US009828361B2

(12) United States Patent
Man et al.

(10) Patent No.: US 9,828,361 B2
(45) Date of Patent: *Nov. 28, 2017

(54) ARYLMETHOXY ISOINDOLINE DERIVATIVES AND COMPOSITIONS COMPRISING AND METHODS OF USING THE SAME

(71) Applicant: Celgene Corporation, Summit, NJ (US)

(72) Inventors: Hon-Wah Man, Princeton, NJ (US); Roger Shen-Chu Chen, Edison, NJ (US); George W. Muller, Rancho Santa Fe, CA (US); Alexander L. Ruchelman, Cream Ridge, NJ (US); Ehab M. Khalil, Whitehouse Station, NJ (US); Weihong Zhang, Highland Park, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,971

(22) Filed: Feb. 10, 2016

(65) Prior Publication Data

US 2016/0159768 A1 Jun. 9, 2016

Related U.S. Application Data

(60) Continuation of application No. 13/952,386, filed on Jul. 26, 2013, now Pat. No. 9,309,219, which is a division of application No. 13/025,105, filed on Feb. 10, 2011, now Pat. No. 8,518,972.

(60) Provisional application No. 61/303,618, filed on Feb. 11, 2010.

(51) Int. Cl.
| | |
|---|---|
| *C07D 401/12* | (2006.01) |
| *C07D 401/04* | (2006.01) |
| *C07D 401/14* | (2006.01) |
| *C07D 407/12* | (2006.01) |
| *C07D 407/14* | (2006.01) |
| *C07D 409/14* | (2006.01) |
| *C07D 413/14* | (2006.01) |
| *C07D 417/14* | (2006.01) |
| *C07D 487/04* | (2006.01) |
| *C07D 491/107* | (2006.01) |
| *C07D 493/04* | (2006.01) |
| *C07D 495/04* | (2006.01) |
| *C07D 471/04* | (2006.01) |

(52) U.S. Cl.
CPC ........ *C07D 401/12* (2013.01); *C07D 401/04* (2013.01); *C07D 401/14* (2013.01); *C07D 407/12* (2013.01); *C07D 407/14* (2013.01); *C07D 409/14* (2013.01); *C07D 413/14* (2013.01); *C07D 417/14* (2013.01); *C07D 471/04* (2013.01); *C07D 487/04* (2013.01); *C07D 491/107* (2013.01); *C07D 493/04* (2013.01); *C07D 495/04* (2013.01)

(58) Field of Classification Search
CPC .......................... C07D 401/04; A61K 31/454
USPC .......... 514/323; 544/58.2, 105, 131; 546/15, 546/122, 146, 175, 184, 200, 201
See application file for complete search history.

(56) References Cited

U.S. PATENT DOCUMENTS

| | | |
|---|---|---|
| 4,421,865 A | 12/1983 | Shen |
| 5,149,820 A | 9/1992 | Borretzen et al. |
| 5,385,901 A | 1/1995 | Kaplan et al. |
| 5,646,154 A | 7/1997 | Irie et al. |
| 6,458,810 B1 | 10/2002 | Muller et al. |
| 8,153,659 B2 | 4/2012 | Ruchelman et al. |
| 8,518,972 B2 * | 8/2013 | Man ..................... C07D 401/04 514/323 |
| 9,090,585 B2 | 7/2015 | Dewitt |
| 9,221,788 B2 | 12/2015 | Cohen et al. |
| 9,309,219 B2 * | 4/2016 | Man ..................... C07D 401/04 514/323 |
| 9,309,220 B2 | 4/2016 | Traverse et al. |
| 9,415,049 B2 | 8/2016 | Tester et al. |
| 2013/0274291 A1 | 10/2013 | Dewitt |
| 2014/0045843 A1 | 2/2014 | Schafer et al. |
| 2014/0045844 A1 | 2/2014 | Schafer et al. |
| 2014/0162282 A1 | 6/2014 | Schafer et al. |
| 2014/0301980 A1 | 10/2014 | Day |
| 2014/0314752 A1 | 10/2014 | Lopez-Girona et al. |
| 2014/0343058 A1 | 11/2014 | Schafer et al. |
| 2015/0038511 A1 | 2/2015 | Schafer et al. |
| 2015/0099745 A1 | 4/2015 | Parikh et al. |
| 2015/0152511 A1 | 6/2015 | Thakurta et al. |
| 2015/0224104 A1 | 8/2015 | Gandhi et al. |
| 2015/0361066 A1 | 12/2015 | Traverse |
| 2015/0374678 A1 | 12/2015 | Chamberlain et al. |
| 2016/0045475 A1 | 2/2016 | Day |
| 2016/0313300 A1 | 10/2016 | Trotter et al. |
| 2016/0324878 A1 | 11/2016 | He |

FOREIGN PATENT DOCUMENTS

| | | |
|---|---|---|
| WO | 99/47512 A1 | 9/1999 |
| WO | 02/059106 A1 | 8/2002 |

(Continued)

OTHER PUBLICATIONS

Leung et al. "TNF-alpha and neuro . . . " K. Neuroinflammation 7:27, 1-11 (2010).*

(Continued)

*Primary Examiner* — Heidi Reese
(74) *Attorney, Agent, or Firm* — Jones Day

(57) ABSTRACT

Provided are 4'-arylmethoxy isoindoline compounds, and pharmaceutically acceptable salts, solvates, clathrates, stereoisomers, and prodrugs thereof. Methods of use, and pharmaceutical compositions of these compounds are disclosed.

10 Claims, No Drawings

(56) References Cited

FOREIGN PATENT DOCUMENTS

| WO | WO 2006/019768 A1 | 2/2006 |
|---|---|---|
| WO | 2006/025991 A2 | 3/2006 |
| WO | WO 2006/028964 A1 | 3/2006 |
| WO | 2007/027527 A1 | 3/2007 |
| WO | 2008/115516 | 9/2008 |
| WO | WO 2012/027065 A2 | 3/2012 |
| WO | WO 2012/079022 A1 | 6/2012 |
| WO | WO 2014/025958 A2 | 2/2014 |
| WO | WO 2015/179276 A1 | 11/2015 |
| WO | WO 2016/060702 A1 | 4/2016 |
| WO | WO 2016/065980 A1 | 5/2016 |

OTHER PUBLICATIONS

Bioactivity Lenalidomide, "Bioactivity Data for Compound lenalidomide (CID 216326)," p. 1, retrieve online <http://pubchem.ncbi.nlm.nih.gov/assay/assay.cgi?cid_216326>. Retrieved on Jun. 22, 2015.

Braga and Grepioni, "Making crystals from crystals: a green route to crystal engineering and polymorphism," Chem. Commun., 3635-3645 (2005).

Brown et al., "A clinical study assessing the tolerability and biological effects of infliximab, a TNF-α inhibitor, in patients with advanced cancer," Ann. Oncol., 19(7):1340-1346 (2008).

Grever et al., "The National Cancer Institute: Cancer drug discovery and development program," Semin. Oncol., 19(6):622-638 (1992).

Hideshima et al., "Current therapeutic uses of lenalidomide in multiple myeloma," Expert Opin. Investig. Drugs, 15(2):171-179 (2006).

Kiran, "Cancer Treatment," Chapter 1, pp. 1-18 (2011).

Latli, "Synthesis of deuterium, tritium, and carbon-14 labeled BIRB 796, a p38 MAP kinase inhibitor," J. Label Compd. Radiopharm., 47:847-856 (2004).

Latli, "Synthesis of deuterium, tritium, and carbon-14 labeled BIRB 796, a p38 MAP kinase inhibitor," CAPLUS, 142:411280 (2004).

Nakamura et al., "Mono- and Dihydroxylated Metabolites of Thalidomide: Synthesis and TNF-α Production-Inhibitory Activity," Chem. Pharm. Bull., 54(12):1709-1714 (2006).

National Cancer Institute, "Targeted cancer therapies," retrieved online <http:www.cancer.gov/cancertopics/factsheet/Therapy/targeted>. Retrieved on Aug. 13, 2014, 6 pages.

National Cancer Institute, "What is Cancer?," retrieved online <http://www.cancer.gov/cancertopics/cancerlibrary/what-is-cancer>. Retrived on Aug. 11, 2014, 3 pages.

Peyrin-Biroulet et al., "Efficacy and safety of tumor necrosis factor antagonists in Crohn's disease: meta-analysis of placebo-controlled trials," Clin. Gasroenterol. Hepatol., 6(6):644-653 (2008).

Seddon, "Pseudopolymorph: a polemic," Crystal Growth Design, 4(6):1087 (2004).

Szlosarek et al., "Tumour necrosis factor-α as a tumour promoter," Eur. J. Cancer, 42(6):745-750 (2006).

Wade, "Deuterium isotope effects on noncovalent interactions between molecules," Chemico-Biological Interactions, 117:191-217 (1999).

Who, "Cancer classification," retrieved on <http://training.seer.cancer.gov/module_...ase/unit3_categories2_by_histology.html>. Retrieved on Jan. 26, 2005, 3 pages.

Wikipedia, "Lenalidomide," retrieved online <http://en.wikipedia.org/wiki/Lenalidomide>. Retrieved on Jan. 14, 2015, pp. 1-5.

Wiltshire et al., "Synthesis of labeled forms of cipemastat," CAPLUS, 134:311151 (2001).

Wiltshire et al., "The Synthesis of labelled forms of cipemastat," J. Labelled Cpd. Rapiopharm., 4:149-164 (2001).

Witzig et al., "A comprehensive review of lenalidomide therapy for B-cell non-Hodgkin lymphoma," Ann. Oncol., 1-10 (2015).

Wu and Zhou, "TNF-α/NF-κB/snail pathway in cancer cell migration and invasion," Br. J. Cancer, 102(4):639-644 (2010).

Zhou et al., "The TNF-alpha-238 polymorphism and cancer risk: a meta-analysis," PloS One, 6(7):e22092 (2011).

Gant, "Using deuterium in drug discovery: leaving the label in the drug," *J. Med. Chem.*, 57:3595-3611 (2014).

Mullard, "Deuterated drugs draw heavier backing," *Nature Rev. Drug Dis.*, 15:219-221 (2016).

\* cited by examiner

ARYLMETHOXY ISOINDOLINE DERIVATIVES AND COMPOSITIONS COMPRISING AND METHODS OF USING THE SAME

This application is a continuation application of U.S. application Ser. No. 13/952,386, filed Jul, 26, 2013, which is a divisional application of U.S. application Ser. No. 13/025,105, filed Feb. 10, 2011, now U.S. Pat. No. 8,518, 972, which claims priority to U.S. Provisional Application No. 61/303,618, filed Feb. 11, 2010, the entirety of each of which is incorporated herein by reference.

1. FIELD

Provided herein are 4'-arylmethoxy isoindoline derivatives. Pharmaceutical compositions comprising the compounds and methods for treating, preventing and managing various disorders using the compounds and compositions are also disclosed.

2. BACKGROUND

2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; arthritis; and proliferative vitreoretinopathy.

Accordingly, compounds that can control angiogenesis or inhibit the production of certain cytokines, including TNF-α, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine, vol*. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health or age of a patient or may be unacceptable to the patient.

Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other, treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance.

Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for safe and effective methods of treating, preventing and managing cancer and other diseases and conditions, including for diseases that are refractory to standard treatments, such as surgery, radiation therapy, chemotherapy and hormonal therapy, while reducing or avoiding the toxicities and/or side effects associated with the conventional therapies.

3. SUMMARY

Provided herein are 4'-arylmethoxy isoindoline compounds, and pharmaceutically acceptable salts, solvates (e.g., hydrates), prodrugs, clathrates, or stereoisomers thereof.

Also provided are methods of treating and managing various diseases or disorders. The methods comprise administering to a patient in need of such treatment or management a therapeutically effective amount of a compound provided herein, or a pharmaceutically acceptable salt, solvate, prodrug, clathrate, or stereoisomer thereof.

Further provided are methods of preventing various diseases and disorders, which comprise administering to a patient in need of such prevention a prophylactically effective amount of a compound provided herein, or a pharmaceutically acceptable salt, solvate, prodrug, clathrate, or stereoisomer thereof.

Also provided herein are pharmaceutical compositions, single unit dosage forms, dosing regimens and kits which comprise a compound provided herein, or a pharmaceutically acceptable salt, solvate, prodrug, clathrate, or stereoisomer thereof.

4. DETAILED DESCRIPTION

In one embodiment, provided are isoindoline compounds, and pharmaceutically acceptable salts, solvates, prodrugs, clathrate, and stereoisomers thereof.

In another embodiment, provided are methods of treating, managing, and preventing various diseases and disorders, which comprises administering to a patient in need of such treatment or prevention a therapeutically or prophylactically effective amount of a compound provided herein, or a pharmaceutically acceptable salt, solvate, prodrug, clathrate, or stereoisomer thereof. Examples of diseases and disorders are described herein.

In other embodiments, a compound provided herein, or a pharmaceutically acceptable salt, solvate, prodrug, clathrate, or stereoisomer thereof, is administered in combination with another drug ("second active agent") or treatment. Second active agents include small molecules and large molecules (e.g., proteins and antibodies), examples of which are provided herein, as well as stem cells. Methods, or therapies, that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable salt, solvate, prodrug, clathrate, or stereoisomer thereof, and optionally a second active agent.

4.1 Compounds

In one embodiment, provided herein is a compound of formula (I):

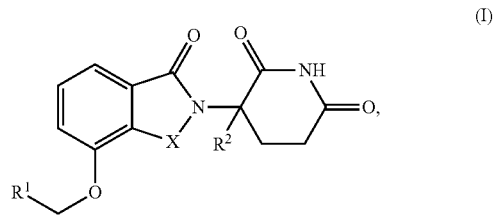

or a pharmaceutically acceptable salt, solvate or stereoisomer thereof, wherein:

X is C=O or CH$_2$;

R$^1$ is —Y—R$^3$;

R$^2$ is H or (C$_1$-C$_6$)alkyl;

Y is: 6 to 10 membered aryl, heteroaryl or heterocycle, each of which may be optionally substituted with one or more halogen; or a bond;

R$^3$ is: —(CH$_2$)$_n$-aryl, —O—(CH$_2$)$_n$-aryl or —(CH$_2$)$_n$—O-aryl, wherein the aryl is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen;

—(CH$_2$)$_n$-heterocycle, —O—(CH$_2$)$_n$-heterocycle or —(CH$_2$)$_n$—O-heterocycle, wherein the heterocycle is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; or —(CH$_2$)$_n$-heteroaryl, —O—(CH$_2$)$_n$-heteroaryl or —(CH$_2$)$_n$—O-heteroaryl, wherein the heteroaryl is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; and n is 0, 1, 2 or 3.

In one embodiment, X is C═O. In another embodiment, C is CH$_2$.

In one embodiment, R$^2$ is H. In another embodiment, R$^2$ is (C$_1$-C$_6$)alkyl.

In one embodiment, Y is aryl. In another embodiment, Y is heteroaryl. In another embodiment, Y is heterocycle. In another embodiment, Y is a bond.

In one embodiment, R$^3$ is unsubstituted —(CH$_2$)$_n$-aryl. In another embodiment, R$^3$ is —(CH$_2$)$_n$-aryl substituted with one or more (C$_1$-C$_6$)alkyl, itself optionally substituted with one or more halogen. In another embodiment, R$^3$ is —(CH$_2$)$_n$-aryl substituted with one or more (C$_1$-C$_6$)alkoxy, itself substituted with one or more halogen. In another embodiment, R$^3$ is —(CH$_2$)$_n$-aryl substituted with one or more oxo. In another embodiment, R$^3$ is —(CH$_2$)$_n$-aryl substituted with one or more amino. In another embodiment, R$^3$ is —(CH$_2$)$_n$-aryl substituted with one or more carboxyl. In another embodiment, R$^3$ is —(CH$_2$)$_n$-aryl substituted with one or more cyano. In another embodiment, R$^3$ is —(CH$_2$)$_n$-aryl substituted with one or more hydroxyl. In another embodiment, R$^3$ is —(CH$_2$)$_n$-aryl substituted with one or more halogen. In another embodiment, R$^3$ is —(CH$_2$)$_n$-aryl substituted with one or more deuterium. In another embodiment, R$^3$ is —(CH$_2$)$_n$-aryl substituted with one or more 6 to 10 membered aryl, optionally substituted with one or more (C$_1$-C$_6$)alkyl. In another embodiment, R$^3$ is —(CH$_2$)$_n$-aryl substituted with one or more 6 to 10 membered heteroaryl, optionally substituted with one or more (C$_1$-C$_6$)alkyl, (C$_1$-C$_6$)alkoxy or halogen. In another embodiment, R$^3$ is —(CH$_2$)$_n$-aryl substituted with one or more —CONH$_2$. In another embodiment, R$^3$ is —(CH$_2$)$_n$-aryl substituted with one or more —COO—(C$_1$-C$_6$)alkyl, wherein the alkyl may be optionally substituted with one or more halogen.

In one embodiment, R$^3$ is unsubstituted —O—(CH$_2$)$_n$-aryl. In another embodiment, R$^3$ is —O—(CH$_2$)$_n$-aryl substituted with one or more (C$_1$-C$_6$)alkyl, itself optionally substituted with one or more halogen. In another embodiment, R$^3$ is —O—(CH$_2$)$_n$-aryl substituted with one or more (C$_1$-C$_6$)alkoxy, itself substituted with one or more halogen. In another embodiment, R$^3$ is —O—(CH$_2$)$_n$-aryl substituted with one or more oxo. In another embodiment, R$^3$ is —O—(CH$_2$)$_n$-aryl substituted with one or more amino. In another embodiment, R$^3$ is —O—(CH$_2$)$_n$-aryl substituted with one or more carboxyl. In another embodiment, R$^3$ is —O—(CH$_2$)$_n$-aryl substituted with one or more cyano. In another embodiment, R$^3$ is —O—(CH$_2$)$_n$-aryl substituted with one or more hydroxyl. In another embodiment, R$^3$ is —O—(CH$_2$)$_n$-aryl substituted with one or more halogen. In another embodiment, R$^3$ is —O—(CH$_2$)$_n$-aryl substituted with one or more deuterium. In another embodiment, R$^3$ is —O—(CH$_2$)$_n$-aryl substituted with one or more 6 to 10 membered aryl, optionally substituted with one or more (C$_1$-C$_6$)alkyl. In another embodiment, R$^3$ is —O—(CH$_2$)$_n$-aryl substituted with one or more 6 to 10 membered heteroaryl, optionally substituted with one or more (C$_1$-C$_6$)alkyl, (C$_1$-C$_6$)alkoxy or halogen. In another embodiment, R$^3$ is —O—(CH$_2$)$_n$-aryl substituted with one or more —CONH$_2$. In another embodiment, R$^3$ is —O—(CH$_2$)$_n$-aryl substituted with one or more —COO—(C$_1$-C$_6$)alkyl, wherein the alkyl may be optionally substituted with one or more halogen.

In one embodiment, R$^3$ is unsubstituted —(CH$_2$)$_n$—O-aryl. In another embodiment, R$^3$ is —(CH$_2$)$_n$—O-aryl substituted with one or more (C$_1$-C$_6$)alkyl, itself optionally substituted with one or more halogen. In another embodiment, R$^3$ is —(CH$_2$)$_n$—O-aryl substituted with one or more (C$_1$-C$_6$)alkoxy, itself substituted with one or more halogen. In another embodiment, R$^3$ is —(CH$_2$)$_n$—O-aryl substituted with one or more oxo. In another embodiment, R$^3$ is —(CH$_2$)$_n$—O-aryl substituted with one or more amino. In another embodiment, R$^3$ is —(CH$_2$)$_n$—O-aryl substituted with one or more carboxyl. In another embodiment, R$^3$ is —(CH$_2$)$_n$—O-aryl substituted with one or more cyano. In another embodiment, R$^3$ is —(CH$_2$)$_n$—O-aryl substituted with one or more hydroxyl. In another embodiment, R$^3$ is —(CH$_2$)$_n$—O-aryl substituted with one or more halogen. In another embodiment, R$^3$ is —(CH$_2$)$_n$—O-aryl substituted with one or more deuterium. In another embodiment, R$^3$ is —(CH$_2$)$_n$—O-aryl substituted with one or more 6 to 10 membered aryl, optionally substituted with one or more (C$_1$-C$_6$)alkyl. In another embodiment, R$^3$ is —(CH$_2$)$_n$—O-aryl substituted with one or more 6 to 10 membered heteroaryl, optionally substituted with one or more (C$_1$-C$_6$)alkyl, (C$_1$-C$_6$)alkoxy or halogen. In another embodiment, R$^3$ is —(CH$_2$)$_n$—O-aryl substituted with one or more —CONH$_2$. In another embodiment, R$^3$ is —(CH$_2$)$_n$—O-aryl substituted with one or more —COO—(C$_1$-C$_6$)alkyl, wherein the alkyl may be optionally substituted with one or more halogen.

In one embodiment, R$^3$ is unsubstituted —(CH$_2$)$_n$-heterocycle. In another embodiment, R$^3$ is —(CH$_2$)$_n$-heterocycle substituted with one or more (C$_1$-C$_6$)alkyl, itself optionally substituted with one or more halogen. In another embodiment, R$^3$ is —(CH$_2$)$_n$-heterocycle substituted with one or more (C$_1$-C$_6$)alkoxy, itself substituted with one or more halogen. In another embodiment, R$^3$ is —(CH$_2$)$_n$-heterocycle substituted with one or more oxo. In another embodiment, R$^3$ is —(CH$_2$)$_n$-heterocycle substituted with one or more amino. In another embodiment, R$^3$ is —(CH$_2$)$_n$-heterocycle substituted with one or more carboxyl. In another embodiment, R$^3$ is —(CH$_2$)$_n$-heterocycle substituted with one or more cyano. In another embodiment, R$^3$ is —(CH$_2$)$_n$-heterocycle substituted with one or more hydroxyl. In another embodiment, R$^3$ is —(CH$_2$)$_n$-heterocycle substituted with one or more halogen. In another embodiment, R$^3$ is —(CH$_2$)$_n$-heterocycle substituted with one or more deuterium. In another embodiment, R$^3$ is —(CH$_2$)$_n$-heterocycle substituted with one or more 6 to 10 membered aryl, optionally substituted with one or more (C$_1$-C$_6$)alkyl. In another embodiment, R$^3$ is —(CH$_2$)$_n$-heterocycle substituted with one or more 6 to 10 membered heteroaryl, optionally substituted with one or more (C$_1$-C$_6$)alkyl, (C$_1$-C$_6$)alkoxy or halogen. In another embodiment, R$^3$ is —(CH$_2$)$_n$-heterocycle substituted with one or more —CONH$_2$. In another embodiment, R$^3$ is —(CH$_2$)$_n$-heterocycle substituted with one or more —COO—(C$_1$-C$_6$)alkyl, wherein the alkyl may be optionally substituted with one or more halogen.

In one embodiment, R$^3$ is unsubstituted —O—(CH$_2$)$_n$-heterocycle. In another embodiment, R$^3$ is —O—(CH$_2$)$_n$-heterocycle substituted with one or more (C$_1$-C$_6$)alkyl, itself optionally substituted with one or more halogen. In another embodiment, R$^3$ is —O—(CH$_2$)$_n$-heterocycle substituted with one or more (C$_1$-C$_6$)alkoxy, itself substituted with one or more halogen. In another embodiment, R$^3$ is —O—(CH$_2$)$_n$-heterocycle substituted with one or more oxo. In another embodiment, R$^3$ is —O—(CH$_2$)$_n$-heterocycle substituted with one or more amino. In another embodiment, R$^3$ is —O—(CH$_2$)$_n$-heterocycle substituted with one or more carboxyl. In another embodiment, R$^3$ is —O—(CH$_2$)$_n$-heterocycle substituted with one or more cyano. In another embodiment, R$^3$ is —O—(CH$_2$)$_n$-heterocycle substituted with one or more hydroxyl. In another embodiment, R$^3$ is —O—(CH$_2$)$_n$-heterocycle substituted with one or more halogen. In another embodiment, $R^3$ is —O—$(CH_2)_n$-heterocycle substituted with one or more deuterium. In another embodiment, $R^3$ is —O—$(CH_2)_n$-heterocycle substituted with one or more 6 to 10 membered aryl, optionally substituted with one or more $(C_1$-$C_6)$alkyl. In another embodiment, $R^3$ is —O—$(CH_2)_n$-heterocycle substituted with one or more 6 to 10 membered heteroaryl, optionally substituted with one or more $(C_1$-$C_6)$alkyl; $(C_1$-$C_6)$alkoxy or halogen. In another embodiment, $R^3$ is —O—$(CH_2)_n$-heterocycle substituted with one or more —$CONH_2$. In another embodiment, $R^3$ is —O—$(CH_2)_n$-heterocycle substituted with one or more —COO—$(C_1$-$C_6)$alkyl, wherein the alkyl may be optionally substituted with one or more halogen.

In one embodiment, $R^3$ is unsubstituted —$(CH_2)_n$—O-heterocycle. In another embodiment, $R^3$ is —$(CH_2)_n$—O-heterocycle substituted with one or more $(C_1$-$C_6)$alkyl, itself optionally substituted with one or more halogen. In another embodiment, $R^3$ is —$(CH_2)_n$—O-heterocycle substituted with one or more $(C_1$-$C_6)$alkoxy, itself substituted with one or more halogen. In another embodiment, $R^3$ is —$(CH_2)_n$—O-heterocycle substituted with one or more oxo. In another embodiment, $R^3$ is —$(CH_2)_n$—O-heterocycle substituted with one or more amino. In another embodiment, $R^3$ is —$(CH_2)_n$—O-heterocycle substituted with one or more carboxyl. In another embodiment, $R^3$ is —$(CH_2)_n$—O-heterocycle substituted with one or more cyano. In another embodiment, $R^3$ is —$(CH_2)_n$—O-heterocycle substituted with one or more hydroxyl. In another embodiment, $R^3$ is —$(CH_2)_n$—O-heterocycle substituted with one or more halogen. In another embodiment, $R^3$ is —$(CH_2)_n$—O-heterocycle substituted with one or more deuterium. In another embodiment, $R^3$ is —$(CH_2)_n$—O-heterocycle substituted with one or more 6 to 10 membered aryl, optionally substituted with one or more $(C_1$-$C_6)$alkyl. In another embodiment, $R^3$ is —$(CH_2)_n$—O-heterocycle substituted with one or more 6 to 10 membered heteroaryl, optionally substituted with one or more $(C_1$-$C_6)$alkyl, $(C_1$-$C_6)$alkoxy or halogen. In another embodiment, $R^3$ is —$(CH_2)_n$—O-heterocycle substituted with one or more —$CONH_2$. In another embodiment, $R^3$ is —$(CH_2)_n$—O-heterocycle substituted with one or more —COO—$(C_1$-$C_6)$alkyl, wherein the alkyl may be optionally substituted with one or more halogen.

In one embodiment, $R^3$ is unsubstituted —$(CH_2)_n$-heteroaryl. In another embodiment, $R^3$ is —$(CH_2)_n$-heteroaryl substituted with one or more $(C_1$-$C_6)$alkyl, itself optionally substituted with one or more halogen. In another embodiment, $R^3$ is —$(CH_2)_n$-heteroaryl substituted with one or more $(C_1$-$C_6)$alkoxy, itself substituted with one or more halogen. In another embodiment, $R^3$ is —$(CH_2)_n$-heteroaryl substituted with one or more oxo. In another embodiment, $R^3$ is —$(CH_2)_n$-heteroaryl substituted with one or more amino. In another embodiment, $R^3$ is —$(CH_2)_n$-heteroaryl substituted with one or more carboxyl. In another embodiment, $R^3$ is —$(CH_2)_n$-heteroaryl substituted with one or more cyano. In another embodiment, $R^3$ is —$(CH_2)_n$-heteroaryl substituted with one or more hydroxyl. In another embodiment, $R^3$ is —$(CH_2)_n$-heteroaryl substituted with one or more halogen. In another embodiment, $R^3$ is —$(CH_2)_n$-heteroaryl substituted with one or more deuterium. In another embodiment, $R^3$ is —$(CH_2)_n$-heteroaryl substituted with one or more 6 to 10 membered aryl, optionally substituted with one or more $(C_1$-$C_6)$alkyl. In another embodiment, $R^3$ is —$(CH_2)_n$-heteroaryl substituted with one or more 6 to 10 membered heteroaryl, optionally substituted with one or more $(C_1$-$C_6)$alkyl, $(C_1$-$C_6)$alkoxy or halogen. In another embodiment, $R^3$ is —$(CH_2)_n$-heteroaryl substituted with one or more —$CONH_2$. In another embodiment, $R^3$ is —$(CH_2)_n$-heteroaryl substituted with one or more —COO—$(C_1$-$C_6)$alkyl, wherein the alkyl may be optionally substituted with one or more halogen.

In one embodiment, $R^3$ is unsubstituted —O—$(CH_2)_n$-heteroaryl. In another embodiment, $R^3$ is —O—$(CH_2)_n$-heteroaryl substituted with one or more $(C_1$-$C_6)$alkyl, itself optionally substituted with one or more halogen. In another embodiment, $R^3$ is —O—$(CH_2)_n$-heteroaryl substituted with one or more $(C_1$-$C_6)$alkoxy, itself substituted with one or more halogen. In another embodiment, $R^3$ is —O—$(CH_2)_n$-heteroaryl substituted with one or more oxo. In another embodiment, $R^3$ is —O—$(CH_2)_n$-heteroaryl substituted with one or more amino. In another embodiment, $R^3$ is —O—$(CH_2)_n$-heteroaryl substituted with one or more carboxyl. In another embodiment, $R^3$ is —O—$(CH_2)_n$-heteroaryl substituted with one or more cyano. In another embodiment, $R^3$ is —O—$(CH_2)_n$-heteroaryl substituted with one or more hydroxyl. In another embodiment, $R^3$ is —O—$(CH_2)_n$-heteroaryl substituted with one or more halogen. In another embodiment, $R^3$ is —O—$(CH_2)_n$-heteroaryl substituted with one or more deuterium. In another embodiment, $R^3$ is —O—$(CH_2)_n$-heteroaryl substituted with one or more 6 to 10 membered aryl, optionally substituted with one or more $(C_1$-$C_6)$alkyl. In another embodiment, $R^3$ is —O—$(CH_2)_n$-heteroaryl substituted with one or more 6 to 10 membered heteroaryl, optionally substituted with one or more $(C_1$-$C_6)$alkyl, $(C_1$-$C_6)$alkoxy or halogen. In another embodiment, $R^3$ is —O—$(CH_2)_n$-heteroaryl substituted with one or more —$CONH_2$. In another embodiment, $R^3$ is —O—$(CH_2)_n$-heteroaryl substituted with one or more —COO—$(C_1$-$C_6)$alkyl, wherein the alkyl may be optionally substituted with one or more halogen.

In one embodiment, $R^3$ is unsubstituted —$(CH_2)_n$—O-heteroaryl. In another embodiment, $R^3$ is —$(CH_2)_n$—O-heteroaryl substituted with one or more $(C_1$-$C_6)$alkyl, itself optionally substituted with one or more halogen. In another embodiment, $R^3$ is —$(CH_2)_n$—O-heteroaryl substituted with one or more $(C_1$-$C_6)$alkoxy, itself substituted with one or more halogen. In another embodiment, $R^3$ is —$(CH_2)_n$—O-heteroaryl substituted with one or more oxo. In another embodiment, $R^3$ is —$(CH_2)_n$—O-heteroaryl substituted with one or more amino. In another embodiment, $R^3$ is —$(CH_2)_n$—O-heteroaryl substituted with one or more carboxyl. In another embodiment, $R^3$ is —$(CH_2)_n$—O-heteroaryl substituted with one or more cyano. In another embodiment, $R^3$ is —$(CH_2)_n$—O-heteroaryl substituted with one or more hydroxyl. In another embodiment, $R^3$ is —$(CH_2)_n$—O-heteroaryl substituted with one or more halogen. In another embodiment, $R^3$ is —$(CH_2)_n$—O-heteroaryl substituted with one or more deuterium. In another embodiment, $R^3$ is —$(CH_2)_n$—O-heteroaryl substituted with one or more 6 to 10 membered aryl, optionally substituted with one or more $(C_1$-$C_6)$alkyl. In another embodiment, $R^3$ is —$(CH_2)_n$—O-heteroaryl substituted with one or more 6 to 10 membered heteroaryl, optionally substituted with one or more $(C_1$-$C_6)$alkyl, $(C_1$-$C_6)$alkoxy or halogen. In another embodiment, $R^3$ is —$(CH_2)_n$—O-heteroaryl substituted with one or more —$CONH_2$. In another embodiment, $R^3$ is —$(CH_2)_n$—O-heteroaryl substituted with one or more —COO—$(C_1$-$C_6)$alkyl, wherein the alkyl may be optionally substituted with one or more halogen.

In one embodiment, n is 0. In another embodiment, n is 1. In another embodiment, n is 2.

All of the specific combinations that can result from the definition provided herein for X, $R^1$, $R^2$, Y, $R^3$ and n are encompassed.

In one embodiment, X is $CH_2$.

In one embodiment, Y is aryl. In another embodiment, Y is phenyl.

In another embodiment wherein Y is phenyl, $R^3$ is —$(CH_2)_n$-heterocycle. In one embodiment, the heterocycle is morpholinyl, piperidinyl or pyrrolidinyl.

In one embodiment, Y is a heteroaryl. In another embodiment, Y is a 10 membered hetero aryl. In another embodiment, Y is benzo[d]thiazole. In another embodiment, Y is benzofuran. In another embodiment, Y is quinoline.

In another embodiment where Y isheteroaryl, $R^3$ is —$(CH_2)_n$-heterocycle. In one embodiment, the heterocycle is morpholinyl, piperidinyl or pyrrolidinyl.

In one embodiment, Y is a bond. In another embodiment where Y is a bond, $R^3$ is —$(CH_2)_n$-heterocycle or —$(CH_2)_n$-heteroaryl.

In one embodiment, examples include, but are not limited to:

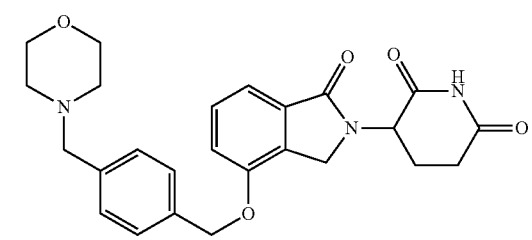

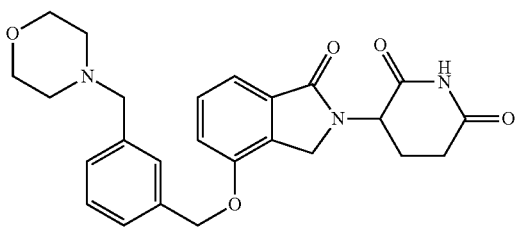

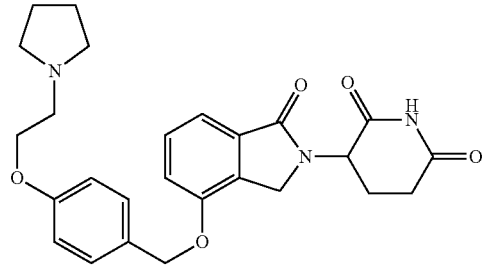

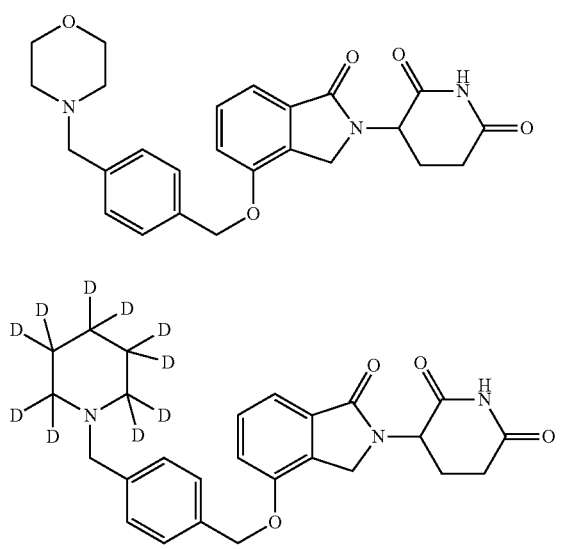

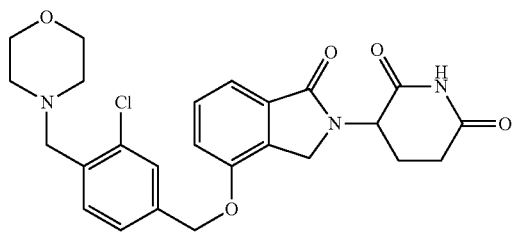

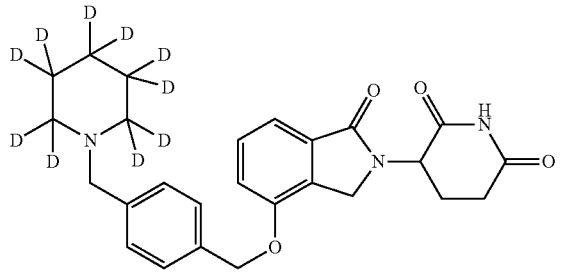

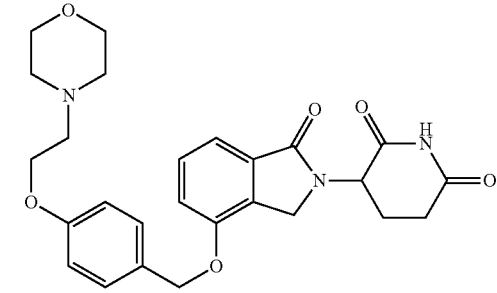

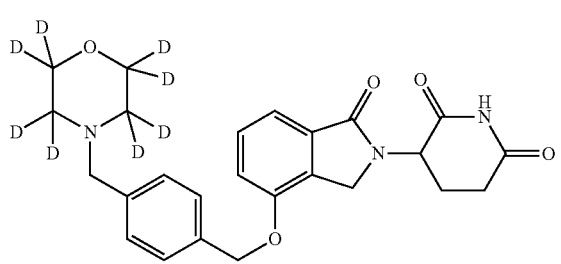

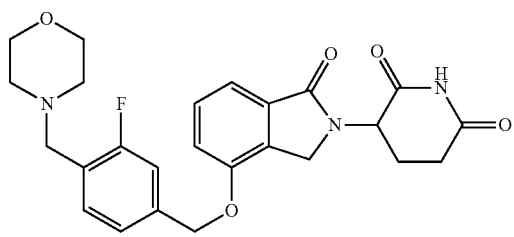

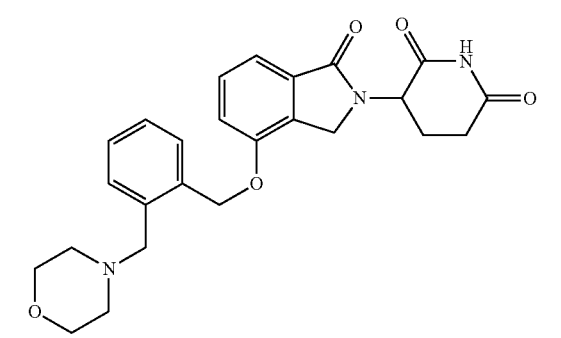

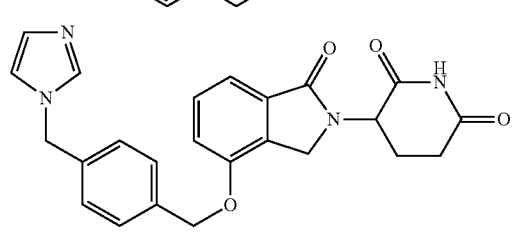

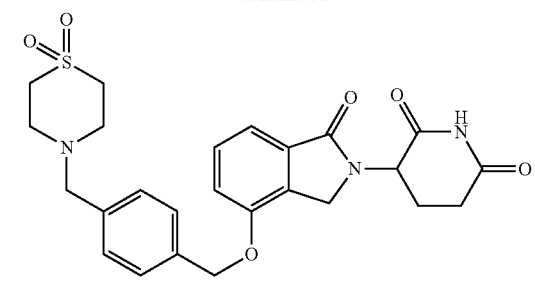
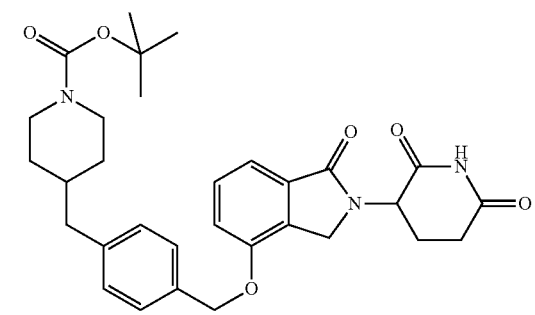
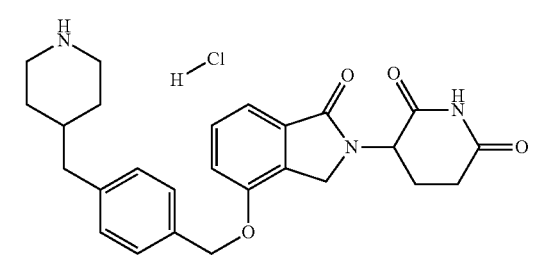
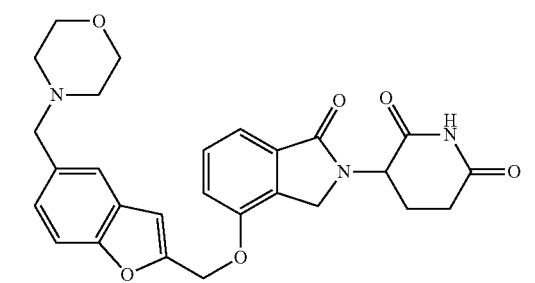
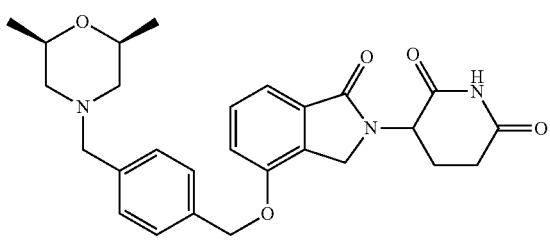
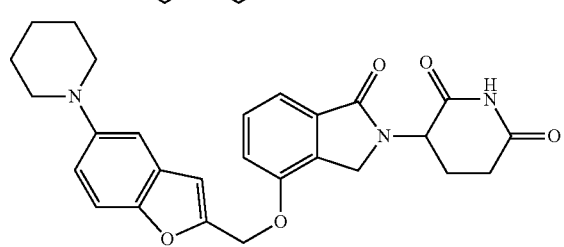
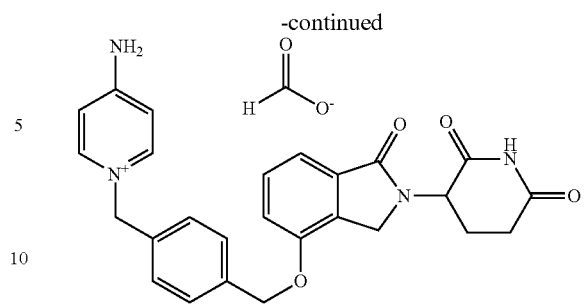
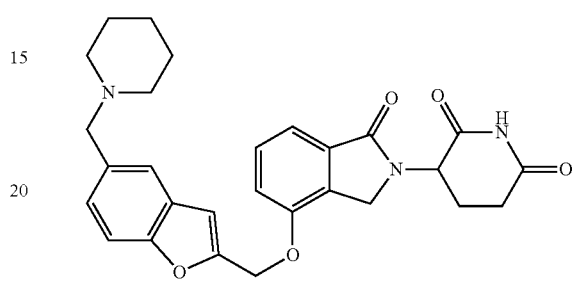
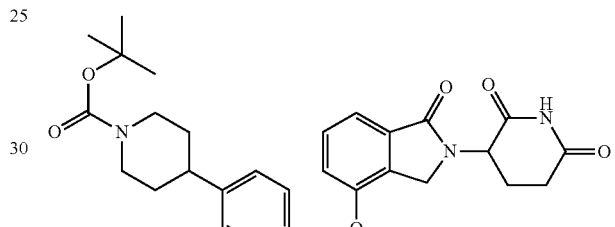
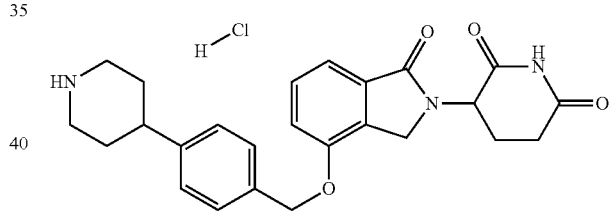
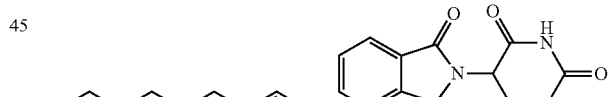
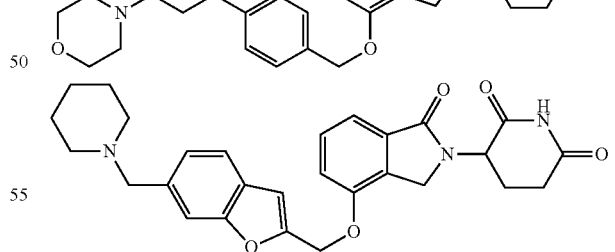
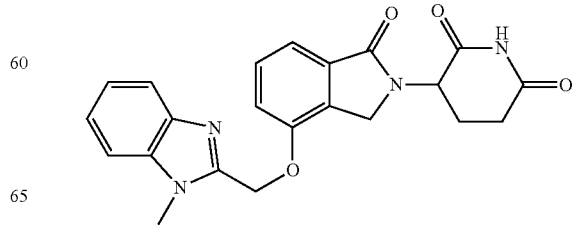

13
-continued
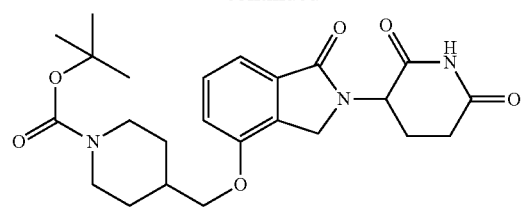
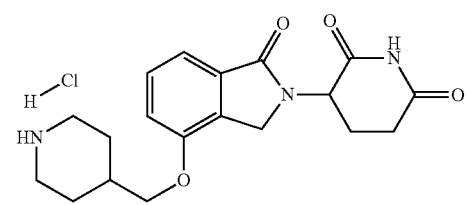
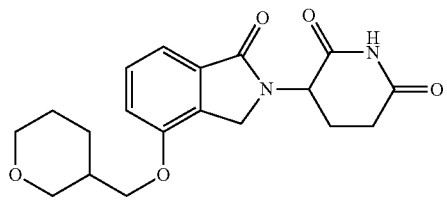
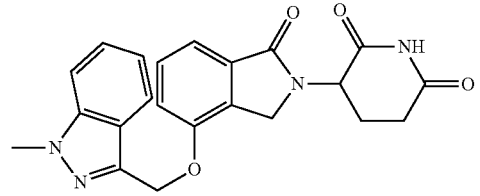
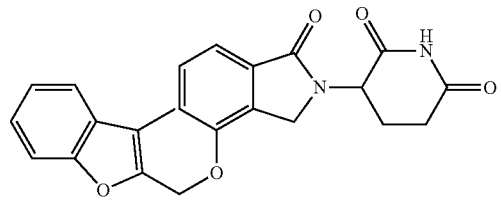
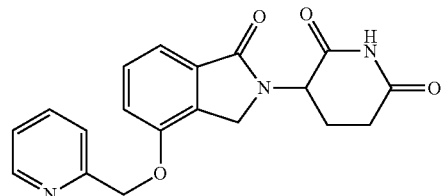
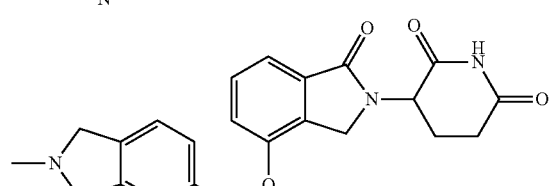
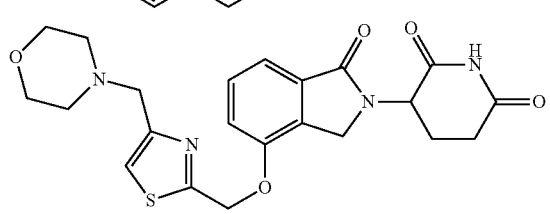
14
-continued
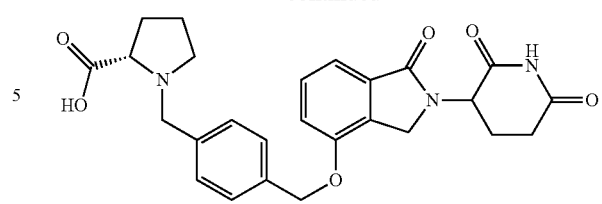
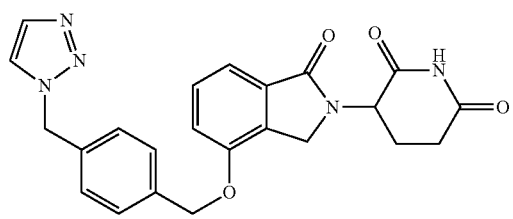
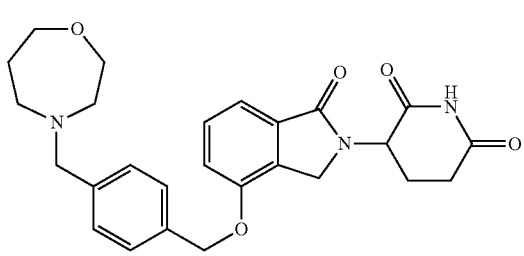
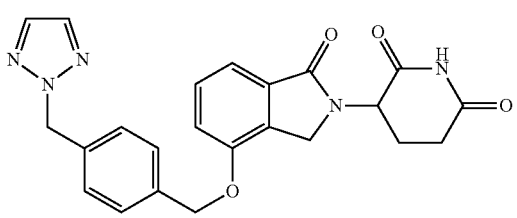
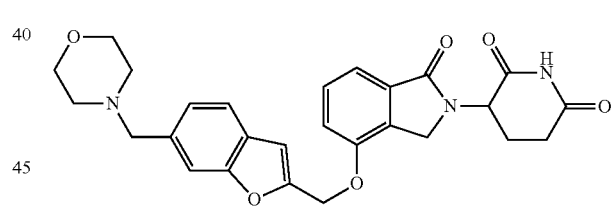
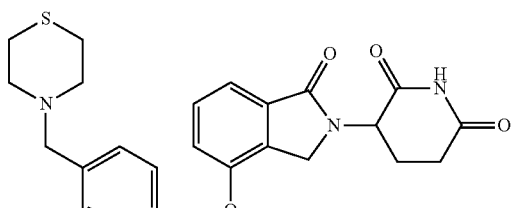
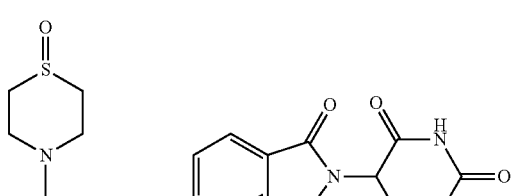

15
-continued
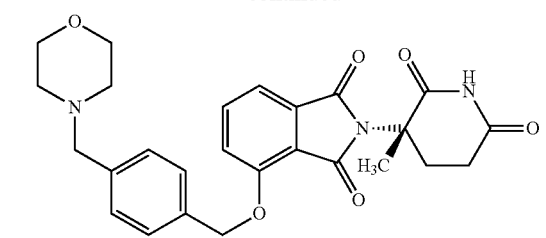
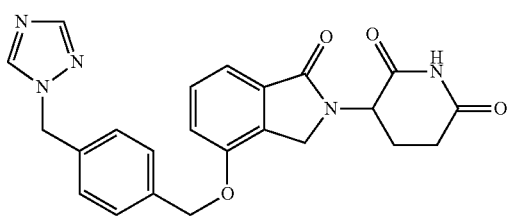
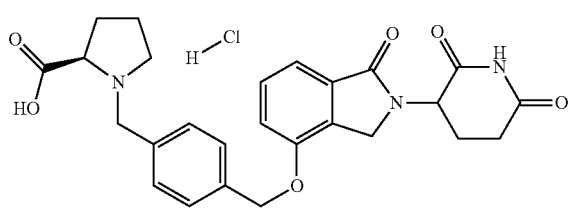
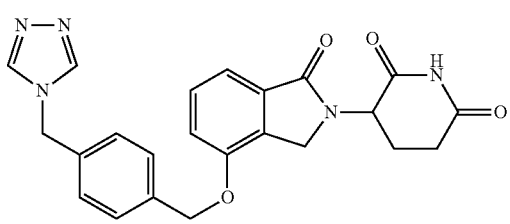
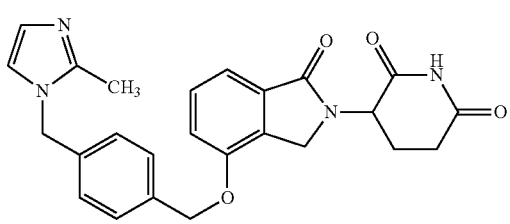
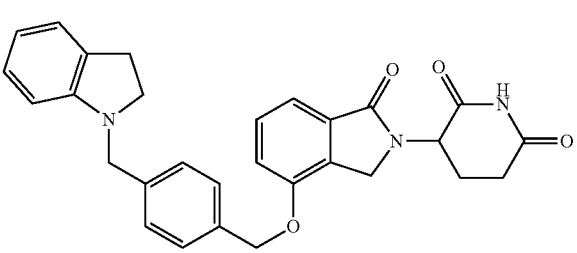
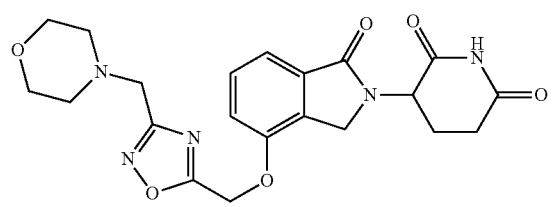
16
-continued
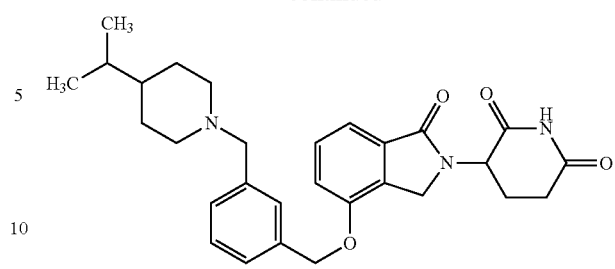
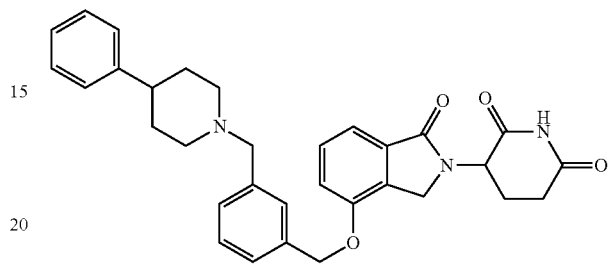
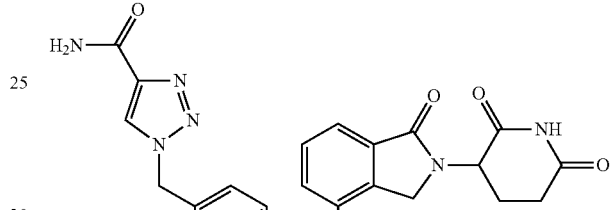
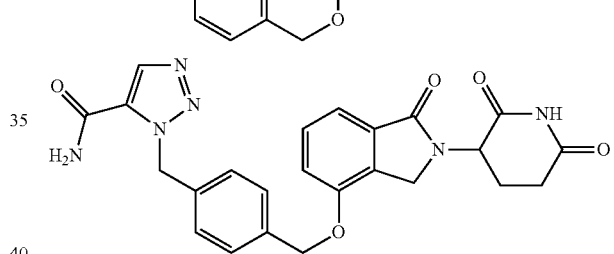
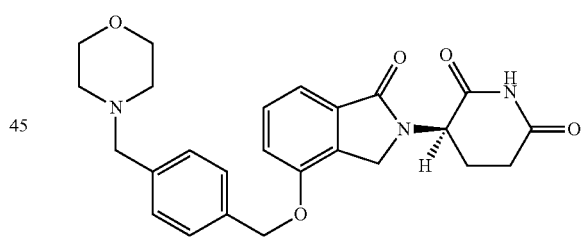
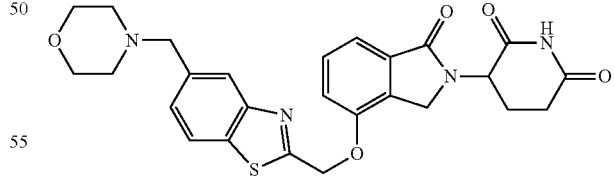
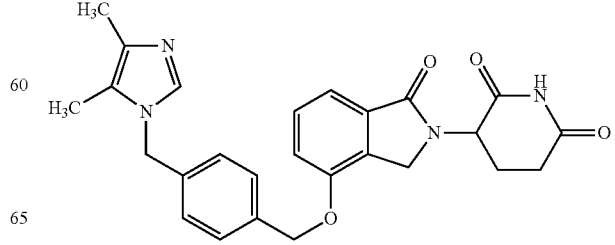

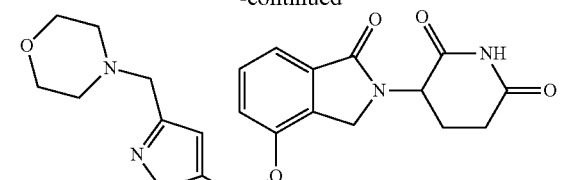

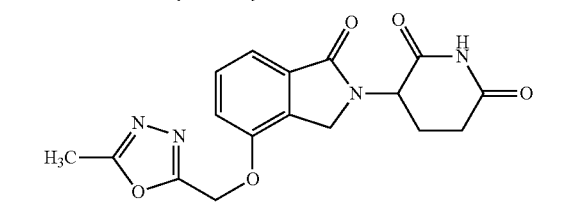
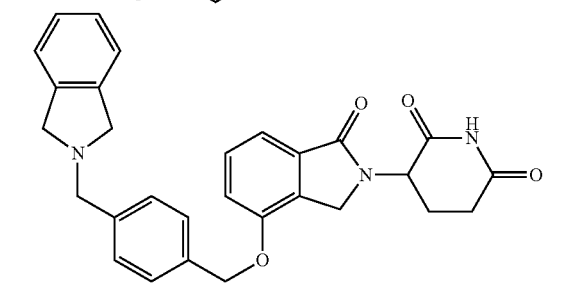
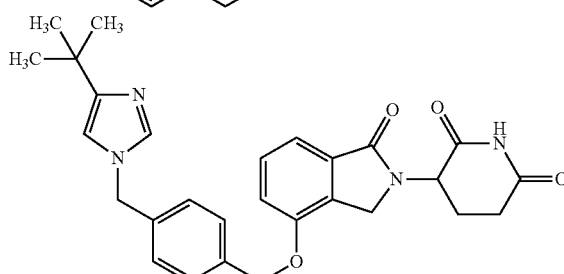
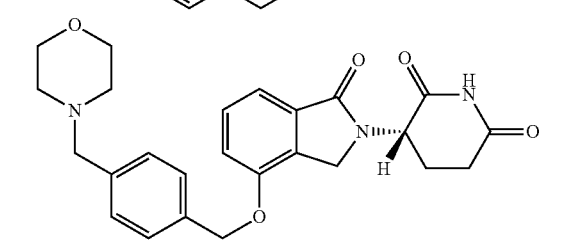
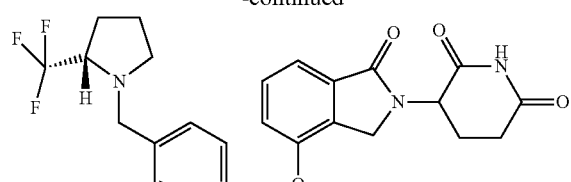
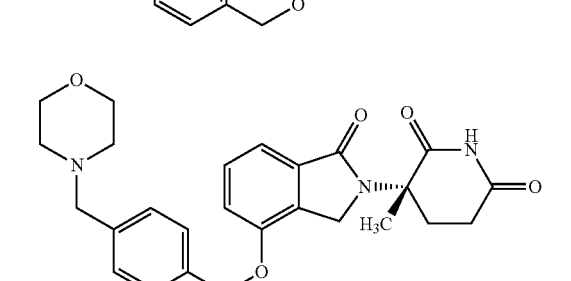
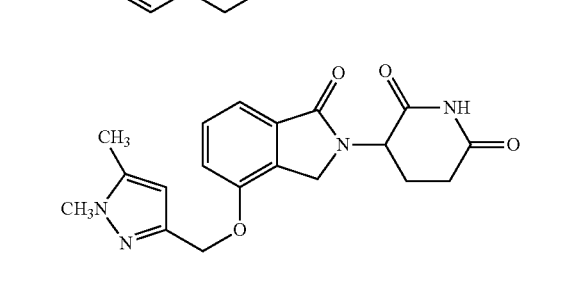
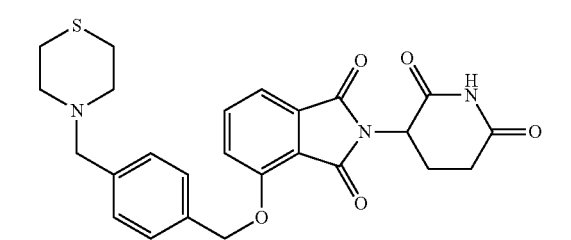
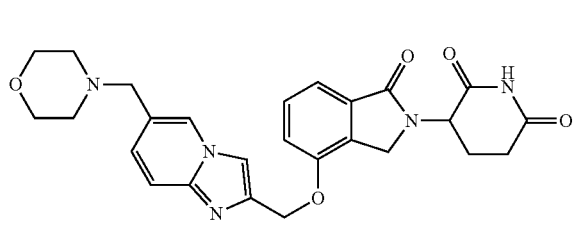
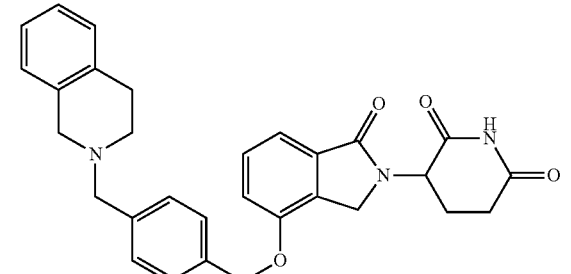
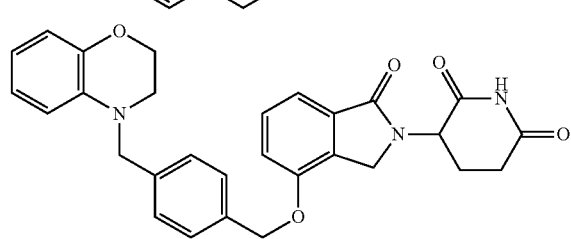

19
-continued
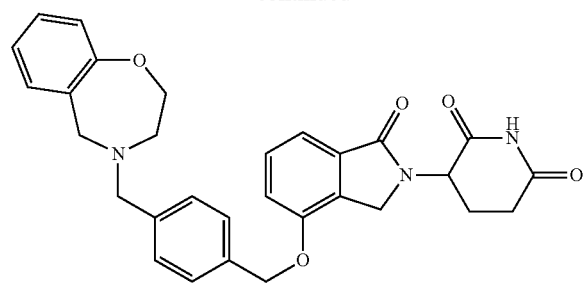
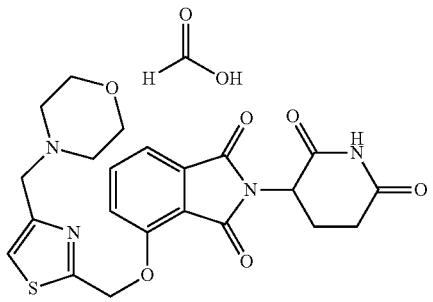
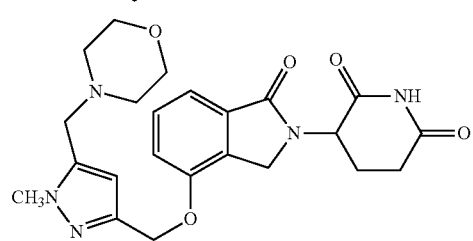
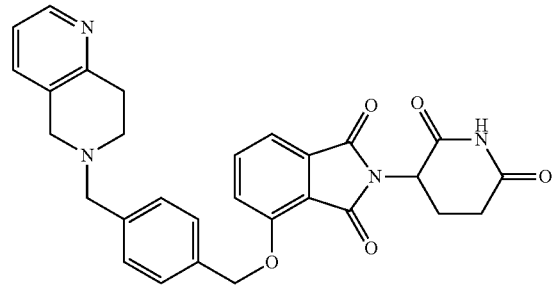
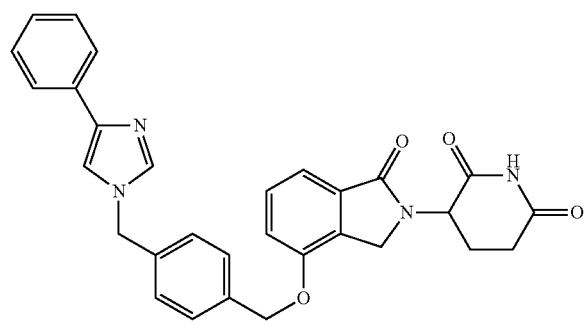
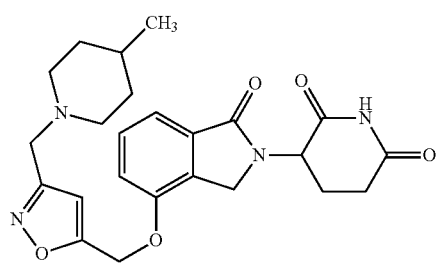
20
-continued
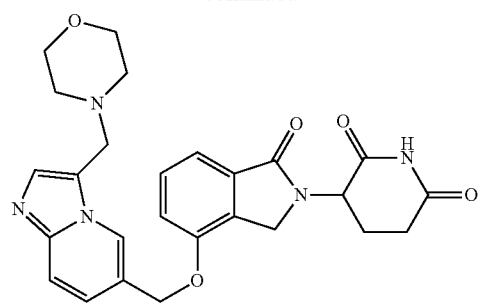
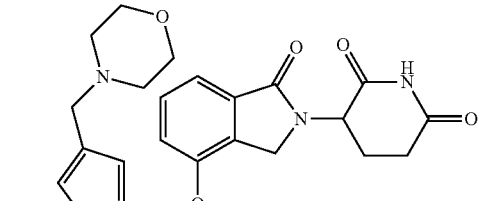
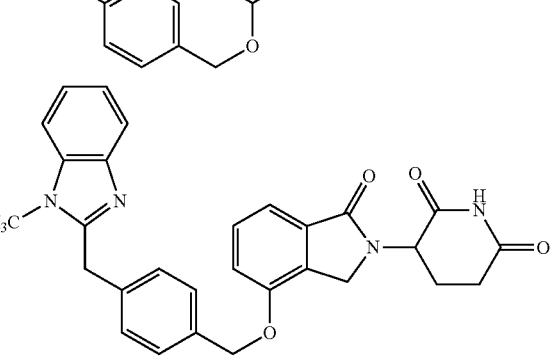
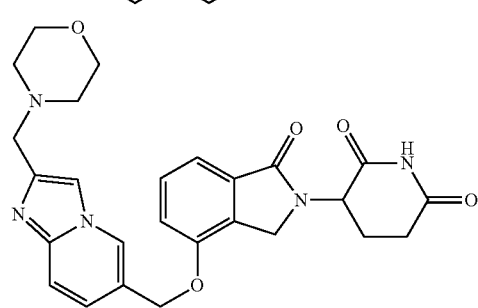
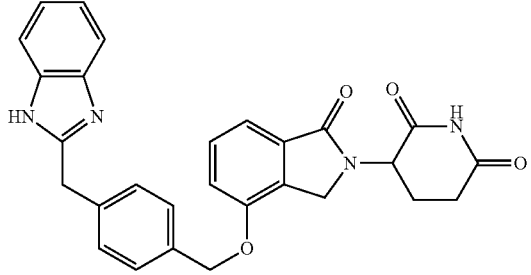

21
-continued
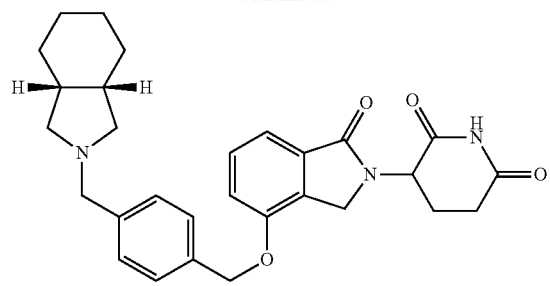
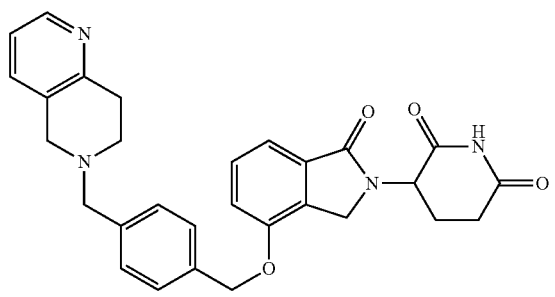
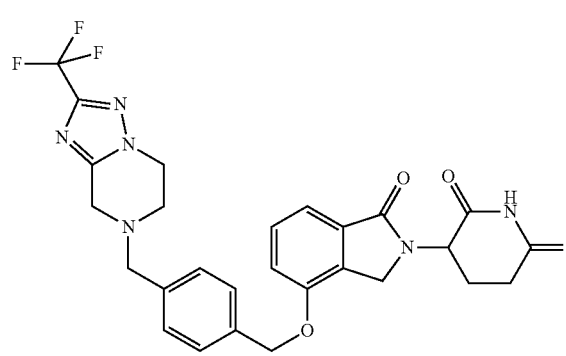
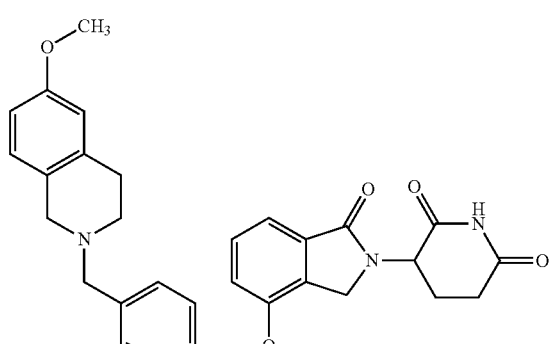
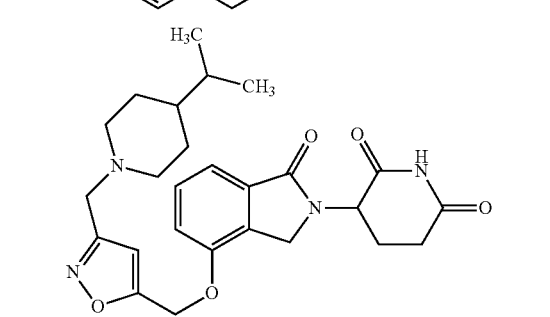
22
-continued
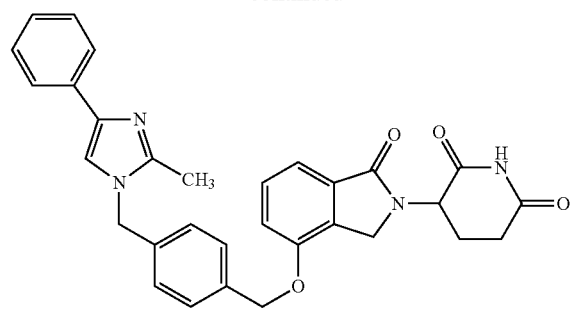
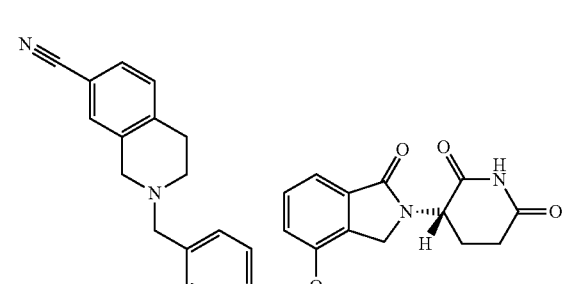
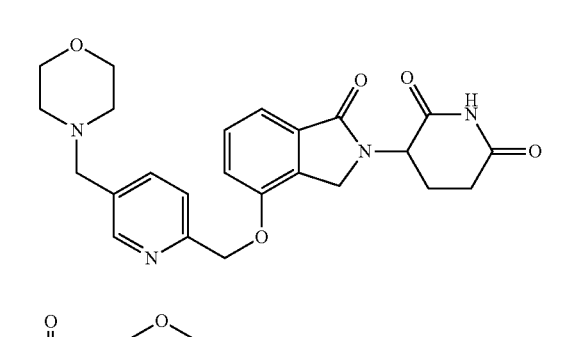
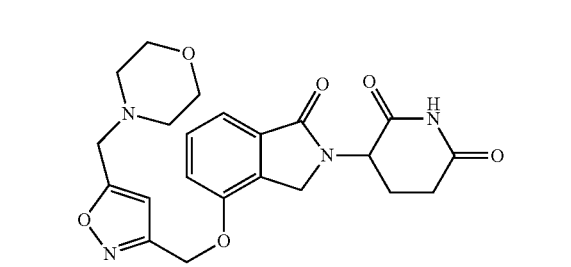
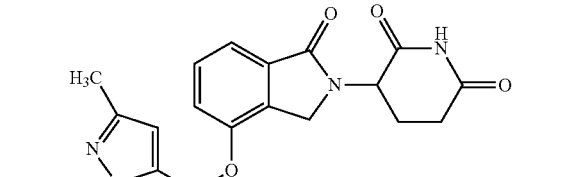

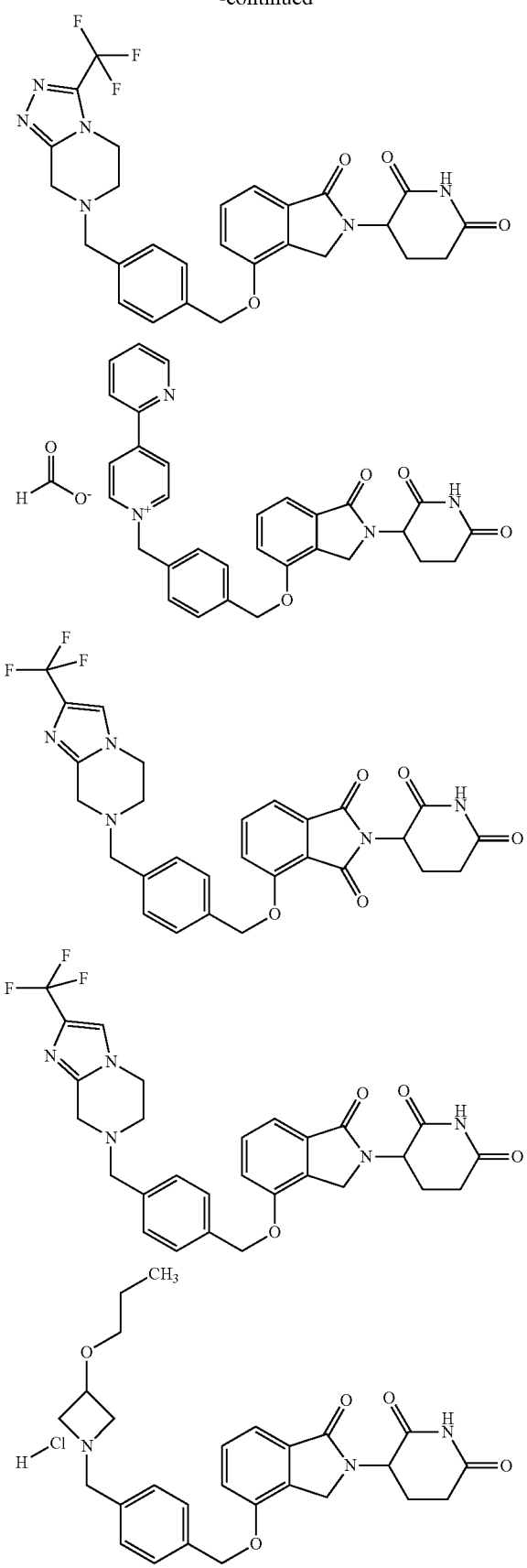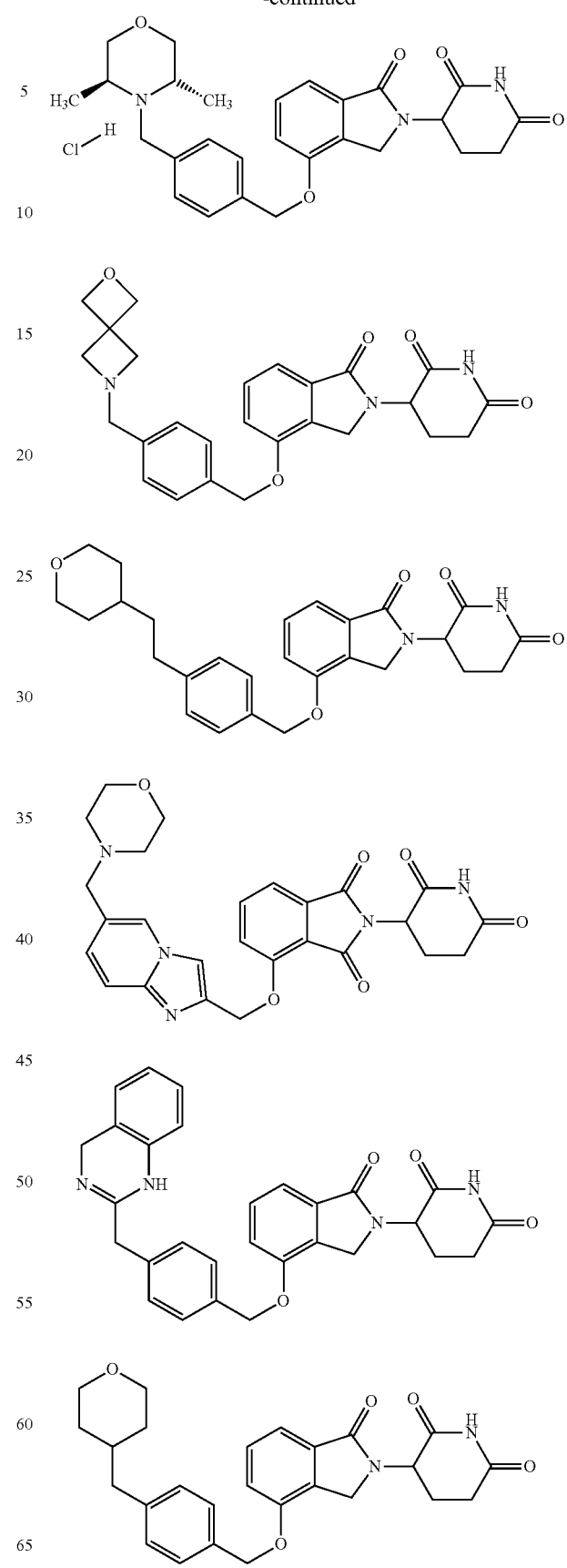

25
-continued
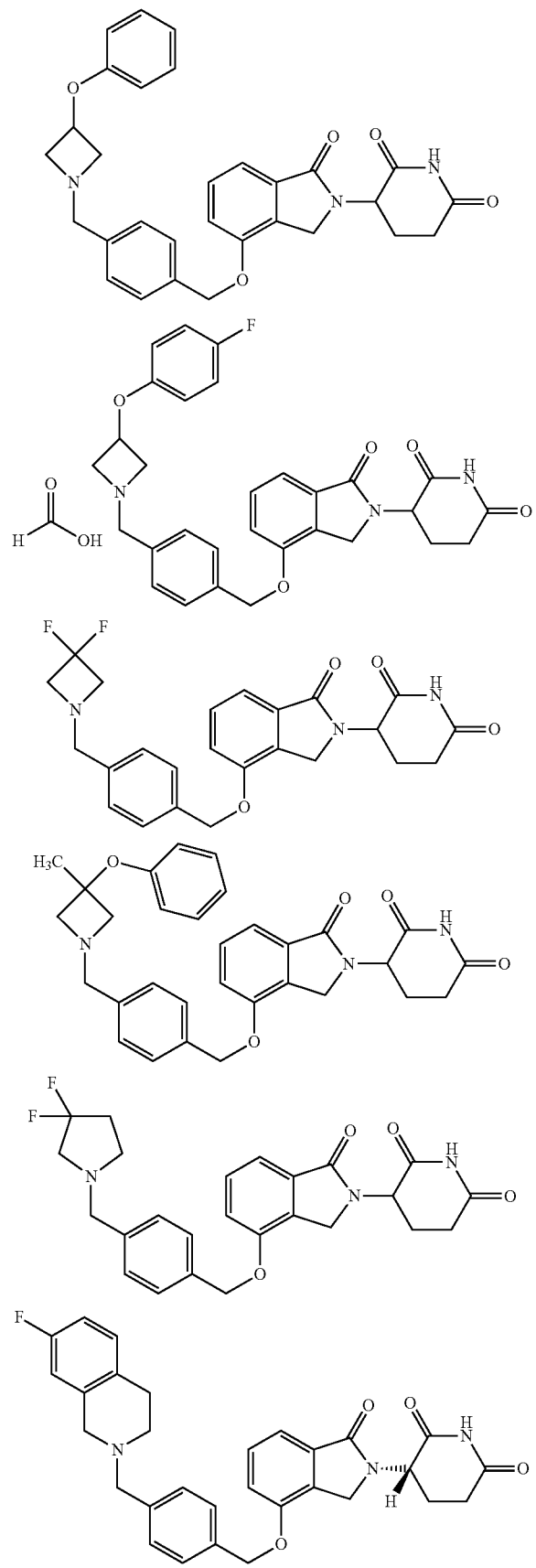
26
-continued
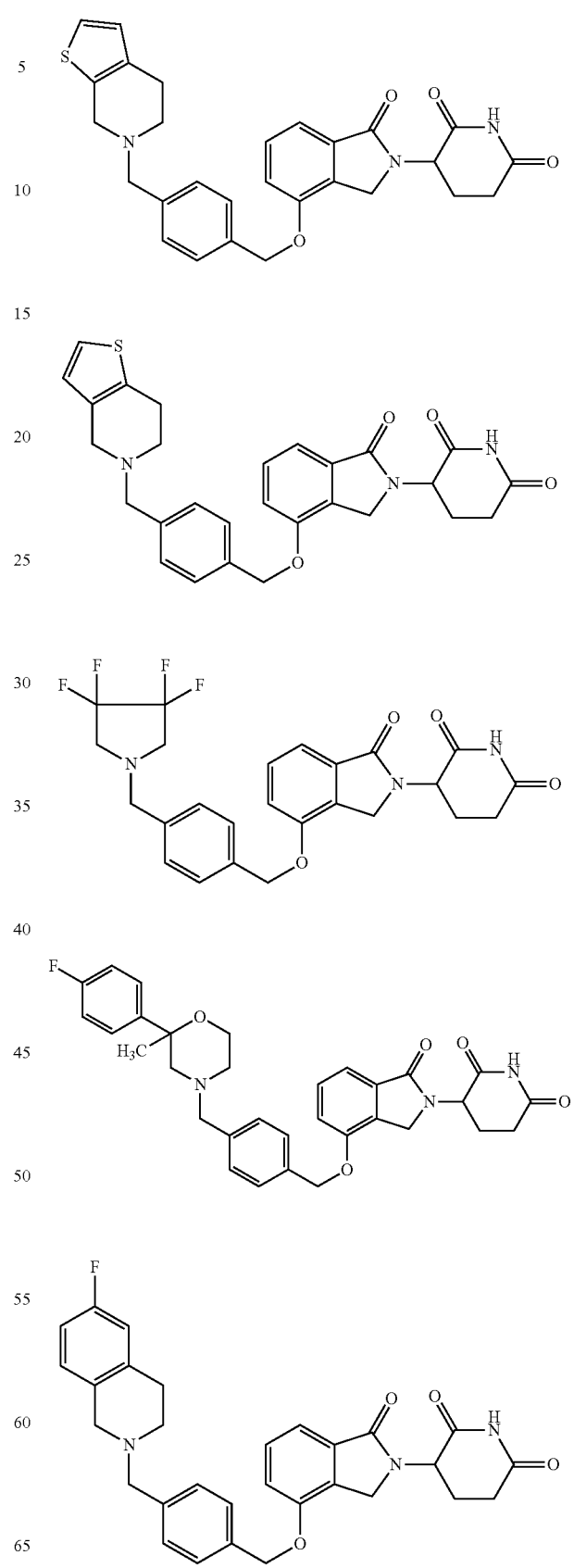

27
-continued
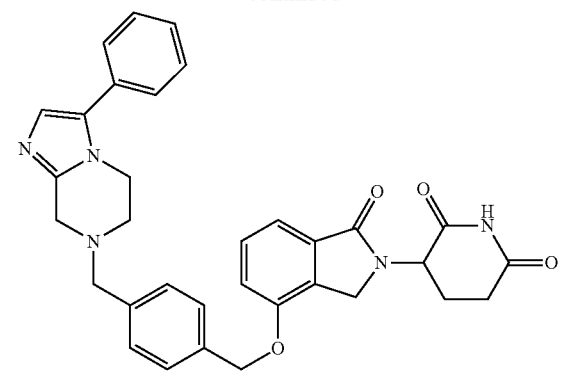
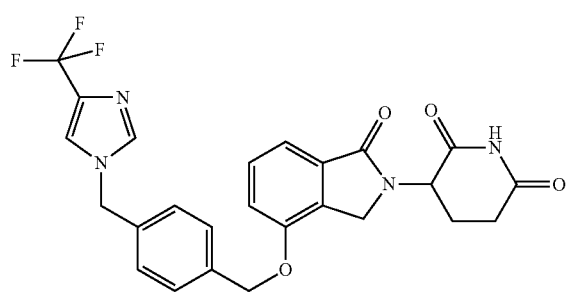
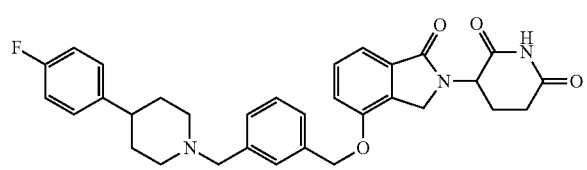
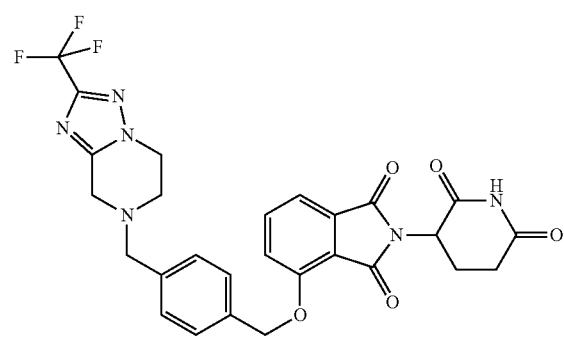
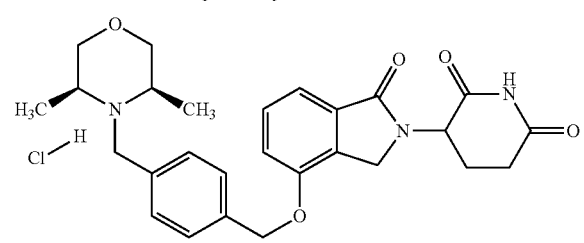
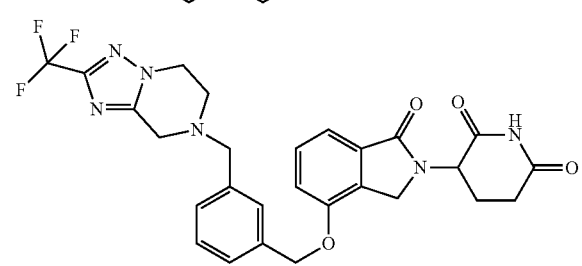
28
-continued
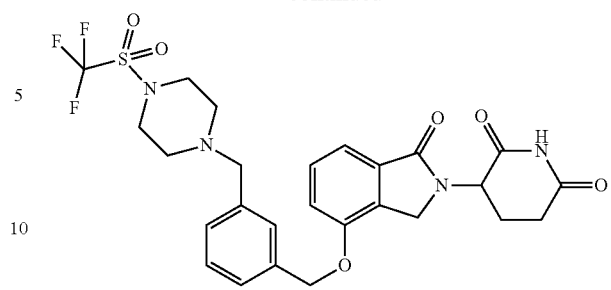
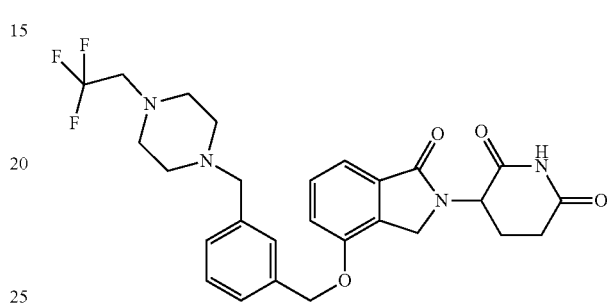
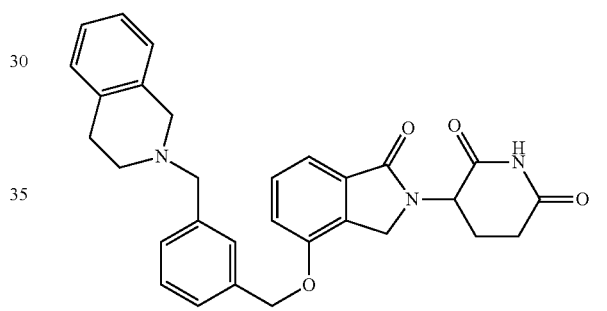
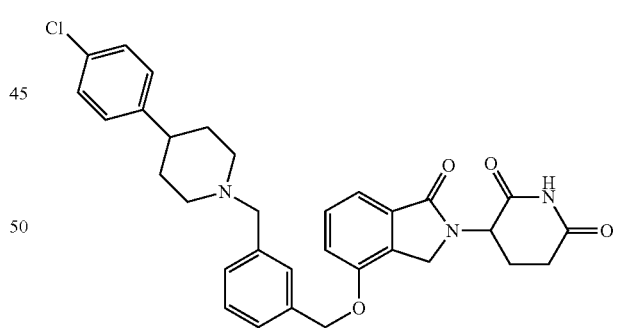
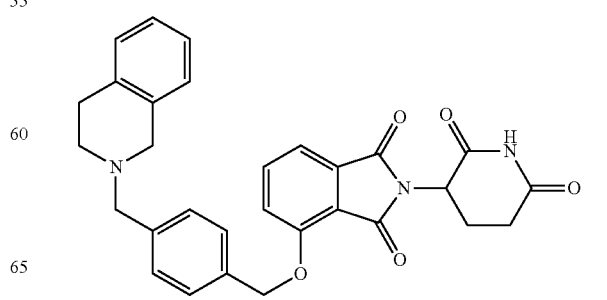

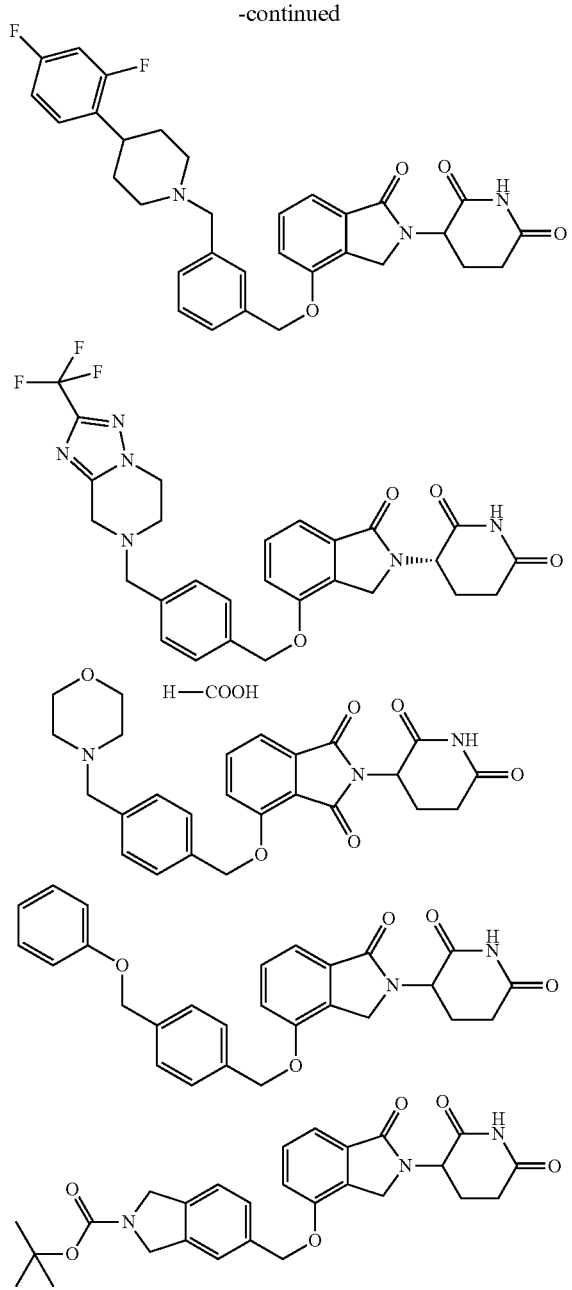

or a pharmaceutically acceptable salt, solvate or stereoisomer thereof.

In another embodiment, provided herein is a compound of formula (II):

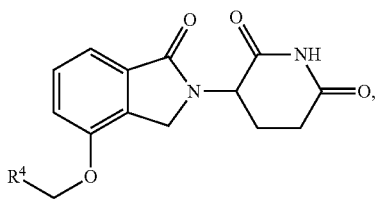

(II)

or a pharmaceutically acceptable salt, solvate or stereoisomer thereof, wherein:

R⁴ is unsubstituted 9 to 10 membered bicyclic ring is benzothiazole, quinoline, isoquinoline, naphthalene, 2,3-dihydro-1H-indene, benzo[d][1,2,3]triazole, imidazo[1,2-a]pyridine, benzofuran, 2,3-dihydrobenzofuran, benzothiophene, benzo[d]oxazole isoindoline or chroman;

with the proviso that if the bicyclic ring is benzofuran or benzothiophene, then the ring is not connected to the isoindole ring through the 2-position.

In one embodiment, R⁴ is benzothiazole. In another embodiment, R⁴ is quinoline. In another embodiment, R⁴ is isoquinoline. In another embodiment, R⁴ is naphthalene. In another embodiment, R⁴ is 2,3-dihydro-1H-indene. In another embodiment, R⁴ is benzo[d][1,2,3]triazole. In another embodiment, R⁴ is imidazo[1,2-a]pyridine. In another embodiment, R⁴ is benzofuran. In another embodiment, R⁴ is 2,3-dihydrobenzofuran. In another embodiment, R⁴ is benzothiophene. In another embodiment, R⁴ is benzo[d]oxazole isoindoline. In another embodiment, R⁴ is chroman.

In one embodiment, specific examples include, but are not limited to:

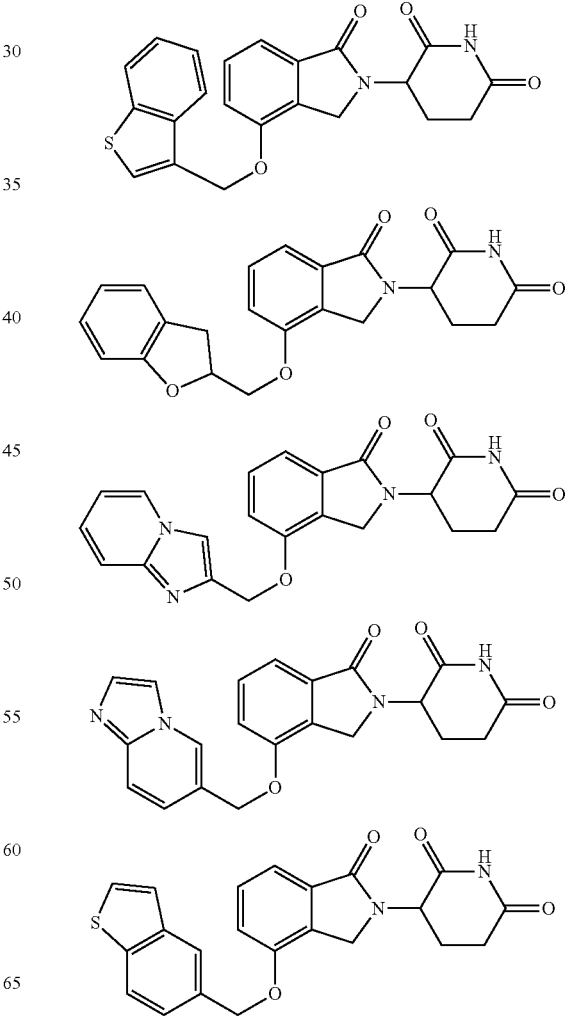

31
-continued

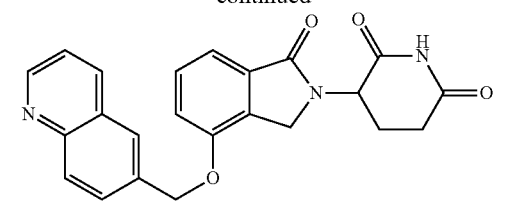
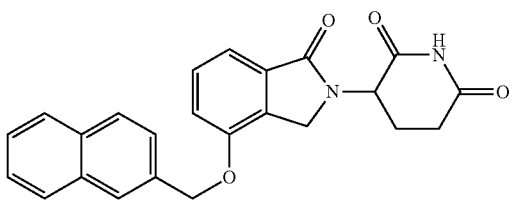
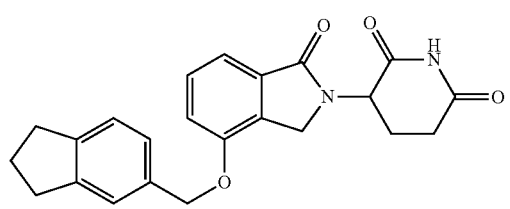
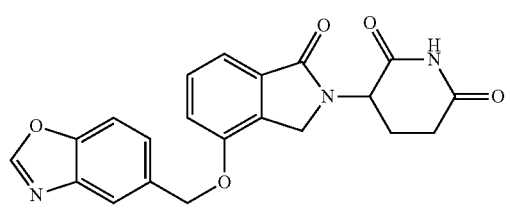
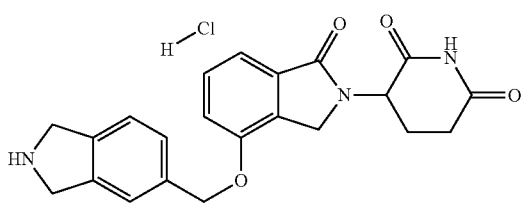
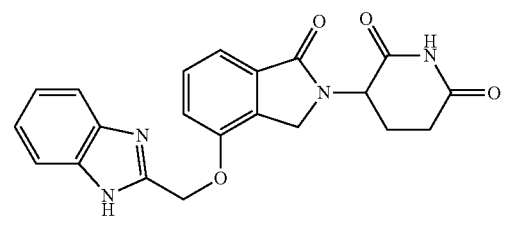
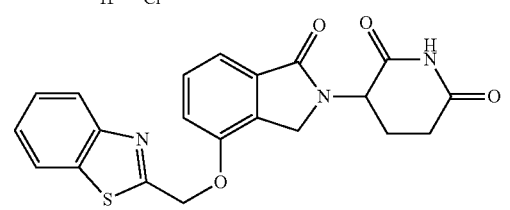
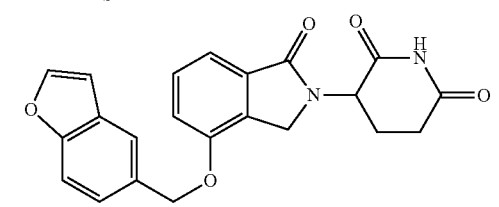

32
-continued

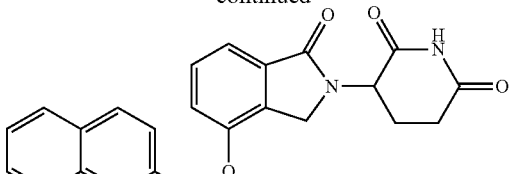
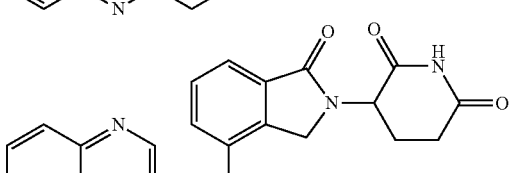
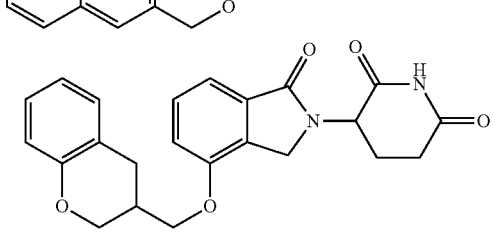
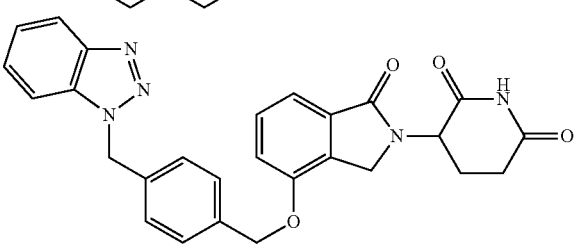

or a pharmaceutically acceptable salt, solvate or stereoisomer thereof.

In another embodiment, provided herein is a compound of formula (III):

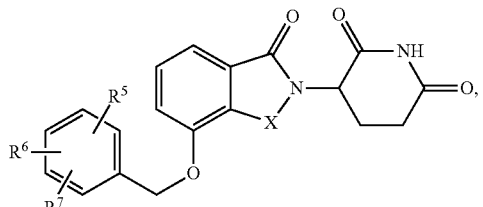

(III)

or a pharmaceutically acceptable salt, solvate or stereoisomer thereof, wherein:

X is $CH_2$ or $C=O$;

$R^5$, $R^6$ and $R^7$ are each independently hydrogen, halogen, nitro, carbamoyl, amino, —$SO_2R^8$, —$CONR^9R^{10}$, —($C_1$-$C_6$)alkyl or —($C_1$-$C_6$)alkoxy, said alkyl or alkoxy may be optionally substituted with one or more halogen, amino, hydroxyl, or $NR^9R^{10}$;

$R^8$ is: ($C_1$-$C_6$)alkyl, optionally substituted with ($C_1$-$C_6$)alkyl or ($C_6$-$C_{10}$)aryl; amino, optionally substituted with ($C_1$-$C_6$)alkyl or ($C_6$-$C_{10}$)aryl; or 6 to 10 membered heterocycle, optionally substituted with ($C_1$-$C_6$)alkyl or ($C_6$-$C_{10}$)aryl;

$R^9$ and $R^{10}$ are each independently hydrogen, 6 to 10 membered aryl, —COO—($C_1$-$C_6$)alkyl, —($C_0$-$C_6$)alkyl-CHO, —($C_0$-$C_6$)alkyl-COOH, —($C_0$-$C_6$)alkyl-$NR^{9'}R^{10'}$, —(C₀-C₆)alkyl-(5 to 10 membered heterocycle), —(C₁-C₆)alkyl-OH, —(C₁-C₆)alkyl-O—(C₁-C₆)alkyl, (C₁-C₆)alkyl, or (C₃-C₆)cycloalkyl; or R⁹ and R¹⁰ together may form an optionally substituted 5 to 6 membered ring containing one or more heteroatoms; and R⁹' and R¹⁰' are each independently hydrogen or (C₁-C₆)alkyl;

with the proviso that all of R⁵-R⁷ cannot be hydrogen; and with the proviso that if one of R⁵-R⁷ is hydrogen and the remaining two of R⁵-R⁷ are both chloride, then the two chloride atoms cannot be on 3 and 4 position of the phenyl ring.

In one embodiment, R⁵ is hydrogen. In another embodiment, R⁵ is halogen. In another embodiment, R⁵ is nitro. In another embodiment, R⁵ is carbamoyl. In another embodiment, R⁵ is amino. In another embodiment, R⁵ is —SO₂R⁸. In another embodiment, R⁵ is —CONR⁹R¹⁰. In another embodiment, R⁵ is —(C₁-C₆)alkyl, optionally substituted with one or more halogen, amino, hydroxyl, or NR⁹R¹⁰. In another embodiment, R⁵ is —(C₁-C₆)alkoxy, optionally substituted with one or more halogen, amino, hydroxyl or NR⁹R¹⁰.

In one embodiment, R⁶ is hydrogen. In another embodiment, R⁶ is halogen. In another embodiment, R⁶ is nitro. In another embodiment, R⁶ is carbamoyl. In another embodiment, R⁶ is amino. In another embodiment, R⁶ is —SO₂R⁸. In another embodiment, R⁶ is —CONR⁹R¹⁰. In another embodiment, R⁶ is —(C₁-C₆)alkyl, optionally substituted with one or more halogen, amino, hydroxyl, or NR⁹R¹⁰. In another embodiment, R⁶ is —(C₁-C₆)alkoxy, optionally substituted with one or more halogen, amino, hydroxyl or NR⁹R¹⁰.

In one embodiment, R⁷ is hydrogen. In another embodiment, R⁷ is halogen. In another embodiment, R⁷ is nitro. In another embodiment, R⁷ is carbamoyl. In another embodiment, R⁷ is amino. In another embodiment, R⁷ is —SO₂R⁸. In another embodiment, R⁷ is —CONR⁹R¹⁰. In another embodiment, R⁷ is —(C₁-C₆)alkyl, optionally substituted with one or more halogen, amino, hydroxyl, or NR⁹R¹⁰. In another embodiment, R⁷ is —(C₁-C₆)alkoxy, optionally substituted with one or more halogen, amino, hydroxyl or NR⁹R¹⁰.

In one embodiment, R⁸ is (C₁-C₆)alkyl, optionally substituted with (C₁-C₆)alkyl or (C₆-C₁₀)aryl. In another embodiment, R⁸ is amino, optionally substituted with (C₁-C₆)alkyl or (C₆-C₁₀)aryl. In another embodiment, R⁸ is 6 to 10 membered heterocycle, optionally substituted with (C₁-C₆)alkyl or (C₆-C₁₀)aryl.

In one embodiment, R⁹ is hydrogen. In another embodiment, R⁹ is 6 to 10 membered aryl. In another embodiment, R⁹ is —COO—(C₁-C₆)alkyl. In another embodiment, R⁹ is —(C₀-C₆)alkyl-CHO. In another embodiment, R⁹ is —(C₀-C₆)alkyl-COOH. In another embodiment, R⁹ is —(C₀-C₆)alkyl-NR⁹'R¹⁰'. In another embodiment, R⁹ is —(C₀-C₆)alkyl-(5 to 10 membered heterocycle). In another embodiment, R⁹ is —(C₁-C₆)alkyl-OH. In another embodiment, R⁹ is —(C₁-C₆)alkyl-O—(C₁-C₆)alkyl. In another embodiment, R⁹ is (C₁-C₆)alkyl. In another embodiment, R⁹ is (C₃-C₆)cycloalkyl.

In one embodiment, R¹⁰ is hydrogen. In another embodiment, R¹⁰ is 6 to 10 membered aryl. In another embodiment, R¹⁰ is —COO—(C₁-C₆)alkyl. In another embodiment, R¹⁰ is —(C₀-C₆)alkyl-CHO. In another embodiment, R¹⁰ is —(C₀-C₆)alkyl-COOH. In another embodiment, R¹⁰ is —(C₀-C₆)alkyl-NR⁹'R¹⁰'. In another embodiment, R¹⁰ is —(C₀-C₆)alkyl-(5 to 10 membered heterocycle). In another embodiment, R¹⁰ is —(C₁-C₆)alkyl-OH. In another embodiment, R¹⁰ is —(C₁-C₆)alkyl-O—(C₁-C₆)alkyl. In another embodiment, R¹⁰ is (C₁-C₆)alkyl. In another embodiment, R¹⁰ is (C₃-C₆)cycloalkyl.

In one embodiment, R⁹ and R¹⁰ together form a 5 to 6 membered ring. In one embodiment, the ring contains one or more heteroatoms. In one embodiment, the heteroatoms are selected from the group consisting of N, S and O.

In one embodiment, R⁹' is hydrogen. In another embodiment, R⁹' is (C₁-C₆)alkyl.

In one embodiment, R¹⁰' is hydrogen. In another embodiment, R¹⁰' is (C₁-C₆)alkyl.

In certain embodiments, provided herein are compounds that result from any combination of R⁵-R¹⁰ and R⁹'-R¹⁰'.

In one embodiment, one of R⁵-R⁷ is hydrogen and the remaining two of R⁵-R⁷ are halogen. In one embodiment, one of R⁵-R⁷ is hydrogen and the remaining two of R⁵-R⁷ are (C₁-C₆)alkoxy. In one embodiment, one of R⁵-R⁷ is hydrogen and the remaining two of R⁵-R⁷ are (C₁-C₆)alkyl. In one embodiment, R⁵ is hydrogen, R⁶ is halogen, and R⁷ is (C₁-C₆)alkoxy.

In one embodiment, two of R⁵-R⁷ are hydrogen and the remaining one of R⁵-R⁷ is halogen. In one embodiment, two of R⁵-R⁷ are hydrogen and the remaining one of R⁵-R⁷ is (C₁-C₆)alkoxy. In one embodiment, two of R⁵-R⁷ are hydrogen and the remaining one of R⁵-R⁷ is (C₁-C₆)alkyl.

In one embodiment, specific examples include, but are not limited to:

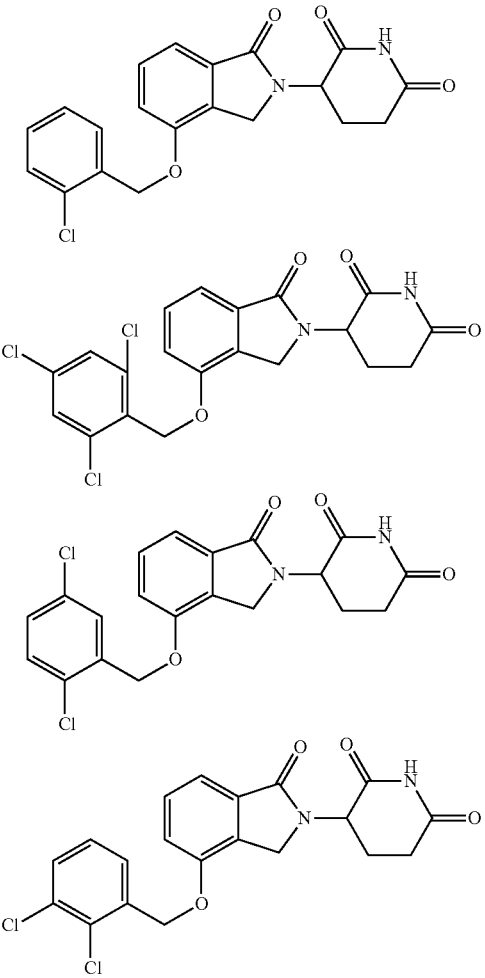

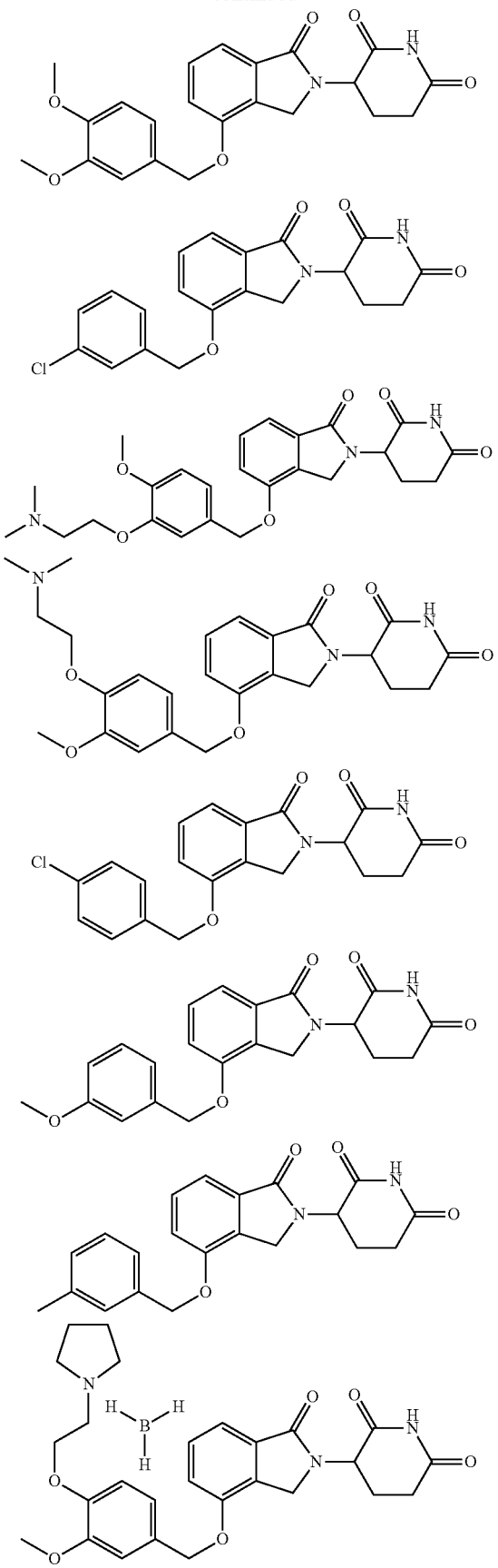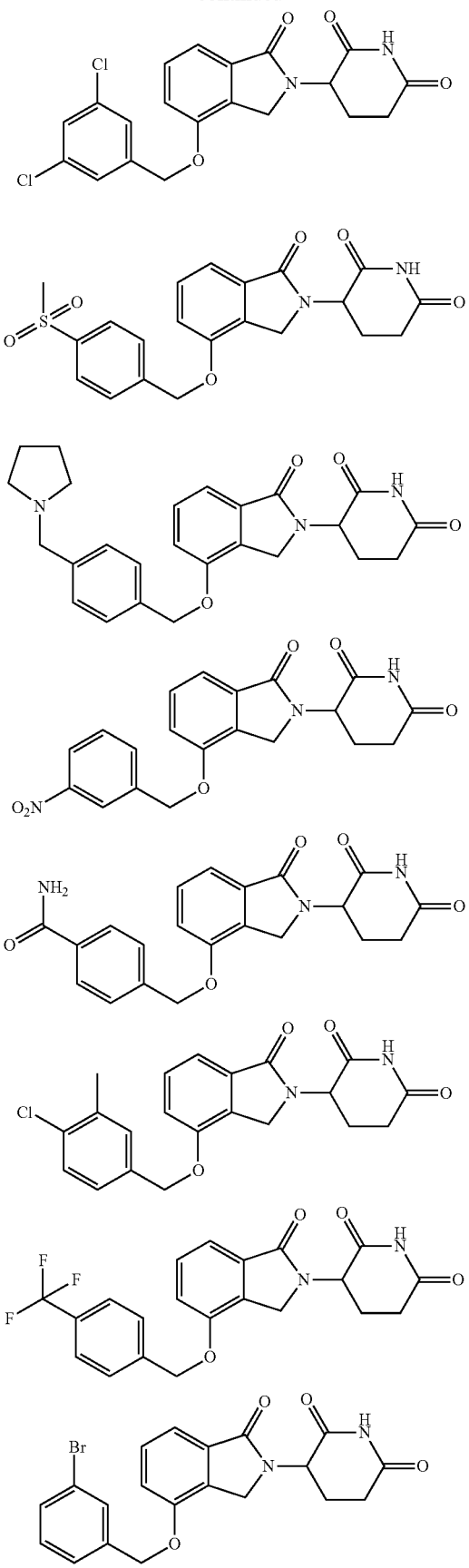

37
-continued
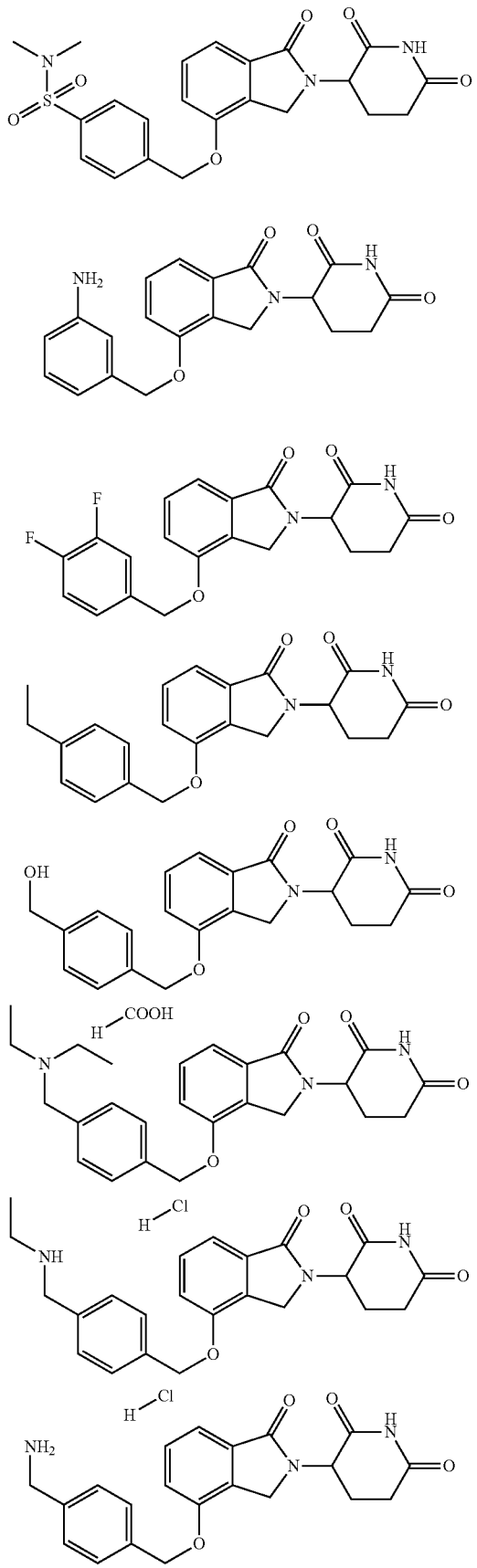
38
-continued
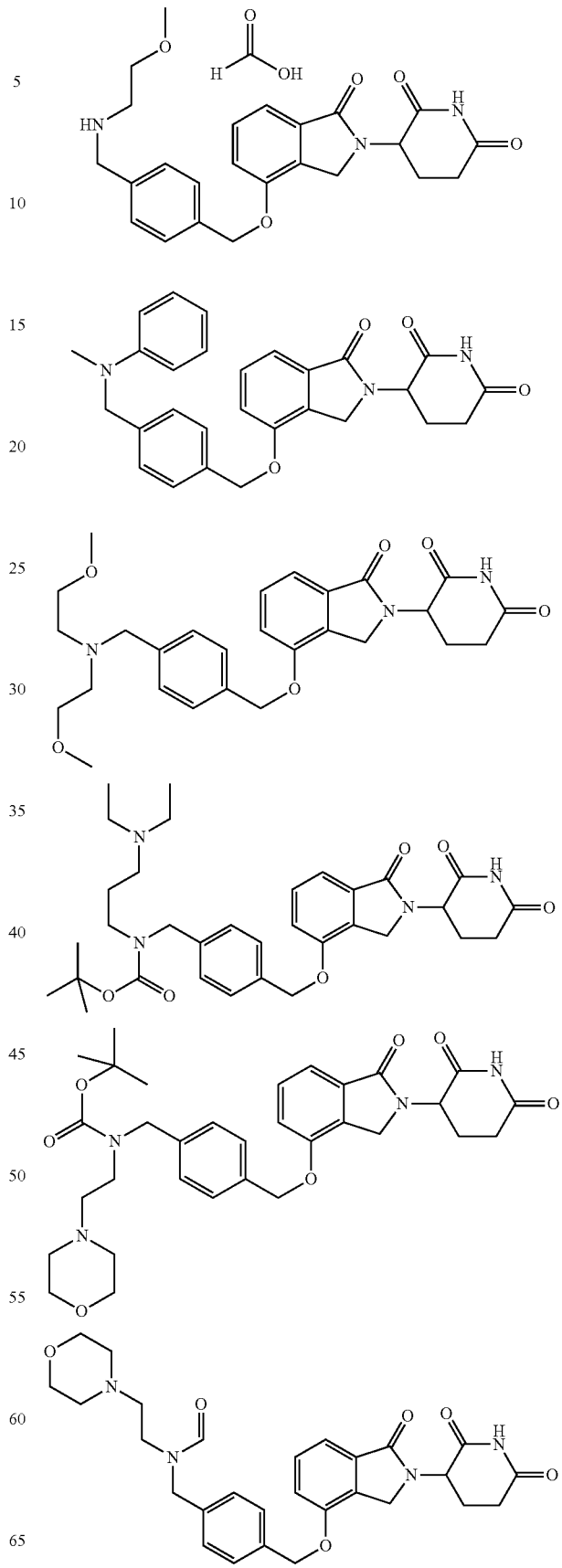

39
-continued
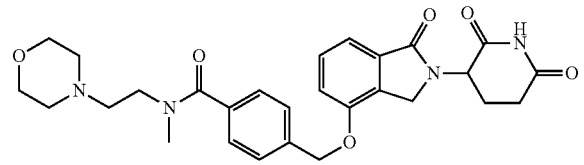
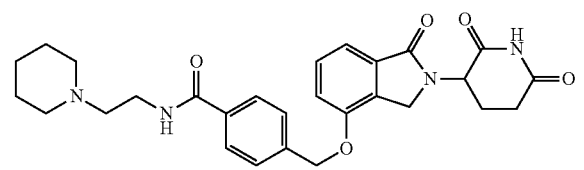
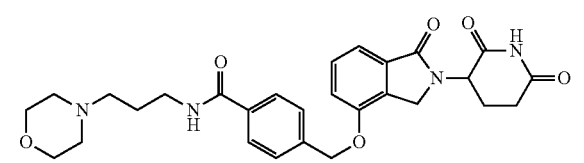
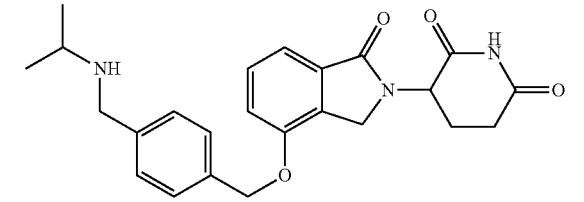
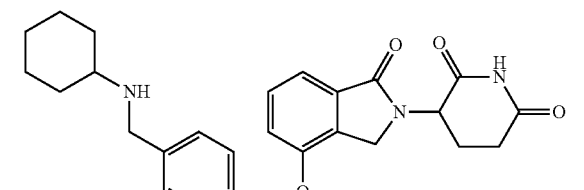
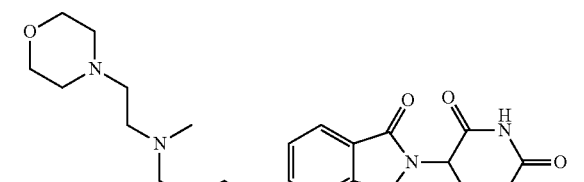
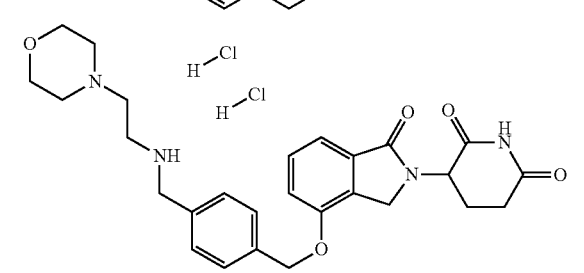
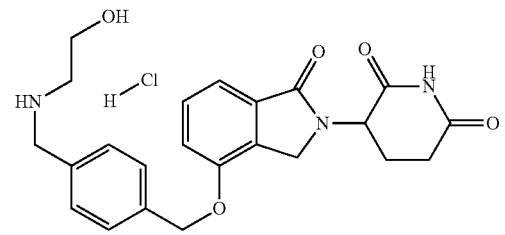
40
-continued
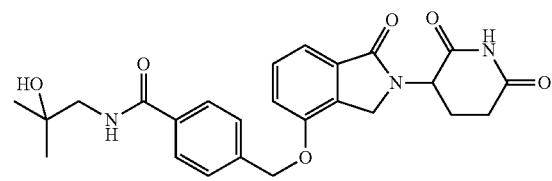
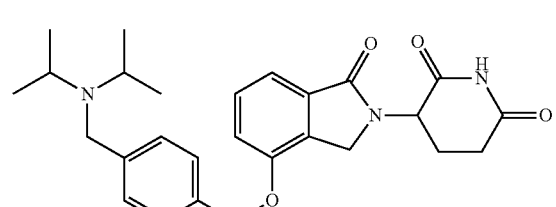
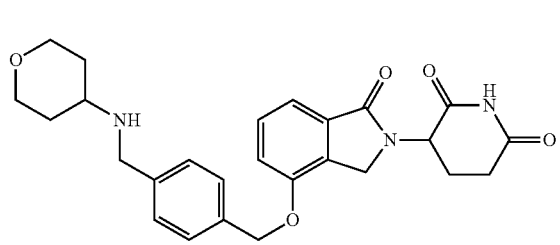
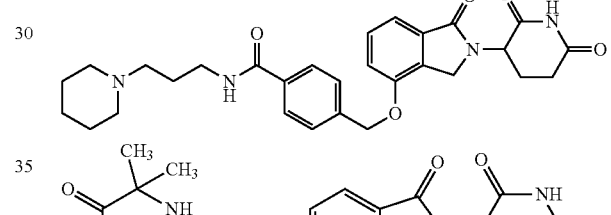
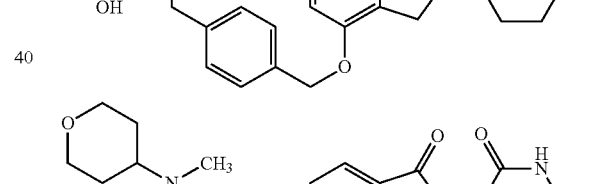
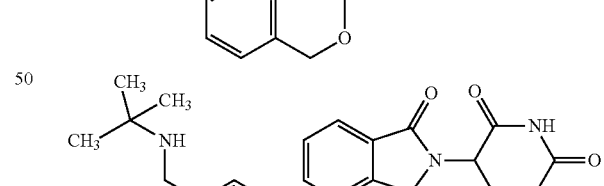
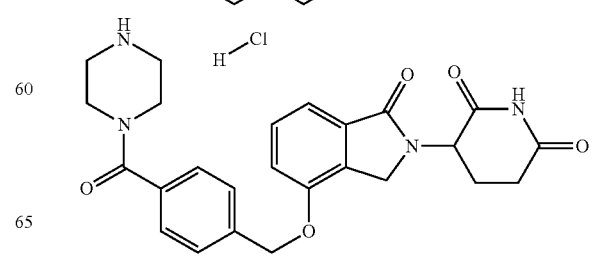

-continued

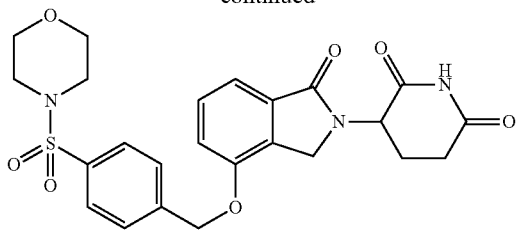

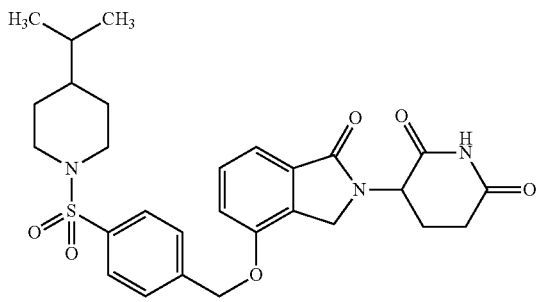

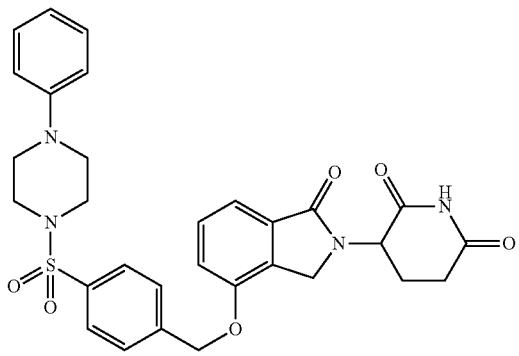

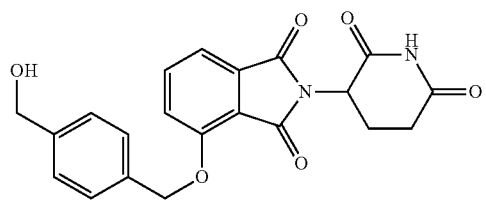

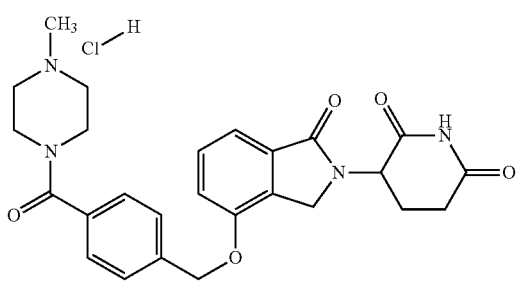

or a pharmaceutically acceptable salt, solvate or stereoisomer thereof.

In another embodiment, provided herein is a compound of formula (IV):

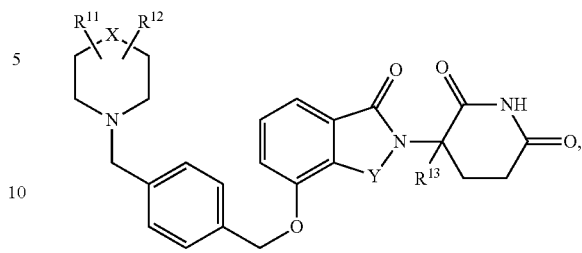

or a pharmaceutically acceptable salt, solvate or stereoisomer thereof, wherein:

X is N or C;
Y is CH$_2$ or C=O;
R$^{11}$ and R$^{12}$ are each independently hydrogen, —(C$_1$-C$_6$)alkyl, —(C$_1$-C$_6$)alkyl-(C$_3$-C$_6$)cycloalkyl, —(C$_1$-C$_6$)alkoxy, —(C$_6$-C$_{10}$)aryl, —CO(C$_1$-C$_6$)alkyl, —CO(C$_3$-C$_6$)cycloalkyl, —CO(C$_6$-C$_{10}$)aryl, —COO(C$_1$-C$_6$)alkyl, halogen, hydroxyl, oxo, 3 to 10 membered heterocycle, 6 to 10 membered heteroaryl, —NHCO(C$_1$-C$_6$)alkyl, —(CH$_2$)$_n$-phenyl, —SO$_2$(C$_1$-C$_6$)alkyl, —SO$_2$(C$_3$-C$_6$)cycloalkyl, —SO$_2$(C$_6$-C$_{10}$)aryl or —NR$^{14}$R$^{15}$, wherein the alkyl, aryl or heteroaryl portion of each of the groups may be optionally substituted with one or more halogen, hydroxyl or —(C$_1$-C$_6$)alkoxy;
R$^{13}$ is hydrogen or —(C$_1$-C$_6$)alkyl;
R$^{14}$ and R$^{15}$ are each independently hydrogen or —(C$_1$-C$_6$)alkyl; and
n is 0, 1, 2 or 3.

In one embodiment, X is N. In another embodiment, X is C.

In one embodiment, Y is CH$_2$. In another embodiment, Y is C=O.

In one embodiment, R$^{11}$ is hydrogen. In another embodiment, R$^{11}$ is —(C$_1$-C$_6$)alkyl. In another embodiment, R$^{11}$ is —(C$_1$-C$_6$)alkyl-(C$_3$-C$_6$)cycloalkyl. In another embodiment, R$^{11}$ is —(C$_1$-C$_6$)alkoxy. In another embodiment, R$^{11}$ is —(C$_6$-C$_{10}$)aryl. In another embodiment, R$^{11}$ is —CO(C$_1$-C$_6$)alkyl. In another embodiment, R$^{11}$ is —CO(C$_3$-C$_6$)cycloalkyl. In another embodiment, R$^{11}$ is —CO(C$_6$-C$_{10}$)aryl. In another embodiment, R$^{11}$ is —COO(C$_1$-C$_6$)alkyl. In another embodiment, R$^{11}$ is halogen. In another embodiment, R$^{11}$ is hydroxyl. In another embodiment, R$^{11}$ is oxo. In another embodiment, R$^{11}$ is 3 to 10 membered heterocycle. In another embodiment, R$^{11}$ is 6 to 10 membered heteroaryl. In another embodiment, R$^{11}$ is —NHCO(C$_1$-C$_6$)alkyl. In another embodiment, R$^{11}$ is —(CH$_2$)$_n$-phenyl. In another embodiment, R$^{11}$ is —SO$_2$(C$_1$-C$_6$)alkyl. In another embodiment, R$^{11}$ is —SO$_2$(C$_3$-C$_6$)cycloalkyl. In another embodiment, R$^{11}$ is —SO$_2$(C$_6$-C$_{10}$)aryl. In another embodiment, R$^{11}$ is —NR$^{14}$R$^{15}$. In another embodiment, is the alkyl, aryl or heteroaryl portion of R$^{11}$ is substituted with one or more halogen, hydroxyl and/or —(C$_1$-C$_6$)alkoxy.

In one embodiment, R$^{12}$ is hydrogen. In another embodiment, R$^{12}$ is —(C$_1$-C$_6$)alkyl. In another embodiment, R$^{12}$ is —(C$_1$-C$_6$)alkyl-(C$_3$-C$_6$)cycloalkyl. In another embodiment, R$^{12}$ is —(C$_1$-C$_6$)alkoxy. In another embodiment, R$^{12}$ is —(C$_6$-C$_{10}$)aryl. In another embodiment, R$^{12}$ is —CO(C$_1$-C$_6$)alkyl. In another embodiment, R$^{12}$ is —CO(C$_3$-C$_6$)cycloalkyl. In another embodiment, R$^{12}$ is —CO(C$_6$-C$_{10}$)aryl. In another embodiment, R$^{12}$ is —COO(C$_1$-C$_6$)alkyl. In another embodiment, R$^{12}$ is halogen. In another embodiment, R$^{12}$ is hydroxyl. In another embodiment, R$^{12}$ is oxo.

In another embodiment, $R^{12}$ is 3 to 10 membered heterocycle. In another embodiment, $R^{12}$ is 6 to 10 membered heteroaryl. In another embodiment, $R^{12}$ is —NHCO($C_1$-$C_6$)alkyl. In another embodiment, $R^{12}$ is —($CH_2$)$_n$-phenyl. In another embodiment, $R^{12}$ is —$SO_2$($C_1$-$C_6$)alkyl. In another embodiment, $R^{12}$ is —$SO_2$($C_3$-$C_6$)cycloalkyl. In another embodiment, $R^{12}$ is —$SO_2$($C_6$-$C_{10}$)aryl. In another embodiment, $R^{12}$ is —$NR^{14}R^{15}$. In another embodiment, is the alkyl, aryl or heteroaryl portion of $R^{12}$ is substituted with one or more halogen, hydroxyl and/or —($C_1$-$C_6$)alkoxy.

In one embodiment, $R^{13}$ is hydrogen. In another embodiment, $R^{13}$ is —($C_1$-$C_6$)alkyl.

In one embodiment, $R^{14}$ is hydrogen. In another embodiment, $R^{14}$ is —($C_1$-$C_6$)alkyl.

In one embodiment, $R^{15}$ is hydrogen. In another embodiment, $R^{15}$ is —($C_1$-$C_6$)alkyl.

In one embodiment, n is 0. In another embodiment, n is 1. In another embodiment, n is 2. In another embodiment, n is 3.

In one embodiment, provided herein are compounds that result from any combination of X, Y, $R^{11}$-$R^{15}$ and n as defined above.

In one embodiment, specific examples include, but are not limited to:

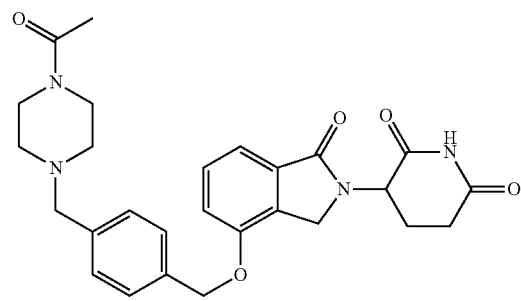

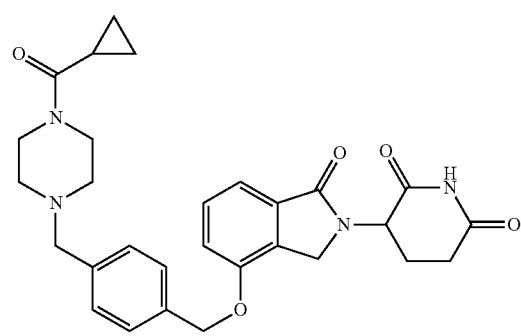

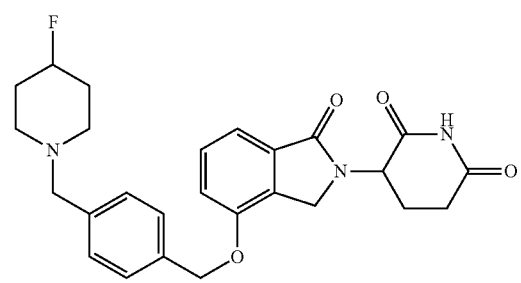

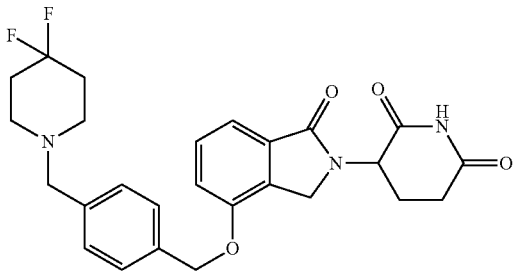

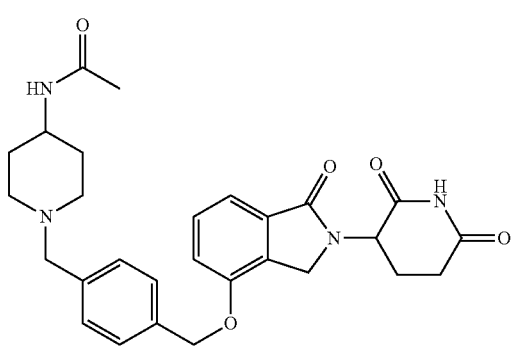

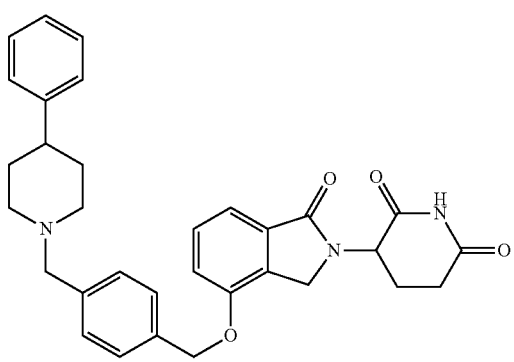

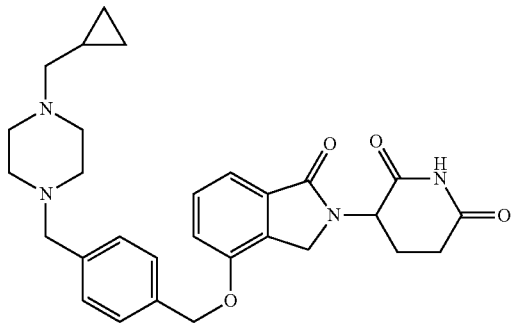

45
-continued
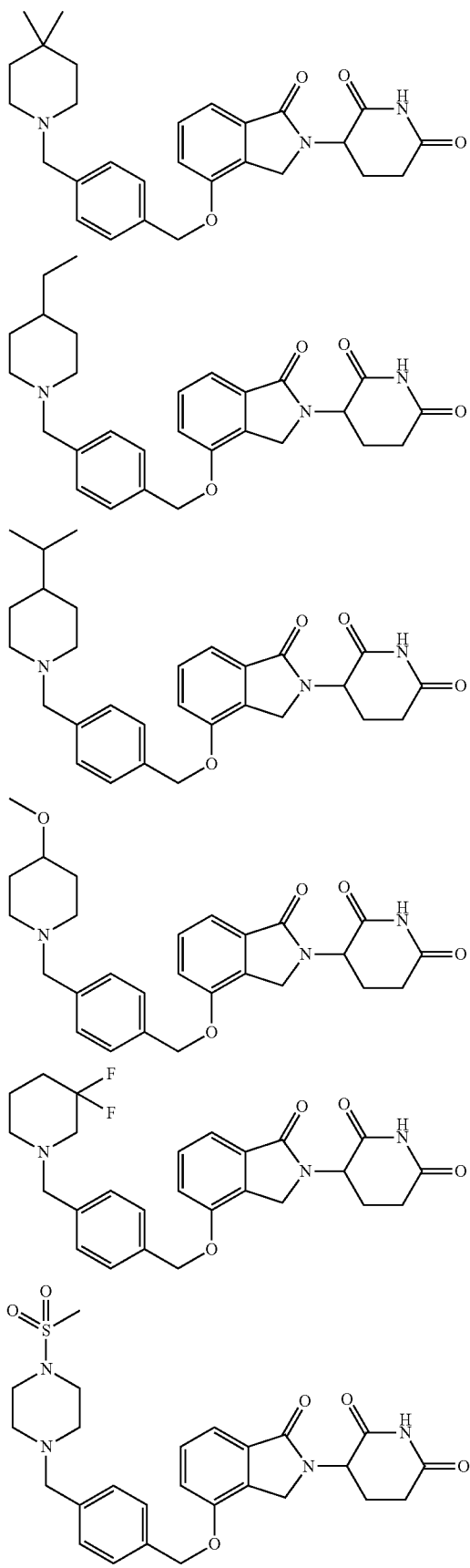
46
-continued
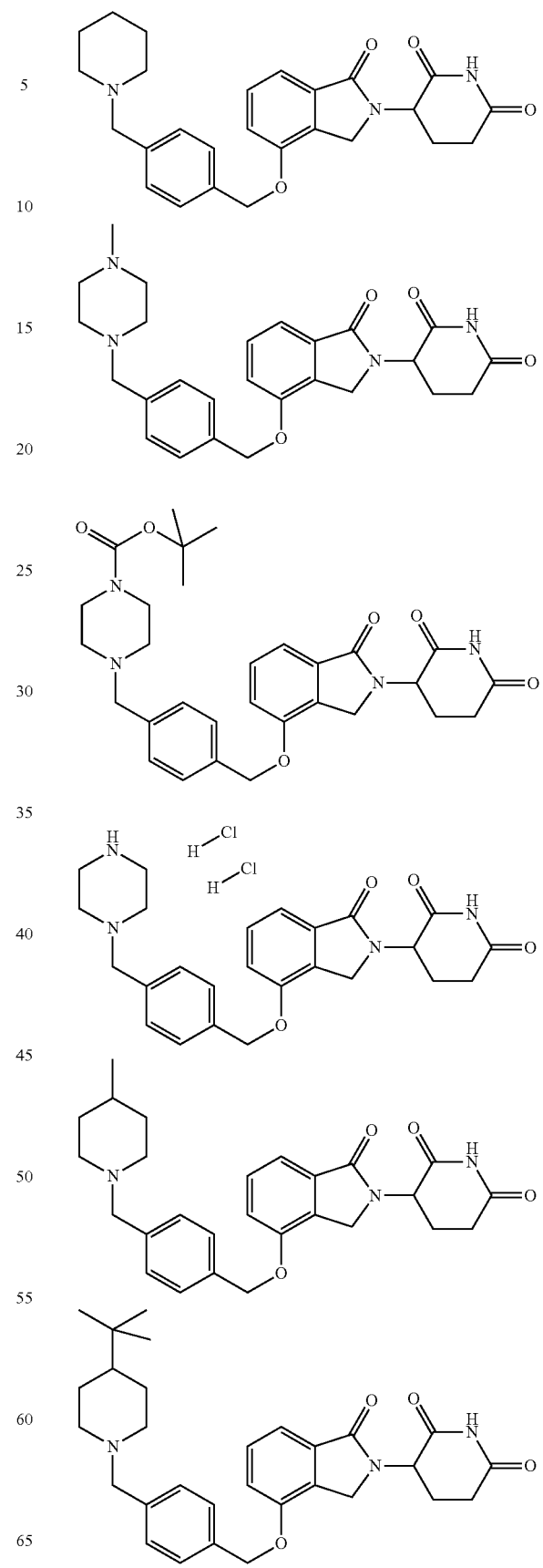

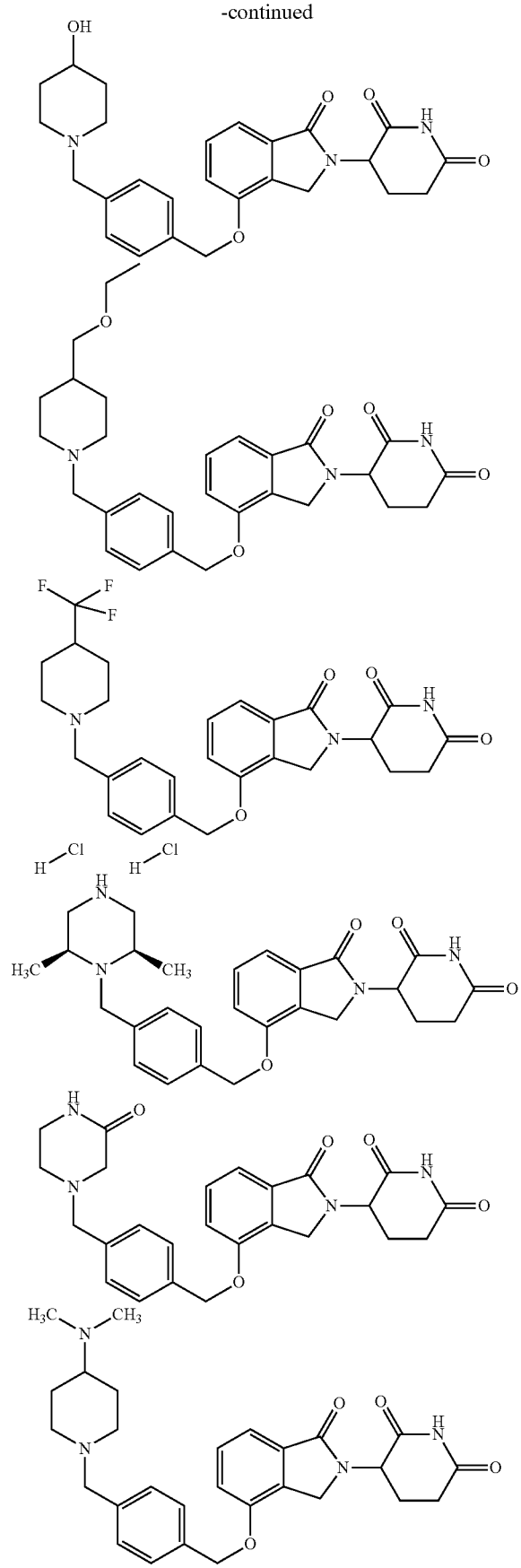
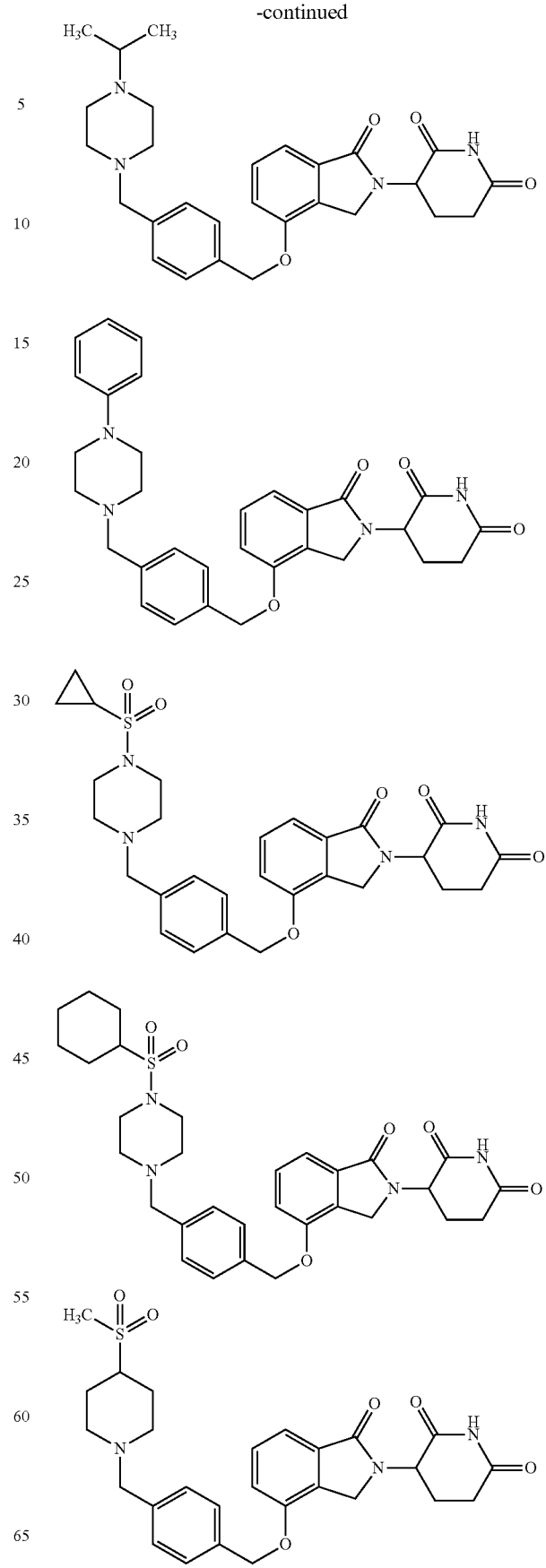

49
-continued
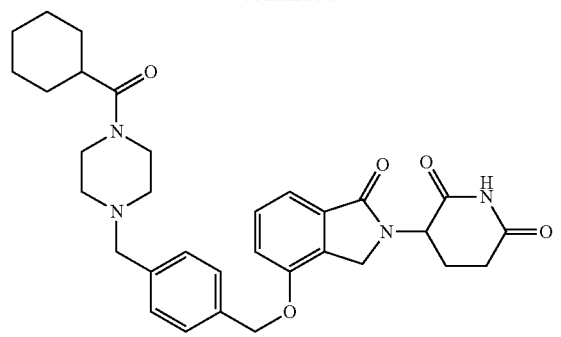
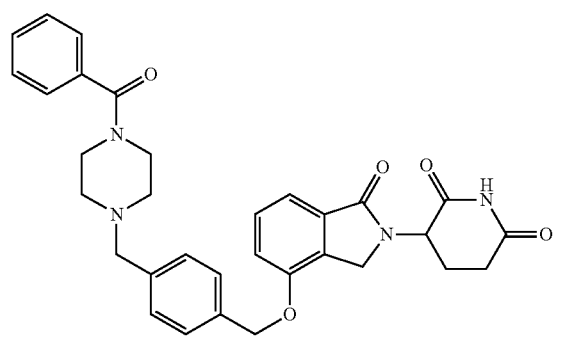
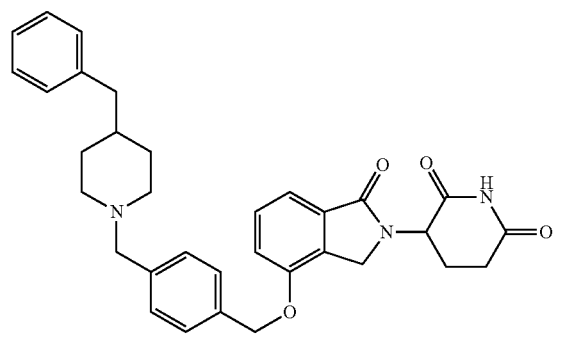
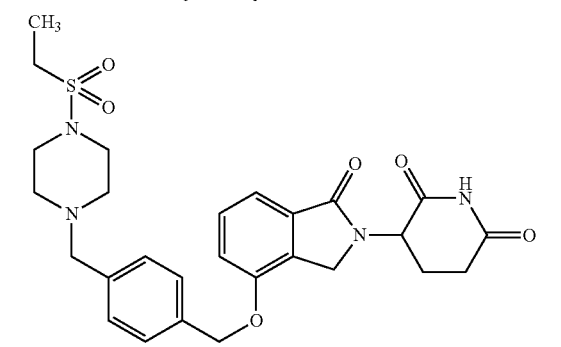
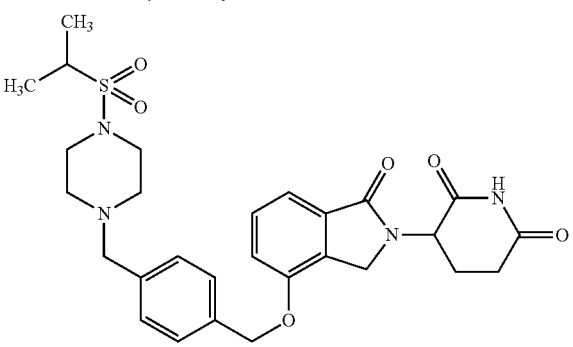
50
-continued
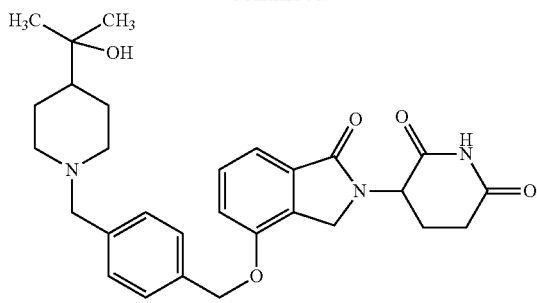
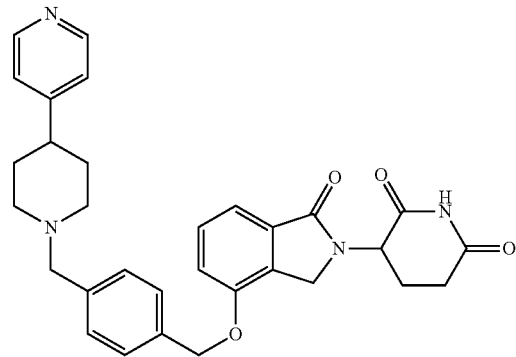
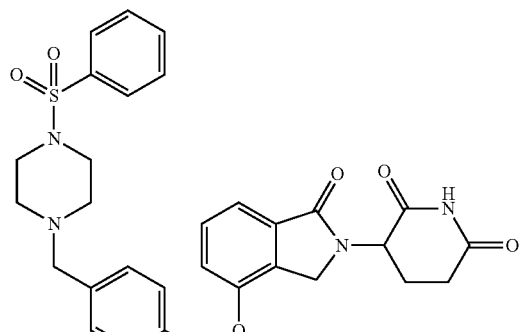
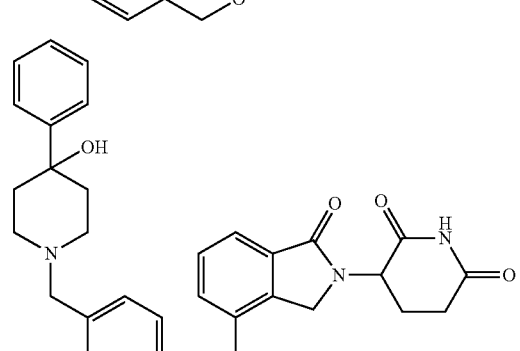
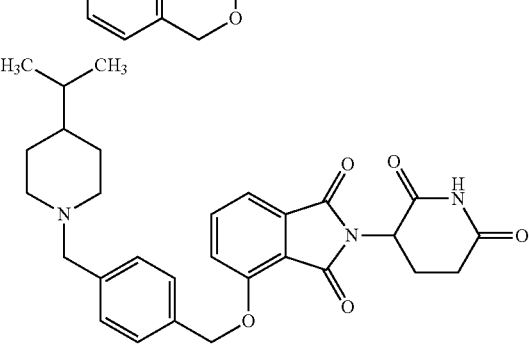

51
-continued
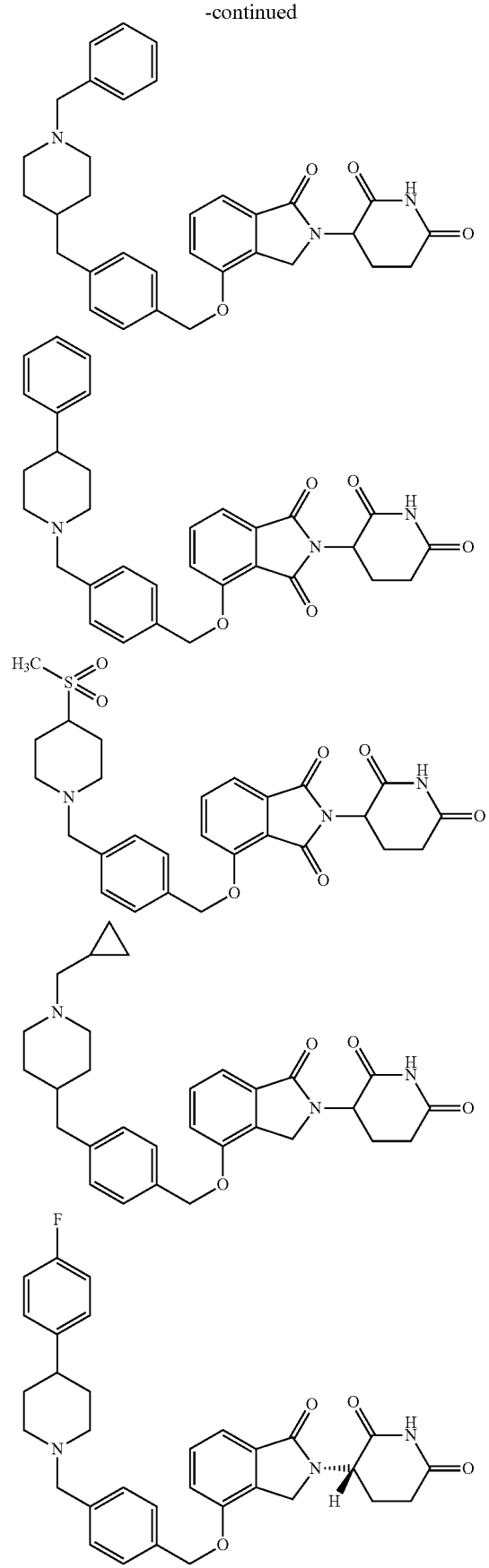
52
-continued
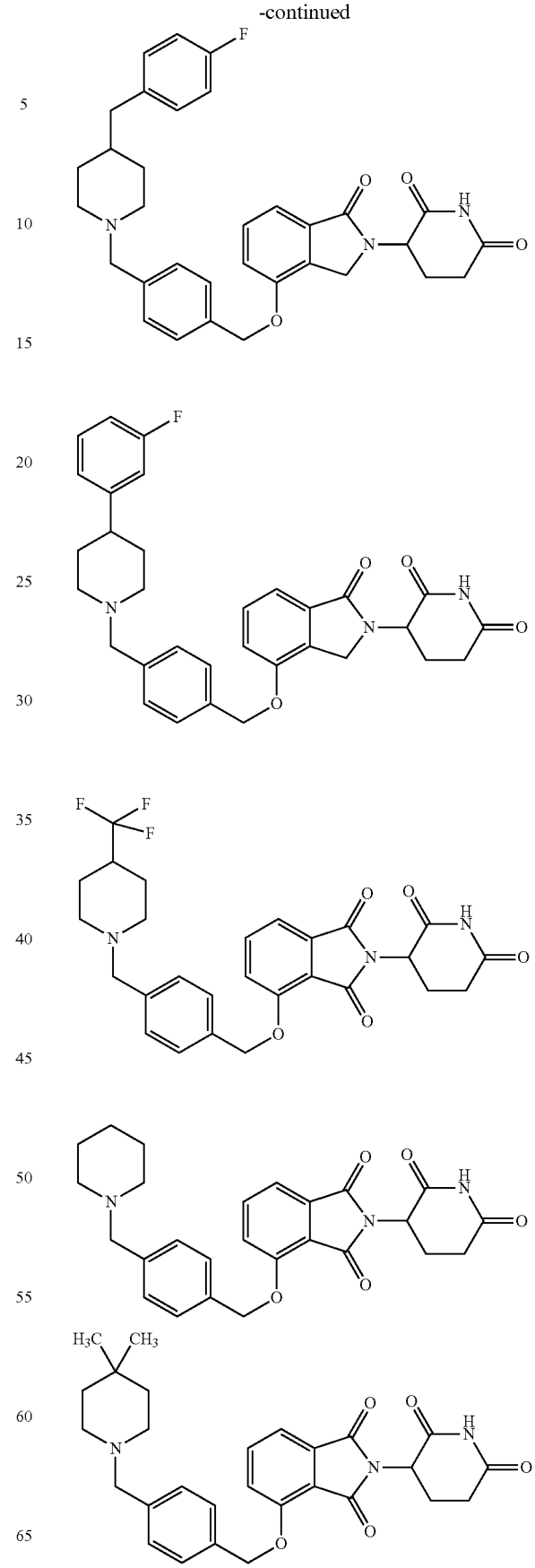

53
-continued
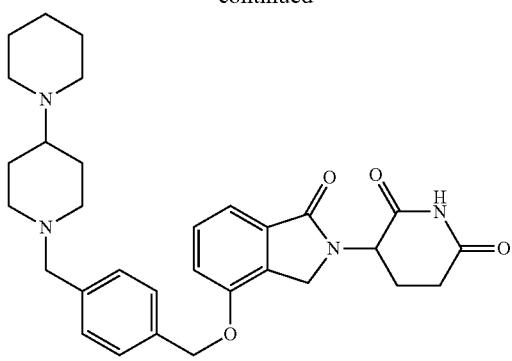
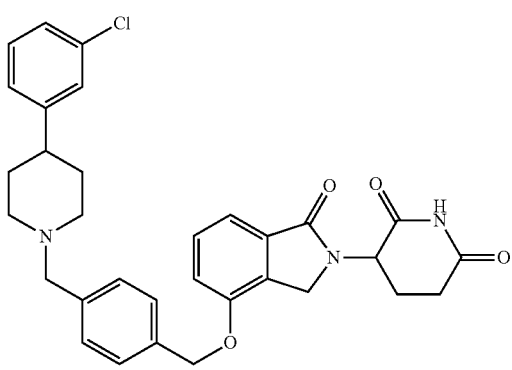
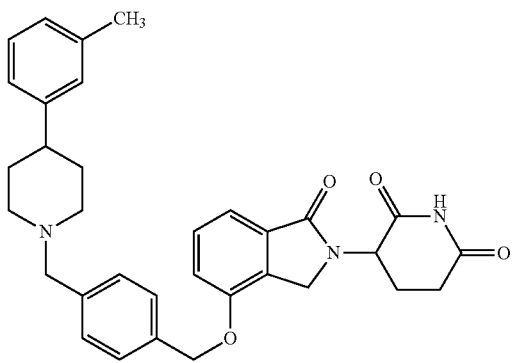
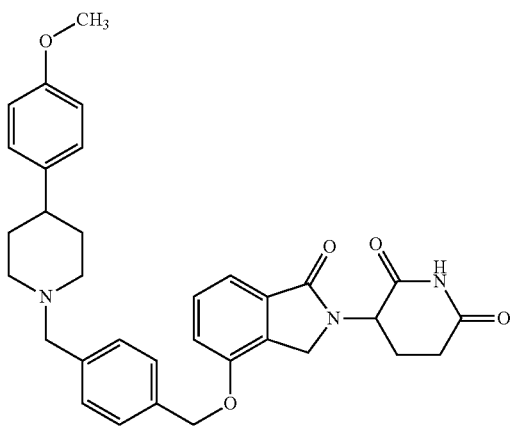
54
-continued
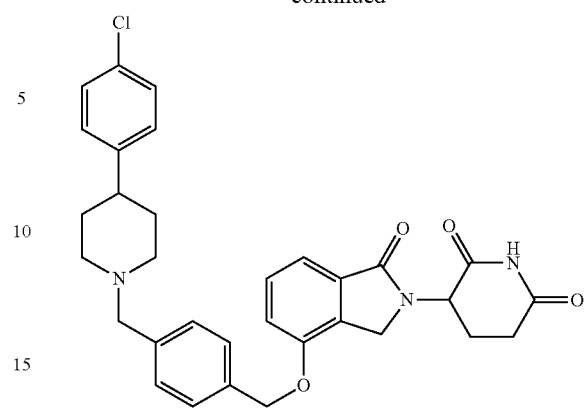
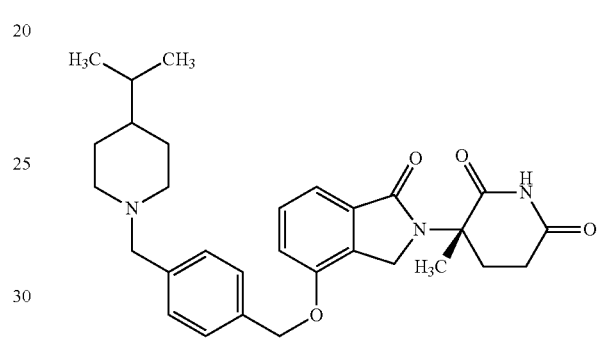
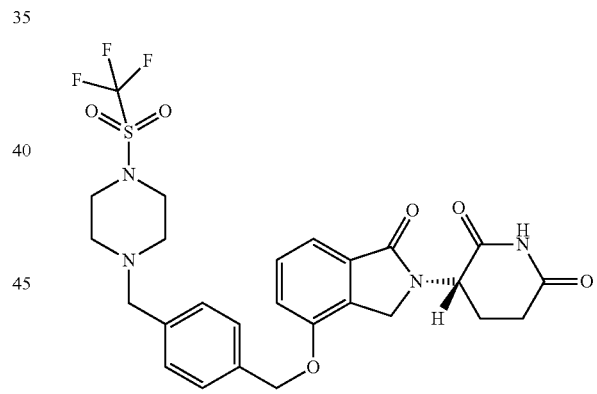
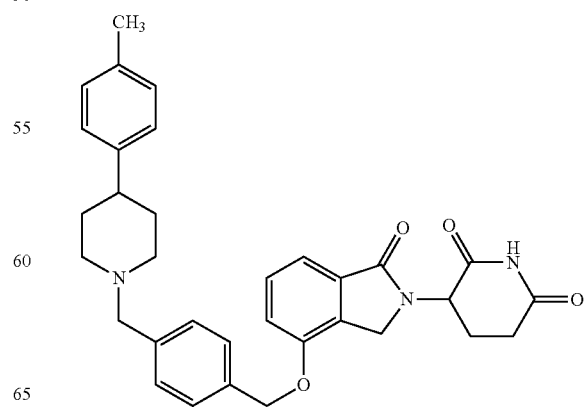

55
-continued
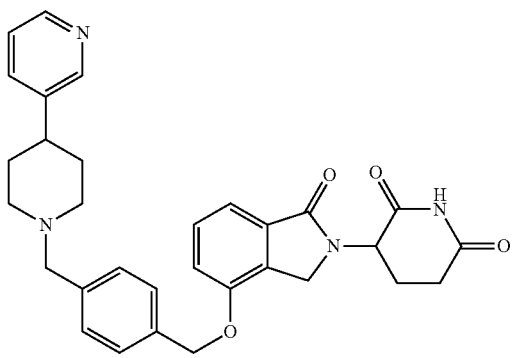
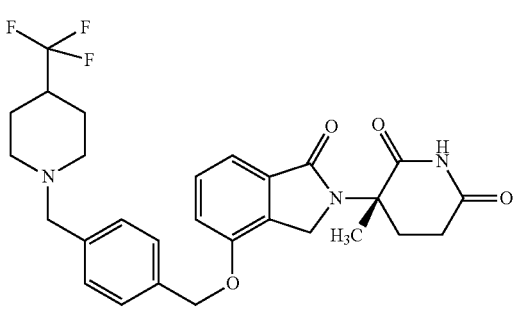
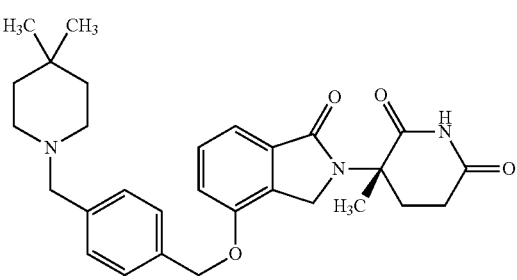
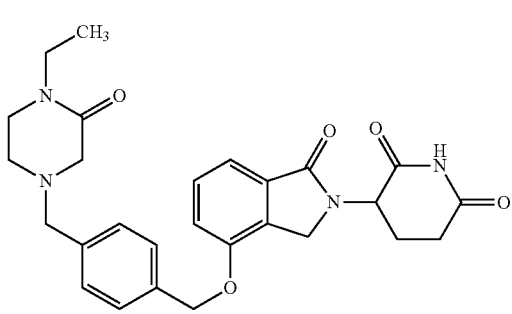
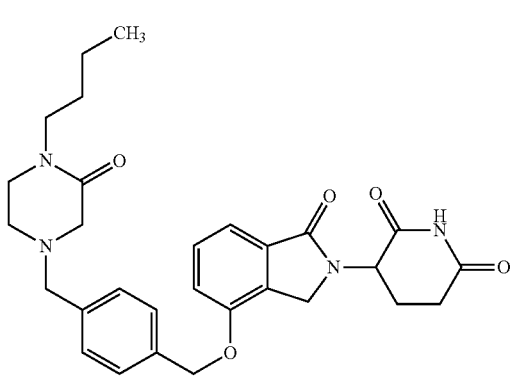
56
-continued
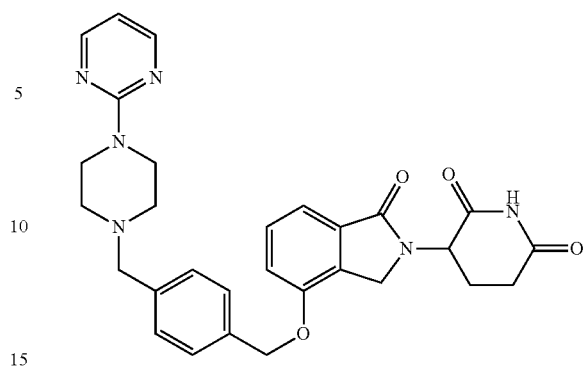
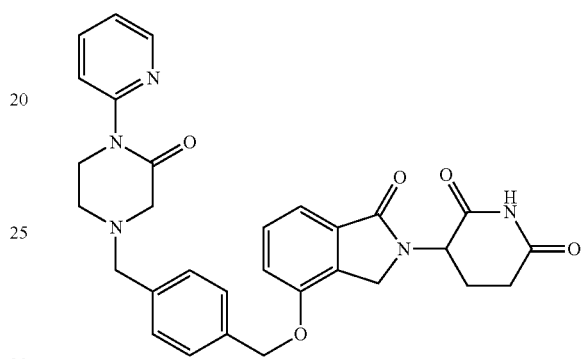
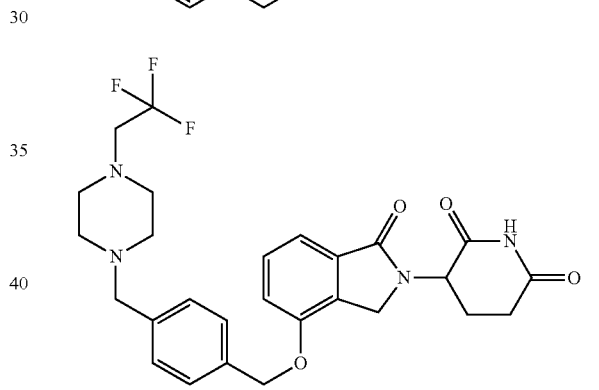
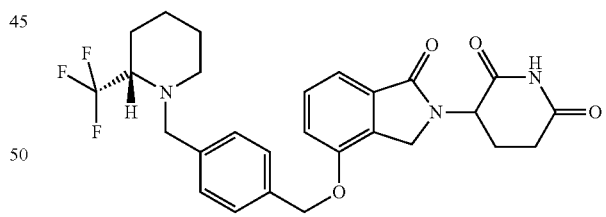
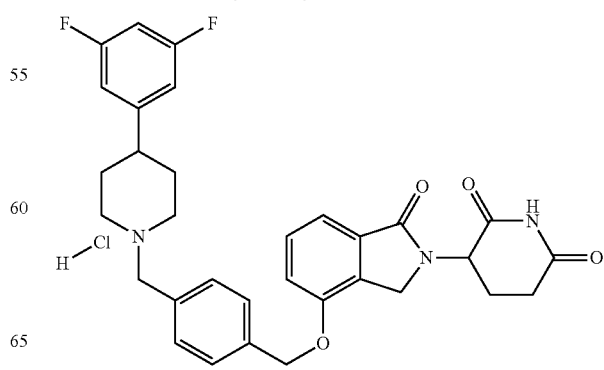

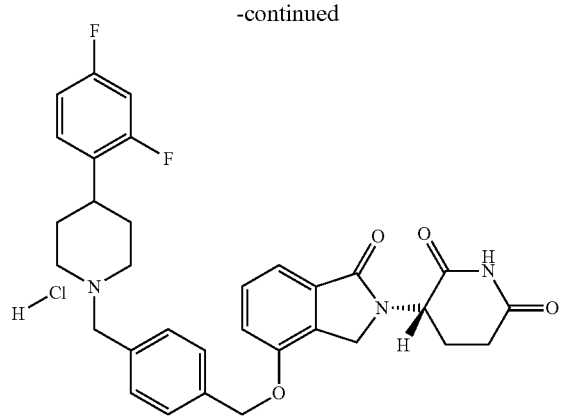
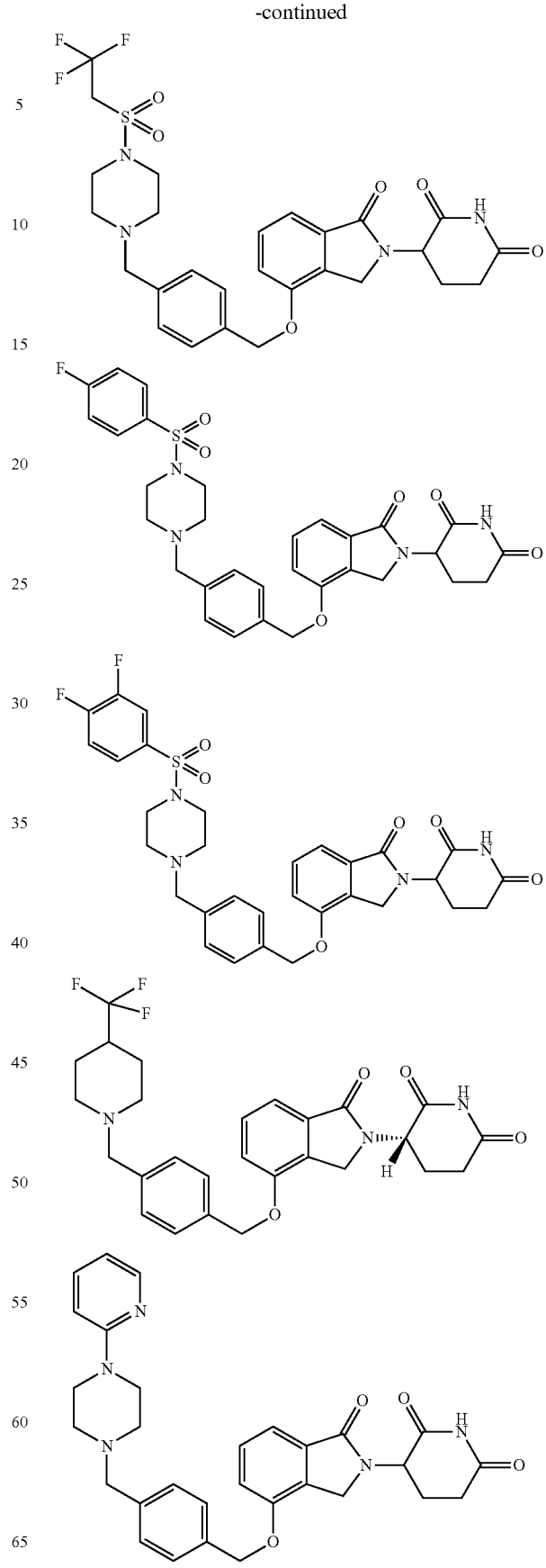

59
-continued
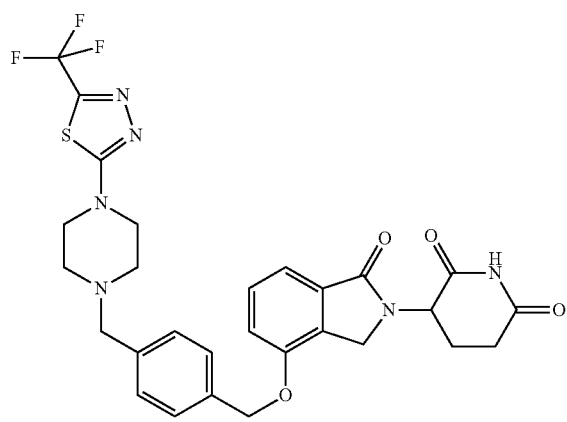
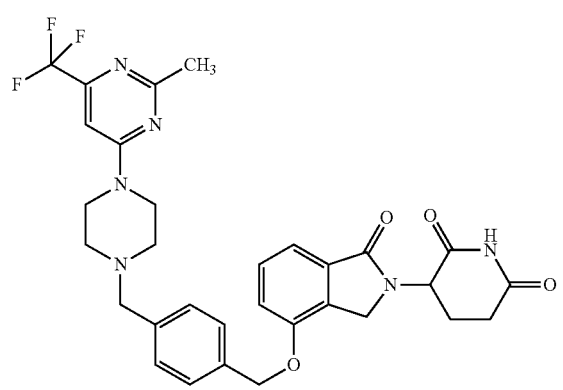
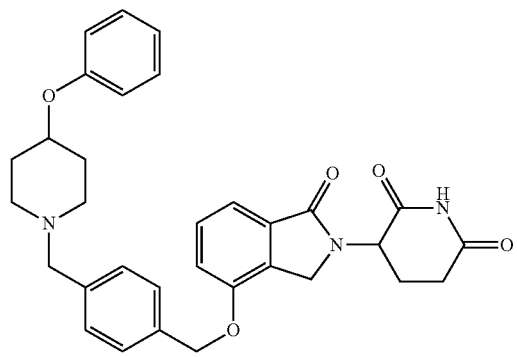
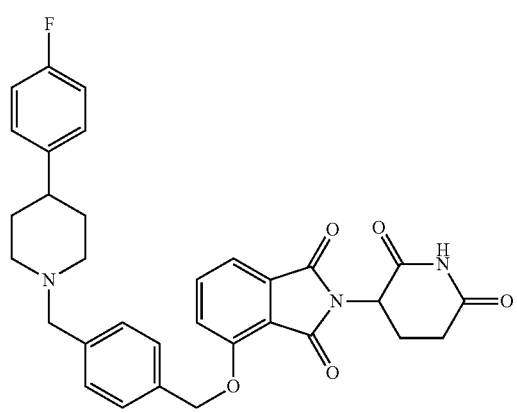
60
-continued
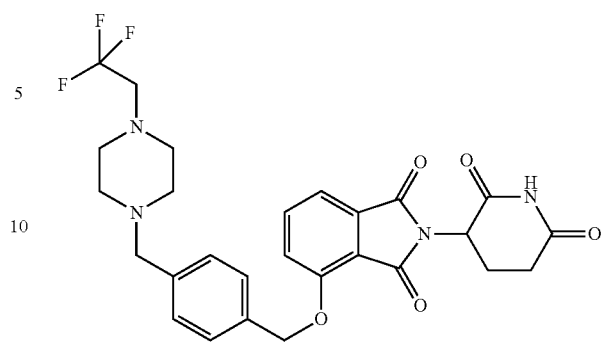
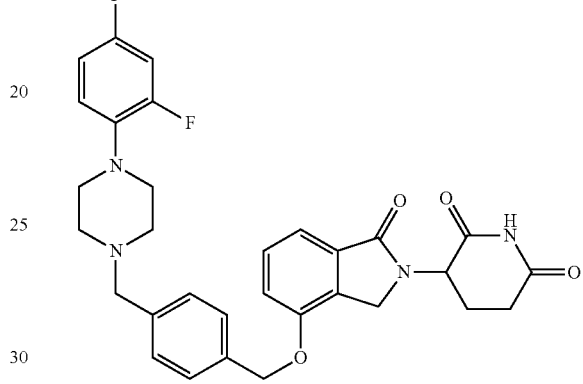
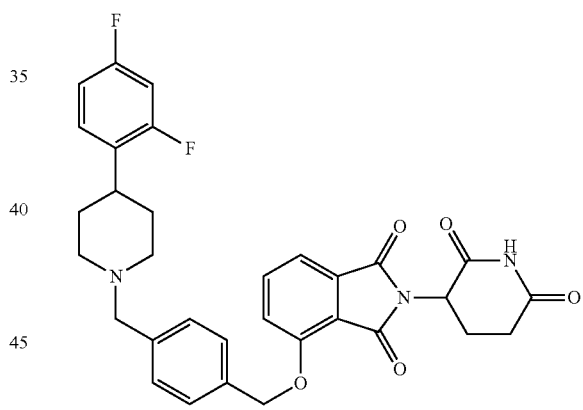
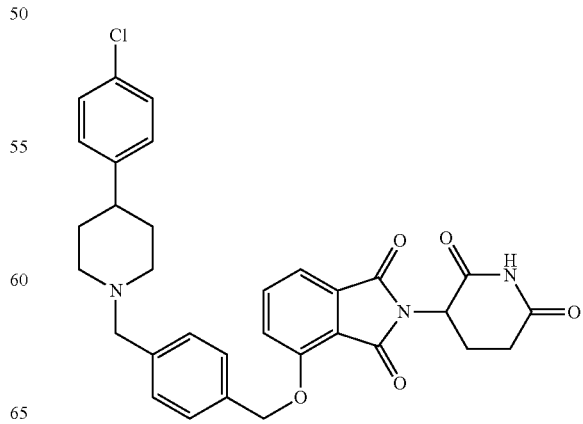

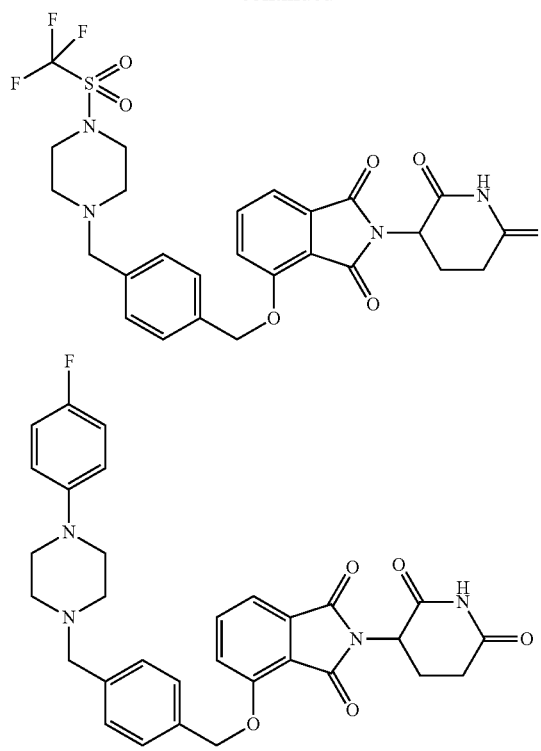
or a pharmaceutically acceptable salt, solvate or stereoisomer thereof.
In another embodiment, provided herein are compounds of formula:
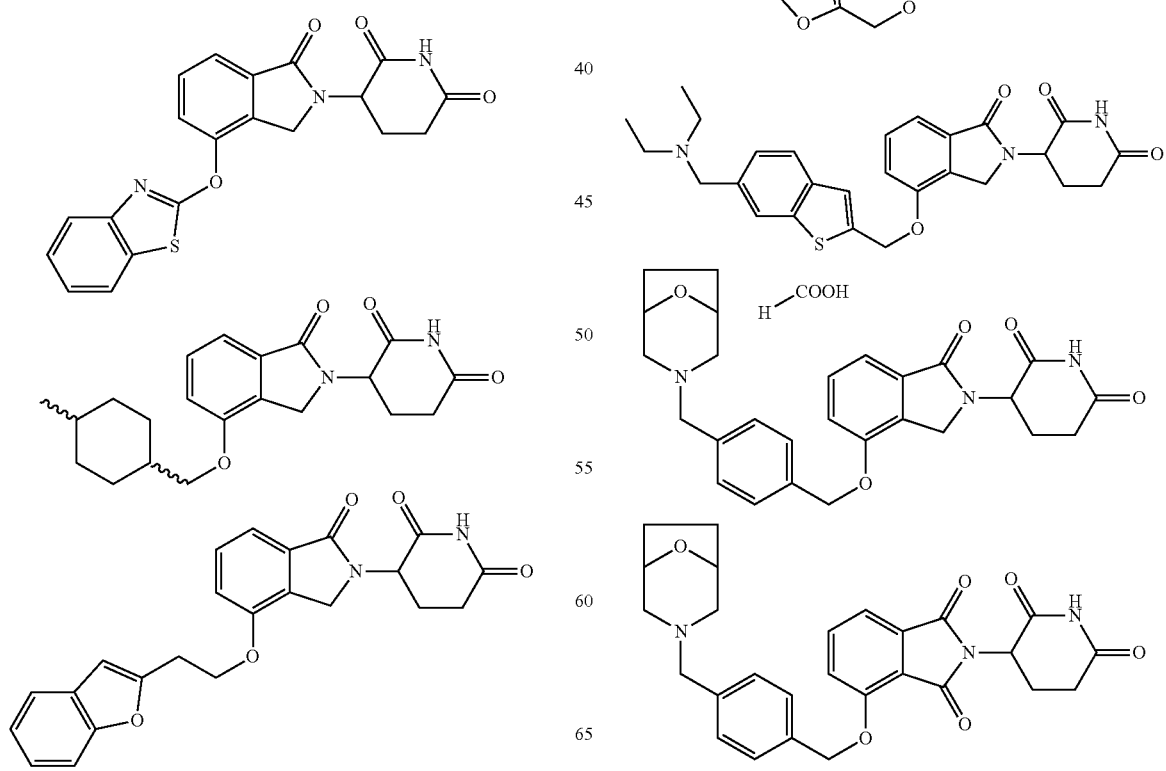
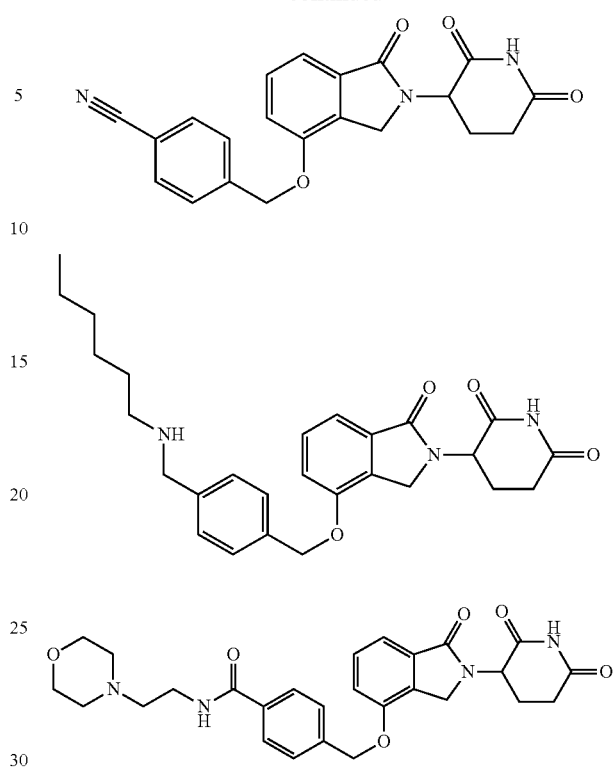

-continued

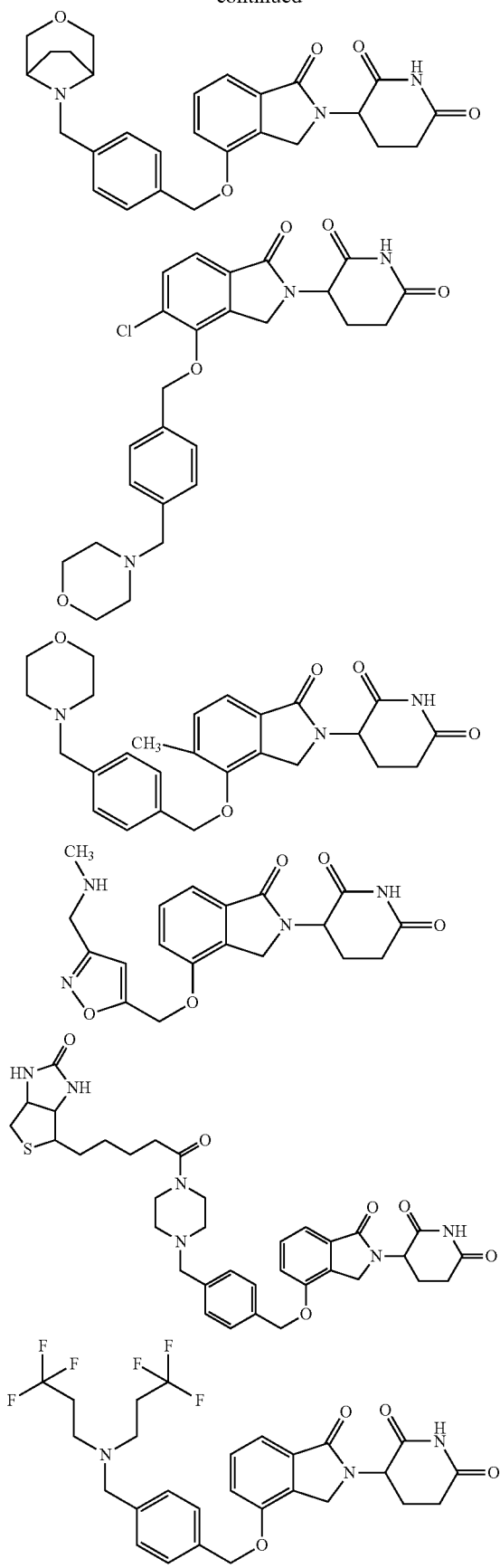

-continued

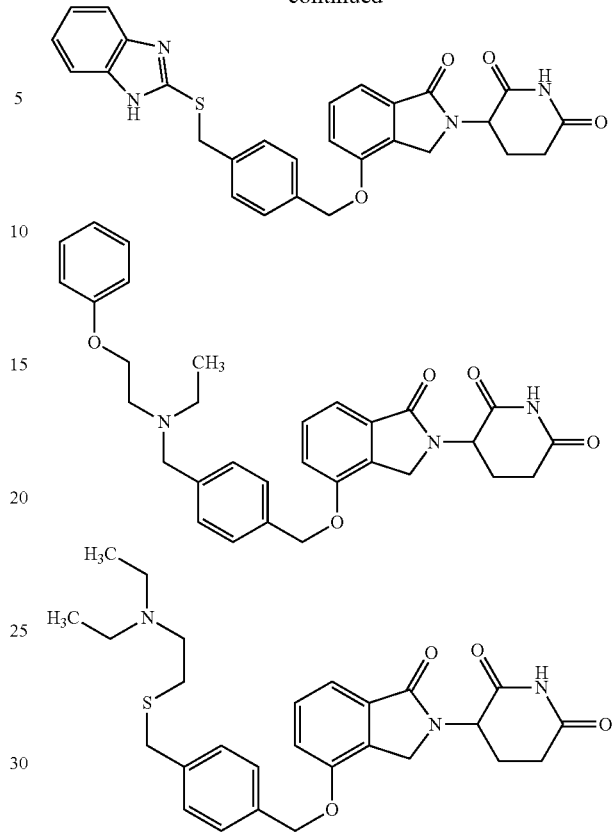

or a pharmaceutically acceptable salt, solvate or stereoisomer thereof.

As used herein, and unless otherwise specified, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucuronic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In one embodiment, suitable are hydrochloric, hydrobromic, phosphoric, and sulfuric acids.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed. 1995), and *Design of Prodrugs* (H. Bundgaard ed., Elsevier, New York 1985).

As used herein, and unless otherwise specified, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, carbamates that include lower alkylamine, substituted ethylenediamine, aminoacid, hydroxyalkylamine, heterocyclic and heteroaromatic amine, and polyether amine moieties.

As used herein, and unless otherwise specified, the term "stereoisomer" encompasses all enantiomerically/stereomerically pure and enantiomerically/stereomerically enriched compounds provided herein.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, greater than about 98% by weight of one stereoisomer of the compound and less than about 2% by weight of the other stereoisomers of the compound or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center.

Similarly, the term "enantiomerically enriched" means a stereomerically enriched composition of a compound having one chiral center.

As used herein, and unless otherwise indicated, the term "alkyl" refers to a saturated straight chain or branched hydrocarbon having a number of carbon atoms as specified herein. In some embodiments, alkyl groups have 1 to 15, 1 to 10, 1 to 6, or 1 to 3 carbon atoms. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The term "alkyl" also encompasses cycloalkyl.

As used herein, alkenyl refers to a straight chain or branched hydrocarbon containing one or more double bonds. Exemplary alkenyl carbon chains contain from 2 to 20 carbons, and in certain embodiments, contain 1 to 8 double bonds, and the alkenyl carbon chains of 2 to 16 carbons, in certain embodiments, contain 1 to 5 double bonds.

As used herein, alkynyl refers to a straight chain or branched hydrocarbon containing one or more triple bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkenyl and alkynyl groups herein include, but are not limited to, ethene, propene, butene, pentene, acetylene and hexyne. As used herein, lower alkyl, lower alkenyl, and lower alkynyl refer to carbon chains having from about 1 or about 2 carbons up to about 6 carbons.

As used herein, and unless otherwise specified, the term "cycloalkyl" means a specie of alkyl, which is cyclic and contains from 3 to 15, 3 to 9, 3 to 6, or 3 to 5 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more substituents. In some embodiments, a cycloalkyl may be a cycloalkyl fused with aryl or heteroaryl groups.

As used herein, and unless otherwise specified, the term "heterocycloalkyl" means a cycloalkyl in which one or more carbon atoms are replaced by heteroatoms such as, but not limited to, N, S, and O. In some embodiments, a heterocycloalkyl group contains contains from 2 to 14, 2 to 8, 2 to 7, 2 to 5, or 2 to 4 carbon atoms. In some embodiments, a heterocycloalkyl may be a heterocycloalkyl fused with aryl or heteroaryl groups.

As used herein, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Specifically, the aryl group may be a mono-, bi-, or tricyclic ring. Representative aryl groups include phenyl, anthracenyl, fluorenyl, indenyl, azulenyl, phenanthrenyl and naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, indolinyl, pyrrolidinyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "alkylaminocarbonyl" refers to C(O)NHR in which R is alkyl, including lower alkyl. As used herein, "dialkylaminocarbonyl" refers to C(O)NR'R in which R' and R are independently alkyl, including lower alkyl; "carboxamide" refers to groups of formula —NR'COR in which R' and R are independently alkyl, including lower alkyl.

As used herein, "arylaminocarbonyl" refers to —C(O)NHR in which R is aryl, including lower aryl, such as phenyl.

As used herein, "halo", "halogen" or "halide" refers to F, Cl, Br or I.

Where the number of any given substituent is not specified (e.g., "haloalkyl"), there may be one or more substituents present. For example, "haloalkyl" may include one or more of the same or different halogens.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Methods of Treatment, Prevention and Management

Provided herein are methods of treating, preventing, and/or managing various diseases or disorders using a compound provided herein, or a pharmaceutically acceptable salt, solvate (e.g., hydrate), prodrug, clathrate, or stereoisomer thereof.

Examples of diseases or disorders include, but are not limited to, cancer, disorders associated with angiogenesis, pain including, but not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα related disorders, and other various diseases and disorders.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

As used herein, unless otherwise specified, the term "preventing" refers to the treatment with or administration of a compound provided herein, with or without other additional active compound, prior to the onset of symptoms, particularly to patients at risk of cancer and/or other disorders described herein. The term "prevention" includes the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. In certain cases, the beneficial effects that a subject derives from a prophylactic or therapeutic agent do not result in a cure of the disease or disorder.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to inhibit or reduce a symptom of a disease or to prevent recurrence of a disease. A prophylactically effective amount of a compound means an amount of therapeutic agent, alone or in combination with other agents, which provides a prophylactic benefit in the inhibition or reduction of a symptom of a disease or recurrence of a disease. The term "prophylactically effective amount" can encompass an amount that improves overall prophylaxis or enhances the prophylactic efficacy of another prophylactic agent.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Specific examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistant to chemotherapy or radiation.

In one embodiment, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another embodiment, provided herein are methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mantle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trelat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vasular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Banesia Gibsoni, Besnoitia darlingi, Cytauxzoonfelis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. application Ser. No. 11/289,723, filed Nov. 30, 2005. Specific examples include, but not limited to, adenosine deaminase deficiency, antibody deficiency with normal or elevated Igs, ataxia-telangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/0122228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post. ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated herein:

TABLE 1

| Artery | Body Areas Supplied |
|---|---|
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | |
| Middle sacral | Esophagus and stomach |

TABLE 1-continued

| Artery | Body Areas Supplied |
|---|---|
| Ovarian | Sacrum |
| Palmar arch | Ovaries |
| Peroneal | Hand |
| Popliteal | Calf |
| Posterior tibial | Knee |
| Pulmonary | Calf |
| Radial | Lungs |
| Renal | Forearm |
| Splenic | Kidney |
| Subclavian | Stomach, pancreas, and spleen |
| Superior mesenteric | Shoulder |
| Testicular | Pancreas, small intestine, ascending and transverse colon |
| Ulnar | Testes Forearm |

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock;

rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, sepsis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other embodiments, the use of compounds provided herein in various immunological applications, i.e., use of compounds provided herein in combination with a vaccination, for example, as vaccine adjuvant. Although any methods and manners of use of compounds provided herein in combination with a vaccine are contemplated herein, a non-limiting example of such uses is the use of compounds provided herein as vaccine adjuvants, according to the administration regimens disclosed in U.S. Provisional Application No. 60/712,823, filed Sep. 1, 2005, which is incorporated herein in its entirety by reference. These embodiments also relate to the uses of compounds provided herein in combination with vaccines to treat or prevent cancer or infectious diseases, and other various uses of compounds provided herein, such as, but not limited to, reduction or desensitization of allergic reactions.

Doses of a compound provided herein, or a pharmaceutically acceptable salt, solvate, clathrate, stereoisomer or prodrug thereof, vary depending on factors such as: specific indication to be treated, prevented, or managed; age and condition of a patient; and amount of second active agent used, if any. Generally, a compound provided herein, or a pharmaceutically acceptable salt, solvate, clathrate, stereoisomer or prodrug thereof, may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

4.3 Second Active Agents

A compound provided herein, or a pharmaceutically acceptable salt, solvate, prodrug, clathrate, or stereoisomer thereof, can be combined with other pharmacologically active compounds ("second active agents") in methods and compositions provided herein. Certain combinations may work synergistically in the treatment of particular types diseases or disorders, and conditions and symptoms associated with such diseases or disorders. A compound provided herein, or a pharmaceutically acceptable salt, solvate, clathrate, stereoisomer or prodrug thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); PI3K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; lapatinib (Tykerb®); acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine;

meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium;

tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0214328, 2005/0239842, 2006/0154880, 2006/0122228, and 2005/0143344; and U.S. provisional application No. 60/631,870.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16, 17-1-methylethylidinebis (oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hypertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cis-platinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises I-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a compound provided herein, or a pharmaceutically acceptable salt, solvate, clathrate, stereoisomer or prodrug thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g., *Physicians' Desk Reference* (60$^{th}$ ed., 2006).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

4.4 Cycling Therapy

In certain embodiments, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

4.5 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed in Section 4.3, above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences*, 20$^{th}$ ed., Mack Publishing, Easton Pa. (2000).

In one embodiment, pharmaceutical compositions and dosage forms comprise one or more excipients. Suitable excipients are well known to those skilled in the art of pharmacy, and non-limiting examples of suitable excipients are provided herein.

Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

4.5.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 20th ed., Mack Publishing, Easton Pa. (2000).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

4.5.2 Controlled Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus, the compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body.

Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, CRC Crit. Ref Biomed. Eng. 14:201 (1987); Buchwald et al., Surgery 88:507 (1980); Saudek et al., N. Engl. J. Med. 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

4.5.3 Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

4.5.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16$^{th}$, 18$^{th}$ and 20$^{th}$ eds., Mack Publishing, Easton Pa. (1980, 1990 and 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences*, 16$^{th}$, 18$^{th}$ and 20$^{th}$ eds., Mack Publishing, Easton Pa. (1980, 1990 and 2000).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4.6 KITS

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.3).

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the claimed subject matter are illustrated by the following non-limiting examples.

5.1 4-Carbamoyl-4-(4-Hydroxy-1-Oxo-1,3-Dihydro-Isoindol-2-yl)-Butyric Acid Methyl Ester

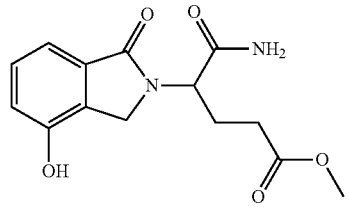 [SMILES: COC(=O)CCC(C(N)=O)N1Cc2c(O)cccc2C1=O]

5.1.1 3-Hydroxy-2-methyl-benzoic acid methyl ester

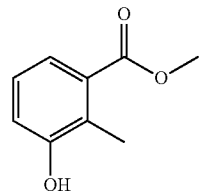

3-Hydroxy-2-methylbenzoic acid (105 g, 690 mmol) was added to MeOH (800 mL) in a 2 L three neck round bottom flask equipped with condenser, thermometer and stirring bar followed by the addition of MeOH (250 ml). H$_2$SO$_4$ (10 mL, 180 mmol) was added to above solution. The reaction mixture was stirred at 62° C. for 17 hours. The solvent was removed in vacuo. The residue (200 mL) was added to water (600 mL) slowly at room temperature and a white solid was formed. The suspension was stirred in an ice bath for 30 minutes and filtered. The solid was washed with water (5×250 mL) and dried to give 3-hydroxy-2-methyl-benzoic acid methyl ester as a white solid (100 g, 87% yield). The compound was used in the next step without further purification: LCMS MH=167; $^1$H NMR (DMSO-d$_6$) δ 2.28 (s, 3H, CH$_3$), 3.80 (s, 3H, CH$_3$), 6.96-7.03 (m, 1H, Ar), 7.09 (t, J=7.8 Hz, 1H, Ar), 7.14-7.24 (m, 1H, Ar), 9.71 (s, 1H, OH).

5.1.2 3-(tert-Butyl-dimethyl-silanyloxy)-2-methyl-benzoic acid methyl ester

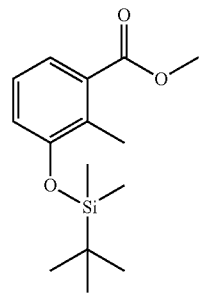 [SMILES: COC(=O)c1cccc(O[Si](C)(C)C(C)(C)C)c1C]

To a 1 L three neck RB flask equipped with stirring bar and thermometer, were added DMF (300 mL), methyl 3-hydroxy-2-methylbenzoate (90 g, 542 mmol) and imidazole (92 g, 1,354 mmol). TBDMS-Cl (90 g, 596 mmol) was added to the above solution in portions to control the internal temp between 15-19° C. over 20 minutes, and after addition, the internal temp dropped below 1° C. The ice bath was removed and the reaction mixture was stirred at room temperature for 16 hours. The reaction mixture was added to ice water (500 mL), and the resulting solution was divided into two portions (700 mL×2). Each portion was extracted with EtOAc (700 mL). Each organic layer was washed with cold water (350 mL) and brine (350 mL). Organic layers were combined and dried by MgSO$_4$. The combined organic layer was concentrated to give 3-(tert-butyl-dimethyl-silanyloxy)-2-methyl-benzoic acid methyl ester as a light brown oil (160 g, 100% crude yield). The compound was used in the next step without further purification: LCMS MH=281; $^1$H NMR (DMSO-d$_6$) δ −0.21 (s, 6H, CH$_3$, CH$_3$), 0.73-0.84 (m, 9H, CH$_3$, CH$_3$, CH$_3$), 2.10 (s, 3H, CH$_3$), 3.60 (s, 3H, CH$_3$), 6.82 (dd, 1H, Ar), 6.97 (t, J=0.7.9 Hz, 1H, Ar), 7.13 (dd, J=1.1, 7.7 Hz, 1H, Ar).

5.1.3 2-Bromomethyl-3-(tert-butyl-dimethyl-silanyloxy)-benzoic acid methyl ester

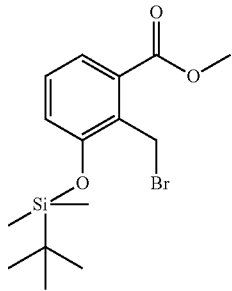

NBS (49.8 g, 280 mmol) was added to methyl 3-(tert-butyl dimethylsilyloxy)-2-methylbenzoate (78.4 g, 280 mmol) in methyl acetate (500 mL) at room temperature to give an orange colored suspension. The resulting reaction mixture was heated in an oil bath at 40° C. and shined by 300 wt sunlight bulb at reflux for 4 hours. The reaction mixture was cooled down and washed by Na$_2$SO$_3$ solution (2×600 mL, 50% saturated concentration), water (500 mL) and brine (600 mL). The organic layer was dried by MgSO$_4$ and decolorized by charcoal. The organic layer was concentrated to give 2-bromomethyl-3-(tert-butyl-dimethyl-silanyloxy)-benzoic acid methyl ester as a light brown oil (96 g, 91% crude yield). The compound was used in the next step without further purification: LCMS M-Br=279; $^1$H NMR (DMSO-d$_6$) δ 0.05-0.11 (m, 6H, CH$_3$, CH$_3$), 0.82 (s, 9H, CH$_3$, CH$_3$, CH$_3$), 3.65 (s, 3H, CH$_3$), 4.74 (s, 2H, CH$_2$), 6.94 (dd, J=1.3, 8.1 Hz, 1H, Ar), 7.10-7.20 (m, 1H, Ar), 7.21-7.29 (m, 1H, Ar).

5.1.4 4-Carbamoyl-butyric acid methyl ester

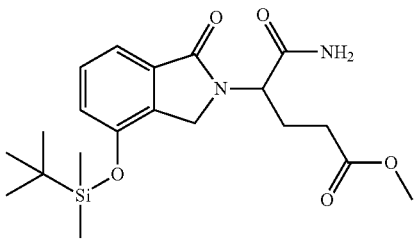 [SMILES: COC(=O)CCC(C(N)=O)N1Cc2c(O[Si](C)(C)C(C)(C)C)cccc2C1=O]

To a stirred solution of methyl 2-(bromomethyl)-3-(tert-butyldimethylsilyloxy)benzoate (137.5 g, 325 mmol) in acetonitrile (1100 mL) in a 2 L round bottom flask, was added methyl 4,5-diamino-5-oxopentanoate hydrochloride (70.4 g, 358 mmol). To the suspension was added DIPEA (119 ml, 683 mmol) through an addition funnel over 10 minutes and the suspension was stirred at room temperature for 1 hour before the mixture was heated in an oil bath at 40° C. for 23 hours. The reaction mixture was concentrated under vacuo. The residue was stirred in ether (600 mL), and a white solid precipitated out. The mixture was filtered and the solid was washed with ether (400 mL). The filtrate was washed with HCl (1N, 200 mL), NaHCO$_3$ (sat. 200 mL) and brine (250 mL). The aqueous acid layer and basic layer were kept separately. Then the solid was further washed with ether (250 mL) and the liquid was washed with above acid solution and basic solution. The two organic layers were combined and concentrated under vacuo to give 4-[4-(tert-Butyl-dimethyl-silanyloxy)-1-oxo-1,3-dihydro-isoindol-2-yl]-4-carbamoyl-butyric acid methyl ester as a brown oil (152 g, 115% crude yield, 77% purity by H NMR). The compound was used in the next step without further purification: LCMS MH=407.

5.1.5 4-Carbamoyl-4-(4-hydroxy-1-oxo-1,3-dihydro-isoindol-2-yl)-butyric acid methyl ester

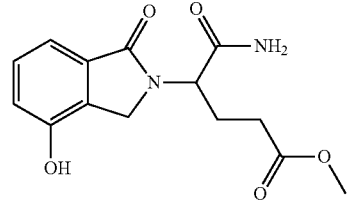 [SMILES: COC(=O)CCC(C(N)=O)N1Cc2c(O)cccc2C1=O]

To a stirred cold solution of methyl 5-amino-4-(4-(tert-butyldimethylsilyloxy)-1-oxoisoindolin-2-yl)-5-oxopentanoate (152 g, 288 mmol) in DMF (500 mL) and water (55 mL), was added by K$_2$CO$_3$ (19.89 g, 144 mmol) by portions over 5 minutes. The resulting reaction mixture was stirred at room temperature for 40 minutes. The reaction mixture was cooled in an ice bath. To the mixture, HCl (12M, 23.99 ml, 288 mmol) was added slowly. After the addition, acetonitrile (280 mL) was added to the mixture and a solid precipitated out. The mixture was stirred at room temperature for 10 minutes and filtered. The solid was washed with acetonitrile (50 mL×4). The filtrate was concentrated under high vacuo to give a yellow oil (168 g). The oil was dissolved in acetonitrile (600 mL) and stirred at room temperature for 10 minutes. The mixture was filtered and the solid was washed with acetonitrile (25 mL×2). The filtrate was concentrated under high vacuo to give a yellow oil (169 g), which was added to a mixture of water (1200 mL) and ether (1000 mL). The mixture was stirred for 3 minutes and the layers were separated. The aqueous solution was concentrated under high vacuo and the residue was stirred in acetonitrile (160 mL) and a white solid was formed after overnight stirring. The mixture was filtered to give 4-carbamoyl-4-(4-hydroxy-1-oxo-1,3-dihydro-isoindol-2-yl)-butyric acid methyl ester as a white solid (46 g, 54% yield). The filtrate was concentrated and the residue was further crystallized in acetonitrile (60 mL) to give more 4-carbamoyl-4-(4-hydroxy-1-oxo-1,3-dihydro-isoindol-2-yl)-butyric acid methyl ester as a white solid (11.7 g, 14% yield). The filtrate was concentrated and the residue was purified by ISCO chromatography to give more 4-carbamoyl-4-(4-hydroxy-1-oxo-1,3-dihydro-isoindol-2-yl)-butyric acid methyl ester as a white solid (13.2 g, 15% yield). The total product obtained was 70.9 g in 83% yield: LCMS MH=293; $^1$H NMR (DMSO-$d_6$) δ 1.95-2.34 (m, 4H, $CH_2$, $CH_2$), 3.51 (s, 3H, $CH_3$), 4.32 (d, J=17.6 Hz, 1H, CHH), 4.49 (d, J=17.4 Hz, 1H, CHH), 4.73 (dd, J=4.7, 10.2 Hz, 1H, CHH), 6.99 (dd, J=0.8, 7.9 Hz, 1H, Ar), 7.10-7.23 (m, 2H, Ar, NHH), 7.25-7.38 (m, 1H, Ar), 7.58 (s, 1H, NHH), 10.04 (s, 1H, OH).

5.2 3-[4-(4-Morpholin-4-ylmethyl-Benzyloxy)-1-Oxo-1,3-Dihydro-Isoindol-2-yl]-Piperidine-2,6-Dione

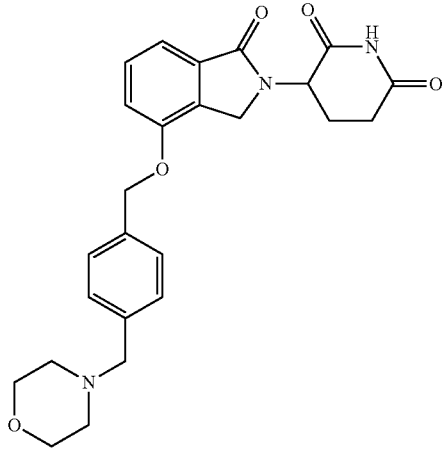 [SMILES: O=C1CCC(N2Cc3c(OCc4ccc(CN5CCOCC5)cc4)cccc3C2=O)C(=O)N1]

5.2.1 Procedure 1

Step 1: To the solution of 3-(4-hydroxy-1-oxo-1,3-dihydro-isoindol-2-yl)-piperidine-2,6-dione (2.5 g, 8.56 mmol) in THF (60 mL) was added triphenyl phosphine (polymer supported 1.6 mmol/g, 12 g, 18.8 mmol). The mixture was stirred at room temperature for 15 minutes. Diisopropyl azodicarboxylate (3.96 mL, 18.8 mmol) was added at 0° C., and the mixture was stirred at 0° C. for 30 minutes. (4-Morpholin-4-ylmethyl-phenyl)-methanol (2.62 g, 12.4 mmol) was added at 0° C., and the mixture was allowed to warm to room temperature and stirred at room temperature overnight. The reaction mixture was filtered, and the filtrate was concentrated. The resulting oil was purified on silica gel column eluted with methylene chloride and methanol (gradient, product came out at 6% methanol) to give 4-carbamoyl-4-[4-(4-morpholin-4-ylmethyl-benzyloxy)-1-oxo-1,3-dihydro-isoindol-2-yl]-butyric acid methyl ester (2.2 g, 54% yield). The product was used in the next step without further purification.

Step 2: To the THF solution (50 mL) of 4-carbamoyl-4-[4-(4-morpholin-4-ylmethyl-benzyloxy)-1-oxo-1,3-dihydro-isoindol-2-yl]-butyric acid methyl ester (2.2 g, 4.57 mmol) was added potassium tert-butoxide (0.51 g, 4.57 mmol) at 0° C. The mixture was stirred at 0° C. for 10 minutes and was quenched with 1N HCl (5 mL, 5 mmol) followed by saturated $NaHCO_3$ (25 mL). The mixture was extracted with EtOAc (2×50 mL). The organic layer was washed with water (30 mL), brine (30 mL), dried over $MgSO_4$ and concentrated. To the resulting solid was added EtOAc (10 mL) followed by hexane (10 mL) under stirring. The suspension was filtered to give 3-[4-(4-morpholin-4-ylmethyl-benzyloxy)-1-oxo-1,3-dihydro-isoindol-2-yl]-piperidine-2,6-dione as white solid (1.5 g, 73% yield). HPLC: Waters Symmetry $C_{18}$, 5 μm, 3.9×150 mm, 1 mL/min, 240 nm, gradient to 95/5 acetonitrile/0.1% $H_3PO_4$ in 5 min: $t_R$=4.78 min (97.5%); mp: 210-212° C.; $^1$H NMR (DMSO-$d_6$) δ 1.86-2.09 (m, 1H, CHH), 2.29-2.38 (m, 4H, $CH_2$, $CH_2$), 2.44 (dd, J=4.3, 13.0 Hz, 1H, CHH), 2.53-2.64 (m, 1H, CHH), 2.82-2.99 (m, 1H, CHH), 3.46 (s, 2H, $CH_2$), 3.52-3.61 (m, 4H, $CH_2$, $CH_2$), 4.18-4.51 (m, 2H, $CH_2$), 5.11 (dd, J=5.0, 13.3 Hz, 1H, NCH), 5.22 (s, 2H, $CH_2$), 7.27-7.38 (m, 5H, Ar), 7.40-7.53 (m, 3H, Ar), 10.98 (s, 1H, NH) $^{13}$C NMR (DMSO-$d_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for $C_{25}H_{27}N_3O_5$+0.86 $H_2O$: C, 64.58; H, 6.23; N, 9.04. Found: C, 64.77; H, 6.24; N, 8.88.

5.2.2 Procedure 2

Step 1: To a 2-L round bottom flask, were charged methyl 5-amino-4-(4-hydroxy-1-oxoisoindolin-2-yl)-5-oxopentanoate (30 g, 103 mmol), 1,4-bis(bromomethyl)benzene (81 g, 308 mmol) and potassium carbonate (14.19 g, 103 mmol) and acetonitrile (1.2 L). The mixture was stirred at room temperature for 10 minutes and heated to 50° C. for 12 hours. The reaction mixture was allowed to cool to room temperature. The mixture was filtered and the filtrate was concentrated on rota-vap. The resulting solid was dissolved in $CH_2Cl_2$ and loaded on 2 silica gel columns (330 g each) and eluted using $CH_2Cl_2$/MeOH to give 4-[4-(4-bromomethyl-benzyloxy)-1-oxo-1,3-dihydro-isoindol-2-yl]-4-carbamoyl-butyric acid methyl ester as white solid (40 g, 82% yield): $^1$H NMR (DMSO-$d_6$) δ 1.98-2.13 (m, 1H, CHH), 2.14-2.23 (m, 1H, CHH), 2.23-2.32 (m, 2H, CHH, CHH), 3.50 (s, 3H, $CH_3$), 4.34-4.63 (m, 2H, $CH_2$), 4.67-4.80 (m, 3H, $CH_2$, NCH), 5.25 (s, 4H, $CH_2$), 7.19 (s, 1H, NHH), 7.24-7.34 (m, 2H, Ar), 7.41-7.54 (m, 5H, Ar), 7.58 (br. s., 1H, NHH).

Step 2: To the $CH_2Cl_2$ solution of methyl 5-amino-4-(4-(4-(bromomethyl)benzyloxy)-1-oxoisoindolin-2-yl)-5-oxopentanoate (36.5 g, 77 mmol), was added morpholine (14.72 ml, 169 mmol) at room temperature. The mixture was stirred at room temperature for 1 hour. The resulting suspension was filtered, and the filtrate was concentrated on rota-vap. The resulting oil was dissolved in 350 mL of EtOAc and washed with water (50 mL×3). The organic layer was concentrated on rota-vap to give 4-carbamoyl-4-[4-(4-morpholin-4-ylmethyl-benzyloxy)-1-oxo-1,3-dihydro-isoindol-2-yl]-butyric acid methyl ester as a foamy solid (39 g, 100% yield): $^1$H NMR (DMSO-$d_6$) δ 2.00-2.12 (m, 1H, CHH), 2.14-2.22 (m, 1H, CHH), 2.22-2.29 (m, 2H, CHH, CHH), 2.30-2.39 (m, 4H, $CH_2$, $CH_2$), 3.46 (s, 2H, $CH_2$), 3.50 (s, 3H, $CH_3$), 3.53-3.63 (m, 4H, $CH_2$, $CH_2$), 4.28-4.59 (m, 2H, $CH_2$), 4.73 (dd, J=4.7, 10.2 Hz, 1H, NCH), 5.22 (s, 2H, $CH_2$), 7.14-7.23 (m, 1H, NHH), 7.26-7.39 (m, 4H, Ar), 7.41-7.51 (m, 3H, Ar), 7.58 (s, 1H, NHH).

Step 3: To the THF solution of methyl 5-amino-4-(4-(4-(morpholinomethyl)benzyloxy)-1-oxoisoindolin-2-yl)-5-oxopentanoate (40 g, 83 mmol), was added potassium 2-methylpropan-2-olate (9.80 g, 87 mmol) portion wise at 0° C. The mixture was stirred at this temperature for 30 minutes. To the reaction mixture, was added 45 mL of 1N HCl solution, followed by 200 mL of saturated $NaHCO_3$ solution. The mixture was diluted with 500 mL of EtOAc at 0° C., stirred for 5 minutes and separated. The organic layer was washed with water (50 mL×3) and brine (100 mL), and concentrated on rota-vap to give a white solid, which was stirred in diethyl ether (300 mL) to give a suspension. The suspension was filtered to give 3-[4-(4-morpholin-4-ylm-ethyl-benzyloxy)-1-oxo-1,3-dihydro-isoindol-2-yl]-piperidine-2,6-dione as white solid (28.5 g, 72% yield): HPLC: Waters Symmetry $C_{18}$, 5 μm, 3.9×150 mm, 1 mL/min, 240 nm, gradient to 95/5 acetonitrile/0.1% $H_3PO_4$ in 5 min: $t_R$=4.78 min (98.5%); mp: 209-211° C.; $^1$H NMR (DMSO-$d_6$) δ 1.86-2.09 (m, 1H, CHH), 2.29-2.38 (m, 4H, $CH_2$, $CH_2$), 2.44 (dd, J=4.3, 13.0 Hz, 1H, CHH), 2.53-2.64 (m, 1H, CHH), 2.82-2.99 (m, 1H, CHH), 3.46 (s, 2H, $CH_2$), 3.52-3.61 (m, 4H, $CH_2$, $CH_2$), 4.18-4.51 (m, 2H, $CH_2$), 5.11 (dd, J=5.0, 13.3 Hz, 1H, NCH), 5.22 (s, 2H, $CH_2$), 7.27-7.38 (m, 5H, Ar), 7.40-7.53 (m, 3H, Ar), 10.98 (s, 1H, NH); $^{13}$C NMR (DMSO-$d_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for $C_{25}H_{27}N_3O_5$+0.86 $H_2O$: C, 64.63; H, 6.22; N, 9.04; Found: C, 64.39; H, 6.11; N, 8.89; $H_2O$, 3.24.

5.3 3-{4-[4-(2,2,3,3,4,4,5,5,6,6-Decadeutero-Piperidin-1-ylmethyl)-Benzyloxy]-1-Oxo-1,3-Dihydro-Isoindol-2-yl}-Piperidine-2,6-Dione

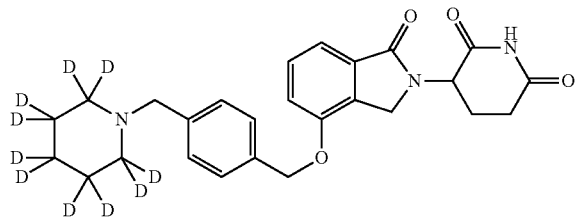 [SMILES: [2H]C1([2H])N(Cc2ccc(COc3cccc4c3CN(C3CCC(=O)NC3=O)C4=O)cc2)C([2H])([2H])C([2H])([2H])C([2H])([2H])C1([2H])[2H]]

Step 1: Perdeutero-piperidine ($d_{11}$, 98% D, 136 mg, 1.42 mmol) was added to a solution of tert-butyl 5-amino-2-(4-(4-(chloromethyl)benzyloxy)-1-oxoisoindolin-2-yl)-5-oxopentanoate (450 mg, 0.95 mmol) and N,N-diisopropylethylamine (0.24 mL, 1.42 mmol) in dry MeCN (9 mL). The reaction mixture was warmed up to 60° C. with stirring for 2 hours. The mixture was allowed to cool down to room temperature and then stored at 4° C. overnight. A solid formed upon cooling and the slurry was partitioned between EtOAc (150 mL) and 1N $NaHCO_3$ (40 mL). The aqueous layer was washed with EtOAc (100 mL) and the combined organic layer was washed with brine, dried ($Na_2SO_4$), and concentrated in vacuo to provide 4-carbamoyl-2-{4-[4-(2,2,3,3,4,4,5,5,6,6-decadeutero-piperidin-1-ylmethyl)-benzyloxy]-1-oxo-1,3-dihydro-isoindol-2-yl}-butyric acid tert-butyl ester as a white solid (490 mg, 97% yield): LCMS MH=532. The solid was used in the next step without further purification.

Step 2: To a solution of 4-carbamoyl-2-{4-[4-(2,2,3,3,4,4,5,5,6,6-decadeutero-piperidin-1-ylmethyl)-benzyloxy]-1-oxo-1,3-dihydro-isoindol-2-yl}-butyric acid tert-butyl ester (490 mg, 0.92 mmol) in THF (10 mL) at room temperature, was added KOtBu (109 mg, 0.96 mmol) as a solid in one portion. The solution changed color from pale to a deep yellow upon addition, and the mixture was stirred at room temperature for about 30 minutes. More KOtBu (14 mg) was added to the reaction and stirring was continued overnight. After about 17 hours, added another portion of KOtBu (28 mg), and the reaction was allowed to stir at room temperature for an additional 2 hours. The reaction mixture was quenched with acetic acid (0.158 mL, 2.76 mmol) at 0° C. The resulting slurry was concentrated in vacuo and the residue partitioned between EtOAc (75 mL) and 1N $NaHCO_3$ (30 mL). The aqueous layer was washed with more EtOAc (75 mL). The combined organic layers was washed with brine, dried ($Na_2SO_4$), and concentrated in vacuo to give a tan solid. $Et_2O$ (20 mL) was added to the solid crude product and the slurry was triturated by sonication, followed by filtration and washing of the solid with additional $Et_2O$. The cake was suction dried to give 3-{4-[4-(2,2,3,3,4,4,5,5,6,6-Decadeutero-piperidin-1-ylmethyl)-benzyloxy]-1-oxo-1,3-dihydro-isoindol-2-yl}-piperidine-2,6-dione as a pale yellow solid (205 mg, 49% yield): HPLC: Waters Symmetry $C_{18}$, 5 μm, 3.9×150 mm, 1 ml/min, 240 nm, 5% grad 95% in 5 min, acetonitrile/0.1% $H_3PO_4$, 4.69 min (95.6%); mp: 186-188° C.; $^1$H NMR (DMSO-$d_6$) δ 1.88-2.06 (m, 1H, CHH), 2.37-2.48 (m, 1H, CHH), 2.52-2.63 (m, 1H, CHH), 2.81-3.02 (m, 1H, CHH), 3.41 (s, 2H, $CH_2$), 4.25 (d, J=17.6 Hz, 1H, CHH), 4.41 (d, J=17.6 Hz, 1H, CHH), 5.11 (dd, J=5.0, 13.1 Hz, 1H, CH), 5.22 (s, 2H, $CH_2$), 7.26-7.37 (m, 4H, Ar), 7.38-7.57 (m, 3H, Ar), 10.97 (s, 1H, NH); $^{13}$C NMR (DMSO-$d_6$) δ 22.33, 31.18, 45.07, 51.55, 62.42, 69.42, 114.94, 115.19, 127.57, 128.78, 129.78, 129.93, 133.28, 135.00, 138.58, 153.51, 167.99, 170.95, 172.80; $CD_2$ carbon signals are not observed in the $^{13}$C NMR; LCMS MH=458; Anal Calcd for $C_{26}H_{19}D_{10}N_3O_4$+0.25 $H_2O$: C, 67.58; H, 6.43; N, 9.09. Found: C, 67.51; H, 6.32; N, 9.16.

5.4 3-{4-[4-(2,2,3,3,5,5,6,6-Octadeutero-Morpholin-4-ylmethyl)-Benzyloxy]-1-Oxo-1,3-Dihydro-Isoindol-2-yl}-Piperidine-2,6-Dione

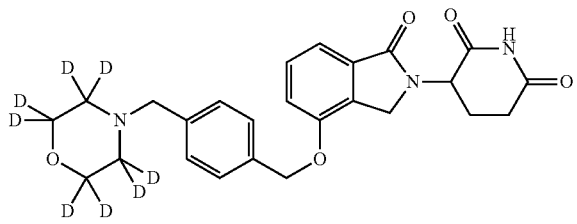

Step 1: To a solution of tert-butyl 5-amino-2-(4-(4-(chloromethyl)benzyloxy)-1-oxoisoindolin-2-yl)-5-oxopentanoate (450 mg, 0.95 mmol) and N,N-diisopropylethylamine (0.24 mL, 1.42 mmol) in MeCN (9 mL), was added 2,2,3,3,5,5,6,6-octadeutero-morpholine (ds, 98% D, 136 mg, 1.42 mmol). The reaction was stirred at 60° C. for 2.5 hours. The mixture (a white slurry) was concentrated to dryness and the solid residue was partitioned between EtOAc (150 mL) and 1N $NaHCO_3$ (35 mL). The aqueous layer was washed with additional EtOAc (150 mL). The organic layers were combined, washed with brine, dried ($Na_2SO_4$), and concentrated in vacuo to provide 4-carbamoyl-2-{4-[4-(2,2,3,3,5,5,6,6-octadeutero-morpholin-4-ylmethyl)-benzyloxy]-1-oxo-1,3-dihydro-isoindol-2-yl}-butyric acid tert-butyl ester as a white solid (0.5 g, 99% yield): LCMS MH=532. The solid was used in the next step without Step 2: To a cooled solution of 4-carbamoyl-2-{4-[4-(2,2,3,3,5,5,6,6-octadeutero-morpholin-4-ylmethyl)-benzyloxy]-1-oxo-1,3-dihydro-isoindol-2-yl}-butyric acid tert-butyl ester (0.5 g, 0.94 mmol) in THF (10 mL) at 0° C., was added KOtBu (0.137 g, 1.22 mmol) as a solid in one portion. The solution turned deep yellow. The ice bath was immediately removed and the reaction mixture was stirred at room temperature for about 90 minutes. The mixture was cooled in an ice bath and quenched by addition of acetic acid (0.162 mL, 2.82 mmol).

The volatiles were removed in vacuo to give a white solid that was partitioned between EtOAc (125 mL) and 1N NaHCO₃ (30 mL). The aqueous layer was washed with additional EtOAc (about 75 mL). The EtOAc layers were combined, washed with brine, dried (Na₂SO₄), and concentrated in vacuo to give 400 mg of a solid. This white solid was slurried in Et₂O (25 mL) and vigorously vortexed and sonicated to aid with trituration. The slurry was then filtered and suction dried on filter funnel for about ½ hour. The cake was stored in a vacuum oven at 60° C. for several hours to give 3-{4-[4-(2,2,3,3,5,5,6,6-Octadeutero-morpholin-4-ylmethyl)-benzyloxy]-1-oxo-1,3-dihydro-isoindol-2-yl}-piperidine-2,6-dione as a white solid (236 mg, 55% yield): HPLC: Waters Symmetry C₁₈, 5 µm, 3.9×150 mm, 1 ml/min, 240 nm, 5% grad 95% in 10 min, acetonitrile/0.1% H₃PO₄, 5.55 min (96.5%); mp: 206-208° C.; $^1$H NMR (DMSO-d₆) δ 1.88-2.07 (m, 1H, CHH), 2.34-2.49 (m, 1H, CHH), 2.52-2.65 (m, 1H, CHH), 2.80-3.01 (m, 1H, CHH), 3.46 (s, 2H, CH₂), 4.25 (d, J=17.6 Hz, 1H, CHH), 4.41 (d, J=17.6 Hz, 1H, CHH), 5.11 (dd, J=5.2, 13.1 Hz, 1H, CH), 5.23 (s, 2H, CH₂), 7.23-7.38 (m, 4H, Ar), 7.39-7.54 (m, 3H, Ar), 10.97 (s, 1H, CH); $^{13}$C NMR (DMSO-d₆) δ 22.33, 31.16, 45.06, 51.55, 62.01, 69.38, 114.96, 115.20, 127.61, 128.97, 129.78, 129.93, 133.28, 135.25, 137.72, 153.48, 167.99, 170.96, 172.81; CD2 carbon signals are not observed due to coupling and splitting with deuteriums; LCMS MH=458; Anal Calcd for C₂₅H₁₉D₈N₃O₅+0.25 H₂O: C, 64.98; H, 6.00; N, 9.09. Found: C, 64.91; H, 5.71; N, 9.04.

5.5 3-[4-(2-Morpholin-4-ylmethyl-Benzyloxy)-1-Oxo-1,3-Dihydro-Isoindol-2-yl]-Piperidine-2,6-Dione

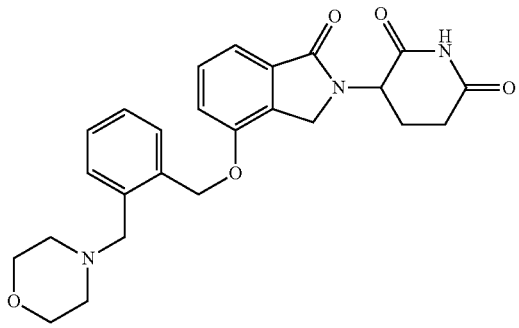 [SMILES: O=C1CCC(N2Cc3c(OCc4ccccc4CN4CCOCC4)cccc3C2=O)C(=O)N1]

Step 1: To the THF solution (15 mL) of 4-carbamoyl-4-(4-hydroxy-1-oxo-1,3-dihydro-isoindol-2-yl)-butyric acid methyl ester (0.3 g, 1 mmol), was added triphenyl phosphine resin (1.38 g, 2.2 mmol/g loading, 2.2 mmol) and DIAD (0.43 mL, 2.2 mmol) at 0° C., and kept for 10 minutes. To the mixture was added (2-morpholin-4-ylmethyl-phenyl)-methanol (0.31 g, 1.5 mmol), and the mixture was stirred at room temperature overnight. The mixture was filtered and the filtrate was concentrated and extracted with EtOAc (30 mL) and Na₂CO₃ (20 mL). The organic layer was washed with water (20 mL), brine (20 mL), and concentrated. The resulting oil was purified on silica gel column to give 4-carbamoyl-4-[4-(2-morpholin-4-ylmethyl-benzyloxy)-1-oxo-1,3-dihydro-isoindol-2-yl]-butyric acid methyl ester (0.07 g, 15% yield).

Step 2: To the THF solution (20 mL) of 4-carbamoyl-4-[4-(2-morpholin-4-ylmethyl-benzyloxy)-1-oxo-1,3-dihydro-isoindol-2-yl]-butyric acid methyl ester (0.07 g, 0.15 mmol), was added potassium t-butoxide (20 mg, 0.18 mmol) at 0° C. The mixture was stirred for 15 minutes at 0° C. and quenched with 5 mL of 1N HCl solution, followed by 15 mL of saturated NaHCO₃ solution. The mixture was extracted with EtOAc (20 mL). The organic layer was concentrated in vacuo. The resulting oil was purified on silica gel column eluted with CH₂Cl₂ and methanol to give 3-[4-(2-morpholin-4-ylmethyl-benzyloxy)-1-oxo-1,3-dihydro-isoindol-2-yl]-piperidine-2,6-dione as a white solid (30 mg, 50% yield): mp: 188-190° C.; HPLC: Waters Symmetry C-18, 3.9×150 mm, 5 micro, 1 mL/min, 240 nm, gradient acetonitrile/0.1% H₃PO₄ in H₂O from 5/95 to 100/0 in 5 min and stayed at 100/0 for 5 min: t$_R$=4.8 min (96%). $^1$H NMR (DMSO-d₆) δ 1.84-2.11 (m, 1H, CHH), 2.22-2.44 (m, 5H, CHH, CH₂CH₂), 2.54-2.64 (m, 1H, CHH), 2.89 (d, J=12.5 Hz, 1H, CHH), 3.42-3.62 (m, 6H, CH₂CH₂, CH₂), 4.17-4.52 (m, 2H, CH₂), 5.12 (dd, J=5.0, 13.1 Hz, 1H, NCH), 5.43 (s, 2H, CH₂), 7.17-7.40 (m, 5H, Ar), 7.42-7.65 (m, 2H, Ar), 10.97 (s, 1H, NH); $^{13}$C NMR (DMSO-d₆) δ 0.03, 22.29, 31.13, 45.05, 51.52, 53.13, 60.10, 66.15, 67.17, 114.77, 115.09, 127.29, 127.54, 127.90, 129.76, 130.08, 133.25, 135.62, 135.75, 153.46, 167.94, 170.91, 172.75; LCMS MH=450; Anal Calcd for C₂₅H₂₇N₃O₅+0.2 H₂O: C, 66.27; H, 6.10; N, 9.27; Found: C, 66.06%; H, 5.85; N, 9.14%.

5.6 3-[4-(3-Morpholin-4-ylmethyl-Benzyloxy)-1-Oxo-1,3-Dihydro-Isoindol-2-yl]-Piperidine-2,6-Dione

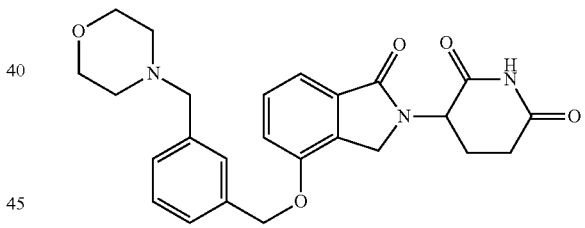

Step 1: To the THF (10 mL) solution of 4-carbamoyl-4-(4-hydroxy-1-oxo-1,3-dihydro-isoindol-2-yl)-butyric acid methyl ester (1.0 g, 3.42 mmol), were added triphenyl phosphine resin (2.3 g, 2.2 mmol/g loading, 6.84 mmol) and DIAD (1.33 mL, 6.84 mmol) at 0° C. and kept for 10 minutes. To the mixture was added (3-morpholin-4-ylmethyl-phenyl)-methanol (1.06 g, 3.42 mmol) and stirred at room temperature overnight. The mixture was filtered and the filtrate was concentrated and extracted with EtOAc (30 mL) and Na₂CO₃ (20 mL). The organic layer was washed with water (20 mL) and brine (20 mL), and concentrated. The resulting oil was purified on silica gel column to give 4-carbamoyl-4-[4-(3-morpholin-4-ylmethyl-benzyloxy)-1-oxo-1,3-dihydro-isoindol-2-yl]-butyric acid methyl ester (0.50 g, 30%).

Step 2: To the THF solution (20 mL) of 4-carbamoyl-4-[4-(3-morpholin-4-ylmethyl-benzyloxy)-1-oxo-1,3-dihydro-isoindol-2-yl]-butyric acid methyl ester (0.3 g, 0.6 mmol), was added potassium t-butoxide (0.6 mL g, 0.6 mmol) at 0° C. The mixture was stirred for 15 minutes at 0°

C. and quenched with 5 mL of 1N HCl solution followed by 15 mL of saturated NaHCO$_3$ solution. The mixture was extracted with EtOAc (20 mL). The organic layer was concentrated in vacuo. The resulting oil was purified on silica gel column eluted with CH$_2$Cl$_2$ and methanol to give 3-[4-(3-morpholin-4-ylmethyl-benzyloxy)-1-oxo-1,3-dihydro-isoindol-2-yl]-piperidine-2,6-dione as a white solid (120 mg, 44% yield): mp: 247-249° C.; HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: $t_R$=4.8 min (96%); $^1$H NMR (DMSO-d$_6$) δ 1.93-2.03 (m, 1H, CHH), 2.26-2.38 (m, 4H, CH$_2$, CH$_2$), 2.40-2.48 (m, 1H, CHH), 2.54-2.63 (m, 1H, CHH), 2.84-2.98 (m, 1H, CHH), 3.48-3.59 (m, 4H, CH$_2$, CH$_2$), 4.20-4.48 (m, 2H, CH$_2$), 5.11 (dd, J=5.1, 13.4 Hz, 1H, NCH), 5.25 (s, 2H, CH$_2$), 7.24-7.42 (m, 6H, Ar), 7.44-7.51 (m, 1H, Ar), 10.97 (s, 1H, NH); $^{13}$C NMR (DMSO-d$_6$) δ 22.36, 31.20, 45.10, 51.59, 53.11, 62.21, 66.16, 69.58, 115.20, 115.27, 126.37, 128.09, 128.38, 128.53, 129.79, 129.98, 133.31, 136.54, 138.06, 153.44, 167.99, 170.98, 172.85; LCMS MH=450; Anal Calcd for C$_{25}$H$_{27}$N$_3$O$_5$+0.4 H$_2$O: C, 65.75; H, 6.14; N, 9.20; Found: C, 65.38%; H, 5.95; N, 9.21.

5.7 3-(1-Oxo-4-(4-(2-(Pyrrolidin-1-yl)Ethoxy) Benzyloxy)Isoindolin-2-yl)-Piperidine-2,6-Dione

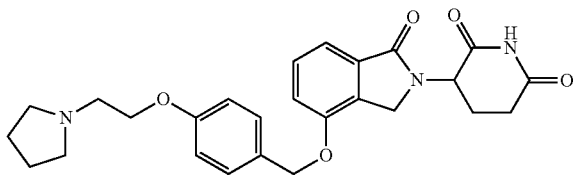 [SMILES: O=C1CCC(N2Cc3c(OCc4ccc(OCCN5CCCC5)cc4)cccc3C2=O)C(=O)N1]

Step 1: A mixture of 4-hydroxybenzaldehyde (4.0 g, 32.8 mmol) and Cs$_2$CO$_3$ (26.7 g, 81.9 mmol) in DMF (80 mL) was stirred for 10 minutes at room temperature. To this mixture, was added 1-(2-chloroethyl)pyrrolidine hydrochloride (6.7 g, 39.3 mmol). The mixture was warmed at 60° C. for 2 hours then at 80° C. overnight. The reaction mixture was cooled and filtered, and the solid was washed with EtOAc (100 mL). The filtrate was stirred with cold water (200 mL) and the aqueous layer was extracted with EtOAC (3×50 mL). The combined EtOAc solutions was washed with 2N NaOH (40 mL), water (3×40 mL) and brine (40 mL) and dried (K$_2$CO$_3$). The solvent was removed to give 4-(2-pyrrolidin-1-yl-ethoxy)benzaldehyde (5.9 g, 81% yield): $^1$H NMR (CDCl$_3$) δ 1.76-1.84 (m, 4H), 2.60-2.65 (m, 4H), 2.91-2.95 (m, 2H), 4.19 (t, J=6.0 Hz, 2H), 7.00-7.04 (m, 2H), 7.80-7.95 (m, 2H), 9.88 (s, 1H).

Step 2: A solution of 4-(2-pyrrolidin-1-yl-ethoxy)benzaldehyde (5.8 g, 26.5 mmol) in reagent alcohol (60 mL) was cooled to −60° C. in dry ice/acetone bath. LiBH4/THF (2M, 15.9 mL, 31.9 mmol) was added slowly at −60° C. The mixture was stirred at −60° C. for 1 hour. The reaction mixture was quenched with water (20 mL) slowly and then warmed to room temperature. The mixture was concentrated and the residue was stirred with EtOAc (80 mL) and 2N NaOH (20 mL). The aqueous layer was extracted with EtOAc (2×30 mL), and the combined EtOAc solutions was washed with water (30 mL) and brine (30 mL) and dried. The solvent was removed and the residue was purified by chromatography (SiO$_2$, NH$_4$OH:CH$_3$OH:CH$_2$Cl$_2$ 0.5:3:97) to give 4-[(2-pyrrolidin-1-yl-ethoxy)-phenyl]-methanol (2.5 g, 42% yield): $^1$H NMR (CDCl$_3$) δ 1.74-1.83 (m, 4H), 2.56-2.63 (m, 4H), 2.86 (t, J=6.1 Hz, 2H), 4.03 (t, J=6.0 Hz, 2H), 4.57 (s, 2H), 6.82-6.87 (m, 2H), 7.23-7.27 (m, 2H).

Step 3: Diisopropyl azodicarboxylate (1.1 g, 5.5 mmol) was added slowly to a stirred suspension of methyl 5-amino-4-(4-hydroxy-1-oxoisoindolin-2-yl)-5-oxopentanoate (0.8 g, 2.7 mmol), 4-[(2-pyrrolidin-1-yl-ethoxy)-phenyl]-methanol (0.9 g, 4.1 mmol) and triphenylphosphine-polymer bound (1.8 g, 5.5 mmol) in THF (60 mL) at 5-8° C. After addition, the mixture was stirred at room temperature overnight. The reaction mixture was filtered and the solid was washed with CH$_2$Cl$_2$ (30 mL). The filtrate was concentrated and the residue was purified by chromatography (SiO$_2$, CH$_3$OH:CH$_2$Cl$_2$=3:97) to give methyl 5-amino-5-oxo-4-(1-oxo-4-(4-(2-pyrrolidin-1-yl)ethoxy)benzyloxy)isoindolin-2-yl)pentanoate (1.0 g, 77%).

Step 4: A solution of KO-t-Bu/THF (1M, 2.5 mL, 2.5 mmol) was added slowly to a stirred solution of methyl 5-amino-5-oxo-4-(1-oxo-4-(4-(2-pyrrolidin-1-yl)ethoxy)benzyloxy)isoindolin-2-yl)pentanoate (1.0 g, 2.1 mmol) in THF (30 mL) at 5° C. The mixture was stirred at 5° C. for 10 minutes then warmed to room temperature for 2 hours. The reaction mixture was cooled in an ice bath and quenched with 4N HCl (4 mL). The mixture was stirred with EtOAc (40 mL) and sat Na$_2$CO$_3$ (25 mL). The aqueous layer was extracted with EtOAc (3×40 mL) and combined EtOAc solution was washed with water (40 mL) and brine (40 mL) and dried (K$_2$CO$_3$). The solvent was removed and the residue was purified by chromatography (SiO$_2$, CH$_3$OH:CH$_2$Cl$_2$=5:95) to give 3-(1-oxo-4-(4-(2-pyrrolidin-1-yl)ethoxy)-benzyloxy)isoindolin-2-yl)piperidine-2,6-dione (0.2 g, 20% yield): mp 153-155° C.; 1H NMR (DMSO-d6) δ 1.66-1.69 (m, 4H), 1.94-1.99 (m, 1H), 2.40-2.59 (m, 2H), 2.77 (t, J=5.7 Hz, 2H), 2.84-2.90 (m, 1H), 4.06 (t, J=6.0 Hz, 2H), 4.24 (d, J=17.4 Hz, 1H), 4.35 (d, J=17.7 Hz, 1H), 5.07-5.13 (dd, J=5.1 and 13.2 Hz, 1H), 5.15 (s, 2H), 6.92-6.97 (m, 2H), 7.30-7.50 (m, 5H), 10.96 (s, 1H); 13C NMR (DMSO-d6) δ 22.33, 23.09, 31.17, 45.06, 51.54, 53.93, 54.24, 66.69, 69.34, 114.35, 115.04, 115.12, 128.42, 129.50, 129.75, 129.95, 133.25, 153.50, 158.33, 168.00, 170.96, 172.81; Calcd for C$_{26}$H$_{29}$N$_3$O$_5$+0.5 Et2O: C, 66.65; H, 6.63; N, 8.64. Found: C, 66.95; H, 6.62; N, 8.71.

5.8 3-[4-(3-Chloro-4-Morpholin-4-ylmethyl-Benzyloxy)-1-Oxo-1,3-Dihydro-Isoindol-2-yl]-Piperidine-2,6-Dione

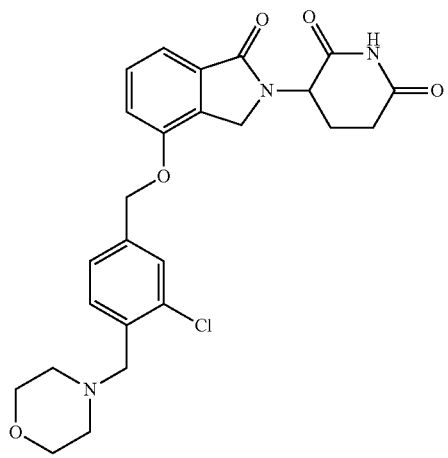 [SMILES: O=C1CCC(N2Cc3c(OCc4ccc(CN5CCOCC5)c(Cl)c4)cccc3C2=O)C(=O)N1]

Step 1: To a round bottom flask, were charged 3-chloro-4-methyl-benzoic acid (1.5 g, 9 mmol) and trimethyl orthoacetate (25 mL). The mixture was heated at 100° C. overnight. The reaction mixture was concentrated in vacuo. The resulting oil, 3-chloro-4-methyl-benzoic acid methyl ester, was used in next step without purification.

Step 2: To the CCl$_4$ solution (50 mL) of 3-chloro-4-methyl-benzoic acid methyl ester (1.66 g, 0.9 mmol), was added NBS (1.58 g, 9 mol). The suspension was bathed in the light of 300-W sun lamp and heated at 65° C. for 1 hour. The mixture was filtered and the filtrate was concentrated in vacuo. The resulting oil, 4-bromomethyl-3-chloro-benzoic acid methyl ester, was used in next step without further purification.

Step 3: To the acetonitrile solution (30 mL) of 4-bromomethyl-3-chloro-benzoic acid methyl ester, was added morpholine (3 mL). The mixture was stirred at room temperature for 0.5 hour and concentrated on rota-vap. The resulting oil was extracted with EtOAc (30 mL) and water (20 mL). The organic layer was concentrated and purified on silica gel column eluted with EtOAc and hexane to give 3-chloro-4-morpholin-4-ylmethyl-benzoic acid methyl ester (1.0 g, 42% for three steps) as yellow oil.

Step 4: To the THF solution (30 mL) of 3-chloro-4-morpholin-4-ylmethyl-benzoic acid methyl ester (1.0 g, 3.7 mmol), was added LiAlH$_4$ (3.7 mL, 1 M in THF, 3.7 mmol) dropwise at 0° C. The mixture was stirred at 0° C. for 30 minutes. The reaction mixture was quenched with sat. NaHCO3 (5 mL), and then was diluted with EtOAc (30 mL) and water (20 mL). After extraction, the organic layer was concentrated and purified on silica gel column eluted with EtOAc and hexane to give (3-chloro-4-morpholin-4-ylmethyl-phenyl)-methanol as an oil (0.6 g, 70%).

Step 5: To the THF solution of 4-carbamoyl-4-(4-hydroxy-1-oxo-1,3-dihydro-isoindol-2-yl)-butyric acid methyl ester (0.32 g, 1.1 mmol), was added triphenyl phosphine resin (1.94 g, 1.6 mmol/g loading, 2.42 mmol) and DIAD (0.477 mL, 2.42 mmol) at 0° C. After being stirred at 0° C. for 10 minutes, to the mixture was added (3-chloro-4-morpholin-4-ylmethyl-phenyl)-methanol (0.40 g, 1.66 mmol). The mixture was stirred at room temperature overnight. The mixture was filtered and the filtrate was concentrated and extracted with EtOAc (30 mL) and Na2CO3 (20 mL). The organic layer was washed with water (20 mL) and brine (20 mL), and concentrated. The resulting oil was purified on silica gel column to give 4-carbamoyl-4-[4-(3-chloro-4-morpholin-4-ylmethyl-benzyloxy)-1-oxo-1,3-dihydro-isoindol-2-yl]-butyric acid methyl ester (0.40 g, 73%).

Step 6: To the THF solution (20 mL) of 4-carbamoyl-4-[4-(3-chloro-4-morpholin-4-ylmethyl-benzyloxy)-1-oxo-1,3-dihydro-isoindol-2-yl]-butyric acid methyl ester (0.64 g, 1.2 mmol), was added potassium t-butoxide (0.14 g, 1.2 mmol) at 0° C. The mixture was stirred for 15 minutes at 0° C. and quenched with 5 mL of 1N HCl solution, followed by 15 mL of saturated NaHCO$_3$ solution. The mixture was extracted with EtOAc (20 mL). The organic layer was concentrated in vacuo. The resulting solid was stirred in MeOH (5 ml) and filtered to give 3-[4-(3-chloro-4-morpholin-4-ylmethyl-benzyloxy)-1-oxo-1,3-dihydro-isoindol-2-yl]-piperidine-2,6-dione (300 mg, 50%) as white solid: mp: 240-242° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=4.81 min (96%); $^1$H NMR (DMSO-d$_6$) δ 1.86-2.10 (m, 1H, CHH), 2.37-2.45 (m, 5H, CH$_2$, CH$_2$, CHH), 2.54-2.63 (m, 1H, CHH), 2.84-2.99 (m, 1H, CHH), 3.42-3.69 (m, 6H, CH$_2$, CH$_2$, CH$_2$), 4.07-4.58 (m, 2H, CHH), 4.98-5.17 (m, 1H, NCH), 5.25 (s, 2H, CH$_2$), 7.22-7.38 (m, 2H, Ar), 7.40-7.61 (m, 4H, Ar), 10.97 (s, 1H, NH); $^{13}$C NMR (DMSO-d$_6$) δ 22.26, 31.10, 44.99, 51.49, 53.10, 58.68, 66.09, 68.38, 114.86, 115.31, 126.13, 128.22, 129.75, 129.88, 130.91, 133.23, 133.32, 134.85, 137.37, 153.19, 167.86, 170.88, 172.75; LCMS MH=484; Anal Calcd for C$_{25}$H$_{26}$N$_3$O$_5$Cl, C, 62.05; H, 5.42; N, 8.68; Found: C, 61.71; H, 5.08; N, 8.62.

5.9 3-(4-(4-(2-Morpholin-4-yl-Ethoxy)-Benzyloxy)-1-Oxoisoindolin-2-yl)-Piperidine-2,6-Dione

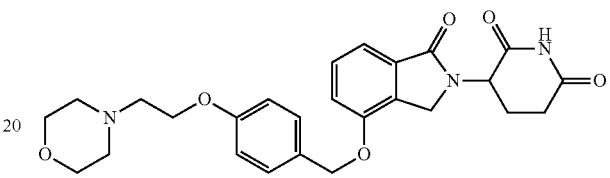

Step 1: A mixture of 4-hydroxybenzaldehyde (4.0 g, 32.8 mmol) and Cs$_2$CO$_3$ (26.7 g, 81.9 mmol) in DMF (80 mL) was stirred at room temperature for 10 minutes. To this mixture was added 4-(2-chloroethyl)morpholine hydrochloride (7.3 g, 39.3 mmol). The resulting mixture was heated at 80° C. in an oil bath overnight. The reaction mixture was cooled to room temperature and filtered, and the solid was washed with EtOAc (100 mL). Filtrate was diluted with cold water (200 mL) and aqueous layer was extracted with EtOAc (3×50 mL). Combined EtOAc solution was washed with 2N NaOH (25 mL), water (3×40 mL) and brine (40 mL), and dried (K$_2$CO$_3$). The solvent was removed to give 4-(2-morpholin-4-yl-ethoxy)-benzaldehyde (6.2 g, 81% yield): $^1$H NMR (CDCl$_3$) δ 2.57-2.60 (m, 4H), 2.83 (t, J=5.7 Hz, 2H), 3.70-3.75 (m, 4H), 4.19 (t, J=5.7 Hz, 2H), 6.98-7.03 (m, 2H), 7.81-7.85 (m, 2H), 9.88 (s, 1H); $^{13}$C NMR (CDCl$_3$) δ 53.52, 56.73, 65.77, 66.11, 114.93, 129.58, 131.73, 163.40, 191.21.

Step 2: LiBH$_4$/THF (2M, 15.9 mL, 31.7 mmol) was added slowly to a stirred solution of 4-(2-morpholin-4-yl-ethoxy)-benzaldehyde (6.2 g, 26.4 mmol) in reagent alcohol (60 mL) at −60° C. The resulting mixture was stirred at −60° C. for 1 hour then quenched with water (20 mL). The mixture was concentrated and the residue was stirred with EtOAc (80 mL) and 1N NaOH (30 mL). The aqueous layer was extracted with EtOAc (2×30 mL) and combined EtOAc solution was washed with water (40 mL) and brine (40 mL) and dried. The solvent was removed and the residue was purified by chromatography (SiO$_2$, NH$_4$OH:CH$_3$OH:CH$_2$Cl$_2$ 0.5:3:100) to give [4-(2-morpholin-4-yl-ethoxy)-phenyl]-methanol (4.2 g, 67% yield): $^1$H NMR (CDCl$_3$) δ 2.25 (s, 1H), 2.54-2.57 (m, 4H), 2.78 (t, J=5.7 Hz, 2H), 3.70-3.73 (m, 4H), 4.08 (t, J=5.7 Hz, 2H), 4.59 (s, 2H), 6.85-6.89 (m, 2H), 7.25-7.29 (m, 2H); $^{13}$C NMR (CDCl$_3$) δ 54.06, 57.61, 65.79, 66.85, 114.62, 128.57, 133.52, 158.24.

Step 3: Triphenylphosphine-polymer bound (1.8 g, 5.5 mmol) was stirred with dry CH$_2$Cl$_2$ (20 mL) for 10 minutes. To this mixture was added a solution of methyl 5-amino-4-(4-hydroxy-1-oxoisoindolin-2-yl)-5-oxopentanoate (0.8 g, 2.7 mmol) and [4-(2-morpholin-4-yl-ethoxy)-phenyl]-methanol (1.0 g, 4.1 mmol) in THF (60 mL). The resulting mixture was cooled to 5° C. and diisopropyl azodicarboxylate (1.1 g, 5.5 mmol) was added slowly at 5-8° C. After addition, the mixture was stirred at room temperature overnight. The reaction mixture was filtered and solid was washed with $CH_2Cl_2$ (30 mL). Filtrate was concentrated and the residue was purified by chromatography ($SiO_2$, $CH_3OH$: $CH_2Cl_2$ 3:97) to give methyl 5-amino-4-(4-(4-(2-morpholinoethoxy)benzyloxy)-1-oxoisoindolin-2-yl)-5-oxo-pentanoate (1.0 g, 71%).

Step 4: A solution of potassium t-butoxide/THF (1M, 2.6 mL, 2.6 mmol) was added slowly at 5° C. to a stirred solution of methyl 5-amino-4-(4-(4-(2-morpholinoethoxy)benzyloxy)-1-oxoisoindolin-2-yl)-5-oxopentanoate (1.1 g, 2.1 mmol) in THF (30 mL). The reaction mixture was stirred at 5° C. for 10 minutes then warmed to room temperature for 2 hours. The reaction mixture was cooled in an ice bath and quenched with 4N HCl (4 mL). The mixture was stirred with EtOAc (40 mL) and sat. $Na_2CO_3$ (25 mL). The aqueous layer was extracted with EtOAc (3×40 mL) and combined EtOAc solution was washed with water (40 mL) and brine (40 mL), and dried ($K_2CO_3$). The solvent was removed and the residue was purified by chromatography ($Al_2O_3$, $CH_3OH:CH_2Cl_2$ 3:97) to 3-(4-(4-(2-morpholinoethoxy)benzyloxy)-1-oxoisoindolin-2-yl)-piperidine-2,6-dione (0.2 g, 16% yield): mp: 203-205° C.; $^1H$ NMR (DMSO-$d_6$) δ 1.90-2.05 (m, 1H), 2.40-2.70 (m, 8H), 2.84-2.96 (m, 1H), 3.55-3.58 (m, 4H), 4.06-4.10 (m, 2H), 4.24 (d, J=17.4 Hz, 1H), 4.35 (d, J=17.4 Hz, 1H), 5.07-5.15 (m, 3H), 6.97 (d, J=8.4 Hz, 2H), 7.30-7.5.0 (m, 5H), 10.96 (s, 1H); $^{13}C$ NMR (DMSO-$d_6$) δ 22.32, 31.17, 45.06, 51.55, 53.56, 56.92, 65.29, 66.11, 63.31, 114.41, 115.04, 115.11, 128.50, 129.47, 129.74, 129.94, 133.25, 153.49, 158.27, 167.99, 170.94, 172.80; Calcd for $C_{26}H_{29}N_3O_6$+0.2 $H_2O$: C, 64.64; H, 6.10; N, 8.70. Found: C, 64.54; H, 6.06; N, 8.63.

5.10 3-[4-(3-Fluoro-4-Morpholin-4-ylmethyl-Benzyloxy)-1-Oxo-1,3-Dihydro-Isoindol-2-yl]-Piperidine-2,6-Dione

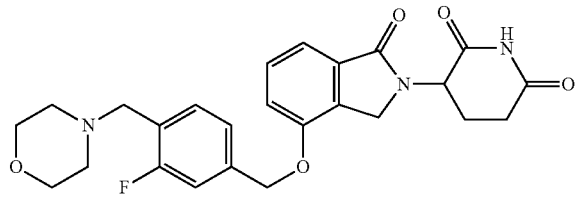 [SMILES: O=C1CCC(N2Cc3c(OCc4ccc(CN5CCOCC5)c(F)c4)cccc3C2=O)C(=O)N1]

Step 1: To a stirred solution of 3-fluoro-4-methyl-benzoic acid methyl ester (5.45 g, 32.4 mmol) in carbon tetrachloride (30 mL), was added N-bromosuccinimide (5.48 g, 30.8 mmol). The mixture was heated to 80° C., with a 300 W light shined. The mixture was heated for two hours and then filtered. The filtrated was evaporated to give 4-bromomethyl-3-fluoro-benzoic acid methyl ester as a light green oil (9.1 g, 113% crude yield).

Step 2: Morpholine (28.3 mL, 324.4 mmol) was added to a stirred solution of 4-bromomethyl-3-fluoro-benzoic acid methyl ester (8.01 g, 32.4 mmol) in acetonitrile (40 mL) at room temperature. The mixture was stirred for ten minutes and the solvent was evaporated. To the residue was added water (40 mL), and then the mixture was extracted with ethyl acetate (3×50 mL). The combined organic phases were evaporated and purified on silica gel column (EtOAc/Hexanes gradient from 10% to 40% in 40 min) to give 3-fluoro-4-morpholin-4-ylmethyl-benzoic acid methyl ester as a yellow solid (5.58 g, 68% yield): $^1H$ NMR (DMSO-$d_6$) δ 2.35-2.44 (m, 4H, $CH_2$, $CH_2$), 3.53-3.65 (m, 6H, $CH_2$, $CH_2$, $CH_2$), 3.87 (s, 3H, $CH_3$), 7.55-7.63 (m, 1H, Ar), 7.63-7.70 (m, 1H, Ar), 7.75-7.82 (m, 1H, Ar); $^{13}C$ NMR (DMSO-$d_6$) δ 52.36, 52.98, 53.22, 54.64, 65.84, 66.10, 66.35, 115.45, 115.75, 124.97, 129.95, 130.16, 130.44, 130.54, 131.72, 131.78, 158.73, 162.00, 165.09.

Step 3: Lithium aluminum hydride (1.0 M in THF, 8.06 mL, 8.06 mmol) was added to a stirred solution of 3-fluoro-4-morpholin-4-ylmethyl-benzoic acid methyl ester (1.02 g, 4.03 mmol) in THF (20 mL) at 0° C. It was stirred for 30 minutes and quenched with dropwise addition of saturated sodium bicarbonate. To the mixture was added water (30 mL), and the mixture was extracted by ethyl acetate (3×100 mL). The resulting precipitate was filtered. The combined ethyl acetate filtrate was evaporated and purified on silica gel column (EtOAc/Hexanes gradient from 20% to 90% in 35 min) to give (3-fluoro-4-morpholin-4-ylmethyl-phenyl)-methanol as an oily solid (0.81 g, 89% yield): $^1H$ NMR (DMSO-$d_6$) δ 2.31-2.42 (m, 4H, $CH_2$, $CH_2$), 3.46-3.50 (m, 2H, $CH_2$), 3.51-3.59 (m, 4H, $CH_2$, $CH_2$), 4.49 (br. s., 2H, $CH_2$), 5.27 (br. s., 1H, OH), 7.04-7.14 (m, 2H, Ar), 7.29-7.38 (m, 1H, Ar); $^{13}C$ NMR (DMSO-$d_6$) δ 2.89, 54.80, 62.02, 66.13, 112.63, 112.93, 121.80, 121.96, 122.17, 131.31, 131.38, 144.40, 144.50, 159.14, 162.38.

Step 4: Polymer-supported triphenylphosphene (1.6 mmol/g, 1.60 g, 2.60 mmol) was added to a stirred suspension of (3-fluoro-4-morpholin-4-ylmethyl-phenyl)-methanol (0.39 g, 1.71 mmol) in THF (20 mL) at 0° C., followed by addition of diisopropyl diazene-1,2-dicarboxylate (0.37 ml, 1.88 mmol). After stirring for 30 minutes, 4-carbamoyl-4-(4-hydroxy-1-oxo-1,3-dihydro-isoindol-2-yl)-butyric acid methyl ester (0.50 g, 1.71 mmol) was added. The mixture was stirred for three hours then filtered, washed with MeOH (3×20 mL) and methylene chloride (3×20 mL). The combined filtrate was evaporated in vacuo to give an oil, which was purified on silica gel column (MeOH/$CH_2Cl_2$ gradient from 1% to 5% in 40 min) to give 4-carbamoyl-4-[4-(3-fluoro-4-morpholin-4-ylmethyl-benzyloxy)-1-oxo-1,3-dihydro-isoindol-2-yl]-butyric acid methyl ester as a clear oil (0.54 g, 63% yield).

Step 5: Potassium tert-butoxide (0.12 g, 1.08 mmol) was added to a stirred solution of 4-carbamoyl-4-[4-(3-fluoro-4-morpholin-4-ylmethyl-benzyloxy)-1-oxo-1,3-dihydro-isoindol-2-yl]-butyric acid methyl ester (0.54 g, 1.08 mmol) in THF (15 mL) at 0° C. The mixture was stirred for ten minutes and quenched with 1N HCl (3 mL), neutralized by saturated sodium bicarbonate (4 mL to pH=7), and quickly extracted by ethyl acetate (2×30 mL). The combined ethyl acetate phases were evaporated and purified on silica gel column (MeOH/$CH_2Cl_2$, gradient from 1% to 5% in 90 min) to give 3-[4-(3-fluoro-4-morpholin-4-ylmethyl-benzyloxy)-1-oxo-1,3-dihydro-isoindol-2-yl]-piperidine-2,6-dione as a white solid (0.36 g, 72% yield): HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% $H_3PO_4$), 4.90 min (97.8%); mp: 263-265° C.; $^1H$ NMR (DMSO-$d_6$) δ 1.91-2.05 (m, 1H, CHH), 2.32-2.48 (m, 5H, CHH, $CH_2CH_2$), 2.54-2.65 (m, 1H, CHH), 2.82-3.02 (m, 1H, CHH), 3.47-3.61 (m, 6H, $CH_2CH_2$, $CH_2$), 4.23-4.50 (m, 2H, $CH_2$), 5.12 (dd, J=5.2, 13:3 Hz, 1H, NCH), 5.25 (s, 2H, $CH_2$), 7.25-7.56 (m, 6H, Ar), 10.98 (s, 1H, NH); $^{13}C$ NMR (DMSO-$d_6$) δ 22.36, 31.20, 45.09, 51.59, 52.93, 54.74, 66.13, 68.56, 114.09, 114.40, 114.92, 115.39, 123.22, 123.70, 123.89, 129.84, 130.00, 131.69, 131.75, 133.37, 138.16, 138.26, 153.28, 159.08, 162.33, 167.98, 170.96, 172.83; LCMS MH=468; Anal. Calcd for $C_{25}H_{26}N_3O_5F$: C, 64.23; H, 5.61; N, 8.99. Found: C, 63.95; H, 5.41; N, 8.92.

5.11 3-{4-[4-(2-Morpholin-4-yl-Ethyl)-Benzyloxy]-1-Oxo-1,3-Dihydro-Isoindol-2-yl}-Piperidine-2,6-Dione

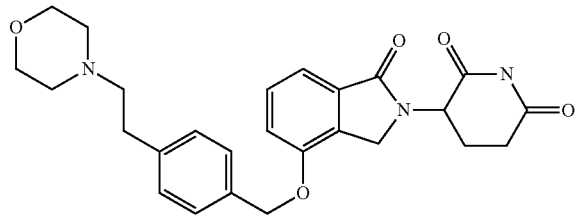 [SMILES: O=C1CCC(N2Cc3c(OCc4ccc(CCN5CCOCC5)cc4)cccc3C2=O)C(=O)N1]

Step 1: To the THF solution of 4-(2-bromoethyl)benzoic acid (25 g, 109 mmol) and trifluoroborane etherate (13.71 ml, 109 mmol), was added borane (196 ml, 196 mmol) dropwise through a dripping funnel at 0° C. during 2 hours. The mixture was stirred at room temperature overnight, and MeOH was added dropwise at room temperature until the cloudy suspension become clear and no more bubbles formed. The clear solution was concentrated on rota-vap and the resulting solid was stirred in water (100 mL) for 30 minutes at room temperature. The suspension was filtered to give 4-(2-chloro-ethyl)-benzoic acid as white solid (25 g, 107%).

Step 2: To the acetonitrile solution of (4-(2-bromoethyl)phenyl)methanol (25 g, 116 mmol), was added morpholine (25.3 ml, 291 mmol). NaI was added all at once. The mixture was stirred at room temperature over-weekend. The reaction suspension was filtered. The filtrate was concentrated and stirred in ether (100 mL) at room temperature for 30 minutes. The suspension was filtered. The resulting solid was dissolved in 1N HCl and was extracted with EtOAc (50 mL×2). The aqueous layer was neutralized with 1N NaOH to pH=7-8. The resulting suspension was filtered to give [4-(2-morpholin-4-yl-ethyl)-phenyl]-methanol as white solid (13 g, 60%).

Step 3: To the THF solution of 4-carbamoyl-4-(4-hydroxy-1-oxo-1,3-dihydro-isoindol-2-yl)-butyric acid methyl ester (0.5 g, 1.7 mmol), was added triphenyl phosphine resin (2.3 g, 1.6 mmol/g loading, 3.74 mmol) and DIAD (0.73 mL, 3.74 mmol) at 0° C. After being stirred at 0° C. for 10 minutes, the mixture was added [4-(2-morpholin-4-yl-ethyl)-phenyl]-methanol (0.65 g, 2.94 mmol) and was stirred at room temperature overnight. The mixture was filtered and the filtrate was concentrated and extracted with EtOAc (30 mL) and Na2CO3 (20 mL). The organic layer was washed with water (20 mL) and brine (20 mL), and concentrated. The resulting oil was purified on silica gel column to give 4-carbamoyl-4-{4-[4-(2-morpholin-4-yl-ethyl)-benzyloxy]-1-oxo-1,3-dihydro-isoindol-2-yl}-butyric acid methyl ester as white solid (0.74 g, 88%).

Step 4: To the THF solution (20 mL) of 4-carbamoyl-4-{4-[4-(2-morpholin-4-yl-ethyl)-benzyloxy]-1-oxo-1,3-dihydro-isoindol-2-yl}-butyric acid methyl ester (0.74 g, 1.5 mmol) was added potassium t-butoxide (0.16 g, 1.5 mmol) at 0° C. The mixture was stirred for 15 minutes at 0° C. and quenched with 5 mL of 1N HCl solution followed by 15 mL of saturated NaHCO3 solution. The mixture was extracted with EtOAc (20 mL). The organic layer was concentrated in vacuo. The resulting oil was purified on silica gel column eluted with $CH_2Cl_2$ and methanol to give 3-{4-[4-(2-morpholin-4-yl-ethyl)-benzyloxy]-1-oxo-1,3-dihydro-isoindol-2-yl}-piperidine-2,6-dione as a white solid (620 mg, 87% yield): mp: 230-232° C. HPLC: Waters Symmetry C-18, 3.9×150 mm, 5 micro, 1 mL/min, 240 nm, gradient acetonitrile/0.1% $H_3PO_4$ in $H_2O$ from 5/95 to 100/0 in 5 min and stayed at 100/0 for 5 min: $t_R$=4.86 min (97%); $^1$H NMR (DMSO-$d_6$) δ 1.80-2.12 (m, 1H, CHH), 2.40-2.44 (m, 4H, $CH_2$, $CH_2$), 2.45-2.48 (m, 1H, CHH), 2.55-2.64 (m, 1H, CHH), 2.69-2.80 (m, 2H, $CH_2$), 2.81-3.00 (m, 1H, CHH), 3.52-3.61 (m, 4H, $CH_2$, $CH_2$), 4.18-4.48 (m, 2H, $CH_2$), 5.11 (dd, J=5.1, 13.2 Hz, 1H, NCH), 5.20 (s, 2H, $CH_2$), 7.19-7.54 (m, 7H, Ar), 10.97 (s, 1H, NH); $^{13}$C NMR (DMSO-$d_6$) δ 22.36, 31.21, 32.04, 45.10, 51.58, 53.21, 59.93, 66.13, 69.47, 114.98, 115.19, 127.80, 128.70, 128.74, 129.79, 129.95, 133.29, 134.08, 140.25, 153.50, 168.01, 170.96, 172.82; LCMS MH=464; Anal Calcd for $C_{26}H_{29}N_3O_5$+0.5 $H_2O$: C, 66.09; H, 6.40; N, 8.89; Found: C, 65.96; H, 6.33; N, 9.07.

5.12 3-[4-(4-Imidazol-1-ylmethyl-Benzyloxy)-1-Oxo-1,3-Dihydro-Isoindol-2-yl]-Piperidine-2,6-Dione

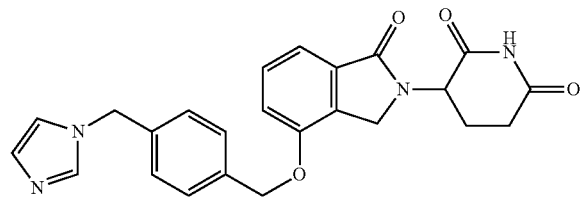 [SMILES: O=C1CCC(N2Cc3c(OCc4ccc(Cn5ccnc5)cc4)cccc3C2=O)C(=O)N1]

Step 1: Polymer-supported triphenylphosphine (1.6 mmol/g, 10 g, 16 mmol) was added to a stirred suspension of methyl 5-amino-4-(4-hydroxy-1-oxoisoindolin-2-yl)-5-oxopentanoate (2.49 g, 8.52 mmol) in THF (100 mL) at 0° C., followed by diisopropyl diazene-1,2-dicarboxylate (3.36 ml, 17.04 mmol). After stirring for 30 minutes, (4-(chloromethyl)phenyl)methanol (2.00 g, 12.78 mmol) was added. The mixture was stirred for one hour then filtered. The resin was washed with methanol (3×30 mL) and methylene chloride (3×30 mL). The combined filtrate was evaporated in vacuo to give an oil, which was purified on silica gel column (MeOH/$CH_2Cl_2$ gradient from 1% to 5% in 30 min) to give 4-carbamoyl-4-[4-(4-chloromethyl-benzyloxy)-1-oxo-1,3-dihydro-isoindol-2-yl]-butyric acid methyl ester as an oil (3.38 g, 92% yield): $^1$H NMR (DMSO-$d_6$) δ 1.97-2.35 (m, 4H, $CH_2CH_2$), 3.50 (s, 3H, $CH_3$), 4.35-4.62 (m, 2H, $CH_2$), 4.73 (dd, J=4.8, 10.3 Hz, 1H, NCH), 4.78 (s, 2H, $CH_2$), 5.26 (s, 2H, $CH_2$), 7.19 (d, 1H, NHH), 7.25-7.35 (m, 2H, Ar), 7.41-7.54 (m, 5H, Ar), 7.58 (d, J=0.4 Hz, 1H, NHH).

Step 2: Imidazole (0.19 g, 2.84 mmol), and diisopropylethylamine (0.24 mL, 1.42 mmol) were added to a stirred solution of 4-carbamoyl-4-[4-(4-chloromethyl-benzyloxy)-1-oxo-1,3-dihydro-isoindol-2-yl]-butyric acid methyl ester (0.61 g, 1.42 mmol) in acetonitrile (15 mL). The mixture was heated at 70° C. overnight. To the mixture was, added potassium carbonate (0.20 g, 1.48 mmol), and the mixture was heated at 80° C. for three hours. The mixture was concentrated and then purified on silica gel column (MeOH/$CH_2Cl_2$ from 1% to 10% in 30 minutes) to give 3-[4-(4-Imidazol-1-ylmethyl-benzyloxy)-1-oxo-1,3-dihydro-isoindol-2-yl]-piperidine-2,6-dione as a white solid (0.12 g, 37% yield): HPLC: Waters Symmetry C-18, 3.9×150 mm, 5 μm, 1 mL/min, 240 nm, isocratic at 18/2 in 10 min (acetonitrile/ 0.1% H₃PO₄), 2.50 min (96.8%); mp: 248-250° C.; ¹H NMR (DMSO-d₆) δ 1.88-2.07 (m, 1H, CHH), 2.36-2.47 (m, 1H, CHH), 2.53-2.63 (m, 1H, CHH), 2.82-2.99 (m, 1H, CHH), 4.17-4.47 (m, 2H, CH₂), 5.10 (dd, J=5.2, 13.3 Hz, 1H, NCH), 6.92 (s, 1H, Ar), 7.20 (t, J=1.2 Hz, 1H, Ar), 7.24-7.37 (m, 4H, Ar), 7.42-7.54 (m, 3H, Ar), 7.78 (s, 1H, Ar), 10.96 (s, 1H, NH); ¹³C NMR (DMSO-d₆) δ 22.35, 31.20, 45.08, 49.20, 51.58, 69.19, 114.95, 115.27, 119.56, 127.58, 128.07, 128.54, 129.81, 129.97, 133.31, 136.14, 137.35, 137.59, 153.40, 167.99, 170.96, 172.83; LCMS MH=431; Anal. Calcd for C₂₄H₂₂N₄O₄+0.5 H₂O: C, 65.59; H, 5.28; N, 12.75. Found: C, 65.43; H, 5.15; N, 12.64.

5.13 3-{4-[4-(1,1-Dioxo-1-Thiomorpholin-4-ylmethyl)-Benzyloxy]-1-Oxo-1,3-Dihydro-Isoindol-2-yl}-Piperidine-2,6-Dione

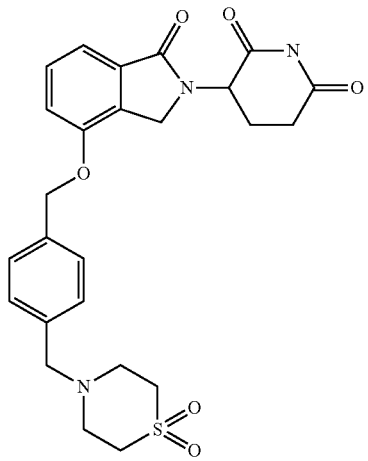 [SMILES: O=C1CCC(N2Cc3c(OCc4ccc(CN5CCS(=O)(=O)CC5)cc4)cccc3C2=O)C(=O)N1]

Step 1: A slurry of 4-carbamoyl-4-(4-hydroxy-1-oxo-1,3-dihydro-isoindol-2-yl)-butyric acid tert-butyl ester (1.5 g, 4.49 mmol), N,N-diisopropylethylamine (784 µl, 4.49 mmol), and K₂CO₃ (620 mg, 4.49 mmol) in DMF (15 mL) was stirred for 5 minutes at room temperature, followed by addition of (4-chloromethyl-phenyl)-methanol (902 mg, 4.49 mmol). The mixture was stirred at room temperature for about 15 hours then heated to 70° C. for 3 hours. Piperidine (800 µl) was added to the mixture to scavenge unconsumed (4-chloromethyl-phenyl)-methanol. The mixture was stirred for an additional 18 hours at 70° C. The mixture was diluted with water (50 mL) and EtOAc (200 mL). The pH of the aqueous was adjusted to about 4 using 1 N HCl, and the phases were split in a separatory funnel. The aqueous layer was saturated with NaCl and extracted with additional EtOAc (200 mL). The organic layers were combined, washed with brine, dried (Na₂SO₄), and concentrated on rotovap to give 3.5 g of a tan oil. A portion of this oil (2.1 g) was purified on a SiO₂ flash column (CombiFlash, 80 g SiO₂ prepacked column, MeOH/dichloromethane gradient) to give 4-carbamoyl-2-[4-(4-hydroxymethyl-benzyloxy)-1-oxo-1,3-dihydro-isoindol-2-yl]-butyric acid tert-butyl ester as a white foam (1.1 g, 90% yield, based on portion purified): ¹H NMR (DMSO-d₆) δ 1.39 (s, 9H, tBu), 2.00-2.13 (m, 3H, CHH, CH₂), 2.13-2.31 (m, 1H, CHH), 4.41 (s, 2H, CH₂), 4.50 (d, J=5.7 Hz, 2H, CH₂), 4.69 (dd, J=4.6, 10.3 Hz, 1H, CH), 5.19 (t, J=5.7 Hz, 1H, OH), 5.24 (s, 2H, CH₂), 6.75 (br. s., 1H, NH), 7.22 (br. s., 1H, NH), 7.25-7.37 (m, 4H, Ar), 7.42-7.53 (m, 3H, Ar); ¹³C NMR (DMSO-d₆) δ 24.69, 27.56, 31.50, 44.78, 54.08, 62.60, 69.45, 81.42, 114.97, 115.18, 126.52, 127.57, 129.71, 130.03, 133.27, 134.86, 142.40, 153.42, 168.12, 169.85, 172.94; LCMS MH=455.

Step 2: To a solution of 4-carbamoyl-2-[4-(4-hydroxymethyl-benzyloxy)-1-oxo-1,3-dihydro-isoindol-2-yl]-butyric acid tert-butyl ester (250 mg, 0.55 mmol) in dichloromethane (5 mL), cooled in an ice bath to 0° C., was added N,N-diisopropylethylamine (115 µl, 0.66 mmol) followed by methanesulfonyl chloride (47 µl, 0.605 mmol). After 5 minutes, the mixture was allowed to warm up to room temperature. The mixture was stirred for about 45 minutes at room temperature, then more MsCl (20 µl) was added. The reaction was complete after 10 minutes as judged by LCMS. The crude mixture was concentrated and the residue was dried further in vacuum oven at 40° C. overnight to give the crude product as a white solid (320 mg). LCMS indicated that the obtained solid contained about 5:1 mixture of 4-carbamoyl-2-[4-(4-methanesulfonyloxymethyl-benzyloxy)-1-oxo-1,3-dihydro-isoindol-2-yl]-butyric acid tert-butyl ester and 4-carbamoyl-2-[4-(4-chloromethyl-benzyloxy)-1-oxo-1,3-dihydro-isoindol-2-yl]-butyric acid tert-butyl ester (MH=533 and 473, respectively). The mixture was used in the next step without further purification. To a solution of the crude product (293 mg, 0.55 mmol, assuming quantitative yield from previous step) and N,N-diisopropylethylamine (240 µl, 1.375 mmol) in acetonitrile (5 mL), was added thiomorpholine 1,1-dioxide (82 mg, 0.605 mmol). The mixture was stirred at room temperature for about 45 minutes and then more thiomorpholine 1,1-dioxide (82 mg, 0.605 mmol) was added. After 3 hours, the mixture was heated to reflux for about 4 hours and then stirred at room temperature for 2 days. The volatiles were removed in vacuo and the residue was partitioned between EtOAc (150 mL) and 1 N NaHCO₃ (30 mL). The aqueous layer was washed with additional EtOAc (150 mL). The organic layers were combined, washed with brine, dried (Na₂SO₄), and concentrated on a rotovap to give 4-carbamoyl-2-{4-[4-(1,1-dioxo-1-thiomorpholin-4-ylmethyl)-benzyloxy]-1-oxo-1,3-dihydro-isoindol-2-yl}-butyric acid tert-butyl ester as an off-white solid (340 mg). LCMS MH=572. The solid was used in the next step without further purification.

Step 3: To a stirred solution of 4-carbamoyl-2-{4-[4-(1,1-dioxo-1-thiomorpholin-4-ylmethyl)-benzyloxy]-1-oxo-1,3-dihydro-isoindol-2-yl}-butyric acid tert-butyl ester (230 mg, 0.40 mmol) in THF (10 mL), was added a 1 M solution of KOtBu (402 µl, 0.402 mmol). The resulting mixture was stirred at room temperature for about 2 hours, then more KOtBu (100 µl) was added. After approximately another 2.5 hours, the reaction mixture was cooled in an ice bath and then transferred to a 1 N aqueous HCl solution. The mixture was concentrated to dryness and the residue was redissolved in minimal DMF and 1 N HCl (1:1) and filtered. The filtrate containing the crude product was purified by injection onto a C-18 preparatory HPLC column. The product was eluted with an acetonitrile/water gradient (0.1% formic acid in both mobile phases) and fractions were collected by mass trigger. The desired fractions were combined and concentrated in vacuo to give 3-{4-[4-(1,1-Dioxo-1-thiomorpholin-4-ylmethyl)-benzyloxy]-1-oxo-1,3-dihydro-isoindol-2-yl}-piperidine-2,6-dione as a white solid (113 mg, 56% yield): HPLC: Waters Symmetry C₁₈, 5 µm, 3.9×150 mm, 1 ml/min, 240 nm, 20/80 acetonitrile/0.1% H₃PO₄, 4.91 min (97.5%); mp: 156-158° C.; ¹H NMR (DMSO-d₆) δ 1.89-2.04 (m, 1H, CHH), 2.35-2.48 (m, 1H, CHH), 2.52-2.64 (m, 1H, CHH), 2.74-3.01 (m, 5H, 2CH₂, CHH), 3.03-3.16 (m, 4H, 2CH₂), 3.68 (s, 2H, CH$_2$), 4.25 (d, J=17.6 Hz, 1H, CHH), 4.42 (d, J=17.4 Hz, 1H, CHH), 5.11 (dd, J=5.1, 13.2 Hz, 1H, CH), 5.23 (s, 2H, CH$_2$), 7.25-7.40 (m, 4H, Ar), 7.42-7.56 (m, 3H, Ar), 10.97 (s, 1H, NH); $^{13}$C NMR (DMSO-d$_6$) δ 21.24, 30.06, 43.97, 48.93, 49.12, 50.46, 58.16, 68.23, 113.87, 114.13, 126.60, 127.76, 128.70, 128.83, 132.18, 134.44, 136.40, 152.36, 166.87, 169.84, 171.71; LCMS MH=498; Anal Calcd for C$_{25}$H$_{27}$N$_3$O$_6$S: C, 60.35; H, 5.47; N, 8.44; S, 6.44. Found: C, 55.59; H, 5.24; N, 7.92; S, 5.96.

5.14 4-{4-[2-(2,6-Dioxo-Piperidin-3-yl)-1-Oxo-2,3-Dihydro-1H-Isoindol-4-yloxymethyl]-Benzyl}-Piperidine-1-Carboxylic Acid Tert-Butyl Ester

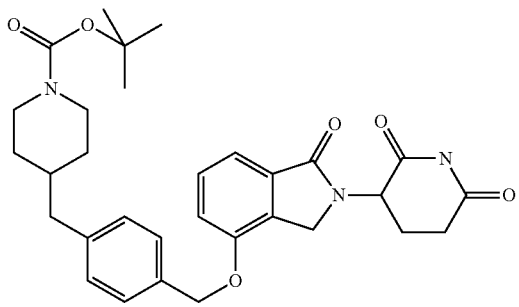 [SMILES: CC(C)(C)OC(=O)N1CCC(Cc2ccc(COc3cccc4c3CN(C3CCC(=O)NC3=O)C4=O)cc2)CC1]

Step 1: To the THF solution of 4-carbamoyl-4-(4-hydroxy-1-oxo-1,3-dihydro-isoindol-2-yl)-butyric acid methyl ester (0.45 g, 1.5 mmol), was added triphenyl phosphine resin (1.75 g, 1.6 mmol/g loading, 2.86 mmol) and DIAD (0.55 mL, 2.86 mmol) at 0° C. After being stirred at 0° C. for 10 minutes 4-(4-hydroxymethyl-benzyl)-piperidine-1-carboxylic acid tert-butyl ester was added to the mixture, and the resulting mixture was stirred at room temperature overnight. The mixture was filtered and the filtrate was concentrated and extracted with EtOAc (30 mL) and Na$_2$CO$_3$ (20 mL). The organic layer was washed with water (20 mL) and brine (20 mL), and concentrated. The resulting oil was purified on silica gel column to give 4-{4-[2-(1-carbamoyl-3-methoxycarbonyl-propyl)-1-oxo-2,3-dihydro-1H-isoindol-4-yloxymethyl]-benzyl}-piperidine-1-carboxylic acid tert-butyl ester as an oil (0.85 g, 90%).

Step 2: To the THF solution (20 mL) of 4-{4-[2-(1-carbamoyl-3-methoxycarbonyl-propyl)-1-oxo-2,3-dihydro-1H-isoindol-4-yloxymethyl]-benzyl}-piperidine-1-carboxylic acid tert-butyl ester (0.85 g, 1.5 mmol), was added potassium t-butoxide (0.16 g, 1.5 mmol) at 0° C. The mixture was stirred for 15 minutes at 0° C. and quenched with 5 mL of 1N HCl solution followed by 15 mL of saturated NaHCO$_3$ solution. The mixture was extracted with EtOAc (20 mL). The organic layer was concentrated in vacuo. The resulting oil was purified on silica gel column eluted with CH$_2$Cl$_2$ and methanol to give 4-{4-[2-(2,6-dioxo-piperidin-3-yl)-1-oxo-2,3-dihydro-1H-isoindol-4-yloxymethyl]-benzyl}-piperidine-1-carboxylic acid tert-butyl ester as a oil (660 mg, 80%). mp: 180-182° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=7.69 min (98%). $^1$H NMR (DMSO-d$_6$) δ 0.92-1.12 (m, 2H, CH$_2$), 1.16-1.24 (m, 1H, CHH), 1.38 (s, 9H, CH$_3$, CH$_3$, CH$_3$), 1.46-1.58 (m, 2H, CH$_2$), 1.59-1.74 (m, 1H, CH), 1.89-2.06 (m, 1H, CHH), 2.35-2.47 (m, 1H, CHH), 2.56-2.71 (m, 4H, CH$_2$, CHH, CHH), 2.79-3.01 (m, 1H, CHH), 3.79-4.00 (m, 2H, CH$_2$), 4.18-4.51 (m, 2H, CH$_2$), 5.01-5.16 (m, 1H, NCH), 5.20 (s, 2H, CH$_2$), 7.20 (d, J=8.1 Hz, 2H, Ar), 7.28-7.36 (m, 2H, Ar), 7.32-7.32 (m, 1H, Ar), 7.40 (d, J=8.1 Hz, 2H, Ar), 7.43-7.56 (t, J=8.3 Hz, 1H, Ar), 10.91-11.07 (m, 1H, NH). $^{13}$C NMR (DMSO-d$_6$) δ 22.29, 28.01, 31.13, 31.39, 37.18, 41.74, 45.02, 51.51, 69.40, 78.31, 114.90, 115.13, 127.64, 129.06, 129.74, 129.89, 133.24, 134.00, 139.87, 153.46, 153.74, 167.94, 170.91, 172.76; LCMS MH=548. Anal Calcd for C$_{31}$H$_{37}$N$_3$O$_6$+0.8 H$_2$O: C, 66.25; H, 6.92; N, 7.48; Found: C, 66.09; H, 6.83; N, 7.67.

5.15 3-[1-Oxo-4-(4-Piperidin-4-ylmethyl-Benzyloxy)-1,3-Dihydro-Isoindol-2-yl]-Piperidine-2,6-Dione Hydrogen Chloride

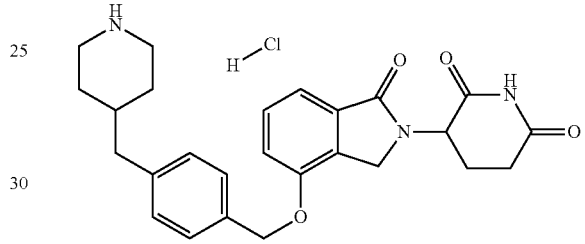

To the CH$_2$Cl$_2$ solution (10 mL) of 4-{4-[2-(2,6-dioxo-piperidin-3-yl)-1-oxo-2,3-dihydro-1H-isoindol-4-yloxymethyl]-benzyl}-piperidine-1-carboxylic acid tert-butyl ester (0.5 g, 1.0 mmol), was added hydrogen chloride in ether solution (2.0 M, 5 mL, 10 mmol). The mixture was stirred at room temperature overnight. The mixture was filtered. The resulting solid was stirred with ether to give 3-[1-oxo-4-(4-piperidin-4-ylmethyl-benzyloxy)-1,3-dihydro-isoindol-2-yl]-piperidine-2,6-dione hydrogen chloride as white solid (194 mg, 50%). mp: 200-202° C. HPLC: Waters Symmetry C-18, 3.9×150 mm, 5 micro, 1 mL/min, 240 nm, gradient acetonitrile/0.1% H3PO4 in H2O from 5/95 to 100/0 in 5 min and stayed at 100/0 for 5 min: t$_R$=4.90 min (96%). 1H NMR (DMSO-d6) δ 1.35 (d, J=11.9 Hz, 2H, CH2), 1.62-1.73 (m, 2H, CH2), 1.74-1.87 (m, 1H, CH), 1.91-2.05 (m, 1H, CHH), 2.33-2.48 (m, 1H, CHH), 2.52-2.64 (m, 3H, CH2, CHH), 2.77 (d, J=10.8 Hz, 2H, CH$_2$), 2.84-3.01 (m, 1H, CHH), 3.21 (d, J=12.1 Hz, 2H, CH$_2$), 4.11-4.51 (m, 2H, CH2), 5.12 (dd, J=5.1, 13.2 Hz, 1H, NCH), 5.21 (s, 2H, CH2), 7.21 (d, J=8.1 Hz, 2H, Ar), 7.28-7.37 (m, 2H, Ar), 7.42 (d, J=8.1 Hz, 2H, Ar), 7.45-7.54 (m, 1H, Ar), 8.50-8.75 (m, 1H, HCl), 8.80-9.02 (m, 1H, HCl), 10.97 (s, 1H, NH); 13C NMR (DMSO-d6) δ 22.31, 28.04, 31.14, 34.82, 41.23, 42.89, 45.01, 51.51, 69.34, 114.93, 115.16, 127.71, 129.09, 129.76, 129.87, 133.24, 134.25, 139.25, 153.43, 167.92, 170.91, 172.78; LCMS MH=448. Anal Calcd for C26H29N3O4HCl+1.1 H2O: C, 61.98; H, 6.44; N, 8.34; Cl, 7.04; Found: C, 61.96; H, 6.63; N, 8.00; Cl, 7.06.

5.16 3-(4-((5-(Morpholinomethyl)Benzofuran-2-yl)Methyoxy)-1-Oxosioindolin-2-yl)Piperidine-2,6-Dione

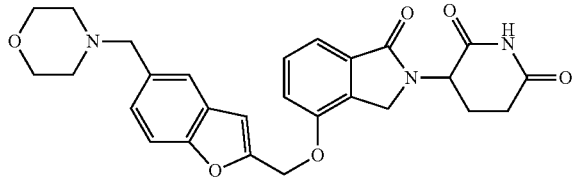 [SMILES: O=C1CCC(N2Cc3c(OCc4cc5cc(CN6CCOCC6)ccc5o4)cccc3C2=O)C(=O)N1]

Step 1: Hexamethylenetetramine (14.0 g, 100 mmol) was added in one portion under $N_2$ to a stirred solution of 4-hydroxybenzaldehyde (12.2 g, 100 mmol) in trifluoroacetic acid (100 mL). After addition, the mixture was heated in oil bath at 90° C. for 24 hours. The reaction was quenched with 140 mL of 3N HCl and cooled to room temperature over 1 hour. The mixture was extracted with $CH_2Cl_2$ (4×100 mL) and combined $CH_2Cl_2$ solution was concentrated. Ethanol (15 mL) was added to the residue at 40° C. and then cooled in an ice bath for 30 minutes. The mixture was filtered and solid was washed with cold ethanol (10 mL) to give 5-formylsalicylaldehyde (5.0 g, 33% yield): $^1$H NMR (DMSO-$d_6$) δ 7.16 (d, J=8.4 Hz, 1H), 8.00-8.04 (dd, J=2.4 and 8.7 Hz, 1H), 8.21 (d, J=2.4 Hz, 1H), 9.89 (s, 1H), 10.34 (s, 1H), 11.79 (s, 1H).

Step 2: A mixture of 5-formylsalicylaldehyde (3.9 g, 26.0 mmol), ethyl bromoacetate (4.4 g, 26.0 mmol), potassium carbonate (5.4 g, 39.0 mmol) and molecular sieve (3.9 g) in DMF (40 mL) was heated at 85° C. oil bath for 2 hours then at 120° C. for 5 hours. The reaction mixture was cooled to room temperature and diluted with EtOAc (100 mL). The mixture was filtered and solid was washed EtOAc (50 mL). Filtrate was washed with water (3×50 mL) and brine (50 mL), and dried. The solvent was removed and the residue was stirred with ether (20 mL) and hexane (20 mL) to give ethyl 5-formylbenzofuran-2-carboxylate (3.3 g, 59% yield): $^1$H NMR (DMSO-$d_6$) δ 1.35 (t, J=7.2 Hz, 3H), 4.35-4.42 (q, J=6.9 Hz, 2H), 7.92-7.95 (m, 2H), 8.03-8.07 (dd, J=1.5 and 8.7 Hz, 1H), 8.42 (b, 1H), 10.10 (s, 1H).

Step 3: Morpholine (1.2 g, 13.8 mmol) was added to a stirred solution of ethyl 5-formylbenzofuran-2-carboxylate (1.5 g, 6.9 mmol) in methanol (60 mL). Molecular sieve (4 A, 1.5 g) was added, followed by acetic acid (0.4 g, 6.9 mmol) and sodium cyanoborohydride (0.7 g, 10.3 mmol). The resulting mixture was stirred at room temperature for 2 hours. The reaction mixture was filtered and solid was washed with methanol (40 mL). Filtrate was concentrated and the residue was dissolved in EtOAc (100 mL). EtOAc solution was washed with sat. $NaHCO_3$ (30 mL) and brine (30 mL), and dried ($K_2CO_3$). The solvent was removed and the residue was purified by chromatography ($SiO_2$, EtOAc:$CH_2Cl_2$ 40:60) to give 5-morpholin-4-ylmethyl-benzofuran-2-carboxylic acid ethyl ester (1.2 g, 61% yield): $^1$H NMR (CDCl$_3$) δ 1.43 (t, J=6.9 Hz, 3H), 2.45 (t, J=4.5 Hz, 4H), 3.58 (s, 2H), 3.71 (t, J=4.5 Hz, 4H), 4.41-4.48 (q, J=6.9 Hz, 2H), 7.42-7.45 (dd, J=1.8 and 8.7 Hz, 1H), 7.49 (d, J=0.9 Hz, 1H), 7.52 (d, J=8.4 Hz, 1H), 7.61 (d, J=0.9 Hz, 1H).

Step 4: A solution of LiAlH$_4$/THF (1M, 8 mL, 8.0 mmol) in THF (10 mL) was cooled in an ice bath to 5° C. A solution of 5-morpholin-4-ylmethyl-benzofuran-2-carboxylic acid ethyl ester (1.8 g, 6.2 mmol) in THF (20 mL) was added dropwise at 5-10° C. After addition, the mixture was stirred in an ice bath for 30 minutes. The reaction mixture was carefully quenched with sat. $Na_2CO_3$ (50 mL) in an ice bath and mixture was diluted with $CH_2Cl_2$ (50 mL). The aq. layer was extracted $CH_2Cl_2$ (3×40 mL) and combined $CH_2Cl_2$ solution was washed with sat. $NaHCO_3$ (40 mL) and brine (40 mL) and dried. The solvent was removed and the residue was purified by chromatography ($SiO_2$, $CH_3OH$:$CH_2Cl_2$ 5:95) to give (5-morpholin-4-ylmethyl-benzofuran-2-yl)-methanol (1.3 g, 86% yield): $^1$H NMR (CDCl$_3$) δ 2.45 (t, J=4.5 Hz, 4H), 2.70 (b, 1H), 3.55 (s, 2H), 3.71 (t, J=4.8 Hz, 4H), 4.74 (s, 2H), 6.59 (s, 1H), 7.20-7.24 (dd, J=1.5 and 8.4 Hz, 1H), 7.32 (d, J=8.4 Hz, 1H), 7.47 (d, J=1.2 Hz, 1H).

Step 5: Diisopropyl azodicarboxylate (0.8 g, 4.1 mmol) was added slowly to a stirred suspension of triphenylphosphine-polymer bound (3.5 g, 4.4 mmol) in THF (40 mL) at 3-5° C. After stirred at 3° C. for 10 minutes, a solution of methyl 5-amino-4-(4-hydroxy-1-oxoisoindolin-2-yl)-5-oxopentanoate (0.8 g, 2.7 mmol) and 5-morpholin-4-ylmethyl-benzofuran-2-yl)-methanol (0.9 g, 3.6 mmol) in THF (60 mL) was added slowly at 3-6° C. After stirred at 3° C. for 5 minutes, mixture was stirred at room temperature overnight. The reaction mixture was filtered and solid was washed with $CH_2Cl_2$ (40 mL). Filtrate was concentrated and the residue was dissolved in $CH_2Cl_2$ (100 mL) and washed with sat $NaHCO_3$ (40 mL), water (2×30 mL) and brine (30 mL), and dried ($K_2CO_3$). The solvent was removed and the residue was purified by chromatography ($SiO_2$, $CH_3OH$:$CH_2Cl_2$ 5:95) to give methyl 5-amino-4-(4-((5-morpholinomethyl)benzofuran-2-yl)methoxy)-1-oxoisoindolin-2-yl)-5-oxopentanoate (0.9 g, 64% yield): $^1$H NMR (CDCl$_3$)δ 2.13-2.47 (m, 8H), 3.57 (s, 2H), 3.63 (s, 3H), 3.70-3.72 (m, 4H), 4.35 (d, J=17.7 Hz, 1H), 4.44 (d, J=17.7 Hz, 1H), 4.86-4.91 (d, J=5.7 and 8.7 Hz, 1H), 5.24 (s, 2H), 5.36 (s, 1H), 6.30 (b, 1H), 6.77 (s, 1H), 7.17-7.19 (dd, J=1.8 and 6.9 Hz, 1H), 7.28-7.31 (dd, J=1.5 and 8.4 Hz, 1H), 7.41-7.48 (m, 3H), 7.52 (d, J=1.2 Hz, 1H).

Step 6: A solution of potassium t-butoxide/THF (1 M, 1.9 mL, 1.9 mmol) was added slowly to a stirred solution of methyl 5-amino-4-(4-((5-morpholinomethyl)benzofuran-2-yl)methoxy)-1-oxoisoindolin-2-yl)-5-oxopentanoate (0.9 g, 1.7 mmol) in THF (25 mL) at 5° C. The reaction mixture was stirred at 5° C. for 1 h then quenched with sat. $NH_4Cl$ (5 mL). The mixture was stirred with $CH_2Cl_2$ (50 mL) and water (15 mL). The aqueous layer was extracted with $CH_2Cl_2$ (30 mL), and combined $CH_2Cl_2$ solution was washed with brine (30 mL) and dried ($K_2CO_3$). The solvent was removed and the residue was purified by chromatography ($SiO_2$, $CH_3OH$:$CH_2Cl_2$ 5:95) to give 3-(4-((5-morpholinomethyl)benzofuran-2-yl)methoxy)-1-oxoisoindolin-2-yl)piperidine-2,6-dione (0.2 g, 25% yield): mp 233-235° C.; $^1$H NMR (DMSO-$d_6$) δ 1.95-2.09 (m, 1H), 2.35-2.59 (m, 6H), 2.89-2.92 (m, 1H), 3.54-3.57 (m, 6H), 4.25 (d, J=15 Hz, 1H), 4.36 (d, J=18 Hz, 1H), 5.07-5.13 (dd, J=6 and 12 Hz, 1H), 5.42 (s, 2H), 7.08 (s, 1H), 7.27-7.57 (m, 6H), 10.96 (s, 1H); $^{13}$C NMR (DMSO-$d_6$) δ 22.28, 31.16, 45.03, 51.56, 53.06, 62.32, 62.52, 66.15, 107.05, 110.80, 115.14, 115.66, 121.61, 126.00, 127.48, 129.81, 129.95, 132.58, 133.41, 152.80, 152.95, 153.82, 167.88, 170.93, 172.79; Calcd for $C_{27}H_{27}N_3O_6$+1.0 $H_2O$: C, 63.90; H, 5.76; N, 8.28. Found: C, 63.97; H, 5.40; N, 8.20.

5.17 3-(4-(4-(((2S,6R)-2,6-Dimethylmorpholino)Methyl)Benzyloxy)-1-Oxoisoindolin-2-yl)Piperidine-2,6-Dione

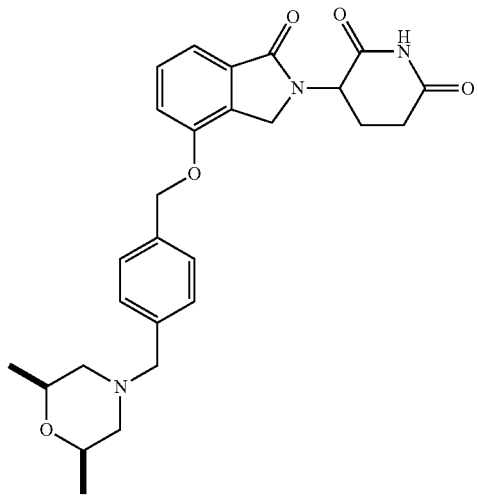 [SMILES: C[C@@H]1CN(Cc2ccc(COc3cccc4c3CN(C3CCC(=O)NC3=O)C4=O)cc2)C[C@H](C)O1]

Step 1: In a 250-mL RB flask, L-glutamine α-tert-butyl ester (7.83 g, 32.8 mmol) and N,N-diisopropylethylamine (11.46 ml, 65.6 mmol) were slurried in acetonitrile (100 mL) at room temperature. The suspension was stirred for about 10 minutes and then a solution of methyl 2-(bromomethyl)-3-(tert-butyldimethylsilyloxy)benzoate (11.4 g, 29.8 mmol) in acetonitrile (20 mL) was added dropwise over about 10 minutes. The reaction mixture was heated in an oil bath to a slow reflux (80° C.) for 4 hours. The reaction mixture was allowed to cool to room temperature for about 1 hour and then a solution of cesium fluoride (4.53 g, 29.8 mmol) in water (15 mL) was added. The resulting mixture was vigorously stirred at room temperature for about 1 hour at which point LCMS indicated desilylation was complete. The reaction mixture was diluted with acetonitrile and filtered to remove undissolved solids. The solids were washed with additional acetonitrile. The filtrate and washes (total volume 200 mL) were diluted further with EtOAc (300 mL), transferred to a 1-L separatory funnel, and washed with 0.5 N Aqueous $KH_2PO_4$ (100 mL, pH~5). To the aqueous layer was added 1 N HCl in portions (~20 mL, pH changed from pH 7-8 to pH~5 using pH paper). NaCl (~10 g) and EtOAc (~200 mL) were added to aqueous layer. The mixture was shaken vigorously in a separatory funnel. The organic layers were combined, washed with brine (50 mL), dried ($Na_2SO_4$), and concentrated on rotovap to give 15 g of an off-white solid. This solid containing the crude product was slurried in acetonitrile (200 mL) and the suspension was heated in an oil bath to reflux (85° C.) for 30 minutes with stirring. The mixture was allowed to cool down to room temperature over 1 hour then aged at 4° C. for another 2 hours. The solid formed was collected by suction filtration. The remaining solid in the flask was transferred onto a filter funnel using some MTBE. The cake was washed with additional MTBE (total filtrate volume ~300 mL), suction dried, and then placed in a vacuum oven at 40° C. for several hours to afford tert-butyl 5-amino-2-(4-hydroxy-1-oxoisoindolin-2-yl)-5-oxopentanoate as a white solid (7.3 g 72% yield, adjusted for purity of starting material and product): HPLC: Waters Symmetry $C_{18}$, 5 μm, 3.9×150 mm, 1 ml/min, 240 nm, 30/70 acetonitrile/0.1% $H_3PO_4$, 2.91 min (96.9%); mp: 198-200° C.; $^1$H NMR (DMSO-$d_6$) δ 1.39 (s, 9H, tBu), 1.93-2.14 (m, 3H, $CH_2$, CHH), 2.15-2.33 (m, 1H, CHH), 4.35 (s, 2H, $CH_2$), 4.61-4.83 (m, 1H, CH), 6.76 (br. s., 1H, NH), 6.97-7.07 (m, 1H, Ar), 7.11-7.20 (m, 1H, Ar), 7.26 (br. s., 1H, NH), 7.29-7.36 (m, 1H, Ar), 10.10 (s, 1H, OH); $^{13}$C NMR (DMSO-$d_6$) δ 24.81, 27.56, 31.44, 44.71, 54.02, 81.38, 113.72, 117.96, 127.99, 129.36, 133.36, 152.50, 168.36, 169.88, 172.94; LCMS MH=335; Anal Calcd for $C_{17}H_{22}N_2O_5$+0.19 $H_2O$: C, 60.45; H, 6.68; N, 8.29. Found: C, 60.44; H, 6.62; N, 8.27.

Step 2: In a 250-mL RB flask, tert-butyl 5-amino-2-(4-hydroxy-1-oxoisoindolin-2-yl)-5-oxopentanoate (3 g, 8.79 mmol) and triphenyl phosphine on polystyrene (1.6 mmol/g resin, 10.99 g, 17.59 mmol) were slurried in THF (100 mL, 1220 mmol) at room temperature. The resin was allowed to swell with gentle stirring for 5 minutes then the mixture was cooled in an ice bath at 0° C. To the mixture, DIAD (3.42 mL, 17.59 mmol) was added using a syringe in a rapid dropwise fashion. After 10 minutes, (4-(chloromethyl)phenyl)methanol (2.066 g, 13.19 mmol) was added as a solid in one portion. The ice bath was removed and the mixture was stirred at room temperature for 6 hours. The resin was suction filtered and rinsed on filter funnel with successive washes of dichloromethane and MeOH (2×, ~50 mL each wash). The combined filtrates and washes were concentrated in vacuo to a syrup which was partitioned between EtOAc (~300 mL) and water (~100 mL). The organic layer was washed with brine, dried ($Na_2SO_4$), and concentrated in vacuo to give the crude product as a tan oil (~10 g). The oil was purified on a $SiO_2$ flash column (CombiFlash, 330 g $SiO_2$ prepacked column, 0% to 5% MeOH in dichloromethane gradient) to give tert-butyl 5-amino-2-(4-(4-(chloromethyl)benzyloxy)-1-oxoisoindolin-2-yl)-5-oxopentanoate as a white foam which was crushed to a fine powder (3.6 g, 87% yield); $^1$H NMR (DMSO-$d_6$) δ 1.39 (s, 9H, tBu), 2.00-2.14 (m, 3H, CHH, $CH_2$), 2.14-2.35 (m, 1H, CHH), 4.43 (s, 2H, $CH_2$), 4.70 (dd, J=4.7, 10.4 Hz, 1H, CH), 4.78 (s, 2H, $CH_2$), 5.27 (s, 2H, $CH_2$), 6.66-6.83 (m, 1H, NH), 7.18-7.28 (m, 1H, NH), 7.29 (d, J=2.3 Hz, 1H, Ar), 7.32 (d, J=2.6 Hz, 1H, Ar), 7.40-7.58 (m, 5H, Ar); $^{13}$C NMR (DMSO-$d_6$) δ 24.69, 27.56, 31.50, 44.78, 45.83, 54.08, 69.13, 81.41, 114.91, 115.26, 127.92, 129.00, 129.73, 130.03, 133.31, 136.78, 137.38, 153.35, 168.09, 169.85, 172.93.

Step 3: To a solution of tert-butyl 5-amino-2-(4-(4-(chloromethyl)benzyloxy)-1-oxoisoindolin-2-yl)-5-oxopentanoate (250 mg, 0.529 mmol) in acetonitrile (10 mL), was added (2S,6R)-2,6-dimethylmorpholine (183 mg, 1.586 mmol) and DIEA (0.138 ml, 0.793 mmol). The resulting mixture was stirred at 60° C. for 3 hours. The reaction mixture was concentrated in vacuo and further dried in a vacuum oven to give tert-butyl 5-amino-2-(4-(4-(((2S,6R)-2,6-dimethylmorpholino)methyl)benzyloxy)-1-oxoisoindolin-2-yl)-5-oxopentanoate as a clear glassy solid (360 mg). LCMS MH=552. The solid was used in the next step without further purification Step 4: tert-Butyl 5-amino-2-(4-(4-(((2S,6R)-2,6-dimethylmorpholino)methyl)benzyloxy)-1-oxoisoindolin-2-yl)-5-oxopentanoate (0.528 mmol, assume theoretical yield from previous step) was taken up in dry THF (5 mL). To the stirred solution at room temperature, was added KOtBu (0.581 ml, 0.581 mmol, 1.0 M in THF) dropwise. The resulting mixture (pale yellow clear solution) was stirred for 1 hour at room temperature. Another 1.1 eq of KOtBu was added (0.581 ml, 0.581 mmol, 1.0 M THF) and the mixture was stirred for another 1 hour (LCMS indicated reaction complete). The reaction mixture was cooled on ice and then transferred portionwise to a flask with 2 M formic acid in MeCN (50 mL). The crude reaction mixture was concentrated in vacuo to give an oily residue which was dissolved in minimal water/DMF mixture (~2 mL/8 mL) and filtered, and the filtrate containing the crude product was purified by injection onto a C-18 preparatory HPLC column. The product was eluted with an acetonitrile/water gradient (0.1% formic acid in both mobile phases, 5 to 30% MeCN over 12 minutes) and fractions were collected by mass trigger. The desired fractions were combined and concentrated in vacuo to give 3-(4-(4-(((2S,6R)-2,6-dimethylmorpholino)methyl) benzyloxy)-1-oxoisoindolin-2-yl)piperidine-2,6-dione as a white solid (55 mg, 22% yield over step 3 and step 4): HPLC: Waters Symmetry $C_{18}$, 5 µm, 3.9×150 mm, 1 ml/min, 240 nm, 5% grad 95% in 10 min, acetonitrile/0.1% $H_3PO_4$, 5.84 min (95.6%); mp: 164-166° C.; $^1$H NMR (DMSO-$d_6$) δ 1.00 (s, 3H, $CH_3$), 1.02 (s, 3H, $CH_3$), 1.52-1.74 (m, 2H, CHH, CHH), 1.88-2.12 (m, 1H, CHH), 2.32-2.47 (m, 1H, CHH), 2.53-2.62 (m, 1H, CHH), 2.62-2.71 (m, 2H, CHH, CHH), 2.83-3.03 (m, 1H, CHH), 3.44 (s, 2H, $CH_2N$), 3.48-3.63 (m, 2H, 2×CH), 4.25 (d, J=17.4 Hz, 1H, CHH), 4.42 (d, J=17.6 Hz, 1H, CHH), 5.11 (dd, J=5.1, 13.2 Hz, 1H, CH), 5.23 (s, 2H, C $H_2O$), 7.20-7.39 (m, 4H, Ar), 7.39-7.59 (m, 3H, Ar), 10.97 (s, 1H, NH); $^{13}$C NMR (DMSO-$d_6$) δ 18.93, 22.33, 31.18, 45.06, 51.55, 58.89, 61.66, 69.39, 70.94, 114.96, 115.22, 127.63, 128.95, 129.80, 129.92, 133.30, 135.25, 137.69, 153.49, 167.99, 170.96, 172.81; LCMS MH=478; Anal Calcd for $C_{27}H_{31}N_3O_5$+0.34 $H_2O$: C, 67.05; H, 6.60; N, 8.69; $H_2O$, 1.27. Found: C, 67.20; H, 6.63; N, 8.52; $H_2O$, 1.27.

5.18 3-(1-Oxo-4-((5-(Piperidin-1-yl)Benzofuran-2-yl)Methoxy)Isoindolin-2-yl)-Piperidine-2,6-Dione

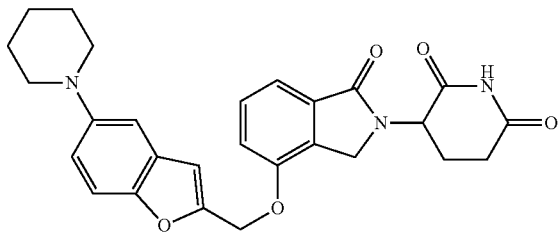 [SMILES: O=C1CCC(N2Cc3c(OCc4cc5cc(N6CCCCC6)ccc5o4)cccc3C2=O)C(=O)N1]

Step 1: A mixture of ethyl 5-nitrobenzofuran-2-carboxylate (5.0 g, 21.2 mmol) and 10% Pd/C (05.g) in EtOAc (300 mL) was hydrogenated at 50 psi overnight. The reaction mixture was filtered through celite and washed with EtOAc (100 mL). Filtrate was concentrated and the residue was purified by chromatography (SiO$_2$, EtOAc:Hexane 4:6) to give ethyl 5-aminobenzofuran-2-carboxylate (4.5 g, 100% yield): $^1$H NMR (CDCl$_3$) δ 1.41 (t, J=7.2 Hz, 3H), 3.68 (b, 2H), 4.38-4.45 (q, J=7.2 Hz, 2H), 6.80-6.84 (dd, J=2.4 and 9.0 Hz, 1H), 6.88 (d, J=2.1 Hz, 1H), 7.35-7.36 (d, J=3.3 Hz, 1H), 7.38 (s, 1H).

Step 2: N,N-Diisopropylethylamine (3.8 g, 29.2 mmol) was added to a stirred solution of ethyl 5-aminobenzofuran-2-carboxylate (2.5 g, 12.2 mmol) and 1,5-dibromopentane (5.0 g, 21.9 mmol) in toluene (40 mL). The resulting mixture was heated at 110° C. oil bath overnight. The reaction mixture was cooled to room temperature and filtered and solid was washed with toluene (25 mL). Filtrate was concentrated and the residue was purified by chromatography (SiO$_2$, EtOAc:Hexane 1:9) to give ethyl 5-piperidin-1-yl-benzofuran-2-carboxylate (3.0 g, 89%); $^1$H NMR (CDCl$_3$) δ 1.42 (t, J=6.2 Hz, 3H), 1.53-1.61 (m, 2H), 1.71-1.79 (m, 4H), 3.09-3.13 (t, J=5.4 Hz, 4H), 4.39-4.46 (q, J=6.9 Hz, 2H), 7.09-7.10 (d, J=2.4 Hz, 1H), 7.15-7.19 (dd, J=2.7 and 9.3 Hz, 1H), 7.42-7.46 (m, 2H).

Step 3: A solution of LiAlH$_4$/THF (1M, 11 mL, 11 mmol) in THF (10 mL) was cooled to 3° C. A solution of ethyl 5-piperidin-1-yl-benzofuran-2-carboxylate (2.9 g, 10.7 mmol) in THF (30 mL) was added slowly at 3-10° C. The reaction mixture was stirred at 3° C. for 30 minutes then quenched with sat. Na$_2$CO$_3$ (50 mL). The mixture was stirred with CH$_2$Cl$_2$ (50 mL) and aqueous layer was extracted with CH$_2$Cl$_2$ (3×40 mL). Combined CH$_2$Cl$_2$ solution was washed with sat. NaHCO$_3$ (40 mL) and brine (40 mL), and dried. The solvent was removed and the residue was purified by chromatography (SiO$_2$, EtOAc: CH$_2$Cl$_2$ 3:7) to give (5-piperidin-1-yl-benzofuran-2-yl)-methanol (2.4 g, 95% yield): $^1$H NMR (CDCl$_3$) δ 1.23-1.27 (m, 2H), 1.54-1.60 (m, 4H), 2.82 (b, 1H), 3.07 (t, J=6.0 Hz, 4H), 4.68 (s, 2H), 6.45 (s, 1H), 6.95-7.00 (m, 2H), 7.29 (d, J=9.0 Hz, 1H); $^{13}$C NMR (CDCl$_3$) δ 24.20, 26.14, 53.10, 58.11, 104.20, 108.83, 111.19, 117.01, 128.53, 149.07, 150.30, 156.94.

Step 4: Diisopropyl azodicarboxylate (0.8 g, 4.1 mmol) was added slowly to a stirred suspension of triphenylphosphine-polymer bound (3.5 g, 4.4 mmol) in THF (40 mL) at 3-6° C. After stirred at 3° C. for 10 minutes, a solution of methyl 5-amino-4-(4-hydroxy-1-oxoisoindolin-2-yl)-5-oxopentanoate (0.8 g, 2.7 mmol) and (5-piperidin-1-yl-benzofuran-2-yl)-methanol (0.8 g, 3.6 mmol) in THF (60 mL) was added slowly at 3-6° C. After stirred at 3° C. for 10 minutes, mixture was stirred at room temperature overnight. The reaction mixture was filtered and solid was washed with CH$_2$Cl$_2$ (30 mL). Filtrate was concentrated and the residue was dissolved in CH$_2$Cl$_2$ (80 mL) and washed with sat. NaHCO$_3$ (40 mL), water (2×35 mL) and brine (35 mL), and dried. The solvent was removed and the residue was purified by chromatography (SiO$_2$, CH$_3$OH:CH$_2$Cl$_2$ 3:97) to give methyl 5-amino-5-oxo-4-(1-oxo-4-((5-piperidin-1-yl)benzofuran-2-yl)methoxy)isoindolin-2-yl)pentanoate (0.7 g, 51% yield): $^1$H NMR (CDCl$_3$) δ 1.55-1.59 (m, 2H), 1.72-1.77 (m, 4H), 2.31-2.39 (m, 4H), 3.08-3.11 (m, 4H), 4.40 (d, J=18 Hz, 1H), 4.44 (d, J=18 Hz, 1H), 4.87-4.92 (dd, J=6.0 and 9.0 Hz, 1H), 5.21 (s, 2H), 5.49 (s, 1H), 6.38 (s, 1H), 6.71 (s, 1H), 7.02-7.18 (m, 3H), 7.36-7.46 (m, 2H).

Step 5: A solution of potassium t-butoxide/THF (1M, 1.5 mL, 1.5 mmol) was added slowly to a stirred solution of methyl 5-amino-5-oxo-4-(1-oxo-4-((5-piperidin-1-yl)benzofuran-2-yl)methoxy)isoindolin-2-yl)pentanoate (0.6 g, 1.2 mmol) in THF (20 mL) at 5° C. and stirred for 30 minutes then quenched with sat. NH$_4$Cl (5 mL). The mixture was stirred with CH$_2$Cl$_2$ (50 mL) and water (15 mL). The aqueous layer was extracted with CH$_2$Cl$_2$ (30 mL) and combined CH$_2$C$_2$ solution was washed with water (30 mL) and dried. The solvent was removed and the residue was purified by chromatography (SiO$_2$, CH$_3$OH: CH$_2$Cl$_2$ 3:97) to give 3-(1-oxo-4-((5-(piperidin-1-yl)benzofuran-2-yl) methoxy)isoindolin-2-yl)piperidine-2,6-dione (0.3 g, 43% yield): mp 242-244° C.; $^1$H NMR (DMSO-$d_6$) δ 1.09 (m, 2H), 1.50-1.64 (m, 4H), 1.90-2.02 (m, 2H), 2.49-2.51 (m, 2H), 2.80-2.95 (m, 1H), 3.03-3.07 (m, 4H), 4.25 (d, J=17.7 Hz, 1H), 4.35 (d, J=17.4 Hz, 1H), 5.05-5.15 (m, 1H), 5.37 (s, 2H), 6.97-7.09 (m, 3H), 7.35-7.51 (m, 4H), 10.96 (s, 1H); $^{13}$C NMR (DMSO-$d_6$) δ 22.28, 23.78, 25.53, 31.16, 45.04, 51.51, 62.61, 107.29, 107.71, 111.12, 115.15, 116.69, 127.96, 129.78, 129.95, 133.40, 148.89, 149.23, 152.57, 152.99, 167.88, 170.93, 172.70; Calcd for $C_{27}H_{27}N_3O_5$+0.2 $H_2O$: C, 67.97; H, 5.79; N, 8.81. Found: C, 67.88; H, 5.75; N, 8.62.

5.19 4-Amino-1-{4-[2-(2,6-Dioxo-Piperidin-3-yl)-1-Oxo-2,3-Dihydro-1H-Isoindol-4-yloxymethyl]-Benzyl}-Pyridinium Formate

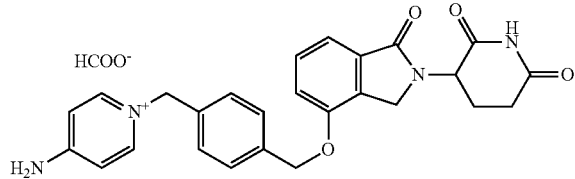 [SMILES: Nc1cc[n+](Cc2ccc(COc3cccc4c3CN(C3CCC(=O)NC3=O)C4=O)cc2)cc1 ; "HCOO-"]

Pyridin-4-amine (0.82 g, 8.70 mmol) was added to a stirred solution of methyl 5-amino-4-(4-(4-(chloromethyl)benzyloxy)-1-oxoisoindolin-2-yl)-5-oxopentanoate (0.75 g, 1.74 mmol) in DMF (15 ml) at 50° C. for three hours. To the mixture was added potassium carbonate (0.24 g, 1.74 mmol), and the mixture was heated at 75° C. for five hours. The mixture was purified by preparative HPLC to give 4-amino-1-{4-[2-(2,6-dioxo-piperidin-3-yl)-1-oxo-2,3-dihydro-1H-isoindol-4-yloxymethyl]-benzyl}-pyridinium formate as a brown solid (0.20 g, 26% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H3PO4): 5.00 min (99.1%); mp: 300-302° C.; 1H NMR (DMSO-d6) δ 1.92-2.05 (m, 1H, CHH), 2.35-2.47 (m, 1H, CHH), 2.54-2.64 (m, 1H, CHH), 2.83-3.00 (m, 1H, CHH), 4.19-4.47 (m, 2H, CH2), 5.11 (dd, J=5.1, 13.2 Hz, 1H, NCH), 5.26 (s, 2H, NH2 or CH2), 5.36 (s, 2H, CH2 or NH2), 6.86 (d, J=7.4 Hz, 2H, CH2), 7.27-7.58 (m, 7H, Ar), 8.22-8.43 (m, 4H, Ar), 11.00 (br. s., 1H, NH); 13C NMR (DMSO-d6) δ 22.35, 31.15, 45.09, 51.58, 59.39, 69.00, 109.56, 115.00, 115.36, 128.12, 128.32, 129.85, 129.94, 133.29, 135.35, 137.21, 142.93, 153.31, 158.57, 158.67, 168.02, 170.89, 172.80; LCMS M+=457; Anal. Calcd for C26H25N4O4 HCOO: C, 64.53; H, 5.22; N, 11.15; Found: C, 56.18; H, 5.07; N, 10.01.

5.20 3-(1-Oxo-4-((5-Piperidin-1-ylmethyl)Benzofuran-2-yl)Methoxy)Isoindolin-2-yl)Piperidine-2,6-Dione

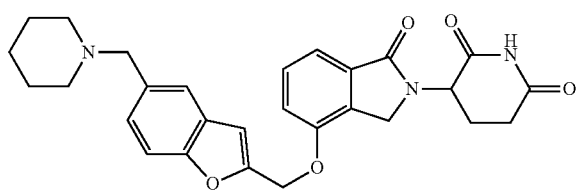 [SMILES: O=C1CCC(N2Cc3c(OCc4cc5cc(CN6CCCCC6)ccc5o4)cccc3C2=O)C(=O)N1]

Step 1: Piperidine (1.2 g, 14.1 mmol) was added to a stirred solution of ethyl 5-formylbenzofuran-2-carboxylate (1.5 g, 6.9 mmol) in methanol (60 mL). Molecular sieve (1.5 g) was added, followed by acetic acid (0.4 g, 6.9 mmol) and sodium cyanoborohydride (0.7 g, 10.3 mmol). The resulting mixture was stirred at room temperature for 3 hours. The mixture was filtered and solid was washed with methanol (40 mL). Filtrate was concentrated and the residue was dissolved in EtOAc (100 mL) and washed with sat. NaHCO3 (35 mL) and brine (35 mL), and dried (K2CO3). The solvent was removed and the residue was purified by chromatography (SiO2, CH3OH:CH2Cl2 3:97) to give 5-piperidin-1-ylmethyl-benzofuran-2-carboxylic acid ethyl ester (1.0 g, 49% yield): 1H NMR (CDCl3) δ 1.40-1.48 (m, 3H), 1.57-1.64 (m, 4H), 2.44 (b, 1H), 3.60 (s, 2H), 3.97-3.98 (m, 2H), 4.40-4.47 (q, 2H), 7.40-7.63 (m, 4H).

Step 2: A solution of 5-piperidin-1-ylmethyl-benzofuran-2-carboxylic acid ethyl ester (1.0 g, 3.4 mmol) in THF (15 mL0 was added slowly to a stirred solution of LiAlH4/THF (1M, 4.4 mL, 4.4 mmol) in THF (10 mL) at 5-8° C. After addition, the mixture was stirred at 5° C. for 30 minutes then quenched with sat. Na2CO3 (50 mL). The mixture was stirred with CH2Cl2 (50 mL) and aqueous layer was extracted with CH2Cl2 (2×30 mL). Combined CH2Cl2 solution was washed with sat. NaHCO3 (30 mL) and brine (30 mL), and dried. The solvent was removed and the residue was purified by chromatography (SiO2, CH3OH:CH2Cl2 3:97) to give (5-piperidin-1-ylmethyl-benzofuran-2-yl)-methanol (0.5 g, 63% yield): 1H NMR (CDCl3) δ 1.45-1.46 (m, 2H), 1.55-1.62 (m, 4H), 2.40 (s, 4H), 3.46 (s, 1H), 3.52 (s, 2H), 4.71 (s, 2H), 6.55 (s, 1H), 7.20 (d, J=8.4 Hz, 1H), 7.26 (d, J=8.4 Hz, 1H), 7.45 (s, 1H).

Step 3: Diisopropyl azodicarboxylate (0.6 g, 3.1 mmol) was added slowly to a stirred suspension of triphenylphosphine-polymer bound (2.5 g, 3.1 mmol) in THF (40 mL) at 3-5° C. After stirred at 3° C. for 10 minutes, a solution of methyl 5-amino-4-(4-hydroxy-1-oxoisoindolin-2-yl)-5-oxopentanoate (0.6 g, 2.0 mmol) and (5-piperidin-1-ylmethyl-benzofuran-2-yl)-methanol (0.5 g, 2.0 mmol) in THF (40 mL) was added slowly at 3-6° C. The reaction mixture was stirred at 3° C. for 5 minutes then warmed to room temperature overnight. The reaction mixture was filtered and solid was washed with CH2Cl2 (40 mL). Filtrate was concentrated and the residue was dissolved in CH2Cl2 (100 mL) and washed with sat. NaHCO3 (30 mL), water (30 mL) and brine (30 mL), and dried. The solvent was removed and the residue was purified by chromatography (SiO2, CH3OH:CH2Cl2 3:97) to give methyl 5-amino-5-oxo-4-(1-oxo-4-((5-(piperidin-1-ylmethyl)benzofuran-2-yl)methoxy)isoindolin-2-yl)pentanoate (0.6 g, 56% yield): 1H NMR (CDCl3) δ 1.42-1.46 (m, 2H), 1.53-1.60 (m, 4H), 2.12-2.45 (m, 8H), 3.55 (s, 2H), 3.62 (s, 3H), 4.40 (d, J=17.7 Hz, 1H), 4.44 (d, J=17.7 Hz, 1H), 4.87-4.92 (dd, J=5.7 and 8.7 Hz, 1H), 5.23 (s, 2H), 5.47 (s, 1H), 6.40 (s, 1H), 6.77 (s, 1H), 7.15-7.18 (dd, J=2.1 and 6.6 Hz, 1H), 7.26-7.32 (m, 1H), 7.40-7.51 (m, 4H).

Step 4: A mixture of methyl 5-amino-5-oxo-4-(1-oxo-4-((5-piperidin-1-ylmethyl)benzofuran-2-yl)methoxy)isoindolin-2-yl)pentanoate (0.6 g, 1.1 mmol) and K2CO3 (0.2 g, 1.1 mmol) in DMF (10 mL) was heated at 80° C. oil bath for 3 hours. The reaction mixture was concentrated and the residue was stirred with water (10 mL) and EtOAc (10 mL). Solid was collected and reslurried in acetone (10 mL) and hexane (10 mL) to give 3-(1-oxo-4-((5-piperidin-1-ylmethyl)benzofuran-2-yl)methoxy)isoindolin-2-yl)piperidine-2,6-dione (0.2 g, 50% yield): mp 202-204° C.; 1H NMR (DMSO-d6) δ 1.46-1.47 (m, 6H), 1.96-2.00 (m, 1H), 2.31-2.58 (m, 6H), 2.84-2.96 (m, 1H), 3.48 (s, 2H), 4.25 (d, J=17.4 Hz, 1H), 4.35 (d, J=17.4 Hz, 1H), 5.06-5.13 (dd, J=5.1 and 13.2 Hz, 1H), 5.41 (s, 2H), 7.07 (s, 1H), 7.23-7.27 (dd, J=1.5 and 8.4 Hz, 1H), 7.34-7.37 (dd, J=0.9 and 6.9 Hz, 1H), 7.46-7.53 (m, 4H), 10.96 (s, 1H); 13C NMR (DMSO-d6) δ 22.25, 23.98, 25.50, 31.16, 45.03, 51.55, 53.74, 62.55, 62.70, 107.05, 110.68, 115.13, 115.65, 121.39, 125.89, 127.42, 129.81, 129.94, 133.41, 152.72, 152.97, 153.74, 167.88, 170.93, 172.79; Calcd for C28H29N3O5: C, 68.98; H, 6.00; N, 8.62. Found: C, 68.67; H, 6.03; N, 8.53.

5.21 Tert-Butyl 4-(4-((2-(2,6-Dioxopiperidin-3-yl)-1-Oxoisoindolin-4-yloxy)Methyl)Phenyl)Piperidine-1-Carboxylate

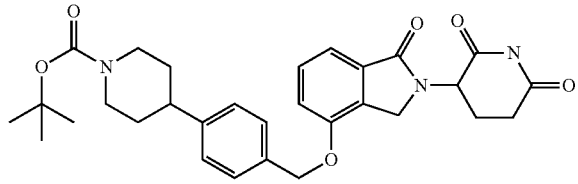 [SMILES: CC(C)(C)OC(=O)N1CCC(c2ccc(COc3cccc4c3CN(C3CCC(=O)NC3=O)C4=O)cc2)CC1]

Step 1: BH$_3$ THF (2.88 ml, 2.88 mmol, 1.0 M in THF) was added dropwise to a solution of 4-(1-(tert-butoxycarbonyl)piperidin-4-yl)benzoic acid (800 mg, 2.62 mmol) in THF (10 ml) at 0° C. After 15 minutes, the ice bath was removed and the clear solution was allowed to stir overnight (~17 hours). The reaction mixture was cooled in an ice bath and quenched with H$_2$O (25 mL). EtOAc (100 mL) was added and the mixture was washed with 1 N NaHCO$_3$ (~40 mL) and brine, dried (Na$_2$SO$_4$), and concentrated in vacuo. The oily residue was dissolved in dichloromethane and concentrated again and then dried in a vacuum oven at 40° C. to give tert-butyl 4-(4-(hydroxymethyl)phenyl)piperidine-1-carboxylate as a clear oil (707 mg, 93% yield). The oil solidified upon standing and was used in the next step without further purification. LCMS MH=292, 218; $^1$H NMR (CHLOROFORM-d) δ 1.48 (s, 9H, tBu), 1.56-1.72 (m, 3H, CHH, CHH, OH), 1.75-1.89 (m, 2H, CHH, CHH), 2.53-2.71 (m, 1H, CH), 2.73-2.92 (m, 2H, CHH, CHH), 4.17-4.32 (m, 2H, CHH, CHH), 4.67 (d, J=5.9 Hz, 2H, CH$_2$), 7.21 (d, J=8.1 Hz, 2H, Ar), 7.32 (d, J=8.3 Hz, 2H, Ar); $^{13}$C NMR (CHLOROFORM-d) δ 28.50, 33.22, 42.49, 65.21, 77.22, 79.47, 127.02, 127.34, 138.96, 145.40. Carbamate carbon signal is not observed.

Step 2: To a solution of tert-butyl 5-amino-2-(4-hydroxy-1-oxoisoindolin-2-yl)-5-oxopentanoate (0.7 g, 1.96 mmol) in THF (25 ml), was added triphenyl phosphine on polystyrene (1.6 gm/mmol, 1.845 g, 2.95 mmol). The resin was allowed to swell for several minutes at room temperature, and then the reaction mixture was cooled in an ice bath at 0° C. DIAD (0.574 ml, 2.95 mmol) was added dropwise while stirring. After about 15 minutes, tert-butyl 4-(4-(hydroxymethyl)phenyl)piperidine-1-carboxylate (0.70 g, 2.40 mmol) was added as a solution in dry THF (5 mL). After about 10 minutes, the ice bath was removed and the resulting mixture was stirred at room temperature for 48 hours. The reaction mixture was filtered with suction and the resin was washed successively with dichloromethane then MeOH (3× swell/shrink cycles). After the final MeOH wash, the combined filtrate was concentrated in vacuo. The oily residue was partitioned between EtOAc (~200 mL) and Na$_2$CO$_3$ (sat. ~70 mL). The EtOAc layer was washed with brine, dried (Na$_2$SO$_4$), and concentrated in vacuo to give a foam which was stored in a vacuum oven at 40° C. overnight to afford tert-butyl 4-(4-((2-(5-amino-1-tert-butoxy-1,5-dioxopentan-2-yl)-1-oxoisoindolin-4-yloxy)methyl)phenyl)piperidine-1-carboxylate) (1.9 g, assume theoretical yield). The foam obtained was used in the next step without further purification.

Step 3: KOtBu (0.722 mL, 0.722 mmol, 1.0 M in THF) was added dropwise to a solution of tert-butyl 4-(4-((2-(5-amino-1-tert-butoxy-1,5-dioxopentan-2-yl)-1-oxoisoindolin-4-yloxy)methyl)phenyl)piperidine-1-carboxylate (400 mg, 0.408 mmol) in dry THF (5 mL) at room temperature. More KOtBu (0.722 mL, 0.722 mmol) was added to reaction mixture after 2.5 hours and stirring was continued at room temperature. After about 20 minutes, the mixture transferred to a chilled 0.5 N aq. HCl (~50 mL). EtOAc (250 mL) was added and the mixture transferred to a separatory funnel. The EtOAc layer was washed with brine, dried (Na$_2$SO$_4$), and concentrated in vacuo and the residue was dried further in a vacuum oven to give 380 mg of a tan oil. The crude product was dissolved in minimal DMF (~10 mL) and purified by injection onto a C-18 preparatory HPLC column. The product was eluted with an acetonitrile/water gradient (0.1% formic acid in both mobile phases, 30 to 80% MeCN over 20 minutes) and fractions were collected by mass trigger. The desired fractions were combined and concentrated in vacuo to give tert-butyl 4-(4-((2-(2,6-dioxopiperidin-3-yl)-1-oxoisoindolin-4-yloxy)methyl)phenyl)piperidine-1-carboxylate as a white solid (84 mg, 39% yield for step 2 and step 3): HPLC: Waters Symmetry C$_{18}$, 5 µm, 3.9×150 mm, 1 ml/min, 240 nm, 60/40 acetonitrile/0.1% H$_3$PO$_4$, 4.76 min (98.7%); mp: 214-216° C.; $^1$H NMR (DMSO-d$_6$) δ 1.29-1.44 (m, 9H, tBu), 1.44-1.58 (m, 2H, 2×CHH), 1.72 (br. s., 2H, CHH, CHH), 1.87-2.08 (m, 1H, CHH), 2.35-2.48 (m, 1H, CHH), 2.52-2.99 (m, 5H, 5×CHH), 3.89-4.14 (m, 2H, 2×CHH), 4.24 (d, J=17.6 Hz, 1H, CHH), 4.40 (d, J=17.4 Hz, 1H, CHH), 5.10 (dd, J=5.1, 13.2 Hz, 1H, CH), 5.20 (s, 2H, CH$_2$), 7.18-7.37 (m, 4H, Ar), 7.37-7.55 (m, 3H, Ar), 10.96 (s, 1H, NH); $^{13}$C NMR (DMSO-d$_6$) δ 22.33, 28.07, 31.18, 32.66, 41.35, 43.89, 45.06, 51.55, 69.35, 78.53, 114.90, 115.16, 126.81, 127.95, 129.78, 129.92, 133.28, 134.39, 145.62, 153.48, 153.86, 167.99, 170.97, 172.84; LCMS MH=534; Anal Calcd for C$_{30}$H$_{35}$N$_3$O$_6$+1.5 H$_2$O: C, 64.27; H, 6.83; N, 7.49. Found: C, 64.22; H, 6.72; N, 7.36.

5.22 3-(1-Oxo-4-(4-(Piperidin-4-yl)Benzyloxy)Isoindolin-2-yl)Piperidine-2,6-Dione Hydrogen Chloride

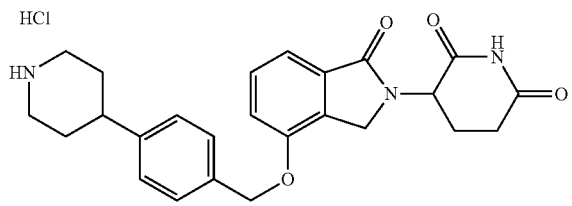 [SMILES: Cl ; O=C1CCC(N2Cc3c(OCc4ccc(C5CCNCC5)cc4)cccc3C2=O)C(=O)N1]

A 2 N HCl (10 mL, 20.00 mmol) in Et$_2$O was added to tert-butyl 4-(4-((2-(2,6-dioxopiperidin-3-yl)-1-oxoisoindolin-4-yloxy)methyl)phenyl)piperidine-1-carboxylate (54 mg, 0.101 mmol). The reaction flask was sonicated to loosen solid adhering on side of flask and the resulting suspension was sealed and stirred at room temperature. After about 4 hours, LCMS indicated reaction was complete. The reaction mixture was diluted with additional Et$_2$O and then filtered through a fritted funnel with suction. The remaining solid in reaction flask was transferred to funnel and washed with additional Et$_2$O. The cake was dried in vacuum oven at 40° C. to afford 3-(1-oxo-4-(4-(piperidin-4-yl)benzyloxy)isoindolin-2-yl)piperidine-2,6-dione hydrochloride as a fluffy off-white solid hydrochloride salt (47 mg, 99% yield): HPLC: Waters Symmetry C18, 5 µm, 3.9×150 mm, 1 ml/min, 240 nm, 20/80 acetonitrile/0.1% H3PO4, 3.62 min (96.0%); mp: 280-282° C.; 1H NMR (DMSO-d6) □ 1.67-

2.12 (m, 5H, 5×CHH), 2.32-2.48 (m, 1H, CHH), 2.52-2.64 (m, 1H, CHH), 2.76-3.08 (m, 4H, 4×CHH), 3.26-3.46 (m, 2H, 2×CHH), 4.24 (d, J=17.6 Hz, 1H, CHH), 4.41 (d, J=17.4 Hz, 1H, CHH), 5.11 (dd, J=5.1, 13.2 Hz, 1H, CH), 5.22 (s, 2H, C H2O), 7.26 (d, J=8.1 Hz, 2H, Ar), 7.33 (d, J=7.7 Hz, 2H, Ar), 7.40-7.54 (m, 3H, Ar), 8.48-9.01 (m, 2H, 2×NH), 10.96 (s, 1H, NH); 13C NMR (DMSO-d6) □ 22.34, 29.30, 31.18, 43.48, 45.03, 51.55, 69.28, 114.94, 115.22, 126.61, 128.08, 129.80, 129.92, 133.28, 134.86, 144.42, 153.45, 167.97, 170.96, 172.81. 1 carbon signal is not observed due to overlap with DMSO-d6; LCMS MH=434; Anal Calcd for $C_{25}H_{27}N_3O_4$+2 HCl+1.7 H2O: C, 55.91; H, 6.08; N, 7.82. Found: C, 55.84; H, 5.82; N, 7.70.

5.23 3-{4-[4-(3-Morpholin-4-yl-Propyl)-Benzyloxy]-1-Oxo-1,3-Dihydro-Isoindol-2-yl}-Piperidine-2,6-Dione

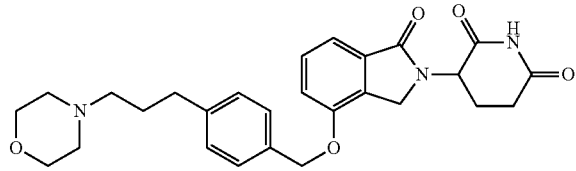 [SMILES: O=C1CCC(N2Cc3c(OCc4ccc(CCCN5CCOCC5)cc4)cccc3C2=O)C(=O)N1]

Step 1: (Triphenylphosphoranylidene)acetaldehyde (500 mg, 1.64 mmol) was added to the stirred solution of methyl 4-formylbenzoate (2.0 g, 12.18 mmol) in tetrahydrofuran (50 mL). The reaction mixture was heated at reflux for two hours before (triphenylphosphoranylidene)acetaldehyde (500 mg, 1.64 mmol) was added to the reaction mixture. The reaction mixture was kept at reflux for 21 hours and then (triphenyl phosphoranylidene)acetaldehyde (3.5 g, 11.45 mmol) was added to the reaction mixture which was kept at reflux for 8 hours. The reaction mixture was diluted by EtOAc (80 mL) and then washed by NH4Cl (Sat. 40 mL), water (40 mL) and brine (40 mL) respectively. The organic layer was dried by MgSO4 and concentrated to give dark solid. The dark solid was suspended in diethyl ether (50 mL) and filtered through celite and the solid was washed by diethyl ether (50 mL×3). The filtrate was concentrated and purified by silica chromatography to give 4-(3-Oxo-propenyl)-benzoic acid methyl ester as an off white solid (1.04 g, 33% yield); LCMS MH=191; $^1$H NMR (DMSO-$d_6$) δ 3.88 (s, 3H, CH$_3$), 6.97 (dd, J=7.6, 16.0 Hz, 1H, CH), 7.82 (d, J=16.1-Hz, 1H, CH), 7.90 (d, J=8.5 Hz, 2H, Ar), 8.02 (d, J=8.3 Hz, 2H, Ar), 9.72 (d, J=7.6 Hz, 1H, CHO).

Step 2: Morpholine (0.715 ml, 8.20 mmol) was added to the stirred solution of (E)-methyl 4-(3-oxoprop-1-enyl)benzoate (520 mg, 2.73 mmol). The clear solution was added by molecular sieves (2.2 g) and acetic acid (0.157 ml, 2.73 mmol). Thirty minutes later, sodium cyanoborohydride (258 mg, 4.10 mmol) was added to above yellow reaction suspension. The reaction was complete in 15 minutes at room temperature. The reaction mixture combined with another batch of reaction started with (E)-methyl 4-(3-oxoprop-1-enyl)benzoate (512 mg) was added by water (2 mL) and stirred for 10 minutes before it was filtered through celite. The filtrate was concentrated and purified by ISCO chromatography to give 4-(3-Morpholin-4-yl-propenyl)-benzoic acid methyl ester as yellow liquid (550 mg, 39% yield); LCMS MH=262.

Step 3: Palladium on carbon (120 mg, 0.056 mmol) was added to the stirred solution of (E)-methyl 4-(3-morpholinoprop-1-enyl)benzoate (710 mg, 2.72 mmol) in MeOH (20 mL). The reaction flask was sealed and vacuumed. The reaction charged with H$_2$ (1 atm) was stirred at room temperature and the reaction was complete in 1 hour. The reaction mixture combined with another batch of reaction started with (E)-methyl 4-(3-morpholinoprop-1-enyl)benzoate (50 mg) was filtered through celite. And the solid was washed by MeOH (20 mL×3). The filtrate was concentrated and was purified by ISCO chromatography to give 4-(3-Morpholin-4-yl-propyl)-benzoic acid methyl ester as clear solid (690 mg, 90% yield) and the compound was put to next step without further purification; LCMS MH=264.

Step 4: LiAlH$_4$ (1.3 mL, 2.62 mmol) in THF (2 M) solution was added to the stirred solution of methyl 4-(3-morpholinopropyl)benzoate (690 mg, 2.62 mmol) in tetrahydrofuran (25 mL) under −78° C. drop wise. The reaction mixture was stirred under −78° C. for 30 minutes and then allowed to 0° C. slowly. Two hours later, the reaction mixture was cooled down to −78° C. and 1.3 mL LiAlH$_4$ (2M in THF) was added to the reaction mixture. And the cold bath was removed after addition and the reaction mixture was stirred at room temperature for 1 hour and the reaction was complete. To the reaction mixture, NaOH (0.6 mL, 10 N) and water (0.4 mL) were added. The resulting suspension was stirred at room temperature for 20 minutes before it was filtered through celite. The solid was washed by EtOAc (40 mL×4) and concentrated under vacuo to give [4-(3-morpholin-4-yl-propyl)-phenyl]-methanol as a clear oil (600 mg, 97% crude yield) which was used without further purification; LCMS MH=236.

Step 5: Polymer bonded PPh$_3$ (727 mg, 2.77 mmol, 1.6 mmol/g) was added to the stirred suspension of methyl 5-amino-4-(4-hydroxy-1-oxoisoindolin-2-yl)-5-oxopentanoate (450 mg, 1.540 mmol) in THF (17 mL) at 0° C. The reaction mixture was stirred at 0° C. for 20 minutes before DIAD (0.539 ml, 2.77 mmol) was added drop wise. The resulting reaction mixture was stirred for 20 minutes, and (4-(3-morpholinopropyl) phenyl)methanol (471 mg, 2.001 mmol) in THF (3 mL) was added to the mixture. Thirty minutes later, the ice bath was removed and the reaction mixture was stirred at room temperature for 2 hours before the reaction stopped progressing. The reaction mixture combined with another batch of reaction started with methyl 5-amino-4-(4-hydroxy-1-oxoisoindolin-2-yl)-5-oxopentanoate (100 mg) was filtered and washed with dichloromethane (25 mL×6). The filtrate was concentrated and purified by ISCO chromatography to give 4-Carbamoyl-4-{4-[4-(3-morpholin-4-yl-propyl)-benzyloxy]-1-oxo-1,3-dihydro-isoindol-2-yl}-butyric acid methyl ester as glass like solid (450 mg, 47% yield); LCMS MH=510; $^1$H NMR (DMSO-$d_6$) δ 1.72 (quin, J=7.5 Hz, 2H, CH$_2$), 2.00-2.21 (m, 2H, CHH, CHH), 2.21-2.40 (m, 8H, CH$_2$, CH$_2$, CH$_2$, CH$_2$), 2.60 (t, J=7.6 Hz, 2H, CH$_2$), 3.50 (s, 3H, CH$_3$), 3.52-3.62 (m, 4H, CH$_2$, CH$_2$), 4.31-4.45 (m, 1H, CHH), 4.45-4.61 (m, 1H, CHH), 4.72 (dd, J=4.7, 10.2 Hz, 1H, CHH), 5.20 (s, 2H, CH$_2$), 7.11-7.32 (m, 5H, Ar, NH), 7.35-7.49 (m, 3H, Ar), 7.58 (s, 1H, NH).

Step 6: To the stirred solution of methyl 5-amino-4-(4-(4-(3-morpholinopropyl)benzyloxy)-1-oxoisoindolin-2-yl)-5-oxopentanoate (400 mg, 0.785 mmol) in tetrahydrofuran (18 mL) at 0° C., was added potassium 2-methylpropan-2-olate (88 mg, 0.785 mmol). The mixture was stirred at 0° C. for 1.5 hours and the reaction was complete. The cold reaction mixture was diluted by EtOAc (30 mL), followed by the addition of HCl (aq, 1N, 1 mL), NaHCO$_3$ (sat. 0.6 mL) and brine (3 mL). The mixture was extracted and organic layer was washed by brine (5 mL). The organic layer was combined with the organic layer from anther batch of reaction mixture started with methyl 5-amino-4-(4-(4-(3-morpholinopropyl) benzyloxy)-1-oxoisoindolin-2-yl)-5-oxopentanoate (50 mg). The mixture was dried by MgSO$_4$ and concentrated to give solid (460 mg). The solid was triturated in ether (15 mL) to give 3-{4-[4-(3-Morpholin-4-yl-propyl)-benzyloxy]-1-oxo-1,3-dihydro-isoindol-2-yl}-piperidine-2,6-dione as a white solid (165 mg, 41% yield). HPLC: Waters Symmetry C-18, 3.9×150 mm, 5 μm, 1 mL/min, 240 nm, 20/80, (acetonitrile/0.1% H$_3$PO$_4$), 4.0 min (97%); mp: 190-192° C.; $^1$H NMR (DMSO-d$_6$) δ 1.71 (quin, J=7.5 Hz, 2H, CH$_2$), 1.91-2.04 (m, 1H, CHH), 2.21-2.36 (m, 6H, M$_{01}$), 2.39-2.47 (m, 1H, CHH), 2.59 (t, J=7.6 Hz, 3H, CHH, CH$_2$), 2.81-3.00 (m, 1H, CHH), 3.50-3.62 (m, 4H, CH$_2$, CH$_2$), 4.19-4.30 (m, 1H, CHH), 4.33-4.48 (m, 1H, CHH), 5.11 (dd, J=5.0, 13.1 Hz, 1H, CHH), 5.20 (s, 2H, CH$_2$), 7.23 (d, J=7.9 Hz, 2H, Ar), 7.32 (d, J=7.7 Hz, 2H, Ar), 7.39 (d, J=7.9 Hz, 2H, Ar), 7.43-7.55 (m, 1H, Ar), 10.97 (s, 1H, NH); $^{13}$C NMR (DMSO-d$_6$) δ 22.33, 27.72, 31.16, 32.53, 45.07, 51.56, 53.28, 57.52, 66.17, 69.45, 114.97, 115.16, 127.79, 128.39, 129.77, 129.93, 133.27, 133.87, 141.92, 153.49, 168.00, 170.95, 172.81; LCMS MH=478; Anal. Calcd for C$_{27}$H$_{31}$N$_3$O$_5$+1 H$_2$O+0.26 Ether: C, 65.42; H, 6.97; N, 8.16; Found: C, 65.41; H, 6.77; N, 8.19.

5.24 3-(1-Oxo-4-(((6-Piperidin-1-ylmethyl)Benzofuran-2-yl)Methoxy)Isoindolin-2-yl)Piperidine-2,6-Dione

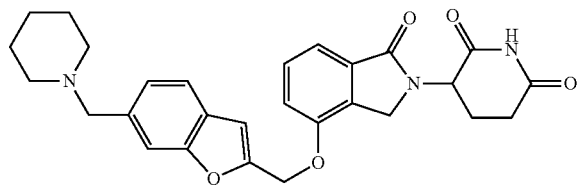 [SMILES: O=C1CCC(N2Cc3c(OCc4cc5ccc(CN6CCCCC6)cc5o4)cccc3C2=O)C(=O)N1]

Step 1: A mixture of 2-hydroxy-4-methylbenzaldehyde (4.6 g, 33.9 mmol), ethyl 2-bromoacetate (5.7 g, 33.9 mmol), K$_2$CO$_3$ (7.0 g, 50.9 mmol) and molecular sieve (4.6 g) in DMF (40 mL) was heated at 85° C. for 2 hours then at 120° C. for 5 hours. The reaction mixture was cooled and diluted with EtOAc (100 mL). The mixture was filtered, and filtrate was washed with water (3×50 mL) and brine (50 mL), and dried. The solvent was removed and the residue was purified by chromatography (SiO$_2$, EtOAc:Hexane=1:9) to give ethyl 6-methylbenzofuran-2-carboxylate (3.1 g, 44% yield): $^1$H NMR (DMSO-d$_6$) δ 1.34 (t, J=7.2 Hz, 3H), 4.32-4.39 (q, J=6.9 Hz, 2H), 7.35-7.58 (m, 2H), 7.66-7.70 (m, 2H).

Step 2: N-Bromosuccinimide (5.6 g, 31.5 mmol) was added to a stirred solution of ethyl 6-methylbenzofuran-2-carboxylate (3.1 g, 15.0 mmol) in CCl$_4$ (50 mL). The resulting mixture was heated at 70° C. oil bath with a 300 W bulb shining for 5 hours. The reaction mixture was cooled and filtered. Filtrate was concentrated and the residue was purified by chromatography (SiO$_2$, EtOAC: Hexane=1:9) to give ethyl 6-(bromomethyl)benzofuran-2-carboxylate (2.8 g, 66% yield): $^1$H NMR (DMSO-d$_6$) δ 1.34 (t, J=7.2 Hz, 3H), 4.38 (q, J=7.2 Hz, 2H), 4.86 (s, 2H), 7.40-7.45 (m, 1H), 7.76-7.84 (m, 3H).

Step 3: A mixture of piperidine (1.0 g, 11.3 mmol), K$_2$CO$_3$ (3.6 g, 26 mmol) and 18-crown-6 (catalytic amount) in acetone (10 mL) was heated at 60° C. oil bath. A solution of ethyl 6-(bromomethyl)benzofuran-2-carboxylate (2.0 g, 7.1 mmol) in acetone (10 mL) was added dropwise and the mixture was stirred at 60° C. oil bath for 3 hours. The reaction mixture was cooled and filtered. Filtrate was concentrated and the residue was dissolved in EtOAc (100 mL) and washed with water (2×35 mL) and brine (35 mL), and dried. The solvent was removed and the residue was purified by chromatography (SiO$_2$, CH$_3$OH:CH$_2$Cl$_2$ 3:97) to give ethyl 6-(piperidin-1-ylmethyl)benzofuran-2-carboxylate (1.5 g, 73% yield): $^1$H NMR (CDCl$_3$) δ 1.40-1.46 (m, 5H), 1.53-1.61 (m, 4H), 2.37-2.40 (m, 4H), 3.59 (s, 2H), 4.40-4.47 (q, J=6.9 Hz, 2H), 7.26-7.30 (m, 1H), 7.49 (d, J=0.9 Hz, 1H), 7.56-7.60 (m, 2H).

Step 4: A solution of ethyl 6-(piperidin-1-ylmethyl)benzofuran-2-carboxylate (1.5 g, 5.2 mmol) in THF (20 mL) was added slowly to a stirred solution of LiAlH$_4$/THF (1M, 6.7 mL, 6.7 mmol) in THF (10 mL) at 3-8° C. After addition, the mixture was stirred at 3° C. for 30 minutes then quenched with sat. Na$_2$CO$_3$ (50 mL). The mixture was diluted with CH$_2$Cl$_2$ (50 mL) and aqueous layer was extracted with CH$_2$Cl$_2$ (3×40 mL). Combined CH$_2$Cl$_2$ solution was washed with brine (35 mL) and dried. The solvent was removed and the residue was purified by chromatography (SiO$_2$, CH$_3$OH:CH$_2$Cl$_2$ 3:97) to give [6-(piperidin-1-ylmethyl)benzofuran-2-yl]methanol (0.9 g, 68% yield): $^1$H NMR (CDCl$_3$) δ 1.41-1.46 (m, 2H), 1.54-1.61 (m, 4H), 2.39 (m, 4H), 3.56 (s, 2H), 4.72 (s, 2H), 6.60 (s, 1H), 7.14-7.17 (dd, J=1.2 and 7.8 Hz, 1H), 7.42-7.47 (m, 2H); $^{13}$C NMR (CDCl$_3$) δ 24.34, 25.83, 54.42, 57.92, 63.95, 103.88, 111.95, 120.36, 124.36, 127.09, 135.02, 155.38, 156.71.

Step 5: Diisopropyl azodicarboxylate (0.8 g, 4.0 mmol) was added to a stirred suspension of triphenylphosphine-polymer bound (3.4 g, 4.3 mmol) in THF (40 mL) at 3-6° C. After stirred at 3° C. for 10 minutes, a solution of methyl 5-amino-4-(4-hydroxy-1-oxoisoindolin-2-yl)-5-oxopentanoate (0.8 g, 2.7 mmol) and [6-(piperidin-1-ylmethyl)benzofuran-2-yl]methanol (0.9 g, 3.5 mmol) in THF (60 mL) was added slowly at 3-6° C. After stirred at 3° C. for 5 minutes, the mixture was stirred at room temperature overnight. The reaction mixture was filtered and solid was washed with CH$_2$Cl$_2$ (30 mL). Filtrate was concentrated and the residue was dissolved in CH$_2$Cl$_2$ (100 mL) and washed with sat. NaHCO$_3$ (40 mL), water (40 mL), brine (40 mL) and dried. The solvent was removed and the residue was purified by chromatography (SiO$_2$, CH$_3$OH:CH$_2$Cl$_2$ 3:97) to give methyl 5-amino-5-oxo-4-(1-oxo-4-((6-piperidin-1-ylmethyl)benzofuran-2-yl)methoxy)isoindolin-2-yl)pentanoate (0.9 g, 64%).

Step 6: A mixture of methyl 5-amino-5-oxo-4-(1-oxo-4-((6-piperidin-1-ylmethyl)benzofuran-2-yl)methoxy)isoindolin-2-yl)pentanoate (0.9 g, 1.7 mmol) and K$_2$CO$_3$ (0.2 g, 1.7 mmol) in DMF (10 mL) was heated at 80° C. oil bath for 2.5 hours. The reaction mixture was cooled and concentrated. Residue was stirred with water (20 mL) and EtOAc (10 mL). Solid was collected and reslurried with hot acetone (10 mL) to give 3-(1-oxo-4-((6-piperidin-1-ylmethyl)benzofuran-2-yl)methoxy)isoindolin-2-yl)piperidine-2,6-dione (0.19 g, 22% yield): mp 216-218° C.; $^1$H NMR (DMSO-d$_6$) δ 1.39-1.49 (m, 6H), 1.95-1.99 (m, 1H), 2.33-2.58 (m, 6H), 2.86-2.94 (m, 1H), 3.53 (s, 2H), 4.25 (d, J=15 Hz, 1H), 4.36 (d, J=18 Hz, 1H), 5.07-5.13 (dd, J=6 and 15 Hz, 1H), 5.41 (s, 2H), 7.08 (s, 1H), 7.22 (d, J=9 Hz, 1H), 7.37 (d, J=6 Hz, 1H), 7.49-7.59 (m, 4H), 10.96 (s, 1H); $^{13}$C NMR (DMSO-d$_6$) δ 22.28, 23.92, 25.47, 31.16, 45.04, 51.55, 53.74, 62.52, 62.70, 107.01, 111.17, 115.09, 115.63, 120.86, 124.05, 126.34, 129.80, 129.93, 133.41, 135.94, 152.41, 152.97, 154.73, 167.88, 170.92, 172.79; Calcd for $C_{28}H_{29}N_3O_5$+0.8 $H_2O$: C, 67.00; H, 6.14; N, 8.37. Found: C, 66.96; H, 5.96; N, 8.03.

5.25 3-(4-((1-Methyl-1H-Benzo[D]Imidazol-2-yl)Methoxy)-1-Oxoisoindolin-2-yl)Piperidine-2,6-Dione

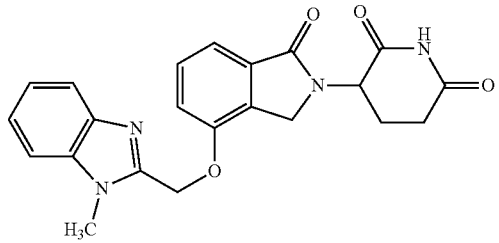 [SMILES: Cn1c(COc2cccc3c2CN(C2CCC(=O)NC2=O)C3=O)nc2ccccc21]

Step 1: A mixture of N-methyl 1,2-phenylenediamine (5.4 g, 44.0 mmol) and glycolic acid (5.0 g, 66.0 mmol) in 4N HCl (50 mL) was refluxed for 45 minutes then cooled to room temperature. The reaction mixture was filtered and filtrate was diluted with water (100 mL). The mixture was cooled in an ice bath with vigorous stirring and neutralized with solid sodium bicarbonate carefully. Solid was collected and recrystallized from 1,4-dioxane (40 mL) to give (1-methyl-1H-benzo[d]imidazol-2-yl)methanol (5.7 g, 80% yield): $^1$H NMR (DMSO-$d_6$) δ 3.82 (s, 3H, N—$CH_3$), 4.70 (d, J=5.7 Hz, 2H, $CH_2O$), 5.75 (t, J=5.7 Hz, 1H, OH), 7.14-7.26 (m, 2H, Ar), 7.50-7.57 (m, 2H, Ar); $^{13}$C NMR (DMSO-$d_6$) δ 29.75, 56.39, 109.83, 118.85, 121.28, 122.01, 136.02, 141.77, 153.90.

Step 2: Diisopropyl azodicarboxylate (1.0 g, 4.9 mmol) was added to a stirred suspension of methyl 5-amino-2-(4-hydroxy-1-oxoisoindolin-2-yl)-5-oxopentanoate (0.7 g, 2.5 mmol), (1-methyl-1H-benzo[d]imidazol-2-yl)methanol (0.6 g, 3.7 mmol) and triphenylphosphine-polymer bound (1.6 g, 4.9 mmol) in THF (150 mL) at room temperature. After addition, mixture was stirred for 2 hours. The reaction mixture was filtered and solid was washed with methylene chloride (30 mL). Filtrate was concentrated and the residue was purified by chromatography (SiO$_2$, CH$_3$OH:CH$_2$Cl$_2$ 3:97) to give methyl 5-amino-2-(4-((1-methyl-1H-benz0[d]imidazol-2-yl)methoxy)-1-oxoisoindolin-2-yl)-5-oxopentanoate (0.7 g, 60%).

Step 3: Potassium t-butoxide/THF (1M, 1.5 mL, 1.5 mmol) was added to a stirred solution of methyl 5-amino-2-(4-((1-methyl-1H-benzo[d]imidazol-2-yl)methoxy)-1-oxoisoindolin-2-yl)-5-oxopentanoate (0.7 g, 1.5 mmol) in THF (30 mL) and DMF (10 mL). After addition, mixture was stirred at room temperature for 2 hours. The reaction mixture was cooled in an ice bath and quenched with water (30 mL). The mixture was stirred with methylene chloride (30 mL) and aqueous layer was extracted with methylene chloride (2×35 mL). Combined organic solution was washed with water (40 mL) and brine (40 mL), and dried. The solvent was removed and the residue was stirred with water (20 mL). Solid was collected and reslurried with ether (10 mL) to give 3-(4-((1-methyl-1H-benzo[d]imidazol-2-yl)methoxy)-1-oxoisoindolin-2-yl)piperidine-2,6-dione (0.3 g, 42%) as a white solid: mp 233-235° C.; $^1$H NMR (DMSO-$d_6$) δ 1.94-1.99 (m, 1H), 2.39-2.59 (m, 2H), 2.86-2.90 (m, 1H), 3.88 (s, 3H), 4.28 (d, J=17.4 Hz, 1H), 4.38 (d, J=17.4 Hz, 1H), 5.06-5.13 (dd, J=5.1 and 13.2 Hz, 1H), 5.57 (s, 2H), 7.22 (dt, J=1.1 and 7.3 Hz, 1H), 7.30 (dt, J=1.3 and 8.1 Hz, 1H), 7.36 (t, J=4.3 Hz, 1H), 7.53 (d, J=3.8 Hz, 2H), 7.58 (d, J=7.7 Hz, 1H), 7.65 (d, J=7.6 Hz, 1H), 10.96 (s, 1H); $^{13}$C NMR (DMSO-$d_6$) δ 22.29, 30.30, 31.13, 44.99, 51.56, 62.87, 110.26, 115.17, 115.76, 119.29, 121.78, 122.74, 129.83, 129.95, 133.40, 135.98, 141.70, 149.16, 152.91, 167.84, 170.88, 172.79; Calcd. For $C_{22}H_{20}N_4O_4$+0.1 $H_2O$: C, 65.05; H, 5.01; N, 13.79. Found: C, 65.01; H, 5.08; N, 13.58.

5.26 4-[2-(2,6-Dioxo-Piperidin-3-yl)-1-Oxo-2,3-Dihydro-1H-Isoindol-4-yloxymethyl]-Piperidine-1-Carboxylic Acid Tert-Butyl Ester

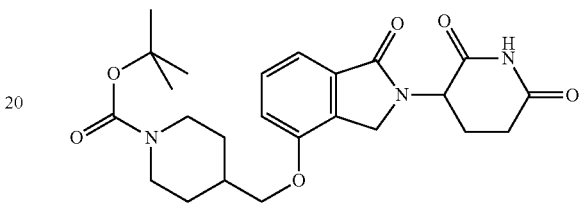

Step 1: Polymer-supported triphenylphosphene (1.6 mmol/g, 1.76 g, 2.19 mmol) was added to a stirred solution of 4-carbamoyl-4-(4-hydroxy-1-oxo-1,3-dihydro-isoindol-2-yl)-butyric acid methyl ester (0.29 g, 1.01 mmol) in THF (15 mL) at 0° C., followed by addition of diisopropyl diazene-1,2-dicarboxylate (0.44 ml, 2.19 mmol). After stirring for 30 minutes, 4-hydroxymethyl-piperidine-1-carboxylic acid tert-butyl ester (0.43 g, 2.00 mmol) was added. The mixture was stirred overnight at room temperature then filtered, washed with methanol (3×10 mL), then with methylene chloride (3×10 mL). The combined filtrate was evaporated in vacuo to give an oil, which was purified on silica gel column (MeOH/CH$_2$Cl$_2$ gradient from 0% to 5% in 60 min) to give 4-[2-(1-carbamoyl-3-methoxycarbonyl-propyl)-1-oxo-2,3-dihydro-1H-isoindol-4-yloxymethyl]-piperidine-1-carboxylic acid tert-butyl ester as a clear oil (0.27 g, 55% yield).

Step 2: Potassium tert-butoxide (0.06 g, 0.55 mmol) was added to a stirred solution of 4-[2-(1-carbamoyl-3-methoxycarbonyl-propyl)-1-oxo-2,3-dihydro-1H-isoindol-4-yloxymethyl]-piperidine-1-carboxylic acid tert-butyl ester (0.27 g, 0.55 mmol) in THF (10 mL) at 0° C. for 10 minutes. The mixture was quenched with 1N HCl (2 ml) and neutralized with saturated sodium bicarbonate (4 ml to pH=8). The mixture was washed with ethyl acetate (3×20 mL). The combined ethyl acetate phases were evaporated and then purified on silica gel column (MeOH/CH$_2$Cl$_2$ gradient from 0% to 5% in 40 min) to give 4-[2-(2,6-dioxo-piperidin-3-yl)-1-oxo-2,3-dihydro-1H-isoindol-4-yloxymethyl]-piperidine-1-carboxylic acid tert-butyl ester as an off-white solid (0.15 g, 60% yield); HPLC: Waters Symmetry C-18, 3.9× 150 mm, 5 μm, 1 mL/min, 240 nm, isocratic at 50/50 in 10 min (acetonitrile/0.1% $H_3PO_4$), 3.81 min (96.5%); mp: 233-235° C.; $^1$H NMR (DMSO-$d_6$) δ 1.07-1.29 (m, 2H, $CH_2$), 1.40 (s, 9H, ($CH_3$)$_3$), 1.71-1.83 (m, 2H, $CH_2$), 1.87-2.06 (m, 2H, CHH, CHH), 2.36-2.47 (m, 1H, CHH), 2.54-2.64 (m, 1H, CHH), 2.66-2.82 (m, 2H, $CH_2$), 2.83-3.01 (m, 1H, CHH), 3.92-4.07 (m, 4H, $CH_2CH_2$), 4.17-4.45 (m, 2H, ArCH$_2$), 5.11 (dd, J=5.1, 13.2 Hz, 1H, NCH), 7.23 (d, J=7.9 Hz, 1H, Ar), 7.30 (d, J=7.4 Hz, 1H, Ar), 7.43-7.53 (m, 1H, Ar), 10.97 (s, 0.1H, NH); $^{13}$C NMR (DMSO-$d_6$) δ 22.39, 28.09, 28.14, 31.20, 35.28, 43.11 (brs due to rotamer), 44.94, 51.55, 71.97, 78.50, 114.51, 114.98, 129.74, 129.84, 133.21, 153.73, 153.89, 168.03, 170.99, 172.83; LCMS MH=358; Anal Calcd for $C_{24}H_{31}N_3O_6+0.1\ H_2O$: C, 62.76; H, 6.85; N, 9.15; Found: C, 62.75; H, 6.92; N, 8.90.

5.27 3-[1-Oxo-4-(Piperidin-4-ylmethoxy)-1,3-Dihydro-Isoindol-2-yl]-Piperidine-2,6-Dione Hydrochloride

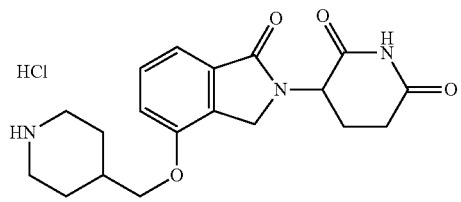 [SMILES: Cl ; O=C1CCC(N2Cc3c(OCC4CCNCC4)cccc3C2=O)C(=O)N1]

Step 1: Polymer-supported triphenylphosphene (1.6 mmol/g, 1.76 g, 2.19 mmol) was added to a stirred solution of 4-carbamoyl-4-(4-hydroxy-1-oxo-1,3-dihydro-isoindol-2-yl)-butyric acid methyl ester (0.29 g, 1.01 mmol) in THF (15 mL) at 0° C., followed by addition of diisopropyl diazene-1,2-dicarboxylate (0.44 ml, 2.19 mmol). After stirring for 30 minutes, 4-hydroxymethyl-piperidine-1-carboxylic acid tert-butyl ester (0.43 g, 2.00 mmol) was added. The mixture was stirred overnight at room temperature then filtered, washed with methanol (3×10 mL), then with methylene chloride (3×10 mL). The combined filtrate was evaporated in vacuo to give an oil, which was purified on silica gel column (MeOH/CH$_2$Cl$_2$ gradient from 0% to 5% in 60 min) to give 4-[2-(1-carbamoyl-3-methoxycarbonyl-propyl)-1-oxo-2,3-dihydro-1H-isoindol-4-yloxymethyl]-piperidine-1-carboxylic acid tert-butyl ester as a clear oil (0.27 g, 55% yield).

Step 2: Potassium tert-butoxide (0.060 g, 0.55 mmol) was added to a stirred solution of 4-[2-(1-carbamoyl-3-methoxycarbonyl-propyl)-1-oxo-2,3-dihydro-1H-isoindol-4-yloxymethyl]-piperidine-1-carboxylic acid tert-butyl ester (0.27 g, 0.55 mmol) in THF (10 mL) at 0° C. for 10 minutes. The mixture was quenched with 1N HCl (2 ml) and neutralized with saturated sodium bicarbonate (4 ml to pH=8). The mixture was washed with ethyl acetate (3×20 mL). The combined ethyl acetate phases were evaporated and then purified on silica gel column (MeOH/CH$_2$Cl$_2$ gradient from 0% to 5% in 40 min) to give 4-[2-(2,6-dioxo-piperidin-3-yl)-1-oxo-2,3-dihydro-1H-isoindol-4-yloxymethyl]-piperidine-1-carboxylic acid tert-butyl ester as an off-white solid (0.15 g, 60% yield); HPLC: Waters Symmetry C-18, 3.9×150 mm, 5 μm, 1 mL/min, 240 nm, isocratic at 50/50 in 10 min (acetonitrile/0.1% H$_3$PO$_4$), 3.81 min (96.5%); mp: 233-235° C.; $^1$H NMR (DMSO-d$_6$) δ 1.07-1.29 (m, 2H, CH$_2$), 1.40 (s, 9H, (CH$_3$)$_3$), 1.71-1.83 (m, 2H, CH$_2$), 1.87-2.06 (m, 2H, CHH, CHH), 2.36-2.47 (m, 1H, CHH), 2.54-2.64 (m, 1H, CHH), 2.66-2.82 (m, 2H, CH$_2$), 2.83-3.01 (m, 1H, CHH), 3.92-4.07 (m, 4H, CH$_2$CH$_2$), 4.17-4.45 (m, 2H, ArCH$_2$), 5.11 (dd, J=5.1, 13.2 Hz, 1H, NCH), 7.23 (d, J=7.9 Hz, 1H, Ar), 7.30 (d, J=7.4 Hz, 1H, Ar), 7.43-7.53 (m, 1H, Ar), 10.97 (s, 1H, NH); $^{13}$C NMR (DMSO-d$_6$) δ 22.39, 28.09, 28.14, 31.20, 35.28, 43.11 (brs due to rotamer), 44.94, 51.55, 71.97, 78.50, 114.51, 114.98, 129.74, 129.84, 133.21, 153.73, 153.89, 168.03, 170.99, 172.83; LCMS MH=358; Anal Calcd for $C_{24}H_{31}N_3O_6+0.1\ H_2O$: C, 62.76; H, 6.85; N, 9.15; Found: C, 62.75; H, 6.92; N, 8.90.

Step 3: 2 M HCl/ether (20 mL) was added to a stirred solution of 4-[2-(2,6-dioxo-piperidin-3-yl)-1-oxo-2,3-dihydro-1H-isoindol-4-yloxymethyl]-piperidine-1-carboxylic acid tert-butyl ester (0.090 g, 0.196 mmol) in dichloromethane (3 mL). The mixture was stirred for three hours and filtered, then dried to give 3-[1-oxo-4-(piperidin-4-ylmethoxy)-1,3-dihydro-isoindol-2-yl]-piperidine-2,6-dione hydrochloride as a white solid (0.076 g, 98% yield); HPLC: Waters Symmetry C-18, 3.9×150 mm, 5 μm, 1 mL/min, 240 nm, isocratic at 9/91 in 10 min (acetonitrile/0.1% H$_3$PO$_4$), 6.22 min (98.0%); mp: 298-300° C.; $^1$H NMR (DMSO-d$_6$) δ 1.43-1.66 (m, 2H, CH$_2$), 1.83-2.20 (m, 3H, CH$_2$, CHH), 2.32-2.46 (m, 1H, CHH), 2.58 (d, J=16.8 Hz, 1H, CHH), 2.80-3.02 (m, 2H, CH$_2$), 3.19-3.44 (m, 2H, CH$_2$), 4.02 (d, J=6.2 Hz, 2H, OCH$_2$), 4.16-4.48 (m, 2H, ArCH$_2$), 5.13 (dd, J=5.1, 13.2 Hz, 1H, NCH), 7.26 (d, J=8.1 Hz, 1H, Ar), 7.32 (d, J=7.4 Hz, 1H, Ar), 7.42-7.55 (m, 1H, Ar), 8.69 (d, J=3.4 Hz, 2H, NH$_2$Cl), 10.99 (s, 1H, NH); $^{13}$C NMR (DMSO-d$_6$) δ 22.49, 25.00, 31.18, 33.00, 42.60, 44.91, 51.55, 71.39, 114.60, 115.13, 129.72, 129.88, 133.22, 153.60, 168.01, 171.02, 172.85; LCMS MH=358; Anal Calcd for $C_{19}H_{24}N_3O_4Cl+1.0\ H_2O$: C, 55.41; H, 6.36; N, 10.20; Cl, 8.61; Found: C, 55.72; H, 6.16; N, 9.82; Cl, 8.69.

5.28 3-[1-Oxo-4-(Tetrahydro-Pyran-3-ylmethoxy)-1,3-Dihydro-Isoindol-2-yl]-Piperidine-2,6-Dione

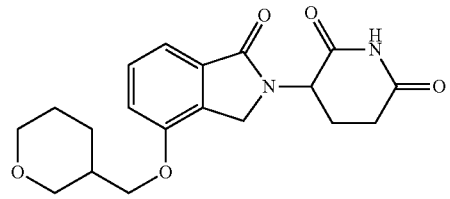 [SMILES: O=C1CCC(N2Cc3c(OCC4CCCOC4)cccc3C2=O)C(=O)N1]

Step 1: Polymer bonded triphenylphosphine (1.6 g, 2.06 mmol, 1.25 mmol/g) was added to the stirred solution of 4-carbamoyl-4-(4-hydroxy-1-oxo-1, 3-dihydro-isoindol-2-yl)-butyric acid methyl ester (300 mg, 1.03 mmol) in THF (10 mL) at 0° C. The resulting mixture was stirred at 0° C. for 10 minutes, followed by the addition of DIAD (412 mg, 2.06 mmol). Fifteen minutes later, (tetrahydro-pyran-3-yl)-methanol (239 mg, 2.06 mmol) was added to the mixture. The reaction was stirred at room temperature for 17 hours and the reaction was complete. The reaction mixture was filtered and the solid was washed with dichloromethane (6×20 mL). The filtrate was concentrated and the residue was purified by ISCO chromatography to give 4-carbamoyl-4-[1-oxo-4-(tetrahydro-pyran-3-ylmethoxy)-1,3-dihydro-isoindol-2-yl]-butyric acid methyl ester as a clear oil (256 mg, 64% yield): LCMS MH=391.

Step 2: KOtBu (72 mg, 0.64 mmol) was added to the stirred solution of 4-carbamoyl-4-[1-oxo-4-(tetrahydro-pyran-3-ylmethoxy)-1,3-dihydro-isoindol-2-yl]-butyric acid methyl ester (250 mg, 0.0.64 mmol) in tetrahydrofuran (18 mL) at 0° C. The mixture was stirred at room temperature for 1 hour and the reaction was added by HCl (aq. 0.1N, 6 mL) followed by the addition of water (10 mL). The mixture was extracted with dichloromethane (2×20 mL). Organic layers were dried by MgSO$_4$ and concentrated under vacuo. The residue was purified by ISCO chromatography and prep HPLC to give 3-[1-oxo-4-(tetrahydro-pyran-3-ylmethoxy)-1,3-dihydro-isoindol-2-yl]-piperidine-2,6-dione as a white solid (36 mg, 16% yield). HPLC: Waters Symmetry C-18, 3.9×150 mm, 5 µm, 1 mL/min, 240 nm, 30/70, (acetonitrile/ 0.1% H$_3$PO$_4$): t$_R$=4.5 (100%); mp: 118-120° C.; $^1$H NMR (DMSO-d$_6$) δ 1.25-1.72 (m, 3H, CH$_2$, CHH), 1.79-1.92 (m, 1H, CHH), 1.92-2.09 (m, 2H, CH$_2$), 2.36-2.48 (m, 1H, CHH), 2.53-2.64 (m, 1H, CHH), 2.74-3.10 (m, 1H, CHH), 3.66-3.81 (m, 1H, CHH), 3.83-4.08 (m, 3H, CH$_2$, CHH), 4.13-4.47 (m, 2H, CH$_2$), 5.11 (dd, J=5.0, 13.1 Hz, 1H, NCH), 7.23 (d, J=7.9 Hz, 1H, Ar), 7.31 (d, J=7.0 Hz, 1H, Ar), 7.43-7.53 (m, 1H, Ar), 10.97 (s, 1H, NH) * two protons are overlapped with DMSO's Me peak and it was confirmed by HMQC; $^{13}$C NMR (DMSO-d$_6$) δ 22.32, 24.59, 25.42, 31.16, 35.42, 44.90, 51.53, 67.48, 69.26, 69.44, 114.45, 115.00, 129.73, 129.81, 133.07, 153.43, 167.98, 170.99, 172.83; LCMS MH=359; Anal. Calcd for C$_{19}$H$_{22}$N$_2$O$_5$+ 0.57 H$_2$O+0.015CH$_2$Cl$_2$+0.04HCOOH: C, 61.56; H, 6.3; N, 7.53; Found: C, 61.16; H, 5.9; N, 7.35.

5.29 3-(4-((1-Methyl-1H-Indazol-3-yl)Methoxy)-1-Oxoisoindolin-2-yl)Piperidine-2,6-Dione

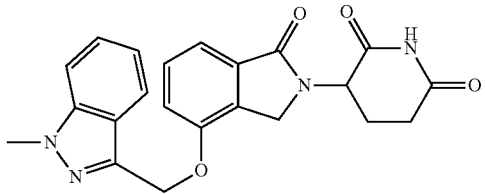 [SMILES: Cn1nc(COc2cccc3c2CN(C2CCC(=O)NC2=O)C3=O)c2ccccc21]

Step 1: Iodomethane (10.9 g, 77.1 mmol) was added slowly to a stirred mixture of 1H-indazole-3-carboxylic acid (5.0 g, 30.8 mmol) and potassium carbonate (12.8 g, 92.5 mmol) in DMF (30 mL). The resulting mixture was heated at 50° C. oil bath for 4 hours. The reaction mixture was cooled and poured into ice water (200 mL). The mixture was extracted with EtOAc (4×50 mL) and the combined EtOAc solution was washed with water (3×40 mL) and brine (40 mL), and dried (MgSO$_4$). The solvent was removed and the residue was purified by chromatography (SiO$_2$, EtOAc: Hexane 2:8) to give methyl 1-methyl-1H-indazole-3-carboxylate (3.9 g, 66% yield): $^1$H NMR (DMSO-d$_6$) δ 3.93 (s, 3H), 4.17 (s, 3H), 7.33-7.38 (ddd, J=1.8, 6.9 and 8.1 Hz, 1H), 7.48-7.53 (ddd, J=1.1, 6.9 and 8.4 Hz, 1H), 7.77-7.80 (td, J=0.8 and 8.5 Hz, 1H), 8.06-8.09 (td, J=1.0 and 8.2 Hz, 1H); $^{13}$C NMR (DMSO-d$_6$) δ 36.26, 51.54, 110.75, 120.99, 122.75, 123.10, 126.61, 133.25, 140.64, 162.28.

Step 2: A solution of methyl 1-methyl-1H-indazole-3-carboxylate (3.8 g, 20.0 mmol) in ether (100 mL) was cooled to 5° C. A solution of LiBH$_4$/THF (2M, 15.0 mL, 30 mmol) was added slowly at 5-10° C. The mixture was stirred at room temperature for 2.5 hours and then cooled in an ice bath and quenched with water (30 mL). The aqueous layer was extracted with CH$_2$Cl$_2$ (50 mL) and combined organic solution was washed with water (2×40 mL) and brine (40 mL), and dried. The solvent was removed and the residue was purified by chromatography (SiO$_2$, EtOAc:Hexane 4:6) to give (1-methyl-1H-indazol-3-yl)-methanol (2.8 g, 86% yield): $^1$H NMR (DMSO-d$_6$) δ 3.98 (s, 3H), 4.79 (d, J=6.0 Hz, 2H), 5.24 (t, J=6.0 Hz, 1H), 7.09-7.14 (dt, J=0.9 and 6.0 Hz, 1H), 7.35-7.40 (dt, J=1.2 and 6.0 Hz, 1H), 7.54-7.58 (dt, J=9.0 and 0.6 Hz, 1H), 7.83-7.86 (dt, J=9.0 and 0.9 Hz, 1H); $^{13}$C NMR (DMSO-d$_6$) δ 34.96, 56.43, 109.39, 119.71, 120.72, 121.90, 125.91, 140.58, 144.42.

Step 3: Diisopropyl azodicarboxylate (1.3 g, 6.4 mmol) was added to a stirred suspension of methyl 5-amino-4-(4-hydroxy-1-oxoisoindolin-2-yl)-5-oxopentanoate (0.9 g, 3.2 mmol), (1-methyl-1H-indazol-3-yl)-methanol (0.8 g, 4.8 mmol), and triphenylphosphine-polymer bound (2.1 g, 6.4 mmol) in THF (60 mL) at 5-8° C. After addition, the mixture was stirred at room temperature overnight. The reaction mixture was filtered and solid was washed with CH$_2$Cl$_2$ (30 mL). Filtrate was concentrated and the residue was purified by chromatography (SiO$_2$, CH$_3$OH:CH$_2$Cl$_2$ 3:97) to give methyl 5-amino-4-(4-((1-methyl-1H-indazol-3-yl) methoxy)-1-oxoisoindolin-2-yl)-5-oxopentanoate (0.5 g, 36%).

Step 4: A solution of potassium t-butoxide/THF (1M, 0.9 mL, 0.9 mmol) was added to a stirred solution of methyl 5-amino-4-(4-((1-methyl-1H-indazol-3-yl)methoxy)-1-oxoisoindolin-2-yl)-5-oxopentanoate (0.4 g, 0.9 mmol) in THF (30 mL) at 5° C. The reaction mixture was stirred at 5° C. for 5 minutes then warmed to room temperature for 2 hours. The reaction mixture was cooled in an ice bath and quenched with sat. NH$_4$Cl (10 mL). The mixture was diluted with CH$_2$Cl$_2$ (50 mL) and water (20 mL). The aqueous layer was extracted with CH$_2$Cl$_2$ (30 mL) and combined CH$_2$Cl$_2$ solution was washed with water (40 mL) and brine (40 mL), and dried. The solvent was removed and the residue was purified by chromatography (SiO$_2$, CH$_3$OH:CH$_2$Cl$_2$ 3:97) to give 3-(4-((1-methyl-1H-indazol-3-ylmethoxy)-1-oxoisoindolin-2-yl)-piperidine-2,6-dione (0.2 g, 51% yield): mp 14-142° C.; $^1$H NMR (DMSO-d$_6$) δ 1.93-1.97 (m, 1H), 2.38-2.57 (m, 2H), 2.84-2.88 (m, 1H), 4.05 (s, 3H), 4.21 (d, J=17.4 Hz, 1H), 4.31 (d, J=17.4 Hz, 1H), 5.04-5.10 (dd, J=4.8 and 13.2 Hz, 1H), 5.56 (s, 2H), 7.14-7.19 (dt, J=0.6 and 6.9 Hz, 1H), 7.31-7.34 (dd, J=3.9 and 4.8 Hz, 1H), 7.30-7.45 (dt, J=3.9 and 4.8 Hz, 1H), 7.39-7.45 (dt, J=0.9 and 6.6 Hz, 1H), 7.50-7.52 (m, 2H), 7.63 (d, J=8.7 Hz, 1H), 7.83 (d, J=7.2 Hz, 1H), 10.93 (s, 1H); $^{13}$C NMR (DMSO-d$_6$) δ 22.24, 31.15, 35.32, 45.08, 51.56, 63.13, 109.88, 115.10, 115.32, 120.06, 120.67, 122.15, 126.28, 129.78, 129.90, 133.30, 139.14, 140.58, 153.45, 167.92, 170.91, 172.77; Calcd for C$_{22}$H$_{20}$N$_4$O$_4$: C, 65.34; H, 4.98; N, 13.85. Found: C, 64.96; H, 4.96; N, 13.74.

5.30 3-(4-((3-Methylbenzofuran-2-yl)Methoxy)-1-Oxoisoindolin-2-yl)-Piperidine-2,6-Dione

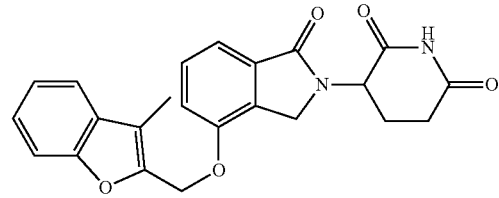 [SMILES: Cc1c(COc2cccc3c2CN(C2CCC(=O)NC2=O)C3=O)oc2ccccc12]

Step 1: Borane/THF (1M, 22.7 mL, 22.7 mmol) was added slowly to a stirred solution of 3-methylbenzofuran-2-carboxylic acid (2 g, 11.4 mmol) in THF (30 mL) at 5-7° C. After addition, mixture was stirred at 5° C. for 10 minutes then warmed to room temperature for 5 hours. The reaction mixture was cooled in an ice bath and quenched with water (15 mL) slowly. The mixture was diluted with CH$_2$Cl$_2$ (35 mL) and water (15 mL) and aqueous layer was extracted with CH$_2$Cl$_2$ (2×35 mL). Combined CH$_2$Cl$_2$ solution was washed with sat. NaHCO$_3$ (25 mL), water (25 mL) and brine (25 mL), and dried. The solvent was removed and the residue was purified by chromatography (SiO$_2$, CH$_2$Cl$_2$) to give (3-methyl-benzofuran-2-yl)-methanol (1.4 g 78%); $^1$H NMR (DMSO-d$_6$) δ 2.21 (s, 3H), 4.56 (d, J=5.7 Hz, 2H), 5.29 (t, J=5.7 Hz, 1H), 7.20-7.31 (m, 2H), 7.47-7.56 (m, 2H); $^{13}$C NMR (DMSO-d$_6$) δ 7.46, 53.83, 110.71, 111.33, 119.48, 122.20, 124.14, 129.51, 152.98, 153.27.

Step 2: Diisopropyl azodicarboxylate (1.3 g, 6.2 mmol) was added to a stirred suspension of methyl 5-amino-4-(4-hydroxy-1-oxo-isoindolin-2-yl)-5-oxo-pentanoate (0.9 g, 3.1 mmol), (3-methyl-benzofuran-2-yl)-methanol (0.8 g, 4.6 mmol) and triphenylphosphine-polymer bound (2.1 g, 6.2 mmol) in THF (60 mL) at 5-8° C. After addition, the mixture was stirred at room temperature overnight. The reaction mixture was filtered and solid was washed with CH$_2$Cl$_2$ (30 mL). Filtrate was concentrated and the residue was purified by chromatography (SiO$_2$, CH$_3$OH:CH$_2$Cl$_2$ 3:97) to give methyl 5-amino-4-(4-((3-methyl-benzofuran-2-yl) methoxy)-1-oxoisoindolin-2-yl)-oxopentanoate (1.0 g, 72%).

Step 3: A solution of potassium t-butoxide/THF (1M, 2.2 mL, 2.2 mmol) was added slowly to a stirred solution of methyl 5-amino-4-(4-((3-methyl-benzofuran-2-yl) methoxy)-1-oxoisoindolin-2-yl)-5-oxopentanoate (1.0 g, 2.2 mmol) in THF (30 mL) at 5° C. The mixture was stirred at 5° C. for 5 minutes then warmed to room temperature for 2 hours. The reaction mixture was cooled in an ice bath and quenched with 1N HCl (10 mL). The mixture was diluted with CH$_2$Cl$_2$ (50 mL) and water (10 mL). The aqueous layer was extracted with CH$_2$Cl$_2$ (30 mL) and combined CH$_2$Cl$_2$ solution was washed with water (40 mL) and brine (40 mL), and dried. The solvent was removed and the residue was purified by chromatography (SiO$_2$, CH$_3$OH:CH$_2$Cl$_2$ 3:97) to give 3-(4-((3-methylbenzofuran-2-yl)methoxy)-1-oxoisoindolin-2-yl)piperidine-2,6-dione (0.5 g, 60% yield): mp 210-212° C.; $^1$H NMR (DMSO-d$_6$) δ 1.96-1.98 (m, 1H), 2.28 (s, 3H), 2.27-2.57 (m, 2H), 2.83-2.90 (m, 1H), 4.23 (d, J=17.4 Hz, 1H), 4.33 (d, J=17.7 Hz, 1H), 5.06-5.12 (dd, J=5.1 and 13.2 Hz, 1H), 5.40 (s, 2H), 7.25-7.37 (m, 3H), 7.45-7.48 (dd, J=0.6 and 8.1 Hz, 1H), 7.51-7.56 (dt, J=0.9 and 8.1 Hz, 2H), 7.61-7.63 (dd, J-0.9 and 7.8 Hz, 1H), 10.94 (s, 1H); $^{13}$C NMR (DMSO-d$_6$) δ 7.55, 22.25, 31.16, 45.04, 51.54, 60.93, 111.04, 115.23, 115.64, 119.98, 122.60, 125.08, 128.95, 129.81, 130.00, 133.38, 147.64, 153.17, 153.68, 167.89, 170.82, 170.91, 172.78; Calcd for C$_{23}$H$_{20}$N$_2$O$_5$: C, 68.31; H, 4.98; N, 6.93. Found: C, 68.09; H, 5.00; N, 6.81.

5.31 3-(1-Oxo-4-(Pyridine-2-ylmethoxy)Isoindolin-2-yl)Piperidine-2,6-Dione

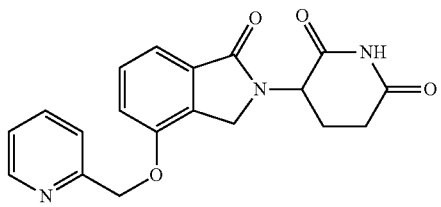 [SMILES: O=C1CCC(N2Cc3c(OCc4ccccn4)cccc3C2=O)C(=O)N1]

To a mixture of triphenylphosphine polymer supported (0.63 g, 1.88 mmol) and methyl 5-amino-4-(4-hydroxy-1-oxoisoindolin-2-yl)-5-oxopentanoate (0.25 g, 0.86 mmol) in THF (15 mL) cooled down to 0° C., was added drop wise DIAD (0.37 ml, 1.88 mmol). 3-Pyridyl carbinol (0.10 mL, 1.03 mmol) was then added. The reaction mixture was stirred at 0° C. for 1 hour and then at room temperature overnight. The reaction mixture was then filtered through celite. Celite was washed with ethyl acetate (100 mL). The ethyl acetate phase was washed with water, dried with MgSO$_4$, and solvent was evaporated. The residue was purified by ISCO flash (40 g column, gradient MeOH/CH$_2$Cl$_2$ 0/100 to 5/95 in 30 min, eluting product at 5/95). The solvent was evaporated and crude product was carried over to next step.

To the crude product stirred in THF (10 mL) and cooled down to 0° C., was added KOtBu (0.064 g, 0.57 mmol) and the reaction mixture was stirred for 1 hour and 30 minutes. Acetic acid (5 drops) was added to reaction mixture. Ethyl acetate (100 mL) was added and it was washed with a saturated solution of sodium bicarbonate (2×100 mL) and brine (100 mL), and dried (MgSO$_4$). After filtration of the drying agent, solvent was concentrated down to give 3-(1-oxo-4-(pyridine-2-ylmethoxy)isoindolin-2-yl)piperidine 2,6-dione as a white solid (0.13 g, 43% yield): HPLC: Waters XTerra RP18, 3.9×150 mm, 5 μm, 1 mL/min, 240 nm, 25/75 acetonitrile/0.1% HCOONH4, 3.58 min (98.63%); mp: 235-237° C.; 1H NMR (DMSO-d6) δ 1.86-2.16 (m, 1H, CHH), 2.18-2.47 (m, 1H, CHH), 2.53-2.70 (m, 1H, CHH), 2.78-3.06 (m, 1H, CHH), 4.16-4.35 (m, 1H, CHH), 4.36-4.52 (m, 1H, CHH), 5.11 (dd, J=5.0, 13.1 Hz, 1H, CH), 5.31 (s, 2H, CH2), 7.36 (dd, J=4.3, 7.7 Hz, 2H, Ar), 7.41-7.69 (m, 2H, Ar), 7.93 (d, J=7.7 Hz, 1H, Ar), 8.65 (d, J=49.3 Hz, 2H, Ar), 10.97 (s, 1H, NH); 13C NMR (DMSO-d6) δ 22.33, 31.16, 45.03, 51.56, 67.25, 114.97, 115.47, 123.62, 129.83, 130.02, 132.25, 133.36, 135.69, 148.94, 149.19, 153.23, 167.93, 170.93, 172.81; LCMS MH=352; Anal. Calcd for C$_{19}$H$_{17}$N$_3$O$_4$+0.4 H2O: C, 63.64; H, 5.00; N, 11.72; Found: C, 63.34; H, 5.12; N, 11.48.

5.32 3-(4-((2-Methylisoindolin-5-yl)Methoxy)-1-Oxoisoindolin-2-yl)-Piperidine-2,6-Dione

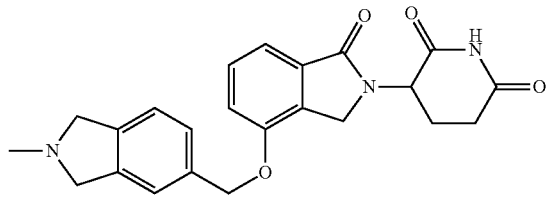 [SMILES: CN1Cc2ccc(COc3cccc4c3CN(C3CCC(=O)NC3=O)C4=O)cc2C1]

Step 1: A solution of LiAlH$_4$/THF (1 M, 24 mL, 24 mmol) was added slowly to a stirred solution of 5-hydroxymethyl-1,3-dihydro-isoindole-2-carboxylic acid tert-butyl ester (3.0 g, 12.0 mmol) in THF (30 mL) at 5° C. After addition, the reaction mixture was warmed slowly to reflux for 2 hours. The reaction mixture was cooled in an ice bath and quenched with water (20 mL). The mixture was diluted with EtOAc (25 mL) and filtered through celite. Filtrate was concentrated and the residue was dissolved in EtOAc (100 mL). EtOAc solution was washed with water (2×25 mL) and brine (25 mL), and dried. The solvent was removed to give (2-methyl-2,3-dihydro-1H-isoindol-5-yl)-methanol (1.2 g, 62% yield): $^1$H NMR (CDCl$_3$) δ 2.55 (s, 3H), 3.76 (s, 2H), 3.85 (s, 2H), 4.10 (b, 1H), 4.55 (s, 2H), 6.96 (s, 1H), 7.04-7.10 (m, 2H).

Step 2: Diisopropyl azodicarboxylate (0.9 g, 4.6 mmol) was added slowly to a stirred suspension of triphenylphosphine-polymer bound (3.9 g, 4.9 mmol) in THF (40 mL) at 3-5° C. After stirred at 3° C. for 10 minutes, a solution of methyl 5-amino-4-(4-hydroxy-1-oxoisoindolin-2-yl)-5-oxopentanoate (0.9 g, 3.1 mmol) and (2-methyl-2,3-dihydro-1H-isoindol-5-yl)-methanol (0.7 g, 4.0 mmol) in THF (60 mL) was added slowly at 3-6° C. The reaction mixture was stirred at 3° C. for 5 minutes then warmed to room temperature and stirred overnight. The reaction mixture was filtered and solid washed with CH₂Cl₂ (30 mL). Filtrate was concentrated and the residue was dissolved in CH₂Cl₂ (100 mL). CH₂Cl₂ solution was washed with sat. NaHCO₃ (40 mL), water (2×30 mL), and brine (30 mL), and dried. The solvent was removed and the residue was purified by chromatography (SiO₂, CH₃OH:CH₂Cl₂ 3:97) to give methyl 5-amino-4-(4-((2-methylisoindolin-5-yl)methoxy)-1-oxoisoindolin-2-yl)-5-oxopentanoate (0.5 g, 39% yield): ¹H NMR (CDCl₃) δ 2.14-2.46 (m, 4H), 2.60 (s, 3H), 3.63 (s, 3H), 3.92 (s, 4H), 4.34-4.48 (m, 2H), 4.88-4.92 (dd, J=3.3 and 8.7 Hz, 1H), 5.12 (s, 2H), 5.56 (s, 1H), 6.34 (s, 1H), 7.05-7.08 (dd, J=1.5 and 6.9 Hz, 1H), 7.22-7.26 (m, 3H), 7.36-7.44 (m, 2H).

Step 3: A mixture of methyl 5-amino-4-(4-((2-methylisoindolin-5-yl)methoxy)-1-oxo-isoindolin-2-yl)-5-oxopentanoate (0.3 g, 0.6 mol) and K₂CO₃ (0.09 g, 0.6 mmol) in DMF (10 mL) was heated at 80° C. oil bath for 3 hours. The reaction mixture was cooled and concentrated and the residue was stirred with water (20 mL). Solid was collected and reslurried with acetone (10 mL) to give 3-(4-((2-methylisoindolin-5-yl)methoxy)-1-oxoisoindolin-2-yl)piperidine-2,6-dione (0.2 g, 66% yield): mp 262-264° C.; ¹H NMR (DMSO-d₆) δ 1.97-1.99 (m, 1H), 2.41-2.59 (m, 5H), 2.91 (m, 1H), 3.80 (s, 4H), 4.27 (d, J=17.7 Hz, 1H), 4.37 (d, J=17.7 Hz, 1H), 5.07-5.13 (dd, J=5.1 and 13.2 Hz, 1H), 5.21 (s, 2H), 7.22-7.51 (m, 6H), 10.96 (s, 1H); ¹³C NMR (DMSO-d₆) δ 22.31, 31.16, 41.83, 45.08, 51.56, 60.01, 60.13, 69.65, 115.00, 115.17, 121.54, 122.02, 126.25, 129.77, 129.93, 133.28, 134.96, 140.64, 141.08, 153.46, 167.98, 170.96, 172.81; Calcd for C₂₃H₂₃N₃O₄+0.4 H₂O: C, 66.94; H, 5.81; N, 10.18. Found: C, 66.80; H, 5.52; N, 10.14.

5.33 3-(4-((4-(Morpholinomethyl)Thiazol-2-yl)Methoxy)-1-Oxoisoindolin-2-yl)Piperidine-2,6-Dione

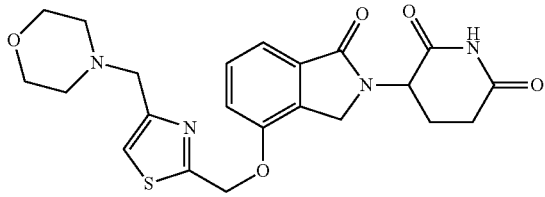 [SMILES: O=C1CCC(N2Cc3c(OCc4nc(CN5CCOCC5)cs4)cccc3C2=O)C(=O)N1]

Step 1: The mixture of ethyl 2-amino-2-thioxoacetate (2 g, 15.02 mmol) and 1,3-dichloropropan-2-one (2.193 g, 17.27 mmol) in toluene (20 mL) was heated under reflux for 3 hours. The mixture was cooled to room temperature, ethyl acetate (50 mL) was added. The mixture was washed with saturated aqueous NaHCO₃ (30 mL) and brine (30 mL), and dried over MgSO₄. The solvent was evaporated and the product was purified by ISCO (120 g silica gel column, EtOAc/hexanes gradient from 0% to 20% in 30 min) to give ethyl 4-(chloromethyl)thiazole-2-carboxylate as a yellow oil (2.07 g, 67% yield); ¹H NMR (CHLOROFORM-d) 1.45 (t, J=7.2 Hz, 3H, CH₃), 4.50 (q, J=7.1 Hz, 2H, CH₂), 4.78 (s, 2H, CH₂), 7.64 (s, 1H, Ar).

Step 2: To a solution of ethyl 4-(chloromethyl)thiazole-2-carboxylate (1.5 g, 7.29 mmol) in acetonitrile (30 ml) were added morpholine (1.27 g, 14.59 mmol) and triethyl amine (2.03 ml, 14.59 mmol). The mixture was stirred at room temperature overnight. The solvent was removed under vacuum, the residue was dissolved in ethyl acetate (100 mL), washed with saturated aqueous sodium bicarbonate (2×20 ml), water (2×50 mL), brine (30 ml), and dried over MgSO₄. The solvent was removed to give ethyl 4-(morpholinomethyl)thiazole-2-carboxylate (1.72 g, 92% yield); ¹H NMR (CHLOROFO-RM-d) δ 1.45 (t, J=7.1 Hz, 3H, CH₃), 2.47-2.66 (m, 4H, CH₂, CH₂), 3.68-3.78 (m, 4H, CH₂, CH₂), 3.80 (s, 2H, CH₂), 4.49 (q, J=7.1 Hz, 2H, CH₂), 7.53 (s, 1H, Ar).

Step 3: To a solution of ethyl 4-(morpholinomethyl)thiazole-2-carboxylate (0.8 g, 3.12 mmol) in THF (10 ml) was slowly added a solution of Diisobutylaluminium hydride (1 M in toluene, 9.36 mL, 9.36 mmol) at 0° C. The mixture was stirred at room temperature overnight. A solution of Rochelle's salt (1.0 M, 50 ml) and ethyl acetate (50 ml) were added. The resulting suspension was stirred at room temperature for 2 hours. The clear phase separation was achieved. The organic phase was separated and the aqueous phase was extracted with ethyl acetate (3×40 ml). The combined organic layers were washed with saturated aqueous NaHCO₃ (5 mL) and brine, dried over MgSO₄, and concentrated to give (4-(morpholinomethyl)thiazol-2-yl)methanol (600 mg, 90% yield); ¹H NMR (CHLOROFORM-d) δ 2.44-2.63 (m, 4H, CH₂, CH₂), 3.64 (s, 2H, CH₂), 3.71-3.81 (m, 4H, CH₂, CH₂), 4.95 (s, 2H, CH₂), 7.12 (s, 1H, Ar).

Step 4: Polymer-supported triphenylphosphine (1.6 mmol/g, 4.13 g, 6.61 mmol) was added to a stirred suspension of methyl 5-amino-4-(4-hydroxy-1-oxoisoindolin-2-yl)-5-oxopentanoate (966 mg, 3.31 mmol) in THF (40 mL) at 0° C., followed by diisopropyl azodicarboxylate (1.34 g, 6.61 mmol). After stirring for 10 minutes, (4-(morpholinomethyl)thiazol-2-yl)methanol (850 mg, 3.97 mmol) was added. The mixture was stirred at room temperature overnight and filtered. The resin was rinsed with dichloromethane and methanol (2×50 ml each wash). The combined filtrates and washes were concentrated and purified by ISCO (80 g silica gel column, MeOH/CH₂Cl₂ gradient from 0% to 5% in 40 min) to give methyl 5-amino-4-(4-((4-(morpholinomethyl)thiazol-2-yl)methoxy)-1-oxoisoindolin-2-yl)-5-oxopentanoate (360 mg, 22% yield); ¹H NMR (DMSO-d₆) δ 1.98-2.34 (m, 4H, CH₂, CH₂), 2.34-2.46 (m, 4H, CH₂, CH₂), 3.50 (s, 3H, CH₃), 3.53-3.59 (m, 4H, CH₂, CH₂), 3.60 (s, 2H, CH₂), 4.33-4.65 (m, 2H, CH₂), 4.74 (d, J=5.5 Hz, 1H, CH), 5.55 (s, 2H, CH₂), 7.20 (s, 1H, NHH), 7.35 (t, J=7.2 Hz, 2H, Ar), 7.44-7.57 (m, 2H, Ar), 7.61 (s, 1H, NHH).

Step 5: To a solution of methyl 5-amino-4-(4-((4-(morpholinomethyl)thiazol-2-yl)methoxy)-1-oxoisoindolin-2-yl)-5-oxopentanoate (320 mg, 0.65 mmol) in THF (10 mL) was added potassium tert-butoxide (73 mg, 0.65 mmol) at 0° C. The formed mixture was warmed to room temperature and stirred for 2 hours. The reaction was quenched with acetic acid (0.5 mL). The solvent was removed under vacuum. The residue was partitioned between ethyl acetate (20 mL) and aqueous saturated sodium bicarbonate (10 mL). The organic phase was washed with brine and dried over magnesium sulfate. The solvent was evaporated and the crude was reslurried with acetonitrile (4 mL) to give 3-(4-((4-(morpholinomethyl)thiazol-2-yl)methoxy)-1-oxoisoindolin-2-yl)piperidine-2,6-dione as a white solid (200 mg, 67% yield); mp: 218-220° C.; ¹H NMR (DMSO-d₆) δ 1.89-2.05 (m, 1H, CHH), 2.42 (d, J=4.5 Hz, 4H, CH₂), 2.44-2.49 (m, 1H, CHH), 2.55 (br. s, 1H, CHH), 2.82-3.08 (m, 1H, CHH), 3.57 (dd, J=5.2, 9.7 Hz, 6H, CH₂, CH₂, CH₂), 4.18-4.55 (m, 2H, CH₂), 5.12 (dd, J=5.0, 13.1 Hz, 1H, CH), 5.56 (s, 2H, CH₂), 7.38 (dd, J=5.6, 7.5 Hz, 2H, Ar), 7.45-7.65 (m, 2H, Ar), 10.98 (s, 1H, NH); ¹³C NMR (DMSO-d$_6$) δ 22.31, 31.18, 45.03, 51.62, 52.97, 57.52, 66.10, 66.93, 115.47, 115.99, 118.09, 129.86, 129.99, 133.46, 152.71, 152.88, 165.07, 167.81, 170.93, 172.81; LCMS MH=457; HPLC: Waters Xterra C-18, 3.9×150 mm, 5 μm, 1 mL/min, 240 nm, Gradient (CH$_3$CN/0.1% HCOONH$_4$) 5/95 to 95/5 in 5 min, 95/5 10 min: t$_R$=3.95 (99.07%); Anal. Calcd for C$_{22}$H$_{24}$N$_4$O$_5$S: C, 57.88; H, 5.30; N, 12.27; Found: C, 57.64; H, 5.36; N, 12.14.

5.34 1-{4-[2-(2,6-Dioxo-Piperidin-3-yl)-1-Oxo-2,3-Dihydro-1H-Isoindol-4-yl Oxy Methyl]-Benzyl}-Pyrrolidine-2-Carboxylic Acid

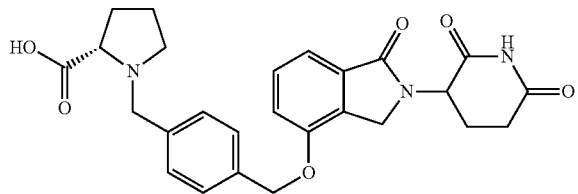 [SMILES: O=C1CCC(N2Cc3c(OCc4ccc(CN5CCC[C@H]5C(=O)O)cc4)cccc3C2=O)C(=O)N1]

Step 1: To the stirred solution of methyl 5-amino-4-(4-(4-(bromomethyl)benzyloxy)-1-oxoisoindolin-2-yl)-5-oxopentanoate (900 mg, 1.89 mmol) in Acetonitrile (18 mL) was added (S)-tert-butyl pyrrolidine-2-carboxylate (357 mg, 2.08 mmol) and DIPEA (0.661 ml, 3.79 mmol). The resulting yellow solution was stirred at room temperature over night and the reaction was complete. The reaction mixture was concentrated and dissolved in DCM (30 mL). The solution was washed by NaHCO$_3$ (aq, sat., 15 mL). Organic layer was dried by MgSO$_4$ and concentrated to give crude 1-{4-[2-(1-Carbamoyl-3-methoxycarbonyl-propyl)-1-oxo-2,3-dihydro-1H-isoindol-4-yloxymethyl]-benzyl}-pyrrolidine-2-carboxylic acid tert-butyl ester as a light brown oil (1.23 g). The compound was used in the next step without further purification: LCMS MH=566.

Step 2: To the stirred solution of (2S)-tert-butyl 1-(4-((2-(1-amino-5-methoxy-1,5-dioxopentan-2-yl)-1-oxoisoindolin-4-yloxy)methyl)benzyl)pyrrolidine-2-carboxylate (1.071 g, 1.89 mmol) in Tetrahydrofuran (18 ml) was added Potassium t-butyloxide (0.212 g, 1.89 mmol) in one portion at 0° C. The solution turned to yellow immediately. The mixture was stirred at 0° C. for 10 min and room temperature for 1 hr before the reaction mixture was diluted with DCM (70 mL). The mixture was acidified by HCl (1N, aq, 3 mL) and then basified with NaHCO$_3$ (aq, sat., 3 mL). The mixture was added by brine (15 mL) and extracted. The aqueous layer was extracted with DCM (25 mL). Organic layers were combined and dried over MgSO$_4$. The mixture was filtered and concentrated to give a white solid. The white solid was stirred in DCM (2 mL) and ether (40 mL) overnight and filtered to give 1-{4-[2-(2,6-Dioxo-piperidin-3-yl)-1-oxo-2,3-dihydro-1H-isoindol-4-yloxymethyl]-benzyl}-pyrrolidine-2-carboxylic acid tert-butyl ester as a white solid (700 mg, 69% yield). The filtrate was concentrated to give second crop of 1-{4-[2-(2,6-Dioxo-piperidin-3-yl)-1-oxo-2,3-dihydro-1H-isoindol-4-yloxymethyl]-benzyl}-pyrrolidine-2-carboxylic acid tert-butyl ester with some impurities as an off white solid (301 mg, 30% yield): $^1$H NMR (DMSO-d$_6$) δ 1.38 (s, 9H, CH$_3$, CH$_3$, CH$_3$), 1.62-1.88 (m, 3H, CHH, CH$_2$), 1.91-2.10 (m, 2H, CH$_2$), 2.29-2.48 (m, 2H, CHH, CHH), 2.52-2.64 (m, 2H, CHH, CHH), 2.75-3.00 (m, 2H, CHH, CHH), 3.06-3.21 (m, 1H, CHH), 3.45-3.59 (m, 1H, CHH), 3.89 (d, J=13.0 Hz, 1H, CHH), 4.18-4.48 (m, 2H, CHH, CHH), 5.11 (dd, J=5.1, 13.2 Hz, 1H, CHH), 5.22 (s, 2H, CH$_2$), 7.32 (d, J=7.6 Hz, 4H, Ar), 7.39-7.54 (m, 3H, Ar), 10.97 (s, 1H, NH); LCMS MH=534.

Step 3: To the stirred solution of (2S)-tert-butyl 1-(4-((2-(2,6-dioxopiperidin-3-yl)-1-oxoisoindolin-4-yloxy)methyl)benzyl)pyrrolidine-2-carboxylate (620 mg, 1.16 mmol) in DCM (5 ml) was added hydrogen chloride, 2M in diethyl ether (5.81 ml, 11.62 mmol). The reaction mixture was stirred at room temperature for 2 days and the reaction was complete.

The reaction mixture was concentrated and the residue was purified by ISCO chromatography and prep HPLC to give 1-{4-[2-(2,6-Dioxo-piperidin-3-yl)-1-oxo-2,3-dihydro-1H-isoindol-4-yloxy methyl]-benzyl}-pyrrolidine-2-carboxylic acid (170 mg, 31% yield) as an off white solid: HPLC: Waters Symmetry C-18, 3.9×150 mm, 5 μm, 1 mL/min, 240 nm, 20/80 (CH$_3$CN/0.1% H$_3$PO$_4$): t$_R$=3.81 (96.0%); mp: 260-262° C.; $^1$H NMR (DMSO-d$_6$) δ 1.66-1.81 (m, 1H, CHH), 1.82-2.09 (m, 3H, CHH, CHH, CHH), 2.21 (dq, J=8.5, 12.7 Hz, 1H, CHH), 2.36-2.50 (m, 1H, CHH), 2.57-2.69 (m, 1H, CHH), 2.80-3.02 (m, 1H, CHH), 3.24-3.38 (m, 1H, CHH), 3.47-3.56 (m, 1H, CHH), 4.04 (d, J=12.8 Hz, 1H, CHH), 4.04-4.04 (m, 1H, CHH), 4.21-4.36 (m, 2H, CHH, CHH), 4.47 (d, J=17.6 Hz, 1H, CHH), 5.11 (dd, J=5.1, 13.2 Hz, 1H, CHH), 5.28 (s, 2H, CH$_2$), 7.32-7.41 (m, 2H, Ar), 7.47-7.58 (m, 5H, Ar); $^{13}$C NMR (DMSO-d$_6$) δ 22.33, 22.72, 28.52, 31.18, 45.10, 51.56, 52.81, 56.90, 65.76, 69.32, 114.99, 115.25, 127.67, 129.38, 129.80, 129.95, 133.30, 135.95, 136.03, 153.45, 167.97, 170.96, 172.35, 172.81; LCMS MH=478; Anal. Calcd for C$_{26}$H$_{27}$N$_3$O$_6$+3H$_2$O+0.2CH$_2$Cl$_2$: C, 57.37; H, 6.14; N, 7.66; Found: C, 57.08; H, 5.74; N, 7.36.

5.35 3-[1-Oxo-4-(4-[1,2,3]Triazol-1-ylmethyl-Benzyloxy)-1,3-Dihydro-Isoindol-2-yl]-Piperidine-2,6-Dione

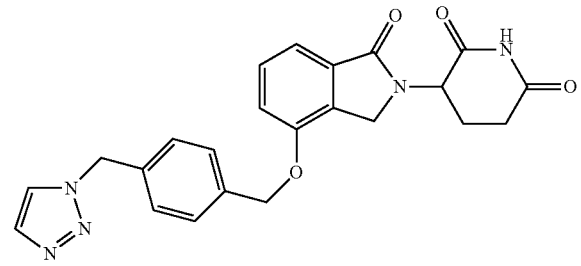 [SMILES: O=C1CCC(N2Cc3c(OCc4ccc(Cn5ccnn5)cc4)cccc3C2=O)C(=O)N1]

Step 1: To the stirred solution of 1H-1,2,3-triazole (139 mg, 2.020 mmol) in Acetonitrile (15 mL) was added methyl 5-amino-4-(4-(4-(bromomethyl)benzyloxy)-1-oxoisoindolin-2-yl)-5-oxopentanoate (800 mg, 1.683 mmol) and DIPEA (0.588 ml, 3.37 mmol) at room temperature. The resulting clear solution was stirred at room temperature for 19 hrs. To the mixture was added DCM (50 mL). The organic layer was extracted with NaHCO$_3$ (sat. aq, 5 mL) and brine (10 mL). The organic layer was concentrated for ISCO purification to give 4-Carbamoyl-4-[1-oxo-4-(4-[1,2,3]triazol-1-ylmethyl-benzyloxy)-1,3-dihydro-isoindol-2-yl]-butyric acid methyl ester as a white solid (710 mg, 70% yield); LCMS MH=464; $^1$H NMR (DMSO-d$_6$) δ 1.96-2.31 (m, 4H, CH$_2$, CH$_2$), 3.50 (s, 3H, CH$_3$), 4.39 (d, J=17.8 Hz, 1H, CHH), 4.52 (d, J=17.6 Hz, 1H, CHH), 4.67-4.78 (m, 1H, CHH), 5.23 (s, 2H, CH$_2$), 5.63 (s, 2H, CH$_2$), 7.18 (s, 1H, Ar), 7.23-7.37 (m, 4H, Ar), 7.40-7.53 (m, 3H, Ar), 7.57 (s, 1H, NHH), 7.75 (d, J=0.8 Hz, 1H, Ar), 8.20 (d, J=0.8 Hz, 1H, Ar).

Step 2: To the stirred solution of methyl 4-(4-(4-((1H-1,2,3-triazol-1-yl)methyl)benzyloxy)-1-oxoisoindolin-2-yl)-5-amino-5-oxopentanoate (710 mg, 1.53 mmol) in Tetrahydrofuran (15 ml) was added KOtBu (200 mg, 1.78 mmol) at 0° C. The reaction mixture was stirred at 0° C. for 4 hrs, KOtBu (40 mg, 0.36 mmol) was added. 30 mins later, the reaction mixture was diluted by EtOAc (50 mL) and acidified by HCl (1N, aq, 4 mL) followed by the addition of NaHCO$_3$ (sat., aq, 4 mL) and brine (15 mL). The mixture was extracted and the organic layer was dried over MgSO$_4$. The mixture was filtered and the filtrate was concentrated under vacuo to give a white solid. The white solid was suspended in ether (30 mL) and stirred over weekend. The suspension was filtered to give 3-[1-Oxo-4-(4-[1,2,3]triazol-1-ylmethyl-benzyloxy)-1,3-dihydro-isoindol-2-yl]-piperidine-2,6-dione as a white solid (440 mg, 67% yield); HPLC: Waters Symmetry C-18, 3.9×150 mm, 5 μm, 1 mL/min, 240 nm, 30/70, CH$_3$CN/0.1% H$_3$PO$_4$), 4.84 min (98.4%); mp: 133-135° C.; $^1$H NMR (DMSO-d$_6$) δ 1.90-2.03 (m, 1H, M$_{01}$), 2.35-2.48 (m, 1H, CHH), 2.53-2.63 (m, 1H, CHH), 2.81-3.00 (m, 1H, CHH), 4.24 (d, J=17.6 Hz, 1H, CHH), 4.40 (d, J=17.6 Hz, 1H, CHH), 5.10 (dd, J=5.1, 13.2 Hz, 1H, CHH), 5.23 (s, 2H, CH$_2$), 5.63 (s, 2H, CH$_2$), 7.26-7.37 (m, 4H, Ar), 7.43-7.53 (m, 3H, Ar), 7.75 (d, J=0.8 Hz, 1H, CH), 8.20 (d, J=0.9 Hz, 1H, CH), 10.96 (s, 1H, NH); $^{13}$C NMR (DMSO-d$_6$) δ 22.31, 31.18, 45.06, 51.56, 52.26, 69.12, 114.90, 115.26, 124.94, 127.95, 128.06, 129.78, 129.93, 133.30, 133.52, 135.95, 136.51, 153.36, 167.97, 170.95, 172.81; LCMS MH=432; Anal. Calcd for C$_{23}$H$_{21}$N$_5$O$_4$+0.7H$_2$O: C, 62.21; H, 5.08; N, 15.77; Found: C, 62.07; H, 4.88; N, 15.46.

5.36 3-[4-(4-[1,4]Oxazepan-4-ylmethyl-Benzyloxy)-1-Oxo-1,3-Dihydro-Isoindol-2-yl]-Piperidine-2,6-Dione

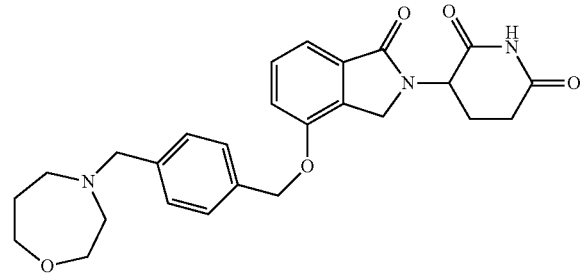 [SMILES: O=C1CCC(N2Cc3c(OCc4ccc(CN5CCCOCC5)cc4)cccc3C2=O)C(=O)N1]

Step 1: To the stirred solution of methyl 5-amino-4-(4-(4-(bromomethyl)benzyloxy)-1-oxoisoindolin-2-yl)-5-oxopentanoate (600 mg, 1.26 mmol) in Acetonitrile (10 mL) at room temperature was added by 1,4-oxazepane hydrochloride (208 mg, 1.51 mmol) and DIPEA (0.44 ml, 2.52 mmol). The reaction mixture was stirred at room temperature overnight and diluted by DCM (50 mL). The mixture was washed with NaHCO$_3$ (aq, sat. 5 mL) and brine (15 ml). The organic layer was dried by MgSO$_4$ and concentrated under vacuo to give crude 4-Carbamoyl-4-[4-(4-[1,4]oxazepan-4-ylmethyl-benzyloxy)-1-oxo-1,3-dihydro-isoindol-2-yl]-butyric acid methyl ester as a sticky oil (810 mg). The compound was used in the next step without further purification; LCMS MH=496.

Step 2: To the stirred suspension of methyl 4-(4-(4-((1,4-oxazepan-4-yl)methyl)benzyloxy)-1-oxoisoindolin-2-yl)-5-amino-5-oxopentanoate (625 mg, 1.26 mmol) in Tetrahydrofuran (10 mL) at 0° C. was added KOtBu (142 mg, 1.26 mmol) in one portion. The reaction mixture was stirred at 0° C. for 1 hour and KOtBu (70 mg) was added. 15 minutes later, the reaction mixture was diluted by EtOAc (50 mL) and acidified by HCl (aq, 1N, 3 mL) followed by the addition of NaHCO$_3$ (aq, sat., 3 mL) and brine (10 mL). The mixture was extracted and the organic layer was dried by MgSO$_4$. The mixture was filtered and the filtrate was concentrated down to give white solid. The solid was stirred in diethyl ether (20 mL) and filtered to give 3-[4-(4-[1,4]Oxazepan-4-ylmethyl-benzyloxy)-1-oxo-1,3-dihydro-isoindol-2-yl]-piperidine-2,6-dione as a white solid (484 mg, 83% yield); HPLC: Waters Symmetry C-18, 3.9×150 mm, 5 μm, 1 mL/min, 240 nm, 5 to 95% in 10 mins, (CH$_3$CN/0.1% H$_3$PO$_4$), 5.7 min (95.9%); mp: 119-121° C.; $^1$H NMR (DMSO-d$_6$) δ 1.72-1.88 (m, 2H, CH$_2$), 1.92-2.04 (m, 1H, CHH), 2.35-2.47 (m, 1H, CHH), 2.53-2.69 (m, 5H, CH$_2$, CH$_2$, CHH), 2.83-2.99 (m, 1H, CHH), 3.54-3.65 (m, 4H, CH$_2$, CH$_2$), 3.69 (t, J=6.0 Hz, 2H, CH$_2$), 4.25 (d, J=17.6 Hz, 1H, CHH), 4.42 (d, J=17.6 Hz, 1H, CHH), 5.11 (dd, J=5.1, 13.2 Hz, 1H, CHH), 5.23 (s, 2H, CH$_2$), 7.26-7.39 (m, 2H, Ar), 7.40-7.54 (m, 3H, Ar), 10.97 (s, 1H, NH); $^{13}$C NMR (DMSO-d$_6$) δ 22.34, 29.28, 31.18, 45.07, 51.55, 53.24, 57.10, 60.98, 67.69, 68.33, 69.38, 114.94, 115.22, 127.66, 128.73, 129.78, 129.93, 133.30, 135.24, 139.05, 153.49, 167.99, 170.96, 172.81; LCMS MH=464; Anal. Calcd for C$_{26}$H$_{29}$N$_3$O$_5$+0.5 H$_2$O: C, 66.09; H, 6.40; N, 8.89, Found: C, 65.83; H, 6.04; N, 8.60.

5.37 3-[1-Oxo-4-(4-[1,2,3]Triazol-2-ylmethyl-Benzyloxy)-1,3-Dihydro-Isoindol-2-yl]-Piperidine-2,6-Dione

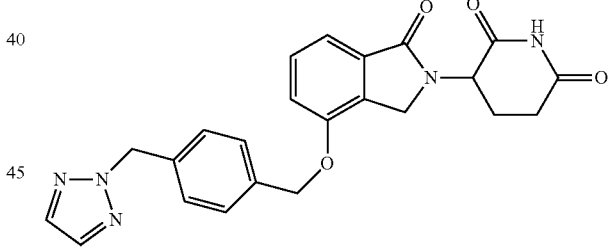

Step 1. To the stirred solution of 1H-1,2,3-triazole (139 mg, 2.020 mmol) in Acetonitrile (15 mL) was added by methyl 5-amino-4-(4-(4-(bromomethyl)benzyloxy)-1-oxoisoindolin-2-yl)-5-oxopentanoate (800 mg, 1.683 mmol) and DIPEA (0.588 ml, 3.37 mmol) at room temperature. The resulting clear solution was stirred at room temperature for 19 hrs and another same reaction mixture (12.5% scale of this one) followed by 1H-1,2,3-trazole (60 mg, 0.87 mmol) was added. The combined reaction mixture was stirred at room temperature overnight and then added by DCM (50 mL), NaHCO$_3$ (sat. aq, 5 mL) and brine (10 mL). The mixture was extracted and the organic layer was concentrated for ISCO purification to give 4-Carbamoyl-4-[1-oxo-4-(4-[1,2,3]triazol-2-ylmethyl-benzyloxy)-1,3-dihydro-isoindol-2-yl]-butyric acid methyl ester as a sticky clear oil (102 mg, 9% yield); LCMS MH=464; $^1$H NMR (DMSO-d$_6$) δ 1.97-2.31 (m, 4H, CH$_2$, CH$_2$), 3.50 (s, 3H, CH$_3$), 4.39 (d, J=17.6 Hz, 1H, CHH), 4.52 (d, J=17.8 Hz, 1H, CHH), 4.66-4.78 (m, 1H, CHH), 5.23 (s, 2H, CH$_2$), 5.67 (s, 2H, CH$_2$), 7.13-7.22 (m, 1H, NHH), 7.23-7.32 (m, 4H, Ar), 7.40-7.52 (m, 3H, Ar), 7.58 (s, 1H, NHH), 7.81 (s, 2H, Ar).

Step 2. To the stirred solution of methyl 4-(4-(4-((2H-1,2,3-triazol-2-yl)methyl)benzyloxy)-1-oxoisoindolin-2-yl)-5-amino-5-oxopentanoate (100 mg, 0.216 mmol) in Tetrahydrofuran (Volume: 4 ml) at 0° C. was added KOtBu (29.1 mg, 0.259 mmol) in one portion. The reaction mixture was stirred at 0° C. for 1 hr. KOtBu (30 mg, 0.26 mmol) was added to the reaction mixture. The reaction mixture was stirred at 0° C. for 30 minutes and then diluted by EtOAc (40 mL). The resulting solution was acidified by HCl (aq, 1N, 2 mL) and then basified by NaHCO$_3$ (aq, sat., 2 mL), and followed by the addition of brine (10 mL). The mixture was extracted and the organic layer was dried over MgSO$_4$. The suspension was filtered and concentrated to give a white solid. The white solid was suspended in diethyl ether (10 mL) and stirred at room temperature overnight. The mixture was filtered to give 3-[1-oxo-4-(4-[1,2,3]triazol-2-ylmethyl-benzyloxy)-1,3-dihydro-isoindol-2-yl]-piperidine-2,6-dione as a white solid (56 mg, 32% yield); HPLC: Waters Symmetry C-18, 3.9×150 mm, 5 μm, 1 mL/min, 240 nm, 40/60, (CH$_3$CN/0.1% H$_3$PO$_4$), 3.71 min (96.8%); mp: N/A; $^1$H NMR (DMSO-d$_6$) δ 1.90-2.04 (m, 1H, CHH), 2.35-2.47 (m, 1H, CHH), 2.54-2.63 (m, 1H, CHH), 2.81-3.00 (m, 1H, CHH), 4.24 (d, J=17.6 Hz, 1H, CHH), 4.40 (d, J=17.6 Hz, 1H, CHH), 5.10 (dd, J=5.1, 13.2 Hz, 1H, CHH), 5.23 (s, 2H, CH$_2$), 5.67 (s, 2H, CH$_2$), 7.21-7.38 (m, 4H, Ar), 7.41-7.54 (m, 3H, Ar), 7.81 (s, 2H, triazole), 10.96 (s, 1H, NH); $^{13}$C NMR (DMSO-d$_6$) δ 22.31, 31.16, 45.04, 51.55, 57.23, 69.14, 114.90, 115.25, 127.95, 129.78, 129.94, 133.19, 134.70, 135.70, 136.39, 152.69, 167.98, 170.93, 172.80; LCMS MH=432; Anal. Calcd for C$_{23}$H$_{21}$N$_5$O$_4$: C, 64.03; H, 4.91; N, 16.23; Found: N/A.

5.38 Preparation of 3-(4-((6-(Morpholinomethyl)Benzofuran-2-yl)Methoxy)-1-Oxoisoindolin-2-yl)Piperidine-2,6-Dione

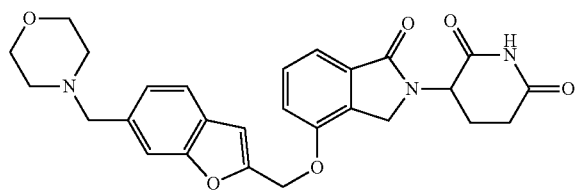 [SMILES: O=C1CCC(N2Cc3c(OCc4cc5ccc(CN6CCOCC6)cc5o4)cccc3C2=O)C(=O)N1]

Step 1: A mixture of 2-hydroxy-4-methylbenzaldehyde (4.2 g, 31.1 mmol), potassium carbonate (5.6 g, 40.5 mmol) and molecular sieve (4.0 g) in DMF (40 mL) was heated to 50° C. Ethyl bromoacetate (5.2 g, 31.1 mmol) was added slowly at 50-55° C. The reaction mixture was heated at 75° C. for 20 min then at 1 10° C. for 1 h. The reaction mixture was cooled to room temperature and diluted with EtOAc (100 mL). The mixture was filtered and the solid was washed with EtOAc (50 mL). The filtrate was washed with water (3×60 mL), brine (60 mL) and dried. The solvent was removed in vacuo and the crude mixture was purified by chromatography (SiO$_2$, CH$_2$Cl$_2$) to give ethyl 6-methylbenzofuran-2-carboxylate (1 g, 16%): $^1$H NMR (CDCl$_3$) δ 1.42 (t, J=6 Hz, 3H), 2.49 (s, 3H), 4.40-4.47 (q, J=6 Hz, 2H), 7.11-7.14 (d, J=9 Hz, 1H), 7.38 (s, 1H), 7.48 (s, 1H), 7.53-7.56 (t, J=9 Hz, 1H).

Step 2: A mixture of ethyl 6-methylbenzofuran-2-carboxylate (0.9 g, 4.6 mmol) and N-bromosuccinimide (1 g, 6.0 mmol) in CCl$_4$ (20 mL) was heated at 70° C. in an oil bath with a 300 W bulb shining to reaction mixture for 4 h. The reaction mixture was cooled and filtered and the solid was washed with CH$_2$Cl$_2$ (30 mL). The filtrate was concentrated in vacuo and the crude mixture was purified by chromatography (SiO$_2$, 10% EtOAc/hexane) to give ethyl 6-(bromomethyl)benzofuran-2-carboxylate (1.3 g, 100%): $^1$H NMR (DMSO-d$_6$) δ 1.34 (t, J=6 Hz, 3H), 4.34-4.41 (q, J=6 Hz, 2H), 4.87 (s, 2H), 7.44-7.53 (m, 1H), 7.76-7.96 (m, 3H).

Step 3: A mixture of potassium carbonate (3.6 g, 26 mmol), morpholine (1.0 g, 11.3 mmol) and catalytic amount of 18-crown-6 in acetone (15 mL) was heated at 60° C. in an oil bath. A solution of ethyl 6-(bromomethyl)benzofuran-2-carboxylate (2.0 g, 7.1 mmol) in acetone (15 mL) was added slowly and the mixture was heated at 60° C. oil bath for 3 h. The reaction mixture was cooled to room temperature and filtered. The filtrate was concentrated and the residue was dissolved in EtOAc (100 mL) and washed with water (2×30 mL), brine (30 mL) and dried. Solvent was removed in vacuo and the residue was purified by chromatography (SiO$_2$, 30% EtOAc/hexane for 15 min then to 60% over 20 min and hold for 15 min) to give ethyl 6-(morpholinomethyl)benzofuran-2-carboxylate (1.2 g, 60%): $^1$H NMR (CDCl$_3$) δ 1.43 (t, 6 Hz, 3H), 2.45-2.48 (m, 4H), 3.62 (s, 2H), 3.71-3.73 (m, 4H), 4.41-4.48 (q, J=6 Hz, 2H), 7.27-7.31 (m, 1H), 7.50 (s, 1H), 7.58-7.62 (m, 2H).

Step 4: A solution of LiAlH$_4$/THF (1M, 5.4 mL, 5.4 mmol) in THF (10 mL) was cooled in an ice bath to 5° C. A solution of ethyl 6-(morpholinomethyl)benzofuran-2-carboxylate (1.2 g, 4.2 mmol) in THF (20 mL) was added dropwise at 5-10° C. The reaction mixture was stirred in an ice bath for 30 min then carefully quenched with water (10 mL). The mixture was diluted with sat. Na$_2$CO$_3$ (40 mL) and CH$_2$Cl$_2$ (50 mL) and the aq. layer was extracted with CH$_2$Cl$_2$ (3×30 mL). The combined CH$_2$Cl$_2$ solution was washed with water (40 mL), brine (40 mL) and dried. Solvent was removed to give (6-(morpholinomethyl)benzofuran-2-yl)methanol (0.9 g, 88%): $^1$H NMR (CDCl$_3$) δ 2.40 (b, 1H), 2.44-2.47 (m, 4H), 3.59 (s, 2H), 3.71-3.72 (m, 4H), 4.75 (s, 2H), 6.63 (s, 1H), 7.18-7.20 (m, 1H), 7.45-7.48 (m, 2H).

Step 5: A mixture of Triphenylphosphine-polymer bound (3.5 g, 4.3 mmol) in THF (40 mL) was cooled in an ice bath to 3° C. Diisopropyl azodicarboxylate (0.8 g, 4.6 mmol) was added slowly at 3-5° C. After stirred at 3° C. for 10 min, a solution of (6-(morpholinomethyl)benzofuran-2-yl)methanol (0.9 g, 3.6 mmol) and methyl 5-amino-4-(4-hydroxy-1-oxoisoindolin-2-yl)-5-oxopentanoate (0.9 g, 3.1 mmol) in THF (60 mL) was added at 3-8° C. After stirred for 10 min, the ice bath was removed and the mixture was stirred at room temperature overnight. The reaction mixture was filtered and the solid was washed with CH$_2$Cl$_2$ (30 mL). The combined filtrates was concentrated and the resulting residue was dissolved in CH$_2$Cl$_2$ (80 mL) and washed with sat. NaHCO$_3$ (40 mL), water (40 mL), brine (40 mL) and dried. The solvent was removed in vacuo and the residue was purified by chromatography (SiO$_2$, CH$_2$Cl$_2$ for 5 min then to 3% CH$_3$OH/CH$_2$Cl$_2$ over 5 in and hold for 20 min then to 5% over 5 in and hold for 20 min) to give methyl 5-amino-4-(4-((6-(morpholinomethyl)benzofuran-2-yl)methoxy)-1-oxoisoindolin-2-yl)-5-oxopentanoate (1.0 g, 44%).

Step 6: A mixture of methyl 5-amino-4-(4-((6-(morpholinomethyl)benzofuran-2-yl)methoxy)-1-oxoisoindolin-2-yl)-5-oxopentanoate (1.0 g, 1.9 mmol) and potassium carbonate (0.3 g, 1.9 mmol) in DMF (10 mL) was heated at 80° C. oil bath for 3 h. The reaction mixture was cooled to room temperature and diluted with EtOAc (80 mL). The mixture was filtered and the filtrate was washed with water (3×35 mL), brine (35 mL) and dried. The solvent was removed and the residue was purified by chromatography (SiO$_2$, CH$_2$Cl$_2$ for 5 min then to 3% CH$_3$OH/CH$_2$Cl$_2$ over 5 min and hold for 15 min then to 5% over 5 min and hold for 20 min) to give 3-(4-((6-(morpholinomethyl)benzufuran-2-yl)methoxy)-1-oxoisoindolin-2-yl)piperidine-2,6-dione (0.24 g, 26%): mp 142-144° C.; $^1$H NMR (DMSO-d$_6$) δ 1.95-1.99 (m, 1H), 2.35-2.59 (m, 1H), 2.84-2.96 (m, 1H), 3.33 (s, 4H), 3.56 (b, 2H), 4.26 (d, J=17.7 Hz, 1H), 4.36 (d, J=17.4 Hz, 1H), 5.07-5.13 (dd, J=5.1 and 13.2 Hz, 1H), 5.42 (s, 2H), 7.09 (s, 1H), 7.23 (b, 1H), 7.34-7.37 (dd, J=0.9 and 6.9 Hz, 1H), 7.46-7.61 (m, 4H), 10.96 (s, 1H); $^{13}$C NMR (DMSO-d$_6$) δ 22.29, 31.17, 45.04, 51.56, 53.05, 62.50, 66.15, 107.01, 111.38, 115.10, 115.66, 121.02, 124.22, 126.55, 129.81, 129.93, 133.43, 135.00, 152.55, 152.96, 154.67, 167.87, 170.93, 172.80; Calcd for C$_{27}$H$_{27}$N$_3$O$_6$+0.5H$_2$O: C, 65.06; H, 5.66; N, 8.43. Found: C, 64.97; H, 5.49; N, 8.39.

5.39 3-(1-Oxo-4-(4-(Thiomorpholinomethyl)Benzyloxy)Isoindolin-2-yl)Piperidine-2,6-Dione

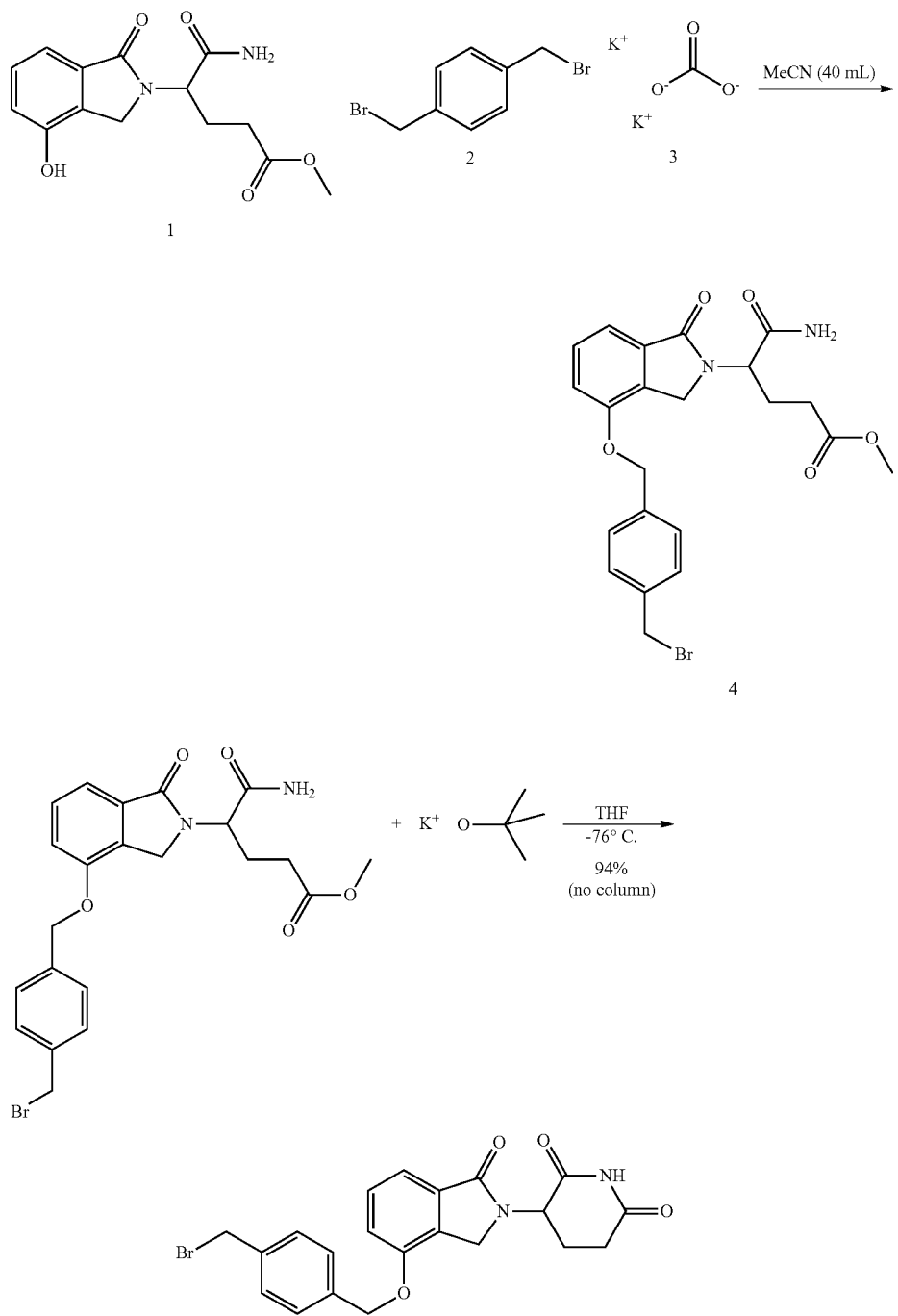

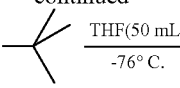

Step 1 Methyl 5-amino-4-(4-(4-(bromomethyl)benzyloxy)-1-oxoisoindolin-2-yl)-5-oxopentanoate: 1,4-bis(Bromomethyl)benzene (2.71 g, 10.26 mmol) was suspended in dry acetonitrile (40 mL). The slurry was warmed up to 60° C. until full dissolution occurred (~15 min). The temperature was reduced to 50° C. and to the solution was added $K_2CO_3$ (0.473 g, 3.42 mmol) as a solid followed by methyl 5-amino-4-(4-hydroxy-1-oxoisoindolin-2-yl)-5-oxopentanoate (1 g, 3.42 mmol, preparation described herein). The resulting white slurry was stirred at 50° C. for ~3 h at which time LCMS indicated the phenol starting material was consumed. The crude reaction mixture was swirled and filtered with suction. The remaining solid in flask and on the filter funnel was rinsed with minimal MeCN (~5 mL). The filtrate was concentrated in vacuo to give 2.6 g of a white solid. The solid was dissolved in minimal DCM and purified using a $SiO_2$ flash column (CombiFlash, 40 g $SiO_2$ prepacked column). The column was eluted with 100% DCM for ~15 min, a gradient to 5% MeOH in DCM over 5 min, and then held at 5% MeOH in DCM. Fractions were combined and concentrated to give methyl 5-amino-4-(4-(4-(bromomethyl)benzyloxy)-1-oxoisoindolin-2-yl)-5-oxopentanoate as a white solid (1.3 g, 80% yield): $^1$H NMR (DMSO-$d_6$) δ 1.94-2.34 (m, 4H, $CH_2$, $CH_2$), 3.50 (s, 3H, $CH_3$), 4.33-4.62 (m, 2H, $CH_2$), 4.72 (s, 2H, $CH_2$,), 5.25 (s, 2H, $CH_2$), 5.27-5.36 (m, 1H, CH), 7.19 (br. s., 1H, NH), 7.23-7.36 (m, 2H, Ar), 7.40-7.70 (m, 6H, Ar, NH); LC/MS M+H=475, 477.

Step 2. 3-(4-(4-(Bromomethyl)benzyloxy)-1-oxoisoindolin-2-yl)piperidine-2,6-dione: Methyl 5-amino-4-(4-(4-(bromomethyl)benzyloxy)-1-oxoisoindolin-2-yl)-5-oxopentanoate (2.05 g, 4.31 mmol) was dissolved in THF (50 mL) and the solution was cooled in dry ice/acetone bath to −76° C. While stirring, solid KO$^t$Bu (0.532 g, 4.74 mmol) was added in one portion to the clear solution. The reaction mixture became a pale yellow color and was stirred for ~90 min at −76° C. A cooled solution of 1 N aq HCl (20 mL) was rapidly transferred to the reaction mixture, maintaining temperature at −76° C. The mixture immediately turned milky white and the dry $CO_2$/acetone bath was removed, allowing the mixture to warm up to while stirring. The mixture was concentrated on a rotovap to remove most of THF (concentrated to a fixed volume at 160 mbar and water bath ~35° C.). Upon concentration of reaction mixture, a white solid precipitated out. The white slurry was diluted with more water (~80 mL) and then suction filtered. The cake was washed with copious water (total filtrate volume ~150 mL) and suction dried. The cake was washed with $Et_2O$ (~50 mL), suction dried and then placed in vacuum oven at 40° C. overnight to give 3-(4-(4-(Bromomethyl)benzyloxy)-1-oxoisoindolin-2-yl)piperidine-2,6-dione as a white solid (1.8 g, 94% yield): HPLC: Waters Symmetry $C_{18}$, 5 µm, 3.9×150 mm, 1 ml/min, 240 nm, 50/50 $CH_3CN$/0.1% $H_3PO_4$, 3.70 min (97.9%); mp, 123-125° C.; $^1$H NMR (DMSO-$d_6$) δ 1.89-2.05 (m, 1H, CHH), 2.32-2.48 (m, 1H, CHH), 2.52-2.64 (m, 1H, CHH), 2.78-3.04 (m, 1H, CHH), 4.26 (d, J=17.6 Hz, 1H, CHH), 4.43 (d, J=17.6 Hz, 1H, CHH), 4.72 (s, 2H, $CH_2$), 5.11 (dd, J=5.0, 13.1 Hz, 1H, CH), 5.25 (s, 2H, $CH_2$), 7.24-7.36 (m, 2H, Ar), 7.41-7.54 (m, 5H, Ar), 10.83-11.07 (m, 1H, NH); $^{13}$C NMR (DMSO-$d_6$) δ 22.33, 31.18, 34.15, 45.06, 51.56, 69.12, 114.94, 115.28, 127.95, 128.33, 129.41, 129.80, 131.93, 133.31, 136.78, 153.36, 167.97, 170.95, 172.81; LC/MS M+H=443, 445. The solid was used in the next step without further purification.

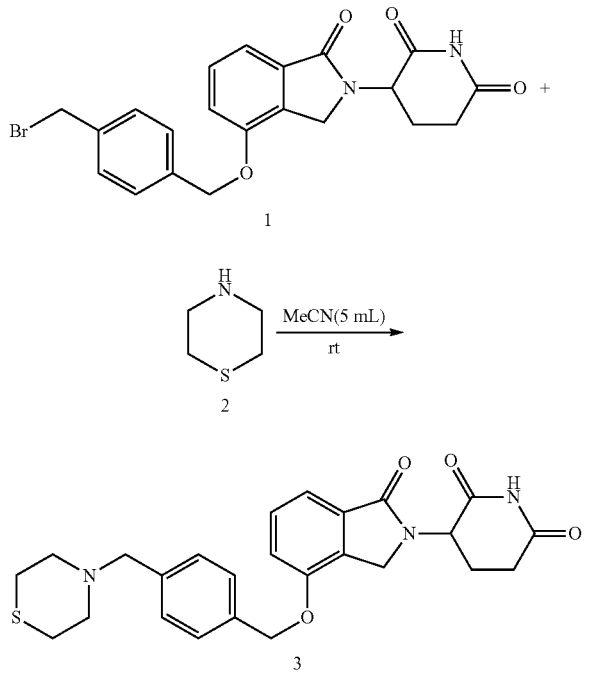 [SMILES: O=C1CCC(N2Cc3c(OCc4ccc(CBr)cc4)cccc3C2=O)C(=O)N1 ; C1CSCCN1 ; O=C1CCC(N2Cc3c(OCc4ccc(CN5CCSCC5)cc4)cccc3C2=O)C(=O)N1]

Step 3. 3-(1-Oxo-4-(4-(thiomorpholinomethyl)benzyloxy)isoindolin-2-yl)piperidine-2,6-dione: In a 20-mL reaction vial, thiomorpholine (62.8 mg, 0.609 mmol) was added to a solution of 3-(4-(4-(bromomethyl)benzyloxy)-1-oxoisoindolin-2-yl)piperidine-2,6-dione (150 mg, 0.338 mmol) in MeCN (5 mL). The clear reaction mixture was stirred at room temperature for 2 h. The reaction mixture was cooled to 0° C. and quenched with addition of 1.5 mL of glatial acetic acid. A slurry formed which was partitioned between EtOAc (100 mL) and 1N NaHCO$_3$ (30 mL). The organic layer was washed with brine, dried (Na$_2$SO$_4$), and concentrated in vacuo to give a glassy solid. The solid was triturated with water and sonicated to give a free flowing solid. This solid was collected by filtration, suction dried, and then dried in vacuum oven at 40° C. to give 3-(1-oxo-4-(4-(thiomorpholinomethyl)benzyloxy)isoindolin-2-yl)piperidine-2,6-dione as a white solid (127 mg, 81% yield): HPLC: Waters Symmetry C$_{18}$, 5 µm, 3.9×150 mm, 1 ml/min, 240 nm, 17/83 CH$_3$CN/0.1% H$_3$PO$_4$, 5.05 min (97.0%); mp: 134-136° C.; $^1$H NMR (DMSO-d$_6$) δ 1.86-2.05 (m, 1H, CHH), 2.32-2.47 (m, 1H, CHH), 2.60 (s, 9H, 4×CH$_2$, CHH), 2.80-3.00 (m, 1H, CHH), 3.49 (s, 2H, CH$_2$), 4.25 (d, J=17.6 Hz, 1H, CHH), 4.42 (d, J=17.4 Hz, 1H, CHH), 5.11 (dd, J=4.8, 12.9 Hz, 1H, CH), 5.22 (s, 2H, CH$_2$), 7.01-7.38 (m, 4H, Ar), 7.38-7.65 (m, 3H, Ar), 10.97 (s, 1H, NH); $^{13}$C NMR (DMSO-d$_6$) δ 22.33, 27.14, 31.16, 45.06, 51.55, 54.36, 62.23, 69.38, 114.94, 115.20, 127.63, 128.84, 129.78, 129.93, 133.28, 135.22, 137.89, 153.48, 167.97, 170.95, 172.81; LC/MS M+H=466; Anal Calcd for C$_{25}$H$_{27}$N$_3$O$_4$S+0.25 H$_2$O: C, 63.88; H, 5.90; N, 8.94; S, 6.82. Found: C, 63.85; H, 5.93; N, 8.67; S, 6.50.

5.40 3-{1-Oxo-4-[4-(1-Oxo-Thiomorpholin-4-ylmethyl)-Benzyloxy]-1,3-Dihydro-Isoindol-2-yl}-Piperidine-2,6-Dione

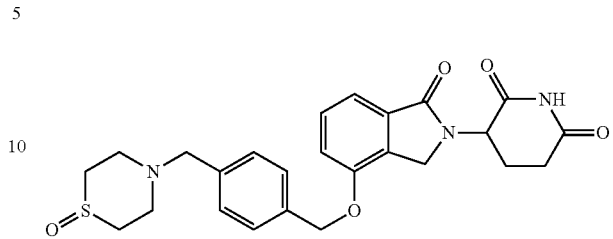

In a 20-mL reaction vial, N,N-diisopropylethylamine (0.197 mL, 1.128 mmol) was added to a suspension of 1-oxo-thiomorpholine hydrochloride (97 mg, 0.620 mmol) in MeCN (5 mL). The mixture was sonicated at room temperature to break up solid. Upon full dissolution of the, 3-(4-(4-(bromomethyl)benzyloxy)-1-oxoisoindolin-2-yl)piperidine-2,6-dione (250 mg, 0.564 mmol) was added to the solution in one portion and the resulting mixture was stirred at room temperature. After about 1 hour, MeCN (~5 mL) was added to improve stirring. The mixture was stirred for another 4 hours at room temperature and then diluted with EtOAc (15 mL). The slurry was stirred for a few minutes then filtered on a fine-pore filter funnel with suction. The cake was washed with a small portion of EtOAc (~5 mL), suction dried, and then dried further in vacuum oven at 40° C. to give 3-{1-oxo-4-[4-(1-oxo-thiomorpholin-4-ylmethyl)-benzyloxy]-1,3-dihydro-isoindol-2-yl}-piperidine-2, 6-dione as a white solid (110 mg, 40% yield): HPLC: Waters Symmetry C$_{18}$, 5 µm, 3.9×150 mm, 1 m/min, 240 nm, 15/85 CH$_3$CN/0.1% H$_3$PO$_4$, 4.25 min (98.9%); mp: 170-172° C., $^1$H NMR (DMSO-d$_6$) δ 1.90-2.05 (m, 1H, CHH), 2.36-2.47 (m, 1H, CHH), 2.53-2.66 (m, 3H, CH$_2$, CHH), 2.66-2.77 (m, 2H, CH$_2$), 2.79-3.01 (m, 5H, CH$_2$, CH$_2$, CHH), 3.57 (s, 2H, CH$_2$), 4.25 (d, J=17.6 Hz, 1H, CHH), 4.42 (d, J=17.6 Hz, 1H, CHH), 5.11 (dd, J=5.1, 13.2 Hz, 1H, CH), 5.23 (s, 2H, CH$_2$), 7.26-7.39 (m, 4H, Ar), 7.40-7.54 (m, 3H, Ar), 10.97 (s, 1H, NH); $^{13}$C NMR (DMSO-d$_6$) δ 22.33, 31.16, 43.56, 45.07, 45.51, 51.55, 61.15, 69.36, 114.96, 115.22, 127.67, 128.92, 129.80, 129.95, 133.28, 135.38, 137.67, 153.48, 167.97, 170.96, 172.81; LC/MS M+H=482; Anal Calcd for C$_{25}$H$_{27}$N$_3$O$_5$S+1.0 H$_2$O: C, 60.10; H, 5.85; N, 8.41; S, 6.42. Found: C, 59.94; H, 5.52; N, 8.26; S, 6.45.

5.41 (S)-2-(3-Methyl-2,6-Dioxopiperidin-3-yl)-4-(4-Morpholinomethyl)Benzyloxy)Isoindoline-1,3-Dione

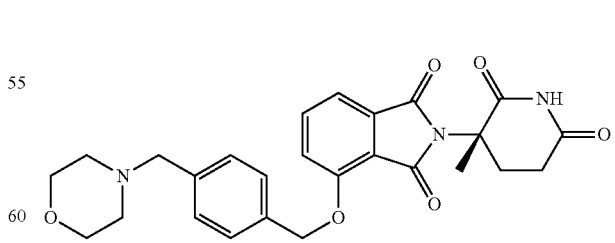

Step 1: In a 250 ml RBF, dimethyl 3-hydroxyphthalate (1 g, 4.76 mmol) and triphenyl phosphine on polystyrene (1.6 mmol/g resin) (2.98 g, 4.76 mmol) were slurried in THF (40 ml) at room temperature. The mixture was cooled at 0° C. and DIAD (1.850 ml, 9.52 mmol) was added via syringe, after 10 minutes, (4-(morpholinomethyl)phenyl) methanol (0.986 g, 4.76 mmol) in THF (10 ml) was added, and the mixture was stirred at room temperature overnight. The reaction mixture was filtered, the resin was rinsed with washes of DCM and MeOH (2×50 ml each wash), the combined filtrates and washes were concentrated in vacuo to a syrup. The residue was purified by ISCO (80 g column, MeOH in DCM gradient from 0-5 in 50 min, 5% MeOH in DCM 20 min) to give dimethyl 3-(4-(morpholinomethyl) benzyloxy)phthalate (770 mg, 41% yield). $^1$H NMR (DMSO-$d_6$) δ 2.29-2.40 (m, 4H, $CH_2$, $CH_2$), 3.45 (s, 2H, $CH_2$), 3.53-3.60 (m, 4H, $CH_2$, $CH_2$), 3.79 (s, 3H, $CH_3$), 3.82 (s, 3H, $CH_3$), 5.21 (s, 2H, $CH_2$), 7.33 (d, J=0.9 Hz, 4H, Ar), 7.44-7.59 (m, 3H, Ar).

Step 2: To a solution of dimethyl 3-(4-(morpholinomethyl)benzyloxy) phthalate (770 mg, 1.928 mmol) in EtOH (20 ml, 343 mmol), was added NaOH (3N, 10 mL, pre-made from 12 N solution). The mixture was refluxed for 1 hour. The reaction mixture was evaporated to dryness in vacuum. HCl (1N) was added to the residue and adjusted pH to 3, and the precipitate was collected by filtration to give 3-(4-(morpholinomethyl)benz yloxy)phthalic acid as a white solid (350 mg, 49% yield). $^1$H NMR (DMSO-$d_6$) δ 2.27-2.43 (m, 4H, $CH_2$, $CH_2$), 3.49 (s, 2H, $CH_2$), 3.53-3.65 (m, 4H, $CH_2$, $CH_2$), 5.17 (s, 2H, $CH_2$), 7.16-7.63 (m, 7H, Ar).

Step 3: The mixture of 3-(4-(morpholinomethyl)benzyloxy)phthalic acid (300 mg, 0.808 mmol) and (S)-3-amino-3-methylpiperidine-2,6-dione hydrobromide (198 mg, 0.889 mmol) in pyridine (20 ml) was heated to reflux for 2 days and cooled to room temperature. Pyridine was stripped of under reduced pressure, the residue was partitioned between EtOAc (50 ml) and sodium bicarbonate (10 ml), the organic layer was separated and washed with water (2×10 ml), brine (10 ml), and dried ($MgSO_4$). The solvent was evaporated under reduced pressure, the residue was purified by ISCO (12 g column, MeOH in DCM gradient from 0-3% in 25 min) to give (S)-2-(3-methyl-2,6-dioxopiperidin-3-yl)-4-(4-(morpholinomethyl)benzyloxy)isoindoline-1,3-dione (100 mg, 26% yield). mp: 178-180° C.; $^1$H NMR (DMSO-$d_6$) δ 1.88 (s, 3H, $CH_3$), 1.98-2.12 (m, 1H, CHH), 2.29-2.42 (m, 4H, $CH_2$, $CH_2$), 2.52-2.83 (m, 3H, CHH, CHH, CHH), 3.47 (s, 2H, $CH_2$), 3.53-3.66 (m, 4H, $CH_2$, $CH_2$), 5.31 (s, 2H, $CH_2$), 7.29-7.51 (m, 5H, Ar), 7.57 (d, J=8.5 Hz, 1H, Ar), 7.80 (dd, J=7.4, 8.5 Hz, 1H, Ar), 10.98 (s, 1H, NH); $^{13}$C NMR (DMSO-$d_6$) δ 20.96, 28.55, 29.03, 53.11, 58.53, 62.06, 66.13, 69.93, 115.09, 116.14, 119.86, 127.35, 129.01, 133.24, 134.74, 136.83, 137.69, 155.33, 166.06, 167.42, 172.10, 172.27; MH=478; HPLC: Waters Xterra C-18, 3.9×150 mm, 5 µm, 1 mL/min, 240 nm, Gradient ($CH_3CN$/0.1% $HCOONH_4$) 5/95 to 95/5 in 5 min, 95/5 10 min: $t_R$=3.72 (100%); Anal. Calcd for $C_{26}H_{27}N_3O_6$ C, 65.40; H, 5.70; N, 8.80; Found: C, 65.28; H, 5.67; N, 8.60.

5.42 3-[1-Oxo-4-(4-[1,2,4]Triazol-1-ylmethyl-Benzyloxy)-1,3-Dihydro-Isoindol-2-yl]-Piperidine-2,6-Dione Step 1: Preparation of 4-Carbamoyl-4-[1-oxo-4-(4-[1,2,4]triazol-1-ylmethyl-benzyloxy)-1,3-dihydro-isoindol-2-yl]-butyric acid methyl ester To a solution of methyl 5-amino-4-(4-(4-(bromomethyl)benzyloxy)-1-oxoisoindolin-2-yl)-5-oxopentanoate (0.804 g, 1.691 mmol) in acetonitrile (20 ml) was added 1H-1,2,4-triazole (0.350 g, 5.07 mmol) and N-ethyl-N-isopropylpropan-2-amine (0.839 ml, 5.07 mmol) at room temperature. The mixture was stirred at room temperature for two days and then diluted by methylene chloride (50 mL) and washed with saturated sodium bicarbonate (10 mL) and brine (O1 mL). Organic layer was concentrated and purified on silica gel column (MeOH/$CH_2Cl_2$ gradient from 1% to 9% in 50 min) to give 4-Carbamoyl-4-[1-oxo-4-(4-[1,2,4]triazol-1-ylmethyl-benzyloxy)-1,3-dihydro-isoindol-2-yl]-butyric acid methyl ester as an oil (0.53 g, 67% yield); $^1$H NMR (DMSO-$d_6$) δ 1.96-2.36 (m, 4H, CHH, CHH, CHH, CHH), 3.50 (s, 3H, $CH_3$), 4.32-4.58 (m, 2H, $CH_2$), 4.72 (dd, J=4.9, 10.4 Hz, 1H, NCH), 5.23 (s, 2H, $CH_2$), 5.37-5.50 (m, 2H, $CH_2$), 7.13-7.21 (m, 1H, NHH), 7.24-7.36 (m, 4H, Ar), 7.40-7.53 (m, 3H, Ar), 7.57 (br. s., 1H, NHH), 7.98 (s, 1H, Ar), 8.66 (s, 1H, Ar). It was used in the next step without further purification.

Step 2: Preparation of 3-[1-Oxo-4-(4-[1,2,4]triazol-1-ylmethyl-benzyloxy)-1,3-dihydro-isoindol-2-yl]-piperidine-2,6-dione To a stirred solution of methyl 4-(4-(4-((1H-1,2,4-triazol-1-yl)methyl)benzyloxy)-1-oxoisoindolin-2-yl)-5-amino-5-oxopentanoate (0.49 g, 1.057 mmol) in THF (20 ml) in an ice-bath was added potassium 2-methylpropan-2-olate (0.119 g, 1.057 mmol). After stirring for 10 minutes, 1 N HCl (2 ml) was added, neutralized by saturated sodium bicarbonate (3 ml), and stirred with ethyl acetate (50 ml). The organic phase was separated, washed with brine (10 ml) and evaporated to a white solid, which was purified on silica gel column (MeOH/$CH_2Cl_2$ gradient from 0% to 4% in 40 min) to give 3-[1-Oxo-4-(4-[1,2,4]triazol-1-ylmethyl-benzyloxy)-1,3-dihydro-isoindol-2-yl]-piperidine-2,6-dione as a white solid (0.177 g, 39% yield); mp, 233-235° C.; HPLC: Waters Symmetry C-18, 3.9×150 mm, 5 µm, 1 mL/min, 240 nm, gradient from 10/90 to 95/5 in 5 min, isocratic at 95/5 in 5 min ($CH_3CN$/0.1% $H_3PO_4$), 5.43 min (96.4%); $^1$H NMR (DMSO-$d_6$) δ 1.90-2.05 (m, 1H, CHH), 2.36-2.48 (m, 1H, CHH), 2.53-2.64 (m, 1H, CHH), 2.82-2.99 (m, 1H, CHH), 4.17-4.48 (m, 2H, $CH_2$), 5.10 (dd, J=5.1, 13.2 Hz, 1H, NCH), 5.23 (s, 2H, $CH_2$), 5.43 (s, 2H, $CH_2$), 7.25-7.37 (m, 4H, Ar), 7.42-7.55 (m, 3H, Ar), 7.98 (s, 1H, Ar), 8.67 (s, 1H, Ar), 10.96 (s, 1H, NH); $^{13}$C NMR (DMSO-$d_6$) δ 22.35, 31.20, 45.08, 51.58, 51.78, 69.19, 114.95, 115.27, 128.02, 129.81, 129.97, 133.32, 136.09, 136.35, 144.23, 151.72, 153.40, 167.99, 170.96, 172.82; LC/MS (M+1)+=432; Anal Calcd for $C_{23}H_{21}N_5O_4$+0.2 $H_2O$: C, 63.50; H, 4.96; N, 16.10. Found: C, 63.11; H, 4.89; N, 16.00.

5.43 1-{4-[2-(2,6-Dioxo-Piperidin-3-yl)-1-Oxo-2,3-Dihydro-1H-Isoindol-4-yl Oxymethyl]-Benzyl}-Pyrrolidine-2-Carboxylic Acid

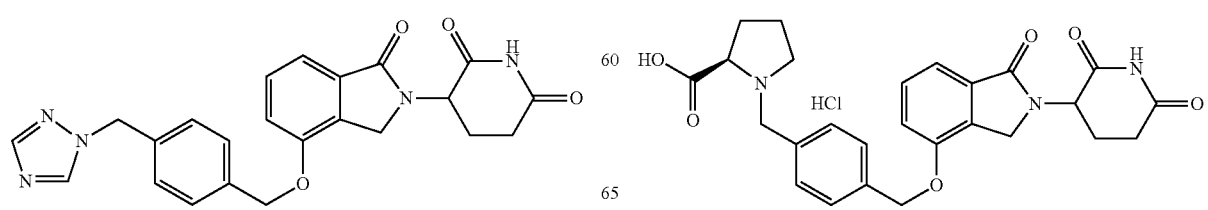

Step 1: 1-{4-[2-(1-Carbamoyl-3-methoxycarbonyl-propyl)-1-oxo-2,3-dihydro-1H-isoindol-4-yloxymethyl]-benzyl}-pyrrolidine-2-carboxylic acid tert-butyl ester To the stirred mixture of methyl 5-amino-4-(4-(4-(bromomethyl)benzyloxy)-1-oxoiso indolin-2-yl)-5-oxopentanoate (798 mg, 1.679 mmol) and (R)-tert-butyl pyrrolidine-2-carboxylate hydrochloride (418 mg, 2.015 mmol) in Acetonitrile (12 mL) at room temperature was added by DIPEA (0.586 ml, 3.36 mmol). The resulting solution was stirred at room temperature for 19 hrs before it was diluted by DCM (50 mL). The solution was washed with NaHCO$_3$ (sat, aq, 5 mL) and brine (15 mL). Organic layer was dried by MgSO$_4$ and concentrated under vacuo. The residue was purified by ISCO chromatography to give 1-{4-[2-(1-Carbamoyl-3-methoxycarbonyl-propyl)-1-oxo-2,3-dihydro-1H-isoindol-4-yloxymethyl]-benzyl}-pyrrolidine-2-carboxylic acid tert-butyl ester as a clear oil (840 mg, 88% yield) which was used in the next step without further purification; LCMS MH=566; $^1$H NMR (DMSO-d$_6$) δ 1.38 (s, 9H, CH$_3$, CH$_3$), 1.64-1.86 (m, 3H, CH, CH$_2$), 1.93-2.12 (m, 2H, CH$_2$), 2.13-2.22 (m, 1H, CHH), 2.22-2.30 (m, 2H, CH$_2$), 2.36 (q, J=7.7 Hz, 1H, CHH), 2.77-2.92 (m, 1H, CHH), 3.13 (dd; J=5.0, 8.8 Hz, 1H, CHH), 3.44-3.59 (m, 4H, CHH, CH$_3$), 3.88 (d, J=13.2 Hz, 1H, CHH), 4.39 (d, J=17.8 Hz, 1H, CHH), 4.53 (d, J=17.6 Hz, 1H, CHH), 4.72 (dd, J=4.7, 10.2 Hz, 1H, CHH), 5.21 (s, 2H, CH$_2$), 7.18 (s, 1H, NHH), 7.24-7.37 (m, 4H, Ar), 7.39-7.53 (m, 3H, Ar), 7.58 (s, 1H, NHH).

1-{4-[2-(2,6-Dioxo-piperidin-3-yl)-1-oxo-2,3-dihydro-1H-isoindol-4-yloxymethyl]-benzyl}-pyrrolidine-2-carboxylic acid tert-butyl ester To the stirred solution of (2R)-tert-butyl 1-(4-((2-(1-amino-5-methoxy-1,5-dioxopentan-2-yl)-1-oxoisoindolin-4-yloxy)methyl)benzyl)pyrrolidine-2-carboxylate (840 mg, 1.485 mmol) in Tetrahydrofuran (13 mL) at 0° C. was added KOtBu (167 mg, 1.485 mmol). The reaction mixture was stirred at 0° C. for 20 mins before it was diluted by EtOAc (50 mL). The mixture was acidified by HCl (1N, aq, 3 mL) followed by addition of NaHCO$_3$ (aq, sat, 3 mL) and brine (15 mL). The mixture was extracted and the organic layer was washed with NaCl (10 ml brine+10 mL water). Organic layer was dried by MgSO$_4$ and concentrated under vacuo to give 1-{4-[2-(2,6-Dioxo-piperidin-3-yl)-1-oxo-2,3-dihydro-1H-isoindol-4-yloxymethyl]-benzyl}-pyrrolidine-2-carboxylic acid tert-butyl ester as a sticky clear oil (810 mg, 102% crude yield) which was used in the next step without further purification; LCMS MH=534.

Step 3: 1-{4-[2-(2,6-Dioxo-piperidin-3-yl)-1-oxo-2,3-dihydro-1H-isoindol-4-yl oxymethyl]-benzyl}-pyrrolidine-2-carboxylic acid To the solution of (2R)-tert-butyl 1-(4-((2-(2,6-dioxopiperidin-3-yl)-1-oxoisoindolin-4-yloxy)methyl)benzyl)pyrrolidine-2-carboxylate (0.795 g, 1.489 mmol) in DCM (Volume: 5 ml) was added by HCl, 2M in diethyl ether (11.17 ml, 22.34 mmol) at room temperature for 4 days and the reaction mixture was concentrated in vacuo and then added fresh 2M HCl (ether, 15 mL). The suspension was stirred at room temperature for at room temperature over night. The reaction mixture was concentrated in vacuo and the residue was stirred in acetonitrile (15 mL) for 4 hrs. The mixture was filtered to give 1-{4-[2-(2,6-Dioxo-piperidin-3-yl)-1-oxo-2,3-dihydro-1H-isoindol-4-yloxymethyl]-benzyl}-pyrrolidine-2-carboxylic acid as an off white solid (420 mg, 57.5% yield); HPLC: Waters Symmetry C-18, 3.9×150 mm, 5 µm, 1 mL/min, 240 nm, 18/82, (CH$_3$CN/0.1% H$_3$PO$_4$), 4.84 min (96.67%); mp: 233-235° C.; $^1$H NMR (DMSO-d$_6$) δ 1.75-2.06 (m, 4H, CHH, CHH, CH$_2$), 2.45 (d, J=13.4 Hz, 2H, CHH, CHH), 2.54-2.65 (m, 1H, CHH), 2.83-3.02 (m, 1H, CHH), 3.11-3.27 (m, 1H, CHH), 3.32-3.46 (m, 1H, CHH), 4.18-4.34 (m, 3H, CHH, CHH, CHH), 4.39-4.52 (m, 2H, CHH, CHH), 5.12 (dd, J=5.0, 13.1 Hz, 1H, CHH), 5.29 (s, 2H, CH$_2$), 7.33 (dd, J=4.9, 7.7 Hz, 2H, Ar), 7.45-7.53 (m, 1H, Ar), 7.56 (s, 4H, Ar), 10.98 (s, 1H, NH); $^{13}$C NMR (DMSO-d$_6$) δ 21.95, 22.36, 27.90, 31.18, 45.06, 51.58, 54.00, 56.96, 65.32, 69.01, 115.00, 115.36, 127.79, 129.81, 129.95, 130.78, 130.95, 133.34, 137.83, 153.33, 167.94, 169.95, 170.96, 172.83; LCMS MH=478; Anal. Calcd for C$_{26}$H$_{27}$N$_3$O$_6$ 0.95HCl+1.2H2O: C, 58.51; H, 5.73; N, 7.87; Cl, 6.31; Found: C, 58.57; H, 5.46; N, 7.89; Cl, 6.14.

5.44 3-[1-Oxo-4-(4-[1,2,4]Triazol-4-ylmethyl-Benzyloxy)-1,3-Dihydro-Isoindol-2-yl]-Piperidine-2,6-Dione

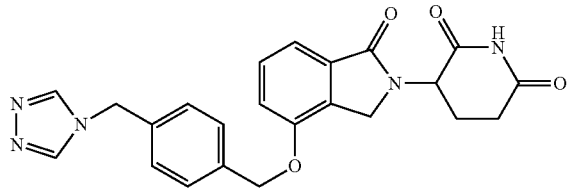 [SMILES: O=C1CCC(N2Cc3c(OCc4ccc(Cn5cnnc5)cc4)cccc3C2=O)C(=O)N1]

Step 1: Preparation of 4-Carbamoyl-4-[1-oxo-4-(4-[1,2,4]triazol-4-ylmethyl-benzyloxy)-1,3-dihydro-isoindol-2-yl]-butyric acid methyl ester To a solution of methyl 5-amino-4-(4-(4-(bromomethyl)benzyloxy)-1-oxoisoindolin-2-yl)-5-oxopentanoate (0.804 g, 1.691 mmol) in acetonitrile (20 ml) was added 1H-1,2,4-triazole (0.350 g, 5.07 mmol) and N-ethyl-N-isopropylpropan-2-amine (0.839 ml, 5.07 mmol) at room temperature. The mixture was stirred at room temperature for two days and then diluted by methylene chloride (50 mL) and washed with saturated sodium bicarbonate (10 mL) and brine (10 mL). The organic layer was concentrated and purified on silica gel column (MeOH/CH$_2$Cl$_2$ gradient from 1% to 9% in 50 min) to give 4-Carbamoyl-4-[1-oxo-4-(4-[1,2,4]triazol-4-ylmethyl-benzyloxy)-1,3-dihydro-isoindol-2-yl]-butyric acid methyl ester as an oil (0.25 g, 32% yield); $^1$H NMR (DMSO-d$_6$) δ 1.98-2.33 (m, 4H, CHH, CHH, CHH, CHH), 3.50 (s, 3H, CH$_3$), 4.34-4.58 (m, 2H, CH$_2$), 4.72 (dd, J=4.9, 10.4 Hz, 1H, NCH), 5.26 (d, J=17.9 Hz, 4H, CH$_2$, CH$_2$), 7.18 (br. s., 1H, NHH), 7.22-7.38 (m, 4H, Ar), 7.39-7.53 (m, 3H, Ar), 7.58 (br. s., 1H, NHH), 8.62 (s, 2H, Ar). It was used in the next step without further purification.

Step 2: Preparation of 3-[1-Oxo-4-(4-[1,2,4]triazol-4-ylmethyl-benzyloxy)-1,3-dihydro-isoindol-2-yl]-piperidine-2,6-dione To a stirred solution of methyl 4-(4-(4-((4H-1,2,4-triazol-4-yl)methyl)benzyloxy)-1-oxoisoindolin-2-yl)-5-amino-5-oxopentanoate (0.23 g, 0.496 mmol) in THF (15 ml) in an ice-bath was added potassium 2-methylpropan-2-olate (0.134 g, 1.19 mmol). The mixture was stirred for 10 minutes and 1N HCl (2 ml to pH=2) was added, then neutralized by saturated sodium bicarbonate (3 ml to pH=7). Ethyl acetate (40 ml) was added to the mixture and stirred for five minutes. The organic phase was separated, washed with brine (10 ml), and evaporated to give a white solid, which was purified on silica gel column (MeOH/CH$_2$Cl$_2$ from 0% to 10% in 30 min) to give 3-[1-Oxo-4-(4-[1,2,4]triazol-4-ylmethyl-benzyloxy)-1,3-dihydro-isoindol-2-yl]-piperidine-2,6-dione as a white solid (58 mg, 27% yield); mp 173-175° C.; HPLC: Waters Symmetry C-18, 3.9×150 mm, 5 µm, 1 mL/min, 240 nm, gradient from 10/90 to 95/5 in 5 min, isocratic at 95/5 in 5 min (CH₃CN/0.1% H₃PO₄), 5.05 min (95.2%); ¹H NMR (DMSO-d₆) δ 1.91-2.04 (m, 1H, CHH), 2.35-2.48 (m, 1H, CHH), 2.53-2.65 (m, 1H, CHH), 2.83-2.99 (m, 1H, CHH), 4.18-4.46 (m, 2H, CH₂), 5.10 (dd, J=5.1, 13.2 Hz, 1H, NCH), 5.23 (s, 2H, CH₂), 5.29 (s, 2H, CH₂), 7.26-7.38 (m, 4H, Ar), 7.43-7.54 (m, 3H, Ar), 8.62 (s, 2H, 2NH), 10.97 (s, 1H, NH); ¹³C NMR (DMSO-d₆) δ 22.35, 31.20, 45.08, 47.26, 51.59, 69.13, 114.97, 115.29, 127.81, 128.18, 129.81, 129.97, 133.32, 136.53, 143.22, 153.37, 167.98, 170.96, 172.83. LC/MS (M+1)⁺=432; Anal Calcd for $C_{23}H_{21}N_5O_4$ C, 64.03; H, 4.91; N, 16.23. Found: C, 61.85; H, 5.06; N, 14.92.

5.45 3-(4-((4-((2-Methyl-1H-Imidazol-1-yl)Methyl) Benzyl)Oxy)-1-Oxoisoindolin-2-yl)Piperidine-2,6-Dione

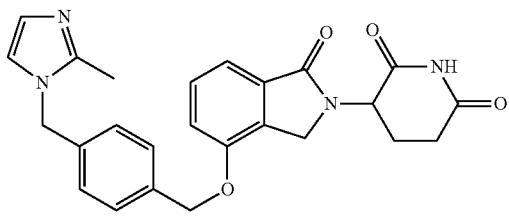 [SMILES: Cc1nccn1Cc1ccc(COc2cccc3c2CN(C2CCC(=O)NC2=O)C3=O)cc1]

To the suspension of 3-(4-(4-(bromomethyl)benzyloxy)-1-oxoisoindolin-2-yl)piperidine-2,6-dione (0.5 g, 1.128 mmol) and 2-methyl-1H-imidazole (0.108 g, 1.315 mmol) in acetonitrile (5 mL) was added DIEA (0.22 ml, 1.260 mmol) at room temperature. The suspension was stirred at room temperature overnight. To the suspension was added water (15 mL). The suspension was stirred at room temperature for 15 min. The suspension was filtered and washed with water (3×10 mL) to give a solid. The solid purified with Prep HPLC (Xbridge C18, 10 μm, 50×250 mm, 143 mL/min, 240 nM, 2/98/2 min, gradient to 95/5 0.1% formic acid in CH₃CN/0.1% formic acid in H2O in 13 min), and desired factions were collected. The solvent was removed in vacuo to give an oil, To the oil was added EtOAc (20 mL) to give a solid and the suspension was stirred at room temperature for 30 min. The suspension was filtered and washed with EtOAc (10 mL) and ether (10 mL) to give 3-(4-((4-((2-methyl-1H-imidazol-1-yl)methyl)benzyl)oxy)-1-oxoisoindolin-2-yl)piperidine-2,6-dione as a white solid (43 mg, 8.6% yield): HPLC: (Waters Symmetry $C_{18}$, 5 μm, 3.9×150 mm, 1 mL/min, 240 nm, 20/80 CH₃CN/0.1% H₃PO₄): RT=3.18 min (99.4%); mp: 275-277° C.; ¹H NMR (DMSO-d₆) δ 1.86-2.07 (m, 1H, CHH), 2.22 (s, 3H, CH₃), 2.33-2.49 (m, 1H, CHH), 2.52-2.63 (m, 1H, CHH), 2.79-3.03 (m, 1H, CHH), 4.16-4.30 (m, 1H, CHH), 4.33-4.46 (m, 1H, CHH), 5.10 (dd, J=5.1, 13.2 Hz, 1H, NCH), 5.15 (s, 2H, CH₂), 5.22 (s, 2H, CH₂), 6.76 (brs, 1H, Ar), 7.08-7.20 (m, 3H, Ar), 7.26-7.36 (m, 2H, Ar), 7.43-7.52 (m, 3H, Ar), 10.97 (s, 1H, NH); ¹³C NMR (DMSO-d₆) δ 12.70, 22.31, 31.16, 45.04, 48.31, 51.53, 69.16, 114.93, 115.25, 120.23, 126.46, 127.04, 128.06, 129.78, 129.95, 133.28, 135.88, 137.34, 153.39, 167.97, 170.95, 172.81; LCMS: MH=445; Anal. Calcd for $C_{25}H_{24}N_4O_4$+0.3 H₂O: C, 66.74; H, 5.51; N, 12.45; Found: C, 66.69; H, 5.24; N, 12.23.

5.46 3-{4-[4-(2,3-Dihydro-Indol-1-ylmethyl)-Benzyloxy]-1-Oxo-1,3-Dihydro-Isoindol-2-yl}-Piperidine-2,6-Dione

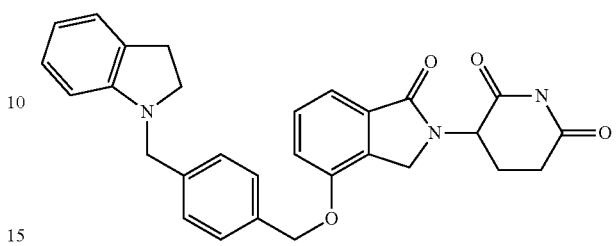

Step 1 Preparation of 4-[4-(4-Bromomethyl-benzyloxy)-1-oxo-1,3-dihydro-isoindol-2-yl]-4-carbamoyl-butyric acid methyl ester To a 1000 mL RBF were charged methyl 5-amino-4-(4-hydroxy-1-oxoisoindolin-2-yl)-5-oxopentanoate (9.76 g, 33.4 mmol), 1,4-bis(bromomethyl)benzene (26.4 g, 100 mmol) and potassium carbonate (4.61 g, 33.4 mmol), was added 500 mL of CH₃CN. The mixture was stirred at 50° C. for five hours and filtered, rinsed with CH₃CN (20 ml). The filtrate was evaporated to give a white solid, which was purified by silica gel column (MeOH/CH₂Cl₂) to give 4-[4-(4-Bromomethyl-benzyloxy)-1-oxo-1,3-dihydro-isoindol-2-yl]-4-carbamoyl-butyric acid methyl ester as a white solid (13.4 g, 84% yield). ¹H NMR (DMSO-d₆) δ 1.97-2.13 (m, 1H, CHH), 2.13-2.35 (m, 3H, CH₂, CHH), 3.50 (s, 3H, CH₂), 4.32-4.63 (m, 2H, CH₂), 4.65-4.84 (m, 3H, CH₂, NCH), 5.25 (s, 2H, CH₂), 7.19 (s, 1H, NHH), 7.23-7.36 (m, 2H, Ar), 7.38-7.52 (m, 5H, Ar), 7.58 (br. s., 1H, NHH).

Step 2: Preparation of 4-Carbamoyl-4-{4-[4-(2,3-dihydro-indol-1-ylmethyl)-benzyloxy]-1-oxo-1, 3-dihydro-isoindol-2-yl}-butyric acid methyl ester To the CH₃CN solution of methyl 5-amino-4-(4-(4-(bromomethyl)benzyloxy)-1-oxoisoindolin-2-yl)-5-oxopentanoate (0.5 g, 1.052 mmol) was added indoline (0.142 ml, 1.262 mmol) and DIPEA (0.220 ml, 1.262 mmol). The mixture was stirred overnight. The mixture was concentrated and extracted with water (15 mL) and EtOAc (20 mL). The organic layer was washed with NaHCO₃ (sat. 15 mL), brine (15 mL) and concentrated on rota-vap to give 4-Carbamoyl-4-{4-[4-(2, 3-dihydro-indol-1-ylmethyl)-benzyloxy]-1-oxo-1, 3-dihydro-isoindol-2-yl}-butyric acid methyl ester a solid (0.5 g, 93%). It was used in the next step directly.

Step 3: Preparation of 3-{4-[4-(1,3-Dihydro-isoindol-2-ylmethyl)-benzyloxy]-1-oxo-1,3-dihydro-1-isoindol-2-yl}-piperidine-2,6-dione To the THF solution of methyl 5-amino-4-(4-(4-(indolin-1-ylmethyl)benzyloxy)-1-oxoisoindolin-2-yl)-5-oxopentanoate (0.5 g, 0.974 mmol) was added KOtBu (0.131 g, 1.168 mmol) at 0° C. After stirring at 0° C. for 15 min., the mixture was added 2 mL of 1N HCl followed by 10 mL of sat. NaHCO₃ and 25 mL of EtOAc. The mixture was separated and the organic layer was washed with water (10 mL), brine (10 mL) and concentrated. The resulted white solid was purified on silica gel column eluted with DCM and MeOH to give 3-{4-[4-(1,3-Dihydro-isoindol-2-ylmethyl)-benzyloxy]-1-oxo-1,3-dihydro-1-isoindol-2-yl}-, piperidine-2,6-dione as white solid (200 mg, 43%). melting point: 173-175° C. LC-MS m/e=482. HPLC Waters Symmetry C-18, 3.9×150 mm, 5 micro, 1 mL/min, 240 nm, gradient 5/95 to 5/95 CH₃CN/0.1% H₃PO₄ in H₂O during 5 min and stay at 95/5 for 5 min: 7.58 min (93%). ¹H NMR (DMSO-d$_6$) δ 1.90-2.04 (m, 1H, CHH), 2.33-2.47 (m, 1H, CHH), 2.56-2.65 (m, 1H, CHH), 2.79-3.02 (m, 4H, CH$_2$, CHH), 3.13-3.30 (m, 2H, CH$_2$), 3.32 (s, 3H, CH$_2$), 4.10-4.59 (m, 4H, CH$_2$, CH$_2$), 4.99-5.18 (m, 1H, NCH), 5.23 (s, 2H, CH$_2$), 6.49-6.65 (m, 2H, Ar), 6.82-7.16 (m, 2H, Ar), 7.25-7.43 (m, 4H, Ar), 7.42-7.62 (m, 3H, Ar), 10.96 (s, 1H, NH). $^{13}$C NMR (DMSO-d$_6$) δ 22.35, 27.92, 31.20, 45.09, 51.58, 52.15, 52.76, 69.39, 106.89, 114.98, 115.24, 117.20, 124.24, 127.04, 127.85, 128.07, 129.47, 129.81, 129.97, 133.31, 135.30, 138.16, 152.16, 153.48, 168.01, 170.96, 172.83. Anal Calcd for C$_{27}$H$_{29}$N$_3$O$_4$: C %:72.33, H %:5.65, N %:,8.73. Found: C %:72.14, H %:5.51, N %:,8.47.

5.47 3-(4-((3-(Morpholinomethyl)-1,2,4-Oxadiazol-5-yl)Methoxy)-1-Oxoisoindolin-2-yl)Piperidine-2,6-Dione

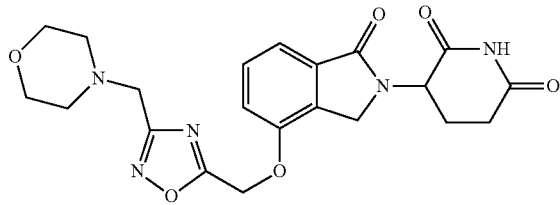 [SMILES: O=C1CCC(N2Cc3c(OCc4nc(CN5CCOCC5)no4)cccc3C2=O)C(=O)N1]

Step 1: Sodium borohydride (179 mg, 4.72 mmol) was added to the solution of ethyl 3-(chloromethyl)-1,2,4-oxadiazole-5-carboxylate (900 mg, 4.72 mmol) in ethanol (10 mL) at 0° C. The mixture was stirred at 0° C. for 1 hour, and then quenched with HCl (1N, 5 mL). The solvent was evaporated, the residue was partitioned between ethyl acetate (30 mL) and water (10 mL), the organic layer was washed with brine, dried over magnesium sulfat, and the solvent was evaporated to give 510 mg of (3-(chloromethyl)-1,2,4-oxadiazol-5-yl)methanol, the crude was used in the next step without further purification.

Step 2: Polymer-supported triphenylphosphine (1.6 mmol/g, 3.16 g, 5.05 mmol) was added to a stirred suspension of methyl 5-amino-4-(4-hydroxy-1-oxoisoindolin-2-yl)-5-oxopentanoate (984 mg, 3.37 mmol) in THF (30 mL) at 0° C., followed by diisopropyl azodicarboxylate (1.02 g, 5.05 mmol), after stirring for 10 minutes, (3-(chloromethyl)-1,2,4-oxadiazol-5-yl)methanol (500 mg, 3.37 mmol) was added, the mixture was stirred at room temperature overnight and filtered. The resin was washed with ethyl acetate (10×20 mL). The combined filtrate was evaporated to dryness. The crude was purified by ISCO (80 g column, MeOH/CH$_2$Cl$_2$ gradient from 0% to 5% in 40 min) to give methyl 5-amino-4-(4-((3-(chloromethyl)-1,2,4-oxadiazol-5-yl)methoxy)-1-oxoisoindolin-2-yl)-5-oxopentanoate (480 mg, 34% yield). $^1$H NMR (DMSO-d$_6$) δ 1.20 (d, J=7.0 Hz, 2H, CH$_2$), 1.95-2.22 (m, 2H, CH$_2$), 3.50 (s, 3H, CH$_3$), 4.38-4.62 (m, 2H, CH$_2$), 4.73 (d, J=5.7 Hz, 1H, CH), 4.94 (s, 2H, CH$_2$), 5.72 (s, 2H, CH$_2$), 7.21 (br. s., 1H, NHH), 7.32-7.41 (m, 2H, Ar), 7.49 (d, J=7.7 Hz, 1H, Ar), 7.61 (br. s., 1H, NHH).

Step 3: To a solution of methyl 5-amino-4-(4-((3-(chloromethyl)-1,2,4-oxadiazol-5-yl)methoxy)-1-oxoisoindolin-2-yl)-5-oxopentanoate (460 mg, 1.088 mmol) in acetonitrile (10 mL) were added morpholine (0.114 mL, 1.306 mmol) and triethyl amine (0.182 mL, 1.306 mmol). The formed mixture was stirred at room temperature overnight. The solvent was evaporated t dryness, the crude was partitioned between ethyl acetate (50 mL) and water (10 mL) the organic layer was separated and washed with brine, dried over magnesium sulfate. The solvent was evaporated to give methyl 5-amino-4-(4-((3-(morpholinomethyl)-1,2,4-oxadiazol-5-yl)methoxy)-1-oxoisoindolin-2-yl)-5-oxopentanoate (410 mg, 80% yield). $^1$H NMR (DMSO-d$_6$) δ 1.18 (d, J=5.3 Hz, 2H, CH$_2$), 1.96-2.23 (m, 2H, CH$_2$), 2.42-2.50 (m, 4H, CH$_2$, CH$_2$), 3.50 (s, 3H, CH$_3$), 3.53-3.62 (m, 4H, CH$_2$, CH$_2$), 3.68 (s, 2H, CH$_2$), 4.30-4.65 (m, 2H, CH$_2$), 4.67-4.83 (m, 1H, CH), 5.68 (s, 2H, CH$_2$), 7.21 (br. s., 1H, NHH), 7.28-7.42 (m, 2H, Ar), 7.48 (d, J=7.7 Hz, 1H, Ar), 7.61 (br. s., 1H, NHH).

Step 4: To a solution of methyl 5-amino-4-(4-((3-(morpholinomethyl)-1,2,4-oxadiazol-5-yl)methoxy)-1-oxoisoindolin-2-yl)-5-oxopentanoate (350 mg, 0.739 mmol) in THF was added was added potassium tert-butoxide (83 mg, 0.739 mmol) at 0° C. The mixture was stirred at 0° C. for 1 hour, additional potassium tert-butoxide (20 mg, 0.27 mmol) was added, the mixture was stirred at room temperature for another 1 hour. The reaction was quenched with acetic acid (1 mL), the solvent was evaporated to dryness, the residue was partitioned between ethyl acetate (50 mL) and saturated sodium bicarbonate (10 mL). The organic layer was separated and washed with brine, dried over magnesium sulfate, the solvent was evaporated under vacuo, the crude was purified by ISCO (40 g column, MeOH/CH$_2$Cl$_2$ gradient from 0% to 5% in 40 min) to give 3-(4-((3-(morpholinomethyl)-1,2,4-oxadiazol-5-yl)methoxy)-1-oxoisoindolin-2-yl)piperidine-2,6-dione as a white solid (230 mg, 70% yield). mp: 150-152° C.; $^1$H NMR (DMSO-d$_6$) δ 1.90-2.08 (m, 1H, CHH), 2.31-2.44 (m, 1H, CHH), 2.44-2.49 (m, 4H, CH$_2$, CH$_2$), 2.53 (br. s., 1H, CHH), 2.79-3.05 (m, 1H, CHH), 3.48-3.63 (m, 4H, CH$_2$, CH$_2$), 3.69 (s, 2H, CH$_2$), 4.21-4.52 (m, 2H, CH$_2$), 5.12 (dd, J=5.0, 13.3 Hz, 1H, CH), 5.69 (s, 2H, CH$_2$), 7.38 (dd, J=7.6, 11.0 Hz, 2H, Ar), 7.47-7.66 (m, 1H, Ar); $^{13}$C NMR (DMSO-d$_6$) δ 22.28, 31.18, 45.00, 51.62, 51.93, 52.58, 61.11, 65.95, 115.25, 116.41, 129.90, 130.00, 133.58, 152.43, 166.98, 167.69, 170.92, 172.81, 174.88; HPLC: Waters Xterra C-18, 3.9×150 mm, 5 µm, 1 mL/min, 240 nm, 20/80 CH$_3$CN/0.1% HCOONH$_4$ t$_R$=4.65 (100%); Anal. Calcd for C$_{21}$H$_{23}$N$_5$O$_6$ C, 57.14; H, 5.26; N, 15.86; Found: C, 56.99; H, 4.95; N, 15.90.

5.48 3-{4-[3-(4-Isopropyl-Piperidin-1-ylmethyl)-Benzyloxy]-1-Oxo-1,3-Dihydro-Isoindol-2-yl}-Piperidine-2,6-Dione

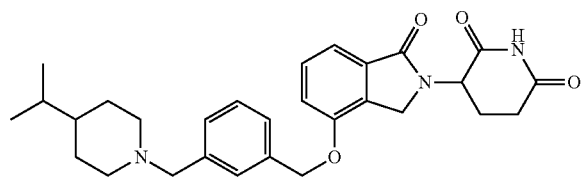 [SMILES: CC(C)C1CCN(Cc2cccc(COc3cccc4c3CN(C3CCC(=O)NC3=O)C4=O)c2)CC1]

To the CH$_3$CN solution (15 ml) of 3-(4-(3-(bromomethyl)benzyloxy)-1-oxoisoindolin-2-yl)piperidine-2,6-dione (0.43 g, 0.970 mmol) was added 4-isopropylpiperidine (0.160 g, 1.261 mmol) and N-ethyl-N-isopropylpropan-2-amine (0.321 ml, 1.940 mmol) at room temperature. The cloudy mixture was stirred at room temperature for 2 hours. The white suspension was evaporated under vacuum to get rid of CH$_3$CN. The resulting white solid was stirred in water (50 ml) and extracted with methylene chloride (3×80 ml). The combined methylene chloride phases was washed by saturated sodium bicarbonate (2×50 ml), dried over sodium sulfate and concentrated to give as an off-white solid (72 mg, 50% yield); mp, 153-155° C. HPLC: Waters Symmetry C-18, 3.9×150 mm, 5 μm, 1 mL/min, 240 nm, gradient from 10/90 to 95/5 in 5 min, isocratic at 95/5 in 5 min (CH$_3$CN/ 0.1% H$_3$PO$_4$), 4.74 min (96.3%). $^1$H NMR (DMSO-d$_6$) δ 0.83 (d, J=6.8 Hz, 6H, 2CH$_3$), 0.89-1.02 (m, 1H, CH), 1.14 (qd, J=3.9, 12.2 Hz, 2H, CH$_2$), 1.37 (dq, J=6.6, 13.2 Hz, 1H, CH), 1.55 (dd, J=1.4, 10.9 Hz, 2H, CH$_2$), 1.75-1.91 (m, 2H, CH$_2$), 1.92-2.05 (m, 1H, CHH), 2.34-2.48 (m, 1H, CHH), 2.53-2.64 (m, 1H, CHH), 2.80 (d, J=11.5 Hz, 2H, CH$_2$), 2.84-3.00 (m, 1H, CHH), 3.43 (s, 2H, CH$_2$), 4.20-4.47 (m, 2H, CH$_2$), 5.11 (dd, J=5.1, 13.2 Hz, 1H, NCH), 5.25 (s, 2H, CH$_2$), 7.20-7.28 (m, 1H, Ar), 7.28-7.41 (m, 5H, Ar), 7.43-7.53 (m, 1H, Ar), 10.97 (s, 1H, NH). $^{13}$C NMR (DMSO-d$_6$) δ 19.68, 22.39, 28.89, 31.21, 31.95, 41.85, 45.09, 51.59, 53.62, 62.25, 69.63, 115.17, 115.26, 126.13, 127.87, 128.29, 129.78, 129.95, 133.31, 136.44, 139.01, 153.46, 167.99, 170.95, 172.80. LC/MS (M+1)$^+$=490; Anal Calcd for C$_{29}$H$_{35}$N$_3$O$_4$+0.2 H2O: C, 70.62; H, 7.23; N, 8.52; Found: C, 70.41; H, 7.26; N, 8.44.

5.49 3-{1-Oxo-4-[3-(4-Phenyl-Piperidin-1-ylmethyl)-Benzyloxy]-1,3-Dihydro-Isoindol-2-yl}-Piperidine-2,6-Dione

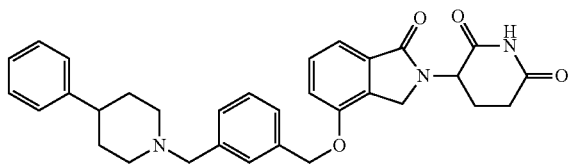 [SMILES: O=C1CCC(N2Cc3c(OCc4cccc(CN5CCC(c6ccccc6)CC5)c4)cccc3C2=O)C(=O)N1]

To the CH$_3$CN solution (15 ml) of 3-(4-(3-(bromomethyl) benzyloxy)-1-oxoisoindolin-2-yl)piperidine-2,6-dione (0.442 g, 0.997 mmol) was added 4-phenylpiperidine (0.209 g, 1.296 mmol) and N-ethyl-N-isopropylpropan-2-amine (0.330 ml, 1.994 mmol) at room temperature. The cloudy mixture was stirred at room temperature overnight. The solvent was evaporated in vacuo to give an off-white solid, which was stirred in water (50 ml) and extracted with methylene chloride (3×50 ml). The combined methylene chloride phases were back washed with water (50 ml), brine (50 ml), dried over sodium sulfate and evaporated to an off-white solid (~0.5 g), which was stirred in acetonitrile (10 ml) at 50° C. oil bath for 10 minutes then filtered and dried vacuum oven to give 3-{1-Oxo-4-[3-(4-phenyl-piperidin-1-ylmethyl)-benzyloxy]-1,3-dihydro-isoindol-2-yl}-piperidine-2,6-dione as a white solid (0.36 g, 69% yield); mp, 226-228° C. HPLC: Waters Symmetry C-18, 3.9×150 mm, 5 μm, 1 mL/min, 240 nm, gradient from 10/90 to 95/5 in 5 min, isocratic at 95/5 in 5 min (CH$_3$CN/0.1% H$_3$PO$_4$), 4.79 min, 96.0%. $^1$H NMR (DMSO-d$_6$) δ 1.53-1.79 (m, 4H, 2CH$_2$), 1.89-2.11 (m, 3H, CHH, CH$_2$), 2.33-2.47 (m, 2H, CHH, CHH), 2.53-2.62 (m, 1H, CHH), 2.80-2.99 (m, 3H, CH$_2$, CHH), 3.51 (s, 2H, CH$_2$), 4.21-4.49 (m, 2H, CH$_2$), 5.11 (dd, J=5.1, 13.2 Hz, 1H, NCH), 5.27 (s, 2H, CH$_2$), 7.12-7.53 (m, 12H, Ar), 10.97 (s, 1H, NH). $^{13}$C NMR (DMSO-d$_6$) δ 22.36, 31.20, 33.05, 41.81, 45.13, 51.59, 53.57, 62.23, 69.63, 115.19, 115.26, 125.94, 126.24, 126.67, 128.04, 128.29, 128.45, 129.78, 129.97, 133.32, 136.49, 138.82, 146.21, 153.46, 167.99, 170.95, 172.80. LC/MS (M+1)$^+$=524; Anal Calcd for C$_{32}$H$_{33}$N$_3$O$_4$+0.3 H2O: C, 72.65; H, 6.40; N, 7.94. Found: C, 72.48; H, 6.33; N, 7.78.

5.50 1-{4-[2-(2,6-Dioxo-Piperidin-3-yl)-1-Oxo-2,3-Dihydro-1H-Isoindol-4-yl Oxymethyl]-Benzyl}-1H-[1,2,3]Triazole-4-Carboxylic Acid Amide

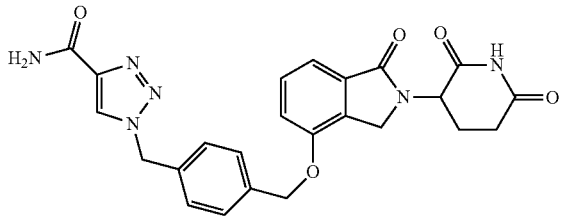 [SMILES: NC(=O)c1cn(Cc2ccc(COc3cccc4c3CN(C3CCC(=O)NC3=O)C4=O)cc2)nn1]

Step 1: 4-[4-(4-Azidomethyl-benzyloxy)-1-oxo-1,3-dihydro-isoindol-2-yl]-4-carbamoyl-butyric acid methyl ester To the mixture of sodium azide (0.226 g, 3.47 mmol) in Ethanol (40 mL) at room temperature was added methyl 5-amino-4-(4-(4-(bromomethyl)benzyloxy)-1-oxoisoindolin-2-yl)-5-oxopentanoate (1.5 g, 3.16 mmol). The resulting suspension was heated to reflux for 4 hrs before it was cooled and added by water (50 mL) and EtOAc (200 mL). The mixture was extracted and the organic layer was washed with brine (50 mL). Organic layer was dried by MgSO$_4$ and concentrated under vacuo to give 4-[4-(4-Azidomethyl-benzyloxy)-1-oxo-1,3-dihydro-isoindol-2-yl]-4-carbamoyl-butyric acid methyl ester as a yellow sticky solid (1.5 g, 109% crude yield)). The compound was used in the next step without further purification; LCMS MH=439.

Step 2: Propynoic Acid Amide Ethyl propiolate (2 g, 20.39 mmol) was added to the stirred aqueous AMMONIA (5.99 g, 102 mmol) at -78° C. drop wise over 7 mins. The resulting mixture was stirred under -78° C. for 1 hrs and was allowed to room temperature. The reaction mixture was concentrated under high vacuo to give Propynoic acid amide as a yellow oil (1.41 g, 100% crude yield). The compound was used in the next step without further purification; $^1$H NMR (DMSO-d$_6$) δ 4.07 (s, 1H, CH), 7.62 (br. s., 1H, NHH), 8.07 (br. s., 1H, NHH); $^{13}$C NMR (DMSO-d$_6$) δ 75.37, 78.51, 153.23.

Step 3: 4-Carbamoyl-4-{4-[4-(4-carbamoyl-[1,2,3]triazol-1-ylmethyl)-benzyloxy]-1-oxo-1,3-dihydro-isoindol-2-yl}-butyric acid methyl ester To a microwave vial was added methyl 5-amino-4-(4-(4-(azidomethyl)benzyloxy)-1-oxoisoindolin-2-yl)-5-oxopentanoate (300 mg, 0.69 mmol) and propiolamide (81 mg, 1.17 mmol) in Ethanol (2 mL). The mixture was heated in microwave oven for 15 mins at 150° C. The reaction mixture was concentrated and stirred in EtOAc (20 mL). The mixture was filtered to give 4-Carbamoyl-4-{4-[4-(4-carbamoyl-[1,2,3]triazol-1-ylmethyl)-benzyloxy]-1-oxo-1,3-dihydro-isoindol-2-yl}-butyric acid methyl ester as a solid (255 mg, 73% crude yield); LCMS MH=507.

Step 4: 1-{4-[2-(2,6-Dioxo-piperidin-3-yl)-1-oxo-2,3-dihydro-1H-isoindol-4-yl oxymethyl]-benzyl}-1H-[1,2,3]triazole-4-carboxylic acid amide To the stirred suspension of methyl 5-amino-4-(4-(4-((4-carbamoyl-1H-1,2,3-triazol-1-yl)methyl)benzyloxy)-1-oxoisoindolin-2-yl)-5-oxopentanoate (250 mg, 0.49 mmol) in Tetrahydrofuran (15 mL) at room temperature was added POTASSIUM TERT-BUTOXIDE (55.4 mg, 0.49 mmol). The resulting suspension was stirred at room temperature for two hrs and kept in fridge overnight. The reaction mixture was added by POTASSIUM TERT-BUTOXIDE (110 mg, 1.0 mmol) two portions and stirred at room temperature for 1 hr before it was diluted by EtOAc (30 mL). The suspension was added by HCl (aq, 1N, 4 mL) and filtered. The filtrate was extracted and the organic layer was dried by MgSO$_4$ and concentrated under vacuo. The residue was purified by ISCO chromatography and the product was stirred in CH$_3$CN (5 mL). The mixture was filtered to give 1-{4-[2-(2,6-Dioxo-piperidin-3-yl)-1-oxo-2,3-dihydro-1H-isoindol-4-yloxymethyl]-benzyl}-1H-[1,2,3]triazole-4-carboxylic acid amide As a white solid (21 mg, 9% yield); HPLC: Waters Symmetry C-18, 3.9×150 mm, 5 μm, 1 mL/min, 240 nm, 30/70, (CH$_3$CN/0.1% H$_3$PO$_4$), 3.5 min (97.4%); mp: N/A; $^1$H NMR (DMSO-d$_6$) δ 1.90-2.03 (m, 1H, CHH), 2.44 (dd, J=4.3, 13.2 Hz, 1H, CHH), 2.54-2.63 (m, 1H, CHH), 2.82-2.98 (m, 1H, CHH), 4.24 (d, J=17.4 Hz, 1H, CHH), 4.40 (d, J=17.6 Hz, 1H, CHH), 5.10 (dd, J=5.0, 13.3 Hz, 1H, CHH), 5.24 (s, 2H, CH$_2$), 5.66 (s, 2H, CH$_2$), 7.25-7.41 (m, 4H, Ar), 7.42-7.57 (m, 4H, NHH, Ar), 7.85 (s, 1H, NHH), 8.61 (s, 1H, triazole), 10.96 (s, 1H, NH); $^{13}$C NMR (DMSO-d$_6$) δ 22.32, 31.19, 45.07, 51.57, 52.75, 69.12, 114.94, 115.29, 126.66, 128.15, 129.82, 129.97, 133.32, 135.45, 136.73, 143.12, 153.38, 161.39, 167.99, 170.97, 172.83; LCMS MH=475; Anal. Calcd for C$_{24}$H$_{22}$N$_6$O$_5$: C, 60.75; H, 4.67; N, 17.71; Found: N/A.

5.51 3-{4-[2-(2,6-Dioxo-Piperidin-3-yl)-1-Oxo-2,3-Dihydro-1H-Isoindol-4-yl Oxymethyl]-Benzyl}-3H-[1,2,3]Triazole-4-Carboxylic Acid Amide

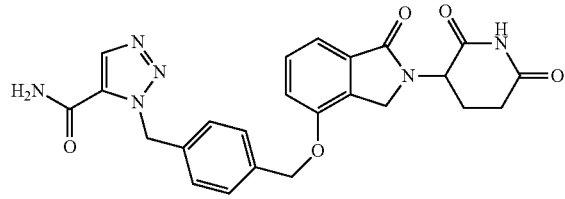 [SMILES: NC(=O)c1cnnn1Cc1ccc(COc2cccc3c2CN(C2CCC(=O)NC2=O)C3=O)cc1]

Step 1: 4-[4-(4-Azidomethyl-benzyloxy)-1-oxo-1,3-dihydro-isoindol-2-yl]-4-carbamoyl-butyric acid methyl ester To the mixture of sodium azide (0.226 g, 3.47 mmol) in Ethanol (40 mL) at room temperature was added methyl 5-amino-4-(4-(4-(bromomethyl)benzyloxy)-1-oxoisoindolin-2-yl)-5-oxopentanoate (1.5 g, 3.16 mmol). The resulting suspension was heated to reflux for 4 hrs before it was cooled and added by water (50 mL) and EtOAc (200 mL). The mixture was extracted and the organic layer was washed with brine (50 mL). Organic layer was dried by MgSO$_4$ and concentrated under vacuo to give 4-[4-(4-Azidomethyl-benzyloxy)-1-oxo-1,3-dihydro-isoindol-2-yl]-4-carbamoyl-butyric acid methyl ester as a yellow sticky solid (1.5 g, 109% crude yield)). The compound was used in the next step without further purification; LCMS MH=439.

Step 2: Propynoic Acid Amide Ethyl propiolate (2 g, 20.39 mmol) was added to the stirred aqueous AMMONIA (5.99 g, 102 mmol) at −78° C. drop wise over 7 mins. The resulting mixture was stirred under −78° C. for 1 hrs and was allowed to room temperature. The reaction mixture was concentrated under high vacuo to give Propynoic acid amide as a yellow oil (1.41 g, 100% crude yield). The compound was put to next step without further purification; $^1$H NMR (DMSO-d$_6$) δ 4.07 (s, 1H, CH), 7.62 (br. s., 1H, NHH), 8.07 (br. s., 1H, NHH); $^{13}$C NMR (DMSO-d$_6$) δ 75.37, 78.51, 153.23.

Step 3: 4-Carbamoyl-4-{4-[4-(5-carbamoyl-[1,2,3]triazol-1-ylmethyl)-benzyloxy]-1-oxo-1,3-dihydro-isoindol-2-yl}-butyric acid methyl ester To a microwave vial was added methyl 5-amino-4-(4-(4-(azidomethyl)benzyloxy)-1-oxoisoindolin-2-yl)-5-oxopentanoate (300 mg, 0.686 mmol) and propiolamide (81 mg, 1.166 mmol) in Ethanol (2 mL). The mixture was heated in microwave oven for 15 mins at 150° C. The reaction mixture was concentrated and stirred in EtOAc (20 mL). The mixture was filtered and the filtrate was concentrated under vacuo and the residue was purified by ISCO chromatography to give 4-Carbamoyl-4-{4-[4-(5-carbamoyl-[1,2,3]triazol-1-ylmethyl)-benzyloxy]-1-oxo-1,3-dihydro-isoindol-2-yl}-butyric acid methyl ester as a solid (50 mg, 14% yield); LCMS MH=507.

Step 4: 3-{4-[2-(2,6-Dioxo-piperidin-3-yl)-1-oxo-2,3-dihydro-1H-isoindol-4-yl oxymethyl]-benzyl}-3H-[1,2,3]triazole-4-carboxylic acid amide To the stirred solution of methyl 5-amino-4-(4-(4-((5-carbamoyl-1H-1,2,3-triazol-1-yl)methyl)benzyloxy)-1-oxoisoindolin-2-yl)-5-oxopentanoate (50.0 mg, 0.099 mmol) in Tetrahydrofuran (10 mL) at room temperature was added potassium 2-methylpropan-2-olate (41.00 mg, 0.37 mmol). The reaction mixture was stirred at room temperature for 2 hrs before it was added by EtOAc (15 mL) followed by the addition of HCl (1N, aq, 2 mL). The mixture was extracted and the organic layer was washed with NaHCO$_3$ (aq, sat., 5 mL) and brine (5 mL). The organic layer was dried by MgSO$_4$ and concentrated under vacuo to give a white solid. The white solid was stirred in CH$_3$CN (4 mL) and ether (15 mL). The mixture was filtered to give 3-{4-[2-(2,6-Dioxo-piperidin-3-yl)-1-oxo-2,3-dihydro-1H-isoindol-4-yl oxymethyl]-benzyl}-3H-[1,2,3]triazole-4-carboxylic acid amide as a white solid (40 mg, 85% yield); HPLC: Waters Symmetry C-18, 3.9×150 mm, 5 μm, 1 mL/min, 240 nm, 30/70, (CH$_3$CN/0.1% H$_3$PO$_4$), 3.88 min (95.7%); mp: 280-282° C.; $^1$H NMR (DMSO-d$_6$) δ 1.89-2.03 (m, 1H, CHH), 2.34-2.48 (m, 1H, CHH), 2.59 (br. s., 1H, CHH), 2.81-2.99 (m, 1H, CHH), 4.23 (d, J=17.6 Hz, 1H, NHH), 4.40 (d, J=17.6 Hz, 1H, CHH), 5.10 (dd, J=5.0, 13.1 Hz, 1H, CHH), 5.21 (s, 2H, CH$_2$), 5.94 (s, 2H, CH$_2$), 7.24 (d, J=8.1 Hz, 2H, M$_{01}$), 7.31 (dd, J=4.2, 7.6 Hz, 2H, Ar), 7.41-7.53 (m, 3H, Ar), 7.81 (s, 1H, NHH), 8.23 (s, 1H, NHH), 8.26 (s, 1H, triazole), 10.96 (s, 1H, NH); $^{13}$C NMR (DMSO-d$_6$) δ 22.30, 31.16, 45.04, 51.53, 51.65, 69.14, 114.85, 115.25, 127.69, 127.98, 129.78, 129.93, 130.34, 133.28, 134.67, 136.10, 136.27, 153.39, 158.90, 167.97, 170.93, 172.81; LCMS MH=475; Anal. Calcd for C$_{24}$H$_{22}$N$_6$O$_5$+0.5H$_2$O: C, 59.62; H, 4.80; N, 17.38; Found: C, 59.82; H, 4.65; N, 17.09.

5.52 (R)-3-[4-(4-Morpholin-4-ylmethyl-Benzyloxy)-1-Oxo-1,3-Dihydro-Isoindol-2-yl]-Piperidine-2,6-Dione

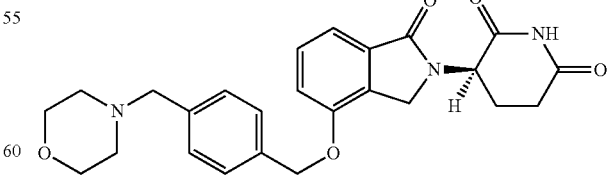

Step 1: 3-Hydroxy-2-methyl-benzoic acid methyl ester 3-hydroxy-2-methylbenzoic acid (105 g, 690 mmol) was added to MeOH (800 mL) in 2 L three neck RB flask equipped with condenser, thermometer and stirring bar followed by the addition of MeOH (250 ml). And H$_2$SO$_4$ (10 mL, 180 mmol) was added to above solution. The reaction mixture was stirred at 62° C. for 17 hrs before it was concentrated. The residue (200 mL) was added to water (600 mL) slowly at room temperature and white solid was formed. The suspension was stirred in ice bath for 30 mins and filtered. The solid was washed by water (5×250 mL) and dried to give 3-Hydroxy-2-methyl-benzoic acid methyl ester as a white solid (100 g, 87% yield). The compound was put to next step without further purification: LCMS MH=167; $^1$H NMR (DMSO-$d_6$) δ 2.28 (s, 3H, $CH_3$), 3.80 (s, 3H, $CH_3$), 6.96-7.03 (m, 1H, Ar), 7.09 (t, J=7.8 Hz, 1H, Ar), 7.14-7.24 (m, 1H, Ar), 9.71 (s, 1H, OH).

Step 2: 3-(tert-Butyl-dimethyl-silanyloxy)-2-methyl-benzoic acid methyl ester To a 1 L three neck RB flask equipped with stirring bar and thermometer was added DMF (300 mL), methyl 3-hydroxy-2-methylbenzoate (90 g, 542 mmol) and imidazole (92 g, 1354 mmol). TBDMS-Cl (90 g, 596 mmol) was added to above solution in portions to control the internal temp between 15-19° C. over 20 mins and after addition the internal temp dropped below 10° C. The ice bath was removed and the reaction mixture was stirred at room temperature for 16 hrs. The reaction mixture was added to ice water (500 mL) and the resulting solution was divided to two portions (700 ml×2). Each portion was extracted with EtOAc (700 mL). And each organic layer was washed with cold water (350 ml) and brine (350 ml). Organic layers were combined and dried by $MgSO_4$. Organic layer was concentrated to give 3-(tert-Butyl-dimethyl-silanyloxy)-2-methyl-benzoic acid methyl ester as a light brown oil (160 g, 100% crude yield). The compound was put to next step without further purification: LCMS MH=281; $^1$H NMR (DMSO-$d_6$) δ −0.21 (s, 6H, $CH_3$, $CH_3$), 0.73-0.84 (m, 9H, $CH_3$, $CH_3$, $CH_3$), 2.10 (s, 3H, $CH_3$), 3.60 (s, 3H, $CH_3$), 6.82 (dd, 1H, Ar), 6.97 (t, J=7.9 Hz, 1H, Ar), 7.13 (dd, J=1.1, 7.7 Hz, 1H, Ar)

Step 3: 2-Bromomethyl-3-(tert-butyl-dimethyl-silanyloxy)-benzoic acid methyl ester NBS (49.8 g, 280 mmol) was added to methyl 3-(tert-butyl dimethylsilyloxy)-2-methylbenzoate (78.4 g, 280 mmol) in methyl acetate (500 mL) at room temperature to give an orange colored suspension. The resulting reaction mixture was heated in oil bath to 40° C. and shined by 300 wt sunlight bulb at reflux for 4 hrs. The reaction mixture was cooled down and washed by $Na_2SO_3$ solution 2×(600 mL, 50% saturated concentration), water (500 mL) and brine (600 mL). Organic layer was dried by $MgSO_4$ and decolored by charcoal. Organic layer was concentrated to give 2-Bromomethyl-3-(tert-butyl-dimethyl-silanyloxy)-benzoic acid methyl ester as a light brown oil (96 g, 91% crude yield). The compound was put to next step without further purification: LCMS M-Br=279; $^1$H NMR (DMSO-$d_6$) δ 0.05-0.11 (m, 6H, $CH_3$, $CH_3$), 0.82 (s, 9H, $CH_3$, $CH_3$, $CH_3$), 3.65 (s, 3H, $CH_3$), 4.74 (s, 2H, $CH_2$), 6.94 (dd, J=1.3, 8.1 Hz, 1H, Ar), 7.10-7.20 (m, 1H, Ar), 7.21-7.29 (m, 1H, Ar); LCMS Step 4: (R) 4-[4-(tert-Butyl-dimethyl-silanyloxy)-1-oxo-1,3-dihydro-isoindol-2-yl]-4-carbamoyl-butyric acid benzyl ester To the stirred solution of methyl 2-(bromomethyl)-3-(tert-butyldimethylsilyloxy)benzoate (15.32 g, 36.7 mmol) in Acetonitrile (130 mL) was added (R)-benzyl 4,5-diamino-5-oxopentanoate hydrochloride (10 g, 36.7 mmol) at room temperature. The resulting suspension was added by DIPEA (13.45 ml, 77 mmol) through an addition funnel over 5 mins and the suspension became clear solution. The reaction mixture was heated at 40° C. for 31 hrs and room temperature 18 hrs before it was concentrated under vacuo. The residue was stirred in diethyl ether (120 mL) and white solid was formed. The mixture was filtered and solid was washed with diethyl ether (80 mL×4). Filtrates was washed with HCl (1N aq, 80 mL) and $NaHCO_3$ (aq., sat., 80 mL) consecutively before it was concentrated under vacuo. The residue was purified by ISCO chromatography to give (R) 4-[4-(tert-Butyl-dimethyl-silanyloxy)-1-oxo-1,3-dihydro-isoindol-2-yl]-4-carbamoyl-butyric acid benzyl ester as a light yellow sticky solid (15.0 g, 101% crude yield). The compound was put to next step without further purification; $^1$H NMR (DMSO-$d_6$) δ 0.00 (s, 3H, $CH_3$), 0.01 (s, 3H, $CH_3$), 0.75 (s, 9H, $CH_3$, $CH_3$, $CH_3$), 1.73-2.16 (m, 4H, $CH_2$, $CH_2$), 4.03-4.35 (m, 2H, CHH, CHH), 4.53 (dd, J=5.1, 10.4 Hz, 1H, CHH), 4.64-4.82 (m, 2H, $CH_2$), 6.77-6.89 (m, 1H, Ar), 6.97 (s, 1H, NHH), 7.01-7.23 (m, 7H, Ar), 7.37 (s, 1H, NHH); LCMS MH=483.

Step 5: (R) 4-Carbamoyl-4-(4-hydroxy-1-oxo-1,3-dihydro-isoindol-2-yl)-butyric acid benzyl ester To the stirred solution of (R)-benzyl 5-amino-4-(4-(tert-butyldimethylsilyloxy)-1-oxoisoindolin-2-yl)-5-oxopentanoate (8.37 g, 17.3 mmol) in DMF (40 mL) and Water (4.4 mL) at ~15° C. was added potassium carbonate (1.20 g, 8.7 mmol) in one portion. The resulting light yellow suspension was stirred at room temperature for 1 hr before it was added by acetonitrile (50 mL) followed by the addition of hydrogen chloride (aq, 12 N, 1.7 mol, 20.8 mmol) and white solid was formed. The mixture was filtered and the filtrate was concentrated in vacuo. The residue purified by ISCO to give (R) 4-Carbamoyl-4-(4-hydroxy-1-oxo-1,3-dihydro-isoindol-2-yl)-butyric acid benzyl ester as a glass like sticky solid (5.75 g, 90% yield). $^1$H NMR (DMSO-$d_6$) δ 2.01-2.39 (m, 4H, $CH_2$, $CH_2$), 4.34 (d, J=17.4 Hz, 1H, CHH), 4.49 (d, J=17.4 Hz, 1H, CHH), 4.75 (dd, J=5.0, 10.3 Hz, 1H, CHH), 4.96 (d, J=12.5 Hz, 1H, CHH), 5.03 (d, J=12.5 Hz, 1H, CHH), 6.99 (d, J=7.7 Hz, 1H, Ar), 7.10-7.24 (m, 2H, NHH, Ar), 7.25-7.41 (m, 6H, Ar), 7.58 (s, 1H, NHH), 10.03 (s, 1H, OH); LCMS: MH=369.

Step 6: (R) 4-[4-(4-Bromomethyl-benzyloxy)-1-oxo-1,3-dihydro-isoindol-2-yl]-4-carbamoyl-butyric acid benzyl ester To the stirred solution of (R)-benzyl 5-amino-4-(4-hydroxy-1-oxoisoindolin-2-yl)-5-oxopentanoate (1 g, 2.71 mmol) in Acetonitrile (35 mL) at room temperature was added 1,4-bis(bromomethyl)benzene (2.15 g, 8.1 mmol) and POTASSIUM CARBONATE (0.375 g, 2.7 mmol). The resulting suspension was stirred at 50° C. for 1 hr and room temperature overnight before it was filtered. The filtrate was concentrated and the residue was purified by ISCO to give (R) 4-[4-(4-Bromomethyl-benzyloxy)-1-oxo-1,3-dihydro-isoindol-2-yl]-4-carbamoyl-butyric acid benzyl ester as a clear sticky solid (1.18 g, 78% yield); $^1$H NMR (DMSO-$d_6$) δ 2.04-2.42 (m, 4H, $CH_2$, $CH_2$), 4.44 (d, J=17.8 Hz, 1H, CHH), 4.55 (d, J=17.8 Hz, 1H, CHH), 4.68-4.80 (m, 3H, CHH, $CH_2$), 4.96 (d, J=12.5 Hz, 1H, CHH), 5.03 (d, J=12.5 Hz, 1H, CHH), 5.25 (s, 2H, $CH_2$), 7.20 (s, 1H, NHH), 7.24-7.38 (m, 7H, Ar), 7.40-7.52 (m, 5H, Ar), 7.58 (s, 1H, NHH); LCMS MH=551, 553

Step 7: (R) 4-Carbamoyl-4-[4-(4-morpholin-4-ylmethyl-benzyloxy)-1-oxo-1,3-dihydro-isoindol-2-yl]-butyric acid benzyl ester To the solution of (R)-benzyl 5-amino-4-(4-(4-(bromomethyl)benzyloxy)-1-oxoisoindolin-2-yl)-5-oxopentanoate (395 mg, 0.716 mmol) in Acetonitrile (10 mL) was added MORPHOLINE (0.187 ml, 2.1 mmol) at room temperature. The resulting solution was stirred at room temperature for 2.5 hrs and the reaction was completed. The reaction mixture was added by EtOAc (50 mL) and $NaHCO_3$ (sat. aq, 15 mL). The mixture was extracted and organic layer was dried by $MgSO_4$ and concentrated down to give (R) 4-Carbamoyl-4-[4-(4-morpholin-4-ylmethyl-benzyloxy)-1-oxo-1,3-dihydro-isoindol-2-yl]-butyric acid benzyl ester as a sticky solid (350 mg, 88% crude yield). The product was put to next step without further purification. $^1$H NMR (DMSO-d$_6$) δ 2.01-2.40 (m, 8H, CH$_2$, CH$_2$, CH$_2$, CH$_2$), 3.46 (s, 2H, CH$_2$), 3.56 (t, J=4.5 Hz, 4H, CH$_2$, CH$_2$), 4.42 (d, J=17.8 Hz, 1H, CHH), 4.54 (d, J=17.8 Hz, 1H, CHH), 4.75 (dd, J=5.0, 10.5 Hz, 1H, CHH), 4.95 (d, J=12.5 Hz, 1H, CHH), 5.02 (d, J=12.5 Hz, 1H, CHH), 5.22 (s, 2H, CH$_2$), 7.19 (s, 1H, NHH), 7.26-7.38 (m, 9H, Ar), 7.41-7.50 (m, 3H, Ar), 7.59 (s, 1H, NHH); LCMS MH=558.

Step 8: (R)-3-[4-(4-Morpholin-4-ylmethyl-benzyloxy)-1-oxo-1,3-dihydro-isoindol-2-yl]-piperidine-2,6-dione To the stirred solution of (R)-benzyl 5-amino-4-(4-(4-(morpholinomethyl)benzyloxy)-1-oxoisoindolin-2-yl)-5-oxopentanoate (350 mg, 0.6 mmol) in Tetrahydrofuran (10 mL) at 0° C. was added POTASSIUM TERT-BUTOXIDE (70.4 mg, 0.6 mmol). The mixture was stirred at 0° C. for 1 hr and KOtBu (10 mg) was added. And the reaction was completed in 1 more hour. The reaction mixture was diluted by EtOAc (40 mL) and acidified by HCl (2 mL, 1N) and neutralized by NaHCO$_3$ (sat. aq, 5 mL). The mixture was added by brine (10 mL) and extracted. Organic layer was dried by MgSO$_4$ and concentrated under vacuo. The sticky white solid which was stirred in ether (40 mL) to give (R) 3-[4-(4-morpholin-4-ylmethyl-benzyloxy)-1-oxo-1,3-dihydro-isoindol-2-yl]-piperidine-2,6-dione as a white solid (252 mg, 89% yield). HPLC: Waters Symmetry C-18, 3.9×150 mm, 5 μm, 1 mL/min, 240 nm, 15/85, (CH$_3$CN/0.1% H$_3$PO$_4$), 5.41 min (99.7%); mp: 141-143° C.; $^1$H NMR (DMSO-d$_6$) δ 1.89-2.06 (m, 1H, CHH), 2.25-2.47 (m, 5H, CHH, CH$_2$, CH$_2$), 2.53-2.65 (m, 1H, CHH), 2.81-3.02 (m, 1H, CHH), 3.46 (s, 2H, CH$_2$), 3.50-3.62 (m, 4H, CH$_2$, CH$_2$), 4.25 (d, J=17.4 Hz, 1H, CHH), 4.41 (d, J=17.4 Hz, 1H, CHH), 5.11 (dd, J=4.9, 13.2 Hz, 1H, CHH), 5.22 (s, 2H, CH$_2$), 7.33 (d, J=7.6 Hz, 4H, Ar), 7.39-7.54 (m, 3H, Ar), 10.97 (s, 1H, NH); $^{13}$C NMR (DMSO-d$_6$) δ 22.33, 31.16, 45.06, 51.55, 53.11, 62.07, 66.14, 69.38, 114.94, 115.20, 127.61, 128.97, 129.78, 129.93, 133.28, 135.27, 137.66, 153.48, 167.99, 170.96, 172.81; LCMS MH=450; Anal. Calcd for C$_{25}$H$_{27}$N$_3$O$_5$+ 0.3H$_2$O: C, 66.01; H, 6.12; N, 9.24; Found: C, 66.00; H, 6.03; N, 9.12; Chiral HPLC Chiral AGP, 4×150 mm, 5 μm, 0.8 mL, 240 nm, 5/95 iPOH/10 mM NH4OAc; R isomer=92% ee.

5.53 3-(4-((5-Morpholinomethyl)Benzo[D]Thiazol-2-yl)Methoxy)-1-Oxoisoindolin-2-yl)Piperidine-2,6-Dione

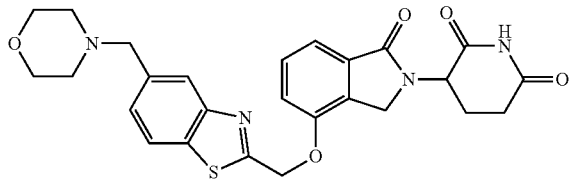

Step 1: 2,3-Dichloro-5H-1,2,3dithiazolium chloride (6.7 g, 32.2 mmol) was added to a stirred solution of 2-bromo-5-methylaniline (6.0 g, 32.2 mmol) in CH$_2$Cl$_2$ (130 mL) and stirred for 2 h. Pyridine (5.1 g, 64.5 mmol) was added and mixture was stirred at room temperature for 2 h. The reaction mixture was washed with water (2×40 mL), brine (40 mL) and dried. Solvent was removed and residue was stirred with ether (20 mL) and hexane (20 mL) to give (Z)-2-bromo-N-(4-chloro-5H-1,2,3-dithiazol-5-ylidene)-5-methylaniline (7.9 g, 76%): $^1$H NMR (CDCl$_3$) δ 2.33 (s, 3H), 6.90=6.92 (m, 2H), 7.53-7.56 (d, J=9 Hz, 1H).

Step 2: A mixture of (Z)-2-bromo-N-(4-chloro-5H-1,2,3-dithiazol-5-ylidene)-5-methylaniline (7.9 g, 24.6 mmol) and copper (I) iodide (5.2 g, 27.1 mmol) in pyridine (100 mL) was heated to reflux for 2 h. The reaction mixture was cooled and concentrated. Residue was dissolved in EtOAc (150 mL) and water (100 mL). EtOAc layer was washed with water (3×50 mL), brine (50 mL) and dried. Solvent was removed and residue was purified by chromatography (SiO$_2$, 4/6 hecane/CH$_2$Cl$_2$ for 20 min then to 2/8 for 15 min) to give 5-methylbenzo[d]thiazole-2-carbonitrile (3.1 g, 71%): $^1$H NMR (CDCl$_3$) δ 2.56 (s, 3H), 7.44-7.48 (dd, J=3 and 9 Hz, 1H), 7.84-7.87 (d, J=9 Hz, 1H), 8.01 (s, 1H).

Step 3: A mixture of 5-methylbenzo[d]thiazole-2-carbonitrile (3.0 g, 17.2 mmol) in methanol (100 mL) was cooled in ice bath. A solution of sodium methoxide/methanol (25% wt, 13 mL) was added slowly and mixture was stirred at room temperature for 1 h. The reaction mixture was cooled in ice bath and quenched with 6N HCl (15 mL). The mixture was concentrated and residue was dissolved in CH$_2$Cl$_2$ (100 mL) and washed with water (2×35 mL), brine (35 mL) and dried. Solvent was removed and residue was purified by chromatography (SiO$_2$, 2/8 hexane/CH$_2$Cl$_2$ for 15 min then to CH$_2$Cl$_2$ over 10 min and hold for 10 min) to give methyl 5-methylbenzo[d]thiazole-2-carboxylate (3.2 g, 88%): $^1$H NMR (CDCl$_3$) δ 2.54 (s, 3H), 4.08 (s, 3H), 7.36-7.39 (dd, J=3 and 9 Hz, 1H), 7.83-7.86 (d, J=9 Hz, 1H), 8.02 (s, 1H).

Step 4: A mixture of methyl 5-methylbenzo[d]thiazole-2-carboxylate (3.1 g, 15.1 mmol) and N-bromosuccinimide (3.0 g, 16.6 mmol) in methyl acetate (50 mL) was heated at 60° C. oil bath with a 300 W bulb shining to reaction mixture for 3 h. The Reaction mixture was cooled to room temperature and diluted with EtOAc (50 mL). The mixture was washed with water (2×40 mL), brine (40 mL) and dried. Solvent was removed and residue was purified by chromatography (SiO$_2$, 2/8 CH$_2$Cl$_2$/hexane for 15 min then to CH$_2$Cl$_2$ for 15 min) to give methyl 5-(bromomethyl)benzo[d]thiazole-2-carboxylate (2.8 g, 65%): $^1$H NMR (CDCl$_3$) δ 4.09 (s, 3H), 4.66 (s, 2H), 7.59-7.62 (dd, J=3 and 9 Hz, 1H), 7.95-7.98 (d, J=9 Hz, 1H), 8.22-8.23 (d, J=3 Hz, 1H).

Step 5: A solution of methyl 5-(bromomethyl)benzo[d]thiazole-2-carboxylate (2.8 g, 9.8 mmol) in acetone (30 mL) was added slowly to a stirred suspension of morpholine (1.3 g, 14.7 mmol) and potassium carbonate (4.7 g, 34.2 mmol) and catalytic amount of 18-crown-6 in acetone (20 mL) at 60° C. oil bath. The reaction mixture was stirred at 60° C. oil bath for 3 h then cooled and filtered. Filtrate was concentrated and residue was dissolved in EtOAc (100 mL) and washed with water (2×40 mL), brine (40 mL) and dried. Solvent was removed and residue was purified by chromatography (SiO$_2$, CH$_2$Cl$_2$ for 10 min then to 3% CH$_3$OH/CH$_2$Cl$_2$ over 5 min and hold for 15 min then to 5% over 5 min and hold for 20 min) to give methyl 5-(morpholinomethyl)benzo[d]thiazole-2-carboxylate (2.3 g, 80%): $^1$H NMR (CDCl$_3$) δ 2.47-2.50 (m, 4H), 3.67-3.73 (m, 6H), 4.09 (s, 3H), 7.57-7.60 (dd, J=3 and 9 Hz, 1H), 7.91-7.94 (d, J=9 Hz, 1H), 8.19 (s, 1H).

Step 6: A solution of methyl 5-(morpholinomethyl)benzo[d]thiazole-2-carboxylate (2.2 g, 2.5 mmol) in THF (50 mL) was added slowly to a stirred solution of LiAlH (t-BuO)$_3$/THF (1M, 15.3 mL, 15.3 mmol) in THF (20 mL) and reaction mixture was stirred at room temperature for 1 h. The reaction mixture was cooled and quenched with water (20 mL) cautionsly. The mixture was diluted with EtOAc (150 mL) and water (35 mL). The organic layer was washed with water (40 mL), brine (40 mL) and dried. Solvent was removed and residue was purified by chromatography (SiO$_2$, CH$_2$Cl$_2$ for 10 min then to 3% CH$_3$OH/CH$_2$Cl$_2$ over 5 min and hold for 15 min then to 5% over 5 min and hold for 20 min) to give (5-(morpholinomethyl)benzo[d]thiazol-2-yl) methanol (1.8 g, 90%): $^1$H NMR (CDCl$_3$) δ 2.46-2.49 (m, 4H), 3.63 (s, 2H), 3.71-3.73 (m, 4H), 3.94 (b, 1H), 5.04 (s, 2H), 7.37-7.41 (dd, J=3 and 9 Hz, 1H), 7.81-7.83 (d, J=9 Hz, 1H), 7.91 (s, 1H); $^{13}$C NMR (CDCl$_3$) δ 553.56, 62.56, 63.16, 66.98, 121.55, 123.14, 126.38, 133.51, 136.31, 153.13, 173.12.

Step 7: A suspension mixture of triphenylphosphine-polymer bound (4.1 g, 4.9 mmol) in THF (40 mL) was cooled to 3° C. Diisopropyl azodicarboxylate (0.9 g, 4.6 mmol) was added slowly at 3-5° C. After stirred at 3° C. for 10 min, a solution of methyl 5-amino-4-(4-hydroxy-1-oxoisoindolin-2-yl)-5-oxopentanoate (1.0 g, 3.4 mmol) and (5-(morpholinomethyl)benzo[d]thiazol-2-yl)methanol (1.1 g, 4.1 mmol) in THF (60 mL) was added slowly at 3-8° C. The reaction mixture was stirred at 3° C. for 10 in then warmed to room temperature and stirred overnight. The reaction mixture was filtered and filtrate was concentrated. Residue was dissolved in CH$_2$Cl$_2$ (80 mL) and washed with sat. NaHCO$_3$ (30 mL), water (30 mL), brine (30 mL) and dried. Solvent was removed and residue was purified by chromatography (SiO$_2$, CH$_2$Cl$_2$ for 10 min then to 3% CH$_3$OH/CH$_2$Cl$_2$ over 5 min and hold for 15 min then to 5% over 5 min and hold for 20 min) to give methyl 5-amino-4-(4-((5-(morpholinomethyl)benzo[d]thiazol-2-yl) methoxy)-1-oxoisoindolin-2-yl)-5-oxopentanoate (0.95 g, 52%); $^1$H NMR (CDCl$_3$) δ 2.23 (m, 1H), 2.35-2.50 (m, 7H), 3.64-3.74 (m, 6H), 4.46-4.52 (d, J=18 Hz, 1H), 4.57-4.63 (d, J=18 Hz, 1H), 4.92-4.95 (1H), 5.30 (s, 3H), 5.58 (s, 2H), 5.65 (b, 1HO, 6.53 (b, 1H), 7.11-7.14 (d, J=9 Hz, 1H), 7.40-7.48 (m, 2H), 7.81-7.87 (m, 2H), 7.99 (s, 1H).

Step 8: Potassium tert-butoxide/THF (1M, 1.7 mL, 1.7 mmol) was added slowly to a stirred solution of methyl 5-amino-4-(4-((5-(morpholinomethyl)benzo[d]thiazol-2-yl) methoxy)-1-oxoisoindolin-2-yl)-5-oxopentanoate (0.9 g, 1.7 mmol) in THF (25 mL) at 5° C. The reaction mixture was stirred at 5° C. for 1 h then quenched with sat. NH$_4$Cl (5 mL). The mixture was diluted with CH$_2$C$_2$ (50 mL) and water (15 mL). Aq. layer was extracted with CH$_2$Cl$_2$ (30 mL) and combined CH$_2$Cl$_2$ solution was washed with brine (40 mL) and dried. Solvent was removed and residue was recrystallized from acetone to give 3-(4-((5-(morpholinomethyl)benzo[d]thiazol-2-yl)methoxy)-1-oxoisoindolin-2-yl) piperidine-2,6-dione (0.4 g, 55%): mp 228-230° C.; $^1$H NMR (DMSO-d$_6$) δ 2.00-2.04 (m, 1H), 2.37-2.63 (m, 6H), 2.88-2.94 (m, 1H), 3.56-3.62 (m, 6H), 4.32-4.38 (d, J=18 Hz, 1H), 4.47-4.53 (d, J=18 Hz, 1H), 5.11-5.17 (dd, J=3 and 12 Hz, 1H), 5.75 (s, 2H), 7.38-7.52 (m, 4H), 7.94 (s, 1H), 8.04-8.07 (d, J=9 Hz, 1H), 11.00 (s, 1H); $^{13}$C NMR (DMSO-d$_6$) δ 22.33, 31.18, 45.00, 51.63, 53.08, 62.00, 66.17, 67.41, 115.29, 116.12, 122.00, 122.74, 126.50, 129.96, 132.95, 133.52, 136.61, 152.60, 152.68, 167.80, 168.03, 170.96, 172.83; Calcd for C$_{26}$H$_{26}$N$_4$O$_5$S+0.35H$_2$O: C, 60.89; H, 5.25; N, 10.92; S, 6.25. Found: C, 60.59; H, 5.11; N, 10.85; S, 6.30.

5.54 3-(4-((4-((4,5-Dimethyl-1H-Imidazol-1-yl) Methyl)Benzyl)Oxy)-1-Oxoisoindolin-2-yl)Piperidine-2,6-Dione

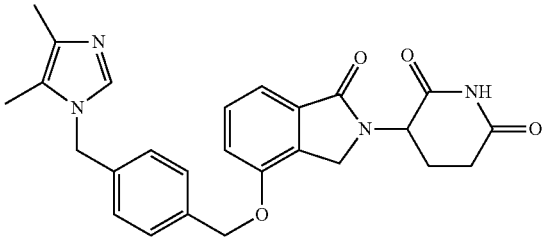 [SMILES: Cc1ncn(Cc2ccc(COc3cccc4c3CN(C3CCC(=O)NC3=O)C4=O)cc2)c1C]

To a mixture of 3-(4-(4-(bromomethyl)benzyloxy)-1-oxoisoindolin-2-yl)piperidine-2,6-dione (0.40 g, 0.90 mmol) and 4,5-dimethyl-1H-imidazole (0.24 g, 2.49 mmol) in acetonitrile (10 mL) was added N,N-diisopropylethyl amine (0.16 ml, 0.90 mmol) at room temperature. The solution was stirred at room temperature for 24 h. To the suspension was added 0.2 M Phosphate Buffer pH 7.4 (50 mL) to give a suspension. To the suspension was added EtOAc (30 mL) and the suspension was stirred for 10 min. Part of solvent was removed to give a suspension. The suspension was filtered and washed with water to give a solid. The solid was purified with Prep HPLC (Xbridge C18, 10 µm, 50×250 mm, 143 mL/min, 240 nM, 2/98/2 min, gradient to 98/2 CH$_3$CN 0.1% formic acid/H2O 0.1% formic acid in 13 min) to give an oil. To the oil was added ether (10 mL) and EtOAc (10 mL) to give a suspension. The suspension was filtered and washed with ether (10 mL) to give 3-(4-((4-((4,5-dimethyl-1H-imidazol-1-yl)methyl)benzyl)oxy)-1-oxoisoindolin-2-yl)piperidine-2,6-dione as a white solid (110 mg, 27% yield): HPLC: Waters Symmetry C$_{18}$, 5 µm, 3.9×150 mm, 1 mL/min, 240 nm, 5.95 gradient to 95/5 in 5 min CH$_3$CN/ 0.1% H$_3$PO$_4$, 4.91 (97.5%); mp: 180-182° C.; $^1$H NMR (DMSO-d$_6$) δ 1.87-2.09 (m, 7H, CHH, CH$_3$, CH$_3$), 2.31-2.48 (m, 1H, CHH), 2.52-2.65 (m, 1H, CHH), 2.81-3.02 (m, 1H, CHH), 4.14-4.30 (m, J=17.6 Hz, 1H, CHH), 4.40 (d, J=17.6 Hz, 1H, CHH), 5.01-5.17 (m, 3H, CH$_2$, NCH), 5.22 (s, 2H, CH$_2$), 7.12 (d, J=8.1 Hz, 2H, Ar), 7.25-7.38 (m, 2H, Ar), 7.41-7.54 (m, 3H, Ar), 7.56 (s, 1H, Ar), 10.97 (s, 1H, NH); $^{13}$C NMR (DMSO-d$_6$) δ 8.05, 12.67, 22.31, 31.16, 45.03, 47.19, 51.53, 69.17, 114.93, 115.25, 121.69, 126.87, 128.04, 129.78, 129.95, 132.92, 133.28, 135.54, 135.79, 137.53, 153.39, 167.97, 170.95, 172.81; LCMS MH=459; Anal. Calcd for C$_{26}$H$_{26}$N$_4$O$_4$+0.5 H$_2$O: C, 66.80; H, 5.82; N, 11.98; Found: C, 66.81; H, 5.66; N, 11.91.

5.55 3-(4-((3-(Morpholinomethyl)Isoxazol-5-yl) Methoxy)-1-Oxoisoindolin-2-yl)Piperidine-2,6-Dione

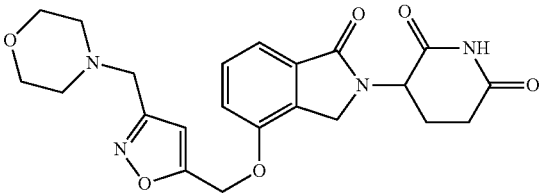 [SMILES: O=C1CCC(N2Cc3c(OCc4cc(CN5CCOCC5)no4)cccc3C2=O)C(=O)N1]

Step 1: (3-((Tetrahydro-2H-pyran-2-yloxy)methyl)isoxazol-5-yl)methanol A solution of ethyl 3-((tetrahydro-2H-pyran-2-yloxy)methyl)isoxazole-5-carboxylate (3.7 g, 14.49 mmol) in THF (100 mL) was cooled to 0° C., and then a 1M solution of DIBALH in toluene (43.5 mL) was added dropwise over 30 min, and then the mixture was stirred at room temperature for 16 h. The mixture was quenched a 1M aqueous solution of sodium potassium tartrate (100 mL) and was then extracted with EtOAc (3×100 mL). The combined organic layers were washed with water (150 mL) and brine (150 mL), dried (MgSO$_4$) and evaporated, providing 2.5 g of the product as an orange oil, in 81% yield; $^1$H NMR (CDCl$_3$) δ 1.56-1.86 (m, 6H), 2.31 (br, 1H), 3.50-3.61 (m, 1H), 3.83-3.95 (m, 1H), 4.61 (d, J=12.8 Hz, 1H), 4.68-4.83 (m, 4H), 6.32 (s, 1H).

Step 2: (4S)-Methyl 5-amino-5-oxo-4-(1-oxo-4-((3-((tetrahydro-2H-pyran-2-yloxy)methyl)-isoxazol-5-yl)methoxy)isoindolin-2-yl)pentanoate A mixture of (S)-methyl 5-amino-4-(4-hydroxy-1-oxoisoindolin-2-yl)-4-methyl-5-oxopentanoate (3.4 g, 11.7 mmol), (3-((tetrahydro-2H-pyran-2-yloxy)methyl)isoxazol-5-yl)methanol (2.5 g, 11.7 mmol), and triphenylphosphine, polymer-bound, 3 mmol/g (7.8 g, 23 mmol) in THF (200 mL) was cooled to 0° C., and DIAD (4.6 ml, 23.5 mmol) was added. After 60 min, the ice bath was removed, and the mixture was stirred for 16 h at ambient temperature. Then, the mixture was filtered and the filtrate was evaporated. The residue was chromatographed in methylene chloride-methanol gradient. The product eluted at 2% MeOH, 3.4 g, in 60% yield; $^1$H NMR (CDCl$_3$) δ 1.51-1.87 (m, 6H), 2.09-2.51 (m, 4H), 3.46-3.60 (m, 1H), 3.64 (s, 3H), 3.81-3.94 (m, 1H), 4.31-4.57 (m, 2H), 4.59-4.66 (m, 1H), 4.67-4.85 (m, 2H), 4.87-4.98 (m, 1H), 5.12-5.32 (m, 2H), 5.52 (br. s., 1H), 6.30-6.53 (m, 2H), 7.08 (d, J=7.6 Hz, 1H), 7.35-7.52 (m, 2H).

Step 3: 3-(4-((3-(Hydroxymethyl)isoxazol-5-yl)methoxy)-1-oxoisoindolin-2-yl)piperidine-2,6-dione A solution of (4S)-methyl 5-amino-5-oxo-4-(1-oxo-4-((3-((tetrahydro-2H-pyran-2-yloxy)methyl)isoxazol-5-yl)methoxy)isoindolin-2-yl)pentanoate (2.75 g, 5.64 mmol) was cooled to 0° C., and potassium tert-butoxide (0.633 g, 5.64 mmol) was added. After 30 min, AcOH (100 mL) and water (25 mL) were added, and the mixture was heated to 45° C. The mixture stirred at this temperature for 24 h, and was then evaporated under vacuum. A portion of the dried intermediate (1.86 g, 5.0 mmol) was dissolved in acetonitrile (100 mL) and treated with methanesulfonyl chloride (0.389 ml, 5.00 mmol) and TEA (0.730 ml, 5.25 mmol). After 2 hrs stirring at room temperature methanesulfonyl chloride (0.438 ml, 5.64 mmol) and TEA (0.823 ml, 5.92 mmol) were again added. After an additional 1 h, the mixture was quenched with AcOH (1 mL) and evaporated under vacuum. The residue was partitioned between EtOAc (100 mL) and saturated aqueous NaHCO$_3$ (100 mL), and the aqueous layer was extracted with EtOAc (50 mL). The combined organic phases were washed with saturated aqueous NaHCO$_3$ (100 mL), water (100 mL), and dried (MgSO$_4$). The mixture was evaporated and chromatographed using a methylene chloride-methanol gradient. The product eluted at ~2% MeOH. The yield after drying was 1.6 g (71%); $^1$H NMR (DMSO-d$_6$) δ 1.93-2.05 (m, 1H), 2.35-2.48 (m, 1H), 2.55-2.63 (m, 1H), 2.83-3.00 (m, 1H), 3.33 (s, 3H), 4.19-4.30 (m, 1H), 4.35-4.48 (m, 1H), 5.11 (dd, J=4.9, 13.2 Hz, 1H), 5.38 (s, 2H), 5.49 (s, 2H), 6.84 (s, 1H), 7.40 (t, J=8.0 Hz, 2H), 7.48-7.57 (m, 1H).

Step 4: 3-(4-((3-(morpholinomethyl)isoxazol-5-yl)methoxy)-1-oxoisoindolin-2-yl)piperidine-2,6-dione A mixture of (5-((2-(2,6-dioxopiperidin-3-yl)-1-oxoisoindolin-4-yloxy)methyl)isoxazol-3-yl)methyl methanesulfonate (0.5 g, 1.113 mmol) in acetonitrile (10 mL) was cooled to 0° C. Morpholine (0.116 ml, 1.335 mmol) and DIEA (0.252 ml, 1.446 mmol) were added, and the mixture stirred at that temperature. After 16 h, the resultant suspension was filtered, and the solid was dried under vacuum. The product was obtained as a white solid, 0.4 g in 82% yield; mp 228-230° C. HPLC: Waters Symmetry C-18, 3.9×150 mm, 5 μm, 1 mL/min, 240 nm, 10/90 gradient to 90/10 CH$_3$CN/0.1% H$_3$PO$_4$ in 10 min: 4.38 (99.82%). $^1$H NMR (DMSO-d$_6$) δ 1.82-2.12 (m, 1H), 2.22-2.48 (m, 5H), 2.54-2.67 (m, 1H), 2.79-3.05 (m, 1H), 3.55 (br., 6H), 4.16-4.49 (m, 2H), 5.11 (dd, J=4.9, 13.2 Hz, 1H), 5.43 (s, 2H), 6.64 (s, 1H), 7.32-7.46 (m, 2H), 7.46-7.61 (m, 1H), 10.98 (s, 1H). $^{13}$C NMR (DMSO-d$_6$) δ 22.30, 31.16, 45.00, 51.58, 52.51, 52.87, 60.67, 65.98, 104.55, 115.09, 115.96, 129.84, 129.96, 133.49, 152.63, 167.26, 167.80, 170.92, 172.81 Anal. Calcd for C$_{22}$H$_{24}$N$_4$O$_6$: C, 59.99%; H, 5.49%; N, 12.72%. Found: C, 59.69%; H, 5.43%; N, 12.66%.

5.56 3-{4-[4-(4-Tert-Butyl-[1,2,3]Triazol-1-ylmethyl)-Benzyloxy]-1-Oxo-1,3-Dihydro-Isoindol-2-yl}-Piperidine-2,6-Dione

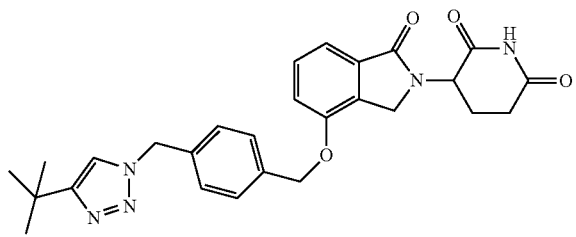 [SMILES: CC(C)(C)c1cn(Cc2ccc(COc3cccc4c3CN(C3CCC(=O)NC3=O)C4=O)cc2)nn1]

Step 1: 4-[4-(4-Azidomethyl-benzyloxy)-1-oxo-1,3-dihydro-isoindol-2-yl]-4-carbamoyl-butyric acid methyl ester To the mixture of sodium azide (0.226 g, 3.47 mmol) in Ethanol (40 mL) at room temperature was added methyl 5-amino-4-(4-(4-(bromomethyl)benzyloxy)-1-oxoisoindolin-2-yl)-5-oxopentanoate (1.5 g, 3.16 mmol). The resulting suspension was heated to reflux for 4 hrs before it was cooled and added by water (50 mL) and EtOAc (200 mL). The mixture was extracted and the organic layer was washed with brine (50 mL). Organic layer was dried by MgSO$_4$ and concentrated under vacuo to give 4-[4-(4-Azidomethyl-benzyloxy)-1-oxo-1,3-dihydro-isoindol-2-yl]-4-carbamoyl-butyric acid methyl ester as a yellow sticky solid (1.5 g, 109% crude yield)). The compound was used in the next step without further purification; LCMS MH=439.

Step 2: 4-{4-[4-(4-tert-Butyl-[1,2,3]triazol-1-ylmethyl)-benzyloxy]-1-oxo-1,3-dihydro-isoindol-2-yl}-4-carbamoyl-butyric acid methyl ester 3,3-dimethylbut-1-yne (752 mg, 9.2 mmol), methyl 5-amino-4-(4-(4-(azidomethyl) benzyloxy)-1-oxoisoindolin-2-yl)-5-oxopentanoate (400 mg, 0.9 mmol) and Toluene (4 mL) were sealed in a microwave vial and heated in a microwave oven at 125° C. for 3 hrs. The reaction mixture was concentrated and the residue was purified by ISCO give 4-{4-[4-(4-tert-Butyl-[1,2,3]triazol-1-ylmethyl)-benzyloxy]-1-oxo-1,3-dihydro-isoindol-2-yl}-4-carbamoyl-butyric acid methyl ester as a light glass like solid (160 mg, 34% yield). The compound was used in the next step without further purification; LCMS MH=520.

Step 3: 3-{4-[4-(4-tert-Butyl-[1,2,3]triazol-1-ylmethyl)-benzyloxy]-1-oxo-1,3-dihydro-isoindol-2-yl}-piperidine-2,6-dione To the stirred solution of methyl 5-amino-4-(4-(4-(4-

((4-tert-butyl-1H-1,2,3-triazol-1-yl)methyl)benzyloxy)-1-oxoisoindolin-2-yl)-5-oxopentanoate (160 mg, 0.3 mmol) in Tetrahydrofuran (5 mL) at 0° C. was added potassium tert-butoxide (34.6 mg, 0.3 mmol). The resulting solution was stirred at 0° C. for 10 mins and the reaction was completed. The reaction mixture was diluted by EtOAC (30 mL) and then acidified by HCl (1N, aq, 2 mL). The resulting mixture was added by NaHCO$_3$ (aq., sat., 2 mL) and brine (5 mL). The mixture was extracted and organic layer was dried by MgSO$_4$ and concentrated. The residue was purified by ISCO and prep HPLC to give 3-{4-[4-(4-tert-Butyl-[1,2,3]triazol-1-ylmethyl)-benzyloxy]-1-oxo-1,3-dihydro-isoindol-2-yl}-piperidine-2,6-dione as a white solid (15 mg, 10% yield). HPLC: Waters Symmetry C-18, 3.9×150 mm, 5 μm, 1 mL/min, 240 nm, 45/55, (CH$_3$CN/0.1% H$_3$PO$_4$), 3.67 min (97.5%); mp: N/A; $^1$H NMR (DMSO-d$_6$) δ 1.26 (s, 9H, CH$_3$, CH$_3$, CH$_3$), 1.86-2.04 (m, 1H, CHH), 2.33-2.45 (m, 1H, CHH), 2.54-2.66 (m, 1H, CHH), 2.79-3.02 (m, 1H, CHH), 4.24 (d, J=17.6 Hz, 1H, CHH), 4.41 (d, J=17.6 Hz, 1H, CHH), 5.10 (dd, J=5.0, 13.1 Hz, 1H, CHH), 5.23 (s, 2H, CH$_2$), 5.53 (s, 2H, CH$_2$), 7.24-7.40 (m, 4H, Ar), 7.41-7.56 (m, 3H, Ar), 7.92 (s, 1H, triazole H), 10.96 (s, 1H, NH); $^{13}$C NMR (DMSO-d$_6$) δ 22.31, 30.24, 31.16, 45.06, 51.55, 52.33, 69.12, 114.88, 115.25, 119.84, 128.04, 129.78, 129.93, 133.30, 136.01, 136.45, 153.38, 156.50, 167.96, 170.95, 172.81; LCMS MH=488.

5.57 3-(1-Oxo-4-((4-((2,4,5-Trimethyl-1H-Imidazol-1-yl)Methyl)Benzyl)Oxy)Isoindolin-2-yl)Piperidine-2,6-Dione Formate

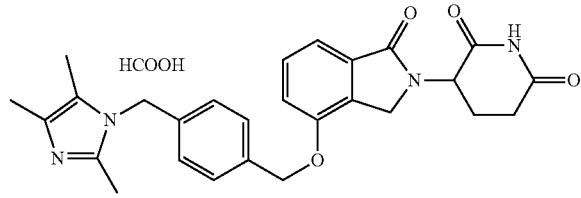 [SMILES: Cc1nc(C)n(Cc2ccc(COc3cccc4c3CN(C3CCC(=O)NC3=O)C4=O)cc2)c1C ; "HCOOH"]

Step 1: 2,4,5-Trimethyl-1H-imidazole Acetaldehyde (0.32 ml, 5.8 mmol) was added to the mixture of biacetyl (0.51 ml, 5.8 mmol), ammonium acetate (4.03 g, 52.3 mmol) and Acetic Acid (8 mL) in a microwave vial (20 mL). The vial was sealed and put on microwave oven for 5 mins at 180° C. The reaction mixture was added to mixture of ice and NH4OH aq (30 mL) slowly and the resulting brown solution was diluted by water (50 mL) and the mixture was extracted with EtOAC (3×35 mL). Organic layer was dried by MgSO$_4$ and concentrated under vacuo to give 2,4,5-Trimethyl-1H-imidazole as a brown oil (460 mg, 77% crude yield). The compound was put to next step without further purification; $^1$H NMR (DMSO-d$_6$) δ 1.75 (s, 3H, CH$_3$), 1.96 (s, 3H, CH$_3$), 2.12 (s, 3H, CH$_3$), 11.10 (br. s., 1H, NH).

Step 2: 3-(1-oxo-4-((4-((2,4,5-trimethyl-1H-imidazol-1-yl)methyl)benzyl)oxy) isoindolin-2-yl)piperidine-2,6-dione formate To the stirred solution of 2,4,5-trimethyl-1H-imidazole (447 mg, 4.1 mmol) in Acetonitrile (8 mL) was added 3-(4-(4-(bromomethyl)benzyloxy)-1-oxoisoindolin-2-yl)piperidine-2,6-dione (400 mg, 0.9 mmol) and N-ethyl-N-isopropylpropan-2-amine (0.482 ml, 2.7 mmol). The resulting solution was stirred at room temperature 18 hrs before it was added by EtOAC (70 mL) and NaHCO$_3$ (aq, sat, 25 mL). Some solid was formed and filtered. The filtrate was extracted and organic layer was concentrated. The residue combined with the solid was purified by Prep HPLC to give a light brown solid which was further purified by be stirred in CH$_3$CN (4 mL) and diethyl ether (30 mL) to give 3-(1-oxo-4-((4-((2,4,5-trimethyl-1H-imidazol-1-yl)methyl)benzyl)oxy)isoindolin-2-yl) piperidine-2,6-dione formate as an off white solid (93 mg, 20% yield). HPLC: Waters Symmetry C-18, 3.9×150 mm, 5 μm, 1 mL/min, 240 nm, 20/80, (CH$_3$CN/0.1% H$_3$PO$_4$), 6.09 min (99.8%); 254-256° C.; $^1$H NMR (DMSO-d$_6$) δ 1.98 (d, J=9.1 Hz, 7H, CHH, CH$_3$, CH$_3$), 2.18 (s, 3H, CH$_3$), 2.34-2.47 (m, 1H, CHH), 2.60 (br. s., 1H, CHH), 2.82-3.00 (m, 1H, CHH), 4.24 (d, J=17.6 Hz, 1H, CHH), 4.40 (d, J=17.6 Hz, 1H, CHH), 4.99-5.16 (m, 3H, CHH, CH$_2$), 5.22 (s, 2H, CH$_2$), 7.00 (d, J=8.1 Hz, 2H, Ar), 7.25-7.38 (m, 2H, Ar), 7.46 (d, J=8.3 Hz, 3H, Ar), 8.20 (s, 1H, HCOOH), 10.97 (s, 1H, NH); $^{13}$C NMR (DMSO-d$_6$) δ 12.31, 12.78, 22.33, 31.16, 45.03, 45.89, 51.53, 69.16, 114.91, 115.23, 121.53, 126.10, 128.11, 129.78, 129.93, 130.18, 133.28, 135.60, 137.32, 141.81, 153.41, 163.55, 167.97, 170.95, 172.81; LCMS MH=473; Anal. Calcd for C$_{27}$H$_{28}$N$_4$O$_4$.HCOOH+1H$_2$O: C, 62.68; H, 6.01; N, 10.44; Found: C, 62.54; H, 5.63; N, 10.35.

5.58 3-(4-((5-Methyl-1,3,4-Oxadiazol-2-yl)Methoxy)-1-Oxoisoindolin-2-yl)Piperidine-2,6-Dione

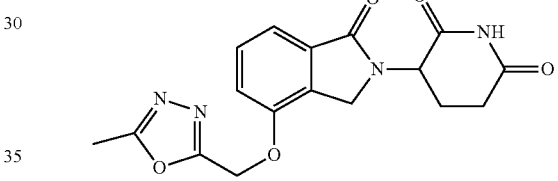

Step 1: To a solution of 2-(chloromethyl)-5-methyl-1,3,4-oxadiazole (500 mg, 3.77 mmol) in DMF (10 mL) were added methyl 5-amino-4-(4-hydroxy-1-oxoisoindolin-2-yl)-5-oxopentanoate (1103 mg, 3.77 mmol) and K$_2$CO$_3$ (573 mg, 4.15 mmol), the formed mixture was stirred at room temperature overnight. The solvent was evaporated under vacuum, the residue was partitioned between water (10 mL) and ethyl acetate (100 mL), the organic layer was washed with saturated sodium carbonate (10 mL), brine, dried over magnesium sulfate, and the solvent was evaporated to dryness. The residue was purified by ISCO (80 g column, MeOH/CH$_2$Cl$_2$ gradient from 0% to 5% in 50 min) to give methyl 5-amino-4-(4-((5-methyl-1,3,4-oxadiazol-2-yl)methoxy)-1-oxoisoindolin-2-yl)-5-oxopentanoate (860 mg, 59% yield); $^1$H NMR (DMSO-d$_6$) δ 2.25 (d, J=6.8 Hz, 4H, CH$_2$, CH$_2$), 2.53 (s, 3H, CH$_3$), 3.49 (s, 3H, CH$_3$), 4.29-4.61 (m, 2H, CH$_2$), 4.68-4.80 (m, 1H, CH), 5.52 (s, 2H, CH$_2$), 7.20 (s, 1H, NHH), 7.31-7.45 (m, 2H, Ar), 7.49 (d, J=7.7 Hz, 1H, Ar), 7.59 (s, 1H, NHH)

Step 2: To a mixture of methyl 5-amino-4-(4-((5-methyl-1,3,4-oxadiazol-2-yl)methoxy)-1-oxoisoindolin-2-yl)-5-oxopentanoate (422 mg, 1.087 mmol) in THF (20 mL) was added potassium tert-butoxide (146 mg, 1.304 mmol) at 0° C. The formed mixture was warmed to room temperature and stirred at room temperature for 2 hours. The reaction was quenched with aqueous HCl (1N, 1.5 mL), the solvent was evaporated, the residue was partitioned between satu-

5.59 3-{4-[4-(1,3-Dihydro-Isoindol-2-ylmethyl)-Benzyloxy]-1-Oxo-1,3-Dihydro-Isoindol-2-yl}-Piperidine-2,6-Dione

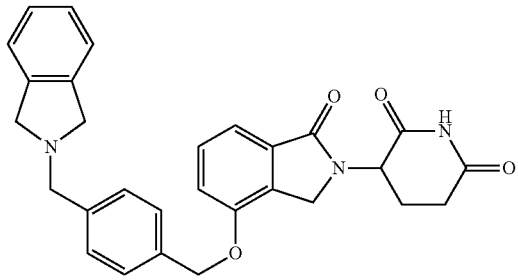 [SMILES: O=C1CCC(N2Cc3c(OCc4ccc(CN5Cc6ccccc6C5)cc4)cccc3C2=O)C(=O)N1]

To the THF solution of methyl 5-amino-4-(4-(4-(isoindolin-2-ylmethyl)benzyloxy)-1-oxoisoindolin-2-yl)-5-oxopentanoate (0.5 g, 0.974 mmol) was added potassium tert-butoxide (0.131 g, 1.168 mmol) at 0° C. The mixture was stirred for 30 min and was added 2 mL of 1N HCl followed by 10 mL of sat. NaHCO$_3$ and 25 mL of EtOAc. The mixture was extracted and the organic layer was concentrated and the resulted solid was purified on silica gel column eluted with DCM and MeOH to give a solid. The solid was recrystallized from 2 mL of CH$_3$CN to give 3-{4-[4-(1,3-dihydro-isoindol-2-ylmethyl)-benzyloxy]-1-oxo-1,3-dihydro-1-isoindol-2-yl}-piperidine-2,6-dione (60 mg, 0.13%). m.p.: 153-155° C. LC-MS m/e=482. HPLC Waters Symmetry C-18, 3.9×150 mm, 5 micro, 1 mL/min, 240 nm, gradient 5/95 to 5/95 CH$_3$CN/0.1% H$_3$PO$_4$ in H$_2$O during 5 min and stay at 95/5 for 5 min: 4.99 min (95%); $^1$H NMR (DMSO-d$_6$) δ 1.89-2.04 (m, 1H, CHH), 2.35-2.45 (m, 1H, CHH), 2.54-2.64 (m, 1H, CHH), 2.82-3.00 (m, 1H, CHH), 3.83 (s, 4H, CH$_2$, CH$_2$), 3.87 (s, 2H, CH$_2$), 4.19-4.50 (m, 2H, CH$_2$), 5.11 (dd, J=5.0, 13.1 Hz, 1H, NCH), 5.25 (s, 2H, CH$_2$), 7.10-7.25 (m, 4H, Ar), 7.27-7.54 (m, 8H, Ar), 10.97 (s, 1H, NH). $^{13}$CNMR (DMSO): δ 22.32, 31.17, 45.08, 49.30, 51.54, 58.16, 69.32, 114.89, 115.24, 122.29, 122.84, 123.50, 127.78, 127.82, 127.89, 129.94, 131.38, 133.50, 136.30, 137.50, 170.96, 172.82. Anal Calcd for C$_{29}$H$_{27}$N$_3$O$_4$: C % 72.33, H % 5.65, N % 8.73. Found: C % 70.89, H % 5.31, N % 8.37.

5.60 3-{4-[4-(4-Tert-Butyl-Imidazol-1-ylmethyl)-Benzyloxy]-1-Oxo-1,3-Dihydro-Isoindol-2-yl}-Piperidine-2,6-Dione

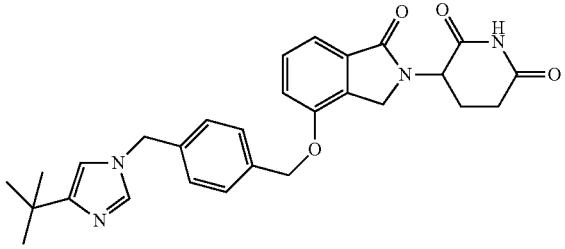 [SMILES: CC(C)(C)c1cn(Cc2ccc(COc3cccc4c3CN(C3CCC(=O)NC3=O)C4=O)cc2)cn1]

Step 1: 5-tert-Butyl-1H-imidazole 1-bromo-3,3-dimethylbutan-2-one (2.0 g, 11.2 mmol) and formamide (1.11 g, 24.6 mmol) were mixed microwave vial and heated at 147° C. in the sealed tube for 5.5 hrs. The reaction mixture was cooled down and diluted by water (40 mL). The mixture was extracted with heptane (50 mL). Aq layer was added by K$_2$CO$_3$ (10% wt aq, ~25 mL) to pH 10. The resulting solution was extracted with DCM (3×50 mL). Organic layer was dried by MgSO$_4$ and concentrated to give 5-tert-Butyl-1H-imidazole as a sticky yellow oil (560 mg, 40% yield). The compound was used in the next step without further purification; $^1$H NMR (DMSO-d$_6$) δ 1.21 (s, 9H, CH$_3$, CH$_3$, CH$_3$), 6.66 (s, 1H, Ar), 7.47 (d, J=0.9 Hz, 1H, Ar), 11.70 (br. s., 1H, NH).

Step 2: 4-{4-[4-(4-tert-Butyl-imidazol-1-ylmethyl)-benzyloxy]-1-oxo-1,3-dihydro-isoindol-2-yl}-4-carbamoyl-butyric acid methyl ester To the stirred solution of 4-tert-butyl-1H-imidazole (549 mg, 4.4 mmol) in Acetonitrile (10 mL) was added methyl 5-amino-4-(4-(4-(bromomethyl) benzyloxy)-1-oxoisoindolin-2-yl)-5-oxopentanoate (600 mg, 1.3 mmol) and DIPEA (0.66 mL, 3.8 mmol). The resulting solution was stirred at room temperature for 2 days. The reaction mixture was diluted by EtOAc (60 mL) and the mixture was washed with NaHCO$_3$ (aq, sat, 20 mL) and brine (20 mL). Organic layer was dried by MgSO$_4$ and concentrated. The residue was purified by ISCO to give 4-{4-[4-(4-tert-Butyl-imidazol-1-ylmethyl)-benzyloxy]-1-oxo-1,3-dihydro-isoindol-2-yl}-4-carbamoyl-butyric acid methyl ester as a white solid (540 mg, 82% yield). $^1$H NMR (DMSO-d$_6$) δ 1.17 (s, 9H, CH$_3$, CH$_3$, CH$_3$), 1.95-2.33 (m, 4H, CH$_2$, CH$_2$), 3.49 (s, 3H, CH$_3$), 4.31-4.58 (m, 2H, CHH, CHH), 4.72 (dd, J=4.5, 10.2 Hz, 1H, CHH), 5.11 (s, 2H, CH$_2$), 5.23 (s, 2H, CH$_2$), 6.83 (d, J=1.3 Hz, 1H, Ar), 7.18 (s, 1H, NHH), 7.24-7.35 (m, 4H, Ar), 7.38-7.53 (m, 3H, Ar), 7.53-7.64 (m, 2H, NHH, Ar); LCMS MH=519.

Step 3: 3-{4-[4-(4-tert-Butyl-imidazol-1-ylmethyl)-benzyloxy]-1-oxo-1,3-dihydro-isoindol-2-yl}-piperidine-2,6-dione To the stirred solution of methyl 5-amino-4-(4-(4-((4-tert-butyl-1H-imidazol-1-yl)methyl)benzyloxy)-1-oxoisoindolin-2-yl)-5-oxopentanoate (540 mg, 1.0 mmol) in Tetrahydrofuran (15 mL) at 0° C. The reaction mixture was stirred at 0° C. for 25 mins before it was diluted by EtOAc (50 mL) and then acidified by HCl (1N, aq, 4 mL) followed by the addition of NaHCO$_3$ (aq, sat, 10 mL). The mixture was extracted and the organic layer was washed with brine (20 mL). The organic layer was dried by MgSO$_4$ and concentrated to give a white solid. The solid was purified by being stirred in acetonitrile (5 mL) and diethyl ether (30 mL) give 3-{4-[4-(4-tert-Butyl-imidazol-1-ylmethyl)-benzyloxy]-1-oxo-1,3-dihydro-isoindol-2-yl}-piperidine-2,6-dione as a white solid (327, 64% yield). HPLC: Waters Symmetry C-18, 3.9×150 mm, 5 µm, 1 mL/min, 240 nm, 25/75, (CH$_3$CN/0.1% H$_3$PO$_4$), 3.71 min (97.9%); 227-229° C.; $^1$H NMR (DMSO-d$_6$) δ 1.17 (s, 9H, CH$_3$, CH$_3$, CH$_3$), 1.88-2.04 (m, 1H, CHH), 2.33-2.47 (m, 1H, CHH), 2.53-2.64 (m, 1H, CHH), 2.82-3.00 (m, 1H, CHH), 4.24 (d, J=17.6 Hz, 1H, CHH), 4.40 (d, J=17.6 Hz, 1H, CHH), 5.11 (s, 3H, CHH, CH$_2$), 5.22 (s, 2H, CH$_2$), 6.83 (d, J=1.3 Hz, 1H, imidazole H), 7.31 (t, J=7.4 Hz, 4H, Ar), 7.48 (d, J=8.1 Hz, 3H, Ar), 7.60 (d, J=1.1 Hz, 1H, imidazole H), 10.97 (s, 1H, NH); $^{13}$C NMR (DMSO-d$_6$) δ 22.24, 30.10, 31.11, 31.34, 44.99, 49.04, 51.48, 69.11, 112.48, 114.83, 115.17, 127.65, 127.97, 129.72, 129.86, 133.23, 135.97, 136.21, 137.62, 151.40, 153.32, 167.90, 170.88, 172.74; LCMS MH=487; Anal. Calcd for C$_{28}$H$_{30}$N$_4$O$_4$: C, 69.12; H, 6.21; N, 11.51; Found: C, 69.02; H, 6.05; N, 11.45. Structure of the compound was confirmed by NOSEY.

5.61 (S)-3-[4-(4-Morpholin-4-ylmethyl-Benzyloxy)-1-Oxo-1,3-Dihydro-Isoindol-2-yl]-Piperidine-2,6-Dione

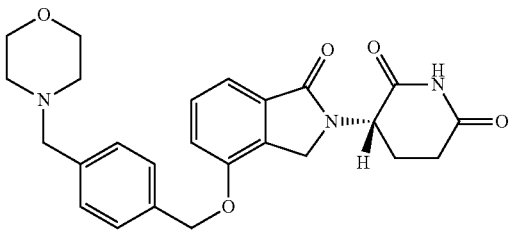 [SMILES: O=C1CC[C@H](N2Cc3c(OCc4ccc(CN5CCOCC5)cc4)cccc3C2=O)C(=O)N1]

Step 1: Preparation of (S)-4-[4-(4-Bromomethyl-benzyloxy)-1-oxo-1,3-dihydro-isoindol-2-yl]-4-carbamoyl-butyric acid methyl ester To a 2-L round bottom flask was charged methyl 5-amino-4-(4-hydroxy-1-oxoisoindolin-2-yl)-5-oxopentanoate (30 g, 103 mmol), 1,4-bis(bromomethyl)benzene (81 g, 308 mmol) and potassium carbonate (14.19 g, 103 mmol) and acetonitrile (1.2 L). The mixture was stirred at room temperature for 10 min and heated to 50° C. for 12 hours. The reaction mixture was allowed to cool to room temperature. The mixture was filtered and the filtrate was concentrated on rota-vap. The resulted solid was dissolved in CH$_2$Cl$_2$ and loaded on 2 silica gel columns (330 g each) eluted using CH2Cl2/MeOH to give 4-[4-(4-bromomethyl-benzyloxy)-1-oxo-1,3-dihydro-isoindol-2-yl]-4-carbamoyl-butyric acid methyl ester as white solid (40 g, 82%). $^1$H NMR (DMSO-d$_6$) δ 1.98-2.13 (m, 1H, CHH), 2.14-2.23 (m, 1H, CHH), 2.23-2.32 (m, 2H, CHH, CHH), 3.50 (s, 3H, CH$_3$), 4.34-4.63 (m, 2H, CH$_2$), 4.67-4.80 (m, 3H, CH$_2$, NCH), 5.25 (s, 4H, CH$_2$), 7.19 (s, 1H, NHH), 7.24-7.34 (m, 2H, Ar), 7.41-7.54 (m, 5H, Ar), 7.58 (br. s., 1H, NHH)

Step 2: Preparation of (S)-4-Carbamoyl-4-[4-(4-morpholin-4-ylmethyl-benzyloxy)-1-oxo-1,3-dihydro-isoindol-2-yl]-butyric acid methyl ester To the CH$_2$Cl$_2$ solution of methyl 5-amino-4-(4-(4-(bromomethyl)benzyloxy)-1-oxoisoindolin-2-yl)-5-oxopentanoate (36.5 g, 77 mmol) was added morpholine (14.72 ml, 169 mmol) at 0° C. The mixture was stirred at 0° C. for 1 hr. The mixture was added 200 mL of CH$_2$Cl$_2$, washed with water (100 mL×2) and brine (100 ml), dried in Na$_2$SO$_4$ and concentrated to give (S)-4-Carbamoyl-4-[4-(4-morpholin-4-ylmethyl-benzyloxy)-1-oxo-1,3-dihydro-isoindol-2-yl]-butyric acid methyl ester as white foam (39 g, 100%). M.p. 66-68° C.; Waters Symmetry C-18, 3.9×150 mm, 5 micro, 1 mL/min, 240 nm, isocratic 15/85 CH$_3$CN/0.1% H$_3$PO$_4$ in H$_2$O: 7.92 min (99%). $^1$H NMR (DMSO-d$_6$) δ 2.00-2.12 (m, 1H, CHH), 2.14-2.22 (m, 1H, CHH), 2.22-2.29 (m, 2H, CHH, CHH), 2.30-2.39 (m, 4H, CH$_2$, CH$_2$), 3.46 (s, 2H, CH$_2$), 3.50 (s, 3H, CH$_3$), 3.53-3.63 (m, 4H, CH$_2$, CH$_2$), 4.28-4.59 (m, 2H, CH$_2$), 4.73 (dd, J=4.7, 10.2 Hz, 1H, NCH), 5.22 (s, 2H, CH$_2$), 7.14-7.23 (m, 1H, NHH), 7.26-7.39 (m, 4H, Ar), 7.41-7.51 (m, 3H, Ar), 7.58 (s, 1H, NHH). $^{13}$C NMR (DMSO-d$_6$) δ 24.82, 30.33, 44.78, 51.24, 53.12, 53.38, 62.09, 66.14, 69.35, 114.66, 115.12, 127.60, 129.00, 129.55, 130.18, 133.43, 135.31, 137.66, 153.42, 167.84, 171.73, 172.46; Anal Calcd for C$_{26}$H$_{31}$N$_3$O$_6$+0.3 H$_2$O: C % 64.13; H % 6.54; N % 8.63; Found: C % 63.89; H % 6.39; N % 8.56.

Step 3: Preparation of (S)-3-[4-(4-morpholin-4-ylmethyl-benzyloxy)-1-oxo-1,3-dihydro-isoindol-2-yl]-piperidine-2,6-dione To the THF solution of (S)-methyl 5-amino-4-(4-(4-(morpholinomethyl)benzyloxy)-1-oxoisoindolin-2-yl)-5-oxopentanoate (45 g, 93 mmol) was added potassium 2-methylpropan-2-olate (10.49 g, 93 mmol) portion wise (2 g×5) at –78° C. The mixture was stirred at this temperature for 30 min then was added 250 mL of 1N HCl solution followed by 200 mL of saturated NaHCO$_3$ solution. The mixture was extracted with CH$_2$Cl$_2$ (150 mL×2). The organic layer was washed with water (50 mL×3) and brine (100 mL), concentrated on rota-vap to give a white solid, which was then recrystallized from CH$_3$CN (100 mL) to give (S)-3-[4-(4-morpholin-4-ylmethyl-benzyloxy)-1-oxo-1,3-dihydro-isoindol-2-yl]-piperidine-2,6-dione as white solid (32 g, 76%). mp: 140-142° C. LC-MS m/e=450. HPLC: Waters Symmetry C$_{18}$, 5 μm, 3.9×150 mm, 1 mL/min, 240 nm, isocratic 15/85 CH$_3$CN/0.1% H$_3$PO$_4$ in 5 min: t$_R$=5.61 min (99.5%); Chiral AGP C$_{18}$ 4.0×150 mm, 5 μm 10/90 i-propanol/10 mM NH$_4$Ac in 20 min: t$_R$=10.07 min (99.5%); $^1$H NMR (DMSO-d$_6$) δ 2.28-2.38 (m, 4H, CH$_2$, CH$_2$), 2.44 (dd, J=4.2, 13.1 Hz, 1H, CHH), 2.53-2.63 (m, 1H, CHH), 2.79-3.02 (m, 1H, CHH), 3.49-3.69 (m, 4H, CH$_2$, CH$_2$), 4.11-4.52 (m, 2H, CH$_2$), 5.11 (dd, J=5.1, 13.2 Hz, 1H, NCH), 5.22 (s, 2H, CH$_2$), 7.33 (d, J=7.7 Hz, 4H, Ar), 7.40-7.52 (m, 3H, Ar), 10.97 (s, 1H, NH). $^{13}$C NMR (DMSO-d$_6$) δ 22.33, 31.18, 45.06, 51.55, 53.11, 62.07, 66.14, 69.38, 114.96, 115.20, 127.61, 128.97, 129.78, 129.93, 133.28, 135.27, 137.67, 153.48, 167.97, 170.95, 172.80. LC-MS: 465; Anal Calcd for C$_{25}$H$_{27}$N$_3$O$_5$ C: 66.80%; H: 6.05%; N: 9.35%. Found: C: 66.59%; H: 5.79%; N: 9.26%.

5.62 3-(1-Oxo-4-((4-(((S)-2-(Trifluoromethyl)Pyrrolidin-1-yl)Methyl)Benzyl)Oxy)Isoindolin-2-yl)Piperidine-2,6-Dione

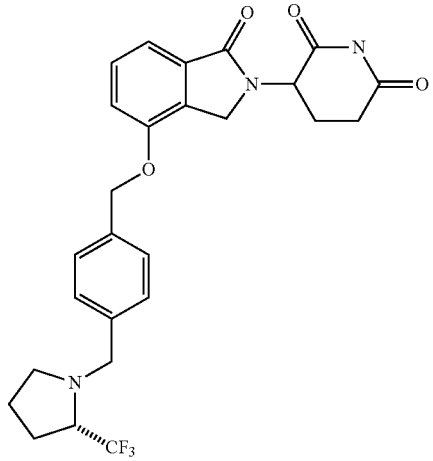 [SMILES: O=C1CCC(N2Cc3c(OCc4ccc(CN5CCC[C@H]5C(F)(F)F)cc4)cccc3C2=O)C(=O)N1]

Step 1: (S)-2-(Trifluoromethyl)pyrrolidine (198 mg, 1.420 mmol) was added as solid to a solution of methyl 5-amino-4-(4-(4-(bromomethyl)benzyloxy)-1-oxoisoindolin-2-yl)-5-oxopentanoate (450 mg, 0.947 mmol) in acetonitrile (5 ml). The resulting solution was stirred for 4 h at room temperature and then for 24 h at 70° C. Additional portions of DIEA (0.165 ml, 0.947 mmol) and (S)-2-(trifluoromethyl) pyrrolidine (60 mg, 0.43 mmol) were charged and the resulting mixture was stirred at 70° C. for an additional ~16 h. The mixture was cooled and then concentrated in vacuo. The residue was partitioned between EtOAc (50 mL) and 1N NaHCO$_3$ (30 mL) and the aqueous layer was washed with additional EtOAc (50 mL). The combined organic layer was washed with brine, dried (Na$_2$SO$_4$), and concentrated in vacuo to give methyl 5-amino-5-oxo-4-(1-oxo-4-((4-(((S)-2-(trifluoromethyl)pyrrolidin-1-yl)methyl)benzyl)oxy)isoindolin-2-yl)pentanoate as a yellow glassy solid (500 mg, 99% crude yield). The crude product was used in the next step without further purification: LCMS:MH=534.

Step 2: To a solution of methyl 5-amino-5-oxo-4-(1-oxo-4-(4-(((S)-2-(trifluoromethyl)pyrrolidin-1-yl)methyl)benzyloxy)isoindolin-2-yl)pentanoate (500 mg, 0.937 mmol) in DMF (5 mL), was added anhydrous potassium carbonate (155 mg, 1.125 mmol) and the mixture was stirred at 85° C. for ~17 h. The reaction mixture was cooled to room temperature, diluted with EtOAc (~150 mL), and washed with 1N aq. NaHCO$_3$ (30 mL). The organic layer was washed with water (30 mL) and brine, dried (Na$_2$SO$_4$), and concentrated in vacuo to give a tan oil. The oil was dissolved in DMF (6 mL) and purified using reversed-phase preparative HPLC. The product was eluted with an acetonitrile/water gradient (0.1% formic acid in both mobile phases, 5 to 80% MeCN over 30 minutes) and fractions were collected by mass trigger. The desired fractions were combined and then concentrated in vacuo to give a white solid. Further drying of this solid in a vacuum oven provided 3-(1-oxo-4-((4-(((S)-2-(trifluoromethyl)pyrrolidin-1-yl)methyl)benzyl)oxy)isoindolin-2-yl)piperidine-2,6-dione as a white solid (275 mg, 58% yield): HPLC: Waters Symmetry C$_{18}$, 5 µm, 3.9×150 mm, 1 ml/min, 240 nm, 45/55 CH$_3$CN/0.1% H$_3$PO$_4$, 5.80 min (99.6%); mp: 178-180° C.; $^1$H NMR (DMSO-d$_6$) δ 1.57-1.91 (m, 3H, CHH, CHH, CHH), 1.92-2.15 (m, 2H, CHH, CHH), 2.31-2.48 (m, 2H, CHH, CHH), 2.53-2.65 (m, 1H, CHH), 2.75-3.03 (m, 2H, CHH, CHH), 3.44-3.60 (m, 1H, CHH), 3.65 (d, J=13.6 Hz, 1H, CHH), 4.07 (d, J=13.6 Hz, 1H, CHH), 4.25 (d, J=17.6 Hz, 1H, CHH), 4.42 (d, J=17.6 Hz, 1H, CHH), 5.11 (dd, J=5.1, 13.2 Hz, 1H, CH), 5.23 (s, 2H, CH$_2$), 7.33 (d, J=7.7 Hz, 4H, Ar), 7.40-7.54 (m, 3H, Ar), 10.97 (s, 1H, NH); $^{13}$C NMR (DMSO-d$_6$) δ 22.33, 24.12, 25.84, 31.18, 45.04, 51.55, 53.56, 59.08, 62.79 (q, J=27.5 Hz, CCF$_3$), 69.38, 114.94, 115.20, 127.66 (q, J=280.6 Hz, CF$_3$), 127.71, 128.27, 129.78, 129.95, 133.28, 135.24, 139.00, 153.48, 167.99, 170.96, 172.81; LCMS: MH=502; Anal Calcd for C$_{26}$H$_{26}$F$_3$N$_3$O$_4$: C, 62.27; H, 5.23; N, 8.38; F, 11.36; Found: C, 61.99; H, 5.17; N, 8.32; F, 11.37.

5.63 (S)-3-Methyl-3-(4-((4-(Morpholinomethyl) Benzyl)Oxy)-1-Oxoisoindolin-2-yl)Piperidine-2,6-Dione

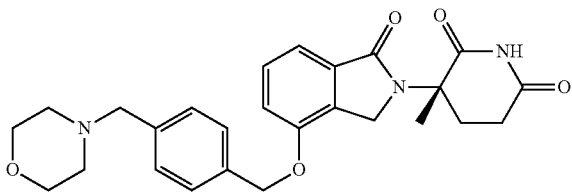 [SMILES: C[C@]1(N2Cc3c(OCc4ccc(CN5CCOCC5)cc4)cccc3C2=O)CCC(=O)NC1=O]

Step 1: (S)-3-(4-hydroxy-1-oxoisoindolin-2-yl)-3-methylpiperidine-2,6-dione To a mixture of methyl 2-(bromomethyl)-3-(tert-butyldimethylsilyloxy)benzoate (4.31 g, 12 mmol and (S)-3-methyl-2,6-dioxopiperidin-3-aminium bromide (2.68 g, 12.00 mmol) in acetonitrile (100 mL) was added DIEA (3.4 g, 26.4 mmol). The mixture was heated to 60° C. for 48 h. Then, 50 mL of AcOH was added, and the mixture was heated to 80° C., After 15 min, the mixture was evaporated to remove the acetonitrile, and the remaining acetic acid solution was then heated to reflux. After 1 h, the mixture was cooled to room temperature and filtered, and the filter was rinsed with acetic acid (30 mL) and water (50 mL), and dried under vacuum, providing 2.6 g (79%) as a white solid. $^1$H NMR (DMSO-d$_6$) δ 1.68 (s, 3H), 1.81-1.97 (m, 1H), 2.51-2.84 (m, 3H), 4.48 (d, J=17.2 Hz, 1H), 4.59 (d, J=17.4 Hz, 1H), 7.00 (d, J=7.9 Hz, 1H), 7.09 (d, J=7.4 Hz, 1H), 7.31 (t J=7.7 Hz, 1H), 10.13 (s, 1H), 10.85 (s, 1H).

Step 2: (S)-3-(4-((4-(bromomethyl)benzyl)oxy)-1-oxoisoindolin-2-yl)-3-methylpiperidine-2,6-dione A mixture of (S)-3-(4-hydroxy-1-oxoisoindolin-2-yl)-3-methylpiperidine-2,6-dione (0.3 g, 1.094 mmol), 1,4-bis(bromomethyl) benzene (0.866 g, 3.28 mmol), and sodium carbonate (0.116 g, 1.094 mmol) in DMF (10 mL) were stirred at room temperature under nitrogen for 16 h. The mixture was partitioned between water (75 mL) and ethyl acetate (75 mL), and the organic phase was evaporated under vacuum. The residue was chromatographed using a methylene chloride-methanol gradient. The product eluted at 2% MeOH. After drying, the yield was 190 mg (38% yield). $^1$H NMR (DMSO-d$_6$) δ 1.69 (s, 3H), 1.82-1.94 (m, 1H), 2.52-2.76 (m, 3H), 4.50-4.76 (m, 4H), 5.27 (s, 2H), 7.26 (dd, J=7.8, 18.2 Hz, 2H), 7.39-7.59 (m, 5H), 10.84 (s, 1H).

Step 3: (S)-3-methyl-3-(4-((4-(morpholinomethyl)benzyl)oxy)-1-oxoisoindolin-2-yl)piperidine-2,6-dione (S)-3-(4-4-(bromomethyl)benzyloxy)-1-oxoisoindolin-2-yl)-3-methylpiperidine-2,6-dione (100 mg, 0.219 mmol) was dissolved in acetonitrile (5 mL), and morpholine (0.021 ml, 0.241 mmol) and DIEA (0.046 ml, 0.262 mmol) were added. The mixture was stirred at room temperature for 16 h. Then, the mixture was partitioned between EtOAc (50 mL) and water (50 mL) and the organic phase was washed with water (50 mL), and then extracted with 1N HCl (2×50 mL). The combined acidic aqueous extracts were washed with EtOAc (2×50 mL) and then made basic by the addition of solid sodium carbonate, and were then extracted with EtOAc (2×50 mL). The combined organic extracts were dried (MgSO$_4$) and evaporated, providing 90 mg as a white solid, in 89% yield; mp 178-180° C. HPLC: Waters X-Terra, 3.9×150 mm, 5 µm, 1 mL/min, 240 nm, 5/95 to 95/5 CH$_3$CN-0.1% NH$_4$ (HCO$_2$) over 5 min then 10 min 95/5 CH$_3$CN-0.1% NH$_4$(HCO$_2$): 4.63 (96.34%). $^1$H NMR (DMSO-d$_6$) δ 1.68 (s, 3H), 1.83-1.93 (m, 1H), 2.28-2.40 (m, 4H), 2.52-2.80 (m, 3H), 3.46 (s, 2H), 3.51-3.62 (m, 4H), 4.55 (d, J=17.8 Hz, 1H), 4.68 (d, J=17.8 Hz, 1H), 5.24 (s, 2H), 7.22 (d, J=7.4 Hz, 1H), 7.27-7.38 (m, 3H), 7.40-7.50 (m, 3H), 10.85 (s, 1H). $^{13}$C NMR (DMSO-d$_6$) δ 20.68, 27.77, 29.01, 45.60, 53.15, 57.19, 62.10, 66.17, 69.39, 114.79, 127.71, 129.01, 129.74, 129.98, 133.91, 135.28, 137.72, 153.35, 167.00, 172.47, 173.53. Anal. Calcd for C$_{26}$H$_{29}$N$_3$O$_5$+2.0 H$_2$O: C, 62.51%; H, 6.66%; N, 8.41%; Found: C, 62.52%; H, 6.29%; N, 8.19%.

5.64 3-(4-((1,5-Dimethyl-1H-Pyrazol-3-yl)Methoxy)-1-Oxoisoindolin-2-yl)Piperidine-2,6-Dione

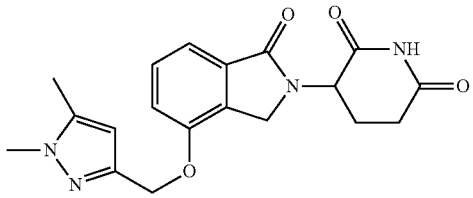 [SMILES: Cc1cc(COc2cccc3c2CN(C2CCC(=O)NC2=O)C3=O)nn1C]

Step 1: To the solution of methyl 1,5-dimethyl-1H-pyrazole-3-carboxylate (1 g, 6.49 mmol) in THF (20 mL) was added dibal-H (1 M in toluene, 19.46 mL, 19.46 mmol) at 0° C., the mixture was stirred at room temperature overnight. A solution of Rochelle's salt (1.0 M, 50 ml) was added; followed by ethyl acetate (50 mL), the resulting suspension was stirred at room temperature until the clear phase separation was achieved, the organic phase was separated and the aqueous phase was extracted with EtOAc (3×40 ml). The combined organic layers were washed with saturated aqueous $NaHCO_3$ (5 mL) and brine, dried over $MgSO_4$, and concentrated to give (1,5-dimethyl-1H-pyrazol-3-yl)methanol (700 mg, 86% yield); $^1$H NMR (DMSO-$d_6$) δ 2.20 (s, 3H, $CH_3$), 3.63 (s, 3H, $CH_3$), 4.29 (d, J=5.9 Hz, 2H, $CH_2$), 4.84 (t, J=5.8 Hz, 1H, OH), 5.93 (s, 1H, Ar)

Step 2: Polymer-supported thiphenylphosphine (1.6 mmol/g, 3.96 g, 6.34 mmol) was added to a stirred suspension of methyl 5-amino-4-(4-hydroxy-1-oxoisoindolin-2-yl)-5-oxopentanoate (927 mg, 3.17 mmol) in THF (30 mL) at 0° C., followed by diisopropyl azodicarboxylate (1.28 g, 6.34 mmol), after stirring for 10 minutes, (1,5-dimethyl-1H-pyrazol-3-yl)methanol (400 mg, 3.17 mmol) was added, the mixture was stirred at room temperature overnight and filtered. The resin was washed with ethyl acetate (10×20 mL). The combined filtrate was evaporated to dryness, the residue was purified by ISCO (40 g column, MeOH/$CH_2Cl_2$ gradient from 0% to 5% in 40 min) to give methyl 5-amino-4-(4-((1,5-dimethyl-1H-pyrazol-3-yl)methoxy)-1-oxoisoindolin-2-yl)-5-oxopentanoate (340 mg 27% yield); $^1$H NMR (DMSO-$d_6$) δ 1.99-2.29 (m, 7H, $CH_2$, $CH_2$, $CH_3$), 3.50 (s, 3H, $CH_3$), 3.70 (s, 2H, $CH_3$), 4.26-4.57 (m, 2H, $CH_2$), 4.70 (s, 1H, CH), 5.06 (s, 2H, $CH_2$), 6.14 (s, 1H, Ar), 7.18 (br. s., 1H, NHH), 7.27 (d, J=7.2 Hz, 1H, Ar), 7.32-7.40 (m, 1H, Ar), 7.41-7.50 (m, 1H, Ar), 7.57 (s, 1H, NHH)

Step 3: To a solution of methyl 5-amino-4-(4-((1,5-dimethyl-1H-pyrazol-3-yl)methoxy)-1-oxoisoindolin-2-yl)-5-oxopentanoate (340 mg, 0.849 mmol) in THF (20 mL) was added potassium tert-butoxide (105 mg, 0.934 mmol) at 0° C. The mixture was warmed up to room temperature and stirred at room temperature for 1 hour. HCl (1N, 1.5 mL) was added to quenche the reaction, the solvent was evaporated, the residue was partitioned between ethyl acetate (50 mL) and aqueous saturated sodium bicarbonate (5 mL). the organic layer was separated, washed with brine, dried over magnesium sulfate, the solvent was removed under vacuum, the residue was dissolved in ethyl acetate (3 mL), hexanes (5 mL) was added dropwise, the formed precipitate was collected by filtration to give 3-(4-((1,5-dimethyl-1H-pyrazol-3-yl)methoxy)-1-oxoisoindolin-2-yl)piperidine-2,6-dione (150 mg, 48% yield); mp: 214-216° C.; $^1$H NMR (DMSO-$d_6$) δ 1.89-2.04 (m, 1H, CHH), 2.22 (s, 3H, $CH_3$), 2.34-2.48 (m, 1H, CHH), 2.53-2.67 (m, 1H, CHH), 2.80-3.01 (m, 1H, CHH), 3.70 (s, 3H, $CH_3$), 4.11-4.43 (m, 2H, $CH_2$), 5.00-5.18 (m, 3H, CH, $CH_2$), 6.13 (s, 1H, Ar), 7.31 (d, J=7.2 Hz, 1H, Ar), 7.35-7.43 (m, 1H, Ar), 7.43-7.59 (m, 1H, Ar), 10.97 (s, 1H, NH); $^{13}$C NMR (DMSO-$d_6$) δ 10.62, 22.31, 31.19, 35.78, 45.07, 51.55, 64.00, 104.81, 114.93, 115.07, 129.73, 129.84, 133.21, 139.29, 145.31, 153.46, 168.00, 170.96, 172.81; HPLC: Waters Xterra C-18, 3.9× 150 mm, 5 μm, 1 mL/min, 240 nm, 25/75 $CH_3CN$/0.1% $HCOONH_4$ $t_R$=4.51 (98.77%); Anal. Calcd for $C_{19}H_{20}N_4O_4$+0.2 $H_2O$ C, 61.35; H, 5.53; N, 15.06; Found: C, 61.29; H, 5.30; N, 14.86.

5.65 2-(2,6-Dioxopiperidin-3-yl)-4-((4-(Thiomorpholinomethyl)Benzyl)Oxy)Isoindoline-1 3-Dione

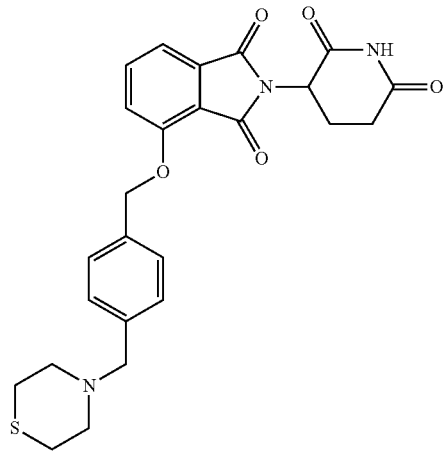 [SMILES: O=C1CCC(N2C(=O)c3cccc(OCc4ccc(CN5CCSCC5)cc4)c3C2=O)C(=O)N1]

Step 1: Dimethyl 3-((4-(hydroxymethyl)benzyl)oxy) phthalate Dimethyl 3-hydroxyphthalate (10 g, 47.6 mmol) and (4-(chloromethyl)phenyl)methanol (7.82 g, 50.0 mmol) were dissolved in dry DMF (60 mL). To the solution was added $K_2CO_3$ (6.90 g, 50.0 mmol) and the mixture was stirred at 80° C. for 16 h. The DMF was removed in vacuo and the residue was partitioned between EtOAc (300 mL) and water (100 mL). The organic layer was washed with additional water (100 mL) and brine, dried ($Na_2SO_4$), and concentrated in vacuo to dimethyl 3-((4-(hydroxymethyl)benzyl)oxy)-phthalate as a viscous amber oil (19 g): LCMS: MH=331; The crude product was used in the next step without further purification Step 2: 3-((4-(Hydroxymethyl)benzyl)oxy)phthalic acid Dimethyl 3-(4-(hydroxymethyl)benzyloxy)phthalate (19 g actual wt, 15.72 g, 47.6 mmol, assuming quantitative yield from previous step) was dissolved in THF (30 mL). To the solution was added water (30 mL). Aqueous NaOH (10 N, 25 mL, 250 mmol) was added and the mixture was vigorously stirred at 70° C. for 2.5 h. The mixture was allowed to cool to rt, concentrated in vacuo to a syrup, and then transferred to a flask containing 6 N HCl (45 mL) over ice. Immediately, solid precipitated out and the slurry was diluted with water (~60 mL). The mixture was filtered on a medium fritted funnel with suction. The cake was washed with additional water (~60 mL), suction dried, and then placed in a vacuum oven at 60° C. for 4 h to give 3-((4-(hydroxymethyl)benzyl)oxy)phthalic acid as a pale yellow solid (13.9 g, 97% yield from dimethyl 3-hydroxyphthalate): $^1$H NMR (DMSO-$d_6$) δ 4.41-4.58 (m, 2H, $CH_2$), 5.17 (s, 3H, $CH_2$, OH), 7.20-7.64 (m, 7H, Ar), 13.02 (br. s., 2H, 2×COOH); $^{13}$C NMR (DMSO-d$_6$) δ 62.63, 69.73, 1 17.03, 121.56, 126.46, 126.88, 127.13, 128.91, 129.57, 134.87, 142.19, 154.50, 166.45, 167.71; LCMS: MH=303, 94 area % at 240 nm. The solid was used in the next step without further purification.

Step 3: 2-(2,6-Dioxopiperidin-3-yl)-4-((4-(hydroxymethyl)benzyl)oxy)isoindoline-1,3-dione 3-Aminopiperidine-2,6-dione hydrochloride (0.915 g, 5.56 mmol) was added to a solution of 3-(4-(hydroxymethyl)benzyloxy)phthalic acid (1.4 g, 4.63 mmol) in dry pyridine (15 mL) and the mixture was heated to 118° C. in an oil bath for 16 h. The dark reaction mixture was allowed to cool to room temperature and was acidified with slow addition of 1 N HCl (~25 mL). The mixture was further diluted with water (~170 mL) and then sonicated for ~30 minutes to help break up solid aggregates. The resulting dark slurry was filtered on a medium pore fritted funnel and the dark solid was washed with additional water (70 mL). The cake was suction dried and then placed in vacuum oven at 60° C. for 2.5 h to give 1.6 g of a dark blue solid. The solid was dissolved in a mixture of DCM, MeCN, and MeOH (~100 mL each) and treated decolorizing charcoal. The mixture was swirled around and then gravity-filtered using filter paper. The filtrate/wash (dark amber color) was treated once again with decolorizing charcoal and then filtered on a bed of celite. The clear filtrate was concentrated in vacuo to dryness to give a solid which was triturated with water and filtered with suction. The cake was washed with additional water (~100 mL), suction dried, and then placed in vacuum oven at 60° C. for 4 h to give 2-(2,6-dioxopiperidin-3-yl)-4-((4-(hydroxymethyl)benzyl)oxy)isoindoline-1,3-dione as an off-white solid (1.2 µm, 68% yield): HPLC: Waters Symmetry C$_{18}$, 5 µm, 3.9×150 mm, 1 ml/min, 240 nm, 15/85 CH$_3$CN/0.1% H$_3$PO$_4$, 5.08 min (99.9%); mp: 250-252; $^1$H NMR (DMSO-d$_6$) δ 1.95-2.07 (m, 1H, CHH), 2.41-2.67 (m, 2H, CHH, CHH), 2.78-3.00 (m, 1H, CHH), 4.50 (d, J=5.1 Hz, 2H, CH$_2$OH), 5.09 (dd, J=5.4, 12.7 Hz, 1H, CH), 5.19 (t, J=5.6 Hz, 1H, OH), 5.36 (s, 2H, CH$_2$O), 7.24-7.40 (m, 2H, Ar), 7.41-7.53 (m, 3H, Ar), 7.59 (d, J=8.5 Hz, 1H, Ar), 7.82 (dd, J=7.4, 8.5 Hz, 1H, Ar), 11.11 (s, 1H, NH); $^{13}$C NMR (DMSO-d$_6$) δ 21.88, 30.83, 48.67, 62.53, 69.91, 115.40, 116.52, 120.18, 126.44, 127.09, 133.17, 134.31, 136.86, 142.32, 155.42, 165.21, 166.68, 169.81, 172.66. LCMS: M+Na=417; MH is not observed in positive ionization mode; Anal Calcd for C$_{21}$H$_{18}$N$_2$O$_6$: C, 63.96; H, 4.60; N, 7.10; Found: C, 63.77; H, 4.52; N, 7.32.

Step 4: 4-((4-(Bromomethyl)benzyl)oxy)-2-(2,6-dioxopiperidin-3-yl)isoindoline-1,3-dione A suspension of 2-(2,6-dioxopiperidin-3-yl)-4-(4-(hydroxymethyl)benzyloxy)isoindoline-1,3-dione (1.05 g, 2.66 mmol) in a mixture of DCM and MeCN (25 mL, 10 mL) was stirred in an ice bath. To the mixture was added PBr$_3$ (0.502 mL, 5.32 mmol) in one portion. After 5 min, the ice bath was removed and the reaction mixture was stirred at room temperature for ~20 h. To the reaction mixture was added NaBr (0.822 g, 7.99 mmol) and tetrabutylammonium bromide (0.077 g, 0.240 mmol) and stirring was continued for an additional 14 h at room temperature. The reaction was concentrated in vacuo to an off-white solid and the solid was reslurried in water with vigorous agitation and then filtered (medium fritted funnel). The cake was washed with copious water (~250 mL, total volume of filtrate and washes) and then dried in a vacuum oven at 50° C. to give 4-((4-(bromomethyl)benzyl)-oxy)-2-(2,6-dioxopiperidin-3-yl)isoindoline-1,3-dione as a white solid (1.21 g, 99% yield): HPLC: Waters Symmetry C$_{18}$, 5 µm, 3.9×150 mm, 1 ml/min, 240 nm, 50/50 CH$_3$CN/0.1% H$_3$PO$_4$, 4.85 min (99.5%); $^1$H NMR (DMSO-d$_6$) δ 1.94-2.15 (m, 1H, CHH), 2.42-2.70 (m, 2H, CHH, CHH), 2.79-2.99 (m, 1H, CHH), 4.72 (s, 2H, CH$_2$), 5.10 (dd, J=5.4, 12.9 Hz, 1H, CH), 5.38 (s, 2H, CH$_2$), 7.38-7.54 (m, 5H, Ar), 7.59 (d, J=8.5 Hz, 1H, Ar), 7.83 (dd, J=7.3, 8.4 Hz, 1H, Ar), 11.11 (s, 1H, NH); $^{13}$C NMR (DMSO-d$_6$) δ 21.95, 30.91, 34.12, 48.75, 69.64, 115.57, 116.62, 120.18, 127.48, 129.42, 133.26, 136.33, 136.99, 137.72, 155.37, 165.27, 166.73, 169.87, 172.72; LCMS: M+Na=479, 481; MH is not observed.

Step 5: 2-(2,6-Dioxopiperidin-3-yl)-4-((4-(thiomorpholinomethyl)benzyl) oxy)isoindoline-1,3-dione To a slurry of 4-(4-(bromomethyl)benzyloxy)-2-(2,6-dioxopiperidin-3-yl) isoindoline-1,3-dione (250 mg, 0.547 mmol) in MeCN (10 mL), was added thiomorpholine (62.1 mg, 0.601 mmol) followed by DIEA (0.143 mL, 0.820 mmol). The resulting suspension was stirred at room temperature. The reaction mixture became clear after ~15 min of stirring and then, gradually, solids precipitated out of solution. After ~2 h, the reaction mixture was treated with more DIEA (0.143 mL, 0.820 mmol) and the slurry was heated to 80° C. with constant stirring for ~1 h. The mixture was allowed to cool to room temperature slowly with gentle stirring. After 2 h, the slurry was filtered on a medium fritted funnel with suction. The residual solid in the reaction vial was rinsed onto the funnel with minimal MeCN (1 mL). The cake was washed with water (3×10 mL). The remaining solid was dried in vacuum oven at 60 C for 4 h to give 2-(2,6-dioxopiperidin-3-yl)-4-((4-(thiomorpholinomethyl)-benzyl) oxy)isoindoline-1,3-dione as a white solid (225 mg, 86%): HPLC: Waters Symmetry C$_{18}$, 5 µm, 3.9×150 mm, 1 ml/min, 240 nm, 18/82 CH$_3$CN/0.1% H$_3$PO$_4$, 6.96 min (99.3%); mp: 221-223° C.; $^1$H NMR (DMSO-d$_6$) δ 1.96-2.10 (m, 1H, CHH), 2.41-2.66 (m, 11H, 4×CH$_2$, 3×CHH), 2.80-2.97 (m, 1H, CHH), 3.50 (s, 2H, CH$_2$N), 5.09 (dd, J=5.3, 12.8 Hz, 1H, CH), 5.35 (s, 2H, CH$_2$O), 7.26-7.40 (m, 2H, Ar), 7.42-7.53 (m, 2H, Ar), 7.60 (d, J=8.5 Hz, 1H, Ar), 7.83 (dd, J=7.4, 8.5 Hz, 1H, Ar), 11.11 (s, 1H, NH); $^{13}$C NMR (DMSO-d$_6$) δ 21.21, 26.38, 30.16, 47.99, 53.65, 61.49, 69.19, 114.75, 115.82, 119.45, 126.52, 128.12, 132.51, 134.00, 136.23, 137.16, 154.78, 164.55, 166.00, 169.13, 171.98; LCMS: MH=480; Anal Calcd for C$_{25}$H$_{25}$N$_3$O$_5$S+ 0.28 H$_2$O: C, 61.96; H, 5.32; N, 8.67; S, 6.62; Found: C, 61.97; H, 5.12; N, 8.63; S, 6.55.

5.66 3-(4-((6-(Morpholinomethyl)Imidazo[1,2-A]Pyridine-2-yl)Methoxy)-1-Oxoisoindolin-2-yl)Piperidine-2,6-Dione

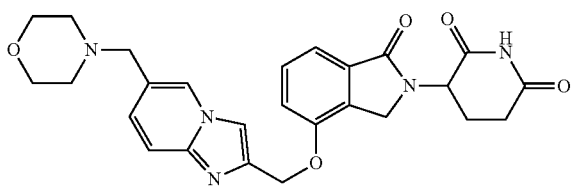 [SMILES: O=C1CCC(N2Cc3c(OCc4cn5cc(CN6CCOCC6)ccc5n4)cccc3C2=O)C(=O)N1]

Step 1: Ethyl 3-bromo-2-oxopropanoate (9.0 g, 46.2 mmol) was added to a stirred solution of 5-methylpyridin-2-amine (5.0 g, 46.2 mmol) in ethanol (50 mL). The resulting mixture was refluxed for 18 h. The reaction mixture was cooled and concentrated. Residue was dissolved in CH$_2$Cl$_2$ (100 mL) and washed with sat. NaHCO$_3$ (40 mL), water (40 mL), brine (40 mL) and dried. Solvent was removed and residue was purified by chromatography (SiO$_2$, 20% EtOAc/

CH$_2$Cl$_2$ for 20 min then to 100% EtOAc over 30 min) to give ethyl 6-methylimidazo[1,2-a]pyridine-2-carboxylate (3.8 g, 40%): $^1$H NMR (CDCl$_3$) δ 1.44 (t, J=6 Hz, 3H), 2.33 (s, 3H), 4.42-4.49 (q, J=6 Hz, 2H), 7.07-7.11 (dd, J=3 and 12 Hz, 1H), 7.56-7.59 (d, J=9 Hz, 1H), 7.90-7.91 (d, J=3 Hz, 1H), 8.10 (s, 1H).

Step 2: A mixture of ethyl 6-methylimidazo[1,2-a]pyridine-2-carboxylate (3.7 g, 18.2 mmol) and N-bromosuccinimide (3.2 g, 18.2 mmol) in methyl acetate (50 mL) was heated at 60° C. oil bath with a 300 W bulb shining on the reaction mixture for 3 h. The reaction mixture was cooled and diluted with EtOAc (50 mL) and washed with water (2×35 mL), brine (35 mL) and dried. Solvent was removed and residue was purified by chromatography (SiO$_2$, 20% EtOAc/CH$_2$Cl$_2$ for 25 min) to give ethyl 3-bromo-6-methylimidazo[1,2-a]pyridine-2-carboxylate (4.7 g, 90%): $^1$H NMR (CDCl$_3$) δ 1.46 (t, J=6 Hz, 3H), 2.41 (s, 3H), 4.45-4.52 (q, J=6 Hz, 2H), 7.16-7.19 (dd, J=3 and 9 Hz, 1H), 7.58-7.61 (d, J=9 Hz, 1H), 7.98 (s, 1H); $^{13}$C NMR (CDCl$_3$) δ 14.41, 18.45, 61.35, 99.75, 118.46, 121.90, 124.57, 129.95, 133.55, 144.27, 162.45.

Step 3: A mixture of ethyl 3-bromo-6-methylimidazo[1,2-a]pyridine-2-carboxylate (4.5 g, 15.8 mmol), N-bromosuccinimide (2.8 g, 17.8 mmol) and 2,2'-azobisisobutyronitrile (0.6 g) in CCl$_4$ (75 mL) was heated at 75° C. oil bath with a 300 W bulb shining on the reaction mixture for 3 h. The reaction mixture was cooled and filtered and washed solid with CH$_2$Cl$_2$ (40 mL). Filtrate was concentrated and residue was dissolved in CH$_2$Cl$_2$ (100 mL) and washed with water (2×30 mL), brine (30 mL) and dried. Solvent was removed and residue was purified by chromatography (SiO$_2$, CH$_2$Cl$_2$ for 5 min then to 10% EtOAc/CH$_2$Cl$_2$ over 5 min and hold for 15 min then to 20% over 5 min and hold for 15 min) to give ethyl 3-bromo-6-(bromomethyl)imidazo[1,2-a]pyridine-2-carboxylate (2.5 g, 44%); $^1$H NMR (CDCl$_3$) δ 1.47 (t, J=6 Hz, 3H), 4.46-4.52 (q, J=6 Hz, 2H), 4.54 (s, 2H), 7.35-7.39 (dd, J=3 and 9 Hz, 1H), 7.68-7.71 (d, J=9 Hz, 1H), 8.23 (s, 1H); $^{13}$C NMR (CDCl$_3$) δ 14.35, 29.60, 61.54, 100.79, 119.60, 123.28, 125.38, 128.28, 134.56, 144.45, 162.09.

Step 4: A solution of ethyl 3-bromo-6-(bromomethyl)imidazo[1,2-a]pyridine-2-carboxylate (2.4 g, 6.7 mmol) in acetone (50 mL) and DMF (40 mL) was added to a stirred mixture of morpholine (0.9 g, 10.1 mol), potassium carbonate (3.3 g, 23.6 mmol) and catalytic amount of 18-crown-6 in acetone (50 mL) at 60° C. oil bath. The reaction mixture was stirred at 60° C. oil bath for 3 h. The reaction mixture was cooled and filtered. Filtrate was concentrated and residue was dissolved in EtOAC (100 mL) and washed with water (2×35 mL), brine (35 mL) and dried. Solvent was removed and solid residue was stirred with ether to give ethyl 3-bromo-6-(morpholinomethyl)imidazo[1,2-a]pyridine-2-carboxylate (1.4 g, 55%): $^1$H NMR (CDCl$_3$) δ 1.47 (t, J=6 Hz, 3H), 2.48-2.51 (m, 4H), 3.55 (s, 2H), 3.72-3.75 (m, 4H), 4.46-4.53 (q, J=6 Hz, 2H), 7.39-7.42 (d, J=9 Hz, 1H), 7.63-7.66 (d, J=9 Hz, 1H), 8.12 (s, 1H).

Step 5: LiAlH$_4$/THF (1M, 3.9 mL, 3.9 mmol) was added slowly to a stirred solution of ethyl 3-bromo-6-(morpholinomethyl)imidazo[1,2-a]pyridine-2-carboxylate (1.2 g, 3.3 mmol) in THF (40 mL) at 0-5° C. The reaction mixture was stirred at 0° C. for 1 h. The reaction mixture was quenched with water (1 mL), 2N NaOH (1 mL), water (4 mL). The mixture was filtered and washed solid with CH$_2$Cl$_2$ (40 mL). Filtrate was washed with brine (35 mL) and dried. Solvent was removed to give (6-(morpholinomethyl)imidazo[1,2-a]pyridine-2-yl)methanol (0.6 g, 75%): $^1$H NMR (CDCl$_3$) δ 2.45-2.50 (m, 4H), 3.46 (s, 2H), 3.70-3.74 (m, 4H), 4.84 (s, 2H), 7.19-7.22 (dd, J=3 and 9 Hz, 1H), 7.47-7.52 (m, 2H), 8.02 (s, 1H).

Step 6: Triphenylphosphine-polymer bound (2.5 g, 3.4 mmol) in THF (30 mL) was cooled in ice bath to 3° C. Diisopropyl azadicarboxylate (0.6 g, 3.2 mmol) was added slowly at 3-5° C. After stirred at 3° C. for 10 min, a solution of methyl 5-amino-4-(4-hydroxy-1-oxoisoindolin-2-yl)-5-oxopentanoate (0.7 g, 2.3 mmol) and (6-(morpholinomethyl)imidazo[1,2-a]pyridine-2-yl)methanol (0.6 g, 2.3 mmol) in THF (70 mL) was added slowly at 5-10° C. After stirred for 5 min, ice bath was removed and mixture was stirred at room temperature overnight. The reaction mixture was filtered and filtrate was concentrated. Residue was dissolved in CH$_2$Cl$_2$ (100 mL) and washed with sat. NaHCO$_3$ (35 mL), water (35 mL), brine (35 mL) and dried. Solvent was removed and residue was purified by chromatography (SiO$_2$, CH$_2$Cl$_2$ for 5 min then to 3% CH$_3$OH/CH$_2$Cl$_2$ over 5 min and hold for 15 min then to 5% over 5 min and hold for 15 min then to 10% over 5 min and hold for 10 min) to give methyl 5-amino-4-(4-((6-(morpholinomethyl)imidazo[1,2-a]pyridine-2-yl)methoxy)-1-oxoisoindolin-2-yl)-5-oxopentanoate (0.5 g, 43%).

Step 7: A solution of methyl 5-amino-4-(4-((-6-(morpholinomethyl)imidazo[1,2-a]pyridine-2-yl)methoxy)-1-oxoisoindolin-2-yl)-5-oxopentanoate (0.5 g, 0.9 mmol) in THF (15 mL) was cooled in dry ice/acetone bath for 5 min. A solution of potassium tert-butoxide/THF (1M, 1.0 mL, 1.0 mmol) was added. The reaction mixture was stirred at −78° C. bath for 1 h. The reaction mixture was quenched with 1N HCl (3 mL) and warmed to room temperature. Water (20 mL) was added and basified with sat. NaHCO$_3$ (8 mL) to pH=8. The mixture was extracted with CH$_2$Cl$_2$ (3×30 mL) and combined organic solution was washed with brine (25 mL) and dried. Solvent was removed and residue was precipitated with ether to give 3-(4-((6-(morpholinomethyl)imidazo[1,2-a]pyridin-2yl)methoxy)-1-oxoisoindolin-2-yl)piperidine-2,6-dione (0.4 g, 83%): mp 155-157° C.; $^1$H NMR (DMSO-d$_6$) δ 1.97-2.01 (m, 1H), 2.36-2.39 (m, 4H), 2.39-2.60 (m, 2H), 2.85-2.96 (m, 1H), 3.44 (s, 2H), 3.55-3.58 (m, 4H), 4.20-4.26 (d, J=18 Hz, 1H), 4.36-4.41 (d, J=18 Hz, 1H), 5.08-5.14 (dd, J=6 and 12 Hz, 1H), 5.34 (s, 2H), 7.21-7.24 (m, 1H), 7.31-7.33 (d, J=9 Hz, 1H), 7.46-7.51 (m, 3H), 8.02 (s, 1H), 8.43 (s, 1H), 10.98 (s, 1H); $^{13}$C NMR (DMSO-d$_6$) δ 22.36, 31.18, 45.06, 51.55, 52.97, 59.13, 64.61, 66.13, 111.89, 115.03, 115.18, 116.24, 122.06, 125.67, 126.91, 129.77, 133.27, 141.58, 143.90, 153.45, 167.99, 170.96, 172.81; Calcd for C$_{26}$H$_{27}$N$_5$O$_5$+0.2CH$_2$Cl$_2$: C, 62.13; H, 5.45; N, 13.83. Found: C, 62.16; H, 5.74; N, 13.13.

5.67 3-{4-[4-(3,4-Dihydro-1H-Isoquinolin-2-ylmethyl)-Benzyloxy]-1-Oxo-1,3-Dihydro-Isoindol-2-yl}-Piperidine-2, 6-Dione

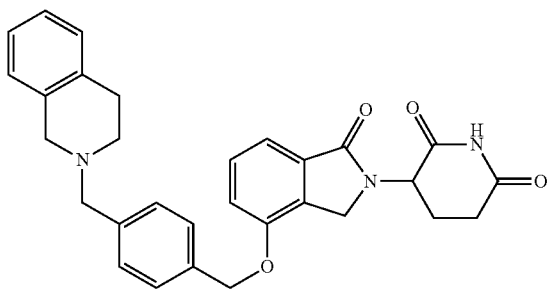 [SMILES: O=C1CCC(N2Cc3c(OCc4ccc(CN5CCc6ccccc6C5)cc4)cccc3C2=O)C(=O)N1]

Step 1 Preparation of 4-Carbamoyl-4-{4-[4-(3,4-dihydro-1H-isoquinolin-2-ylmethyl)-benzyloxy]-1-oxo-1,3-dihydro-isoindol-2-yl}-butyric acid methyl ester To the CH₃CN solution of methyl 5-amino-4-(4-(4-(bromomethyl)benzyloxy)-1-oxoisoindolin-2-yl)-5-oxopentanoate (0.37 g, 0.778 mmol) was added 1,2,3,4-tetrahydroisoquinoline (0.124 g, 0.934 mmol) and DIPEA (0.272 ml, 1.557 mmol). The mixture was stirred at room temperature for 2 hours. The reaction mixture was concentrated then extracted with CH₂Cl₂ and water. The organic layer was concentrated and gave 4-Carbamoyl-4-{4-[4-(3,4-dihydro-1H-isoquinolin-2-ylmethyl)-benzyloxy]-1-oxo-1,3-dihydro-isoindol-2-yl}-butyric acid methyl ester as a white solid (0.4 g, 97%). It was used in next step directly.

Step 2 Preparation of 3-{4-[4-(3,4-Dihydro-1H-isoquinolin-2-ylmethyl)-benzyloxy]-1-oxo-1,3-dihydro-isoindol-2-yl}-piperidine-2, 6-dione To the CH₃CN solution of methyl 5-amino-4-(4-(4-((3,4-dihydroisoquinolin-2(1H)-yl)methyl)benzyloxy)-1-oxoisoindolin-2-yl)-5-oxopentanoate (0.4 g, 0.758 mmol) was added potassium tert-butoxide (0.094 g, 0.834 mmol) at 0° C. The mixture was stirred at 0° C. for 1 hour. The reaction was quenched by adding 5 mL of 1N HCl followed by NaHCO₃ (sat., 5 mL). The mixture was added CH₂Cl₂ (20 mL), water (20 mL) and extracted. The organic layer was concentrated and gave a white solid. The solid was recrystallized from 4 mL of CH₃CN to give a white solid 170 mg (45%). m.p.: 173-175° C. LC-MS m/e=496. HPLC Waters Symmetry C-18, 3.9×150 mm, 5 micro, 1 mL/min, 240 nm, gradient 5/95 to 5/95 CH₃CN/0.1% H₃PO₄ in H₂O during 5 min and stay at 95/5 for 5 min: 6.43 min (97%). $^1$H NMR (DMSO-$d_6$) δ 1.86-2.11 (m, 1H, CHH), 2.35-2.48 (m, J=4.4, 13.3 Hz, 1H, CHH), 2.52-2.62 (m, 1H, CHH), 2.63-2.74 (m, 2H, CH₂), 2.74-2.84 (m, 2H, CH₂), 2.84-3.02 (m, 1H, CHH), 3.54 (s, 2H, CH₂), 3.65 (s, 2H, CH₂), 4.13-4.54 (m, 2H, CH₂), 5.11 (dd, J=5.0, 13.1 Hz, 1H, NCH), 5.24 (s, 2H, CH₂), 6.82-7.20 (m, 4H, Ar), 7.26-7.68 (m, 7H, Ar), 10.97 (s, 1H, NH). $^{13}$C NMR (DMSO-$d_6$) δ 22.36, 28.64, 31.20, 45.10, 50.16, 51.58, 55.40, 61.48, 69.44, 114.98, 115.23, 125.43, 125.94, 126.32, 127.72, 128.41, 128.82, 129.82, 129.95, 134.05, 134.69, 135.29, 138.10, 153.51, 170.98, 172.83. Anal Calcd for $C_{30}H_{29}N_3O_4$+0.3 $H_2O$; C % 71.92; H % 5.96; N % 8.39; Found: C % 71.55; H % 5.72; N % 8.22.

5.68 3-{4-[4-(2,3-Dihydro-Benzo[1,4]Oxazin-4-ylmethyl)-Benzyloxy]-1-Oxo-1,3-Dihydro-Isoindol-2-yl}-Piperidine-2,6-Dione

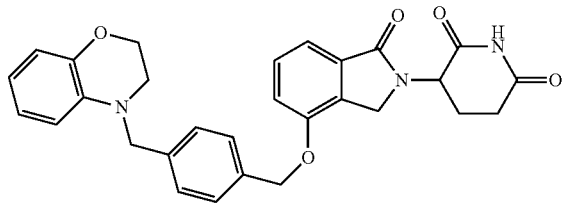 [SMILES: O=C1CCC(N2Cc3c(OCc4ccc(CN5CCOc6ccccc65)cc4)cccc3C2=O)C(=O)N1]

To the stirred solution of 3-(4-(4-(bromomethyl)benzyloxy)-1-oxoisoindolin-2-yl)piperidine-2,6-dione (350 mg, 0.79 mmol) in Acetonitrile (8 mL) was added solution of 3,4-dihydro-2H-benzo[b][1,4]oxazine (128 mg, 0.9 mmol) in acetonitrile (2 mL) and DIPEA (0.21 ml, 1.2 mmol) at room temperature. The resulting light yellow solution was stirred at room temperature for 18 hrs and stirred at 40° C. for 24 hrs. The product was purified by prep HPLC to give 3-{4-[4-(2,3-Dihydro-benzo[1,4]oxazin-4-ylmethyl)-benzyloxy]-1-oxo-1,3-dihydro-isoindol-2-yl}-piperidine-2,6-dione as a white solid (208 mg, 53% yield). HPLC: Waters Symmetry C-18, 3.9×150 mm, 5 μm, 1 mL/min, 240 nm, 55/45, (CH₃CN/0.1% H₃PO₄), 4.50 min (99.0%); mp: 145-147° C.; $^1$H NMR (DMSO-$d_6$) δ 1.91-2.04 (m, 1H, CHH), 2.33-2.47 (m, 1H, CHH), 2.53-2.65 (m, 1H, CHH), 2.80-3.01 (m, 1H, CHH), 3.35-3.43 (m, 2H, CH₂), 4.14-4.45 (m, 4H, CHH, CHH, CH₂), 4.47 (s, 2H, CH₂), 5.10 (dd, J=5.1, 13.2 Hz, 1H, CHH), 5.21 (s, 2H, CH₂), 6.44-6.56 (m, 1H, Ar), 6.57-6.76 (m, 3H, Ar), 7.22-7.39 (m, 4H, Ar), 7.39-7.59 (m, 3H, Ar), 10.96 (s, 1H, NHH); $^{13}$C NMR (DMSO-$d_6$) δ 22.31, 31.16, 45.06, 47.06, 51.55, 53.57, 64.03, 69.32, 112.27, 114.91, 115.20, 115.77, 116.91, 121.24, 127.20, 127.96, 129.78, 129.95, 133.28, 135.17, 135.21, 138.23, 143.46, 153.45, 167.99, 170.95, 172.81; LCMS MH=498; Anal. Calcd for $C_{29}H_{27}N_3O_5$+0.3$H_2O$: C, 69.25; H, 5.53; N, 8.35; Found: C, 69.01; H, 5.29; N, 8.25.

5.69 3-{4-[4-(2,3-Dihydro-5H-Benzo[F][1,4]Oxazepin-4-ylmethyl)-Benzyloxy]-1-Oxo-1,3-Dihydro-Isoindol-2-yl}-Piperidine-2,6-Dione

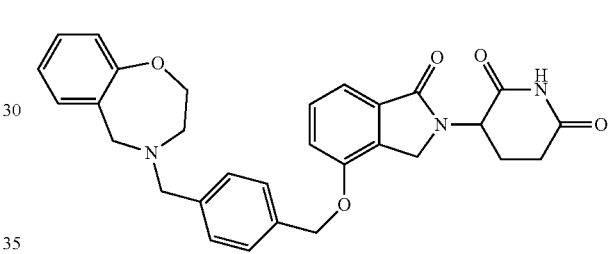

To the stirred solution of 2,3,4,5-tetrahydrobenzo[f][1,4]oxazepine (141 mg, 0.9 mmol) in Acetonitrile (8 mL) was added 3-(4-(4-(bromomethyl)benzyloxy)-1-oxoisoindolin-2-yl)piperidine-2,6-dione (350 mg, 0.79 mmol) and DIPEA (0.21 ml, 1.1 mmol) at room temperature. The reaction mixture was stirred at room temperature for 3.5 hrs before 3-(4-(4-(bromomethyl)benzyl oxy)-1-oxoisoindolin-2-yl)piperidine-2,6-dione (30 mg, 0.07 mmol) was added. The resulting reaction mixture was stirred at room temperature for 17 hrs and the mixture was purified by prep HPLC to give 3-{4-[4-(2,3-Dihydro-5H-benzo[f][1,4]oxazepin-4-ylmethyl)-benzyloxy]-1-oxo-1,3-dihydro-isoindol-2-yl}-piperidine-2,6-dione as a white solid (216 mg, 54% yield); HPLC: Waters Symmetry C-18, 3.9×150 mm, 5 μm, 1 mL/min, 240 nm, 23/77, (CH₃CN/0.1% H₃PO₄), 4.16 min (99.7%); mp: 148-150° C.; $^1$H NMR (DMSO-$d_6$) δ 1.90-2.04 (m, 1H, CHH), 2.34-2.48 (m, 1H, CHH), 2.57 (d, J=17.8 Hz, 1H, CHH), 2.81-3.04 (m, 3H, CH₂, CHH), 3.62 (s, 2H, CH₂), 3.75 (s, 2H, CH₂), 3.95-4.06 (m, 2H, CH₂), 4.26 (d, J=17.6 Hz, 1H, CHH), 4.42 (d, J=17.6 Hz, 1H, CHH), 5.03-5.17 (m, 1H, CHH), 5.24 (s, 2H, CH₂), 6.91-7.09 (m, 3H, Ar), 7.13-7.25 (m, 1H, Ar), 7.33 (d, J=7.2 Hz, 4H, Ar), 7.39-7.54 (m, 3H, Ar), 10.97 (s, 1H, NH); $^{13}$C NMR (DMSO-$d_6$) δ 22.33, 31.16, 45.07, 51.55, 57.28, 57.73, 57.87, 69.41, 69.87, 115.00, 115.22, 120.38, 123.08, 127.66, 128.36, 128.68, 129.78, 129.95, 130.53, 131.62, 133.30, 135.25, 138.62, 153.48, 159.60, 167.99, 170.96, 172.81; LCMS MH=512; Anal. Calcd for $C_{30}H_{29}N_3O_5$+0.4$H_2O$: C, 69.46; H, 5.79; N, 8.10; Found: C, 69.25; H, 5.53; N, 8.35.

5.70 2-(2,6-Dioxopiperidin-3-yl)-4-((4-(Morpholinomethyl)Thiazol-2-yl)Methoxy)Isoindoline-1,3-Dione

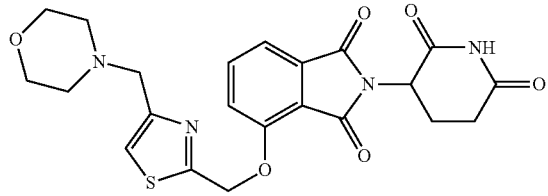 [SMILES: O=C1CCC(N2C(=O)c3cccc(OCc4nc(CN5CCOCC5)cs4)c3C2=O)C(=O)N1]

Step 1: Polymer-supported triphenylphosphine (1.6 mmol/g, 3.5 g, 5.6 mmol) was added to a stirred solution of dimethyl 3-hydroxyphthalate (647 mg, 3.08 mmol) in THF (30 mL) at 0° C., followed by diisopropyl azodicarboxylate (1.13 g, 5.6 mmol), after stirring for 10 minutes, (4-(morpholinomethyl)thiazol-2-yl)methanol (600 mg, 2.80 mmol) was added, the mixture was stirred at room temperature overnight and filtered. The resin was washed with ethyl acetate (10×30 mL). The combined organic layers were evaporated under vacuum. The residue was purified by ISCO (40 g column, MeOH/CH$_2$Cl$_2$ gradient from 0% to 5% in 50 min) to give dimethyl 3-((4-(morpholinomethyl)thiazol-2-yl)methoxy)phthalate (800 mg, 70% yield).

Step 2: The mixture of dimethyl 3-((4-(morpholinomethyl)thiazol-2-yl)methoxy)phthalate (320 mg, 0.787 mmol) and sodium hydroxide (10 ml, 30.0 mmol) in ethanol (20 ml) was heated to reflux for 1 hour. The reaction mixture was evaporated to dryness under vacuum, water (20 mL) was added, the mixture was extracted with ethyl acetate (2×10 mL), the aqueous layer was separated and acidified with HCl (3N, 15 mL), then evaporated under vacuum to dryness. The crude was used for next step without further purification.

Step 3: The mixture of 3-((4-(morpholinomethyl)thiazol-2-yl)methoxy)phthalic acid (298 mg, 0.787 mmol) and 3-aminopiperidine-2,6-dione hydrochloride (155 mg, 0.944 mmol) in pyridine (20 mL) was heated to reflux overnight. Pyridine was evaporated to dryness under vacuum, the residue was partitioned between saturated sodium bicarbonate (20 mL) and ethyl acetate (50 mL), the organic layer was separated, washed with brine, dried over magnesium sulfate, the solvent was evaporated and the product was purified by prep HPLC (gradient condition: 0-20% acetonitrile in water, 0.1% formic acid in 15 min) to give 2-(2,6-dioxopiperidin-3-yl)-4-((4-(morpholinomethyl)thiazol-2-yl)methoxy)isoindoline-1,3-dione (39 mg, 11% yield); mp: 210-212° C.; $^1$H NMR (DMSO-d$_6$) δ 1.92-2.14 (m, 1H, CHH), 2.42 (d, J=4.2 Hz, 5H, CHH, CH$_2$, CH$_2$), 2.55-2.65 (m, 1H, CHH), 2.77-3.02 (m, 1H, CHH), 3.49-3.58 (m, 4H, CH$_2$, CH$_2$), 3.60 (s, 2H, CH$_2$), 4.95-5.22 (m, 1H, CH), 5.66 (s, 2H, CH$_2$), 7.44-7.58 (m, 2H, Ar), 7.65 (d, J=8.5 Hz, 1H, Ar), 7.83 (d, J=7.7 Hz, 1H, Ar), 11.11 (s, 1H, NH); $^{13}$C NMR (DMSO-d$_6$) δ 21.93, 30.90, 48.78, 52.99, 57.52, 66.11, 67.56, 116.18, 116.82, 118.28, 120.45, 133.26, 136.97, 152.88, 154.60, 164.44, 165.07, 166.64, 169.84, 172.72; HPLC: Waters Xterra C-18, 3.9×150 mm, 5 μm, 1 mL/min, 240 nm, 25/75 CH$_3$CN/0.1% HCOONH$_4$ t$_R$=4.34 (99.30%); Anal. Calcd for C$_{23}$H$_{24}$N$_4$O$_8$S C, 53.48; H, 4.68; N, 10.85; Found: C, 49.86; H, 4.42; N, 10.50.

5.71 3-(4-((1-Methyl-5-(Morpholinomethyl)-1H-Pyrazol-3-yl)Methoxy)-1-Oxoisoindolin-2-yl)Piperidine-2,6-Dione

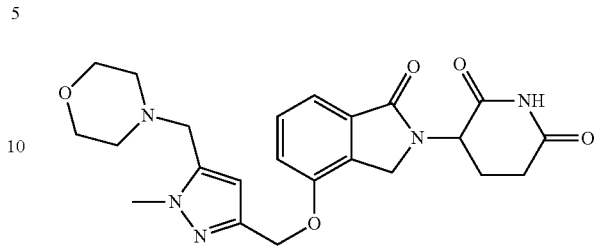

Step 1: A 250 mL round bottle flask was charged with methyl 1,5-dimethyl-1H-pyrazole-3-carboxylate (2 g, 12.97 mmol), NBS (2.309 g, 12.97 mmol), AIBN (0.213 g, 1.297 mmol) as well as CCl4 (40 ml, 415 mmol). The mixture was refluxed under nitrogen overnight. The reaction mixture was cooled down, the solid was filtered off, the filtrate was evaporated to dryness, the residue was purified by ISCO (120 g column, ethyl acetate/hexanes gradient from 0% to 30% in 50 min, 30% 30 min) to give methyl 5-(bromomethyl)-1-methyl-1H-pyrazole-3-carboxylate (500 mg, 17% yield); $^1$H NMR (CHLOROFORM-d) δ 3.93 (s, 3H, CH$_3$), 3.99 (s, 3H, CH$_3$), 4.47 (s, 2H, CH$_2$), 6.83 (s, 1H, Ar).

Step 2: To a solution of methyl 5-(bromomethyl)-1-methyl-1H-pyrazole-3-carboxylate (500 mg, 2.145 mmol) in acetonitrile (30 mL) were added morpholine (0.280 ml, 3.22 mmol) and triethyl amine (0.449 ml, 3.22 mmol). The mixture was stirred at room temperature for 7 hours. The solvent was evaporated to dryness, the residue was partitioned between ethyl acetate (50 mL) and aqueous saturated sodium bicarbonate (20 mL), the organic layer was washed with brine, dried over magnesium sulfate, the solvent was evaporated to give methyl 1-methyl-5-(morpholinomethyl)-1H-pyrazole-3-carboxylate (450 mg, 88% yield); $^1$H NMR (CHLOROFORM-d) δ 2.45 (br. s., 4H, CH$_2$, CH$_2$), 3.52 (br. s., 2H, CH$_2$), 3.70 (br. s., 4H, CH$_2$, CH$_2$), 3.93 (s, 3H, CH$_3$), 4.00 (s, 3H, CH$_3$), 6.54-6.87 (m, 1H, Ar).

Step 3: To the mixture of methyl 1-methyl-5-(morpholinomethyl)-1H-pyrazole-3-carboxylate (450 mg, 1.881 mmol) in THF (15 mL) was added Dibal-H (5.64 mL, 5.64 mmol) at 0° C. The formed mixture was stirred at room temperature overnight. The solvent was evaporated under vacuum, the residue was partitioned between Rochelle's salt (1.0M, 10 ml) and ethyl acetate (50 ml), the organic phase was separated and the aqueous phase was extracted with ethyl acetate (3×20 ml). The combined organic layers were washed with saturated aqueous sodium bicarbonate (5 mL) and brine, dried (MgSO$_4$), and concentrated to give (1-methyl-5-(morpholinomethyl)-1H-pyrazol-3-yl)methanol (300 mg, 76% yield); $^1$H NMR (CHLOROFORM-d) δ 2.47 (br. s., 4H, CH$_2$, CH$_2$), 3.52 (br. s., 2H, CH$_2$), 3.72 (d, J=2.1 Hz, 4H, CH$_2$, CH$_2$), 3.90 (s, 3H, CH$_3$), 4.65 (s, 2H, CH$_2$), 6.17 (br. s., 1H, Ar).

Step 4: Polymer-supported triphenylphosphine (1.6 mmol/g, 1.78 g, 2.84 mmol) was added to a stirred suspension of methyl 5-amino-4-(4-hydroxy-1-oxoisoindolin-2-yl)-5-oxopentanoate (415 mg, 1.420 mmol) in THF (30 mL) at 0° C., followed by DIAD (574 mg, 2.84 mmol), after stirring for 10 min, the solution of (1-methyl-5-(morpholinomethyl)-1H-pyrazol-3-yl)methanol (300 mg, 1.420 mmol) in THF (10 mL) was added, the mixture was stirred at room temperature overnight. The resin was filtered and washed with ethyl acetate (10×30 mL). The combined filtrate was evaporated to dryness, the residue was purified by ISCO (40 g column, MeOH in DCM gradient from 0-5% in 40 min) to give methyl 5-amino-4-(4-((1-methyl-5-(morpholinomethyl)-1H-pyrazol-3-yl)methoxy)-1-oxoisoindolin-2-yl)-5-oxopentanoate (270 mg, 39% yield); $^1$H NMR (DMSO-d$_6$) δ 1.92-2.30 (m, 4H, CH$_2$, CH$_2$), 2.30-2.42 (m, 4H, CH$_2$, CH$_2$), 3.49 (s, 5H, CH$_2$, CH$_3$), 3.52-3.63 (m, 4H, CH$_2$, CH$_2$), 3.80 (s, 3H, CH$_3$), 4.25-4.57 (m, 2H, CH$_2$), 4.25-4.57 (m, 2H, CH$_2$), 4.71 (dd, J=4.7, 10.2 Hz, 1H, CH), 5.09 (s, 2H, CH$_2$), 5.02-5.19 (m, 2H, CH$_2$), 6.27 (s, 1H, Ar), 7.18 (s, 1H, NHH), 7.28 (d, J=7.2 Hz, 1H, Ar), 7.32-7.40 (m, 1H, Ar), 7.40-7.51 (m, 1H, Ar), 7.57 (s, 1H, NHH).

Step 5: To a solution of methyl 5-amino-4-(4-((1-methyl-5-(morpholinomethyl)-1H-pyrazol-3-yl)methoxy)-1-oxoisoindolin-2-yl)-5-oxopentanoate (250 mg, 0.515 mmol) in THF was added potassium tert-butoxide (63.6 mg, 0.566 mmol) at 0° C., the formed mixture was stirred at room temperature for 1 hour. The reaction was quenched by adding aqueous HCl (1N, 1.5 mL). The solvent was removed under vacuum, the residue was partitioned between saturated sodium bicarbonate (5 mL) and ethyl acetate (30 mL), the organic layer was separated and washed with brine, dried over magnesium sulfate and filtered, the filtrate was evaporated to dryness, the solid was reslurried with ether (10 mL) and filtered to give 3-(4-((1-methyl-5-(morpholinomethyl)-1H-pyrazol-3-yl)methoxy)-1-oxoisoindolin-2-yl)piperidine-2,6-dione (130 mg, 56% yield); mp: 125-127° C.; $^1$H NMR (DMSO-d$_6$) δ 1.99 (d, 1H, CHH), 2.35 (d, J=4.0 Hz, 4H, CH$_2$, CH$_2$), 2.46 (br. s., 1H, CHH), 2.52-2.65 (m, 1H, CHH), 2.82-3.02 (m, 1H, CHH), 3.49 (s, 2H, CH$_2$), 3.51-3.62 (m, 4H, CH$_2$, CH$_2$), 3.80 (s, 3H, CH$_3$), 4.12-4.43 (m, 2H, CH$_2$), 5.03-5.17 (m, 3H, CH$_2$, CH), 6.26 (s, 1H, Ar), 7.31 (d, J=7.4 Hz, 1H, Ar), 7.35-7.43 (m, 1H, Ar), 7.43-7.55 (m, 1H, Ar), 10.97 (s, 1H, NH); $^{13}$C NMR (DMSO-d$_6$) δ 22.31, 30.38, 31.18, 36.41, 45.07, 51.55, 52.23, 52.93, 64.00, 66.08, 106.66, 115.07, 115.18, 129.74, 129.89, 133.24, 139.35, 145.27, 153.46, 167.97, 170.96, 172.81; HPLC: Waters Xterra C-18, 3.9×150 mm, 5 μm, 1 mL/min, 240 nm, 25/75 CH$_3$CN/0.1% HCOONH$_4$ t$_R$=3.31 (97.56%); Anal. Calcd for C$_{23}$H$_{27}$N$_5$O$_5$+0.4 EtOAc C, 60.45; H, 6.23; N, 14.33; Found: C, 60.10; H, 6.04; N, 14.70.

5.72 4-((4-((7,8-Dihydro-1,6-Naphthyridin-6(5H)-yl)Methyl)Benzyl)Oxy)-2-(2,6-Dioxopiperidin-3-yl)Isoindoline-1,3-Dione

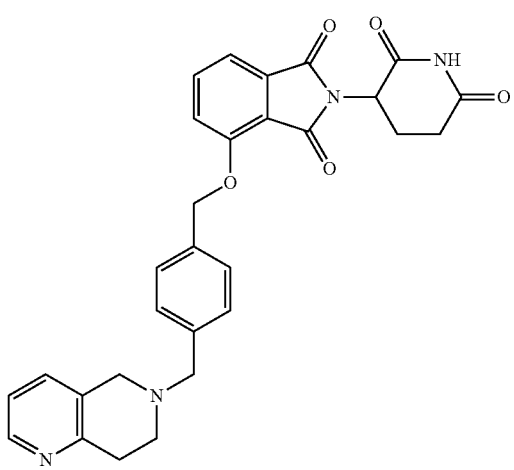 [SMILES: O=C1CCC(N2C(=O)c3cccc(OCc4ccc(CN5CCc6ncccc6C5)cc4)c3C2=O)C(=O)N1]

To a mixture of 4-(4-(bromomethyl)benzyloxy)-2-(2,6-dioxopiperidin-3-yl)isoindoline-1,3-dione (250 mg, 0.547 mmol) and 5,6,7,8-tetrahydro-1,6-naphthyridine (81 mg, 0.601 mmol) in dry MeCN (10 mL), was added DIEA (0.334 mL, 1.914 mmol). The resulting suspension was stirred at room temperature for 17 h. The reaction mixture was warmed to 80° C. with vial cap removed. Most of the solids dissolved and the mixture was concentrated to ~½ original volume. After ~2.5 h, the mixture was allowed to cool to room temperature with gentle stirring. A thick slurry formed which was aged at 4° C. overnight. The slurry was treated with DIEA (250 μL) and the mixture was stirred at room temperature for 30 min. The slurry was then filtered on a medium fritted funnel with suction and the cake was washed with water (~30 mL). The collected solid was suction dried and then dried further in vacuum oven at 50° C. for 6 h to give 4-((4-((7,8-dihydro-1,6-naphthyridin-6(5H)-yl)methyl)benzyl)oxy)-2-(2,6-dioxopiperidin-3-yl)isoindoline-1,3-dione as an off-white solid (275 mg, 99%): HPLC: Waters Symmetry C$_{18}$, 5 μm, 3.9×150 mm, 1 ml/min, 240 nm, 15/85 CH$_3$CN/0.1% H$_3$PO$_4$, 5.08 min (99.9%); mp: 165-167° C.; $^1$H NMR (DMSO-d$_6$) δ 1.93-2.15 (m, 1H, CHH), 2.38-2.65 (m, 2H, CHH, CHH), 2.73-3.01 (m, 5H, CH$_2$, CH$_2$, CHH), 3.58 (s, 2H, CH$_2$), 3.70 (s, 2H, CH$_2$), 5.09 (dd, J=5.4, 12.7 Hz, 1H, CH), 5.37 (s, 2H, CH$_2$O), 7.12 (dd, J=4.7, 7.7 Hz, 1H, Ar), 7.34-7.54 (m, 6H, Ar), 7.61 (d, J=8.3 Hz, 1H, Ar), 7.83 (dd, J=7.4, 8.5 Hz, 1H, Ar), 8.33 (dd, J=1.7, 4.7 Hz, 1H, Ar), 11.11 (s, 1H, NH; $^{13}$C NMR (DMSO-d$_6$) δ 21.95, 30.90, 31.89, 48.73, 50.02, 54.26, 61.13, 69.95, 115.50, 116.58, 120.19, 120.95, 127.36, 128.84, 129.81, 133.26, 134.17, 134.87, 136.99, 138.05, 147.15, 154.38, 155.53, 165.29, 166.75, 169.87, 172.72; LCMS: MH=511; Anal Calcd for C$_{29}$H$_{26}$N$_4$O$_5$+0.6 H$_2$O: C, 66.81; H, 5.26; N, 10.57; Found: C, 66.75; H, 5.28; N, 10.84.

5.73 3-{1-Oxo-4-[4-(4-Phenyl-Imidazol-1-ylmethyl)-Benzyloxy]-1,3-Dihydro-Isoindol-2-yl}-Piperidine-2,6-Dione

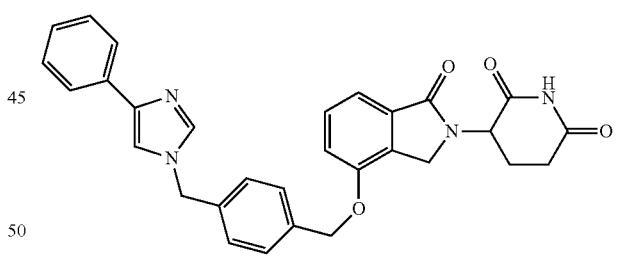

To the stirred solution of 4-phenyl-1H-imidazole (179 mg, 1.2 mmol) in Acetonitrile (15 mL) was added 3-(4-(4-(bromomethyl)benzyloxy)-1-oxoisoindolin-2-yl)piperidine-2,6-dione (500 mg, 1.1 mmol) and DIPEA (0.30 ml, 1.7 mmol) at room temperature. The reaction mixture was stirred at room temperature for 19 hrs and heated at 40° C. for 7 hrs before it was added by EtOAc (60 mL), water (15 mL) and brine (15 mL). Then acetonitrile (20 mL) was added to dissolve solid. The resulting solution was extracted and organic layer was concentrated under vacuo. The residue was purified by ISCO to give 3-{1-Oxo-4-[4-(4-phenyl-imidazol-1-ylmethyl)-benzyloxy]-1,3-dihydro-isoindol-2-yl}-piperidine-2,6-dione as a white solid (190 mg, 33% yield). ROESY confirmed the isomeric structure of the product. HPLC: Waters Symmetry C-18, 3.9×150 mm, 5

μm, 1 mL/min, 240 nm, 25/75, (CH$_3$CN/0.1% H$_3$PO$_4$), 4.84 min (99.9%); mp: 246-248° C.; $^1$H NMR (DMSO-d$_6$) δ 1.99 (br. s., 1H, CHH), 2.33-2.47 (m, 1H, CHH), 2.53-2.60 (m, 1H, CHH), 2.81-2.99 (m, 1H, CHH), 4.23 (d, J=17.6 Hz, 1H, CHH), 4.39 (d, J=17.6 Hz, 1H, CHH), 5.09 (dd, J=5.0, 13.1 Hz, 1H, CHH), 5.23 (s, 4H, CH$_2$, CH$_2$), 7.12-7.23 (m, 1H, Ar), 7.23-7.39 (m, 6H, Ar), 7.39-7.54 (m, 3H, Ar), 7.68 (d, J=1.3 Hz, 1H, imdazole H), 7.70-7.78 (m, 2H, Ar), 7.83 (d, J=1.3 Hz, 1H, imdazole H), 10.95 (s, 1H, NH); $^{13}$C NMR (DMSO-d$_6$) δ 22.30, 31.15, 45.04, 49.45, 51.53, 69.17, 114.90, 115.23, 115.79, 124.11, 126.17, 127.63, 128.12, 128.40, 129.78, 129.93, 133.28, 134.44, 136.17, 137.45, 137.94, 140.90, 153.38, 167.96, 170.93, 172.80; LCMS MH=507; Anal. Calcd for C$_{30}$H$_{26}$N$_4$O$_4$+0.1H$_2$O: C, 70.88; H, 5.19; N, 11.00; Found: C, 70.66; H, 4.87; N, 10.83.

5.74 3-(4-((3-((4-Methylpiperidin-1-yl)Methyl)Isoxazol-5-yl)Methoxy)-1-Oxoisoindolin-2-yl)Piperidine-2,6-Dione

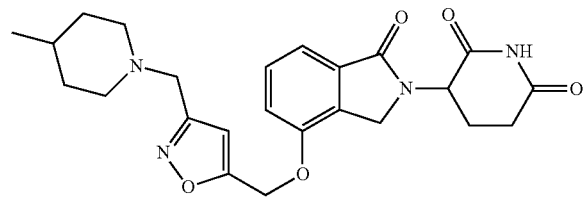 [SMILES: CC1CCN(Cc2cc(COc3cccc4c3CN(C3CCC(=O)NC3=O)C4=O)on2)CC1]

A mixture of (5-((2-(2,6-dioxopiperidin-3-yl)-1-oxoisoindolin-4-yloxy)methyl)isoxazol-3-yl)methyl methanesulfonate (0.25 g, 0.556 mmol) in acetonitrile (10 mL) was cooled to 0° C. 4-Methylpiperidine (0.066 g, 0.668 mmol) and TEA (0.073 g, 0.719 mmol) were added, the ice bath was removed, and the mixture stirred for 16 h. The mixture was partitioned between EtOAc (100 mL) and water (100 mL), and the organic phase was washed with water (100 mL). Then, the organic phase was extracted with 1% aq. HCl (100 mL), and this extract was made basic with 5% aq. Na$_2$CO$_3$ (50 mL) and extracted into EtOAc (2×75 mL). The combined organic extracts were washed with water (100 mL), dried (MgSO$_4$), and evaporated, providing 180 mg (72%), as a white solid; mp 168-170° C. HPLC: Waters Symmetry C-18, 3.9×150 mm, 5 μm, 1 mL/min, 240 nm, 10/90 gradient to 90/10 CH$_3$CN/0.1% H$_3$PO$_4$ in 10 min: 4.95 (97.98%). $^1$H NMR (DMSO-d$_6$) δ 0.87 (d, J=6.4 Hz, 3H), 1.01-1.19 (m, 2H), 1.21-1.38 (m, 1H), 1.49-1.65 (m, 2H), 1.88-2.04 (m, 3H), 2.36-2.47 (m, 1H), 2.54-2.62 (m, 1H), 2.68-2.80 (m, 2H), 2.83-2.99 (m, 1H), 3.50 (s, 2H), 4.24 (d, J=17.6 Hz, 1H), 4.41 (d, J=17.6 Hz, 1H), 5.11 (dd, J=5.1, 13.2 Hz, 1H), 5.42 (s, 2H), 6.60 (s, 1H), 7.33-7.44 (m, 2H), 7.46-7.57 (m, 1H), 10.97 (s, 1H). $^{13}$C NMR (DMSO-d$_6$) δ 21.73, 22.33, 29.97, 31.20, 33.79, 45.05, 51.61, 52.64, 53.14, 60.72, 104.53, 115.10, 115.97, 129.85, 129.98, 133.51, 152.67; 161.56, 167.06, 167.82, 170.94, 172.82. Anal. Calcd for C$_{24}$H$_{28}$N$_4$O$_5$+H$_2$O: C, 61.26%; H, 6.43%; N, 11.91%; Found: C, 61.41%; H, 6.33%; N, 12.10%.

5.75 3-(4-((3-(Morpholinomethyl)Imidazo[1,2-A]Pyridin-6-yl)Methoxy)-1-Oxoisoindolin-2-yl)Piperidine-2,6-Dione

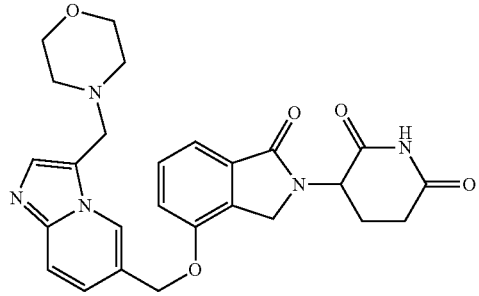 [SMILES: O=C1CCC(N2Cc3c(OCc4ccc5ncc(CN6CCOCC6)n5c4)cccc3C2=O)C(=O)N1]

Step 1: A mixture of ethyl 6-aminonictinate (8.3 g, 49.9 mmol) and chloroacetaldehyde (50% in water, 15.7 g, 99.9 mmol) in CH$_3$CN (200 mL) was refluxed for 17 h. The reaction mixture was cooled and concentrated. Residue was stirred with CH$_2$Cl$_2$ (100 mL) and basified with sat. NaHCO$_3$ (120 mL). Aq. Layer was extracted with CH$_2$Cl$_2$ (2×40 mL) and combined CH$_2$Cl$_2$ solution was washed with water (50 mL), brine (50 mL) and dried. Solvent was removed and residue was purified by chromatography (SiO$_2$, CH$_2$Cl$_2$ for 5 min then to 3% CH$_3$OH/CH$_2$Cl$_2$ over 5 min and hold for 15 min then to 5% over 5 min and hold for 15 min) to give ethyl imidazo[1,2-a]pyridine-6-carboxylate (8.3 g, 87%): $^1$H NMR (CDCl$_3$) δ 1.42 (t, J=6 Hz, 3H), 4.38-4.45 (q, J=6 Hz, 2H), 7.61-7.75 (m, 4H), 8.93 (s, 1H); $^{13}$C NMR (CDCl$_3$) δ 14.33, 61.48, 113.49, 1 16.89, 117.13, 124.09, 130.02, 135.33, 145.93, 164.87.

Step 2: A mixture of ethyl imidazo[1,2-a]pyridine-6-carboxylate (2.9 g, 15.4 mmon), 37% aq. formaldehyde (1.3 g, 15.4 mmol) and morpholine (1.4 g, 15.4 mmol) in glacial acetic acid (5 mL) was warmed at 50° C. for 3 h then stirred at room temperature overnight. The reaction mixture was diluted with CH$_2$Cl$_2$ (40 mL) and basified with 2N NaOH to pH=8. Aq. layer was extracted with CH$_2$Cl$_2$ (2×40 mL) and combined CH$_2$Cl$_2$ solution was washed with brine (40 mL) and dried. Solvent was removed to give ethyl 3-(morpholinomethyl)imidazo[1,2-a]pyridine-6-carboxylate (4.1 g, 92%): $^1$H NMR (CDCl$_3$) δ 1.36 (t, J=6 Hz, 3H), 2.37-2.40 (m, 4H), 3.54-3.57 (m, 4H), 3.92 (s, 2H), 4.33-4.40 (q, J=6 Hz, 2H), 7.63-7.65 (m, 3H), 9.18-9.19 (d, J=3 Hz, 1H); $^{13}$C NMR (CDCl$_3$) δ 14.07, 51.06, 52.81, 60.99, 66.18, 115.12, 116.58, 121.62, 122.95, 129.67, 134.98, 145.71, 164.47.

Step 3: A solution of ethyl 3-(morpholinomethyl)imidazo[1,2-a]pyridine-6-carboxylate (4.1 g, 14.2 mmol) in THF (50 mL) was cooled in ice bath. A solution of lithium tri-tert-butoxyaluminum hydride/THF (1M, 29 mL, 29 mmol) was added slowly. After stirred for 5 min, ice bath was removed and mixture was stirred at room temperature for 2 h. The reaction mixture was cooled and quenched with water (1.5 mL), 2N NaOH (1.5 mL) and water (4.5 mL). The mixture was filtered and washed filter with CH$_2$Cl$_2$ (100 mL). Filtrate was washed sat. NaHCO$_3$ (40 mL), brine (40 mL) and dried. Solvent was removed and residue was purified by chromatography (SiO$_2$, 3% CH$_3$OH/CH$_2$Cl$_2$ for 10 min then to 10% over 10 min and hold for 30 min) to give (3-(morpholinomethyl)imidazo[1,2-a]pyridine-6-yl)methanol (1.5 g, 42%): $^1$H NMR (CDCl$_3$) δ 2.42-2.45 (m, 4H), 3.64-3.67 (m, 4H), 3.78 (s, 2H), 4.75 (s, 2H), 7.18-7.22 (dd, J=3 and 9 Hz, 1H), 7.48 (s, 1H), 7.53-7.56 (d, J=9 Hz, 1H), 8.33 (s, 1H).

Step 4: A mixture of triphenylphosphine-polymer bound (6.2 g, 8.7 mmol) in THF (40 mL) was cooled in ice bath to 3° C. Diisopropylazadicarboxylate (1.5 g, 7.6 mmol) was added slowly at 3-5° C. After stirred at 3° C. for 10 min, a solution of (3-(morpholinomethyl)imidazo[1,2-a]pyridine-6-yl)methanol (1.4 g, 5.8 mmol) and methyl 5-amino-4-(4-hydroxy-1-oxoisoindolin-2-yl)-5-oxopentanoate (1.7 g, 5.8 mmol) in THF (120 mL) was added slowly at 5-8° C. After stirred for 10 min, ice bath was removed and mixture was stirred at room temperature overnight. The reaction mixture was filtered and filtrate was concentrated. Residue was dissolved in $CH_2Cl_2$ (120 mL) and washed with sat. $NaHCO_3$ (40 mL), water (40 mL), brine (40 mL) and dried. Solvent was removed and residue was purified by chromatography ($SiO_2$, $CH_2Cl_2$ for 5 min then to 3% $CH_3OH$/$CH_2Cl_2$ over 5 min and hold for 10 min then to 5% over 5 min and hold for 20 min) to give methyl 5-amino-4-(4-((3-(morpholinomethyl)imidazo[1,2-a]pyridine-6-yl)methoxy)-1-oxoisoindolin-2-yl)-5-oxopentanoate (1.3 g, 43%): $^1$H NMR (CDCl$_3$) δ 2.17-2.18 (m, 1H), 2.37-3.45 (m, 7H), 3.62-3.65 (m, 7H), 3.82 (s, 2H), 4.38-4.43 (d, J=15 Hz, 1H), 4.51-4.57 (d, J=18 Hz, 1H), 4.94-4.96 (m, 1H), 5.18 (s, 2H), 5.68 (b, 1H), 6.51 (b, 1H), 7.13-7.16 (dd, J=6 and 9 Hz, 1H), 7.26-7.28 (m, 1H), 7.42-7.47 (m, 2H), 7.54 (s, 1H), 7.65-7.68 (d, J=9 Hz, 1H), 8.44 (s, 1H); 3C NMR (CDCl$_3$) δ 24.24, 30.45, 45.22, 51.80, 52.61, 53.36, 53.89, 66.93, 68.07, 114.09, 116.25, 118.08, 120.30, 120.59, 123.97, 124.45, 129.92, 130.23, 133.65, 134.44, 146.03, 163.47, 169.14, 171.55, 172.83.

Step 5: A solution of methyl 5-amino-4-(4-((3-(morpholinomethyl)imidazo[1,2-a]pyridin-6-yl)methoxy)-1-oxoisoindolin-2-yl)-5-oxopentanoate (1.2 g, 2.4 mmol) in THF (30 mL) was cooled in dry ice/acetone bath for 15 min. A solution of potassium tert-butoxide/THF (1M, 2.6 mL, 2.6 mmol) was added slowly. The reaction mixture was stirred in −78° C. bath for 1 h then warmed to 0° C. for 1 h. The reaction mixture was quenched with 1N HCl (5 mL) and water (20 mL) was added. The mixture was basified with sat. $NaHCO_3$ to pH=8 and extracted with $CH_2Cl_2$ (3×30 mL). Combined $CH_2Cl_2$ solution was washed with brine (30 mL) and dried. Solvent was removed and residue was purified by chromatography ($SiO_2$, $CH_2Cl_2$ for 5 min then to 3% $CH_3OH/CH_2Cl_2$ over 5 min and hold for 10 min then to 5% over 5 min and hold for 15 min) to give 3-(4-((3-(morpholinomethyl)imidazo[1,2-a]pyridin-6-yl)methoxy)-1-oxoisoindolin-2-yl)piperidine-2,6-dione (0.8 g, 69%): mp 170-172° C.; $^1$H NMR (DMSO-d$_6$) δ 1.96-2.01 (m, 1H), 2.36-2.60 (m, 6H), 2.85-2.93 (m, 1H), 3.33-3.49 (m, 4H), 4.29 (d, J=18 Hz, 1H), 4.40 (d, J=18 Hz, 1H), 5.09-5.15 (dd, J=6 and 12 Hz, 1H), 5.33 (s, 2H), 7.35-7.62 (m, 6H), 8.63 (s, 1H), 10.98 (s, 1H); $^{13}$C NMR (DMSO-d$_6$) δ 22.39, 31.16, 44.98, 51.04, 52.79, 66.07, 67.25, 115.04, 115.44, 116.92, 120.45, 120.58, 124.43, 124.77, 129.83, 133.34, 133.79, 144.80, 153.20, 167.94, 170.93, 172.80; Calcd for $C_{26}H_{27}N_5O_5$+0.2Et$_2$O+ 0.1 $CH_2Cl_2$: C, 63.00; H, 5.74; N, 13.66. Found: C, 62.94; H, 5.98; N, 13.50.

5.76 3-(4-((4-(Morpholinomethyl)Furan-2-yl)Methoxy)-1-Oxoisoindolin-2-yl)Piperidine-2,6-Dione

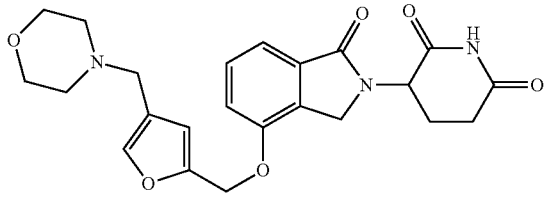

Step 1: Redistilled morpholine (3.81 mL, 43.7 mmol) was dissolved in THF (300 mL) and cooled to −78° C. under nitrogen gas condition. To this solution n-butyllithium (27.3 mL, 43.7 mmol) (1.6 M in hexanes) was added dropwise and the resulting solution was stirred for further 20 min. subsequently furan-3-carbaldehyde (4 g, 41.6 mmol) in THF (8 mL) was slowly added, after another 20 min sec-butyllithium (31.2 mL, 43.7 mmol) (1.4 M in cyclohexane) was added dropwise, the resulting mixture was stirred −78° C. for 2.5 h. Methyl chloroformate (4.33 g, 45.8 mmoL) dissolved in THF (8 mL) was slowly introduced and the reaction mixture was stirred for 45 min at −78° C. and the additional 20 min at room temperature, the solution was poured into ice cold 10% HCl (400 mL, 2.87 M). The layers were separated and the aqueous phase was extracted with ether (4×100 mL), the combined organic layers were washed with brine, dried over magnesium sulfate, filtered, and concentrated under reduced pressure to dryness, the crude was purified by ISCO (330 g column, EtOAc/hexanes gradient from 0% to 20% in 60 min, 20% for 20 min) to give methyl 4-formylfuran-2-carboxylate (1.5 g, 23% yield); $^1$H NMR (CHLOROFORM-d) δ 3.89 (s, 3H, CH$_3$), 7.09-7.30 (m, 2H, Ar), 9.75 (s, 1H, CHO).

Step 2: To a solution of methyl 4-formylfuran-2-carboxylate (800 mg, 5.19 mmol) in dichloromethane (30 mL) was added morpholine (1.357 mL, 15.57 mmol) and acetic acid (1.783 mL, 31.1 mmol). The reaction mixture was stirred for 10 min, sodium triacetoxyborohydride (3300 mg, 15.57 mmol) was added, the mixture was stirred overnight. The reaction mixture was diluted with dichloromethane (50 mL) and washed with water (2×30 mL), saturated sodium bicarbonate (30 mL), brine (30 mL) and dried over magnesium sulfate, after filtration, the solvent was evaporated under vacuum to give methyl 4-(morpholinomethyl)furan-2-carboxylate; $^1$H NMR (CHLOROFORM-d) δ 2.46-2.59 (m, 4H, CH$_2$, CH$_2$), 3.62 (s, 2H, CH$_2$), 3.69-3.79 (m, 4H, CH$_2$, CH$_2$), 3.89 (s, 3H, CH$_3$), 6.37 (d, J=3.2 Hz, 1H, Ar), 7.14 (d, J=3.4 Hz, 1H, Ar).

Step 3: To the solution of methyl 4-(morpholinomethyl)furan-2-carboxylate (1.12 g, 4.97 mmol) in THF (30 mL) was added Dibal-H (14.92 ml, 14.92 mmol) in toluene at 0° C. The formed mixture was stirred at room temperature overnight. A solution of Rochelle's salt (1.0 M, 50 ml) was added, followed by ethyl acetate (50 mL), the resulting suspension was stirred at room temperature, the organic phase was separated and the aqueous phase was extracted with EtOAc (3×40 ml). The combined organic layers were washed with saturated aqueous sodium bicarbonate (5 mL) and brine, dried (MgSO$_4$), and concentrated to give (4-(morpholinomethyl)furan-2-yl)methanol; $^1$H NMR (CHLOROFORM-d) δ 2.43-2.65 (m, 4H, CH$_2$, CH$_2$), 3.57 (s, 2H, CH$_2$), 3.68-3.85 (m, 4H, CH$_2$, CH$_2$), 4.61 (s, 2H, CH$_2$), 6.17-6.30 (m, 2H, Ar).

Step 4: Polymer-supported triphenylphosphine (1.6 mmol/g, 1.98 g, 3.16 mmol) was added to a stirred suspension of methyl 5-amino-4-(4-hydroxy-1-oxoisoindolin-2-yl)-5-oxopentanoate (615 mg, 2.104 mmol) in THF (50 mL) at 0° C., followed by DIAD (638 mg, 3.16 mmol), after stirring for 10 minutes, (4-(morpholinomethyl)furan-2-yl)methanol (415 mg, 2.104 mmol) in THF (10 mL) was added, the mixture was stirred at room temperature overnight. The mixture was filtered, the resin was washed with ethyl acetate (10×20 mL), methanol (5×10 mL), the combined organic phase was evaporated to dryness, the crude was purified by ISCO (80 g column, MeOH in DCM gradient from 0-5% in 45 min) to give methyl 5-amino-4-(4-((4-(morpholinomethyl)furan-2-yl)methoxy)-1-oxoisoindolin-2-yl)-5-oxopentanoate (440 mg, 44% yield); $^1$H NMR (DMSO-$d_6$) δ 2.24 (d, J=6.6 Hz, 4H, CH$_2$, CH$_2$), 2.32-2.40 (m, 4H, CH$_2$), 3.46-3.52 (m, 5H, CH$_2$, CH$_3$), 3.52-3.57 (m, 4H, CH$_2$, CH$_2$), 4.26-4.55 (m, 2H, CH$_2$), 4.71 (d, J=5.5 Hz, 1H, CHH), 5.18 (s, 2H, CH$_2$), 6.29 (d, J=3.0 Hz, 1H, Ar), 6.56 (d, J=3.2 Hz, 1H, Ar), 7.18 (s, 1H, NHH), 7.30 (d, J=7.4 Hz, 1H, Ar), 7.35-7.42 (m, 1H, Ar), 7.46 (d, J=7.7 Hz, 1H, Ar), 7.57 (s, 1H, NHH).

Step 5: To a solution of methyl 5-amino-4-(4-((4-(morpholinomethyl)furan-2-yl)methoxy)-1-oxoisoindolin-2-yl)-5-oxopentanoate (440 mg, 0.933 mmol) in THF (20 mL) was added potassium tert-butoxide (126 mg, 1.120 mmol) at 0° C., the mixture was stirred at 0° C. for 1 hour, additional potassium tertbutoxide (20 mg, 0.27 mmol) was added, the mixture was stirred at room temperature for 1 hour. The reaction was quenched by adding aqueous HCl (1N, 3 mL). The solvent was removed under vacuum, the residue was partitioned between saturated sodium bicarbonate (10 mL) and ethyl acetate (50 mL), the organic layer was separated and washed with brine, dried over magnesium sulfate and filtered, the filtrate was evaporated to dryness to give a solid, the solid was reslurried in acetonitrile (4 mL) and filtered to give 3-(4-((4-(morpholinomethyl)furan-2-yl)methoxy)-1-oxoisoindolin-2-yl)piperidine-2,6-dione (160 mg, 39% yield); mp: 168-170° C.; $^1$H NMR (DMSO-$d_6$) δ 1.85-2.05 (m, 1H, CHH), 2.17-2.50 (m, 5H, CH$_2$, CH$_2$, CHH), 2.54-2.65 (m, 1H, CHH), 2.88 (d, J=12.3 Hz, 1H, CHH), 3.32 (br. s., 2H, CH$_2$), 3.56 (br. s., 4H, CH$_2$, CH$_2$), 4.13-4.42 (m, 2H, CH$_2$), 5.10 (dd, J=5.1, 13.2 Hz, 1H, CHH), 5.20 (s, 2H, CH$_2$), 6.09-6.52 (m, 1H, Ar), 6.58 (br. s., 1H, Ar), 7.34 (d, J=7.2 Hz, 1H, Ar), 7.38-7.46 (m, 1H, Ar), 7.46-7.56 (m, 1H, Ar), 10.97 (s, 1H, NH); $^{13}$C NMR (DMSO-$d_6$) δ 22.31, 31.18, 45.06, 51.55, 52.44, 54.08, 62.16, 65.81, 109.72, 111.65, 115.42, 115.54, 129.73, 129.99, 133.34, 149.29, 152.31, 152.98, 167.90, 170.95, 172.81; HPLC: Waters Xterra C-18, 3.9×150 mm, 5 μm, 1 mL/min, 240 nm, 30/70 CH$_3$CN/0.1% HCOONH$_4$ $t_R$=3.13 (96.19%); Anal. Calcd for C$_{23}$H$_{25}$N$_3$O$_6$+0.5 H$_2$O C, 61.60; H, 5.84; N, 9.37; Found: C, 61.28; H, 5.79; N, 9.31.

5.77 3-{4-[4-(1-Isopropyl-Piperidin-4-ylmethyl)-Benzyloxy]-1-Oxo-1,3-Dihydro-Isoindol-2-yl}-Piperidine-2,6-Dione

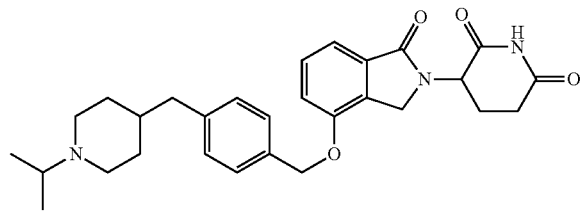 [SMILES: CC(C)N1CCC(Cc2ccc(COc3cccc4c3CN(C3CCC(=O)NC3=O)C4=O)cc2)CC1]

Step 1: Preparation of 4-{4-[2-(1-Carbamoyl-3-methoxycarbonyl-propyl)-1-oxo-2,3-dihydro-1H-isoindol-4-yloxymethyl]-benzyl}-piperidine-1-carboxylic acid tert-butyl ester Triphenyl phosphene (polymer-supported, 1.6 mmol/g, 3.3 g) was added to a stirred white suspension of methyl 5-amino-4-(4-hydroxy-1-oxoisoindolin-2-yl)-5-oxopentanoate (2.444 g, 8.36 mmol) in THF (100 ml) at 0° C. After ten minutes, diisopropyl diazene-1,2-dicarboxylate (2.470 ml, 12.54 mmol) was added and stirred for 40 minutes and then tert-butyl 4-(4-(hydroxymethyl)benzyl)piperidine-1-carboxylate (3.32 g, 10.87 mmol) in THF (20 ml) was added. The mixture was stirred at 0° C. and warmed up to room temperature overnight. The suspension was filtered, rinsed with MeOH (2×20 ml), CH$_2$Cl$_2$ (2×30 ml), and the filtrate was evaporated to give an oil, which was dissolved in CH$_2$Cl$_2$ (80 ml), washed with Sat NaHCO$_3$ (50 ml), concentrated and then purified by silica gel column to give 4-{4-[2-(1-Carbamoyl-3-methoxycarbonyl-propyl)-1-oxo-2,3-dihydro-1H-isoindol-4-yloxymethyl]-benzyl}-piperidine-1-carboxylic acid tert-butyl ester as a foamy oil (2.2 g, 45% yield). It was used in the next step without further purification.

Step 2: Preparation of 4-Carbamoyl-4-[1-oxo-4-(4-piperidin-4-ylmethyl-benzyloxy)-1,3-dihydro-isoindol-2-yl]-butyric acid methyl ester To a stirred solution of tert-butyl 4-(4-((2-(1-amino-5-methoxy-1,5-dioxopentan-2-yl)-1-oxoisoindolin-4-yloxy)methyl)benzyl)piperidine-1-carboxylate (2.2 g, 3.80 mmol) in CH$_2$Cl$_2$ (10 ml) at room temperature was added hydrogen chloride (2 M in ether) (10 ml, 38.0 mmol). After four hours, the suspension was filtered, rinsed with ether and the resulting yellow solid was dried to give 2.02 g, 111% crude yield (HCl salt). The product was used later in the next step without further purification.

Step 3: Preparation of 4-Carbamoyl-4-{4-[4-(1-isopropyl-piperidin-4-ylmethyl)-benzyloxy]-1-oxo-1,3-dihydro-isoindol-2-yl}-butyric acid methyl ester To a stirred solution of methyl 5-amino-5-oxo-4-(1-oxo-4-(4-(piperidin-4-ylmethyl) benzyloxy) isoindolin-2-yl)pentanoate hydrochloride (1.24 g, 2.403 mmol) in MeOH (15 ml) was added N-ethyl-N-isopropylpropan-2-amine (0.397 ml, 2.403 mmol), propan-2-one (1.252 ml, 16.82 mmol), acetic acid (0.069 ml, 1.201 mmol), and Sodium cyanoborohydride (0.302 g, 4.81 mmol). The mixture was stirred at room temperature overnight. Ice-water (30 ml) was poured into the mixture, a precipitate formed, which was extracted with ethyl acetate (100 ml), washed with saturated sodium bicarbonate (2×40 ml), brine (30 ml), dried and concentrated to a brown foamy oil (1.11 g, 89% crude yield). It was used in the next step without further purification.

Step 4: Preparation of 3-{4-[4-(1-Isopropyl-piperidin-4-ylmethyl)-benzyloxy]-1-oxo-1,3-dihydro-isoindol-2-yl}-piperidine-2,6-dione To a stirred solution of methyl 5-amino-4-(4-(4-((1-isopropylpiperidin-4-yl) methyl) benzyloxy)-1-oxoisoindolin-2-yl)-5-oxopentanoate (1.09 g, 2.090 mmol) in Tetrahydrofuran (12 ml) in an ice bath (0° C.) was added potassium 2-methylpropan-2-olate (0.246 g, 2.194 mmol). The mixture was stirred at 0° C. for 10 minutes. To the mixture was added 1 N HCl (to pH=1) then neutralized with saturated sodium bicarbonate (to pH=7) and extracted with ethyl acetate (3×30 ml), washed with brine (20 ml), dried over sodium sulfate, and concentrated to a foamy solid, which was purified by silica gel column (MeOH/CH$_2$Cl$_2$) to give 3-{4-[4-(1-Isopropyl-piperidin-4-ylmethyl)-benzyloxy]-1-oxo-1,3-dihydro-isoindol-2-yl}-piperidine-2,6-dione as an off-white foamy solid (0.33 g, 32% yield); mp, 182-184° C. HPLC: Waters Symmetry C-18, 3.9×150 mm, 5 μm, 1 mL/min, 240 nm, gradient from 10/90 to 70/30 in 5 min, isocratic at 70/30 for 5 min (CH$_3$CN/0.1% H$_3$PO$_4$), 5.19 min (97.4%). $^1$H NMR (DMSO-$d_6$) δ 0.92 (d, J=6.4 Hz, 6H, CH$_3$, CH$_3$), 1.03-1.22 (m, 2H, CH$_2$), 1.35-1.60 (m, 3H, CH, CH$_2$), 1.90-2.10 (m, 3H, CHH, CH$_2$), 2.34-2.48 (m, 2H, CHH, CH), 2.53-2.57 (m, 1H, CHH), 2.57-2.78 (m, 4H, CH$_2$, CH$_2$), 2.83-3.00 (m, 1H, CHH), 4.19-4.47 (m, 2H, CH$_2$), 5.11 (dd, J=5.1, 13.2 Hz, 1H, NCH), 5.20 (s, 2H, CH$_2$), 7.17 (d, J=8.1 Hz, 2H, Ar), 7.36 (dd, J=7.9, 18.9 Hz, 4H, Ar), 7.44-7.54 (m, 1H, Ar), 10.97 (s, 1H, NH). $^{13}$C NMR (DMSO-$d_6$) δ 17.94, 22.36, 31.21, 32.13, 37.77, 42.14, 45.09, 48.18, 51.56, 53.78, 69.49, 114.95, 115.19, 127.67, 129.05, 129.81, 129.94, 133.29, 133.91, 140.32, 153.54, 168.01, 170.96, 172.83. LC/MS m/e=490. Anal Calcd for $C_{29}H_{35}N_3O_4$ (+0.3$H_2O$): C, 70.36; H, 7.26; N, 8.49. Found: C, 70.18; H, 7.06; N, 8.36.

5.78 3-{4-[4-(1-Methyl-1H-Benzoimidazol-2-ylmethyl)-Benzyloxy]-1-Oxo-1,3-Dihydro-Isoindol-2-yl}-Piperidine-2,6-Dione

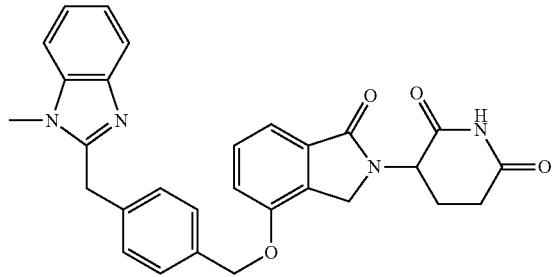 [SMILES: Cn1c(Cc2ccc(COc3cccc4c3CN(C3CCC(=O)NC3=O)C4=O)cc2)nc2ccccc21]

Step 1: (4-Bromomethyl-phenyl)-acetic acid tert-butyl ester The stirred solution of 2-(4-(bromomethyl)phenyl) acetic acid (2.6 g, 11.35 mmol) in thionyl chloride (20 mL, 274 mmol) was heated to reflux for 2.5 hrs. The reaction mixture was concentrated under vacuo to give off white solid. The white solid was added to the stirred solution of 2-methylpropan-2-ol (20 ml, 213 mmol) in DCM (2 mL) under ice/water bath. And the mixture was stirred under ice/water bath for 2 hrs and at room temperature for 18 hrs. The reaction mixture was added to $CH_2Cl_2$ (40 mL). The organic phase was washed successively with $H_2O$ (20 mL), $NaHCO_3$ (sat, aq, 20 mL), and brine (25 mL) and dried over $MgSO_4$. Organic layer was concentrated under vacuo to give (4-bromo methyl-phenyl)-acetic acid tert-butyl ester as a light yellow liquid (2.4 g, 74% crude yield). 1H NMR (DMSO-d6): 1.39 (s, 9H, tBu), 3.54 (s, 2H, $CH_2CO2$), 4.69 (s, 2H, $CH_2Br$), 7.23, 7.39 (m, 4H, due to impurities).

Step 2: 4-[4-(4-tert-Butoxycarbonylmethyl-benzyloxy)-1-oxo-1,3-dihydro-isoindol-2-yl]-4-carbamoyl-butyric acid methyl ester To the stirred mixture of methyl 5-amino-4-(4-hydroxy-1-oxoisoindolin-2-yl)-5-oxopentanoate (1.5 g, 5.13 mmol) and tert-butyl 2-(4-(bromomethyl)phenyl) acetate (2.2 g, 7.7 mmol) in Acetonitrile (30 mL) was added POTASSIUM CARBONATE (1.42 g, 10.3 mmol). The resulting reaction mixture was stirred at 50° C. for 27 hrs and in between tert-butyl 2-(4-(bromomethyl) phenyl) acetate (800 mg, 2.9 mmol) was added in 2 portions. The reaction mixture was filtered and the light brown solid was washed with acetonitrile (2×20 mL). The filtrate was concentrated under vacuo and the residue was purified by ISCO 4-[4-(4-tert-Butoxycarbonylmethyl-benzyloxy)-1-oxo-1,3-dihydro-isoindol-2-yl]-4-carbamoyl-butyric acid methyl ester as a light yellow sticky solid (2.1 g, 82% crude yield) LCMS MH=497.

Step 3: 4-Carbamoyl-4-[4-(4-carboxymethyl-benzyloxy)-1-oxo-1,3-dihydro-isoindol-2-yl]-butyric acid methyl ester To the stirred solution of methyl 5-amino-4-(4-(4-(2-tert-butoxy-2-oxoethyl)benzyloxy)-1-oxoisoindolin-2-yl)-5-oxopentanoate (2.1 g, 4.2 mmol) in DCM (20 mL) at room temperature was added by WATER (0.38 ml, 21.1 mmol) followed by the addition of TFA (1.63 ml, 21.1 mmol) slowly. The resulting solution was stirred at room temperature for 5 hrs and in between TFA (3.2 mL) and water (0.15 mL) were added. The mixture was kept in fridge overnight and the reaction mixture was concentrated under vacuo to give 4-Carbamoyl-4-[4-(4-carboxy methyl-benzyloxy)-1-oxo-1,3-dihydro-isoindol-2-yl]-butyric acid methyl ester as an off white solid (2.3 g, 123% crude yield). $^1$H NMR (DMSO-$d_6$) δ 1.97-2.31 (m, 4H, $CH_2$, $CH_2$), 3.50 (s, 3H, $CH_3$), 3.58 (s, 2H, $CH_2$), 4.41 (d, J=17.8 Hz, 1H, CHH), 4.53 (d, J=17.8 Hz, 1H, CHH), 4.72 (dd, J=4.6, 10.3 Hz, 1H, CHH), 5.23 (s, 2H, $CH_2$), 7.18 (br. s., 1H, NHH), 7.24-7.34 (m, 4H, Ar), 7.40-7.50 (m, 3H, Ar), 7.57 (br. s., 1H, NHH); LCMS MH=441.

Step 4: 4-Carbamoyl-4-{4-[4-(1-methyl-1H-benzoimidazol-2-ylmethyl)-benzyloxy]-1-oxo-1,3-dihydro-isoindol-2-yl}-butyric acid methyl ester The mixture of 2-(4-((2-(1-amino-5-methoxy-1,5-dioxopentan-2-yl)-1-oxoisoindolin-4-yloxy)methyl)phenyl)acetic acid (500 mg, 1.1 mmol) and CDI (166 mg, 1.0 mmol) in THF (3 mL). The mixture was stirred at 50° C. for 25 mins before was added N1-methylbenzene-1,2-diamine (125 mg, 1.022 mmol) in THF (6 mL). The resulting brown solution was stirred at 50° C. for 21 hrs and the reaction mixture was diluted by EtOAc (40 mL) and washed with $NH_4OH$ (aq, 10% wt, 2×20 mL). Organic layer was concentrated under vacuo and the residue was purified by ISCO to give 4-Carbamoyl-4-{4-[4-(1-methyl-1H-benzoimidazol-2-ylmethyl)-benzyloxy]-1-oxo-1,3-dihydro-isoindol-2-yl}-butyric acid methyl ester as a pink solid (185 mg, 31% yield); $^1$H NMR (DMSO-$d_6$) δ 1.96-2.34 (m, 4H, $CH_2$, $CH_2$), 3.49 (s, 3H, $CH_3$), 3.71 (s, 3H, $CH_3$), 4.25-4.58 (m, 4H, CHH, CHH, $CH_2$), 4.65-4.78 (m, 1H, CHH), 5.21 (s, 2H, $CH_2$), 7.09-7.24 (m, J=1.3, 7.4, 7.4, 7.4, 7.4 Hz, 3H, Ar), 7.25-7.37 (m, 4H, Ar, NHH), 7.39-7.51 (m, 4H, Ar, NHH), 7.52-7.62 (m, 2H, Ar); LCMS MH=527.

Step 5: 3-{4-[4-(1-Methyl-1H-benzoimidazol-2-ylmethyl)-benzyloxy]-1-oxo-1,3-dihydro-isoindol-2-yl}-piperidine-2,6-dione To the stirred solution of methyl 5-amino-4-(4-(4-((1-methyl-1H-benzo[d]imidazol-2-yl)methyl)benzyloxy)-1-oxoisoindolin-2-yl)-5-oxopentanoate (660 mg, 1.25 mmol) in Tetrahydrofuran (15 mL) at 0° C. (water/ice bath) was added POTASSIUM TERT-BUTOXIDE (155 mg, 1.4 mmol) in one portion. The resulting mixture was stirred at 0° C. for 1 hr and the reaction mixture was diluted by DCM (100 mL) followed by the addition of HCl (aq, 1N, 5 mL). The mixture was stirred and added by $NaHCO_3$ (aq., sat., 20 mL). The mixture was extracted and aq layer was extracted by DCM (20 mL). Organic layers were combined and washed with brine (2×25 mL). Organic layer was dried by $MgSO_4$ and concentrated down for ISCO purification to give a white solid. The white solid was further purified by be stirred in acetonitrile (5 mL) to give 3-{4-[4-(1-Methyl-1H-benzoimidazol-2-ylmethyl)-benzyloxy]-1-oxo-1,3-dihydro-isoindol-2-yl}-piperidine-2,6-dione as a white solid (328 mg, 34% yield). HPLC: Waters Symmetry C-18, 3.9×150 mm, 5 μm, 1 mL/min, 240 nm, 20/80, ($CH_3CN$/0.1% $H_3PO_4$), 7.80 min (99.2%); Mp: 240-242° C.; $^1$H NMR (DMSO-$d_6$) δ 1.88-2.03 (m, 1H, CHH), 2.35-2.47 (m, 1H, CHH), 2.53-2.64 (m, 1H, CHH), 2.80-2.99 (m, 1H, CHH), 3.71 (s, 3H, $CH_3$), 4.15-4.45 (m, 4H, CHH, CHH, CHH, CHH), 5.09 (dd, J=5.1, 13.2 Hz, 1H, CHH), 5.21 (s, 2H, $CH_2$), 7.10-7.24 (m, J=1.4, 7.4, 7.4, 7.4, 7.4 Hz, 2H, Ar), 7.32 (d, J=7.4 Hz, 4H, Ar), 7.40-7.53 (m, 4H, Ar), 7.53-7.60 (m, 1H, Ar), 10.95 (s, 1H, NH); $^{13}$C NMR (DMSO-$d_6$) δ 22.30, 29.75, 31.16, 32.65, 45.06, 51.53, 69.35, 109.81, 114.91, 115.20, 118.41, 121.24, 121.59, 128.06, 128.84, 129.78, 129.93, 133.27, 134.83, 135.81, 136.74, 142.19, 153.46, 153.59, 167.99, 170.95, 172.80;

LCMS MH=495; Anal. Calcd for $C_{29}H_{26}N_4O_4$: C, 70.43; H, 6.30; N, 11.33. Found: C, 70.16; H, 5.03; N, 11.31.

5.79 3-(4-((2-(Morpholinomethyl)Imidazo[1,2-A]Pyridine-6-yl)Methoxy)-1-Oxoisoindolin-2-yl)Piperidine-2,6-Dione

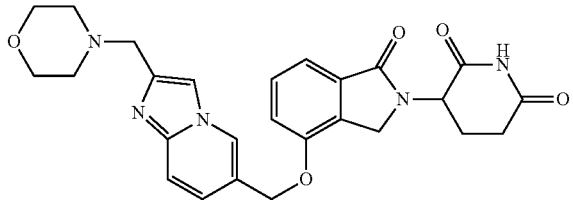 [SMILES: O=C1CCC(N2Cc3c(OCc4ccc5nc(CN6CCOCC6)cn5c4)cccc3C2=O)C(=O)N1]

Step 1: A mixture of ethyl 6-aminonicotinate (5.0 g, 30.1 mmol) and 1,3-dichloropropan-2-one (5.7 g, 45.1 mmol) in acetonitrile (100 mL) was refluxed for 17 h. The mixture was concentrated and residue was stirred with $CH_2Cl_2$ (100 mL) and sat. $NaHCO_3$ (35 mL). The organic layer was washed with brine (40 mL) and dried. Solvent was removed and residue was purified by chromatography ($SiO_2$, 30% EtOAc/$CH_2Cl_2$ for 25 min then to 100% EtOAc over 15 min) to give ethyl 2-(chloromethyl)imidazo[1,2-a]pyridine-6-carboxylate (4.7 g, 65%): $^1$H NMR (CDCl$_3$) δ 1.42 (t, J=6 Hz, 3H), 4.38-4.45 (q, J=6 Hz, 2H), 4.77 (s, 2H), 7.56-7.59 (d, J=9 Hz, 1H), 7.70 (s, 1H), 7.74-7.77 (dd, J=3 and 9 Hz, 1H), 8.86-8.87 (d, J=3 Hz, 1H).

Step 2: Diisobutylaluminum hydride/Toluene (1M, 22.0 mL, 22.0 mmol) was added slowly to a stirred solution of ethyl 2-(chloromethyl)imidazo[1,2-a]pyridine-6-carboxylate (2.1 g, 8.8 mmol) in THF (60 mL) at 0° C. The reaction mixture was stirred at 0° C. for 4 h then quenched with methanol (5 mL). $CH_2Cl_2$ (70 mL) and sat. $NaHCO_3$ (40 mL) was added and mixture was warmed to room temperature. Aq. layer was extracted with $CH_2Cl_2$ (60 mL) and combined $CH_2Cl_2$ solution was washed with brine (40 mL) and dried. Solvent was removed and residue was stirred with ether (25 mL) to give (2-(chloromethyl)imidazo[1,2-a]pyridine-6-yl)methanol (1.1 g, 65%): $^1$H NMR (DMSO-d$_6$) δ 4.60 (s, 2H), 4.75 (s, 2H), 5.22 (b, 1H), 7.19-7.22 (dd, J=3 and 9 Hz, 1H), 7.44-7.47 (d, J=9 Hz, 1H), 7.75 (s, 1H), 8.24 (s, 1H).

Step 3: A suspension mixture of (2-(chloromethyl)imidazo[1,2-a]pyridine-6-yl)methanol (1.5 g, 7.4 mmol), morpholine (1.0 g, 11.1 mmol) and N,N-diisopropylethylamine (1.4 g, 11.1 mmol) in acetonitrile (30 mL) was heated at 70° C. oil bath for 20 min. The reaction mixture was concentrated and residue was dissolved in $CH_2Cl_2$ (80 mL) and washed with brine (30 mL) and dried. Solvent was removed and residue was purified by chromatography ($SiO_2$, 3% $CH_3OH/CH_2Cl_2$ for 10 min then to 10% over 10 min and hold for 40 min) to give (2-(morpholinomethyl)imidazo[1,2-a]pyridine-6-yl)methanol (1.0 g, 54%): $^1$H NMR (CDCl$_3$) δ 2.54-2.57 (m, 4H), 3.66-3.74 (m, 6H), 4.40 (b, 1H), 4.67 (s, 2H), 7.05-7.09 (dd, J=3 and 9 Hz, 1H), 7.30-7.44 (m, 2H), 8.02 (s, 1H).

Step 4: A mixture of triphenylphosphine-polymer bound (4.3 g, 6.1 mmol) in THF (40 mL) was cooled in ice bath to 3° C. Diisopropyl azadicarboxylate (1.1 g, 5.3 mmol) was added slowly at 3-5° C. After stirred at 3° C. for 10 min, a solution of methyl 5-amino-4-(4-hydroxy-1-oxoisoindolin-2-yl)-5-oxopentanoate (1.2 g, 4.0 mmol) and (2-(morpholinomethyl)imidazo[1,2-a]pyridine-6-yl)methanol (1.1 g, 4.0 mmol) in THF (80 mL) was added slowly at 5-8° C. After stirred at 3° C. for 5 min, ice bath was removed and mixture was stirred at room temperature overnight. The reaction mixture was filtered and washed solid with $CH_2Cl_2$ (60 mL). Filtrate was concentrated and residue was dissolved in $CH_2Cl_2$ (120 mL) and washed with sat. $NaHCO_3$ (35 mL), water (35 mL), brine (35 mL) and dried. Solvent was removed and residue was purified by chromatography ($SiO_2$, $CH_2Cl_2$ for 5 min then to 3% $CH_3OH/CH_2Cl_2$ over 5 min and hold for 15 min then to 5% over 5 min and hold for 15 min) to give methyl 5-amino-4-(4-((2-(morpholinomethyl)imidazo[1,2-a]pyridin-6-yl)methoxy)-1-oxoisoindolin-2-yl)-5-oxopentanoate (1.2 g, 57%): $^1$H NMR (CDCl$_3$) δ 2.18-2.44 (m, 4H), 2.57-2.60 (m, 4H), 3.63 (s, 3H), 3.72-3.76 (m, 6H), 4.38-4.44 (d, J=18 Hz, 1H), 4.49-4.55 (d, J=18 Hz, 1H), 4.90-4.95 (dd, J=6 and 9 Hz, 1H), 5.14 (s, 2H), 5.50 (b, 1H), 6.38 (b, 1H), 7.12-7.20 (m, 2H), 7.42-7.47 (m, 2H), 7.50-7.63 (m, 2H), 8.18 (s, 1H); $^{13}$C NMR (CDCl$_3$) δ 24.12, 30.45, 45.21, 51.83, 53.82, 53.90, 57.00, 66.98, 67.75, 111.50, 114.32, 116.64, 117.79, 120.97, 124.13, 124.26, 129.99, 130.20, 133.65, 144.40, 144.75, 153.35, 169.17, 171.46, 172.87.

Step 5: A solution of methyl 5-amino-4-(4-((2-(morpholinomethyl)imidazo[1,2-a]pyridin-6-yl)methyoxy)-1-oxoisoindolin-2-yl)-5-oxopentanoate (1.2 g, 2.2 mmol) in THF (30 mL) was cooled in ice bath for 15 min. A solution of potassium tert-butoxide/THF (1 M, 2.5 mL, 2.5 mmol) was added slowly and mixture was stirred in ice bath for 2 h. The reaction mixture was quenched with 1N HCl (5 mL) and mixture was diluted with $CH_2Cl_2$ (30 mL) and water (20 mL). The mixture was basified with sat. $NaHCO_3$ (7 mL) to pH=8. Aq. layer was extracted with $CH_2Cl_2$ (3×30 mL) and combined $CH_2Cl_2$ solution was washed with brine (30 mL) and dried. Solvent was removed and residue was crystallized from acetone (10 mL) to give 3-(4-((2-(morpholinomethyl)imidazo[1,2-a]pyridin-6-yl)methoxy)-1-oxoisoindolin-2-yl)piperidine-2,6-dione (0.6 g, 53%): mp 278-280° C.; $^1$H NMR (DMSO-d$_6$) δ 1.97-2.01 (m, 1H), 2.40-2.61 (m, 6H), 2.90-2.95 (m, 1H), 3.55-3.59 (m, 6H), 4.29 (d, J=18 Hz, 1H), 4.39 (d, J=15 Hz, 1H), 5.08-5.14 (dd, J=6 and 15 Hz, 1H), 5.25 (s, 2H), 7.30-7.41 (m, 3H), 7.49-7.51 (m, 2H), 7.83 (s, 1H), 8.66 (s, 1H), 10.98 (s, 1H); $^{13}$C NMR (DMSO-d$_6$) δ 22.36, 31.16, 45.04, 51.56, 53.19, 56.27, 66.18, 67.31, 111.68, 115.09, 115.44, 116.34, 120.69, 124.87, 125.69, 129.83, 130.02, 133.34, 134.51, 134.58, 153.26, 167.96, 170.95, 172.80; Calcd for $C_{26}H_{27}N_5O_5$: C, 63.79; H, 5.56; N, 14.31. Found: C, 63.38; H, 5.64; N, 14.09.

5.80 3-{4-[4-(1H-Benzoimidazol-2-ylmethyl)-Benzyloxy]-1-Oxo-1,3-Dihydro-Isoindol-2-yl}-Piperidine-2,6-Dione

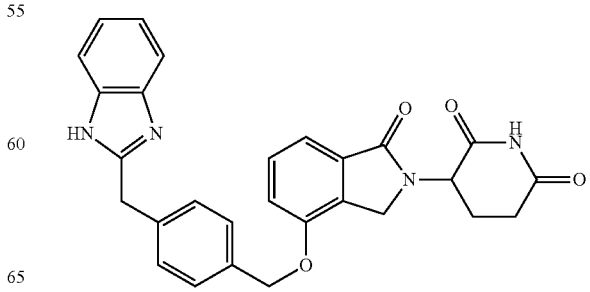

Step 1: (4-Bromomethyl-phenyl)-acetic acid tert-butyl ester The stirred solution of 2-(4-(bromomethyl)phenyl) acetic acid (2.6 g, 1 1.35 mmol) in thionyl chloride (20 mL, 274 mmol) was heated to reflux for 2.5 hrs. The reaction mixture was concentrated under vacuo to give off white solid. The white solid was added to the stirred solution of 2-methylpropan-2-ol (20 ml, 213 mmol) in DCM (2 mL) under ice/water bath. And the mixture was stirred under ice/water bath for 2 hrs and at room temperature for 18 hrs. The reaction mixture was added to $CH_2Cl_2$ (40 mL). The organic phase was washed successively with $H_2O$ (20 mL), $NaHCO_3$ (sat, aq, 20 mL), and brine (25 mL) and dried over $MgSO_4$. Organic layer was concentrated under vacuo to give (4-bromo methyl-phenyl)-acetic acid tert-butyl ester as a light yellow liquid (2.4 g, 74% crude yield). 1H NMR (DMSO-d6): 1.39 (s, 9H, tBu), 3.54 (s, 2H, $CH_2CO_2$), 4.69 (s, 2H, $CH_2Br$), 7.23, 7.39 (m, 4H, due to impurities).

Step 2: 4-[4-(4-tert-Butoxycarbonylmethyl-benzyloxy)-1-oxo-1,3-dihydro-isoindol-2-yl]-4-carbamoyl-butyric acid methyl ester To the stirred mixture of methyl 5-amino-4-(4-hydroxy-1-oxoisoindolin-2-yl)-5-oxopentanoate (1.5 g, 5.13 mmol) and tert-butyl 2-(4-(bromomethyl)phenyl) acetate (2.2 g, 7.7 mmol) in Acetonitrile (30 mL) was added POTASSIUM CARBONATE (1.42 g, 10.3 mmol). The resulting reaction mixture was stirred at 50° C. for 27 hrs and in between tert-butyl 2-(4-(bromomethyl) phenyl) acetate (800 mg, 2.9 mmol) was added in 2 portions. The reaction mixture was filtered and the light brown solid was washed with acetonitrile (2×20 mL). The filtrate was concentrated under vacuo and the residue was purified by ISCO 4-[4-(4-tert-Butoxycarbonylmethyl-benzyloxy)-1-oxo-1,3-dihydro-isoindol-2-yl]-4-carbamoyl-butyric acid methyl ester as a light yellow sticky solid (2.1 g, 82% crude yield) LCMS MH=497.

Step 3: 4-Carbamoyl-4-[4-(4-carboxymethyl-benzyloxy)-1-oxo-1,3-dihydro-isoindol-2-yl]-butyric acid methyl ester To the stirred solution of methyl 5-amino-4-(4-(4-(2-tert-butoxy-2-oxoethyl)benzyloxy)-1-oxoisoindolin-2-yl)-5-oxopentanoate (2.1 g, 4.2 mmol) in DCM (20 mL) at room temperature was added by WATER (0.38 ml, 21.1 mmol) followed by the addition of TFA (1.63 ml, 21.1 mmol) slowly. The resulting solution was stirred at room temperature for 5 hrs and in between TFA (3.2 mL) and water (0.15 mL) were added. The mixture was kept in fridge overnight and the reaction mixture was concentrated under vacuo to give 4-Carbamoyl-4-[4-(4-carboxy methyl-benzyloxy)-1-oxo-1,3-dihydro-isoindol-2-yl]-butyric acid methyl ester as an off white solid (2.3 g, 123% crude yield). $^1$H NMR (DMSO-$d_6$) δ 1.97-2.31 (m, 4H, $CH_2$, $CH_2$), 3.50 (s, 3H, $CH_3$), 3.58 (s, 2H, $CH_2$), 4.41 (d, J=17.8 Hz, 1H, CHH), 4.53 (d, J=17.8 Hz, 1H, CHH), 4.72 (dd, J=4.6, 10.3 Hz, 1H, CHH), 5.23 (s, 2H, $CH_2$), 7.18 (br. s., 1H, NHH), 7.24-7.34 (m, 4H, Ar), 7.40-7.50 (m, 3H, Ar), 7.57 (br. s., 1H, NHH); LCMS MH=441.

Step 4: 4-{4-[4-(1H-Benzoimidazol-2-ylmethyl)-benzyloxy]-1-oxo-1,3-dihydro-isoindol-2-yl}-4-carbamoyl-butyric acid methyl ester The solution of 2-(4-((2-(1-amino-5-methoxy-1,5-dioxopentan-2-yl)-1-oxoisoindolin-4-yloxy) methyl)phenyl)acetic acid (621 mg, 1.4 mmol) in THF (4 mL) was added CDI (208 mg, 1.28 mmol) in one portion. The mixture was stirred at room temperature for 3 hrs and at 50° C. for 1 hr before was added the solution of benzene-1,2-diamine (139 mg, 1.28 mmol) in THF (6 mL). The reaction mixture was stirred at 50° C. for 20 hrs and then stirred at 65° C. for 30 hrs. The reaction mixture was diluted by EtOAc (40 mL) and washed with $NH_4OH$ (aq, 10% wt, 2×20 mL). Organic layer was concentrated under vacuo and the residue was purified by ISCO 4-{4-[4-(1H-Benzoimidazol-2-ylmethyl)-benzyloxy]-1-oxo-1,3-dihydro-isoindol-2-yl}-4-carbamoyl-butyric acid methyl ester as a yellow solid (266 mg, 40% yield). $^1$H NMR (DMSO-$d_6$) δ 1.96-2.32 (m, 4H, $CH_2$, $CH_2$), 3.42-3.57 (m, 3H, $CH_3$), 4.18 (s, 2H, $CH_2$), 4.30-4.58 (m, 2H, CHH, CHH), 4.71 (dd, J=4.7, 10.2 Hz, 1H, CHH), 5.21 (s, 2H, $CH_2$), 7.05-7.22 (m, 3H, NHH, Ar), 7.22-7.32 (m, 2H, Ar), 7.32-7.49 (m, 6H, Ar), 7.49-7.62 (m, 2H, Ar, NHH), 12.26 (s, 1H, NH); LCMS MH=513.

Step 5: 3-{4-[4-(1H-Benzoimidazol-2-ylmethyl)-benzyloxy]-1-oxo-1,3-dihydro-isoindol-2-yl}-piperidine-2,6-dione To the stirred solution of methyl 4-(4-(4-((1H-benzo[d]imidazol-2-yl)methyl)benzyloxy)-1-oxoisoindolin-2-yl)-5-amino-5-oxopentanoate (260 mg, 0.5 mmol) in Tetrahydrofuran (10 mL) at 0° C. was added POTASSIUM TERT-BUTOXIDE (62.6 mg, 0.56 mmol). The resulting mixture was stirred at 0° C. for 2 hrs and in between KOtBu (50 mg, 0.4 mmol) was added in two portions. The resulting reaction mixture was diluted by EtOAc (50 mL) and followed by the addition of HCl (aq, 1N, 3 mL). The resulting mixture was added by $NaHCO_3$ (sat., aq, 20 mL) and extracted. Organic layer was concentrated under vacuo and the residue was purified by ISCO to give an off white solid (110 mg). The offwhite solid was purified by being heated in EtOAc (10 mL) at reflux to give 3-{4-[4-(1H-Benzoimidazol-2-ylmethyl)-benzyloxy]-1-oxo-1,3-dihydro-isoindol-2-yl}-piperidine-2,6-dione as a white solid (33 mg, 14% yield); HPLC: Waters Symmetry C-18, 3.9×150 mm, 5 μm, 1 mL/min, 240 nm, 20/80, ($CH_3CN$/0.1% $H_3PO_4$), 6.03 min (99.3%); mp: 203-205° C.; $^1$H NMR (DMSO-$d_6$) δ 1.86-2.04 (m, 1H, CHH), 2.33-2.47 (m, 1H, CHH), 2.53-2.63 (m, 1H, CHH), 2.81-2.99 (m, 1H, CHH), 4.11-4.44 (m, 4H, CHH, CHH, $CH_2$), 5.09 (dd, J=5.1, 13.2 Hz, 1H, CHH), 5.20 (s, 2H, $CH_2$), 6.99-7.21 (m, 2H, Ar), 7.26-7.60 (m, 9H, Ar), 10.94 (s, 1H, NH), 12.27 (s, 1H, NH); $^{13}$C NMR (DMSO-$d_6$) δ 22.28, 31.16, 34.62, 45.06, 51.55, 69.35, 110.84, 114.90, 115.18, 118.22, 120.89, 121.58, 128.02, 128.88, 129.77, 129.93, 133.27, 134.82, 137.50, 153.38, 153.45, 167.97, 170.93, 172.78; LCMS MH=481; Anal. Calcd for $C_{28}H_{24}N_4O_4$: C, 69.99; H, 5.03; N, 11.66; Found: C, 69.97; H, 4.70; N, 11.58.

5.81 3-{4-[4-(Octahydro-Isoindol-2-ylmethyl)-Benzyloxy]-1-Oxo-1,3-Dihydro-Isoindol-2-yl}-Piperidine-2,6-Dione

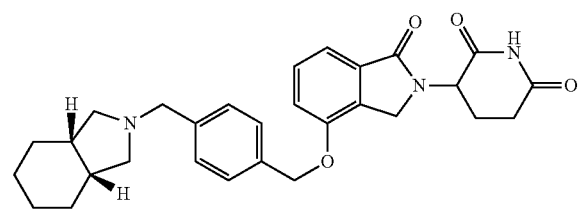 [SMILES: O=C1CCC(N2Cc3c(OCc4ccc(CN5C[C@H]6CCCC[C@H]6C5)cc4)cccc3C2=O)C(=O)N1]

To the $CH_3CN$ (10 ml) solution of 3-(4-(4-(bromomethyl) benzyloxy)-1-oxoisoindolin-2-yl)piperidine-2,6-dione (0.357 g, 0.805 mmol) was added Cis-Octa hydro-isoindole hydrochloride (0.195 g, 1.208 mmol) and N-ethyl-N-isopropylpropan-2-amine (0.466 ml, 2.82 mmol) at room temperature. The mixture was stirred at room temperature overnight. Solvent was evaporated and the resulting off-white solid was stirred in methylene chloride (100 ml), washed with saturated sodium bicarbonate (2×80 ml), brine (50 ml), dried and concentrated to an off-white solid, which was purified by silica gel column (MeOH/CH₂Cl₂) to give 3-{4-[4-(Octa-hydro-isoindol-2-ylmethyl)-benzyloxy]-1-oxo-1,3-dihydro-isoindol-2-yl}-piperidine-2,6-dione as a white solid (20 mg, 5% yield); mp, not determined. HPLC: Waters Symmetry C-18, 3.9×150 mm, 5 μm, 1 mL/min, 240 nm, gradient from 10/90 to 70/30 in 5 min, isocratic at 70/30 for 5 min (CH₃CN/0.1% H₃PO₄), 5.17 min (97.7%). ¹H NMR (DMSO-d₆) δ 1.18-1.34 (m, 2H, CH₂), 1.35-1.62 (m, 6H, CH₂, CH₂, CH₂), 1.92-2.03 (m, 1H, CHH), 2.04-2.22 (m, 2H, CH₂), 2.36-2.48 (m, 1H, CHH), 2.53-2.80 (m, 4H, CH₂, CH, CHH), 2.83-3.00 (m, 1H, CHH), 3.58-3.86 (m, 2H, CH₂), 4.17-4.49 (m, 2H, CH₂), 5.11 (dd, J=5.1, 13.2 Hz, 1H, NCH), 5.22 (s, 2H, CH₂), 7.26-7.54 (m, 7H, Ar), 10.97 (s, 1H, NH). ¹³C NMR (DMSO-d₆) δ 22.27, 22.36, 31.21, 36.52, 45.10, 51.59, 57.64, 69.41, 114.98, 115.23, 127.67, 129.81, 129.95, 133.32, 153.50, 168.01, 170.96, 172.82. LC/MS m/e=488. Anal Calcd for C₂₉H₃₃N₃O₄: C, 71.44; H, 6.82; N, 8.62.

5.82 3-(4-((4-((7,8-Dihydro-1,6-Naphthyridin-6 (5H)-yl)Methyl)Benzyl)Oxy)-1-Oxoisoindolin-2-yl) Piperidine-2,6-Dione

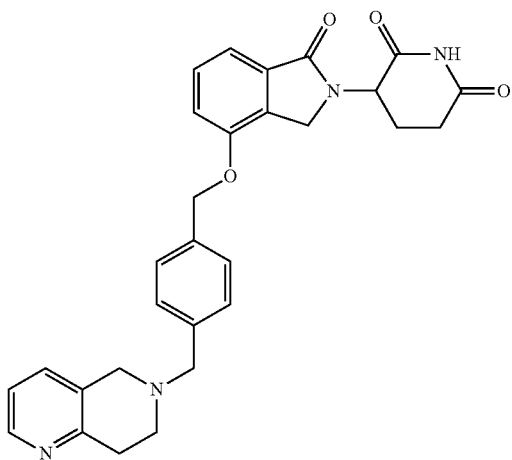 [SMILES: O=C1CCC(N2Cc3c(OCc4ccc(CN5CCc6ncccc6C5)cc4)cccc3C2=O)C(=O)N1]

Step 1: (S)-Methyl 5-amino-4-(4-((4-(bromomethyl)benzyl)oxy)-1-oxoisoindolin-2-yl)-5-oxopentanoate 1,4-bis(Bromomethyl)benzene (2.71 g, 10.26 mmol) was suspended in dry acetonitrile (40 mL). The slurry was warmed up to 60° C. until full dissolution occurred (~15 min). The temperature was reduced to 50° C. and to the solution was added K₂CO₃ (0.473 g, 3.42 mmol) as a solid followed by (S)-methyl 5-amino-4-(4-hydroxy-1-oxoisoindolin-2-yl)-5-oxopentanoate (1 g, 3.42 mmol, preparation described herein). The resulting white slurry was stirred at 50° C. for ~3 h at which time LCMS indicated the phenol starting material was consumed. The crude reaction mixture was swirled and filtered with suction. The remaining solid in flask and on the filter funnel was rinsed with minimal MeCM (~5 mL). The filtrate was concentrated in vacuo to give 2.6 g of a white solid. The solid was dissolved in minimal DCM and purified using a SiO₂ flash column (CombiFlash, 40 g SiO₂ prepacked column). The column was eluted with 100% DCM for ~15 min, a gradient to 5% MeOH in DCM over 5 min, and then held at 5% MeOH in DCM. Fractions were combined and concentrated to give (S) methyl 5-amino-4-(4-(4-(bromomethyl)benzyloxy)-1-oxoisoindolin-2-yl)-5-oxopentanoate as a white solid (1.3 g, 80% yield): ¹H NMR (DMSO-d₆) δ 1.94-2.34 (m, 4H, CH₂, CH₂), 3.50 (s, 3H, CH₃), 4.33-4.62 (m, 2H, CH₂), 4.72 (s, 2H, CH₂,), 5.25 (s, 2H, CH₂), 5.27-5.36 (m, 1H, CH), 7.19 (br. s., 1H, NH), 7.23-7.36 (m, 2H, Ar), 7.40-7.70 (m, 6H, Ar, NH); LCMS: MH=475, 477.

Step 2: (S)-3-(4-(4-(Bromomethyl)benzyloxy)-1-oxoisoindolin-2-yl)piperidine-2,6-dione (S)-Methyl 5-amino-4-(4-(4-(bromomethyl)benzyloxy)-1-oxoisoindolin-2-yl)-5-oxopentanoate (2.05 g, 4.31 mmol) was dissolved in THF (50 mL) and the solution was cooled in dry ice/acetone bath to −76° C. While stirring, solid KOᵗBu (0.532 g, 4.74 mmol) was added in one portion to the clear solution. The reaction mixture became a pale yellow color and was stirred for ~90 min at −76° C. A cooled solution of 1 N aq HCl (20 mL) was rapidly transferred to the reaction mixture, maintaining temperature at −76° C. The mixture immediately turned milky white and the dry CO₂/acetone bath was removed, allowing the mixture to warm up to while stirring. The mixture was concentrated on a rotovap to remove most of THF (concentrated to a fixed volume at 160 mbar and water bath −35° C.). Upon concentration of reaction mixture, a white solid precipitated out. The white slurry was diluted with more water (~80 mL) and then suction filtered. The cake was washed with copious water (total filtrate volume ~150 mL) and suction dried. The cake was washed with Et₂O (~50 mL), suction dried and then placed in vacuum oven at 40° C. overnight to give (S)-3-(4-(4-(bromomethyl)benzyloxy)-1-oxoisoindolin-2-yl)piperidine-2,6-dione as a white solid (1.8 g, 94% yield): HPLC: Waters Symmetry C₁₈, 5 μm, 3.9×150 mm, 1 ml/min, 240 nm, 50/50 CH₃CN/0.1% H₃PO₄, 3.70 min (97.9%); mp: 123-125° C.; ¹H NMR (DMSO-d₆) δ 1.89-2.05 (m, 1H, CHH), 2.32-2.48 (m, 1H, CHH), 2.52-2.64 (m, 1H, CHH), 2.78-3.04 (m, 1H, CHH), 4.26 (d, J=17.6 Hz, 1H, CHH), 4.43 (d, J=17.6 Hz, 1H, CHH), 4.72 (s, 2H, CH₂), 5.11 (dd, J=5.0, 13.1 Hz, 1H, CH), 5.25 (s, 2H, CH₂), 7.24-7.36 (m, 2H, Ar), 7.41-7.54 (m, 5H, Ar), 10.83-11.07 (m, 1H, NH); ¹³C NMR (DMSO-d₆) δ 22.33, 31.18, 34.15, 45.06, 51.56, 69.12, 114.94, 115.28, 127.95, 128.33, 129.41, 129.80, 131.93, 133.31, 136.78, 153.36, 167.97, 170.95, 172.81; LCMS: MH=443, 445. The solid was used in the next step without further purification. The stereochemistry of the benzyl bromide product is deduced from the stereochemical outcome of products derived from it.

Step 3: 3-(4-((4-((7,8-Dihydro-1,6-naphthyridin-6(5H)-yl)methyl)benzyl)oxy)-1-oxoisoindolin-2-yl)piperidine-2,6-dione In a 20-mL scintillation vial, MeCN (5 mL, 96 mmol) was added to a mixture of 3-(4-(4-(bromomethyl)benzyloxy)-1-oxoisoindolin-2-yl)piperidine-2,6-dione (200 mg, 0.451 mmol) and 5,6,7,8-tetrahydro-1,6-naphthyridine (72.6 mg, 0.541 mmol). DIEA (0.236 mL, 1.354 mmol) was added to the mixture. The mixture was stirred at room temperature for 1 h. The suspension was filtered. The solid was washed with Et₂O and dried in vacuum oven to give 3-(4-((4-((7,8-dihydro-1,6-naphthyridin-6(5H)-yl)methyl)benzyl)oxy)-1-oxoisoindolin-2-yl)piperidine-2,6-dione as a white solid (198 mg, 88% yield): mp: 163-165° C.; HPLC: Waters Symmetry C₁₈, 5 μm, 3.9×150 mm, 1 ml/min, 240 nm, 15/85 CH₃CN/0.1% H₃PO₄, 3.66 min (99.2%); ¹H NMR (DMSO-d₆) δ 1.90-2.05 (m, 1H, CHH), 2.34-2.48 (m, 1H, CHH), 2.52-2.64 (m, 1H, CHH), 2.70-2.82 (m, 2H, CH₂), 2.82-3.04 (m, 3H, CHH, CH₂), 3.57 (s, 2H, CH₂), 3.69 (s, 2H, CH₂), 4.26 (d, J=17.4 Hz, 1H, CHH), 4.42 (d, J 17.6 Hz, 1H, CHH), 5.11 (dd, J=5.1, 13.2 Hz, 1H, CH), 5.24 (s, 2H, CH₂O), 7.12 (dd, J=4.8, 7.6 Hz, 1H, Ar), 7.27-7.36 (m, 2H, Ar), 7.37-7.58 (m, 6H, Ar), 8.33 (dd, J=1.5, 4.7 Hz, 1H, Ar), 10.97 (s, 1H, NH); ¹³C NMR (DMSO-d₆) δ 22.33, 31.18, 31.92, 45.07, 50.00, 51.56, 54.27, 61.14, 69.41, 114.97, 115.22, 120.95, 127.73, 128.79, 129.80, 129.83, 129.93, 133.30, 134.16, 135.35, 138.10, 147.15, 153.49, 154.40, 167.99, 170.96, 172.80; LCMS: MH=497; Anal Calcd for $C_{29}H_{28}N_4O_4$+1.14 $H_2O$: C, 67.36; H, 5.90; N, 10.83; Found: C, 67.36; H, 5.93; N, 10.68.

5.83 3-(1-Oxo-4-((4-((2-(Trifluoromethyl)-5,6-Dihydro-[1,2,4]Triazolo[1,5-A]Pyrazin-7(8H)-yl)Methyl)Benzyl)Oxy)Isoindolin-2-yl)Piperidine-2,6-Dione

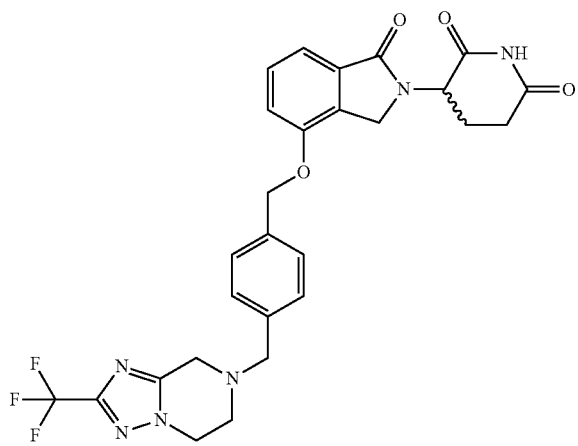 [SMILES: O=C1CCC(N2Cc3c(OCc4ccc(CN5CCn6nc(C(F)(F)F)nc6C5)cc4)cccc3C2=O)C(=O)N1]

Step 1: 3-[4-(4-Hydroxymethyl-benzyloxy)-1-oxo-1,3-dihydro-isoindol-2-yl]-piperidine-2,6-dione To a round bottom flask charged with methyl 5-amino-4-(4-hydroxy-1-oxoisoindolin-2-yl)-5-oxopentanoate (5 g, 17.11 mmol), (4-(chloromethyl)phenyl)methanol (2.81 g, 17.96 mmol), and anhydrous potassium carbonate (2.60 g, 18.82 mmol), was added DMF (50 mL). The reaction mixture was stirred at room temperature and reaction progress was followed by LCMS. After ~3 h, DIEA (3.29 mL, 18.82 mmol) was added and the reaction was stirred overnight. After ~18 h, solid KI (1.6 g, 9.64 mmol) was added and the mixture was warmed to 40° C. and stirred for ~2 days. The reaction mixture, containing a mixture of desired product and uncyclized glutarimide precursor, was warmed further to 80° C. for ~30 h. The crude reaction mixture was cooled to rt, filtered on a fritted funnel, and the removed solids were washed with minimal MeCN. The combined filtrate and washes were concentrated on a rotovap until DMF started to distill. The concentrated mixture was diluted with aqueous 1 N HCl (~150 mL) and water (~700 mL) and extracted with EtOAc (2×700 mL). The combined organic layer was washed with 1 N HCl (200 mL), 1 N $Na_2CO_3$ (2×300 mL), and brine. The solution was dried ($Na_2SO_4$) and concentrated in vacuo to ~400 mL. Activated charcoal (~11 g) was added and the slurry was agitated for ~15 min then filtered on a bed of Celite on a medium fritted funnel with suction. The clear filtrate was concentrated in vacuo to give an off-white solid (4.1 g). The solid was slurried in MeCN (60 mL) with aid of sonication and gentle heating. The mixture was heated for ~30 min at 60° C. with agitation and then allowed to cool to room temperature. $Et_2O$ (~30 mL) was added and the slurry was agitated with intermittent sonication. The solid was collected by filtration on a medium fritted funnel and the cake was washed with additional $Et_2O$ and then suction dried. The remaining solid was dried in a vacuum oven at 40° C. to give 3-[4-(4-hydroxymethyl-benzyloxy)-1-oxo-1,3-dihydro-isoindol-2-yl]-piperidine-2,6-dione as a white solid (3.4 g, 52% yield): $^1$H NMR (DMSO-$d_6$) δ 1.90-2.04 (m, 1H, CHH), 2.34-2.49 (m, 1H, CHH), 2.57 (d, J=18.1 Hz, 1H, CHH), 2.81-3.01 (m, 1H, CHH), 4.25 (d, J=17.6 Hz, 1H, CHH), 4.41 (d, J=17.4 Hz, 1H, CHH), 4.50 (d, J=5.9 Hz, 2H, $CH_2$), 5.11 (dd, J=5.1, 13.0 Hz, 1H, CH), 5.18 (t, J=5.8 Hz, 1H, OH), 5.23 (s, 2H, $CH_2$), 7.28-7.39 (m, 4H, Ar), 7.41-7.56 (m, 3H, Ar), 10.96 (s, 1H, NH); LCMS: MH=381.

Step 2: 3-[4-(4-Bromomethyl-benzyloxy)-1-oxo-1,3-dihydro-isoindol-2-yl]-piperidine-2,6-dione To a well stirred suspension of 3-(4-(4-(hydroxymethyl)benzyloxy)-1-oxoisoindolin-2-yl)piperidine-2,6-dione (2.4 g, 6.31 mmol) in dry MeCN (40 mL) at 0° C., was added $PBr_3$ (1.19 mL, 12.6 mmol) via a syringe. To the stirred mixture was added tetrabutyl ammonium bromide (0.203 g, 0.631 mmol). After ~5 min, the ice bath was removed and the reaction mixture was allowed to stir at room temperature for ~4.5 h. The reaction mixture was poured into a flask with water (200 mL) on ice. The resulting thick slurry was filtered on a medium fritted funnel with suction. Residual solid in the flask was transferred onto the filter funnel with additional water. The cake was washed with copious water and hexanes (~150 mL) and then suction dried. The solid was slurried with Et20 (~50 mL) and agitated for 10 min then collected by suction filtration. The cake was washed with additional $Et_2O$ (~50 mL) and then dried in a vacuum oven at 40° C. overnight to give 3-[4-(4-bromomethyl-benzyloxy)-1-oxo-1,3-dihydro-isoindol-2-yl]-piperidine-2,6-dione as white solid (2.61 g, 93%): HPLC: Waters Symmetry $C_{18}$, 5 μm, 3.9×150 mm, 1 ml/min, 240 nm, 50/50 $CH_3CN$/0.1% $H_3PO_4$, 3.78 min (96.6%); $^1$H NMR (MeCN-$d_3$) δ 2.08-2.22 (m, J=2.5, 5.2, 5.2, 12.8 Hz, 1H, CHH), 2.45 (qd, J=4.9, 13.1 Hz, 1H, CHH), 2.62-2.94 (m, 2H, CHH, CHH), 4.31 (d, J=17.0 Hz, 1H, CHH), 4.41 (d, J=17.2 Hz, 1H, CHH), 4.62 (s, 2H, $CH_2$), 5.09 (dd, J=5.1, 13.4 Hz, 1H, CH), 5.24 (s, 2H, $CH_2$), 7.24 (d, J=8.1 Hz, 1H, Ar), 7.38 (d, J=7.0 Hz, 1H, Ar), 7.42-7.55 (m, 5H, Ar), 8.83 (br. s., 1H, NH); $^{13}$C NMR (MeCN-$d_3$) δ 22.37, 30.89, 33.02, 44.83, 51.64, 69.26, 114.62, 115.21, 127.79, 129.01, 129.55, 130.12, 133.27, 136.87, 137.98, 153.52, 168.29, 170.13, 171.79; LCMS: MH=443, 445.

Step 3: 3-(1-Oxo-4-((4-((2-(trifluoromethyl)-5,6-dihydro-[1,2,4]triazolo[1,5-a]pyrazin-7(8H)-yl)methyl)benzyl)oxy)isoindolin-2-yl)piperidine-2,6-dione To a slurry of (3-(4-(4-(bromomethyl)benzyloxy)-1-oxoisoindolin-2-yl)piperidine-2,6-dione (200 mg, 0.451 mmol)) and 2-(trifluoromethyl)-5,6,7,8-tetrahydro-[1,2,4]triazolo[1,5-a]pyrazine (95 mg, 0.496 mmol) in dry MeCN (5 mL, 96 mmol), was added DIEA (0.197 mL, 1.128 mmol) and the resulting white suspension was stirred at room temperature for 2 h and heat to 40° C. for 4 additional hours The mixture was cooled at 0° C. The suspension was filtered. The solid was washed with water (~50 mL) and dried in vacuum oven at 50° C. to give 3-(1-oxo-4-((4-((2-(trifluoromethyl)-5,6-dihydro-[1,2,4]triazolo[1,5-a]pyrazin-7(8H)-yl)methyl)benzyl)oxy)isoindolin-2-yl)piperidine-2,6-dione as a white solid (135 mg, 54% yield): HPLC: Waters Symmetry $C_{18}$, 5 μm, 3.9×150 mm, 1 ml/min, 240 nm, 40/60 $CH_3CN$/0.1% $H_3PO_4$, 6.33 min (98.2%); mp: 139-142° C.; $^1$H NMR (DMSO-$d_6$) δ 1.89-2.05 (m, 1H, CHH), 2.34-2.48 (m, 1H, CHH), 2.57 (d, J=19.1 Hz, 1H, CHH), 2.82-2.98 (m, 1H, CHH), 3.02 (t, J=5.5 Hz, 2H, $CH_2$), 3.80 (s, 2H, $CH_2$), 3.82 (s, 2H, $CH_2$), 4.20-4.31 (m, 3H, CHH, $CH_2$), 4.42 (d, J=17.6 Hz, 1H, CHH), 5.11 (dd, J=5.1, 13.2 Hz, 1H, CH), 5.25 (s, 2H, $CH_2$), 7.30-7.36 (m, 2H, Ar), 7.38-7.44 (m, 2H, Ar), 7.45-7.54 (m, 3H, Ar), 10.96 (s, 1H, NH); $^{13}$C NMR (DMSO-$d_6$) δ 22.34, 31.16, 45.07, 46.54, 47.73, 49.17, 51.56, 59.42, 69.35, 114.99, 115.23, 127.80, 128.92, 129.80, 129.95, 133.30, 135.73, 137.05, 152.82, 153.46, 167.97, 170.95, 172.80; Two carbon signals are not observed (probably due to splitting of CF$_3$, and CCF$_3$); LCMS: MH=555; Anal Calcd for C$_{27}$H$_{25}$F$_3$N$_6$O$_4$+0.5 H$_2$O: C, 57.55; H, 4.65; N, 14.91; F, 10.11; Found: C, 57.42; H, 4.32; N, 14.60; F, 9.92.

5.84 3-{4-[4-(6-Methoxy-3,4-Dihydro-1H-Isoquinolin-2-ylmethyl)-Benzyloxy]-1-Oxo-1,3-Dihydro-Isoindol-2-yl}-Piperidine-2,6-Dione

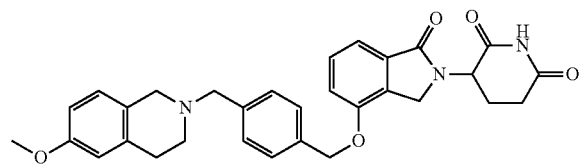 [SMILES: COc1ccc2c(c1)CCN(Cc1ccc(COc3cccc4c3CN(C3CCC(=O)NC3=O)C4=O)cc1)C2]

To the CH$_3$CN (10 ml) solution of 3-(4-(4-(bromomethyl)benzyloxy)-1-oxoisoindolin-2-yl)piperidine-2,6-dione (0.365 g, 0.823 mmol) was added 6-methoxy-1,2,3,4-tetrahydroisoquinoline hydrochloride (0.247 g, 1.235 mmol) and N-ethyl-N-isopropylpropan-2-amine (0.408 ml, 2.470 mmol) at room temperature overnight. Solvent was evaporated and the residue was stirred in CH$_2$Cl$_2$ (100 ml) and washed with sat NaHCO$_3$ (2×30 ml), brine (20 ml) and evaporated to an oil, which was purified by silica gel column (MeOH/CH$_2$Cl$_2$) to give 3-{4-[4-(6-Methoxy-3,4-dihydro-1H-isoquinolin-2-ylmethyl)-benzyloxy]-1-oxo-1,3-dihydroisoindol-2-yl}-piperidine-2,6-dione (0.26 g, 60% yield); mp, 169-171° C. HPLC: Waters Symmetry C-18, 3.9×150 mm, 5 µm, 1 mL/min, 240 nm, gradient from 10/90 to 70/30 in 5 min, isocratic at 70/30 for 5 min (CH$_3$CN/0.1% H$_3$PO$_4$), 4.72 min (98.3%). $^1$H NMR (DMSO-d$_6$) δ 1.90-2.06 (m, 1H, CHH), 2.32-2.46 (m, 1H, CHH), 2.53-2.71 (m, 3H, CH$_2$, CHH), 2.71-2.83 (m, 2H, CH$_2$), 2.83-3.02 (m, 1H, CHH), 3.46 (br. s., 2H, CH$_2$), 3.55-3.81 (m, 5H, CH$_2$, CH$_3$), 4.18-4.50 (m, 2H, CH$_2$), 5.12 (dd, J=5.2, 13.3 Hz, 1H, NCH), 5.23 (br. s., 2H, CH$_2$), 6.58-6.74 (m, 2H, Ar), 6.89 (d, J=9.1 Hz, 1H, Ar), 7.24-7.62 (m, 7H, Ar), 10.98 (br. s., 1H, NH). $^{13}$C NMR (DMSO-d$_6$) δ 22.36, 28.94, 31.21, 45.10, 50.12, 51.58, 54.92, 61.51, 69.45, 111.91, 112.93, 114.97, 115.24, 126.73, 127.26, 127.72, 128.82, 129.81, 129.94, 131.81, 133.31, 135.22, 138.28, 153.51, 157.45, 168.01, 169.07, 170.96, 172.83. LC/MS m/e=526. Anal Calcd for C$_{31}$H$_{31}$N$_3$O$_5$ (+1.1 H$_2$O): C, 68.27; H, 6.14; N, 7.70. Found: C, 68.08; H, 5.92; N, 7.47.

5.85 3-(4-((3-((4-Isopropylpiperidin-1-yl)Methyl)Isoxazol-5-yl)Methoxy)-1-Oxoisoindolin-2-yl)Piperidine-2,6-Dione

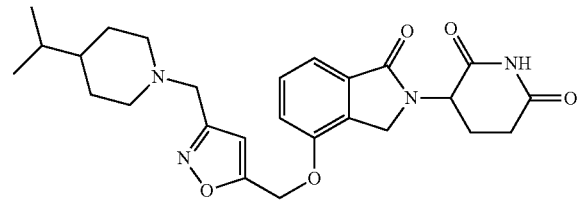 [SMILES: CC(C)C1CCN(Cc2cc(COc3cccc4c3CN(C3CCC(=O)NC3=O)C4=O)on2)CC1]

A mixture of (5-((2-(2,6-dioxopiperidin-3-yl)-1-oxoisoindolin-4-yloxy)methyl)isoxazol-3-yl)methyl methanesulfonate (0.28 g, 0.623 mmol) in acetonitrile (10 mL) was stirred at room temperature. 4-Isopropylpiperidine (0.095 g, 0.748 mmol) and DIEA (0.11 g, 0.810 mmol) were added, and the mixture stirred at room temperature for 3 h. Then, the mixture was evaporated under vacuum. The residue was partitioned between EtOAc (75 mL) and water (75 mL), and the organic phase was washed with water (75 mL). Then the organic phase was extracted with 1N HCl (2×50 mL). The combined aqueous extracts were washed with EtOAc (75 mL) and then made basic with solid sodium carbonate, and the resulting mixture was extracted with EtOAc (2×50 mL). The combined organic extracts were washed with water (75 mL), dried (MgSO$_4$) and evaporated, providing 180 mg (60%) as a white solid; mp 173-175° C. HPLC: Waters Symmetry C-18, 3.9×150 mm, 5 µm, 1 mL/min, 240 nm, 10/90 gradient to 90/10 CH$_3$CN/0.1% H$_3$PO$_4$ in 10 min: 5.65 (96.83%). $^1$H NMR (DMSO-d$_6$) δ 0.83 (d, J=6.6 Hz, 6H), 0.97 (br. s., 1H), 1.09-1.24 (m, 2H), 1.30-1.46 (m, 1H), 1.58 (d, J=11.9 Hz, 2H), 1.80-2.06 (m, 3H), 2.36-2.47 (m, 1H), 2.52-2.64 (m, 1H), 2.72-3.01 (m, 3H), 3.41-3.63 (m, 2H), 4.25 (d, J=17.6 Hz, 1H), 4.41 (d, J=17.6 Hz, 1H), 5.11 (dd, J=5.0, 13.1 Hz, 1H), 5.43 (s, 2H), 6.62 (s, 1H), 7.39 (t, J=7.0 Hz, 2H), 7.46-7.57 (m, 1H), 10.97 (s, 1H). $^{13}$C NMR (DMSO-d$_6$) δ 19.62, 22.35, 28.69, 31.21, 31.85, 41.46, 45.05, 51.61, 52.58, 53.49, 60.72, 104.57, 115.11, 115.99, 129.85, 129.98, 133.51, 152.67, 161.50, 167.12, 167.82, 170.92, 172.80. Anal. Calcd for C$_{26}$H$_{32}$N$_4$O$_5$+0.2 H$_2$O: C, 64.50%; H, 6.75%; N, 11.57%; Found: C, 64.48%; H, 6.73%; N, 11.31%.

5.86 3-{4-[4-(2-Methyl-4-Phenyl-Imidazol-1-ylmethyl)-Benzyloxy]-1-Oxo-1,3-Dihydro-Isoindol-2-yl}-Piperidine-2,6-Dione

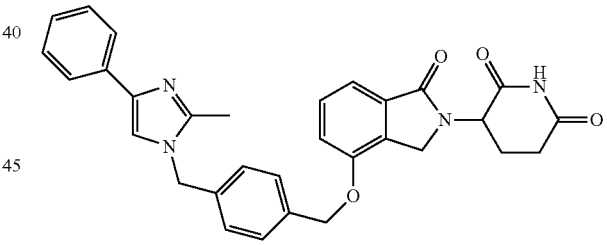

To the stirred solution of 2-methyl-4-phenyl-1H-imidazole (157 mg, 0.99 mmol) in Acetonitrile (15 mL) was added 3-(4-(4-(bromomethyl)benzyloxy)-1-oxoisoindolin-2-yl)piperidine-2,6-dione (400 mg, 0.9 mmol) and DIPEA (0.24 ml, 1.35 mmol) at room temperature. The reaction mixture was stirred at room temperature for 4 days before the reaction mixture was diluted by EtOAc (40 mL) and NaHCO$_3$ (aq, sat., 20 mL). The mixture was extracted. Some solid was formed and the mixture was filtered. And the solid was dissolved in DCM (20 mL) and MeOH (5 mL). All organic layers were combined and dried by MgSO$_4$ and concentrated. The residue was purified by ISCO to give 3-{4-[4-(2-Methyl-4-phenyl-imidazol-1-ylmethyl)-benzyloxy]-1-oxo-1,3-dihydro-isoindol-2-yl}-piperidine-2,6-dione as a white solid (310 mg, 66% yield). HPLC: Waters Symmetry C-18, 3.9×150 mm, 5 µm, 1 mL/min, 240 nm, 25/75, (CH$_3$CN/0.1% H$_3$PO$_4$), 5.26 min (99.6%); mp: 270-272° C.; $^1$H NMR (DMSO-d$_6$) δ 1.91-2.03 (m, 1H, CHH), 2.30 (s, 3H, CH₃), 2.43 (dd, J=4.3, 13.0 Hz, 1H, CHH), 2.53-2.63 (m, 1H, CHH), 2.82-2.97 (m, 1H, CHH), 4.23 (d, J=17.6 Hz, 1H, CHH), 4.39 (d, J=17.6 Hz, 1H, CHH), 5.04-5.16 (m, 1H, CHH), 5.18 (s, 2H, CH₂), 5.23 (s, 2H, CH₂), 7.10-7.20 (m, 1H, Ar), 7.20-7.26 (m, J=8.1 Hz, 2H, Ar), 7.26-7.36 (m, 4H, Ar), 7.42-7.54 (m, 3H, Ar), 7.62 (s, 1H, NH), 7.64-7.75 (m, 2H, Ar), 10.96 (s, 1H, NH); ¹³C NMR (DMSO-d₆) δ 12.76, 22.31, 31.16, 45.04, 48.59, 51.55, 69.17, 114.93, 115.25, 116.49, 123.92, 125.88, 127.15, 128.14, 128.36, 129.78, 129.95, 133.30, 134.58, 135.98, 137.15, 138.50, 144.57, 153.39, 167.97, 170.93, 172.80; LCMS MH=521; Anal. Calcd for C₃₁H₂₈N₄O₄+0.3 H₂O: C, 70.79; H, 5.48; N, 10.65; Found: C, 70.68; H, 5.21; N, 10.52. The regio isomeric structure was confirmed by ROESY.

5.87 2-{4-[2-(2,6-Dioxo-Piperidin-3-yl)-1-Oxo-2,3-Dihydro-1H-Isoindol-4-yloxymethyl]-Benzyl}-1,2,3,4-Tetrahydro-Isoquinoline-7-Carbonitrile

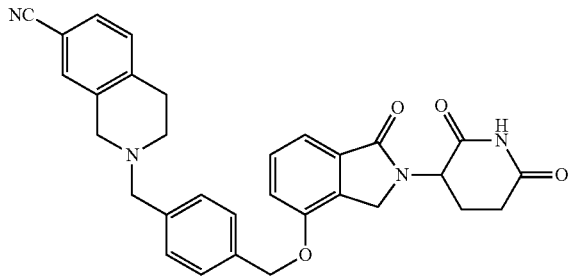 [SMILES: N#Cc1ccc2c(c1)CN(Cc1ccc(COc3cccc4c3CN(C3CCC(=O)NC3=O)C4=O)cc1)CC2]

To the CH₃CN (10 ml) solution of 3-(4-(4-(bromomethyl)benzyloxy)-1-oxoisoindolin-2-yl)piperidine-2,6-dione (0.358 g, 0.808 mmol) was added 1,2,3,4-tetrahydroisoquinoline-7-carbonitrile (0.192 g, 1.211 mmol), a suspension formed. Then N-ethyl-N-isopropylpropan-2-amine (0.267 ml, 1.615 mmol) was added, which became a clear solution. It became turbid again in 10 minutes. The mixture was stirred at room temperature overnight. Solvent was evaporated, to the resulting solid was added ether (30 ml), stirred, filtered and the filter was purified by silica gel column (MeOH/CH₂Cl₂) to give 2-{4-[2-(2,6-Dioxo-piperidin-3-yl)-1-oxo-2,3-dihydro-1H-isoindol-4-yloxymethyl]-benzyl}-1,2,3,4-tetrahydro-isoquinoline-7-carbonitrile (0.324 g, 77% yield); mp, 145-147° C. HPLC: Waters Symmetry C-18, 3.9×150 mm, 5 μm, 1 mL/min, 240 nm, gradient from 10/90 to 90/10 in 5 min, isocratic at 90/10 for 5 min (CH₃CN/0.1% H₃PO₄), 4.62 min (95.8%). ¹H NMR (DMSO-d₆) δ 1.92-2.06 (m, 1H, CHH), 2.35-2.48 (m, 1H, CHH), 2.53-2.64 (m, 1H, CHH), 2.64-2.75 (m, 2H, CH₂), 2.82-3.00 (m, 3H, CHH, CH₂), 3.58 (s, 2H, CH₂), 3.67 (s, 2H, CH₂), 4.20-4.48 (m, 2H, CH₂), 5.12 (dd, J=5.1, 13.2 Hz, 1H, NCH), 5.24 (s, 2H, CH₂), 7.26-7.42 (m, 5H, Ar), 7.43-7.61 (m, 5H, Ar), 10.97 (s, 1H, NH). ¹³C NMR (DMSO-d₆) δ 28.88, 31.20, 45.09, 49.39, 61.14, 69.42, 108.23, 114.98, 115.24, 119.01, 127.77, 128.80, 129.49, 129.69, 129.82, 129.94, 130.32, 133.31, 135.38, 136.40, 137.99, 140.51, 153.51, 168.01, 170.98, 172.83. LC/MS m/e=521. Anal Calcd for C₃₁H₂₈N₄O₄ (+0.8 H₂O): C, 69.60; H, 5.58; N, 10.47. Found: C, 69.21; H, 5.21; N, 10.22.

5.88 3-(4-((5-(Morpholinomethyl)Pyridin-2-yl)Methoxy)-1-Oxoisoindolin-2-yl)Piperidine-2,6-Dione

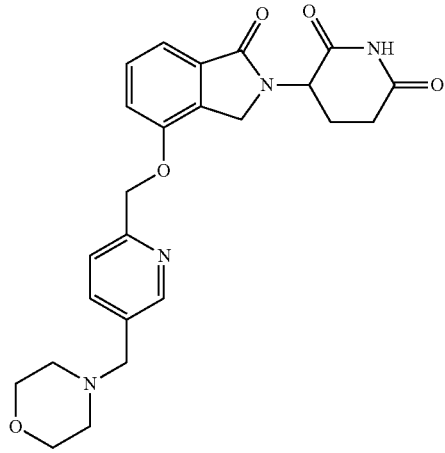 [SMILES: O=C1CCC(N2Cc3c(OCc4ccc(CN5CCOCC5)cn4)cccc3C2=O)C(=O)N1]

Step 1: A solution of methyl 5-(chloromethyl)picolinate (3.00 g, 16.14 mmol) in acetonitrile (30 mL) was added to morpholine (4.5 mL, 51.7 mmol). The resulting dark solution was stirred at room temperature for 3 h. The reaction mixture was diluted with Et₂O (~100 mL) and the solid that formed was removed by filtration. The filtrate was concentrated and the oily residue was partitioned between EtOAc (125 mL) and 1N NaHCO₃ (50 mL). The aqueous layer was washed with more EtOAc (~100 mL). The combined organic layers was washed with brine, dried (Na₂SO₄), and concentrated in vacuo to give methyl 5-(morpholinomethyl)picolinate as a dark oil (3.4 g, 89% yield). ¹H NMR (DMSO-d₆) δ 2.29-2.42 (m, 4H, CH₂, CH₂), 3.54-3.61 (m, 6H, CH₂, CH₂, CH₂), 3.88 (s, 3H, CH₃), 7.91 (dd, J=2.2, 8.0 Hz, 1H, Pyr), 8.03 (d, J=8.5 Hz, 1H, Pyr), 8.64 (d, J=1.5 Hz, 1H, Pyr); ¹³C NMR (DMSO-d₆) δ 52.28, 53.02, 59.03, 66.08, 124.51, 137.47, 137.57, 146.28, 150.08, 165.11. The product was used in the next step without further purification.

Step 2: To a well stirred solution of methyl 5-(morpholinomethyl)picolinate (3.4 g, 14.39 mmol) in THF (30 ml) at 2° C. (in ice bath), a 1 M solution of lithium aluminum hydride (15.83 ml, 15.83 mmol) in THF was added via a syringe. Gas evolved and the reaction mixture changed was stirred at ~2° C. for ~1 h. The reaction was quenched by slow addition of 1N NaHCO₃ (20 mL) at 0° C. and then diluted with EtOAc (~300 mL) and H₂O (100 mL). The mixture was agitated and then 1 N aq. solution of Rochelle's salt was added to break up emulsion. The aqueous layer was extracted with EtOAc (300 mL). The aqueous layer was saturated with solid NaCl and extracted once more with EtOAc. The combined organic layer was washed with minimal brine, dried (Na₂SO₄), and concentrated in vacuo to give the crude (5-(morpholinomethyl)pyridin-2-yl)methanol as an orange oil (1.7 g, 56% crude yield). The crude product was used in the next step without purification. ¹H NMR (DMSO-d₆) δ 2.30-2.38 (m, 4H, CH₂, CH₂), 3.47 (s, 2H, CH₂), 3.51-3.63 (m, 4H, CH₂, CH₂), 4.54 (d, J=5.5 Hz, 2H, CH₂OH), 5.36 (t, J=5.8 Hz, 1H, OH), 7.42 (d, J=7.9 Hz, 1H, Pyr), 7.70 (dd, J=2.2, 8.0 Hz, 1H, Pyr), 8.38 (d, J=1.7 Hz, 1H, Pyr).

Step 3: Methyl 5-amino-4-(4-hydroxy-1-oxoisoindolin-2-yl)-5-oxopentanoate (1.0 g, 3.42 mmol) and triphenyl phosphine on polystyrene (1.6 mmol/g resin) (4.28 g, 6.84 mmol) were slurried in THF (30 mL) at room temperature. The resin was allowed to swell with gentle stirring for about 5 minutes then the mixture was cooled in ice bath at 0° C. and DIAD (1.330 mL, 6.84 mmol) was added using a syringe in a rapid dropwise fashion. After about 10 minutes, (5-(morpholinomethyl)pyridin-2-yl)methanol (1.069 g, 5.13 mmol) in THF (5 mL) was added. The resulting mixture was stirred at room temperature. After about 1.5 h, the resin was filtered on a course fritted funnel and the resin was rinsed 3× with successive swell/shrink cycles (DCM/MeOH washes). The filtrate (amber color) was concentrated in vacuo to give the crude methyl 5-amino-4-((5-(morpholinomethyl)pyridin-2-yl)methoxy)-1-oxoisoindolin-2-yl)-5-oxopentanoate as a brown oil (3.3 g). The crude product was used in the next step without further purification.

Step 4: To a stirred solution of crude methyl 5-amino-4-(4-((5-(morpholinomethyl)pyridin-2-yl)methoxy)-1-oxoisoindolin-2-yl)-5-oxopentanoate (1 g, 1.036 mmol) in dry THF (10 mL) at 0° C. (ice bath) was added potassium tert-butoxide (0.233 g, 2.072 mmol). The resulting mixture was stirred at 0° C. for ~10 min, then allowed to warm up to rt. After ~3 h, the reaction mixture was transferred to a chilled solution of 20% AcOH in MeCN (~50 mL) on ice. The resulting solution was concentrated to dryness and the brown oily residue was partitioned between EtOAc (150 mL) and 1N NaHCO$_3$ (35 mL). The aqueous layer was extracted with additional EtOAc (~150 mL). The combined organic layer was washed with brine, dried (Na$_2$SO$_4$), and concentrated to dryness to give a glassy solid. The solid was recrystallized from MeCN/Et$_2$O, filtered, and washed with additional Et$_2$O to give 3-(4-((5-(morpholinomethyl)pyridin-2-yl)methoxy)-1-oxoisoindolin-2-yl)piperidine-2,6-dione as a light tan solid (78 mg, 17% yield): HPLC: Waters Symmetry C$_{18}$, 5 μm, 3.9×150 mm, 1 ml/min, 240 nm, 10/90 CH$_3$CN/0.1% H$_3$PO$_4$, 6.45 min (97.3%); mp: 194-196° C.; $^1$H NMR (DMSO-d$_6$) δ 1.91-2.05 (m, 1H, CHH), 2.30-2.41 (m, 4H, CH$_2$, CH$_2$), 2.40-2.48 (m, 1H, CHH), 2.55-2.67 (m, 1H, CHH), 2.82-3.01 (m, 1H, CHH), 3.51 (br. s., 2H, CH$_2$N), 3.53-3.70 (m, 4H, CH$_2$, CH$_2$), 4.30 (d, J=17.6 Hz, 1H, CHH), 4.46 (d, J=17.6 Hz, 1H, CHH), 5.12 (dd, J=5.1, 13.2 Hz, 1H, CH), 5.31 (s, 2H, CH$_2$O), 7.25-7.39 (m, 2H, Ar), 7.43-7.52 (m, 1H, Ar), 7.55 (d, J=7.9 Hz, 1H, Ar), 7.76 (d, J=7.6 Hz, 1H, Ar), 8.50 (s, 1H, Ar), 10.98 (s, 1H, NH); $^{13}$C NMR (DMSO-d$_6$) δ 22.36, 31.16, 45.06, 51.56, 52.96, 59.16, 66.08, 70.37, 114.96, 115.41, 121.31, 129.84, 129.92, 132.53, 133.34, 137.50, 149.56, 153.27, 155.02, 167.94, 170.96, 172.83; LCMS: MH=451; Anal Calcd for: C$_{24}$H$_{26}$N$_4$O$_5$: C, 63.99; H, 5.82; N, 12.44; Found: C, 58.77; H, 5.34; N, 11.46; Cl, 1.10.

5.89 4-Carbamoyl-4-(4-Hydroxy-1-Oxo-1,3-Dihydro-Isoindol-2-yl)-Butyric Acid Methyl Ester Formic Acid Step 1: Preparation of 4-Carbamoyl-4-[4-(4-morpholin-4-ylmethyl-benzyloxy)-1-oxo-1,3-dihydro-isoindol-2-yl]-butyric acid methyl ester Polymer-supported triphenylphosphene (1.6 mmol/g, 3.0 g, 3.78 mmol) was added to a stirred solution of 4-carbamoyl-4-(4-hydroxy-1-oxo-1,3-dihydro-isoindol-2-yl)-butyric acid methyl ester (0.50 g, 1.72 mmol) in THF (30 mL) at 0° C. After 5 minutes, diisopropyl diazene-1,2-dicarboxylate (0.75 ml, 3.78 mmol) was added. After 30 minutes, (4-Morpholin-4-ylmethyl-phenyl)-methanol (0.71 g, 3.43 mmol) was added. The mixture was stirred overnight at room temperature then filtered, washed w/ MeOH (10 mL), methylene chloride (10 mL), and repeated three more times w/ MeOH (10 mL), methylene chloride (10 mL). The combined filtrate was evaporated in vacuo to give an oil, which was purified by ISCO flash column chromatography (120 g, MeOH/CH$_2$Cl$_2$ gradient from 0% to 5% in 60 min) to give 4-Carbamoyl-4-[4-(4-morpholin-4-ylmethyl-benzyloxy)-1-oxo-1,3-dihydro-isoindol-2-yl]-butyric acid methyl ester as a foamy white solid (0.62 g, 75% yield). It was used in the next step without further purification.

Step 2: Preparation of 3-[4-(4-Morpholin-4-ylmethyl-benzyloxy)-1-oxo-1,3-dihydro-isoindol-2-yl]-piperidine-2,6-dione Potassium tert-butoxide (0.14 g, 1.25 mmol) was added to a stirred solution of 4-Carbamoyl-4-[4-(4-morpholin-4-ylmethyl-benzyloxy)-1-oxo-1,3-dihydro-isoindol-2-yl]-butyric acid methyl ester (0.60 g, 1.25 mmol) in THF (15 mL) at 0° C. for 10 minutes. The mixture was quenched with a couple pipetful of 1N HCl and neutralized with saturated sodium bicarbonate to pH=8. The mixture was ethyl acetate (3×20 mL). The combined ethyl acetate phases were evaporated and then purified by ISCO flash column chromatography (40 g, MeOH/CH$_2$Cl$_2$ gradient from 0% to 5% in 40 min) to give 3-[4-(4-Morpholin-4-ylmethyl-benzyloxy)-1-oxo-1,3-dihydro-isoindol-2-yl]-piperidine-2,6-dione as an off-white solid (0.13 g, 23% yield); mp, 208-210° C. HPLC: Waters Symmetry C-18, 3.9×150 mm, 5 μm, 1 mL/min, 240 nm, isocratic at 15/85 in 10 min (CH$_3$CN/0.1% H$_3$PO$_4$): t$_R$=3.86 min (98.1%). LC/MS (Acquity UPLC BEH C18, 2.1×50 mm, 0.8 mL/min, 1.7 μm, 5/95 gradient to 85/15 in 5 min, isocratic at 85/15 for 1 min (CH$_3$CN/0.1% HCOOH: water/0.1% HCOOH)): m/e=450. $^1$H NMR (DMSO-d$_6$) δ 1.90-2.05 (m, 1H, CH), 2.28-2.40 (m, 4H, $_2$CH$_2$), 2.40-2.46 (m, 1H, CH), 2.54-2.65 (m, 1H, CH), 2.82-3.00 (m, 1H, CH), 3.46 (s, 2H, CH$_2$), 3.51-3.65 (m, 4H, $_2$CH$_2$), 4.20-4.48 (m, 2H, ArCH$_2$), 5.11 (dd, J=5.1, 13.2 Hz, 1H, NCH), 5.23 (s, 2H, ArCH$_2$O), 7.33 (d, J=7.6 Hz, 4H, Arh), 7.39-7.55 (m, 3H, ArH), 10.97 (s, 1H, NH). $^{13}$C NMR (DMSO-d$_6$) δ 22.36, 31.20, 45.09, 51.58, 53.20, 62.10, 66.17, 69.41, 114.98, 115.24, 127.65, 128.99, 129.82, 129.95, 133.32, 135.30, 137.70, 153.50, 167.99, 170.98, 172.83. Anal Calcd for C$_{25}$H$_{27}$N$_3$O$_5$. C, 66.80; H, 6.05; N, 9.35. Found: C, 66.49; H, 5.90; N, 9.29.

Step 3: Preparation of 4-Carbamoyl-4-(4-hydroxy-1-oxo-1,3-dihydro-isoindol-2-yl)-butyric acid methyl ester formic acid Hydrogen peroxide (10.24 g, 90.2 mmol) was added to a stirred solution of 3-(4-(4-(morpholinomethyl)benzyloxy)-1-oxoisoindolin-2-yl)piperidine-2,6-dione (0.507 g, 1.128 mmol) in acetonitrile (30 ml) and Water (10 ml) at room temperature. The solution was stirred at room temperature overnight. Solvent was evaporated and the residue was purified by preparative HPLC (MeCN/water, with 0.1% HCOOH) to give 4-Carbamoyl-4-(4-hydroxy-1-oxo-1,3-dihydro-isoindol-2-yl)-butyric acid methyl ester formic acid (0.23 g, 44% yield); mp, 154-156° C. HPLC: Waters Symmetry C-18, 3.9×150 mm, 5 μm, 1 mL/min, 240 nm, gradient from 10/90 to 90/10 in 5 min, isocratic at 90/10 for 5 min (CH$_3$CN/0.1% H$_3$PO$_4$), 4.35 min (98.7%). $^1$H NMR

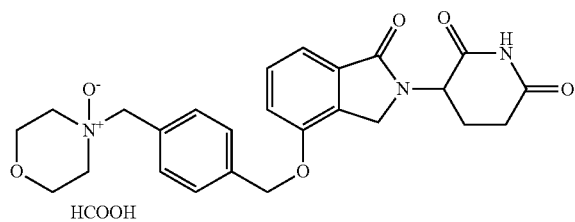 [SMILES: O=C1CCC(N2Cc3c(OCc4ccc(C[N+]5([O-])CCOCC5)cc4)cccc3C2=O)C(=O)N1 ; "HCOOH"]

(DMSO-d$_6$) δ 1.91-2.05 (m, 1H, CHH), 2.35-2.48 (m, 1H, CHH), 2.53-2.65 (m, 1H, CHH), 2.83-2.99 (m, 1H, CHH), 3.04 (d, J=12.3 Hz, 2H, CH$_2$), 3.54 (td, J=3.8, 11.8 Hz, 2H, CH$_2$), 3.71-3.82 (m, 2H, CH$_2$), 3.92-4.07 (m, 2H, CH$_2$), 4.22-4.49 (m, 2H, CH$_2$), 4.63 (s, 2H, CH$_2$), 5.11 (dd, J=5.2, 13.3 Hz, 1H, NCH), 5.28 (s, 2H, CH$_2$), 7.29-7.38 (m, 2H, Ar), 7.44-7.66 (m, 5H, Ar), 11.02 (s, 1H, NH). $^{13}$C NMR (DMSO-d$_6$) δ 22.38, 31.20, 45.08, 51.59, 60.67, 62.05, 69.15, 71.81, 114.95, 115.33, 127.21, 128.77, 129.84, 129.97, 133.12, 133.35, 137.87, 153.40, 164.93, 167.98, 170.98, 172.83. LC/MS m/e=466. Anal Calcd for C$_{25}$H$_{27}$N$_3$O$_6$ ((+1.0HCOOH, +1.3H$_2$O): C, 58.38; H, 5.95; N, 7.85. Found: C, 58.21; H, 6.30; N, 7.81.

5.90 3-(4-((5-(Morpholinomethyl)Isoxazol-3-yl)Methoxy)-1-Oxoisoindolin-2-yl)Piperidine-2,6-Dione

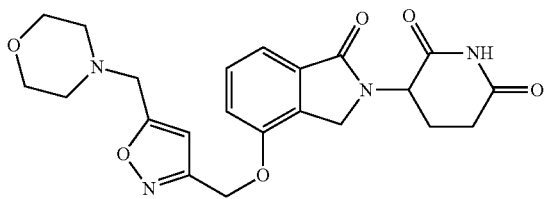 [SMILES: O=C1CCC(N2Cc3c(OCc4cc(CN5CCOCC5)on4)cccc3C2=O)C(=O)N1]

Step 1: ethyl 5-(hydroxymethyl)isoxazole-3-carboxylate (2 g, 11.69 mmol) was dissolved in DCM (30 ml) and triphenylphosphine (3.37 g, 12.85 mmol) and CBr$_4$ (3.68 g, 11.10 mmol) were added at 0° C., The mixture was stirred for 2 hours at 0° C. The mixture was concentrated under vacuum, the residue was purified by ISCO (80 g column, ethyl acetate in hexanes gradient from o-20% in 40 min) to give ethyl 5-(bromomethyl)isoxazole-3-carboxylate (2.5 g, 91% yield); $^1$H NMR (CHLOROFORM-d) δ 1.43 (t, J=7.1 Hz, 3H, CH$_3$), 4.46 (q, J=7.2 Hz, 2H, CH$_2$), 4.50 (s, 2H, CH$_2$), 6.74 (s, 1H, Ar).

Step 2: The mixture of ethyl 5-(bromomethyl)isoxazole-3-carboxylate (2.3 g, 9.83 mmol), morpholine (1.284 ml, 14.74 mmol) and triethyl amine (2.055 ml, 14.74 mmol) in acetonitrile was stirred at room temperature overnight. The solvent was evaporated to dryness under vacuum, the residue was partitioned between ethyl acetate (100 mL) and saturated sodium bicarbonate (30 mL), the organic layer was separated and washed with brine, dried over MgSO$_4$, the solvent was removed under reduced pressure to give ethyl 5-(morpholinomethyl)isoxazole-3-carboxylate (2.3 g, 95% yield); $^1$H NMR (CHLOROFORM-d) δ 1.43 (t, J=7.2 Hz, 3H, CH$_3$), 2.45-2.64 (m, 4H, CH$_2$, CH$_2$), 3.67-3.81 (m, 6H, CH$_2$, CH$_2$, CH$_2$), 4.45 (q, J=7.2 Hz, 2H, CH$_2$), 6.65 (s, 1H, Ar).

Step 3: To the solution of ethyl 5-(morpholinomethyl) isoxazole-3-carboxylate (2.3 g, 9.57 mmol) in THF (50 mL) was added Dibal-H (28.7 ml, 28.7 mmol) at 0° C. The formed mixture was warmed up to room temperature and stirred at room temperature. The mixture was quenched with 1M Rochelle's salt and extracted with EtOAc (3×50) mL, the combined organic layer was washed with saturated sodium bicarbonate, brine and dried over magnesium sulfate. The organic solvent was evaporated to give (5-(morpholinomethyl)isoxazol-3-yl)methanol (1.48 g, 78% yield); $^1$H NMR (CHLOROFORM-d) δ 2.50-2.66 (m, 4H, CH$_2$), 3.70 (s, 2H, CH$_2$), 3.72-3.82 (m, 4H, CH$_2$, CH$_2$), 4.76 (br. s., 2H, CH$_2$), 6.29 (s, 1H, Ar).

Step 3: A mixture of (5-(morpholinomethyl)isoxazol-3-yl)methanol (740 mg, 3.73 mmol), methyl 5-amino-4-(4-hydroxy-1-oxoisoindolin-2-yl)-5-oxopentanoate (1091 mg, 3.73 mmol) and polymer supported triphenylphosphine (1.86 g, 5.6 mmol, 3 mmol/g) in THF (100 mL) was cooled to 0° C., and DIAD (1132 mg, 5.6 mmol) was added, The formed mixture was stirred at room temperature overnight. The reaction mixture was filtered through celite, the resin was washed with ethyl acetate (5×200 mL), the combined organic layer was evaporated to dryness, the residue was purified by ISCO (80 g column, MeOH in DCM gradient from 0-5% in 50 min) to give methyl 5-amino-4-(4-((5-(morpholinomethyl)isoxazol-3-yl)methoxy)-1-oxoisoindolin-2-yl)-5-oxopentanoate (600 mg, 34% yield); $^1$H NMR (DMSO-d$_6$) δ 1.98-2.32 (m, 4H, CH$_2$, CH$_2$), 2.36-2.45 (m, 4H, CH$_2$, CH$_2$), 3.50 (s, 3H, CH$_3$), 3.53-3.62 (m, 4H, CH$_2$, CH$_2$), 3.69 (s, 2H, CH$_2$), 4.29-4.60 (m, 2H, CH$_2$), 4.66-4.82 (m, 1H, CH), 5.33 (s, 2H, CH$_2$), 6.59 (s, 1H, Ar), 7.19 (s, 1H, NHH), 7.33 (dd, J=4.2, 7.6 Hz, 2H, Ar), 7.47 (d, J=7.6 Hz, 1H, Ar), 7.59 (s, 1H, NHH.

Step 4: To a mixture of methyl 5-amino-4-(4-((5-(morpholinomethyl)isoxazol-3-yl)methoxy)-1-oxoisoindolin-2-yl)-5-oxopentanoate (580 mg, 1.228 mmol) in THF (30 ml) was added potassium tert-butoxide (152 mg, 1.350 mmol) at 0° C. The formed mixture was stirred at 0° C. for 0.5 hour and warmed up to room temperature in 0.5 hour. The reaction was quenched with HCl (1N, 3 mL), THF was evaporated under vacuum, saturated sodium bicarbonate (20 mL) was added, the formed precipitate was collected by filtration and reslurried in acetonitrile (7 mL) to give 3-(4-((5-(morpholinomethyl)isoxa-zol-3-yl)methoxy)-1-oxoisoindolin-2-yl)piperidine-2,6-dione as a white solid (325 mg, 60 yield); mp 218-220° C. HPLC: (Waters Xterra C-18, 3.9×150 mm, 5 µm, 1 mL/min, 240 nm, 25/75 CH$_3$CN/0.1% HCOONH$_4$): 3.45 (98.98%). $^1$H NMR (DMSO-d$_6$) δ 1.86-2.08 (m, 1H), 2.31-2.48 (m, 5H), 2.52-2.68 (m, 1H), 2.81-3.01 (m, 1H), 3.48-3.64 (m, 4H), 3.69 (s, 2H), 4.26 (d, J=17.6 Hz, 1H), 4.34-4.53 (m, J=17.6 Hz, 1H), 5.11 (dd, J=5.1, 13.2 Hz, 1H), 5.34 (s, 2H), 6.57 (s, 1H), 7.25-7.43 (m, 2H), 7.44-7.59 (m, 1H), 10.98 (s, 1H). $^{13}$C NMR (DMSO-d$_6$) δ 22.38, 31.20, 45.03, 51.61, 52.51, 52.73, 61.62, 66.03, 103.25, 115.13, 115.83, 129.87, 130.01, 133.42, 152.95, 160.09, 167.86, 169.84, 170.94, 172.82. Anal. Calcd for C$_{22}$H$_{24}$N$_4$O$_6$: C, 59.99%; H, 5.49%; N, 12.72%; Found: C, 59.00%; H, 5.03%; N, 12.14%.

5.91 3-(4-((3-Methylisoxazol-5-yl)Methoxy)-1-Oxoisoindolin-2-yl)Piperidine-2,6-Dione

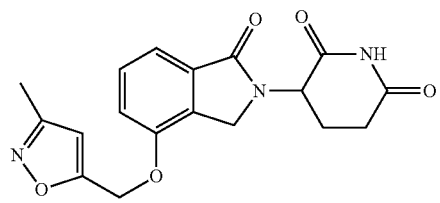 [SMILES: Cc1cc(COc2cccc3c2CN(C2CCC(=O)NC2=O)C3=O)on1]

Step 1: A mixture of methyl 5-amino-4-(4-hydroxy-1-oxoisoindolin-2-yl)-5-oxopentanoate (1 g, 3.42 mmol) and (3-methylisoxazol-5-yl)methanol (0.387 g, 3.42 mmol) in THF (50 mL) was cooled to 0° C. Triphenylphosphine, polymer-bound, 3 mmol/g (2.3 g, 6.84 mmol) was added, followed by DIAD (1.347 ml, 6.84 mmol). The ice bath was allowed to melt and the mixture stirred at ambient temperature for 16 h. The mixture was evaporated to dryness and the residue was loaded dry-loaded directly onto a silica gel column, running a hexanes-EtOAc gradient. The product eluted at 100% EtOAc, and the yield of the crude mixture thus obtained was 0.75 g (57%).

Step 2: The residue from step 1 was dissolved in THF (50 mL) and cooled to 0° C. Then, potassium tert-butoxide (0.230 g, 2.053 mmol) was added. After 30 min, the reaction was quenched by the addition of AcOH (0.5 mL) and the mixture was evaporated under vacuum. Then the mixture was suspended in a mixture of EtOAc (100 mL) and 10% aqueous sodium carbonate solution (100 mL), and this biphasic mixture was stirred for 1 h, and then filtered, and the filter was washed with water (50 mL) and ethyl acetate (50 mL). After drying under vacuum, the product was obtained as a white solid, 510 mg, in 42% yield; mp 278-280° C. HPLC: Waters Symmetry C-18, 3.9×150 mm, 5 μm, 1 mL/min, 240 nm, 30/70 $CH_3CN/0.1\%$ $H_3PO_4$: 3.27 (96.63%). $^1$H NMR (DMSO-$d_6$) δ 1.91-2.07 (m, 1H), 2.24 (s, 3H), 2.34-2.48 (m, 1H), 2.52-2.68 (m, 1H), 2.80-3.01 (m, 1H), 4.24 (d, J=17.6 Hz, 1H), 4.33-4.47 (m, J=17.6 Hz, 1H), 5.10 (dd, J=4.9, 13.0 Hz, 1H), 5.40 (s, 2H), 6.54 (s, 1H), 7.28-7.45 (m, 2H), 7.46-7.60 (m, 1H), 10.99 (s, 1H). $^{13}$C NMR (DMSO-$d_6$) δ 10.89, 22.39, 31.24, 45.00, 51.64, 60.65, 105.05, 115.03, 115.93, 129.85, 129.95, 133.51, 152.68, 159.68, 166.88, 167.83, 171.05, 172.96. Anal. Calcd for $C_{18}H_{17}N_3O_5+0.3$ $CH_2Cl_2$: C, 57.72%; H, 4.66%; N, 11.03%; Found: C, 57.61%; H, 4.47%; N, 10.70%.

5.92 3-(1-Oxo-4-((4-((3-(Trifluoromethyl)-5,6-Dihydro-[1,2,4]Triazolo[4,3-A]Pyrazin-7(8H)-yl) Methyl)Benzyl)Oxy)Isoindolin-2-yl)Piperidine-2,6-Dione

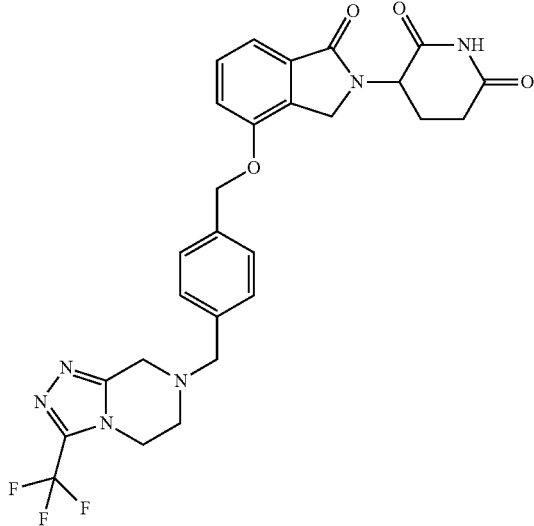 [SMILES: O=C1CCC(N2Cc3c(OCc4ccc(CN5CCn6c(nnc6C(F)(F)F)C5)cc4)cccc3C2=O)C(=O)N1]

To a mixture of 3-(4-(4-(bromomethyl)benzyloxy)-1-oxoisoindolin-2-yl)piperidine-2,6-dione (200 mg, 0.451 mmol) and 3-(trifluoromethyl)-5,6,7,8-tetrahydro-[1,2,4]triazolo[4,3-a]pyrazine hydrochloride (113 mg, 0.496 mmol) in dry MeCN (5 mL, 96 mmol), was added DIEA (0.276 mL, 1.579 mmol) at room temperature and then resulting mix was stirred at room temperature overnight. To the mixture was added tetrabutylammonium bromide (10.18 mg, 0.032 mmol) and raised temp to 40° C. over weekend. The reaction mixture was transferred portionwise with stirring to a flask with water (~50 mL). The resulting suspension was stirred at room temperature with intermittent sonication to break up solid aggregates. After ~1 h of stirring the solid was filtered and washed with small portion of water. The crude mixture was purified by Prep HPLC to give 3-(1-oxo-4-((4-((3-(trifluoromethyl)-5,6-dihydro-[1,2,4]triazolo[4,3-a]pyrazin-7(8H)-yl)methyl)benzyl)oxy)isoindolin-2-yl)piperidine-2,6-dione as an off-white solid (120 mg, 48% yield): HPLC: Waters Symmetry $C_{18}$, 5 Lm, 3.9×150 mm, 1 ml/min, 240 nm, 35/65 $CH_3CN/0.1\%$ $H_3PO_4$, 4.86 min (97.7%); mp: 142-144° C.; $^1$H NMR (DMSO-$d_6$) δ 1.91-2.04 (m, OH, CHH), 2.45 (dd, J=4.3, 13.0 Hz, OH, CHH), 2.57 (dd, J=2.3, 15.5 Hz, OH, CHH), 2.81-2.99 (m, 3H, $CH_2$, CHH), 3.78 (s, 2H, $CH_2$), 3.84 (s, 2H, $CH_2$), 4.15 (t, J=5.4 Hz, 2H, $CH_2$), 4.26 (d, J=17.6 Hz, 1H, CHH), 4.42 (d, J=17.6 Hz, 1H, CHH), 5.11 (dd, J=5.1, 13.2 Hz, 1H, CH), 5.25 (s, 2H, $CH_2$), 7.33 (d, J=7.6 Hz, 2H, Ar), 7.38-7.44 (m, 2H, Ar), 7.45-7.58 (m, 3H, Ar), 10.97 (s, 1H, NH); $^{13}$C NMR (DMSO-$d_6$) δ 22.34, 31.16, 43.03, 45.06, 47.30, 48.09, 51.56, 59.51, 69.35, 114.99, 115.23, 116.80 (q, J=269.6 Hz, $M_{10}$), 127.79, 128.94, 129.78, 129.93, 133.30, 135.75, 136.99, 142.31 (q, J=38.5 Hz, $M_{24}$), 152.28, 153.46, 167.97, 170.95, 172.80; LCMS: MH=555; Anal Calcd for $C_{27}H_{25}F_3N_6O_4+0.75$ $H_2O$: C, 57.09; H, 4.70; N, 14.79; F, 10.03; Found: C, 57.09; H, 4.55; N, 14.74; F, 9.76.

5.93 1'-{4-[2-(2,6-Dioxo-Piperidin-3-yl)-1-Oxo-2,3-Dihydro-1H-Isoindol-4-yloxymethyl]-Benzyl}-[2,4'] Bipyridinyl-1'-Ium Formate

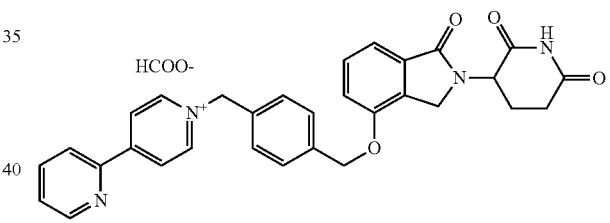

To the $CH_2Cl_2$ (10 ml) solution of 3-(4-(4-(bromomethyl)benzyloxy)-1-oxoisoindolin-2-yl)piperidine-2,6-dione (0.52 g, 1.173 mmol) was added 2,4'-bipyridine (0.220 g, 1.408 mmol) and N-ethyl-N-isopropylpropan-2-amine (0.388 ml, 2.346 mmol). It was a light green clear solution and was stirred at room temperature overnight. The oily solid/oil was stirred in water (20 ml) and $CH_2Cl_2$ (25 ml) for one hour. The aq phase was separated and further washed with $CH_2Cl_2$ (2×30 ml). The combined $CH_2Cl_2$ phases were extracted with water (2×10 ml). The combined water phases were evaporated in a 50° C. water bath to give an off white solid, which was purified by preparative HPLC (MeCN/water in 0.1% HCOOH) to give 1'-{4-[2-(2,6-Dioxo-piperidin-3-yl)-1-oxo-2,3-dihydro-1H-isoindol-4-yloxymethyl]-benzyl}-[2,4']bipyridinyl-1'-ium formate (0.213 g, 35% yield); mp, 132-134° C. HPLC: Waters Symmetry C-18, 3.9×150 mm, 5 μm, 1 mL/min, 240 nm, gradient from 10/90 to 90/10 in 5 min, isocratic at 90/10 in 5 min ($CH_3CN/0.1\%$ $H_3PO_4$), 4.58 min (96.3%). $^1$H NMR (DMSO-$d_6$) δ 1.92-2.05 (m, 1H, CHH), 2.33-2.48 (m, 1H, CHH), 2.53-2.65 (m, 1H, CHH), 2.83-3.00 (m, 1H, CHH), 4.17-4.48 (m, 2H, $CH_2$), 5.11 (dd, J=5.1, 13.2 Hz, 1H, NCH), 5.28 (s, 2H, $CH_2$), 5.91 (s, 2H, $CH_2$), 7.27-7.37 (m, 2H, Ar), 7.43-7.52 (m, 1H, Ar), 7.54-7.64 (m, 4H, Ar), 7.64-7.72 (m, 1H, Ar), 8.08-8.18 (m, 1H, Ar), 8.39-8.50 (m, 2H, Ar), 8.77-8.92 (m, 3H, Ar), 9.33 (d, J=6.8 Hz, 2H, Ar), 10.99 (br. s., 1H, NH). $^{13}$C NMR (DMSO-d$_6$) δ 22.38, 31.18, 45.03, 51.58, 62.47, 68.94, 114.97, 115.36, 123.50, 124.75, 126.66, 128.41, 128.92, 129.82, 129.94, 133.34, 134.04, 137.93, 138.21, 145.31, 149.68, 150.64, 153.22, 153.30, 164.91, 167.93, 170.95, 172.82. LC/MS m/e=519, 520. Anal Calcd for C$_{31}$H$_{27}$N$_4$O$_4^+$·HCOO$^-$: C, 68.08; H, 5.00; N, 9.92. Found: C, 61.92; H, 5.05; N, 8.98.

5.94 2-(2,6-Dioxopiperidin-3-yl)-4-((4-((2-(Trifluoromethyl)-5,6-Dihydroimidazo[1,2-A]Pyrazin-7(8H)-yl)Methyl)Benzyl)Oxy)Isoindoline-1,3-Dione

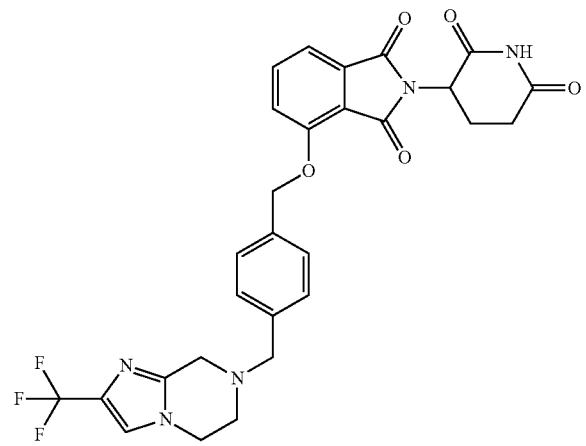 [SMILES: O=C1CCC(N2C(=O)c3cccc(OCc4ccc(CN5CCn6cc(C(F)(F)F)nc6C5)cc4)c3C2=O)C(=O)N1]

To a mixture of 4-(4-(bromomethyl)benzyloxy)-2-(2,6-dioxopiperidin-3-yl)isoindoline-1,3-dione (250 mg, 0.547 mmol) and 2-(trifluoromethyl)-5,6,7,8-tetrahydroimidazo[1,2-a]pyrazine hydrochloride (137 mg, 0.601 mmol) in dry MeCN (10 mL), was added DIEA (0.334 mL, 1.914 mmol) and the resulting slurry was stirred at room temperature for 3 days. Water was added in portions (~35 mL total) to form a precipitate. The mixture was extensively sonicated with gentle warming and then stirred for several hours at room temperature until a finely dispersed solid was obtained. The mixture was filtered on a medium fritted funnel and the cake was washed with additional water (~50 mL), suction dried, and placed in a vacuum oven at 50° C. overnight to give to give 2-(2,6-dioxopiperidin-3-yl)-4-((4-((2-(trifluoromethyl)-5,6-dihydroimidazo[1,2-a]pyrazin-7(8H)-yl)methyl)benzyl)-oxy)isoindoline-1,3-dione as a light tan solid (275 mg, 89% yield): HPLC: Waters Symmetry C$_{18}$, 5 μm, 3.9×150 mm, 1 ml/min, 240 nm, 30/70 CH$_3$CN/0.1% H$_3$PO$_4$, 4.44 min (97.2%); mp: 178-180° C.; $^1$H NMR (DMSO-d$_6$) δ 1.95-2.14 (m, 1H, CHH), 2.42-2.66 (m, 2H, CHH, CHH), 2.80-2.99 (m, 3H, CH$_2$, CHH), 3.62 (s, 2H, CH$_2$), 3.74 (s, 2H, CH$_2$), 4.02 (t, J=5.4 Hz, 2H, CH$_2$), 5.09 (dd, J=5.3, 12.8 Hz, 1H, CH), 5.37 (s, 2H, CH$_2$), 7.35-7.44 (m, 2H, Ar), 7.49 (t, 3H, Ar), 7.61 (d, J=8.5 Hz, 1H, Ar), 7.73 (d, J=1.1 Hz, 1H, Ar), 7.83 (dd, J=7.4, 8.5 Hz, 1H, Ar), 11.11 (s, 1H, NH); $^{13}$C NMR (DMSO-d$_6$) δ 21.95, 30.90, 44.10, 48.37, 48.73, 50.63, 60.16, 69.89, 115.51, 116.58, 119.35, 119.40, 120.19, 123.68, 127.38, 128.92, 133.34, 135.15, 136.99, 137.31, 144.00, 155.49, 165.27, 166.75, 169.87, 172.72. Not all Ar carbon signals are observed due to splitting with Fluorine; LCMS: MH=568; Anal Calcd for C$_{28}$H$_{24}$F$_3$N$_5$O$_5$+0.2 H$_2$O: C, 58.89; H, 4.31; N, 12.26; F, 9.98; Found: C, 58.91; H, 3.99; N, 11.91; F, 9.37.

5.95 3-(1-Oxo-4-((4-((2-(Trifluoromethyl)-5,6-Dihydroimidazo[1,2-a]Pyrazin-7(8H)-yl)Methyl)Benzyl)Oxy)Isoindolin-2-yl)Piperidine-2,6-Dione

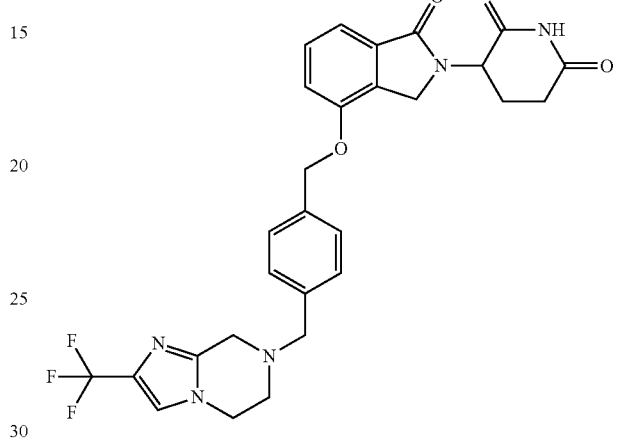

To a suspension of (S)-(4-(4-(bromomethyl)benzyloxy)-1-oxoisoindolin-2-yl)piperidine-2,6-dione (200 mg, 0.451 mmol) and 2-(trifluoromethyl)-5,6,7,8-tetrahydroimidazo[1,2-a]pyrazine hydrochloride (113 mg, 0.496 mmol) in dry MeCN (5 mL), was added DIEA (0.276 mL, 1.579 mmol). The resulting solution was stirred for 3 days at room temperature and then heated to 50° C. for 16 h. The reaction mixture was diluted with water (~35 mL) and the precipitated solid was extensively sonicated at 50° C. to help break up solid aggregates. The resulting slurry was filtered and the solid was washed with additional water (~50 mL) and Et$_2$O (~50 mL). The solid was again washed with water (~75 mL) and Et$_2$O (~30 mL) and then dried in a vacuum oven at 50° C. overnight to give 3-(1-oxo-4-((4-((2-(trifluoromethyl)-5,6-dihydroimidazo[1,2-a]pyrazin-7(8H)-yl)methyl)benzyl)oxy)isoindolin-2-yl)piperidine-2,6-dione as a tan solid (189 mg, 76% yield): HPLC: Waters Symmetry Cis, 5 μm, 3.9×150 mm, 1 ml/min, 240 nm, 25/75 CH$_3$CN/0.1% H$_3$PO$_4$, 6.99 min (95.8%); mp: 148-150° C.; $^1$H NMR (DMSO-d$_6$) δ 1.89-2.09 (m, 1H, CHH), 2.35-2.48 (m, 1H, CHH), 2.53-2.65 (m, 1H, CHH), 2.80-3.06 (m, 3H, CH$_2$, CHH), 3.61 (s, 2H, CH$_2$), 3.73 (s, 2H, CH$_2$), 4.02 (t, J=5.4 Hz, 2H, CH$_2$), 4.26 (d, J=17.4 Hz, 1H, CHH), 4.44 (d, J=17.6 Hz, 1H, CHH), 5.11 (dd, J=5.1, 13.2 Hz, 1H, CH), 5.25 (s, 2H, CH$_2$), 7.30-7.37 (m, 2H, Ar), 7.37-7.45 (m, 2H, Ar), 7.45-7.56 (m, 3H, Ar), 7.73 (d, J=1.3 Hz, 1H, Imidazole), 10.97 (s, 1H, NH); $^{13}$C NMR (DMSO-d$_6$) δ 22.33, 31.16, 44.10, 45.07, 48.44, 50.55, 51.55, 60.18, 69.36, 114.96, 115.23, 123.98 (q, J=266.3 Hz, CF$_3$), 119.37 (q, J=4.4 Hz, CCF$_3$), 127.79, 128.93 (q, J=37.4 Hz, CCF$_3$), 128.90, 129.80, 129.93, 133.30, 135.63, 137.31, 143.99, 153.48, 167.97, 170.96, 172.81. Quartets at 119.37 and 127.79 are incomplete; LCMS: MH=554; Anal Calcd for C$_{28}$H$_{26}$F$_3$N$_5$O$_4$+0.58 H2O: C, 59.63; H, 4.85; N, 12.42; F, 10.11; Found: C, 59.25; H, 4.46; N, 12.41; F, 10.85.

5.96 3-(1-Oxo-4-((4-((3-Propoxyazetidin-1-yl)Methyl)Benzyl)Oxy)Isoindolin-2-yl)Piperidine-2,6-Dione Hydrochloride

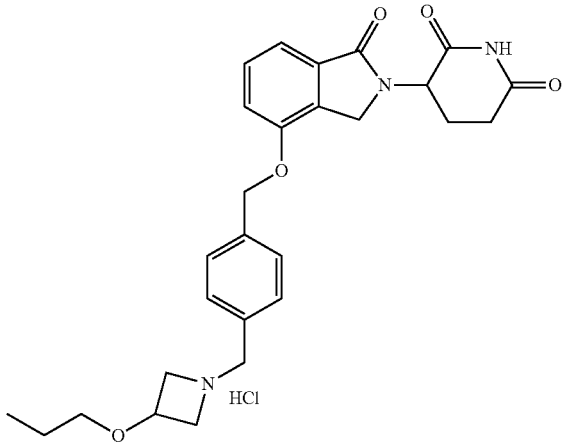 [SMILES: CCCOC1CN(Cc2ccc(COc3cccc4c3CN(C3CCC(=O)NC3=O)C4=O)cc2)C1 ; Cl]

To a solution of (S)-3-(4-(4-(bromomethyl)benzyloxy)-1-oxoisoindolin-2-yl)piperidine-2,6-dione (200 mg, 0.451 mmol) in dry MeCN (5 mL), was added 3-propoxyazetidine hydrochloride (75 mg, 0.496 mmol) and DIEA (0.276 mL, 1.579 mmol). The mixture was stirred at room temperature for 3 h and LCMS indicated benzyl bromide starting material was consumed. The mixture was heated to 50° C. for ~30 min, cooled slowly to rt, and then stored at 4° C. overnight. The mixture containing the crude product was concentrated in vacuo and the residue was dissolved in minimal DMF (~5 mL) for Prep HPLC purification. The product was eluted with an acetonitrile/water gradient (0.1% formic acid in both mobile phases, 5% to 60% MeCN over 20 minutes) and fractions were collected by mass trigger. The desired fractions were combined and concentrated in vacuo to give a clear glass residue. 1 N HCl (2-3 mL) was added and the mixture was concentrated in vacuo to dryness. This process was repeated twice to obtain HCl salt. To the clear residue, MeCN and Et2O were added in small portions and the mixture was sonicated until a white solid was obtained. The slurry was concentrated in vacuo to dryness and twice evaporated from Et$_2$O (3-4 mL portions) until a free flowing white solid was obtained. The solid was dried in a vacuum oven overnight to give 3-(1-oxo-4-((4-((3-propoxyazetidin-1-yl)methyl)benzyl)oxy)isoindolin-2-yl)piperidine-2,6-dione hydrochloride as a white solid (52 mg, 22%): HPLC: Waters Symmetry $C_{18}$, 5 µm, 3.9×150 mm, 1 ml/min, 240 nm, 20/80 CH$_3$CN/0.1% H$_3$PO$_4$, 6.60 min (99.8%); mp: 142-144° C.; $^1$H NMR (DMSO-d$_6$) δ 0.87 (t, J=7.4 Hz, 3H, CH$_3$), 1.40-1.59 (m, 2H, CH$_2$), 1.91-2.06 (m, 1H, CHH), 2.35-2.47 (m, 1H, CHH), 2.53-2.65 (m, 1H, CHH), 2.84-3.01 (m, 1H, CHH), 3.28-3.39 (m, 2H, CH$_2$O, overlapped with DMSO), 3.89 (br. s., 2H, CH$_2$), 4.06-4.23 (m, 2H, CH$_2$), 4.23-4.32 (m, 2H, CHH, CHH), 4.36 (s, 2H, CH$_2$), 4.44 (d, J=17.6 Hz, 1H, CHH), 5.12 (dd, J=5.1, 13.2 Hz, 1H, CH), 5.28 (s, 2H, CH$_2$), 7.27-7.38 (m, 2H, Ar), 7.44-7.53 (m, 1H, Ar), 7.55 (s, 4H, Ar), 10.97 (s, 1H, NH), 11.09 (br. s., 1H, HCl); $^{13}$C NMR (DMSO-d$_6$) δ −0.01, 12.34, 24.22, 32.97, 47.32, 53.70, 62.70, 63.30, 69.33, 71.21, 71.67, 117.13, 117.29, 129.67, 130.77, 131.82, 131.96, 134.99, 137.66, 138.23, 155.27, 170.35, 172.81, 174.98; LCMS: MH=478; Anal Calcd for $C_{27}H_{31}N_3O_5$.+3.2 H$_2$O+1.3 HCl: C, 55.66; H, 6.70; N, 7.21; Cl, 7.91; H$_2$O, 9.89; Found: C, 53.73; H, 6.33; N, 6.90; Cl, 7.63; H$_2$O, 9.62.

5.97 ((S)-3-(4-((4-(((3S,5S)-3,5-Dimethylmorpholino)Methyl)Benzyl)Oxy)-1-Oxoisoindolin-2-yl)Piperidine-2,6-Dione Hydrochloride

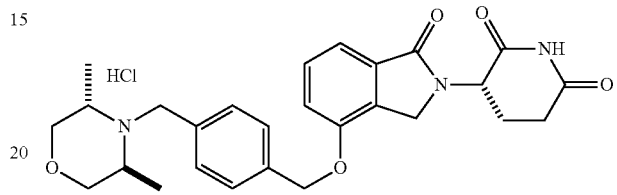

To a suspension of (S)-3-(4-(4-(bromomethyl)benzyloxy)-1-oxoisoindolin-2-yl)piperidine-2,6-dione (250 mg, 0.564 mmol) in MeCN (5 mL), was added (3S,5S)-3,5-dimethylmorpholine (71.4 mg, 0.620 mmol). The mixture was stirred and sonicated briefly to give a clear solution then DIEA (0.197 mL, 1.128 mmol) was immediately added and the resulting mixture was stirred at room temperature for 2 days. The reaction mixture was concentrated in vacuo and the oily residue was partitioned between EtOAc (150 mL) and 1N NaHCO$_3$ (30 mL). The organic layer was washed with brine, dried (Na$_2$SO$_4$), and concentrated in vacuo to give a white solid. The solid was dissolved in DMF (8 mL) and purified using reversed-phase preparatory HPLC. The product was eluted with an acetonitrile/water gradient (0.1% formic acid in both mobile phases, 5% to 50% MeCN over 20 minutes) and fractions were collected by mass trigger. The desired fractions were combined and concentrated in vacuo. 1N HCl (8 mL) was added to the concentrate and all solvents were evaporated to give a gummy solid. The solid was redissolved in minimal water, frozen and lyophilized to give ((S)-3-(4-((4-(((3S,5S)-3,5-dimethylmorpholino)methyl)benzyl)oxy)-1-oxoisoindolin-2-yl)piperidine-2,6-dione hydrochloride as a white fluffy solid (160 mg, 55% yield): HPLC: Waters Symmetry $C_{18}$, 5 µm, 3.9×150 mm, 1 ml/min, 240 nm, 5% grad 95% in 10 min, CH$_3$CN/0.1% H$_3$PO$_4$, 5.89 min (97.0%); mp: 230-232; $^1$H NMR (DMSO-d$_6$) δ 1.28 (d, J=6.8 Hz, 3H, CH$_3$), 1.38 (d, J=6.2 Hz, 3H, CH$_3$), 1.86-2.08 (m, 1H, CHH), 2.36-2.48 (m, 1H, CHH), 2.58 (d, J=17.4 Hz, 1H, CHH), 2.80-3.01 (m, 1H, CHH), 3.03-3.22 (m, 1H, CH), 3.48-3.84 (m, 3H, CH$_2$, CH), 3.91 (dd, J=3.2, 12.3 Hz, 1H, CHH), 3.98-4.18 (m, 2H, CHH, CHH), 4.29 (d, J=17.4 Hz, 1H, CHH), 4.45 (d, J=17.6 Hz, 1H, CHH), 4.72 (dd, J=3.8, 13.6 Hz, 1H, CHH), 5.12 (dd, J=5.1, 13.2 Hz, 1H, CH), 5.29 (s, 2H, CH$_2$), 7.28-7.41 (m, 2H, Ar), 7.45-7.54 (m, 1H, Ar), 7.58 (d, J=8.1 Hz, 2H, Ar), 7.83 (d, J=8.1 Hz, 2H, Ar), 10.97 (s, 1H, NH), 11.40 (dd, J=1.2, 3.1 Hz, 1H, HCl); $^{13}$C NMR (DMSO-d$_6$) δ 9.35, 11.92, 22.27, 31.09, 44.99, 51.38, 51.49, 53.34, 67.65, 67.88, 68.90, 114.89, 115.30, 127.81, 129.25, 129.75, 129.89, 130.93, 133.27, 137.63, 153.29, 167.87, 170.89, 172.76; LCMS: MH=478; Anal Calcd for $C_{27}H_{31}N_3O_5$.+1.3 H$_2$O+2 HCl: C, 56.46; H, 6.25; N, 7.31; Found: C, 56.55; H, 5.93; N, 7.33.

5.98 3-{4-[4-(2-Oxa-6-Aza-Spiro[3.3]Hept-6-ylmethyl)-Benzyloxy]-1-Oxo-1,3-Dihydro-Isoindol-2-yl}-Piperidine-2,6-Dione

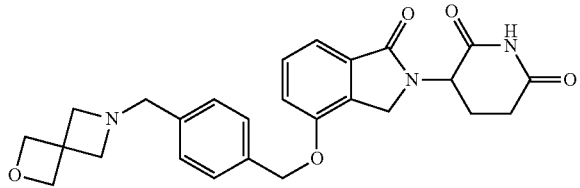 [SMILES: O=C1CCC(N2Cc3c(OCc4ccc(CN5CC6(COC6)C5)cc4)cccc3C2=O)C(=O)N1]

To the dichloromethane (10 ml) suspension of 2-oxa-6-azaspiro[3.3]heptane oxalate (0.124 g, 0.857 mmol) was added N-ethyl-N-isopropylpropan-2-amine (0.425 ml, 2.57 mmol). The mixture was stirred at room temperature for 5 min. Then 3-(4-(4-(bromomethyl)benzyloxy)-1-oxoisoindolin-2-yl)piperidine-2,6-dione (0.380 g, 0.857 mmol) was added, which was still a suspension. About 3 ml of acetonitrile was added and the mixture was stirred at room temperature overnight. The mixture was purified by preparative HPLC (MeCN/water in 0.1% HCOOH) to give 3-{4-[4-(2-Oxa-6-aza-spiro[3.3]hept-6-ylmethyl)-benzyloxy]-1-oxo-1,3-dihydro-isoindol-2-yl}-piperidine-2,6-dione (39 mg, 10% yield); mp, not determined. HPLC: Waters Symmetry C-18, 3.9×150 mm, 5 μm, 1 mL/min, 240 nm, gradient from 10/90 to 90/10 in 5 min, isocratic at 90/10 in 5 min (CH$_3$CN/0.1% H$_3$PO$_4$), 4.32 min (95.2%). $^1$H NMR (DMSO-d$_6$) δ 1.93-2.04 (m, 1H, CHH), 2.36-2.48 (m, 1H, CHH), 2.53-2.64 (m, 1H, CHH), 2.84-2.99 (m, 1H, CHH), 3.30 (s, 3H, CH$_2$CH$_2$), 3.51 (s, 1H, CH$_2$), 4.20-4.47 (m, 2H, CH$_2$), 4.59 (s, 3H, CH$_2$CH$_2$), 5.11 (dd, J=5.1, 13.2 Hz, 1H, NCH), 5.22 (s, 1H, CH$_2$), 7.23-7.36 (m, 4H, Ar), 7.38-7.53 (m, 3H, Ar), 10.97 (br. s., 1H, NH). $^{13}$C NMR (DMSO-d$_6$) δ 22.39, 31.21, 38.54, 45.13, 51.66, 61.97, 62.85, 69.47, 79.96, 115.05, 115.26, 127.62, 128.35, 129.79, 130.00, 133.35, 135.23, 137.96, 153.51, 167.99, 170.92, 172.76. LC/MS m/e=462.

5.99 3-(1-Oxo-4-{4-[2-(Tetrahydro-Pyran-4-yl)-Ethyl]-Benzyloxy}-1,3-Dihydro-Isoindol-2-yl)-Piperidine-2,6-Dione

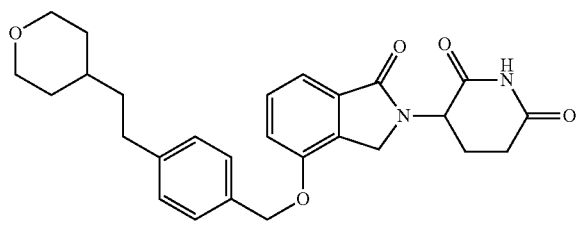 [SMILES: O=C1CCC(N2Cc3c(OCc4ccc(CCC5CCOCC5)cc4)cccc3C2=O)C(=O)N1]

Step 1: Preparation of 4-[2-(Tetrahydro-pyran-4-yl)-vinyl]-benzoic acid methyl ester Sodium hydride (60% in oil) (0.378 g, 9.46 mmol) was added into a stirred solution of anhydrous DMSO (50 ml). The mixture was stirred at room temperature for 20 min. Added (4-Methoxycarbonylbenzyl)triphenylphosphonium bromide (4.65 g, 9.46 mmol) (white powder) to the mixture in an 5~12° C. cold water bath. After two hours, tetrahydro-2H-pyran-4-carbaldehyde (0.9 g, 7.88 mmol) was added. The mixture was stirred at room temperature for two days. Water (50 ml) was added to the mixture, and was extracted with ethyl acetate (2×30 ml), washed with brine (50 ml), dried and concentrated to an oily solid, which was purified by silica gel column (EtOAc/Hexanes) to give 4-[2-(tetrahydro-pyran-4-yl)-vinyl]-benzoic acid methyl ester as a white solid (1.2 g, 61% yield). LC/MS m/e=247. The product was used in the next step without further purification.

Step 2: Preparation of 4-[2-(tetrahydro-pyran-4-yl)-ethyl]-benzoic acid methyl ester A mixture of 4-[2-(tetrahydro-pyran-4-yl)-vinyl]-benzoic acid methyl ester (1.36 g, 5.52 mmol) and palladium on activated carbon 10 wt % (50% wet) (0.21 g, 8.92 mmol) in methanol (50 ml) was hydrogenated with a hydrogen balloon at room temperature overnight. The black suspension was filtered through Celite, the filtrate was evaporated to give 4-[2-(tetrahydro-pyran-4-yl)-ethyl]-benzoic acid methyl ester as a white solid (1.33 g, 97% yield). LC/MS m/e=217. It was used in the next step without further purification.

Step 3: Preparation of {4-[2-(tetrahydro-pyran-4-yl)-ethyl]-phenyl}-methanol Lithium Aluminum Hydride (2.0M in THF) (2.29 ml, 4.58 mmol) was added dropwise to a stirred solution of 4-[2-(tetrahydro-pyran-4-yl)-ethyl]-benzoic acid methyl ester (0.64 g, 2.58 mmol) in tetrahydrofuran (8 ml) in an ice-bath at 0° C. The mixture was stirred at 0° C. for 30 min, the solution was cooled in an ice-bath and added water dropwise to form a white gel, gas was evolved out. More water (30 ml) was added. It was extracted with EtOAc (3×30 ml) and separated the two phases by adding "1N Rochelle salt solution". The organic phase was evaporated to give {4-[2-(tetrahydro-pyran-4-yl)-ethyl]-phenyl}-methanol as a white solid (0.58 g, 102% crude yield). LC/MS m/e=203. It was used in the next step without further purification.

Step 4: Preparation of 4-[2-(4-Bromomethyl-phenyl)-ethyl]-tetrahydro-pyran To a stirred slurry of (4-(2-(tetrahydro-2H-pyran-4-yl)ethyl)phenyl)methanol (0.57 g, 2.59 mmol) in dry MeCN (8 mL) at 0° C., was added tribromophosphine (0.466 ml, 4.94 mmol). The resulting mixture was stirred at 0° C. for 20 minutes, then allowed to warm up to room temperature. The cloudy suspension was quenched with water (~5 ml) in an ice-bath, added more water (20 ml), extracted with ethyl acetate (2×30 ml). The combined organic phases were washed with brine (20 ml), dried over sodium sulfate and concentrated to give 4-[2-(4-Bromomethyl-phenyl)-ethyl]-tetrahydro-pyran as an oil (0.74 g, 101% crude yield). It was used in the next step without further purification.

Step 5: Preparation of 4-Carbamoyl-4-(1-oxo-4-{4-[2-(tetrahydro-pyran-4-yl)-ethyl]-benzyloxy}-1,3-dihydro-isoindol-2-yl)-butyric acid methyl ester A white suspension of methyl 5-amino-4-(4-hydroxy-1-oxoisoindolin-2-yl)-5-oxopentanoate (0.764 g, 2.61 mmol), 4-(4-(bromomethyl)phenethyl)tetrahydro-2H-pyran (0.74 g, 2.61 mmol), and potassium carbonate (0.361 g, 2.61 mmol) in acetonitrile (15 ml) was stirred in a 50° C. oil bath overnight. The white suspension was filtered, and the filtrate was evaporated to a white solid, which was purified by silica gel column (MeOH/CH$_2$Cl$_2$) to give 4-Carbamoyl-4-(1-oxo-4-{4-[2-(tetrahydro-pyran-4-yl)-ethyl]-benzyloxy}-1,3-dihydro-isoindol-2-yl)-butyric acid methyl ester as a white solid (0.96 g, 74% yield). LC/MS m/e=495. It was used in the next step without further purification.

Step 6: Preparation of 3-(1-Oxo-4-{4-[2-(tetrahydro-pyran-4-yl)-ethyl]-benzyloxy}-1,3-dihydro-isoindol-2-yl)-piperidine-2,6-dione To a stirred solution of methyl 5-amino-5-oxo-4-(1-oxo-4-(4-(2-(tetrahydro-2H-pyran-4-yl)ethyl)benzyloxy)isoindolin-2-yl)pentanoate (0.96 g, 1.941 mmol) in tetrahydrofuran (10 ml) at 0° C. in an ice-bath was added potassium 2-methylpropan-2-olate (0.218 g, 1.941 mmol). The mixture was stirred for ten minutes then quenched with 1 N HCl (to pH=1), neutralized with saturated sodium bicarbonate to pH=7, extracted with methylene chloride (3×30 ml). The combined methylene chloride phases were washed with (2×20 ml), dried and concentrated to a white solid. It was stirred in ether (20 ml) for a couple of hours, and filtered to give 3-(1-Oxo-4-{4-[2-(tetrahydro-pyran-4-yl)-ethyl]-benzyloxy}-1,3-dihydro-isoindol-2-yl)-piperidine-2,6-dione as a white solid (0.64 g, 71% yield); mp, 254-256° C. HPLC: Waters Symmetry C-18, 3.9×150 mm, 5 μm, 1 mL/min, 240 nm, gradient from 10/90 to 90/10 in 5 min, isocratic at 90/10 in 5 min ($CH_3CN/0.1\%$ $H_3PO_4$), 7.18 min (96.7%). $^1$H NMR (DMSO-$d_6$) δ 1.13-1.28 (m, 2H, $CH_2$), 1.45-1.54 (m, 3H, $CH_2$, CH), 1.61 (d, J=13.0 Hz, 2H, $CH_2$), 1.87-2.09 (m, 1H, CHH), 2.33-2.44 (m, 1H, CHH), 2.60 (t, J=7.6 Hz, 3H, $CH_2$, CHH), 2.91 (br. s., 1H, CHH), 3.24 (td, J=1.7, 11.6 Hz, 2H, $CH_2$), 3.82 (dd, J=3.0, 11.1 Hz, 2H, $CH_2$), 4.14-4.48 (m, 2H, $CH_2$), 5.11 (dd, J=5.1, 13.2 Hz, 1H, NCH), 5.20 (s, 2H, $CH_2$), 7.22 (d, J=8.1 Hz, 2H, Ar), 7.31-7.67 (m, 5H, Ar), 10.96 (s, 1H, NH). $^{13}$C NMR (DMSO-$d_6$) δ 522.36, 31.21, 31.63, 32.64, 33.89, 38.24, 45.10, 51.59, 67.03, 69.49, 115.01, 115.20, 127.85, 128.34, 129.79, 129.97, 133.31, 133.86, 142.20, 153.53, 168.01, 170.96, 172.82. LC/MS m/e=463. Anal Calcd for $C_{27}H_{30}N_2O_5$ (+0.1 $H_2O$): C, 69.84; H, 6.56; N, 6.03. Found: C, 69.57; H, 6.64; N, 5.93.

5.100 2-(2,6-Dioxopiperidin-3-yl)-4-((6-(Morpholinomethyl)Imidazo[1,2-A]Pyridine-2-yl)Methoxy)Isoindoline-1,3-Dione

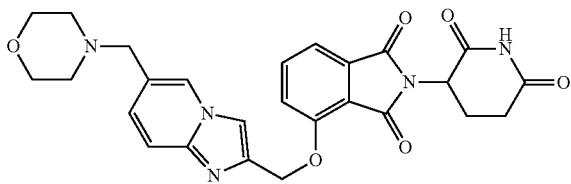 [SMILES: O=C1CCC(N2C(=O)c3cccc(OCc4cn5cc(CN6CCOCC6)ccc5n4)c3C2=O)C(=O)N1]

Step 1: A mixture of 3-hydroxyphthalic anhydride (1.6 g, 9.8 mmol) in methanol (25 mL) was refluxed for 3 h. The mixture was cooled and concentrated. Residue and $NaHCO_3$ (2.3 g, 27.3 mmol) were stirred in DMF (20 mL). Iodomethane (3.3 g, 23.4 mmol) was added and reaction mixture was heated at 50° C. oil bath for 3 h. The reaction mixture was cooled and diluted with EtOAc (80 mL) and water (40 mL). The mixture was acidified with 4N HCl and aq. layer was extracted with EtOAc (2×40 mL). Combined EtOAc solution was washed with water (2×40 mL), brine (40 mL) and dried. Solvent was removed and residue was purified by chromatography ($SiO_2$, 10% EtOAc/hexane for 15 min then to 20% over 5 min and hold for 15 min then to 30% over 5 min and hold for 15 min) to give dimethyl 3-hydroxyphthalate (1.8 g, 89%): $^1$H NMR ($CDCl_3$) δ 3.89 (s, 3H), 3.92 (s, 3H), 6.95-6.98 (dd, J=3 and 9 Hz, 1H), 7.06-7.10 (dd, J=3 and 9 Hz, 1H), 7.41-7.48 (t, J=9 Hz, 1H), 10.55 (s, 1H); $^{13}$C NMR ($CDCl_3$) δ 52.64, 52.90, 110.19, 119.11, 119.83, 134.58, 135.46, 161.08, 169.33, 169.39.

Step 2: A mixture of ethyl 6-aminonicotinate (5.0 g, 30.1 mmol) and 1,3-dichloropropan-2-one (5.7 g, 45.1 mmol) in acetonitrile (100 mL) was refluxed for 17 h. The mixture was concentrated and residue was stirred with $CH_2Cl_2$ (100 mL) and sat. $NaHCO_3$ (35 mL). The organic layer was washed with brine (40 mL) and dried. Solvent was removed and residue was purified by chromatography ($SiO_2$, 30% EtOAc/$CH_2Cl_2$ for 25 min then to 100% EtOAc over 15 min) to give ethyl 2-(chloromethyl)imidazo[1,2-a]pyridine-6-carboxylate (4.7 g, 65%): $^1$H NMR ($CDCl_3$) δ 1.42 (t, J=6 Hz, 3H), 4.38-4.45 (q, J=6 Hz, 2H), 4.77 (s, 2H), 7.56-7.59 (d, J=9 Hz, 1H), 7.74-7.77 (dd, J=3 and 9 Hz, 1H), 8.86-8.87 (d, J=3 Hz, 1H).

Step 3: A solution of ethyl 2-(chloromethyl)imidazo[1,2-a]pyridine-6-carboxylate (2.1 g, 8.8 mmol) in anhydrous $CH_2Cl_2$ (60 mL) was cooled in dry ice/acetone bath. A solution of diisobutylaluminum hydride/$CH_2Cl_2$ (1 M, 26.4 mL, 26.4 mmol) was added slowly at −70° C. After addition, reaction mixture was stirred at −70° C. for 1.5 h then quenched with methanol (5 mL). The mixture was diluted with $CH_2Cl_2$ (40 mL), and sat. $NaHCO_3$ (40 mL) and warmed to room temperature. The mixture was filtered and washed solid with $CH_2Cl_2$ (50 mL). Layers were separated and organic layer was washed with water (35 mL), brine (35 mL) and dried. Solvent was removed to give 2-(chloromethyl)imidazo[1,2-a]pyridine-6-carbaldehyde (1.5 g, 89%), which was used in next step without purification.

Step 4: A solution of 2-(chloromethyl)imidazo[1,2-a]pyridine-6-carbaldehyde (1.5 g, 7.9 mmol), morpholine (0.7 g, 7.9 mmol) and acetic acid (0.6 g, 9.4 mmol) in THF (60 mL) was stirred at room temperature for 15 min. Sodium triacetoxyborohydride (3.3 g, 15.7 mmol) was added and mixture was stirred at room temperature for 1 h, Reaction mixture was diluted with $CH_2Cl_2$ (50 mL) and cooled in ice bath and quenched with sat. $NaHCO_3$ (40 mL). The organic layer was washed with brine (30 mL) and dried. Solvent was removed and residue was purified by chromatography ($SiO_2$, $CH_2Cl_2$ for 5 min then to 3% $CH_3OH/CH_2Cl_2$ over 5 min and hold for 15 min then to 5% over 5 min and hold for 15 min) to give 4-((2-(chloromethyl)imidazo[1,2-a]pyridine-6-yl)methyl)morpholine (1. g, 53%): $^1$H NMR ($CDCl_3$) δ 2.45-2.49 (m, 4H), 3.47 (s, 2H), 3.70-3.73 (m, 4H), 4.76 (s, 2H), 7.22-7.25 (dd, J=3 and 9 Hz, 1H), 7.53-7.57 (m, 2H), 8.03 (s, 1H).

Step 5: A mixture of 4-((2-(chloromethyl)imidazo[1,2-a]pyridin-6-yl)methyl)morpholine (1.1 g, 4.2 mmol), dimethyl 3-hydroxyphthalate (0.9 g, 4.2 mmol) and potassium carbonate (0.6 g, 4.2 mmol) in DMF (20 mL) was heated at 55° C. oil bath for 7 h. The reaction mixture was cooled and diluted with EtOAc (100 mL) and washed with water (3×30 mL), brine (30 mL) and dried. Solvent was removed and residue was purified by chromatography ($SiO_2$, $CH_2Cl_2$ for 5 min then to 3% $CH_3OH/CH_2Cl_2$ over 5 min and hold for 15 min then to 5% over 5 min and hold for 15 min) to give dimethyl 3-((6-(morpholinomethyl)imidazo[1,2-a]pyridine-2-yl)methoxy)phthalate (0.6 g, 32%): $^1$H NMR ($CDCl_3$) δ 2.43-2.45 (m, 4H), 3.45 (s, 2H), 3.70-3.73 (m, 4H), 3.89 (s, 3H), 3.91 (s, 3H), 5.39 (s, 2H), 7.19 (m, 1H), 7.30-7.38 (m, 2H), 7.45-7.61 (m, 3H), 8.01 (s, 1H).

Step 6: Sodium hydroxide (0.3 g, 6.5 mmol) was added to a stirred solution of dimethyl 3-((6-(morpholinomethyl)imidazo[1,2-a]pyridin-2-yl)methoxy)phthalate (1.0 g, 2.3 mmol) in ethanol (20 mL). The resulting mixture was refluxed for 1 h then cooled and neutralized with acetic acid (0.5 g, 8.3 mmol). The mixture was concentrated and residue was dissolved in pyridine (30 mL). To this solution was added α-aminoglutarimide hydrochloride (0.4 g, 2.3 mmol) and the resulting mixture was refluxed for 5 h. The reaction mixture was cooled and concentrated. Residue was stirred with EtOAc (50 mL) and water (30 mL). The mixture was filtered and solid was washed with EtOAc (20 mL). Layers were separated and aq. layer was extracted with EtOAc (2×40 mL). Combined EtOAc solution was washed with water (2×30 mL), brine (30 mL) and dried. Solvent was removed and residue was purified by chromatography (SiO$_2$, CH$_2$Cl$_2$ for 5 min then to 3% CH$_3$OH/CH$_2$Cl$_2$ over 5 min and hold for 10 min then to 5% over 5 min and hold for 15 min) to give 2-(2,6-dioxopiperidin-3-yl)-4-((6-(morpholinomethyl)imidazo[1,2-a]pyridin-2-yl)methoxy)isoindoline-1,3-dione (0.12 g, 10%): mp 255-257° C.; $^1$H NMR (DMSO-d$_6$) δ 1.99-2.05 (m, 1H), 2.36-2.39 (m, 4H), 2.54-2.61 (m, 2H), 2.85-2.89 (m, 1H), 3.44-3.58 (m, 6H), 5.05-5.11 (dd, J=6 and 15 Hz, 1H), 5.46 (s, 2H), 7.22-7.25 (dd, J=3 and 6 Hz, 1H), 7.45-7.49 (m, 2H), 7.73-7.82 (m, 2H), 8.01 (s, 1H), 8.47 (s, 1H), 11.11 (s, 1H); $^{13}$C NMR (DMSO-d$_6$) δ 21.95, 30.89, 48.72, 52.97, 59.11, 65.32, 66.13, 111.95, 115.41, 116.24, 115.40, 120.31, 122.31, 125.79, 127.03, 133.21, 136.87, 141.13, 143.91, 155.55, 165.24, 166.76, 169.87, 172.74; Calcd for C$_{26}$H$_{25}$N$_5$O$_6$+ 0.9H$_2$O: C, 60.09; H, 5.20; N, 13.47. Found: C, 60.05; H, 5.01; N, 13.22.

5.101 3-{4-[4-(1,4-Dihydro-Quinazolin-2-ylmethyl)-Benzyloxy]-1-Oxo-1,3-Dihydro-Isoindol-2-yl}-Piperidine-2,6-Dione

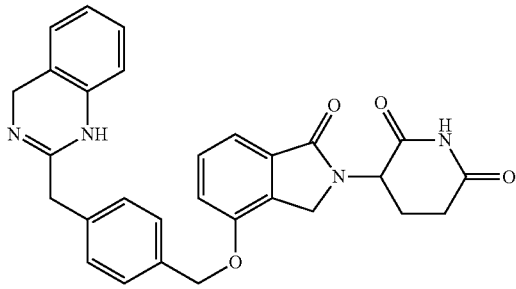 [SMILES: O=C1CCC(N2Cc3c(OCc4ccc(CC5=NCc6ccccc6N5)cc4)cccc3C2=O)C(=O)N1]

Step 1: (4-Bromomethyl-phenyl)-acetic acid tert-butyl ester The stirred solution of 2-(4-(bromomethyl)phenyl) acetic acid (2.6 g, 11.35 mmol) in thionyl chloride (20 mL, 274 mmol) was heated to reflux for 2.5 hrs. The reaction mixture was concentrated under vacuo to give off white solid. The white solid was added to the stirred solution of 2-methylpropan-2-ol (20 ml, 213 mmol) in DCM (2 mL) under ice/water bath. And the mixture was stirred under ice/water bath for 2 hrs and at room temperature for 18 hrs. The reaction mixture was added to CH$_2$Cl$_2$ (40 mL). The organic phase was washed successively with H$_2$O (20 mL), NaHCO$_3$ (sat, aq, 20 mL), and brine (25 mL) and dried over MgSO$_4$. Organic layer was concentrated under vacuo to give (4-bromo methyl-phenyl)-acetic acid tert-butyl ester as a light yellow liquid (2.4 g, 74% crude yield). 1H NMR (DMSO-d6): 1.39 (s, 9H, tBu), 3.54 (s, 2H, CH$_2$CO2), 4.69 (s, 2H, CH$_2$Br), 7.23, 7.39 (m, 4H, due to impurities).

Step 2: 4-[4-(4-tert-Butoxycarbonylmethyl-benzyloxy)-1-oxo-1,3-dihydro-isoindol-2-yl]-4-carbamoyl-butyric acid methyl ester To the stirred mixture of methyl 5-amino-4-(4-hydroxy-1-oxoisoindolin-2-yl)-5-oxopentanoate (1.5 g, 5.13 mmol) and tert-butyl 2-(4-(bromomethyl)phenyl) acetate (2.2 g, 7.7 mmol) in Acetonitrile (30 mL) was added POTASSIUM CARBONATE (1.42 g, 10.3 mmol). The resulting reaction mixture was stirred at 50° C. for 27 hrs and in between tert-butyl 2-(4-(bromomethyl) phenyl) acetate (800 mg, 2.9 mmol) was added in 2 portions. The reaction mixture was filtered and the light brown solid was washed with acetonitrile (2×20 mL). The filtrate was concentrated under vacuo and the residue was purified by ISCO 4-[4-(4-tert-Butoxycarbonylmethyl-benzyloxy)-1-oxo-1,3-dihydro-isoindol-2-yl]-4-carbamoyl-butyric acid methyl ester as a light yellow sticky solid (2.1 g, 82% crude yield) LCMS MH=497.

Step 3: 4-Carbamoyl-4-[4-(4-carboxymethyl-benzyloxy)-1-oxo-1,3-dihydro-isoindol-2-yl]-butyric acid methyl ester To the stirred solution of methyl 5-amino-4-(4-(4-(2-tert-butoxy-2-oxoethyl)benzyloxy)-1-oxoisoindolin-2-yl)-5-oxopentanoate (2.1 g, 4.2 mmol) in DCM (20 mL) at room temperature was added by WATER (0.38 ml, 21.1 mmol) followed by the addition of TFA (1.63 ml, 21.1 mmol) slowly. The resulting solution was stirred at room temperature for 5 hrs and in between TFA (3.2 mL) and water (0.15 mL) were added. The mixture was kept in fridge overnight and the reaction mixture was concentrated under vacuo to give 4-Carbamoyl-4-[4-(4-carboxy methyl-benzyloxy)-1-oxo-1,3-dihydro-isoindol-2-yl]-butyric acid methyl ester as an off white solid (2.3 g, 123% crude yield). $^1$H NMR (DMSO-d$_6$) δ 1.97-2.31 (m, 4H, CH$_2$, CH$_2$), 3.50 (s, 3H, CH$_3$), 3.58 (s, 2H, CH$_2$), 4.41 (d, J=17.8 Hz, 1H, CHH), 4.53 (d, J=17.8 Hz, 1H, CHH), 4.72 (dd, J=4.6, 10.3 Hz, 1H, CHH), 5.23 (s, 2H, CH$_2$), 7.18 (br. s., 1H, NHH), 7.24-7.34 (m, 4H, Ar), 7.40-7.50 (m, 3H, Ar), 7.57 (br. s., 1H, NHH); LCMS MH=441.

Step 4: 5-amino-4-(4-(4-(2-(2-aminobenzylamino)-2-oxoethyl)benzyl oxy)-1-oxoisoindolin-2-yl)-5-oxopentanoate To the stirred solution of 2-(4-((2-(1-amino-5-methoxy-1,5-dioxopentan-2-yl)-1-oxoisoindolin-4-yloxy)methyl) phenyl)acetic acid (820 mg, 1.9 mmol) in DMF (10 mL at room temperature was added HOBT (285 mg, 1.9 mmol). A minute later, 2-(aminomethyl)aniline (227 mg, 1.9 mmol), EDC (357 mg, 1.9 mmol) and DIEA (0.81 ml, 4.65 mmol) were added.

The resulting solution was stirred at room temperature for 17 hrs before it was added by water (40 mL) and EtOAc (60 mL). The mixture was extracted and the aq layer was extracted with EtOAc (50 mL). The organic layers were combined, dried by MgSO$_4$ and concentrated under vacuo. The residue was purified by ISCO to give 5-amino-4-(4-(4-(2-(2-amino benzylamino)-2-oxoethyl)benzyl oxy)-1-oxoisoindolin-2-yl)-5-oxopentanoate as a sticky oil (300 mg, 30% yield). The compound was put to next step without further purification. LCMS MH=545.

Step 5: Methyl 5-amino-4-(4-((4-(2-((2-aminobenzyl)amino)-2-oxoethyl)benzyl)oxy)-1-oxoisoindolin-2-yl)-5-oxopentanoate The solution of methyl 5-amino-4-(4-(4-(2-(2-aminobenzylamino)-2-oxoethyl)benzyl oxy)-1-oxoisoindolin-2-yl)-5-oxopentanoate (300 mg, 0.55 mmol) in ACETIC ACID (4 ml, 69.9 mmol) was heated at microwave oven at 125° C. for 10 mins. The reaction mixture was added to NaHCO$_3$ (aq, sat, 50 mL) slowly to control the formation of CO$_2$. The resulting mixture was extracted with DCM (100 mL). Organic layer was washed with NaHCO$_3$ (aq, sat, 15 mL) and brine (20 mL). Organic layer was dried by MgSO$_4$ and concentrated under vacuo to give methyl 5-amino-4-(4-((4-(2-((2-aminobenzyl) amino)-2-oxoethyl) benzyl)oxy)-1-oxoisoindolin-2-yl)-5-oxopentanoate as a light brown solid (240 mg, 83% yield); $^1$H NMR (DMSO-d$_6$) δ 2.00-2.31 (m, 4H, CH$_2$, CH$_2$), 3.46 (s, 2H, CH$_2$), 3.49 (s, 3H, CH$_3$), 4.33-4.57 (m, 4H, CHH, CHH, CH$_2$), 4.71 (dd, J=4.8, 10.3 Hz, 1H, CHH), 5.21 (s, 2H, CH$_2$), 6.75 (d, J=7.7 Hz, 1H, Ar), 6.88 (d, J=4.2 Hz, 2H, Ar), 7.00-7.13 (m, 1H, Ar), 7.13-7.23 (m, 1H, NHH), 7.23-7.33 (m, 2H, Ar), 7.33-7.49 (m, 6H, Ar), 7.57 (s, 1H, NHH); LCMS MH=527.

Step 6: 3-{4-[4-(1,4-Dihydro-quinazolin-2-ylmethyl)-benzyloxy]-1-oxo-1,3-dihydro-isoindol-2-yl}-piperidine-2, 6-dione To the stirred suspension of methyl 5-amino-4-(4-(4-((1,4-dihydroquinazolin-2-yl)methyl)benzyloxy)-1-oxoisoindolin-2-yl)-5-oxopentanoate (240 mg, 0.46 mmol) in Tetrahydrofuran (10 mL) at 0° C. (ice/water bath) was added POTASSIUM TERT-BUTOXIDE (56.3 mg, 0.5 mmol). The resulting mixture was stirred at 0° C. for 2 hrs and KOtBu (37 mg, 0.33 mmol) was added to the reaction mixture for further reaction at 0° C. 1.5 hrs later, the reaction mixture was diluted by DCM (50 mL) followed by the addition of HCl (2 mL, 1N, aq). The mixture was stirred for 1 min and NaHCO$_3$ (aq, sat., 20 mL) was added. The mixture was filtered to get some yellow solid. The filtrate was extracted and aq layer was extracted with DCM (30 mL). Combined organic layers were dried by MgSO$_4$ and filtered. The filtrate was concentrated and the residue was purified by ISCO to give 3-{4-[4-(1,4-Dihydro-quinazolin-2-ylmethyl)-benzyloxy]-1-oxo-1,3-dihydro-isoindol-2-yl}-piperidine-2,6-dione as a white solid (25 mg, 11% yield); HPLC: Waters Symmetry C-18, 3.9×150 mm, 5 μm, 1 mL/min, 240 nm, 23/77, (CH$_3$CN/0.1% H$_3$PO$_4$), 3.90 min (96.3%); mp: 153-155° C. (in house); $^1$H NMR (DMSO-d$_6$) δ 1.98 (br. s., 1H, CHH), 2.35-2.46 (m, 1H, CHH), 2.54-2.62 (m, 1H, CHH), 2.87 (dd, J=4.7, 12.8 Hz, 1H, CHH), 3.45 (s, 2H, CH$_2$), 4.23 (d, J=17.6 Hz, 1H, CHH), 4.40 (d, J=17.6 Hz, 1H, CHH), 4.48 (s, 2H, CH$_2$), 5.09 (dd, J=5.1, 13.2 Hz, 1H, CHH), 5.20 (s, 2H, CH$_2$), 6.74 (d, J=7.7 Hz, 1H, Ar), 6.88 (d, J=4.2 Hz, 2H, Ar), 6.99-7.10 (m, 1H, Ar), 7.25-7.56 (m, 8H, Ar, NH), 10.95 (s, 1H, NH); $^{13}$C NMR (DMSO-d$_6$) δ 22.23, 31.09, 40.98, 45.02, 51.48, 69.32, 114.83, 115.11, 122.98, 125.44, 127.34, 127.78, 127.88, 128.75, 129.10, 129.72, 129.88, 133.22, 134.62, 137.18, 153.41, 167.92, 170.86, 172.73; LCMS MH=495; Anal. Calcd for C$_{29}$H$_{25}$N$_4$O$_4$: C, 70.43; H, 5.30; N, 11.33; Found: N/A.

5.102 3-(1-Oxo-4-{4-[2-(Tetrahydro-Pyran-4-yl)-Ethyl]-Benzyloxy}-1,3-Dihydro-Isoindol-2-yl)-Piperidine-2,6-Dione

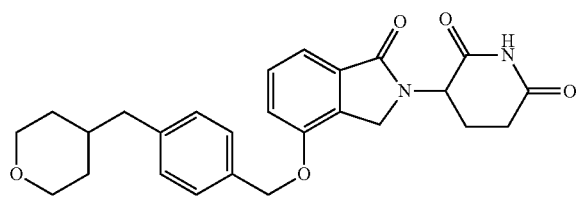 [SMILES: O=C1CCC(N2Cc3c(OCc4ccc(CC5CCOCC5)cc4)cccc3C2=O)C(=O)N1]

Step 1: Preparation of 4-(Tetrahydro-pyran-4-ylidenemethyl)-benzoic acid methyl ester Sodium hydride (60% in oil) (0.240 g, 5.99 mmol) was added into a stirred solution of anhydrous DMSO (50 ml). The mixture was stirred at room temperature for 20 minutes. To the mixture was added (4-Methoxycarbonylbenzyl) triphenylphosphonium bromide (2.94 g, 5.99 mmol) (white powder) in an 5~12° C. cold water bath. After two hours, dihydro-2H-pyran-4(3H)-one (0.5 g, 4.99 mmol) in DMSO (3 ml) was added. The mixture was stirred at room temperature overnight, then diluted with water (80 ml) slowly and extracted with ethyl acetate (3×80 ml). The combined ethyl acetate phases were further washed with water (2×100 ml). The ethyl acetate phase was evaporated to an off-white solid and purified by silica gel column (EtOAc/Hexanes) to give 4-(Tetrahydro-pyran-4-ylidenemethyl)-benzoic acid methyl ester as an oil (0.74 g, 63% yield). HNMR showed 72% pure. The product was used in the next step without further purification.

Step 2: Preparation of 4-(Tetrahydro-pyran-4-ylmethyl)-benzoic acid methyl ester A mixture of 4-(tetrahydro-pyran-4-ylidenemethyl)-benzoic acid methyl ester (0.743 g, 3.20 mmol) and palladium on activated carbon 10 wt % (50% wet) (0.14 g, 69.4 mmol) in methanol (30 ml) was hydrogenated with two hydrogen balloons for three hours. The suspension was filtered through a Celite pad, the filtrate was evaporated to give 4-(Tetrahydro-pyran-4-ylmethyl)-benzoic acid methyl ester as an oily solid (0.71 g, 95% yield). HNMR showed 70% pure. It was used in the next step without further purification.

Step 3: Preparation of [4-(Tetrahydro-pyran-4-ylmethyl)-phenyl]-methanol Lithium Aluminum Hydride (2.0 M in THF) (1.494 ml, 2.99 mmol) was added dropwise to a stirred solution of 4-(Tetrahydro-pyran-4-ylmethyl)-benzoic acid methyl ester (0.7 g, 2.99 mmol) in tetrahydrofuran (8 ml) in an ice-bath at 0° C. The mixture was stirred for 20 minutes. The solution was cooled in an ice-bath and added water (30 ml) dropwise to form a white gel, gas was evolved out. It was extracted with EtOAc (2×40 ml) and separated the two phases by adding "1N Rochelle salt solution". The organic phase was evaporated and purified by silica gel column (EtOAc/Hexanes) to give [4-(Tetrahydro-pyran-4-ylmethyl)-phenyl]-methanol as an oil (0.16 g, 26% yield). It was used in the next step without further purification.

Step 4: Preparation of 4-(4-Bromomethyl-benzyl)-tetrahydro-pyran To a stirred slurry of (4-((tetrahydro-2H-pyran-4-yl)methyl)phenyl)methanol (0.16 g, 0.776 mmol) in acetonitrile (anhydrous) (8 ml, 0.776 mmol) at 0° C., was added tribromophosphine (0.110 ml, 1.163 mmol). The resulting mixture was stirred at 0° C. for 10 minutes. The suspension was quenched with water (25 ml) in an ice-bath, extracted with ethyl acetate (2×30 ml). The combined org phases were washed with brine (20 ml), dried over sodium sulfate and concentrated to give 4-(4-Bromomethyl-benzyl)-tetrahydro-pyran as an oil (0.206 g, 99% crude yield). It was used in the next step without further purification.

Step 5: Preparation of 4-Carbamoyl-4-{1-oxo-4-[4-(tetrahydro-pyran-4-ylmethyl)-benzyloxy]-1,3-dihydro-isoindol-2-yl}-butyric acid methyl ester A white suspension of methyl 5-amino-4-(4-hydroxy-1-oxoisoindolin-2-yl)-5-oxopentanoate (0.195 g, 0.669 mmol), 4-(4-(bromomethyl)benzyl)tetrahydro-2H-pyran (0.18 g, 0.669 mmol), and potassium carbonate (0.092 g, 0.669 mmol) in acetonitrile (10 ml) was stirred in a 50° C. oil bath overnight. The suspension was filtered and the filtrate was evaporated to an oil, which was purified by silica gel column (MeOH/CH$_2$Cl$_2$) to give 4-Carbamoyl-4-{1-oxo-4-[4-(tetrahydro-pyran-4-ylmethyl)-benzyloxy]-1,3-dihydro-isoindol-2-yl}-butyric acid methyl ester as an oil (~0.15 g, 46% yield). It was used in the next step without further purification.

Step 6: Preparation of 3-{-Oxo-4-[4-(tetrahydro-pyran-4-ylmethyl)-benzyloxy]-1,3-dihydro-isoindol-2-yl}-piperidine-2,6-dione To a stirred solution of methyl 5-amino-5-oxo-4-(1-oxo-4-(4-((tetrahydro-2H-pyran-4-yl)methyl)benzyloxy)isoindolin-2-yl)pentanoate (0.15 g, 0.312 mmol) in tetrahydrofuran (8 ml) at 0° C. in an ice-bath was added potassium 2-methylpropan-2-olate (0.035 g, 0.312 mmol). The solution was stirred for ten minutes and quenched with 1 N HCl to pH=1 then neutralized with saturated sodium bicarbonate to pH=7, and extracted with ethyl acetate (2×30 ml). The EtOAc phases were washed with water (20 ml), brine (20 ml), dried and concentrated to an oil, which was purified by silica gel column (40 g, MeOH/CH$_2$Cl$_2$) to give 3-(1-Oxo-4-{4-[2-(tetrahydro-pyran-4-yl)-ethyl]-benzyloxy}-1,3-dihydro-isoindol-2-yl)-piperidine-2,6-dione as a white solid (64 mg, 46% yield); mp, 172-174° C. HPLC:

Waters Symmetry C-18, 3.9×150 mm, 5 μm, 1 mL/min, 240 nm, gradient from 10/90 to 90/10 in 5 min, isocratic at 90/10 in 5 min (CH$_3$CN/0.1% H$_3$PO$_4$), 6.88 (96.1%). $^1$H NMR (DMSO-d$_6$) δ 1.12-1.29 (m, 2H, CH$_2$), 1.39-1.53 (m, 2H, CH$_2$), 1.61-1.82 (m, 1H, CH), 1.91-2.04 (m, 1H, CHH), 2.35-2.48 (m, 1H, CHH), 2.53-2.64 (m, 1H, CHH), 2.83-3.00 (m, 1H, CHH), 3.16-3.28 (m, OH, CH$_2$), 3.75-3.87 (m, J=0.9, 0.9, 4.7, 11.4 Hz, OH, CH$_2$), 4.18-4.47 (m, 2H, CH$_2$), 5.11 (dd, J=5.1, 13.2 Hz, 1H, NCH), 5.20 (s, 2H, CH$_2$), 7.20 (d, J=7.9 Hz, 2H, Ar), 7.32 (d, J=7.7 Hz, 2H, Ar), 7.40 (d, J=8.1 Hz, 2H, Ar), 7.44-7.54 (m, 1H, Ar), 10.97 (s, 1H, NH). $^{13}$C NMR (DMSO-d$_6$) δ 22.36, 31.20, 32.46, 36.36, 42.28, 45.09, 51.58, 66.91, 69.48, 114.97, 115.20, 127.68, 129.11, 129.81, 129.94, 133.29, 134.04, 139.81, 153.53, 168.01, 170.96, 172.82. LC/MS m/e=449. Anal Calcd for C$_{26}$H$_{28}$N$_2$O$_5$ (+0.4 H$_2$O): C, 68.53; H, 6.37; N, 6.15. Found: C, 68.35; H, 6.44; N, 6.03.

5.103 3-{1-Oxo-4-[4-(3-Phenoxy-Azetidin-1-ylmethyl)-Benzyloxy]-1,3-Dihydro-Isoindol-2-yl}-Piperidine-2,6-Dione

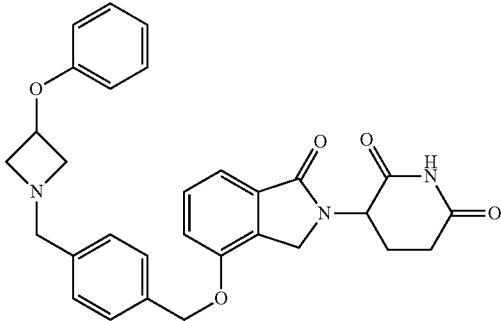 [SMILES: O=C1CCC(N2Cc3c(OCc4ccc(CN5CC(Oc6ccccc6)C5)cc4)cccc3C2=O)C(=O)N1]

To the CH$_3$CN (10 ml) solution of 3-(4-(4-(bromomethyl)benzyloxy)-1-oxoisoindolin-2-yl)piperidine-2,6-dione (0.36 g, 0.812 mmol) was added 3-phenoxyazetidine (0.158 g, 1.056 mmol) and N-ethyl-N-isopropylpropan-2-amine (0.268 ml, 1.624 mmol). The solution was stirred at room temperature for one hour. Solvent was evaporated and mixed with methylene chloride (80 ml). It was washed with water (2×40 ml), dried and concentrated to an oil, which was purified by solica gel column (MeOH/CH$_2$Cl$_2$) to give 3-{1-Oxo-4-[4-(3-phenoxy-azetidin-1-ylmethyl)-benzyloxy]-1,3-dihydro-isoindol-2-yl}-piperidine-2,6-dione as a white solid (0.237 g, 57% yield); mp, 150-152° C. HPLC: Waters Symmetry C-18, 3.9×150 mm, 5 μm, 1 mL/min, 240 nm, gradient from 10/90 to 90/10 in 5 min, isocratic at 90/10 for 5 min (CH$_3$CN/0.1% H$_3$PO$_4$), 4.83 min (96.0%). $^1$H NMR (DMSO-d$_6$) δ 1.91-2.06 (m, 1H, CHH), 2.36-2.48 (m, 1H, CHH), 2.53-2.64 (m, 1H, CHH), 2.83-2.98 (m, 1H, CHH), 3.04 (ddd, J=1.8, 5.3, 6.9 Hz, 2H, CH$_2$), 3.65 (s, 2H, CH$_2$), 3.68-3.79 (m, 2H, CH$_2$), 4.19-4.48 (m, 2H, CH$_2$), 4.80 (quin, J=5.7 Hz, 1H, CH), 5.11 (dd, J=5.1, 13.2 Hz, 1H, NCH), 5.22 (s, 2H, CH$_2$), 6.82 (dd, J=1.0, 8.8 Hz, 2H, Ar), 6.89-6.98 (m, 1H, Ar), 7.22-7.37 (m, 5H, Ar), 7.40-7.53 (m, 3H, Ar), 10.97 (s, 1H, NH). $^{13}$C NMR (DMSO-d$_6$) δ 22.36, 31.21, 45.10, 51.59, 60.56, 62.35, 66.23, 69.41, 114.49, 114.98, 115.23, 120.89, 127.68, 128.39, 129.60, 129.81, 129.95, 133.32, 135.23, 138.05, 153.50, 156.68, 168.01, 170.96, 172.82. LC/MS m/e=512. Anal Calcd for C$_{30}$H$_{29}$N$_3$O$_5$ (+0.9 H$_2$O): C, 68.27; H, 5.88; N, 7.96. Found: C, 67.93; H, 5.69; N, 7.84.

5.104 3-(4-{4-[3-(4-Fluoro-Phenoxy)-Azetidin-1-ylmethyl]-Benzyloxy}-1-Oxo-1,3-Dihydro-Isoindol-2-yl)-Piperidine-2,6-Dione Formate

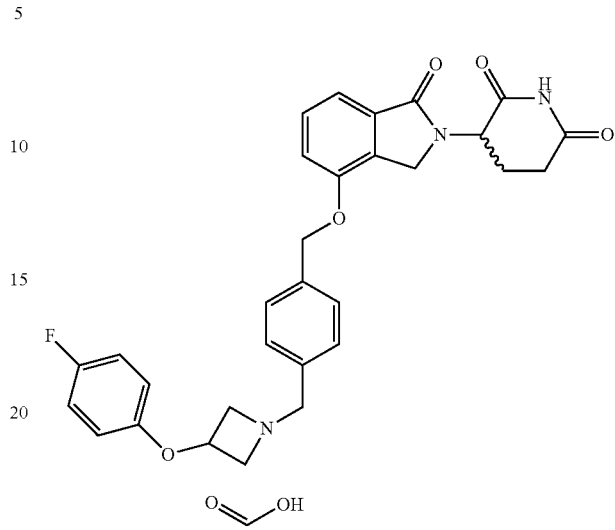

To a 20-mL reaction vial charged with 3-(4-((4-(bromomethyl)benzyl)oxy)-1-oxoisoindolin-2-yl)piperidine-2,6-dione (300 mg, 0.677 mmol) and 3-(4-fluorophenoxy)azetidine hydrochloride (145 mg, 0.711 mmol), was added dry MeCN (10 mL) followed by DIEA (0.355 mL, 2.0 mmol). The resulting suspension was warmed to 50° C. to give a clear solution. After ~30 min, the temperature was raised further to 70° C. and the reaction mixture was stirred for ~16 h at 70° C. The reaction mixture was cooled to room temperature and then concentrated under vacuum. The residue was diluted in EtOAc (~100 mL) and then extracted with 1N NaHCO$_3$ (2×35 mL) and brine. Drying (Na$_2$SO$_4$) and concentration on a rotovap gave a glassy solid. Et$_2$O (~15 mL) was added to the glass in small portions and with intermittent sonication until a well-dispersed solid was formed. The slurry was agitated vigorously and then filtered on a 15-mL fine fritted funnel. The solid was dissolved in DMF (7 mL) and purified using reversed-phase preparatory HPLC. The product was eluted with an acetonitrile/water gradient (0.1% formic acid in both mobile phases, 5% to 95% MeCN over 20 minutes) and fractions were collected by mass trigger. The desired fractions were combined and concentrated in vacuo to give 3-(4-{4-[3-(4-fluoro-phenoxy)-azetidin-1-ylmethyl]-benzyloxy}-1-oxo-1,3-dihydro-isoindol-2-yl)-piperidine-2,6-dione formate as a white solid (204 mg, 52% yield): HPLC: Waters Symmetry C$_{18}$, 5 μm, 3.9×150 mm, 1 ml/min, 240 nm, 27/73 CH$_3$CN/0.1% H$_3$PO$_4$, 3.62 min (98.4%); mp: 166-168° C.; $^1$H NMR (DMSO-d$_6$) δ 1.88-2.04 (m, 1H, CHH), 2.36-2.49 (m, 1H, CHH), 2.52-2.63 (m, 1H, CHH), 2.91 (ddd, J=5.3, 13.5, 17.4 Hz, 1H, CHH), 3.03 (dd, J=5.6, 8.2 Hz, 2H, CHH, CHH), 3.64 (s, 2H, CH$_2$N), 3.71 (dd, J=6.2, 8.3 Hz, 2H, CHH, CHH), 4.25 (d, J=17.4 Hz, 1H, CHH), 4.41 (d, J=17.6 Hz, 1H, CHH), 4.77 (quin, J=5.7 Hz, 1H, OCH), 5.11 (dd, J=5.1, 13.2 Hz, 1H, CH), 5.22 (s, 2H, CH$_2$), 6.75-6.91 (m, 2H, Ar), 7.00-7.21 (m, 2H, Ar), 7.28-7.38 (m, 4H, Ar), 7.39-7.62 (m, 3H, Ar), 8.16 (s, 1H, HCOOH), 10.97 (s, 1H, NH). ~1.8 equiv. of HCOOH at 8.16 ppm is observed. $^{13}$C NMR (DMSO-d$_6$) δ 22.33, 31.18, 45.07, 51.56, 60.41, 62.29, 66.70, 69.36, 114.97, 115.20, 115.70, 115.80, 116.09, 127.66, 128.39, 129.78, 129.93, 133.30, 135.24, 137.98, 153.23 (d, J=35.2 Hz, CF), 158.22, 163.15, 167.97, 170.95, 172.80; LCMS: MH=530; Anal Calcd for $C_{30}H_{28}FN_3O_5$+ 1.8 HCOOH+1.25 $H_2O$: C, 60.16; H, 5.41; N, 6.62; Found: C, 60.08; H, 5.05; N, 6.56.

5.105 3-{4-[4-(3,3-Difluoro-Azetidin-1-ylmethyl)-Benzyloxy]-1-Oxo-1,3-Dihydro-Isoindol-2-yl}-Piperidine-2,6-Dione

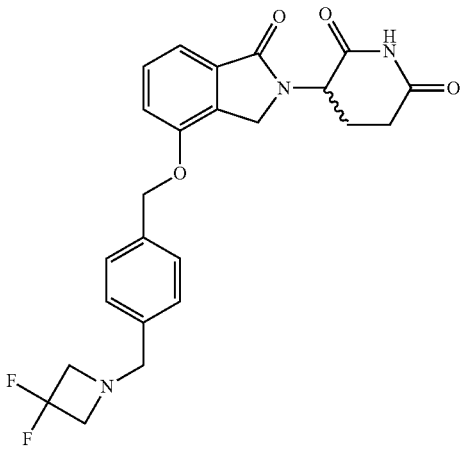 [SMILES: O=C1CCC(N2Cc3c(OCc4ccc(CN5CC(F)(F)C5)cc4)cccc3C2=O)C(=O)N1]

To a 20-mL reaction vial charged with 3-(4-((4-(bromomethyl)benzyl)oxy)-1-oxoisoindolin-2-yl)piperidine-2,6-dione (300 mg, 0.677 mmol) and 3,3-difluoroazetidine hydrochloride (92 mg, 0.711 mmol), was added dry MeCN (10 mL) followed by DIEA (0.355 mL, 2.0 mmol). The resulting suspension was warmed to 50° C. After ~30 min, the temperature was raised further to 70° C. and the reaction mixture became clear. Stirring was continued for ~16 h at 70° C. The reaction mixture was cooled to room temperature and then concentrated under vacuum. The residue was diluted in EtOAc (~100 mL) and then extracted with 1N $NaHCO_3$ (2×35 mL) and brine. Drying ($Na_2SO_4$) and concentration on a rotovap gave a glassy solid. $Et_2O$ (~20 mL) was added to the glass in small portions and with intermittent sonication until a well-dispersed solid was formed. The slurry was agitated vigorously and then filtered on a 15-mL medium fritted funnel. The cake was washed with additional $Et_2O$ (~50 mL) and then water (~50 mL). The remaining solid was suction dried and then dried further in a vacuum oven at 60° C. for several hours to give 3-{4-[4-(3,3-difluoro-azetidin-1-ylmethyl)-benzyloxy]-1-oxo-1,3-dihydro-isoindol-2-yl}-piperidine-2,6-dione as an off-white solid (187 mg, 61% yield): HPLC: Waters Symmetry $C_{18}$, 5 μm, 3.9×150 mm, 1 ml/min, 240 nm, 18/82 $CH_3CN$/0.1% $H_3PO_4$, 4.20 min (99.1%); mp: 175-177° C.; $^1H$ NMR (DMSO-$d_6$) δ 1.89-2.06 (m, 1H, CHH), 2.34-2.49 (m, 1H, CHH), 2.52-2.64 (m, 1H, CHH), 2.81-3.04 (m, 1H, CHH), 3.59 (t, J=12.5 Hz, 4H, $CH_2CF_2$, $CH_2CF_2$), 3.72 (s, 2H, $CH_2$), 4.25 (d, J=17.4 Hz, 1H, CHH), 4.42 (d, J=17.4 Hz, 1H, CHH), 5.11 (dd, J=5.1, 13.2 Hz, 1H, CH), 5.23 (s, 2H, $CH_2$), 7.25-7.39 (m, 4H, Ar), 7.41-7.59 (m, 3H, Ar), 10.97 (s, 1H, NH); $^{13}C$ NMR (DMSO-$d_6$) δ 22.33, 31.16, 45.06, 51.56, 61.30, 63.55 (t, J=22.0 Hz, $CF_2(CH_2)_2$), 69.31, 117.29 (t, J=275.1 Hz, $CF_2$), 1 14.96, 115.22, 127.71, 128.36, 129.78, 129.93, 133.30, 135.49, 137.59, 153.45, 167.97, 170.95, 172.80; LCMS: MH=456; Anal Calcd for $C_{24}H_{23}F_2N_3O_4$+0.65 $H_2O$: C, 61.70; H, 5.24; N, 8.99; Found: C, 61.70; H, 5.01; N, 8.77.

5.106 3-{4-[4-(3-Methyl-3-Phenoxy-Azetidin-1-ylmethyl)-Benzyloxy]-1-Oxo-1,3-Dihydro-Isoindol-2-yl}-Piperidine-2,6-Dione

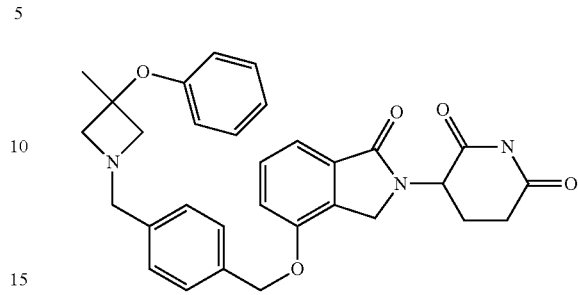

To the $CH_2Cl_2$ solution of 3-(4-(4-(bromomethyl)benzyloxy)-1-oxoisoindolin-2-yl)piperidine-2,6-dione (0.35 g, 0.790 mmol) was added 3-methyl-3-phenoxyazetidine (0.142 g, 0.869 mmol) and N-ethyl-N-isopropylpropan-2-amine (0.336 ml, 1.974 mmol). The mixture was stirred at room temperature overnight. The reaction mixture was added water (10 mL) and $CH_2Cl_2$ (10 mL) then extracted. The organic layer was concentrated and purified on silica gel column to give 3-{4-[4-(3-methyl-3-phenoxy-azetidin-1-ylmethyl)-benzyloxy]-1-oxo-1,3-dihydro-isoindol-2-yl}-piperidine-2,6-dione as a white solid (250 mg, 60%). Melting point: 127-129° C. LC-MS m/e=526. HPLC Waters Symmetry C-18, 3.9×150 mm, 5 micro, 1 mL/min, 240 nm, gradient 5/95 to 5/95 $CH_3CN$/0.1% $H_3PO_4$ in H2O during 5 min and stay at 95/5 for 5 min: 6.82 min (94%); $^1H$ NMR (DMSO-$d_6$) δ 1.58 (s, 3H, $CH_3$), 1.87-2.14 (m, 1H, CHH), 2.36-2.44 (m, OH, CHH), 2.54-2.64 (m, 1H, CHH), 2.82-3.01 (m, 1H, CHH), 3.17 (d, J=7.6 Hz, 2H, $CH_2$), 3.49 (d, J=7.9 Hz, 2H, $CH_2$), 3.64 (s, 2H, $CH_2$), 4.16-4.50 (m, 2H, $CH_2$), 5.11 (dd, J=5.1, 13.2 Hz, 1H, NCH), 5.22 (s, 2H, $CH_2$), 6.71 (d, J=7.7 Hz, 2H, Ar), 6.84-7.00 (m, 1H, Ar), 7.18-7.29 (m, 2H, Ar), 7.29-7.37 (m, 4H, Ar), 7.39-7.60 (m, 3H, Ar), 10.97 (s, 1H, NH); $^{13}C$ NMR (DMSO-$d_6$) δ 21.57, 22.33, 31.16, 45.06, 51.55, 62.12, 65.47, 69.36, 73.05, 114.94, 115.20, 116.40, 120.69, 127.67, 128.41, 129.48, 129.78, 129.93, 133.28, 135.21, 138.05, 153.46, 154.73, 167.97, 170.95, 172.80; Anal Calcd for $C_{31}H_{31}N_3O_5$+0.5 $H_2O$: C: 69.65%; H: 6.03%; N:7.83%; Found: C: 69.52%; H: 5.87%; N: 7.80%.

5.107 3-{4-[4-(3,3-Difluoro-Pyrrolidin-1-ylmethyl)-Benzyloxy]-1-Oxo-1,3-Dihydro-Isoindol-2-yl}-Piperidine-2,6-Dione

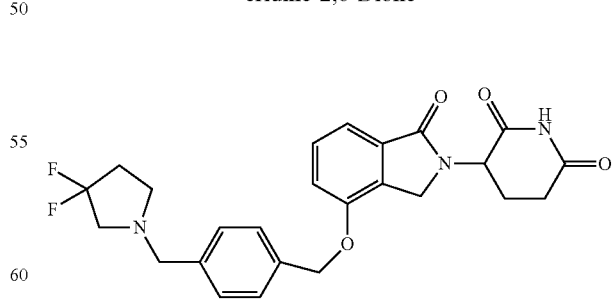

To the stirred mixture of 3-(4-(4-(bromomethyl)benzyloxy)-1-oxoisoindolin-2-yl)piperidine-2,6-dione (350 mg, 0.8 mmol) and 3,3-difluoropyrrolidine hydrochloride (136 mg, 0.8 mmol) in DCM (10 mL) was added DIPEA (0.28 ml, 1.6 mmol). The resulting mixture was stirred at room temperature for 22 hrs and the reaction mixture was diluted by DCM (30 mL). The mixture was washed with water (20 mL) and brine (20 mL). Organic layer was dried by MgSO$_4$ and concentrated. The residue was purified by ISCO to give 3-{4-[4-(3,3-Difluoro-pyrrolidin-1-ylmethyl)-benzyloxy]-1-oxo-1,3-dihydro-isoindol-2-yl}-piperidine-2,6-dione as a white solid (256 mg, 69% yield. HPLC: Waters Symmetry C-18, 3.9×150 mm, 5 μm, 1 mL/min, 240 nm, 20/80, (CH$_3$CN/0.1% H$_3$PO$_4$), 3.59 min (98.6%); mp: 126-128° C.; $^1$H NMR (DMSO-d$_6$) δ 1.91-2.04 (m, 1H, CHH), 2.15-2.34 (m, 2H, CH$_2$), 2.35-2.44 (m, 1H, CHH), 2.60 (br. s., 1H, CHH), 2.69 (t, J=7.0 Hz, 2H, CH$_2$), 2.76-3.01 (m, 3H, CHH, CH$_2$), 3.62 (s, 2H, CH$_2$), 4.20-4.32 (m, J=17.6 Hz, 1H, CHH), 4.42 (d, J=17.4 Hz, 1H, CHH), 5.11 (dd, J=5.1, 13.2 Hz, 1H, CHH), 5.23 (s, 2H, CH$_2$), 7.22-7.37 (m, 4H, Ar), 7.39-7.63 (m, 3H, Ar), 10.97 (s, 1H, NH); $^{13}$C NMR (DMSO-d$_6$) δ 22.33, 31.16, 34.92, 35.55 (t, J$_{C-F}$=22.50 Hz), 51.30, 51.56, 58.24, 60.99 (t, J$_{C-F}$=27.57 Hz), 69.35, 114.97, 115.22, 127.69, 128.62, 129.78, 129.93, 130.38, 133.30, 135.44, 137.63, 153.46, 167.97, 170.95, 172.80; LCMS MH=470; Anal. Calcd for C$_{25}$H$_{25}$F$_2$N$_3$O$_4$+0.2H$_2$O: C, 63.47; H, 5.41; N, 8.88; Found: C, 63.41; H, 5.46; N, 8.78.

5.108 3-{4-[4-(7-Fluoro-3,4-Dihydro-1H-Isoquinolin-2-ylmethyl)-Benzyloxy]-1-Oxo-1,3-Dihydro-Isoindol-2-yl}-Piperidine-2,6-Dione

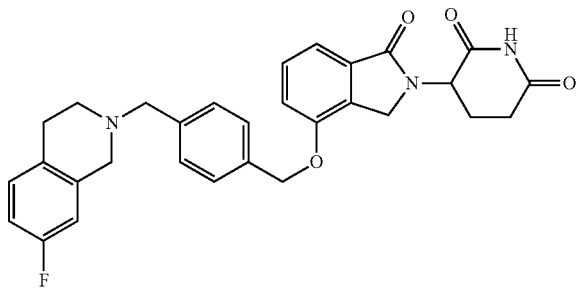 [SMILES: O=C1CCC(N2Cc3c(OCc4ccc(CN5CCc6ccc(F)cc6C5)cc4)cccc3C2=O)C(=O)N1]

To the CH$_3$CN (10 ml) solution of 3-(4-(4-(bromomethyl)benzyloxy)-1-oxoisoindolin-2-yl)piperidine-2,6-dione (0.36 g, 0.812 mmol) was added 7-fluoro-1,2,3,4-tetrahydroisoquinoline hydrochloride (0.198 g, 1.056 mmol) and N-ethyl-N-isopropylpropan-2-amine (0.403 ml, 2.436 mmol). The resulting solution was stirred at room temperature overnight. Solvent was evaporated, and methylene chloride (100 ml) was added. The mixture was washed with water (2×50 ml), brine (50 ml), dried and concentrated to a foamy solid, which was purified by silica gel column (MeOH/CH$_2$Cl$_2$) to give 3-{4-[4-(7-Fluoro-3,4-dihydro-1H-isoquinolin-2-ylmethyl)-benzyloxy]-1-oxo-1,3-dihydro-isoindol-2-yl}-piperidine-2,6-dione as a white solid (0.205 g, 49% yield); mp, 132-134° C. HPLC: Waters Symmetry C-18, 3.9×150 mm, 5 μm, 1 mL/min, 240 nm, gradient from 10/90 to 90/10 in 5 min, isocratic at 90/10 for 5 min (CH$_3$CN/0.1% H$_3$PO$_4$), 4.75 min (95.6%). $^1$H NMR (DMSO-d$_6$) δ 1.90-2.08 (m, 1H, CHH), 2.36-2.48 (m, 1H, CHH), 2.53-2.63 (m, 1H, CHH), 2.63-2.72 (m, 2H, CH$_2$), 2.73-2.82 (m, 2H, CH$_2$), 2.83-3.00 (m, 1H, CHH), 3.54 (s, 2H, CH$_2$), 3.65 (s, 2H, CH$_2$), 4.21-4.49 (m, 2H, CH$_2$), 5.11 (dd, J=5.1, 13.2 Hz, 1H, NCH), 5.24 (s, 2H, CH$_2$), 6.84-7.00 (m, 2H, Ar), 7.09-7.17 (m, 1H, Ar), 7.29-7.42 (m, 4H, Ar), 7.43-7.54 (m, 3H, Ar), 10.97 (s, 1H, NH). $^{13}$C NMR (DMSO-d$_6$) δ 22.36, 27.90, 31.20, 45.10, 50.02, 51.59, 61.21, 69.44, 112.49, 112.78, 113.07, 115.00, 115.24, 127.74, 128.80, 129.82, 129.93 (d, J$_{C-F}$=18), 130.19, 133.32, 135.33, 136.95 (d, J$_{C-F}$=8), 138.13, 153.51, 160.20 (d, J$_{C-F}$=240), 168.01, 170.96, 172.82.). LC/MS m/e=514. Anal Calcd for C$_{30}$H$_{28}$N$_3$O$_4$F (+0.2 H$_2$O): C, 69.67; H, 5.54; N, 8.12. Found: C, 69.34; H, 5.57; N, 7.96.

5.109 3-{4-[4-(4,7-Dihydro-5H-Thieno[2,3-C]Pyridin-6-ylmethyl)-Benzyloxy]-1-Oxo-1,3-Dihydro-Isoindol-2-yl}-Piperidine-2,6-Dione

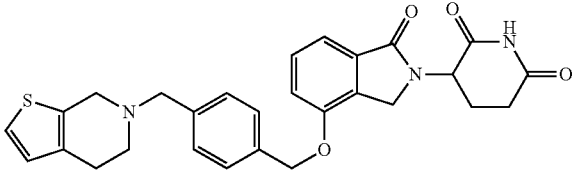 [SMILES: O=C1CCC(N2Cc3c(OCc4ccc(CN5CCc6ccsc6C5)cc4)cccc3C2=O)C(=O)N1]

To the CH$_3$CN (10 ml) solution of 3-(4-(4-(bromomethyl)benzyloxy)-1-oxoisoindolin-2-yl)piperidine-2,6-dione (0.359 g, 0.810 mmol) was added 4,5,6,7-tetrahydrothieno[2,3-c]pyridine hydrochloride (0.171 g, 0.972 mmol) and N-ethyl-N-isopropylpropan-2-amine (0.402 ml, 2.430 mmol). It became a clear solution after DIPEA was added. The mixture was stirred at room temperature overnight. Solvent was evaporated and to the residue was added methylene chloride (80 ml). The mixture was washed with water (2×60 ml), brine (50 ml), dried and concentrated to an off-white solid, which was purified by silica gel column (MeOH/CH$_2$Cl$_2$) to give 3-{4-[4-(4,7-Dihydro-5H-thieno[2,3-c]pyridin-6-ylmethyl)-benzyloxy]-1-oxo-1,3-dihydro-isoindol-2-yl}-piperidine-2,6-dione as a white solid (0.304 g, 74% yield). HPLC: Waters Symmetry C-18, 3.9×150 mm, 5 μm, 1 mL/min, 240 nm, gradient from 10/90 to 90/10 in 5 min, isocratic at 90/10 for 5 min (CH$_3$CN/0.1% H$_3$PO$_4$), 4.61 min (98.1%). $^1$H NMR (DMSO-d$_6$) δ 1.89-2.08 (m, 1H, CHH), 2.35-2.48 (m, 1H, CHH), 2.53-2.68 (m, 3H, CHH, CH$_2$), 2.68-2.77 (m, 2H, CH$_2$), 2.82-3.00 (m, 1H, CHH), 3.59 (s, 2H, CH$_2$), 3.68 (s, 2H, CH$_2$), 4.20-4.48 (m, 2H, CH$_2$), 5.11 (dd, J=5.2, 13.3 Hz, 1H, NCH), 5.24 (s, 2H, CH$_2$), 6.82 (d, J=5.1 Hz, 1H, Ar), 7.28 (d, J=5.1 Hz, 1H, Ar), 7.31-7.42 (m, 4H, Ar), 7.43-7.56 (m, 3H, Ar), 10.97 (s, 1H, NH). $^{13}$C NMR (DMSO-d$_6$) δ 22.36, 25.12, 31.20, 45.10, 49.59, 51.36, 51.59, 60.50, 69.45, 115.00, 115.24, 122.61, 126.99, 127.72, 128.83, 129.81, 129.95, 132.46, 133.32, 133.47, 135.35, 138.29, 153.53, 168.01, 170.96, 172.82. LC/MS m/e=502. Anal Calcd for C$_{28}$H$_{27}$N$_3$O$_4$S (+0.5 H$_2$O): C, 65.86; H, 5.53; N, 8.23. Found: C, 65.64; H, 5.44; N, 8.04.

5.110 3-{4-[4-(6,7-Dihydro-4H-Thieno[3,2-C]Pyridin-5-ylmethyl)-Benzyloxy]-1-Oxo-1,3-Dihydro-Isoindol-2-yl}-Piperidine-2,6-Dione

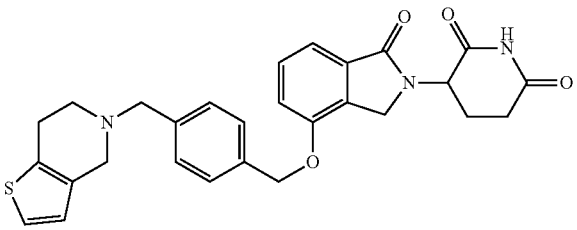 [SMILES: O=C1CCC(N2Cc3c(OCc4ccc(CN5CCc6sccc6C5)cc4)cccc3C2=O)C(=O)N1]

To the CH₃CN (10 ml) suspension of 4,5,6,7-tetrahydrothieno[3,2-c]pyridine (0.145 g, 1.038 mmol) was added 3-(4-(4-(bromomethyl)benzyloxy)-1-oxoisoindolin-2-yl)piperidine-2,6-dione (0.354 g, 0.799 mmol) and N-ethyl-N-isopropylpropan-2-amine (0.264 ml, 1.597 mmol). It became a clear solution after DIPEA was added. The mixture was stirred at room temperature for two hours. Solvent was evaporated, and methylene chloride (80 ml) was added. The mixture was washed with water (2×50 ml), brine (50 ml), dried and concentrated to an oil, which was purified by silica gel column (MeOH/CH₂Cl₂) to give 3-{4-[4-(6,7-Dihydro-4H-thieno[3,2-c]pyridin-5-ylmethyl)-benzyloxy]-1-oxo-1,3-dihydro-isoindol-2-yl}-piperidine-2,6-dione as a white solid (0.312 g, 78% yield); mp, 143-145° C. HPLC: Waters Symmetry C-18, 3.9×150 mm, 5 μm, 1 mL/min, 240 nm, gradient from 10/90 to 90/10 in 5 min, isocratic at 90/10 for 5 min (CH₃CN/0.1% H₃PO₄), 4.51 min (97.0%). ¹H NMR (DMSO-d₆) δ 1.89-2.06 (m, 1H, CHH), 2.35-2.48 (m, 1H, CHH), 2.53-2.64 (m, 1H, CHH), 2.68-2.83 (m, 4H, CH₂, CH₂), 2.84-3.00 (m, 1H, CHH), 3.42-3.49 (m, 2H, CH₂), 3.68 (s, 2H, CH₂), 4.20-4.48 (m, 2H, CH₂), 5.11 (dd, J=5.1, 13.2 Hz, 1H, NCH), 5.24 (s, 2H, CH₂), 6.76 (d, J=5.1 Hz, 1H, Ar), 7.25 (d, J=5.1 Hz, 1H, Ar), 7.30-7.41 (m, 4H, Ar), 7.43-7.53 (m, 3H, Ar), 10.97 (s, 1H, NH). ¹³C NMR (DMSO-d₆) δ 22.36, 24.99, 31.20, 45.10, 50.18, 51.59, 52.42, 60.91, 69.45, 115.00, 115.24, 122.91, 125.42, 127.72, 128.82, 129.82, 129.95, 132.77, 133.32, 133.96, 135.30, 138.38, 153.53, 168.01, 170.96, 172.83. LC/MS m/e=502. Anal Calcd for $C_{28}H_{27}N_3O_4S$ (+0.4 H₂O): C, 66.10; H, 5.51; N, 8.26. Found: C, 65.92; H, 5.45; N, 8.00.

5.111 3-{1-Oxo-4-[4-(3,3,4,4-Tetrafluoro-Pyrrolidin-1-ylmethyl)-Benzyloxy]-1,3-Dihydro-Isoindol-2-yl}-Piperidine-2,6-Dione

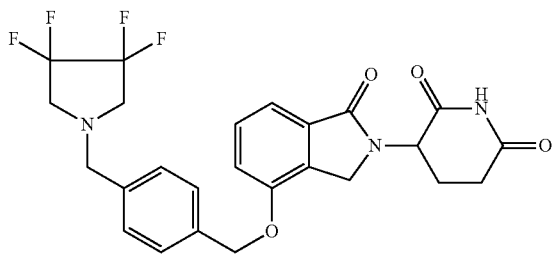 [SMILES: O=C1CCC(N2Cc3c(OCc4ccc(CN5CC(F)(F)C(F)(F)C5)cc4)cccc3C2=O)C(=O)N1]

To the CH₂Cl₂ solution of 3-(4-(4-(bromomethyl)benzyloxy)-1-oxoisoindolin-2-yl)piperidine-2,6-dione (0.35 g, 0.790 mmol) was added 3,3,4,4-tetrafluoropyrrolidine hydrochloride (0.142 g, 0.79 mmol), and N-ethyl-N-isopropylpropan-2-amine (336 μl, 1.974 mmol). The mixture was heated to 70° C. for 3 days. The reaction mixture was concentrated and the resulted solid was taken up in CH₂Cl₂ (20 mL) and extracted with water (20 mL). Organic layer was concentrated and purified on silica gel column eluted with CH₂Cl₂ and MeOH to give 3-{1-Oxo-4-[4-(3,3,4,4-tetrafluoro-pyrrolidin-1-ylmethyl)-benzyloxy]-1,3-dihydro-isoindol-2-yl}-piperidine-2,6-dione as white a solid (120 mg, 30%). Melting point: 164-166° C. LC-MS m/e=506. HPLC Waters Symmetry C-18, 3.9×150 mm, 5 micro, 1 mL/min, 240 nm, gradient 5/95 to 5/95 CH₃CN/0.1% H₃PO₄ in H₂O during 5 min and stay at 95/5 for 5 min: 6.67 min (96%). ¹H NMR (DMSO-d₆) δ 1.86-2.09 (m, 1H, CHH), 2.34-2.44 (m, 1H, CHH), 2.55-2.67 (m, 1H, CHH), 2.81-3.03 (m, 1H, CHH), 3.15 (t, J=13.4 Hz, 4H, CH₂, CH₂), 3.72 (s, 2H, CH₂), 4.19-4.48 (m, 2H, CH₂), 5.11 (dd, J=5.1, 13.2 Hz, 1H, NCH), 5.24 (s, 2H, CH₂), 7.26-7.39 (m, 4H, Ar), 7.43-7.58 (m, 3H, Ar), 10.97 (s, 1H, NH); ¹³C NMR (DMSO-d₆) δ 22.33, 31.16, 45.06, 51.56, 57.01, 57.47, 57.82, 58.15, 69.29, 114.97, 115.25, 119.39, 122.84, 127.80, 128.75, 129.80, 129.95, 133.30, 135.88, 136.13, 153.45, 167.97, 170.95, 172.80; Anal Calcd for $C_{25}H_{23}F_4N_3O_4$+0.4 H₂O: C; 58.57%; H: 4.67%; N: 8.20%; Found: C; 58.46%; H: 4.35%; N: 8.08%.

5.112 3-(4-{4-[2-(4-Fluoro-Phenyl)-2-Methyl-Morpholin-4-ylmethyl]-Benzyloxy}-1-Oxo-1,3-Dihydro-Isoindol-2-yl)-Piperidine-2,6-Dione

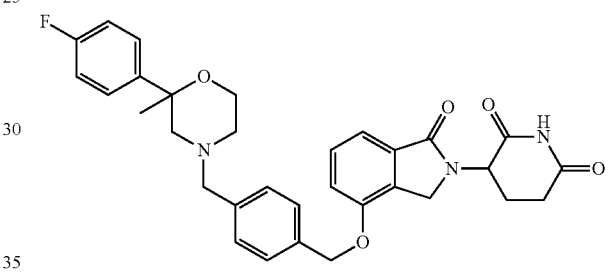

To the CH₂Cl₂ solution of 3-(4-(4-(bromomethyl)benzyloxy)-1-oxoisoindolin-2-yl)piperidine-2,6-dione (0.35 g, 0.790 mmol) was added 2-(4-fluorophenyl)-2-methylmorpholine (0.170 g, 0.869 mmol) and N-ethyl-N-isopropylpropan-2-amine (0.336 ml, 1.974 mmol). The mixture was stirred at room temperature overnight. The mixture was added water and CH2Cl2 then extracted. The organic layer was concentrated and purified on silica gel column eluted with CH₂Cl₂ and MeOH to give 3-(4-{4-[2-(4-fluoro-phenyl)-2-methyl-morpholin-4-ylmethyl]-benzyloxy}-1-oxo-1,3-dihydro-isoindol-2-yl)-piperidine-2,6-dione as a white solid (0.27 g, 61%). Melting point: 118-120° C. LC-MS m/e=558. HPLC Waters Symmetry C-18, 3.9×150 mm, 5 micro, 1 mL/min, 240 nm, gradient 5/95 to 5/95 CH₃CN/0.1% H₃PO₄ in H₂O during 5 min and stay at 95/5 for 5 min: 6.90 min (94%); ¹H NMR (DMSO-d₆) δ 1.32 (s, 3H, CH₃), 1.87-2.09 (m, 1H, CHH), 2.22-2.46 (m, 4H, CHH, CH₂, CHH), 2.57 (d, J=18.5 Hz, 1H, CHH), 2.93 (br. s., 2H, CHH, CHH), 3.35-3.55 (m, J=1.9 Hz, 3H, CH₂, CHH), 3.57-3.76 (m, 1H, CHH), 4.16-4.54 (m, 2H, CH₂), 5.00-5.19 (m, 1H, NCH), 5.24 (s, 2H, CH₂), 7.12 (td, J=1.5, 8.9 Hz, 2H, Ar), 7.27-7.41 (m, 6H, Ar), 7.41-7.56 (m, 3H, Ar), 10.97 (s, 1H, NH); ¹³C NMR (DMSO-d₆) δ 22.33, 27.95, 31.16, 45.06, 51.56, 52.70, 60.63, 61.07, 61.77, 69.39, 74.52, 114.40, 114.68, 115.00, 115.22, 127.57, 127.76, 127.86, 128.98, 129.77, 129.95, 133.30, 135.37, 137.59, 141.20, 153.46, 159.21, 162.42, 167.97, 170.93, 172.80. Anal Calcd for $C_{32}H_{32}FN_3O_5$: C: 68.93%; H: 5.78%; N: 7.54%; Found: C: 67.20%; H: 5.26%; N: 7.17%.

5.113 3-{4-[4-(6-Fluoro-3,4-Dihydro-1H-Isoquinolin-2-ylmethyl)-Benzyloxy]-1-Oxo-1,3-Dihydro-Isoindol-2-yl}-Piperidine-2,6-Dione

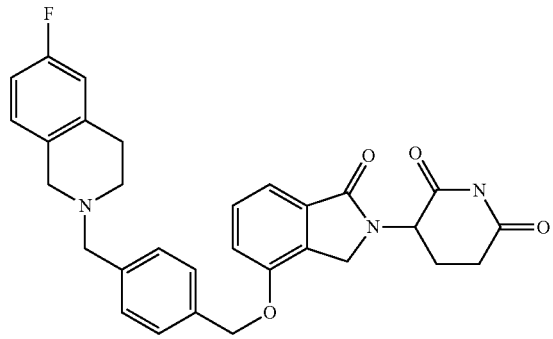 [SMILES: O=C1CCC(N2Cc3c(OCc4ccc(CN5CCc6cc(F)ccc6C5)cc4)cccc3C2=O)C(=O)N1]

To the CH$_2$Cl$_2$ of 3-(4-(4-(bromomethyl)benzyloxy)-1-oxoisoindolin-2-yl)piperidine-2,6-dione (0.35 g, 0.790 mmol) was added 6-fluoro-1,2,3,4-tetrahydroisoquinoline hydrochloride (0.163 g, 0.869 mmol) and N-ethyl-N-isopropylpropan-2-amine (0.336 ml, 1.974 mmol). The mixture was stirred at room temperature overnight. The mixture was added water and CH$_2$Cl$_2$ and extracted. The organic layer was concentrated to give a solid. The solid was stirred with ether and the suspension was filtered to give 3-{4-[4-(6-Fluoro-3,4-dihydro-1H-isoquinolin-2-ylmethyl)-benzyloxy]-1-oxo-1,3-dihydro-isoindol-2-yl}-piperidine-2,6-dione as white solid (0.28 g, 69%). Melting point: 123-125° C. LC-MS m/e=514. HPLC Waters Symmetry C-18, 3.9×150 mm, 5 micro, 1 mL/min, 240 nm, gradient 5/95 to 5/95 CH$_3$CN/0.1% H$_3$PO$_4$ in H$_2$O during 5 min and stay at 95/5 for 5 min: 6.6 min (94%). $^1$H NMR (DMSO-d$_6$) δ 1.88-2.06 (m, 1H, CHH), 2.34-2.48 (m, J=13.4 Hz, 1H, CHH), 2.57 (d, J=18.3 Hz, 1H, CHH), 2.62-2.71 (m, 2H, CH$_2$), 2.76-3.00 (m, 3H, CH$_2$, CHH), 3.51 (s, 2H, CH$_2$), 3.65 (s, 2H, CH$_2$), 4.11-4.49 (m, 2H, CH$_2$), 5.11 (dd, J=5.1, 13.2 Hz, 1H, NCH), 5.24 (s, 2H, CH$_2$), 6.93 (d, J=9.3 Hz, 2H, Ar), 6.99-7.12 (m, 1H, Ar), 7.28-7.43 (m, 4H, Ar), 7.43-7.56 (m, 3H, Ar), 10.97 (s, 1H, NH); $^{13}$C NMR (DMSO-d$_6$) δ 22.33, 28.70, 31.16, 45.07, 49.65, 51.55, 54.75, 61.33, 69.42, 112.29, 112.57, 114.36, 114.64, 114.97, 115.22, 127.70, 128.02, 128.14, 128.78, 129.78, 129.93, 130.78, 133.30, 135.30, 136.51, 136.61, 138.17, 153.49, 158.83, 162.04, 167.97, 170.95, 172.80; Anal Calcd for C$_{30}$H$_{28}$FN$_3$O$_4$+0.5 H$_2$O: C: 68.95%; H: 5.59%; N: 8.04%. Found: C: 68.68%; H: 5.31%; N: 7.89%.

5.114 3-{1-Oxo-4-[4-(3-Phenyl-5,6-Dihydro-8H-Imidazo[1,2-a]Pyrazin-7-ylmethyl)-Benzyloxy]-1,3-Dihydro-Isoindol-2-yl}-Piperidine-2,6-Dione

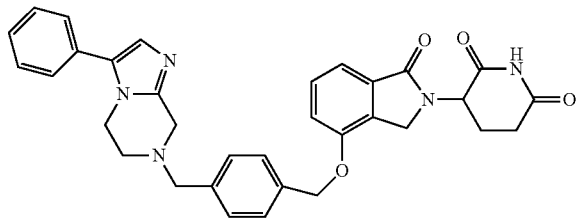 [SMILES: O=C1CCC(N2Cc3c(OCc4ccc(CN5CCn6c(-c7ccccc7)cnc6C5)cc4)cccc3C2=O)C(=O)N1]

The mixture of 3-(4-(4-(bromomethyl)benzyloxy)-1-oxoisoindolin-2-yl)piperidine-2,6-dione (350 mg, 0.8 mmol) and 3-phenyl-5,6,7,8-tetrahydroimidazo[1,2-a]pyrazine (157 mg, 0.8 mmol) in DCM (10 mL) was added DIPEA (0.28 mL, 1.6 mmol). The resulting mixture was stirred at room temperature for 23 hrs and then added by 3-phenyl-5,6,7,8-tetrahydroimidazo[1,2-a]pyrazine (94 mg, 0.45 mmol) and DIPEA (0.1 mL, 0.6 mmol). The mixture was concentrated and stirred in acetonitrile (7 mL), DCM (2 mL) and DIPEA (0.2 mL) at 60° C. for 16 hrs. The reaction mixture was diluted by DCM (30 mL) and washed with water (20 mL) and brine (20 mL). The organic layer was dried by MgSO$_4$ and concentrated. The residue was purified by ISCO to give 3-{1-Oxo-4-[4-(3-phenyl-5,6-dihydro-8H-imidazo[1,2-a]pyrazin-7-ylmethyl)-benzyloxy]-1,3-dihydro-isoindol-2-yl}-piperidine-2,6-dione as a light yellow solid (82 mg, 18% yield). HPLC: Waters Symmetry C-18, 3.9×150 mm, 5 μm, 1 mL/min, 240 nm, 27/73, (CH$_3$CN/0.1% H$_3$PO$_4$), 4.89 min (98.3%); mp: 131-133° C. (in house); $^1$H NMR (DMSO-d$_6$) δ 1.92-2.05 (m, 1H, CHH), 2.36-2.47 (m, 1H, CHH), 2.54-2.64 (m, 1H, CHH), 2.84 (t, J=5.4 Hz, 2H, CH$_2$), 2.88-2.99 (m, 1H, CHH), 3.64 (s, 2H, CH$_2$), 3.74 (s, 2H, CH$_2$), 4.03 (t, J=5.2 Hz, 2H, CH$_2$), 4.26 (d, J=17.6 Hz, 1H, CHH), 4.43 (d, J=17.6 Hz, 1H, CHH), 5.11 (dd, J=4.9, 13.2 Hz, 1H, CHH), 5.26 (s, 2H, CH$_2$), 7.02 (s, 1H, Ar), 7.29-7.38 (m, 3H, Ar), 7.39-7.46 (m, 4H, Ar), 7.46-7.54 (m, 5H, Ar), 10.98 (s, 1H, NH); $^{13}$C NMR (DMSO-d$_6$) δ 21.43, 30.26, 42.58, 44.17, 48.31, 50.64, 59.57, 68.52, 114.13, 114.33, 125.24, 126.26, 126.33, 126.87, 127.83, 128.04, 128.83, 128.90, 129.06, 130.23, 132.40, 134.69, 136.60, 142.49, 152.59, 167.08, 170.04, 171.90; LCMS MH=562; Anal. Calcd for C$_{33}$H$_{31}$N$_5$O$_4$+ 0.8H$_2$O+0.31 CH$_2$Cl$_2$: C, 66.42; H, 5.56; N, 11.63; Found: C, 66.10; H, 5.25; N, 11.49.

5.115 3-{1-Oxo-4-[4-(4-Trifluoromethyl-Imidazol-1-ylmethyl)-Benzyloxy]-1,3-Dihydro-Isoindol-2-yl}-Piperidine-2,6-Dione

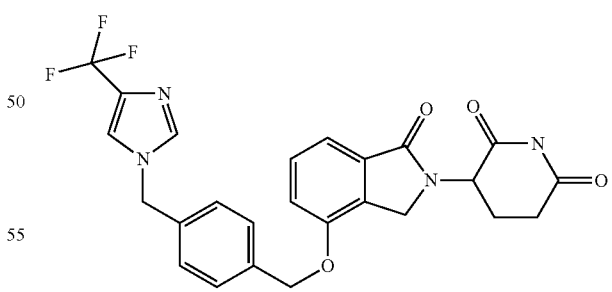

To the CH$_3$CN solution of 3-(4-(4-(bromomethyl)benzyloxy)-1-oxoisoindolin-2-yl)piperidine-2,6-dione (0.35 g, 0.790 mmol) was added 4-(trifluoromethyl)-1H-imidazole (0.118 g, 0.869 mmol) and N-ethyl-N-isopropylpropan-2-amine (0.336 ml, 1.974 mmol). The mixture was heated at 70° C. for 2 days. The reaction mixture was then added CH$_2$Cl$_2$ and water and extracted. The organic layer was concentrated and the resulted oil was purified on silica gel column eluted with CH₂Cl₂ and MeOH to give 3-{1-Oxo-4-[4-(4-trifluoromethyl-imidazol-1-ylmethyl)-benzyloxy]-1,3-dihydro-isoindol-2-yl}-piperidine-2, 6-dione as a white solid (80 mg, 20%). Melting point 148-150° C. LC-MS m/e=499. HPLC Waters Symmetry C-18, 3.9×150 mm, 5 micro, 1 mL/min, 240 nm, gradient 5/95 to 5/95 CH₃CN/0.1% H₃PO₄ in H₂O during 5 min and stay at 95/5 for 5 min: 8.89 min (96%). ¹H NMR (DMSO-d₆) δ 1.90-2.05 (m, 1H, CHH), 2.33-2.48 (m, J=4.3, 13.0 Hz, 1H, CHH), 2.57 (d, J=17.9 Hz, 1H, CHH), 2.80-2.99 (m, 1H, CHH), 4.18-4.47 (m, 2H, CH₂), 5.10 (dd, J=5.1, 13.2 Hz, 1H, NCH), 5.23 (s, 2H, CH₂), 5.27 (s, 2H, CH₂), 7.25-7.41 (m, 4H, Ar), 7.43-7.57 (m, 3H, Ar), 7.91 (d, J=1.1 Hz, 1H, Ar), 8.00 (s, 1H, Ar), 10.96 (s, 1H, NH); ¹³C NMR (DMSO-d₆) δ 22.31, 31.16, 45.04, 49.62, 51.55, 69.10, 114.91, 115.26, 120.53, 127.83, 128.14, 129.78, 129.95, 133.30, 136.49, 136.64, 139.07, 153.36, 167.96, 170.93, 172.80. Anal Calcd for C₂₅H₂₁F₃N₄O₄₊₀.₅ H₂O: C; 59.17%; H, 4.37%; N, 11.04%. Found: C; 59.21%; H, 4.11%; N, 10.90%.

5.116 3-(4-{3-[4-(4-Fluoro-Phenyl)-Piperidin-1-ylmethyl]-Benzyloxy}-1-Oxo-1,3-Dihydro-Isoindol-2-yl)-Piperidine-2,6-Dione

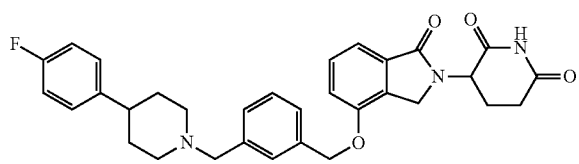 [SMILES: O=C1CCC(N2Cc3c(OCc4cccc(CN5CCC(c6ccc(F)cc6)CC5)c4)cccc3C2=O)C(=O)N1]

To the CH₃CN (10 ml) solution of 3-(4-(3-(bromomethyl)benzyloxy)-1-oxoisoindolin-2-yl)piperidine-2,6-dione (0.31 g, 0.699 mmol) was added 4-(4-fluorophenyl)piperidine hydrochloride (0.181 g, 0.839 mmol) and N-ethyl-N-isopropylpropan-2-amine (0.347 ml, 2.098 mmol) at room temperature. The cloudy mixture was stirred at room temperature for one hour. Solvent was evaporated and the resulting residue was purified by silica gel column (MeOH/CH₂Cl₂) to give 3-(4-{3-[4-(4-Fluoro-phenyl)-piperidin-1-ylmethyl]-benzyloxy}-1-oxo-1,3-dihydro-isoindol-2-yl)-piperidine-2, 6-dione as a white solid (0.176 g, 47% yield); mp, 139-141° C. HPLC: Waters Symmetry C-18, 3.9×150 mm, 5 μm, 1 mL/min, 240 nm, gradient from 10/90 to 90/10 in 5 min, isocratic at 90/10 for 5 min (CH₃CN/0.1% H₃PO₄), 4.95 min (95.5%). ¹H NMR (DMSO-d₆) δ 1.49-1.77 (m, 4H, CH₂, CH₂), 1.89-2.09 (m, 3H, CH₂, CHH), 2.35-2.47 (m, 1H, CHH), 2.53-2.62 (m, 1H, CHH), 2.81-2.99 (m, 3H, CH₂, CHH), 3.51 (s, 2H, CH₂), 4.20-4.49 (m, 2H, CH₂), 5.11 (dd, J=5.1, 13.2 Hz, 1H, NCH), 5.27 (s, 2H, CH₂), 7.04-7.15 (m, 2H, Ar), 7.21-7.53 (m, 9H, Ar), 10.97 (s, 1H, NH). ¹³C NMR (DMSO-d₆) δ 15.14, 22.36, 31.18, 33.13, 41.01, 45.12, 51.59, 53.50, 62.18, 69.63, 114.75, 115.01, 115.20, 115.26, 126.22, 128.00, 128.34, 128.44, 129.76, 129.98, 133.31, 136.47, 138.79, 142.35, 153.44, 160.58 (d, J_{C-F}=242 Hz), 167.99, 170.95, 172.79. LC/MS m/e=542. Anal Calcd for C₃₂H₃₂N₃O₄F (+0.2 H₂O): C, 70.49; H, 5.99; N, 7.71. Found: C, 70.24; H, 6.14; N, 7.58.

5.117 2-(2,6-Dioxo-Piperidin-3-yl)-4-[4-(2-Trifluoromethyl-5,6,8,8A-Tetrahydro-1H-[1,2,4]Triazolo[1,5-A]Pyrazin-7-ylmethyl)-Benzyloxy]-Isoindole-1,3-Dione

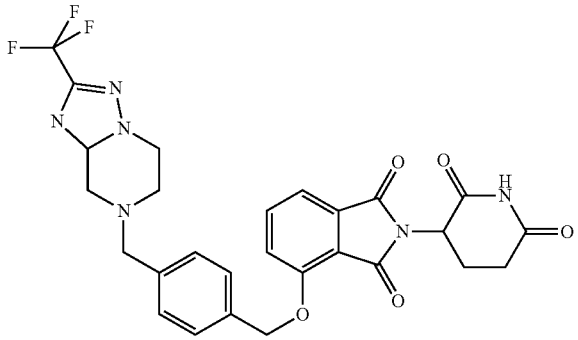 [SMILES: O=C1CCC(N2C(=O)c3cccc(OCc4ccc(CN5CCN6N=C(C(F)(F)F)NC6C5)cc4)c3C2=O)C(=O)N1]

Step 1: Preparation of dimethyl 3-((4-(hydroxymethyl)benzyl)oxy)phthalate Dimethyl 3-hydroxyphthalate (10 g, 47.6 mmol) and (4-(chloromethyl)phenyl)methanol (7.82 g, 50.0 mmol) were dissolved in dry DMF (60 mL). To the solution was added K₂CO₃ (6.90 g, 50.0 mmol) and the mixture was stirred at 80° C. for 16 h. The DMF was removed in vacuo and the residue was partitioned between EtOAc (300 mL) and water (100 mL). The organic layer was washed with additional water (100 mL) and brine, dried (Na₂SO₄), and concentrated in vacuo to dimethyl 3-((4-(hydroxymethyl)benzyl)oxy)-phthalate as a viscous amber oil (19 g): LCMS: MH=331; The crude product was used in the next step without further purification Step 2: Preparation of 3-((4-(Hydroxymethyl)benzyl)oxy) phthalic acid Dimethyl 3-(4-(hydroxymethyl)benzyloxy) phthalate (19 g actual wt, 15:72 g, 47.6 mmol, assuming quantitative yield from previous step) was dissolved in THF (30 mL). To the solution was added water (30 mL). Aqueous NaOH (10 N, 25 mL, 250 mmol) was added and the mixture was vigorously stirred at 70° C. for 2.5 h. The mixture was allowed to cool to rt, concentrated in vacuo to a syrup, and then transferred to a flask containing 6 N HCl (45 mL) over ice. Immediately, solid precipitated out and the slurry was diluted with water (~60 mL). The mixture was filtered on a medium fritted funnel with suction. The cake was washed with additional water (~60 mL), suction dried, and then placed in a vacuum oven at 60° C. for 4 h to give 3-((4-(hydroxymethyl)benzyl)oxy)phthalic acid as a pale yellow solid (13.9 g, 97% yield from dimethyl 3-hydroxyphthalate): ¹H NMR (DMSO-d₆) δ 4.41-4.58 (m, 2H, CH₂), 5.17 (s, 3H, CH₂, OH), 7.20-7.64 (m, 7H, Ar), 13.02 (br. s., 2H, 2×COOH); ¹³C NMR (DMSO-d₆) δ 62.63, 69.73, 117.03, 121.56, 126.46, 126.88, 127.13, 128.91, 129.57, 134.87, 142.19, 154.50, 166.45, 167.71; LCMS: MH=303, 94 area % at 240 nm. The solid was used in the next step without further purification.

Step 3: Preparation of 2-(2,6-Dioxopiperidin-3-yl)-4-((4-(hydroxymethyl)benzyl) oxy)isoindoline-1,3-dione 3-Aminopiperidine-2,6-dione hydrochloride (0.915 g, 5.56 mmol) was added to a solution of 3-(4-(hydroxymethyl)benzyloxy)phthalic acid (1.4 g, 4.63 mmol) in dry pyridine (15 mL) and the mixture was heated to 118° C. in an oil bath for 16 h. The dark reaction mixture was allowed to cool to room temperature and was acidified with slow addition of 1 N HCl (~25 mL). The mixture was further diluted with water (~170 mL) and then sonicated for ~30 minutes to help break up solid aggregates. The resulting dark slurry was filtered on a medium pore fritted funnel and the dark solid was washed with additional water (70 mL). The cake was suction dried and then placed in vacuum oven at 60° C. for 2.5 h to give 1.6 g of a dark blue solid. The solid was dissolved in a mixture of DCM, MeCN, and MeOH (~100 mL each) and treated with decolorizing charcoal. The mixture was swirled around and then gravity-filtered using filter paper. The filtrate/wash (dark amber color) was treated once again with decolorizing charcoal and then filtered on a bed of celite. The clear filtrate was concentrated in vacuo to dryness to give a solid which was triturated with water and filtered with suction. The cake was washed with additional water (~100 mL), suction dried, and then placed in vacuum oven at 60° C. for 4 h to give 2-(2,6-dioxopiperidin-3-yl)-4-((4-(hydroxymethyl)benzyl)oxy)isoindoline-1,3-dione as an off-white solid (1.2 μm, 68% yield): HPLC: Waters Symmetry $C_{18}$, 5 μm, 3.9×150 mm, 1 ml/min, 240 nm, 15/85 $CH_3CN$/0.1% $H_3PO_4$, 5.08 min (99.9%); mp: 250-252; $^1$H NMR (DMSO-$d_6$) δ 1.95-2.07 (m, 1H, CHH), 2.41-2.67 (m, 2H, CHH, CHH), 2.78-3.00 (m, 1H, CHH), 4.50 (d, J=5.1 Hz, 2H, $CH_2OH$), 5.09 (dd, J=5.4, 12.7 Hz, 1H, CH), 5.19 (t, J=5.6 Hz, 1H, OH), 5.36 (s, 2H, $CH_2O$), 7.24-7.40 (m, 3H, Ar), 7.41-7.53 (m, 3H, Ar), 7.59 (d, J=8.5 Hz, 1H, Ar), 7.82 (dd, J=7.4, 8.5 Hz, 1H, Ar), 11.11 (s, 1H, NH); $^{13}$C NMR (DMSO-$d_6$) δ 21.88, 30.83, 48.67, 62.53, 69.91, 115.40, 116.52, 120.18, 126.44, 127.09, 133.17, 134.31, 136.86, 142.32, 155.42, 165.21, 166.68, 169.81, 172.66. LCMS: M+Na=417; MH is not observed in positive ionization mode; Anal Calcd for $C_{21}H_{18}N_2O_6$: C, 63.96; H, 4.60; N, 7.10; Found: C, 63.77; H, 4.52; N, 7.32.

Step 4 Preparation of 4-((4-(Bromomethyl)benzyl)oxy)-2-(2,6-dioxopiperidin-3-yl)isoindoline-1,3-dione A suspension of 2-(2,6-dioxopiperidin-3-yl)-4-(4-(hydroxymethyl)benzyloxy)isoindoline-1,3-dione (1.05 g, 2.66 mmol) in a mixture of DCM and MeCN (25 mL, 10 mL) was stirred in an ice bath. To the mixture was added $PBr_3$ (0.502 mL, 5.32 mmol) in one portion. After 5 min, the ice bath was removed and the reaction mixture was stirred at room temperature for ~20 h. To the reaction mixture was added NaBr (0.822 g, 7.99 mmol) and tetrabutylammonium bromide (0.077 g, 0.240 mmol) and stirring was continued for an additional 14 h at room temperature. The reaction was concentrated in vacuo to an off-white solid and the solid was reslurried in water with vigorous agitation and then filtered (medium fritted funnel). The cake was washed with copious water (~250 mL, total volume of filtrate and washes) and then dried in a vacuum oven at 50° C. to give 4-((4-(bromomethyl)benzyl)-oxy)-2-(2,6-dioxopiperidin-3-yl)isoindoline-1,3-dione as a white solid (1.21 g, 99% yield): HPLC: Waters Symmetry $C_{18}$, 5 μm, 3.9×150 mm, 1 ml/min, 240 nm, 50/50 $CH_3CN$/0.1% $H_3PO_4$, 4.85 min (99.5%); $^1$H NMR (DMSO-$d_6$) δ 1.94-2.15 (m, 1H, CHH), 2.42-2.70 (m, 2H, CHH, CHH), 2.79-2.99 (m, 1H, CHH), 4.72 (s, 2H, $CH_2$), 5.10 (dd, J=5.4, 12.9 Hz, 1H, CH), 5.38 (s, 2H, $CH_2$), 7.38-7.54 (m, 5H, Ar), 7.59 (d, J=8.5 Hz, 1H, Ar), 7.83 (dd, J=7.3, 8.4 Hz, 1H, Ar), 11.11 (s, 1H, NH); $^{13}$C NMR (DMSO-$d_6$) δ 21.95, 30.91, 34.12, 48.75, 69.64, 115.57, 116.62, 120.18, 127.48, 129.42, 133.26, 136.33, 136.99, 137.72, 155.37, 165.27, 166.73, 169.87, 172.72; LCMS: M+Na=479, 481; MH is not observed.

Step 5: Preparation of 2-(2,6-dioxo-piperidin-3-yl)-4-[4-(2-trifluoromethyl-5,6,8,8a-tetrahydro-1H-[1,2,4]triazolo[1,5-a]pyrazin-7-ylmethyl)-benzyloxy]-isoindole-1,3-dione To the $CH_2Cl_2$ solution of 4-(4-(bromomethyl)benzyloxy)-2-(2,6-dioxopiperidin-3-yl)isoindoline-1,3-dione (0.13 g, 0.284 mmol) was added 2-(trifluoromethyl)-5,6,7,8-tetrahydro-[1,2,4]triazolo[1,5-a]pyrazine (0.060 g, 0.313 mmol) and N-ethyl-N-isopropylpropan-2-amine (0.152 ml, 0.853 mmol). The mixture was stirred at room temperature overnight. To the reaction mixture was added water (10 mL) and $CH_2Cl_2$ (10 mL) and extracted. The organic layer was concentrated and the resulted oil was purified on silica gel column eluted with MeOH and $CH_2Cl_2$ to give 2-(2,6-dioxopiperidin-3-yl)-4-[4-(2-trifluoromethyl-5,6,8,8a-tetrahydro-1H-[1,2,4]triazolo[1,5-a]pyrazin-7-ylmethyl)-benzyloxy]-isoindole-1,3-dione as a white solid (120 mg, 74%). Melting point: 128-130° C. LC-MS m/e=569. HPLC Waters Symmetry C-18, 3.9×150 mm, 5 micro, 1 mL/min, 240 nm, isocratic 50/50 $CH_3CN$/0.1% $H_3PO_4$ in $H_2O$: $t_R$=3.64 min (99%); $^1$H NMR (DMSO-$d_6$) δ 1.94-2.12 (m, 1H, CHH), 2.41-2.47 (m, 1H, CHH), 2.54-2.67 (m, 1H, CHH), 2.77-2.95 (m, 1H, CHH), 3.01 (t, J=5.4 Hz, 2H, $CH_2$), 3.81 (d, J=7.6 Hz, 4H, $CH_2$, $CH_2$), 4.24 (t, J=5.1 Hz, 2H, $CH_2$), 5.09 (dd, J=5.4, 12.7 Hz, 1H, NCH), 5.37 (s, 2H, $CH_2$), 7.37-7.55 (m, 5H, Ar), 7.61 (d, J=8.5 Hz, 1H, Ar), 7.76-7.88 (m, 1H, Ar), 11.11 (s, 1H, NH); $^{13}$C NMR (DMSO-$d_6$) δ 21.95, 30.90, 46.54, 47.67, 48.73, 49.21, 59.42, 69.89, 115.53, 116.59, 120.21, 127.42, 128.95, 133.26, 135.25, 136.99, 137.06, 152.84, 155.50, 165.29, 166.75, 169.87, 172.71. Anal Calcd for $C_{27}H_{23}F_3N_6O_5$+0.5 $H_2O$+0.2 $Et_2O$: C: 56.37%; H: 4.42%; N: 14.19%; Found C: 56.27%; H: 4.20%; N: 14.05%.

5.118 3-(4-((4-(((3R,5S)-3,5-Dimethylmorpholino) Methyl)Benzyl)Oxy)-1-Oxoisoindolin-2-yl)Piperidine-2,6-Dione Hydrochloride

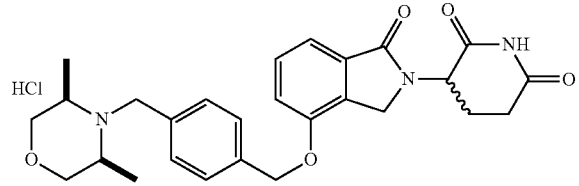 [SMILES: Cl ; C[C@@H]1COC[C@H](C)N1Cc1ccc(COc2cccc3c2CN(C2CCC(=O)NC2=O)C3=O)cc1]

Step 1: To a slurry of methyl 5-amino-4-(4-(4-(bromomethyl)benzyloxy)-1-oxoisoindolin-2-yl)-5-oxopentanoate (250 mg, 0.526 mmol) in acetonitrile (5 mL) was added (3R,5S)-3,5-dimethylmorpholine (79 mg, 0.684 mmol) as a solid. The mixture was stirred with intermittent sonication to give a clear solution and then DIEA (0.197 mL, 1.128 mmol) was added. The resulting clear solution was stirred at room temperature. After about 24 h, more (3R,5S)-3,5-dimethylmorpholine (79 mg, 0.526 mmol) was added and the mixture was allowed to stir for an additional 24 h at room temperature. The reaction mixture was concentrated in vacuo to give (S)-methyl 5-amino-4-(4-((4-(((3R,5S)-3,5-dimethylmorpholino)methyl)benzyl)oxy)-1-oxoisoindolin-2-yl)-5-oxopentanoate as an oily residue (268 mg). The crude product was used in the next step without further purification, LCMS: MH=510.

Step 2: The oil obtained in step 1, methyl 5-amino-4-(4-(4-(((3R,5S)-3,5-dimethylmorpholino)methyl)benzyloxy)-1-oxoisoindolin-2-yl)-5-oxopentanoate (268 mg, 0.526 mmol, assuming quantitative yield from previous step) was dissolved in DMF (5 mL). To the solution was added anhydrous potassium carbonate (189 mg, 1.367 mmol) and the mixture was stirred at 85° C. for about 6 h. Heating was discontinued over weekend (sample stored at 4° C.) and then resumed again for an additional 24 h. The cooled reaction mixture was diluted with EtOAc (~100 mL) and then washed with 1N aq. NaHCO$_3$ (30 mL) and brine. The organic layer was dried over Na$_2$SO$_4$ and then concentrated in vacuo to give a tan oil. The oil was dissolved in DMF (8 mL) and purified using reversed-phase preparative HPLC. The product was eluted with an acetonitrile/water gradient (0.1% formic acid in both mobile phases, 5 to 50% MeCN over 20 minutes) and fractions were collected by mass trigger. The desired fractions were combined, treated with 1 N HCl (3 mL), and then concentrated in vacuo to give a glassy solid. The solid was treated with 2 N HCl in Et$_2$O (1 mL) and concentrated in vacuo. The resulting solid was placed in vacuum oven at 60° C. for several hours to give 3-(4-((4-(((3R,5S)-3,5-dimethylmorpholino)methyl)benzyl)oxy)-1-oxoisoindolin-2-yl)piperidine-2,6-dione hydrochloride as a white solid (130 mg, 48% yield): HPLC: Waters Symmetry C$_{18}$, 5 µm, 3.9×150 mm, 1 ml/min, 240 nm, 5% grad 95% in 10 min, CH$_3$CN/0.1% H$_3$PO$_4$, 5.90 min (96.2%); mp: 235-237° C.; $^1$H NMR (DMSO-d$_6$ with D$_2$O) δ 0.89 (d, J=6.2 Hz, 6H, CH$_3$, CH$_3$), 1.96-2.15 (m, 1H, CHH), 2.41-2.53 (m, 3H, CHH, CH, CH), 2.58-2.70 (m, 1H, CHH), 2.80-2.98 (m, 1H, CHH), 3.00-3.19 (m, 2H, morph. CHH, CHH), 3.65 (dd, J=2.9, 11.2 Hz, 2H, morph. CHH, CHH), 3.78 (br. s., 2H, CH$_2$), 4.31 (d, J=17.6 Hz, 1H, CHH), 4.45 (d, J=17.6 Hz, 1H, CHH), 5.09 (dd, J=5.1, 13.2 Hz, 1H, CH), 5.23 (s, 2H, CH$_2$), 7.29-7.58 (m, 7H, Ar); $^{13}$C NMR (DMSO-d$_6$) δ 17.73, 24.16, 32.97, 47.23, 50.90, 53.61, 55.17, 56.71, 71.34, 74.46, 117.03, 117.20, 129.39, 129.90, 131.81, 131.90, 134.99, 136.37, 142.45, 155.36, 170.27, 172.80, 174.91; LCMS: MH=478; Anal Calcd for C$_{27}$H$_{31}$N$_3$O$_5$.+0.95 HCl: C, 63.31; H, 6.29; N, 8.20; Found: C, 63.51; H, 6.20; N, 7.91.

5.119 3-(1-Oxo-4-((3-((2-(Trifluoromethyl)-5,6-Dihydro-[1,2,4]Triazolo[1,5-A]Pyrazin-7(8H)-yl)Methyl)Benzyl)Oxy)Isoindolin-2-yl)Piperidine-2,6-Dione

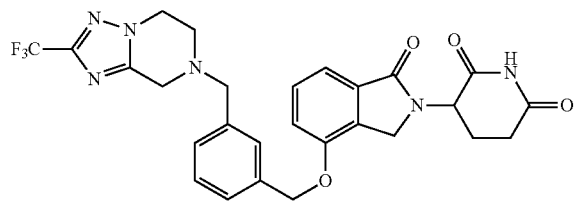 [SMILES: O=C1CCC(N2Cc3c(OCc4cccc(CN5CCn6nc(C(F)(F)F)nc6C5)c4)cccc3C2=O)C(=O)N1]

To the stirred solution of 3-(4-(3-(bromomethyl)benzyloxy)-1-oxoisoindolin-2-yl)piperidine-2,6-dione (500 mg, 1.13 mmol) in DCM (10 mL) was added 2-(trifluoromethyl)-5,6,7,8-tetrahydro-[1,2,4]triazolo[1,5-a]pyrazine (238 mg, 1.24 mmol) and DIPEA (0.59 mL, 3.38 mmol). The resulting solution was stirred at 40° C. for 27 hrs. The reaction mixture was added by DCM (30 mL) and brine (20 mL). The mixture was extracted and organic layer was dried by MgSO$_4$ and concentrated. The residue was purified by give a glass like solid. The solid was stirred in EtOAc (5 mL) and stirred in diethyl ether (40 mL) to give 3-(1-oxo-4-((3-((2-(trifluoromethyl)-5,6-dihydro-[1,2,4]triazolo[1,5-a]pyrazin-7(8H)-yl)methyl) benzyl)oxy)isoindolin-2-yl)piperidine-2,6-dione as a white solid (391 mg, 62% yield); HPLC: Waters Symmetry C-18, 3.9×150 mm, 5 µm, 1 mL/min, 240 nm, 50/50, (CH$_3$CN/0.1% H$_3$PO$_4$), 3.25 min (95.7%); mp: 213-215° C.; $^1$H NMR (DMSO-d$_6$) δ 1.92-2.06 (m, 1H, CHH), 2.34-2.47 (m, 1H, CHH), 2.53-2.64 (m, 1H, CHH), 2.82-3.07 (m, 3H, CHH, CH$_2$), 3.81 (s, 4H, CH$_2$, CH$_2$), 4.17-4.49 (m, 4H, CHH, CHH, CH$_2$), 5.05-5.16 (m, 1H, CHH), 5.27 (s, 2H, CH$_2$), 7.28-7.54 (m, 7H, Ar), 10.97 (s, 1H, NH); $^{13}$C NMR (DMSO-d$_6$) δ 22.33, 31.16, 45.09, 46.52, 47.73, 49.14, 51.58, 59.55, 69.55, 115.13, 115.28, 126.72, 128.06, 128.44, 128.59, 129.77, 129.96, 133.30, 136.81, 137.47, 152.82, 153.45, 167.96, 170.95, 172.78; LCMS MH=555; Anal. Calcd for C$_{27}$H$_{25}$F$_3$N$_6$O$_4$: C, 58.48; H, 4.54; N, 15.16; Found: C, 58.53; H, 4.21; N, 14.89.

5.120 3-{1-Oxo-4-[3-(4-Trifluoromethanesulfonyl-Piperazin-1-ylmethyl)-Benzyloxy]-1,3-Dihydro-Isoindol-2-yl}-Piperidine-2,6-Dione

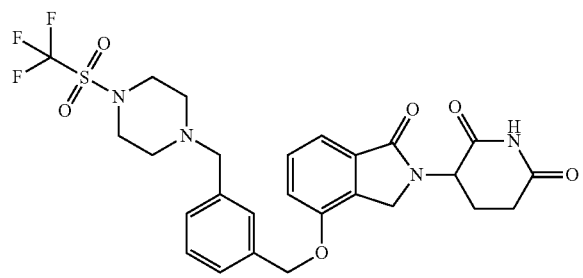 [SMILES: O=C1CCC(N2Cc3c(OCc4cccc(CN5CCN(S(=O)(=O)C(F)(F)F)CC5)c4)cccc3C2=O)C(=O)N1]

To the stirred solution of 3-(4-(3-(bromomethyl)benzyloxy)-1-oxoisoindolin-2-yl)piperidine-2,6-dione (500 mg, 1.13 mmol) in DCM (10 ml) was added by 1-(trifluoromethylsulfonyl)piperazine (320 mg, 1.47 mmol) and DIPEA (0.59 ml, 3.38 mmol). The resulting solution was stirred at 40° C. for 22 hrs. The reaction mixture was added by DCM (30 mL) and brine (20 mL). The mixture was extracted and organic layer was dried by MgSO$_4$ and concentrated. The residue was purified by ISCO give a glass like solid. The solid was stirred in EtOAc (5 mL) and diethyl ether (40 mL) to give 3-{1-Oxo-4-[3-(4-trifluoromethanesulfonyl-piperazin-1-ylmethyl)-benzyloxy]-1,3-dihydro-isoindol-2-yl}-piperidine-2,6-dione as a white solid (257 mg, 39% yield); HPLC: Waters Symmetry C-18, 3.9×150 mm, 5 µm, 1 mL/min, 240 nm, 27/73, (CH$_3$CN/0.1% H$_3$PO$_4$), 4.82 min (99.9%); mp: 150-152° C.; $^1$H NMR (DMSO-d$_6$) δ 1.92-2.05 (m, 1H, CHH), 2.35-2.48 (m, 5H, CH$_2$, CH$_2$, CHH), 2.52-2.64 (m, 1H, CHH), 2.83-3.00 (m, 1H, CHH), 3.41-3.53 (m, 4H, CH$_2$, CH$_2$), 3.57 (s, 2H, CH$_2$), 4.26 (d, J=17.4 Hz, 1H, CHH), 4.42 (d, J=17.4 Hz, 1H, CHH), 5.11 (dd, J=5.0, 13.3 Hz, 1H, CHH), 5.25 (s, 2H, CH$_2$), 7.25-7.35 (m, 3H, Ar), 7.35-7.43 (m, 3H, Ar), 7.44-7.53 (m, 1H, Ar), 10.97 (s, 1H, NH); $^{13}$C NMR (DMSO-d$_6$) δ 22.33, 31.16, 45.06, 46.36, 51.56, 51.81, 61.11, 69.54, 115.13, 115.26, 126.49, 128.04, 128.46, 129.77, 129.95, 133.30, 136.64, 137.67, 153.43, 167.96, 170.93, 172.78; LCMS MH=581; Anal. Calcd for C$_{26}$H$_{27}$F$_3$N$_4$O$_6$S+0.1 EtOAC+0.1 Et$_2$O: C, 53.94; H, 4.86; N, 9.39; Found: C, 54.05; H, 4.77; N, 9.16.

5.121 3-(1-Oxo-4-{3-[4-(2,2,2-Trifluoro-Ethyl)-Piperazin-1-ylmethyl]-Benzyloxy}-1,3-Dihydro-Isoindol-2-yl)-Piperidine-2,6-Dione

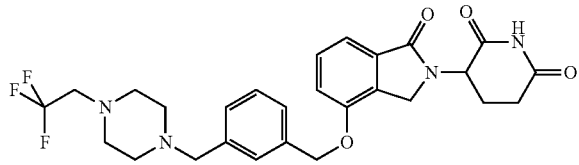 [SMILES: O=C1CCC(N2Cc3c(OCc4cccc(CN5CCN(CC(F)(F)F)CC5)c4)cccc3C2=O)C(=O)N1]

To the CH$_3$CN (10 ml) solution of 3-(4-(3-(bromomethyl)benzyloxy)-1-oxoisoindolin-2-yl)piperidine-2,6-dione (0.495 g, 1.117 mmol) (in fact 0.55 g but deducted 10% wt THF) was added 1-(2,2,2-trifluoroethyl)piperazine dihydrochloride (0.323 g, 1.340 mmol) and N-ethyl-N-isopropylpropan-2-amine (0.738 ml, 4.47 mmol) at room temperature. The cloudy mixture became clear as soon as DIPEA added. The solution was stirred for 15 minutes and evaporated under vacuum to get rid of CH$_3$CN. The resulting residue was purified by silica gel column (MeOH/CH$_2$Cl$_2$) to give 3-(1-Oxo-4-{3-[4-(2,2,2-trifluoro-ethyl)-piperazin-1-ylmethyl]-benzyloxy}-1,3-dihydro-isoindol-2-yl)-piperidine-2,6-dione as a white solid (0.485 g, 82% yield); mp, 112-114° C. HPLC: Waters Symmetry C-18, 3.9×150 mm, 5 μm, 1 mL/min, 240 nm, isocratic at 20/80 for 10 minutes, (CH$_3$CN/0.1% H$_3$PO$_4$), 5.64 min (99.9%). $^1$H NMR (DMSO-d$_6$) δ 1.92-2.06 (m, 1H, CHH), 2.28-2.48 (m, 5H, CHH, CH$_2$, CH$_2$), 2.53-2.66 (m, 5H, CHH, CH$_2$, CH$_2$), 2.83-3.00 (m, 1H, CHH), 3.12 (q, J=10.3 Hz, 2H, CH$_2$), 3.47 (s, 2H, CH$_2$), 4.21-4.48 (m, 2H, CH$_2$), 5.11 (dd, J=5.1, 13.2 Hz, 1H, NCH), 5.25 (s, 2H, CH$_2$), 7.20-7.28 (m, 1H, Ar), 7.28-7.41 (m, 5H, Ar), 7.44-7.52 (m, 1H, Ar), 10.97 (s, 1H, NH). $^{13}$C NMR (DMSO-d$_6$) δ 22.38, 31.20, 45.10, 51.59, 52.42, 53.09, 56.27, 56.65, 57.04, 57.42, 61.67, 69.58, 115.17, 115.26, 124.09, 126.27, 127.81, 127.93, 128.35, 129.78, 129.97, 133.32, 136.53, 138.37, 153.44, 167.99, 170.95, 172.80. LCMS: m/e=531. Anal Calcd for C$_{27}$H$_{29}$N$_4$O$_4$F$_3$ (+0.1 H$_2$O, +0.1 EtOAc): C, 60.81; H, 5.59; N, 10.35. Found: C, 60.72; H, 5.65; N, 10.09.

5.122 3-{4-[3-(3,4-Dihydro-1H-Isoquinolin-2-ylmethyl)-Benzyloxy]-1-Oxo-1,3-Dihydro-Isoindol-2-yl}-Piperidine-2,6-Dione

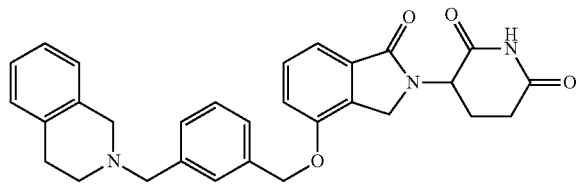 [SMILES: O=C1CCC(N2Cc3c(OCc4cccc(CN5CCc6ccccc6C5)c4)cccc3C2=O)C(=O)N1]

To the CH$_3$CN (10 ml) solution of 3-(4-(3-(bromomethyl)benzyloxy)-1-oxoisoindolin-2-yl)piperidine-2,6-dione (0.222 g, 0.501 mmol) was added 1,2,3,4-tetrahydroisoquinoline hydrochloride (0.102 g, 0.601 mmol) and N-ethyl-N-isopropylpropan-2-amine (0.207 ml, 1.253 mmol) at room temperature. The cloudy mixture was stirred at room temperature for 40 minutes and was evaporated under vacuum to get rid of CH$_3$CN. The resulting residue was purified by silica gel column (MeOH/CH$_2$Cl$_2$) to give 3-{4-[3-(3,4-Dihydro-1H-isoquinolin-2-ylmethyl)-benzyloxy]-1-oxo-1,3-dihydro-isoindol-2-yl}-piperidine-2,6-dione as an off-white solid (0.198 g, 80% yield); mp; 117-119° C. HPLC: Waters Symmetry C-18, 3.9×150 mm, 5 μm, 1 mL/min, 240 nm, isocratic at 20/80 for 10 minutes, (CH$_3$CN/0.1% H$_3$PO$_4$), 6.88 min (99.9%). $^1$H NMR (DMSO-d$_6$) δ 1.90-1.99 (m, 1H, CHH), 2.32-2.47 (m, 1H, CHH), 2.53-2.62 (m, 1H, CHH), 2.63-2.71 (m, 2H, CH$_2$), 2.75-2.83 (m, 2H, CH$_2$), 2.84-2.98 (m, 1H, CHH), 3.53 (s, 2H, CH$_2$), 3.67 (s, 2H, CH$_2$), 4.20-4.45 (m, 2H, CH$_2$), 5.10 (dd, J=5.1, 13.2 Hz, 1H, NCH), 5.26 (s, 2H, CH$_2$), 6.94-7.15 (m, 4H, Ar), 7.28-7.53 (m, 7H, Ar), 10.97 (s, 1H, NH). $^{13}$C NMR (DMSO-d$_6$) δ 14.07, 22.35, 28.64, 31.21, 45.09, 50.15, 51.59, 55.38, 61.58, 69.63, 115.14, 115.26, 125.43, 125.93, 126.29, 126.35, 127.88, 128.34, 128.42, 129.79, 129.95, 133.32, 134.05, 134.74, 136.62, 138.70, 153.47, 167.99, 170.95, 172.80. LC/MS m/e=496. Anal Calcd for C$_{30}$H$_{29}$N$_3$O$_4$ (+0.3 H$_2$O, +0.3 EtOAc): C, 71.05; H, 6.12; N, 7.97. Found: C, 71.00; H, 6.14; N, 7.91.

5.123 3-(4-((3-((4-(4-Chlorophenyl)Piperidin-1-yl)Methyl)Benzyl)Oxy)-1-Oxoisoindolin-2-yl)Piperidine-2,6-Dione

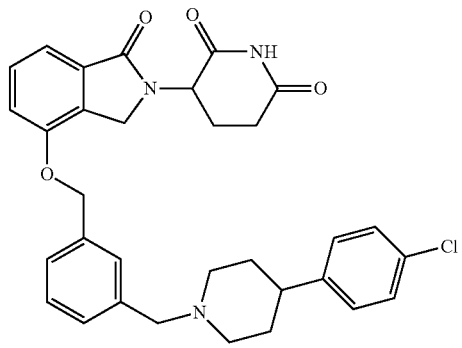 [SMILES: O=C1CCC(N2Cc3c(OCc4cccc(CN5CCC(c6ccc(Cl)cc6)CC5)c4)cccc3C2=O)C(=O)N1]

To the CH$_2$Cl$_2$ solution of 3-(4-(3-(bromomethyl)benzyloxy)-1-oxoisoindolin-2-yl)piperidine-2,6-dione (0.5 g, 1.128 mmol) was added 4-(4-chlorophenyl)piperidine (0.232 g, 1.184 mmol) and N-ethyl-N-isopropylpropan-2-amine (0.602 ml, 3.38 mmol). The solution was stirred at room temperature overnight. The mixture was added water (10 mL), CH$_2$Cl$_2$ (15 mL) and extracted. The organic layer was concentrated then purified on silica gel column eluted with CH$_2$Cl$_2$ and MeOH to give 3-(4-((3-((4-(4-chlorophenyl)piperidin-1-yl)methyl)benzyl)oxy)-1-oxoisoindolin-2-yl)piperidine-2,6-dione as white solid (340 mg, 54%). Melting point: 180-182° C. LC-MS m/e=558, 560. HPLC Waters Symmetry C-18, 3.9×150 mm, 5 micro, 1 mL/min, 240 nm, isocratic 30/70 CH$_3$CN/0.1% H$_3$PO$_4$ in H$_2$O: 4.34 min (99%). $^1$H NMR (DMSO-d$_6$) δ 1.49-1.78 (m, 4H, CH$_2$, CH$_2$), 1.89-2.10 (m, 3H, CHH, CH$_2$), 2.33-2.47 (m, 2H, CHH, CH), 2.53-2.61 (m, J=13.8 Hz, 1H, CHH), 2.79-2.98 (m, J=11.5 Hz, 3H, CH$_2$, CHH), 3.51 (s, 2H, CH$_2$), 4.20-4.50 (m, 2H, CH$_2$), 5.11 (dd, J=5.0, 13.1 Hz, 1H, NCH), 5.27 (s, 2H, CH$_2$), 7.19-7.53 (m, 11H, Ar), 10.97 (s, 1H, NH). $^{13}$C NMR (DMSO-d$_6$) δ 22.34, 31.16, 32.85, 41.09, 45.09, 51.55, 53.40, 62.13, 69.58, 115.16, 115.23, 126.20, 127.95, 128.17, 128.30, 128.40, 128.56, 129.74, 129.96, 130.41, 133.30, 136.46, 138.75, 145.17, 153.42, 167.97, 170.93, 172.78. Anal Calcd for C$_{32}$H$_{32}$ClN$_3$O$_4$: C %: 68.87; H %: 5.78; N %: 7.53; Found: C %: 68.59; H %: 5.83; N %: 7.39.

5.124 4-((4-((3,4-Dihydroisoquinolin-2(1H)-yl)Methyl)Benzyl)Oxy)-2-(2,6-Dioxopiperidin-3-yl)Isoindoline-1,3-Dione

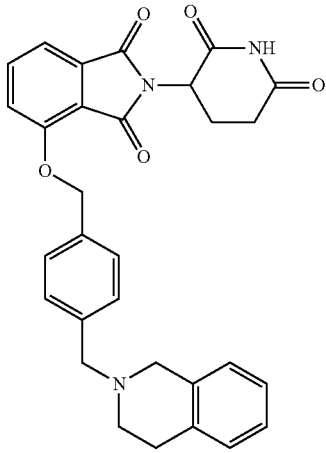 [SMILES: O=C1CCC(N2C(=O)c3cccc(OCc4ccc(CN5CCc6ccccc6C5)cc4)c3C2=O)C(=O)N1]

To the CH$_2$Cl$_2$ suspension of 4-(4-(bromomethyl)benzyloxy)-2-(2,6-dioxopiperidin-3-yl)isoindoline-1,3-dione (0.25 g, 0.547 mmol) was added 1,2,3,4-tetrahydroisoquinoline (0.080 g, 0.601 mmol) and N-ethyl-N-isopropylpropan-2-amine (0.212 g, 1.640 mmol). The mixture was stirred at room temperature overnight. The mixture was added CH$_2$Cl$_2$ and water and extracted. The organic layer was concentrated and purified on silica gel column eluted with CH$_2$Cl$_2$ and MeOH to give a solid. The solid was recrystallized from CH$_3$CN (3 mL) to give 4-((4-((3,4-dihydroisoquinolin-2(1H)-yl)methyl)benzyl)oxy)-2-(2,6-dioxopiperidin-3-yl)isoindoline-1,3-dione as a yellow solid (90 mg, 32%). Melting point (determined in house): 124-126° C. LC-MS m/e=510. HPLC Waters Symmetry C-18, 3.9×150 mm, 5 micro, 1 mL/min, 240 nm, isocratic 30/70 CH$_3$CN/0.1% H$_3$PO$_4$ in H$_2$O: 3.52 min (98.5%). $^1$H NMR (DMSO-d$_6$) δ 1.97-2.11 (m, 1H, CHH), 2.42-2.47 (m, 1H, CHH), 2.54-2.62 (m, 3H, CHH, CH$_2$), 2.64-2.71 (m, 2H, CH$_2$), 2.76-2.98 (m, 3H, CHH, CH$_2$), 3.54 (s, 2H, CH$_2$), 3.66 (s, 2H, CH$_2$), 5.03-5.16 (m, 1H, NCH), 5.37 (s, 2H, CH$_2$), 6.94-7.12 (m, 3H, Ar), 7.37-7.44 (m, 2H, Ar), 7.45-7.53 (m, 3H, Ar), 7.61 (d, J=8.3 Hz, 1H, Ar), 7.83 (d, J=7.5, 8.4 Hz, 1H, Ar), 11.11 (s, 1H, NH). $^{13}$C NMR (DMSO-d$_6$) δ 21.09, 27.77, 30.06, 47.89, 49.30, 54.57, 60.62, 69.13, 114.65, 119.38, 124.57, 125.06, 125.46, 126.48, 127.54, 127.95, 132.41, 133.21, 133.87, 133.94, 136.13, 137.43, 154.69, 164.45, 165.90, 169.02, 171.87. Anal Calcd for C$_{30}$H$_{27}$N$_3$O$_5$ C: 70.71%; H: 5.34%; N: 8.25%. Found: C: 67.07%; H: 5.12%; N: 7.81%.

5.125 3-(4-((3-((4-(2,4-Difluorophenyl)Piperidin-1-yl)Methyl)Benzyl)Oxy)-1-Oxoisoindolin-2-yl)Piperidine-2,6-Dione

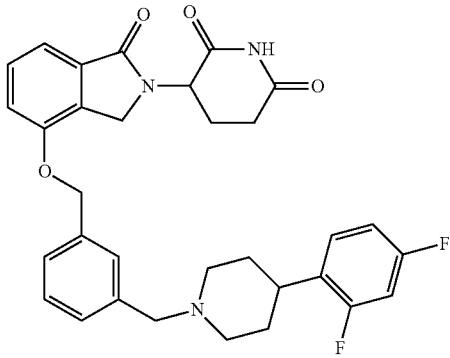 [SMILES: O=C1CCC(N2Cc3c(OCc4cccc(CN5CCC(c6ccc(F)cc6F)CC5)c4)cccc3C2=O)C(=O)N1]

To the CH$_2$Cl$_2$ solution of 3-(4-(3-(bromomethyl)benzyloxy)-1-oxoisoindolin-2-yl)piperidine-2,6-dione (0.45 g, 1.015 mmol) was added 4-(2,4-difluorophenyl)piperidine (0.210 g, 1.066 mmol) and N-ethyl-N-isopropylpropan-2-amine (0.542 ml, 3.05 mmol). The mixture was stirred at room temperature overnight. The mixture was added water and CH$_2$Cl$_2$, extracted and purified on silica gel column eluted with MeOH and CH$_2$Cl$_2$ to give 3-(4-((3-((4-(2,4-difluorophenyl)piperidin-1-yl)methyl)benzyl)oxy)-1-oxoisoindolin-2-yl)piperidine-2,6-dione as a white solid (250 mg, 44%). Melting point: 211-213° C. LC-MS m/e=560. HPLC: Waters Symmetry C$_{18}$, 5 m, 3.9×150 mm, 1 ml/min, 240 nm, isocratic 30/70 CH$_3$CN/0.1% H$_3$PO$_4$: 4.68 min (97.6%). $^1$H NMR (DMSO-d$_6$) δ 1.66 (br. s., 4H, CH$_2$, CH$_2$), 1.89-2.07 (m, 3H, CH$_2$, CHH), 2.43 (dd, J=4.3, 13.0 Hz, 1H, CHH), 2.53-2.61 (m, J=19.3 Hz, 1H, CHH), 2.73 (quin, J=7.5 Hz, 1H, CH), 2.82-3.03 (m, 3H, CH$_2$, CHH), 3.51 (s, 2H, CH$_2$), 4.11-4.52 (m, 2H, CH$_2$), 5.11 (dd, J=5.1, 13.2 Hz, 1H, NCH), 5.27 (s, 2H, CH$_2$), 7.02 (td, J=2.2, 8.5 Hz, 1H, Ar), 7.10-7.21 (m, 1H, Ar), 7.24-7.54 (m, 8H, Ar), 10.97 (s, 1H, NH). $^{13}$C NMR (DMSO-d$_6$) δ 22.34, 31.16, 31.61, 34.62, 51.58, 53.43, 62.12, 69.60, 103.20, 103.54, 103.90, 111.21, 111.49, 115.16, 115.25, 126.21, 127.96, 128.31, 128.41, 128.62, 128.68, 128.87, 128.98, 129.07, 129.74, 129.96, 133.30, 136.48, 138.74, 153.43, 158.17, 158.33, 158.84, 159.02, 161.42, 161.58, 162.08, 162.26, 167.97, 170.93, 172.77. Anal Calcd for C$_{32}$H$_{31}$F$_2$N$_3$O$_4$: C %: 68.68; H %: 5.58; N %: 7.51. Found: C %: 68.57; H %: 5.52; N %: 7.60.

5.126 3-{1-Oxo-4-[4-(2-Trifluoromethyl-5,6-Dihydro-8H-[1,2,4]Triazolo[1,5-A]Pyrazin-7-ylmethyl)-Benzyloxy]-1,3-Dihydro-Isoindol-2-yl}-Piperidine-2,6-Dione

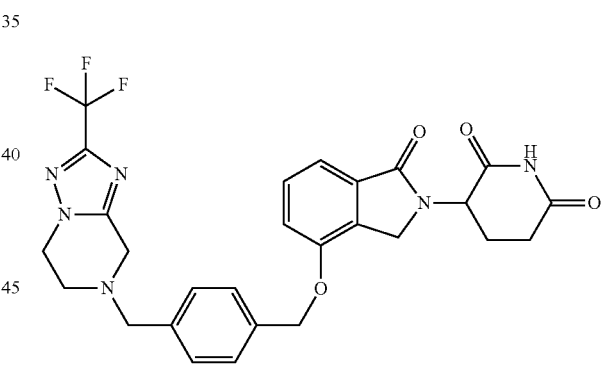

To the stirred mixture of 3-(4-(4-(bromomethyl)benzyloxy)-1-oxoisoindolin-2-yl)piperidine-2,6-dione (1.0 g, 2.256 mmol) and 2-(trifluoromethyl)-5,6,7,8-tetrahydro-[1,2,4]triazolo[1,5-a]pyrazine (0.477 g, 2.481 mmol) in MeCN (15 mL) was added DIPEA (1.0 mL, 5.6 mmol). The resulting mixture was heated at 50° C. for 16 hrs and concentrated to around 3 mL followed by the addition of Et$_2$O (40 mL). The mixture was stirred at room temperature and solid was formed. The solid was purified by being stirred in CH$_3$CN (17 mL) at reflux to give 3-{-Oxo-4-[4-(2-trifluoromethyl-5,6-dihydro-8H-[1,2,4]triazolo[1,5-a]pyrazin-7-ylmethyl)-benzyloxy]-1,3-dihydro-isoindol-2-yl}-piperidine-2,6-dione as a white solid (580 mg, 46% yield). HPLC: Waters Symmetry C-18, 3.9×150 mm, 5 μm, 1 mL/min, 240 nm, 40/60, (CH$_3$CN/0.1% H$_3$PO$_4$), 6.32 min (99.8%); mp: 215-217° C.; $^1$H NMR (DMSO-d$_6$) δ 1.92-2.05 (m, 1H, CHH), 2.35-2.48 (m, 1H, CHH), 2.53-2.63 (m, 1H, CHH), 2.83-2.98 (m, 1H, CHH), 3.02 (t, J=5.4 Hz, 2H, CH$_2$), 3.81 (d, J=5.3 Hz, 4H, CH$_2$, CH$_2$), 4.19-4.32 (m, 3H, CHH, CH$_2$), 4.42 (d, J=17.4 Hz, 1H, CHH), 5.11 (dd, J=5.1, 13.2 Hz, 1H, CHH), 5.25 (s, 2H, CH$_2$), 7.29-7.37 (m, 2H, Ar), 7.37-7.44 (m, 2H, Ar), 7.45-7.53 (m, 3H, Ar), 10.97 (s, 1H, NH); $^{13}$C NMR (DMSO-d$_6$) δ 22.29, 31.11, 45.02, 46.49, 47.67, 49.12, 51.52, 59.38, 69.29, 114.93, 115.19, 127.75, 128.87, 129.75, 129.89, 133.26, 135.69, 136.99, 152.77, 153.42, 167.92, 170.89, 172.74; LCMS MH=555; Anal. Calcd for C$_{27}$H$_{25}$F$_3$N$_6$O$_4$: C, 58.48; H, 4.54; N, 15.16; Found: C, 58.50; H, 4.23; N, 15.08; Chiral HPLC: Chiral AGP/C18, 4.0×150 mm, 5 μm, 0.8 mL/min, UV 240 nm, mobile phase A: MeOH, mobile phase B: NH4OAc 10 mM), 20/80, at 8.78 min (1.37%) and 1 1.51 min (93.56%); ee %=(93.56-1.37)/(93.56+1.37)*100%=97%.

5.127 2-(2,6-Dioxo-Piperidin-3-yl)-4-(4-Morpholin-4-ylmethyl-Benzyloxy)-Isoindole-1,3-Dione

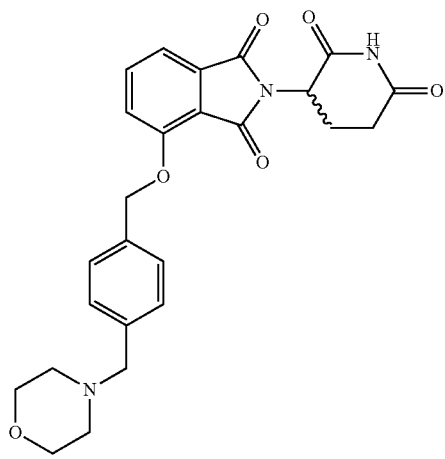 [SMILES: O=C1CCC(N2C(=O)c3cccc(OCc4ccc(CN5CCOCC5)cc4)c3C2=O)C(=O)N1]

Step 1: To a solution of dimethyl 3-hydroxyphthalate (1.0 g, 4.76 mmol) in THF (40 ml, 488 mmol), was added triphenyl phosphine on polystyrene resin (1.6 gm/mmol, 4.76 g, 7.61 mmol). After allowing the resin to swell for several minutes at room temperature, the reaction mixture was cooled in an ice bath at 0° C. To the stirred mixture, DIAD (1.48 mL, 7.61 mmol) was added dropwise. After about 10 minutes, (4-(morpholinomethyl)phenyl)methanol (1.48 g, 7.14 mmol) was added in one portion. The resulting mixture was stirred at room temperature for 20 min. The resin was removed by filtration and rinsed on a fritted funnel with suction using alternating MeOH and DCM washes twice. The combined filtrate was concentrated in vacuo to give the crude product as a yellow oil (4 g). The oil was partitioned between EtOAc (200 mL) and 0.25 N HCl (150 mL). The organic layer was washed with an additional 100 mL of 0.25 N HCl. The aqueous layer, containing the product, was concentrated on a rotovap to a syrup (about 10 mL). The syrup was partitioned between EtOAc (300 mL) and 1 N NaOH (100 mL). The aqueous layer was washed with another portion of EtOAc (about 200 mL). The combined organic layers was washed with brine, dried (Na$_2$SO$_4$), concentrated in vacuo, and dried in a vacuum oven at 40° C. overnight to give 3-(4-morpholin-4-ylmethyl-benzyloxy)-phthalic acid dimethyl ester as a pale yellow oil (2.6 g). The crude product was used in the next step without further purification.

Step 2: To a solution of dimethyl 3-(4-(morpholinomethyl)benzyloxy)phthalate (1.9 g, 4.76 mmol) in THF (20 ml, 244 mmol), was added water (0.180 ml, 9.99 mmol). With stirring at rt, KO$^t$Bu (9.99 ml, 9.99 mmol, 1M in THF) was added dropwise. After about 24 h, water (1 mL) was added and the mixture was warmed up to 45° C. After about 22 h, the mixture was diluted with Et$_2$O (100 mL) and filtered through a fritted funnel. The solid was acidified with aqueous 1 N HCl (10 mL) and the resulting mixture was concentrated to dryness on rotovap to give a white solid (2.2 g) that was determined by LCMS to be a ~1:3 mixture of 3-(4-morpholin-4-ylmethyl-benzyloxy)-phthalic acid 1-methyl ester and 3-(4-morpholin-4-ylmethyl-benzyloxy)-phthalic acid, respectively. The mixture was used in the next step without further purification.

Step 3: To a suspension of 3-(4-morpholin-4-ylmethyl-benzyloxy)-phthalic acid 1-methyl ester and 3-(4-morpholin-4-ylmethyl-benzyloxy)-phthalic acid (1.7 g, 3.75 mmol, assuming 82 wt %) in pyridine (30 mL), was added rac. 3-aminopiperidine-2,6-dione hydrochloride (0.803 g, 4.88 mmol) as a solid. A reflux condenser was placed on RBF and the resulting mixture was heated in an oil bath at 1 18° C. for about 24 h. The reaction mixture was allowed to cool down to rt and then concentrated in vacuo to remove most of the pyridine. The remaining dark solid residue was slurried in EtOAc (about 100 mL), stirred overnight at room temperature, then filtered on a medium fritted funnel. The solid was washed with copious EtOAc and then suction dried. The remaining solid was transferred to a flask with EtOAc (400 mL) and 0.5 N aq NaHCO$_3$ (100 mL). The mixture was vigorously stirred for overnight. The phases were separated and the aqueous layer was extracted with additional EtOAc (~300 mL). The combined organic layers was washed with brine and then treated with Na$_2$SO$_4$ and decolorizing charcoal. The slurry was mixed and then filtered on a bed of Supercell. The clear filtrate was concentrated in vacuo and the resulting white foam was dissolved in minimal MeCN (~3 mL). To the solution was added Et$_2$O in small portions (about 25 mL, total), resulting in a white precipitate. The slurry was sonicated to break up all solid aggregates into a well-dispersed suspension. The slurry was then filtered and the cake was washed with several small portions of Et$_2$O (~50 mL, total). The cake was suction dried and then further dried in a vacuum oven at 55° C. to give 2-(2,6-dioxo-piperidin-3-yl)-4-(4-morpholin-4-ylmethyl-benzyloxy)-isoindole-1,3-dione as a white solid (950 mg, 55% yield over Step 1-3): HPLC: Waters Symmetry C$_{18}$, 5 μm, 3.9×150 mm, 1 ml/min, 240 nm, 17/83 CH$_3$CN/0.1% H$_3$PO$_4$, 5.34 min (99.8%); mp: 205-207° C.; $^1$H NMR (DMSO-d$_6$) δ 1.92-2.14 (m, 1H, CHH), 2.28-2.42 (m, 4H, CH$_2$, CH$_2$), 2.43-2.66 (m, 2H, CHH, CHH), 2.78-3.00 (m, 1H, CHH), 3.46 (s, 2H, CH$_2$), 3.52-3.64 (m, 4H, CH$_2$, CH$_2$), 5.09 (dd, J=5.4, 12.9 Hz, 1H, CH), 5.35 (s, 2H, CH$_2$), 7.29-7.39 (m, 2H, Ar), 7.42-7.52 (m, 3H, Ar), 7.60 (d, J=8.5 Hz, 1H, Ar), 7.82 (dd, J=7.4, 8.5 Hz, 1H, Ar), 1 1.11 (s, 1H, NH); $^{13}$C NMR (DMSO-d$_6$) δ 21.88, 30.84, 48.67, 53.06, 62.01, 66.08, 69.85, 115.42, 116.50, 120.11, 127.18, 128.93, 133.18, 134.72, 136.91, 137.61, 155.44, 165.21, 166.68, 169.80, 172.66; LCMS: MH=464; Anal Calcd for C$_{25}$H$_{25}$N$_3$O$_6$+0.06 H$_2$O: C, 64.64; H, 5.45; N, 9.04; H$_2$O, 0.23; Found: C, 64.75; H, 5.13; N, 8.91; H$_2$O, 0.23.

5.128 3-[1-Oxo-4-(4-Phenoxymethyl-Benzyloxy)-1,3-Dihydro-Isoindol-2-yl]-Piperidine-2,6-Dione

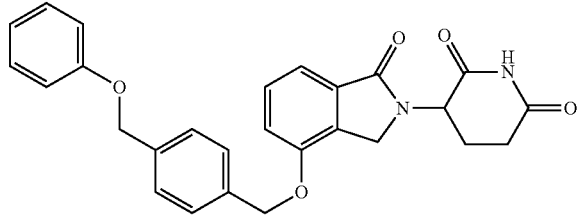 [SMILES: O=C1CCC(N2Cc3c(OCc4ccc(COc5ccccc5)cc4)cccc3C2=O)C(=O)N1]

Step 1: Preparation of methyl 5-amino-5-oxo-4-(1-oxo-4-(4-(phenoxymethyl) benzyloxy)isoindolin-2-yl)pentanoate To the acetonitrile solution of methyl 5-amino-4-(4-hydroxy-1-oxoisoindolin-2-yl)-5-oxopentanoate (0.5 g, 1.711 mmol) was added 1-(bromomethyl)-4-(phenoxymethyl)benzene (0.474 g, 1.711 mmol) and potassium carbonate (0.236 g, 1.711 mmol). The mixture was stirred at 50° C. for 3 days. The mixture was cooled down to room temperature, concentrated and purified on silica gel column eluted with $CH_2Cl_2$ and MeOH to give methyl 5-amino-5-oxo-4-(1-oxo-4-(4-(phenoxymethyl)benzyloxy)isoindolin-2-yl) pentanoate as white solid (0.8 g, 47%).

Step 2: Preparation of 3-[1-Oxo-4-(4-phenoxymethyl-benzyloxy)-1,3-dihydro-isoindol-2-yl]-piperidine-2,6-dioneT o the THF solution of methyl 5-amino-5-oxo-4-(1-oxo-4-(4-(phenoxymethyl)benzyloxy) isoindolin-2-yl) pentanoate (0.8 g, 1.638 mmol) was added potassium tert-butoxide (0.202 g, 1.801 mmol) at −78° C. The mixture was stirred at this temperature for 1 hr then was added water and $CH_2Cl_2$. After extraction, the organic layer was concentrated to give 3-[1-Oxo-4-(4-phenoxymethyl-benzyloxy)-1,3-dihydro-isoindol-2-yl]-piperidine-2,6-dione as white solid (0.70 g, 94%). Melting point determined in house: 110-112° C. LC-MS m/e=457. HPLC Waters Symmetry C-18, 3.9×150 mm, 5 micro, 1 mL/min, 240 nm, gradient 5/95 to 5/95 $CH_3CN/0.1\%$ $H_3PO_4$ in $H_2O$ during 5 min and stay at 95/5 for 5 min: 10.48 min (96%). $^1H$ NMR (DMSO-$d_6$) δ 1.90-2.04 (m, 1H, CHH), 2.31-2.48 (m, J=4.3, 13.2 Hz, 1H, CHH), 2.52-2.65 (m, 1H, CHH), 2.80-3.01 (m, 1H, CHH), 4.16-4.50 (m, 2H, $CH_2$), 5.03-5.16 (m, 3H, NCH, $CH_2$), 5.26 (s, 2H, $CH_2$), 6.88-7.05 (m, 3H, Ar), 7.21-7.37 (m, 4H, Ar), 7.42-7.56 (m, 5H, Ar), 10.97 (s, 1H, NH); CNMR (DMSO-$d_6$): δ 15.11, 22.33, 31.17, 45.077, 51.57, 68.72, 69.28, 114.73, 114.97, 115.25, 120.68, 127.76, 129.45, 129.79, 129.96, 133.31, 136.16, 136.94, 153.41, 158.22, 167.98, 170.94, 170.94, 172.80. Anal Calcd for $C_{27}H_{24}N_2O_5+0.3$ $H_2O$, C 71.04%, H 5.30%, N 6.14%. Found: C 69.89%, H 5.48%, N 5.82%.

5.129 Tert-Butyl 5-((2-(2,6-Dioxopiperidin-3-yl)-1-Oxoisoindolin-4-yloxy)Methyl)Isoindololine-2-Carboxylate

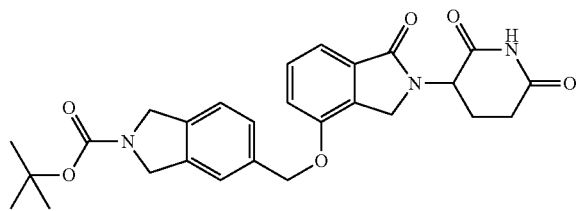 [SMILES: CC(C)(C)OC(=O)N1Cc2ccc(COc3cccc4c3CN(C3CCC(=O)NC3=O)C4=O)cc2C1]

Step 1: Sodium hydride (60%, 3.6 g, 90.5 mmol) was added to a stirred solution of N-BOC-propargylamine (10.8 g, 69.6 mmol) in THF (80 mL). The resulting suspension was stirred at room temperature for 30 minutes and a solution of propargyl bromide/toluene (80%, 16.6 g, 111.3 mmol) was added dropwise (slight exothermic!). The mixture was stirred at room temperature for 3 hours. The reaction mixture was concentrated and the residue was dissolved in EtOAc (150 mL) and washed with water (4×40 mL) and brine (40 mL), and dried. The solvent was removed and the residue was purified by chromatography ($SiO_2$, EtOAc:Hexane 30:70 to 80:20) to give N-BOC-diprop-2-ynyl-amine (8.5 g, 63% yield): $^1H$ NMR (CDCl$_3$) δ 1.48 (s, 9H), 2.22 (s, 2H), 4.17 (b, 4H).

Step 2: Propargyl alcohol (7.3 g, 144.9 mmol) was added dropwise to a stirred solution of N-BOC-diprop-2-ynyl-amine (7.0 g, 36.2 mmol) in absolute ethanol (150 mL) at 3° C. Tris(triphenylphosphine)rhodium dichloride (1.0 g) was added in one portion. The resulting mixture was stirred at room temperature overnight. The reaction mixture was concentrated and the residue was purified by chromatography ($SiO_2$, EtOAc:Hexane 10:90 to 40:60) to give 5-hydroxymethyl-1,3-dihydro-isoindole-2-carboxylic acid tert-butyl ester (5.2 g, 57% yield): $^1H$ NMR (CDCl$_3$) δ 1.51 (s, 9H), 2.07 (b, 1H), 4.62 (s, 4H), 4.68 (d, J=5.7 Hz, 2H), 7.20-7.27 (m, 3H).

Step 3: Diisopropyl azodicarboxylate (1.0 g, 5.0 mmol) was added to a stirred suspension of triphenylphosphine-polymer bound (4.3 g, 5.3 mmol) in THF (40 mL) at 3-5° C. The mixture was stirred at 3° C. for 10 minutes and a solution of methyl 5-amino-4-(4-hydroxy-1-oxoisoindolin-2-yl)-5-oxopentanoate (1.0 g, 3.3 mmol) and 5-hydromethyl-1,3-dihydro-isoindole-2-carboxylic acid tert-butyl ester (1.1 g, 4.3 mmol) in THF (60 mL) at 3-6° C. After stirred at 3° C. for 5 minutes, the mixture was stirred at room temperature overnight. The reaction mixture was filtered and solid was washed with $CH_2Cl_2$ (30 mL). Filtrate was concentrated and the residue was dissolved in $CH_2Cl_2$ (80 mL) and washed with sat. $NaHCO_3$ (25 mL), water (2×25 mL), and brine (25 mL), and dried. The solvent was removed and the residue was purified by chromatography ($SiO_2$, $CH_3OH$:$CH_2Cl_2$ 3:97) to give tert-butyl 5-((2-(1-amino-5-methoxy-1,5-dioxopentan-2-yl)-1-oxoisoindolin-4-yloxy)methyl) isoindoline-2-carboxylate (1.3 g, 73% yield): $^1H$ NMR (CDCl$_3$) δ 1.52 (s, 9H), 2.17-2.41 (m, 4H), 3.64 (s, 3H), 4.36-4.46 (dd, J=17.7 and 29.4 Hz, 2H), 4.67-4.71 (m, 4H), 4.91 (m, 1H), 5.15 (s, 2H), 5.43 (s, 1H), 6.35 (s, 1H), 7.05-7.08 (m, 1H), 7.26-7.32 (m, 3H), 7.40-7.45 (m, 2H); $^{13}C$ NMR (CDCl$_3$) δ 24.04, 28.55, 30.45, 45.28, 51.82, 52.27, 53.89, 70.02, 70.16, 79.81, 114.44, 116.18, 121.59, 121.98, 122.93, 123.08, 126.64, 129.90, 133.43, 135.50, 137.69, 153.70, 154.51, 169.36, 171.49, 172.88. Step 4: A solution of potassium t-butoxide/THF (1M, 2.4 mL, 2.4 mmol) was added slowly to a stirred solution of tert-butyl 5-((2-(1-amino-5-methoxy-1,5-dioxopentan-2-yl)-1-oxoisoindolin-4-yloxy)methyl)isoindoline-2-carboxylate (1.3 g, 2.4 mmol) in THF (20 mL) at 5° C. The reaction mixture was stirred at 5° C. for 30 minutes then quenched with sat. $NH_4Cl$ (5 mL). The mixture was stirred with $CH_2Cl_2$ (50 mL) and water (15 mL) and aqueous layer was extracted with $CH_2Cl_2$ (30 mL). Combined $CH_2Cl_2$ solution was washed with sat. $NaHCO_3$ (30 mL), water (2×30 mL), and brine (30 mL), and dried. The solvent was removed and the residue was purified by chromatography ($SiO_2$, $CH_3OH$: $CH_2Cl_2$ 3:97) to give tert-butyl 5-((2-(2,6-dioxo-piperidin-3-yl)-1-oxoisoindolin-4-yloxy)methyl)isoindoline-2-carboxylate (0.6 g, 50% yield): mp 178-180° C.; $^1H$ NMR (DMSO-$d_6$) δ 1.45 (s, 9H), 1.96-2.02 (m, 1H), 2.41-2.60 (m, 2H), 2.86-2.91 (m, 1H), 4.28 (d, J=17.4 Hz, 1H), 4.38 (d, J=17.4 Hz, 1H), 4.59 (b, 4H), 5.07-5.14 (dd, J=5.1 and 13.5 Hz, 1H), 5.24 (s, 2H), 7.31-7.51 (m, 6H), 10.97 (s, 1H); $^{13}$C NMR (DMSO-$d_6$) δ 22.34, 28.12, 31.18, 45.08, 51.48, 51.65, 69.42, 78.80, 115.01, 115.25, 122.15, 122.88, 126.94, 129.79, 129.95, 133.30, 135.82, 136.41, 136.96, 137.44, 138.40, 167.97, 170.96, 172.82; Calcd for $C_{27}H_{29}N_3O_6$: C, 65.98; H, 5.95; N, 8.55. Found: C, 65.76; H, 6.10; N, 8.33.

5.130 3-(4-(Benzo[B]Thiophen-3-ylmethoxy)-1-Oxoisoindolin-2-yl)-Piperidine-2,6-Dione

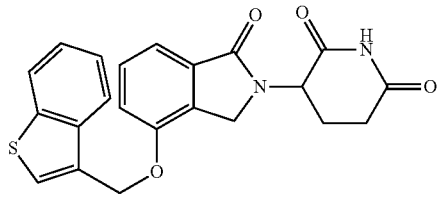 [SMILES: O=C1CCC(N2Cc3c(OCc4csc5ccccc45)cccc3C2=O)C(=O)N1]

Step 1: Diisopropyl azodicarboxylate (1.1 g, 5.5 mmol) was added to a stirred suspension of methyl 5-amino-4-(4-hydroxy-1-oxoisoindolin-2-yl)-5-oxopentanoate (0.8 g, 2.7 mmol), 1-benzothiophen-3-ylmethanol (0.7 g, 4.1 mmol) and triphenylphosphine-polymer bound (1.8 g, 5.5 mmol) in THF (60 mL) at 5-8° C. After addition, the mixture was stirred at room temperature overnight. The reaction mixture was filtered and solid was washed with $CH_2Cl_2$ (30 mL). Filtrate was concentrated and the residue was purified by chromatography ($SiO_2$, $CH_3OH:CH_2Cl_2$ 3:97) to give methyl 5-amino-4-(4-(benzo[b]thiophen-3-ylmethoxy)-1-oxoisoindolin-2-yl)-5-oxopentanoate (1 g, 77%).

Step 2: A solution of potassium t-butoxide/THF (1M, 2.3 mL, 2.3 mmol) was added to a stirred solution of methyl 5-amino-4-(4-(benzo[b]thiophen-3-ylmethoxy)-1-oxoisoindolin-2-yl]-5-oxopentanoate (1.0 g, 2.3 mmol) in THF (30 mL) at 5° C. The mixture was stirred at 5° C. for 10 minutes then warmed to room temperature for 2 hours. The reaction mixture was cooled in an ice bath and quenched with 1N HCl (10 mL). The mixture was stirred with $CH_2Cl_2$ (50 mL) and water (10 mL) and aqueous layer was extracted with $CH_2Cl_2$ (30 mL). Combined $CH_2Cl_2$ solution was washed with water (2×40 mL), brine (40 mL) and dried. The solvent was removed and the residue was purified by chromatography ($SiO_2$, $CH_3OH:CH_2Cl_2$ 3:97) to give 3-(4-benzo[b]thiophen-3-ylmethoxy)-1-oxoisoindolin-2yl)-piperidine-2,6-dione (0.3 g, 32% yield): mp 231-233° C.; $^1$H NMR (DMSO-$d_6$) δ 1.94-1.98 (m, 1H), 2.28-2.58 (m, 2H), 2.85-2.95 (m, 1H), 4.24 (d, J=17.4 Hz, 1H), 4.34 (d, J=17.7 Hz, 1H), 5.06-5.12 (dd, J=5.1 and 13.2 Hz, 1H), 5.52 (s, 2H), 7.33-7.52 (m, 5H), 7.92-8.03 (m, 3H), 10.94 (s, 1H); $^{13}$C NMR (DMSO-$d_6$) δ 22.28, 31.13, 45.04, 51.52, 64.29, 115.05, 115.31, 122.11, 122.96, 124.04, 124.64, 126.79, 129.80, 129.93, 131.36, 133.31, 137.71, 139.76, 153.34, 167.94, 170.94, 172.78; Calcd for $C_{22}H_{18}N_2O_4S$+0.5 $H_2O$: C, 63.30; H, 4.61; N, 6.74; S, 7.72. Found: C, 63.85; H, 4.41; N, 6.75; S, 7.96.

5.131 3-[4-(2,3-Dihydro-Benzofuran-2-ylmethoxy)-1-Oxo-1,3-Dihydro-Isoindol-2-yl]-Piperidine-2,6-Dione

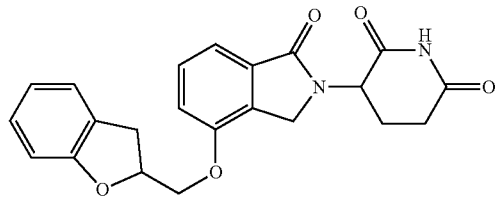 [SMILES: O=C1CCC(N2Cc3c(OCC4Cc5ccccc5O4)cccc3C2=O)C(=O)N1]

Step 1: Polymer bonded triphenylphosphine (1.6 g, 2.06 mmol, 1.25 mmol/g) was added to the stirred solution of 4-carbamoyl-4-(4-hydroxy-1-oxo-1, 3-dihydro-isoindol-2-yl)-butyric acid methyl ester (300 mg, 1.03 mmol) in THF (10 mL) at 0° C. The resulting mixture was stirred at 0° C. for 10 minutes, followed by the addition of DIAD (412 mg, 2.06 mmol). Ten minutes later, (2,3-Dihydro-benzofuran-2-yl)-methanol (250 mg, 1.66 mmol) was added to the mixture. The reaction was stirred at room temperature for 7.5 hours and the reaction was complete. The reaction mixture was filtered, and the solid was washed with dichloromethane (7×20 mL). The filtrate was concentrated and the residue was purified by ISCO chromatography to give 4-Carbamoyl-4-[4-(2,3-dihydro-benzofuran-2-ylmethoxy)-1-oxo-1,3-dihydro-isoindol-2-yl]-butyric acid methyl ester as an oil (380 mg, 87% yield): LCMS MH=425.

Step 2: KOtBu (100.5 mg, 0.89 mmol) was added to the stirred solution of 4-carbamoyl-4-[4-(2,3-dihydro-benzofuran-2-ylmethoxy)-1-oxo-1,3-dihydro-isoindol-2-yl]-butyric acid methyl ester (380 mg, 0.89 mmol) in tetrahydrofuran (18 mL) at 0° C. The mixture was stirred at 0° C. for 0.5 hour and the reaction was complete. The cold reaction mixture was added by HCl (aq. 0.1N, 10 mL), followed by the addition of dichloromethane (25 mL) and brine (10 mL). The mixture was extracted and organic layer was dried by $MgSO_4$ and concentrated under vacuo. The residue was purified by ISCO chromatography to give 3-[4-(2,3-dihydro-benzofuran-2-ylmethoxy)-1-oxo-1,3-dihydro-isoindol-2-yl]-piperidine-2,6-dione as a white solid (243 mg, 70% yield). HPLC: Waters Symmetry C-18, 3.9×150 mm, 5 μm, 1 mL/min, 240 nm, 40/60 (acetonitrile/0.1% $H_3PO_4$): $t_R$=4.32 (98%); mp: 258-260° C.; $^1$H NMR (DMSO-$d_6$) δ 1.90-2.05 (m, 1H, CHH), 2.28-2.46 (m, 1H, CHH), 2.54-2.66 (m, 1H, CHH), 2.82-2.99 (m, 1H, CHH), 3.04-3.20 (m, 1H, CHH), 3.35-3.43 (m, 1H, CHH), 3.97-4.45 (m, 4H, CHH, CHH, CHH, CHH), 5.03-5.22 (m, 2H, CNH, COH), 6.75 (d, J=7.9 Hz, 1H, Ar), 6.79-6.88 (m, 1H, Ar), 7.02-7.13 (m, 1H, Ar), 7.19-7.37 (m, 3H, Ar), 7.42-7.55 (m, 1H, Ar), 10.98 (s, 1H, NH); $^{13}$C NMR (DMSO-$d_6$) δ 22.39, 44.75, 51.52, 70.33, 80.31, 108.89, 114.88, 115.36, 120.29, 124.94, 126.61, 127.74, 127.79, 129.72, 129.76, 129.84, 133.24, 153.54, 159.08, 167.93, 170.96, 172.81; LCMS MH=393; Anal. Calcd for $C_{22}H_{20}N_2O_5$+0.3 $H_2O$: C, 66.42; H, 5.22; N, 7.04. Found: C, 66.28; H, 5.12; N, 7.34.

5.132 3-(4-(Imidazo[1,2-A]Pyridin-2-ylmethoxy)-1-Oxoisoindolin-2-Yl)Piperidine-2,6-Dione

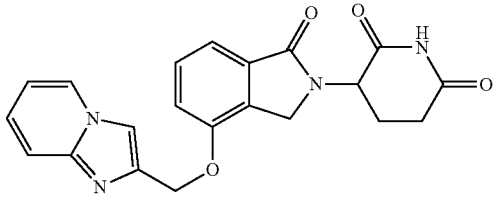 [SMILES: O=C1CCC(N2Cc3c(OCc4cn5ccccc5n4)cccc3C2=O)C(=O)N1]

Step 1: Diisopropyl azodicarboxylate (1.1 g, 5.5 mmol) was added to a stirred suspension of methyl 5-amino-4-(4-hydroxy-1-oxoisoindolin-2-yl)-5-oxopentanoate (0.8 g, 2.7 mmol), imidazo[1,2-a]pyridin-2-ylmethanol (0.6 g, 4.1 mmol) and triphenylphosphine-polymer bound (1.8 g, 5.5 mmol) in THF (100 mL) at 5-8° C. After addition, the mixture was stirred at room temperature overnight. The reaction mixture was filtered and solid was washed with methylene chloride (30 mL). Filtrate was concentrated and the residue was purified by chromatography (amine column, $CH_3OH:CH_2Cl_2$ 3:97) to give methyl 5-amino-4-(4-(imidazo[1,2-a]pyridin-2-yl methoxy)-1-oxoisoindolin-2-yl)-5-oxopentanoate (0.5 g, 41% yield): $^1H$ NMR (DMSO-$d_6$) δ 1.99-2.28 (m, 4H), 3.50 (s, 3H), 4.41 (d, J=18.0 Hz, 1H), 4.51 (d, J=18.0 Hz, 1H), 4.71-4.75 (m, 1H), 5.35 (s, 2H), 6.89 (t, J=6.0 Hz, 1H), 7.18-7.30 (m, 3H), 7.41-7.58 (m, 4H), 8.05 (s. 1H), 8.55 (d, J=6.0 Hz, 1H).

Step 2: Potassium t-butoxide/THF (1M, 1.1 mL, 1.1 mmol) was added to a stirred solution of methyl 5-amino-2-(4-(imidazo[1,2-a]pyridine-2-ylmethoxy)-1-oxoisoindolin-2-yl)-5-oxopentanoate (0.4 g, 1.1 mmol) in THF (30 mL) and DMF (20 mL). The resulting mixture was stirred at room temperature for 2 hours. The reaction mixture was cooled in an ice bath and quenched with water (30 mL). The mixture was stirred with methylene chloride (40 mL) and aqueous layer was extracted with methylene chloride (2×40 mL). Combined organic solution was washed with water (40 mL) and brine (40 mL), and dried. The solvent was removed and the residue was stirred with water (20 mL). The mixture was filtered and solid was reslurried with methylene chloride (15 mL) to give 3-(4-(imidazo[1,2-a]pyridin-2-yl methoxy)-1-oxoisoindolin-2-yl)piperidine-2,6-dione (0.1 g, 28%) as a white solid: mp 222-224° C.; $^1H$ NMR (DMSO-$d_6$) δ 1.96-2.01 (m, 1H), 2.35-2.51 (m, 2H), 2.58-2.91 (m, 1H), 4.26 (d, J=17.4 Hz, 1H), 4.36 (d, J=17.4 Hz, 1H), 5.08-5.14 (dd, J=5.1 and 13.5 Hz, 1H), 5.36 (s, 2H), 6.87-6.91 (dt, J=0.9 and 6.6 Hz, 1H), 7.21-7.55 (m, 5H), 8.03 (s, 1H), 8.51-8.53 (dd, J=0.9 and 6.6 Hz, 1H), 10.97 (s, 1H); $^{13}C$ NMR (DMSO-$d_6$) δ 22.35, 31.17, 45.06, 51.54, 64.63, 111.79, 112.14, 115.01, 115.18, 116.65, 124.90, 126.95, 129.78, 129.84, 133.26, 141.54, 144.28, 153.45, 167.98, 170.96, 172.81; Calcd. For $C_{21}H_{18}N_4O_4$+0.25 $H_2O$: C, 63.87; H, 4.72; N, 14.19. Found: C, 63.99; H, 4.60; N, 14.20.

5.133 3-(4-(Imidazo[1,2-A]Pyridin-6-ylmethoxy)-1-Oxoisoindolin-2-yl)-Piperidine-2,6-Dione

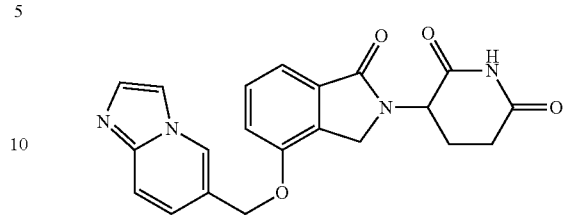

Step 1: Diisopropyl azodicarboxylate (1.3 g, 6.2 mmol) was added to a stirred suspension of methyl 5-amino-4-(4-hydroxy-1-oxo-isoindolin-2-yl)-5-oxo-pentanonate (0.9 g, 3.1 mmol), imidazo[1,2-a]pyridine-6-ylmethanol (0.7 g, 4.6 mmol) and triphenylphosphine-polymer bound (2.1 g, 6.2 mmol) in THF (70 mL) at 5-8° C. After addition, the mixture was stirred at 5° C. for 5 minutes then warmed to room temperature overnight. The reaction mixture was filtered and solid was washed with $CH_2Cl_2$ (30 mL). Filtrate was concentrated and the residue was purified by chromatography ($SiO_2$, $CH_3OH:CH_2Cl_2$ 3:97) to give methyl 5-amino-4-(4-(imidazo[1,2-a]pyridin-6-ylmethoxy)-1-oxoisoindolin-2-yl)-5-oxopentanoate (0.8 g, 65%).

Step 2: A solution of potassium t-butoxide/THF (1M, 2.0 mL, 2.0 mmol) was added to a stirred solution of methyl 5-amino-4-(4-(imidazo[1,2-a]pyridin-6-ylmryhoxy)-1-oxoisoindolin-2-yl)-5-oxopentanoate (0.8 g, 2.0 mmol) in THF (50 mL) at 5° C. The mixture was stirred at 5° C. for 10 minutes then warmed to room temperature for 2 hours. The reaction mixture was cooled in an ice bath and quenched with water (30 mL). The mixture was extracted with $CH_2Cl_2$ (3×30 mL) and combined $CH_2Cl_2$ solution was washed with brine (40 mL) and dried. The solvent was removed and the residue was purified by chromatography ($SiO_2$, $CH_3OH: CH_2Cl_2$ 3:97) to give 3-(4-(imidazo[1,2-a]pyridin-6-ylmethoxy)-1-oxoisoindolin-2-yl)-piperidine-2,6-dione (0.25 g, 32% yield): mp 270-272° C.; $^1H$ NMR (DMSO-$d_6$) δ 2.00 (m, 1H), 2.26-2.53 (m, 2H), 2.85-2.97 (m, 1H), 4.29 (d, J=17.4 Hz, 1H), 4.39 (d, J=17.7 Hz, 1H), 5.08-5.14 (dd, J=5.1 and 13.2 Hz, 1H), 5.26 (s, 2H), 7.28-7.41 (m, 3H), 7.51 (t, J=7.8 Hz, 1H), 7.58-7.61 (m, 2H), 7.97 (s, 1H), 8.72 (s, 1H), 10.97 (s, 1H); $^{13}C$ NMR (DMSO-$d_6$) δ 22.35, 31.15, 45.04, 51.54, 67.26, 113.45, 115.07, 115.45, 116.84, 120.99, 125.10, 125.95, 129.83, 130.01, 133.34, 133.44, 144.01, 153.26, 167.94, 170.94, 172.80; Calcd for $C_{21}H_{18}N_4O_4$+ 0.15 $H_2O$: C, 64.19; H, 4.69; N, 14.25. Found: C, 64.10; H, 4.60; N, 14.32.

5.134 3-(4-(Benzo[B]Thiophen-3-ylmethoxy)-1-Oxoisoindolin-2-yl)-Piperidine-2,6-Dione

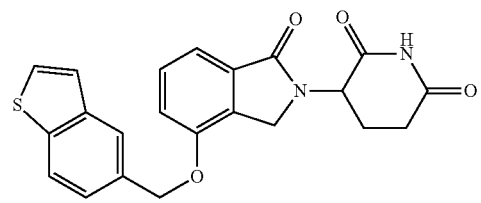 [SMILES: O=C1CCC(N2Cc3c(OCc4ccc5sccc5c4)cccc3C2=O)C(=O)N1]

Step 1: Diisopropyl azodicarboxylate (1.1 g, 5.47 mmol) was added to a stirred solution of methyl 5-amino-4-(4-hydroxy-1-oxoisoindolin-2-yl)-5-oxopentanoate (0.8 g, 2.7 mmol), 1-benzothiophen-5-ylmethanol (0.7 g, 4.1 mmol) and triphenylphosphine-polymer bound (1.8 g, 5.5 mmol) in THF (60 mL) at 5-8° C. After addition, the mixture was stirred at room temperature overnight. The reaction mixture was filtered and solid was washed with $CH_2Cl_2$ (30 mL). Filtrate was concentrated and the residue was purified by chromatography ($SiO_2$, $CH_3OH:CH_2Cl_2$ 3:97) to give methyl 5-amino-4-(4-(benzo[b]thiophen-5-ylmethoxy)-1-oxoisoindolin-2-yl)-5-oxopentanoate (0.8 g, 56%).

Step 2: A solution of potassium t-butoxide/THF (I M, 2.3 ml, 2.3 mmol) was added to a stirred solution of methyl 5-amino-4-(4-(benzo[b]thiophen-5-ylmethoxy)-1-oxoisoindolin-2-yl)-5-oxopentanoate (1.0 g, 2.3 mmol) in THF (30 mL) at 5° C. The mixture was stirred at 5° C. for 10 minutes then warmed to room temperature for 2 hours. The reaction mixture was cooled in an ice bath and quenched with 1N HCl (10 mL). The mixture was diluted with $CH_2Cl_2$ (50 mL) and water (10 mL). The aqueous layer was extracted with $CH_2Cl_2$ (30 mL) and combined $CH_2Cl_2$ solution was washed with water (2×40 mL) and brine (40 mL), and dried. The solvent was removed and the residue was purified by chromatography ($SiO_2$, $CH_3OH:CH_2C_2$ 3:97) to give 3-(4-benzo[b]thiophen-5-ylmethoxy)-1-oxoisoindolin-2-yl)-piperidine-2,6-dione (0.4 g, 36% yield): mp 213-215° C.; $^1H$ NMR (DMSO-$d_6$) δ 1.95-2.01 (m, 1H), 2.36-2.52 (m, 2H), 2.85-2.95 (m, 1H), 4.30 (d, J=17.4 Hz, 1H), 4.40 (d, J=17.4 Hz, 1H), 5.08-5.14 (dd, J=5.1 and 13.5 Hz, 1H), 5.37 (s, 2H), 7.31-7.37 (2d, J=8.1 and 7.5 Hz, 2H), 7.46-7.51 (m, 3H), 7.79 (d, J=5.4 Hz, 1H), 8.00-8.04 (m, 2H), 10.97 (s, 1H); $^{13}C$ NMR (DMSO-$d_6$) δ 22.33, 31.17, 45.09, 51.57, 69.67, 115.05, 115.23, 122.68, 122.77, 123.89, 124.11, 128.09, 129.79, 129.97, 132.84, 133.31, 138.75, 139.50, 153.46, 167.98, 170.95, 172.80; Calcd for $C_{22}H_{18}N_2O_4S$: C, 65.01; H, 4.46; N, 6.89; S, 7.89. Found: C, 64.66; H, 4.07; N, 6.76; S, 7.87.

5.135 3-(1-Oxo-4-(Quinolin-6-ylmethoxy)-Isoindolin-2-yl)Piperidine-2,6-Dione

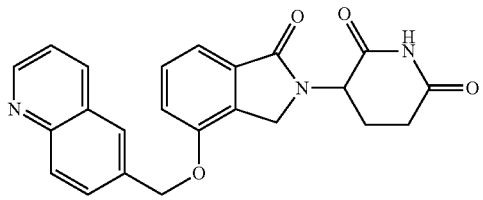 [SMILES: O=C1CCC(N2Cc3c(OCc4ccc5ncccc5c4)cccc3C2=O)C(=O)N1]

Step 1: DIBAL/toluene (1M, 16 mL, 16 mmol) was added slowly to a stirred solution of methyl quinoline-6-carboxylate (1.0 g, 5.3 mmol) in THF (30 mL) at −60° C. The resulting solution was stirred at −20° C. for 1.5 hours and then carefully quenched with water (15 mL). The mixture was concentrated and the residue was stirred in EtOAc (80 mL) and sat. $NaHCO_3$ (20 mL). The mixture was filtered and aqueous layer was extracted with EtOAc (2×30 mL). Combined EtOAc solution was washed with water (30 mL) and brine (30 mL) and dried ($MgSO_4$). The solvent was removed and the residue was purified by chromatography ($SiO_2$, EtOAc: $CH_2Cl_2$ 1:1) to give quinolin-6-yl-methanol (0.5 g, 62% yield): $^1H$ NMR (DMSO-$d_6$) δ 4.69 (d, J=5.1 Hz, 2H), 5.42 (t, J=5.4 Hz, 1H), 7.49-7.53 (dd, J=4.5 and 8.4 Hz, 1H), 7.69-7.72 (dd, J=1.8 and 8.7 Hz, 1H), 7.88 (d, J=0.9 Hz, 1H), 7.96 (d, J=8.7 Hz, 1H), 8.32-8.36 (dd, J=0.9 and 8.4 Hz, 1H), 8.85-8.87 (dd, J=1.8 and 4.2 Hz, 1H).

Step 2: Diisopropyl azodicarboxylate (0.7 g, 3.6 mmol) was added to a stirred suspension of triphenylphosphine-polymer bound (3 g, 3.8 mmon) in THF (40 mL) at 3-6° C. After stirred for 10 minutes at 3° C., a solution of methyl 5-amino-4-(4-hydroxy-1-oxoisoindolin-2-yl)-5-oxopentanoate (0.7 g, 2.4 mmol) and quinolin-6-yl-methanol (0.5 g, 3.1 mmol) in THF (40 mL) was added slowly at 3-7° C. The resulting mixture was stirred at room temperature overnight. The reaction mixture was filtered and solid was washed with $CH_2Cl_2$ (30 mL). Filtrate was concentrated and the residue was purified by chromatography ($SiO_2$, $CH_3OH:CH_2Cl_2$ 5:95) to give methyl 5-amino-5-oxo-4-(1-oxo-4-(quinolin-6-ylmethoxy)-isoindolin-2-yl)pentanoate (0.5 g, 46%).

Step 3: KO-t-Bu/THF (1M, 1.1 mL, 1.1 mmol) was added slowly to a stirred solution of methyl 5-amino-5-oxo-4-(1-oxo-4-(quinolin-6-ylmethoxy)isoindolin-2-yl)pentanoate (0.5 g, 1.1 mmol) at 5° C. The reaction mixture was stirred 30 minutes at 5° C. then quenched with sat. $NH_4Cl$ (5 mL). The mixture was stirred with $CH_2Cl_2$ (50 mL) and sat. $NaHCO_3$ (15 mL). The aqueous layer was extracted with $CH_2Cl_2$ (30 mL) and combined $CH_2Cl_2$ solution was washed with water (20 mL) and brine (30 mL), and dried ($MgSO_4$). The solvent was removed and the residue was stirred with $CH_2Cl_2$ (3 mL) and ether (3 mL). Solid was collected to give 3-(1-oxo-4-(quinolin-6-ylmethoxy)isoindolin-2-yl)piperidine-2,6-dione (0.3 g, 60% yield): mp 267-269° C.; $^1H$ NMR (DMSO-d6) δ 1.97-2.02 (m, 1H), 2.42-2.62 (m, 2H), 2.86-2.92 (m, 1H), 4.35 (d, J=17.4 Hz, 1H), 4.45 (d, J=17.4 Hz, 1H), 5.10-5.16 (dd, J=5.1 and 13.2 Hz, 1H), 5.47 (s, 2H), 7.33-7.37 (m, 2H), 7.47-7.57 (m, 2H), 7.86-7.89 (dd, J=1.8 and 8.7 Hz, 1H), 8.04-8.09 (m, 2H), 8.38-8.41 (dd, J=0.9 and 8.4 Hz, 1H), 8.90-8.92 (dd, J=1.8 and 4.2 Hz, 1H), 10.98 (s, 1H); $^{13}C$ NMR (DMSO-$d_6$) δ 22.36, 31.17, 45.10, 51.58, 69.27, 115.08, 115.39, 121.74, 126.41, 127.60, 129.02, 129.22, 129.84, 120.02, 133.37, 134.96, 136.01, 147.36, 150.71, 153.40, 167.97, 170.98, 172.82; Calcd for $C_{23}H_{19}N_3O_4+0.2 H_2O$: C, 68.21; H, 4.83; N, 10.37. Found: C, 68.04; H, 4.78; N, 10.10.

5.136 3-(4-(Naphthalen-2-ylmethoxy)-1-Oxoisoindolin-2-yl)-Piperidine-2,6-Dione

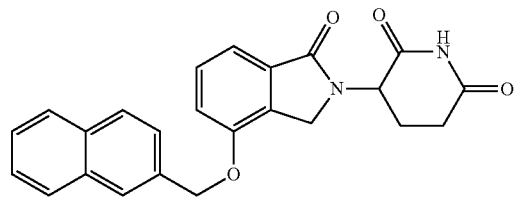 [SMILES: O=C1CCC(N2Cc3c(OCc4ccc5ccccc5c4)cccc3C2=O)C(=O)N1]

Step 1: Diisopropyl azodicarboxylate (0.8 g, 4.1 mmol) was added slowly to a stirred suspension of triphenylphosphine-polymer bound (3.0 g, 4.5 mmol) in THF (40 mL) at 3-6° C. After stirred at 3° C. for 10 minutes, a solution of methyl 5-amino-4-(4-hydroxy-1-oxoisoindolin-2-yl)-5-oxopentanoate (0.8 g, 2.7 mmol), 2-naphthalene-methanol (0.7 g, 4.1 mmol) and triethylamine (0.4 g, 4.1 mmol) in THF (40 mL) was added at 3-6° C. After addition, the mixture was stirred at room temperature overnight. The reaction mixture was filtered and solid was washed with $CH_2Cl_2$ (30 mL). Filtrate was concentrated and the residue was purified by chromatography (SiO$_2$, CH$_3$OH:CH$_2$Cl$_2$ 3:97) to give methyl 5-amino-4-(4-(naphthalen-2-ylmethoxy)-1-oxoisoindolin-2-yl)-5-oxopentanoate (0.6 g, 50%).

Step 2: A solution of potassium t-butoxide/THF (1M, 1.4 mmol) was added slowly to a stirred solution of methyl 5-amino-4-(4-(naphthalen-2-ylmethoxy)-1-oxoisoindolin-2-yl)-5-oxopentanoate (0.6 g, 1.4 mmol) in THF (20 mL) at 5° C. The resulting solution was stirred at 5° C. for 30 minutes then quenched with sat. NH$_4$Cl (5 mL). The mixture was stirred with CH$_2$Cl$_2$ (40 mL) and water (15 mL). The aqueous layer was extracted with CH$_2$Cl$_2$ (40 mL) and combined CH$_2$Cl$_2$ solution was washed with water (20 mL) and brine (20 mL), and dried. The solvent was removed and the residue was purified by chromatography (SiO$_2$, CH$_3$OH:CH$_2$Cl$_2$ 3:97) to give 3-(4-(naphthalen-2-ylmethoxy)-1-oxoisoindolin-2-yl)-piperidine-2,6-dione (0.2 g, 36% yield): mp 277-279° C.; $^1$H NMR (DMSO-d$_6$) δ 1.97-2.02 (m, 1H), 2.42-2.61 (m, 2H), 2.85-2.95 (m, 1H), 4.33 (d, J=17.4 Hz, 1H), 4.43 (d, J=17.4 Hz, 1H), 5.09-5.15 (dd, J=5.1 and 13.2 Hz, 1H), 5.42 (s, 2H), 7.32-7.39 (m, 2H), 7.46-7.56 (m, 3H), 7.60-7.64 (m, 1H), 7.91-7.96 (m, 3H), 8.02 (s, 1H), 10.97 9s, 1H); $^{13}$C NMR (DMSO-d$_6$) δ 22.34, 31.17, 45.11, 51.58, 69.67, 115.08, 115.29, 125.58, 126.18, 126.31, 127.57, 127.77, 128.12, 129.81, 130.00, 132.57, 132.71, 133.34, 134.21, 153.47, 167.98, 170.96, 172.81; Calcd for C$_{24}$H$_{20}$N$_2$O$_4$: C, 71.99; H, 5.03; N, 7.00. Found: C, 71.71; H, 5.09; N, 6.93.

5.137 3-(4-((2,3-Dihydro-1H-Indan-5-yl)Methoxy)-1-Oxoisoindolin-2-yl)-Piperidine-2,6-Dione

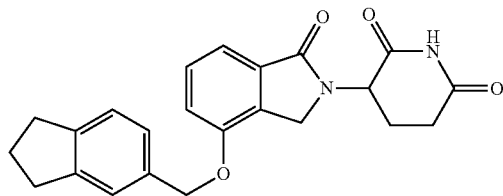 [SMILES: O=C1CCC(N2Cc3c(OCc4ccc5c(c4)CCC5)cccc3C2=O)C(=O)N1]

Step 1: Diisopropyl azodicarboxylate (0.8 g, 4.1 mmol) was added to a stirred suspension of triphenylphosphine-polymer bound (3.5 g, 4.4 mmol) in THF (40 mL) at 3-5° C. After stirred at 3° C. for 10 minutes, a solution of methyl 5-amino-4-(4-hydroxy-1-oxoisoindolin-2-yl)-5-oxopentanoate (0.8 g, 2.7 mmol) and 5-hydroxymethylindane (0.5 g, 3.6 mmol) in THF (40 mL) was added slowly at 3-5° C. The resulting mixture was stirred at room temperature overnight. The reaction mixture was filtered and solid was washed with CH$_2$Cl$_2$ (30 mL). Filtrate was concentrated and the residue was dissolved in CH$_2$Cl$_2$ (80 mL) and washed with sat. NaHCO$_3$ (30 mL), water (2×30 mL) and brine (30 mL), and dried. The solvent was removed and the residue was purified by chromatography (SiO$_2$, CH$_3$OH:CH$_2$Cl$_2$ 3:97) to give methyl 5-amino-4-(4-((2,3-dihydro-1H-indan-5-yl)methoxy)-1-oxoisoindolin-2-yl)-5-oxopentanoate (0.7 g, 60% yield): $^1$H NMR (CDCl$_3$) δ 2.05-2.45 (m, 6H), 2.89-2.96 (m, 4H), 3.64 (s, 3H), 4.35-4.49 (dd, J=17.4 and 26.4 Hz, 2H), 4.87-4.92 (dd, J=6.0 and 8.7 Hz, 1H), 5.10 (s, 2H), 5.37 (s, 1H), 6.33 (s, 1H), 7.08-7.28 (m, 4H), 7.37-7.44 (m, 2H).

Step 2: A solution of potassium t-butoxide/THF (1M, 1.5 mL, 1.5 mmol) was added slowly to a stirred solution of methyl 5-amino-4-(4-((2,3-dihydro-1H-indan-5-yl)methoxy)-1-oxoisoindolin-2-yl)-5-oxopentanoate (0.6 g, 1.5 mmol) in THF (20 mL) at 5° C. The resulting solution was stirred at 5° C. for 30 minutes then quenched with sat. NH$_4$Cl (5 mL). The mixture was stirred with CH$_2$Cl$_2$ (50 mL) and water (15 mL) and aqueous layer was extracted with CH$_2$Cl$_2$ (30 mL). Combined CH$_2$Cl$_2$ solution was washed with water (20 mL) and brine (20 mL), and dried. The solvent was removed and solid residue was stirred with acetone (10 mL) to give 3-(4-((2,3-dihydro-1H-indan-5-yl)methoxy)-1-oxoisoindolin-2-yl)piperidine-2,6-dione (0.3 g, 58% yield): mp 216-218° C.; $^1$H NMR (DMSO-d$_6$) δ 1.96-2.08 (m, 3H), 2.41-2.60 (m, 2H), 2.82-2.96 (m, 5H), 4.26 (d, J=17.7 Hz, 1H), 4.36 (d, J=17.7 Hz, 1H), 5.07-5.13 (dd, J=5.1 and 13.5 Hz, 1H), 5.19 (s, 2H), 7.23-7.25 (m, 2H), 7.30-7.33 (m, 3H), 7.47 (t, J=7.8 Hz, 1H), 10.86 (s, 1H); $^{13}$C NMR (DMSO-d$_6$) δ 22.31, 25.05, 31.17, 32.00, 32.17, 45.08, 51.56, 69.76, 114.98, 115.11, 123.77, 124.15, 125.84, 129.76, 129.92, 133.26, 134.32, 143.60, 143.98, 153.50, 167.99, 170.96, 172.81; Calcd for C$_{23}$H$_{22}$N$_2$O$_4$+0.3 H$_2$O: C, 69.79; H, 5.75; N, 7.08. Found: C, 69.72; H, 5.67; N, 6.91.

5.138 3-(4-(Benzo[D]Oxazol-5-ylmethoxy)-1-Oxoisoindolin-2-yl)Piperidine-26-Dione

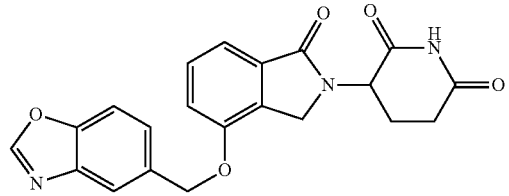 [SMILES: O=C1CCC(N2Cc3c(OCc4ccc5ocnc5c4)cccc3C2=O)C(=O)N1]

Step 1: A mixture of 5-methylbenzo[d]oxazole (2 g, 15 mmol), NBS (2.67 g, 15 mmol) and benzoyl peroxide (50 mg, 0.21 mmol) was heated to reflux in CCl$_4$ (50 mL) overnight. The mixture was cooled to room temperature, and the resulting precipitate was removed by filtration. The filtrate was concentrated under reduced pressure and the residue was purified by ISCO (40 g column, EtOAc/hexanes gradient from 0% to 20% in 40 min) to give 5-(bromomethyl)benzo[d]oxazole (1.6 g, 50% yield); $^1$H NMR (DMSO-d$_6$): 4.88 (s, 2H, CH$_2$), 7.55 (dd, J=1.7, 8.5 Hz, 1H, Ar), 7.77 (d, J=8.5 Hz, 1H, Ar), 7.91 (d, J=1.5 Hz, 1H, Ar), 8.79 (s, 1H, Ar).

Step 2: To a suspension of potassium carbonate (189 mg, 1.37 mmol) in DMF (5 mL), were added 5-(bromomethyl)benzo[d]oxazole (261 mg, 1.23 mmol) and methyl 5-amino-4-(4-hydroxy-1-oxoisoindolin-2-yl)-5-oxopentanoate (400 mg, 1.37 mmol). The formed mixture was stirred at room temperature over weekend. Additional 5-(bromomethyl)benzo[d]oxazole (87 mg, 0.41 mmol) was added, and the mixture was stirred at room temperature overnight. The reaction was quenched with water (40 mL) at 0° C., the product was extracted with ethyl acetate (3×30 mL), and the combined organic layers were washed with water (20 mL) and brine (20 mL). The solvent was evaporated under vacuum and the product was purified with ISCO (40 g column, MeOH/CH$_2$Cl$_2$ gradient from 0% to 5% in 40 min) to give methyl 5-amino-4-(4-(benzo[d]oxazol-5-yl-methoxy)-1-oxoisoindolin-2-yl)-5-oxopentanoate (440 mg, 76% yield); $^1$H NMR (DMSO-d$_6$): 1.82-2.37 (m, 4H, CH$_2$, CH$_2$), 3.50 (s, 3H, CH$_3$), 4.34-4.64 (m, 2H, CH$_2$), 4.67-4.83 (m, 1H, CH), 5.38 (s, 2H, CH$_2$), 7.18 (s, 1H, NHH), 7.26-7.41 (m, 2H, Ar), 7.45 (d, J=7.7 Hz, 1H, Ar), 7.59 (dd, J=1.4, 8.4 Hz, 2H, Ar), 7.81 (d, J=8.3 Hz, 1H, Ar), 7.96 (d, J=0.9 Hz, 1H, NHH), 8.78 (s, 1H, Ar).

Step 3: To a mixture of methyl 5-amino-4-(4-(benzo[d]oxazol-5-ylmethoxy)-1-oxoisoindolin-2-yl)-5-oxopentanoate (450 mg, 1.06 mmol) in THF (20 mL), was added potassium tert-butoxide (119 mg, 1.06 mmol) at 0° C. The formed mixture was warm up to room temperature and stirred overnight. Additional potassium tert-butoxide (48 mg, 0.43 mmol) was added, and the mixture was stirred at room temperature for 3 hours. The reaction was quenched with acetic acid (1 mL) at 0° C., the solvent was evaporated to dryness, the residue was taken in actonitrile (5 mL), and water (10 mL) was added dropwise, then saturated sodium bicarbonate was added to adjust pH to 7. The mixture was stirred overnight, the resulting solid was filtered and resulted with acetonitrile (3 mL) to give 3-(4-(benzo[d]oxazol-5-ylmethoxy)-1-oxoisoindolin-2-yl)piperidine-2,6-dione as a white solid (180 mg, 43% yield); mp: 209-211° C.; $^1$H NMR (DMSO-$d_6$): 1.89-2.07 (m, 1H, CHH), 2.35-2.48 (m, 1H, CHH), 2.60 (br. s., 1H, CHH), 2.82-3.02 (m, 1H, CHH), 4.22-4.54 (m, 2H, CH$_2$), 5.11 (dd, J=5.1, 13.2 Hz, 1H, CH), 5.38 (s, 2H, CH$_2$), 7.35 (dd, J=7.6, 10.6 Hz, 2H, Ar), 7.44-7.55 (m, 1H, Ar), 7.58 (dd, J=1.5, 8.5 Hz, 1H, Ar), 7.80 (d, J=8.5 Hz, 1H, Ar), 7.95 (d, J=0.9 Hz, 1H, Ar), 8.78 (s, 1H, Ar), 10.97 (s, 1H, NH); $^{13}$C NMR (DMSO-$d_6$): 22.33, 31.16, 45.10, 51.58, 69.32, 111.09, 115.03, 115.29, 119.48, 125.56, 129.78, 130.02, 133.33, 133.40, 139.83, 149.05, 153.35, 154.75, 167.99, 170.95, 172.81; LCMS MH=392; HPLC: Waters Symmetry C-18, 3.9×150 mm, 5 μm, 1 mL/min, 240 nm, 25/75 acetonitrile/0.1% H$_3$PO$_4$ $t_R$=4.59 (98.54%); Anal. Calcd for $C_{21}H_{17}N_3O_5$+0.3 H$_2$O: C, 63.57; H, 4.47; N, 10.59; Found: C, 63.54; H, 4.31; N, 10.58.

5.139 3-(4-(Isoindolin-5-yl)Methoxy)-1-Oxoisoindolin-2-yl)Piperidine-2,6-Dione Hydrochloride

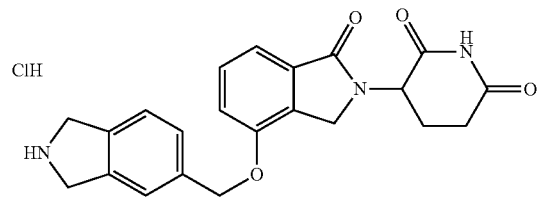 [SMILES: Cl ; O=C1CCC(N2Cc3c(OCc4ccc5c(c4)CNC5)cccc3C2=O)C(=O)N1]

A solution of tert-butyl 5-((2-(2,6-dioxopiperidin-3-yl)-1-oxoisoindolin-4-yloxy)methyl)isoindoline-2-carboxylate (0.6 g, 1.3 mmol) in THF (20 mL) was treated with HCl/ether (2M, 1.9 mL, 3.8 mmol) and stirred at room temperature for 8 hours. Ether (10 mL) was added and solid was collected. Solid was reslurried with CH$_2$Cl$_2$ (15 mL) to give 3-(4-(isoindolin-5-yl)methoxy)-1-oxoisoindolin-2-yl)piperidine-2,6-dione hydrochloride (0.5 g, 88% yield): mp 270-272° C.; $^1$H NMR (DMSO-$d_6$) δ 1.97-2.00 (m, 1H), 2.41-2.61 (m, 2H), 2.87-2.93 (m, 1H), 4.28 (d, J=15 Hz, 1H), 4.39 (d, J=18 Hz, 1H), 4.50 (s, 4H), 5.08-5.14 (dd, J=6 and 15 Hz, 1H), 5.28 (s, 2H), 7.32-7.52 (m, 6H), 10.01 (s, 2H), 10.98 (s, 1H); $^{13}$C NMR (DMSO-$d_6$) δ 22.35, 31.18, 45.08, 49.73, 49.79, 51.57, 69.19, 115.01, 115.33, 122.14, 123.01, 127.77, 129.81, 129.93, 133.32, 134.89, 135.47, 136.95, 153.31, 167.95, 170.96, 172.83; Calcd for $C_{22}H_{23}N_3O_4Cl$+ 0.5 H$_2$O: C, 60.48; H, 5.31; N, 9.62; Cl, 8.11. Found: C, 60.11; H, 5.21; N, 9.38; Cl, 8.27.

5.140 3-(4-((1H-Benzo[D]Imidazol-2-yl)Methoxy)-1-Oxoisoindolin-2-yl)Piperidine-2,6-Dione Hydrogen Chloride

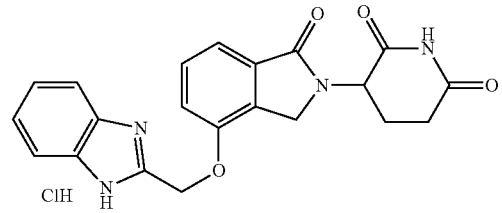 [SMILES: O=C1CCC(N2Cc3c(OCc4nc5ccccc5[nH]4)cccc3C2=O)C(=O)N1 ; Cl]

Step 1: To a stirred solution of 2-(chloromethyl)-1H-benzo[d]imidazole (1 g, 6.00 mmol) in DMF (10 ml, 129 mmol), was added di-tert-butyl dicarbonate (1.375 g, 6.30 mmol) at room temperature. After about 10 minutes, cat amounts of DMAP (0.05 g, 0.409 mmol) was added to the rxn mixture. The resulting solution was stirred for an additional 5 minutes at room temperature (LCMS indicated reaction has gone to completion) and the mixture was incubated at 4° C. overnight. The reaction mixture was concentrated in vacuo to an oil which was diluted with EtOAc (~200 mL), transferred to a separatory funnel, and washed with aqueous 1 M KH$_2$PO$_4$ (pH~5, 2×50 mL). The organic layer was washed with brine, dried (Na$_2$SO$_4$), and concentrated in vacuo. The residue was dried in a vacuum oven to give tert-butyl 2-(chloromethyl)-1H-benzo[d]imidazole-1-carboxylate as an amber oil (1.6 g, 97% yield). The oil was used in the next step without further purification. $^1$H NMR (DMSO-$d_6$) δ 1.59-1.76 (m, 9H, tBu), 5.13 (s, 2H, CH$_2$), 7.33-7.51 (m, 2H, Ar), 7.62-7.84 (m, 1H, Ar), 7.87-8.10 (m, 1H, Ar); $^{13}$C NMR (DMSO-$d_6$) δ 27.36, 86.28, 114.88, 119.99, 124.52, 125.61, 132.77, 141.16, 147.47, 150.23; One carbon signal (CH$_2$Cl) is not observed due to overlap with DMSO-$d_6$; confirmed by HMQC; LCMS MH=267, 269 (mainly see -Boc fragmentation Step 2: tert-Butyl 5-amino-2-(4-hydroxy-1-oxoisoindolin-2-yl)-5-oxopentanoate (500 mg, 1.495 mmol) and potassium carbonate (227 mg, 1.645 mmol) were suspended in DMF (7 mL) at room temperature. To the stirred mixture at room temperature, was added tert-butyl 2-(chloromethyl)-1H-benzo[d]imidazole-1-carboxylate (439 mg, 1.645 mmol) as a solution in DMF (3 mL). The resulting suspension was stirred at room temperature for about 15 hours. The crude reaction mixture was partitioned between EtOAc (150 mL) and water (~50 mL). The organic layer was washed with brine (50 mL), dried (Na$_2$SO$_4$), and concentrated in vacuo. The oily residue was diluted with dichloromethane (~10 mL), concentrated to dryness (2× from dichloromethane) and the resulting oil was placed in a vacuum oven at 40° C. for several hours to afford tert-butyl 2-((2-(5-amino-1-tert-butoxy-1,5-dioxopentan-2-yl)-1-oxoisoindolin-4-yloxy)methyl)-1H-benzo [d]imidazole-1-carboxylate (1 g) as a tan oil, which was used in the next step without further purification. LCMS MH (-Boc)=465.

Step 3: tert-Butyl 2-((2-(5-amino-1-tert-butoxy-1,5-dioxopentan-2-yl)-1-oxoisoindolin-4-yloxy)methyl)-1H-benzo[d]imidazole-1-carboxylate (844 mg, 1.495) was dissolved in THF (10 ml, 122 mmol). To the stirred solution at room temperature, was added KOtBu (2 ml, 2.0 mmol, 1.0 M in THF) in a rapid dropwise fashion via syringe and reaction progress was closely monitored by LCMS. After about 50 minutes, additional KOtBu (1 mL, 1 mmol) was added, and the mixture stirring was continued at room temperature for about 15 minutes. The reaction mixture was stored at −20° C. overnight. The following morning, additional KOtBu (0.5 mL, 5 mmol) was added, followed by another treatment of KOtBu (0.5 mL, 0.5 mmol) after 3 hours. After about 80 minutes, the reaction mixture was transferred to a solution of 2 N HCl in Et$_2$O (50 mL). The resulting pale yellow slurry was stirred at room temperature. After about 1 hour, the slurry was filtered and the solid was washed with additional Et$_2$O and then suction dried on filter funnel. Oven drying gave ~1 g of crude product as a tan solid. The solid was dissolved in DMF/water (10 mL/3 mL), sonicated and then filtered. The filtrate was purified by injection onto a C-18 preparatory HPLC column. The product was eluted with an acetonitrile/water gradient (0.1% formic acid in both mobile phases, 5% to 30% MeCN over 12 minutes) and fractions were collected by mass trigger. The desired fractions were combined and concentrated in vacuo to give a solid residue which was redissolved in 1 N HCl/acetonitrile (~1:1, 40 mL). The mixture was concentrated in vacuo and the solid was transferred to a scintillation vial. The suspension was frozen and lyophilized to give and off-white solid (145 mg). This solid was slurried in water (5 mL), and the mixture was stirred for several hours then filtered. The solid was suction dried and then stored in vacuum oven overnight to give 3-(4-((1H-benzo [d]imidazol-2-yl)methoxy)-1-oxoisoindolin-2-yl)piperidine-2,6-dione hydrochloride as a white solid (90 mg, 15% yield). HPLC: Waters Symmetry C$_{18}$, 5 μm, 3.9×150 mm, 1 ml/min, 240 nm, 13/87 acetonitrile/0.1% H$_3$PO$_4$, 4.01 min (96.6%); mp: 229-231° C.; $^1$H NMR (DMSO-d$_6$) δ 1.91-2.12 (m, 1H, CHH), 2.32-2.47 (m, 1H, CHH), 2.54-2.70 (m, 1H, CHH), 2.84-3.04 (m, 1H, CHH), 4.41 (d, J=17.6 Hz, 1H, CHH), 4.55 (d, J=17.6 Hz, 1H, CHH), 5.16 (dd, J=5.0, 13.3 Hz, 1H, CH), 5.73 (s, 2H, CH$_2$), 7.29-7.65 (m, 5H, Ar), 7.68-7.85 (m, 2H, Ar), 11.02 (s, 1H, NH); $^{13}$C NMR (DMSO-d$_6$) δ 22.49, 31.18, 45.13, 51.58, 62.19, 114.56, 114.93, 116.34, 124.67, 129.97, 130.21, 133.50, 133.55, 149.24, 152.50, 167.74, 170.99, 172.81; LCMS MH=391; Anal Calcd for C$_{21}$H$_{18}$N$_4$O$_4$+0.76 HCl+3.4 H$_2$O: C, 52.62; H, 5.37; N, 11.69; Cl, 5.62. Found: C, 52.72; H, 4.98; N, 11.33; Cl, 5.45.

5.141 3-(4-(Benzo[D]Thiazol-2-ylmethoxy)-1-Oxoisoindolin-2-Y1)Piperidine-2,6-Dione

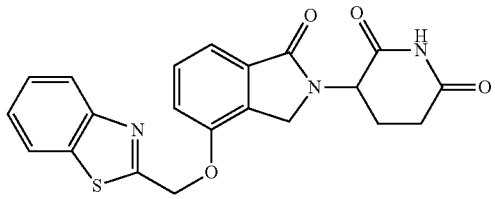 [SMILES: O=C1CCC(N2Cc3c(OCc4nc5ccccc5s4)cccc3C2=O)C(=O)N1]

Step 1: Diisopropyl azodicarboxylate (1.3 g, 6.2 mmol) was added to a stirred suspension of methyl 5-amino-4-(4-hydroxy-1-oxoisoindolin-2-yl)-5-oxopentanoate (0.9 g, 3.1 mmol), 1,3-benzothiazole-2-methanol (0.8 g, 4.7 mmol) and triphenylphosphne-polymer bound (2.1 g, 6.2 mmol) in THF (80 mL) at 5-8° C. After addition, the mixture was stirred at room temperature overnight. The reaction mixture was filtered and the solid was washed with methylene chloride (20 mL). Filtrate was concentrated and the residue was purified by chromatography (SiO$_2$, CH$_3$OH:CH$_2$Cl$_2$ 3:97) to give methyl 5-amino-4-(4-benzo[d]ythiazol-2-ylmethoxy)-1-oxoisoindolin-2-yl)-5-oxopentanoate (0.6 g, 42%).

Step 2: Potassium t-butoxide (0.2 g, 1.4 mmol) was added to a stirred solution of methyl 5-amino-4-(4-benzo[d]triazol-2-ylmethoxy) 1-oxoisoindolin-2-yl)-5-oxopentanoate (0.6 g, 1.4 mmol) in THF (40 mL) at 5° C. The mixture was stirred at 5° C. for 10 minutes then warmed to room temperature for 2 hours. The reaction mixture was cooled in an ice bath and quenched with 4N HCl (3 mL). The mixture was diluted with CH$_2$Cl$_2$ (80 mL) and washed with water (20 mL), brine (20 mL) and dried. The solvent was removed and the residue was stirred with CH$_2$Cl$_2$ (10 mL) to give 0.4 g of solid. The solid was reslurried with hot methanol (1 5 mL) to give 3-(4-(benzo[d]thiazol-2-ylmethoxy)-1-osoisoindolin-2-yl) piperidine-2,6-dione (0.35 g, 63% yield): mp 253-255° C.; $^1$H NMR (DMSO-d$_6$) δ 1.99-2.04 (m, 1H), 2.45-2.62 (m, 2H), 2.86-2.94 (m, 1H), 4.39 (d, J=17.4 Hz, 1H), 4.47 (d, J=17.7 Hz, 1H), 5.11-5.17 (dd, J=5.1 and 13.2 Hz, 1H), 5.76 (s, 2H), 7.32-7.75 (m, 5H), 8.02-8.05 (dd, J=0.6 and 8.1 Hz, 1H), 8.11-8.14 (dd, J=0.6 and 7.8 Hz, 1H), 11.00 (s, 1H); $^{13}$C NMR (DMSO-d$_6$) δ 22.44, 31.28, 45.10, 51.73, 67.53, 115.41, 116.24, 122.48, 122.86, 125.52, 126.47, 130.07, 133.63, 134.47, 152.58, 152.72, 167.89, 171.07, 172.94; Calcd. For C$_{21}$H$_{17}$N$_3$O$_4$S: C, 61.91; H, 4.21; N, 10.31; S, 7.87. Found: C, 61.76; H, 4.01; N, 10.24; S, 7.85.

5.142 3-(4-(Benzofuran-5-ylmethoxy)-1-Oxoisoindolin-2-Y1)Piperidine-2,6-Dione

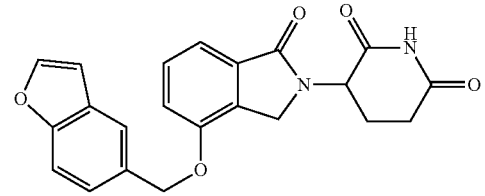

Step 1: A solution of 1-benzofuran-5-carboxylic acid (1.0 g, 6.2 mmol) and trimethyl borate (5 mL) in THF (20 mL) was stirred for 10 minutes. BH$_3$(CH$_3$)$_2$S/THF (2M, 3.7 mL, 7.4 mmol) was added dropwise. The resulting mixture was stirred at room temperature overnight. The reaction mixture was quenched with methanol (5 mL) and concentrated. The residue was dissolved in methylene chloride (75 mL) and washed with water (25 mL) and brine (25 mL) and dried. The solvent was removed to give benzofuran-5-methanol (2.6 g, 95%).

Step 2: Diisopropyl azodicarboxylate (1.4 g, 6.8 mmol) was added to a stirred suspension of methyl 5-amino-4-(4-hydroxy-1-oxoisoindolin-2-yl)-5-oxopentanoate (1.0 g, 3.4 mmol), benzofuran-5-methanol (0.8 g, 5.1 mmol) and triphenylphosphine-polymer bound (2.3 g, 6.8 mmol) in THF (80 mL) at 3-6° C. After addition, reaction mixture was stirred at room temperature overnight. The reaction mixture was filtered and solid was washed with methylene chloride (20 mL). Filtrate was concentrated and the residue was purified by chromatography (SO$_2$, CH$_3$OH:CH$_2$Cl$_2$ 3:97) to give methyl 5-amino-4-(4-(benzofuran-5-ylmethoxy)-1-oxoisoindolin-2-yl)-5-oxopentanoate (0.9 g, 63% yield): $^1$H NMR (DMSO-d$_6$) δ 1.09-1.30 (m, 1H), 2.08-2.25 (m, 3H), 3.49 (s, 3H), 4.43 (d, J=17.7 Hz, 1H), 4.50 (d, J=17.6 Hz, 1H), 4.71-4.75 (dd, J=5.0 and 10.4 Hz, 1H), 5.33 (s, 2H), 6.98-6.99 (dd, J=1.0 and 2.2 Hz, 1H), 7.18 (s, 1H), 7.27-7.35 (m, 2H), 7.43-7.48 (m, 2H), 7.58-7.79 (m, 2H), 8.01 (s, 1H), 8.02 (s, 1H).

Step 3: Potassium t-butoxide (0.3 g, 2.1 mmol) was added to a stirred solution of methyl 5-amino-4-(4-benzofuran-5-ylmethoxy)-1-oxoisoindolin-2-yl)-5-oxopentano ate (0.9 g, 2.1 mmol) in THF (40 mL) at 5° C. The reaction mixture was stirred at 5° C. for 10 minutes then warmed to room temperature for 2 hours. The reaction mixture was cooled in an ice bath and quenched with 4N HCl (3 mL). The mixture was diluted with methylene chloride (80 mL) and washed with water (20 mL) and brine (20 mL) and dried. The solvent was removed and the residue was purified by chromatography (SiO$_2$, CH$_3$OH:CH$_2$Cl$_2$ 3:97) to give 3-(4-(benzofuran-5-ylmethoxy)-1-oxoisoindolin-2-yl)piperidine-2,6-dione (0.5 g, 57%) as a white solid: mp 168-170° C.; $^1$H NMR (DMSO-d$_6$) δ 1.97-2.00 (m, 1H), 2.42-2.59 (m, 2H), 2.90-2.91 (m, 1H), 4.28 (d, J=17.4 Hz, 1H), 4.39 (d, J=17.4 Hz, 1H), 5.08-5.14 (dd, J=5.4 and 13.5 Hz, 1H), 5.33 (s, 2H), 6.97-6.98 (dd, J=0.9 and 2.1 Hz, 1H), 7.31-7.51 (m, 4H), 7.60 (d, J=8.4 Hz, 1H), 7.79 (d, J=0.9 Hz, 1H), 8.0 (d, J=2.1 Hz, 1H), 10.97 (s, 1H); $^{13}$C NMR (DMSO-d$_6$) δ 22.32, 31.16, 45.09, 51.56, 69.75, 106.70, 111.23, 115.03, 115.18, 120.79, 124.40, 127.28, 129.78, 129.95, 131.25, 133.28, 146.55, 153.49, 153.99, 168.00, 170.96, 172.81; Calcd. For C$_{22}$H$_{18}$N$_2$O$_5$+0.2 H$_2$O: C, 67.07; H, 4.71; N, 7.11. Found: C, 67.05; H, 4.57; N, 6.97.

5.143 3-(1-Oxo-4-(Quinolin-2-ylmethoxy)Isoindolin-2-yl)Piperidine-2,6-Dione

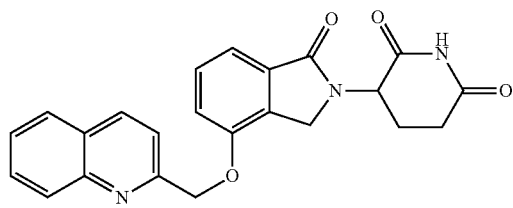 [SMILES: O=C1CCC(N2Cc3c(OCc4ccc5ccccc5n4)cccc3C2=O)C(=O)N1]

Step 1: A solution of 2-quinoline carboxaldehyde (1.0 g, 6.4 mmol) in reagent alcohol (40 mL) was cooled in dry ice/acetone bath to −60° C. LiBH$_4$/THF (2M, 3.8 mL, 7.6 mmol) was added dropwise at −60° C. The reaction mixture was stirred at −60° C. for 1 hour then quenched with water (10 mL). The mixture was concentrated and the residue was dissolved in EtOAc (60 mL). EtOAc solution was washed with brine (35 mL) and dried. The solvent was removed to give quinolin-2-ylmethanol (0.9 g, 89%).

Step 2: Diisopropyl azodicarboxylate (1.4 g, 6.8 mmol) was added to a stirred suspension of methyl 5-amino-4-(4-hydroxy-1-oxoisoindolin-2-yl)-5-oxopentanoate (1.0 g, 3.4 mmol), quinolin-2-ylmethanol (0.9 g, 5.7 mmol) and triphenylphosphine-polymer bound (2.3 g, 6.8 mmol) in THF (80 mL) at 5-8° C. After addition, the mixture was stirred at room temperature overnight. The reaction mixture was filtered and solid was washed with methylene chloride (25 mL). Filtrate was concentrated and the residue was purified by chromatography (SiO$_2$, CH$_3$OH:CH$_2$Cl$_2$ 3:97) to give methyl 5-amino-5-oxo-4-(1-oxo-4(quinolin-2-ylmethoxy)isoindolin-2-yl)pentanoate (0.7 g, 47% yield): $^1$H NMR (DMSO-d$_6$) δ 2.08-2.31 (m, 4H), 3.51 (s, 3H), 4.54 (d, J=17.4 Hz, 1H), 4.61 (d, J=17.6 Hz, 1H), 4.73-4.78 (dd, J=5.0 and 10.4 Hz, 1H), 5.52 (s, 2H), 7.21 (s, 1H), 7.29-7.32 (m, 2H), 7.45 (t, J=7.8 Hz, 1H), 7.60-7.65 (m, 2H), 7.73-7.82 (m, 2H), 7.99-8.05 (t, J=8.4 Hz, 2H), 8.42 (d, J=8.5 Hz, 1H); $^{13}$C NMR (DMSO-d$_6$) δ 24.83, 30.34, 44.82, 51.25, 53.42, 71.05, 114.79, 115.44, 119.44, 126.63, 127.21, 127.94, 128.51, 129.63, 129.90, 130.29, 133.54, 137.16, 146.90, 153.23, 157.13, 167.81, 171.74, 172.48.

Step 3: Potassium t-butoxide (0.2 g, 1.6 mmol) was added to a stirred solution of methyl 5-amino-5-oxo-4-(1-oxo-4-(quinolin-2-ylmethoxy)isoindolin-2-yl)pentanoate (0.7 g, 1.6 mmol) in THF (50 mL) at 5° C. The reaction mixture was stirred at 5° C. for 10 minutes then warmed to room temperature for 2 hours. The reaction mixture was cooled in an ice bath and quenched with 4N HCl (3 mL). The mixture was diluted with methylene chloride (80 mL) and washed with saturated NaHCO$_3$ (25 mL). The organic layer was washed with water (40 mL) and brine (40 mL) and dried. The solvent was removed and solid residue was slurried with CH$_2$Cl$_2$ (20 mL) to give 3-(1-oxo-4-(quinolin-2-ylmethoxy)isoindolin-2-yl)piperidine-2,6-dione (0.2 g, 26%) as a white solid: mp 269-271° C.; $^1$H NMR (DMSO-d$_6$) δ 1.99-2.04 (m, 1H), 2.44-2.63 (m, 2H), 2.88-2.93 (m, 1H), 4.39 (d, J=17.5 Hz, 1H), 4.50 (d, J=17.5 Hz, 1H), 5.11-5.17 (dd, J=5.1 and 13.3 Hz, 1H), 5.25 (s, 2H), 7.32-7.36 (dd, J=2.6 and 6.9 Hz, 2H), 7.48 (t, J=7.8 Hz, 1H), 7.60-7.65 (dt, J=1.2 and 6.9 Hz, 1H), 7.72-7.82 (m, 2H), 7.99-8.04 (t, J=8.0 Hz, 2H), 8.41-8.44 (d, J=8.5 Hz, 1H), 10.99 (s, H); $^{13}$C NMR (DMSO-d$_6$) δ 22.37, 31.17, 45.12, 51.60, 71.05, 115.05, 115.52, 119.44, 126.64, 127.20, 127.93, 128.51, 129.87, 129.91, 130.03, 133.40, 137.11, 146.89, 153.29, 157.09, 167.94, 170.97, 172.83; Calcd. For C$_{23}$H$_{19}$N$_3$O$_4$: C, 68.82; H, 4.77; N, 10.47. Found: C, 68.66; H, 4.49; N, 10.24.

5.144 3-(1-Oxo-4-(Quinolin-3-ylmethoxy)Isoindolin-2-yl)Piperidine-2,6-Dione

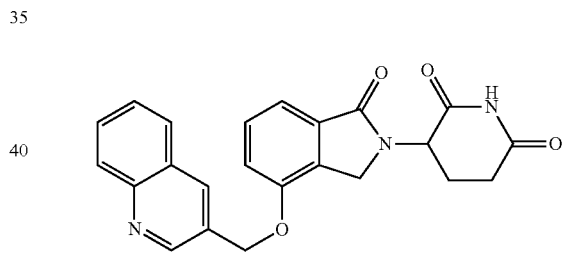

Step 1: A solution of 3-quinolinecarboxaldehyde (1.2 g, 7.6 mmol) in reagent alcohol (60 mL) was cooled in dry ice/acetone bath to −40° C. LiBH$_4$/THF (2 M, 4.6 mL, 9.2 mmol) was added dropwise at −40 to −60° C. The reaction mixture was stirred at −60° C. for 1 hour then quenched with water (10 mL). The mixture was concentrated and the residue was dissolved in EtOAc (90 mL). EtOAc solution was washed with saturated NaHCO$_3$ (30 mL) and brine (30 mL) and dried. The solvent was removed to give quinolin-3-ylmethanol (1.2 g, 100%).

Step 2: Diisopropyl azodicarboxylate (1.6 g, 7.7 mmol) was added to a stirred suspension of methyl 5-amino-4-(4-hydroxy-1-oxoisoindolin-2-yl)-5-oxopenatnoate (1.1 g, 3.8 mmol), quinolin-3-ylmethanol (1.2 g, 7.9 mmol) and triphenylphosphine-polymer bound (2.6 g, 7.7 mmol) in THF (80 mL) at 5-8° C. After addition, the mixture was stirred at room temperature overnight. The reaction mixture was filtered and solid was washed with methylene chloride (25 mL). Filtrate was concentrated and the residue was purified by chromatography (SiO$_2$, CH$_3$OH:CH$_2$Cl$_2$ 3:97) to give methyl 5-amino-5-oxo-4-(1-oxo-4-(quinolin-3-ylmethoxy) isoindolin-2-yl)pentanoate (1.0 g, 24%).

Step 3: Potassium t-butoxide (0.3 g, 2.4 mmol) was added to a stirred solution of methyl 5-amino-5-oxo-4-(1-oxo-4-(quinolin-3-ylmethoxy)isoindolin-2-yl)pentanoate (1.0 g, 2.4 mmol) in THF (50 mL) at 5° C. The reaction mixture was stirred at 5° C. for 10 minutes then warmed to room temperature for 2 hours. The reaction mixture was cooled in an ice bath and quenched with 4N HCl (4 mL). The mixture was diluted with methylene chloride (80 mL) and washed with saturated NaHCO$_3$ (30 mL) and water (40 mL) and dried. The solvent was removed and solid was slurried with hot methanol (10 mL) to give 3-(1-oxo-4-(quinolin-3-ylmethoxy)isoindolin-2-yl)piperidine-2,6-dione (0.1 g, 47%) as a white solid: mp 270-273° C.; $^1$H NMR (DMSO-d6) δ 1.99-2.01 (m, 1H), 2.43-2.60 (m, 2H), 2.91 (m, 1H), 4.33 (d, J=17.4 Hz, 1H), 4.40 (d, J=17.7 Hz, 1H), 5.09-5.15 (dd, J=5.1 and 13.2 Hz, 1H), 5.49 (s, 2H), 7.37 (d, J=7.2 Hz, 1H), 7.44 (d, J=7.7 Hz, 1H), 7.52 (t, J=7.8 Hz, 1H), 7.64 (dt, J=1.0 and 8.0 Hz, 1H), 7.79 (dt, J=1.5 and 6.9 Hz, 1H), 8.03 (t, J=8.5 Hz, 2H), 8.48 (d, J=1.3 Hz, 1H), 9.04 (d, J=2.1 Hz, 1H), 10.98 (s, 1H); $^{13}$C NMR (DMSO-d$_6$) δ 22.33, 31.16, 45.08, 51.57, 67.52, 115.07, 115.51, 126.94, 127.24, 128.09, 128.72, 129.68, 129.72, 129.87, 130.06, 133.38, 134.68, 147.22, 150.52, 153.28, 167.95, 170.94, 172.81; Calcd for C$_{23}$H$_{19}$N$_3$O$_4$+0.2 H$_2$O: C, 68.21; H, 4.83; N, 10.37. Found: C, 68.29; H, 4.87; N, 10.15.

5.145 3-[4-(Chroman-3-ylmethoxy)-1-Oxo-1,3-Dihydro-Isoindol-2-yl]-Piperidine-2,6-Dione

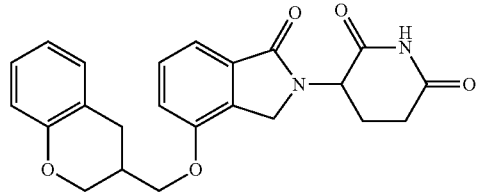 [SMILES: O=C1CCC(N2Cc3c(OCC4COc5ccccc5C4)cccc3C2=O)C(=O)N1]

Step 1: Polymer bonded triphenylphosphine (1.6 g, 2.04 mmol, 1.25 mmol/g) was added to the stirred solution of 4-carbamoyl-4-(4-hydroxy-1-oxo-1,3-dihydro-isoindol-2-yl)-butyric acid methyl ester (300 mg, 1.02 mmol) in THF (10 mL) at 0° C. The resulting mixture was stirred at 0° C. for 10 minutes, followed by the addition of DIAD (412 mg, 2.04 mmol). Ten minutes later, chroman-3-yl-methanol (336 mg, 2.04 mmol) was added to the mixture. The reaction was stirred at room temperature for 16 hours and the reaction was complete. The reaction mixture was filtered and the solid was washed with dichloromethane (5×20 mL). The filtrate was concentrated and the residue was purified by ISCO chromatography to give 4-carbamoyl-4-[4-(chroman-3-ylmethoxy)-1-oxo-1,3-dihydro-isoindol-2-yl]-butyric acid methyl ester as a yellow glass like solid (400 mg, 90% yield): LCMS MH=439.

Step 2: KOtBu (102.4 mg, 0.91 mmol) was added to the stirred solution of 4-carbamoyl-4-[4-(chroman-3-ylmethoxy)-1-oxo-1,3-dihydro-isoindol-2-yl]-butyric acid methyl ester (400 mg, 0.91 mmol) in tetrahydrofuran (20 mL) at 0° C. The mixture was stirred at room temperature for 5 hours, followed by the addition of HCl (aq. 1N, 1.3 mL) and then water (10 mL). The mixture was extracted with dichloromethane (2×25 mL). Organic layers were dried by MgSO$_4$ and concentrated under vacuo. The residue was purified by ISCO chromatography and prep HPLC to give 3-[4-(Chroman-3-ylmethoxy)-1-oxo-1,3-dihydro-isoindol-2-yl]-piperidine-2,6-dione as a white solid (30 mg, 7.9% yield). HPLC: Waters Symmetry C-18, 3.9×150 mm, 5 µm, 1 mL/min, 240 nm, 40/60 (acetonitrile/0.1% H$_3$PO$_4$): t$_R$=7.07 (100%); mp: 258-260° C.; $^1$H NMR (DMSO-d$_6$) δ 1.92-2.08 (m, 1H, CHH), 2.34-2.45 (m, 1H, CHH), 2.54-2.65 (m, 2H, CH$_2$), 2.66-2.81 (m, 1H, CHH), 2.82-3.02 (m, 2H, CH$_2$), 3.97-4.48 (m, 6H, CH$_2$, CH$_2$, CH$_2$), 5.04-5.19 (m, 1H, CHN), 6.70-6.89 (m, 2H, Ar), 7.01-7.15 (m, 2H, Ar), 7.29 (dd, J=7.7, 18.1 Hz, 2H, Ar), 7.42-7.52 (m, 1H, Ar), 10.99 (s, 1H, NH). *one proton is overlapped with DMSO, which was proved by HMQC; $^{13}$C NMR (DMSO-d$_6$) δ 22.37, 26.66, 31.15, 31.72, 31.75, 44.89, 51.52, 66.88, 68.18, 114.48, 115.18, 116.14, 120.26, 121.02, 127.07, 129.86, 129.99, 133.20, 153.52, 154.11, 167.99, 170.97, 172.83; LCMS MH=407.

5.146 3-[4-(4-Benzotriazol-1-ylmethyl-Benzyloxy)-1-Oxo-1,3-Dihydro-Isoindol-2-yl]-Piperidine-2,6-Dione

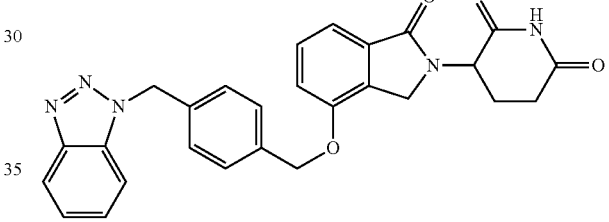

Step 1: To a solution of methyl 5-amino-4-(4-(4-(bromomethyl)benzyloxy)-1-oxoisoindolin-2-yl)-5-oxopentanoate (0.683 g, 1.43 mmol) in acetonitrile (10 ml) was added 1H-benzo[d][1,2,3]triazole (0.205 g, 1.72 mmol) and N-ethyl-N-isopropylpropan-2-amine (0.285 ml, 1.724 mmol). The mixture was stirred overnight and then concentrated to give crude methyl 4-(4-(4-(4-((1H-benzo[d][1,2,3]triazol-1-yl)methyl)benzyloxy)-1-oxoisoindolin-2-yl)-5-amino-5-oxopentanoate as a white foamy solid (1.30 g). It was used in the next step without further purification.

Step 2: To a stirred white suspension of methyl 4-(4-(4-((1H-benzo [d][1,2,3]triazol-1-yl)methyl)benzyloxy)-1-oxoisoindolin-2-yl)-5-amino-5-oxopentanoate (0.73 g, 1.43 mmol) in THF (12 ml) in an ice bath was added potassium 2-methylpropan-2-olate (0.46 g, 4.11 mmol). The mixture was stirred for 15 minutes and was quenched with 1 N HCl (~3 ml) and then neutralized by saturated sodium bicarbonate (6 ml to pH=7). The mixture was stirred with ethyl acetate (20 ml), and then filtered to give a white solid. It was purified on silica gel column (MeOH/CH$_2$Cl$_2$ gradient from 1% to 5% in 30 min) to give 3-[4-(4-benzotriazol-1-ylmethyl-benzyloxy)-1-oxo-1,3-dihydro-isoindol-2-yl]-piperidine-2,6-dione as a white powder (340 mg, 49% yield); mp, 228-230° C.; HPLC: Waters Symmetry C-18, 3.9×150 mm, 5 µm, 1 mL/min, 240 nm, gradient from 10/90 to 95/5 in 5 min, isocratic at 95/5 in 5 min (CH$_3$CN/0.1% H$_3$PO$_4$), 6.44 min (98.2%); $^1$H NMR (DMSO-d$_6$) δ 1.89-2.03 (m, 1H, CH), 2.33-2.47 (m, 1H, CH), 2.52-2.62 (m, 1H, CH), 2.81-2.98 (m, 1H, CH), 4.14-4.45 (m, 2H, CH$_2$), 5.09 (dd, J=5.1, 13.2 Hz, 1H, NCH), 5.20 (s, 2H, CH$_2$), 6.00 (s, 2H, CH$_2$), 7.26-7.58 (m, 11H, ArH), 7.86 (d, J=8.5 Hz, 1H, ArH), 8.06 (d, J=8.3 Hz, 1H, ArH), 10.95 (s, 1H, NH); $^{13}$C NMR (DMSO-d$_6$) δ 22.33, 31.20, 45.06, 50.64, 51.55, 69.12, 110.65, 114.89, 115.27, 119.22, 124.04, 127.45, 127.88, 128.15, 129.79, 129.94, 132.64, 133.31, 135.65, 136.53, 145.31, 153.37, 167.98, 170.94, 172.82. LC/MS MH=482; Anal Calcd for C$_{27}$H$_{23}$N$_5$O$_4$+0.7 H$_2$O: C, 65.63; H, 4.98; N, 14.17. Found: C, 65.39; H, 4.79; N, 13.96.

5.147 3-(4-(2-Chlorobenzyloxy)-1-Oxoisoindolin-2-yl)Piperidine-2,6-Dione

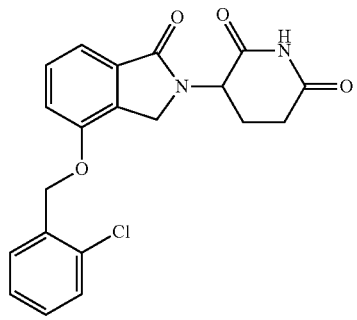 [SMILES: O=C1CCC(N2Cc3c(OCc4ccccc4Cl)cccc3C2=O)C(=O)N1]

To a slurry of methyl 5-amino-4-(4-hydroxy-1-oxoisoindolin-2-yl)-5-oxopentanoate (200 mg, 0.684 mmol,) and Cs$_2$CO$_3$ (233 mg, 0.677 mmol) in dry DMF (5 mL), was added 1-chloro-2-chloromethyl-benzene (820 μl, 10% solution in DMF, 0.650 mmol). The reaction mixture was stirred at room temperature and progress was monitored by LCMS. After 2 hours, N,N-diisopropylethylamine (120 μL, 0.684 mmol) was added, and the mixture was stirred at room temperature overnight. After 14 hours, the mixture was warmed up in oil bath to 80° C. and stirred for 8 hours. The crude reaction mixture was cooled on an ice bath and then transferred in small portions to a cooled 0.5 N aqueous HCl solution (40 mL). A white solid formed was collected by filtration, washed with additional water on filter funnel, and dried in vacuum oven to give 220 mg of crude product. The solid was dissolved in minimal DMF and purified by injection onto a C-18 preparatory HPLC column. The product was eluted with an acetonitrile/water gradient (0.1% formic acid in both mobile phases, 30% to 75% acetonitrile over 20 min) and fractions were collected by mass trigger. The desired fractions were combined and concentrated in vacuo to give 3-(4-(2-chlorobenzyloxy)-1-oxoisoindolin-2-yl)piperidine-2,6-dione as a white solid (175 mg, 70% yield): HPLC: Waters Symmetry C18, 5 μm, 3.9×150 mm, 1 ml/min, 240 nm, 50/50 acetonitrile/0.1% H3PO4, 4.08 min (98.7%); mp: 213-215° C.; 1H NMR (DMSO-d6) δ 1.87-2.05 (m, 1H, CHH), 2.32-2.48 (m, 1H, CHH), 2.53-2.65 (m, 1H, CHH), 2.82-3.00 (m, 1H, CHH), 4.26 (d, J=17.6 Hz, 1H, CHH), 4.46 (d, J=17.6 Hz, 1H, CHH), 5.11 (dd, J=5.0, 13.1 Hz, 1H, CH), 5.31 (s, 2H, CH2), 7.27-7.46 (m, 4H, Ar), 7.48-7.59 (m, 2H, Ar), 7.62-7.72 (m, 1H, Ar), 10.96 (s, 1H, NH); 13C NMR (DMSO-d6) δ 22.30, 31.16, 45.03, 51.55, 67.25, 114.93, 115.51, 127.38, 129.42, 129.90, 129.95, 130.03, 130.22, 132.72, 133.37, 133.85, 153.26, 167.91, 170.96, 172.80; LCMS MH=385, 387; Anal. Calcd. For C$_{20}$H$_{17}$ClN$_2$O$_4$+0.35 H$_2$O: C, 61.42; H, 4.56; N, 7.16; Cl, 9.06. Found: C, 61.26; H, 4.32; N, 7.19; Cl, 9.18.

5.148 3-(1-Oxo-4-(2,4,6-Trichlorobenzyloxy)Isoindolin-2-yl)Piperidine-2,6-Dione

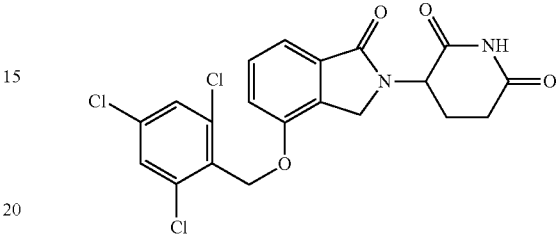

Step 1: A solution of methyl 5-amino-4-(4-hydroxy-1-oxoisoindolin-2-yl)-5-oxopentanoate (0.50 g, 1.7 mmol) and 2,4,6-trichlorobenzyl alcohol (0.72 g, 3.4 mmol) in THF (30 mL) was cooled to 0° C. Polymer bound triphenyl phosphine (3 mmol/g loading, 1.2 g, 3.7 mmol) was added, followed by DIAD (0.76 gm 3.7 mmol). After one hour, the cooling bath was removed, and the mixture stirred under nitrogen for 20 hours. The mixture was filtered, and the filter was rinsed with ethyl acetate (50 mL). The filtrate was diluted with additional ethyl acetate (50 mL) and washed with brine (3×100 mL) and evaporated. The residue was chromatographed in a methylene chloride-methanol gradient, eluting the product at 5% methanol. Crude methyl 5-amino-5-oxo-4-(1-oxo-4-(2,4,6-trichlorobenzyloxy)isoindolin-2-yl)pentanoate (1.15 g (>100%)) was obtained as a glue.

Step 2: The crude material obtained in Step 1 was dissolved in THF (25 mL) and cooled to 0° C. Then, potassium tert-butoxide (0.19 g, 1.7 mmol) was added, and the mixture was stirred under nitrogen for 3 hours. The mixture was quenched by the addition of 5 drops acetic acid. The resulting mixture was diluted with ethyl acetate (75 mL) and washed with saturated aqueous sodium bicarbonate solution (75 mL) and evaporated under vacuum. The residue was chromatographed in a methylene chloride-methanol gradient, eluting the product at 5% methanol. After evaporation of the appropriate fractions, the residue was slurried in ether (15 mL) for 1 hour, filtered, and dried under vacuum, providing the product as a white solid, 0.53 g, in 68% yield over two steps; HPLC: Waters Symmetry C-18, 3.9×150 mm, 5 μm, 1 mL/min, 240 nm, 50/50 (acetonitrile/0.1% H$_3$PO$_4$): t$_R$=6.94 (97.86%); mp 138-140° C.; $^1$H NMR (DMSO-d$_6$) δ 1.88-2.02 (m, 1H, CHH), 2.33-2.47 (m, 1H, CHH), 2.53-2.62 (m, 1H, CHH), 2.79-2.98 (m, 1H, CHH), 4.16 (d, J=17.6 Hz, 1H, CHH), 4.32 (d, J=17.6 Hz, 1H, CHH), 5.09 (dd, J=5.0, 13.1 Hz, 1H, CH), 5.33 (d, J=10.6 Hz, 1H, CHH), 5.39 (d, J=10.8 Hz, 1H, CHH), 7.39 (d, J=7.2 Hz, 1H, Ar), 7.45-7.61 (m, 2H, Ar), 7.81 (s, 2H, Ar), 10.94 (s, 1H, NH); $^{13}$C NMR (DMSO-d$_6$) δ 22.26, 31.18, 44.99, 51.58, 65.00, 115.07, 115.89, 128.58, 129.90, 130.03, 130.62, 133.44, 135.09, 136.85, 153.40, 167.83, 170.95, 172.79; LCMS MH=453/455/457; Anal. Calcd for C$_{20}$H$_{15}$Cl$_3$N$_2$O$_4$·0.4 Et$_2$O: C, 53.67; H, 3.96; N, 5.80; Found: C, 53.65; H, 3.89; N, 5.71.

5.149 3-[4-(2,5-Dichloro-Benzyloxy)-1-Oxo-1,3-Dihydro-Isoindol-2-yl]-Piperidine-2,6-Dione

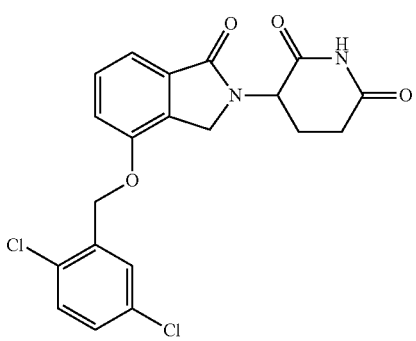 [SMILES: O=C1CCC(N2Cc3c(OCc4cc(Cl)ccc4Cl)cccc3C2=O)C(=O)N1]

Step 1: To the solution of 3-(4-hydroxy-1-oxo-1,3-dihydro-isoindol-2-yl)-piperidine-2,6-dione (0.5 g, 1.7 mmol) in THF (30 mL), was added triphenyl phosphine (polymer supported 2.2 mmol/g, 1.64 g, 3.74 mmol). The mixture was stirred at room temperature for 15 minutes. Diisopropyl azodicarboxylate (0.76 mL, 3.74 mmol) was added at 0° C. and the mixture was stirred at 0° C. for 30 minutes. 2,5-Dichloro phenylmethanol (0.45 g, 2.57 mmol) was added at 0° C., and the mixture was allowed to warm to room temperature and stirred at room temperature overnight. The reaction mixture was filtered and the filtrate was concentrated. The resulting oil was purified on silica gel column eluted with methylene chloride and methanol (gradient, product came out at 6% methanol) to give 4-carbamoyl-4-[4-(2,5-dichloro-benzyloxy)-1-oxo-1,3-dihydro-isoindol-2-yl]-butyric acid methyl ester (0.7 g, 92%).

Step 2: To the THF solution (30 mL) of 4-carbamoyl-4-[4-(2,5-dichloro-benzyloxy)-1-oxo-1,3-dihydro-isoindol-2-yl]-butyric acid methyl ester (0.7 g, 1.5 mmol) was added potassium tert-butoxide (0.17 g, 1.7 mmol) at 0° C. The mixture was stirred at 0° C. for 10 minutes and was quenched with 1N HCl (5 mL, 5 mmol), followed by saturated NaHCO$_3$ (25 mL). The mixture was extracted with EtOAc (50 mL×2). The organic layer was washed with water (30 mL) and brine (30 mL), dried over MgSO$_4$, and concentrated. To the resulting solid was added EtOAc (10 mL) followed by hexane (10 mL) under stirring. The suspension was filtered to give 3-[4-(2,5-Dichloro-benzyloxy)-1-oxo-1,3-dihydro-isoindol-2-yl]-piperidine-2,6-dione as white solid (0.26 g, 37%). mp: 256-258° C.; HPLC: Waters Symmetry C$_{18}$, 5 µm, 3.9×150 mm, 1 mL/min, 240 nm, gradient to 95/5 acetonitrile/0.1% H$_3$PO$_4$ in 5 min: $t_R$=6.87 min (96.5%); $^1$H NMR (DMSO-d$_6$) δ 1.67-2.16 (m, 1H, CHH), 2.36-2.46 (m, J=4.2 Hz, 1H, CHH), 2.53-2.65 (m, J=19.5 Hz, 1H, CHH), 2.76-3.09 (m, 1H, CHH), 4.13-4.60 (m, 2H, CH$_2$), 5.11 (dd, J=5.0, 13.1 Hz, 1H, NCH), 5.29 (s, 2H, CH$_2$), 7.34-7.43 (m, 2H, Ar), 7.46-7.63 (m, 3H, Ar), 7.73 (d, J=2.5 Hz, 1H, Ar), 10.97 (s, 1H, NH). $^{13}$C NMR (DMSO-d$_6$) δ 22.27, 31.14, 45.02, 51.56, 66.75, 114.95, 115.68, 129.66, 129.78, 129.88, 129.94, 131.11, 131.37, 131.91, 133.41, 136.01, 153.05, 167.83, 170.91, 172.76; LCMS: 465; Anal Calcd for C$_{26}$H$_{16}$Cl$_2$N$_2$O$_4$+0.2 H$_2$O: C, 56.81; H, 3.91; N, 6.62; Found: C, 56.75; H, 4.19; N, 6.70.

5.150 3-[4-(3-Methyl-Benzyloxy)-1-Oxo-1,3-Dihydro-Isoindol-2-yl]-Piperidine-2,6-Dione

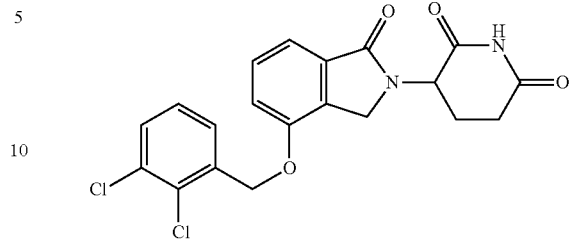

Step 1: Polymer-supported triphenylphosphene (1.6 mmol/g, 2.40 g, 3.80 mmol) was added to a stirred solution of methyl 5-amino-4-(4-hydroxy-1-oxoisoindolin-2-yl)-5-oxopentanoate (0.50 g, 1.71 mmol) in THF (10 mL) at 0° C., followed by addition of diisopropyl diazene-1,2-dicarboxylate (0.75 ml, 3.80 mmol). After stirring for 30 minutes, (2,3-dichloro-phenyl)-methanol (0.45 g, 2.60 mmol) was added. The mixture was stirred for one hour then filtered, washed with methanol (3×10 mL), methylene chloride (3×10 mL). The combined filtrate was evaporated in vacuo to give an oil, which was purified on silica gel column (EtOAc/Hexanes gradient from 20% to 100% in 90 min) to give 4-carbamoyl-4-[4-(2,3-dichloro-benzyloxy)-1-oxo-1,3-dihydro-isoindol-2-yl]-butyric acid methyl ester as a white solid (0.35 g, 45% yield).

Step 2: Potassium tert-butoxide (0.17 g, 1.50 mmol) was added to a stirred suspension of 4-carbamoyl-4-[4-(2,3-dichloro-benzyloxy)-1-oxo-1,3-dihydro-isoindol-2-yl]-butyric acid methyl ester (0.34 g, 0.75 mmol) in THF (20 mL) at 0° C. The mixture was stirred for ten minutes and quenched with 1N HCl (3 mL), neutralized by saturated sodium bicarbonate (4 mL to pH=7), and quickly extracted by ethyl acetate (2×30 mL). The combined ethyl acetate phases were evaporated and purified on silica gel column (MeOH/CH$_2$Cl$_2$, gradient from 1% to 9% in 60 min) to give 3-[4-(2,3-dichloro-benzyloxy)-1-oxo-1,3-dihydro-isoindol-2-yl]-piperidine-2,6-dione as a white solid (0.03 g, 9% yield); HPLC: Waters Symmetry C-18, 3.9×150 mm, 5 µm, 1 mL/min, 240 nm, isocratic at 50/50 in 10 min (CH$_3$CN/0.1% H$_3$PO$_4$), 5.84 min (96.1%); mp: 272-274° C.; $^1$H NMR (DMSO-d$_6$) δ 1.90-2.05 (m, 1H, CHH), 2.37-2.47 (m, H, CHH), 2.53-2.65 (m, 1H, CHH), 2.83-3.01 (m, 1H, CHH), 4.22-4.50 (m, 2H, CH$_2$), 5.12 (dd, J=5.2, 13.1 Hz, 1H, NCH), 5.35 (s, 2H, CH$_2$), 7.32-7.73 (m, 6H, Ar), 10.97 (s, 1H, NH); $^{13}$C NMR (DMSO-d$_6$) δ 22.35, 31.20, 45.05, 51.59, 67.56, 114.97, 115.68, 128.41, 128.51, 129.95, 130.30, 130.60, 131.98, 133.44, 136.57, 153.09, 167.90, 170.96, 172.83; LCMS MH=419, 421; Anal Calcd for C$_{20}$H$_{16}$N$_2$O$_4$Cl$_2$: C, 57.30; H, 3.85; N, 6.68; Cl, 16.91; Found: C, 57.31; H, 3.86; N, 6.46; Cl, 17.02.

5.151 3-(4-(3,4-Dimethoxybenzyloxy)-1-Oxoisoindolin-2-yl)Piperidine-2,6-Dione

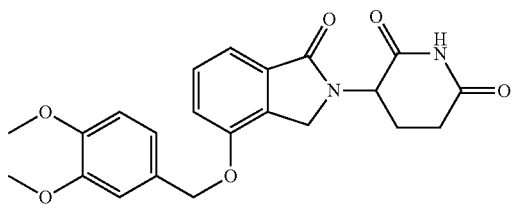 [SMILES: COc1ccc(COc2cccc3c2CN(C2CCC(=O)NC2=O)C3=O)cc1OC]

Step 1: Diisopropyl azodicarboxylate (1.3 g, 6.1 mmol) was added to a stirred suspension of methyl 5-amino-4-(4-hydroxy-1-oxoisoindolin-2-yl)-5-oxopentanoate (0.9 g, 3.1 mmol), 3,4-dimethoxybenzyl alcohol (0.8 g, 4.6 mmol) and triphenylphosphine-polymer bound (2.1 g, 6.2 mmol) in THF (80 mL) at 5-8° C. After addition, the mixture was stirred at room temperature overnight. The reaction mixture was filtered and solid was washed with methylene chloride (30 mL). The filtrate was concentrated and the residue was purified by chromatography (SiO$_2$, CH$_3$OH:CH$_2$Cl$_2$ 3:97) to give methyl 5-amino-4-(4-(3,4-dimethoxybenzyloxy)-1-oxoisoindolin-2-yl)-5-oxopentanoate (0.5 g, 3.8%).

Step 2: A solution of potassium t-butoxide in THF (I M, 1.2 mL, 1.2 mmol), was added to a stirred solution of methyl 5-amino-4-(4-(3,4-dimethoxybenzyloxy)-1-oxoisoindolin-2-yl)-5-oxopentanoate (0.5 g, 1.2 mmol) in THF (30 mL) at 5° C. The mixture was stirred at 5° C. for 10 minutes then warmed to room temperature for 2 hours. The reaction mixture was cooled in an ice bath and quenched with 4N HCl (4 mL). The mixture was diluted with methylene chloride (70 mL) and water (20 mL). The organic layer was washed with brine (40 mL) and dried. The solvent was removed and the residue was purified by chromatography (SiO$_2$, CH$_3$OH:CH$_2$Cl$_2$ 3:97) to give 3-(4-(3,4-dimethoxybenzyloxy)-1-oxoisoindolin-2-yl)piperidine-2,6-dione (0.2 g, 32%) as a white solid: mp 205-207° C.; $^1$H NMR (DMSO-d$_6$) δ 6 1.96-2.00 (m, 1H), 2.41-2.60 (m, 2H), 2.91 (m, 1H), 3.76 (s, 6H), 4.26 (d, J=17.7 Hz, 1H), 4.37 (d, J=17.4 Hz, 1H), 5.07-5.13 (m, 3H), 6.94-7.09 (m, 3H), 7.31-7.35 (m, 2H), 7.48 (t, J=7.8 Hz, 1H), 10.96 (s, 1H); $^{13}$C NMR (DMSO-d$_6$) δ 22.30, 31.17; 45.11, 51.56, 55.47, 69.67, 111.59, 111.90, 115.07, 115.12, 120.51, 128.80, 129.75, 129.96, 133.24, 148.65, 153.51, 168.00, 170.96, 172.82; Calcd. For C$_{22}$H$_{22}$N$_2$O$_6$: C, 64.38; H, 5.40; N, 6.83. Found: C, 64.36; H, 5.25; N, 6.85.

5.152 3-[4-(3-Chloro-Benzyloxy)-1-Oxo-1,3-Dihydro-Isoindol-2-yl]-Piperidine-2,6-Dione

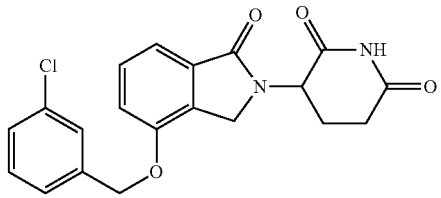

Step 1: To the THF solution of 4-carbamoyl-4-(4-hydroxy-1-oxo-1,3-dihydro-isoindol-2-yl)-butyric acid methyl ester (1.0 g, 3.42 mmol), was added triphenyl phosphine resin (2.3 g, 2.2 mmol/g loading, 6.84 mmol) and DIAD (1.33 mL, 6.84 mmol) at 0° C. After being stirred at 0° C. for 10 minutes, the mixture was added (3-chloro-4-ylmethyl-phenyl)-methanol (0.61 mL, 5.13 mmol) and stirred at room temperature overnight. The mixture was filtered and the filtrate was concentrated and extracted with EtOAc (30 mL) and Na$_2$CO$_3$ (20 mL). The organic layer was washed with water (20 mL) and brine (20 mL), and concentrated. The resulting oil was purified on silica gel column to give 4-carbamoyl-4-[4-(3-chloro-benzyloxy)-1-oxo-1,3-dihydro-isoindol-2-yl]-butyric acid methyl ester as an oil (0.24 g, 20%).

Step 2: To the THF solution (20 mL) of 4-carbamoyl-4-[4-(3-chloro-benzyloxy)-1-oxo-1,3-dihydro-isoindol-2-yl]-butyric acid methyl ester (0.24 g, 0.57 mmol), was added potassium t-butoxide (0.57 mL g, 0.57 mmol) at 0° C. The mixture was stirred for 15 minutes at 0° C. and quenched with 5 mL of 1N HCl solution followed by 15 mL of saturated NaHCO$_3$ solution. The mixture was extracted with EtOAc (20 mL). The organic layer was concentrated in vacuo. The resulting oil was purified on silica gel column eluted with CH$_2$Cl$_2$ and methanol to give 3-[4-(4-Chlorobenzyloxy)-1-oxo-1,3-dihydro-isoindol-2-yl]-piperidine-2,6-dione as a white solid (60 mg, 27%). mp: 224-226° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=4.9 min (97%). $^1$H NMR (DMSO-d$_6$) δ 1.88-2.05 (m, J=1.9 Hz, 1H, CHH), 2.34-2.46 (m, 1H, CHH), 2.57-2.65 (m, J=3.6 Hz, 1H, CHH), 2.79-3.02 (m, 1H, CHH), 4.16-4.61 (m, 2H, CH$_2$), 5.11 (dd, J=5.2, 13.1 Hz, 1H, NCH), 5.27 (s, 2H, CH$_2$), 7.19-7.38 (m, 2H, Ar), 7.38-7.54 (m, 4H, Ar), 7.56 (s, 1H, Ar), 10.97 (s, 1H, NH). $^{13}$C NMR (DMSO-d$_6$) δ 22.36, 31.21, 45.09, 51.61, 68.59, 114.95, 115.43, 126.19, 127.33, 127.91, 129.84, 129.98, 130.42, 133.13, 133.39, 139.20, 153.24, 167.95, 170.99, 172.87; LCMS MH=385. Anal Calcd for C$_{20}$H$_{17}$N$_2$O$_4$Cl, C, 62.42; H, 4.45; N, 7.28; Found: C, 61.51%; H, 4.04; N, 7.12.

5.153 3-(4-(3-(2-(Dimethylamino)Ethoxy)-4-Methoxybenzyloxy)-1-Oxoisoindolin-2-yl)Piperidine-2,6-Dione

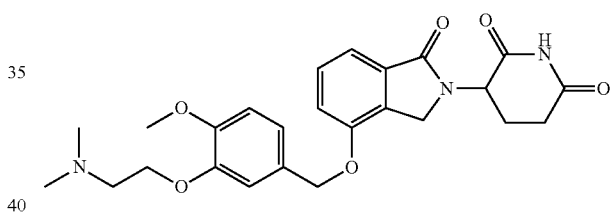

Step 1: A mixture of 3-hydroxy-4-methoxybenzaldehyde (4.2 g, 27.3 mmol) and Cs$_2$CO$_3$ (22.2 g, 68.2 mmol) in DMF (80 mL) was stirred for 10 minutes. To this mixture was added dimethylaminoethyl chloride hydrochloride (4.7 g, 32.7 mmol). The reaction mixture was stirred at 50° C. oil bath for 18 hours. The reaction mixture was cooled and filtered. Filtrate was diluted with water (200 mL) and extracted with EtOAc (4×50 mL). Combined EtOAc solution was washed with water (3×50 mL) and brine (50 mL), and dried. The solvent was removed to give 3-(2-(dimethylamino)ethoxy)-4-methoxybenzaldehyde (3.8 g, 62%).

Step 2: A solution of 3-(2-(dimethylamino)ethoxy)-4-methoxybenzaldehyde (3.8 g, 16.8 mmol) in THF (20 mL) was added to a stirred solution of LiBH$_4$/THF (2.0M, 10.1 mL) in THF (20 mL) at 6-10° C. After addition, the mixture was stirred at room temperature for 1 hour. The reaction mixture was cooled in an ice bath and quenched with water (15 mL). The mixture was extracted with EtOAc (3×50 mL) and combined EtOAc solution was washed with water (40 mL) and brine (40 mL), and dried. The solvent was removed and the residue was purified by chromatography (SiO$_2$, EtOAc: CH$_2$C$_2$3:7) to give 3-(2-(dimethylamino)ethoxy-4-methoxyphenyl)methanol (3.6 g, 94% yield): $^1$H NMR (DMSO-d$_6$) δ 2.62 (s, 6H). 3.13 (t, J=5.4 Hz, 2H), 3.73 (s, 3H), 4.31 (t, J=5.4 Hz, 2H), 4.42 (d, J=5.7 Hz, 2H), 5.08 (t, J=5.7 Hz, 1H), 6.84-6.97 (m, 3H); $^{13}$C NMR (DMSO-d$_6$) δ 51.74, 55.70, 61.89, 62.63, 64.07, 111.91, 112.38, 119.38, 135.12, 147.15, 147.97.

Step 3: Diisopropyl azodicarboxylate (0.9 g, 4.4 mmol) was added to a stirred suspension of methyl 5-amino-4-(4-hydroxy-1-oxoisoindolin-2-yl)-5-oxopentanoate (0.7 g, 2.2 mmol), 3-(2-(dimethylamino)ethoxy-4-methoxyphenyl)methanol (0.8 g, 3.3 mmol) and triphenylphosphine-polymer bound (1.5 g, 4.4 mmol) in THF (80 mL) at 5-8° C. After addition, the mixture was stirred at room temperature overnight. The reaction mixture was filtered and solid was washed with methylene chloride (30 mL). Filtrate was concentrated, and the residue was purified by chromatography (SiO$_2$, CH$_3$OH:CH$_2$Cl$_2$ 3:97) to give methyl 5-amino-4-(4-(3-(2-(dimethylamino)ethoxy)-4-methoxybenzyloxy)-1-oxoisoindolin-2-yl)-5-oxopentanoate (0.6 g, 54%).

Step 4: Potassium t-butoxide/THF (1 M, 1.3 mL, 1.3 mmol) was added to a stirred solution of methyl 5-amino-4-(4-(3-(2-(dimethylamino)ethoxy)-4-methoxybenzyloxy)-1-oxoisoindolin-2-yl)-5-oxopentanoate (0.6 g, 1.3 mmol) in THF (20 mL) at 5° C. The mixture was stirred at 5° C. for 10 minutes then warmed to room temperature for 2 hours. The reaction mixture was cooled in an ice bath and quenched with saturated NH$_4$Cl (6 mL). The mixture was diluted with methylene chloride (70 mL) and saturated NaHCO$_3$ (20 mL). The organic layer was washed with water (40 mL) and brine (40 mL), and dried. The solvent was removed and the residue was purified by chromatography (SiO$_2$, CH$_3$OH:CH$_2$Cl$_2$ 3:97) to give 3-(4-(3-(2-(dimethylamino)ethoxy)-4-methoxybenzyloxy)-1-oxoisoindolin-2-yl)piperidine-2,6-dione (0.2 g, 39%) as a white solid: mp 201-203° C.; $^1$H NMR (DMSO-d6) δ 8 1.95-2.00 (m, 1H), 2.40-2.52 (m, 2H), 2.61 (s, 6H), 2.84-2.95 (m, 1H), 3.11-3.17 (m, 2H), 3.76 (s, 3H), 4.26 (d, J=17.7 Hz, 1H), 4.34 (t, J=5.4 Hz, 2H), 4.37 (d, J=17.7 Hz, 1H), 5.07-5.13 (dd, J=5.1 and 13.2 Hz, 1H), 5.15 (s, 2H), 7.00 (d, J=8.4 Hz, 1H), 7.05-7.08 (dd, J=1.8 and 8.1 Hz, 1H), 7.16 (d, J=1.8 Hz, 1H), 7.31-7.35 (m, 2H), 7.48 (t, J=7.8 Hz, 1H), 10.96 (s, 1H); $^{13}$C NMR (DMSO-d$_6$) δ 22.33, 31.16, 45.09, 51.54, 51.73, 55.67, 61.76, 64.10, 69.55, 112.01, 113.75, 115.09, 115.16, 121.31, 128.89, 129.77, 129.96, 133.25, 147.25, 149.00, 153.50, 168.00, 170.95, 172.80; Calcd. For C$_{25}$H$_{29}$N$_3$O$_6$+0.1 H$_2$O: C, 61.84; H, 6.44; N, 8.65; Found: C, 62.02; H, 6.67; N, 8.58.

5.154 3-(4-(4-(2-(Dimethylamino)Ethoxy)-3-Methoxybenzyloxy)-1-Oxoisoindolin-2-yl)Piperidine-2,6-Dione

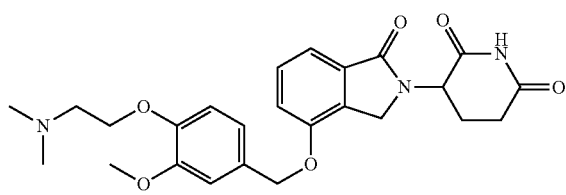 [SMILES: COc1cc(COc2cccc3c2CN(C2CCC(=O)NC2=O)C3=O)ccc1OCCN(C)C]

Step 1: A mixture of vanillin (2 g, 27.3 mmol) and Cs$_2$CO$_3$ (22.2 g, 68.2 mmol) in DMF (80 mL) was stirred for 10 minutes. To this mixture was added diemthylaminoethyl chloride (4.7 g, 32.7 mmol). The mixture was stirred at 50° C. oil bath for 18 hours. The reaction mixture was filtered. Filtrate was diluted with water (100 mL) and extracted with EtOAc (4×50 mL). EtOAc solution was washed with water (3×50 mL) and brine (50 mL), and dried. The solvent was removed to give 4-(2-(dimethylamino)ethoxy)-3-methoxybenzaldehyde (2.1 g, 34%).

Step 2: A solution of 4-(2-(dimethylamino)ethoxy)-3-methoxybenzaldehyde (1.8 g, 8.1 mmol) in THF (15 mL) was added to a stirred solution of LiBH$_4$/THF (2M, 4.8 mL, 9.7 mmol) in THF (15 mL) at 8 to 10° C. After addition, reaction mixture was stirred at room temperature for 1 hour. The reaction mixture was cooled in an ice bath and quenched with water (10 mL). The mixture was stirred with saturated NaHCO$_3$ (25 mL) and EtOAc (50 mL). The aqueous layer was extracted with EtOAc (2×30 mL). Combined EtOAc solution was washed with brine (40 mL) and dried. The solvent was removed and the residue was purified by chromatography (SiO$_2$, EtOAc: CH$_2$Cl$_2$ 3:7) to give (4-(2-(dimethylamino)ethoxy)-3-methoxyphenyl)methanol (2.6 g, 93% yield): $^1$H NMR (DMSO-d$_6$) δ 2.61 (s, 6H), 3.11 (t, J=5.4 Hz, 2H), 3.75 (s, 3H), 4.30 (t, J=5.4 Hz, 2H), 4.41 (d, J=5.7 Hz, 2H), 5.09 (t, J=5.7 Hz, 1H), 6.81-6.96 (m, 3H); $^{13}$C NMR (DMSO-d$_6$) δ 51.69, 55.48, 61.85, 62.69, 64.29, 110.81, 113.61, 118.51, 136.02, 146.11, 149.01.

Step 3: Diisopropyl azodicarboxylate (1.4 g, 6.8 mmol) was added to a stirred suspension of methyl 5-amino-4-(4-hydroxy-1-oxoisoindolin-2-yl)-5-oxopenatnoate (1.0 g, 3.4 mmol), (4-(2-(dimethylamino)ethoxy)-3-methoxyphenyl)methanol (1.2 g, 5.1 mmol) and triphenphosphine-polymer bound (2.3 g, 6.8 mmol) in THF (80 mL) at 5-8° C. After addition, the mixture was stirred at room temperature overnight. The reaction mixture was filtered and solid was washed with methylene chloride (30 mL). Filtrate was concentrated and the residue was purified by chromatography (SiO$_2$, CH$_3$OH:CH$_2$Cl$_2$ 3:97) to give methyl 5-amino-4-(4-(4-(2-dimethylamino)ethoxy)-3-methoxybenzyloxy)-1-oxoisoindolin-2-yl)-5-oxopentanoate (1.4 g, 81%).

Step 4: A solution of potassium t-butoxide/THF (1 M, 3.0 mL, 3.0 mmol) was added to a stirred solution of methyl 5-amino-4-(4-(4-(2-(dimethylamino)ethoxy)-3-methoxybenzyloxy)-1-oxoisoindolin-2-yl)-5-oxopentanoate (1.5 g, 3.0 mmol) in THF (30 mL) at 5° C. The mixture was stirred at 5° C. for 10 minutes then warmed to room temperature for 2 hours. The reaction mixture was cooled in an ice bath and quenched with saturated NH$_4$Cl (10 mL). The mixture was diluted with CH$_2$Cl$_2$ (50 mL) and saturated NaHCO$_3$ (25 mL). The aqueous layer was extracted with CH$_2$Cl$_2$ (2×30 mL) and combined CH$_2$Cl$_2$ solution was washed with brine (40 mL) and dried. The solvent was removed and the residue was purified by chromatography (SiO$_2$, CH$_3$OH:CH$_2$Cl$_2$ 3:97) to give 3-(4-(4-(2-(dimethylamino)ethoxy)-3-methoxybenzyloxy)-1-oxoisoindolin-2-yl)piperidine-2,6-dione (0.6 g, 39%) as a white solid: mp 190-192° C.; $^1$H NMR (DMSO-d$_6$) δ 1.95-2.00 (m, 1H), 2.41-2.55 (m, 2H), 2.61 (s, 6H), 2.84-2.91 (m, 1H), 3.13 (t, J=5.4 Hz, 2H), 3.77 (s, 3H), 4.27 (d, J=17.5 Hz, 1H), 4.33 (t, J=5.4 Hz, 2H), 4.37 (d, J=17.5 Hz, 1H), 5.07-5.13 (dd, J=5.1 and 13.2 Hz, 1H), 5.16 (s, 2H), 7.02 (m, 2H), 7.12 (b, 1H), 7.31-7.35 (m, 2H), 7.48 (t, J=7.8 Hz, 1H), 10.96 (s, 1H); $^{13}$C NMR (DMSO-d$_6$) δ 22.31, 31.17, 45.11, 51.56, 51.72, 55.67, 61.77, 64.14, 69.59, 112.24, 113.42, 115.05, 115.16, 120.50, 129.77, 129.95, 133.25, 147.22, 149.06, 153.50, 168.00, 170.96, 172.82; Calcd. For C$_{25}$H$_{29}$N$_3$O$_6$+1.0 H$_2$O: C, 61 34; H, 6.44; N, 8.65; Found: C, 61.98; H, 6.84; N, 8.67.

5.155 3-[4-(4-Chloro-Benzyloxy)-1-Oxo-1,3-Dihydro-Isoindol-2-yl]-Piperidine-2,6-Dione

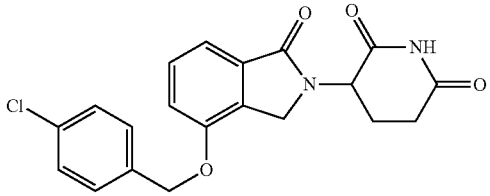 [SMILES: O=C1CCC(N2Cc3c(OCc4ccc(Cl)cc4)cccc3C2=O)C(=O)N1]

Step 1: To the THF solution of 4-carbamoyl-4-(4-hydroxy-1-oxo-1,3-dihydro-isoindol-2-yl)-butyric acid methyl ester (1.0 g, 3.42 mmol), were added triphenyl phosphine resin (2.3 g, 2.2 mmol/g loading, 6.84 mmol) and DIAD (1.33 mL, 6.84 mmol) at 0° C. After being stirred at 0° C. for 10 minutes, the mixture was added (4-chloro-4-ylmethyl-phenyl)-methanol (0.73 g, 5.13 mmol) and stirred at room temperature overnight. The mixture was filtered and the filtrate was concentrated and extracted with EtOAc (30 mL) and Na$_2$CO$_3$ (20 mL). The organic layer was washed with water (20 mL) and brine (20 mL), and concentrated. The resulting oil was purified on silica gel column to give 4-carbamoyl-4-[4-(4-chloro-benzyloxy)-1-oxo-1,3-dihydroisoindol-2-yl]-butyric acid methyl ester (0.13 g, 13%).

Step 2: To the THF solution (20 mL) of 4-carbamoyl-4-[4-(3-morpholin-4-ylmethyl-benzyloxy)-1-oxo-1,3-dihydro-isoindol-2-yl]-butyric acid methyl ester (0.18 g, 0.43 mmol), was added potassium t-butoxide (0.6 mL g, 0.6 mmol) at 0° C. The mixture was stirred for 15 minutes at 0° C. and quenched with 5 mL of 1N HCl solution, followed by 15 mL of saturated NaHCO$_3$ solution. The mixture was extracted with EtOAc (20 mL).

The organic layer was concentrated in vacuo. The resulting oil was purified on silica gel column eluted with CH$_2$Cl$_2$ and methanol to give 3-[4-(4-chloro-benzyloxy)-1-oxo-1,3-dihydro-isoindol-2-yl]-piperidine-2,6-dione as a white solid (70 mg, 42%). mp: 238-240° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: $t_R$=3.9 min (97%). $^1$H NMR (DMSO-d$_6$) δ 1.81-2.08 (m, 1H, CHH), 2.34-2.48 (m, 1H, CHH), 2.53-2.65 (m, 1H, CHH), 2.80-3.01 (m, 1H, CHH), 4.15-4.51 (m, 2H, CH$_2$), 5.11 (dd, J=5.1, 13.2 Hz, 1H, NCH), 5.26 (s, 2H, CH$_2$), 7.13-7.39 (m, 2H, Ar), 7.41-7.58 (m, 5H, Ar), 10.97 (s, 1H, NH). $^{13}$C NMR (DMSO-d$_6$) δ 22.38, 31.20, 45.06, 51.58, 68.65, 115.00, 115.38, 128.47, 129.47, 129.82, 129.97, 132.55, 133.35, 135.70, 153.27, 167.96, 170.98, 172.83; LCMS MH=385. Anal Calcd for C$_{20}$H$_{17}$ClN$_2$O$_4$+0.1 H$_2$O: C, 62.13; H, 4.48; N, 7.25; Found: C, 61.76%; H, 4.45; N, 7.28.

5.156 3-[4-(3-Methoxy-Benzyloxy)-1-Oxo-1,3-Dihydro-Isoindol-2-yl]-Piperidine-2,6-Dione

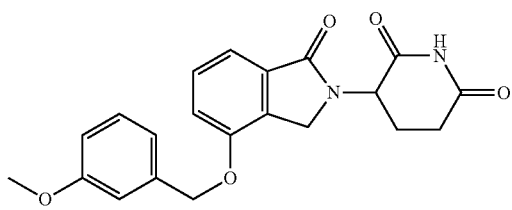 [SMILES: COc1cccc(COc2cccc3c2CN(C2CCC(=O)NC2=O)C3=O)c1]

Step 1: Polymer-supported triphenylphosphene (1.6 mmol/g, 3.84 g, 4.78 mmol) was added to a stirred solution of 4-carbamoyl-4-(4-hydroxy-1-oxo-1,3-dihydro-isoindol-2-yl)-butyric acid methyl ester (0.78 g, 2.66 mmol) in THF (15 mL) at 0° C., followed by addition of diisopropyl diazene-1,2-dicarboxylate (0.95 ml, 4.78 mmol). After stirring for 30 minutes, (3-methoxy-phenyl)-methanol (0.56 mL, 4.52 mmol) was added. The mixture was stirred for one hour then filtered, washed with methanol (3×10 mL), then methylene chloride (3×10 mL). The combined filtrate was evaporated in vacuo to give an oil, which was purified on silica gel column (MeOH/CH$_2$Cl$_2$ gradient from 0% to 5% in 60 min) to give 4-carbamoyl-4-[4-(3-methoxy-benzyloxy)-1-oxo-1,3-dihydro-isoindol-2-yl]-butyric acid methyl ester as an oil (0.32 g, 36% yield).

Step 2: Potassium tert-butoxide (0.10 g, 0.92 mmol) was added to a stirred solution of 4-carbamoyl-4-[4-(3-methoxy-benzyloxy)-1-oxo-1,3-dihydro-isoindol-2-yl]-butyric acid methyl ester (1.13 g, 2.60 mmol) in THF (10 mL) at 0° C. for 10 minutes. The mixture was quenched with 1N HCl (2 mL) and neutralized with saturated sodium bicarbonate (4 ml to pH=8). The mixture was extracted with ethyl acetate (3×20 mL). The combined ethyl acetate phases were evaporated and then purified on silica gel column (MeOH/CH$_2$Cl$_2$ gradient from 0% to 5% in 40 min) to give 3-[4-(3-methoxy-benzyloxy)-1-oxo-1,3-dihydro-isoindol-2-yl]-piperidine-2,6-dione as a white solid (0.23 g, 65% yield); HPLC: Waters Symmetry C-18, 3.9×150 mm, 5 μm, 1 mL/min, 240 nm, isocratic at 40/60 in 10 min (acetonitrile/0.1% H$_3$PO$_4$), 5.32 min (98.9%); mp: 225-227° C.; $^1$H NMR (DMSO-d$_6$) δ 1.88-2.09 (m, 1H, CHH), 2.37-2.47 (m, 1H, CHH), 2.53-2.65 (m, 1H, CHH), 2.82-3.00 (m, 1H, CHH), 3.76 (s, 3H, CH$_3$), 4.20-4.52 (m, 2H, ArCH$_2$N), 5.11 (dd, J=5.0, 13.1 Hz, 1H, NCH), 5.23 (s, 2H, ArCH$_2$O), 6.91 (dd, J=1.7, 8.1 Hz, 1H, Ar), 7.00-7.12 (m, 2H, Ar), 7.23-7.38 (m, 3H, Ar), 7.43-7.55 (m, 1H, Ar), 10.97 (s, 1H, NH); $^{13}$C NMR (DMSO-d$_6$) δ 22.35, 31.21, 45.12, 51.61, 55.05, 69.38, 113.26, 115.00, 115.26, 119.68, 129.59, 129.79, 129.97, 133.32, 138.19, 153.41, 159.35, 167.99, 170.98, 172.83 (missing one aromatic carbon due to overlapping, confirmed by HMQC); LCMS MH=381; Anal. Calcd for C$_{21}$H$_{20}$N$_2$O$_5$+0.1 H2O: C, 65.99; H, 5.33; N, 7.33. Found: C, 65.71; H, 5.36; N, 7.25.

5.157 3-[4-(3-Methyl-Benzyloxy)-1-Oxo-1,3-Dihydro-Isoindol-2-yl]-Piperidine-2,6-Dione

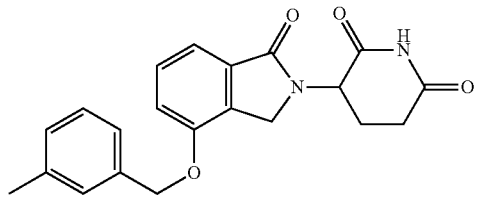 [SMILES: Cc1cccc(COc2cccc3c2CN(C2CCC(=O)NC2=O)C3=O)c1]

Step 1: Polymer-supported triphenylphosphene (1.6 mmol/g, 3.76 g, 4.68 mmol) was added to a stirred solution of 4-carbamoyl-4-(4-hydroxy-1-oxo-1,3-dihydro-isoindol-2-yl)-butyric acid methyl ester (0.75 g, 2.60 mmol) in THF (15 mL) at 0° C., followed by addition of diisopropyl diazene-1,2-dicarboxylate (0.93 ml, 4.68 mmol). After stirring for 30 minutes, m-tolyl-methanol (0.53 mL, 4.40 mmol) was added. The mixture was stirred for one hour then filtered, washed with methanol (3×10 mL), then methylene chloride (3×10 mL). The combined filtrate was evaporated in vacuo to give an oil, which was purified on silica gel column (MeOH/CH$_2$Cl$_2$ gradient from 0% to 5% in 60 min) to give 4-carbamoyl-4-[4-(3-methyl-benzyloxy)-1-oxo-1,3-dihydro-isoindol-2-yl]-butyric acid methyl ester as an oil (1.13 g, 137% crude yield).

Step 2: Potassium tert-butoxide (0.30 g, 2.60 mmol) was added to a stirred solution of 4-carbamoyl-4-[4-(3-methyl-benzyloxy)-1-oxo-1,3-dihydro-isoindol-2-yl]-butyric acid methyl ester (1.13 g, 2.60 mmol) in THF (10 mL) at 0° C. for 10 minutes. The mixture was quenched with 1N HCl (2 mL) and neutralized with saturated sodium bicarbonate (4 ml to pH=8). The mixture was extracted with ethyl acetate (3×20 mL). The combined ethyl acetate phases were evaporated and purified on silica gel column (MeOH/CH$_2$Cl$_2$ gradient from 0% to 5% in 40 min) to give 3-[4-(3-methyl-benzyloxy)-1-oxo-1,3-dihydro-isoindol-2-yl]-piperidine-2,6-dione as a white solid (0.21 g, 29% yield over two steps); HPLC: Waters Symmetry C-18, 3.9×150 mm, 5 µm, 1 mL/min, 240 nm, isocratic at 40/60 in 10 min (acetonitrile/0.1% H$_3$PO$_4$), 7.89 min (99.4%); mp: 244-246° C.; $^1$H NMR (DMSO-d$_6$) δ 1.90-2.06 (m, 1H, CHH), 2.32 (s, 3H, CH$_3$), 2.36-2.47 (m, 1H, CHH), 2.53-2.64 (m, 1H, CHH), 2.81-3.00 (m, 1H, CHH), 4.19-4.49 (m, 2H, ArCH$_2$N), 5.11 (dd, J=5.1, 13.2 Hz, 1H, NCH), 5.21 (s, 2H, ArCH$_2$O), 7.11-7.20 (m, 1H, Ar), 7.23-7.37 (m, 5H, Ar), 7.43-7.55 (m, 1H, Ar), 10.97 (s, 1H, NH); $^{13}$C NMR (DMSO-d$_6$) δ 20.99, 22.36, 31.21, 45.12, 51.59, 69.61, 114.98, 115.23, 124.78, 128.25, 128.38, 128.61, 129.81, 129.94, 133.32, 136.53, 137.64, 153.50, 168.01, 170.98, 172.83; LCMS MH=365; Anal. Calcd for C$_{21}$H$_{20}$N$_2$O$_4$+0.2 H$_2$O: C, 68.54; H, 5.59; N, 7.61. Found: C, 68.18; H, 5.49; N, 7.52.

5.158 3-(4-(3-Methoxy-4-(2-Pyrrolidin-1-yl) Ethoxy)-Benzyloxy)-1-Oxo-Isoindolin-2-yl)-Piperidine-2,6-Dione

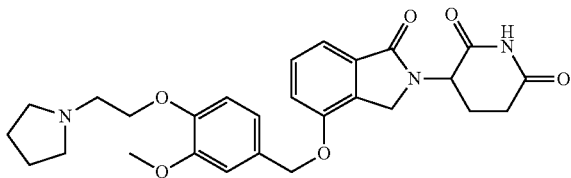 [SMILES: COc1cc(COc2cccc3c2CN(C2CCC(=O)NC2=O)C3=O)ccc1OCCN1CCCC1]

Step 1: A mixture of Vanillin (4.2 g, 27.3 mmol) and Cs$_2$CO$_3$ (22.2 g, 68.3 mmol) in DMF (80 mL) was stirred for 10 minutes at room temperature. To this mixture was added 1-(2-chloroethyl)pyrrolidine hydrochloride (5.6 g, 32.7 mmol). The mixture was heated at 50° C. overnight. The reaction mixture was cooled and filtered and washed solid with EtOAc (100 mL). Filtrate was diluted with water (200 mL) and aqueous layer was extracted with EtOAc (3×50 mL). Combined EtOAc solution was washed with water (2×50 mL) and brine (50 mL), and dried. The solvent was removed to give 3-methoxy-4-(2-pyrrolidin-1-yl-ethoxy) benzaldehyde (6.2 g, 91% yield): $^1$H NMR (DMSO-d$_6$) δ 1.65-1.71 (m, 4H), 2.50-2.55 (m, 4H), 2.81 (t, J=6.0 Hz, 2H), 4.17 (t, J=6.0 Hz, 2H), 7.20 (d, J=8.1 Hz, 1H), 7.40 (d, J=1.8 Hz, 1H), 7.52-7.55 (dd, J=1.8 and 8.1 Hz, 1H), 9.84 (s, 1H).

Step 2: A solution of LiBH$_4$/THF (2.0M, 14.7 mL, 29.4 mmol) in THF (20 mL) was cooled in an ice bath to 5° C. A solution of 3-methoxy-4-(2-pyrrolidin-1-yl-ethoxy)benzaldehyde (6.1 g, 24.5 mmol) in THF (20 mL) was added slowly at 5-8° C. After addition, the mixture was stirred at room temperature for 1 hour. The reaction mixture was cooled in an ice bath and quenched with water (15 mL). The mixture was stirred with EtOAc (50 mL) and sat. NaHCO$_3$ (25 mL). The aqueous layer was extracted with EtOAc (2×40 mL) and combined EtOAc solution was washed with water (40 mL) and brine (40 mL), and dried (MgSO$_4$). The solvent was removed and the residue was purified by chromatography (SiO$_2$, EtOAc: CH$_2$Cl$_2$ 2:8) to give [3-methoxy-4-(2-pyrrolidin-1-yl-ethoxy)-phenyl]-methanol (4.8 g, 77% yield): $^1$H NMR (DMSO-d$_6$) δ 1.85-2.01 (m, 4H), 2.96-3.08 (m, 4H), 3.12 (t, J=5.7 Hz, 2H), 3.74 (s, 3H), 4.34 (t, J=5.7 Hz, 2H), 4.41 (d, J=5.6 Hz, 2H), 5.07 (t, J=5.7 Hz, 1H), 6.80-6.84 (dd, J=1.8 and 8.1 Hz, 1H), 6.94 (d, J=8.1 Hz, 2H); $^{13}$C NMR (DMSO-d$_6$) δ 22.28, 55.48, 61.34, 62.58, 62.70, 64.65, 110.78, 113.26, 118.52, 135.84, 146.23, 148.91.

Step 3: Diisopropyl azodicarboxylate (1.1 g, 5.5 mmol) was added slowly to a stirred suspension of methyl 5-amino-4-(4-hydroxy-1-oxoisoindolin-2-yl)-5-oxopentanoate (0.8 g, 2.7 mmol), [3-methoxy-4-(2-pyrrolidine-1-yl-ethoxy)-phenyl]-methanol (1.0 g, 4.1 mmol) and triphenylphosphine-polymer bound (1.8 g, 5.5 mmol) in THF (60 mL) at 5-7° C. After addition, the mixture was stirred at room temperature overnight. The reaction mixture was filtered and solid was washed with CH$_2$Cl$_2$ (30 mL). Filtrate was concentrated and the residue was purified by chromatography (SiO$_2$, CH$_3$OH: CH$_2$Cl$_2$ 3:97) to give methyl 5-amino-4-(4-(3-methoxy-4-(2-(pyrrolidin-1-yl)ethoxy)benzyloxy)-1-oxoisoindolin-2-yl)-5-oxopentanoate (0.9 g, 59%).

Step 4: A solution of potassium t-butoxide/THF (1M, 1.6 mL, 1.6 mmol) was added slowly to a stirred solution of methyl 5-amino-4-(4-(3-methoxy-4-(2-(pyrrolidin-1-yl) ethoxy)benzoyloxy)-1-oxoisoindolin-2-yl)-5-oxopentanoate (0.8 g, 1.6 mmol) in THF (30 mL) at 5° C. The mixture was stirred at 5° C. for 10 minutes then warmed to room temperature for 2 hours. The reaction mixture was cooled in an ice bath and quenched with 4N HCl (3 mL). The mixture was stirred with CH$_2$Cl$_2$ (40 mL) and sat. NaHCO$_3$ (25 mL). The aqueous layer was extracted with CH$_2$Cl$_2$ (40 mL) and combined CH$_2$Cl$_2$ solution was washed with water (2×25 mL) and brine (25 mL), and dried (MgSO$_4$). The solvent was removed and the residue was purified by chromatography (SiO$_2$, CH$_3$OH:CH$_2$Cl$_2$ 3:97) to give 3-(4-(3-methoxy-4-(2-(pyrrolidin-1-yl)ethoxy)benzyloxy)-1-oxoisoindolin-2-yl)-piperidine-2,6-dione (0.4 g, 49% yield): mp 160-162° C.; $^1$H NMR (DMSO-d$_6$) δ 1.96-2.01 (m, 5H), 2.42-2.59 (m, 2H), 2.95-3.16 (m, 7H), 3.76 (s, 3H), 4.27 (d, J=17.4 Hz, 1H), 4.35-4.42 (m, 3H), 5.07-5.13 (dd, J=5.4 and 13.5 Hz, 1H), 5.16 (s, 2H), 6.98-7.02 (m, 2H), 7.11 (d, J=1.2 Hz, 1H), 7.30-7.35 (m, 2H), 7.48 (t, J=7.8 Hz, 1H), 10.96 (s, 1H); $^{13}$C NMR (DMSO-d$_6$) δ 22.27, 31.17, 45.12, 51.56, 55.57, 55.67, 60.48, 61.38, 64.55, 69.62, 112.24, 113.14, 115.05, 115.15, 120.54, 129.53, 129.77, 129.95, 133.25, 147.34, 149.00, 153.52, 168.00, 170.96, 172.81; Calcd for C$_{27}$H$_{31}$N$_3$O$_6$+BH$_3$: C, 63.91; H, 6.75; N, 8.28. Found: C, 63.90; H, 6.76; N, 8.17.

5.159 3-[4-(3,5-Dichloro-Benzyloxy)-1-Oxo-1,3-Dihydro-Isoindol-2-yl]-Piperidine-2,6-Dione

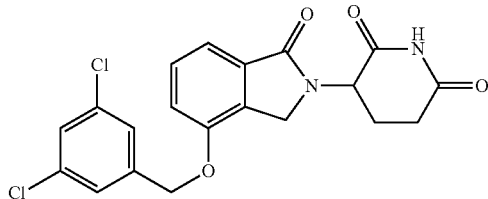 [SMILES: O=C1CCC(N2Cc3c(OCc4cc(Cl)cc(Cl)c4)cccc3C2=O)C(=O)N1]

Step 1: Polymer bonded triphenylphosphine (1.6 g, 1.92 mmol) was added to the stirred solution of 4-carbamoyl-4-(4-hydroxy-1-oxo-1, 3-dihydro-isoindol-2-yl)-butyric acid methyl ester (300 mg, 1.03 mmol) in THF (10 mL) at 0° C. The resulting mixture was stirred at 0° C. for 10 minutes, followed by the addition of DIAD (412 mg, 2.06 mmol). Ten minutes later, (3,5-dichloro-phenyl)-methanol (364.7 mg, 2.06 mmol) was added to the mixture. The reaction was stirred at room temperature for 1 hour and the reaction was complete. The reaction mixture was filtered and the solid was washed with dichloromethane (5×25 mL). The filtrate was concentrated and the residue was purified by ISCO chromatography to give 4-carbamoyl-4-[4-(3,5-dichloro-benzyloxy)-1-oxo-1,3-dihydro-isoindol-2-yl]-butyric acid methyl ester as a white solid (410 mg, 88% yield): LCMS MH=451, 453.

Step 2: KOtBu (102 mg, 0.91 mmol) was added to the stirred solution of 4-carbamoyl-4-[4-(3,5-dichloro-benzyloxy)-1-oxo-1,3-dihydro-isoindol-2-yl]-butyric acid methyl ester (410 mg, 0.91 mmol) in THF (20 mL) at 0° C. The resulting mixture was stirred at 0° C. for 5 minutes and the reaction was complete. To the reaction mixture was added by HCl (0.1N aq, 14 mL), and the mixture was extracted with dichloromethane (25 mL×2). The organic layer was dried by MgSO$_4$ and concentrated under vacuo. The residue was purified by ISCO chromatography to give a solid. The solid was triturated with diethyl ether (15 mL) to give 3-[4-(3,5-Dichloro-benzyloxy)-1-oxo-1,3-dihydro-isoindol-2-yl]-piperidine-2,6-dione as a white solid (230 mg, 60% yield); HPLC: Waters Symmetry C-18, 3.9×150 mm, 5 µm, 1 mL/min, 240 nm, 60/40 (acetonitrile/0.1% H$_3$PO$_4$): $t_R$=3.5 (98%); mp: 271-273° C.; $^1$H NMR (DMSO-d$_6$) δ 1.92-2.07 (m, 1H, CHH), 2.37-2.47 (m, 1H, CHH), 2.54-2.66 (m, 1H, CHH), 2.81-3.02 (m, 1H, CHH), 4.22-4.56 (m, 2H, CHH, CHH), 5.12 (dd, J=5.1, 13.0 Hz, 1H, NCH), 5.27 (s, 2H, CH$_2$), 7.29 (d, J=7.9 Hz, 1H, Ar), 7.35 (d, J=7.2 Hz, 1H, Ar), 7.46-7.54 (m, 1H, Ar), 7.57 (d, 2H, Ar), 7.58-7.63 (m, 1H, Ar), 10.98 (s, 1H, NH); $^{13}$C NMR (DMSO-d$_6$) δ 22.33, 31.18, 45.09, 51.60, 67.92, 114.88, 115.57, 126.15, 127.57, 129.83, 129.99, 133.43, 134.14, 140.97, 153.03, 167.90, 170.95, 172.81; LCMS MH=419, 421; Anal. Calcd for C$_{20}$H$_{16}$Cl$_2$N$_2$O$_4$+0.045 CH$_2$Cl$_2$+0.06 MeOH: C, 56.82; H, 3.87; N, 6.59; Cl, 17.43; Found: C, 56.58; H, 3.86; N, 6.52; Cl, 17.15.

5.160 3-[4-(4-Methanesulfonyl-Benzyloxy)-1-Oxo-1,3-Dihydro-Isoindol-2-yl]-Piperidine-2,6-Dione

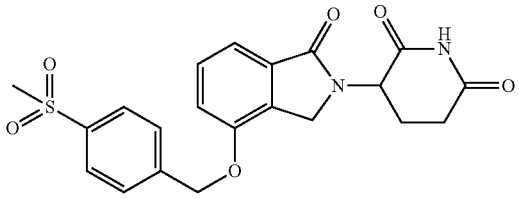 [SMILES: CS(=O)(=O)c1ccc(COc2cccc3c2CN(C2CCC(=O)NC2=O)C3=O)cc1]

Step 1: Polymer bonded triphenylphosphine (1.5 g, 1.92 mmol) was added to the stirred solution of 4-carbamoyl-4-(4-hydroxy-1-oxo-1, 3-dihydro-isoindol-2-yl)-butyric acid methyl ester (280 mg, 0.96 mmol) in THF (10 mL) at 0° C. The resulting mixture was stirred at 0° C. for 15 minutes, followed by the addition of DIAD (388 mg, 1.92 mmol). Five minutes later, (4-methanesulfonyl-phenyl)-methanol (357 mg, 1.92 mmol) was added to above mixture. The reaction mixture was stirred at room temperature for 4 hours and then at 0° C. overnight, and the reaction was complete. The reaction mixture was filtered and the solid was washed with dichloromethane (20 mL×5). The filtrate was concentrated and the residue was purified by ISCO chromatography to give 4-carbamoyl-4-[4-(4-methanesulfonyl-benzyloxy)-1-oxo-1,3-dihydro-isoindol-2-yl]-butyric acid methyl ester as a white solid (310 mg, 70% yield): LCMS MH=461.

Step 2: KOtBu (75.2 mg, 0.67 mmol) was added to the stirred solution of 4-carbamoyl-4-[4-(4-methanesulfonyl-benzyloxy)-1-oxo-1,3-dihydro-isoindol-2-yl]-butyric acid methyl ester (310 mg, 0.67 mmol) in THF (18 mL) at 0° C. The resulting mixture was stirred at 0° C. for 1.5 hours and KOtBu (35 mg, 0.31 mmol) was added to the reaction mixture. The reaction was stopped in 30 minutes. To the reaction mixture was added by HCl (1N aq, 10 mL) and the mixture was extracted with dichloromethane (30 mL×2). Organic layer was dried by MgSO$_4$ and concentrated under vacuo. The residue was purified by ISCO chromatography to give a solid. The solid was triturated with diethyl ether (30 ml) to give 3-[4-(4-ethanesulfonyl-benzyloxy)-1-oxo-1,3-dihydro-isoindol-2-yl]-piperidine-2,6-dione as a white solid (195 mg, 68% yield): HPLC: Waters Symmetry C-18, 3.9×150 mm, 5 µm, 1 mL/min, 240 nm, 30/70 (acetonitrile/0.1% H$_3$PO$_4$): $t_R$=3.98 (98%); mp: 248-250° C.; $^1$H NMR DMSO-d$_6$) δ 1.90-2.08 (m, 1H, CHH), 2.35-2.47 (m, 1H, CHH), 2.54-2.66 (m, 1H, CHH), 2.81-3.04 (m, 1H, CHH), 3.22 (s, 3H, CH$_3$), 4.20-4.57 (m, 2H, CHH, CHH), 5.13 (dd, J=5.1, 13.2 Hz, 1H, NCH), 5.40 (s, 2H, CH$_2$), 7.26-7.39 (m, 2H, Ar), 7.48 (d, 1H, Ar), 7.76 (d, J=8.3 Hz, 2H, Ar), 7.96 (d, J=8.3 Hz, 2H, Ar), 10.98 (s, 1H, NH); $^{13}$C NMR (DMSO-d$_6$) δ 22.37, 31.16, 43.45, 45.04, 51.58, 68.52, 114.94, 115.51, 127.16, 128.05, 129.86, 129.97, 133.40, 140.27, 142.62, 153.13, 167.91, 170.95, 172.81; LCMS MH=429; Anal. Calcd for C$_{21}$H$_{20}$N$_2$O$_6$S: C, 58.87; H, 4.71; N, 6.54; Found: C, 58.98; H, 4.97; N, 6.21.

5.161 3-[1-Oxo-4-(4-Pyrrolidin-1-ylmethyl-Benzyloxy)-1,3-Dihydro-Isoindol-2-yl]-Piperidine-2,6-Dione

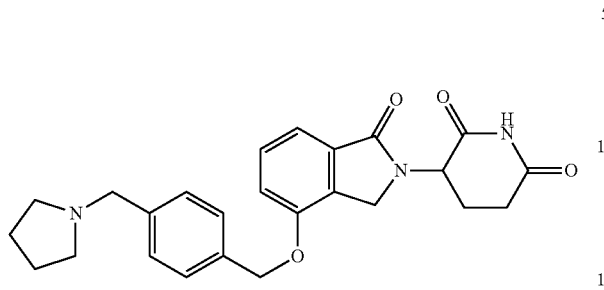

Step 1: Polymer-supported triphenylphosphene (1.6 mmol/g, 1.83 g, 2.30 mmol) was added to a stirred solution of 4-carbamoyl-4-(4-hydroxy-1-oxo-1,3-dihydro-isoindol-2-yl)-butyric acid methyl ester (0.31 g, 1.04 mmol) in THF (20 mL) at 0° C., followed by addition of diisopropyl diazene-1,2-dicarboxylate (0.46 ml, 2.30 mmol). After stirring for 30 minutes, (4-pyrrolidin-1-ylmethyl-phenyl)-methanol (0.40 g, 2.09 mmol) was added. The mixture was stirred for one hour then filtered, washed with methanol (3×10 mL), then methylene chloride (3×10 mL). The combined filtrate was evaporated in vacuo to give an oil, which was purified by preparative HPLC to give 4-carbamoyl-4-[1-oxo-4-(4-pyrrolidin-1-ylmethyl-benzyloxy)-1,3-dihydro-isoindol-2-yl]-butyric acid methyl ester as a clear oil (0.17 g, 35% yield).

Step 2: Potassium tert-butoxide (0.08 g, 0.74 mmol) was added to a stirred solution of 4-carbamoyl-4-[1-oxo-4-(4-pyrrolidin-1-ylmethyl-benzyloxy)-1,3-dihydro-isoindol-2-yl]-butyric acid methyl ester (0.17 g, 0.37 mmol) in THF (10 mL) at 0° C. The mixture was stirred for ten minutes and quenched with 1N HCl (3 mL), neutralized by saturated sodium bicarbonate (6 mL to pH=7), and quickly extracted by ethyl acetate (2×15 mL). The combined ethyl acetate phases were evaporated to a light green foamy oil, which was stirred in water (15 mL) for one hour, filtered and dried to give 3-[1-oxo-4-(4-pyrrolidin-1-ylmethyl-benzyloxy)-1,3-dihydro-isoindol-2-yl]-piperidine-2,6-dione as an off-white solid (0.033 g, 20% yield); HPLC: Waters Symmetry C-18, 3.9×150 mm, 5 µm, 1 mL/min, 240 nm, isocratic at 15/85 in 10 min (acetonitrile/0.1% $H_3PO_4$), 5.51 min (98.2%); mp: N/A due to limited sample available; $^1$H NMR (DMSO-$d_6$) δ 1.64-1.84 (m, 4H, $CH_2CH_2$), 1.97-2.12 (m, 1H, CHH), 2.53-2.72 (m, 6H, CHH, CHH, $CH_2CH_2$), 2.85-3.09 (m, 1H, CHH), 3.63 (s, 2H, $CH_2$), 4.24-4.56 (m, 2H, $CH_2$), 5.17 (dd, J=5.1, 13.2 Hz, 1H, NCH), 5.28 (s, 2H, $CH_2$), 7.30-7.62 (m, 7H, Ar), 11.03 (s, 1H, NH); $^{13}$C NMR (DMSO-$d_6$) δ 22.36, 23.10, 31.21, 45.10, 51.58, 53.47, 59.29, 69.45, 115.00, 115.21, 127.61, 128.51, 129.81, 129.95, 133.31, 135.00, 139.36, 153.51, 168.01, 170.98, 172.83; LCMS MH=434.

5.162 3-(4-(3-Nitrobenzyloxy)-1-Oxoisoindolin-2-yl)Piperidine-2,6-Dione

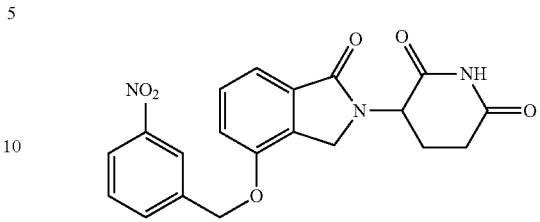

To a mixture of methyl 5-amino-4-(4-hydroxy-1-oxoisoindolin-2-yl)-5-oxopentanoate (600 mg, 2.05 mmol,) and N,N-diisopropylethylamine (358 µL, 2.05 mmol) in anhydrous DMF (10 mL), was added 1-(bromomethyl)-3-nitrobenzene (421 mg, 1.95 mmol). The mixture was stirred at room temperature for 16 hours then heated to 80° C. for 24 hours. The reaction mixture was cooled on an ice bath and then transferred to a chilled 0.5 N HCl solution (~120 mL). A solid formed was collected by filtration and dried in vacuum oven to give 720 mg of crude product. A portion of the crude product was purified by injection onto a C-18 preparatory HPLC column. The product was eluted with an acetonitrile/water gradient (0.1% formic acid in both mobile phases) and fractions were collected by mass trigger. The desired fractions were combined and concentrated in vacuo to give 3-(4-(3-nitrobenzyloxy)-1-oxoisoindolin-2-yl)piperidine-2,6-dione as a white solid (60 mg, 37% yield based on portion purified): HPLC: Waters Symmetry C18, 5 µm, 3.9×150 mm, 1 ml/min, 240 nm, 40/60 acetonitrile/0.1% $H_3PO_4$, 4.20 min (99.0%); mp: 237-240° C.; 1H NMR (DMSO-d6) δ 1.86-2.05 (m, 1H, CHH), 2.35-2.48 (m, 1H, CHH), 2.53-2.67 (m, 1H, CHH), 2.82-3.01 (m, 1H, CHH), 4.30 (d, J=17.6 Hz, 1H, CHH), 4.46 (d, J=17.4 Hz, 1H, CH), 5.12 (dd, J=5.0, 13.1 Hz, 1H, CH), 5.42 (s, 2H, Ar), 7.23-7.45 (m, 2H, Ar), 7.45-7.59 (m, 1H, Ar), 7.66-7.84 (m, 1H, Ar), 7.98 (d, J=7.7 Hz, 1H, Ar), 8.15-8.29 (m, 1H, Ar), 8.29-8.43 (m, 1H, Ar), 10.98 (br. s., 1H, NH); 13C NMR (DMSO-d6) δ 22.38, 31.20, 45.10, 51.62, 68.33, 115.08, 115.61, 122.18, 122.90, 129.90, 130.00, 130.14, 133.45, 134.14, 139.01, 147.86, 153.15, 167.92, 170.96, 172.83; LCMS MH=396; Anal. Calcd. For $C_{20}H_{17}N_3O_6$+0.9 $H_2O$: C, 58.36; H, 4.60; N, 10.21. Found: C, 58.30; H, 4.21; N, 10.05.

5.163 4-((2-(2,6-Dioxopiperidin-3-yl)-1-Oxoisoindolin-4-yloxy)Methyl)Benzamide

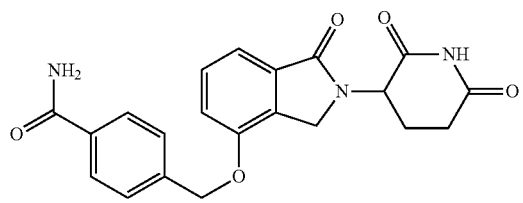 [SMILES: NC(=O)c1ccc(COc2cccc3c2CN(C2CCC(=O)NC2=O)C3=O)cc1]

Step 1: In a 250-mL RB flask, L-glutamine α-tert-butyl ester (7.83 g, 32.8 mmol) and N,N-diisopropylethylamine (11.46 ml, 65.6 mmol) were slurried in acetonitrile (100 mL) at room temperature. The suspension was stirred for about 10 minutes and then a solution of methyl 2-(bromomethyl)-

3-(tert-butyldimethylsilyloxy)benzoate (11.4 g, 29.8 mmol,) in acetonitrile (20 mL) was added dropwise over 10 minutes. The reaction mixture was heated in an oil bath to a slow reflux (~80° C.) for 4 hours. The reaction mixture was allowed to cool to room temperature for about 1 hour and then a solution of cesium fluoride (4.53 g, 29.8 mmol) in water (15 mL) was added. The resulting mixture was vigorously stirred at room temperature for 1 hour at which point LCMS indicated desilylation was complete. The reaction mixture was diluted with acetonitrile and filtered to remove undissolved solids. The solids were washed with additional acetonitrile. The filtrate and washes (total volume 200 mL) were diluted further with EtOAc (300 mL), transferred to a 1-L separatory funnel, and washed with 0.5 N Aqueous $KH_2PO_4$ (100 mL, pH~5). To the aqueous layer was added 1 N HCl in portions (~20 mL, pH changed from pH 7-8 to pH~5 using pH paper). NaCl (~10 g) and EtOAc (~200 mL) were added to aqueous layer. The mixture was shaken vigorously in a separatory funnel. The organic layers were combined, washed with brine (50 mL), dried ($Na_2SO_4$), and concentrated on rotovap to give 15 g of an off-white solid. This solid containing the crude product was slurried in acetonitrile (200 mL) and the suspension was heated in an oil bath to reflux (~85° C.) for about 30 minutes with stirring. The mixture was allowed to cool down to room temperature over 1 hour then aged at 4° C. for another 2 hours. The solid formed was collected by suction filtration. The remaining solid in the flask was transferred onto a filter funnel using some MTBE. The cake was washed with additional MTBE (total filtrate volume ~300 mL), suction dried, and then placed in a vacuum oven at 40° C. for several hours to afford tert-butyl 5-amino-2-(4-hydroxy-1-oxoisoindolin-2-yl)-5-oxopentanoate as a white solid (7.3 g 72% yield, adjusted for purity of starting material and product): mp: 198-200° C.; $^1$H NMR (DMSO-$d_6$) δ 1.39 (s, 9H, tBu), 1.93-2.14 (m, 3H, $CH_2$, CHH), 2.15-2.33 (m, 1H, CHH), 4.35 (s, 2H, $CH_2$), 4.61-4.83 (m, 1H, CH), 6.76 (br. s., 1H, NH), 6.97-7.07 (m, 1H, Ar), 7.11-7.20 (m, 1H, Ar), 7.26 (br. s., 1H, NH), 7.29-7.36 (m, 1H, Ar), 10.10 (s, 1H, OH); $^{13}$C NMR (DMSO-$d_6$) δ 24.81, 27.56, 31.44, 44.71, 54.02, 81.38, 113.72, 117.96, 127.99, 129.36, 133.36, 152.50, 168.36, 169.88, 172.94; LCMS MH=335; Anal Calcd for $C_{17}H_{22}N_2O_5$+0.19 $H_2O$: C, 60.45; H, 6.68; N, 8.29. Found: C, 60.44; H, 6.62; N, 8.27.

Step 2: tert-Butyl 5-amino-2-(4-hydroxy-1-oxoisoindolin-2-yl)-5-oxopentanoate (300 mg, 0.897 mmol), N,N-diisopropylethylamine (157 μL, 0.897 mmol), and $K_2CO_3$ (124 mg, 0.897 mmol) were slurried in DMF (5 mL). After 10 minutes, 4-(bromomethyl)benzamide (192 mg, 0.897 mmol) was added and the reaction mixture was stirred at room temperature for 2 days. Removal of DMF in vacuo gave a residue that was partitioned between EtOAc and 0.2 N aqueous HCl. The aqueous layer was saturated with NaCl and washed with additional EtOAc. The organic layers were combined (total volume ~400 mL), washed with brine, dried ($Na_2SO_4$), and concentrated in vacuo to give 400 mg of tert-butyl 5-amino-2-(4-hydroxy-1-oxoisoindolin-2-yl)-5-oxopentanoate as an oil. LCMS MH=420. The oil was used in the next step without further purification.

Step 3: To a solution of tert-butyl 5-amino-2-(4-hydroxy-1-oxoisoindolin-2-yl)-5-oxopentanoate (400 mg) in dichloromethane (5 mL) was added TFA (1.5 mL) and the resulting mixture was stirred at room temperature for 3.5 hours (LCMS indicated deprotection was complete). The reaction mixture was concentrated in vacuo and trace volatiles were chased with a small portion of dichloromethane (2×) and concentrated again to give 400 mg of 4-carbamoyl-2-[4-(4-carbamoyl-benzyloxy)-1-oxo-1,3-dihydro-isoindol-2-yl]-butyric acid as a white solid. This material was used without further purification. 4-Carbamoyl-2-[4-(4-carbamoyl-benzyloxy)-1-oxo-1,3-dihydro-isoindol-2-yl]-butyric acid (369 mg, 0.897 mmol, assuming theoretical yield from previous step) was dissolved in DMF (10 mL). To the solution was added CDI (167 mg, 1.03 mmol), and the mixture was stirred at room temperature for 12 hours and then heated to 80° C. for 6 hours. The reaction mixture was cooled on an ice bath and a 0.1 N HCl solution was slowly added until a white precipitate was obtained. The solid was filtered and washed with minimal water, then dried in a vacuum oven to give 150 mg of crude product. The crude product was dissolved in DMF and purified by injection onto a C-18 preparatory HPLC column. The product was eluted with an acetonitrile/water gradient (0.1% formic acid in both mobile phases, 5% to 60% acetonitrile over 30 minutes) and fractions were collected by mass trigger. The desired fractions were combined and concentrated in vacuo to give 4-((2-(2,6-dioxopiperidin-3-yl)-1-oxoisoindolin-4-yloxy)methyl)benzamide as a white solid (85 mg, 24% combined yield for step 2 and step 3): HPLC: Waters Symmetry $C_{18}$, 5 μm, 3.9×150 mm, 1 ml/min, 240 nm, 25/75 acetonitrile/0.1% $H_3PO_4$, 3.41 min (98.8%); mp: 278-280° C.; $^1$H NMR (DMSO-$d_6$) δ 1.89-2.05 (m, 1H, CHH), 2.34-2.48 (m, 1H, CHH), 2.52-2.68 (m, 1H, CHH), 2.83-3.01 (m, 1H, CHH), 4.29 (d, J=17.4 Hz, 1H, CHH), 4.45 (d, J=17.4 Hz, 1H, CHH), 5.12 (dd, J=5.0, 13.1 Hz, 1H, CH), 5.32 (s, 2H, $CH_2$), 7.19-7.41 (m, 3H, Ar, NH), 7.43-7.52 (m, 1H, Ar), 7.56 (d, J=8.1 Hz, 2H, Ar), 7.89 (d, J=8.3 Hz, 2H, Ar), 7.97 (br. s., 1H, NH), 10.98 (s, 1H, NH); $^{13}$C NMR (DMSO-$d_6$) δ 3 21.27, 30.11, 44.00, 50.50, 67.88, 113.91, 114.26, 126.08, 126.53, 128.72, 128.91, 132.26, 132.79, 138.72, 152.21, 166.42, 166.87, 169.88, 171.73; LCMS MH=394; Anal. Calcd. For $C_{21}H_{19}N_3O_5$+0.8 $H_2O$+0.28 acetonitrile+1.1 HCOOH: C, 57.57; H, 4.68; N, 9.95. Found: C, 57.92; H, 5.07; N, 9.78.

5.164 3-(4-(4-Chloro-3-Methylbenzyloxy)-1-Oxoisoindolin-2-yl)Piperidine-2,6-Dione

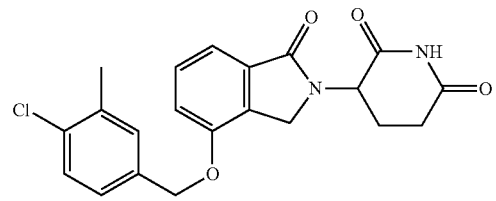 [SMILES: Cc1cc(COc2cccc3c2CN(C2CCC(=O)NC2=O)C3=O)ccc1Cl]

Step 1: To a solution of 4-chloro-3-methylbenzoic acid (1 g, 5.86 mmol) in THF (10 mL), was slowly added the borane solution in THF (1M, 8.79 mL, 8.79 mmol), and the mixture was stirred at room temperature overnight. The reaction was quenched by adding water (1 mL) dropwise, and then 30 mL of water was added. The mixture was saturated with excess potassium carbonate, extracted with ethyl acetate (2×50 mL), the combined organic layers were dried over $MgSO_4$, and the solvent was evaporated under vacuum to give (4-chloro-3-methylphenyl)methanol (900 mg, 98% yield). $^1$H NMR (DMSO-$d_6$) δ 2.32 (s, 3H, $CH_3$), 4.45 (d, J=5.7 Hz, 2H, $CH_2$), 5.22 (t, J=5.7 Hz, 1H, OH), 7.15 (dd, J=1.6, 8.2 Hz, 1H, Ar), 7.28 (s, 1H, Ar), 7.34 (d, J=8.1 Hz, 1H, Ar).

Step 2: Polymer-supported triphenylphosphine (3 mmol/g, 0.69 g, 2.06 mmol) was added to a stirred suspension of methyl 5-amino-4-(4-hydroxy-1-oxoisoindolin-2-yl)-5-opentanoate (300 mg, 1.03 mmol) in THF (10 mL) at 0° C., followed by diisopropyl azodicarboxylate (416 mg, 2.06 mmol). After stirring for 10 minutes, (4-chloro-3-methylphenyl)methanol (322 mg, 1.03 mmol) was added. The mixture was stirred at room temperature overnight and filtered. The resin was washed with ethyl acetate (7×10 mL). The combined filtrate was washed with water and brine, the solvent was evaporated, and the crude was purified by ISCO (40 g column, MeOH/CH$_2$Cl$_2$ gradient from 0% to 3% in 40 min) to give methyl 5-amino-4-(4-(4-chloro-3-methylbenzyloxy)-1-oxoisoindolin-2-yl)-5-oxopentanoate (430 mg, 97% yield). $^1$H NMR (DMSO-d$_6$) δ 2.25 (d, 4H, CH$_2$, CH$_2$), 2.35 (s, 3H, CH$_3$), 3.50 (s, 3H, CH$_3$), 4.33-4.63 (m, 2H, CH$_2$), 4.69-4.78 (m, 1H, CH), 5.21 (s, 2H, CH$_2$), 7.19 (s, H, NH), 7.24-7.39 (m, 3H, Ar), 7.39-7.51 (m, 3H, Ar), 7.59 (br. s., 1H, NH).

Step 3: To a solution of methyl 5-amino-4-(4-(4-chloro-3-methylbenzyloxy)-1-oxoisoindolin-2-yl)-5-oxopentanoate in THF (10 mL), was added potassium tert-butoxide (112 mg, 1 mmol) at 0° C., and the mixture was stirred at 0° C. for 10 minutes, warmed up to room temperature, and stirred for 3 hours. The reaction was quenched by adding aqueous HCl (1N, 2 mL). The mixture was diluted with water (30 mL) and extracted with ethyl acetate (3×50 mL). The combined organic layers were washed with brine (20 mL), dried over MgSO$_4$, the solvent was evaporated under vacuum, and the crude was reslurried in acetonitrile (5 mL) for 2 hours and filtered to give 3-(4-(4-chloro-3-methylbenzyloxy)-1-oxoisoindolin-2-yl)piperidine-2,6-dione as a white solid (180 mg, 45% yield); mp: 217-219° C.; $^1$H NMR (DMSO-d$_6$) δ 2.35 (s, 3H, CH$_3$), 2.48 (br. s., 1H, CHH), 2.61 (br. s., 1H, CHH), 2.80-3.03 (m, 1H, CHH), 4.19-4.52 (m, 2H, CH$_2$), 5.11 (dd, J=5.1, 13.2 Hz, 1H, CHH), 5.21 (s, 2H, CH$_2$), 7.25-7.39 (m, 3H, Ar), 7.39-7.57 (m, 3H, Ar), 10.97 (s, 1H, NH); $^{13}$C NMR (DMSO-d$_6$) δ 19.56, 22.34, 31.16, 45.07, 51.58, 68.77, 114.97, 115.32, 126.87, 128.88, 129.80, 129.95, 130.43, 132.77, 133.33, 135.52, 135.66, 153.32, 167.96, 170.96, 172.81; LCMS MH=399; HPLC: Waters Symmetry C-18, 3.9×150 mm, 5 μm, 1 mL/min, 240 nm, 50/50 acetonitrile/0.1% H$_3$PO$_4$ t$_R$=5.29 (99.50%); Anal. Calcd for C$_{21}$H$_{19}$ClN$_2$O$_4$: C, 63.24; H, 4.80; N, 7.02; Found: C, 62.99; H, 4.94; N, 6.86.

5.165 3-(1-Oxo-4-(4-(Trifluoromethyl)Benzyloxy) Isoindolin-2-yl)Piperidine-2,6-Dione

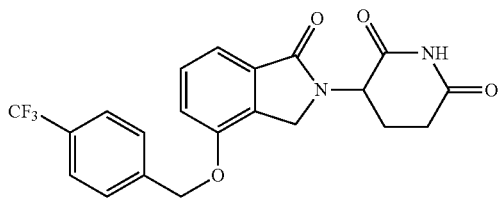 [SMILES: O=C1CCC(N2Cc3c(OCc4ccc(C(F)(F)F)cc4)cccc3C2=O)C(=O)N1]

To a mixture of methyl 5-amino-4-(4-hydroxy-1-oxoisoindolin-2-yl)-5-oxopentanoate (0.10 g, 0.34 mmol) and K$_2$CO$_3$ (0.05 g, 0.34 mmol) in DMF (10 mL), was slowly added 4-(trifluoromethyl)benzyl bromide (0.07 g, 0.31 mmol). The reaction mixture was stirred at room temperature overnight. Additional 4-(trifluoromethyl)benzyl bromide (0.008 g, 0.03 mmol) was added, and the reaction mixture was stirred at room temperature overnight. Additional K$_2$CO$_3$ (0.05 g, 0.34 mmol) was added, and the reaction mixture was heated at 80° C. for 24 hours. Acetic acid (5 drops) was added to the reaction mixture. The solvent was evaporated and ethyl acetate (100 mL) was added to the reaction mixture. It was then washed with a saturated solution of sodium bicarbonate (2×100 mL) and brine (100 mL), and dried (MgSO$_4$). After filtration of the drying agent, solvent was concentrated down and the residue was purified by ISCO flash (40 g column, gradient methanol/methylene chloride 0/100 to 5/95 in 20 min, eluting product at 5/95). The solvent was evaporated. The residue was stirred in ether, and solid was filtered and dried to give 3-(1-oxo-4-(4-(trifluoromethyl)benzyloxy)isoindolin-2-yl)piperidine-2,6-dione as a white solid (0.09 g, 72% yield). This experiment was repeated with 5-amino-4-(4-hydroxy-1-oxoisoindolin-2-yl)-5-oxopentanoate (0.30 g, 1.03 mmol) to give 3-(1-oxo-4-(4-(trifluoromethyl)benzyloxy)isoindolin-2-yl)piperidine-2,6-dione (0.12 g) and another time with 5-amino-4-(4-hydroxy-1-oxoisoindolin-2-yl)-5-oxopentanoate (0.10 g, 0.34 mmol) to give 3-(1-oxo-4-(4-(trifluoromethyl)benzyloxy)isoindolin-2-yl)piperidine-2,6-dione (0.05 g). The 3 batches were combined. Solids were dissolved in ethyl acetate (20 mL). The solvent was evaporated. The residue was stirred in ether, and solid was filtered and dried to give 3-(1-oxo-4-(4-(trifluoromethyl)benzyloxy)isoindolin-2-yl) piperidine-2,6-dione as a white solid (0.24 g): HPLC: Waters Symmetry C-18, 3.9×150 mm, 5 μm, 1 mL/min, 240 nm, acetonitrile/0.1% H3PO4: gradient 10/90 to 90/10 in 15 min; 5 min at 90/10:12.68 min (98.97%); mp: 241-243° C.; 1H NMR (DMSO-d6) □ 1.17 (t, J=7.1 Hz, 1H, Ethyl Acetate (5%)), 1.82-2.18 (m, 1H, CHH), 2.29-2.47 (m, 1H, CHH), 2.58 (d, J=19.1 Hz, 1H, CHH), 2.79-3.12 (m, 1H, CHH), 4.03 (d, J=7.2 Hz, 1H, Ethyl Acetate (5%)), 4.17-4.39 (m, 1H, CHH), 4.38-4.69 (m, 1H, CHH), 5.13 (dd, J=5.0, 13.1 Hz, 1H, CH), 5.38 (s, 2H, CH2), 7.33 (dd, J=7.8, 10.5 Hz, 2H, Ar), 7.41-7.59 (m, 1H, Ar), 7.75 (q, J=8.3 Hz, 4H, Ar), 10.99 (s, 1H, NH); 13C NMR (DMSO-d6) □ 22.37, 31.16, 45.03, 51.56, 68.58, 114.94, 115.47, 124.16 (q, J=270.8 Hz), 125.33 (q, J=3.8 Hz), 128.01, 128.41 (q, J=31.5 Hz), 129.84, 129.96, 133.39, 141.52, 153.17, 167.91, 170.96, 172.81; LCMS MH=419; Anal Calcd for C21H17N2O4F3+0.2 H2O: C, 59.77; H, 4.16; N, 6.64; Found: C, 59.66; H, 4.12; N, 6.52.

5.166 3-[4-(3-Bromo-Benzyloxy)-1-Oxo-1,3-Dihydro-Isoindol-2-yl]-Piperidine-2,6-Dione

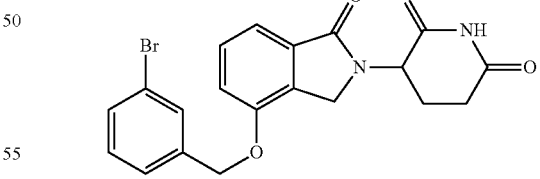

Step 1: tert-Butyl 5-amino-2-(4-hydroxy-1-oxoisoindolin-2-yl)-5-oxopentanoate (300 mg, 0.897 mmol,), N,N-diisopropylethylamine (157 μL, 0.897 mmol), and K$_2$CO$_3$ (124 mg, 0.897 mmol) were slurried in DMF (5 mL). After 10 minutes, 1-bromo-3-bromomethyl-benzene (224 mg, 0.897 mmol) was added and the reaction mixture was stirred at room temperature for 2 days. Removal of DMF in vacuo gave a residue that was partitioned between EtOAc and 0.2 N aqueous HCl. The EtOAc layer was washed with brine, dried (Na$_2$SO$_4$), and concentrated in vacuo to give 450 mg of 2-[4-(3-bromo-benzyloxy)-1-oxo-1,3-dihydro-isoindol-2-yl]-4-carbamoyl-butyric acid tert-butyl ester as a tan oil. LCMS MH=503, 505. The oil was used in the next step without further purification.

Step 2: To a solution of 2-[4-(3-bromo-benzyloxy)-1-oxo-1,3-dihydro-isoindol-2-yl]-4-carbamoyl-butyric acid tert-butyl ester (450 mg) in dichloromethane (5 mL), was added TFA (1.5 mL), and the resulting mixture was stirred at room temperature for 4 hours (LCMS indicated deprotection was complete). The reaction mixture was concentrated in vacuo and the resulting solid was triturated with $Et_2O$ and then collected by filtration. Drying of the solid in vacuo provided 400 mg of 2-[4-(3-bromo-benzyloxy)-1-oxo-1,3-dihydro-isoindol-2-yl]-4-carbamoyl-butyric acid as a tan solid. This material was used without further purification.

Step 3: To a solution of 2-[4-(3-bromo-benzyloxy)-1-oxo-1,3-dihydro-isoindol-2-yl]-4-carbamoyl-butyric acid (400 mg, 0.897 mmol, assuming theoretical yield from previous step) in DMF (5 mL), was added CDI (145 mg, 0.897 mmol). The reaction mixture was warmed to 70° C. and stirred overnight. After 21 hours, catalytic DMAP was added, followed by another equivalent of CDI. The mixture was stirred at 80° C. for an additional 15 hours. The reaction mixture was cooled on an ice bath and the crude product was precipitated by addition of 0.2 N aqueous HCl. The solid was collected by filtration, washed with copious water, and dried in vacuo to give 150 mg of crude product. The crude product was dissolved in DMF and purified by injection onto a C-18 preparatory HPLC column. The product was eluted with an acetonitrile/water gradient (0.1% formic acid in both mobile phases) and fractions were collected by mass trigger. The desired fractions were combined and concentrated in vacuo to give 3-[4-(3-bromo-benzyloxy)-1-oxo-1,3-dihydro-isoindol-2-yl]-piperidine-2,6-dione as a white solid (80 mg, 21% combined yield for step 1 and step 2): HPLC: Waters Symmetry $C_{18}$, 5 μm, 3.9×150 mm, 1 ml/min, 240 nm, 50/50 acetonitrile/0.1% $H_3PO_4$, 4.59 min (95.5%); mp: 238-240° C.; $^1H$ NMR (DMSO-$d_6$) δ 1.89-2.05 (m, 1H, CHH), 2.36-2.48 (m, 1H, CHH), 2.53-2.65 (m, 1H, CHH), 2.81-3.02 (m, 1H, CHH), 4.28 (d, J=17.4 Hz, 1H, CHH), 4.45 (d, J=17.6 Hz, 1H, CHH), 5.11 (dd, J=5.1, 13.2 Hz, 1H, CH), 5.26 (s, 2H, $CH_2$), 7.25-7.42 (m, 3H, Ar), 7.45-7.59 (m, 3H, Ar), 7.70 (d, J=1.7 Hz, 1H, Ar), 10.97 (s, 1H, NH); $^{13}C$ NMR (DMSO-$d_6$) δ 22.26, 31.09, 45.00, 51.51, 68.48, 114.87, 115.34, 121.61, 126.52, 129.75, 129.88, 130.15, 130.61, 130.74, 133.30, 139.36, 153.15, 167.86, 170.88, 172.74; LCMS MH=429, 431; Anal Calcd for $C_{20}H_{17}N_2O_4$+ 0.8 $H_2O$: C, 54.14; H, 4.23; N, 6.31; Br, 18.01. Found: C, 53.92; H, 3.88; N, 6.32; Br, 18.16.

5.167 4-((2-(2,6-Dioxopiperidin-3-yl)-1-Oxoisoindolin-4-yloxy)Methyl)-N,N-Dimethylbenzene Sulfonamide Step 1: To a solution of 4-(N,N-dimethylsulfamoyl)benzoic acid (1 g, 4.36 mmol) in THF (10 mL), was slowly added the borane solution in THF (1M, 8.72 mL, 8.72 mmol), and the mixture was stirred at room temperature overnight. The reaction was quenched by adding water (1 mL) dropwise, and then 30 mL of water was added. The mixture was saturated with excess potassium carbonate and extracted with ethyl acetate (3×40 mL), and the combined organic layers were dried over $MgSO_4$. The solvent was evaporated under vacuum to give 4-(hydroxymethyl)-N,N-dimethylbenzenesulfonamide (700 mg, 75% yield). $^1H$ NMR (DMSO-$d_6$) δ 2.59 (s, 6H, $CH_3$, $CH_3$), 4.61 (d, J=5.9 Hz, 2H, $CH_2$), 5.44 (s, 1H, OH), 7.54-7.62 (m, 2H, Ar), 7.67-7.75 (m, 2H, Ar).

Step 2: Polymer-supported triphenylphosphine (3 mmol/g, 0.69 g, 2.06 mmol) was added to a stirred suspension of methyl 5-amino-4-(4-hydroxy-1-oxoisoindolin-2-yl)-5-opentanoate (300 mg, 1.03 mmol) in THF (10 mL) at 0° C., followed by diisopropyl azodicarboxylate (416 mg, 2.06 mmol). After stirring for 10 minutes, 4-(hydroxymethyl)-N,N-dimethylbenzenesulfonamide (443 mg, 2.06 mmol) was added. The mixture was stirred at room temperature overnight and filtered. The resin was washed with ethyl acetate (7×10 mL). The combined filtrate was washed with water and brine, the solvent was evaporated, and the crude was purified by ISCO (40 g column, MeOH/$CH_2Cl_2$ gradient from 0% to 4% in 40 min) to give methyl 5-amino-4-(4-(4-(N,N-dimethylsulfamoyl)benzylox-yl)-1-oxoisoindolin-2-yl)-5-oxopentanoate (340 mg, 68% yield). $^1H$ NMR (DMSO-$d_6$) δ 1.93-2.36 (m, 4H, $CH_2$, $CH_2$), 2.62 (s, 6H, $CH_3$, $CH_3$), 3.50 (s, 3H, $CH_3$), 4.40-4.66 (m, 2H, $CH_2$), 4.75 (dd, J=4.7, 10.2 Hz, 1H, CHH), 5.39 (s, 2H, $CH_2$), 7.21 (s, 1H, NHH), 7.27-7.36 (m, 2H, Ar), 7.43-7.53 (m, 1H, Ar), 7.60 (s, 1H, NHH), 7.73-7.85 (m, 4H, Ar).

Step 3: To a solution of methyl 5-amino-4-(4-(4-(N,N-dimethylsulfamoyl)benzyloxyl)-1-oxoisoindolin-2-yl)-5-oxopentanoate (573 mg, 1.17 mmol) in THF (20 mL), was added potassium tert-butoxide (131 mg, 1 mmol) at 0° C. The mixture was stirred at 0° C. for 10 minutes, warmed up to room temperature and stirred for 4 hours. Additional potassium t-butoxide (40 mg, 0.4 mmol) was added, and the mixture was kept stirring for 2 hours. The reaction was quenched by adding aqueous HCl (1N, 2 mL), and water (50 mL) was added dropwise. The precipitate formed was corrected by filtration, and the crude was reslurried with acetonitrile (10 mL) to give 4-((2-(2,6-dioxopiperidin-3-yl)-1-oxoisoindolin-4-yloxy)methyl)-N,N-dimethylbenzenesulfonamide as a white solid (260 mg, 48% yield); mp: 261-263° C.; $^1H$ NMR (DMSO-$d_6$) δ 1.90-2.10 (m, 1H, CHH), 2.34-2.48 (m, 1H, CHH), 2.56 (d, J=3.4 Hz, 1H, CHH), 2.62 (s, 6H, $CH_3$, $CH_3$), 2.82-3.03 (m, 1H, CHH), 4.25-4.56 (m, 2H, $CH_2$), 5.13 (dd, J=4.9, 13.2 Hz, 1H, CHH), 5.39 (s, 2H, $CH_2$), 7.28-7.41 (m, 2H, Ar), 7.45-7.57 (m, 1H, Ar), 7.73-7.83 (m, 4H, Ar), 10.99 (s, 1H, NH); $^{13}C$ NMR (DMSO-$d_6$) δ 22.37, 31.15, 37.51, 45.04, 51.56, 68.56, 114.99, 115.54, 127.71, 127.95, 129.87, 129.96, 133.37, 134.20, 142.02, 153.19, 167.94, 170.96, 172.84; LCMS MH=458; HPLC: Waters Symmetry C-18, 3.9×150 mm, 5 μm, 1 mL/min, 240 nm, 40/60 acetonitrile/0.1% $H_3PO_4$ $t_R$=3.61 (98.56%); Anal. Calcd for $C_{22}H_{23}N_3O_6S$+0.5 $H_2O$: C, 56.64; H, 5.19; N, 9.01; Found: C, 56.62; H, 5.18; N, 8.89.

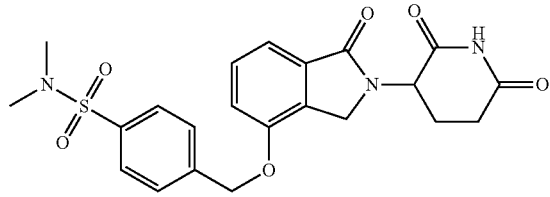 [SMILES: CN(C)S(=O)(=O)c1ccc(COc2cccc3c2CN(C2CCC(=O)NC2=O)C3=O)cc1]

5.168 3-[4-(3-Amino-Benzyloxy)-1-Oxo-1,3-Dihydro-Isoindol-2-yl]-Piperidine-2,6-Dione

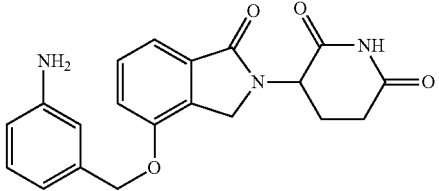 [SMILES: Nc1cccc(COc2cccc3c2CN(C2CCC(=O)NC2=O)C3=O)c1]

To a slurry of 3-(4-(3-nitrobenzyloxy)-1-oxoisoindolin-2-yl)piperidine-2,6-dione (300 mg, 0.759 mmol) in ethanol (10 mL), was added a solution of sodium dithionite (661 mg, 3.79 mmol) in water (5 mL). The mixture was stirred for 20 minutes at room temperature then concentrated in vacuo. The residue was dissolved in DMF, the solution passed through a syringe filter, and the filtrate injected onto a C-18 preparatory HPLC column. The product was eluted with an acetonitrile/water gradient (0.1% formic acid in both mobile phases, 5% to 60% acetonitrile over 20 min) and fractions were collected by mass trigger. The desired fractions were combined and concentrated in vacuo to give 3-[4-(3-amino-benzyloxy)-1-oxo-1,3-dihydro-isoindol-2-yl]-piperidine-2,6-dione (10 mg, 3% yield) as a white solid: HPLC: Waters Symmetry $C_{18}$, 5 µm, 3.9×150 mm, 1 ml/min, 240 nm, 15/85 acetonitrile/0.1% $H_3PO_4$, 4.17 min (95.6%); mp; 109-113° C.; $^1$H NMR (DMSO-$d_6$) δ 1.87-2.07 (m, 1H, CHH), 2.36-2.48 (m, 1H, CHH), 2.53-2.65 (m, 1H, CHH), 2.81-3.02 (m, 1H, CHH), 4.25 (d, J=17.6 Hz, 1H, CHH), 4.41 (d, J=17.4 Hz, 1H, CHH), 5.00-5.20 (m, 5H, $CH_2$, $NH_2$, CH), 6.46-6.55 (m, 1H, Ar), 6.59 (d, J=7.6 Hz, 1H, Ar), 6.62-6.70 (m, 1H, Ar), 7.01 (t, J=7.7 Hz, 1H, Ar), 7.30 (dd, J=7.6, 9.8 Hz, 2H, Ar), 7.41-7.53 (m, 1H, Ar), 10.94 (br. s., 1H, NH); $^{13}$C NMR (DMSO-$d_6$) δ 22.38, 31.21, 45.10, 51.58, 69.95, 112.74, 113.49, 114.84, 114.98, 115.08, 128.93, 129.78, 129.87, 133.26, 137.14, 148.80, 153.60, 168.02, 170.99, 172.83; LCMS MH=366; Anal Calcd for $C_{20}H_{19}N_3O_4$: C, 65.74; H, 5.24; N, 11.50. Found: C, 58.81; H, 5.20; N, 9.99.

5.169 3-[4-(3,4-Difluoro-Benzyloxy)-1-Oxo-1,3-Dihydro-Isoindol-2-yl]-Piperidine-2,6-Dione

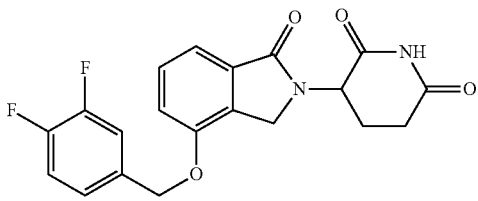 [SMILES: O=C1CCC(N2Cc3c(OCc4ccc(F)c(F)c4)cccc3C2=O)C(=O)N1]

Step 1: A solution of 3-acetoxy-2-bromomethyl-benzoic acid methyl ester (1.0 g, 3.48 mmol) in acetonitrile (10 mL) was added to a stirred suspension of tert-butyl 4,5-diamino-5-oxopentanoate hydrochloride and N,N-diisopropylethylamine (1.4 mL, 7.66 mmol) in acetonitrile (20 mL). The mixture was stirred at room temperature for 3.5 hours at room temperature. Acetic acid (0.5 mL) was added and the temperature was raised to 60° C. After 3 days, water (2 mL) was added to the reaction mixture, the temperature was raised to 80° C., and the mixture stirred for another 3 days. The reaction mixture was cooled to room temperature. Piperidine (1 mL) was added, and stirring was continued for an additional 6 hours at room temperature. The mixture was concentrated in vacuo to remove most volatiles. The resulting viscous oil was partitioned between EtOAc (200 mL) and 0.2 N HCl (50 mL). The aqueous layer was extracted with additional EtOAc (150 mL). The EtOAc layers were combined, dried ($Na_2SO_4$), and concentrated on a rotovap to give 1.16 g of crude product as an off-white foam. Purification of this foam on a $SiO_2$ flash column (CombiFlash, 40 g $SiO_2$ prepacked column, EtOAc/Hexanes gradient) furnished 4-carbamoyl-4-(4-hydroxy-1-oxo-1,3-dihydro-isoindol-2-yl)-butyric acid tert-butyl ester as a white foam (740 mg, 63% yield). LCMS MH=335. $^1$H NMR (DMSO-$d_6$) δ 1.24-1.37 (m, 9H, tBu), 1.81-2.06 (m, 3H, CHH, $CH_2$), 2.08-2.27 (m, 1H, CHH), 4.32 (d, J=17.4 Hz, 1H, CHH), 4.49 (d, J=17.4 Hz, 1H, CHH), 4.71 (dd, J=4.1, 10.1 Hz, 1H, CH), 6.88-7.04 (m, 1H, Ar), 7.08-7.23 (m, 2H, Ar, NH), 7.26-7.40 (m, 1H, Ar), 7.55 (br. s., 1H, NH), 10.02 (s, 1H, OH).

Step 2: A slurry of 4-carbamoyl-4-(4-hydroxy-1-oxo-1,3-dihydro-isoindol-2-yl)-butyric acid tert-butyl ester (250 mg, 0.748 mmol), N,N-diisopropylethylamine (130 µl, 0.748 mmol), and $Cs_2CO_3$ (244 mg, 0.748 mmol) in DMF (5 mL) was stirred for 10 minutes at room temperature, followed by addition of 4-chloromethyl-1,2-difluoro-benzene (122 mg, 0.748 mmol). The mixture was stirred at room temperature for 15 hours then concentrated in vacuo to give crude 4-carbamoyl-4-[4-(3,4-difluoro-benzyloxy)-1-oxo-1,3-dihydro-isoindol-2-yl]-butyric acid tert-butyl ester as a tan solid (344 mg). This solid was taken up in dry THF (5 mL), and solid KOtBu (84 mg, 0.747 mmol) was added in one portion with stirring. The mixture was stirred at room temperature for 40 minutes, then the reaction was quenched by addition of 1 N aqueous HCl (15 mL). The resulting slurry was diluted further with water, and the solid collected by filtration, washed with additional water, and suction dried on filter funnel. The solid was dissolved in minimal DMF and purified by injection onto a C-18 preparatory HPLC column. The product was eluted with an acetonitrile/water gradient (0.1% formic acid in both mobile phases) and fractions were collected by mass trigger. The desired fractions were combined and concentrated in vacuo to give 3-[4-(3,4-difluoro-benzyloxy)-1-oxo-1,3-dihydro-isoindol-2-yl]-piperidine-2,6-dione (140 mg, 48% yield) as a white solid: HPLC: Waters Symmetry $C_{18}$, 5 µm, 3.9×150 mm, 1 ml/min, 240 nm, 40/60 acetonitrile/0.1% $H_3PO_4$, 5.53 min (97.9%); mp: 228-230° C.; $^1$H NMR (DMSO-$d_6$) δ 1.90-2.08 (m, 1H, CHH), 2.32-2.48 (m, 1H, CHH), 2.52-2.67 (m, 1H, CHH), 2.81-3.00 (m, 1H, CHH), 4.28 (d, J=17.6 Hz, 1H, CHH), 4.45 (d, J=17.6 Hz, 1H, CHH), 5.11 (dd, J=5.1, 13.2 Hz, 1H, CH), 5.24 (s, 2H, $CH_2$), 7.23-7.41 (m, 3H, Ar), 7.41-7.54 (m, 2H, Ar), 7.59 (ddd, J=1.9, 8.0, 11.4 Hz, 1H, Ar), 10.97 (s, 1H, NH); $^{13}$C NMR (DMSO-$d_6$) δ 22.34, 31.16, 45.04, 51.56, 68.17, 114.93, 115.44, 116.76 (d, $J_{C-F}$=17.6 Hz), 117.52 (d, $J_{C-F}$=17.6 Hz), 124.52 (dd, $J_{C-F}$=3.3, 6.6 Hz), 129.81, 130.00, 133.36, 134.42 (dd, $J_{C-F}$=3.3, 5.5 Hz), 149.12 (dd, $J_{C-F}$=23.2, 245.3 Hz), 149.44 (dd, $J_{C-F}$=23.2, 245.8 Hz), 153.14, 167.93, 170.95, 172.81; LCMS MH=387; Anal Calcd for $C_{20}H_{16}F_2N_2O_4$+0.7 $H_2O$: C, 60.21; H, 4.39; N, 7.00; F, 9.52. Found: C, 60.13; H, 4.09; N, 6.91; F, 9.45.

5.170 3-(4-(4-Ethylbenzyloxy)-1-Oxoisoindolin-2-yl)Piperidine-2,6-Dione

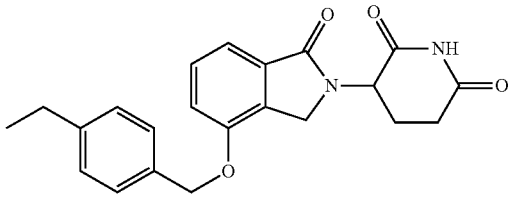 [SMILES: CCc1ccc(COc2cccc3c2CN(C2CCC(=O)NC2=O)C3=O)cc1]

To a mixture of triphenylphosphine polymer supported (0.75 g, 2.26 mmol) and methyl 5-amino-4-(4-hydroxy-1-oxoisoindolin-2-yl)-5-oxopentanoate (0.30 g, 1.03 mmol) in THF (20 mL) cooled down to 0° C., was added drop wise DIAD (0.45 ml, 2.26 mmol). 4-Ethylbenzyl alcohol (0.16 mL, 1.23 mmol) was then added. The reaction mixture was stirred at 0° C. for 1 hour and then at room temperature overnight. The reaction mixture was then filtered through celite. Celite was washed with ethyl acetate (100 mL). The ethyl acetate phase was washed with water, dried with MgSO₄, and solvent was evaporated. The residue was purified by ISCO flash (40 g column, gradient EtOAc/Hexanes 50/50 to 100/0 in 20 min, eluting product at 100/0). The solvent was evaporated and methyl 5-amino-4-(4-(4-ethylbenzyloxy)-1-oxoisoindolin-2-yl)-5-oxopentanoate was obtained as a sticky, transparent solid (0.20 g, 48% yield). To the solid stirred in THF (10 mL) and cooled down to 0° C., was added KOtBu (0.05 g, 0.46 mmol), and the reaction mixture was stirred for 3 hours. Acetic acid (1 mL) was added to reaction mixture. Ethyl acetate (100 mL) was added, and it was washed with a saturated solution of sodium bicarbonate (2×100 mL) and brine (100 mL), and dried (MgSO₄). After filtration of the drying agent, solvent was concentrated down to give 3-(4-(4-ethylbenzyloxy)-1-oxoisoindolin-2-yl)piperidine-2,6-dione as a white solid (0.12 g, 69% yield): HPLC: Waters Symmetry $C_{18}$, 5 µm, 3.9×150 mm, 1 mL/min, 240 nm, gradient: acetonitrile/0.1% H3PO4, 10/90 to 90/10 in 15 min, 90/10 for 5 min, 12.96 min (98.16%); mp: 158-160° C.; 1H NMR (DMSO-d6) δ 1.17 (t, J=7.6 Hz, 3H, CH3), 1.82-2.13 (m, 1H, CHH), 2.31-2.47 (m, 1H, CHH), 2.53-2.72 (m, 3H, CHH, CH₂), 2.78-3.10 (m, 1H, CHH), 4.24 (d, J=17.4 Hz, 1H, CHH), 4.40 (d, J=17.6 Hz, 1H, CHH), 5.11 (dd, J=4.9, 13.2 Hz, 1H, CH), 5.20 (s, 2H, CH₂), 6.83-7.95 (m, 7H, Ar), 10.97 (s, 4H, NH); 13C NMR (DMSO-d6) δ 15.58, 22.33, 27.85, 31.18, 45.06, 51.55, 69.44, 114.96, 115.15, 127.82, 127.86, 129.77, 129.93, 133.27, 133.82, 143.59, 153.48, 167.99, 170.96, 172.81; LCMS MH=379; Anal. Calcd for $C_{22}H_{22}N_2O_4$+0.7 H₂O: C, 67.57; H, 6.03; N, 7.16; Found: C, 67.40; H, 5.87; N, 7.12.

5.171 3-[4-(4-Hydroxymethyl-Benzyloxy)-1-Oxo-1,3-Dihydro-Isoindol-2-yl]-Piperidine-2,6-Dione

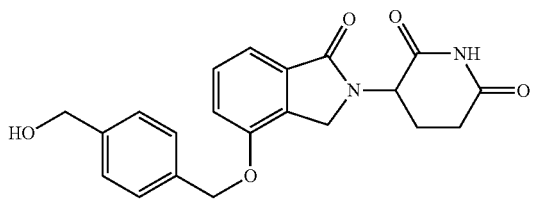 [SMILES: O=C1CCC(N2Cc3c(OCc4ccc(CO)cc4)cccc3C2=O)C(=O)N1]

Step 1: A slurry of 4-carbamoyl-4-(4-hydroxy-1-oxo-1,3-dihydro-isoindol-2-yl)-butyric acid tert-butyl ester (1.5 g, 4.49 mmol), N,N-diisopropylethylamine (784 µl, 4.49 mmol), and K₂CO₃ (620 mg, 4.49 mmol) in DMF (15 mL) was stirred for 5 minutes at room temperature, followed by addition of (4-chloromethyl-phenyl)-methanol (902 mg, 4.49 mmol). The mixture was stirred at room temperature for 15 hours then heated to 70° C. for 3 hours. Piperidine (800 µl) was added to the mixture to scavenge unconsumed (4-chloromethyl-phenyl)-methanol. The mixture was stirred for an additional 18 hours at 70° C. The mixture was diluted with water (50 mL) and EtOAc (200 mL). The pH of the aqueous was adjusted to 4 using 1 N HCl, and the phases were split in a separatory funnel. The aqueous layer was saturated with NaCl and extracted with additional EtOAc (200 mL). The organic layers were combined, washed with brine, dried (Na₂SO₄), and concentrated on rotovap to give 3.5 g of a tan oil. A portion of this oil (2.1 g) was purified on a SiO₂ flash column (CombiFlash, 80 g SiO₂ prepacked column, MeOH/dichloromethane gradient) to give 4-carbamoyl-2-[4-(4-hydroxymethyl-benzyloxy)-1-oxo-1,3-dihydro-isoindol-2-yl]-butyric acid tert-butyl ester as a white foam (1.1 g, 90% yield, based on portion purified): 1H NMR (DMSO-d6) δ 1.39 (s, 9H, tBu), 2.00-2.13 (m, 3H, CHH, CH₂), 2.13-2.31 (m, 1H, CHH), 4.41 (s, 2H, CH₂), 4.50 (d, J=5.7 Hz, 2H, CH₂), 4.69 (dd, J=4.6, 10.3 Hz, 1H, CH), 5.19 (t, J=5.7 Hz, 1H, OH), 5.24 (s, 2H, CH₂), 6.75 (br. s., 1H, NH), 7.22 (br. s., 1H, NH), 7.25-7.37 (m, 4H, Ar), 7.42-7.53 (m, 3H, Ar); 13C NMR (DMSO-d6) δ 24.69, 27.56, 31.50, 44.78, 54.08, 62.60, 69.45, 81.42, 114.97, 115.18, 126.52, 127.57, 129.71, 130.03, 133.27, 134.86, 142.40, 153.42, 168.12, 169.85, 172.94; LCMS MH=455.

Step 2: KOtBu (1.1 mL, 1.1 mmol, 1 M in THF) was added via syringe to a stirred mixture of 4-carbamoyl-2-[4-(4-hydroxymethyl-benzyloxy)-1-oxo-1,3-dihydro-isoindol-2-yl]-butyric acid tert-butyl ester (500 mg, 1.1 mmol) in TNF (20 mL). The resulting mixture was stirred at room temperature for 1 hour and then another 100 µl of KOtBu was added. After 6 hours, the reaction mixture was quenched by transferring to 1 N aqueous HCl solution (10 mL). The mixture was diluted with EtOAc (150 mL) and 1 N NaHCO₃ (35 mL). The aqueous layer was washed with additional EtOAc (100 mL). The organic layers were combined, washed with brine, dried (Na₂SO₄), and concentrated on a rotovap to give the crude product as a solid (300 mg). A portion of the solid (~127 mg) was dissolved in minimal DMF and purified by injection onto a C-18 preparatory HPLC column. The product was eluted with an acetonitrile/water gradient (0.1% formic acid in both mobile phases, 5% to 60% acetonitrile over 20 min) and fractions were collected by mass trigger. The desired fractions were combined, concentrated in vacuo, and residual water was lyophilized to give 3-[4-(4-hydroxymethyl-benzyloxy)-1-oxo-1,3-dihydro-isoindol-2-yl]-piperidine-2,6-dione as white solid (115 mg, 55% yield, based on portion purified): HPLC: Waters Symmetry $C_{18}$, 5 µm, 3.9×150 mm, 1 ml/min, 240 nm, 30/70 acetonitrile/0.1% H₃PO₄, 3.30 min (97.2%); mp: 220-222° C.; 1H NMR (DMSO-d6) δ 1.91-2.04 (m, 1H, CHH), 2.34-2.48 (m, 1H, CHH), 2.52-2.64 (m, 1H, CHH), 2.81-2.99 (m, 1H, CHH), 4.25 (d, J=17.6 Hz, 1H, CHH), 4.41 (d, J=17.6 Hz, 1H, CHH), 4.50 (d, J=5.5 Hz, 2H, CH₂), 5.10 (dd, J=5.2, 13.1 Hz, 1H, CH), 5.18 (t, J=5.8 Hz, 1H, OH), 5.23 (s, 2H, CH₂), 7.25-7.38 (m, 4H, Ar), 7.39-7.53 (m, 3H, Ar), 10.96 (s, 1H, NH); 13C NMR (DMSO-d6) δ 22.31, 31.18, 45.07, 51.56, 62.60, 69.42, 115.01, 115.18, 126.49, 127.52, 129.76, 129.96, 133.28, 134.87, 142.38, 153.43, 167.99, 170.96, 172.81. LCMS MH=381; Anal Calcd for $C_{21}H_{20}N_2O_5$+0.3 $H_2O$: C, 65.38; H, 5.38; N, 7.26. Found: C, 65.44; H, 5.43; N, 7.29.

5.172 3-[4-(4-Diethylaminomethyl-Benzyloxy)-1-Oxo-1 3-Dihydro-Isoindol-2-yl]-Piperidine-2,6-Dione Formic Acid Salt

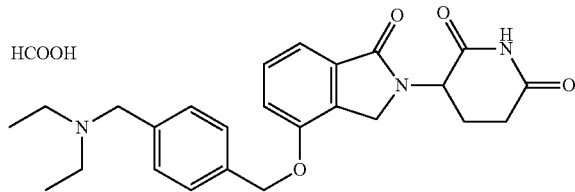 [SMILES: "HCOOH" ; CCN(CC)Cc1ccc(COc2cccc3c2CN(C2CCC(=O)NC2=O)C3=O)cc1]

To a stirred solution of methyl 5-amino-4-(4-hydroxy-1-oxoisoindolin-2-yl)-5-oxopentanoate (0.50 g, 1.72 mmol) in DMF (O1 mL), were added potassium carbonate (0.24 g, 1.72 mmol) and (4-bromomethyl-benzyl)-diethyl-amine (0.88 g, 2.42 mmol) in DMF (3 mL). The mixture was stirred at room temperature overnight and heated at 70° C. for three hours. The mixture was purified by preparative HPLC to give 3-[4-(4-diethylaminomethyl-benzyloxy)-1-oxo-1,3-dihydro-isoindol-2-yl]-piperidine-2,6-dione formic acid salt as an off-white solid (0.15 g, 20% yield); HPLC: Waters Symmetry C-18, 3.9×150 mm, 5 µm, 1 mL/min, 240 nm, isocratic at 15/85 in 10 min (acetonitrile/0.1% H3PO4), 7.31 min (95.5%); mp: 210-212° C.; 1H NMR (DMSO-d6) δ 0.98 (t, J=7.1 Hz, 6H, 2CH3), 1.92-2.04 (m, 1H, CHH), 2.41-2.49 (m, 5H, 2CH$_2$, CH), 2.53-2.63 (m, 1H, CHH), 2.83-2.98 (m, 1H, CHH), 3.56 (s, 2H, CH2), 4.21-4.47 (m, 2H, CH2), 5.11 (dd, J=5.1, 13.2 Hz, 1H, NCH), 5.22 (s, 2H, CH2), 7.29-7.39 (m, 4H, Ar), 7.40-7.53 (m, 3H, Ar), 10.97 (br. s., 1H, NH); 13C NMR (DMSO-d6) δ 11.95, 22.83, 31.68, 45.59, 46.52, 52.06, 56.93, 69.93, 115.46, 115.70, 128.07, 129.14, 130.29, 130.42, 133.77, 135.48, 139.85, 153.98, 168.49, 171.45, 173.31; LCMS MH=436; Anal. Calcd for C25H29N3O4 2.5HCOOH.: C, 59.99; H, 6.22; N, 7.63; Found: C, 51.24; H, 5.88; N, 6.38.

5.173 3-[4-(4-Ethylaminomethyl-Benzyloxy)-1-Oxo-1,3-Dihydro-Isoindol-2-yl]-Piperidine-2,6-Dione Hydrochloride

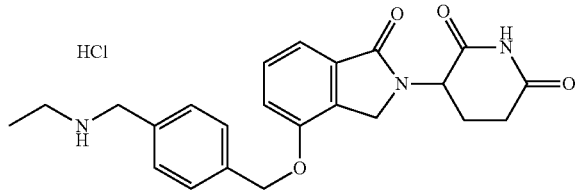 [SMILES: CCNCc1ccc(COc2cccc3c2CN(C2CCC(=O)NC2=O)C3=O)cc1 ; Cl]

Ethyl amine (4.24 mL, 8.48 mmol, 2.0 M in THF) was added to a stirred solution of 4-carbamoyl-4-[4-(4-chloromethyl-benzyloxy)-1-oxo-1,3-dihydro-isoindol-2-yl]-butyric acid methyl ester (0.73 g, 1.70 mmol) in acetonitrile (15 mL) at room temperature overnight. The mixture was concentrated and swapped to DMF (10 mL). To the solution was added potassium carbonate (0.23 g, 1.70 mmol), and the mixture was heated at 80° C. for three hours. The solvent was evaporated and then stirred in 2 M HCl in ether (5 mL) for one hour, filtered and stirred in methylene chloride (8 mL) for two hours, filtered again and dried in vacuum oven to give 3-[4-(4-ethylaminomethyl-benzyloxy)-1-oxo-1,3-dihydro-isoindol-2-yl]-piperidine-2,6-dione hydrochloride as a white solid (0.126 g, 29% yield); HPLC: Waters Symmetry C-18, 3.9×150 mm, 5 µm, 1 mL/min, 240 nm, gradient from 10/90 to 95/5 in 5 min, isocratic at 95/5 in 5 min (acetonitrile/0.1% H3PO4), 4.89 min (93.2%); mp: 273-275° C.; 1H NMR (DMSO-d6) δ 1.93-2.05 (m, 1H, CHH), 2.36-2.47 (m, 1H, CHH), 2.54-2.66 (m, 1H, CHH), 2.83-3.01 (m, 3H, CH2, CHH), 4.11 (t, J=5.9 Hz, 2H, CH2), 4.22-4.51 (m, 2H, CH2), 5.11 (dd, J=5.1, 13.2 Hz, 1H, NCH), 5.29 (s, 2H, CH2), 7.27-7.38 (m, 2H, Ar), 7.43-7.63 (m, 5H, Ar), 9.20 (br. s., 2H, NH2Cl), 10.98 (s, 1H, NH); 13C NMR (DMSO-d6) δ 10.83, 22.38, 31.21, 41.63, 45.12, 49.11, 51.62, 69.01, 115.03, 115.33, 127.80, 129.81, 130.00, 130.10, 131.83, 133.35, 137.37, 153.30, 167.98, 170.98, 172.85; LCMS MH=408; Anal. Calcd for C, 23; H, 25; N, 3; O, 4; HCl+0.5 H2O: C, 60.99; H, 6.01; N, 9.28; Cl, 7.83. Found: C, 60.65; H, 6.01; N, 9.12; Cl, 7.66.

5.174 3-(4-(4-(((Chloroamino)Methyl)Benzyloxy)-1-Oxoisoindolin-2-yl)Piperidine-2,6-Dione Hydrochloride

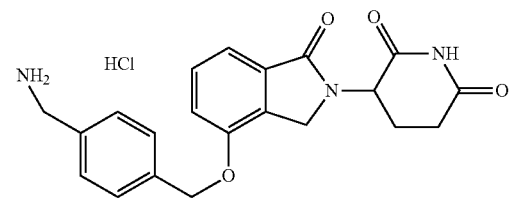 [SMILES: NCc1ccc(COc2cccc3c2CN(C2CCC(=O)NC2=O)C3=O)cc1 ; Cl]

Step 1: To a mixture of triphenylphosphine polymer supported (0.93 g, 3.54 mmol) and methyl 5-amino-4-(4-hydroxy-1-oxoisoindolin-2-yl)-5-oxopentanoate (0.47 g, 1.61 mmol) in THF (20 mL) cooled down to 0° C., was added drop wise DIAD (0.70 ml, 3.54 mmol). 4-Hydroxymethyl-benzyl)-carbamic acid tert-butyl ester (0.46 g, 1.93 mmol) was then added. The reaction mixture was stirred at 0° C. for 1 hour and then at room temperature overnight. The reaction mixture was then filtered through celite. Celite was washed with ethyl acetate (100 mL). The solvent was evaporated. The residue was purified by ISCO flash (40 g column, gradient EtOAc/Hexanes 50/50 to 100/0 in 30 min, eluting product at 80/20). The solvent was evaporated and methyl 5-amino-4-(4-(4-((tert-butoxycarbonylamino) methyl)benzyloxy)-1-oxoisoindolin-2-yl)-5-oxopentanoate was obtained as a sticky, transparent solid (0.34 g, 41% yield). To the solid stirred in THF (15 mL) and cooled down to 0° C., was added KOtBu (0.07 g, 0.65 mmol) and the reaction mixture was stirred for 1.5 hours. Acetic acid (1 mL) was added to reaction mixture. Ethyl acetate (100 mL) was added, and it was washed with a saturated solution of sodium bicarbonate (2×100 mL) and brine (100 mL), and dried (MgSO$_4$). After filtration of the drying agent, solvent was concentrated down to give tert-butyl 4-((2-(2,6-dioxopiperidin-3-yl)-1-oxoisoindolin-4-yloxy)methyl)benzylcarbamate as a light pink solid (0.25 g, 81% yield): HPLC: Waters Symmetry $C_{18}$, 5 µm, 3.9×150 mm, 1 mL/min, 240 nm, gradient: acetonitrile/0.1% $H_3PO_4$, 10/90 to 90/10 in 15 min, 90/10 for 5 min, 12.06 min (98.12%).

Step 2: To a solution of tert-butyl 4-((2-(2,6-dioxopiperidin-3-yl)-1-oxoisoindolin-4-yloxy)methyl)benzylcarbamate (0.10 g, 0.2 mmol) in THF (40 mL), was bubbled HCl gaz for 15 minutes. The solvent was then evaporated. Water (10 mL) was added to the residue, and it was filtered. The filtrate was concentrated down, and the residue was stirred in ether overnight. Solid was then filtered and dried in oven at 40° C. to give 3-(4-(4-((chloroamino)methyl)benzyloxy)-1-oxoisoindolin-2-yl)piperidine-2,6-dione hydrochloride as a white solid (0.08 g, 94% yield); mp: 198-200° C.; $^1$H NMR (DMSO-d$_6$) δ 1.86-2.12 (m, 1H, CHH), 2.34-2.49 (m, 1H, CHH), 2.53-2.69 (m, 1H, CHH), 2.81-3.05 (m, 1H, CHH), 4.02 (q, J=5.6 Hz, 2H, CH$_2$), 4.27 (d, J=17.6 Hz, 1H, CHH), 4.43 (d, J=17.6 Hz, 1H, CHH), 5.11 (dd, J=5.1, 13.2 Hz, 1H, CH), 5.28 (s, 2H, CH$_2$), 7.21-7.40 (m, 2H, Ar), 7.40-7.73 (m, 4H, Ar), 8.45 (br. s., 3H, NH$_3$Cl), 10.97 (s, 1H, NH); $^{13}$C NMR (DMSO-d$_6$) δ 22.33, 31.18, 41.85, 45.09, 51.59, 69.01, 115.00, 115.28, 127.77, 129.06, 129.77, 129.97, 133.33, 133.75, 136.87, 153.26, 167.96, 170.96, 172.83; LCMS MH=380; Anal. Calcd for C$_{21}$H$_{22}$N$_3$O$_4$Cl+1.5 H$_2$O: C, 56.95; H, 5.69; N, 9.49; Found: C, 56.81; H, 5.61; N, 9.37.

5.175 3-(4-(4-((2-Methoxyethylamino)Methyl)Benzyloxy)-1-Oxoisoindolin-2-yl)Piperidine-2,6-Dione Formate

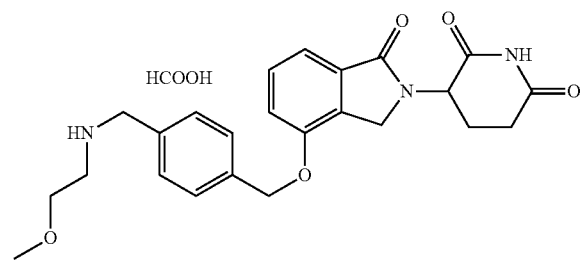 [SMILES: COCCNCc1ccc(COc2cccc3c2CN(C2CCC(=O)NC2=O)C3=O)cc1 ; "HCOOH"]

Step 1: To a solution of tert-butyl 5-amino-2-(4-(4-(chloromethyl) benzyloxy)-1-oxoisoindolin-2-yl)-5-oxopentanoate (250 mg, 0.529 mmol) in acetonitrile (10 mL), were added 2-methoxyethanamine (0.068 ml, 0.793 mmol) and DIEA (0.138 ml, 0.793 mmol). The resulting mixture was stirred at 50° C. for 1.5 hours, then additional 2-methoxyethanamine (150 μl) was added. The temperature was raised to 60° C. and the mixture was stirred for another 2.5 hours. The reaction mixture was concentrated in vacuo using a rotovap to give tert-butyl 5-amino-2-(4-(4-((2-methoxyethylamino)methyl) benzyloxy)-1-oxoisoindolin-2-yl)-5-oxopentanoate as a white foam (295 mg, assume theoretical yield). LCMS MH=512. The solid was used in the next step without further purification.

Step 2: tert-Butyl 5-amino-2-(4-(4-((2-methoxyethylamino)methyl) benzyloxy)-1-oxoisoindolin-2-yl)-5-oxopentanoate (0.528 mmol, assume theoretical yield from previous step) was taken up in dry THF (5 mL). To the stirred suspension at room temperature was added KOtBu (0.581 ml, 0.581 mmol, 1.0 M in THF) dropwise. The resulting mixture was stirred at room temperature for 2 hours and then additional KOtBu (176 μL) was added. The mixture was stirred overnight at room temperature, then treated with additional KOtBu (176 μL). After 6 hours, a final portion of KOtBu was added, and the mixture was stirred for 2 hours. The reaction mixture was quenched by transferring to a 2 M soln of formic acid in MeCN on an ice bath. The mixture was concentrated in vacuo using a rotovap to give an oil which was dissolved in minimal DMF and purified by injection onto a C-18 preparatory HPLC column. The product was eluted with an acetonitrile/water gradient (0.1% formic acid in both mobile phases, 5% to 30% MeCN over 12 minutes) and fractions were collected by mass trigger. The desired fractions were combined and concentrated in vacuo, and residual water was lyophilized to give 3-(4-(4-((2-methoxyethylamino)methyl)benzyloxy)-1-oxoisoindolin-2-yl)piperidine-2,6-dione formate as a white solid (80 mg, 35% yield): HPLC: Waters Symmetry C$_{18}$, 5 μm, 3.9×150 mm, 1 ml/min, 240 nm, 5% grad 95% in 10 min, acetonitrile/0.1% H$_3$PO$_4$, 5.64 min (95.6%); mp: 200-202° C.; $^1$H NMR (DMSO-d$_6$) δ 1.89-2.06 (m, 1H, CHH), 2.35-2.48 (m, 1H, CHH), 2.52-2.62 (m, 1H, CHH), 2.65 (t, J=5.6 Hz, 2H, CH$_2$), 2.82-3.01 (m, 1H, CHH), 3.23 (s, 3H, OCH$_3$), 3.40 (t, J=5.7 Hz, 2H, CH$_2$O), 3.73 (s, 2H, CH$_2$N), 4.28 (d, J=17.6 Hz, 1H, CHH), 4.42 (d, J=17.4 Hz, 1H, CHH), 5.01-5.16 (m, 1H, CH), 5.22 (s, 2H, C H$_2$O), 7.23-7.39 (m, 4H, Ar), 7.40-7.55 (m, 3H, Ar), 8.07-8.55 (m, 1H, HCOOH), 10.39-11.40 (m, 1H, NH); $^{13}$C NMR (DMSO-d$_6$) δ 22.31, 31.18, 45.07, 47.62, 51.56, 52.33, 57.95, 69.41, 71.33, 114.97, 115.18, 127.61, 128.09, 129.77, 129.95, 133.28, 134.92, 140.17, 153.45, 167.99, 170.95, 172.81; LCMS MH=438; Anal Calcd for C$_{24}$H$_{27}$N$_3$O$_5$.HCOOH+2.8 H$_2$O: C, 56.24; H, 6.53; N, 7.87. Found: C, 56.13; H, 6.18; N, 7.75.

5.176 3-(4-{4-[(Methyl-Phenyl-Amino)-Methyl]-Benzyloxy}-1-Oxo-1,3-Dihydro-Isoindol-2-yl)-Piperidine-2,6-Dione

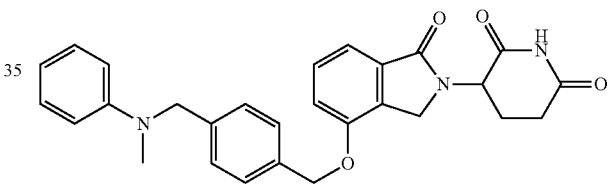

N-methylaniline (0.55 ml, 5.00 mmol) was added to a stirred solution of methyl 5-amino-4-(4-(4-(chloromethyl) benzyloxy)-1-oxoisoindolin-2-yl)-5-oxopentanoate (0.72 g, 1.67 mmol) in DMF (15 ml). The mixture was stirred at 50° C. for two days. To the mixture was added potassium carbonate (0.23 g, 1.67 mmol), and the mixture was heated at 70° C. overnight. The reaction mixture was concentrated in vacuo and the residue was purified on silica gel column (CH$_2$Cl$_2$/EtOAc gradient from 5% EtOAc in CH$_2$Cl$_2$ to 50%) to give 3-(4-{4-[(Methyl-phenyl-amino)-methyl]-benzyloxy}-1-oxo-1,3-dihydro-isoindol-2-yl)-piperidine-2,6-dione as a white solid (0.29 g, 37% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0. % H3PO4): 6.20 min (98.4%); mp: 201-203° C. 1H NMR (DMSO-d6) δ 1.91-1.98 (m, 1H, CHH), 2.35-2.47 (m, 1H, CHH), 2.53-2.62 (m, 1H, CHH), 2.82-2.97 (m, 1H, CHH), 3.01 (s, 3H, CH3), 4.19-4.45 (m, 2H, CH2), 4.57 (s, 2H, CH2), 5.10 (dd, J=5.2, 13.3 Hz, 1H, NCH), 5.20 (s, 2H, CH2), 6.60 (t, J=7.3 Hz, 1H, Ar), 6.70 (dd, J=0.9, 8.9 Hz, 2H, Ar), 7.09-7.18 (m, 2H, Ar), 7.22 (d, J=8.1 Hz, 2H, Ar), 7.29-7.36 (m, 2H, Ar), 7.39-7.53 (m, 3H, Ar), 10.96 (s, 1H, NH); 13C NMR (DMSO-d6) δ 22.33, 31.20, 38.60, 45.09, 51.56, 55.05, 69.36, 111.99, 114.92, 115.21, 115.84, 126.85, 127.97, 128.95, 129.81, 129.95, 133.29, 134.95, 139.02, 148.97, 153.48, 168.01, 170.96, 172.83; LCMS MH=470; Anal. Calcd for C, 28; H, 27; N, 3; O, 4;+0.3 H2O: C, 70.81; H, 5.86; N, 8.85; Found: C, 70.51; H, 5.66; N, 8.71.

5.177 3-(4-(4-((Bis(2-Methoxyethyl)Amino)Methyl)Benzyloxy)-1-Oxoisoindolin-2-yl)Piperidine-2,6-Dione

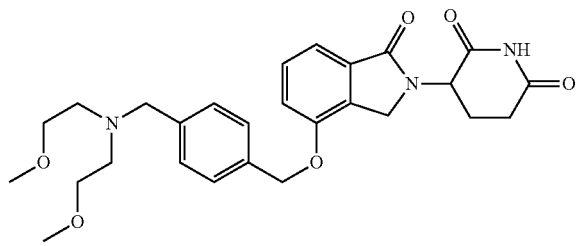 [SMILES: COCCN(CCOC)Cc1ccc(COc2cccc3c2CN(C2CCC(=O)NC2=O)C3=O)cc1]

Step 1: To a solution of tert-butyl 5-amino-2-(4-(4-(chloromethyl) benzyloxy)-1-oxoisoindolin-2-yl)-5-oxopentanoate (250 mg, 0.529 mmol) in acetonitrile (10 mL), were added bis(2-methoxyethyl)amine (106 mg, 0.793 mmol) and N,N-diisopropylethylamine (0.138 ml, 0.793 mmol). The resulting mixture was stirred at 60° C. for 2 days. The mixture was concentrated in vacuo using a rotovap and further dried in a vacuum oven overnight to give tert-butyl 5-amino-2-(4-(4-((bis(2-methoxyethyl)amino) methyl)benzyloxy)-1-oxoisoindolin-2-yl)-5-oxopentanoate as an amber oil (320 mg). The oil was used in the next step without further purification.

Step 2: tert-Butyl 5-amino-2-(4-(4-((bis(2-methoxyethyl)amino)methyl) benzyloxy)-1-oxoisoindolin-2-yl)-5-oxopentanoate (0.528 mmol, assume theoretical yield from previous step) was taken up in dry THF (5 mL). To the stirred suspension at room temperature, KOtBu (0.581 ml, 0.581 mmol, 1.0 M in THF) was added dropwise. The resulting mixture was stirred at room temperature for 48 hours, then additional KOtBu (200 µL, 0.2 mmol) was added to the reaction, and the mixture stirred for 3 hours. Another portion of KOtBu (400 µL, 0.4 mmol) was added (total of 1.18 mmol KOtBu used). After about 15 minutes, LCMS indicated cyclization was complete. The reaction mixture was cooled at 0° C. and quenched with formic acid (500 µL) and concentrated using a rotovap to give an oily residue, which was dissolved in H₂O and DMF (2 mL/6 mL) and filtered on a syringe filter (0.2 g polypropylene). The filtrate was purified by injection onto a C-18 preparatory HPLC column. The product was eluted with an acetonitrile/water gradient (0.1% formic acid in both mobile phases, 5% to 30% MeCN over 12 minutes) and fractions were collected by mass trigger. The desired fractions were combined and concentrated in vacuo and residual water was lyophilized to give 3-(4-(4-((bis(2-methoxyethyl)amino) methyl)benzyloxy)-1-oxoisoindolin-2-yl)piperidine-2,6-dione as an off-white solid (110 mg, 42% yield for step 1 and step 2): HPLC: Waters Symmetry $C_{18}$, 5 µm, 3.9×150 mm, 1 ml/min, 240 nm, 20/80 acetonitrile/0.1% $H_3PO_4$, 3.22 min (95.4%); mp: 105-107° C.; $^1H$ NMR (DMSO-$d_6$) δ 1.89-2.05 (m, 1H, CHH), 2.35-2.48 (m, 1H, CHH), 2.52-2.60 (m, 1H, CHH), 2.62 (t, J=6.1 Hz, 4H, $_2$×$CH_2$), 2.80-2.99 (m, 1H, CHH), 3.20 (s, 6H, $_2$×$CH_3$), 3.39 (t, J=6.1 Hz, 4H, $_2$×$CH_2$), 3.62 (s, 2H, $CH_2$), 4.25 (d, J=17.6 Hz, 1H, CHH), 4.42 (d, J=17.4 Hz, 1H, CHH), 5.11 (dd, J=5.2, 13.1 Hz, 1H, CHH), 5.22 (s, 2H, C $H_2O$), 7.28-7.37 (m, 4H, Ar), 7.38-7.53 (m, 3H, Ar), 10.97 (br. s., 1H, NH); $^{13}C$ NMR (DMSO-$d_6$) δ 22.33, 31.18, 45.07, 51.55, 52.99, 57.98, 58.52, 69.44, 70.57, 114.97, 115.18, 127.55, 128.52, 129.77, 129.93, 133.27, 134.95, 139.67, 153.48, 167.99, 170.95, 172.81; Anal Calcd for $C_{27}H_{33}N_3O_6$.+0.7 HCOOH+2 $H_2O$: C, 59.01; H, 6.86; N, 7.45. Found: C, 58.72; H, 6.49; N, 7.32.

5.178 Tert-Butyl 3-(Diethylamino)Propyl(4-((2-(2,6-Dioxopiperidin-3-yl)-1-Oxoisoindolin-4-yloxy)Methyl)Benzyl)Carbamate

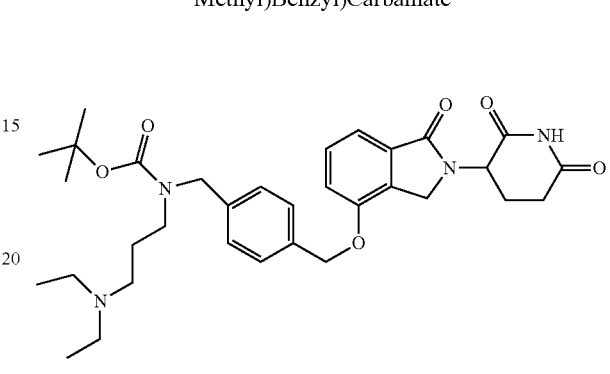

Step. 1: In a round-bottomed flask was methyl 5-amino-4-(4-(4-(chloromethyl)benzyloxy)-1-oxoisoindolin-2-yl)-5-oxopentanoate (1.0 g, 2.321 mmol) in acetonitrile (Volume: 30 ml) to give a colorless solution. N1,N1-diethylpropane-1,3-diamine (0.907 g, 6.96 mmol) was added. The mixture was stirred at room temperature over weekend. The reaction was concentrated on rota-vap. The resulting oil was used in next step without any purification.

Step 2: To the $CH_2Cl_2$ solution (30 mL) of methyl 5-amino-4-(4-(4-((3-(diethylamino)propylamino)methyl)benzyloxy)-1-oxoisoindolin-2-yl)-5-oxopentanoate (1.218 g, 2.32 mmol), was added $BOC_2O$ (2.70 ml, 11.61 mmol). The mixture was stirred at room temperature for 2 hours. The reaction mixture was concentrated and purified on silica gel column eluted with methylene chloride and methanol to give methyl 5-amino-4-(4-(4-((tert-butoxycarbonyl(3-(diethylamino)propyl)amino)methyl)benzyloxy)-1-oxoisoindolin-2-yl)-5-oxopentanoate as a clear oil (500 mg, 35%).

Step 3: To the THF solution (20 mL) of methyl 5-amino-4-(4-(4-((tert-butoxycarbonyl(3-(diethylamino)propyl)amino)methyl)benzyloxy)-1-oxoisoindolin-2-yl)-5-oxopentanoate (0.5 g, 0.80 mmol), was added potassium tert-butoxide (0.090 g, 0.80 mmol). The mixture was stirred at 0° C. for 10 minutes and quenched by adding 1N HCl (2 mL) followed by saturated $NaHCO_3$ (15 mL) and EtOAc (30 mL). The mixture was extracted and separated. The organic layer was washed with brine and concentrated on rota-vap. The resulting oil was purified on silica gel column and eluted with $CH_2Cl_2$/MeOH to give tert-butyl 3-(diethylamino)propyl(4-((2-(2,6-dioxopiperidin-3-yl)-1-oxoisoindolin-4-yloxy)methyl)benzyl)carbamate as a white solid was obtained (0.23 g, 49%). mp: 140-142° C. HPLC: Waters Symmetry C-18, 3.9×150 mm, 5 micro, 1 mL/min, 240 nm, gradient acetonitrile/0.1% $H_3PO_4$ in $H_2O$ from 5/95 to 100/0 in 5 min and stayed at 100/0 for 5 min: $t_R$=5.15 min (95%). $^1H$ NMR (DMSO-$d_6$) δ 0.89 (t, J=7.2 Hz, 6H, $CH_3$, $CH_3$), 1.29-1.47 (m, 9H, $CH_3$, $CH_3$, $CH_3$), 1.48-1.62 (m, 2H, $CH_2$), 1.89-2.06 (m, 1H, CHH), 2.29 (t, J=7.0 Hz, 2H, $CH_2$), 2.37 (q, J=7.2 Hz, 4H, $CH_2$, $CH_2$), 2.42-2.47 (m, 1H, CHH), 2.54-2.63 (m, 1H, CHH), 2.80-2.98 (m, 1H, CHH), 3.00-3.23 (m, 2H, $CH_2$), 4.03-4.61 (m, 4H, $CH_2$, $CH_2$), 4.95-5.18 (m, 1H, NCH), 5.23 (s, 2H, $CH_2$), 7.12-7.38 (m, 4H, Ar), 7.39-7.65 (m, 3H, Ar), 10.97 (s, 1H, NH). $^{13}$C NMR (DMSO-d$_6$) δ 11.52, 28.01, 31.16, 45.06, 46.01, 49.58, 51.55, 69.29, 78.64, 114.94, 115.20, 127.29, 127.83, 129.77, 129.93, 133.28, 135.30, 138.66, 153.42, 167.99, 170.95, 172.81; LCMS MH=593. Anal Calcd for C$_{33}$H$_{44}$N$_4$O$_6$+0.1 H$_2$O: C, 66.87; H, 7.49; N, 9.42; Found: C, 66.40; H, 7.43; N, 9.27.

5.179 [{4-[2-(2,6-Dioxo-Piperidin-3-yl)-1-Oxo-2,3-Dihydro-1H-Isoindol-4-yloxymethyl]-Benzyl}-(2-Morpholin-4-yl-Ethyl)-Amino]-Acetic Acid Tert-Butyl Ester

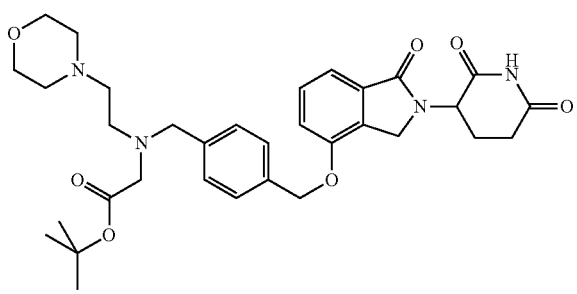 [SMILES: CC(C)(C)OC(=O)CN(CCN1CCOCC1)Cc1ccc(COc2cccc3c2CN(C2CCC(=O)NC2=O)C3=O)cc1]

Step 1: To a stirred colorless solution of methyl 5-amino-4-(4-(4-(chloromethyl)benzyloxy)-1-oxoisoindolin-2-yl)-5-oxopentanoate (1.18 g, 2.75 mmol) in acetonitrile (15 ml) was added 2-morpholinoethanamine (1.08 ml, 8.24 mmol). The reaction mixture immediately turned into a light green solution. The reaction was stirred at room temperature overnight. The solution was evaporated to give a light green oil, which was not further characterized and used in the next step without purification.

Step 2: To a stirred solution of methyl 5-amino-4-(4-(4-((2-morpholinoethylamino)methyl)benzyloxy)-1-oxoisoindolin-2-yl)-5-oxopentanoate (1.442 g, 2.75 mmol) in dichloromethane (15 ml), was added di-tert-butyl dicarbonate (1.80 g, 8.25 mmol). The weight of the limiting SM was assumed as 1.44 g, which was the theoretical yield of the previous step. The oil was purified on silica gel column (MeOH/CH$_2$Cl$_2$ gradient from 1% to 9% in 50 min) to give 4-[4-(4-{[tert-Butoxycarbonylmethyl-(2-morpholin-4-yl-ethyl)-amino]-methyl}-benzyloxy)-1-oxo-1,3-dihydro-isoindol-2-yl]-4-carbamoyl-butyric acid methyl ester as an oily solid (0.88 g, 51% over two steps).

Step 3: To a stirred solution of methyl 5-amino-4-(4-(4-((tert-butoxycarbonyl(2-morpholinoethyl)amino)methyl)benzyloxy)-1-oxoisoindolin-2-yl)-5-oxopentanoate (0.36 g, 0.58 mmol) in THF (10 ml) at 0° C., was added potassium 2-methylpropan-2-olate (0.07 g, 0.58 mmol). The reaction mixture was stirred for ten minutes and quenched with 1 N HCl (2 mL) to give a clear colorless solution. It was neutralized with saturated sodium bicarbonate (to pH=7) to give a cloudy mixture, which was extracted with ethyl acetate (2×20 mL). The ethyl acetate phase was concentrated and purified on silica gel column (MeOH/CH$_2$Cl$_2$ gradient from 1% to 5% in 30 min) to give [{4-[2-(2,6-Dioxo-piperidin-3-yl)-1-oxo-2,3-dihydro-1H-isoindol-4-yloxymethyl]-benzyl}-(2-morpholin-4-yl-ethyl)-amino]-acetic acid tert-butyl ester as a foamy white solid (0.21 g, 62% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 5.38 min (97.4%); mp: 110-112° C.; $^1$H NMR (DMSO-d$_6$) δ 1.29-1.49 (m, 9H, 3CH$_3$), 1.92-2.05 (m, 1H, CHH), 2.25-2.39 (m, 6H, 3CH$_2$), 2.44 (dd, J=4.5, 13.0 Hz, 1H, CHH), 2.53-2.64 (m, 1H, CHH), 2.83-3.00 (m, 1H, CHH), 3.15-3.29 (m, 2H, CH$_2$), 3.52 (t, J=4.6 Hz, 4H, 2CH$_2$), 4.19-4.49 (m, 4H, CH$_2$, CH$_2$), 5.11 (dd, J=5.1, 13.2 Hz, 1H, NCH), 5.23 (s, 2H, CH$_2$), 7.23-7.37 (m, 4H, Ar), 7.41-7.53 (m, 3H, Ar), 10.97 (s, 1H, NH); $^{13}$C NMR (DMSO-d$_6$) δ 22.36, 28.02, 31.21, 43.30, 45.09, 49.37, 50.05, 51.58, 53.33, 55.95, 56.39, 66.17, 69.32, 78.84, 115.00, 115.23, 127.39, 127.83, 129.78, 129.97, 133.31, 135.30, 138.56, 153.43, 155.02, 168.01, 170.96, 172.83 (2 extra peaks in alkyl region possibly from the two alkyl atoms close to the amide nitrogen atom due to the rotamer); LCMS MH=593; Anal. Calcd for C$_{32}$H$_{40}$N$_4$O$_7$+0.1 H$_2$O: C, 64.65; H, 6.82; N, 9.42. Found: C, 64.31; H, 6.82; N, 9.24.

5.180 N-{4-[2-(2,6-Dioxo-Piperidin-3-yl)-1-Oxo-2,3-Dihydro-1H-Isoindol-4-yloxymethyl]-Benzyl}-N-(2-Morpholin-4-yl-Ethyl)-Formamide

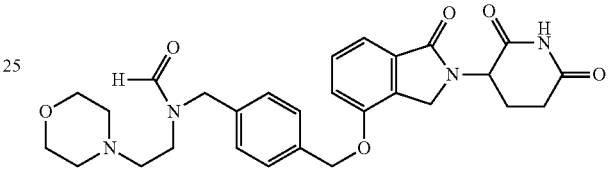

Step 1: To a stirred colorless solution of methyl 5-amino-4-(4-(4-(chloromethyl)benzyloxy)-1-oxoisoindolin-2-yl)-5-oxopentanoate (1.18 g, 2.75 mmol) in acetonitrile (15 ml), was added 2-morpholinoethanamine (1.08 ml, 8.24 mmol). The reaction mixture immediately turned into a light green solution. The reaction was stirred at room temperature overnight. The reaction solution was evaporated to give a light green oil, which was not further characterized and used in the next step without purification.

Step 2: To a stirred solution of methyl 5-amino-4-(4-(4-((2-morpholinoethylamino)methyl)benzyloxy)-1-oxoisoindolin-2-yl)-5-oxopentanoate (1.442 g, 2.75 mmol) in dichloromethane (15 ml), was added di-tert-butyl dicarbonate (1.80 g, 8.25 mmol). The weight of the limiting SM was assumed as 1.44 g, which was the theoretical yield of the previous step. The oil was purified on silica gel column (MeOH/CH$_2$Cl$_2$ gradient from 1% to 9% in 50 min) to give 4-[4-(4-{[tert-Butoxycarbonylmethyl-(2-morpholin-4-yl-ethyl)-amino]-methyl}-benzyloxy)-1-oxo-1,3-dihydro-isoindol-2-yl]-4-carbamoyl-butyric acid methyl ester as an oily solid (0.88 g, 51% yield over two steps).

Step 3: To a stirred solution of methyl 5-amino-4-(4-(4-((tert-butoxycarbonyl(2-morpholinoethyl)amino)methyl)benzyloxy)-1-oxoisoindolin-2-yl)-5-oxopentanoate (0.36 g, 0.58 mmol) in THF (10 ml) at 0° C., was added potassium 2-methylpropan-2-olate (0.07 g, 0.58 mmol). The reaction mixture was stirred for ten minutes and was quenched with 1 N HCl (2 mL) to give a clear colorless solution. It was neutralized with saturated sodium bicarbonate (4 ml to pH=7) to give a cloudy mixture, which was extracted with ethyl acetate (2×20 mL). The ethyl acetate phase was concentrated and purified on silica gel column (MeOH/CH$_2$Cl$_2$ gradient from 1% to 5% in 30 min) to give [{4-[2-(2,6-Dioxo-piperidin-3-yl)-1-oxo-2,3-dihydro-1H-isoindol-4-yloxymethyl]-benzyl}-(2-morpholin-4-yl-ethyl)-amino]-acetic acid tert-butyl ester as a foamy solid (0.213 g, 62% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 5.38 min (97.4%); mp: 110-112° C.; $^1$H NMR (DMSO-d$_6$) δ 1.29-1.49 (m, 9H, 3CH$_3$), 1.92-2.05 (m, 1H, CHH), 2.25-2.39 (m, 6H, 3CH$_2$), 2.44 (dd, J=4.5, 13.0 Hz, 1H, CHH), 2.53-2.64 (m, 1H, CHH), 2.83-3.00 (m, 1H, CHH), 3.15-3.29 (m, 2H, CH$_2$), 3.52 (t, J=4.6 Hz, 4H, 2CH$_2$), 4.19-4.49 (m, 4H, CH$_2$, CH$_2$), 5.11 (dd, J=5.1, 13.2 Hz, 1H, NCH), 5.23 (s, 2H, CH$_2$), 7.23-7.37 (m, 4H, Ar), 7.41-7.53 (m, 3H, Ar), 10.97 (s, 1H, NH); $^{13}$C NMR (DMSO-d$_6$) δ 22.36, 28.02, 31.21, 43.30, 45.09, 49.37, 50.05, 51.58, 53.33, 55.95, 56.39, 66.17, 69.32, 78.84, 115.00, 115.23, 127.39, 127.83, 129.78, 129.97, 133.31, 135.30, 138.56, 153.43, 155.02, 168.01, 170.96, 172.83 (2 extra peaks in alkyl region possibly from the two alkyl atoms close to the amide nitrogen atom due to the rotamer); LCMS MH=593; Anal. Calcd for C$_{32}$H$_{40}$N$_4$O$_7$+0.1 H$_2$O: C, 64.65; H, 6.82; N, 9.42. Found: C, 64.31; H, 6.82; N, 9.24.

Step 5: To a stirred solution of tert-butyl 4-((2-(2,6-dioxopiperidin-3-yl)-1-oxoisoindolin-4-yloxy)methyl)benzyl(2-morpholinoethyl)carbamate (0.42 g, 0.71 mmol) in dichloromethane (5 ml), was added 2M HCl/ether (4 ml). A white precipitate formed almost immediately. The suspension was stirred overnight and filtered to give a white solid, which was purified by prep HPLC to give a clear oil (0.22 g, 58% yield). It was found to be a mixture of the desired product (16% by H NMR) and the amide on the benzyl NH with formic acid (84% by H NMR).

Step 6: To a stirred mixture of 3-(4-(4-((2-morpholinoethylamino)methyl) benzyloxy)-1-oxoisoindolin-2-yl)piperidine-2,6-dione (0.04 g, 0.08 mmol) in dichloromethane (3 ml) at room temperature, was added ethyl formate (6.04 μl, 0.075 mmol). It was stirred for one hour, and 0.12 ml of ethyl formate was added and stirred for six hours. The mixture was evaporated to give a white solid, to which was added diethyl ether (5 mL), stirred and evaporated again to give a white solid. It was stirred in ethyl acetate (2 mL) and evaporated. It was repeated two more times (by adding 2 mL of EtOAc and then evaporated). The resulting white solid was dried in vacuum oven overnight to give N-{4-[2-(2,6-dioxo-piperidin-3-yl)-1-oxo-2,3-dihydro-1H-isoindol-4-yloxymethyl]-benzyl}-N-(2-morpholin-4-yl-ethyl)-formamide as a white solid (0.16 g, 79% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 5.23 min (95.4%); mp: 216-218° C.; $^1$H NMR (DMSO-d$_6$) δ 1.91-2.05 (m, 1H, CH), 2.23-2.36 (m, 6H, CH$_2$, CH$_2$, CH$_2$), 2.36-2.47 (m, 1H, CH), 2.53-2.66 (m, 1H, CH), 2.83-3.00 (m, 1H, CH), 3.20 (t, J=6.6 Hz, 1H, CH), 3.27 (t, J=6.0 Hz, 1H, CH), 3.51 (t, J=4.6 Hz, 4H, ch$_2$, ch$_2$), 4.20-4.46 (m, 2H, CH$_2$), 4.50 (d, J=5.1 Hz, 2H, CH$_2$), 5.11 (dd, J=5.2, 13.3 Hz, 1H, NCH), 5.24 (d, J=6.8 Hz, 2H, CH$_2$), 7.24-7.37 (m, 4H, ArH), 7.41-7.54 (m, 3H, ArH), 8.15 (s, 0.5H, HCON, due to rotamer), 8.29 (s, 0.5H, HCON, due to rotamer), 10.97 (s, 1H, NH); $^{13}$C NMR (DMSO-d$_6$) δ 22.36, 31.20, 38.09, 43.31, 44.74, 45.08, 50.21, 51.58, 53.14, 55.02, 56.11, 66.11, 66.17, 69.29, 115.01, 115.24, 127.78, 127.85, 127.99, 129.79, 129.97, 133.31, 135.47, 136.05, 137.11, 137.36, 153.41, 163.00, 163.31, 167.99, 170.96, 172.83 (4 extra peaks in aromatic region and 6 extra peaks in alkyl region due to rotamer); LCMS MH=521; Anal. Calcd for C$_{28}$H$_{32}$N$_4$O$_6$+0.6 H$_2$O: C, 63.29; H, 6.30; N, 10.54. Found: C, 63.06; H, 6.24; N, 10.35.

5.181 4-((2-(2,6-Dioxopiperidin-3-yl)-1-Oxoisoindolin-4-yloxy)Methyl)-N-Methyl-N-(2-Morpholinoethyl)Benzamide

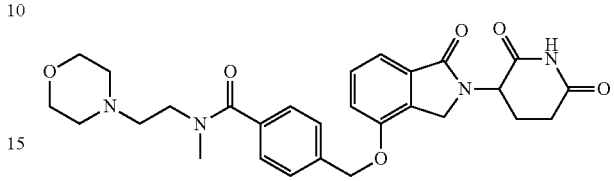

Step 1: 4-(chloromethyl)benzoyl chloride (655 mg, 3.47 mmol) was added to the stirred solution of N-methyl-2-morpholinoethanamine (500 mg, 3.47 mmol) in acetonitrile (20 mL). The reaction mixture was stirred at room temperature for 15 minutes and the reaction was complete. The reaction mixture was added by NaHCO$_3$ (aq. sat. 30 mL). The solution was extracted with EtOAc (40 mL×3). Organic layers were combined and dried by MgSO$_4$. The mixture was filtered and concentrated to give 4-chloromethyl-N-methyl-N-(2-morpholin-4-yl-ethyl)-benzamide as a light brown oil (1.0 g, 97% crude yield): LCMS MH=297; $^1$H NMR (DMSO-d$_6$) δ 2.07-2.25 (m, 2H, CH$_2$), 2.32-2.47 (m, 2H, CH$_2$), 2.82-3.01 (m, 3H, CH$_2$), 3.31 (s, 3H, CH$_3$), 3.39-3.67 (m, 5H, CH$_2$), 4.80 (s, 2H, CH$_2$), 7.39 (d, J=8.1 Hz, 2H, Ar), 7.49 (d, J=8.1 Hz, 2H, Ar).

Step 2: To the stirred mixture of methyl 5-amino-4-(4-hydroxy-1-oxoisoindolin-2-yl)-5-oxopentanoate (400 mg, 1.369 mmol), 4-(chloromethyl)-N-methyl-N-(2-morpholino ethyl)benzamide (406 mg, 1.369 mmol) and K$_2$CO$_3$ (189 mg, 1.369 mmol) in DMF (10 mL), was added DIPEA (0.239 ml, 1.369 mmol). The resulting reaction mixture was stirred at room temperature for 3 days and then heated at 50° C. for 24 hours before it was added by K$_2$CO$_3$ (100 mg, 0.82 mmol) and heated at 80° C. for 3.5 hours. The reaction mixture combined with another batch of reaction with methyl 5-amino-4-(4-hydroxy-1-oxoisoindolin-2-yl)-5-oxopentanoate (100 mg, 0.34 mmol) was concentrated and purified by ISCO chromatography to give 4-((2-(2,6-dioxopiperidin-3-yl)-1-oxoisoindolin-4-yloxy)methyl)-N-methyl-N-(2-morpholinoethyl) benzamide as a white solid (135 mg, 15% yield): HPLC: Waters Symmetry C-18, 3.9×150 mm, 5 μm, 1 mL/min, 240 nm, 20/80, (acetonitrile/0.1% H$_3$PO$_4$), 2.11 min (98%); mp: 120-122° C.; $^1$H NMR (DMSO-d$_6$) δ 1.96-2.09 (m, 1H, CHH), 2.28-2.37 (m, 4H, CH$_2$, CH$_2$), 2.39-2.46 (m, 1H, CHH), 2.44-2.52 (m, 2H, CH$_2$), 2.54-2.66 (m, 1H, CHH), 2.79-2.91 (m, 1H, CHH), 2.94 (s, 3H, CH$_3$), 3.44 (t, J=6.4 Hz, 2H, CH$_2$), 3.52 (t, J=4.7 Hz, 4H, CH$_2$, CH$_2$), 4.32 (d, J=17.2 Hz, 1H, CHH), 4.43 (d, J=17.2 Hz, 1H, CHH), 5.04 (dd, J=5.3, 13.0 Hz, 1H, CHH), 5.28 (s, 2H, CH$_2$), 7.24-7.57 (m, 7H, Ar), 10.62 (s, 1H, NH); $^{13}$C NMR (DMSO-d$_6$) δ 22.36, 31.16, 37.28, 43.50, 45.06, 51.56, 53.28, 55.04, 66.16, 69.03, 114.99, 115.32, 126.87, 127.29, 129.78, 129.96, 133.33, 136.39, 137.66, 153.32, 167.96, 170.95, 172.81; LCMS MH=521; Anal. Calcd for C$_{28}$H$_{32}$N$_4$O$_6$+1.3 H$_2$O: C, 61.82; H, 6.41; N, 10.30; Found: C, 61.73; H, 6.29; N, 10.11.

5.182 4-((2-(2,6-Dioxopiperidin-3-yl)-1-Oxoisoindolin-4-yloxy)Methyl)-N-(2-(Piperidin-1-yl)Ethyl)Benzamide

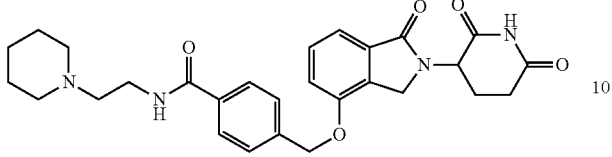

Step 1: 4-(Chloromethyl)benzoyl chloride (1.474 g, 7.80 mmol) was added to the stirred solution of 2-(piperidin-1-yl)ethanamine (1 g, 7.80 mmol) in acetonitrile (20 mL) at room temperature. The resulting clear solution was stirred at room temperature for 20 minutes and the reaction was complete. The reaction mixture was diluted by EtOAc (50 mL) and extracted by NaHCO$_3$ (aq. sat. 30 mL). The aqueous layer was back extracted with EtOAc (2×25 mL). Organic layers were combined and dried by MgSO$_4$. The mixture was filtered and concentrated to give 4-chloromethyl-N-(2-piperidin-1-yl-ethyl)-benzamide as a light brown solid (2.46 g, 109% crude yield): LCMS MH=281; $^1$H NMR (DMSO-d$_6$) δ 1.29-1.57 (m, 6H, CH$_2$, CH$_2$, CH$_2$), 2.30-2.46 (m, 6H, CH$_2$, CH$_2$, CH$_2$), 3.26-3.45 (m, 2H, CH$_2$), 4.80 (s, 2H, CH$_2$), 7.51 (d, J=8.3 Hz, 2H, Ar), 7.82 (d, J=8.3 Hz, 2H, Ar), 8.40 (t, J=5.5 Hz, 1H, NH).

Step 2: K$_2$CO$_3$ (284 mg, 2.053 mmol) was added to the stirred solution of methyl 5-amino-4-(4-hydroxy-1-oxoisoindolin-2-yl)-5-oxopentanoate (600 mg, 2.053 mmol) and 4-(chloromethyl)-N-(2-(piperidin-1-yl)ethyl)benzamide (576 mg, 2.053 mmol) in DMF (12 mL), followed by the addition of DIPEA (0.359 ml, 2.053 mmol) at room temperature. The resulting reaction suspension was stirred at room temperature for 2 days and heated at 50° C. for 1 day before K$_2$CO$_3$ (120 mg, 0.87 mmol) was added to the reaction. The resulting reaction mixture was heated at 80° C. for 3 hrs and the reaction was complete. The reaction mixture was acidified by HCl (1N, 8 mL) to PH=3. The clear solution was added by NaHCO$_3$ (aq, sat., 8 mL) to pH=8 before it was added by dichloromethane (40 mL) and brine (10 mL). The mixture was extracted and the aqueous layer was back extracted with dichloromethane (30 mL×2). Organic layers were combined and dried by MgSO$_4$. The mixture was filtered and the filtrate was concentrated. The residue was purified by ISCO chromatography to give a white solid (220 mg). The solid was dissolved in dichloromethane (2 mL) and precipitated out in EtOAC (10 mL). The solid was filtered and dried to give 4-((2-(2,6-dioxopiperidin-3-yl)-1-oxoisoindolin-4-yloxy)methyl)-N-(2-(piperidin-1-yl)ethyl)benzamide as a white solid (205 mg, 19.8% yield): HPLC: Waters Symmetry C-18, 3.9×150 mm, 5 µm, 1 mL/min, 240 nm, 20/80, (acetonitrile/0.1% H3PO4), 2.91 min (97.6%); mp: 220-222° C.; $^1$H NMR (DMSO-d$_6$) δ 1.31-1.42 (m, 2H, CH$_2$), 1.43-1.56 (m, 4H, CH$_2$, CH$_2$), 1.92-2.06 (m, 1H, CHH), 2.30-2.47 (m, 7H, CHH, CH$_2$, CH$_2$, CH$_2$), 2.58 (d, J=17.6 Hz, 1H, CHH), 2.82-3.00 (m, 1H, CHH), 3.34-3.40 (m, 2H, CH$_2$), 4.28 (d, 1H, CHH), 4.45 (d, J=17.6 Hz, 1H, CHH), 5.12 (dd, J=5.0, 13.1 Hz, 1H, CHH), 5.32 (s, 2H, CH$_2$), 7.26-7.37 (m, 2H, Ar), 7.42-7.52 (m, 1H, Ar), 7.56 (d, J=8.3 Hz, 2H, Ar), 7.84 (d, J=8.3 Hz, 2H, Ar), 8.38 (t, J=5.6 Hz, 1H, NH), 10.98 (s, 1H, NH); $^{13}$C NMR (DMSO-d$_6$) δ 22.34, 23.97, 25.53, 31.18, 36.92, 45.07, 51.58, 54.02, 54.93, 57.61, 68.97, 115.01, 115.35, 127.23, 129.78, 129.97, 133.34, 134.19, 139.64, 153.27, 165.73, 167.97, 170.96, 172.81; LCMS MH=505; C$_{28}$H$_{32}$N$_4$O$_5$+0.1 H$_2$O+0.42CH2Cl2: C, 62.92; H, 6.14; N, 10.34; Found: C, 62.85; H, 6.26; N, 10.17.

5.183 4-[2-(2,6-Dioxo-Piperidin-3-yl)-1-Oxo-2,3-Dihydro-1H-Isoindol-4-yloxymethyl]-N-(3-Morpholin-4-yl-Propyl)-Benzamide

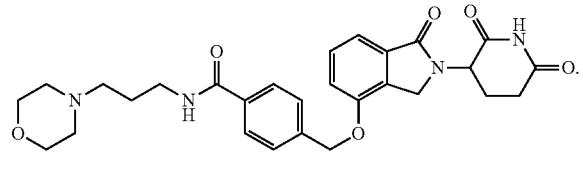 [SMILES: O=C1CCC(N2Cc3c(OCc4ccc(C(=O)NCCCN5CCOCC5)cc4)cccc3C2=O)C(=O)N1]

Step 1: 4-(Chloromethyl)benzoyl chloride (1.311 g, 6.93 mmol) was added to the stirred solution of 3-morpholinopropan-1-amine (1 g, 6.93 mmol) in acetonitrile (20 mL) at room temperature. The resulting reaction solution was stirred at room temperature for 2 hours and the reaction was complete. The reaction mixture was diluted by EtOAc (50 mL) and the solution was extracted with NaHCO$_3$ (aq. sat., 40 mL). The aqueous layer was back extracted with EtOAc (2×20 mL). Organic layers were combined and dried by MgSO$_4$. The mixture was filtered and concentrated to give 4-chloromethyl-N-(3-morpholin-4-yl-propyl)-benzamide as a light red clear liquid (2.23 g, 117% crude yield) which was put to next step without further purification: LCMS MH=297; $^1$H NMR (DMSO-d$_6$) δ 1.68 (quin, J=7.1 Hz, 2H, CH$_2$), 2.24-2.41 (m, 6H, CH$_2$, CH$_2$, CH$_2$), 3.19-3.39 (m, 2H, CH$_2$), 3.48-3.64 (m, 4H, CH$_2$, CH$_2$), 4.81 (s, 2H, M$_{01}$), 7.52 (d, J=8.1 Hz, 2H, Ar), 7.83 (d, J=8.3 Hz, 2H, Ar), 8.51 (t, J=5.4 Hz, 1H, NH).

Step 2: DIPEA (0.359 ml, 2.053 mmol) was added to the stirred mixture of methyl 5-amino-4-(4-hydroxy-1-oxoisoindolin-2-yl)-5-oxopentanoate (600 mg, 2.053 mmol), 4-(chloromethyl)-N-(3-morpholinopropyl)benzamide (640 mg, 2.155 mmol) and K$_2$CO$_3$ (284 mg, 2.053 mmol) in DMF (12 mL) at room temperature. The resulting mixture was reacted at 50° C. for 8 hours and room temperature for 2 days before it was added by K$_2$CO$_3$ (100 mg, 0.72 mmol). The mixture was heated at 80° C. for 9 hours before the reaction stopped proceeding. The reaction mixture was filtered and the filtrate was diluted by dichloromethane (50 mL). The resulting solution was extracted with brine (15 mL). The aqueous layer was back extracted with dichloromethane (25 mL). Organic layers were combined and dried with MgSO$_4$. The mixture was filtered and the filtrate was concentrated. The residue was purified by ISCO chromatography to give a clear solid (480 mg), which was triturated in EtOAC (15 mL) and filtered to give 4-[2-(2,6-dioxo-piperidin-3-yl)-1-oxo-2,3-dihydro-1H-isoindol-4-yloxymethyl]-N-(3-morpholin-4-yl-propyl)-benzamide as a white solid (426 mg, 82% yield): HPLC: Waters Symmetry C-18, 3.9×150 mm, 5 µm, 1 mL/min, 240 nm, 15/85, (acetonitrile/0.1% H$_3$PO$_4$), 6.63 min (99.9%); mp: 160-162° C.; $^1$H NMR (DMSO-d$_6$) δ 1.67 (quin, J=7.0 Hz, 2H, CH$_2$), 1.93-2.06 (m, 1H, CH$_2$), 2.28-2.38 (m, 6H, CH$_2$, CH$_2$, CH$_2$), 2.39-2.47 (m, 1H, CHH), 2.54-2.64 (m, 1H, CHH), 2.83-3.00 (m, 1H, CHH), 3.23-3.31 (m, 2H, CH$_2$), 3.56 (t, J=4.7 Hz, 4H, CH$_2$, CH$_2$), 4.28 (d, J=17.6 Hz, 1H, CHH), 4.45 (d, J=17.6 Hz, 1H, CHH), 5.12 (dd, J=5.1, 13.2 Hz, 1H, CHH), 5.32 (s, 2H, CH$_2$), 7.32 (dd, J=7.6, 8.3 Hz, 2H, Ar), 7.48 (t, J=7.7 Hz, 1H, Ar), 7.56 (d, J=8.1 Hz, 2H, Ar), 7.85 (d, J=8.3 Hz, 2H, Ar), 8.48 (t, J=5.5 Hz, 1H, NH), 10.98 (s, 1H, NH); $^{13}$C NMR (DMSO-d$_6$) δ 22.34, 25.91, 31.18, 37.71, 45.07, 51.58, 53.31, 56.02, 66.17, 68.98, 115.03, 115.35, 127.22, 127.28, 129.78, 129.97, 133.34, 134.22, 139.60, 153.27, 165.76, 167.94, 170.96, 172.81; LCMS MH=521; Anal. Calcd for C$_{28}$H$_{32}$N$_4$O$_6$+1.0 H$_2$O: C, 62.44; H, 6.36; N, 10.40; Found: C, 62.29; H, 6.41; N, 10.26.

5.184 3-{4-[4-(Isopropylamino-Methyl)-Benzyloxy]-1-Oxo-1,3-Dihydro-Isoindol-2-yl}-Piperidine-2,6-Dione

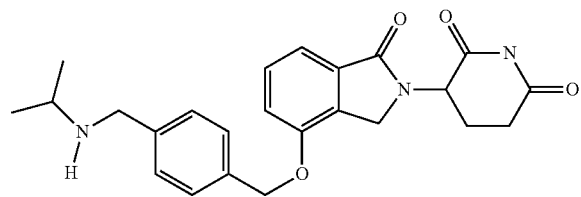 [SMILES: CC(C)NCc1ccc(COc2cccc3c2CN(C2CCC(=O)NC2=O)C3=O)cc1]

Step 1: To the acetonitrile solution of methyl 5-amino-4-(4-(4-(chloromethyl)benzyloxy)-1-oxoisoindolin-2-yl)-5-oxopentanoate (0.5 g, 1.160 mmol), was added propan-2-amine (0.593 ml, 6.96 mmol) dropwise at room temperature. The mixture was stirred at room temperature overnight. The mixture was concentrated on rota-vap and the resulting oil was used in the next step directly.

Step 2: To the THF suspension of methyl 5-amino-4-(4-(4-((isopropylamino)methyl)benzyloxy)-1-oxoisoindolin-2-yl)-5-oxopentanoate (0.45 g, 0.992 mmol), was added potassium tert-butoxide (0.223 g, 1.984 mmol) at 0° C. The mixture was stirred for 5 minutes and quenched by adding 2 mL of 1N HCl followed by 10 mL of sat. NaHCO$_3$ and 20 mL of CH$_2$Cl$_2$. The mixture was extracted and separated. The organic layer was concentrated on rota-vap and the resulting oil was stirred with ether (20 mL) to give 3-{4-[4-(isopropylaminomethyl)-benzyloxy]-1-oxo-1,3-dihydro-isoindol-2-yl}-piperidine-2,6-dione as a yellow solid (150 mg, 31%). mp: 165-167° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=4.56 min (96%). $^1$H NMR (DMSO-d$_6$) δ 0.98 (d, J=6.2 Hz, 6H, CH$_3$, CH$_3$), 1.88-2.05 (m, 1H, CHH), 2.35-2.48 (m, 1H, CHH), 2.53-2.62 (m, 1H, CHH), 2.63-2.74 (m, 1H, CH), 2.80-2.99 (m, 1H, CH), 3.68 (s, 2H, CH$_2$), 4.15-4.51 (m, 2H, CH$_2$), 5.10 (dd, J=5.0, 13.1 Hz, 1H, NCH), 5.22 (s, 2H, CH$_2$), 7.24-7.62 (m, 7H, Ar), 11.00-11.10 (broad, 1H, NH). $^{13}$C NMR (DMSO-d$_6$) δ 22.37, 22.73, 31.21, 45.06, 47.08, 50.10, 51.57, 114.97, 115.16, 127.55, 127.92, 129.76, 129.94, 133.30, 134.56, 141.36, 153.46, 167.98, 171.08, 172.96. LCMS MH=422. Anal Calcd for C$_{24}$H$_{27}$N$_3$O$_4$+0.9 H$_2$O: C, 65.86; H, 6.63; N, 9.60; Found: C, 66.02; H, 6.46; N, 9.25.

5.185 3-[4-(4-Cyclohexylaminomethyl-Benzyloxy)-1-Oxo-1,3-Dihydro-Isoindol-2-yl]-Piperidine-2,6-Dione

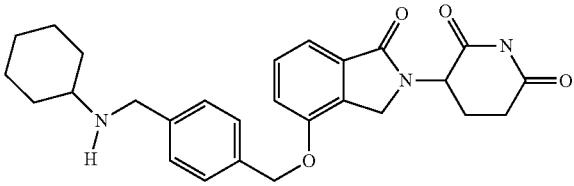 [SMILES: O=C1CCC(N2Cc3c(OCc4ccc(CNC5CCCCC5)cc4)cccc3C2=O)C(=O)N1]

Step 1: To the acetonitrile solution (10 mL) of methyl 5-amino-4-(4-(4-(chloromethyl)benzyloxy)-1-oxoisoindolin-2-yl)-5-oxopentanoate (0.5 g, 1.160 mmol), was added cyclohexanamine (0.798 ml, 6.96 mmol) dropwise at room temperature. The mixture was stirred at room temperature overnight and was concentrated on rota-vap. The resulting mixture was used in the next step directly.

Step 2: To the THF solution (20 mL) of methyl 5-amino-4-(4-(4-((cyclohexylamino)methyl)benzyloxy)-1-oxoisoindolin-2-yl)-5-oxopentanoate (0.4 g, 0.810 mmol), was added potassium 2-methylpropan-2-olate (0.136 g, 1.216 mmol) at 0° C. The mixture was stirred at room temperature for 5 minutes. The mixture was added 2 mL of 1N HCl followed by 10 mL of sat. NaHCO$_3$ and 20 mL of CH$_2$Cl$_2$. The mixture was extracted and separated. The organic layer was concentrated on rota-vap and the resulting solid was stirred with ether (20 mL) to give 3-[4-(4-cyclohexylaminomethyl-benzyloxy)-1-oxo-1,3-dihydro-isoindol-2-yl]-piperidine-2,6-dione as a white solid (250 mg, 47%). mp: 175-177° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=4.80 min (95%). $^1$H NMR (DMSO-d$_6$) δ 0.94-1.20 (m, 4H, CH$_2$, CH$_2$, CHH), 1.42-1.58 (m, 1H, CHH), 1.58-1.73 (m, 2H, CH$_2$), 1.80-1.84 (m, 2H, CH$_2$), 1.91-2.06 (m, 1H, CHH), 2.27-2.40 (m, 1H, CH), 2.40-2.48 (m, 1H, CHH), 2.53-2.64 (m, 1H, CHH), 2.79-3.04 (m, 1H, CHH), 3.71 (s, 2H, CH$_2$), 4.10-4.60 (m, 2H, CH$_2$), 5.11 (dd, J=5.1, 13.2 Hz, 1H, NCH), 5.22 (s, 2H, CH$_2$), 7.24-7.63 (m, 7H, Ar). $^{13}$C NMR (DMSO-d$_6$) δ 22.29, 24.34, 25.84, 31.14, 32.81, 45.04, 49.51, 51.53, 55.05, 69.43, 114.94, 115.12, 127.51, 127.83, 129.71, 129.90, 133.24, 134.50, 141.46, 153.43, 167.94, 170.90, 172.75; LCMS MH=462. Anal Calcd for C$_{27}$H$_{31}$N$_3$O$_4$+0.4 H$_2$O: C, 69.18; H, 6.84; N, 8.96; Found: C, 69.02; H, 7.11; N, 8.79.

5.186 3-(4-(4-((Methyl(2-Morpholinoethyl)Amino)Methyl)Benzyloxy)-1-Oxoisoindolin-2-yl)Piperidine-2,6-Dione

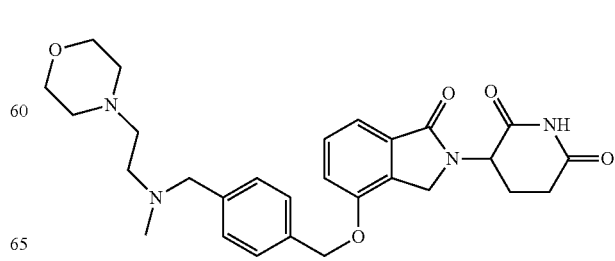

Step 1: To the acetonitrile solution (10 mL) of methyl 5-amino-4-(4-(4-(chloromethyl)benzyloxy)-1-oxoisoindolin-2-yl)-5-oxopentanoate (0.5 g, 1.160 mmol), was added N-methyl-2-morpholinoethanamine (0.201 g, 1.392 mmol) followed by DIPEA (0.243 ml, 1.392 mmol). The mixture was stirred at room temperature overnight. The reaction mixture was concentrated and extracted with $CH_2Cl_2$ (30 mL) and water (30 mL). Organic layer was concentrated on rota-vap to give 4-carbamoyl-4-[4-(4-{[methyl-(2-morpholin-4-yl-ethyl)-amino]-methyl}-benzyloxy)-1-oxo-1,3-dihydro-isoindol-2-yl]-butyric acid methyl ester as a foamy solid. It was used in the next step without further purification.

Step 2: To the THF solution (20 mL) of methyl 5-amino-4-(4-(4-((methyl(2-morpholinoethyl)amino)methyl)benzyloxy)-1-oxoisoindolin-2-yl)-5-oxopentanoate (0.6 g, 1.114 mmol), was added potassium tert-butoxide (0.150 g, 1.337 mmol). The mixture was stirred at 0° C. for 5 minutes. The reaction mixture was added 1N HCl (2 mL), followed by sat. $NaHCO_3$ (10 mL) and $CH_2Cl_2$ (30 mL). The mixture was extracted and separated. The organic layer was dried over $Na_2SO_4$ and concentrated. The resulting foamy solid was purified on silica gel column and eluted with $CH_2Cl_2$/MeOH to give 3-(4-(4-((methyl(2-morpholinoethyl)amino)methyl)benzyloxy)-1-oxoisoindolin-2-yl)piperidine-2,6-dione as white solid (0.34 g, 60%). mp: 193-195° C. HPLC: Waters Symmetry C-18, 3.9×150 mm, 5 micro, 1 mL/min, 240 nm, gradient acetonitrile/0.1% $H_3PO_4$ in $H_2O$ from 5/95 to 100/0 in 5 min and stayed at 100/0 for 5 min: $t_R$ 4.25 min (98%). $^1H$ NMR (DMSO-$d_6$) δ 1.94-2.05 (m, 1H, CHH), 2.14 (s, 3H, $CH_3$), 2.30-2.38 (br. s., 4H, $CH_2$, $CH_2$), 2.38-2.49 (br. s., 5H, $CH_2$, $CH_2$, CHH), 2.54-2.60 (m., 1H, CHH), 2.89 (m, 1H, CHH), 3.43-3.63 (m, 6H, $CH_2$, $CH_2$, $CH_2$), 4.22-4.45 (m, 2H, $CH_2$), 5.11 (dd, J=4.9, 13.2 Hz, 1H, NCH), 5.23 (s, 2H, $CH_2$), 7.31-7.51 (m, 6H, Ar), 10.97 (s, 1H, NH). $^{13}C$ NMR (DMSO-$d_6$) δ 22.36, 31.21, 42.19, 45.10, 51.58, 53.63, 53.88, 56.11, 61.43, 66.16, 69.44, 115.01, 115.23, 127.58, 128.77, 129.79, 129.95, 133.31, 135.13, 139.01, 153.50, 168.01, 170.96, 172.83. Anal Calcd for $C_{28}H_{34}N_4O_5$+0.4 $H_2O$: C, 65.45; H, 6.83; N, 10.90; Found: C, 65.71; H, 7.11; N, 10.95.

5.187 3-(4-{4-[(2-Morpholin-4-yl-Ethylamino)-Methyl]-Benzyloxy}-1-Oxo-1,3-Dihydro-Isoindol-2-yl)-Piperidine-2,6-Dione Bis Hydrochloride

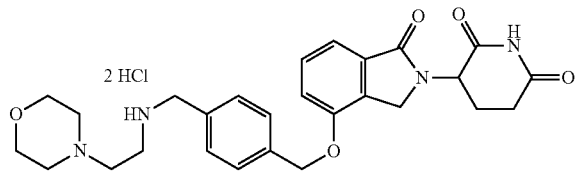 [SMILES: O=C1CCC(N2Cc3c(OCc4ccc(CNCCN5CCOCC5)cc4)cccc3C2=O)C(=O)N1]

Step 1: To a stirred solution of methyl 5-amino-4-(4-(4-(chloromethyl)benzyloxy)-1-oxoisoindolin-2-yl)-5-oxopentanoate (1.18 g, 2.75 mmol) in acetonitrile (15 ml), was added 2-morpholinoethanamine (1.08 ml, 8.24 mmol). The reaction mixture immediately turned into a light green solution. The mixture was stirred at room temperature overnight and then evaporated to give a light green oil, which was not further characterized and used in the next step without purification.

Step 2: To a stirred solution of methyl 5-amino-4-(4-(4-((2-morpholinoethylamino)methyl)benzyloxy)-1-oxoisoindolin-2-yl)-5-oxopentanoate (1.44 g, 2.75 mmol) in dichloromethane (15 ml), was added di-tert-butyl dicarbonate (1.80 g, 8.25 mmol). The weight of the limiting SM was assumed as 1.44 g, which was the theoretical yield of the previous step. The oil was purified on silica gel column (MeOH/$CH_2Cl_2$ gradient from 1% to 9% in 50 min) to give 4-[4-(4-{[tert-butoxycarbonylmethyl-(2-morpholin-4-yl-ethyl)-amino]-methyl}-benzyloxy)-1-oxo-1,3-dihydro-isoindol-2-yl]-4-carbamoyl-butyric acid methyl ester as an oily solid (0.88 g, 51% yield over two steps).

Step 3: To a stirred solution of methyl 5-amino-4-(4-(4-((tert-butoxycarbonyl(2-morpholinoethyl)amino)methyl)benzyloxy)-1-oxoisoindolin-2-yl)-5-oxopentanoate (0.36 g, 0.58 mmol) in THF (10 ml) at 0° C., was added potassium 2-methylpropan-2-olate (0.07 g, 0.58 mmol). The reaction mixture was stirred for ten minutes and was quenched with 1 N HCl (2 mL) to give a clear colorless solution. It was neutralized with saturated sodium bicarbonate (4 ml to pH=8) to give a cloudy mixture, which was extracted with ethyl acetate (2×20 mL). The ethyl acetate phase was concentrated and purified on silica gel column (MeOH/$CH_2Cl_2$ gradient from 1% to 5% in 30 min) to give [{4-[2-(2,6-dioxo-piperidin-3-yl)-1-oxo-2,3-dihydro-1H-isoindol-4-yloxymethyl]-benzyl}-(2-morpholin-4-yl-ethyl)-amino]-acetic acid tert-butyl ester as a foamy solid (0.21 g, 62% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% $H_3PO_4$), 5.38 min (97.4%); mp: 110-112° C.; $^1H$ NMR (DMSO-$d_6$) δ 1.29-1.49 (m, 9H, 3$CH_3$), 1.92-2.05 (m, 1H, CHH), 2.25-2.39 (m, 6H, 3$CH_2$), 2.44 (dd, J=4.5, 13.0 Hz, 1H, CHH), 2.53-2.64 (m, 1H, CHH), 2.83-3.00 (m, 1H, CHH), 3.15-3.29 (m, 2H, $CH_2$), 3.52 (t, J=4.6 Hz, 4H, 2$CH_2$), 4.19-4.49 (m, 4H, $CH_2$, $CH_2$), 5.11 (dd, J=5.1, 13.2 Hz, 1H, NCH), 5.23 (s, 2H, $CH_2$), 7.23-7.37 (m, 4H, Ar), 7.41-7.53 (m, 3H, Ar), 10.97 (s, 1H, NH); $^{13}C$ NMR (DMSO-$d_6$) δ 22.36, 28.02, 31.21, 43.30, 45.09, 49.37, 50.05, 51.58, 53.33, 55.95, 56.39, 66.17, 69.32, 78.84, 115.00, 115.23, 127.39, 127.83, 129.78, 129.97, 133.31, 135.30, 138.56, 153.43, 155.02, 168.01, 170.96, 172.83 (2 extra peaks in alkyl region possibly from the two alkyl atoms close to the amide nitrogen atom due to the rotamer); LCMS MH=593; Anal. Calcd for $C_{32}H_{40}N_4O_7$+0.1 $H_2O$: C, 64.65; H, 6.82; N, 9.42. Found: C, 64.31; H, 6.82; N, 9.24.

Step 4: To a stirred solution of tert-butyl 4-((2-(2,6-dioxopiperidin-3-yl)-1-oxoisoindolin-4-yloxy)methyl)benzyl(2-morpholinoethyl)carbamate (0.27 g, 0.45 mmol) in dichloromethane (3 ml) was added 2M HCl/ether (2.5 ml). A white precipitate formed almost immediately. It was stirred at room temperature overnight and then filtered to give 3-(4-{4-[(2-Morpholin-4-yl-ethylamino)-methyl]-benzyloxy}-1-oxo-1,3-dihydro-isoindol-2-yl)-piperidine-2,6-dione two hydrochloride as a yellow solid (176 mg, 74% yield); HPLC: Waters Symmetry C-18, 3.9×150 mm, 5 μm, 1 mL/min, 240 nm, gradient from 05/95 to 95/5 in 5 min, isocratic at 95/5 in 5 min (acetonitrile/0.1% $H_3PO_4$), 4.89 min (95.4%); mp: 258-260° C.; $^1H$ NMR (DMSO-$d_6$) δ 1.94-2.06 (m, 1H, CHH), 2.36-2.44 (m, 1H, CHH), 2.55-2.66 (m, 1H, CHH), 2.83-3.00 (m, 1H, CHH), 3.03-3.23 (m, 2H, $CH_2$), 3.47 (br. s., 6H, $CH_2$, $CH_2$, $CH_2$), 3.80 (br. s., 2H, $CH_2$), 3.92-4.10 (m, 2H, $CH_2$), 4.15-4.51 (m, 4H, $CH_2$, $CH_2$), 5.12 (dd, J=5.2, 13.1 Hz, 1H, NCH), 5.30 (s, 2H, $CH_2$), 7.27-7.38 (m, 2H, Ar), 7.44-7.52 (m, 1H, Ar), 7.53-7.65 (m, 4H, ArH), 9.43-9.67 (br. s, 1.3H, NH or HCl), 10.97 (s, 1H, NH), 11.06-11.23 (br. s, 0.6H, NH or HCl); $^{13}C$ NMR (DMSO-$d_6$) δ 22.36, 31.22, 40.67, 45.15, 49.89, 51.62, 52.06, 54.93, 63.28, 69.03, 115.01, 115.33, 127.78, 129.81, 130.00, 130.17, 131.44, 133.35, 137.48, 153.30, 167.98, 170.96, 172.85; LCMS MH=493; Anal. Calcd for $C_{27}H_{32}N_4O_5 \cdot 2HCl$: +1.1 $H_2O$, +0.1 $CH_2Cl_2$: C, 54.82; H, 6.18; N, 9.44; Cl, 13.13; Found: C, 54.56; H, 6.04; N, 9.31; Cl, 12.82.

5.188 3-(4-{4-[(2-Hydroxy-Ethylamino)-Methyl]-Benzyloxy}-1-Oxo-1,3-Dihydro-Isoindol-2-yl)-Piperidine-2,6-Dione

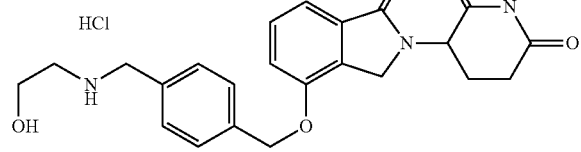

Step 1: To a stirred solution of methyl 5-amino-4-(4-(4-(chloromethyl)benzyloxy)-1-oxoisoindolin-2-yl)-5-oxopentanoate (0.52 g, 1.21 mmol) in acetonitrile (10 ml) at room temperature, were added 2-aminoethanol (0.15 ml, 2.41 mmol) and N-ethyl-N-isopropylpropan-2-amine (0.60 ml, 3.62 mmol). The reaction mixture was heated at 40° C. overnight and evaporated in vacuo to give an oil, which was mixed with methylene chloride (40 mL), washed with water (3×20 mL) and evaporated to a clear oil (0.61 g, 111% crude yield). It was used in the next step without further purification.

Step 2: To a stirred mixture of methyl 5-amino-4-(4-(4-((2-hydroxyethylamino)methyl)benzyloxy)-1-oxoisoindolin-2-yl)-5-oxopentanoate (0.61 g, 1.34 mmol) in THF (15 ml) in an ice bath, was added potassium 2-methylpropan-2-olate (0.65 g, 4.91 mmol), and the mixture was stirred for ten minutes. The mixture was quickly quenched with 1N HCl (~3 mL) and neutralized with saturated sodium bicarbonate (6 ml to pH=7), and then extracted with methylene chloride (3×30 mL). The organic phases were combined, washed with brine (20 mL) and concentrated to an off-white foamy solid (0.31 g, 54% yield). It was stirred in water (15 mL) and extracted with methylene chloride (4×20 mL). The aqueous phase was quickly frozen by acetone/dry ice mixture and lyophilized overnight. The weight of the white fluffy solid after lyophilizing was 83 mg. It was mixed with methylene chloride (2 mL, partially dissolved), added 2M HCl/ether (1.2 mL, 6 eq) and stirred overnight. The suspension was filtered and rinsed with diethyl ether. The filtered off-white solid was dried in vacuum oven to give 3-(4-{4-[(2-hydroxy-ethylamino)-methyl]-benzyloxy}-1-oxo-1,3-dihydro-isoindol-2-yl)-piperidine-2,6-dione (57 mg, 10% yield over two steps); HPLC: Waters Symmetry C-18, 3.9×150 mm, 5 µm, 1 mL/min, 240 nm, gradient from 10/90 to 95/5 in 5 min, isocratic at 95/5 in 5 min (acetonitrile/0.1% $H_3PO_4$), 5.13 min (92.2%); mp: 251-253° C.; $^1H$ NMR (DMSO-$d_6$) δ 1.92-2.06 (m, 1H, CHH), 2.37-2.47 (m, 1H, CHH), 2.54-2.65 (m, 1H, CHH), 2.83-3.00 (m, 3H, $CH_2$, CHH), 3.68 (t, J=5.4 Hz, 2H, $CH_2$), 4.11-4.20 (m, 2H, $CH_2$), 4.23-4.50 (m, 2H, $CH_2$), 5.11 (dd, J=5.1, 13.2 Hz, 1H, NCH), 5.29 (s, 2H, $CH_2$), 7.29-7.37 (m, 2H, Ar), 7.43-7.64 (m, 5H, Ar), 9.18-9.41 (m, 2H, HClNH), 10.97 (s, 1H, NH); $^{13}C$ NMR (DMSO-$d_6$) δ 22.36, 31.21, 45.13, 48.40, 49.49, 51.62, 56.30, 69.07, 115.01, 115.32, 127.74, 129.81, 130.00, 130.33, 131.65, 133.35, 137.30, 153.34, 167.98, 170.98, 172.85; LCMS MH=424; Anal Calcd for $C_{23}H_{25}N_3O_5 \cdot HCl$: C, 60.06; H, 5.70; N, 9.14; Cl, 7.71. Found: C, 48.95; H, 5.00; N, 7.28; Cl, 14.92.

5.189 4-((2-(2,6-Dioxopiperidin-3-yl)-1-Oxoisoindolin-4-yloxy)Methyl)-N-(2-Hydroxy-2Methylpropyl)Benzamide

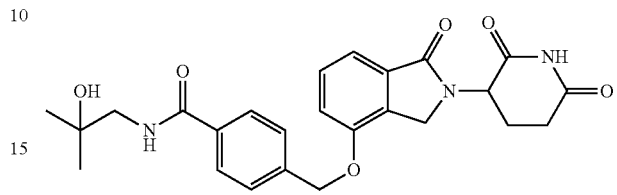

To a solution of 4-(chloromethyl)-N-(2-hydroxy-2-methylpropyl)benzamide (0.73 g, 3.02 mmol) and methyl 5-amino-4-(4-hydroxy-1-oxoisoindolin-2-yl)-5-oxopentanoate (0.839 g, 2.87 mmol) in DMF (10 mL), was added DIEA (0.527 ml, 3.02 mmol) at room temperature. The mixture was stirred at room temperature overnight. The solution was heated to 40° C. To the mixture was added $K_2CO_3$ (0.417 g, 3.02 mmol). The mixture was stirred at room temperature for 4 days. The reaction mixture was heated to 35° C. for 1 day. The mixture was heated to 80° C. overnight. The mixture was cooled to room temperature. The suspension was filtered and washed with acetonitrile (15 mL). The filtrate was acidified with HCOOH (2 mL). The solution was purified with prep HPLC, (Xbridge C18, 10 µm, 50×250 mm, 143 mL/min, 240 nM, 2/98/2 min, gradient to 95/5 acetonitrile 0.1% FA/H2O 0.1% formic acid in 30 min) to give 4-((2-(2,6-dioxopiperidin-3-yl)-1-oxoisoindolin-4-yloxy)methyl)-N-(2-hydroxy-2-methylpropyl)benzamide as a white solid (0.18 g, 12.8% yield): HPLC: (Waters Symmetry C18, 5 µm, 3.9×150 mm, 1 mL/min, 240 nm, 25/75 acetonitrile/0.1% H3PO4) 4.72 (95.2%); mp: 165-167° C.; 1H NMR (DMSO-d6) δ 1.10 (s, 6H, CH3, CH3), 1.87-2.11 (m, 1H, CHH), 2.36-2.47 (m, 1H, CHH), 2.53-2.64 (m, 1H, CHH), 2.77-3.04 (m, 1H, CHH), 3.25 (d, J=6.0 Hz, 2H, CH2), 4.31 (s, 1H, CHH), 4.42 (s, 1H, CHH), 4.55 (s, 1H, OH), 5.00-5.20 (m, 1H, NCH), 5.33 (s, 2H, CH2), 7.33 (dd, J=5.7, 7.0 Hz, 2H, Ar), 7.48 (t, J=7.7 Hz, 1H, Ar), 7.57 (d, J=8.3 Hz, 2H, Ar), 7.88 (d, J=8.3 Hz, 2H, Ar), 8.24 (t, J=6.1 Hz, 1H, NH), 10.98 (s, 1H, NH); 13C NMR (DMSO-d6) δ 22.27, 27.28, 31.11, 45.01, 50.12, 51.52, 68.92, 69.72, 114.96, 115.28, 127.15, 127.40, 129.73, 129.92, 133.28, 134.27, 139.59, 153.21, 166.30, 167.87, 170.89, 172.74; LCMS MH=466; Anal. Calcd for C, 25; H, 27; N, 3; O, 6;+1 H2O: C, 62.10; H, 6.05; N, 8.69; Found: C, 62.00; H, 5.74; N, 8.65.

5.190 3-(4-{4-[(Diisopropylamino)-Methyl]-Benzyloxy}-1-Oxo-1,3-Dihydro-Isoindol-2-yl)-Piperidine-2,6-Dione

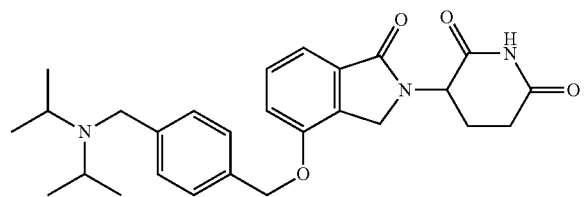 [SMILES: CC(C)N(Cc1ccc(COc2cccc3c2CN(C2CCC(=O)NC2=O)C3=O)cc1)C(C)C]

Step 1: To a stirred colorless solution of methyl 5-amino-4-(4-(4-(chloromethyl)benzyloxy)-1-oxoisoindolin-2-yl)-5-oxopentanoate (1.00 g, 2.32 mmol) in acetonitrile (10 ml) at room temperature, was added diisopropylamine (2.95 ml, 20.88 mmol). The mixture was stirred at 100° C. for two days. The reaction could not go completed and the mixture was used in the next step by a solvent swap to DMF without any purification.

Step 2: A mixture of methyl 5-amino-4-(4-(4-((diisopropylamino)methyl) benzyloxy)-1-oxoisoindolin-2-yl)-5-oxopentanoate (1.15 g, 2.32 mmol) and potassium carbonate (0.32 g, 2.32 mmol) in DMF (15 ml) was heated at 80° C. overnight. The suspension was filtered and rinsed with DMF to give a brown filtrate and off-white solid. The filtrate was evaporated to an oil and purified on silica gel column (MeOH/CH$_2$Cl$_2$ gradient from 1% to 9% in 50 min) to give 3-(4-{4-[(Diisopropylamino)-methyl]-benzyloxy}-1-oxo-1,3-dihydro-isoindol-2-yl)-piperidine-2,6-dione as a white solid (38 mg, 7% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.11% H$_3$PO$_4$), 5.35 min (95.8%); mp: 201-203° C.; $^1$H NMR (DMSO-d$_6$) δ 0.98 (d, J=6.6 Hz, 12H, 4CH$_3$), 1.90-2.05 (m, 1H, CHH), 2.35-2.46 (m, 1H, CHH), 2.53-2.65 (m, 2H, CHH, CHH), 2.82-3.05 (m, 2H, CHH, CHH), 3.61 (s, 2H, CH$_2$), 4.18-4.49 (m, 2H, CH$_2$), 5.11 (dd, J=5.1, 13.2 Hz, 1H, NCH), 5.20 (s, 2H, CH$_2$), 7.26-7.55 (m, 7H, Ar), 10.96 (s, 1H, NH); $^{13}$C NMR (DMSO-d$_6$) δ 20.60, 22.35, 31.21, 45.10, 47.35, 48.03, 51.58, 69.52, 114.95, 115.19, 127.56, 127.64, 129.81, 129.95, 133.29, 134.39, 142.81, 153.56, 168.02, 170.96, 172.83; LCMS MH=464; Anal. Calcd for C$_{27}$H$_{33}$N$_3$O$_4$+1.1 H$_2$O: C, 67.09; H, 7.34; N, 8.69. Found: C, 66.73; H, 6.99; N, 8.56.

5.191 3-(1-Oxo-4-{4-[(Tetrahydro-Pyran-4-ylamino)-Methyl]-Benzyloxy}-1,3-Dihydro-Isoindol-2-yl)-Piperidine-2,6-Dione

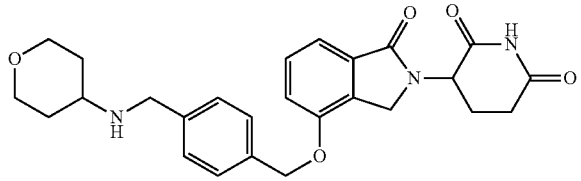 [SMILES: O=C1CCC(N2Cc3c(OCc4ccc(CNC5CCOCC5)cc4)cccc3C2=O)C(=O)N1]

Step 1: To a solution of methyl 5-amino-4-(4-(4-(chloromethyl)benzyloxy)-1-oxoisoindolin-2-yl)-5-oxopentanoate (0.5 g, 1.16 mmol) in THF (10 mL), was added tetrahydro-2H-pyran-4-amine (0.29 g, 2.90 mmol) at room temperature. The mixture was stirred at room temperature overnight and then heated at 45° C. for three hours. The reaction mixture was filtered to get rid of the solid. The filtrate was concentrated and extracted with water and dichloromethane. The organic layer was concentrated to give a yellow foamy solid (0.50 g, 87% yield), which was purified on silica gel (MeOH/CH$_2$Cl$_2$ gradient from 1% to 10% in 30 min) to give 4-carbamoyl-4-(1-oxo-4-{4-[(tetrahydro-pyran-4-ylamino)-methyl]-benzyloxy}-1,3-dihydro-isoindol-2-yl)-butyric acid methyl ester as an oil (0.40 g, 70% yield). It was used in the next step without further purification.

Step 2: To a stirred solution of methyl 5-amino-5-oxo-4-(1-oxo-4-(4-((tetrahydro-2H-pyran-4-ylamino)methyl)benzyloxy)isoindolin-2-yl)pentanoate (0.40 g, 0.81 mmol) in THF (15 ml) in an ice bath, was added potassium 2-methylpropan-2-olate (0.10 g, 0.90 mmol). The mixture was stirred for ten minutes and then quenched with 1N HCl (2 ml) and neutralized with saturated sodium bicarbonate (3 ml to pH=7). The mixture was stirred with ethyl acetate (30 ml) and separated. The organic phase was washed with brine (20 ml) and concentrated to an off-white solid, which was purified on silica gel column (MeOH/CH$_2$Cl$_2$ gradient from 1% to 10% in 30 min) to give 3-(1-oxo-4-{4-[(tetrahydro-pyran-4-ylamino)-methyl]-benzyloxy}-1,3-dihydro-isoindol-2-yl)-piperidine-2,6-dione as a white solid (80.8 mg, 22% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 4.89 min (98.7%); mp: 231-233° C.; $^1$H NMR (DMSO-d$_6$) δ 1.19-1.32 (m, 3H, NH, CH$_2$), 1.74-1.79 (m, 2H, CH$_2$), 1.96-2.00 (m, 1H, CHH), 2.37-2.47 (m, 1H, CHH), 2.51-2.60 (m, 2H, 2CH), 2.85-2.97 (m, 1H, CHH), 3.20-3.28 (m, 2H, CH$_2$), 3.73 (s, 2H, CH$_2$), 3.78-3.84 (m, 2H, CH$_2$), 4.22-4.44 (m, 2H, CH$_2$), 5.11 (dd, J=5.1, 13.2 Hz, 1H, NCH), 5.22 (s, 2H, CH$_2$), 7.31-7.51 (m, 7H, Ar), 10.97 (s, 1H, NH); $^{13}$C NMR (DMSO-d$_6$) δ 22.32, 31.17, 33.10, 45.08, 49.08, 51.56, 52.36, 65.76, 69.45, 115.00, 115.18, 127.57, 127.94, 129.77, 129.95, 133.28, 134.64, 141.20, 153.46, 167.99, 170.95, 172.81; LCMS MH=464; Anal. Calcd for C$_{26}$H$_{29}$N$_3$O$_5$ (0.5 H$_2$O): C, 66.09; H, 6.40; N, 8.89. Found: C, 65.90; H, 6.21; N, 8.62.

5.192 4-[2-(2,6-Dioxo-Piperidin-3-yl)-1-Oxo-2,3-Dihydro-1H-Isoindol-4-yloxymethyl]-N-(3-Piperidin-1-yl-Propyl)-Benzamide

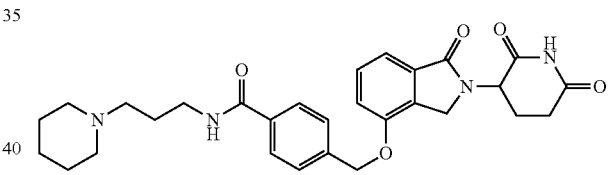

Step 1: 3-(Piperidin-1-yl)propan-1-amine (411 mg, 2.89 mmol) was added to a stirred solution of 4-(chloromethyl)benzoyl chloride (546 mg, 2.89 mmol) in acetonitrile (10 mL) through syringe. After addition the solution was stirred at room temperature for 20 minutes and the reaction was complete. The reaction mixture was added by NaHCO$_3$ (aq. sat., 20 mL). The clear solution was back extracted with EtOAc (3×25 mL). Organic layers were combined and dried by MgSO$_4$. The mixture was filtered and concentrated under vacuo to give 4-chloromethyl-N-(3-piperidin-1-yl-propyl)-benzamide as a light brown oil (700 mg, 82%). The compound was used in the next step as is: $^1$H NMR (DMSO-d$_6$) δ 1.37 (d, J=5.1 Hz, 2H, CH$_2$), 1.42-1.54 (m, 4H, CH$_2$, CH$_2$), 1.66 (t, J=7.0 Hz, 2H, CH$_2$), 2.23-2.39 (m, 6H, CH$_2$, CH$_2$, CH$_2$), 3.19-3.31 (m, 2H, CH$_2$), 4.80 (s, 2H, CH$_2$), 7.51 (d, J=8.1 Hz, 2H, Ar), 7.83 (d, J=8.1 Hz, 2H, Ar), 8.53 (t, J=5.4 Hz, 1H, NH); LCMS MH=295.

Step 2: To the mixture of methyl 5-amino-4-(4-hydroxy-1-oxoisoindolin-2-yl)-5-oxopentanoate (694 mg, 2.374 mmol), 4-(chloromethyl)-N-(3-(piperidin-1-yl)propyl)benzamide (700 mg, 2.374 mmol) and K$_2$CO$_3$ (328 mg, 2.374 mmol), was added DMF (10 mL). The reaction mixture was stirred at 50° C. overnight and K$_2$CO$_3$ (150 mg, 1.08 mmol) was added. The resulting mixture was heated at 80° C. for 2 hours. The reaction mixture was acidified by HCl (1N, aq.

8 mL) followed by addition of NaHCO₃ (aq. sat. 8 mL) and brine (10 mL). The aqueous layer was back extracted with dichloromethane (3×35 mL). The organic layers were combined and dried by MgSO₄. The mixture was filtered and concentrated. The residue was purified by ISCO chromatography to give a white solid. The solid was triturated in dichloromethane (1 mL) and ether (15 mL) to give 4-[2-(2,6-dioxo-piperidin-3-yl)-1-oxo-2,3-dihydro-1H-isoindol-4-yloxymethyl]-N-(3-piperidin-1-yl-propyl)-benzamide as a white solid (84 mg, 6.8% yield): HPLC: Waters Symmetry C-18, 3.9×150 mm, 5 μm, 1 mL/min, 240 nm, 18/82, (acetonitrile/0.1% H₃PO4), 4.54 min (98.5%); mp: 183-185° C.; ¹H NMR (DMSO-d₆) δ 1.37 (d, J=5.1 Hz, 2H, CH₂), 1.43-1.54 (m, 4H, CH₂, CH₂), 1.67 (quin, J=7.0 Hz, 2H, CH₂), 1.93-2.07 (m, 1H, CHH), 2.31 (d, J=5.7 Hz, 5H, CH₂, CH₂), 2.40-2.47 (m, 1H, CHH), 2.53-2.66 (m, 1H, CHH), 2.83-3.01 (m, 1H, CHH), 3.21-3.37 (m, 3H, CH₂, CHH), 4.28 (d, J=17.6 Hz, 1H, CHH), 4.45 (d, J=17.4 Hz, 1H, CHH), 5.12 (dd, J=5.0, 13.1 Hz, 1H, CHH), 5.32 (s, 2H, CH₂), 7.32 (dd, J=7.6, 8.3 Hz, 2H, Ar), 7.48 (t, J=7.7 Hz, 1H, Ar), 7.56 (d, J=8.3 Hz, 2H, Ar), 7.84 (d, J=8.1 Hz, 2H, Ar), 8.50 (t, J=5.4 Hz, 1H, NH), 10.98 (s, 1H, NH); ¹³C NMR (DMSO-d₆) δ 22.34, 24.05, 25.52, 26.19, 31.18, 37.97, 45.07, 51.59, 54.01, 56.43, 68.98, 115.03, 115.35, 127.25, 127.21, 129.78, 129.97, 133.34, 134.29, 139.58, 153.29, 165.73, 167.91, 170.96, 172.81; LCMS MH=519; Anal. Calcd for C₂₉H₃₄N₄O₅+0.4 H₂O: C, 66.24; H, 6.67; N, 10.66; Found: C, 66.17; H, 6.43; N, 10.53.

5.193 2-{4-[2-(2,6-Dioxo-Piperidin-3-yl)-1-Oxo-2,3-Dihydro-1H-Isoindol-4-yl Oxymethyl]-Benzylamino}-2-Methyl-Propionic Acid

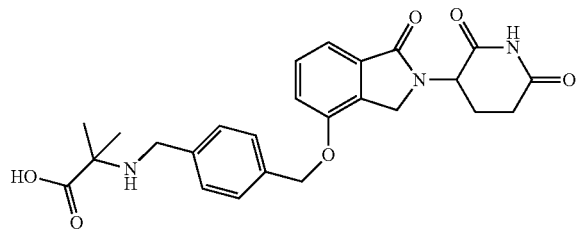 [SMILES: CC(C)(NCc1ccc(COc2cccc3c2CN(C2CCC(=O)NC2=O)C3=O)cc1)C(=O)O]

Step 1: 4-(4-{4-[(1-tert-Butoxycarbonyl-1-methyl-ethylamino)-methyl]-benzyloxy}-1-oxo-1,3-dihydro-isoindol-2-yl)-4-carbamoyl-butyric acid methyl ester To the stirred solution of methyl 5-amino-4-(4-(4-(bromomethyl)benzyloxy)-1-oxoisoindolin-2-yl)-5-oxopentanoate (600 mg, 1.262 mmol) in Acetonitrile (10 mL) at room temperature was added by tert-butyl 2-amino-2-methylpropanoate hydrochloride (272 mg, 1.389 mmol) and DIPEA (0.551 ml, 3.16 mmol). The reaction was stirred at room temperature over night for 5 days and added by EtOAc (50 mL), NaHCO₃ (aq, sat, 5 mL) and brine (15 mL). The mixture was extracted and organic layer was concentrated in vacuo. The residue was purified by ISCO chromatography to give 4-(4-{4-[(1-tert-Butoxycarbonyl-1-methyl-ethylamino)-methyl]-benzyloxy}-1-oxo-1,3-dihydro-isoindol-2-yl)-4-carbamoyl-butyric acid methyl ester as a clear sticky solid (470 mg, 67% yield); LCMS MH=554; ¹H NMR (DMSO-d₆) δ 1.21 (s, 6H, CH₃, CH₃), 1.44 (s, 9H, CH₃, CH₃, CH₃), 1.97-2.32 (m, 4H, CH₂, CH₂, CH), 3.50 (s, 3H, CH₃), 3.58 (d, J=5.7 Hz, 2H, CH₂), 4.39 (d, J=17.6 Hz, 1H, CHH), 4.52 (d, J=17.6 Hz, 1H, CHH), 4.72 (dd, J=4.6, 10.1 Hz, 1H, CHH), 5.22 (s, 2H, CH₂), 7.18 (s, 1H, NHH), 7.25-7.32 (m, 2H, Ar), 7.32-7.39 (m, 2H, Ar), 7.40-7.49 (m, 3H, Ar), 7.58 (s, 1H, NHH).

Step 2: 2-{4-[2-(2,6-Dioxo-piperidin-3-yl)-1-oxo-2,3-dihydro-1H-isoindol-4-yl oxymethyl]-benzylamino}-2-methyl-propionic acid tert-butyl ester To the stirred solution of methyl 5-amino-4-(4-(4-((1-tert-butoxy-2-methyl-1-oxopropan-2-ylamino)methyl)benzyloxy)-1-oxoisoindolin-2-yl)-5-oxopentanoate (470 mg, 0.849 mmol) in Tetrahydrofuran (Volume: 10 ml) at 0° C. was added by potassium tert-butoxide (95 mg, 0.849 mmol) in one portion. The mixture was stirred at 0° C. for 15 mins. The reaction mixture was diluted by EtOAc (50 mL) and quenched by HCl (1N, aq, 3 mL) followed by the addition of NaHCO₃ (aq, sat., 3 mL) and brine (15 mL). The mixture was extracted and the organic layer was dried by MgSO₄. The mixture was filtered and concentrated in vacuo to give 2-{4-[2-(2,6-Dioxo-piperidin-3-yl)-1-oxo-2,3-dihydro-1H-isoindol-4-yloxymethyl]-benzylamino}-2-methyl-propionic acid tert-butyl ester as a white solid (460 mg, 104% crude yield). The compound was used in the next step without further purification; LCMS MH=522.

Step 3: 2-{4-[2-(2,6-Dioxo-piperidin-3-yl)-1-oxo-2,3-dihydro-1H-isoindol-4-yl oxymethyl]-benzylamino}-2-methyl-propionic acid To the suspension of tert-butyl 2-(4-((2-(2,6-dioxopiperidin-3-yl)-1-oxoisoindolin-4-yloxy)methyl)benzylamino)-2-methylpropanoate (360 mg, 0.690 mmol) in DCM (2 mL) was added hydrogen chloride, 2M in ether (8 ml, 16.00 mmol). The resulting suspension was stirred at room temperature for 5 days before it was concentrated under vacuo. The residue was purified by prepH-PLC to give 2-{4-[2-(2,6-Dioxo-piperidin-3-yl)-1-oxo-2,3-dihydro-1H-isoindol-4-yloxymethyl]-benzylamino}-2-methyl-propionic acid as a white solid (125 mg, 39%); HPLC: Waters Symmetry C-18, 3.9×150 mm, 5 μm, 1 mL/min, 240 nm, 5-95% in 10 mins, (CH₃CN/0.1% H₃PO4), 5.96 min (98.4%); mp: 271-272° C.; ¹H NMR (DMSO-d₆) δ 1.32 (s, 6H, CH₃, CH₃), 1.93-2.05 (m, 1H, CHH), 2.35-2.48 (m, 1H, CHH), 2.54-2.64 (m, 1H, CHH), 2.88 (d, J=18.5 Hz, 1H, CHH), 3.89 (s, 2H, CH₂), 4.25 (d, J=17.6 Hz, 1H, CHH), 4.42 (d, J=17.6 Hz, 1H, CHH), 5.11 (dd, J=5.0, 13.1 Hz, 1H, CHH), 5.27 (s, 2H, CH₂), 7.26-7.37 (m, 2H, Ar), 7.40-7.58 (m, 5H, Ar), 10.98 (s, 1H, NH); ¹³C NMR (DMSO-d₆) δ 22.33, 23.26, 23.33, 31.18, 45.07, 46.38, 51.58, 61.65, 69.26, 115.16, 115.29, 127.66, 129.41, 129.77, 130.03, 133.30, 135.37, 136.33, 153.33, 167.97, 170.99, 172.81, 173.07; LCMS MH=466; Anal. Calcd for C₂₅H₂₇N₃O₆+1.9 H₂O: C, 60.09; H, 6.21; N, 8.41; Found: C, 60.01; H, 5.98; N, 8.23.

5.194 3-(4-(4-((Methyl(Tetrahydro-2H-Pyran-4-yl)Amino)Methyl)Benzyloxy)-1-Oxoisoindolin-2-yl)Piperidine-2,6-Dione Formate

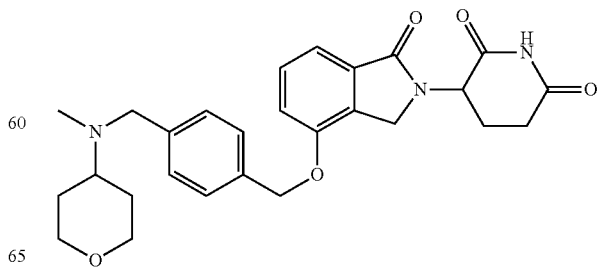

(3-(4-(4-(Bromomethyl)benzyloxy)-1-oxoisoindolin-2-yl)piperidine-2,6-dione (150 mg, 0.338 mmol)) was slurried in MeCN (5 mL). N-methyltetrahydro-2H-pyran-4-amine (136 mg, 1.184 mmol) was added to the mixture and the resulting mixture was stirred at room temperature for ~15 min. The reaction mixture was diluted with EtOAc (100 mL) and 1N NaHCO$_3$ (30 mL). The cloudy organic layer was concentrated in vacuo and the remaining residue was triturated with water (100 mL) and Et$_2$O (~100 mL). The solid was collected by filtration and suction dried on filter funnel and then placed in vacuum oven at 40° C. overnight to give 125 mg of white solid. The solid was dissolved in DMF/1 N HCl (12 mL/1 mL) and purified by injection onto a C-18 preparatory HPLC column. The product was eluted with an acetonitrile/water gradient (0.1% formic acid in both mobile phases, 5% to 50% MeCN over 20 minutes) and fractions were collected by mass trigger. The desired fractions were combined and concentrated in vacuo to give 3-(4-(4-((methyl(tetrahydro-2H-pyran-4-yl)amino)methyl)benzyloxy)-1-oxoisoindolin-2-yl)piperidine-2,6-dione Formate as a white solid (25 mg, 15% yield) as a white solid: HPLC: Waters Symmetry C$_{18}$, 5 μm, 3.9×150 mm, 1 ml/min, 240 nm, 17/83 CH$_3$CN/0.1% H$_3$PO$_4$, 4.48 min (98.1%); $^1$H NMR (DMSO-d$_6$) δ 1.43-1.59 (m, 2H, CHH, CHH), 1.62-1.76 (m, 2H, CHH, CHH), 1.92-2.04 (m, 1H, CHH), 2.09 (s, 3H, CH$_3$), 2.35-2.48 (m, 1H, CHH), 2.52-2.71 (m, 2H, CHH, CH), 2.82-2.99 (m, 1H, CHH), 3.18-3.32 (m, 2H, CHH, CHH), 3.55 (s, 2H, CH$_2$), 3.90 (dd, J=3.8, 11.1 Hz, 2H, CHH, CHH), 4.25 (d, J=17.6 Hz, 1H, CHH), 4.42 (d, J=17.4 Hz, 1H, CHH), 5.11 (dd, J=5.2, 13.1 Hz, 1H, CH), 5.22 (s, 2H, CH$_2$), 7.26-7.37 (m, 4H, Ar), 7.37-7.55 (m, 3H, Ar), 10.96 (s, 1H, NH); $^{13}$C NMR (DMSO-d$_6$) δ 8 22.33, 28.89, 31.18, 37.14, 45.07, 51.55, 56.77, 59.08, 66.61, 69.45, 114.99, 115.19, 127.60, 128.47, 129.78, 129.95, 133.28, 134.92, 139.93, 153.49, 167.99, 170.96, 172.81; LC/MS M+H=478.

5.195 3-{4-[4-(Tert-Butylamino-Methyl)-Benzyloxy]-1-Oxo-1,3-Dihydro-Isoindol-2-yl}-Piperidine-2,6-Dione

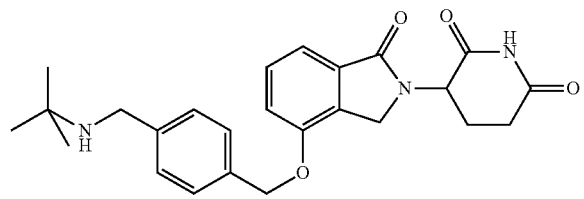 [SMILES: CC(C)(C)NCc1ccc(COc2cccc3c2CN(C2CCC(=O)NC2=O)C3=O)cc1]

Step 1: Preparation of 4-{4-[4-(tert-Butylamino-methyl)-benzyloxy]-1-oxo-1,3-dihydro-isoindol-2-yl}-4-carbamoyl-butyric acid methyl ester To a stirred solution of methyl 5-amino-4-(4-(4-(bromomethyl)benzyloxy)-1-oxoisoindolin-2-yl)-5-oxopentanoate (0.611 g, 1.285 mmol) in acetonitrile (15 ml) was added 2-methylpropan-2-amine (0.406 ml, 3.86 mmol). The mixture was stirred for six hours and then solvent was evaporated to give an oil, which was stirred in water (20 ml) and methylene chloride (30 ml). The resulting white suspension was filtered to give 4-{4-[4-(tert-Butylamino-methyl)-benzyloxy]-1-oxo-1,3-dihydro-isoindol-2-yl}-4-carbamoyl-butyric acid methyl ester as a white solid (0.523 g, 87% yield); $^1$H NMR (DMSO-d$_6$) δ 1.37 (s, 9H, 3CH$_3$), 1.97-2.34 (m, 4H, CH$_2$, CH$_2$), 3.50 (s, 3H, CH$_3$), 4.06-4.22 (m, 2H, CH$_2$), 4.35-4.61 (m, 2H, CH$_2$), 4.74 (dd, J=5.0, 10.3 Hz, 1H, NCH), 5.24-5.37 (m, 2H, CH$_2$), 7.19 (br. s., 1H, NHH), 7.25-7.35 (m, 2H, Ar), 7.41-7.50 (m, 1H, Ar), 7.52-7.70 (m, 5H, NHH, Ar), 8.61 (br. s., 2H, NHHCl); $^{13}$C NMR (DMSO-d$_6$) δ 24.96, 25.17, 30.36, 44.32, 44.77, 51.30, 53.40, 56.96, 69.01, 114.72, 115.24, 127.99, 129.59, 130.26, 132.17, 133.48, 137.55, 153.22, 167.80, 171.75, 172.51. It was used in the next step without further purification.

Step 2: Preparation of 3-{4-[4-(tert-Butylamino-methyl)-benzyloxy]-1-oxo-1,3-dihydro-isoindol-2-yl}-piperidine-2,6-dione To a stirred solution of methyl 5-amino-4-(4-(4-((tert-butylamino)methyl)benzyloxy)-1-oxoisoindolin-2-yl)-5-oxopentanoate (0.5 g, 1.069 mmol) in THF (20 ml) in an ice-bath was added potassium 2-methylpropan-2-olate (0.240 g, 2.14 mmol). The mixture was stirred for ten minutes and 1N HCl (3 ml) was added and neutralized by saturated sodium bicarbonate (6 ml) to pH=7. Ethyl acetate (50 ml) was added to the mixture and stirred for 5 min. The organic phase was separated, washed with brine (10 ml) and evaporated to a white foamy solid (0.38 g). It was stirred in ether (20 ml) for one hour then filtered to give 3-{4-[4-(tert-Butylamino-methyl)-benzyloxy]-1-oxo-1,3-dihydro-isoindol-2-yl}-piperidine-2,6-dione as a white solid (0.279 g, 60% yield); mp 194-196° C.; HPLC: Waters Symmetry C-18, 3.9×150 mm, 5 μm, 1 ml/min, 240 nm, gradient from 10/90 to 95/5 in 5 min, isocratic at 95/5 in 5 min (CH$_3$CN/0.1% H$_3$PO$_4$), 4.42 min (95.4%); $^1$H NMR (DMSO-d$_6$) δ 1.04-1.21 (m, 9H, 3CH$_3$), 1.92-2.06 (m, 1H, CHH), 2.36-2.48 (m, 1H, CHH), 2.53-2.65 (m, 1H, CHH), 2.83-2.99 (m, 1H, CHH), 3.68 (br. s., 2H, CH$_2$), 4.18-4.47 (m, 2H, CH$_2$), 5.11 (dd, J=5.1, 13.2 Hz, 1H, NCH), 5.22 (s, 2H, CH$_2$), 7.27-7.53 (m, 7H, Ar), 10.88-11.20 (weak, OH, NH); $^{13}$C NMR (DMSO-d$_6$) δ 22.36, 28.62, 31.21, 45.10, 45.88, 51.59, 69.45, 115.04, 115.19, 127.55, 128.19, 129.78, 129.97, 133.31, 134.69, 153.46, 168.01, 170.96, 172.82; LC/MS (M+1)$^+$=436; Anal Calcd for C$_{25}$H$_{29}$N$_3$O$_4$+0.2 H$_2$O: C, 68.38; H, 6.75; N, 9.57. Found: C, 68.16; H, 6.62; N, 9.52.

5.196 3-{1-Oxo-4-[4-(Piperazine-1-Carbonyl)-Benzyloxy]-1,3-Dihydro-Isoindol-2-yl}-Piperidine-2,6-Dione Hydrochloride

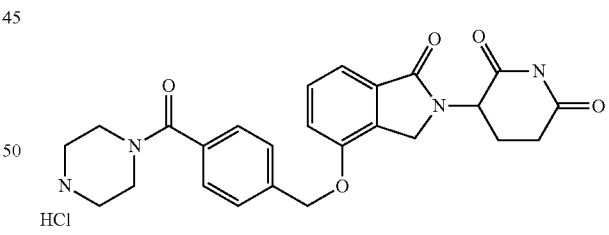

Step 1: To a stirred solution of 4-(chloromethyl)benzoyl chloride (1.890 g, 10 mmol) in MeCN (30 mL) at room temperature, was added tert-butyl piperazine-1-carboxylate (1.9 g, 10.20 mmol) and N-methylmorpholine (1.1 ml, 10.01 mmol). The mixture was stirred for 5 min. The reaction mixture was stored at −20° C. overnight during which a solid formed. The mixture was diluted with equal volume of water (about 30 mL) and the solid was collected by suction filtration and washed with another portion of water (about 20 mL). The remaining solid on the filter was dried in vacuum oven to give a white solid (1.93 g). A second crop of solid formed in the combined filtrate/wash and was collected by filtration and dried to give 4-(4-chloromethyl-benzoyl)-piperazine-1-carboxylic acid tert-butyl ester as a white solid (917 mg, 27% yield). LCMS analysis indicated that the second crop was of higher purity and was used in the next step without further purification. $^1$H NMR (DMSO-$d_6$) δ 1.41 (s, 9H, tBu), 3.11-3.72 (m, 8H, 4×CH$_2$), 4.80 (s, 2H, CH$_2$), 7.42 (d, J=8.3 Hz, 2H, Ar), 7.51 (d, J=8.1 Hz, 2H, Ar); $^{13}$C NMR (DMSO-$d_6$) δ 27.97, 43.35, 45.48, 79.15, 127.32, 128.81, 135.56, 139.00, 153.76, 168.70; LCMS: MH=339, 341.

Step 2: To a solution of methyl 5-amino-2-(4-hydroxy-1-oxoisoindolin-2-yl)-5-oxopentanoate (0.400 g, 1.369 mmol) in DMF (5.01 mL), was added DIEA (0.239 ml, 1.369 mmol), and potassium carbonate (0.189 g, 1.369 mmol). After stirring at room temperature for about 5 min, 4-(4-chloromethyl-benzoyl)-piperazine-1-carboxylic acid tert-butyl ester (0.455 g, 1.342 mmol) was added and the mixture was stirred at room temperature overnight. After about 17 h, the mixture was warmed to 50° C. for 3 h and then 60° C. for 22 h. The mixture was heated further to 80° C. for about 24 h. The crude mixture was transferred to a beaker with a 10% solution of AcOH in H$_2$O (50 mL). Immediately, a white solid formed upon transfer. The slurry was vigorously stirred and sonicated for 5 minutes then filtered on a medium pore fritted filter funnel. The solid was washed with copious water (total filtrate volume about 220 mL) and suction dried to give an off-white solid which was purified by silica gel flash chromatography (80 gm ISCO column, eluted with a MeCN in DCM gradient) to give 4-{4-[2-(2,6-dioxo-piperidin-3-yl)-1-oxo-2,3-dihydro-1H-isoindol-4-yl-oxymethyl]-benzoyl}-piperazine-1-carboxylic acid tert-butyl ester as a white solid (350 mg, 46% yield). LCMS: MH=563. The solid was used in the next step without further purification.

Step 3: To a stirred solution of 4-{4-[2-(2,6-dioxo-piperidin-3-yl)-1-oxo-2,3-dihydro-1H-isoindol-4-yl-oxymethyl]-benzoyl}-piperazine-1-carboxylic acid tert-butyl (350 mg, 0.622 mmol) in DCM (3 mL) at room temperature, was added HCl (2 mL, 4.00 mmol, 2 N in Et$_2$O). The mixture became increasingly cloudy with significant solid forming. The thick slurry was briefly sonicated and then stirred at room temperature for 26 h. The slurry was diluted with Et$_2$O (~40 mL) and then filtered. The collected white solid was suction dried and then washed on filter funnel with EtOAc (50 mL) followed by MeCN (~50 mL). The remaining solid was suction dried on filter funnel, then dried in vacuum oven to give 3-{1-oxo-4-[4-(piperazine-1-carbonyl)-benzyloxy]-1,3-dihydro-isoindol-2-yl}-piperidine-2,6-dione hydrochloride as a white solid (300 mg, 97% yield): HPLC:Waters Symmetry C$_{18}$, 5 μm, 3.9×150 mm, 1 ml/min, 240 nm, 15/85 CH$_3$CN/0.1% H$_3$PO$_4$, 4.73 min (96.7%); mp: 285-287° C.; $^1$H NMR (DMSO-$d_6$) δ 1.92-2.05 (m, 1H, CHH), 2.33-2.46 (m, 1H, CHH), 2.54-2.65 (m, 1H, CHH), 2.83-3.02 (m, 1H, CHH), 3.02-3.24 (m, 4H, CH$_2$, CH$_2$), 3.50-4.03 (m, 4H, CH$_2$, CH$_2$), 4.28 (d, J=17.6 Hz, 1H, CHH), 4.45 (d, J=17.6 Hz, 1H, CHH), 5.13 (dd, J=5.0, 13.3 Hz, 1H, CH), 5.32 (s, 2H, CH$_2$), 7.21-7.39 (m, 2H, Ar), 7.42-7.62 (m, 5H, Ar), 9.11 (br. s., 2H, NH$_2$ salt), 10.98 (s, 1H, NH); $^{13}$C NMR (DMSO-$d_6$) δ 24.11, 32.89, 46.57, 47.35, 53.72, 70.93, 117.11, 117.41, 128.97, 129.46, 131.79, 132.02, 134.89, 137.07, 139.91, 155.13, 171.08, 172.79, 175.11, 179.00; LCMS: MH=463; Anal Calcd for C$_{25}$H$_{26}$N$_4$O$_5$.HCl+0.6 H$_2$O: C, 58.90; H, 5.58; N, 10.99; Found: C, 58.91; H, 5.58; N, 10.78.

5.197 3-{4-[4-(Morpholine-4-Sulfonyl)-Benzyloxy]-1-Oxo-1,3-Dihydro-Isoindol-2-yl}-Piperidine-2,6-Dione

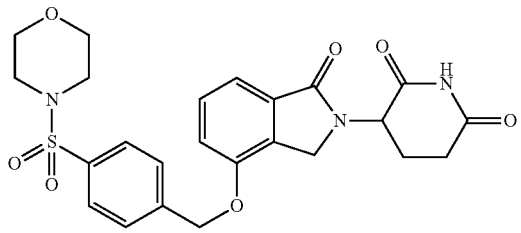 [SMILES: O=C1CCC(N2Cc3c(OCc4ccc(S(=O)(=O)N5CCOCC5)cc4)cccc3C2=O)C(=O)N1]

Step 1: 4-(4-Bromomethyl-benzenesulfonyl)-morpholine To the stirred solution of morpholine (0.30 ml, 3.4 mmol) and TRIETHYLAMINE (0.53 ml, 3.8 mmol) in ether (5 mL) at 0° C. was added solution of 4-(bromomethyl)benzene-1-sulfonyl chloride (0.928 g, 3.4 mmol) in ether (5 mL) drop wise. The resulting suspension was stirred at room temperature for 17.5 hrs before it was dissolved in acetonitrile (80 mL) and EtOAC (20 mL). The mixture was washed with brine (20 mL). Organic layer was dried by MgSO$_4$ and concentrated under vacuo. The residue was purified by ISCO to give 4-(4-Bromomethyl-benzenesulfonyl)-morpholine as a white solid (800 mg, 73%). The compound was put to next step without further purification. $^1$H NMR (DMSO-$d_6$) δ 2.77-2.94 (m, 4H, CH$_2$, CH$_2$), 3.54-3.70 (m, 4H, CH$_2$, CH$_2$), 4.81 (s, 2H, CH$_2$), 7.74 (s, 4H, Ar); LCMS MH=320, 322.

Step 2: 4-Carbamoyl-4-{4-[4-(morpholine-4-sulfonyl)-benzyloxy]-1-oxo-1,3-dihydro-isoindol-2-yl}-butyric acid methyl ester Methyl 5-amino-4-(4-hydroxy-1-oxoisoindolin-2-yl)-5-oxopentanoate (350 mg, 1.2 mmol), 4-(4-(bromomethyl)phenylsulfonyl)morpholine (498 mg, 1.6 mmol) and K$_2$CO$_3$ (165 mg, 1.2 mmol) were mixed in Acetonitrile (15 mL) at room temperature. The resulting mixture was stirred at 50° C. for 16 hrs and K$_2$CO$_3$ (15 mg, 0.1 mmol) was added. The reaction mixture was stirred at 50° C. for 3.5 hrs. The reaction mixture was filtered and the solid was washed with DCM (2×20 mL). The filtrate was concentrated and the residue was purified by ISCO to give 4-Carbamoyl-4-{4-[4-(morpholine-4-sulfonyl)-benzyloxy]-1-oxo-1,3-dihydro-isoindol-2-yl}-butyric acid methyl ester as a white solid (560 mg, 88% yield); $^1$H NMR (DMSO-$d_6$) δ 2.01-2.33 (m, 4H, CH$_2$, CH$_2$), 2.82-2.93 (m, 4H, CH$_2$, CH$_2$), 3.50 (s, 3H, CH$_3$), 3.59-3.68 (m, 4H, CH$_2$, CH$_2$), 4.47 (d, J=17.8 Hz, 1H, CHH), 4.60 (d, J=17.6 Hz, 1H, CHH), 4.75 (dd, J=4.7, 10.2 Hz, 1H, CHH), 5.41 (s, 2H, CH$_2$), 7.20 (s, 1H, NHH), 7.26-7.36 (m, 2H, Ar), 7.42-7.52 (m, 1H, Ar), 7.60 (s, 1H, NHH), 7.79 (s, 4H, Ar); LCMS MH=532.

Step 3: 3-{4-[4-(Morpholine-4-sulfonyl)-benzyloxy]-1-oxo-1,3-dihydro-isoindol-2-yl}-piperidine-2,6-dione To the stirred suspension of methyl 5-amino-4-(4-(4-(morpholinosulfonyl)benzyl oxy)-1-oxoisoindolin-2-yl)-5-oxopentanoate (560 mg, 1.1 mmol) in Tetrahydrofuran (15 mL) at 0° C. was added POTASSIUM TERT-BUTOXIDE (130 mg, 1.2 mmol). The reaction mixture was stirred for 1 hr and POTASSIUM TERT-BUTOXIDE (30 mg, 0.28 mmol) was added. The reaction mixture was stirred at 0° C. for 15 mins and then added by MeOH (20 mL) followed by the addition of HCl (aq, 1N, 5 mL). The mixture was added by brine (15 mL) and EtOAc (25 mL). The mixture was filtered and the filtrate was concentrated until solid started to precipitate out. The mixture was filtered and the solid was purified by stirred in mixed solvents of MeOH (5 mL), DCM (15 mL) and EtOAc (15 mL) to give 3-{4-[4-(Morpholine-4-sulfonyl)-benzyloxy]-1-oxo-1,3-dihydro-isoindol-2-yl}-piperidine-2,6-dione as a white solid (209 mg, 39% yield). HPLC: Waters Symmetry C-18, 3.9×150 mm, 5 µm, 1 mL/min, 240 nm, 35/65, (CH$_3$CN/0.1% H$_3$PO$_4$), 5.06 min (95.4%); mp: 308-310° C.; $^1$H NMR (DMSO-d$_6$) δ 1.93-2.09 (m, 1H, CHH), 2.35-2.47 (m, 1H, CHH), 2.54-2.67 (m, 1H, CHH), 2.80-3.03 (m, 5H, CHH, CH$_2$, CH$_2$), 3.55-3.69 (m, 4H, CH$_2$, CH$_2$), 4.32 (d, J=17.6 Hz, 1H, CHH), 4.48 (d, J=17.4 Hz, 1H, CHH), 5.13 (dd, J=4.9, 13.2 Hz, 1H, CHH), 5.41 (s, 2H, CH$_2$), 7.34 (dd, J=7.7, 10.0 Hz, 2H, Ar), 7.43-7.56 (m, 1H, Ar), 7.78 (s, 4H, Ar), 10.99 (s, 1H, NH); $^{13}$C NMR (DMSO-d$_6$) δ 22.39, 31.16, 45.01, 45.85, 51.56, 65.22, 68.55, 114.97, 115.54, 127.87, 128.04, 129.87, 129.96, 133.40, 133.82, 142.44, 153.19, 167.91, 170.96, 172.83; LCMS MH=500; Anal. Calcd for C$_{24}$H$_{25}$N$_3$O$_7$S+0.5H$_2$O: C, 56.68; H, 5.15; N, 8.26; Found: C, 56.71; H, 5.00; N, 8.16.

5.198 3-{4-[4-(4-Isopropyl-Piperidine-1-Sulfonyl)-Benzyloxy]-1-Oxo-1,3-Dihydro-Isoindol-2-yl}-Piperidine-2,6-Dione

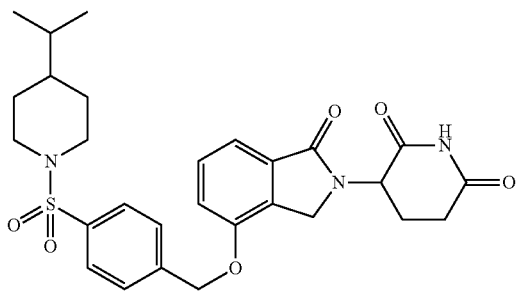 [SMILES: CC(C)C1CCN(S(=O)(=O)c2ccc(COc3cccc4c3CN(C3CCC(=O)NC3=O)C4=O)cc2)CC1]

Step 1: 1-(4-Bromomethyl-benzenesulfonyl)-4-isopropyl-piperidine To the stirred solution of 4-isopropylpiperidine (0.22 g, 1.7 mmol) and TRIETHYL AMINE (0.26 ml, 1.9 mmol) in ether (5 mL) at 0° C. was added solution of 4-(bromomethyl)benzene-1-sulfonyl chloride (0.466 g, 1.7 mmol) in ether (5 mL) drop wise. After addition the reaction mixture was stirred at 0° C. for 3 hrs. The reaction mixture was washed with water (15 mL) and brine (20 mL). Organic layer was dried by MgSO$_4$ and concentrated under vacuo to give 1-(4-Bromomethyl-benzenesulfonyl)-4-isopropyl-piperidine as a white solid (580 mg, 93% yield). The compound was put to next step without further purification. $^1$H NMR (DMSO-d$_6$) δ 0.78 (d, J=6.8 Hz, 6H, CH$_3$, CH$_3$), 0.89-1.04 (m, 1H, CH), 1.06-1.25 (m, 2H, CH$_2$), 1.28-1.46 (m, 1H, CH), 1.55-1.73 (m, 2H, CH$_2$), 2.16 (td, J=2.2, 11.9 Hz, 2H, CH$_2$), 3.68 (d, J=11.7 Hz, 2H, CH$_2$), 4.79 (s, 2H, CH$_2$), 7.71 (d, J=2.6 Hz, 4H, Ar); LCMS MH=360, 362.

Step 2: 4-Carbamoyl-4-{4-[4-(4-isopropyl-piperidine-1-sulfonyl)-benzyloxy]-1-oxo-1,3-dihydro-isoindol-2-yl}-butyric acid methyl ester Methyl 5-amino-4-(4-hydroxy-1-oxoisoindolin-2-yl)-5-oxopentanoate (360 mg, 1.2 mmol), 1-(4-(bromomethyl)phenylsulfonyl)-4-isopropylpiperidine (577 mg, 1.6 mmol) and POTASSIUM CARBONATE (187 mg, 1.4 mmol) were mixed in Acetonitrile (15 mL) at room temperature. The resulting mixture was stirred at 50° C. for 8 hrs and K$_2$CO$_3$ (30 mg, 0.2 mmol) was added the reaction mixture. The resulting mixture was heated at 50° C. for 2 hrs before the reaction mixture was added by EtOAc (60 mL) and water (20 mL). The mixture was extracted and organic layer was washed with brine (20 mL) and dried with MgSO$_4$. The organic layer was concentrated and the residue was purified by ISCO to give 4-Carbamoyl-4-{4-[4-(4-isopropyl-piperidine-1-sulfonyl)-benzyloxy]-1-oxo-1,3-dihydro-isoindol-2-yl}-butyric acid methyl ester as a white solid (700 mg, 99% yield). $^1$H NMR (DMSO-d$_6$) δ 0.78 (d, J=6.8 Hz, 6H, CH$_3$, CH$_3$), 0.88-1.04 (m, 1H, CH), 1.07-1.25 (m, 2H, CH$_2$), 1.29-1.43 (m, 1H, CH), 1.57-1.73 (m, 2H, CH$_2$), 2.02-2.32 (m, 6H, CH$_2$, CH$_2$, CH$_2$), 3.50 (s, 3H, CH$_3$), 3.69 (d, J=11.7 Hz, 2H, CH$_2$), 4.46 (d, J=17.8 Hz, 1H, CHH), 4.59 (d, J=17.6 Hz, 1H, CHH), 4.75 (dd, J=4.7, 10.2 Hz, 1H, CHH), 5.38 (s, 2H, CH$_2$), 7.20 (s, 1H, NHH), 7.26-7.35 (m, 2H, Ar), 7.42-7.52 (m, 1H, Ar), 7.60 (s, 1H, NHH), 7.71-7.83 (m, 4H, Ar); LCMS MH=572.

Step 3: 3-{4-[4-(4-Isopropyl-piperidine-1-sulfonyl)-benzyloxy]-1-oxo-1,3-dihydro-isoindol-2-yl}-piperidine-2,6-dione To the stirred solution of methyl 5-amino-4-(4-(4-(4-isopropylpiperidin-1-ylsulfonyl)benzyloxy)-1-oxoisoindolin-2-yl)-5-oxopentanoate (700 mg, 1.2 mmol) in Tetrahydrofuran (12 mL) at 0° C. was added POTASSIUM TERT-BUTOXIDE (151 mg, 1.3 mmol) in one portion. The solution was stirred at 0° C. for 30 mins. The reaction mixture was diluted by EtOAc (80 mL) and added by HCl (1N, aq, 3 mL). The mixture was added by NaHCO$_3$ (sat. aq, 15 mL) and extracted. Organic layer was washed with brine (30 mL) and dried by MgSO$_4$. The organic layer was concentrated and the resulting white solid was purified by being stirred in EtOAc (10 mL) and Acetonitrile (10 mL) to give 3-{4-[4-(4-Isopropyl-piperidine-1-sulfonyl)-benzyloxy]-1-oxo-1,3-dihydro-isoindol-2-yl}-piperidine-2,6-dione as a white solid (386 mg, 58% yield). HPLC: Waters Symmetry C-18, 3.9×150 mm, 5 µm, 1 mL/min, 240 nm, 55/45, (CH$_3$CN/0.1% H$_3$PO$_4$), 5.76 min (96.6%); mp: 245-247° C.; $^1$H NMR (DMSO-d$_6$) δ 0.78 (d, J=6.8 Hz, 6H, CH$_3$, CH$_3$), 0.97 (dd, J=5.5, 11.7 Hz, 1H, CH), 1.06-1.27 (m, 2H, CH$_2$), 1.36 (dq, J=6.5, 13.1 Hz, 1H, CH), 1.57-1.71 (m, 2H, CH$_2$), 1.93-2.08 (m, 1H, CHH), 2.06-2.24 (m, 2H, CH$_2$), 2.36-2.48 (m, 1H, CHH), 2.54-2.65 (m, 1H, CHH), 2.83-3.01 (m, 1H, CHH), 3.62-3.78 (m, 2H, CH$_2$), 4.31 (d, J=17.4 Hz, 1H, CHH), 4.47 (d, J=17.6 Hz, 1H, CHH), 5.13 (dd, J=5.1, 13.2 Hz, 1H, CHH), 5.38 (s, 2H, CH$_2$), 7.25-7.42 (m, 2H, Ar), 7.43-7.58 (m, 1H, Ar), 7.68-7.86 (m, 4H, Ar), 10.99 (s, 1H, NH); $^{13}$C NMR (DMSO-d$_6$) δ 19.28, 22.30, 27.75, 31.08, 31.39, 44.92, 46.29, 51.43, 68.45, 114.86, 115.44, 127.56, 127.89, 129.80, 129.86, 133.30, 134.91, 141.89, 153.10, 167.84, 170.92, 172.79; LCMS MH=540; Anal. Calcd for C$_{28}$H$_{33}$N$_3$O$_6$S+0.3H$_2$O: C, 61.70; H, 6.21; N, 7.71; Found: C, 61.78; H, 6.00; N, 7.68.

5.199 3-{1-Oxo-4-[4-(4-Phenyl-Piperazine-1-Sulfonyl)-Benzyloxy]-1,3-Dihydro-Isoindol-2-yl}-Piperidine-2,6-Dione

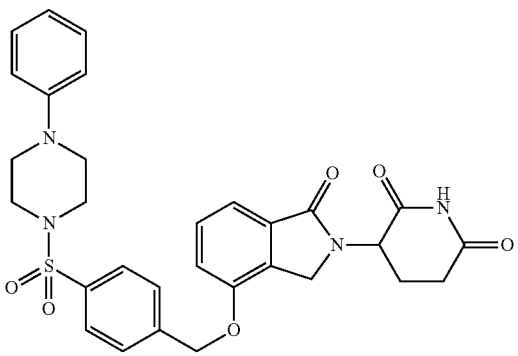 [SMILES: O=C1CCC(N2Cc3c(OCc4ccc(S(=O)(=O)N5CCN(c6ccccc6)CC5)cc4)cccc3C2=O)C(=O)N1]

Step 1:1-(4-Bromomethyl-benzenesulfonyl)-4-phenyl-piperazine To the stirred solution of 1-phenylpiperazine (0.51 g, 3.14 mmol) and TRIETHYL AMINE (0.482 ml, 3.46 mmol) in diethyl ether (10 mL) at 0° C. was added solution of 4-(bromomethyl)benzene-1-sulfonyl chloride (0.847 g, 3.14 mmol) in ether (5 mL) drop wise. The resulting suspension was stirred at 0° C. for 1.5 hr. The reaction mixture was added by acetonitrile (30 mL) and EtOAC (100 mL) followed by the addition of water (30 mL). The mixture was filtered to give a white solid. The filtrate was extracted. Organic layer was dried by $MgSO_4$ and concentrated under vacuo. The residue combined with the white solid was purified by ISCO to give 1-(4-Bromomethyl-benzenesulfonyl)-4-phenyl-piperazine as a white solid (760 mg, 61% yield). $^1H$ NMR (DMSO-$d_6$) δ 2.95-3.08 (m, 4H, $CH_2$, $CH_2$), 3.13-3.25 (m, 4H, $CH_2$, $CH_2$), 4.80 (s, 2H, $CH_2$), 6.75-6.85 (m, 1H, Ar), 6.90 (d, J=7.9 Hz, 2H, Ar), 7.10-7.29 (m, 2H, Ar), 7.57-7.90 (m, 4H, Ar); LCMS MH=395, 397.

Step 2: 4-Carbamoyl-4-{1-oxo-4-[4-(4-phenyl-piperazine-1-sulfonyl)-benzyloxy]-1,3-dihydro-isoindol-2-yl}-butyric acid methyl ester Methyl 5-amino-4-(4-hydroxy-1-oxoisoindolin-2-yl)-5-oxopentanoate (360 mg, 1.2 mmol), 1-(4-(bromomethyl)phenylsulfonyl)-4-phenylpiperazine (584 mg, 1.5 mmol) and POTASSIUM CARBONATE (204 mg, 1.5 mmol) were mixed in Acetonitrile (15 mL) at room temperature. The resulting mixture was stirred at 50° C. for 20 hrs and $K_2CO_3$ (15 mg, 0.1 mmol) was added to the reaction mixture. The resulting mixture was stirred at 50° C. for 1.5 hrs before it was added by EtOAc (50 mL) and water (20 mL). The resulting mixture was extracted and the organic layer was washed with brine (20 mL). The organic layer was concentrated under vacuo and the residue was purified by ISCO to give 4-Carbamoyl-4-{1-oxo-4-[4-(4-phenyl-piperazine-1-sulfonyl)-benzyloxy]-1,3-dihydro-isoindol-2-yl}-butyric acid methyl ester as a white solid (730 mg, 98% yield); $^1H$ NMR (DMSO-$d_6$) δ 2.01-2.33 (m, 4H, $CH_2$, $CH_2$), 2.96-3.09 (m, 4H, $CH_2$, $CH_2$), 3.14-3.26 (m, 4H, $CH_2$, $CH_2$), 3.50 (s, 3H, $CH_3$), 4.46 (d, J=17.8 Hz, 1H, CHH), 4.59 (d, J=17.8 Hz, 1H, CHH), 4.74 (dd, J=4.7, 10.2 Hz, 1H, CHH), 5.40 (s, 2H, $CH_2$), 6.80 (t, J=7.3 Hz, 1H, Ar), 6.90 (d, J=7.9 Hz, 2H, Ar), 7.15-7.24 (m, 3H, Ar, NH), 7.25-7.35 (m, 2H, Ar), 7.40-7.51 (m, 1H, Ar), 7.59 (s, 1H, NHH), 7.74-7.89 (m, 4H, Ar); LCMS MH=607.

Step 3: 3-{-Oxo-4-[4-(4-phenyl-piperazine-1-sulfonyl)-benzyloxy]-1,3-dihydro-isoindol-2-yl}-piperidine-2,6-dione To the stirred solution of methyl 5-amino-5-oxo-4-(1-oxo-4-(4-(4-phenylpiperazin-1-ylsulfonyl)benzyloxy)isoindolin-2-yl)pentanoate (730 mg, 1.2 mmol) in Tetrahydrofuran (15 mL) at 0° C. was added potassium tert-butoxide (127 mg, 1.3 mmol) in one portion. The mixture was stirred at 0° C. for 10 mins before it was added by HCl (1N, aq, 3 mL) at 0° C. followed by the addition of DCM (50 mL) and $NaHCO_3$ (sat. aq, 15 mL). White solid was precipitated out. The mixture was filtered and the filtrate was extracted. The organic layer was concentrated under vacuo. The residue combined with the solid was purified by being stirred in mixed solvent of THF (3 mL) and DCM (25 mL) followed by the triturating in DMF (5 mL) at 80° C. to give 3-{1-Oxo-4-[4-(4-phenyl-piperazine-1-sulfonyl)-benzyloxy]1,3-dihydro-isoindol-2-yl}-piperidine-2,6-dione as a white solid (256 mg, 37% yield). HPLC: Waters Symmetry C-18, 3.9×150 mm, 5 μm, 1 mL/min, 240 nm, 50/50, ($CH_3CN/0.1\%$ $H_3PO_4$), 5.15 min (98.9%); mp: 302-304° C.; $^1H$ NMR (DMSO-$d_6$) δ 1.93-2.06 (m, 1H, CHH), 2.35-2.47 (m, 1H, CHH), 2.53-2.65 (m, 1H, CHH), 2.83-3.08 (m, 5H, $CH_2$, $CH_2$, CHH), 3.14-3.26 (m, 4H, $CH_2$, $CH_2$), 4.30 (d, J=17.6 Hz, 1H, CHH), 4.47 (d, J=17.6 Hz, 1H, CHH), 5.12 (dd, J=5.0, 13.3 Hz, 1H, CHH), 5.40 (s, 2H, $CH_2$), 6.80 (t, J=7.3 Hz, 1H, Ar), 6.90 (d, J=7.9 Hz, 2H, Ar), 7.20 (dd, J=7.3, 8.6 Hz, 2H, Ar), 7.27-7.40 (m, 2H, Ar), 7.44-7.56 (m, 1H, Ar), 7.72-7.85 (m, 4H, Ar), 10.98 (s, 1H, NH); $^{13}C$ NMR (DMSO-$d_6$) δ 22.30, 31.08, 44.95, 45.70, 47.82, 51.46, 68.46, 114.87, 115.46, 116.04, 119.58, 127.79, 127.98, 128.86, 129.79, 129.88, 133.32, 133.96, 142.34, 150.22, 153.10, 167.83, 170.88, 172.74; LCMS MH=575; Anal. Calcd for $C_{30}H_{30}N_4O_6S+0.3H_2O$: C, 62.12; H, 5.32; N, 9.66; Found: C, 62.05; H, 5.18; N, 9.63.

5.200 2-(2,6-Dioxopiperidin-3-yl)-4-((4-(Hydroxymethyl)Benzyl)Oxy)Isoindoline-1,3-Dione

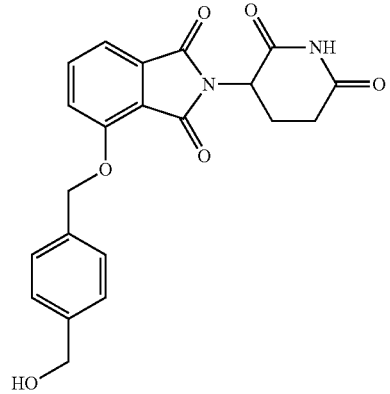 [SMILES: O=C1CCC(N2C(=O)c3cccc(OCc4ccc(CO)cc4)c3C2=O)C(=O)N1]

3-Aminopiperidine-2,6-dione hydrochloride (0.915 g, 5.56 mmol) was added to a solution of 3-(4-(hydroxymethyl)benzyloxy)phthalic acid (1.4 g, 4.63 mmol) in dry pyridine (15 mL) and the mixture was heated to 118° C. in an oil bath for 16 h. The dark reaction mixture was allowed to cool to room temperature and was acidified with slow addition of 1 N HCl (~25 mL). The mixture was further diluted with water (~170 mL) and then sonicated for ~30 minutes to help break up solid aggregates. The resulting dark slurry was filtered on a medium pore fritted funnel and the dark solid was washed with additional water (70 mL). The cake was suction dried and then placed in vacuum oven at 60° C. for 2.5 h to give 1.6 g of a dark blue solid. The solid was dissolved in a mixture of DCM, MeCN, and MeOH (~100 mL each) and treated decolorizing charcoal. The mixture was swirled around and then gravity-filtered using filter paper. The filtrate/wash (dark amber color) was treated once again with decolorizing charcoal and then filtered on a bed of celite. The clear filtrate was concentrated in vacuo to dryness to give a solid which was triturated with water and filtered with suction. The cake was washed with additional water (~100 mL), suction dried, and then placed in vacuum oven at 60° C. for 4 h to give 2-(2,6-dioxopiperidin-3-yl)-4-((4-(hydroxymethyl)benzyl)oxy)isoindoline-1,3-dione as an off-white solid (1.2 μm, 68% yield): HPLC: Waters Symmetry $C_{18}$, 5 μm, 3.9×150 mm, 1 ml/min, 240 nm, 15/85 $CH_3CN/0.1\%$ $H_3PO_4$, 5.08 min (99.9%); mp: 250-252; $^1H$ NMR (DMSO-$d_6$) δ 1.95-2.07 (m, 1H, CHH), 2.41-2.67 (m, 2H, CHH, CHH), 2.78-3.00 (m, 1H, CHH), 4.50 (d, J=5.1 Hz, 2H, $CH_2OH$), 5.09 (dd, J=5.4, 12.7 Hz, 1H, CH), 5.19 (t, J=5.6 Hz, 1H, OH), 5.36 (s, 2H, $CH_2O$), 7.24-7.40 (m, 2H, Ar), 7.41-7.53 (m, 3H, Ar), 7.59 (d, J=8.5 Hz, 1H, Ar), 7.82 (dd, J=7.4, 8.5 Hz, 1H, Ar), 11.11 (s, 1H, NH); $^{13}C$ NMR (DMSO-$d_6$) δ 21.88, 30.83, 48.67, 62.53, 69.91, 115.40, 116.52, 120.18, 126.44, 127.09, 133.17, 134.31, 136.86, 142.32, 155.42, 165.21, 166.68, 169.81, 172.66. LCMS: M+Na=417; MH is not observed in positive ionization mode; Anal Calcd for $C_{21}H18N_2O_6$: C, 63.96; H, 4.60; N, 7.10; Found: C, 63.77; H, 4.52; N, 7.32.

5.201 3-(4-((4-(4-Methylpiperazine-1-Carbonyl)Benzyl)Oxy)-1-Oxoisoindolin-2-yl)Piperidine-2,6-Dione Hydrochloride

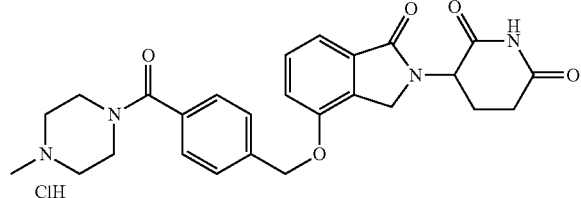 [SMILES: CN1CCN(C(=O)c2ccc(COc3cccc4c3CN(C3CCC(=O)NC3=O)C4=O)cc2)CC1 ; Cl]

To a stirred suspension of 3-(1-oxo-4-(4-(piperazine-1-carbonyl)benzyloxy)isoindolin-2-yl)piperidine-2,6-dione hydrochloride (100 mg, 0.200 mmol) in DMF (2 mL), was added 1 N aq sodium bicarbonate (0.441 mL, 0.441 mmol) followed by iodomethane (0.014 mL, 0.220 mmol). The mixture was stirred at room temperature. After about 24 h, an additional 5 µl of iodomethane was charged and the mixture was stirred at room temperature for 3 days. The reaction mixture was concentrated in vacuo and the residue was partitioned between EtOAc (100 mL) and 1N aq. NaHCO$_3$ (10 mL). The organic layer was washed with additional water (40 mL) and brine, then dried over Na$_2$SO$_4$, and concentrated in vacuo. The crude product was purified by prep HPLC and the product was eluted with an acetonitrile/water gradient (0.1% formic acid in both mobile phases, 5% to 30% MeCN over 20 minutes) and fractions were collected by mass trigger. The desired fractions were combined and treated with 1 N HCl (4 mL). The solution was concentrated to dryness and the residue was treated with 2 N HCl in Et$_2$O (0.5 mL). The volatiles were again concentrated dryness and the remaining solid was dried in a vacuum oven to give 3-(4-((4-(4-methylpiperazine-1-carbonyl)benzyl)oxy)-1-oxoisoindolin-2-yl)piperidine-2,6-dione hydrochloride as an off-white solid (41 mg, 39%): HPLC: Waters Symmetry C$_{18}$, 5 µm, 3.9×150 mm, 1 ml/min, 240 nm, 15/85 CH$_3$CN/0.1% H$_3$PO$_4$, 4.88 min (95.7%): HPLC: Waters Symmetry C$_{18}$, 5 µm, 3.9×150 mm, 1 ml/min, 240 nm, 15/85 CH$_3$CN/0.1% H$_3$PO$_4$, 4.88 min (95.7%); mp: 360-362° C.; $^1$H NMR (DMSO-d$_6$) δ 1.88-2.09 (m, 1H, CHH), 2.33-2.47 (m, 1H, CHH), 2.53-2.67 (m, 1H, CHH), 2.67-2.83 (m, 3H, CH$_3$), 2.83-3.00 (m, 1H, CHH), 3.02-3.22 (m, 2H, CH$_2$), 3.23-3.64 (m, 4H, CH$_2$, CH$_2$), 4.28 (d, J=17.6 Hz, 1H, CHH), 4.45 (d, J=17.6 Hz, 1H, CHH), 4.98-5.21 (m, 0.1H, CH), 5.32 (s, 2H, CH$_2$), 7.22-7.42 (m, 2H, Ar), 7.46-7.55 (m, 3H, Ar), 7.56-7.63 (m, 2H, Ar), 10.98 (s, 1H, NH), 11.31-11.77 (m, 1H, HCl); $^{13}$C NMR (DMSO-d$_6$) δ 24.21, 33.00, 43.95, 47.07, 53.53, 53.79, 70.87, 73.78, 116.96, 117.34, 129.26, 129.44, 131.81, 135.14, 136.04, 140.55, 155.19, 170.00, 170.91, 172.79, 174.75; LCMS: MH=477; Anal Calcd for C$_{26}$H$_{28}$N$_4$O$_5$.HCl: C, 60.88; H, 5.70; N, 10.92; Found: C, 37.90; H, 4.33; N, 6.65.

5.202 3-{4-[4-(4-Acetyl-Piperazin-1-ylmethyl)-Benzyloxy]-1-Oxo-1,3-Dihydro-Isoindol-2-yl}-Piperidine-2,6-Dione

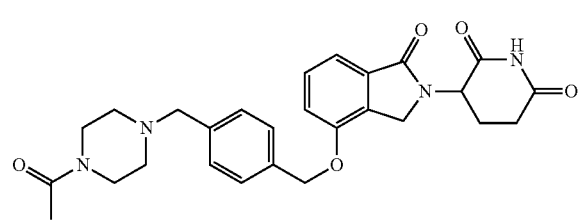 [SMILES: CC(=O)N1CCN(Cc2ccc(COc3cccc4c3CN(C3CCC(=O)NC3=O)C4=O)cc2)CC1]

Step 1: To a stirred solution of 4-carbamoyl-4-[4-(4-chloromethyl-benzyloxy)-1-oxo-1,3-dihydro-isoindol-2-yl]-butyric acid methyl ester (600 mg, 1.392 mmol) in acetonitrile (10 mL), was added 1-(piperazin-1-yl)ethanone (178 mg, 1.392 mmol) and DIPEA (0.608 ml, 3.48 mmol). The reaction was stirred at room temperature for 20 hours, at 40° C. for 2.5 hours and at 50° C. for 3 hours before the reaction stopped proceeding. The reaction mixture was diluted by dichloromethane (40 mL) and washed with water (15 mL) and brine (15 mL). The organic layer was dried by MgSO$_4$ and concentrated to give 4-{4-[4-(4-Acetyl-piperazin-1-ylmethyl)-benzyloxy]-1-oxo-1,3-dihydro-isoindol-2-yl}-4-carbamoyl-butyric acid methyl ester as a clear oil (840 mg, 115% crude yield). The compound was put to next step without further purification; LCMS MH=523.

Step 2: KOtBu (156 mg, 1.393 mmol) was added to the stirred solution of methyl 4-(4-(4-((4-acetylpiperazin-1-yl)methyl)benzyloxy)-1-oxoisoindolin-2-yl)-5-amino-5-oxopentanoate (728 mg, 1.393 mmol) in tetrahydrofuran (10 mL) at 0° C. The reaction mixture was stirred at 0° C. for 1 hour before KOtBu (30 mg, 0.27 mmol) was added. The resulting mixture was stirred at room temperature for 10 minutes and the reaction was complete. The reaction mixture was diluted by dichloromethane (50 mL) and acidified with HCl (1N aq. 4 mL). The mixture was extracted with NaHCO$_3$ (10 mL) and brine (10 mL). The aqueous layer was back extracted with dichloromethane (2×15 mL). Organic layers were combined and dried by MgSO$_4$. The mixture was filtered and concentrated to give a white solid. The solid was triturated in diethyl ether (30 mL) and filtered to give 3-{4-[4-(4-acetyl-piperazin-1-ylmethyl)-benzyloxy]-1-oxo-1,3-dihydro-isoindol-2-yl}-piperidine-2,6-dione as a white solid (500 mg, 67.5% yield): HPLC: Waters Symmetry C-18, 3.9×150 mm, 5 µm, 1 mL/min, 240 nm, 15/85, (acetonitrile/0.1% H$_3$PO$_4$), 4.03 min (99.4%); mp: 208-210° C.; $^1$H NMR (DMSO-d$_6$) δ 1.90-2.05 (m, 4H, CH$_3$, CHH), 2.23-2.40 (m, 4H, CH$_2$, CH$_2$), 2.40-2.48 (m, 1H, CHH), 2.53-2.64 (m, 1H, CHH), 2.80-3.00 (m, 1H, CHH), 3.36-3.46 (m, 4H, CH$_2$, CH$_2$), 3.49 (s, 2H, CH$_2$), 4.26 (d, J=17.6 Hz, 1H, CHH), 4.42 (d, J=17.4 Hz, 1H, CHH), 5.11 (dd, J=5.1, 13.2 Hz, 1H, CHH), 5.23 (s, 2H, CH$_2$), 7.33 (d, J=7.6 Hz, 4H, Ar), 7.37-7.61 (m, 3H, Ar), 10.97 (s, 1H, NH); $^{13}$C NMR (DMSO-d$_6$) δ 21.12, 22.33, 31.18, 40.77, 45.06, 45.60, 51.55, 52.19, 52.74, 61.49, 69.36, 114.96, 115.22, 127.64, 128.94, 129.80, 129.93, 133.28, 135.33, 137.70, 153.48, 167.97, 168.03, 170.96, 172.81; LCMS MH=491; Anal. Calcd for C$_{27}$H$_{30}$N$_4$O$_5$+0.3 H$_2$O: C, 65.39; H, 6.22; N, 11.30; Found: C, 65.31; H, 6.34; N, 11.32.

5.203 3-{4-[4-(4-Cyclopropanecarbonyl-Piperazin-1-ylmethyl)-Benzyloxy]-1-Oxo-1,3-Dihydro-Isoindol-2-yl}-Piperidine-2,6-Dione

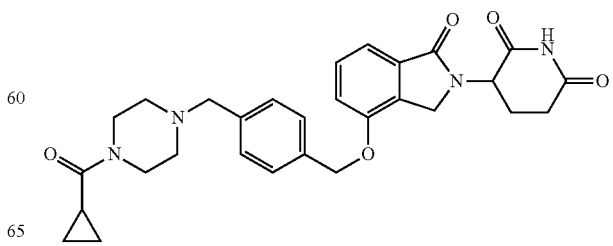

Step 1: To a stirred solution of methyl 5-amino-4-(4-(4-(chloromethyl)benzyloxy)-1-oxoisoindolin-2-yl)-5-oxopentanoate (600 mg, 1.392 mmol) in acetonitrile (10 mL) at room temperature, was added cyclopropyl(piperazin-1-yl)methanone (0.257 ml, 1.810 mmol) and DIPEA (0.608 ml, 3.48 mmol). The resulting light green solution was stirred at room temperature for 3 days and the reaction was complete. The reaction mixture was diluted by dichloromethane (40 mL) and extracted with water (15 mL) and brine (15 mL). The organic layer was dried by $MgSO_4$. The mixture was concentrated to give 4-carbamoyl-4-{4-[4-(4-cyclo propanecarbonyl-piperazin-1-ylmethyl)-benzyloxy]-1-oxo-1,3-dihydro-isoindol-2-yl}-butyric acid methyl ester as a clear oil (900 mg, 118% crude yield). The compound was put to next step without further purification: LCMS MH=549.

Step 2: KOtBu (203 mg, 1.810 mmol) was added to a stirred solution of methyl 5-4-carbamoyl-4-{4-[4-(4-cyclopropanecarbonyl-piperazin-1-ylmethyl)-benzyloxy]-1-oxo-1,3-dihydro-isoindol-2-yl}-butyric acid methyl ester (764 mg, 1.392 mmol) in tetrahydrofuran (10 mL) at 0° C. The resulting yellow solution was stirred at 0° C. for 30 minutes and the reaction was complete. The reaction was diluted by dichloromethane (60 mL) and quenched at 0° C. with HCl (1N, aq, 3 mL) to pH=2. The mixture was added by $NaHCO_3$ (aq. sat., 10 mL) and brine (15 mL). The mixture was extracted and the aqueous layer was back extracted with dichloromethane (2×25 mL). The organic layers were combined and dried by $MgSO_4$. The mixture was filtered and concentrated. The residue was triturated in diethyl ether (50 mL) and filtered to give 3-{4-[4-(4-cyclopropanecarbonyl-piperazin-1-ylmethyl)-benzyloxy]-1-oxo-1,3-dihydro-isoindol-2-yl}-piperidine-2,6-dione as a white solid (578 mg, 80% yield): HPLC: Waters Symmetry C-18, 3.9×150 mm, 5 μm, 1 mL/min, 240 nm, 15/85, (acetonitrile/0.1% $H_3PO_4$), 7.29 min (99.8%); mp: 233-235° C.; $^1$H NMR (DMSO-$d_6$) δ 0.60-0.77 (m, 4H, $CH_2$, $CH_2$), 1.87-2.08 (m, 2H, $CH_2$), 2.24-2.48 (m, 5H, CHH, $CH_2$, $CH_2$), 2.54-2.63 (m, 1H, CHH), 2.82-3.00 (m, 1H, CHH), 3.39-3.55 (m, 4H, $CH_2$, $CH_2$), 3.57-3.74 (m, 2H, $CH_2$), 4.26 (d, J=17.4 Hz, 1H, CHH), 4.42 (d, J=17.6 Hz, 1H, CHH), 5.11 (dd, J=5.1, 13.2 Hz, 1H, CHH), 5.23 (s, 2H, $CH_2$), 7.28-7.39 (m, 4H, Ar), 7.41-7.54 (m, 3H, Ar), 10.97 (s, 1H, NH); $^{13}$C NMR (DMSO-$d_6$) δ 6.83, 10.05, 22.27, 31.11, 41.46, 44.70, 44.99, 51.48, 52.20, 52.87, 61.44, 69.30, 114.89, 115.15, 127.57, 128.89, 129.73, 129.86, 133.23, 135.26, 137.65, 153.41, 167.92, 170.78, 170.89, 172.74; LCMS MH=517; Anal. Calcd for $C_{29}H_{32}N_4O_5$+0.2 $H_2O$: C, 66.96; H, 6.28; N, 10.77; Found: C, 66.90; H, 6.41; N, 10.71.

5.204 3-{4-[4-(4-Fluoro-Piperidin-1-ylmethyl)-Benzyloxy]-1-Oxo-1,3-Dihydro-Isoindol-2-yl}-Piperidine-2,6-Dione

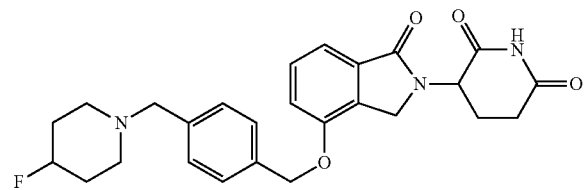 [SMILES: O=C1CCC(N2Cc3c(OCc4ccc(CN5CCC(F)CC5)cc4)cccc3C2=O)C(=O)N1]

Step 1: To the stirred solution of methyl 5-amino-4-(4-(4-(chloromethyl)benzyloxy)-1-oxoisoindolin-2-yl)-5-oxopentanoate (600 mg, 1.392 mmol) and 4-fluoropiperidine hydrochloride (233 mg, 1.671 mmol) in acetonitrile (10 mL) under a $N_2$ atmosphere, was added by DIPEA (0.608 ml, 3.48 mmol). The resulting solution was stirred at room temperature for 2 hours and at 70° C. for 3 hours before $K_2CO_3$ (192 mg, 1.392 mmol) was added to the reaction mixture. The resulting mixture was heated at 50° C. overnight. $K_2CO_3$ (40 mg, 0.29 mmol) and 4-fluoropiperidine hydrochloride (35 mg, 0.25 mmol) were added to the reaction mixture, which was stirred at 60° C. for 7 hours. The reaction mixture was diluted by dichloromethane (50 mL) and extracted with brine (20 mL). Organic layer was dried by $MgSO_4$ and concentrated down to give 4-carbamoyl-4-{4-[4-(4-fluoro-piperidin-1-ylmethyl)-benzyloxy]-1-oxo-1,3-dihydro-isoindol-2-yl}-butyric acid methyl ester as a light green stick oil (760 mg, 1 10% crude yield). The compound was put to next step as is: LCMS MH=498.

Step 2: KOtBu (203 mg, 1.810 mmol) was added to the stirred solution of 4-carbamoyl-4-{4-[4-(4-fluoro-piperidin-1-ylmethyl)-benzyloxy]-1-oxo-1,3-dihydro-isoindol-2-yl}-butyric acid methyl ester (693 mg, 1.392 mmol) in tetrahydrofuran (10 mL) at 0° C. under a $N_2$ atmosphere. The reaction mixture was stirred at 0° C. for 30 minutes and the reaction was complete. The reaction mixture was diluted by dichloromethane (50 mL) and added by HCl (1N, aq, 4 mL) to PH=1. The mixture was extracted with a mixture of $NaHCO_3$ (aq, sat., O1 mL) and brine (15 mL). The aqueous layer was back extracted with dichloromethane (2×25 mL). Organic layers were combined and dried $MgSO_4$. The mixture was filtered and concentrated. The residue was purified by ISCO chromatography to give 3-{4-[4-(4-fluoro-piperidin-1-ylmethyl)-benzyloxy]-1-oxo-1,3-dihydro-isoindol-2-yl}-piperidine-2,6-dione as a white solid (215 mg, 33% yield): HPLC: Waters Symmetry C-18, 3.9×150 mm, 5 μm, 1 mL/min, 240 nm, 18/82, acetonitrile/0.1% $H_3PO_4$), 4.02 min (98.9%); mp: 141-143° C.; $^1$H NMR (DMSO-$d_6$) δ 1.57-2.06 (m, 5H, CHH, $CH_2$, $CH_2$), 2.19-2.34 (m, 2H, $CH_2$), 2.35-2.55 (m, 3H, $CH_2$, CHH), 2.54-2.63 (m, 1H, CHH), 2.82-3.01 (m, 1H, CHH), 3.47 (s, 2H, $CH_2$), 4.25 (d, J=17.6 Hz, 1H, CHH), 4.42 (d, J=17.6 Hz, 1H, CHH), 4.52-4.82 (m, 1H, CHH), 5.11 (dd, J=5.1, 13.2 Hz, 1H, CHH), 5.22 (s, 2H, $CH_2$), 7.26-7.37 (m, 4H, Ar), 7.40-7.56 (m, 3H, Ar), 10.97 (s, 1H, NH); $^{13}$C NMR (DMSO-$d_6$) δ 22.29, 31.09 (d, J=19.8 Hz, $M_{19}$), 31.10, 45.00, 48.92 (d, $J_{C-F}$=6.6 Hz), 51.49, 61.43, 69.34, 88.43 (d, J=168.4 Hz, $M_{14}$), 114.87, 115.15, 127.56, 28.74, 129.73, 129.87, 133.23, 135.12, 138.21, 153.44, 167.93, 170.90, 172.76; LCMS MH=466; Anal. Calcd for $C_{26}H_{28}FN_3O_4$+0.2 $H_2O$: C, 66.57; H, 6.10; N, 8.96; Found: C, 66.35; H, 6.29; N, 8.79.

5.205 3-{4-[4-(4,4-Difluoro-Piperidin-1-ylmethyl)-Benzyloxy]-1-Oxo-1,3-Dihydro-Isoindol-2-yl}-Piperidine-2,6-Dione

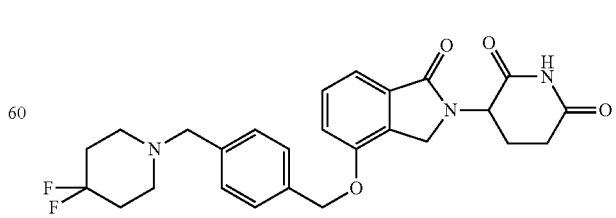

Step 1: To the stirred solution of methyl 5-amino-4-(4-(4-(chloromethyl)benzyloxy)-1-oxoisoindolin-2-yl)-5-oxopentanoate (500 mg, 1.160 mmol) and 4,4-difluoropiperidine hydrochloride (274 mg, 1.741 mmol) in acetonitrile (10 mL) under a N₂ atmosphere, were added Na₂CO₃ (160 mg, 1.160 mmol) and DIPEA (0.507 ml, 2.90 mmol). The resulting solution was stirred at 50° C. for 8 hours and the reaction was stopped. The reaction mixture was diluted by dichloromethane (50 mL) and extracted with brine (20 mL). The organic layer was dried by MgSO₄ and concentrated under vacuo to give 4-carbamoyl-4-{4-[4-(4,4-difluoro-piperidin-1-ylmethyl)-benzyloxy]-1-oxo-1,3-dihydro-isoindol-2-yl}-butyric acid methyl ester as an off white solid (630 mg, 105% crude yield). The product was put to next step as it was: LCMS MH=516.

Step 2: To the stirred solution of 4-carbamoyl-4-{4-[4-(4, 4-difluoro-piperidin-1-ylmethyl)-benzyloxy]-1-oxo-1,3-dihydro-isoindol-2-yl}-butyric acid methyl ester (630 mg, 1.222 mmol) in THF (10 mL) at 0° C., was added by KOtBu (151 mg, 1.344 mmol). The mixture was stirred at 0° C. for 5 minutes and the reaction was complete. The reaction mixture was diluted by dichloromethane (50 mL) and acidified by HCl (1N, aq. 3 mL) to pH=2. The mixture was extracted with the mixture of NaHCO₃ (aq. sat., 5 mL) and brine (10 mL). The organic layer was dried by MgSO₄ and concentrated. The residue was stirred in ether (50 mL) and the mixture filtered to give the white solid. The solid was triturated in EtOAc (5 mL) and filtered to give 3-{4-[4-(4, 4-difluoro-piperidin-1-ylmethyl)-benzyloxy]-1-oxo-1,3-dihydro-isoindol-2-yl}-piperidine-2,6-dione as a white solid (215 mg, 36%): HPLC: Waters Symmetry C-18, 3.9×150 mm, 5 μm, 1 mL/min, 240 nm, 18/82 (acetonitrile/0.1% H₃PO₄): $t_R$=4.17 (99.4%); mp: 193-195° C.; ¹H NMR (DMSO-d₆) δ 1.84-2.09 (m, 5H, CH₂, CH₂, CHH), 2.34-2.49 (m, 5H, CHH, CH₂, CH₂), 2.54-2.64 (m, 1H, CHH), 2.81-3.02 (m, 1H, CHH), 3.55 (s, 2H, CH₂), 4.25 (d, J=17.6 Hz, 1H, CHH), 4.42 (d, J=17.6 Hz, 1H, CHH), 5.11 (dd, J=5.1, 13.2 Hz, 1H, CHH), 5.23 (s, 2H, CH₂), 7.33 (d, 4H, M₀₁), 7.40-7.54 (m, 3H, Ar), 10.97 (s, 1H, NH); ¹³C NMR (DMSO-d₆) δ 22.29, 31.12, 33.25 (t, $J_{C-F}$=20.9 Hz), 45.00, 49.12, 51.51, 60.40, 69.29, 114.89, 115.16, 122.68 (t, $J_{C-F}$=239.9 Hz), 127.60, 128.84, 129.73, 129.88, 133.24, 135.32, 137.72, 153.42, 167.93, 170.91, 172.76; LCMS MH=484; Anal. Calcd for C₂₆H₂₇F₂N₃O₅+1 H₂O: C, 62.27; H, 5.83; N, 8.39, Found: C, 62.09; H, 5.73; N, 8.17.

5.206 N-(1-{4-[2-(2,6-Dioxo-Piperidin-3-yl)-1-Oxo-2,3-Dihydro-1H-Isoindol-4-yloxymethyl]-Benzyl}-Piperidin-4-yl)-Acetamide

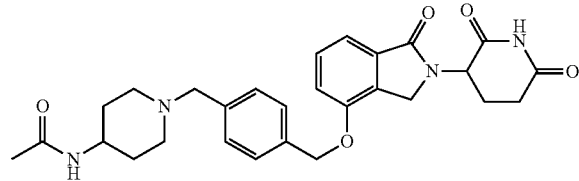 [SMILES: CC(=O)NC1CCN(Cc2ccc(COc3cccc4c3CN(C3CCC(=O)NC3=O)C4=O)cc2)CC1]

Step 1: To the stirred solution of methyl 5-amino-4-(4-(4-(chloromethyl) benzyloxy)-1-oxoiso indolin-2-yl)-5-oxopentanoate (500 mg, 1.160 mmol) in acetonitrile (10 mL), were added N-(piperidin-4-yl)acetamide (215 mg, 1.509 mmol), N-ethyl-N-isopropyl propan-2-amine (0.405 ml, 2.321 mmol) and K₂CO₃ (160 mg, 1.160 mmol). The resulting reaction mixture was stirred at 50° C. for 2 hours and at room temperature overnight. The reaction mixture was diluted by dichloromethane (70 mL) and extracted with brine (20 mL). The organic layer was dried by MgSO₄ and concentrated to give 4-{4-[4-(4-acetylamino-piperidin-1-ylmethyl)-benzyloxy]-1-oxo-1,3-dihydro-isoindol-2-yl}-4-carbamoyl-butyric acid methyl ester as a sticky oil (705 mg, 113% crude yield). The compound was used as it was: LCMS MH=537.

Step 2: KOtBu (130 mg, 1.160 mmol) was added to the suspension of 4-{4-[4-(4-acetylamino-piperidin-1-ylmethyl)-benzyloxy]-1-oxo-1,3-dihydro-isoindol-2-yl}-4-carbamoyl-butyric acid methyl ester (622 mg, 1.16 mmol) in tetrahydrofuran (10 mL) at 0° C. The resulting yellow mixture was stirred at room temperature for 7 hours and KOtBu (60 mg, 0.46 mmol) was added to the reaction mixture at room temperature. The reaction was complete in 10 minutes. The reaction mixture was diluted by dichloromethane (30 mL) and acidified by HCl (1N, aq. 4 mL) and then neutralized by NaHCO₃ (sat., aq. 5 mL). The mixture was extracted with brine (10 mL). The organic layer was dried by MgSO₄ and concentrated to give white solid which was triturated by ether (30 mL). The mixture was filtered to give N-(1-{4-[2-(2,6-dioxo-piperidin-3-yl)-1-oxo-2,3-dihydro-1H-isoindol-4-yloxymethyl]-benzyl}-piperidin-4-yl)-acetamide as a white solid (293 mg, 50% yield): HPLC: Waters Symmetry C-18, 3.9×150 mm, 5 μm, 1 mL/min, 240 nm, 15/85, (acetonitrile/0.1% H₃PO₄), 4.85 min (99.1%); mp: 270-272° C.; ¹H NMR (DMSO-d₆) δ 1.26-1.44 (m, 2H, CH₂), 1.62-1.73 (m, 2H, CH₂), 1.77 (s, 3H, CH₃), 1.89-2.05 (m, 3H, CHH, CH₂), 2.34-2.47 (m, 1H, CHH), 2.54-2.64 (m, 1H, CHH), 2.65-2.79 (m, 2H, CH₂), 2.81-2.99 (m, 1H, CHH), 3.40-3.57 (m, 3H, CH₂, CHH), 4.25 (d, J=17.6 Hz, 1H, CHH), 4.42 (d, J=17.4 Hz, 1H, CHH), 5.11 (dd, J=5.1, 13.2 Hz, 1H, CHH), 5.22 (s, 2H, CH₂), 7.24-7.38 (m, 4H, Ar), 7.38-7.56 (m, 3H, Ar), 7.74 (d, J=7.7 Hz, 1H, NH), 10.97 (s, 1H, NH); ¹³C NMR (DMSO-d₆) δ 22.33, 22.69, 31.18, 31.60, 45.07, 45.86, 51.55, 51.94, 61.80, 69.41, 114.94, 115.20, 127.61, 128.78, 129.80, 129.93, 133.28, 135.12, 138.50, 153.49, 167.99, 168.23, 170.96, 172.81; LCMS MH=505; Anal. Calcd for C₂₈H₃₂N₄O₅+0.5 H₂O: C, 65.48; H, 6.48; N, 10.91; Found: C, 65.58; H, 6.40; N, 10.76.

5.207 3-(4-(4-((2,6-Dimethylpiperidin-1-yl)Methyl) Benzyloxy)-1-Oxoisoindolin-2-yl)Piperidine-2,6-Dione

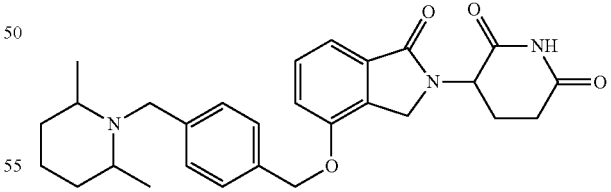

Step 1: To the CNCH₃ solution of methyl 5-amino-4-(4-(4-(bromomethyl)benzyloxy)-1-oxoisoindolin-2-yl)-5-oxopentanoate (0.5 g, 1.052 mmol), was added Cis-2,6-dimethylpiperidine (0.354 ml, 2.63 mmol). The mixture was stirred at 50° C. overnight. The reaction mixture was filtered. The filtrate was concentrated on rota-vap to give methyl 5-amino-4-(4-(4-((2,6-dimethylpiperidin-1-yl)methyl)benzyloxy)-1-oxoisoindolin-2-yl)-5-oxopentanoate as a solid (0.6 g, 112%). It was used in the next step without further purification.

Step 2: To the THF solution of methyl 5-amino-4-(4-(4-((2,6-dimethylpiperidin-1-yl)methyl)benzyloxy)-1-oxoisoindolin-2-yl)-5-oxopentanoate (0.6 g, 1.182 mmol) at 0° C., was added potassium tert-butoxide (0.133 g, 1.182 mmol). The mixture was stirred at 0° C. for 10 minutes. The mixture was quenched with 1N HCl solution (2 mL) followed by 20 mL of NaHCO$_3$ (saturated) and EtOAc (20 mL). After extraction, organic layer was washed with 20 mL of water, then brine (10 mL), and concentrated to give 3-(4-(4-((2,6-dimethylpiperidin-1-yl)methyl)benzyloxy)-1-oxoisoindolin-2-yl)piperidine-2,6-dione as white solid (0.33 g, 59%). mp: 205-207° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: $t_R$=4.74 min (96%). $^1$H NMR (DMSO-d$_6$) δ 0.94 (d, J=6.2 Hz, 6H, CH$_3$, CH$_3$), 1.14-1.38 (m, 3H, CHH, CH$_2$), 1.42-1.74 (m, 3H, CH$_2$, CHH), 1.87-2.06 (m, 1H, CHH), 2.34-2.47 (m, 3H, CH$_2$, CHH), 2.53-2.65 (m, 1H, CHH), 2.81-3.02 (m, 1H, CHH), 3.70 (s, 2H, CH$_2$), 4.19-4.48 (m, 2H, CH$_2$), 5.11 (dd, J=5.0, 13.1 Hz, 1H, NCH), 5.20 (s, 2H, CH$_2$), 7.33 (dd, J=2.6, 7.7 Hz, 2H, Ar), 7.39 (s, 4H, Ar), 7.43-7.56 (m, 1H, Ar), 10.97 (s, 1H, NH). $^{13}$C NMR (DMSO-d$_6$) δ 21.98, 22.31, 23.66, 31.15, 34.04, 45.03, 51.51, 53.56, 57.41, 69.50, 114.88, 115.13, 127.26, 127.41, 129.75, 129.90, 133.24, 134.00, 142.84, 153.52, 167.96, 170.91, 172.76; LCMS: 476; Anal Calcd for C$_{28}$H$_{33}$N$_3$O$_4$+0.4 H$_2$O: C, 69.66; H, 7.06; N, 8.70; Found: C, 69.46; H, 7.10; N, 8.41.

5.208 3-{1-Oxo-4-[4-(4-Phenyl-Piperidin-1-ylmethyl)-Benzyloxy]-1,3-Dihydro-Isoindol-2-yl}-Piperidine-2,6-Dione

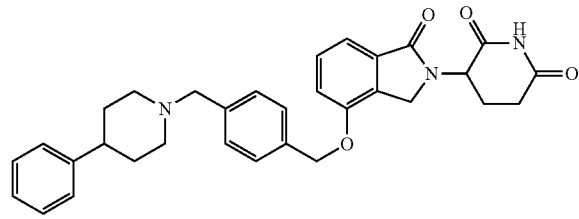 [SMILES: O=C1CCC(N2Cc3c(OCc4ccc(CN5CCC(c6ccccc6)CC5)cc4)cccc3C2=O)C(=O)N1]

Step 1: To a stirred solution of methyl 5-amino-4-(4-(4-(chloromethyl)benzyloxy)-1-oxoisoindolin-2-yl)-5-oxopentanoate (0.60 g, 1.39 mmol) in acetonitrile (15 ml) at room temperature, was added 4-phenylpiperidine (0.27 g, 1.67 mmol) and N-ethyl-N-isopropylpropan-2-amine (0.28 ml, 1.67 mmol). The mixture was stirred at 50° C. for a couple of hours and evaporated to give an oil (1.20 g, 86% crude yield).

Step 2: To a stirred solution of methyl 5-amino-5-oxo-4-(1-oxo-4-(4-((4-phenylpiperidin-1-yl)methyl)benzyloxy)isoindolin-2-yl)pentanoate (0.77 g, 1.39 mmol) in THF (15 ml) in an ice bath, was added potassium 2-methylpropan-2-olate (0.31 g, 2.79 mmol), and the mixture was stirred for ten minutes. The mixture was quickly quenched by 1 N HCl (4 ml) and immediately neutralized by saturated sodium bicarbonate (5.5 ml to pH=7). The mixture was then stirred with ethyl acetate (25 ml). Organic phase was separated, washed with brine (15 ml), and concentrated to a light yellow solid, which was purified on silica gel column (MeOH/CH$_2$Cl$_2$ gradient from 1% to 7% in 20 min) to give 3-{1-Oxo-4-[4-(4-phenyl-piperidin-1-ylmethyl)-benzyloxy]-1,3-dihydro-isoindol-2-yl}-piperidine-2,6-dione as a white solid (0.42 g, 58% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 4.80 min (96.3%); mp: 220-222° C.; $^1$H NMR (DMSO-d$_6$) δ 0.08-0.10 (d, 2H, CH$_2$), 1.64-1.72 (m, 4H, CH$_2$, CH$_2$), 1.96-2.07 (m, 3H, CH, CH$_2$), 2.39-2.42 (m, 1H, CHH), 2.51-2.60 (m, 1H, CHH), 2.85-2.97 (3H, CHH, CH$_2$), 3.52 (br. s, 2H, CH$_2$), 4.23-4.45 (m, 2H, CH$_2$), 5.11 (dd, J=5.1, 13.2 Hz, 1H, NCH), 5.24 (s, 2H, CH$_2$), 7.15-7.52 (m, 12H, Ar), 10.97 (s, 1H, NH); $^{13}$C NMR (DMSO-d$_6$) δ 22.34, 31.18, 32.94, 41.69, 45.07, 51.55, 53.52, 62.05, 69.40, 114.96, 115.22, 125.97, 126.64, 127.64, 128.29, 129.00, 129.81, 129.94, 133.30, 135.21, 138.37, 146.19, 153.50, 167.99, 170.97, 172.82; LCMS MH=524; Anal. Calcd for C$_{32}$H$_{33}$N$_3$O$_4$: (+0.50 H$_2$O): C, 72.16; H, 6.43; N, 7.89. Found: C, 71.83; H, 6.31; N, 7.80.

5.209 3-{4-[4-(4-Cyclopropylmethyl-Piperazin-1-ylmethyl)-Benzyloxy]-1-Oxo-1,3-Dihydro-Isoindol-2-yl}-Piperidine-2,6-Dione

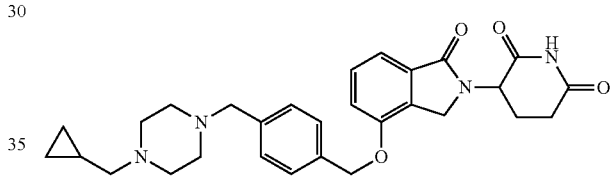

Step 1: To a solution of methyl 5-amino-4-(4-(4-(bromomethyl)benzyloxy)-1-oxoisoindolin-2-yl)-5-oxopentanoate (0.50 g, 1.06 mmol) in acetonitrile (50 mL), was added 1-(cyclopropylmethyl)piperazine (0.35 ml, 2.33 mmol). The mixture was stirred for one and a half hours and then concentrated to give 4-carbamoyl-4-{4-[4-(4-cyclopropylmethyl-piperazin-1-ylmethyl)-benzyloxy]-1-oxo-1,3-dihydro-isoindol-2-yl}-butyric acid methyl ester as a white foamy solid (0.83 g, 146% crude yield). It was used in the next step without further purification.

Step 2: To a stirred solution of methyl 5-amino-4-(4-(4-((4-(cyclopropylmethyl)piperazin-1-yl)methyl)benzyloxy)-1-oxoisoindolin-2-yl)-5-oxopentanoate (0.57 g, 1.06 mmol) in THF (15 ml) in an ice bath was added potassium 2-methylpropan-2-olate (0.29 g, 2.57 mmol). The mixture was stirred for 15 minutes and was quenched with 1 N HCl (~3 ml) and neutralized by saturated sodium bicarbonate (6 ml to pH=7). The mixture was stirred with ethyl acetate (20 ml), and then the organic phase was washed with brine (15 ml), separated and concentrated to an off-white foamy solid. It was purified silica gel column (MeOH/CH$_2$Cl$_2$ gradient from 1% to 9% in 70 min) to give 3-{4-[4-(4-cyclopropylmethyl-piperazin-1-ylmethyl)-benzyloxy]-1-oxo-1,3-dihydro-isoindol-2-yl}-piperidine-2,6-dione as a white powder (270 mg, 51% yield); mp: 176-178° C.; HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 4.05 min (97.0%); $^1$H NMR (DMSO-d$_6$) δ 0.08-0.10 (d, 2H, CH$_2$), 0.45-0.47 (d, 2H, CH$_2$), 0.80-0.83 (m, 1H, CHH), 1.96-2.00 (m, 1H, CHH), 2.27-2.60 (overlapped multiple peaks, 12H, CH$_2$, CH$_2$, CH$_2$, CH$_2$, CH$_2$, CHH, CHH), 2.85-2.97 (m, 1H, CHH), 3.48 (s, 2H, CH$_2$), 4.22-4.44 (m, 2H, CH$_2$), 5.11 (dd, J=5.1, 13.2 Hz, 1H, NCH), 5.22 (s, 2H, CH$_2$), 7.30-7.34 (m, 4H, Ar), 7.45-7.51 (m, 3H, Ar), 10.97 (s, 1H, NH); $^{13}$C NMR (DMSO-d$_6$) δ 3.69, 7.75, 22.34, 31.18, 45.07, 51.55, 52.03, 52.37, 61.54, 62.36, 69.40, 114.96, 115.22, 127.63, 128.89, 129.80, 129.93, 133.29, 135.24, 137.92, 153.49, 167.99, 170.96, 172.82; LCMS MH=503; Anal. Calcd for C$_{29}$H$_{34}$N$_4$O$_4$: (+1.0 H$_2$O): C, 66.90; H, 6.97; N, 10.76. Found: C, 66.67; H, 6.63; N, 10.42.

5.210 3-{4-[4-(4,4-Dimethyl-Piperidin-1-ylmethyl)-Benzyloxy]-1-Oxo-1,3-Dihydro-Isoindol-2-yl}-Piperidine-2,6-Dione

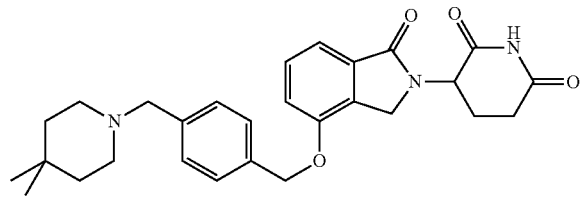 [SMILES: CC1(C)CCN(Cc2ccc(COc3cccc4c3CN(C3CCC(=O)NC3=O)C4=O)cc2)CC1]

Step 1: To a stirred solution of methyl 5-amino-4-(4-(4-(chloromethyl) benzyloxy)-1-oxoisoindolin-2-yl)-5-oxopentanoate (0.55 g, 1.28 mmol) in acetonitrile (15 ml) at room temperature, were added 4,4-dimethylpiperidine hydrochloride (0.23 g, 1.53 mmol) and N-ethyl-N-isopropylpropan-2-amine (0.46 ml, 2.81 mmol). The mixture was stirred overnight and then concentrated to give an oil, which was purified on silica gel column (MeOH/CH$_2$Cl$_2$ gradient from 1% to 9% in 60 min) to give 4-carbamoyl-4-{4-[4-(4,4-dimethyl-piperidin-1-ylmethyl)-benzyloxy]-1-oxo-1,3-dihydro-isoindol-2-yl}-butyric acid methyl ester as a light yellow solid (0.60 g, 92% yield). It was used in the next step without further purification.

Step 2: To a stirred solution of methyl 5-amino-4-(4-(4-((4,4-dimethylpiperidin-1-yl)methyl)benzyloxy)-1-oxoisoindolin-2-yl)-5-oxopentanoate (0.59 g, 1.16 mmol) in THF (15 ml) in an ice bath, was added potassium 2-methylpropan-2-olate (0.33 g, 2.94 mmol). The mixture was stirred for ten minutes and was quickly quenched by 1 N HCl (4 ml) and immediately neutralized by saturated sodium bicarbonate (5.5 ml to pH=7). The mixture was then stirred with ethyl acetate (25 ml). The organic phase was separated, washed with brine (15 ml), and concentrated to an off-white solid, which was purified on silica gel column (MeOH/CH$_2$Cl$_2$ gradient from 1% to 9% in 40 min) to give 3-{4-[4-(4,4-dimethyl-piperidin-1-ylmethyl)-benzyloxy]-1-oxo-1,3-dihydro-isoindol-2-yl}-piperidine-2,6-dione as a fine white powder (150 mg, 27% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 4.64 min (96.2%); mp: 168-170° C.; $^1$H NMR (DMSO-d$_6$) δ 0.95 (s, 6H, 2CH$_3$), 1.49 (br. s, 4H, CH$_2$, CH$_2$), 1.96-2.00 (m, 1H, CHH), 2.37-2.43 (m, 1H, CHH), 2.51-2.60 (m, 1H, CHH), 2.86-2.98 (3H, CHH, CH$_2$), 3.50 (br. s, 2H, CH$_2$), 4.23-4.45 (m, 2H, CH$_2$), 5.11 (dd, J=5.1, 13.2 Hz, 1H, NCH), 5.25 (s, 2H, CH$_2$), 7.31-7.51 (m, 7H, Ar), 10.97 (s, 1H, NH); $^{13}$C NMR (DMSO-d$_6$) δ 22.35, 27.94, 31.18, 37.16, 45.06, 48.91, 51.56, 69.28, 114.97, 115.26, 127.69, 129.80, 129.94, 133.31, 153.44, 167.98, 170.97, 172.82; LCMS MH=476; Anal. Calcd for C$_{28}$H$_{33}$N$_3$O$_4$: C, 70.71; H, 6.99; N, 8.84. Found: C, 66.15; H, 6.50; N, 8.02.

5.211 3-(4-(4-((4-Ethylpiperidin-1-yl)Methyl)Benzyloxy)-1-Oxoisoindolin-2-yl)Piperidine-2,6-Dione

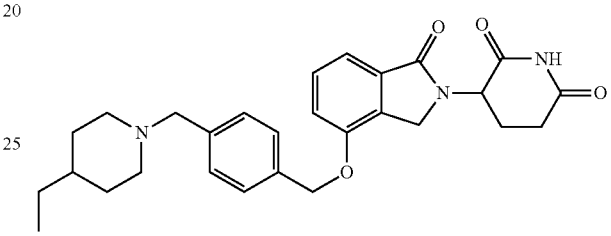

Step 1: To the acetonitrile solution of methyl 5-amino-4-(4-(4-(bromomethyl)benzyloxy)-1-oxoisoindolin-2-yl)-5-oxopentanoate (0.64 g, 1.346 mmol), was added 4-ethylpiperidine (0.34 g, 3.00 mmol). The mixture was stirred at room temperature overnight and concentrated on rota-vap. The resulting solid was extracted with CH$_2$Cl$_2$ (25 mL) and water (25 mL). The organic layer was washed with water (10 mL) then brine (10 mL), dried over Na$_2$SO$_4$, and concentrated to give methyl 5-amino-4-(4-(4-((4-ethylpiperidin-1-yl)methyl)benzyloxy)-1-oxoisoindolin-2-yl)-5-oxopentanoate as an off-white foamy solid (0.67 g, 98%). The solid was used in the next step without further purification.

Step 2: To the THF solution of methyl 5-amino-4-(4-(4-((4-ethylpiperidin-1-yl)methyl)benzyloxy)-1-oxoisoindolin-2-yl)-5-oxopentanoate (0.67 g, 1.320 mmol) was added potassium 2-methylpropan-2-olate (0.148 g, 1.320 mmol) at 0° C. The reaction was quenched by adding sat. NaHCO$_3$ (5 mL) after stirring at 0° C. for 1.5 hours. The mixture was diluted with EtOAc (20 mL) and 10 mL of water, extracted, washed with brine. The organic layer was concentrated on rota-vap to give a yellow solid. The solid was partially dissolved in CH$_2$Cl$_2$ (O1 mL), and ether (5 mL) was added. The mixture was stirred and filtered to give 3-(4-(4-((4-ethylpiperidin-1-yl)methyl)benzyloxy)-1-oxoisoindolin-2-yl)piperidine-2,6-dione as a solid (250 mg, 40%). mp: 180-182° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=4.85 min (96%). $^1$H NMR (DMSO-d$_6$) δ 0.66-0.94 (m, 3H, CH$_3$), 0.99-1.14 (m, 3H, CH, CH$_2$), 1.15-1.29 (m, 2H, CH$_2$), 1.47-1.71 (m, 2H, CH$_2$), 1.78-1.92 (m, 2H, CH$_2$), 1.93-2.06 (m, 1H, CH), 2.36-2.48 (m, 1H, CHH), 2.53-2.65 (m 1H, CHH), 2.77 (d, J=10.8 Hz, 2H, CH$_2$), 2.83-3.03 (m, 1H, CHH), 3.43 (s, 2H, CH$_2$), 4.13-4.50 (m, 2H, CH$_2$), 5.11 (dd, J=4.9, 13.2 Hz, 1H, NCH), 5.22 (s, 2H, CH$_2$), 7.21-7.38 (m, 4H, Ar), 7.39-7.55 (m, 3H, Ar), 10.97 (s, 1H, NH). $^{13}$C NMR (DMSO-d$_6$) δ 11.18, 22.36, 28.76, 31.21, 31.65, 36.97, 45.09, 51.58, 53.37, 62.19, 69.47, 114.97, 115.21, 127.61, 128.79, 129.81, 129.95, 133.31, 135.06, 138.66, 153.53, 168.01, 170.96, 172.82; LCMS: 476; Anal Calcd for C$_{28}$H$_{38}$N$_3$O$_4$+0.8 H$_2$O: C, 68.63; H, 7.12; N, 8.58; Found: C, 68.66; H, 6.83; N, 8.44.

5.212 3-(4-(4-((4-Isopropylpiperidin-1-yl)Methyl) Benzyloxy)-1-Oxoisoindolin-2-yl)Piperidine-2,6-Dione

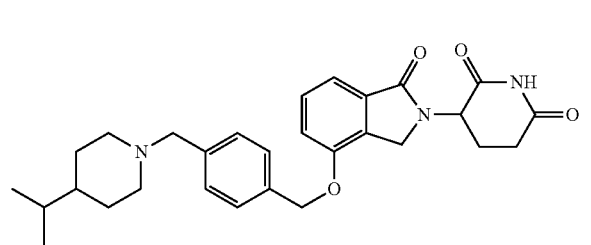 [SMILES: CC(C)C1CCN(Cc2ccc(COc3cccc4c3CN(C3CCC(=O)NC3=O)C4=O)cc2)CC1]

Step 1: To the acetonitrile solution of methyl 5-amino-4-(4-(4-(bromomethyl)benzyloxy)-1-oxoisoindolin-2-yl)-5-oxopentanoate (0.5 g, 1.052 mmol), was added 4-isopropylpiperidine (0.294 g, 2.314 mmol). The mixture was stirred at room temperature overnight. The reaction mixture was concentrated on rota-vap. The resulting oil was taken up in EtOAc (15 mL) and extracted with water (20 mL). The organic layer was washed with brine (10 mL), dried over Na$_2$SO$_4$ and concentrated to give methyl 5-amino-4-(4-(4-((4-isopropylpiperidin-1-yl)methyl)benzyloxy)-1-oxoisoindolin-2-yl)-5-oxopentanoate as an oil. The mixture was used without further purification in the next step.

Step 2: To the THF solution of methyl 5-amino-4-(4-(4-((4-isopropylpiperidin-1-yl)methyl)benzyloxy)-1-oxoisoindolin-2-yl)-5-oxopentanoate (0.548 g, 1.05 mmol), was added potassium 2-methylpropan-2-olate (0.12 g, 1.069 mmol) at 0° C. The mixture was stirred at 0° C. for 30 minutes. The reaction was quenched by adding 2 mL of HCl (1N) and 5 mL of NaHCO$_3$ (saturated) followed by 20 mL of EtOAc and 10 mL of water. The mixture was extracted and the organic layer was washed with water (10 mL) and brine (10 mL), and concentrated. The resulting solid was purified on ISCO column to give 3-(4-(4-((4-isopropylpiperidin-1-yl)methyl)benzyloxy)-1-oxoisoindolin-2-yl)piperidine-2,6-dione as white solid (65 mg, 13%). mp: 124-126° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=4.98 min (96.2%). $^1$H NMR (DMSO-d$_6$) δ 0.83 (d, J=6.8 Hz, 6H, CH$_3$, CH$_3$), 0.90-1.06 (m, 1H, CH), 1.07-1.25 (m, 2H, CH$_2$), 1.31-1.47 (m, 1H, CH), 1.51-1.63 (m, 2H, CH$_2$), 1.76-1.92 (m, 2H, CH$_2$), 1.93-2.04 (m, 1H, CHH), 2.36-2.47 (m, 1H, CHH), 2.53-2.63 (m, 1H, CHH), 2.74-2.88 (m, 2H, CH$_2$), 2.88-3.00 (m, 1H, CHH), 3.40-3.46 (br. s., 2H, CH$_2$), 4.19-4.47 (m, 2H, CH$_2$), 5.11 (dd, J=5.1, 13.2 Hz, 1H, NCH), 5.22 (s, 2H, CH$_2$), 7.25-7.37 (m, 4H, Ar), 7.38-7.54 (m, 3H, Ar), 10.97 (s, 1H, NH). $^{13}$C NMR (DMSO-d$_6$) δ 19.66, 22.36, 28.88, 31.21, 31.94, 41.84, 45.09, 51.58, 53.63, 62.13, 69.45, 114.97, 115.21, 127.61, 128.80, 129.81, 129.95, 133.31, 135.04, 153.51, 168.01, 170.96, 172.82; LCMS: 490; Anal Calcd for C$_{29}$H$_{35}$N$_3$O$_4$+0.4 H$_2$O: C, 70.11; H, 7.26; N, 8.46; Found: C, 70.10; H, 7.37; N, 8.36.

5.213 3-{4-[4-(4-Methoxy-Piperidin-1-ylmethyl)-Benzyloxy]-1-Oxo-1,3-Dihydro-Isoindol-2-yl}-Piperidine-2,6-Dione

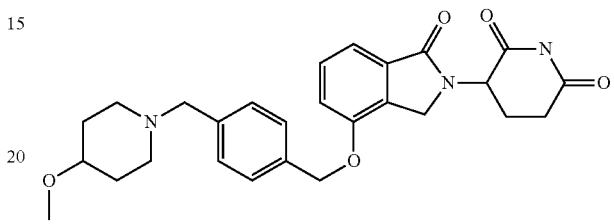

Step 1: To the acetonitrile solution of methyl 5-amino-4-(4-(4-(bromomethyl)benzyloxy)-1-oxoisoindolin-2-yl)-5-oxopentanoate (0.5 g, 1.052 mmol), were added 4-methoxypiperidine (0.133 g, 1.157 mmol) and DIPEA (0.276 ml, 1.578 mmol). After stirred at room temperature overnight, the reaction mixture was concentrated on rota-vap, giving 4-carbamoyl-4-{4-[4-(4-methoxy-piperidin-1-ylmethyl)-benzyloxy]-1-oxo-1,3-dihydro-isoindol-2-yl}-butyric acid methyl ester as an oil. It was used in the next step without further purification.

Step 2: To the THF solution of methyl 5-amino-4-(4-(4-((4-methoxypiperidin-1-yl)methyl)benzyloxy)-1-oxoisoindolin-2-yl)-5-oxopentanoate (0.536 g, 1.052 mmol), was added potassium 2-methylpropan-2-olate (0.236 g, 2.104 mmol) at 0° C. The mixture was stirred at this temperature for 15 minutes. The reaction was quenched by adding 10 mL of 1N HCl followed by 25 mL of NaHCO$_3$ (sat). The mixture was extracted with EtOAc (30 mL). The organic layer was concentrated to give a yellowish solid. The solid was stirred with ether overnight. The resulting suspension was filtered to give 3-{4-[4-(4-methoxy-piperidin-1-ylmethyl)-benzyloxy]-1-oxo-1,3-dihydro-isoindol-2-yl}-piperidine-2,6-dione as white solid (0.34 g, 71%). mp: 149-151° C. HPLC: Waters Symmetry C$_{18}$, 5 μm, 3.9×150 mm, 1 mL/min, 240 nm, gradient to 95/5 acetonitrile/0.1% H$_3$PO$_4$ in 5 min: t$_R$=4.60 min (96%); $^1$H NMR (DMSO-d$_6$) δ 1.28-1.51 (m, 2H, CH$_2$), 1.70-1.87 (m, 2H, CH$_2$), 1.90-2.15 (m, 3H, CHH, CH$_2$), 2.34-2.45 (m, 1H, CHH), 2.56-2.69 (m, 3H, CHH, CH$_2$), 2.80-3.01 (m, 1H, CHH), 3.08-3.19 (m, 1H, CH), 3.21 (s, 3H, OCH$_3$), 3.44 (s, 2H, CH$_2$), 4.18-4.53 (m, 2H, CH$_2$), 5.03-5.16 (m, 1H, NCH), 5.22 (s, 2H, CH$_2$), 7.23-7.38 (m, 4H, Ar), 7.39-7.57 (m, 3H, Ar), 10.97 (s, 1H, NH); $^{13}$C NMR (DMSO-d$_6$) δ 22.36, 30.63, 31.21, 50.48, 51.58, 54.77, 61.72, 69.44, 75.68, 114.95, 115.21, 127.62, 128.79, 128.83, 129.81, 129.95, 133.31, 135.12, 138.51, 153.51, 168.01, 170.96, 172.83; LCMS: 478; Anal Calcd for C$_{27}$H$_{31}$N$_3$O$_5$+0.1 H$_2$O: C, 67.40; H, 6.58; N, 8.73; Found: C, 67.32; H, 6.39; N, 8.52.

5.214 3-{4-[4-(3,3-Difluoro-Piperidin-1-ylmethyl)-Benzyloxy]-1-Oxo-1,3-Dihydro-Isoindol-2-yl}-Piperidine-2,6-Dione

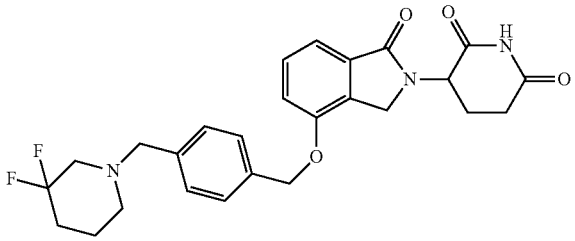 [SMILES: O=C1CCC(N2Cc3c(OCc4ccc(CN5CCCC(F)(F)C5)cc4)cccc3C2=O)C(=O)N1]

Step 1: To the stirred solution of methyl 5-amino-4-(4-(4-(bromomethyl)benzyloxy)-1-oxoisoindolin-2-yl)-5-oxopentanoate (600 mg, 1.262 mmol) in acetonitrile (10 mL), were added 3,3-difluoropiperidine hydrochloride (199 mg, 1.262 mmol) and DIPEA (0.441 ml, 2.52 mmol). The resulting solution was stirred at room temperature for two days. The mixture was concentrated and dissolved in dichloromethane (30 mL) and back extracted with NaHCO$_3$ (aq, sat. 15 mL). The organic layer was concentrated to give 4-carbamoyl-4-{4-[4-(3,3-difluoro-piperidin-1-ylmethyl)-benzyloxy]-1-oxo-1,3-dihydro-isoindol-2-yl}-butyric acid methyl ester as an off-white solid (651. mg, 100% crude yield). The solid was put to next step without further purification: LCMS MH=516.

Step 2: KOtBu (142 mg, 1.262 mmol) was added to a stirred solution of 4-carbamoyl-4-{4-[4-(3,3-difluoro-piperidin-1-ylmethyl)-benzyl oxy]-1-oxo-1,3-dihydro-isoindol-2-yl}-butyric acid methyl ester (651 mg, 1.262 mmol) in tetrahydrofuran (10 mL) at 0° C. The resulting reaction mixture was stirred at 0° C. for 30 minutes before it was diluted with dichloromethane (20 mL). The mixture was acidified with HCl (1N, 2 mL, aq.) and neutralized with NaHCO$_3$ (sat. aq. 2 mL) followed by the addition of brine (8 mL) and dichloromethane (30 mL). The mixture was extracted and the aqueous layer was back extracted with dichloromethane (2×40 mL). Organic layers were combined and dried with MgSO$_4$. The mixture was filtered and the filtrate was concentrated. The residue was triturated in diethyl ether (50 mL) and filtered to give 3-{4-[4-(3,3-difluoro-piperidin-1-ylmethyl)-benzyloxy]-1-oxo-1,3-dihydro-isoindol-2-yl}-piperidine-2,6-dione as a white solid (540 mg, 77% yield): HPLC: Waters Symmetry C-18, 3.9×150 mm, 5 µm, 1 mL/min, 240 nm, 18/82, (acetonitrile/0.1% H$_3$PO$_4$), 4.44 min (99.9%); mp: 140-142° C.; $^1$H NMR (DMSO-d$_6$) δ 1.57-1.71 (m, 2H, CH$_2$), 1.76-2.08 (m, 3H, CH$_2$, CHH), 2.34-2.45 (m, 2H, CH$_2$), 2.45-2.47 (m, 1H, CHH), 2.53-2.68 (m, 3H, CH$_2$, CHH), 2.81-3.01 (m, 1H, CHH), 3.57 (s, 2H, CH$_2$), 4.20-4.32 (m, J=17.6 Hz, 1H, CHH), 4.42 (d, J=17.4 Hz, 1H, CHH), 5.11 (dd, J=5.1, 13.2 Hz, 1H, CHH), 5.23 (s, 2H, CH$_2$), 7.28-7.38 (m, 4H, Ar), 7.41-7.54 (m, 3H, Ar), 10.97 (s, 1H, NH); $^{13}$C NMR (DMSO-d$_6$) δ 21.38-21.71, 22.33, 31.18, 31.61 (t, J$_{C-F}$=23.1 Hz), 45.07, 51.12, 51.55, 57.48 (t, J$_{C-F}$=27.5 Hz), 60.56, 69.38, 114.94, 115.22, 121.05 (t, J$_{C-F}$=241.0 Hz), 127.67, 128.82, 129.78, 129.93, 133.30, 135.40, 137.34, 153.49, 167.99, 170.96, 172.81; LCMS MH=484; Anal. Calcd for C$_{26}$H$_{27}$F$_2$N$_3$O$_4$+1.3 H$_2$O: C, 61.6; H, 5.89; N, 8.29; Found: C, 61.39; H, 5.61; N, 8.00.

5.215 3-(4-(4-((4-(Methylsulfonyl)Piperazin-1-yl)Methyl)Benzyloxy)-1-Oxoisoindolin-2-yl)Piperidine-2,6-Dione

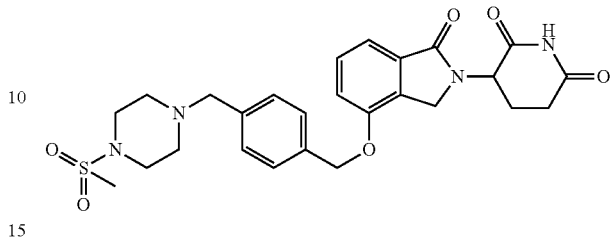

To a stirred solution of methyl 5-amino-4-(4-(4-(chloromethyl)benzyloxy)-1-oxoisoindolin-2-yl)-5-oxopentanoate (0.455 g, 1.056 mmol) in acetonitrile (10 ml), were added 1-(methylsulfonyl)piperazine (0.225 g, 1.373 mmol) and DIPEA (0.436 ml, 2.64 mmol). The reaction mixture was stirred at room temperature for 5.5 days. The reaction mixture was diluted by dichloromethane (40 mL) and washed with water (20 mL) and brine (20 mL). The organic layer was then dried (MgSO$_4$) and after filtration of drying agent, solvent was concentrated down to give methyl 5-amino-4-(4-(4-((4-(methylsulfonyl) piperazin-1-yl) methyl)benzyloxy)-1-oxoisoindolin-2-yl)-5-oxopentanoate. The crude product was used in the next step without further purification.

Potassium tert-butoxide (0.154 g, 1.373 mmol) was added to the stirred solution of methyl 5-amino-4-(4-(4-((4-(methylsulfonyl)piperazin-1-yl)methyl)benzyloxy)-1-oxoisoindolin-2-yl)-5-oxopentanoate (0.590 g, 1.056 mmol) in THF (20 mL) at 0° C. The reaction mixture was stirred at 0° C. for 1 hour. The reaction mixture was then diluted by dichloromethane (50 mL) and acidified with HCl (1N aq. 4 mL). The mixture was washed with NaHCO$_3$ (20 mL) and brine (20 mL). The aqueous layer was extracted back with dichloromethane (2×30 mL). Combined organic layers were dried with MgSO$_4$. After filtration of drying agent, solvent was evaporated. The residue was stirred in a mixture of methanol/dichloromethane: 50/50. The filtrate was purified by Isco Flash (dry loading, gradient, Methanol/dichloromethane: 0/100 to 5/95 in 30 min), eluting product at 5/95. The solvent was then evaporated and the residue was stirred in ether. Solid was filtered and dried to give 3-(4-(4-((4-(methylsulfonyl)piperazin-1-yl)methyl)benzyloxy)-1-oxoisoindolin-2-yl)piperidine-2,6-dione (0.32 g, 2 steps 58% yield); HPLC: Waters Symmetry C-18, 3.9×150 mm, 5 µm, 1 mL/min, 240 nm, acetonitrile/0.1% H3PO4: gradient 10/90 to 90/10 in 15 min; 5 min at 90/10:6.23 min (97.27%), 8.02 min (2.25%); mp: 158-160° C.; 1H NMR (DMSO-d6) δ 1.87-2.08 (m, 1H, CHH), 2.31-2.48 (m, 5H, CH2, CH2, CHH), 2.53-2.69 (m, 1H, CHH), 2.86 (s, 3H, CH3), 2.89-3.02 (m, 1H, CHH), 3.02-3.20 (m, 4H, CH2, CH2), 3.53 (s, 2H, CH2), 4.16-4.33 (m, 1H, CHH), 4.34-4.53 (m, 1H, CHH), 5.11 (dd, J=5.1, 13.2 Hz, 1H, CH), 5.23 (s, 2H, CH2), 7.25-7.40 (m, 4H, Ar), 7.40-7.55 (m, 3H, Ar), 10.97 (s, 1H, NH); 13C NMR (DMSO-d6) δ 22.34, 31.18, 33.55, 45.06, 45.41, 51.55, 51.71, 61.14, 69.35, 114.96, 115.22, 127.66, 128.90, 129.80, 129.93, 133.28, 135.38, 137.69, 153.46, 167.97, 170.96, 172.81; Anal Calcd for C$_{26}$H$_{30}$N$_4$O$_6$S+0.2 H2O: C, 58.90; H, 5.78; N, 10.57; Found: C, 58.62; H, 5.51; N, 10.40.

5.216 3-[1-Oxo-4-(4-Piperidin-1-ylmethyl-Benzyloxy)-1,3-Dihydro-Isoindol-2-yl]-Piperidine-2,6-Dione

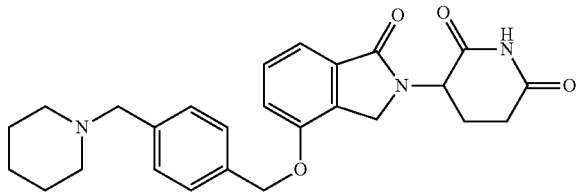 [SMILES: O=C1CCC(N2Cc3c(OCc4ccc(CN5CCCCC5)cc4)cccc3C2=O)C(=O)N1]

Step 1: Polymer-supported triphenylphosphene (1~1.5 mmol/g, 2.10 g, 2.63 mmol) was added to a stirred solution of 4-carbamoyl-4-(4-hydroxy-1-oxo-1,3-dihydro-isoindol-2-yl)-butyric acid methyl ester in THF (20 mL) at 0° C., followed by addition of diisopropyl azodicarboxylate (0.52 mL, 2.63 mmol). After stirring for 15 minutes, (4-piperidin-1-ylmethyl-phenyl)-methanol (0.49 g, 2.39 mmol) was added. The mixture was stirred at room temperature overnight and then filtered. The filtrate was evaporated and purified on silica gel column to give 4-carbamoyl-4-[1-oxo-4-(4-piperidin-1-ylmethyl-benzyloxy)-1,3-dihydro-isoindol-2-yl]-butyric acid methyl ester as an oil (0.51 g, 88% yield).

Step 2: Potassium tert-butoxide (0.12 g, 1.06 mmol) was added to a stirred solution of 4-carbamoyl-4-[1-oxo-4-(4-piperidin-1-ylmethyl-benzyloxy)-1,3-dihydro-isoindol-2-yl]-butyric acid methyl ester (0.51 g, 1.06 mmol) in THF (8 mL) at 0° C. for 10 minutes. The mixture was quenched with 1N HCl (2 ml) and neutralized with saturated sodium bicarbonate (4 ml to pH=8). The mixture was washed with ethyl acetate (3×20 mL). The combined ethyl acetate phases were evaporated and purified by PREP HPLC to give 3-[1-oxo-4-(4-piperidin-1-ylmethyl-benzyloxy)-1,3-dihydro-isoindol-2-yl]-piperidine-2,6-dione as a white solid (0.07 g, 15% yield); HPLC: Waters Symmetry $C_{18}$, 5 µm, 3.9×150 mm, 1 ml/min, 240 nm, 17/83 acetonitrile/0.1% $H_3PO_4$, 4.88 min (98.8%); mp: 186-188° C.; $^1$H NMR (DMSO-$d_6$) δ, 1.30-1.60 (m, 6H, 3CH$_2$), 1.91-2.05 (m, 1H, CHH), 2.22-2.36 (m, 4H, 2CH$_2$), 2.37-2.47 (m, 1H, CHH), 2.53-2.63 (m, 1H, CHH), 2.83-2.99 (m, 1H, CHH), 3.41 (s, 2H, CH$_2$), 4.19-4.48 (m, 2H, ArCH$_2$), 5.11 (dd, J=5.1, 13.2 Hz, 1H, NCH), 5.22 (s, 2H, CH$_2$), 7.26-7.37 (m, 4H, Ar), 7.39-7.53 (m, 3H, Ar), 10.97 (s, 1H, NH); $^{13}$C NMR (DMSO-$d_6$) δ 22.36, 23.99, 25.55, 31.21, 45.10, 51.58, 53.88, 62.54, 69.45, 114.97, 115.21, 127.59, 128.80, 129.81, 129.95, 133.31, 135.03, 138.58, 153.51, 168.01, 170.96, 172.83; LCMS MH=448; Anal. Calcd for $C_{26}H_{29}N_3O_4$: C, 69.78; H, 6.53; N, 9.39. Found: C, 66.86; H, 6.15; N, 8.99.

5.217 3-{4-[4-(4-Methyl-Piperazin-1-ylmethyl)-Benzyloxy]-1-Oxo-1,3-Dihydro-Isoindol-2-yl}-Piperidine-2,6-Dione

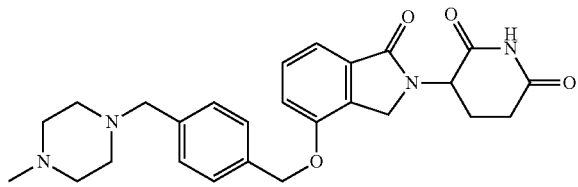

Step 1: Polymer-supported triphenylphosphene (1.6 mmol/g, 1.36 g, 1.85 mmol) was added to a stirred solution of 4-carbamoyl-4-(4-hydroxy-1-oxo-1,3-dihydro-isoindol-2-yl)-butyric acid methyl ester (0.45 g, 1.54 mmol) in THF (20 mL) at 0° C., followed by addition of diisopropyl diazene-1,2-dicarboxylate (0.37 ml, 1.88 mmol). After stirring for 30 minutes, [4-(4-methyl-piperazin-1-ylmethyl)-phenyl]-methanol (0.41 g, 1.85 mmol) was added. The mixture was stirred for three hours then filtered, washed with methanol (3×10 mL) and methylene chloride (3×10 mL). The combined filtrate was evaporated in vacuo to give an oil, which was purified on silica gel column (amine column, MeOH/CH$_2$Cl$_2$ gradient from 0% to 2% in 60 min) to give 4-carbamoyl-4-{4-[4-(4-methyl-piperazin-1-ylmethyl)-benzyloxy]-1-oxo-1,3-dihydro-isoindol-2-yl}-butyric acid methyl ester as a clear oil (0.50 g, 66% yield).

Step 2: Potassium tert-butoxide (0.11 g, 1.01 mmol) was added to a stirred solution of 4-carbamoyl-4-{4-[4-(4-methyl-piperazin-1-ylmethyl)-benzyloxy]-1-oxo-1,3-dihydro-isoindol-2-yl}-butyric acid methyl ester (0.50 g, 1.01 mmol) in THF (15 mL) at 0° C. The mixture was stirred for ten minutes and quenched with 1N HCl (3 mL), neutralized by saturated sodium bicarbonate (4 mL to pH=7), and quickly extracted by ethyl acetate (2×30 mL). The combined ethyl acetate phases were evaporated to give an off-white solid, which was stirred in ethyl acetate (10 mL) for one hour. The suspension was filtered to give 3-{4-[4-(4-methyl-piperazin-1-ylmethyl)-benzyloxy]-1-oxo-1,3-dihydro-isoindol-2-yl}-piperidine-2,6-dione as an off-white solid (0.12 g, 26% yield): HPLC: Waters Symmetry C-18, 3.9×150 mm, 5 µm, 1 mL/min, 240 nm, isocratic at 10/90 in 15 min (acetonitrile/0.1% $H_3PO_4$), 9.82 min (99.7%); mp: 188-190° C.; $^1$H NMR (DMSO-$d_6$) δ 1.90-2.04 (m, 1H, CHH), 2.14 (s, 3H, CH$_3$), 2.20-2.46 (m, 9H, CHH, CH$_2$CH$_2$, CH$_2$CH$_2$), 2.55-2.66 (m, 1H, CHH), 2.80-3.05 (m, 1H, CHH), 3.45 (s, 2H, CH$_2$), 4.17-4.50 (m, 2H, CH$_2$), 5.11 (dd, J=5.2, 13.1 Hz, 1H, NCH), 5.22 (s, 2H, CH$_2$), 7.23-7.56 (m, 7H, Ar), 10.97 (s, 1H, NH); $^{13}$C NMR (DMSO-$d_6$) δ 22.36, 31.21, 45.09, 45.72, 51.58, 52.52, 54.71, 61.74, 69.44, 114.98, 115.23, 127.62, 128.88, 129.81, 129.95, 133.31, 135.17, 138.18, 153.51, 168.01, 170.96, 172.82; LCMS MH=463; Anal. Calcd for $C_{26}H_{30}N_4O_4$: C, 67.51; H, 6.54; N, 12.11; Found: C, 67.23; H, 6.67; N, 11.78.

5.218 4-{4-[2-(2,6-Dioxo-Piperidin-3-yl)-1-Oxo-2,3-Dihydro-1H-Isoindol-4-yloxymethyl]-Benzyl}-Piperazine-1-Carboxylic Acid Tert-Butyl Ester

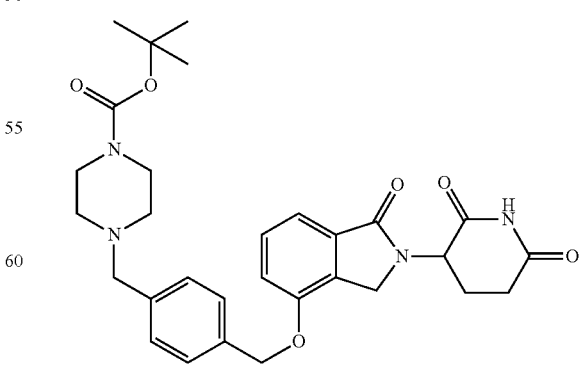

Step 1: To the acetonitrile solution of 4-carbamoyl-4-[4-(4-chloromethyl-benzyloxy)-1-oxo-1,3-dihydro-isoindol-2- yl]-butyric acid methyl ester (0.8 g, 1.8 mmol), was added t-butyl-piperazine-carboxylate (0.86 g, 4.6 mmol) and DIPEA (0.62 mL, 4.6 mmol). After stirred at room temperature overnight, the mixture was concentrated and extracted with EtOAc (30 mL) and Na$_2$CO$_3$ (20 mL). The organic layer was washed with water (20 mL) and brine (20 mL), concentrated to give 4-{4-[2-(1-carbamoyl-3-methoxycarbonyl-propyl)-1-oxo-2,3-dihydro-1H-isoindol-4-yloxymethyl]-benzyl}-piperazine-1-carboxylic acid tert-butyl ester as an oil, which was used in next step without purification.

Step 2: To the THF solution (20 mL) of 4-{4-[2-(1-carbamoyl-3-methoxycarbonyl-propyl)-1-oxo-2,3-dihydro-1H-isoindol-4-yloxymethyl]-benzyl}-piperazine-1-carboxylic acid tert-butyl ester (1.04 g, 1.8 mmol), was added potassium t-butoxide (0.3 g, 2.7 mmol) at 0° C. The mixture was stirred for 15 minutes at 0° C. and quenched with 5 mL of 1N HCl solution followed by 15 mL of saturated NaHCO$_3$ solution. The mixture was extracted with EtOAc (20 mL). The organic layer was concentrated in vacuo. The resulting oil was purified on silica gel column eluted with CH$_2$Cl$_2$ and methanol to give 4-{4-[2-(2,6-Dioxo-piperidin-3-yl)-1-oxo-2,3-dihydro-1H-isoindol-4-yloxymethyl]-benzyl}-piperazine-1-carboxylic acid tert-butyl ester as a oil (170 mg, 18%). mp: 180-182° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: $t_R$ 5.03 min (94%); LCMS MH=549. $^1$H NMR (DMSO-d$_6$) δ 1.38 (s, 9H, CH$_3$, CH$_3$, CH$_3$), 1.87-2.13 (m, 1H, CHH), 2.30 (t, J=4.8 Hz, 4H, CH$_2$, CH$_2$), 2.40-2.48 (m, 1H, CHH), 2.53-2.64 (m, 1H, CHH), 2.81-3.00 (m, 1H, CHH), 3.30 (br. s., 4H, CH$_2$, CH$_2$), 3.48 (s, 2H, CH$_2$), 4.14-4.57 (m, 2H, CH$_2$), 5.00-5.17 (m, 1H, NCH), 5.23 (s, 2H, CH$_2$), 7.33 (d, J=7.7 Hz, 4H, Ar), 7.45 (d, J=8.7 Hz, 3H, Ar), 10.97 (s, 1H, NH); $^{13}$C NMR (DMSO-d$_6$) δ 22.29, 27.96, 31.13, 45.02, 51.51, 52.28, 61.55, 69.33, 78.64, 114.91, 115.18, 127.58, 128.90, 129.76, 129.89, 133.25, 135.25, 137.70, 153.43, 153.71, 167.92, 170.91, 172.76; Anal Calcd for C$_{30}$H$_{36}$N$_4$O$_6$+0.2 H$_2$O: C, 65.25; H, 6.64; N, 10.15; Found: C, 64.96; H, 6.51; N, 10.11.

5.219 3-[1-Oxo-4-(4-Piperazin-1-ylmethyl-Benzyloxy)-1,3-Dihydro-Isoindol-2-yl]-Piperidine-2,6-Dione

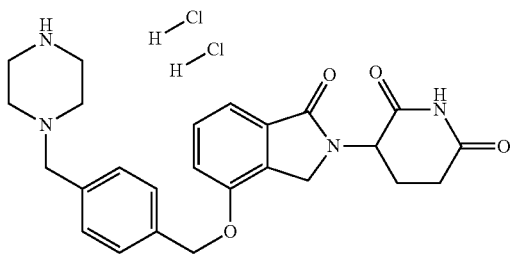

Step 1: To the acetonitrile solution of 4-carbamoyl-4-[4-(4-chloromethyl-benzyloxy)-1-oxo-1,3-dihydro-isoindol-2-yl]-butyric acid methyl ester (0.8 g, 1.8 mmol), were added t-butyl-piperazine-carboxylate (0.86 g, 4.6 mmol) and DIPEA (0.62 mL, 4.6 mmol). After being stirred at room temperature overnight, the mixture was concentrated and extracted with EtOAc (30 mL) and Na$_2$CO$_3$ (20 mL). The organic layer was washed with water (20 mL) and brine (20 mL), and concentrated to give 4-{4-[2-(1-Carbamoyl-3-methoxycarbonyl-propyl)-1-oxo-2,3-dihydro-1H-isoindol-4-yloxymethyl]-benzyl}-piperazine-1-carboxylic acid tert-butyl ester as an oil, which was used in next step without purification.

Step 3: To the THF solution (20 mL) of 4-{4-[2-(1-carbamoyl-3-methoxycarbonyl-propyl)-1-oxo-2,3-dihydro-1H-isoindol-4-yloxymethyl]-benzyl}-piperazine-1-carboxylic acid tert-butyl ester (1.04 g, 1.8 mmol), was added potassium t-butoxide (0.3 g, 2.7 mmol) at 0° C. The mixture was stirred for 15 minutes at 0° C. and quenched with 5 mL of 1N HCl solution followed by 15 mL of saturated NaHCO$_3$ solution. The mixture was extracted with EtOAc (20 mL). The organic layer was concentrated in vacuo. The resulting oil was purified on silica gel column eluted with CH$_2$Cl$_2$ and methanol to give 4-{4-[2-(2,6-Dioxo-piperidin-3-yl)-1-oxo-2,3-dihydro-1H-isoindol-4-yloxymethyl]-benzyl}-piperazine-1-carboxylic acid tert-butyl ester as a oil (170 mg, 18%). mp: 180-182° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: $t_R$=5.03 min (94%); LCMS MH=549. $^1$H NMR (DMSO-d$_6$) δ 1.38 (s, 9H, CH$_3$, CH$_3$, CH$_3$), 1.87-2.13 (m, 1H, CHH), 2.30 (t, J=4.8 Hz, 4H, CH$_2$, CH$_2$), 2.40-2.48 (m, 1H, CHH), 2.53-2.64 (m, 1H, CHH), 2.81-3.00 (m, 1H, CHH), 3.30 (br. s., 4H, CH$_2$, CH$_2$), 3.48 (s, 2H, CH$_2$), 4.14-4.57 (m, 2H, CH$_2$), 5.00-5.17 (m, 1H, NCH), 5.23 (s, 2H, CH$_2$), 7.33 (d, J=7.7 Hz, 4H, Ar), 7.45 (d, J=8.7 Hz, 3H, Ar), 10.97 (s, 1H, NH); $^{13}$C NMR (DMSO-d$_6$) δ 22.29, 27.96, 31.13, 45.02, 51.51, 52.28, 61.55, 69.33, 78.64, 114.91, 115.18, 127.58, 128.90, 129.76, 129.89, 133.25, 135.25, 137.70, 153.43, 153.71, 167.92, 170.91, 172.76. Anal Calcd for C$_{30}$H$_{36}$N$_4$O$_6$+0.2 H$_2$O: C, 65.25; H, 6.64; N, 10.15; Found: C, 64.96; H, 6.51; N, 10.11.

Step 4: To the CH$_2$Cl$_2$ solution (10 mL) of 4-{4-[2-(2,6-dioxo-piperidin-3-yl)-1-oxo-2,3-dihydro-1H-isoindol-4-yloxymethyl]-benzyl}-piperazine-1-carboxylic acid tert-butyl ester (0.37 g, 0.675 mmol), was added hydrogen chloride in ether solution (2.0 M, 1.6 mL, 8 mmol). The mixture was stirred at room temperature overnight. The mixture was filtered. The resulting solid was stirred with ether to give 3-[1-oxo-4-(4-piperazin-1-ylmethyl-benzyloxy)-1,3-dihydro-isoindol-2-yl]-piperidine-2,6-dione as white solid (240 mg, 69%). mp: 196-198° C.; HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: $t_R$=5.10 min (96%); $^1$H NMR (DMSO-d$_6$) δ 1.90-2.07 (m, 1H, CHH), 2.35-2.45 (m, 1H, CHH), 2.59 (d, J=15.7 Hz, 1H, CHH), 2.84-3.02 (m, 1H, CHH), 3.09-3.32 (b, 2H, CH$_2$), 3.41-3.51 (b, 4H, CH$_2$, CH$_2$), 4.22-4.53 (m, 4H, CH$_2$, CH$_2$), 5.12 (dd, J=5.1, 13.2 Hz, 1H, NCH), 5.29 (s, 7H, CH$_2$), 7.28-7.38 (m, 7H, Ar), 7.43-7.54 (m, 4H, Ar), 7.55-7.71 (m, 14H, Ar), 10.98 (s, 1H, NH); $^{13}$C NMR (DMSO-d$_6$) δ 15.05, 22.32, 31.13, 45.02, 47.29, 51.52, 68.94, 114.90, 115.31, 127.79, 129.78, 129.90, 131.44, 133.30, 153.30, 167.89, 170.91, 172.76; LCMS MH=449. Anal Calcd for C$_{25}$H$_{28}$N$_4$O$_4$ 2.1HCl+1H$_2$O: C, 55.29; H, 5.96; N, 10.32; Cl, 13.71%. Found: C, 55.39; H, 6.13; N, 10.19; Cl, 13.61.

5.220 3-{4-[4-(4-Methyl-Piperidin-1-ylmethyl)-Benzyloxy]-1-Oxo-1,3-Dihydro-Isoindol-2-yl}-Piperidine-2,6-Dione

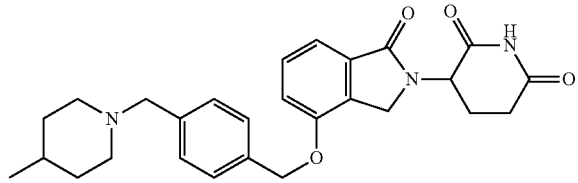 [SMILES: CC1CCN(Cc2ccc(COc3cccc4c3CN(C3CCC(=O)NC3=O)C4=O)cc2)CC1]

4-Methylpiperidine (0.49 g, 4.94 mmol) was added to a stirred solution of methyl 5-amino-4-(4-(4-(chloromethyl)benzyloxy)-1-oxoisoindolin-2-yl)-5-oxopentanoate (0.71 g, 1.65 mmol) in DMF (15 mL) at 50° C. overnight. To the mixture was added potassium carbonate (0.23 g, 1.65 mmol), and the mixture was heated at 90° C. overnight. The mixture was concentrated to give an oil, which was stirred in ethyl acetate (10 mL) overnight. The suspension was filtered to give a brown filtrate, which was evaporated and purified on silica gel column with MeOH (solvent B)/dichloromethane (solvent A) as eluents to give 3-{4-[4-(4-Methyl-piperidin-1-ylmethyl)-benzyloxy]-1-oxo-1,3-dihydro-isoindol-2-yl}-piperidine-2,6-dione as a white solid (0.22 g, 30% yield over 3 steps); HPLC: Waters Symmetry C-18, 3.9×150 mm, 5 µm, 1 mL/min, 240 nm, gradient from 10/90 to 95/5 in 5 min, isocratic at 95/5 in 5 min (acetonitrile/0.1% H3PO4), 5.16 min (98.1%); mp: 189-191° C.; 1H NMR (DMSO-d6) δ 0.88 (d, J=6.4 Hz, 3H, CH3), 1.04-1.20 (m, 2H, CHH), 1.23-1.41 (m, 1H, CHH), 1.49-1.63 (m, 2H, CH2), 1.81-2.04 (m, 3H, CH, CH2), 2.36-2.48 (m, 1H, CHH), 2.53-2.63 (m, 1H, CHH), 2.69-2.82 (m, 2H, CH2), 2.83-2.99 (m, 1H, CHH), 3.38-3.52 (m, 2H, CH2), 4.19-4.47 (m, 2H, CH2), 5.11 (dd, J=5.1, 13.2 Hz, 1H, NCH), 5.22 (s, 2H, CH2), 7.26-7.37 (m, 4H, Ar), 7.39-7.53 (m, 3H, Ar), 10.97 (s, 1H, NH); 13C NMR (DMSO-d6) δ 21.79, 22.36, 30.23, 31.21, 33.89, 45.10, 51.58, 53.22, 62.10, 69.44, 114.97, 115.23, 127.61, 128.86, 129.81, 129.94, 133.31, 135.12, 153.51, 168.01, 170.96, 172.83; LCMS MH=462; Anal. Calcd for C27H31N3O4+0.1 H2O: C, 69.99; H, 6.79; N, 9.07. Found: C, 69.84; H, 6.81; N, 9.12.

5.221 3-{4-[4-(4-Tert-Butyl-Piperidin-1-ylmethyl)-Benzyloxy]-1-Oxo-1,3-Dihydro-Isoindol-2-yl}-Piperidine-2,6-Dione

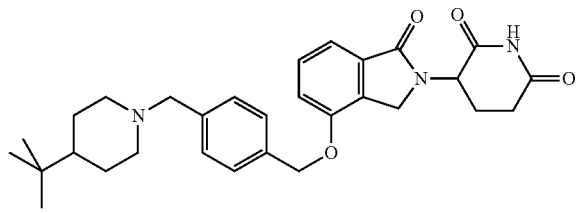 [SMILES: CC(C)(C)C1CCN(Cc2ccc(COc3cccc4c3CN(C3CCC(=O)NC3=O)C4=O)cc2)CC1]

Step 1: 4-Carbamoyl-4-[4-(4-chloromethyl-benzyloxy)-1-oxo-1,3-dihydro-isoindol-2-yl]-butyric acid methyl ester (0.63 g, 1.46 mmol) was added to a stirred solution of 4-tert-butylpiperidine hydrochloride (0.78 g, 4.37 mmol) and diisopropylethylamine (0.96 mL, 5.83 mmol) in DMF (15 mL) at 70° C. The mixture was heated for 5 hours and then evaporated and purified on silica gel column (MeOH/CH2Cl2 gradient from 1% to 9% in 50 min) to give 4-{4-[4-(4-tert-Butyl-piperidin-1-ylmethyl)-benzyloxy]-1-oxo-1,3-dihydro-isoindol-2-yl}-4-carbamoyl-butyric acid methyl ester as a light brown oily solid (1.23 g), which was used in the next step without further purification.

Step 2: To a stirred solution of 4-{4-[4-(4-tert-Butyl-piperidin-1-ylmethyl)-benzyloxy]-1-oxo-1,3-dihydro-isoindol-2-yl}-4-carbamoyl-butyric acid methyl ester in THF (15 ml) at room temperature was added potassium tert-butoxide (0.33 g, 2.90 mmol). The mixture was stirred for 30 minutes or until LCMS showed no starting material. The mixture was quenched with 1 N HCl (2 ml) to give a clear brown solution and then neutralized with saturated sodium bicarbonate (4 ml to pH=7). The mixture was extracted with ethyl acetate (2×30 mL), washed with brine and concentrated to a brown solid. It was purified on silica gel column (MeOH/CH2Cl2 gradient from 1% to 9% in 50 min) to give 3-{4-[4-(4-tert-Butyl-piperidin-1-ylmethyl)-benzyloxy]-1-oxo-1,3-dihydro-isoindol-2-yl}-piperidine-2,6-dione as a light brown solid (0.56 g, 76% yield); HPLC: Waters Symmetry C-18, 3.9×150 mm, 5 µm, 1 mL/min, 240 nm, gradient from 10/90 to 95/5 in 5 min, isocratic at 95/5 in 5 min (acetonitrile/0.1% H3PO4), 5.62 min (96.6%); mp: 208-210° C.; 1H NMR (DMSO-d6) δ 0.82 (s, 9H, 3CH3), 0.88-1.05 (m, 1H, CHH), 1.09-1.31 (m, 2H, CH2), 1.49-1.65 (m, 2H, CH2), 1.83 (t, J=11.5 Hz, 2H, CH2), 1.92-2.06 (m, 1H, CHH), 2.34-2.47 (m, 1H, CHH), 2.54-2.65 (m, 1H, CHH), 2.79-3.00 (m, 3H, CH, CH2), 3.38-3.47 (m, 2H, CH2), 4.20-4.47 (m, 2H, CH2), 5.11 (dd, J=5.1, 13.2 Hz, 1H, NCH), 5.22 (s, 2H, CH2), 7.25-7.37 (m, 4H, Ar), 7.39-7.55 (m, 3H, Ar), 10.97 (s, 1H, NH); 13C NMR (DMSO-d6) δ 22.36, 26.44, 27.19, 31.21, 31.84, 45.09, 45.94, 51.58, 53.98, 62.09, 69.45, 114.97, 115.21, 127.61, 128.77, 129.81, 129.94, 133.31, 135.04, 138.64, 153.51, 168.01, 170.96, 172.82; LCMS MH=504; Anal. Calcd for C30H37N3O4+0.1 H2O: C, 71.29; H, 7.42; N, 8.31. Found: C, 70.96; H, 7.63; N, 8.32.

5.222 3-{4-[4-(4-Hydroxy-Piperidin-1-ylmethyl)-Benzyloxy]-1-Oxo-1,3-Dihydro-Isoindol-2-yl}-Piperidine-2,6-Dione

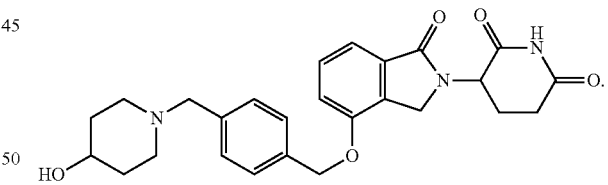

Step 1: To a stirred colorless solution of methyl 5-amino-4-(4-(4-(chloromethyl)benzyloxy)-1-oxoisoindolin-2-yl)-5-oxopentanoate (0.51 g, 1.19 mmol) in acetonitrile (15 ml) was added piperidin-4-ol hydrochloride (0.16 g, 1.19 mmol) and N-ethyl-N-isopropylpropan-2-amine (0.49 ml, 2.98 mmol). It was stirred at room temperature overnight. To the mixture was added piperidin-4-ol hydrochloride (0.09 g) and DIPEA (0.4 mL) and heated at 50° C. overnight. The mixture was purified on silica gel column (MeOH/CH2Cl2 gradient from 1% to 9% in 50 minutes) to give 4-carbamoyl-4-{4-[4-(4-hydroxy-piperidin-1-ylmethyl)-benzyloxy]-1-oxo-1,3-dihydro-isoindol-2-yl}-butyric acid methyl ester as an off-white solid (0.75 g, 78% yield).

Step 2: To a stirred solution of methyl 5-amino-4-(4-(4-((4-hydroxypiperidin-1-yl)methyl)benzyloxy)-1-oxoisoindolin-2-yl)-5-oxopentanoate (0.67 g, 1.35 mmol) in THF (30 ml) at room temperature, was added potassium 2-methyl-propan-2-olate (0.61 g, 5.41 mmol). It was stirred for ten minutes and then quenched with 1N HCl (2 ml), and neutralized by saturated sodium bicarbonate (4 ml to pH=7). The mixture was extracted with ethyl acetate (2×20 mL). The combined ethyl acetate phases were purified on silica gel column (MeOH/CH$_2$Cl$_2$ gradient from 1% to 9% in 50 min) to give 3-{4-[4-(4-Hydroxy-piperidin-1-ylmethyl)-benzyloxy]-1-oxo-1,3-dihydro-isoindol-2-yl}-piperidine-2,6-dione as a white solid (0.24 g, 38% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 5.16 min (97.3%); mp: 204-206° C.; $^1$H NMR (DMSO-d$_6$) δ 1.28-1.48 (m, 2H, CH$_2$), 1.58-1.79 (m, 2H, CH$_2$), 1.89-2.15 (m, 3H, CHH, CH$_2$), 2.37-2.47 (m, 1H, CHH), 2.53-2.71 (m, 4H, CH$_2$, CHH, CHH), 2.83-2.99 (m, 1H, CHH), 3.39-3.49 (m, 3H, CH$_2$, CHH), 4.21-4.47 (m, 2H, CH$_2$), 4.53 (d, J=4.2 Hz, 1H, OH), 5.11 (dd, J=5.0, 13.1 Hz, 1H, NCH), 5.22 (s, 2H, CH$_2$), 7.26-7.37 (m, 4H, Ar), 7.39-7.53 (m, 3H, Ar), 10.97 (s, 1H, NH); $^{13}$C NMR (DMSO-d$_6$) δ 22.36, 31.21, 34.37, 45.10, 50.82, 51.58, 61.77, 66.26, 69.44, 114.97, 115.21, 127.62, 128.80, 129.81, 129.95, 133.31, 135.10, 138.58, 153.51, 168.01, 170.98, 172.83; LCMS MH=464; Anal. Calcd for C$_{26}$H$_{29}$N$_3$O$_5$+0.5 H$_2$O: C, 66.09; H, 6.40; N, 8.89. Found: C, 65.95; H, 6.31; N, 8.74.

5.223 3-{4-[4-(4-Ethoxymethyl-Piperidin-1-ylmethyl)-Benzyloxy]-1-Oxo-1,3-Dihydro-Isoindol-2-yl}-Piperidine-2,6-Dione

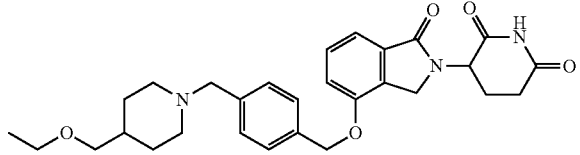 [SMILES: CCOCC1CCN(Cc2ccc(COc3cccc4c3CN(C3CCC(=O)NC3=O)C4=O)cc2)CC1]

Step 1: To a stirred solution of methyl 5-amino-4-(4-(4-(chloromethyl)benzyloxy)-1-oxoisoindolin-2-yl)-5-oxopentanoate (0.67 g, 1.54 mmol) in acetonitrile (15 ml) in an ice bath, was added 4-(ethoxymethyl)piperidine (0.44 g, 3.09 mmol). It was stirred at room temperature for half an hour, followed by addition of one equivalent of DIPEA (0.26 mL), and the solution was stirred at room temperature overnight. To the reaction mixture were added 0.17 g of 4-(ethoxymethyl)piperidine and 0.30 mL of DIPE. The mixture was heated at 70° C. for three hours and then cooled to room temperature. The solution was evaporated to an oil, which was purified on silica gel column (MeOH/CH$_2$Cl$_2$ gradient from 1% to 9% in 50 min) to give 4-carbamoyl-4-{4-[4-(4-ethoxymethyl-piperidin-1-ylmethyl)-benzyloxy]-1-oxo-1,3-dihydro-isoindol-2-yl}-butyric acid methyl ester as a foamy solid, which was used in the next step without further purification.

Step 2: To a stirred solution of methyl 5-amino-4-(4-(4-((4-(ethoxymethyl)piperidin-1-yl)methyl)benzyloxy)-1-oxoisoindolin-2-yl)-5-oxopentanoate (0.83 g, 1.54 mmol) in THF (10 ml) in an ice bath, was added potassium 2-methylpropan-2-olate (0.52 g, 6.18 mmol). The mixture was stirred for ten minutes and quenched with 1 N HCl (4 mL) to form clear solution then neutralized with saturated sodium bicarbonate (7 ml to pH=8). The resulting mixture was extracted with ethyl acetate (2×20 mL) and purified on silica gel column (MeOH/CH$_2$Cl$_2$ gradient from 1% to 9% in 50 min) to give 3-{4-[4-(4-ethoxymethyl-piperidin-1-ylmethyl)-benzyloxy]-1-oxo 1,3-dihydro-isoindol-2-yl}-piperidine-2,6-dione as a white solid (0.45 g, 58% yield); HPLC: Waters Symmetry C-18, 3.9×150 mm, 5 μm, 1 mL/min, 240 nm, gradient from 10/90 to 95/5 in 5 min, isocratic at 95/5 in 5 min (acetonitrile/0.1% H$_3$PO$_4$), 5.38 min (96.7%); mp: 168-170° C.; $^1$H NMR (DMSO-d$_6$) δ 1.08 (t, J=7.0 Hz, 3H, CH$_3$), 1.12-1.23 (m, 2H, CH$_2$), 1.40-1.54 (m, 1H, CHH), 1.55-1.67 (m, 2H, CH$_2$), 1.81-2.04 (m, 3H, CHH, CH$_2$), 2.36-2.48 (m, 1H, CHH), 2.53-2.64 (m, 1H, CHH), 2.72-2.82 (m, 2H, CH$_2$), 2.84-2.99 (m, 1H, CHH), 3.19 (d, J=6.2 Hz, 2H, CH$_2$), 3.34-3.48 (m, 4H, CH$_2$, CH$_2$), 4.19-4.47 (m, 2H, CH$_2$), 5.11 (dd, J=5.2, 13.3 Hz, 1H, NCH), 5.22 (s, 2H, CH$_2$), 7.26-7.37 (m, 4H, Ar), 7.39-7.54 (m, 3H, Ar), 10.97 (s, 1H, NH); $^{13}$C NMR (DMSO-d$_6$) δ 15.10, 22.36, 28.92, 31.20, 35.80, 45.10, 51.58, 52.93, 62.19, 65.44, 69.45, 74.83, 114.97, 115.23, 127.61, 128.80, 129.81, 129.95, 133.31, 135.07, 138.64, 153.53, 168.01, 170.98, 172.83; LCMS MH=506; Anal. Calcd for C$_{29}$H$_{35}$N$_3$O$_5$+0.5 H$_2$O: C, 67.68; H, 7.05; N, 8.17. Found: C, 67.42; H, 7.20; N, 8.05.

5.224 3-(1-Oxo-4-(4-((4-(Trifluoromethyl)Piperidin-1-yl)Methyl)Benzyloxy)Isoindolin-2-yl)Piperidine-2,6-Dione

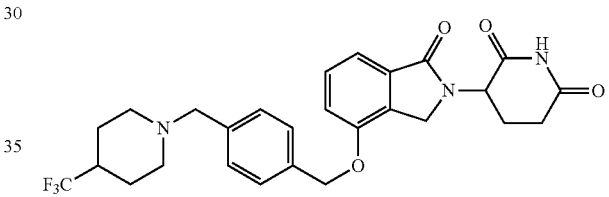

Step 1: tert-Butyl 5-amino-5-oxo-2-(1-oxo-4-(4-((4-(trifluoromethyl)piperidin-1-yl)methyl)benzyloxy)isoindolin-2-yl)pentanoate To a solution of tert-butyl 5-amino-2-(4-(4-(chloromethyl)benzyloxy)-1-oxoisoindolin-2-yl)-5-oxopentanoate (450 mg, 0.95 mmol) and N,N-diisopropylethylamine (0.42 mL, 2.38 mmol) in MeCN (9 mL), was added 4-(trifluoromethyl)piperidine hydrochloride (271 mg, 1.43 mmol). The mixture was stirred for 5 h at 60° C. The crude mixture was partitioned between EtOAc (150 mL) and 1N NaHCO$_3$ (30 mL). The basic aq layer was washed with additional EtOAc (~100 mL). The organic layers were combined, washed with brine, dried (Na$_2$SO$_4$), and concentrated in vacuo to give tert-butyl 5-amino-5-oxo-2-(1-oxo-4-(4-((4-(trifluoromethyl)piperidin-1-yl)methyl) benzyloxy)isoindolin-2-yl)pentanoate as an oil (570 mg). LC/MS M+H=590. The crude product was used in the next step without further purification.

Step 2: 3-(1-Oxo-4-(4-((4-(trifluoromethyl)piperidin-1-yl)methyl)benzyloxy) isoindolin-2-yl)piperidine-2,6-dione To a cooled solution of tert-butyl 5-amino-5-oxo-2-(1-oxo-4-(4-((4-(trifluoromethyl)piperidin-1-yl)methyl)benzyloxy) isoindolin-2-yl)pentanoate (561 mg, 0.95 mmol) in THF (10 mL) in an ice bath, was added KO$^t$Bu (128 mg, 1.14 mmol) as a solid in one portion. The ice bath was removed and the reaction mixture was stirred for ~2 h at room temperature. More KO$^t$Bu (28 mg) was added and the reaction mixture was stirred for ~2 h. The reaction mixture was cooled in an ice bath and quenched with acetic acid (0.163 mL, 2.85 mmol). The mixture was concentrated in vacuo and the resulting solid was partitioned between EtOAc (100 mL) and 1N NaHCO₃ (30 mL). The aq. layer was extracted with EtOAc (50 mL), and the combined organic layer was washed with brine, dried (Na₂SO₄), and concentrated in vacuo to give a white solid (~400 mg). The solid was triturated with Et₂O (40 mL) with the aid of sonication, collected by filtration, and washed with additional Et₂O. The solid was suction dried and a second trituration was carried out using water (120 mL). The remaining solid was suction dried and then dried in vacuum oven at 40° C. overnight to give 3-(1-oxo-4-(4-((4-(trifluoromethyl)piperidin-1-yl) methyl)benzyloxy)isoindolin-2-yl)piperidine-2,6-dione as a white solid (328 mg, 67% yield): HPLC: Waters Symmetry $C_{18}$, 5 μm, 3.9×150 mm, 1 ml/min, 240 nm, 20/80 CH₃CN/ 0.1% H₃PO₄, 6.16 min (96.5%); mp: 178-180° C.; ¹H NMR (DMSO-d₆) δ 1.34-1.55 (m, 2H, CHH, CHH), 1.66-1.82 (m, 2H, CHH, CHH), 1.87-2.05 (m, 3H, CHH, CHH, CHH), 2.14-2.35 (m, 1H, CHH), 2.35-2.48 (m, 1H, CHH), 2.52-2.65 (m, 1H, CHH), 2.78-3.00 (m, 3H, CHH, CHH, CHH), 3.48 (s, 2H, CH₂), 4.25 (d, J=17.6 Hz, 1H, CHH), 4.42 (d, J=17.4 Hz, 1H, CHH), 5.11 (dd, J=5.0, 13.3 Hz, 1H, CHH), 5.17-5.28 (m, 2H, CH₂), 7.21-7.39 (m, 4H, Ar), 7.39-7.55 (m, 3H, Ar), 10.97 (s, 1H, NH); ¹³C NMR (DMSO-d₆) δ 22.33, 24.19, 31.18, 38.35, 39.07, 45.06, 51.39, 51.55, 61.59, 69.39, 114.96, 115.20, 127.64, 127.82 (q, J=278 Hz, CF₃), 128.79, 129.80, 129.93, 133.30, 135.22, 138.11, 153.49, 167.99, 170.96, 172.81; Part of quartet (2 signals) arising from CF₃C are masked by DMSO peak around 8 40 ppm. LC/MS M+H=516; Anal Calcd for $C_{27}H_{28}F_3N_3O_4$+ 0.35 H2O: C, 62.15; H, 5.54; N, 8.05; F, 10.92. Found: C, 62.13; H, 5.48; N, 8.06; F, 9.84.

5.225 3-(4-(4-(((2R,6S)-2,6-Dimethylpiperazin-1-yl) Methyl)Benzyloxy)-1-Oxoisoindolin-2-yl)Piperidine-2,6-Dione

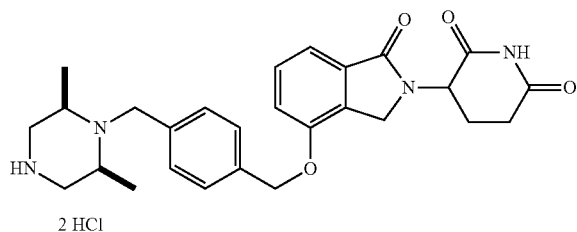

2 HCl

Step 1: To a solution of tert-butyl 5-amino-2-(4-(4-(chloromethyl)benzyloxy)-1-oxoisoindolin-2-yl)-5-oxopentanoate (400 mg, 0.846 mmol) in acetonitrile (10 ml) were added (3R,5S)-tert-butyl 3,5-dimethylpiperazine-1-carboxylate (236 mg, 1.099 mmol), N,N-Diisopropylethylamine (328 mg, 2.54 mmol) and sodium iodide (25 mg, 0.17 mmol). The formed mixture was heated at 70° C. for 2 days. The reaction mixture was concentrated, the residue was partitioned between ethyl acetate (50 ml) and aqueous saturated sodium bicarbonate (10 ml), the organic layer was washed with water, brine and dried over MgSO₄, and the solvent was evaporated under vacuum, the residue was purified by ISCO (40 g column, MeOH/CH₂Cl₂ gradient from 0% to 5% in 50 min) to give (3R,5S)-tert-butyl 4-(4-((2-(5-amino-1-tert-butoxy-1,5-dioxopentan-2-yl)-1-oxoisoindolin-4-yloxy) methyl)benzyl)-3,5-dimethylpiperazine-1-carboxylate (480 mg, 87% yield).

Step 2: To a mixture of (3R,5S)-tert-butyl 4-(4-((2-(5-amino-1-tert-butoxy-1,5-dioxopent-an-2-yl)-1-oxoisoindolin-4-yloxy)methyl)benzyl)-3,5-dimethylpiperazine-1-carboxylate (480 mg, 0.738 mmol) in THF was added potassium tert-butoxide (83 mg, 0.738 mmol) at 0° C. The mixture was stirred at 0° C. for 10 minutes, warmed up to room temperature and stirred for 4 hours. Additional potassium tert-butoxide (25 mg, 0.22 mmol) was added and the mixture was stirred for another 2 hours. The reaction was quenched with acetic acid (0.2 ml), THF was evaporated, and the residue was partitioned between ethyl acetate (100 ml) and aqueous saturated sodium bicarbonate (10 ml). The organic phase was washed with brine, dried over MgSO₄. The solvent was removed and the residue was purified by ISCO (40 g column, MeOH/CH₂Cl₂ gradient from 0% to 5% in 50 min) to give (3R,5S)-tert-butyl 4-(4-((2-(2,6-dioxopiperidin-3-yl)-1-oxoisoindolin-4-yloxy)meth-yl)benzyl)-3,5-dimethylpiperazine-1-carboxylate (120 mg, 28% yield); ¹H NMR (DMSO-d₆) δ 0.94 (d, J=6.0 Hz, 6H, CH₃, CH₃), 1.38 (s, 9H, CH₃, CH₃, CH₃), 1.84-2.11 (m, 1H, CHH), 2.36-2.49 (m, 3H, CHH, CH₂), 2.52-2.75 (m, 3H, CHH, CH₂), 2.81-3.06 (m, 1H, CHH), 3.62-3.80 (m, 4H, CH₂, CH, CH), 4.18-4.51 (m, 2H, CH₂), 5.06-5.16 (m, 1H, CH), 5.18-5.26 (m, 2H, CH₂), 7.29-7.52 (m, 7H, Ar), 10.84-11.10 (m, 1H, NH).

Step 3: To the mixture of (3R,5S)-tert-butyl 4-(4-((2-(2, 6-dioxopiperidin-3-yl)-1-oxoisoindolin-4-yloxy)methyl) benzyl)-3,5-dimethylpiperazine-1-carboxylate (120 mg, 0.208 mm-ol) in dichloromethane (40 mL) was added HCl solution in ether (2 N, 5 ml, 10 mmol), The mixture was stirred at room temperature for 2 days. The formed precipitate was separated by filtration to give 3-(4-(4-(((2R,6S)-2, 6-dimethylpiperazin-1-yl)methyl)-benzyloxy)-1-oxoisoindolin-2-yl)piperidine-2,6-dione as a white solid (80 mg, 75% yield); mp: 253-255° C.; ¹H NMR (DMSO-d₆) δ 1.16-1.40 (m, 6H, CH₃, CH₃), 1.97 (d, J=5.3 Hz, 1H, CHH), 2.24-2.43 (m, 1H, CHH), 2.58 (d, J=2.1 Hz, 1H, CHH), 2.71-3.06 (m, 3H, CH₂, CHH), 3.07-3.59 (m, 4H, CH₂, CH, CH), 4.04-4.54 (m, 4H, CH₂, CH₂), 5.02 (dd, J=5.1, 13.2 Hz, 1H, CH), 5.22 (s, 2H, CH₂), 7.21-7.34 (m, 2H, Ar), 7.38-7.56 (m, 5H, Ar); ¹³C NMR (DMSO-d₆) δ 15.82, 22.27, 31.03, 38.23, 45.25, 45.90, 50.32, 51.69, 68.96, 115.10, 115.39, 127.82, 129.70, 129.86, 129.97, 133.11, 136.86, 153.24, 168.25, 170.87, 172.94; LCMS MH-2HCl=477; HPLC: Waters Xterra C-18, 3.9×150 mm, 5 μm, 1 mL/min, 240 nm, Gradient (CH₃CN/0.1% HCOONH₄) 5/95 to 95/5 in 5 min, 95/5 10 min: $t_R$=4.21 (100%); Anal. Calcd for $C_{27}H_{34}N_4O_4Cl_2$+0.9 H₂O: C, 57.33; H, 6.38; N, 9.90; Found: C, 57.36; H, 6.36; N, 9.80.

5.226 3-(1-Oxo-4-(4-((3-Oxopiperazin-1-yl)Methyl) Benzyloxy)Isoindolin-2-yl)Piperidine-2,6-Dione

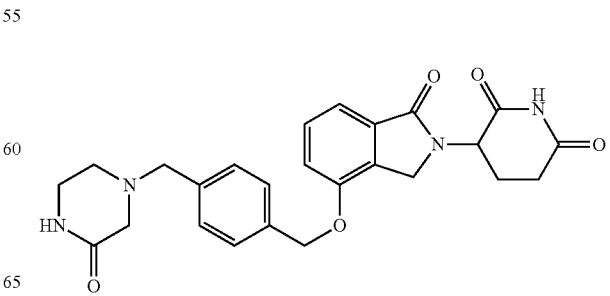

To a suspension of tert-butyl 5-amino-2-(4-(4-(chloromethyl)benzyloxy)-1-oxoisoindolin-2-yl)-5-oxopentanoate (450 mg, 0.951 mmol, preparation described herein) in MeCN (9 mL) was added piperazin-2-one (191 mg, 1.903 mmol) and N,N-diisopropylethylamine (0.249 mL, 1.427 mmol). The mixture was warmed up to 60° C. and stirred for ~18 h and then allowed to cool to room temperature. A solid formed upon cooling which was dispersed by addition of DMF (3 mL) and sonication. The mixture was cooled in ice bath and solid KO$^t$Bu (299 mg, 2.66 mmol) was added in one portion. Dry THF (2 mL) was added and the ice bath was removed. The mixture was stirred at room temperature overnight. The mixture was cooled to 0° C. in an ice bath and then quenched with acetic acid (254 μl, 4.44 mmol). The mixture was concentrated in vacuo and the oily residue was partitioned between EtOAc (200 mL) and 1N NaHCO$_3$ (40 mL). The product partitioned in both aqueous and organic layers. All layers were combined, acidified with HCl, and concentrated to give a solid. The solid was triturated with copious DMF, the mixture was filtered, and the undissolved solids were washed with additional DMF (total filtrate volume ~150 mL). The filtrate was concentrated to an oily residue which was redissolved in DMF/1 N HCl (6 mL/4 mL) and then purified by injection onto a C-18 preparatory HPLC column. The product was eluted with an acetonitrile/water gradient (0.1% formic acid in both mobile phases, 5% to 30% MeCN over 20 minutes) and fractions were collected by mass trigger. The desired fractions were combined and concentrated in vacuo to give 3-(1-oxo-4-(4-((3-oxopiperazin-1-yl)methyl)benzyloxy)isoindolin-2-yl)piperidine-2,6-dione as an off-white solid (177 mg, 43% yield): HPLC: Waters Symmetry C$_{18}$, 5 μm, 3.9×150 mm, 1 ml/min, 240 nm, 15/85 CH$_3$CN/0.1% H$_3$PO$_4$, 4.58 min (98.3%); mp: 245-247° C.; $^1$H NMR (DMSO-d$_6$) δ 1.91-2.04 (m, 1H, CHH), 2.35-2.48 (m, 1H, CHH), 2.51-2.63 (m, 3H, CHH, CH$_2$), 2.80-2.99 (m, 3H, CHH, CH$_2$), 3.06-3.23 (m, 2H, CH$_2$), 3.54 (s, 2H, CH$_2$), 4.25 (d, J=17.6 Hz, 1H, CHH), 4.42 (d, J=17.6 Hz, 1H, CHH), 5.11 (dd, J=5.1, 13.2 Hz, 1H, CH), 5.24 (s, 2H, CH$_2$), 7.21-7.39 (m, 4H, Ar), 7.41-7.56 (m, 3H, Ar), 7.74 (s, 1H, NH), 10.96 (br. s., 1H, NH); $^{13}$C NMR (DMSO-d$_6$) δ 22.33, 31.16, 45.07, 48.35, 51.55, 56.62, 60.40, 69.38, 114.97, 115.22, 127.70, 128.91, 129.80, 129.95, 133.30, 135.49, 137.28, 153.48, 167.56, 167.99, 170.96, 172.81; LC/MS M+H=463; Anal Calcd for C$_{25}$H$_{26}$N$_4$O$_5$: C, 64.92; H, 5.67; N, 12.11. Found: C, 61.40; H, 5.38; N, 11.45.

5.227 3-{4-[4-(4-Dimethylamino-Piperidin-1-ylmethyl)-Benzyloxy]-1-Oxo-1,3-Dihydro-Isoindol-2-yl}-Piperidine-2,6-Dione

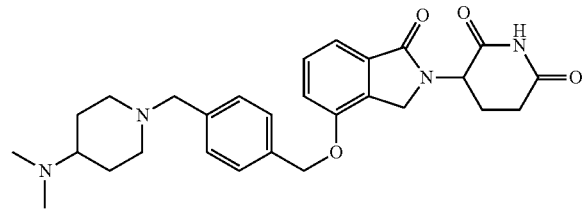 [SMILES: CN(C)C1CCN(Cc2ccc(COc3cccc4c3CN(C3CCC(=O)NC3=O)C4=O)cc2)CC1]

Step 1: Preparation of 4-Carbamoyl-4-{4-[4-(4-isopropyl-piperazin-1-ylmethyl)-benzyloxy]-1-oxo-1,3-dihydro-isoindol-2-yl}-butyric acid methyl ester To a solution of methyl 5-amino-4-(4-(4-(bromomethyl)benzyloxy)-1-oxoisoindolin-2-yl)-5-oxopentanoate (0.674 g, 1.418 mmol) in acetonitrile (15 ml) at room temperature was added N,N-dimethylpiperidin-4-amine (0.545 g, 4.25 mmol). The mixture was stirred for ten minutes and was evaporated to give an oil. It was stirred in methylene chloride (30 ml) and water (10 ml). The methylene chloride phase was separated and evaporated to give 4-Carbamoyl-4-{4-[4-(4-isopropyl-piperazin-1-ylmethyl)-benzyloxy]-1-oxo-1,3-dihydro-isoindol-2-yl}-butyric acid methyl ester as an oil (0.76 g, 103% crude yield). It was used in the next step without further purification.

Step 2: Preparation of 3-{4-[4-(4-Dimethylamino-piperidin-1-ylmethyl)-benzyloxy]-1-oxo-1,3-dihydro-isoindol-2-yl}-piperidine-2,6-dione To a stirred solution of methyl 5-amino-4-(4-(4-((4-(dimethylamino)piperidin-1-yl)methyl)benzyloxy)-1-oxoisoindolin-2-yl)-5-oxopentanoate (0.76 g, 1.454 mmol) in THF (20 ml) in an ice-bath was added potassium 2-methylpropan-2-olate (0.32 g, 2.90 mmol). The mixture was stirred for ten minutes and 1 N HCl (2 ml to pH=3) was added, then neutralized by saturated sodium bicarbonate (4 ml to pH=7). The mixture was stirred with ethyl acetate (50 ml). The organic phase was separated and washed with brine (20 ml) to and concentrated to give an off-white solid. It was stirred in acetonitrile (4 ml) at 70° C. for half hour and filtered to give 3-{4-[4-(4-Dimethyl-amino-piperidin-1-ylmethyl)-benzyloxy]-1-oxo-1,3-dihydro-isoindol-2-yl}-piperidine-2,6-dione as a white solid (0.18 g, 25% yield); mp 209-211° C.; $^1$H NMR (DMSO-d$_6$) δ 1.35 (qd, J=3.8, 11.8 Hz, 2H, CH$_2$), 1.61-1.76 (m, 2H, CH$_2$), 1.82-2.08 (m, 4H, CH$_2$, CHH, CH), 2.14 (s, 6H, $_2$CH$_3$), 2.34-2.47 (m, 1H, CHH), 2.53-2.64 (m, 1H, CHH), 2.74-3.01 (m, 3H, CH$_2$, CHH), 3.43 (s, 2H, CH$_2$), 4.19-4.49 (m, 2H, CH$_2$), 5.11 (dd, J=5.1, 13.2 Hz, 1H, NCH), 5.22 (s, 2H, CH$_2$), 7.27-7.37 (m, 4H, Ar), 7.39-7.54 (m, 3H, Ar), 10.97 (s, 1H, NH); $^{13}$C NMR (DMSO-d$_6$) δ 22.36, 28.05, 31.21, 41.49, 45.09, 51.58, 52.41, 61.61, 61.80, 69.45, 114.97, 115.21, 127.62, 128.77, 129.81, 129.95, 133.31, 135.09, 138.58, 153.51, 168.01, 170.96, 172.82. LC/MS (M+1)$^+$=491; Anal Calcd for C$_{28}$H$_{34}$N$_4$O$_4$+0.2H$_2$O: C, 68.05; H, 7.02; N, 11.34. Found: C, 67.88; H, 6.88; N, 11.19.

5.228 3-{4-[4-(4-Isopropyl-Piperazin-1-ylmethyl)-Benzyloxy]-1-Oxo-1,3-Dihydro-Isoindol-2-yl}-Piperidine-2,6-Dione

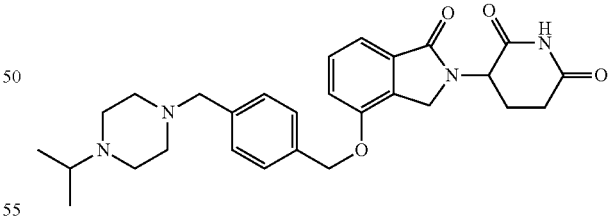

To the acetonitrile solution of the mixture (~1:1) of 3-(4-(4-(bromomethyl)benzyloxy)-1-oxoisoindolin-2-yl)piperidine-2,6-dione (0.25 g, 0.564 mmol) and 3-(4-(4-(chloromethyl)benzyloxy)-1-oxoisoindolin-2-yl)piperidine-2,6-dione (0.225 g, 0.564 mmol) was added N-ethyl-N-isopropylpropan-2-amine (0.292 g, 2.256 mmol) followed by 1-isopropylpiperazine (0.174 g, 1.354 mmol) at room temperature. The cloudy mixture was stirred at room temperature overnight. The white suspension was evaporated under vacuum to get rid of acetonitrile. The resulting white solid was stirred in water (40 ml) and methylene chloride (2×40 ml). The combined methylene chloride phases were back washed with water (50 ml) and then evaporated in vacuo to give a white oily solid, which was stirred in diethyl ether (25 ml) overnight. The suspension was filtered to give an off-white solid, which was mixed with acetonitrile (4 ml) and stirred in a 50° C. oil bath for half hour then the suspension was filtered to give 3-{4-[4-(4-Isopropyl-piperazin-1-ylmethyl)-benzyloxy]-1-oxo-1,3-dihydro-isoindol-2-yl}-piperidine-2,6-dione as a white solid (0.187 g, 34% yield); HPLC: Waters Symmetry C-18, 3.9×150 mm, 5 μm, 1 mL/min, 240 nm, gradient from 10/90 to 95/5 in 5 min, isocratic at 95/5 in 5 min ($CH_3CN/0.1\%$ $H_3PO_4$), 3.94 min (95.8%); mp, 193-195° C.; $^1$H NMR (DMSO-$d_6$) δ 0.94 (d, J=6.4 Hz, 6H, 2$CH_3$), 1.91-2.04 (m, 1H, CHH), 2.21-2.48 (m, 9H, 4$CH_2$, CH), 2.53-2.67 (m, 2H, CHH, CHH), 2.82-2.99 (m, 1H, CHH), 3.44 (s, 2H, $CH_2$), 4.20-4.47 (m, 2H, $CH_2$), 5.11 (dd, J=5.2, 13.1 Hz, 1H, NCH), 5.22 (s, 2H, $CH_2$), 7.26-7.36 (m, 4H, Ar), 7.38-7.54 (m, 3H, Ar), 10.97 (s, 1H, NH); $^{13}$C NMR (DMSO-$d_6$) δ 18.22, 22.36, 31.21, 45.09, 47.95, 51.58, 53.04, 53.55, 61.81, 69.44, 114.97, 115.23, 127.62, 128.86, 129.81, 129.95, 133.31, 135.13, 138.24, 153.51, 168.01, 170.98, 172.83. Anal Calcd for $C_{28}H_{34}N_4O_4+0.1H_2O$: C, 68.30; H, 7.00; N, 11.38. Found: C, 68.21; H, 6.61; N, 11.19.

5.229 3-{1-Oxo-4-[4-(4-Phenyl-Piperazin-1-ylmethyl)-Benzyloxy]-1,3-Dihydro-Isoindol-2-yl}-Piperidine-2,6-Dione

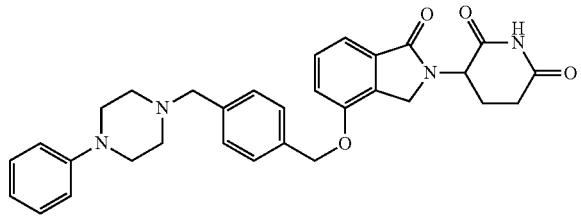

To the $CH_3CN$ solution (15 ml) of 3-(4-(4-(bromomethyl)benzyloxy)-1-oxoisoindolin-2-yl)piperidine-2,6-dione (0.50 g, 1.13 mmol) and was added N-ethyl-N-isopropylpropan-2-amine (0.373 ml, 2.256 mmol) followed by 1-phenylpiperazine (0.257 ml, 1.692 mmol) at room temperature. The cloudy mixture was stirred at room temperature overnight. Solvent was evaporated and the resulting white solid was stirred in water (50 ml) and extracted with methylene chloride (2×80 ml). The combined methylene chloride phases were back washed with water (50 ml), brine (30 ml) and evaporated to a white solid which was stirred in acetonitrile (8 ml) at 50° C. for one hour then filtered, dried in vacuum oven to give 3-{1-Oxo-4-[4-(4-phenyl-piperazin-1-ylmethyl)-benzyloxy]-1,3-dihydro-isoindol-2-yl}-piperidine-2,6-dione as a white solid (0.316 g, 53% yield); mp, 195-197° C. HPLC: Waters Symmetry C-18, 3.9×150 mm, 5 μm, 1 mL/min, 240 nm, gradient from 10/90 to 95/5 in 5 min, isocratic at 95/5 in 5 min ($CH_3CN/0.1\%$ $H_3PO_4$), 4.70 min (95.43%). $^1$H NMR (DMSO-$d_6$) δ 1.92-2.06 (m, 1H, CHH), 2.36-2.47 (m, 1H, CHH), 2.53-2.65 (m, 2H, CHH, CHH), 2.83-2.99 (m, 1H, CHH), 3.12 (t, J=5.1 Hz, 4H, $CH_2$, $CH_2$), 3.50-3.62 (m, 2H, $CH_2$), 4.20-4.48 (m, 2H, $CH_2$), 5.11 (dd, J=5.1, 13.2 Hz, 1H, NCH), 5.20-5.30 (m, 2H, $CH_2$), 6.76 (t, J=7.3 Hz, 1H, Ar), 6.91 (d, J=7.9 Hz, 2H, Ar), 7.15-7.25 (m, 2H, Ar), 7.28-7.41 (m, 4H, Ar), 7.42-7.55 (m, 3H, Ar), 10.98 (s, 1H, NH); $^{13}$C NMR (DMSO-$d_6$) δ 22.36, 31.21, 45.09, 48.18, 51.58, 52.52, 61.71, 69.41, 114.97, 115.24, 115.35, 118.76, 127.68, 128.86, 129.01, 129.82, 129.95, 133.32, 135.30, 137.93, 150.98, 153.50, 168.01, 170.98, 172.83. LC/MS (M+1)$^+$=525; Anal Calcd for $C_{31}H_{32}N_4O_4$: C, 70.97; H, 6.15; N, 10.68. Found: C, 70.69; H, 6.01; N, 10.49.

5.230 3-{4-[4-(4-Cyclopropanesulfonyl-Piperazin-1-ylmethyl)-Benzyloxy]-1-Oxo-1,3-Dihydro-Isoindol-2-yl}-Piperidine-2,6-Dione

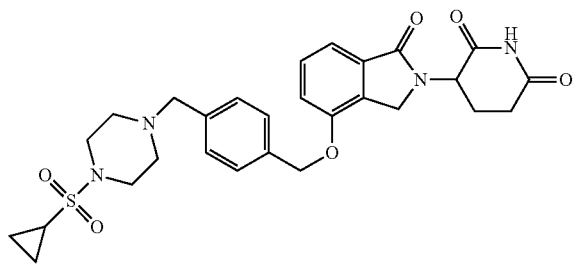 [SMILES: O=C1CCC(N2Cc3c(OCc4ccc(CN5CCN(S(=O)(=O)C6CC6)CC5)cc4)cccc3C2=O)C(=O)N1]

Step 1: 4-Cyclopropanesulfonyl-piperazine-1-carboxylic acid tert-butyl ester To the stirred solution of tert-butyl piperazine-1-carboxylate (1.3 g, 6.98 mmol) in DCM anhydrous (10 mL) was added TEA (1.167 ml, 8.38 mmol) and cyclopropanesulfonyl chloride (1.079 g, 7.68 mmol) at room temperature. White solid was formed and the mixture wad stirred for 2 hrs. The reaction mixture was diluted by DCM (40 mL) and washed with water (25 mL). Organic layer was dried by $MgSO_4$ and concentrated to give 4-Cyclopropanesulfonyl-piperazine-1-carboxylic acid tert-butyl ester as a white solid (2.3 g, 113% crude yield). The compound was used in the next step without further purification. LCMS MH=291.

Step 2: 1-(cyclopropylsulfonyl)piperazine hydrochloride To the stirred solution of tert-butyl 4-(cyclopropylsulfonyl)piperazine-1-carboxylate (2.3 g, 7.92 mmol) in DCM (Volume: 10 ml) at room temperature was added HCl in ether (11.88 ml, 23.76 mmol). The reaction mixture was stirred at room temperature for 22 hrs and solid was formed during the reaction. The suspension was added by diethyl ether (20 mL) and stirred for 10 mins before it was filtered. The white solid was washed with diethyl ether (2×15 mL) and dried under suction to give 1-(cyclopropylsulfonyl)piperazine hydrochloride as a solid (1.51 g, 84% yield); LCMS MH=191; $^1$H NMR (DMSO-$d_6$) δ 0.85-1.09 (m, 4H, $CH_2$, $CH_2$), 2.63-2.81 (m, 1H, CH), 3.06-3.23 (m, 4H, $CH_2$, $CH_2$), 3.33-3.57 (m, 4H, $CH_2$, $CH_2$), 9.54 (br. s., 2H, $NH_2Cl$).

Step 3: 3-{4-[4-(4-Cyclopropanesulfonyl-piperazin-1-yl-methyl)-benzyloxy]-1-oxo-1,3-dihydro-isoindol-2-yl}-piperidine-2,6-dione To the stirred suspension of 3-(4-(4-(bromomethyl)benzyloxy)-1-oxoisoindolin-2-yl)piperidine-2,6-dione (300 mg, 0.677 mmol) and 1-(cyclopropylsulfonyl)piperazine hydrochloride (230 mg, 1.015 mmol) in Acetonitrile (Volume: 10 ml) at room temperature was added DIPEA (0.355 ml, 2.030 mmol). The suspension turned to be clear and the resulting mixture was stirred at room temperature for further reaction. The reaction mixture was stirred at room temperature for 20 hrs before it was added by EtOAc (50 mL) and $NaHCO_3$ (aq, sat, 20 mL). The mixture was extracted and the organic layer was dried by $MgSO_4$. The organic layer was concentrated and the residue was purified by silica gel chromatography to give 3-{4-[4-

(4-Cyclopropanesulfonyl-piperazin-1-ylmethyl)-benzyloxy]-1-oxo-1,3-dihydro-isoindol-2-yl}-piperidine-2,6-dione as a white solid (227 mg, 61% yield); HPLC: Waters Symmetry C-18, 3.9×150 mm, 5 μm, 1 mL/min, 240 nm, 20/80, $CH_3CN/0.1\% H_3PO_4$), 4.09 min (99.9%); m.p. 145-147° C.; $^1H$ NMR (DMSO-$d_6$) δ 0.86-1.05 (m, 4H, $CH_2$, $CH_2$), 1.91-2.04 (m, 1H, CHH), 2.34-2.47 (m, 5H, $CH_2$, $CH_2$, CHH), 2.53-2.66 (m, 2H, CHH, CH), 2.81-3.01 (m, 1H, CHH), 3.11-3.24 (m, 4H, $CH_2$, $CH_2$), 3.52 (s, 2H, $CH_2$), 4.25 (d, J=17.6 Hz, 1H, CHH), 4.42 (d, J=17.6 Hz, 1H, CHH), 5.11 (dd, J=5.1, 13.2 Hz, 1H, CHH), 5.23 (s, 2H, $CH_2$), 7.27-7.38 (m, 4H, Ar), 7.40-7.56 (m, 3H, Ar), 10.97 (s, 1H, NH); $^{13}C$ NMR (DMSO-$d_6$) δ 3.75, 22.34, 24.46, 31.16, 45.06, 45.80, 51.55, 51.85, 61.20, 69.35, 114.94, 115.22, 127.67, 128.90, 129.80, 129.93, 133.28, 135.37, 137.69, 153.46, 167.97, 170.96, 172.81; LCMS MH=553; Anal. Calcd for $C_{28}H_{32}N_4O_6S+0.5H_2O+0.15CH_2Cl_2$: C, 58.86; H, 5.84; N, 9.75; Found: C, 58.53; H, 5.47; N, 9.57.

5.231 3-{4-[4-(4-Cyclohexanesulfonyl-Piperazin-1-ylmethyl)-Benzyloxy]-1-Oxo-1,3-Dihydro-Isoindol-2-yl}-Piperidine-2,6-Dione

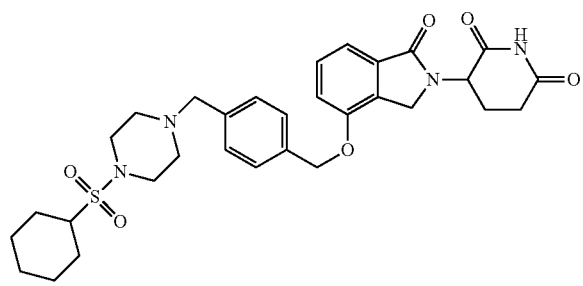 [SMILES: O=C1CCC(N2Cc3c(OCc4ccc(CN5CCN(S(=O)(=O)C6CCCCC6)CC5)cc4)cccc3C2=O)C(=O)N1]

Step 1: 4-Cyclohexanesulfonyl-piperazine-1-carboxylic acid tert-butyl ester To the stirred solution of tert-butyl piperazine-1-carboxylate (450 mg, 2.416 mmol) in DCM anhydrous (10 mL) was added cyclohexanesulfonyl chloride (485 mg, 2.66 mmol) and triethylamine (0.370 ml, 2.66 mmol). The resulting solution was stirred at room temperature for 20 mins and the reaction was completed. The reaction mixture was diluted by DCM (40 mL) and the mixture was washed by water (20 mL) and brine (20 mL). The mixture was extracted and organic layer was dried by $MgSO_4$ and concentrated under vacuo to give 4-Cyclohexanesulfonyl-piperazine-1-carboxylic acid tert-butyl ester as a off white solid (750 mg, 93% crude yield). The compound was put to next step without further purification; LCMS MH (without boc group)=233.

Step 2: 1-Cyclohexanesulfonyl-piperazine hydrochloride To the solution of tert-butyl 4-(cyclohexylsulfonyl)piperazine-1-carboxylate (750 mg, 2.256 mmol) in DCM (5 mL) was added HCl (2M in ether, 5 mL, 10.00 mmol) and diethyl ether (5.0 mL). The resulting solution was stirred at room temperature for 4 days and was concentrated under vacuo. The residue was added by HCl (2M in ether, 15 mL) and the resulting suspension was stirred at room temperature over night and the reaction was completed. The reaction mixture was filtered and the solid was washed with ether (2×15 mL) to give 1-Cyclohexanesulfonyl-piperazine hydrochloride as an off white solid (450 mg, 74% yield). and HNMR were tested for the compound. $^1H$ NMR (DMSO-$d_6$) δ 1.03-1.45 (m, 5H, $CH_2$, $CH_2$, CH), 1.54-1.69 (m, 1H, CH), 1.70-1.84 (m, 2H, $CH_2$), 1.90-2.05 (m, 2H, $CH_2$), 3.03-3.16 (m, 4H, $CH_2$, $CH_2$), 3.17-3.28 (m, 1H, CHH), 3.41-3.57 (m, 4H, $CH_2$, $CH_2$), 9.42 (br. s., 2H, $NH_2Cl$); LCMS MH=233.

Step 3: 3-{4-[4-(4-Cyclohexanesulfonyl-piperazin-1-ylmethyl)-benzyloxy]-1-oxo-1,3-dihydro-isoindol-2-yl}-piperidine-2,6-dione To the stirred suspension of 1-(cyclohexylsulfonyl)piperazine hydrochloride (273 mg, 1.01 mmol) in Acetonitrile (8 mL) at room temperature was added DIPEA (0.36 ml, 2.03 mmol). The suspension became clear solution immediately. And to the clear solution was added 3-(4-(4-(bromomethyl)benzyloxy)-1-oxoisoindolin-2-yl)piperidine-2,6-dione (300 mg, 0.68 mmol). The resulting mixture was stirred at room temperature for 20 hrs. The reaction mixture was added by EtOAc (50 mL) and $NaHCO_3$ (sat. aq. 20 mL). The mixture was extracted and the organic layer was dried by $MgSO_4$. The organic layer was concentrated and the residue was purified by ISCO to gave 3-{4-[4-(4-Cyclohexanesulfonyl-piperazin-1-ylmethyl)-benzyloxy]-1-oxo-1,3-dihydro-isoindol-2-yl}-piperidine-2,6-dione as a white solid (150 mg, 37% yield); HPLC: Waters Symmetry C-18, 3.9×150 mm, 5 μm, 1 mL/min, 240 nm, 25/75, $CH_3CN/0.1\%$ $H_3PO_4$), 5.03 min (99.9%); mp: 245-247° C.; $^1H$ NMR (DMSO-$d_6$) δ 1.03-1.21 (m, 1H, CHH), 1.21-1.45 (m, 4H, $CH_2$, $CH_2$), 1.59 (br. s., 1H, CHH), 1.78 (br. s., 2H, $CH_2$), 1.97 (d, J=7.6 Hz, 3H, CHH, $CH_2$), 2.32-2.47 (m, 5H, CHH, $CH_2$, $CH_2$), 2.53-2.65 (m, 1H, CHH), 2.82-3.00 (m, 1H, CHH), 3.09 (t, J=11.4 Hz, 1H, CH), 3.17-3.28 (m, 4H, $CH_2$, $CH_2$), 3.51 (s, 2H, $CH_2$), 4.18-4.32 (m, J=17.6 Hz, 1H, CHH), 4.42 (d, J=17.6 Hz, 1H, CHH), 5.11 (dd, J=5.1, 13.2 Hz, 1H, CHH), 5.23 (s, 2H, $CH_2$), 7.33 (d, J=7.6 Hz, 4H, Ar), 7.40-7.56 (m, 3H, Ar), 10.97 (s, 1H, NH); $^{13}C$ NMR (DMSO-$d_6$) δ 22.34, 24.43, 24.75, 26.18, 31.16, 45.06, 45.52, 51.55, 52.54, 59.29, 61.31, 69.35, 114.96, 115.22, 127.64, 128.92, 129.80, 129.93, 133.28, 135.35, 137.64, 153.48, 167.97, 170.96, 172.81; LCMS MH=595; Anal. Calcd for $C_{31}H_{38}N_4O_6S$: C, 62.61; H, 6.44; N, 9.42; Found: C, 62.63; H, 6.21; N, 9.56.

5.232 3-(4-((4-((4-(Methylsulfonyl)Piperidin-1-yl)Methyl)Benzyl)Oxy)-1-Oxoisoindolin-2-yl)Piperidine-2,6-Dione

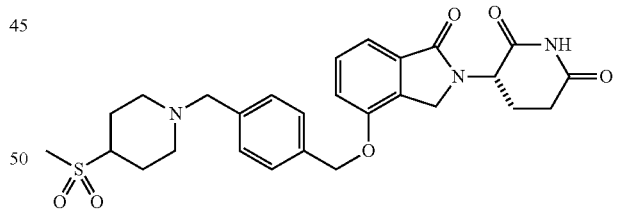

To a clear solution of 3-(4-(4-(bromomethyl)benzyloxy)-1-oxoisoindolin-2-yl)piperidine-2,6-dione (200 mg, 0.451 mmol) in ACETONITRILE (5 mL, 96 mmol), was added 4-(methylsulfonyl)piperidine (110 mg, 0.677 mmol) and the resulting slurry was stirred at room temperature overnight. The reaction mixture was diluted with EtOAc (10 mL), stirred for 5 min, then filtered. The solid was washed with EtOAc (2 mL) and water (2 mL) and dried further in vacuum oven at 50° C. to gave 3-(4-((4-((4-(methylsulfonyl)piperidin-1-yl)methyl)benzyl)oxy)-1-oxoisoindolin-2-yl)piperidine-2,6-dione as a white solid (140 mg, 59% yield): HPLC: Waters Symmetry $C_{18}$, 5 μm, 3.9×150 mm, 1 ml/min, 240 nm, 17/83 $CH_3CN/0.1\% H_3PO_4$, 3.92 min (98.2%); mp: 1.73-175° C.; $^1H$ NMR (DMSO-$d_6$) δ 1.47-1.69 (m, 2H, CHH, CHH), 1.84-2.07 (m, 5H, CHH, CHH, CHH, CHH, CHH), 2.35-2.48 (m, 1H, CHH), 2.53-2.63 (m, 1H, CHH), 2.83-2.97 (m, 6H, CHH, CHH, CHH, CH$_3$), 2.98-3.11 (m, 1H, CH), 3.49 (s, 2H, CH$_2$), 4.25 (d, J=17.4 Hz, 1H, CHH), 4.42 (d, J=17.6 Hz, 1H, CHH), 5.11 (dd, J=5.0, 13.1 Hz, 1H, CH), 5.23 (s, 2H, CH$_2$), 7.33 (d, J=7.2 Hz, 4H, Ar), 7.41-7.55 (m, 3H, Ar), 10.97 (s, 1H, NH); $^{13}$C NMR (DMSO-d$_6$) δ 22.26, 24.34, 31.09, 37.25, 44.99, 51.38, 51.48, 58.64, 61.29, 69.31, 114.90, 115.15, 127.57, 128.71, 129.73, 129.86, 133.23, 135.17, 138.03, 153.41, 167.90, 170.89, 172.74; LCMS: MH=526; Anal Calcd for C$_{27}$H$_{31}$N$_3$O$_6$S+0.4 H$_2$O: C, 60.86; H, 6.02; N, 7.89; S, 6.02; Found: C, 60.79; H, 5.77; N, 7.78; S, 5.82.

5.233 3-{4-[4-(4-Cyclohexanecarbonyl-Piperazin-1-ylmethyl)-Benzyloxy]-1-Oxo-1,3-Dihydro-Isoindol-2-yl}-Piperidine-2,6-Dione

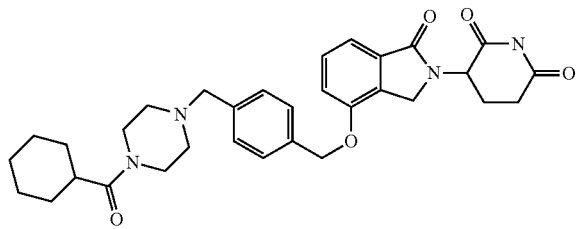 [SMILES: O=C1CCC(N2Cc3c(OCc4ccc(CN5CCN(C(=O)C6CCCCC6)CC5)cc4)cccc3C2=O)C(=O)N1]

Step 1: 4-Cyclohexanecarbonyl-piperazine-1-carboxylic acid tert-butyl ester To the stirred solution of tert-butyl piperazine-1-carboxylate (1.207 g, 6.48 mmol) in DCM (Volume: 15 ml) was added cyclohexanecarbonyl chloride (1 g, 6.82 mmol) and DIPEA (1.187 ml, 6.82 mmol). The resulting solution was stirred at room temperature for 1.5 hrs before it was diluted by DCM (20 mL). The mixture was washed with water (20 mL) and brine (20 mL) respectively. Organic layer was dried by MgSO$_4$ and concentrated under vacuo to give 4-Cyclohexanecarbonyl-piperazine-1-carboxylic acid tert-butyl ester as a white solid (1.92 g, 95% crude yield); LCMS MH=296.

Step 2: Cyclohexyl(piperazin-1-yl)methanone hydrochloride The suspension of tert-butyl 4-(cyclohexanecarbonyl) piperazine-1-carboxylate (1.92 g, 6.48 mmol) in HCl (2M in ether, 25 mL) was stirred at room temperature over weekend and filtered. The white solid was washed with diethyl ether (15 mL×2) and dried under suction to give cyclohexyl (piperazin-1-yl)methanone hydrochloride (1.5 g, 99% crude yield). $^1$H NMR (DMSO-d$_6$) δ 0.99-1.46 (m, 5H, CH$_2$, CH$_2$, CHH), 1.52-1.82 (m, 5H, CH$_2$, CH$_2$, CHH), 2.54-2.68 (m, 1H, CHH), 2.85-3.19 (m, 4H, CH$_2$, CH$_2$), 3.53-3.94 (m, 4H, CH$_2$, CH$_2$), 9.52 (br. s., 2H, NHHCl); LCMS MH=197.

Step 3: 3-{4-[4-(4-Cyclohexanecarbonyl-piperazin-1-ylmethyl)-benzyloxy]-1-oxo-1,3-dihydro-isoindol-2-yl}-piperidine-2,6-dione To the stirred mixture of cyclohexyl(piperazin-1-yl)methanone hydrochloride (239 mg, 1.03 mmol) in Acetonitrile (10 mL) was added DIPEA (0.345 ml, 1.97 mmol) followed by the addition of 3-(4-(4-(bromomethyl) benzyloxy)-1-oxoisoindolin-2-yl)piperidine-2,6-dione (350 mg, 0.79 mmol) and stirred at room temperature overnight. The reaction mixture was diluted by EtOAc (70 mL) and washed with NaHCO$_3$ (aq, sat. 25 mL) and brine (15 mL). Organic layer was dried by MgSO$_4$ and filtered. The filtrate was concentrated under vacuo and the residue was purified by ISCO chromatography to give 3-{4-[4-(4-Cyclohexanecarbonyl-piperazin-1-ylmethyl)-benzyloxy]-1-oxo-1,3-dihydro-isoindol-2-yl}-piperidine-2,6-dione as a white solid (271 mg, 61% yield); HPLC: Waters Symmetry C-18, 3.9×150 mm, 5 μm, 1 mL/min, 240 nm, 25/75, (CH$_3$CN/0.1% H$_3$PO$_4$), 3.18 min (98.9%); mp: 215-217° C.; $^1$H NMR (DMSO-d$_6$) δ 1.05-1.41 (m, 5H, CH$_2$, CH$_2$, CHH), 1.52-1.76 (m, 5H, CH$_2$, CH$_2$, CHH), 1.91-2.05 (m, 1H, CHH), 2.21-2.40 (m, 5H, CHH, CH$_2$, CH$_2$), 2.60 (br. s., 2H, CHH, CHH), 2.82-3.01 (m, 1H, CHH), 3.37-3.54 (m, 6H, CH$_2$, CH$_2$, CH$_2$), 4.26 (d, J=17.4 Hz, 1H, CHH), 4.42 (d, J=17.6 Hz, 1H, CHH), 5.11 (dd, J=5.1, 13.2 Hz, 1H, CHH), 5.23 (s, 2H, CH$_2$), 7.33 (d, J=7.4 Hz, 4H, Ar), 7.38-7.55 (m, 3H, Ar), 10.97 (s, 1H, NH); $^{13}$C NMR (DMSO-d$_6$) δ 22.34, 25.10, 25.52, 29.08, 31.18, 44.74, 45.06, 51.55, 52.36, 53.18, 61.50, 69.36, 114.94, 115.20, 127.63, 128.97, 129.78, 129.93, 133.28, 135.31, 137.70, 153.46, 167.97, 170.96, 172.81, 173.22; LCMS MH=559; Anal. Calcd for C$_{32}$H$_{38}$N$_4$O$_5$+0.2H$_2$O: C, 68.36; H, 6.88; N, 9.96; Found: C, 68.39; H, 6.75; N, 9.89.

5.234 3-{4-[4-(4-Benzoyl-Piperazin-1-ylmethyl)-Benzyloxy]-1-Oxo-1,3-Dihydro-Isoindol-2-yl}-Piperidine-2,6-Dione

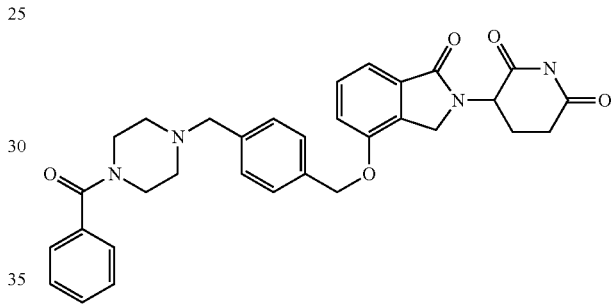

To a stirred solution of 3-(4-(4-(bromomethyl)benzyloxy)-1-oxoisoindolin-2-yl)piperidine-2,6-dione (0.422 g, 0.952 mmol) in acetonitrile (10 ml) at room temperature was added phenyl(piperazin-1-yl)methanone hydrochloride (0.324 g, 1.428 mmol) and N-ethyl-N-isopropylpropan-2-amine (0.472 ml, 2.86 mmol). The mixture was stirred at room temperature overnight. Solvent was evaporated and the resulting solid was stirred in water (30 ml) and methylene chloride (50 ml). The org phase was washed with saturated sodium bicarbonate (2×20 ml), brine (20 ml), dried and concentrated to a light yellow foamy solid (0.55 g) and stirred in diethyl ether (15 ml) at room temperature overnight. The ether suspension was filtered and stirred in acetonitrile (8 ml) at 55° C. for one hour then cooled and filtered to give 3-{4-[4-(4-Benzoyl-piperazin-1-ylmethyl)-benzyloxy]-1-oxo-1,3-dihydro-isoindol-2-yl}-piperidine-2,6-dione as a white solid (0.258 g, 49% yield); mp, 194-196° C. HPLC: Waters Symmetry C-18, 3.9×150 mm, 5 μm, 1 mL/min, 240 nm, gradient from 10/90 to 95/5 in 5 min, isocratic at 95/5 in 5 min (CH$_3$CN/0.1% H$_3$PO$_4$), 4.67 min (95.3%). $^1$H NMR (DMSO-d$_6$) δ 1.90-2.05 (m, 1H, CHH), 2.23-2.48 (m, 5H, $_2$CH$_2$, CHH), 2.57 (d, J=14.9 Hz, 1H, CHH), 2.81-3.01 (m, 1H, CHH), 3.18-3.44 (m, 3H, CH$_2$, CH), 3.55-3.77 (m, 1H, CH), 4.18-4.48 (m, 2H, CH$_2$), 5.11 (dd, J=5.2, 13.3 Hz, 1H, NCH), 5.17-5.28 (m, 2H, CH$_2$), 7.25-7.54 (m, 12H, Ar), 10.97 (s, 1H, NH). $^{13}$C NMR (DMSO-d$_6$) δ 22.36, 31.20, 45.09, 41.53, 47.14, 51.58, 52.58, 61.51, 69.38, 114.97, 115.23, 126.85, 127.68, 127.90, 128.38, 128.98, 129.44, 129.81, 129.94, 133.31, 135.36, 135.89, 137.68, 153.50, 167.99, 168.87, 170.87, 170.98, 172.73, 172.83. LC/MS (M+1)⁺=553; Anal Calcd for $C_{32}H_{32}N_4O_5$+0.6 $H_2O$: C, 68.22; H, 5.94; N, 9.94. Found: C, 67.95; H, 5.68; N, 9.84.

5.235 3-{4-[4-(4-Benzyl-Piperidin-1-ylmethyl)-Benzyloxy]-1-Oxo-1,3-Dihydro-Isoindol-2-yl}-Piperidine-2,6-Dione

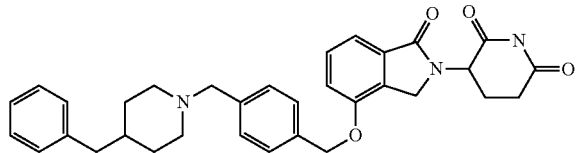 [SMILES: O=C1CCC(N2Cc3c(OCc4ccc(CN5CCC(Cc6ccccc6)CC5)cc4)cccc3C2=O)C(=O)N1]

To a stirred solution of 3-(4-(4-(bromomethyl)benzyloxy)-1-oxoisoindolin-2-yl)piperidine-2,6-dione (0.44 g, 0.993 mmol) in acetonitrile (10 ml) at room temperature was added 4-benzylpiperidine (0.230 ml, 1.290 mmol) and N-ethyl-N-isopropylpropan-2-amine (0.328 ml, 1.985 mmol). The mixture became cloudy in a couple of minutes. It was stirred at room temperature overnight. Solvent was evaporated to give a white solid, which was stirred in water (30 ml) and methylene chloride (50 ml). The org phase was washed with saturated sodium bicarbonate (2×20 ml), brine (20 ml), dried and concentrated to a light yellow solid (0.5 g). The solid was stirred in acetonitrile (8 ml) at 55° C. for one hour then filtered to give 3-{4-[4-(4-Benzyl-piperidin-1-ylmethyl)-benzyloxy]-1-oxo-1,3-dihydro-isoindol-2-yl}-piperidine-2,6-dione as an off-white solid (0.245 g, 46% yield); mp, 169-171° C. HPLC: Waters Symmetry C-18, 3.9×150 mm, 5 μm, 1 mL/min, 240 nm, gradient from 10/90 to 95/5 in 5 min, isocratic at 95/5 in 5 min ($CH_3CN$/0.1% $H_3PO_4$), 5.15 min (94.1%). ¹H NMR (DMSO-$d_6$) δ 1.08-1.29 (m, 2H, $CH_2$), 1.38-1.62 (m, 3H, $CH_2$, CH), 1.77-1.91 (m, 2H, $CH_2$), 1.92-2.05 (m, 1H, CHH), 2.35-2.48 (m, 2H, CHH, CH), 2.57 (dd, J=1.3, 11.7 Hz, 1H, CHH), 2.69-2.81 (m, 2H, $CH_2$), 2.83-3.01 (m, 1H, CHH), 3.41 (s, 2H, $CH_2$), 4.19-4.49 (m, 2H, $CH_2$), 5.11 (dd, J=5.1, 13.2 Hz, 1H, NCH), 5.21 (s, 2H, $CH_2$), 7.10-7.20 (m, 3H, Ar), 7.21-7.37 (m, 7H, Ar), 7.38-7.53 (m, 3H, Ar), 10.97 (s, 1H, NH). ¹³C NMR (DMSO-$d_6$) δ 22.36, 31.21, 31.72, 37.32, 42.36, 45.09, 51.56, 53.18, 62.09, 69.45, 114.97, 115.21, 125.68, 127.62, 128.07, 128.73, 128.93, 129.81, 129.94, 133.31, 135.03, 138.66, 140.32, 153.51, 168.01, 170.98, 172.83. LC/MS (M+1)⁺=538; Anal Calcd for $C_{33}H_{35}N_3O_4$: C, 73.72; H, 6.56; N, 7.82. Found: C, 72.17; H, 6.08; N, 7.53.

5.236 3-{4-[4-(4-Ethanesulfonyl-Piperazin-1-ylmethyl)-Benzyloxy]-1-Oxo-1,3-Dihydro-Isoindol-2-yl}-Piperidine-2,6-Dione

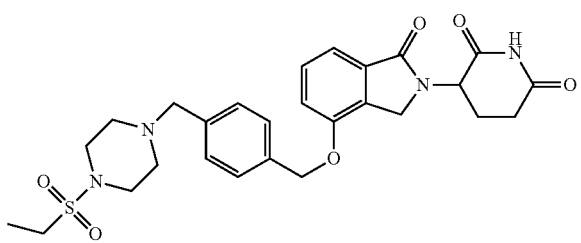 [SMILES: CCS(=O)(=O)N1CCN(Cc2ccc(COc3cccc4c3CN(C3CCC(=O)NC3=O)C4=O)cc2)CC1]

Step 1: 4-Ethanesulfonyl-piperazine-1-carboxylic acid tert-butyl ester To the stirred solution of tert-butyl piperazine-1-carboxylate (1.0 g, 5.37 mmol) in DCM anhydrous (10 mL) at room temperature was added ethanesulfonyl chloride (0.56 ml, 5.91 mmol) and TEA (0.898 ml, 6.44 mmol). The resulting mixture was stirred at room temperature for 22.5 hrs before it was diluted by DCM (40 mL). The mixture was washed with water (20 mL) and brine (20 mL). The organic layer was concentrated under vacuo to give 4-ethane sulfonyl-piperazine-1-carboxylic acid tert-butyl ester as a light yellow oil (1.7 g, 114% crude yield). LCMS MH (without boc)=179.

Step 2: 1-(Ethylsulfonyl)piperazine hydrochloride To the stirred solution of tert-butyl 4-(ethylsulfonyl)piperazine-1-carboxylate (1.7 g, 6.11 mmol) in DCM (5 mL) was added HCl (2M in diethyl ether, 30 ml, 60.0 mmol). The reaction mixture was stirred at room temperature for 22.5 hrs and filtered. The white solid was washed with diethyl ether (2×15 mL) and dried under suction to give 1-(ethylsulfonyl)piperazine hydrochloride as a white solid (1.03 g, 79% yield). The product was put to next step without further purification. HNMR spectra data ¹H NMR (DMSO-$d_6$) δ 1.21 (t, J=7.4 Hz, 3H, $CH_3$), 3.04-3.25 (m, 6H, $CH_2$, $CH_2$, $CH_2$), 3.33-3.54 (m, 4H, $CH_2$, $CH_2$), 9.50 (br. s., 2H, NHHCl); LCMS MH=179

Step 3: 3-{4-[4-(4-Ethanesulfonyl-piperazin-1-ylmethyl)-benzyloxy]-1-oxo-1,3-dihydro-isoindol-2-yl}-piperidine-2,6-dione To the stirred suspension of 1-(ethylsulfonyl)piperazine hydrochloride (203 mg, 0.947 mmol) in Acetonitrile (10 mL) was added DIPEA (0.414 ml, 2.369 mmol) followed by the addition of 3-(4-(4-(bromomethyl)benzyloxy)-1-oxoisoindolin-2-yl)piperidine-2,6-dione (350 mg, 0.790 mmol). The resulting clear solution was stirred at room temperature for further reaction. The reaction mixture was stirred at room temperature for 16 hrs before it was diluted by EtOAc (70 mL) and NaHCO₃ (sat., aq., 20 mL). Some solid was formed in the mixture. The mixture was filtered and the filtrate was extracted. Organic layer was dried by MgSO₄ and filtered. The filtrate combined with the solid was concentrated and the residue was purified by ISCO chromatography to give 3-{4-[4-(4-Ethanesulfonyl-piperazin-1-ylmethyl)-benzyloxy]-1-oxo-1,3-dihydro-isoindol-2-yl}-piperidine-2,6-dione as a white solid (240 mg, 56% yield). HPLC: Waters Symmetry C-18, 3.9×150 mm, 5 μm, 1 mL/min, 240 nm, 20/80, ($CH_3CN$/0.1% $H_3PO_4$), 3.82 min (99.9%); mp: 135-137° C.; ¹H NMR (DMSO-$d_6$) δ 1.20 (t, J=7.4 Hz, 3H, $CH_3$), 1.90-2.06 (m, 1H, CHH), 2.32-2.48 (m, 5H, CHH, $CH_2$, $CH_2$), 2.60 (br. s., 1H, CHH), 2.82-2.99 (m, 1H, CHH), 3.04 (q, J=7.4 Hz, 2H, $CH_2$), 3.11-3.21 (m, 4H, $CH_2$, $CH_2$), 3.52 (s, 2H, $CH_2$), 4.25 (d, J=17.4 Hz, 1H, CHH), 4.42 (d, J=17.6 Hz, 1H, CHH), 5.11 (dd, J=5.1, 13.2 Hz, 1H, CHH), 5.23 (s, 2H, $CH_2$), 7.26-7.38 (m, 4H, Ar), 7.40-7.55 (m, 3H, Ar), 10.97 (s, 1H, NH); ¹³C NMR (DMSO-$d_6$) δ 7.40, 22.34, 31.16, 42.16, 45.06, 45.22, 51.55, 52.07, 61.23, 69.35, 114.96, 115.22, 127.66, 128.92, 129.80, 129.93, 133.30, 135.37, 137.64, 153.48, 167.97, 170.96, 172.81; LCMS MH=541; Anal. Calcd for $C_{27}H_{32}N_4O_6S$: C, 59.98; H, 5.97; N, 10.36; Found: C, 59.67; H, 5.93; N, 10.21.

5.237 3-(1-Oxo-4-{4-[4-(Propane-2-Sulfonyl)-Piperazin-1-ylmethyl]-Benzyloxy}-1,3-Dihydro-Isoindol-2-yl)-Piperidine-2,6-Dione

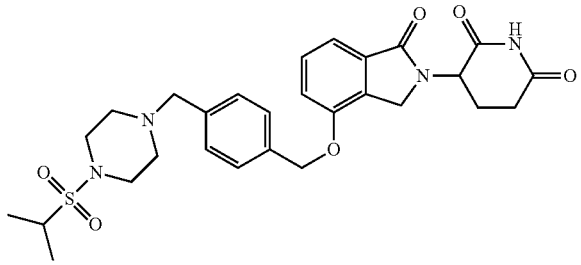 [SMILES: CC(C)S(=O)(=O)N1CCN(Cc2ccc(COc3cccc4c3CN(C3CCC(=O)NC3=O)C4=O)cc2)CC1]

Step 1: 4-(Propane-2-sulfonyl)-piperazine-1-carboxylic acid tert-butyl ester To the stirred solution of tert-butyl piperazine-1-carboxylate (1.0 g, 5.4 mmol) in DCM anhydrous (10 mL) at room temperature was added propane-2-sulfonyl chloride (0.7 ml, 5.9 mmol) and TEA (0.89 ml, 6.44 mmol). The resulting mixture was stirred at room temperature for 16 hrs before it was diluted by DCM (40 mL), which was washed with water (20 mL) and brine (20 mL). The organic layer was concentrated under vacuo to give 4-(Propane-2-sulfonyl)-piperazine-1-carboxylic acid tert-butyl ester as a light brown solid (1.63 g, 104% crude yield). The crude product was put to next step without further purification; LCMS MH=293.

Step 2: 1-(Isopropylsulfonyl)piperazine hydrochloride To the stirred solution of tert-butyl 4-(isopropylsulfonyl)piperazine-1-carboxylate (1.63 g, 5.6-mmol) in DCM (5 mL) was added HCl (2M in diethyl ether, 30 ml, 60.0 mmol). The resulting reaction mixture was stirred at room temperature for 21 hrs before it was filtered. The white solid was washed with diethyl ether (2×15 mL) and dried under suction to give 1-(isopropylsulfonyl)piperazine hydrochloride as a white solid (0.84 g, 66% crude yield). The product was put to next step without further purification; $^1$H NMR (DMSO-$d_6$) δ 1.23 (d, J=6.8 Hz, 6H, $CH_3$, $CH_3$), 2.99-3.21 (m, 4H, $CH_2$, $CH_2$), 3.28-3.57 (m, 5H, CH, $CH_2$, $CH_2$), 9.35-9.66 (m, 2H, NHHCl); LCMS MH=179.

Step 3: 3-(1-Oxo-4-{4-[4-(propane-2-sulfonyl)-piperazin-1-ylmethyl]-benzyloxy}-1,3-dihydro-isoindol-2-yl)-piperidine-2,6-dione To the stirred suspension of 1-(isopropylsulfonyl)piperazine hydrochloride (217 mg, 0.9 mmol) in Acetonitrile (10 mL) was added DIPEA (0.4 ml, 2.4 mmol) followed by the addition of 3-(4-(4-(bromomethyl)benzyloxy)-1-oxoisoindolin-2-yl)piperidine-2,6-dione (350 mg, 0.8 mmol). The resulting clear solution was stirred at room temperature for 17 hrs before it was added by EtOAc (70 mL) and $NaHCO_3$ (sat., aq., 20 mL). Some solid was formed in the mixture. The mixture was filtered and the filtrate was extracted. Organic layer was dried by $MgSO_4$ and filtered. The filtrate combined with the solid was concentrated and the residue was purified by ISCO to give 3-(1-Oxo-4-{4-[4-(propane-2-sulfonyl)-piperazin-1-ylmethyl]-benzyloxy}-1,3-dihydro-isoindol-2-yl)-piperidine-2,6-dione as a white solid (249 mg, 57% yield). HPLC: Waters Symmetry C-18, 3.9×150 mm, 5 μm, 1 mL/min, 240 nm, 20/80, ($CH_3CN$/ 0.1% $H_3PO_4$), 5.03 min (99.2%); mp: 233-235° C.; $^1$H NMR (DMSO-$d_6$) δ 1.21 (d, J=6.8 Hz, 6H, $CH_3$, $CH_3$), 1.91-2.06 (m, 1H, CHH), 2.34-2.48 (m, 5H, CHH, $CH_2$, $CH_2$), 2.54 (br. s., 1H, CHH), 2.82-3.00 (m, 1H, CHH), 3.17-3.28 (m, 4H, $CH_2$, $CH_2$), 3.28-3.37 (m, 1H, CH), 3.52 (s, 2H, $CH_2$), 4.25 (d, J=17.6 Hz, 1H, CHH), 4.42 (d, J=17.6 Hz, 1H, CHH), 5.11 (dd, J=5.1, 13.2 Hz, 1H, CHH), 5.23 (s, 2H, $CH_2$), 7.33 (d, J=7.6 Hz, 4H, Ar), 7.39-7.54 (m, 3H, Ar), 10.97 (s, 1H, NH); $^{13}$C NMR (DMSO-$d_6$) δ 16.41, 22.34, 31.16, 45.06, 45.60, 51.55, 51.62, 52.52, 61.33, 69.35, 114.94, 115.22, 127.64, 128.94, 129.80, 129.93, 133.28, 135.37, 137.60, 153.48, 167.97, 170.96, 172.81; LCMS MH=555; Anal. Calcd for $C_{28}H_{34}N_4O_6S$: C, 60.63; H, 6.18; N, 10.10; Found: C, 60.41; H, 6.03; N, 9.94.

5.238 3-(4-{4-[4-(1-Hydroxy-1-Methyl-Ethyl)-Piperidin-1-ylmethyl]-Benzyloxy}-1-Oxo-1,3-Dihydro-Isoindol-2-yl)-Piperidine-2,6-Dione

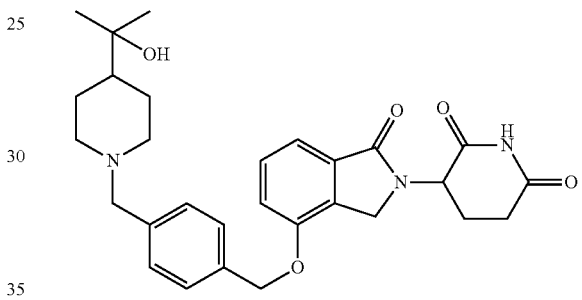

To the $CH_3CN$ solution of the mixture 3-(4-(4-(bromomethyl)benzyloxy)-1-oxoisoindolin-2-yl)piperidine-2,6-dione (0.50 g, 1.12 mmol) was added DIPEA (0.394 ml, 2.256 mmol) followed by 2-(piperidin-4-yl)propan-2-ol (0.194 g, 1.354 mmol) at room temperature. The mixture was stirred at room temperature overnight. The reaction mixture was concentrated then extracted using water (20 mL) and DCM (20 mL). The organic layer was concentrated and the resulted solid recrystallized from 2 mL of $CH_3CN$ to give 3-(4-{4-[4-(1-Hydroxy-1-methyl-ethyl)-piperidin-1-ylmethyl]-benzyloxy}-1-oxo-1,3-dihydro-isoindol-2-yl)-piperidine-2,6-dione (240 mg, 42%). m.p.: 160-162° C. LC_MS m/e=506. HPLC Waters Symmetry C-18, 3.9×150 mm, 5 micro, 1 mL/min, 240 nm, gradient 5/95 to 5/95 $CH_3CN$/ 0.1% $H_3PO_4$ in $H_2O$ during 5 min and stay at 95/5 for 5 min: 4.78 min (95.2%). $^1$H NMR (DMSO-$d_6$) δ 0.94-1.06 (m, 6H, $CH_3$, $CH_3$), 1.07-1.33 (m, 3H, CH, $CH_2$), 1.62 (d, J=10.8, Hz, 2H, $CH_2$), 1.82 (t, J=10.9 Hz, 2H, $CH_2$), 1.91-2.07 (m, 1H, CHH), 2.35-2.47 (m, 1H, CHH), 2.57 (d, J=18.3 Hz, 1H, CHH), 2.84 (d, J=11.7 Hz, 2H, $CH_2$), 2.89-2.99 (m, 1H, CHH), 3.42 (s, 2H, $CH_2$), 4.02 (s, 1H, OH), 4.18-4.47 (m, 2H, $CH_2$), 5.11 (dd, J=5.0, 13.1 Hz, 1H, NCH), 5.22 (s, 2H, $CH_2$), 7.23-7.38 (m, 4H, Ar), 7.39-7.58 (m, 3H, Ar), 10.96 (s, 1H, Ar) $^{13}$C NMR (DMSO-$d_6$) δ 22.33, 26.54, 26.86, 31.18, 45.07, 46.94, 51.55, 53.82, 62.10, 69.44, 70.19, 114.96, 115.19, 127.58, 128.75, 129.78, 129.93, 133.28, 135.00, 138.71, 153.51, 167.99, 170.96, 172.81; Anal Calcd for $C_{29}H_{35}N_3O_5$+0.2 $H_2O$ C %: 68.40; H %: 7.01; N %: 8.25; Found: C %: 68.20; H %: 7.05; N %: 8.12.

5.239 3-{1-Oxo-4-[4-(3,4,5,6-Tetrahydro-2H-[4,4'] Bipyridinyl-1-ylmethyl)-Benzyloxy]-1,3-Dihydro-Isoindol-2-yl}-Piperidine-2,6-Dione

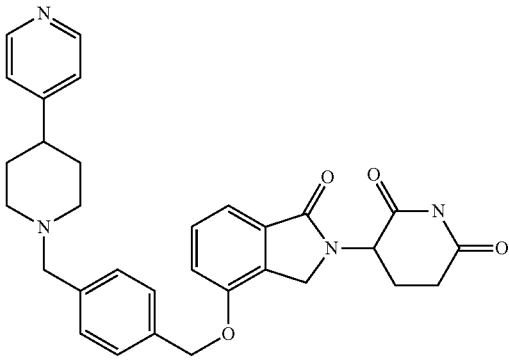 [SMILES: O=C1CCC(N2Cc3c(OCc4ccc(CN5CCC(c6ccncc6)CC5)cc4)cccc3C2=O)C(=O)N1]

To the $CH_3CN$ solution of mixture of 3-(4-(4-(bromomethyl)benzyloxy)-1-oxoisoindolin-2-yl)piperidine-2,6-dione (0.36 g, 0.82 mmol) was added N-ethyl-N-isopropylpropan-2-amine (0.284 ml, 1.624 mmol) and 4-(piperidin-4-yl)pyridine (0.158 g, 0.975 mmol). The mixture was stirred at room temperature for overnight then concentrated on rotavap. The resulted solid was added water 30 mL and stirred at room temperature for 2 hours. The suspension was filtered then was recrystallized from $CH_3CN$ (3 mL) to give 3-{1-Oxo-4-[4-(3,4,5,6-tetrahydro-2H-[4,4']bipyridinyl-1-ylmethyl)-benzyloxy]-1,3-dihydro-isoindol-2-yl}-piperidine-2,6-dione as a white solid. m.p.: 198-200° C. LC-MS m/e=525. HPLC Waters Symmetry C-18, 3.9×150 mm, 5 micro, 1 mL/min, 240 nm, gradient 5/95 to 5/95 $CH_3CN$/ 0.1% $H_3PO_4$ in $H_2O$ during 5 min and stay at 95/5 for 5 min: 4.36 min (96%). $^1H$ NMR (DMSO-$d_6$) δ 1.48-1.86 (m, 4H, $CH_2$, $CH_2$), 1.90-2.17 (m, 3H, $CH_2$, CHH), 2.32-2.44 (m, OH, CHH), 2.51-2.65 (m, 2H, CHH, CH), 2.80-3.08 (m, 3H, CHH, $CH_2$), 3.41-3.63 (m, 2H, $CH_2$), 4.15-4.57 (m, 2H, $CH_2$), 5.11 (dd, J=5.0, 13.1 Hz, 1H, NCH), 5.23 (s, 2H, $CH_2$), 7.12-7.70 (m, 9H, Ar), 8.45 (dd, J=1.5, 4.5 Hz, 2H, Ar), 10.97 (s, 1H, NH); $^{13}C$ NMR (DMSO-$d_6$) δ 22.36, 31.20, 31.98, 40.86, 45.09, 51.58, 53.21, 69.42, 114.98, 115.23, 122.31, 127.65, 129.01, 129.82, 129.95, 133.32, 135.25, 149.56, 153.51, 168.01, 170.98, 172.83; Anal Calcd for $C_{31}H_{32}N_4O_4$+0.3$H_2O$ C %: 70.25; H %: 6.20; N %: 10.57; Found C %: 70.05; H %: 5.92; N %: 10.25.

5.240 3-{4-[4-(4-Benzenesulfonyl-Piperazin-1-ylmethyl)-Benzyloxy]-1-Oxo-1,3-Dihydro-Isoindol-2-yl}-Piperidine-2,6-Dione

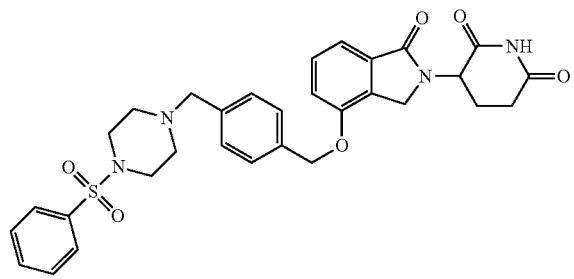 [SMILES: O=C1CCC(N2Cc3c(OCc4ccc(CN5CCN(S(=O)(=O)c6ccccc6)CC5)cc4)cccc3C2=O)C(=O)N1]

Step 1: 4-Benzenesulfonyl-piperazine-1-carboxylic acid tert-butyl ester To the stirred solution of tert-butyl piperazine-1-carboxylate (1.0 g, 5.4 mmol) in DCM anhydrous (10 mL) at room temperature was added benzenesulfonyl chloride (0.75 ml, 5.9 mmol) and TEA (0.90 ml, 6.4 mmol). The resulting mixture was stirred at room temperature for 18 hrs before it was diluted by EtOAc (40 mL) and $NaHCO_3$ (aq, sat, 15 mL). The mixture was extracted and organic layer was washed with brine (20 mL) and dried by $MgSO_4$. The organic layer was concentrated under vacuo to give 4-Benzenesulfonyl-piperazine-1-carboxylic acid tert-butyl ester as a white solid (2.0 g, 114% crude yield). It was used in the next step without further purification; LCMS MH (226, loss of BOC group during LCMS).

Step 2: 1-(Phenylsulfonyl)piperazine hydrochloride To the stirred solution of tert-butyl 4-(phenylsulfonyl)piperazine-1-carboxylate (crude) (1.75 g, 5.4 mmol) in DCM (4 5 mL) was added HCl (2M in diethyl ether) (20 ml, 40.0 mmol). The resulting mixture was stirred at room temperature for 3 days before it was filtered and the white solid was washed with Ether (2×30 mL) and dried under suction to give 1-(phenylsulfonyl)piperazine hydrochloride as a white solid (1.4 g, 100% crude yield). The compound was used in the next step without further purification. $^1H$ NMR (DMSO-$d_6$) δ 3.16 (s, 8H, $CH_2$, $CH_2$, $CH_2$, $CH_2$), 7.61-7.84 (m, 5H, Ar), 9.42 (br. s., 2H, NHHCl); LCMS MH=227.

Step 3: 3-{4-[4-(4-Benzenesulfonyl-piperazin-1-ylmethyl)-benzyloxy]-1-oxo-1,3-dihydro-isoindol-2-yl}-piperidine-2,6-dione To the stirred suspension of 3-(4-(4-(bromomethyl)benzyloxy)-1-oxoisoindolin-2-yl) piperidine-2,6-dione (360 mg, 0.8 mmol) in Acetonitrile (10 mL) was added DIPEA (0.43 ml, 2.4 mmol) and 1-(phenylsulfonyl)piperazine hydrochloride (256 mg, 0.98 mmol) at room temperature. The resulting mixture was stirred at room temperature for 21 hrs before it was added by EtOAc (50 mL) and $NaHCO_3$ (sat., aq., 20 mL). The mixture was extracted and organic layer was dried by $MgSO_4$. Organic layer was concentrated and the residue was purified by ISCO. The solid product was further purified by being stirred in DCM (5 mL) and diethyl ether (30 mL) to give 3-{4-[4-(4-Benzenesulfonyl-piperazin-1-ylmethyl)-benzyloxy]-1-oxo-1,3-dihydro-isoindol-2-yl}-piperidine-2,6-dione as a white solid (392 mg, 82% yield). HPLC: Waters Symmetry C-18, 3.9×150 mm, 5 μm, 1 mL/min, 240 nm, 25/75, ($CH_3CN$/ 0.1% $H_3PO_4$), 3.79 min (99.0%); mp: 220-222° C.; $^1H$ NMR (DMSO-$d_6$) δ 1.90-2.04 (m, 1H, CHH), 2.33-2.47 (m, 5H, CHH, $CH_2$, $CH_2$), 2.54-2.63 (m, 1H, CHH), 2.80-2.94 (m, 5H, $CH_2$, $CH_2$, CHH), 3.46 (s, 2H, $CH_2$), 4.23 (d, J=17.6 Hz, 1H, CHH), 4.40 (d, J=17.6 Hz, 1H, CHH), 5.11 (dd, J=5.0, 13.3 Hz, 1H, CHH), 5.20 (s, 2H, $CH_2$), 7.14-7.54 (m, 7H, Ar), 7.56-7.86 (m, 5H, Ar), 10.97 (s, 1H, NH); $^{13}C$ NMR (DMSO-$d_6$) δ 22.33, 31.16, 45.04, 45.92, 51.37, 51.53, 60.98, 69.32, 114.93, 115.20, 127.51, 127.63, 128.78, 129.36, 129.78, 129.90, 133.23, 133.28, 134.68, 135.33, 137.53, 153.45, 167.97, 170.95, 172.81; LCMS MH=589; Anal. Calcd for $C_{31}H_{32}N_4O_6S$+0.4$H_2O$: C, 62.49; H, 5.55; N, 9.40; Found: C, 62.59; H, 5.40; N, 9.33.

5.241 3-{4-[4-(4-Hydroxy-4-Phenyl-Piperidin-1-ylmethyl)-Benzyloxy]-1-Oxo-1,3-Dihydro-Isoindol-2-yl}-Piperidine-2,6-Dione

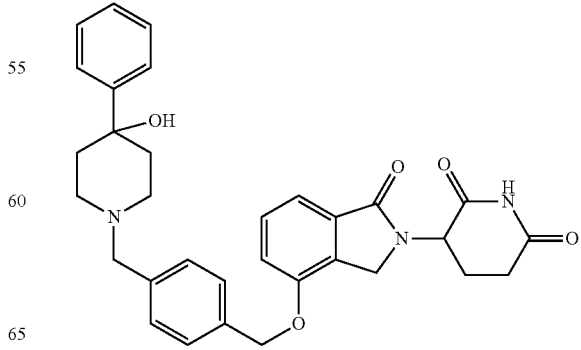

To the CH₃CN solution (10 mL) 3-(4-(4-(bromomethyl)benzyloxy)-1-oxoisoindolin-2-yl)piperidine-2,6-dione (0.28 g, 0.62 mmol) was added N-ethyl-N-isopropylpropan-2-amine (0.22 ml, 1.24 mmol) followed by 4-phenylpiperidin-4-ol (0.13 g, 0.76 mmol). The mixture was stirred at room temperature overnight. The reaction mixture was concentrated on rota-vap and the resulted solid was extracted using CH₂Cl₂ and Water. The organic layer was concentrated to give a solid which was recrystallized from CH₃CN (3 mL) to give 3-{4-[4-(4-Hydroxy-4-phenyl-piperidin-1-ylmethyl)-benzyloxy]-1-oxo-1,3-dihydro-isoindol-2-yl}-piperidine-2,6-dione as a white solid (154 mg, 44%). Melting point: 140-142° C. LC-MS m/e=540. HPLC Waters Symmetry C-18, 3.9×150 mm, 5 micro, 1 mL/min, 240 nm, gradient 5/95 to 5/95 CH₃CN/0.1% H₃PO₄ in H₂O during 5 min and stay at 95/5 for 5 min: 5.02 min (95%). ¹H NMR (DMSO-d₆) δ 1.58 (d, J=13.0 Hz, 2H, CH₂), 1.80-2.10 (m, 3H, CH₂, CHH), 2.32-2.43 (m, 3H, CHH, CH₂), 2.60 (br. s., 3H, CHH, CH₂), 2.79-3.06 (m, 1H, CHH), 3.57 (br. s., 2H, CH₂), 4.04-4.56 (m, 2H, CHH), 4.80 (br. s., 1H, OH), 5.11 (d, J=8.1 Hz, 1H, NCH), 5.24 (s, 2H, CH₂), 7.06-7.66 (m, 12H, Ar), 10.97 (s, 1H, NH). ¹³C NMR (DMSO-d₆) δ 22.33, 31.18, 31.25, 45.06, 48.89, 51.55, 69.41, 114.94, 115.20, 124.71, 126.13, 127.63, 127.77, 129.80, 129.93, 133.28, 153.49, 161.07, 167.99, 170.96. 172.81. Anal Calcd for C₃₂H₃₃N₃O₅+0.6H₂O C %: 69.64; H %: 5.70; N %: 7.27; Found C %: 69.83; H %: 6.26; N %: 7.63.

5.242 2-(2,6-Dioxopiperidin-3-yl)-4-((4-((4-Isopropylpiperidin-1-yl)Methyl)Benzyl)Oxy)Isoindoline-1,3-Dione

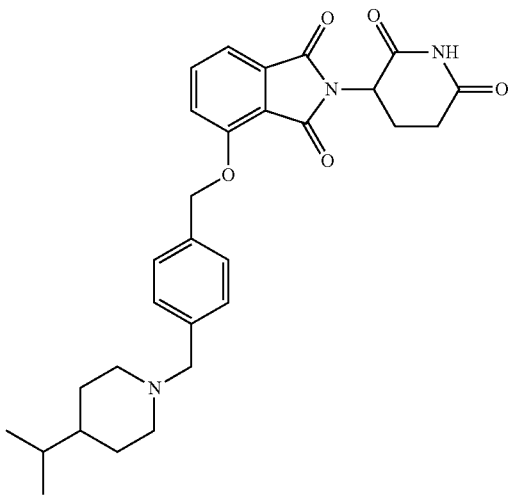 [SMILES: CC(C)C1CCN(Cc2ccc(COc3cccc4c3C(=O)N(C3CCC(=O)NC3=O)C4=O)cc2)CC1]

4-(4-(Bromomethyl)benzyloxy)-2-(2,6-dioxopiperidin-3-yl)isoindoline-1,3-dione (250 mg, 0.547 mmol) was slurried in dry MeCN (10 mL). To the slurry, was added 4-isopropylpiperidine (139 mg, 1.093 mmol) and the mixture was stirred at room temperature resulting in a clear solution within several minutes. After ~1 h, a thick precipitate was formed. The volatiles were removed in vacuo and the residue was partitioned between aq 1N NaHCO₃ (40 mL) and EtOAc (~100 mL). The aqueous layer was saturated with solid Na₂CO₃ and then extracted once more with EtOAc (~50 mL). The combined organic layer was washed with brine, dried (Na₂SO₄), and concentrated in vacuo to give a yellowish solid. The solid was triturated with water, filtered, and then washed with additional water (~200 mL, total). The remaining solid was washed with hexanes (~1500 L, total), suction dried, and then dried further in a vacuum oven at 60° C. to give 2-(2,6-dioxopiperidin-3-yl)-4-((4-((4-isopropylpiperidin-1-yl)methyl)benzyl)-oxy)isoindoline-1,3-dione as a pale yellow solid (220 mg, 80%): HPLC: Waters Symmetry C₁₈, 5 μm, 3.9×150 mm, 1 ml/min, 240 nm, 25/75 CH₃CN/0.1% H₃PO₄, 6.86 min (96.4%). mp: 220-222° C.; ¹H NMR (DMSO-d₆) δ 0.82 (s, 3H, CH₃), 0.85 (s, 3H, CH₃), 0.89-1.06 (m, 1H, CHH), 1.08-1.26 (m, 2H, CHH, CHH, CHH), 1.31-1.46 (m, 1H, CHH), 1.48-1.66 (m, 2H, CH₂), 1.85 (t, J=10.7 Hz, 2H, CH₂), 1.95-2.13 (m, 1H, CHH), 2.52-2.66 (m, 2H, CHH, CHH), 2.72-3.00 (m, 3H, CHH, CHH, CHH), 3.42 (s, 2H, CH₂), 5.09 (dd, J=5.5, 12.8 Hz, 1H, CH), 5.35 (s, 2H, CH₂), 7.25-7.38 (m, 2H, Ar), 7.40-7.52 (m, 3H, Ar), 7.60 (d, J=8.5 Hz, 1H, Ar), 7.74-7.92 (m, 1H, Ar), 11.09 (br. s., 1H, NH); ¹³C NMR (DMSO-d₆) δ 19.64, 21.93, 28.86, 30.90, 31.92, 41.84, 48.73, 53.65, 62.15, 69.98, 115.48, 116.56, 120.21, 127.20, 128.78, 133.26, 134.52, 136.97, 138.65, 155.53, 165.29, 166.75, 169.87, 172.71; LCMS: MH=504; Anal Calcd for C₂₉H₃₃N₃O₅+0.16 H₂O; C, 68.77; H, 6.63; N, 8.30; Found: C, 68.77; H, 6.88; N, 8.22.

5.243 3-{4-[4-(1-Benzyl-Piperidin-4-ylmethyl)-Benzyloxy]-1-Oxo-1,3-Dihydro-Isoindol-2-yl}-Piperidine-2,6-Dione

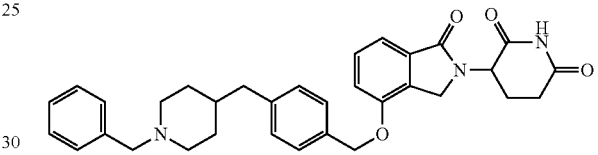

Step 1: Preparation of 4-{4-[2-(1-Carbamoyl-3-methoxycarbonyl-propyl)-1-oxo-2,3-dihydro-1H-isoindol-4-yloxymethyl]-benzyl}-piperidine-1-carboxylic acid tert-butyl ester Triphenyl phosphene (polymer-supported, 1.6 mmol/g, 3.3 g) was added to a stirred white suspension of methyl 5-amino-4-(hydroxy-1-oxoisoindolin-2-yl)-5-oxopentanoate (2.444 g, 8.36 mmol) in THF (100 ml) at 0° C. After ten minutes, diisopropyl diazene-1,2-dicarboxylate (2.470 ml, 12.54 mmol) was added and stirred for 40 minutes and then tert-butyl 4-(4-(hydroxymethyl)benzyl)piperidine-1-carboxylate (3.32 g, 10.87 mmol) in THF (20 ml) was added. The mixture was stirred at 0° C. and warmed up to room temperature overnight. The suspension was filtered, rinsed with MeOH (2×20 ml), CH₂Cl₂(2×30 ml), and the filtrate was evaporated to give an oil, which was dissolved in CH₂Cl₂ (80 ml), washed with Sat NaHCO₃ (50 ml), concentrated and then purified by silica gel column to give 4-{4-[2-(1-Carbamoyl-3-methoxycarbonyl-propyl)-1-oxo-2,3-dihydro-1H-isoindol-4-yloxymethyl]-benzyl}-piperidine-1-carboxylic acid tert-butyl ester as a foamy oil (2.2 g, 45% yield). It was used in the next step without further purification.

Step 2: Preparation of 4-Carbamoyl-4-[1-oxo-4-(4-piperidin-4-ylmethyl-benzyloxy)-1,3-dihydro-isoindol-2-yl]-butyric acid methyl ester To a stirred solution of tert-butyl 4-(4-((2-(1-amino-5-methoxy-1,5-dioxopentan-2-yl)-1-oxoisoindolin-4-yloxy)methyl)benzyl)piperidine-1-carboxylate (2.2 g, 3.80 mmol) in CH₂Cl₂ (10 ml) at room temperature was added hydrogen chloride (2 M in ether) (10 ml, 38.0 mmol). After four hours, the suspension was filtered, rinsed with ether and the resulting yellow solid was dried to give 2.02 g, 111% crude yield (HCl salt). The product was used later in the next step without further purification.

Step 3: Preparation of 4-{4-[4-(1-Benzyl-piperidin-4-ylmethyl)-benzyloxy]-1-oxo-1,3-dihydro-isoindol-2-yl}-4-carbamoyl-butyric acid methyl ester To a stirred mixture of methyl 5-amino-5-oxo-4-(1-oxo-4-(4-(piperidin-4-ylmethyl)benzyloxy)isoindolin-2-yl)pentanoate hydrochloride (0.321 g, 0.622 mmol) and N-ethyl-N-isopropylpropan-2-amine (0.411 ml, 2.488 mmol) in acetonitrile (10 ml) was added (bromomethyl)benzene (0.074 ml, 0.622 mmol). After 15 minutes, the solvent was evaporated to give an oil, which was stirred in water (20 ml), sat NaHCO3 (10 ml), and ethyl acetate (30 ml). The org phase was dried and evaporated to give an oil (0.33 g, 93% yield). It was used in the next step without further purification.

Step 4: Preparation of 3-{4-[4-(1-Benzyl-piperidin-4-yl-methyl)-benzyloxy]-1-oxo-1,3-dihydro-isoindol-2-yl}-piperidine-2,6-dione To a stirred solution of methyl 5-amino-4-(4-(4-((1-benzylpiperidin-4-yl)methyl)benzyloxy)-1-oxoisoindolin-2-yl)-5-oxopentanoate (0.33 g, 0.579 mmol) in THF (8 ml) in an ice-water bath was added potassium 2-methylpropan-2-olate (0.065 g, 0.579 mmol). After ten minutes, the mixture was quenched with 1 N HCl (to pH=1~2), neutralized with Sat NaHCO$_3$ (to pH=7-8), and stirred in water (10 ml) and CH$_2$Cl$_2$ (30 ml). The organic phase was washed with water (20 ml), brine (20 ml), dried over Na$_2$SO$_4$ and concentrated to an oil, which was purified on silica gel column to give 3-{4-[4-(1-Benzyl-piperidin-4-ylmethyl)-benzyloxy]-1-oxo-1,3-dihydro-isoindol-2-yl}-piperidine-2,6-dione as an off-white solid (121 mg, 39% yield); mp, 110-112° C. HPLC: Waters Symmetry C-18, 3.9×150 mm, 5 µm, 1 mL/min, 240 nm, isocratic at 27/73 in 10 min (CH$_3$CN/0.1% H$_3$PO$_4$): 5.48 min (96.8%). $^1$H NMR (DMSO-d$_6$) δ 1.10-1.30 (m, 2H, CH$_2$), 1.39-1.60 (m, 3H, CH$_2$, CHH), 1.84 (t, J=11.4 Hz, 2H, CH$_2$), 1.92-2:03 (m, 1H, CHH), 2.35-2.47 (m, 1H, CHH), 2.57 (d, J=10.8 Hz, 1H, CHH), 2.69-2.81 (m, 2H, CH$_2$), 2.82-3.00 (m, 1H, CHH), 3.40 (s, 2H, CH$_2$), 4.18-4.46 (m, 2H, CH$_2$), 5.11 (dd, J=5.1, 13.2 Hz, 1H, NCH), 5.19 (s, 2H, CH$_2$), 7.13-7.35 (m, 9H, Ar), 7.38 (d, J=8.1 Hz, 2H, Ar), 7.44-7.52 (m, 1H, Ar), 10.96 (s, 1H, NH). $^{13}$C NMR (DMSO-d$_6$) δ 22.36, 31.20, 31.72, 37.30, 42.04, 45.09, 51.56, 53.17, 62.39, 69.49, 114.95, 115.19, 126.72, 127.68, 128.06, 128.61, 129.06, 129.81, 129.94, 133.29, 133.95, 138.72, 140.26, 153.54, 168.01, 170.96, 172.82. LC/MS m/e=538. Anal Calcd for C$_{33}$H$_{35}$N$_3$O$_4$ (+0.6 H$_2$O): C, 72.27; H, 6.65; N, 7.66. Found: C, 72.10; H, 6.38; N, 7.49.

5.244 2-(2,6-Dioxopiperidin-3-yl)-4-((4-((4-Phenylpiperidin-1-yl)Methyl)Benzyl)Oxy)Isoindoline-1,3-Dione

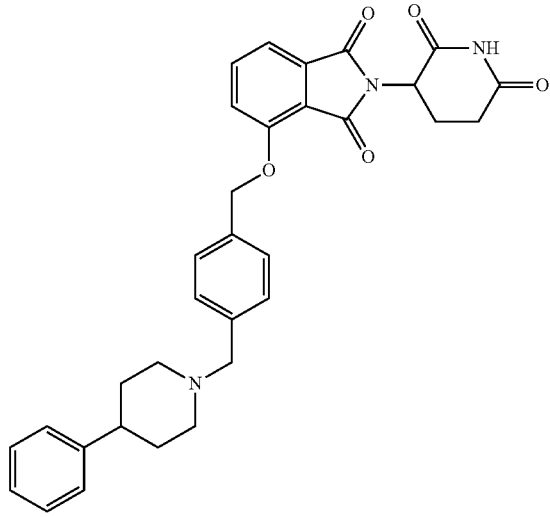 [SMILES: O=C1CCC(N2C(=O)c3cccc(OCc4ccc(CN5CCC(c6ccccc6)CC5)cc4)c3C2=O)C(=O)N1]

To a mixture of 4-(4-(bromomethyl)benzyloxy)-2-(2,6-dioxopiperidin-3-yl)isoindoline-1,3-dione (250 mg, 0.547 mmol) and 4-phenylpiperidine (93 mg, 0.574 mmol) in dry MeCN (10 mL), was added DIEA (0.143 mL, 0.820 mmol) and the resulting suspension was stirred at room temperature. After ~20 h more 4-phenylpiperidine (10 mg, 0.06 mmol) was added and stirring was continued for 1 day. To push reaction to completion, more DIEA (100 µL) was added and the mixture was stirred at room temperature overnight. The crude reaction mixture was treated with additional DIEA (0.143 mL) and then warmed to 80° C. for ~1 h. The mixture was allowed to cool slowly with gentle stirring. After 2 h, the slurry was filtered on a medium fritted funnel with suction. Residual solid the reaction vial was rinsed onto funnel with minimal MeCN (~1 mL). The solid cake on the funnel was washed with water (3×10 mL). The remaining solid was suction dried, then further dried in vacuum oven at 60° C. for 4 h to give 2-(2,6-dioxopiperidin-3-yl)-4-((4-((4-phenylpiperidin-1-yl)methyl)benzyl)-oxy)isoindoline-1,3-dione as a white solid (254 mg, 86%): HPLC: Waters Symmetry C$_{18}$, 5 lam, 3.9×150 mm, 1 ml/min, 240 nm, 30/70 CH$_3$CN/0.1% H$_3$PO$_4$, 3.34 min (99.6%); mp: 142-144° C.; $^1$H NMR (DMSO-d$_6$) δ 1.52-1.83 (m, 4H, CHH, CHH, CHH, CHH), 1.93-2.17 (m, 3H, CHH, CHH, CHH), 2.39-2.68 (m, 3H, CHH, CHH, CHH), 2.77-3.02 (m, 3H, CHH, CHH, CHH), 3.51 (s, 2H, CH$_2$N), 5.09 (dd, J=5.4, 12.7 Hz, 1H, CH), 5.36 (s, 2H, CH$_2$), 7.08-7.33 (m, 5H, Ar), 7.33-7.42 (m, 2H, Ar), 7.47 (d, J=7.9 Hz, 3H, Ar), 7.61 (d, J=8.5 Hz, 1H, Ar), 7.83 (dd, J=7.4, 8.5 Hz, 1H, Ar), 11.11 (s, 1H, NH); $^{13}$C NMR (DMSO-d$_6$) δ 21.95, 30.90, 33.06, 41.81, 48.73, 53.60, 62.10, 69.98, 115.48, 116.56, 120.21, 125.92, 126.66, 127.23, 128.25, 128.92, 133.26, 134.63, 136.99, 138.45, 146.23, 155.55, 165.29, 166.75, 169.87, 172.72; LCMS: MH=538; Anal Calcd for C$_{32}$H$_{31}$N$_3$O$_5$+0.5 H$_2$O: C, 70.31; H, 5.90; N, 7.69; Found: C, 70.39; H, 5.71; N, 7.65.

5.245 2-(2,6-Dioxopiperidin-3-yl)-4-((4-((4-(Methylsulfonyl)Piperidin-1-yl)Methyl) Benzyl)Oxy) Isoindoline-1,3-Dione

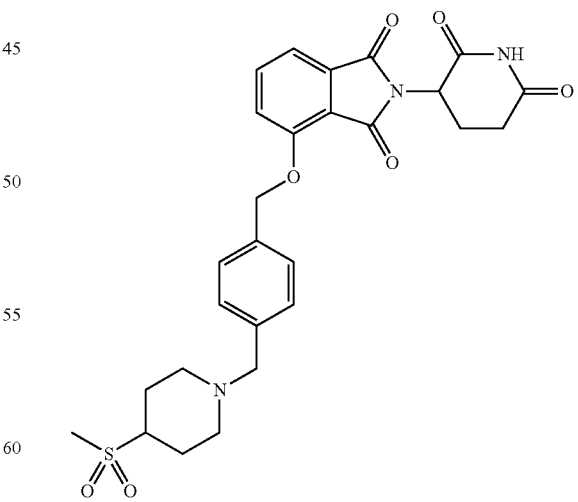

To a mixture of 4-(4-(bromomethyl)benzyloxy)-2-(2,6-dioxopiperidin-3-yl)isoindoline-1,3-dione (250 mg, 0.547 mmol) and 4-(methylsulfonyl)piperidine (98 mg, 0.601 mmol) in MeCN (10 mL, 191 mmol) was added DIEA (0.143 mL, 0.820 mmol) and the resulting mixture (white suspension) was stirred at room temperature. To the reaction mixture was added DIEA (0.143 mL, 0.820 mmol) and the slurry was heated to 80° C. and kept at that temperature for ~1 h, then allowed to cool to room temperature slowly with gentle stirring. After 2 h, the slurry was filtered. The solid cake on the funnel was washed with water (3×10 mL). The remaining solid was suction dried, then further dried in vacuum oven at 60° C. for 4 h. to give 2-(2,6-Dioxopiperidin-3-yl)-4-((4-((4-(methylsulfonyl)piperidin-1-yl)methyl)benzyl)oxy)isoindoline-1,3-dione as a white solid (270 mg, 92% yield): HPLC: Waters Symmetry $C_{18}$, 5 µm, 3.9×150 mm, 1 ml/min, 240 nm, 18/82 $CH_3CN/0.1\%$ $H_3PO_4$, 4.85 min (98.9%); mp: 204-206; ° C. $^1H$ NMR (DMSO-$d_6$) δ 1.60 (qd, J=4.0, 12.6 Hz, 2H, CHH, CHH), 1.88-2.12 (m, 4H, CHH, CHH, CHH, CHH), 2.41-2.66 (m, 3H, CHH, CHH, CHH), 2.81-2.97 (m, 6H, $CH_3$, CHH, CHH, CHH), 2.98-3.13 (m, 1H, CH), 3.49 (s, 2H, $CH_2$), 5.09 (dd, J=5.4, 12.7 Hz, 1H, CH), 5.35 (s, 2H, $CH_2$), 7.34 (d, J=8.1 Hz, 2H, Ar), 7.47 (dd, J=2.0, 7.6 Hz, 3H, Ar), 7.60 (d, J=8.5 Hz, 1H, Ar), 7.83 (dd, J=7.4, 8.3 Hz, 1H, Ar), 11.11 (s, 1H, NH). $^{13}C$ NMR (DMSO-$d_6$) 5 21.95, 24.43, 30.90, 37.30, 48.73, 51.43, 58.73, 61.36, 69.95, 115.50, 116.56, 120.19, 127.29, 128.82, 133.26, 134.76, 136.97, 138.07, 155.53, 165.29, 166.75, 169.87, 172.72; LCMS: MH=540; Anal Calcd for $C_{27}H_{29}N_3O_7S+0.6\ H_2O+0.3$ MeCN, C, 58.91; H, 5.57; N, 8.21; S, 5.70; Found: C, 58.93; H, 5.41; N, 8.11; S, 5.61.

5.246 3-{4-[4-(1-Cyclopropylmethyl-Piperidin-4-ylmethyl)-Benzyloxy]-1-Oxo-1,3-Dihydro-Isoindol-2-yl}-Piperidine-2,6-Dione

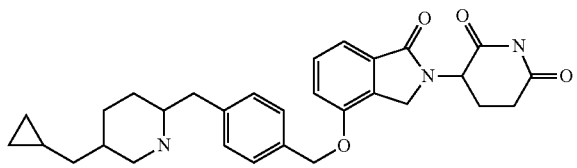 [SMILES: O=C1CCC(N2Cc3c(OCc4ccc(CC5CCC(CC6CC6)CN5)cc4)cccc3C2=O)C(=O)N1]

Step 1: Preparation of 4-{4-[2-(1-Carbamoyl-3-methoxycarbonyl-propyl)-1-oxo-2,3-dihydro-1H-isoindol-4-yloxymethyl]-benzyl}-piperidine-1-carboxylic acid tert-butyl Ester Triphenyl phosphene (polymer-supported, 1.6 mmol/g, 3.3 g) was added to a stirred white suspension of methyl 5-amino-4-(4-hydroxy-1-oxoisoindolin-2-yl)-5-oxopentanoate (2.444 g, 8.36 mmol) in THF (100 ml) at 0° C. After ten minutes, diisopropyl diazene-1,2-dicarboxylate (2.470 ml, 12.54 mmol) was added and stirred for 40 minutes and then tert-butyl 4-(4-(hydroxymethyl)benzyl)piperidine-1-carboxylate (3.32 g, 10.87 mmol) in THF (20 ml) was added. The mixture was stirred at 0° C. and warmed up to room temperature overnight. The suspension was filtered, rinsed with MeOH (2×20 ml), $CH_2Cl_2$(2×30 ml), and the filtrate was evaporated to give an oil, which was dissolved in $CH_2Cl_2$ (80 ml), washed with Sat $NaHCO_3$ (50 ml), concentrated and then purified by silica gel column to give 4-{4-[2-(1-Carbamoyl-3-methoxycarbonyl-propyl)-1-oxo-2,3-dihydro-1H-isoindol-4-yloxymethyl]-benzyl}-piperidine-1-carboxylic acid tert-butyl ester as a foamy oil (2.2 g, 45% yield). It was used in the next step without further purification.

Step 2: Preparation of 4-Carbamoyl-4-[1-oxo-4-(4-piperidin-4-ylmethyl-benzyloxy)-1,3-dihydro-isoindol-2-yl]-butyric acid methyl ester To a stirred solution of tert-butyl 4-(4-((2-(1-amino-5-methoxy-1,5-dioxopentan-2-yl)-1-oxoisoindolin-4-yloxy)methyl)benzyl)piperidine-1-carboxylate (2.2 g, 3.80 mmol) in $CH_2Cl_2$ (10 ml) at room temperature was added hydrogen chloride (2 M in ether) (10 ml, 38.0 mmol). After four hours, the suspension was filtered, rinsed with ether and the resulting yellow solid was dried to give 2.02 g, 111% crude yield (HCl salt). The product was used later in the next step without further purification.

Step 3: Preparation of 4-Carbamoyl-4-{4-[4-(1-cyclopropylmethyl-piperidin-4-ylmethyl)-benzyloxy]-1-oxo-1,3-dihydro-isoindol-2-yl}-butyric acid methyl ester To a stirred mixture of methyl 5-amino-5-oxo-4-(1-oxo-4-(4-(piperidin-4-ylmethyl)benzyloxy)isoindolin-2-yl)pentanoate hydrochloride (0.325 g, 0.630 mmol)) and N-ethyl-N-isopropylpropan-2-amine (0.416 ml, 2.52 mmol) in acetonitrile (10 ml) was added (bromomethyl)cyclopropane (0.061 ml, 0.630 mmol)). The mixture was heated at 55° C. for 5 hours and then at room temperature overnight. The solvent was evaporated to give an oil, which was stirred in water (20 ml), sat $NaHCO_3$ (10 ml), and ethyl acetate (40 ml). The organic phase was washed with water (20 ml), brine (20 ml), dried and evaporated to give 4-Carbamoyl-4-{4-[4-(1-cyclopropylmethyl-piperidin-4-ylmethyl)-benzyloxy]-1-oxo-1,3-dihydro-isoindol-2-yl}-butyric acid methyl ester as an oil (0.28 g, 83% yield). It was used in the next step without further purification.

Step 4: Preparation of 3-{4-[4-(1-Cyclopropylmethyl-piperidin-4-ylmethyl)-benzyloxy]-1-oxo-1,3-dihydro-isoindol-2-yl}-piperidine-2,6-dione To a stirred solution of methyl 5-amino-4-(4-(4-((1-(cyclopropylmethyl)piperidin-4-yl)methyl)benzyloxy)-1-oxoisoindolin-2-yl)-5-oxopentanoate (0.28 g, 0.525 mmol) in THF (10 ml) in an ice-water bath was added potassium 2-methylpropan-2-olate (0.059 g, 0.525 mmol) and stirred for 10 minutes. To the mixture was added 1 N HCl (to pH=1) then neutralized with Sat $NaHCO_3$ (to pH=7). Water (10 ml) and $CH_2Cl_2$ (20 ml) was added and the mixture was washed with water (15 ml), brine (10 ml), dried over $Na_2SO_4$ and concentrated to a brown oil, which was purified by silica gel column to give 3-{4-[4-(1-Cyclopropylmethyl-piperidin-4-ylmethyl)-benzyloxy]-1-oxo-1,3-dihydro-isoindol-2-yl}-piperidine-2,6-dione as a foamy solid (20 mg, 8% yield); mp, N/A. HPLC: Waters Symmetry C-18, 3.9×150 mm, 5 µm, 1 mL/min, 240 nm, gradient from 10/90 to 95/5 in 5 min, isocratic at 95/5 in 5 min ($CH_3CN/0.1\%$ $H_3PO_4$), 4.62 min (98.7%). HPLC: Waters Symmetry C-18, 3.9×150 mm, 5 µm, 1 mL/min, 240 nm, isocratic at 27/73 in 10 min ($CH_3CN/0.1\%$ $H_3PO_4$): 4.58 min (95.4%). $^1H$ NMR (DMSO-$d_6$) δ 0.05-0.14 (m, 2H, $CH_2$), 0.44-0.57 (m, 2H, $CH_2$), 0.78-0.96 (m, 1H, CH), 1.28-1.46 (m, 2H, $CH_2$), 1.47-1.58 (m, 1H, CH), 1.59-1.72 (m, 2H, $CH_2$), 1.86-2.01 (m, 2H, $CH_2$), 2.12-2.43 (m, 4H, $CH_2CH_2$), 2.57 (d, J=6.6 Hz, 2H, $CH_2$), 2.73-2.96 (m, 2H, $CH_2$), 3.09 (dt, J=3.1, 11.8 Hz, 2H, $CH_2$), 4.21-4.55 (m, 2H, $CH_2$), 5.10 (s, 2H, $CH_2$), 5.21 (dd, J=5.3, 13.2 Hz, 1H, NCH), 7.06-7.21 (m, 3H, Ar), 7.31 (d, J=7.9 Hz, 2H, Ar), 7.38-7.56 (m, 2H, Ar). (The NH proton was barely seen). $^{13}C$ NMR (CHLOROFORM-d) δ 0.03, 4.05, 8.18, 23.49, 31.64, 31.72, 37.75, 42.79, 45.15, 51.86, 53.75, 63.90, 70.30, 114.61, 116.40, 127.58, 129.55, 129.90, 130.12, 133.17, 133.68, 140.88, 153.91, 169.39, 169.74, 171.41. LC/MS m/e=502.

5.247 3-(4-{4-[4-(4-Fluoro-Phenyl)-Piperidin-1-ylmethyl]-Benzyloxy}-1-Oxo-1,3-Dihydro-Isoindol-2-yl)-Piperidine-2,6-Dione

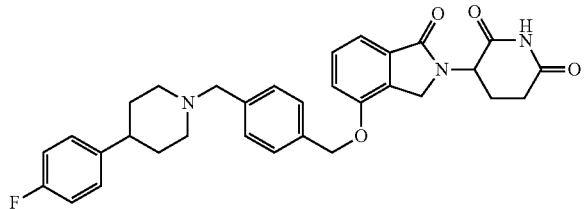 [SMILES: O=C1CCC(N2Cc3c(OCc4ccc(CN5CCC(c6ccc(F)cc6)CC5)cc4)cccc3C2=O)C(=O)N1]

To the CH$_3$CN (10 ml) solution of 3-(4-(4-(bromomethyl)benzyloxy)-1-oxoisoindolin-2-yl)piperidine-2,6-dione (0.513 g, 1.157 mmol) was added 4-(4-fluorophenyl)piperidine hydrochloride (0.311 g, 1.736 mmol) and N-ethyl-N-isopropylpropan-2-amine (0.574 ml, 3.47 mmol) at room temperature. The cloudy mixture was stirred at room temperature starting for two hours. Solvent CH$_3$CN was evaporated, and to the residue was added water (20 ml) and methylene chloride (40 ml). It was washed with saturated sodium bicarbonate (2×15 ml), water (20 ml), brine (20 ml), dried over Na$_2$SO$_4$ and concentrated to an oil, which was purified by silica gel column (MeOH/EtOAc) to give 3-(4-{4-[4-(4-Fluoro-phenyl)-piperidin-1-ylmethyl]-benzyloxy}-1-oxo-1,3-dihydro-isoindol-2-yl)-piperidine-2,6-dione as a white solid (0.315 g, 50% yield); mp, 180-182° C. HPLC: Waters Symmetry C-18, 3.9×150 mm, 5 µm, 1 mL/min, 240 nm, gradient from 10/90 to 95/5 in 5 min, isocratic at 95/5 in 5 min (CH$_3$CN/0.1% H$_3$PO$_4$), 4.79 min (95.7%). $^1$H NMR (DMSO-d$_6$) δ 1.51-1.80 (m, 4H, CH$_2$CH$_2$), 1.89-2.12 (m, 3H, CH, CH$_2$), 2.35-2.47 (m, 1H, CHH), 2.53-2.63 (m, 2H, CH, CHH), 2.83-2.99 (m, 3H, CHH, CH$_2$), 3.50 (s, 2H, CH$_2$), 4.19-4.48 (m, 2H, CH$_2$), 5.11 (dd, J=5.2, 13.3 Hz, 1H, NCH), 5.23 (s, 2H, CH$_2$), 7.04-7.15 (m, 2H, Ar), 7.22-7.39 (m, 6H, Ar), 7.41-7.53 (m, 3H, Ar), 10.97 (s, 1H, NH). $^{13}$C NMR (DMSO-d$_6$) δ 22.36, 31.21, 33.16, 41.02, 45.09, 51.58, 53.55, 62.10, 69.45, 114.75, 115.03, 115.23, 127.62, 128.35, 128.45, 128.92, 129.82, 129.95, 133.31, 135.14, 138.44, 142.35, 153.51, 159.00, 162.19, 168.01, 170.98, 172.83. LC/MS m/e$^+$=542. Anal Calcd for C$_{32}$H$_{32}$N$_3$O$_4$F: C, 70.96; H, 5.96; N, 7.76; F, 3.51. Found: C, 70.68; H, 5.90; N, 7.64; F, 3.54.

5.248 3-(4-{4-[4-(4-Fluoro-Benzyl)-Piperidin-1-ylmethyl]-Benzyloxy}-1-Oxo-1,3-Dihydro-Isoindol-2-yl)-Piperidine-2,6-Dione

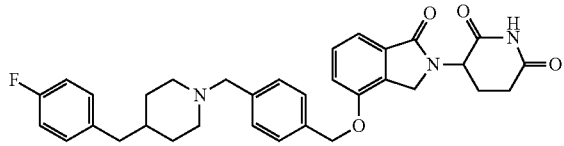 [SMILES: O=C1CCC(N2Cc3c(OCc4ccc(CN5CCC(Cc6ccc(F)cc6)CC5)cc4)cccc3C2=O)C(=O)N1]

To the CH$_3$CN (10 ml) solution of 3-(4-(4-(bromomethyl)benzyloxy)-1-oxoisoindolin-2-yl)piperidine-2,6-dione (0.528 g, 1.191 mmol) was added 4-(4-fluorobenzyl)piperidine (0.345 g, 1.787 mmol) and N-ethyl-N-isopropylpropan-2-amine (0.394 ml, 2.382 mmol) at room temperature. The cloudy mixture was stirred at room temperature starting for two hours. Solvent CH$_3$CN was evaporated, and to the residue was stirred in a mixture of water (20 ml), saturated sodium bicarbonate (10 ml) and methylene chloride (50 ml). The mixture was washed with water (2×20 ml), brine (10 ml), dried over sodium sulfate and concentrated to a white solid, which was purified by silica gel column (MeOH/CH$_2$Cl$_2$) to give 3-(4-{4-[4-(4-Fluoro-benzyl)-piperidin-1-ylmethyl]-benzyloxy}-1-oxo-1,3-dihydro-isoindol-2-yl)-piperidine-2,6-dione as a white foamy solid (0.224 g, 34% yield); mp, 148-150° C. HPLC: Waters Symmetry C-18, 3.9×150 mm, 5 µm, 1 mL/min, 240 nm, gradient from 10/90 to 90/10 in 5 min, isocratic at 90/10 in 5 min (CH$_3$CN/0.1% H$_3$PO$_4$), 4.86 min (95.8%). $^1$H NMR (DMSO-d$_6$) δ 1.08-1.27 (m, 2H, CH$_2$), 1.36-1.59 (m, 3H, CHH, CH$_2$), 1.77-1.91 (m, 2H, CH$_2$), 1.93-2.04 (m, 1H, CHH), 2.35-2.48 (m, 2H, CHH, CHH), 2.53-2.63 (m, 1H, CHH), 2.70-2.81 (m, 2H, CH$_2$), 2.83-3.00 (m, 1H, CHH), 3.41 (s, 2H, CH$_2$), 4.18-4.47 (m, 2H, CH$_2$), 5.11 (dd, J=5.1, 13.2 Hz, 1H, NCH), 5.21 (s, 2H, CH$_2$), 7.02-7.12 (m, 2H, Ar), 7.13-7.22 (m, 2H, Ar), 7.25-7.36 (m, 4H, Ar), 7.38-7.53 (m, 3H, Ar), 10.97 (s, 1H, NH). $^{13}$C NMR (DMSO-d$_6$) δ 22.36, 31.21, 31.60, 37.32, 41.37, 45.09, 51.58, 53.15, 62.07, 69.45, 114.57, 114.85, 114.97, 115.21, 127.61, 128.73, 129.81, 129.94, 130.55, 130.65, 133.31, 135.04, 136.46, 138.66, 153.51, 158.98, 162.17, 168.01, 170.98, 172.83. LC/MS m/e$^+$=556. Anal Calcd for C$_{33}$H$_{34}$N$_3$O$_4$F: C, 71.33; H, 6.17; N, 7.56. Found: C, 71.02; H, 5.84; N, 7.47.

5.249 3-(4-{4-[4-(3-Fluoro-Phenyl)-Piperidin-1-ylmethyl]-Benzyloxy}-1-Oxo-1, 3-Dihydro-Isoindol-2-yl)-Piperidine-2,6-Dione

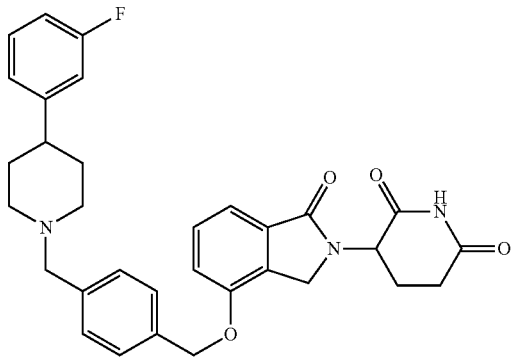 [SMILES: O=C1CCC(N2Cc3c(OCc4ccc(CN5CCC(c6cccc(F)c6)CC5)cc4)cccc3C2=O)C(=O)N1]

To the CH$_2$Cl$_2$ solution of 3-(4-(4-(bromomethyl)benzyloxy)-1-oxoisoindolin-2-yl)piperidine-2,6-dione (0.5 g, 1.128 mmol) was added 4-(3-fluorophenyl)piperidine (0.101 g, 0.564 mmol) and DIPEA (0.146 g, 1.13 mmol). The resulted solution was stirred at room temperature for 2 hours. The mixture was added water (15 mL) and extracted. The organic layer was concentrated and purified on silica gel column eluted with CH$_2$Cl$_2$ and MeOH. The resulted solid was recrystallized from CH$_3$CN (5 mL) to give 3-(4-{4-[4-(3-fluoro-phenyl)-piperidin-1-ylmethyl]-benzyloxy}-1-oxo-1, 3-dihydro-isoindol-2-yl)-piperidine-2,6-dione (430 mg, 70%). Melting Point: 200-202° C. LC-MS m/e=542. HPLC Waters Symmetry C-18, 3.9×150 mm, 5 micro, 1 mL/min, 240 nm, gradient 5/95 to 5/95 CH$_3$CN/0.1% H$_3$PO$_4$ in H$_2$O during 5 min and stay at 95/5 for 5 min:6.95 min (94.75%). $^1$H NMR (DMSO-d$_6$) δ 1.38-1.80 (m, 4H, CH$_2$, CH$_2$), 1.86-2.15 (m, 3H, CHH, CH$_2$), 2.30-2.45 (m, J=4.2 Hz, 1H, CHH), 2.55-2.68 (m, 1H, CHH), 2.76-3.05 (m, 3H, CHH, CH$_2$), 3.50 (s, 2H, CH$_2$), 4.09-4.53 (m, 2H, CH$_2$), 5.11 (dd, J=5.1, 13.2 Hz, 1H, NCH), 5.23 (s, 2H, CH$_2$), 6.79-7.19 (m, 3H, Ar), 7.24-7.60 (m, 8H, Ar), 10.97 (s, 1H, NH); $^{13}$C NMR (DMSO-d$_6$) δ 22.38, 31.21, 32.80, 41.50, 45.09, 51.58, 53.46, 62.07, 69.45, 112.53, 112.81, 113.30, 113.58, 114.97, 115.23, 122.84, 127.62, 128.93, 129.82, 129.95, 130.06, 130.16, 133.32, 135.16, 138.41, 149.26, 149.34, 153.51, 160.69, 163.89, 168.01, 170.98, 172.83. Anal Calcd for C$_{32}$H$_{32}$FN$_3$O$_4$, C, 70.96%; H, 5.96%; N, 7.76%. Found: C, 70.57%; H, 6.01%; N, 7.67%.

5.250 2-(2,6-Dioxopiperidin-3-yl)-4-((4-((4-(Trifluoromethyl)Piperidin-1-yl)Methyl)Benzyl)-Oxy)Isoindoline-1,3-Dione

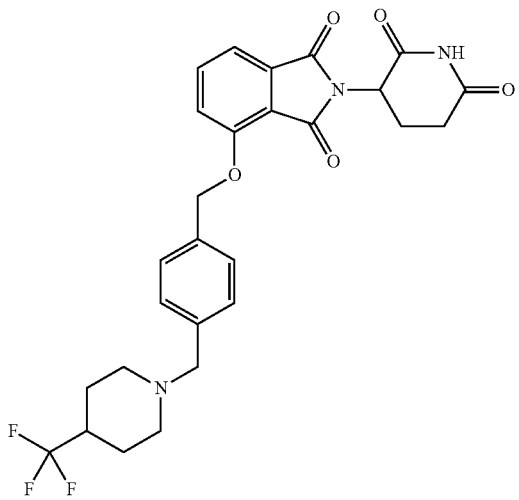 [SMILES: O=C1CCC(N2C(=O)c3cccc(OCc4ccc(CN5CCC(C(F)(F)F)CC5)cc4)c3C2=O)C(=O)N1]

To a mixture of 4-(4-(bromomethyl)benzyloxy)-2-(2,6-dioxopiperidin-3-yl)isoindoline-1,3-dione (250 mg, 0.547 mmol) and 4-(trifluoromethyl)piperidine hydrochloride (114 mg, 0.601 mmol) in MeCN (10 mL), was added DIEA (0.334 mL, 1.914 mmol) and the resulting suspension was stirred at room temperature for ~15 h. The reaction vial cap was removed and the mixture was heated to 80° C. for ~4.5 h. The concentrated reaction mixture (~5 mL) was partitioned between EtOAc (~150 mL) and water (~30 mL). The organic layer was washed with 1N NaHCO$_3$ (2×30 mL). and brine, dried (Na$_2$SO$_4$), and concentrated in vacuo to give a solid residue. MeCN (~3 mL) and water ((~25 mL) were added and the solid was sonicated at room temperature with agitation until a finely dispersed suspension was obtained. The solid was collected on a medium fritted funnel and dried in a vacuum oven at 60° C. to give 2-(2,6-dioxopiperidin-3-yl)-4-((4-((4-(trifluoromethyl)piperidin-1-yl)methyl)benzyl)-oxy)isoindoline-1,3-dione as an off-white solid (243 mg, 84% yield): HPLC: Waters Symmetry C$_{18}$, 5 μm, 3.9×150 mm, 1 ml/min, 240 nm, 25/75 CH$_3$CN/0.1% H$_3$PO$_4$, 3.53 min (99.2%); mp: 190-192° C.; $^1$H NMR (DMSO-d$_6$) δ 1.36-1.55 (m, 2H, CHH, CHH), 1.66-1.83 (m, 2H, CHH, CHH), 1.87-2.14 (m, 3H, CHH, CHH, CHH), 2.15-2.38 (m, 1H, CH), 2.40-2.68 (m, 2H, CHH, CHH), 2.77-3.00 (m, 3H, CHH, CHH, CHH), 3.48 (s, 2H, CH$_2$N), 5.09 (dd, J=5.5, 12.8 Hz, 1H, CH), 5.35 (s, 2H, CH$_2$O), 7.25-7.40 (m, 2H, Ar), 7.44-7.53 (m, 3H, Ar), 7.60 (d, J=8.5 Hz, 1H, Ar), 7.83 (dd, J=7.4, 8.5 Hz, 1H, Ar), 11.11 (s, 1H, NH); residual EtOAc (~0.07 eq); $^{13}$C NMR (DMSO-d$_6$) δ 21.95, 24.19, 30.90, 39.07, 48.73, 51.39, 61.61, 69.95, 115.50, 116.56, 120.19, 127.29, 128.84, 133.26, 134.73, 136.99, 138.12, 155.53, 165.29, 166.75, 169.87, 172.72; signal for CF3 and CCF3 is partially masked by DMSO-d$_6$; $^{19}$F NMR (DMSO-d$_6$) δ -72.35; LCMS: MH=530; Anal Calcd for C$_{27}$H$_{26}$F$_3$N$_3$O$_5$+0.1 H$_2$O+0.07 EtOAc: C, 60.96; H, 5.02; N, 7.82; F, 10.60: Found: C, 61.17; H, 4.98; N, 7.46; F, 10.24.

5.251 2-(2,6-Dioxopiperidin-3-yl)-4-((4-(Piperidin-1-ylmethyl)Benzyl)Oxy)Isoindoline-1,3-Dione

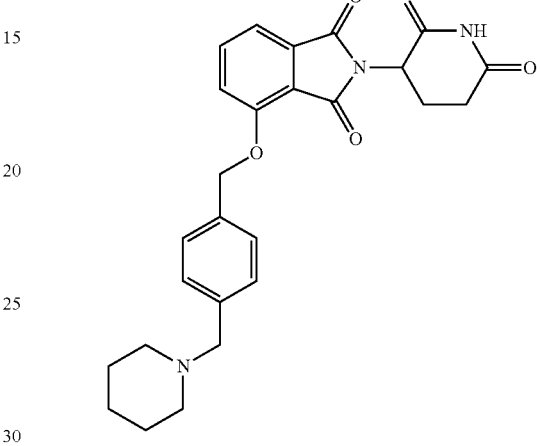

To a suspension of 4-(4-(bromomethyl)benzyloxy)-2-(2,6-dioxopiperidin-3-yl)isoindoline-1,3-dione (230 mg, 0.503 mmol) and piperidine (0.055 mL, 0.553 mmol) in dry MeCN (15 mL, 287 mmol), was added DIEA (0.307 mL, 1.760 mmol) and the resulting suspension was stirred at room temperature for 2.5 h. The reaction mixture was concentrated in vacuo to glassy solid. Trituration of the solid with a solution of ~1:1 MeCN/Et$_2$O (~10 mL) produced a well-dispersed slurry. The solid was filtered and washed with additional Et$_2$O (40 mL). The remaining was partitioned between EtOAc (~150 mL) and 1 N Na$_2$CO$_3$ (~30 mL). The organic layer was washed with additional 1 N Na$_2$CO$_3$ (~30 mL) and brine, then dried (Na$_2$SO$_4$) and concentrated in vacuo to glassy solid. The solid was triturated with extensive sonication in a solution of MeCN (~2 mL) and Et$_2$O (~20 mL) until a finely dispersed solid was formed. The solid was collected on a medium fritted funnel with suction, then washed with additional Et$_2$O (~20 mL). The cake was dried in a vacuum oven overnight at 50° C. give 2-(2,6-dioxopiperidin-3-yl)-4-((4-(piperidin-1-ylmethyl)benzyl)oxy)isoindoline-1,3-dione as a tan solid (110 mg, 47%): HPLC: Waters Symmetry C$_{18}$, 5 Gm, 3.9×150 mm, 1 ml/min, 240 nm, 20/80 CH$_3$CN/0.1% H$_3$PO$_4$, 4.47 min (98.9%); mp: 153-155° C.; $^1$H NMR (DMSO-d$_6$) δ 1.38 (d, J=4.7 Hz, 2H, CH$_2$), 1.43-1.59 (m, 4H, CH$_2$, CH$_2$), 1.94-2.13 (m, 1H, CHH), 2.19-2.40 (m, 4H, CH$_2$, CH$_2$), 2.42-2.67 (m, 2H, CHH, CHH), 2.77-2.99 (m, 1H, CHH), 3.42 (s, 2H, CH$_2$N), 5.09 (dd, J=5.4, 12.9 Hz, 1H, CH), 5.35 (s, 2H, CH$_2$O), 7.26-7.37 (m, 2H, Ar), 7.40-7.53 (m, 3H, Ar), 7.60 (d, J=8.5 Hz, 1H, Ar), 7.82 (dd, J=7.4, 8.3 Hz, 1H, Ar), 11.11 (s, 1H, NH); $^{13}$C NMR (DMSO-d$_6$) δ 21.95, 23.96, 25.51, 30.90, 48.73, 53.85, 62.50, 69.98, 1 15.47, 116.56, 120.19, 127.19, 128.82, 133.24, 134.54, 136.97, 138.52, 155.53, 165.27, 166.75, 169.87, 172.71; LCMS: MH=462; Anal Calcd for C$_{26}$H$_{27}$N$_3$O$_5$+0.18 H$_2$O: C, 67.19; H, 5.93; N, 9.04; Found: C, 67.18; H, 5.78; N, 8.84.

5.252 4-((4-((4,4-Dimethylpiperidin-1-yl)Methyl)Benzyl)Oxy)-2-(2,6-Dioxopiperidin-3-yl)Isoindoline-1,3-Dione

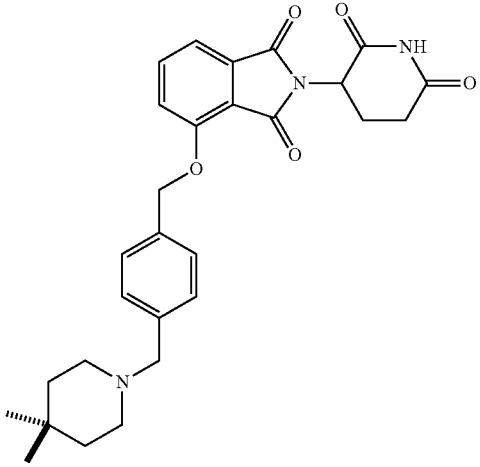

To a mixture of 4-(4-(bromomethyl)benzyloxy)-2-(2,6-dioxopiperidin-3-yl)isoindoline-1,3-dione (250 mg, 0.547 mmol) and 4,4-dimethylpiperidine hydrochloride (90 mg, 0.601 mmol) in dry MeCN (10 mL), was added DIEA (0.334 mL, 1.914 mmol). The resulting suspension was stirred at room temperature for 17 h then the vial cap was removed and the mixture was warmed up to 75° C. After ~2.5 h, ~½ the volume remained as a thick suspension. The mixture was cooled with gentle stirring and then aged 4° C. overnight. To the mixture was added DIEA (250 µL) with stirring for 30 min. The slurry was filtered on a medium fritted funnel with suction and the cake was washed with water (~30 mL). The collected solid was suction dried and then dried further in vacuum oven at 50° C. for 6 h to give 4-((4-((4,4-dimethylpiperidin-1-yl)methyl)benzyl)oxy)-2-(2,6-dioxopiperidin-3-yl)isoindoline-1,3-dione as an off-white solid (230 mg, 86%): HPLC: Waters Symmetry C$_{18}$, 5 µm, 3.9×150 mm, 1 ml/min, 240 nm, 25/75 CH$_3$CN/0.1% H$_3$PO$_4$, 3.88 min (97.8%); mp: 208-210° C.: $^1$H NMR (DMSO-d$_6$) δ 0.89 (s, 6H, CH$_3$, CH$_3$), 1.19-1.41 (m, 4H, CH$_2$, CH$_2$), 1.95-2.15 (m, 1H, CHH), 2.20-2.42 (m, 4H, CH$_2$, CH$_2$), 2.42-2.66 (m, 2H, CHH, CHH), 2.79-2.98 (m, 1H, CHH), 3.46 (s, 2H, CH$_2$), 5.09 (dd, J=5.5, 12.8 Hz, 1H, CH), 5.34 (s, 2H, CH$_2$O), 7.28-7.39 (m, 2H, Ar), 7.39-7.52 (m, 3H, Ar), 7.60 (d, J=8.5 Hz, 1H, Ar), 7.82 (dd, J=7.4, 8.5 Hz, 1H, Ar), 11.11 (s, 1H, NH); $^{13}$C NMR (DMSO-d$_6$) δ 21.95, 28.04, 28.14, 30.90, 38.25, 48.73, 49.32, 62.03, 69.98, 115.48, 116.56, 120.19, 127.20, 128.81, 133.24, 134.57, 136.97, 138.68, 155.53, 165.27, 166.75, 169.87, 172.72; LCMS: MH=490; Anal Calcd for C$_{28}$H$_{31}$N$_3$O$_5$+0.3 H$_2$O: C, 67.94; H, 6.43; N, 8.49; Found: C, 67.91; H, 6.42; N, 8.60.

5.253 3-[4-(4-Bromomethyl-Benzyloxy)-1-Oxo-1,3-Dihydro-Isoindol-2-yl]-Piperidine-2,6-Dione

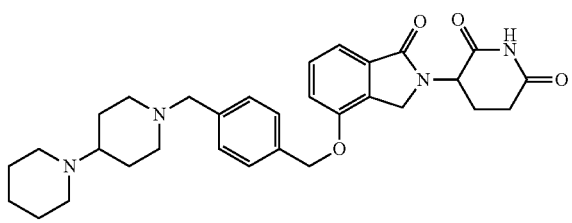 [SMILES: O=C1CCC(N2Cc3c(OCc4ccc(CN5CCC(N6CCCCC6)CC5)cc4)cccc3C2=O)C(=O)N1]

To the CH$_3$CN (10 ml) solution of 3-(4-(4-(bromomethyl)benzyloxy)-1-oxoisoindolin-2-yl)piperidine-2,6-dione (0.486 g, 1.096 mmol) was added 1,4'-bipiperidine dihydrochloride (0.397 g, 1.645 mmol) and N-ethyl-N-isopropylpropan-2-amine (0.725 ml, 4.39 mmol) at room temperature. The cloudy mixture was stirred at room temperature for two hours. Solvent was evaporated to give a white solid, which was stirred in water (20 ml) and methylene chloride (40 ml). It was washed with saturated sodium bicarbonate (2×80 ml), brine (50 ml), dried over sodium sulfate and concentrated to an white foamy solid (0.5 g), which was purified by preparative HPLC (acetonitrile/water in 0.1% formic acid) to give 3-[4-(4-Bromomethyl-benzyloxy)-1-oxo-1,3-dihydro-isoindol-2-yl]-piperidine-2,6-dione as an off-white solid (0.25 g, 43% yield); mp, 202-204° C. HPLC: Waters Symmetry C-18, 3.9×150 mm, 5 µm, 1 mL/min, 240 nm, gradient from 10/90 to 70/30 in 5 min, isocratic at 70/30 in 5 min (CH$_3$CN/0.1% H$_3$PO$_4$), 3.64 min (98.5%). $^1$H NMR (DMSO-d$_6$) δ 1.29-1.40 (m, 3H, CH$_2$, CH), 1.41-1.51 (m, 5H, CH$_2$, CH$_2$, CH), 1.63 (dd, J=3.3, 12.0 Hz, 2H, CH$_2$), 1.81-1.93 (m, 2H, CH$_2$), 1.94-2.04 (m, 1H, CHH), 2.08-2.21 (m, 1H, CH), 2.35-2.48 (m, 5H, CHH, CH$_2$, CH$_2$), 2.53-2.63 (m, 1H, CHH), 2.75-2.99 (m, 3H, CHH, CH$_2$), 3.42 (s, 2H, CH$_2$), 4.19-4.48 (m, 2H, CH$_2$), 5.11 (dd, J=5.1, 13.2 Hz, 1H, NCH), 5.22 (s, 2H, CH$_2$), 7.26-7.36 (m, 3H, Ar), 7.39-7.53 (m, 3H, Ar), 10.97 (s, 1H, NH). $^{13}$C NMR (DMSO-d$_6$) δ 22.36, 24.58, 26.08, 27.54, 31.21, 45.09, 49.70, 51.56, 52.85, 61.84, 61.99, 69.44, 114.95, 115.21, 127.61, 128.82, 129.81, 129.94, 133.31, 135.09, 138.56, 153.51, 168.01, 170.98, 172.83. LC/MS m/e=531. Anal Calcd for C$_{31}$H$_{38}$N$_4$O$_4$ (+0.7 H$_2$O): C, 68.54; H, 7.31; N, 10.31. Found: C, 68.29; H, 7.49; N, 10.16.

5.254 3-(4-{4-[4-(3-Chloro-Phenyl)-Piperidin-1-ylmethyl]-Benzyloxy}-1-Oxo-1,3-Dihydro-Isoindol-2-yl)-Piperidine-2,6-Dione

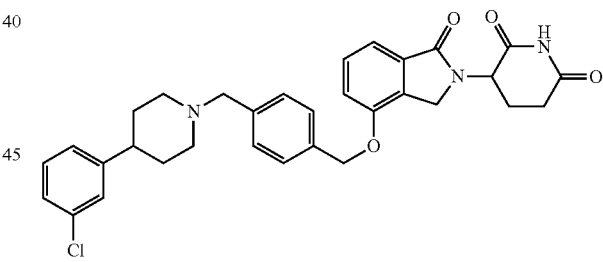

To the CH$_3$CN (10 ml) solution of 3-(4-(4-(bromomethyl)benzyloxy)-1-oxoisoindolin-2-yl)piperidine-2,6-dione (0.354 g, 0.799 mmol) was added 4-(3-chlorophenyl)piperidine hydrochloride (0.278 g, 1.198 mmol) and N-ethyl-N-isopropylpropan-2-amine (0.396 ml, 2.396 mmol) at room temperature. The cloudy mixture was stirred at room temperature overnight. Solvent was evaporated and the residue was stirred in methylene chloride (120 ml), washed with saturated sodium bicarbonate (2×50 ml), brine (50 ml), dried over sodium sulfate, concentrated and purified by Silica Gel Column (MeOH/CH$_2$Cl$_2$) to give 3-(4-{4-[4-(3-Chloro-phenyl)-piperidin-1-ylmethyl]-benzyloxy}-1-oxo-1,3-dihydro-isoindol-2-yl)-piperidine-2,6-dione as a white solid (0.246 g, 55% yield); mp, 218-220° C. HPLC: Waters Symmetry C-18, 3.9×150 mm, 5 µm, 1 mL/min, 240 nm, gradient from 10/90 to 70/30 in 5 min, isocratic at 70/30 in 5 min (CH$_3$CN/0.1% H$_3$PO$_4$), 5.63 min (95.9%). $^1$H NMR (DMSO-$d_6$) δ 1.54-1.80 (m, 4H, CH$_2$, CH$_2$), 1.92-2.11 (m, 3H, CHH, CH$_2$), 2.36-2.48 (m, 1H, CHH), 2.53-2.64 (m, 1H, CHH), 2.83-2.99 (m, 3H, CHH, CH$_2$), 3.50 (s, 2H, CH$_2$), 4.21-4.49 (m, 2H, CH$_2$), 5.11 (dd, J=5.1, 13.2 Hz, 1H, NCH), 5.23 (s, 2H, CH$_2$), 7.18-7.26 (m, 2H, Ar), 7.27-7.39 (m, 6H, Ar), 7.42-7.54 (m, 3H, Ar), 10.96 (s, 1H, NH). $^{13}$C NMR (DMSO-$d_6$) δ 22.38, 31.21, 32.78, 41.44, 45.10, 51.59, 53.43, 62.03, 69.45, 114.98, 115.23, 125.43, 125.96, 126.70, 127.62, 128.93, 129.82, 129.95, 130.16, 132.97, 133.32, 135.16, 138.41, 148.83, 153.53, 168.01, 170.96, 172.82. LC/MS m/e=558, 560. Anal Calcd for C$_{32}$H$_{32}$N$_3$O$_4$Cl (+0.3 H$_2$O): C, 68.21; H, 5.83; N, 7.46. Found: C, 67.93; H, 5.64; N, 7.29.

5.255 3-{1-Oxo-4-[4-(4-M-Tolyl-Piperidin-1-ylmethyl)-Benzyloxy]-1,3-Dihydro-Isoindol-2-yl}-Piperidine-2,6-Dione

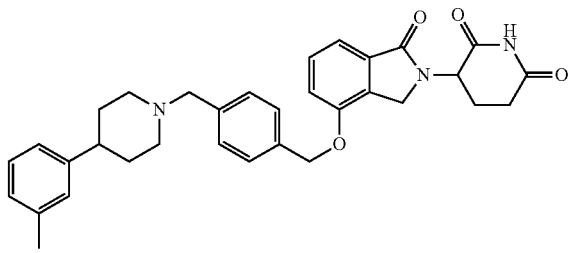 [SMILES: Cc1cccc(C2CCN(Cc3ccc(COc4cccc5c4CN(C4CCC(=O)NC4=O)C5=O)cc3)CC2)c1]

To the CH$_3$CN (10 ml) solution of 3-(4-(4-(bromomethyl)benzyloxy)-1-oxoisoindolin-2-yl)piperidine-2,6-dione (0.352 g, 0.794 mmol) was added 4-m-tolylpiperidine (0.209 g, 1.191 mmol) and N-ethyl-N-isopropylpropan-2-amine (0.394 ml, 2.382 mmol) at room temperature. The solution became cloudy in ~5 minutes and was stirred at room temperature overnight. Solvent was evaporated to give an off-white solid, which was stirred in methylene chloride (120 ml), washed with saturated sodium bicarbonate (2×50 ml), brine (50 ml), dried and concentrated to an off-white solid. It was purified by silica gel column (MeOH/CH$_2$Cl$_2$) to give 3-{1-Oxo-4-[4-(4-m-tolyl-piperidin-1-ylmethyl)-benzyloxy]-1,3-dihydro-isoindol-2-yl}-piperidine-2,6-dione as a white solid (0.272 g, 63% yield); mp, 227-229° C. HPLC: Waters Symmetry C-18, 3.9×150 mm, 5 µm, 1 mL/min, 240 nm, gradient from 10/90 to 70/30 in 5 min, isocratic at 70/30 for 5 min (CH$_3$CN/0.1% H$_3$PO$_4$), 5.45 min (98.6%). $^1$H NMR (DMSO-$d_6$) δ 1.54-1.78 (m, 4H, CH$_2$, CH$_2$), 1.92-2.11 (m, 3H, CHH, CH$_2$), 2.27 (s, 3H, CH$_3$), 2.36-2.48 (m, 2H, CHH, CH), 2.53-2.63 (m, 1H, CHH), 2.83-2.99 (m, 3H, CHH, CH$_2$), 3.50 (s, 2H, CH$_2$), 4.20-4.47 (m, 2H, CH$_2$), 5.11 (dd, J=5.1, 13.2 Hz, 1H, NCH), 5.23 (s, 2H, CH$_2$), 6.95-7.07 (m, 3H, Ar), 7.12-7.20 (m, 1H, Ar), 7.29-7.39 (m, 4H, Ar), 7.41-7.54 (m, 3H, Ar), 10.96 (s, 1H, NH). $^{13}$C NMR (DMSO-$d_6$) δ 21.06, 22.36, 31.21, 33.12, 41.79, 45.10, 51.59, 53.65, 62.12, 69.47, 114.98, 115.23, 123.69, 126.59, 127.40, 127.64, 128.18, 128.90, 129.82, 129.95, 133.32, 135.13, 137.23, 138.53, 146.17, 153.53, 168.01, 170.96, 172.82. LC/MS m/e=538. Anal Calcd for C$_{33}$H$_{35}$N$_3$O$_4$: C, 73.72; H, 6.56; N, 7.82. Found: C, 73.37; H, 5.53; N, 7.52.

5.256 3-{1-Oxo-4-[4-(4-M-Tolyl-Piperidin-1-ylmethyl)-Benzyloxy]-1,3-Dihydro-Isoindol-2-yl}-Piperidine-2,6-Dione

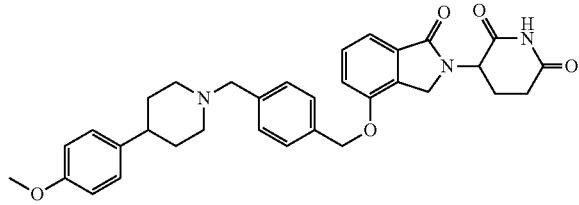 [SMILES: COc1ccc(C2CCN(Cc3ccc(COc4cccc5c4CN(C4CCC(=O)NC4=O)C5=O)cc3)CC2)cc1]

To the CH$_3$CN (10 ml) solution of 3-(4-(4-(bromomethyl)benzyloxy)-1-oxoisoindolin-2-yl)piperidine-2,6-dione (0.354 g, 0.799 mmol) was added 4-(4-methoxyphenyl)piperidine (0.229 g, 1.198 mmol) and N-ethyl-N-isopropylpropan-2-amine (0.396 ml, 2.396 mmol) at room temperature. The mixture was stirred at room temperature overnight. Solvent was evaporated and the resulting off-white solid was stirred in methylene chloride (100 ml), washed with saturated sodium bicarbonate (2×80 ml), brine (50 ml), dried and concentrated to an off-white solid, which was purified by silica gel column (MeOH/CH$_2$Cl$_2$) to give 3-{-Oxo-4-[4-(4-m-tolyl-piperidin-1-ylmethyl)-benzyloxy]-1,3-dihydro-isoindol-2-yl}-piperidine-2,6-dione as a white solid (0.34 g, 77% yield); mp, 189-191° C. HPLC: Waters Symmetry C-18, 3.9×150 mm, 5 µm, 1 mL/min, 240 nm, gradient from 10/90 to 70/30 in 5 min, isocratic at 70/30 for 5 min (CH$_3$CN/0.1% H$_3$PO$_4$), 5.42 min (98.2%). $^1$H NMR (DMSO-$d_6$) δ 1.51-1.77 (m, 4H, CH$_2$, CH$_2$), 1.92-2.11 (m, 3H, CHH, CH$_2$), 2.34-2.48 (m, 2H, CHH, CH), 2.53-2.64 (m, 1H, CHH), 2.82-3.01 (m, 3H, CHH, CH$_2$), 3.44-3.55 (m, 2H, CH$_2$), 3.71 (s, 3H, CH$_3$), 4.20-4.49 (m, 2H, CH$_2$), 5.11 (dd, J=5.1, 13.2 Hz, 1H, NCH), 5.23 (s, 2H, CH$_2$), 6.78-6.90 (m, 2H, Ar), 7.09-7.19 (m, 2H, Ar), 7.28-7.39 (m, 4H, Ar), 7.41-7.55 (m, 3H, Ar), 10.97 (s, 1H, NH). $^{13}$C NMR (DMSO-$d_6$) δ 22.36, 31.21, 33.34, 40.93, 45.10, 51.59, 53.68, 54.96, 62.15, 69.47, 113.68, 114.97, 115.23, 127.52, 127.62, 128.90, 129.82, 129.95, 133.32, 135.13, 138.24, 138.51, 153.53, 157.49, 168.01, 170.96, 172.82. LC/MS m/e=554. Anal Calcd for C$_{33}$H$_{35}$N$_3$O$_5$: C, 71.59; H, 6.37; N, 7.59. Found: C, 71.29; H, 6.30; N, 7.57.

5.257 3-(4-{4-[4-(4-Chloro-Phenyl)-Piperidin-1-ylmethyl]-Benzyloxy}-1-Oxo-1,3-Dihydro-Isoindol-2-yl)-Piperidine-2,6-Dione

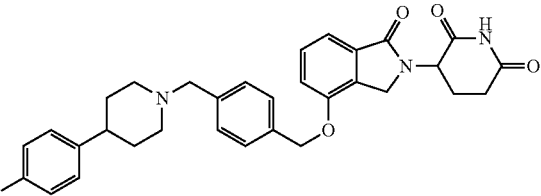

To the CH$_3$CN (10 ml) solution of 3-(4-(4-(bromomethyl)benzyloxy)-1-oxoisoindolin-2-yl)piperidine-2,6-dione (0.354 g, 0.799 mmol) was added 4-(4-chlorophenyl)piperidine hydrochloride (0.278 g, 1.198 mmol) and N-ethyl-N-isopropylpropan-2-amine (0.396 ml, 2.396 mmol) at room temperature. The mixture was stirred at room temperature overnight. Solvent was evaporated to an off-white solid, which was stirred in methylene chloride (100 ml), washed with saturated sodium bicarbonate (2×80 ml), brine (80 ml), dried and concentrated to an off-white solid, which was purified by silica gel column (MeOH/CH$_2$Cl$_2$) to give 3-(4-{4-[4-(4-Chloro-phenyl)-piperidin-1-ylmethyl]-benzyloxy}-1-oxo-1,3-dihydro-isoindol-2-yl)-piperidine-2,6-dione as a white solid (0.286 g, 52% yield); mp, 198-200° C. HPLC: Waters Symmetry C-18, 3.9×150 mm, 5 μm, 1 mL/min, 240 nm, gradient from 10/90 to 70/30 in 5 min, isocratic at 70/30 for 5 min (CH$_3$CN/0.1% H$_3$PO$_4$), 5.63 min (98.9%). $^1$H NMR (DMSO-d$_6$) δ 1.52-1.78 (m, 4H, CH$_2$, CH$_2$), 1.92-2.11 (m, 3H, CHH, CH$_2$), 2.36-2.48 (m, 1H, CHH), 2.53-2.64 (m, 1H, CHH), 2.82-3.00 (m, 3H, CHH, CH$_2$), 3.50 (s, 2H, CH$_2$), 4.20-4.49 (m, 2H, CH$_2$), 5.11 (dd, J=5.1, 13.2 Hz, 1H, NCH), 5.23 (s, 2H, CH$_2$), 7.22-7.39 (m, 8H, Ar), 7.41-7.54 (m, 3H, Ar), 10.97 (s, 1H, NH). $^{13}$C NMR (DMSO-d$_6$) δ 22.38, 31.21, 32.93, 41.12, 45.10, 51.58, 53.47, 62.07, 69.45, 114.98, 115.23, 127.62, 128.19, 128.60, 128.90, 129.82, 129.95, 130.45, 133.32, 135.14, 138.44, 145.20, 153.53, 168.01, 170.96, 172.82. LC/MS m/e=558, 560. Anal Calcd for C$_{32}$H$_{32}$N$_3$O$_4$Cl (+0.1 H$_2$O): C, 68.65; H, 5.80; N, 7.51. Found: C, 68.44; H, 5.73; N, 7.41.

5.258 (S)-3-(4-((4-((4-Isopropylpiperidin-1-yl)Methyl)Benzyl)Oxy)-1-Oxoisoindolin-2-yl)-3-Methylpiperidine-2,6-Dione

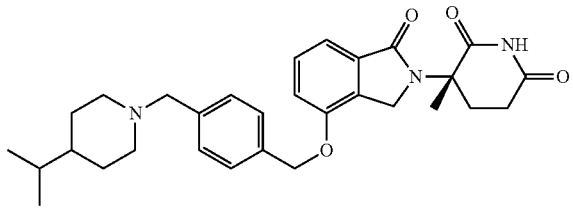 [SMILES: CC(C)C1CCN(Cc2ccc(COc3cccc4c3CN([C@@]3(C)CCC(=O)NC3=O)C4=O)cc2)CC1]

(S)-3-(4-(4-(bromomethyl)benzyloxy)-1-oxoisoindolin-2-yl)-3-methylpiperidine-2,6-dione (500 mg, 0.765 mmol) was dissolved in acetonitrile (5 mL), and 4-isopropylpiperidine (107 mg, 0.842 mmol) and DIEA (0.160 ml, 0.918 mmol) were added. The mixture was stirred at room temperature for 16 h. Then, the mixture was partitioned between water (75 mL) and EtOAc (75 mL), and the organic phase was washed with water (75 mL) and extracted with 1N HCl (2×75 mL). The combined aqueous extracts were washed with EtOAc (2×75 mL), made basic (solid Na$_2$CO$_3$) and then extracted into EtOAc (2×75 mL). The combined extracts were washed with water (75 mL), dried (MgSO$_4$), providing the product as a white solid, 230 mg (60% yield); mp 160-162° C. HPLC: Waters Symmetry C-18, 3.9×150 mm, 5 μm, 1 mL/min, 240 nm, 10/90 gradient to 90/10 CH$_3$CN/0.1% H$_3$PO$_4$ in 10 min: 6.05 (96.32%). $^1$H NMR (DMSO-d$_6$) δ 0.84 (d, J=6.6 Hz, 6H), 0.91-1.07 (m, 1H), 1.13-1.26 (m, 2H), 1.31-1.46 (m, 1H), 1.49-1.63 (m, 2H), 1.68 (s, 3H), 1.76-1.97 (m, 3H), 2.52-2.91 (m, 5H), 3.43 (s, 2H), 4.55 (d, J=17.6 Hz, 1H), 4.67 (d, J=17.6 Hz, 1H), 5.24 (s, 2H), 7.22 (d, J=7.4 Hz, 1H), 7.26-7.37 (m, 3H), 7.39-7.52 (m, 3H), 10.84 (s, 1H). $^{13}$C NMR (DMSO-d$_6$) δ 19.66, 20.70, 27.77, 28.86, 29.01, 31.94, 41.82, 45.59, 53.65, 57.18, 62.13, 69.45, 114.79, 127.67, 128.82, 129.74, 129.97, 133.91, 135.06, 138.6, 138.7, 153.38, 167.00, 172.41, 173.49. Anal. Calcd for C$_{30}$H$_{37}$N$_3$O$_4$: C, 71.54%; H, 7.40%; N, 8.34%; Found: C, 71.23%; H, 7.61%; N, 8.12%.

5.259 3-{1-Oxo-4-[4-(4-Trifluoromethanesulfonyl-Piperazin-1-ylmethyl)-Benzyloxy]-1,3-Dihydro-Isoindol-2-yl}-Piperidine-2,6-Dione

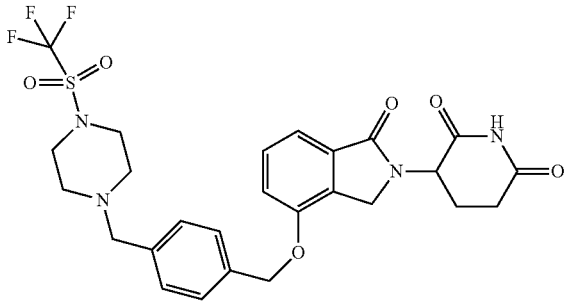 [SMILES: O=C1CCC(N2Cc3c(OCc4ccc(CN5CCN(S(=O)(=O)C(F)(F)F)CC5)cc4)cccc3C2=O)C(=O)N1]

Step 1: 4-Trifluoromethanesulfonyl-piperazine-1-carboxylic acid tert-butyl ester To the stirred solution of tert-butyl piperazine-1-carboxylate (4.6 g, 24.7 mmol) and triethylamine (4.1 ml, 29.6 mmol) in THF (50 mL) was added trifluoromethanesulfonyl chloride (3.1 ml, 29.6 mmol) at 0° C. through a syringe. The resulting suspension was stirred at 0° C. for 2 hrs. The reaction mixture was diluted by EtOAc (100 mL) and washed with water (50 mL), HCl (1N, aq, 50 mL), NaHCO$_3$ (sat. aq., 50 mL) and brine (50 mL). The organic layer was dried by MgSO$_4$ and concentrated under vacuo to give 4-Trifluoromethanesulfonyl-piperazine-1-carboxylic acid tert-butyl ester as clear oil (5.9 g, 87% crude yield). The compound was put to next step without further purification; LCMS MH=319.

Step 2: 1-Trifluoromethanesulfonyl-piperazi To the stirred solution of tert-butyl 4-(trifluoromethylsulfonyl)piperazine-1-carboxylate (5.9 g, 18.54 mmol) in DCM (20 ml) was added TFA (10.00 ml, 130 mmol) at room temperature. Bubbles were evolved immediately and the reaction mixture was cooled in ice/water bath. The reaction mixture was stirred at room temperature for 17 hrs and the reaction mixture was added by diethyl ether (100 mL) and stirred at room temperature for 30 min. The suspension was filtered and the white solid was washed with diethyl ether (2×25 mL). The solid (5.5 g) was added by NaHCO$_3$ (aq, sat, 35 mL) and EtOAC (80 mL). The mixture was extracted and the aqueous layer was extracted with EtOAc (80 mL). Organic layers were combined and dried by MgSO$_4$. The organic layer was concentrated under vacuo to give 1-Trifluoro methanesulfonyl-piperazi as a light brown oil (1.9 g, 47% yield). $^1$H NMR (DMSO-d$_6$) δ 2.76 (t, J=5.0 Hz, 4H, CH$_2$, CH$_2$), 3.36 (br. s., 4H, CH$_2$, CH$_2$); LCMS MH=219.

Step 3: 3-{-Oxo-4-[4-(4-trifluoromethanesulfonyl-piperazin-1-ylmethyl)-benzyloxy]-1,3-dihydro-isoindol-2-yl}-piperidine-2,6-dione To the stirred solution of 3-(4-(4-(bromomethyl)benzyloxy)-1-oxoisoindolin-2-yl)piperidine-2,6-dione (1 g, 2.2 mmol) in DCM (10 mL) at ice/water bath was added solution of 1-(trifluoromethylsulfonyl)piperazine (0.640 g, 2.9 mmol) in DCM (10 mL) followed by the addition of DIPEA (0.79 ml, 4.5 mmol). The resulting solution was kept in fridge for two days and the reaction mixture was added by DCM (80 mL) and water (30 mL). The mixture was extracted and organic layer was dried by MgSO$_4$ and concentrated under vacuo. The residue was purified by ISCO to give a white solid. The solid was purified by being stirred in diethyl ether (20 mL) to give 3-{1-Oxo-4-[4-(4-trifluoromethane sulfonyl-piperazin-1-yl-methyl)-benzyloxy]-1,3-dihydro-isoindol-2-yl}-piperidine- 2,6-dione as a white solid (700 mg, 53% yield). mp: 135-137° C.; $^1$H NMR (DMSO-d$_6$) δ 1.91-2.04 (m, 1H, CHH), 2.34-2.48 (m, 5H, CH$_2$, CH$_2$, CHH), 2.54-2.64 (m, 1H, CHH), 2.82-3.01 (m, 1H, CHH), 3.40-3.52 (m, 4H, CH$_2$, CH$_2$), 3.55 (s, 2H, CH$_2$), 4.25 (d, J=17.6 Hz, 1H, CHH), 4.42 (d, J=17.4 Hz, 1H, CHH), 5.11 (dd, J=5.1, 13.2 Hz, 1H, CHH), 5.23 (s, 2H, CH$_2$), 7.27-7.41 (m, 4H, Ar), 7.41-7.56 (m, 3H, Ar), 10.97 (s, 1H, NH); $^{13}$C NMR (DMSO-d$_6$) δ 22.29, 31.11, 45.00, 46.33, 51.51, 51.80, 60.95, 69.28, 118.06 (q, J=324.6 Hz, CF$_3$), 114.90, 115.22, 127.62, 128.90, 129.73, 129.88, 133.24, 135.45, 137.25, 153.41, 167.92, 170.89, 172.74; LCMS MH=581.

Step 4: 3-(1-oxo-4-((4-((4-(((trifluoromethyl)sulfonyl)piperazin-1-yl)methyl)benzyl)oxy) isoindolin-2-yl)piperidine-2,6-dione hydrochloride To the stirred mixture of 3-(1-oxo-4-(4-((4-((trifluoromethylsulfonyl)piperazin-1-yl)methyl)benzyloxy)isoindolin-2-yl)piperidine-2,6-dione (680 mg, 1.17 mmol) in Acetonitrile (10 mL) was added HCl in diethyl ether (2 M, 1.7 ml, 3.5 mmol). The resulting suspension was stirred at room temperature for 7 hrs and the mixture was filtered. The white solid was washed with acetonitrile (2×10 mL) and dried under vacuum oven to give 3-(1-oxo-4-((4-((4-(((trifluoromethyl)sulfonyl)piperazin-1-yl)methyl) benzyl)oxy) isoindolin-2-yl)piperidine-2,6-dione hydrochloride as a white solid (650 mg, 90% yield); HPLC: Waters Symmetry C-18, 3.9×150 mm, 5 µm, 1 mL/min, 240 nm, 25/75, (CH$_3$CN/0.1% H$_3$PO$_4$), 6.53 min (99.9%); mp: 228-230° C.; $^1$H NMR (DMSO-d$_6$) δ 1.93-2.05 (m, 1H, CHH), 2.41-2.47 (m, 1H, CHH), 2.54-2.65 (m, 1H, CHH), 2.82-3.02 (m, 1H, CHH), 3.12-3.42 (m, 4H, CH$_2$, CH$_2$), 3.67-4.09 (m, 4H, CH$_2$, CH$_2$), 4.22-4.50 (m, 4H, CHH, CHH, CH$_2$), 5.12 (dd, J=5.1, 13.2 Hz, 1H, CHH), 5.29 (s, 2H, CH$_2$), 7.34 (d, J=7.6 Hz, 2H, Ar), 7.50 (t, J=7.9 Hz, 1H, Ar), 7.58 (d, J=7.9 Hz, 2H, Ar), 7.66 (d, J=8.1 Hz, 2H, Ar), 10.98 (s, 1H, CHH), 1 1.83 (s, br, 1H, HCl); $^{13}$C NMR (DMSO-d$_6$) δ 22.30, 31.11, 43.11, 45.00, 49.90, 51.52, 58.21, 68.90, 114.86, 115.29, 119.34 (q, J=321 Hz, CF$_3$), 127.82, 128.95, 129.77, 129.89, 131.43, 133.27, 138.00, 153.28, 167.90, 170.90, 172.77; LCMS MH=581; Anal. Calcd for C$_{26}$H$_{27}$F$_3$N$_4$O$_6$S+HCl+2H$_2$O: C, 47.82; H, 4.94; N, 8.58; Cl, 5.43; Found: C, 47.51; H, 5.01; N, 8.37; Cl, 5.24.

5.260 3-{1-Oxo-4-[4-(4-P-Tolyl-Piperidin-1-ylmethyl)-Benzyloxy]-1,3-Dihydro-Isoindol-2-yl}-Piperidine-2,6-Dione

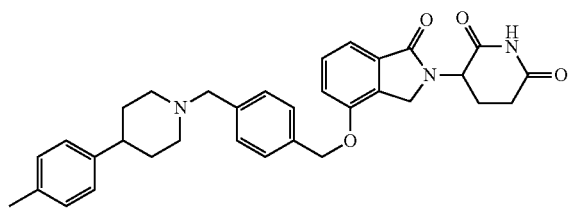 [SMILES: Cc1ccc(C2CCN(Cc3ccc(COc4cccc5c4CN(C4CCC(=O)NC4=O)C5=O)cc3)CC2)cc1]

To the CH$_3$CN (10 ml) solution of 3-(4-(4-(bromomethyl)benzyloxy)-1-oxoisoindolin-2-yl)piperidine-2,6-dione (0.352 g, 0.794 mmol) was added 4-p-tolylpiperidine (0.209 g, 1.191 mmol) and N-ethyl-N-isopropylpropan-2-amine (0.394 ml, 2.382 mmol) at room temperature. The mixture was stirred at room temperature overnight. Solvent was evaporated and the resulting off-white solid was stirred in methylene chloride (100 ml), washed with saturated sodium bicarbonate (2×80 ml), brine (50 ml), dried and concentrated to an off-white solid, which was purified by silica gel column (MeOH/CH$_2$Cl$_2$) to give 3-{-Oxo-4-[4-(4-p-tolyl-piperidin-1-ylmethyl)-benzyloxy]-1,3-dihydro-isoindol-2-yl}-piperidine-2,6-dione as a white solid (0.144 g, 33% yield); mp, 208-210° C. HPLC: Waters Symmetry C-18, 3.9×150 mm, 5 µm, 1 mL/min, 240 nm, gradient from 10/90 to 70/30 in 5 min, isocratic at 70/30 for 5 min (CH$_3$CN/0.1% H$_3$PO$_4$), 5.60 min (96.6%). $^1$H NMR (DMSO-d$_6$) δ 1.52-1.77 (m, 4H, CH$_2$CH$_2$), 1.91-2.10 (m, 3H, CHH, CH$_2$), 2.25 (s, 3H, CH$_3$), 2.36-2.48 (m, 2H, CHH, CH), 2.53-2.63 (m, 1H, CHH), 2.82-3.00 (m, 3H, CHH, CH$_2$), 3.49 (s, 2H, CH$_2$), 4.20-4.48 (m, 2H, CH$_2$), 5.11 (dd, J=5.1, 13.2 Hz, 1H, NCH), 5.23 (s, 2H, CH$_2$), 7.04-7.15 (m, 4H, Ar), 7.30-7.39 (m, 4H, Ar), 7.41-7.54 (m, 3H, Ar), 10.97 (s, 1H, NH). $^{13}$C NMR (DMSO-d$_6$) δ 20.57, 22.36, 31.21, 33.18, 41.39, 45.10, 51.58, 53.65, 62.13, 69.47, 114.98, 115.23, 126.50, 127.64, 128.83, 128.90, 129.82, 129.95, 133.32, 134.81, 135.13, 138.51, 143.19, 153.53, 168.01, 170.98, 172.82. LC/MS m/e=538. Anal Calcd for C$_{33}$H$_{35}$N$_3$O$_4$ (+0.2 H$_2$O): C, 73.23; H, 6.59; N, 7.76. Found: C, 73.01; H, 6.38; N, 7.54.

5.261 3-{1-Oxo-4-[4-(3',4',5',6'-Tetrahydro-2'H-[3,4']Bipyridinyl-1'-ylmethyl)-Benzyloxy]-1,3-Dihydro-Isoindol-2-yl}-Piperidine-2,6-Dione

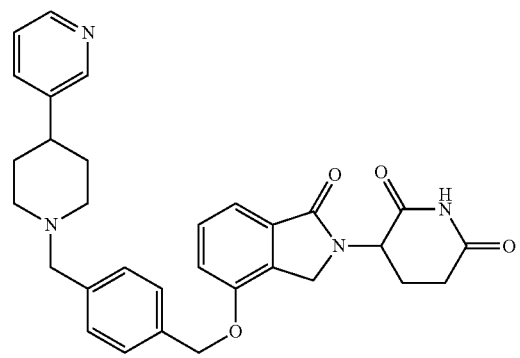 [SMILES: O=C1CCC(N2Cc3c(OCc4ccc(CN5CCC(c6cccnc6)CC5)cc4)cccc3C2=O)C(=O)N1]

To the CH$_2$Cl$_2$ solution of 3-(4-(4-(bromomethyl)benzyloxy)-1-oxoisoindolin-2-yl)piperidine-2,6-dione (0.5 g, 1.128 mmol) was added 3-(piperidin-4-yl)pyridine (0.192 g, 1.184 mmol) followed by DIPEA (0.591 ml, 3.38 mmol). The mixture was stirred at room temperature for 5 hours then was added water (15 mL) After extraction, the organic layer was concentrated to give a yellow solid. The solid was recrystallized from CH3CN (5 mL) to give 3-{1-Oxo-4-[4-(3',4',5',6'-tetrahydro-2'H-[3,4']bipyridinyl-1'-ylmethyl)-benzyloxy]-1,3-dihydro-isoindol-2-yl}-piperidine-2,6-dione as a solid (200 mg, 34%). m.p: 161-163° C. LC-MS m/e=525. HPLC Waters Symmetry C-18, 3.9×150 mm, 5 micro, 1 mL/min, 240 nm, gradient 5/95 to 5/95 CH$_3$CN/ 0.1% H$_3$PO$_4$ in H$_2$O during 5 min and stay at 95/5 for 5 min: 5.11 min (94%). $^1$H NMR (DMSO-d$_6$) δ 1.57-1.80 (m, 5H, CH$_2$, CH$_2$, CH), 1.89-2.15 (m, 3H, CH$_2$, CHH), 2.43-2.50 (m., 1H, CHH), 2.55-2.65 (m, 1H, CHH), 2.80-3.04 (m, 3H, CHH, CH$_2$), 3.51 (s, 2H, CH$_2$), 4.12-4.48 (m, 2H, CH$_2$), 5.11 (dd, J=5.1, 13.2 Hz, 1H, NCH), 5.23 (s, 2H, CH$_2$), 7.23-7.39 (m, 5H, Ar), 7.40-7.54 (m, 3H, Ar), 7.67 (dt, J=1.9, 7.7 Hz, 1H, Ar), 8.40 (dd, J=1.5, 4.7 Hz, 1H, Ar), 8.47 (d, J=1.9 Hz, 1H, Ar), 10.97 (s, 1H, NH). $^{13}$C NMR (DMSO-d$_6$) δ 14.09, 21.30, 30.15, 31.60, 44.03, 50.52, 52.38, 61.01, 68.38, 113.93, 114.17, 122.41, 126.58, 127.89, 128.77, 128.90, 132.27, 133.06, 134.12, 137.34, 140.29, 146.32, 147.48, 152.46, 166.96, 169.93, 171.78. Anal Calcd for C$_{31}$H$_{32}$N$_4$O$_4$: C % 70.97 H % 6.15 N % 10.68. Found, C % 68.36 H % 5.89 N % 10.08.

5.262 (S)-3-Methyl-3-(1-Oxo-4-((4-((4-(Trifluoromethyl)Piperidin-1-yl)Methyl)Benzyl)Oxy)Isoindolin-2-yl)Piperidine-2,6-Dione

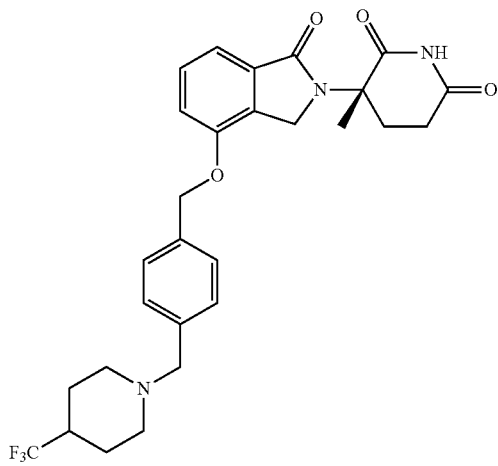 [SMILES: C[C@]1(N2Cc3c(OCc4ccc(CN5CCC(C(F)(F)F)CC5)cc4)cccc3C2=O)CCC(=O)NC1=O]

Step 1: (S)-3-(4-((4-(hydroxymethyl)benzyl)oxy)-1-oxoisoindolin-2-yl)-3-methylpiperidine-2,6-dione A mixture of (S)-3-(4-hydroxy-1-oxoisoindolin-2-yl)-3-methylpiperidine-2,6-dione (1.9 g, 6.93 mmol), (4-(chloromethyl)phenyl)methanol (1.085 g, 6.93 mmol), potassium iodide (0.115 g, 0.693 mmol) and potassium carbonate (1.053 g, 7.62 mmol) in DMF (50 mL) was stirred at room temperature for 9 days. The mixture was evaporated under vacuum. To the residue was added water (150 mL) and EtOAc (150 mL), and the resulting suspension was stirred for 16 h. The suspension was filtered, and the filter was rinsed with water (50 mL) and EtOAc (2×50 mL). The organic phase was washed with 10% aqueous sodium carbonate solution (2×75 mL), 1N HCl (100 mL), and brine (100 mL), was dried (MgSO$_4$) and evaporated. The residue was combined with the solid precipitate that had been filtered off, to afford a total of 2.09 g of a crude product.

Step 2: (S)-4-(((2-(3-methyl-2,6-dioxopiperidin-3-yl)-1-oxoisoindolin-4-yl)oxy)methyl)benzyl methanesulfonate The residue was suspended in 50 mL of acetonitrile and the mixture was cooled to 0° C. Methanesulfonyl chloride (0.538 mL, 6.93 mmol) and DIEA (1.448 ml, 8.31 mmol) were added, and the mixture stirred at 0° C. for 30 min. Then, the mixture was quenched by the addition of AcOH (0.5 mL) and then water (5 mL), and was evaporated. The residue was partitioned between EtOAc (125 mL) and brine (125 mL). A solid that did not dissolve in either phase was filtered off, and the phases were separated. The solid was combined with the organic layer and evaporated. The residue was chromatographed using a methylene chloride-acetonitrile gradient. The product eluted at ~40% ACN. The yield after drying was 1.3 g (40% over the two steps); $^1$H NMR (DMSO-d$_6$) δ 1.69 (s, 3H), 1.82-1.95 (m, 1H), 2.52-2.83 (m, 3H), 3.24 (s, 3H), 5.27 (s, 2H), 5.30 (s, 2H), 7.17-7.35 (m, 2H), 7.39-7.62 (m, 5H), 10.85 (s, 1H).

Step 3: (S)-3-methyl-3-(1-oxo-4-((4-((4-(trifluoromethyl) piperidin-1-yl)methyl)benzyl)oxy)isoindolin-2-yl)piperidine-2,6-dione A mixture of (S)-4-((2-(3-methyl-2,6-dioxopiperidin-3-yl)-1-oxoisoindolin-4-yloxy)methyl)benzyl methanesulfonate (0.40 g, 0.847 mmol) and 4-(trifluoromethyl)piperidine hydrochloride (0.161 g, 0.847 mmol) was cooled to 0° C., and then DIEA (0.310 ml, 1.778 mmol) was added. After 6 h, the rxn was evaporated under vacuum, and the residue was dissolved partitioned between EtOAc (50 mL) and water (50 mL), and the aqueous phase was extracted with EtOAc (50 mL). The combined organic fractions were extracted with 1N HCl (2×50 mL). The combined aqueous extracts were washed with EtOAc (50 mL), and then made basic using 10% aqueous sodium carbonate. This mixture was then extracted with EtOAc (2×50 mL), and the combined extracts were washed with brine (100 mL), dried (MgSO$_4$), and evaporated under vacuum, providing 0.39 g as a white solid, in 87% yield; mp 168-170° C. HPLC: Waters X-Terra, 3.9×150 mm, 5 μm, 1 mL/min, 240 nm, 5/95 to 95/5 CH$_3$CN-0.1% NH$_4$(HCO$_2$) over 5 min then 10 min 95/5 CH$_3$CN-0.1% NH$_4$(HCO$_2$): 5.73 (100%). $^1$H NMR (DMSO-d$_6$) δ 1.33-1.54 (m, 2H), 1.68 (s, 3H), 1.73-1.81 (m, 2H), 1.83-2.04 (m, 3H), 2.16-2.35 (m, 1H), 2.51-2.80 (m, 3H), 2.81-2.95 (m, 2H), 3.48 (s, 2H), 4.56 (d, J=17.6 Hz, 1H), 4.68 (d, J=17.6 Hz, 1H), 5.24 (s, 2H), 7.23 (d, J=7.4 Hz, 1H), 7.27-7.37 (m, 3H), 7.40-7.52 (m, 3H), 10.85 (s, 1H). $^{13}$C NMR (DMSO-d$_6$) δ 20.68, 24.24, 27.77, 28.99, 38.93, (q, J=38.9 Hz), 45.59, 51.43, 57.18, 61.62, 69.41, 114.79, 114.81, 127.71, 127.87 (q, J=278 Hz), 128.82, 129.74, 129.97, 133.91, 135.22, 138.18, 153.38, 167.00, 172.39, 173.47. Anal. Calcd for C$_{28}$H$_{30}$F$_3$N$_3$O$_4$+0.3 H$_2$O: C, 62.87%; H, 5.77%; N, 7.85%; Found: C, 62.87%; H, 5.67%; N, 7.86%.

5.263 (S)-3-(4-((4-((4,4-Dimethylpiperidin-1-yl) Methyl)Benzyoxy)-1-Oxoisoindolin-2-yl)-3-Methylpiperidine-2,6-Dione

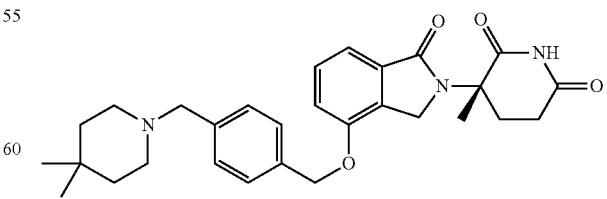

A mixture of (S)-4-((2-(3-methyl-2,6-dioxopiperidin-3-yl)-1-oxoisoindolin-4-yloxy)methyl)benzyl methanesulfonate (0.33 g, 0.698 mmol) and 4,4-dimethylpiperidine hydrochloride (0.105 g, 0.698 mmol) was cooled to 0° C., and then DIEA (0.255 ml, 1.467 mmol) was added. After 16 h, the mixture was evaporated under vacuum. The residue was partitioned between EtOAc (100 mL) and water (100 mL), and the aqueous phase was extracted with EtOAc (100 mL). The combined organic phases were extracted with 1N HCl (2×75 mL), and the combined extracts were wash with EtOAc (100 mL) and then made basic using solid sodium carbonate. The aqueous mixture was then extracted with EtOAc (2×75 mL), and the combined extracts were washed with water (100 mL), dried (MgSO$_4$), and evaporated, providing the product as a white solid, 250 mg, in 73% yield; mp 158-160° C. HPLC: Waters Symmetry C-18, 3.9×150 mm, 5 μm, 1 mL/min, 240 nm, 10/90 gradient to 90/10 CH$_3$CN/0.1% H$_3$PO$_4$ in 10 min then 90/10 CH$_3$CN/0.1% H$_3$PO$_4$ for 5 min: 5.79 (95.52%). $^1$H NMR (DMSO-d$_6$) δ 0.89 (s, 6H), 1.20-1.38 (m, 4H), 1.68 (s, 3H), 1.81-1.94 (m, 1H), 2.22-2.41 (m, 4H), 2.53-2.83 (m, 3H), 3.46 (s, 2H), 4.56 (d, J=17.6 Hz, 1H), 4.61-4.75 (m, J=17.8 Hz, 1H), 5.23 (s, 2H), 7.22 (d, J=7.4 Hz, 1H), 7.26-7.37 (m, 3H), 7.38-7.50 (m, 3H), 10.85 (s, 1H). $^{13}$C NMR (DMSO-d$_6$) δ 20.68, 27.77, 28.04, 28.18, 28.99, 38.32, 45.59, 49.38, 57.18, 62.09, 69.45, 114.78, 114.79, 127.67, 128.79, 129.72, 129.97, 133.89, 135.03, 138.76, 153.38, 167.00, 172.39, 173.47. Anal. Calcd for C$_{29}$H$_{35}$N$_3$O$_4$+0.3 H$_2$O: C, 70.36%; H, 7.25%; N, 8.49%; Found: C, 70.41%; H, 7.18%; N, 8.41%.

5.264 3-(4-((4-((4-Ethyl-3-Oxopiperazin-1-yl)Methyl)Benzyl)Oxy)-1-Oxoisoindolin-2-yl)Piperidine-2,6-Dione A solution of 1-ethylpiperazin-2-one hydrochloride (83 mg, 0.496 mmol) and DIEA (0.276 mL, 1.579 mmol) in dry MeCN (5 mL, 96 mmol) was added to 3-(4-(4-(bromomethyl)benzyloxy)-1-oxoisoindolin-2-yl)piperidine-2,6-dione (200 mg, 0.451 mmol). The resulting solution (pale amber) was stirred at 40° C. for 1 h. The mixture was extracted with ethyl acetate and 1N NaHCO$_3$. The organic layer was washed with brine and dried (Na$_2$SO$_4$), filtered, and concentrated in vacuo to give 3-(4-((4-((4-ethyl-3-oxopiperazin-1-yl)methyl)benzyl)oxy)-1-oxoisoindolin-2-yl)piperidine-2,6-dione as a white solid (169 mg, 76% yield): HPLC: Waters Symmetry C$_{18}$, 5 μm, 3.9×150 mm, 1 ml/min, 240 nm, 15/85 CH$_3$CN/0.1% H$_3$PO$_4$, 7.41 min (99.5%); mp: 163-165° C.; $^1$H NMR (DMSO-d$_6$) δ 1.01 (t, J=7.2 Hz, 3H, CH$_3$), 1.87-2.08 (m, 1H, CHH), 2.34-2.48 (m, 1H, CHH), 2.52-2.68 (m, 3H, CH$_2$, CHH), 2.81-3.02 (m, 1H, CHH), 2.94 (s, 2H, CH$_2$), 3.17-3.31 (m, 4H, CH$_2$, CH$_2$), 3.53 (s, 2H, CH$_2$), 4.25 (d, J=17.4 Hz, 1H, CHH), 4.42 (d, J=17.6 Hz, 1H, CHH), 5.11 (dd, J=5.1, 13.2 Hz, 1H, CH), 5.24 (s, 2H, CH$_2$), 7.24-7.40 (m, 4H, Ar), 7.41-7.61 (m, 3H, Ar), 10.96 (s, 1H, NH). $^{13}$C NMR (DMSO-d$_6$) δ 11.89, 22.33, 31.16, 45.07, 45.17, 48.86, 51.56, 56.81, 60.27, 69.36, 114.97, 115.22, 127.70, 128.95, 129.78, 129.93, 133.28, 135.52, 137.15, 153.48, 165.23, 167.97, 170.93, 172.78; One carbon signal is overlapped with DMSO; LCMS: MH=491; Anal Calcd for C$_{27}$H$_{30}$N$_4$O$_5$+0.35 H$_2$O: C, 65.27; H, 6.23; N, 11.28; Found: C, 65.27; H, 6.25; N, 11.06.

5.265 3-(4-((4-((4-Butyl-3-Oxopiperazin-1-yl)Methyl)Benzyl)Oxy)-1-Oxoisoindolin-2-yl)Piperidine-2,6-Dione

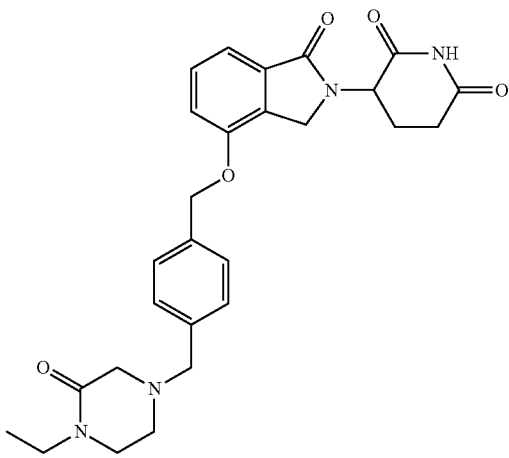 [SMILES: CCN1CCN(Cc2ccc(COc3cccc4c3CN(C3CCC(=O)NC3=O)C4=O)cc2)CC1=O]

To a solution of 3-(4-(4-(bromomethyl)benzyloxy)-1-oxoisoindolin-2-yl)piperidine-2,6-dione (200 mg, 0.451 mmol) in dry MeCN (5 mL, 96 mmol), was added 1-butylpiperazin-2-one (82 mg, 0.496 mmol) and DIEA (0.158 mL, 0.902 mmol). The yellowish clear solution was stirred at room temperature for 3 h. The crude mixture in ethyl acetate was extracted with 1N NaHCO$_3$, then brine. The organic layer was dried (Na$_2$SO$_4$), filtered, and concentrated in vacuo to give 3-(4-((4-((4-butyl-3-oxopiperazin-1-yl)methyl)benzyl)oxy)-1-oxoisoindolin-2-yl)piperidine-2,6-dione as a white solid (160 mg, 68% yield): HPLC: Waters Symmetry C$_{18}$, 5 μm, 3.9×150 mm, 1 ml/min, 240 nm, 20/80 CH$_3$CN/0.1% H$_3$PO$_4$, 6.52 min (99.5%); mp: 138-140° C.; $^1$H NMR (DMSO-d$_6$) δ 0.88 (t, J=7.2 Hz, 3H, CH$_3$), 1.14-1.33 (m, 2H, CH$_2$), 1.36-1.55 (m, 2H, CH$_2$), 1.88-2.05 (m, 1H, CHH), 2.34-2.47 (m, 1H, CHH), 2.52-2.68 (m, 3H, CH$_2$, CHH), 2.80-3.01 (m, 3H, CH$_2$, CHH), 3.17-3.29 (m, 4H, CH$_2$, CH$_2$), 3.53 (s, 2H, CH$_2$), 4.25 (d, J=17.6 Hz, 1H, CHH), 4.42 (d, J=17.6 Hz, 1H, CHH), 5.11 (dd, J=5.1, 13.2 Hz, 1H, CH), 5.24 (s, 2H, CH$_2$), 7.25-7.41 (m, 4H, Ar), 7.42-7.57 (m, 3H, Ar), 10.96 (s, 1H, NH); $^{13}$C NMR (DMSO-d$_6$) δ 13.64, 19.44, 22.33, 28.41, 31.16, 44.85, 45.07, 45.73, 48.88, 51.56, 56.81, 60.27, 69.36, 114.97, 115.22, 127.70, 128.95, 129.78, 129.95, 133.30, 135.53, 137.13, 153.48, 165.48, 167.97, 170.95, 172.80; LCMS: MH=519; Anal Calcd for C$_{27}$H$_{30}$N$_4$O$_5$+0.6 H$_2$O: C, 65.79; H, 6.70; N, 10.58; Found: C, 65.76; H, 6.59; N, 10.56.

5.266 3-(1-Oxo-4-((4-((4-(Pyrimidin-2-yl)Piperazin-1-yl)Methyl)Benzyl)Oxy)Isoindolin-2-yl)Piperidine-2,6-Dione

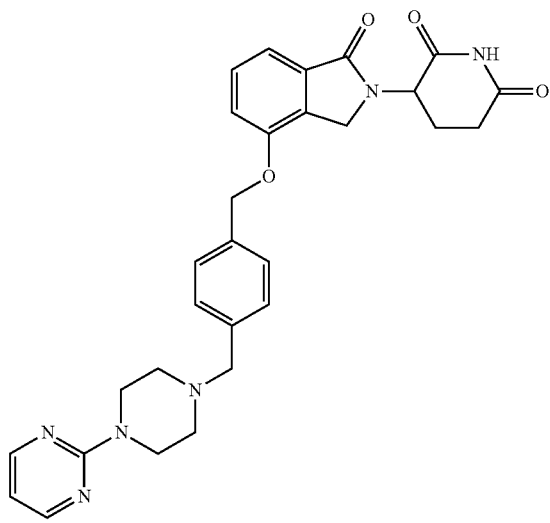 [SMILES: O=C1CCC(N2Cc3c(OCc4ccc(CN5CCN(c6ncccn6)CC5)cc4)cccc3C2=O)C(=O)N1]

A mixture of 3-(4-(4-(bromomethyl)benzyloxy)-1-oxoisoindolin-2-yl)piperidine-2,6-dione (205 mg, 0.462 mmol) in MeCN (8 mL) was stirred at room temperature. To the solution was added 2-(piperazin-1-yl)pyrimidine (81 mg, 0.495 mmol), followed by DIEA (0.145 mL, 0.832 mmol). The mixture was kept at room temperature for 4 h. The crude rxn mixture was diluted with EtOAc. The organic layer was washed with 1N NaHCO$_3$ (2×25 mL), brine and dried over Na$_2$SO$_4$. The solvent was removed in vacuo to give 3-(1-oxo-4-((4-((4-(pyrimidin-2-yl)piperazin-1-yl)methyl)benzyl)oxy)isoindolin-2-yl)piperidine-2,6-dione as a white solid (244 mg, 100% yield): HPLC: Waters Symmetry C$_{18}$, 5 μm, 3.9×150 mm, 1 ml/min, 240 nm, 20/80 CH$_3$CN/0.1% H$_3$PO$_4$, 4.26 min (97.3%), mp: 142-144° C.; $^1$H NMR (DMSO-d$_6$) δ 1.89-2.06 (m, 1H, CHH), 2.41 (t, J=4.9 Hz, 4H, CH$_2$, CH$_2$), 2.47 (br. s., 1H, CHH), 2.53-2.63 (m, 1H, CHH), 2.83-2.99 (m, 1H, CHH), 3.52 (s, 2H, CH$_2$), 3.72 (t, J=4.7 Hz, 4H, CH$_2$, CH$_2$), 4.26 (d, J=17.6 Hz, 1H, CHH), 4.43 (d, J=17.6 Hz, 1H, CHH), 5.11 (dd, J=5.2, 13.1 Hz, 1H, CH), 5.24 (s, 2H, CH$_2$), 6.61 (t, J=4.7 Hz, 1H, Pyr), 7.27-7.39 (m, 4H, Ar), 7.42-7.55 (m, 3H, Ar), 8.34 (d, J=4.7 Hz, 2H, Pyr), 10.97 (s, 1H, NH). See ~0.15 eq. of EtOAc in H-NMR. $^{13}$C NMR (DMSO-d$_6$) δ 22.33, 31.16, 43.26, 45.07, 51.56, 52.35, 61.72, 69.39, 110.01, 114.96, 115.20, 127.64, 128.94, 129.78, 129.93, 133.30, 135.30, 137.89, 153.49, 157.82, 161.16, 167.97, 170.95, 172.80; LCMS: MH=527; Anal Calcd for C$_{29}$H$_{30}$N$_6$O$_4$+0.49 H$_2$O+0.15 EtOAc: C, 64.80; H, 5.91; N, 15.32; Found: C, 64.80; H, 5.75; N, 15.32.

5.267 3-(1-Oxo-4-((4-((3-Oxo-4-(Pyridin-2-yl)Piperazin-1-yl)Methyl)Benzyl)Oxy)Isoindolin-2-yl)Piperidine-2,6-Dione

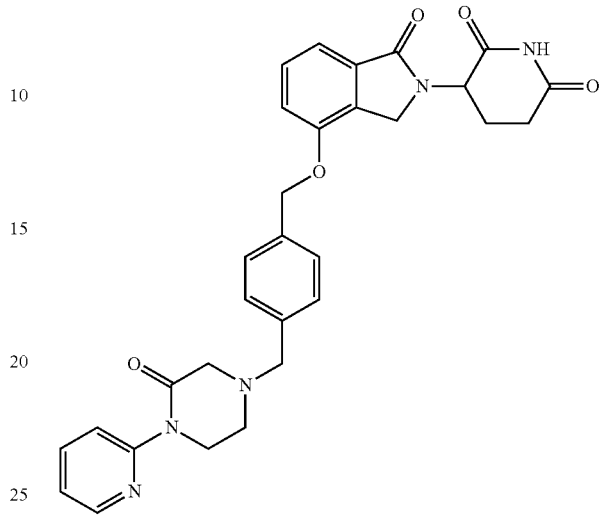

To a suspension of (S)-(4-(4-(bromomethyl)benzyloxy)-1-oxoisoindolin-2-yl)piperidine-2,6-dione (200 mg, 0.451 mmol) and 1-(pyridin-2-yl)piperazin-2-one dihydrochloride (124 mg, 0.496 mmol) in dry MeCN (5 mL), was added DIEA (0.276 mL, 1.579 mmol). The solids dissolved with agitation to give a yellow solution which was warmed up to 40° C. for 3 days. The reaction mixture was diluted with EtOAc (~150 mL) and washed with 1 N NaHCO$_3$ (2×30 mL) and brine. The clear organic layer was dried over Na$_2$SO$_4$, filtered, and concentrated in vacuo to give a glassy residue. The residue was treated with water (30 mL) and the mixture was sonicated extensively to give a well-dispersed solid that was collected by filtration and washed with additional water (~45 mL). The cake was slurried in Et$_2$O, triturated with aid of a spatula, and then filtered. This process was repeated 4 times (total Et$_2$O filtrate volume ~125 mL). The cake was suction dried and then dried in a vacuum oven to give an off-white solid (143 mg). The solid was dissolved in DMF (10 mL) and purified using reversed-phase preparatory HPLC. The product was eluted with an acetonitrile/water gradient (0.1% formic acid in both mobile phases, 5% to 80% MeCN over 20 minutes) and fractions were collected by mass trigger. The desired fractions were combined and concentrated in vacuo and the residue was treated with water and sonicated to give a white slurry. The solid was filtered and then dried in a vacuum oven at 50° C. overnight to give 3-(1-oxo-4-((4-((3-oxo-4-(pyridin-2-yl)piperazin-1-yl)methyl)benzyl)oxy)isoindolin-2-yl)piperidine-2,6-dione as a white solid (72 mg, 30% yield): HPLC: Waters Symmetry C$_{18}$, 5 μm, 3.9×150 mm, 1 ml/min, 240 nm, 20/80 CH$_3$CN/0.1% H$_3$PO$_4$, 4.98 min (97.9%); mp: 224-226° C.; $^1$H NMR (DMSO-d$_6$) δ 1.85-2.05 (m, 1H, CHH), 2.35-2.48 (m, 1H, CHH), 2.57 (d, J=18.3 Hz, 1H, CHH), 2.80 (t, J=5.0 Hz, 2H, CH$_2$), 2.84-3.00 (m, 1H, CHH), 3.23 (s, 2H, CH$_2$), 3.64 (s, 2H, CH$_2$), 3.87 (t, J=5.4 Hz, 2H, CH$_2$), 4.26 (d, J=17.6 Hz, 1H, CHH), 4.43 (d, J=17.6 Hz, 1H, CHH), 5.11 (dd, J=5.2, 13.1 Hz, 1H, CH), 5.25 (s, 2H, CH$_2$), 7.22 (ddd, J=2.3, 4.9, 6.0 Hz, 1H, Ar), 7.33 (dd, J=1.6, 7.8 Hz, 2H, Ar), 7.37-7.44 (m, 2H, Ar), 7.44-7.55 (m, 3H, Ar), 7.74-7.88 (m, 2H, Ar), 8.44 (dt, J=1.4, 4.7 Hz, 1H, Ar), 10.96 (s, 1H, NH); $^{13}$C NMR (DMSO-d$_6$) δ 22.33, 31.16, 45.07, 46.11, 48.89, 51.56, 57.64, 60.09, 69.38, 114.99, 115.23, 119.62, 120.83, 127.74, 129.01, 129.80, 129.95, 133.30, 135.62, 136.99, 137.31, 147.70, 153.07, 153.48, 166.92, 167.97, 170.95, 172.80; LCMS: MH=540; Anal Calcd for C$_{30}$H$_{29}$N$_5$O+0.49 H$_2$O+ 0.15 EtOAc: C, 64.80; H, 5.91; N, 15.31; Found: C, 64.80; H, 5.75; N, 15.32.

5.268 3-(1-Oxo-4-((4-((4-(2,2,2-Trifluoroethyl)Piperazin-1-yl)Methyl)Benzyl)Oxy)Isoindolin-2-yl)Piperidine-2,6-Dione

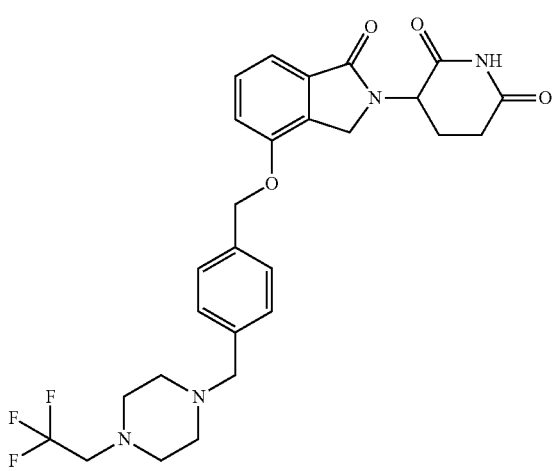 [SMILES: O=C1CCC(N2Cc3c(OCc4ccc(CN5CCN(CC(F)(F)F)CC5)cc4)cccc3C2=O)C(=O)N1]

A 20-mL reaction vial was charged with (S)-3-(4-(4-(bromomethyl)benzyloxy)-1-oxoisoindolin-2-yl)piperidine-2,6-dione (307 mg, 0.693 mmol), 1-(2,2,2-trifluoroethyl)piperazine (170 mg, 0.706 mmol), and catalytic tetrabutylammonium bromide (22.33 mg, 0.069 mmol). To the mixture was added dry MeCN (5 mL) followed by DIEA (0.423 mL, 2.424 mmol). Agitation resulted in a clear yellow solution that stirred at room temperature overnight. The crude mixture was partitioned between EtoAc (~150 mL) and 1N NaHCO$_3$ (~50 mL). The organic layer was washed twice more with 1 N NaHCO$_3$ (2×35 mL) and brine, dried (Na$_2$SO$_4$), and concentrated in vacuo to give a glassy solid. Et$_2$O (~30 mL) was added and the mixture was sonicated extensively until a well-dispersed slurry was obtained. To the mixture, n-hexanes (~30 mL) were added with intermittent sonication to further break up remaining solid aggregates. The mixture was stirred at room temperature overnight and then filtered on a medium fritted funnel with suction. Residual solid in flask was transferred to funnel with more n-hexanes (~30 mL). The solid was suction dried and then triturated with H$_2$O (20 mL). The remaining solid was collected on a filter funnel and the cake washed with water (~250 mL), suction dried, and then dried further in vacuum oven at 50° C. to give 3-(1-oxo-4-((4-((4-(2,2,2-trifluoroethyl)piperazin-1-yl)methyl)benzyl)oxy)isoindolin-2-yl)piperidine-2,6-dione as a pale yellow solid (262 mg, 71% yield): HPLC: Waters Symmetry C$_{18}$, 5 μm, 3.9×150 mm, 1 ml/min, 240 nm, 22/78 CH$_3$CN/0.1% H$_3$PO$_4$, 4.49 min (94.7%); mp: 133-135° C.; $^1$H NMR (DMSO-d$_6$) δ 1.88-2.05 (m, 1H, CHH), 2.22-2.48 (m, 5H, CH$_2$, CH$_2$, CHH), 2.52-2.71 (m, 5H, CH$_2$, CH$_2$, CHH), 2.82-3.02 (m, 1H, CHH), 3.13 (q, J=10.3 Hz, 2H, CH$_2$CF$_3$), 3.46 (s, 2H, CH$_2$N), 4.25 (d, J=17.4 Hz, 1H, lactam CHH), 4.42 (d, J=17.6 Hz, 1H, lactam CHH), 5.11 (dd, J=4.9, 13.2 Hz, 1H, alpha-CH), 5.22 (s, 2H, CH$_2$O), 7.26-7.39 (m, 4H, Ar), 7.40-7.56 (m, 3H, Ar), 10.97 (s, 1H, NH); $^{13}$C NMR (DMSO-d$_6$) δ 22.33, 31.16, 45.06, 51.55, 52.42, 53.06, 56.81 (q, J=29.7 Hz, CCF$_3$), 61.56, 69.39, 114.96, 115.20, 125.90 (q, J=280.6 Hz, CF$_3$), 127.58, 128.85, 129.78, 129.93, 133.28, 135.21, 137.95, 153.49, 167.97, 170.95, 172.80. Outer signals of quartet at 125.90 are too weak to be observed. LCMS: MH=531; Anal Calcd for C$_{27}$H$_{29}$F$_3$N$_4$O$_4$.+0.24 H$_2$O: C, 60.63; H, 5.56; N, 10.47; F, 10.66; Found: C, 60.64; H, 5.49; N, 10.20; F, 9.56.

5.269 3-(1-Oxo-4-((4-(((S)-2-(Trifluoromethyl)Piperidin-1-yl)Methyl)Benzyl)Oxy)Isoindolin-2-yl)Piperidine-2,6-Dione

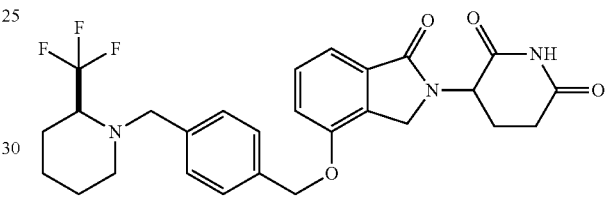

In a 20-mL reaction vial, (S)-3-(4-(4-(bromomethyl)benzyloxy)-1-oxoisoindolin-2-yl)piperidine-2,6-dione (350 mg, 0.790 mmol) was dissolved in dry MeCN (5 m). To the solution was added (S)-2-(trifluoromethyl)piperidine (140 mg, 0.916 mmol) followed by DIEA (0.345 mL, 1.974 mmol). The mixture was stirred at room temperature for 15 h and then at 70° C. for 8 h overnight. The reaction mixture was partitioned between EtOAc (~100 mL) and water (~25 mL). The organic layer was washed with 1 N NaHCO$_3$ (~75 mL) and brine, dried (Na$_2$SO$_4$), and concentrated in vacuo to give a white solid. The solid was dissolved in DMF (8 mL), passed through a syringe filter, and the filtrate injected onto a reversed-phase preparatory HPLC. The product was eluted with an acetonitrile/water gradient (0.1% formic acid in both mobile phases, 5% to 95% MeCN over 20 minutes) and fractions were collected by mass trigger. The desired fractions were combined and concentrated in vacuo to remove all the MeCN and most of the water, producing a white slurry (~20 mL). The solid was collected by filtration, the cake suction dried, and then dried in a vacuum oven at 50° C. for 5 h to give 3-(1-oxo-4-((4-(((S)-2-(trifluoromethyl)piperidin-1-yl)methyl)benzyl)oxy)isoindolin-2-yl)piperidine-2,6-dione as a white solid (506 mg, 51% yield): HPLC: Waters Symmetry C$_{18}$, 5 μm, 3:9×150 mm, 1 ml/min, 240 nm, 45/55 CH$_3$CN/0.1% H$_3$PO$_4$, 3.46 min (97.6%); mp: 120-122; $^1$H NMR (DMSO-d$_6$) δ 1.38-1.63 (m, 4H, CH$_2$, CH$_2$), 1.67-1.90 (m, 2H, CH$_2$), 1.91-2.05 (m, 1H, CHH), 2.36-2.48 (m, 2H, CHH, CHH), 2.53-2.62 (m, 1H, CHH), 2.64-2.78 (m, 1H, CHH), 2.82-2.99 (m, 1H, CHH), 3.46 (qt, J=4.9, 9.5 Hz, 1H, CHCF$_3$), 3.84 (s, 2H, CH$_2$), 4.25 (d, J=17.4 Hz, 1H, CHH), 4.42 (d, J=17.4 Hz, 1H, CHH), 5.11 (dd, J=5.2, 13.1 Hz, 1H, CH), 5.23 (s, 2H, CH$_2$), 7.29-7.39 (m, 4H, Ar), 7.41-7.54 (m, 3H, Ar), 10.97 (s, 1H, NH); $^{13}$C NMR (DMSO-d$_6$) δ 19.64, 22.31, 22.94, 31.16, 45.06, 46.15, 51.55, 58.03 (q, J=24.2 Hz, CCF$_3$), 57.84, 69.39, 114.94, 115.20, 126.02, 127.70, 128.14, 129.78, 129.87, 129.95, 133.28, 135.25, 139.12, 153.49, 167.97, 170.95, 172.80. CF$_3$ quartet is not assigned. One carbon signal in aliphatic region is not observed; possibly overlapped with another signal; LCMS: MH=516; Anal Calcd for C$_{27}$H$_{28}$F$_3$N$_3$O$_4$.+0.5 H$_2$O: C, 61.83; H, 5.57; N, 8.01; F, 10.87; Found: C, 61.92; H, 5.48; N, 7.94; F, 10.08.

5.270 3-(4-{4-[4-(3,5-Difluoro-Phenyl)-Piperidin-1-ylmethyl]-Benzyloxy}-1-Oxo-1,3-Dihydro-Isoindol-2-yl)-Piperidine-2,6-Dione, Hydrochloride

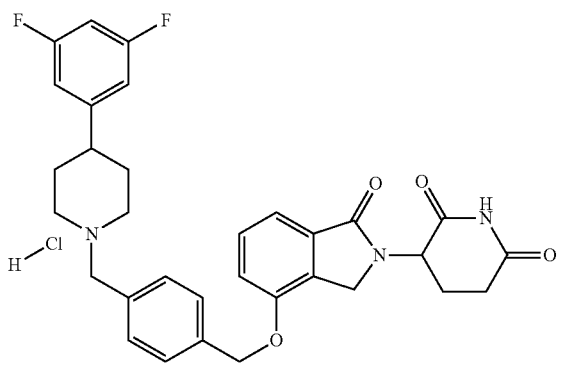

To the CH$_2$Cl$_2$ solution of 3-(4-(4-(bromomethyl)benzyloxy)-1-oxoisoindolin-2-yl)piperidine-2,6-dione (350 mg, 0.790 mmol) was added DIPEA (0.414 ml, 2.369 mmol) and 4-(3,5-difluorophenyl)piperidine (156 mg, 0.790 mmol) at room temperature overnight, added water (20 mL) and extracted. The organic layer was concentrated and the resulted solid was purified on silica gel column eluted with CH$_2$Cl$_2$/MeOH to give a white solid. The solid was dissolved in CH$_2$Cl$_2$ (20 mL) and to it was added 3 mL of HCl (2.0M in ether). The mixture was stirred at room temperature for 1 hour. The resulted suspension was filtered to give 3-(4-{4-[4-(3,5-difluoro-phenyl)-piperidin-1-ylmethyl]-benzyloxy}-1-oxo-1,3-dihydro-isoindol-2-yl)-piperidine-2,6-dione, hydrochloride as a white solid (0.27 g, 61%). Melting point: 281-283° C. LC-MS m/e=560. HPLC Waters Symmetry C-18, 3.9×150 mm, 5 micro, 1 mL/min, 240 nm, gradient 5/95 to 5/95 CH$_3$CN/0.1% H$_3$PO$_4$ in H$_2$O during 5 min and stay at 95/5 for 5 min: 7.05 min (98.6%). $^1$H NMR (DMSO-d$_6$) δ 1.89-2.14 (m, 5H, CH$_2$, CH$_2$, CHH), 2.36-2.45 (m, 1H, CHH), 2.55-2.64 (m, 1H, CHH), 2.79-2.95 (m, 2H, CHH), 2.95-3.10 (m, J=18.5 Hz, 2H, CH$_2$), 3.42 (d, J=11.9 Hz, 2H, CH$_2$), 4.22-4.50 (m, 4H, CH$_2$, CH$_2$), 5.12 (dd, J=5.1, 13.2 Hz, 1H, NCH), 5.31 (s, 2H, CH$_2$), 6.96 (dd, J=2.1, 8.9 Hz, 2H, Ar), 7.04-7.16 (m, 1H, Ar), 7.29-7.38 (m, 2H, Ar), 7.43-7.54 (m, 1H, Ar), 7.55-7.69 (m, 4H, Ar), 10.66 (br. s., 1H, HCl), 10.97 (s, 1H, NH). $^{13}$C NMR (DMSO-d$_6$) δ 22.40, 29.02, 31.21, 38.24, 45.09, 51.30, 51.61, 58.65, 69.03, 101.73, 102.06, 102.40, 109.69, 109.79, 109.91, 110.01, 115.00, 115.39, 127.85, 128.03, 129.36, 129.85, 129.98, 131.09, 131.63, 133.38, 138.07, 148.79, 148.91, 153.37, 160.92, 164.00, 164.17, 167.96, 170.98, 172.83; Anal Calcd for C$_{32}$H$_{31}$F$_2$N$_3$O$_4$HCl+1.3 H$_2$O, C: 62.04; H: 5.63%; N: 6.78%; Found: C: 61.73; H: 5.56%; N: 6.72%.

5.271 3-(4-{4-[4-(2,4-Difluoro-Phenyl)-Piperidin-1-ylmethyl]-Benzyloxy}-1-Oxo-1,3-Dihydro-Isoindol-2-yl)-Piperidine-2,6-Dione Hydrochloride

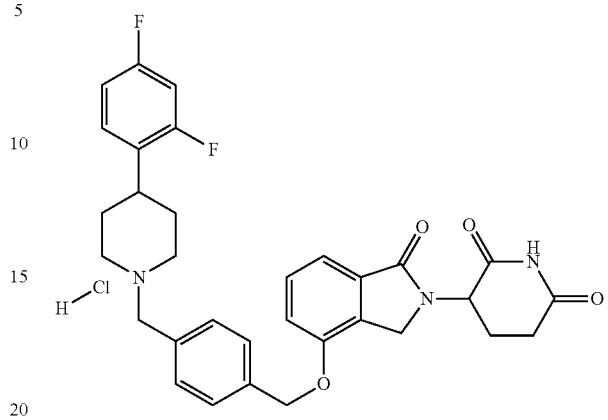

To the CH$_2$Cl$_2$ solution of 3-(4-(4-(bromomethyl)benzyloxy)-1-oxoisoindolin-2-yl)piperidine-2,6-dione (350 mg, 0.790 mmol) and 4-(2,4-difluorophenyl)piperidine (171 mg, 0.869 mmol) was added N-ethyl-N-isopropylpropan-2-amine (0.422 ml, 2.369 mmol). The mixture was stirred at room temperature for 4 hours. Water (15 mL) was added to the reaction mixture and extracted. The organic layer was concentrated and the solid was dissolved in CH$_2$Cl$_2$. The solution was added HCl (2 mL, 2.0 M in ether) and stirred for 1 hours. The suspension was filtered to give 3-(4-{4-[4-(2,4-Difluoro-phenyl)-piperidin-1-ylmethyl]-benzyloxy}-1-oxo-1,3-dihydro-isoindol-2-yl)-piperidine-2,6-dione hydrochloride as a white solid (0.18 g, 40%). Melting point: 274-276° C. LC-MS m/e=560. HPLC Waters Symmetry C-18, 3.9×150 mm, 5 micro, 1 mL/min, 240 nm, gradient 5/95 to 5/95 CH$_3$CN/0.1% H$_3$PO$_4$ in H$_2$O during 5 min and stay at 95/5 for 5 min:7.03 min (94%). $^1$H NMR (DMSO-d$_6$) δ 1.81-2.21 (m, 5H, CH$_2$, CH$_2$, CH), 2.35-2.48 (m, 1H, CHH), 2.53-2.66 (m, 1H, CHH), 2.82-2.99 (m, 1H, CHH), 3.09 (d, J=10.0 Hz, 3H, CH$_2$, CHH), 3.42 (d, J=11.7 Hz, 2H, CH$_2$), 4.22-4.50 (m, 4H, CH$_2$, CH$_2$), 5.12 (dd, J=4.9, 13.2 Hz, 1H, CHN), 5.31 (s, 2H, CH$_2$), 7.04-7.15 (m, 1H, Ar), 7.16-7.27 (m, 1H, Ar), 7.27-7.37 (m, 2H, Ar), 7.44-7.54 (m, 1H, Ar), 7.56-7.67 (m, 3H, Ar), 10.52 (br. s., 1H, HCl), 10.97 (s, 1H, NH); $^{13}$C NMR (DMSO-d$_6$) δ 22.40, 28.37, 31.21, 32.04, 45.09, 51.48, 51.61, 58.84, 69.03, 103.60, 103.95, 104.30, 111.58, 111.83, 115.00, 115.39, 127.85, 128.73, 128.85, 128.93, 129.36, 129.85, 129.98, 131.62, 133.38, 138.09, 153.37, 161.62, 167.96, 170.98, 172.83; Anal Calcd for C$_{32}$H$_{31}$F$_2$N$_3$O$_4$HCl+0.8 H$_2$O; C: 62.96%; H: 5.55%; N: 6.88%; Found: C: 62.83%; H: 5.38%; N: 6.87%.

5.272 3-(1-Oxo-4-{4-[4-(2,2,2-Trifluoro-Acetyl)-Piperazin-1-ylmethyl]-Benzyloxy}-1,3-Dihydro-Isoindol-2-yl)-Piperidine-2,6-Dione

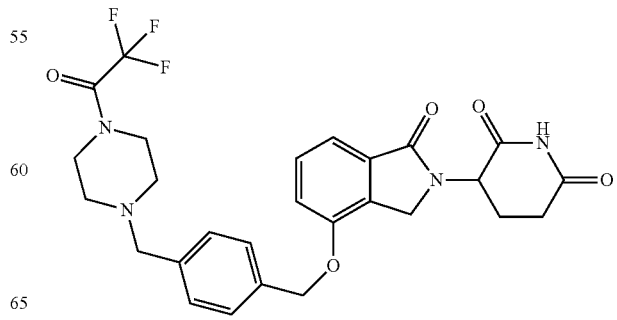

To the stirred solution of 3-(4-(4-(bromomethyl)benzyloxy)-1-oxoisoindolin-2-yl)piperidine-2,6-dione (300 mg, 0.68 mmol) in DCM (7 mL) at room temperature was added the solution of 2,2,2-trifluoro-1-(piperazin-1-yl)ethanone (185 mg, 1.0 mmol) in DCM (1 mL) followed by the addition of DIPEA (0.236 ml, 1.4 mmol). The resulting solution was stirred at room temperature for 7.5 hrs and the reaction mostly completed. The reaction mixture was added by DCM (30 mL) and water (20 mL). The mixture was extracted. The organic layer was dried by $MgSO_4$ and concentrated under vacuo. The residue was purified by ISCO to give a white solid which was further purified by being stirred in EtOAc (3 mL) to give 3-(1-Oxo-4-{4-[4-(2,2,2-trifluoro-acetyl)-piperazin-1-ylmethyl]-benzyloxy}-1,3-dihydro-isoindol-2-yl)-piperidine-2,6-dione as a white solid (180 mg, 49% yield). HPLC: Waters Symmetry C-18, 3.9×150 mm, 5 am, 1 mL/min, 240 nm, 20/80, ($CH_3CN$/0.1% $H_3PO_4$), 5.21 min (99.9%); mp: 125-127° C.; $^1H$ NMR (DMSO-$d_6$) δ 1.91-2.05 (m, 1H, CHH), 2.38-2.48 (m, 5H, CHH, $CH_2$, $CH_2$), 2.53-2.65 (m, 1H, CHH), 2.85-3.01 (m, 1H, CHH), 3.47-3.70 (m, 6H, $CH_2$, $CH_2$, $CH_2$), 4.17-4.55 (m, 2H, CHH, CHH), 5.11 (dd, J=5.1, 13.2 Hz, 1H, CHH), 5.23 (s, 2H, $CH_2$), 7.33 (dd, J=4.1, 7.8 Hz, 4H, Ar), 7.40-7.56 (m, 3H, Ar), 10.97 (s, 1H, NH); $^{13}C$ NMR (DMSO-$d_6$) δ 21.82, 30.65, 42.42, 44.54, 44.81, 51.02, 51.14, 51.81, 60.57, 68.81, 114.43, 114.70, 127.15, 128.45, 129.28, 129.41, 132.78, 134.93, 136.90, 152.96, 167.46, 170.44, 172.29; LCMS MH=545; Anal. Calcd for $C_{27}H_{27}F_3N_4O_5$+0.3$H_2O$: C, 58.97; H, 5.06; N, 10.19; Found: C, 58.85; H, 4.82; N, 10.03.

5.273 3-(4-{4-[4-(4-Fluoro-Phenyl)-Piperazin-1-ylmethyl]-Benzyloxy}-1-Oxo-1, 3-Dihydro-Isoindol-2-yl)-Piperidine-2,6-Dione, Dihydrochloride

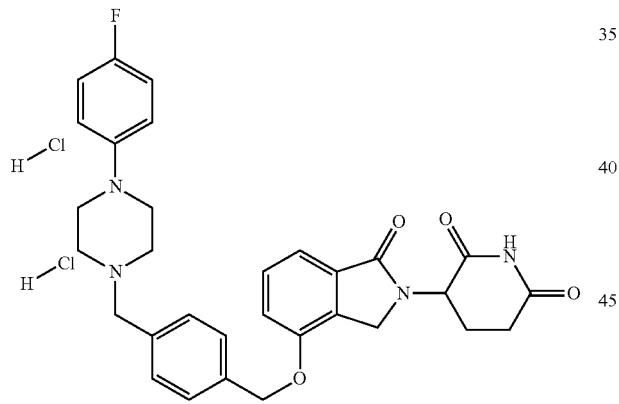

The mixture was stirred at room temperature overnight. The reaction mixture was added water (15 mL) and extracted. The organic layer was concentrated and the resulted solid was dissolved in $CH_2Cl_2$ (35 mL) and 2M HCl in ether was added dropwise. The mixture was stirred at room temperature for 2 hours. The suspension was filtered to give 3-(4-{4-[4-(4-fluoro-phenyl)-piperazin-1-ylmethyl]-benzyloxy}-1-oxo-1, 3-dihydro-isoindol-2-yl)-piperidine-2,6-dione, dihydrochloride as white solid (230 mg, 54%). Melting point: 191-193° C. LC-MS m/e=543. HPLC Waters Symmetry C-18, 3.9×150 mm, 5 micro, 1 mL/min, 240 nm, gradient 5/95 to 5/95 $CH_3CN$/0.1% $H_3PO_4$ in $H_2O$ during 5 min and stay at 95/5 for 5 min: 6.67 min (96%). $^1H$ NMR (DMSO-$d_6$) δ 1.80-2.09 (m, 1H, CHH), 2.36-2.45 (m, J=4.3 Hz, 1H, CHH), 2.58 (d, J=18.5 Hz, 1H, CHH), 2.81-3.00 (m, 1H, CHH), 3.16 (d, J=8.9 Hz, 4H, $CH_2$, $CH_2$), 3.34 (d, J=8.1 Hz, 2H, $CH_2$), 3.63-3.80 (m, 2H, $CH_2$), 4.15-4.62 (m, 4H, $CH_2$, $CH_2$), 5.12 (dd, J=5.1, 13.2 Hz, 1H, CHN), 5.30 (s, 2H, $CH_2$), 6.89-7.06 (m, 2H, Ar), 7.04-7.16 (m, 2H, Ar), 7.26-7.42 (m, 2H, Ar), 7.42-7.55 (m, 1H, Ar), 7.54-7.64 (m, 2H, Ar), 7.64-7.79 (m, 2H, Ar), 10.97 (s, 1H, nh), 11.46 (br. s., 1H, HCl); $^{13}C$ NMR (DMSO-$d_6$) δ 22.39, 31.21, 45.10, 45.91, 50.16, 51.61, 58.05, 69.03, 114.98, 115.36, 115.65, 117.78, 117.88, 127.85, 129.24, 129.85, 130.00, 131.69, 133.37, 138.06, 146.34, 153.37, 154.99, 158.12, 167.98, 170.96, 172.83; Anal Calcd for $C_{31}H_{31}FN_4O_4$+1.8 HCl+2$H_2O$: C, 57.79%; H, 5.76%; N, 8.70%; Cl, 9.90%; Found: C, 57.61%; H, 5.64%; N, 8.60%; Cl, 9.54%.

5.274 3-(4-{4-[4-(4-Fluoro-Benzyl)-Piperazin-1-ylmethyl]-Benzyloxy}-1-Oxo-1,3-Dihydro-Isoindol-2-yl)-Piperidine-2,6-Dione

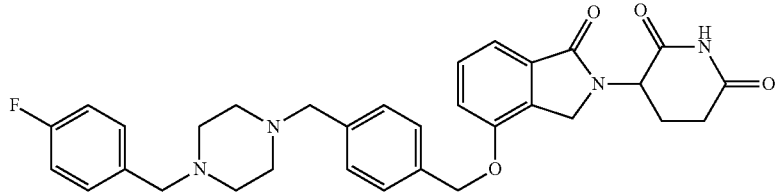 [SMILES: O=C1CCC(N2Cc3c(OCc4ccc(CN5CCN(Cc6ccc(F)cc6)CC5)cc4)cccc3C2=O)C(=O)N1]

To the $CH_2Cl_2$ solution of 3-(4-(4-((4-(4-fluorophenyl)piperazin-1-yl)methyl)benzyloxy)-1-oxoisoindolin-2-yl)piperidine-2,6-dione (0.23 g, 0.424 mmol) and 1-(4-fluorophenyl)piperazine (142 mg, 0.790 mmol) was added N-ethyl-N-isopropylpropan-2-amine (422 μl, 2.369 mmol).

To the $CH_3CN$ (10 ml) solution of 3-(4-(4-(bromomethyl)benzyloxy)-1-oxoisoindolin-2-yl)piperidine-2,6-dione (0.40 g, 0.902 mmol) was added 1-(4-fluorobenzyl)piperazine (0.193 g, 0.993 mmol) and N-ethyl-N-isopropylpropan-2-amine (0.298 ml, 1.805 mmol). The solution was stirred at room temperature for two hours. Water (20 ml) was added to the reaction solution and extracted with methylene chloride (2×30 ml), washed with brine, evaporated and the off-white solid was purified by silica gel column (MeOH/CH$_2$Cl$_2$) to give 3-(4-{4-[4-(4-Fluoro-benzyl)-piperazin-1-ylmethyl]-benzyloxy}-1-oxo-1,3-dihydro-isoindol-2-yl)-piperidine-2,6-dione as a white solid (0.336 g, 66.9% yield); mp, 222-224° C. HPLC: Waters Symmetry C-18, 3.9×150 mm, 5 μm, 1 mL/min, 240 nm, gradient from 10/90 to 95/05 in 5 min, isocratic at 95/05 for 5 min (CH$_3$CN/0.1% H$_3$PO$_4$), 4.67 min (97.01%). $^1$H NMR (DMSO-d$_6$) δ 1.92-2.04 (m, 1H, CHH), 2.20-2.47 (m, 8H, 2CHH, 3CH$_2$), 2.55-2.66 (m, 1H, CHH), 2.82-3.01 (m, 1H, CHH), 3.30-3.35 (m, 2H, CH$_2$), 3.45 (s, 2H, CH$_2$), 4.19-4.47 (m, 2H, CH$_2$), 5.11 (dd, J=5.1, 13.2 Hz, 1H, NCH), 5.22 (s, 2H, CH$_2$), 7.07-7.17 (m, 2H, Ar), 7.26-7.37 (m, 6H, Ar), 7.40-7.53 (m, 3H, Ar), 10.97 (s, 1H, NH). $^{13}$C NMR (DMSO-d$_6$) δ 22.36, 31.21, 45.10, 51.59, 52.48, 52.58, 61.08, 61.71, 69.44, 114.68, 114.95, 115.23, 127.62, 128.86, 129.81, 129.95, 130.55 (d, J$_{C-F}$=10), 133.31, 134.37, 135.19, 138.12, 153.51, 161.17 (d, J$_{C-F}$=250), 168.01, 170.96, 172.82. LC/MS m/e=557. Anal Calcd for C$_{32}$H$_{33}$N$_4$O$_4$F: C, 69.05; H, 5.98; N, 10.07. Found: C, 68.93; H, 5.99; N, 10.01.

5.275 3-(1-Oxo-4-{4-[4-(2,2,2-Trifluoro-Ethanesulfonyl)-Piperazin-1-ylmethyl]-Benzyloxy}-1,3-Dihydro-Isoindol-2-yl)-Piperidine-2,6-Dione

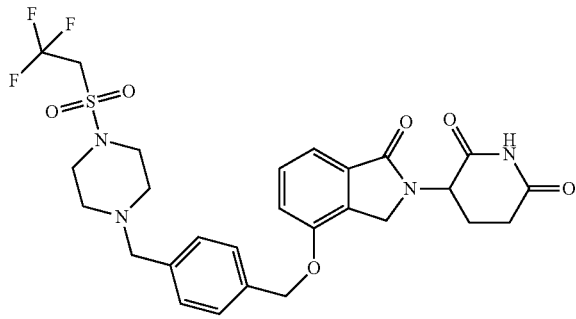 [SMILES: O=C1CCC(N2Cc3c(OCc4ccc(CN5CCN(S(=O)(=O)CC(F)(F)F)CC5)cc4)cccc3C2=O)C(=O)N1]

Step 1: 4-(2,2,2-Trifluoro-ethanesulfonyl)-piperazine-1-carboxylic acid tert-butyl ester To the stirred solution of tert-butyl piperazine-1-carboxylate (0.850 g, 4.56 mmol) and TEA (0.76 ml, 5.48 mmol) in THF (10 mL) at 0° C. was added 2,2,2-trifluoroethane sulfonyl chloride (1.0 g, 5.48 mmol) in THF (0.5 mL). The resulting suspension was stirred at 0° C. for 1.5 hrs and the reaction mixture was diluted by EtOAC (30 mL). The mixture was washed with water (15 mL), HCl (1N, aq, 15 mL) and NaHCO$_3$ (15 mL) and brine (20 mL). Organic layer was dried by MgSO$_4$ and concentrated under vacuo to give 4-(2,2,2-Trifluoro-ethanesulfonyl)-piperazine-1-carboxylic acid tert-butyl ester as a white solid (1.3 g, 86% yield). The compound was put to next step without further purification. $^1$H NMR (DMSO-d$_6$) δ 1.41 (s, 9H, tButyl), 3.12-3.26 (m, 4H, CH$_2$, CH$_2$), 3.36-3.48 (m, 4H, CH$_2$, CH$_2$), 4.52 (q, J=10.1 Hz, 2H, CH$_2$); LCMS MH (without boc)=233.

Step 2: 1-(2,2,2-Trifluoro-ethanesulfonyl)-piperazine To the stirred solution of tert-butyl 4-(2,2,2-trifluoroethylsulfonyl)piperazine-1-carboxylate (1.3 g, 3.9 mmol) in DCM (20 mL) at room temperature was added TFA (3.0 mL, 39.1 mmol). The resulting solution was stirred at room temperature 15 hrs and the reaction mixture was diluted by DCM (30 mL) and added by NaHCO$_3$ (sat., aq, 15 mL) slowly to control the gas emission. The resulting mixture was stirred at room temperature for 10 mins and partitioned. The organic layer was washed with NaHCO$_3$ (sat., aq, 5 mL) and brine (20 mL). The combined aqueous layer was extracted with DCM (4×40 mL). Combined layers were dried by MgSO$_4$ and concentrated under vacuo to give 1-(2,2,2-Trifluoro-ethanesulfonyl)-piperazine as white solid (930 mg, 102% crude yield). $^1$H NMR (DMSO-d$_6$) δ 2.41 (br. s., 1H, NH), 2.64-2.85 (m, 4H, CH$_2$, CH$_2$), 3.02-3.20 (m, 4H, CH$_2$, CH$_2$), 4.46 (q, J=10.2 Hz, 2H, CH$_2$); LCMS MH=233.

Step 3: 3-(1-Oxo-4-{4-[4-(2,2,2-trifluoro-ethanesulfonyl)-piperazin-1-ylmethyl]-benzyloxy}-1,3-dihydro-isoindol-2-yl)-piperidine-2,6-dione To the stirred mixture of 3-(4-(4-(bromomethyl)benzyloxy)-1-oxoisoindolin-2-yl) piperidine-2,6-dione (350 mg, 0.79 mmol) and 1-(2,2,2-trifluoroethylsulfonyl) piperazine (183 mg, 0.79 mmol) in DCM (10 mL) was added DIPEA (0.28 ml, 1.56 mmol). The resulting mixture was stirred at room temperature for 3 days. The reaction mixture was diluted by DCM (30 mL) and the solution was washed with water (20 mL) and brine (20 mL). Organic layer was dried by MgSO$_4$ and concentrated under vacuo. The residue was purified by ISCO to give a glasslike solid. The solid was further purified by being stirred in acetonitrile (2 mL) and diethyl ether (30 mL) to give 3-(1-Oxo-4-{4-[4-(2,2,2-trifluoroethanesulfonyl)-piperazin-1-ylmethyl]-benzyloxy}-1,3-dihydro-isoindol-2-yl)-piperidine-2,6-dione as a white solid (277 mg, 59% yield). HPLC: Waters Symmetry C-18, 3.9×150 mm, 5 μm, 1 mL/min, 240 nm, 25/75, (CH$_3$CN/0.1% H$_3$PO$_4$), 3.10 min (99.2%); 213-215° C. (in house); $^1$H NMR (DMSO-d$_6$) δ 1.91-2.05 (m, 1H, CHH), 2.45 (d, J=8.7 Hz, 5H, CH$_2$, CH$_2$, CHH), 2.53-2.63 (m, 1H, CHH), 2.83-2.99 (m, 1H, CHH), 3.17-3.27 (m, 4H, CH$_2$, CH$_2$), 3.53 (s, 2H, CH$_2$), 4.25 (d, J=17.4 Hz, 1H, CHH), 4.36-4.58 (m, 3H, CH$_2$, CHH), 5.11 (dd, J=5.0, 13.1 Hz, 1H, CHH), 5.23 (s, 2H, CH$_2$), 7.33 (d, J=7.6 Hz, 4H, Ar), 7.39-7.53 (m, 3H, Ar), 10.97 (s, 1H, NH); $^{13}$C NMR (DMSO-d$_6$) δ 22.34, 31.18, 45.06, 45.15, 50.02 (q, J=29.2 Hz, CF$_3$), 51.56, 51.81, 61.10, 69.36, 114.97, 115.22, 123.22 (q, J=275.2 Hz, CF$_3$), 127.67, 128.91, 129.80, 129.93, 133.30, 135.43, 137.57, 153.48, 167.97, 170.96, 172.81; LCMS MH=595; Anal. Calcd for C$_{27}$H$_{29}$F$_3$N$_4$O$_6$S+0.5H$_2$O: C, 53.73; H, 5.01; N, 9.28; Found: C, 53.67; H, 5.03; N, 9.17.

5.276 3-(4-{4-[4-(4-Fluoro-Benzenesulfonyl)-Piperazin-1-ylmethyl]-Benzyloxy}-1-Oxo-1,3-Dihydro-Isoindol-2-yl)-Piperidine-2,6-Dione

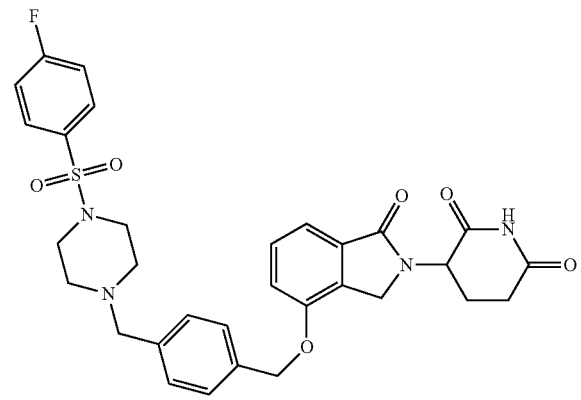 [SMILES: O=C1CCC(N2Cc3c(OCc4ccc(CN5CCN(S(=O)(=O)c6ccc(F)cc6)CC5)cc4)cccc3C2=O)C(=O)N1]

To the stirred solution of 3-(4-(4-(bromomethyl)benzyloxy)-1-oxoisoindolin-2-yl)piperidine-2,6-dione (330 mg, 0.7 mmol) in DCM (10 mL) was added 1-(4-fluoro phenylsulfonyl)piperazine (236 mg, 0.97 mmol) and DIPEA (0.26 mL, 1.5 mmol). The resulting solution was stirred at room temperature for 20 hrs and then were added DCM (20 mL) and water (20 mL). The mixture was extracted and the organic layer was washed with brine (20 mL). Organic layer was dried by MgSO$_4$ and concentrated under vacuo. The residue was purified by ISCO to give a white solid. The solid was further purified by being stirred in acetonitrile and diethyl ether to give 3-(4-{4-[4-(4-Fluoro-benzene sulfonyl)-piperazin-1-ylmethyl]-benzyloxy}-1-oxo-1,3-dihydro-isoindol-2-yl)-piperidine-2,6-dione as a white solid (245 mg, 54% yield). HPLC: Waters Symmetry C-18, 3.9×150 mm, 5 μm, 1 mL/min, 240 nm, 25/75, (CH$_3$CN/0.1% H$_3$PO$_4$), 4.70 min (98.9%); mp: 192-194° C.; $^1$H NMR (DMSO-d$_6$) δ 1.91-2.04 (m, 1H, CHH), 2.34-2.47 (m, 5H, CH$_2$, CH$_2$, CHH), 2.53-2.63 (m, 1H, CHH), 2.82-3.01 (m, 5H, CHH, CH$_2$, CH$_2$), 3.47 (s, 2H, CH$_2$), 4.24 (d, J=17.6 Hz, H, CHH), 4.40 (d, J=17.6 Hz, 1H, CHH), 5.08 (dd, J=4.9, 8.1 Hz, 1H, CHH), 5.21 (s, 2H, CH$_2$), 7.25 (d, 2H, Ar), 7.29-7.34 (m, 2H, Ar), 7.40 (d, J=7.9 Hz, 2H, Ar), 7.44-7.56 (m, 3H, Ar), 7.73-7.87 (m, 2H, Ar), 10.96 (s, 1H, NH); $^{13}$C NMR (DMSO-d$_6$) δ 22.33, 31.16, 45.04, 45.90, 51.33, 51.53, 60.95, 69.31, 114.93, 115.20, 116.60 (d, J=23.25 Hz, Ar), 127.63, 128.79, 129.78, 129.90, 130.60 (d, J=9.75 Hz, Ar), 131.17, 133.27, 135.34, 137.51, 153.45, 162.62 (d, J=249.75 Hz, Ar), 167.97, 170.96, 172.81; LCMS MH=607; Anal. Calcd for C$_{31}$H$_{31}$FN$_4$O$_6$S+0.6H$_2$O: C, 60.30; H, 5.26; N, 9.07; Found: C, 60.18; H, 5.18; N, 9.09.

5.277 3-(4-{4-[4-(3,4-Difluoro-Benzenesulfonyl)-Piperazin-1-ylmethyl]-Benzyloxy}-1-Oxo-1,3-Dihydro-Isoindol-2-yl)-Piperidine-2,6-Dione

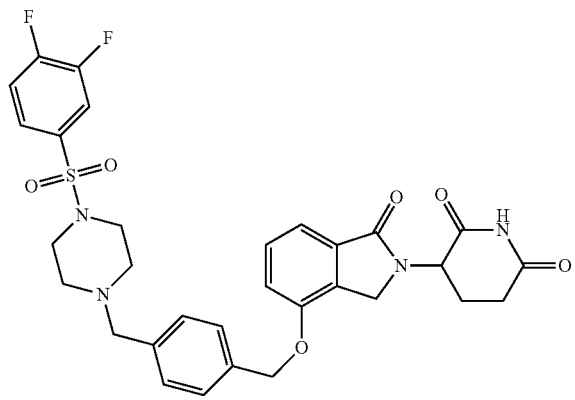 [SMILES: O=C1CCC(N2Cc3c(OCc4ccc(CN5CCN(S(=O)(=O)c6ccc(F)c(F)c6)CC5)cc4)cccc3C2=O)C(=O)N1]

To the stirred mixture of 3-(4-(4-(bromomethyl)benzyloxy)-1-oxoisoindolin-2-yl)piperidine-2,6-dione (350 mg, 0.79 mmol) and 1-(3,4-difluorophenylsulfonyl) piperazine (269 mg, 1.0 mmol) in DCM (10 mL) was added DIPEA (0.25 ml, 1.6 mmol). The resulting mixture was stirred at room temperature for 3 days. The reaction mixture was diluted by DCM (30 mL) and the solution was washed with water (20 mL), brine (2×20 mL). Organic layer was dried by MgSO$_4$ and filtered. The filtrate was concentrated under vacuo. And the residue was purified by ISCO to give a white solid. The solid was further purified by being stirred in acetonitrile and diethyl ether to give 3-(4-{4-[4-(3,4-Difluoro-benzenesulfonyl)-piperazin-1-ylmethyl]-benzyloxy}-1-oxo-1,3-dihydro-isoindol-2-yl)-piperidine-2,6-dione as a white solid (296 mg, 60% yield). HPLC: Waters Symmetry C-18, 3.9×150 mm, 5 μm, 1 mL/min, 240 nm, 25/75, (CH$_3$CN/0.1% H$_3$PO$_4$), 6.70 min (99.9%); mp: 225-227° C.; $^1$H NMR (DMSO-d$_6$) δ 1.91-2.04 (m, 1H, CHH), 2.35-2.47 (m, 5H, CHH, CH$_2$, CH$_2$), 2.53-2.63 (m, 1H, CHH), 2.82-3.02 (m, 5H, CHH, CH$_2$, CH$_2$), 3.48 (s, 2H, CH$_2$), 4.24 (d, J=17.4 Hz, 1H, CHH), 4.40 (d, J=17.6 Hz, 1H, CHH), 5.11 (dd, J=5.1, 13.2 Hz, 1H, CHH), 5.21 (s, 2H, CH$_2$), 7.26 (d, J=7.9 Hz, 2H, Ar), 7.30 (d, J=3.0 Hz, 1H, Ar), 7.33 (d, J=2.1 Hz, 1H, Ar), 7.41 (d, J=8.1 Hz, 2H, Ar), 7.48 (t, J=7.7 Hz, 1H, Ar), 7.62 (dd, J=2.0, 4.1 Hz, 1H, Ar), 7.73 (dd, J=7.7, 10.2 Hz, 1H, Ar), 7.84 (ddd, J=2.1, 7.5, 9.7 Hz, 1H, Ar), 10.97 (s, 1H, NH); $^{13}$C NMR (DMSO-d$_6$) δ 22.34, 31.16, 45.03, 45.90, 51.30, 51.53, 60.92, 69.31, 114.93, 115.20, 17.45 (d, J=19.5, CF), 118.84 (d, J=17.2, CF), 125.43, 127.63, 128.81, 129.78, 129.90, 132.11, 133.28, 135.35, 137.50, 149.25 (dd, J=228.0 Hz, J=12.0 Hz), 152.60 (dd, J=230.2 Hz, J=13.5 Hz), 153.43, 167.97, 170.96, 172.83; LCMS MH=625; Anal. Calcd for C$_{31}$H$_{30}$F$_2$N$_4$O$_6$S: C, 59.61; H, 4.84; N, 8.97; Found: C, 59.34; H, 4.72; N, 8.88.

5.278 (S)-3-(1-Oxo-4-((4-((4-(Trifluoromethyl)Piperidin-1-yl)Methyl)Benzyl)Oxy)Isoindolin-2-yl) Piperidine-2,6-Dione

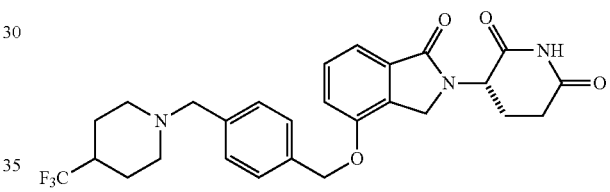

To a suspension of (S)-3-(4-(4-(bromomethyl)benzyloxy)-1-oxoisoindolin-2-yl)piperidine-2,6-dione (1 g, 2.256 mmol) in MeCN (20 mL) at 0° C., was added 4-(trifluoromethyl)piperidine hydrochloride (0.470 g, 2.481 mmol). DIEA (0.788 mL, 4.51 mmol) was immediately added and the resulting mixture was stirred at 0° C. for 3 h. Tetrabutylammonium bromide (0.036 g, 0.113 mmol) was added to the reaction mixture and stirring was continued for 1 h at 0° C. then at room temperature for ~18 h. The reaction slurry was concentrated to dryness under vacuum to give ~1.2 g of a yellow solid. This solid was partitioned between EtOAc (~250 mL) and aq 1N NaHCO$_3$ (~100 mL). The organic layer was washed with another 100 mL of 1N NaHCO$_3$, water (~25 mL), and Brine (~50 mL). The solution was dried over Na$_2$SO$_4$, filtered, and concentrated on rotovap to a minimum volume of EtOAc (~5-7 mL) at 40° C. to first sign of cloudiness. The flask was removed from rotovap and allowed to stand at room temperature. More solids formed upon standing.

An equal volume of MTBE (5-7 mL) was added to the slurry. The mixture was swirled and then filtered on 30-mL fine fritted funnel with suction. Additional MTBE was used to wash the cake and transfer residual solid from flask (~25 mL). The cake was suction dried and then placed in vacuum oven overnight at 50° C. to give 850 mg (73% yield) of a white to light cream colored solid. To remove unwanted residual solvents (EtOAc and MTBE), a second recrystallization was carried out from warm MeCN/water.

The solid was collected on a fine fritted funnel, washed with water (~25 mL), and the cake was dried in a vacuum oven at 60° C. overnight to give (S)-3-(1-oxo-4-((4-((4-(trifluoromethyl)piperidin-1-yl)methyl)benzyl)oxy)isoindolin-2-yl)piperidine-2,6-dione as a white solid (485 mg, 61% recovery): HPLC:Waters Symmetry C$_{18}$, 5 μm, 3.9×150 mm, 1 ml/min, 240 nm, 20/80 CH$_3$CN/0.1% H$_3$PO$_4$, 6.33 min (99.0%); Chiral HPLC: Chiral Technologies, AGP analytical column, 99% ee by comparison with a racemic sample previously synthesized; mp: 158-160; $^1$H NMR (DMSO-d$_6$) δ 1.33-1.56 (m, 2H, CHH, CHH), 1.67-1.84 (m, 2H, CHH, CHH), 1.86-2.09 (m, 3H, CHH, CH$_2$), 2.14-2.34 (m, 1H, CH), 2.35-2.48 (m, 1H, CHH), 2.53-2.64 (m, 1H, CHH), 2.78-3.00 (m, 3H, CH$_2$, CHH), 3.48 (br. s., 2H, CH$_2$), 4.25 (d, J=17.4 Hz, 1H, CHH), 4.42 (d, J=17.6 Hz, 1H, CHH), 5.11 (dd, J=5.0, 13.3 Hz, 1H, CH), 5.23 (s, 2H, CH$_2$), 7.25-7.39 (m, 4H, Ar), 7.40-7.55 (m, 3H, Ar), 10.97 (s, 1H, NH); $^{13}$C NMR (DMSO-d$_6$) δ 22.34, 24.21, 31.18, 45.06, 51.37, 51.56, 61.59, 69.38, 114.96, 115.22, 127.72 (q, J=280.6 Hz, CF$_3$), 127.64, 128.81, 129.78, 129.93, 133.30, 135.22, 138.12, 153.48, 167.97, 170.95, 172.80. CF$_3$C is overlapped with DMSO and not observed; LCMS: MH=516; Anal Calcd for C$_{27}$H$_{28}$F$_3$N$_3$O$_4$+0.5 H$_2$O: C, 61.83; H, 5.57; N, 8.01; F, 10.87; Found: C, 61.81; H, 5.40; N, 8.06; F, 10.51.

5.279 3-{1-Oxo-4-[4-(4-Pyridin-2-yl-Piperazin-1-ylmethyl)-Benzyloxy]-1,3-Dihydro-Isoindol-2-yl}-Piperidine-2,6-Dione

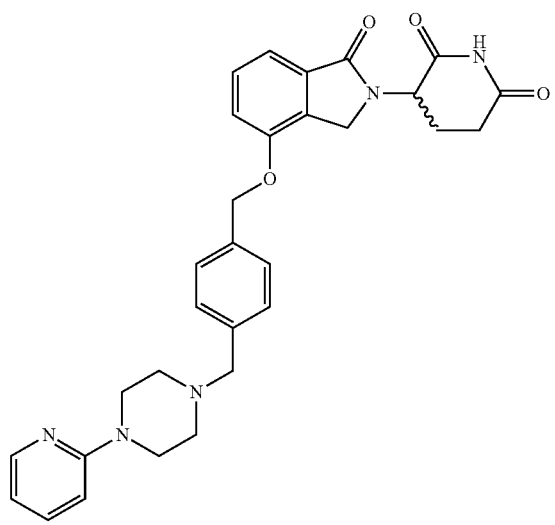 [SMILES: O=C1CCC(N2Cc3c(OCc4ccc(CN5CCN(c6ccccn6)CC5)cc4)cccc3C2=O)C(=O)N1]

To a suspension 3-(4-(4-(bromomethyl)benzyloxy)-1-oxoisoindolin-2-yl)piperidine-2,6-dione (300 mg, 0.677 mmol) in dry MeCN (10 mL), was added 1-(pyridin-2-yl)piperazine (116 mg, 0.711 mmol) followed by DIEA (0.236 mL, 1.354 mmol). The resulting mixture was stirred at room temperature for 16 h. The thick slurry was then warmed to 50° C., resulting in a clear yellow solution. After ~7 h at 50° C., the heat was removed and the solution was stirred gently for about 1 h and then allowed to stand at room temperature overnight. The resulting slurry was gently agitated and then filtered on a 30-mL medium fritted funnel with suction. The residual solid remaining in reaction vial was transferred onto funnel with additional MeCN (~2 mL). The cake was washed with several portions of Et$_2$O (total volume ~70 mL) and then slurried in water and then suctioned dried. The solid was washed with small portions of water (total volume ~50 mL). The remaining white solid was reslurried in water on funnel and then suctioned dried. The solid was washed with additional water (total volume ~50 mL) and then placed in vacuum oven at 60° C. overnight to give 3-{1-oxo-4-[4-(4-pyridin-2-yl-piperazin-1-ylmethyl)-benzyloxy]-1,3-dihydro-isoindol-2-yl}-piperidine-2,6-dione as a white solid (260 mg, 73% yield): HPLC: Waters Symmetry C$_{18}$, 5 μm, 3.9×150 mm, 1 ml/min, 240 nm, 13/87 CH$_3$CN/0.1% H$_3$PO$_4$, 5.11 min (99.2%); mp: 165-167° C.; $^1$H NMR (DMSO-d$_6$) δ 1.89-2.07 (m, 1H, CHH), 2.34-2.49 (m, 5H, CHH, CH$_2$, CH$_2$), 2.57 (d, J=18.7 Hz, 1H, CHH), 2.81-3.03 (m, 1H, CHH), 3.38-3.51 (m, 4H, CH$_2$, CH$_2$), 3.53 (br. s., 2H, CH$_2$), 4.26 (d, J=17.4 Hz, 1H, CHH), 4.43 (d, J=17.6 Hz, 1H, CHH), 5.11 (dd, J=5.0, 13.1 Hz, 1H, CH), 5.24 (s, 2H, CH$_2$), 6.63 (dd, J=5.1, 6.8 Hz, 1H, Ar), 6.79 (d, J=8.7 Hz, 1H, Ar), 7.25-7.42 (m, 4H, Ar), 7.42-7.66 (m, 4H, Ar), 8.09 (dd, J=1.4, 4.8 Hz, 1H, Pyr), 10.97 (s, 1H, NH); $^{13}$C NMR (DMSO-d$_6$) δ 22.34, 31.18, 44.53, 45.07, 51.55, 52.29, 61.69, 69.36, 107.01, 112.94, 114.96, 115.22, 127.66, 129.03, 129.80, 129.93, 133.30, 135.33, 137.44, 137.86, 147.49, 153.48, 158.95, 167.99, 170.96, 172.83; LCMS: MH=526; Anal Calcd for C$_{30}$H$_{31}$N$_5$O$_4$+1.2 H$_2$O: C, 65.87; H, 6.15; N, 12.80; Found: C, 65.87; H, 5.93; N, 12.68.

5.280 3-(1-Oxo-4-{4-[4-(5-Trifluoromethyl-[1,3,4]Thiadiazol-2-yl)-Piperazin-1-ylmethyl]-Benzyloxy}-1,3-Dihydro-Isoindol-2-yl)-Piperidine-2,6-Dione

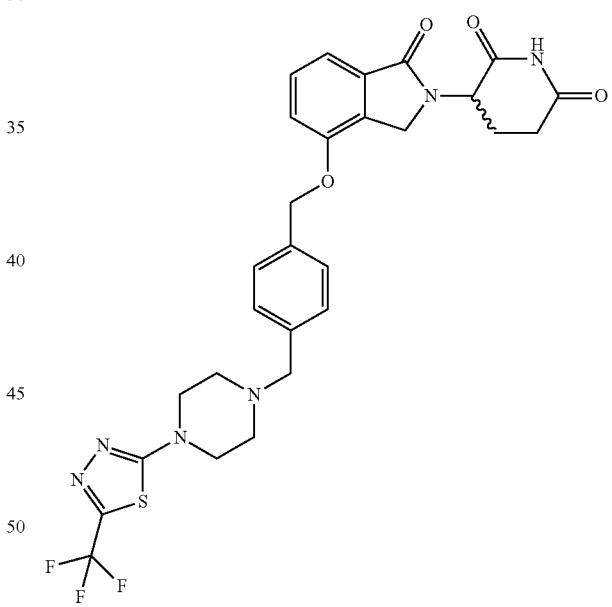

To a suspension of 3-(4-(4-(bromomethyl)benzyloxy)-1-oxoisoindolin-2-yl)piperidine-2,6-dione (300 mg, 0.677 mmol) in dry MeCN (10 mL), was added 2-(piperazin-1-yl)-5-(trifluoromethyl)-1,3,4-thiadiazole (169 mg, 0.711 mmol) followed by DIEA (0.236 mL, 1.354 mmol). The resulting mixture was stirred at room temperature for 16 h. The mixture was heated to 50° C. for 8 h and then to 80° C. for 1 h. The reaction mixture was allowed to stand overnight at room temperature then swirled gently to resuspend solids at bottom of vial. The solid was collected on a 30-mL medium fritted funnel with suction. Residual solid in the vial was transferred onto funnel with additional MeCN (~1 mL). The white cake was washed with several portions of Et$_2$O (total volume ~30 mL). The remaining white solid was reslurried in water on funnel and then suctioned dried. The solid was washed with additional water (total volume ~50 mL) and then placed in vacuum oven at 60° C. overnight to give 3-(1-oxo-4-{4-[4-(5-trifluoromethyl-[1,3,4]thiadiazol-2-yl)-piperazin-1-ylmethyl]-benzyloxy}-1,3-dihydro-isoindol-2-yl)-piperidine-2,6-dione as a white solid (332 mg, 82% yield): HPLC: Waters Symmetry $C_{18}$, 5 μm, 3.9×150 mm, 1 ml/min, 240 nm, 22/78 $CH_3CN/0.1\%$ $H_3PO_4$, 7.89 min (99.9%); mp: 160-162° C.; $^1H$ NMR (DMSO-$d_6$) δ 1.90-2.08 (m, 1H, CHH), 2.36-2.47 (m, 1H, CHH), 2.50-2.63 (m, 5H, CHH, pip $CH_2$, $CH_2$), 2.82-3.04 (m, 1H, CHH), 3.44-3.70 (m, 6H, $CH_2$, pip $CH_2$, $CH_2$), 4.26 (d, J=17.6 Hz, 1H, CHH), 4.42 (d, J=17.4 Hz, 1H, CHH), 5.11 (dd, J=5.0, 13.1 Hz, 1H, CH), 5.24 (s, 2H, $CH_2$), 7.35 (t, J=8.3 Hz, 4H, Ar), 7.43-7.54 (m, 3H, Ar), 10.97 (s, 1H, NH); $^{13}C$ NMR (DMSO-$d_6$) δ 22.34, 31.18, 45.06, 49.58, 51.27, 51.55, 61.29, 69.35, 114.97, 115.23, 121.36, 127.69, 129.00, 129.80, 129.95, 133.30, 135.47, 137.48, 153.48, 167.99, 170.96, 172.81, 173.95. One carbon signal is missing, possibly $CF_3$ due to splitting; LCMS: MH=601; Anal Calcd for $C_{28}H_{27}F_3N_6O_4S+0.9\ H_2O$: C, 54.52; H, 4.71; N, 13.62; F, 9.24; Found: C, 54.50; H, 4.57; N, 13.52; F, 9.24.

5.281 3-(4-((4-((4-(2-Methyl-6-(Trifluoromethyl)Pyrimidin-4-yl)Piperazin-1-yl)Methyl)Benzyl)Oxy)-1-Oxoisoindolin-2-yl)Piperidine-2,6-Dione

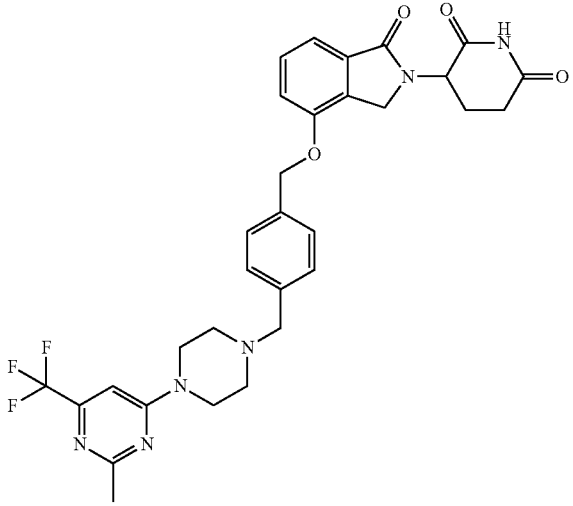 [SMILES: Cc1nc(N2CCN(Cc3ccc(COc4cccc5c4CN(C4CCC(=O)NC4=O)C5=O)cc3)CC2)cc(C(F)(F)F)n1]

To a suspension of 3-(4-(4-(bromomethyl)benzyloxy)-1-oxoisoindolin-2-yl)piperidine-2,6-dione (300 mg, 0.677 mmol) in dry MeCN (10 mL), was added 2-methyl-4-(piperazin-1-yl)-6-(trifluoromethyl)pyrimidine (175 mg, 0.711 mmol) followed by DIEA (0.236 mL, 1.354 mmol). The resulting mixture was stirred at room temperature for 16 h. The mixture was heated to 50° C. until it became a clear solution and was then allowed to cool to room temperature with gentle stirring overnight. A white solid formed upon standing. The mixture was agitated and the solid was collected on a 15-mL fine fritted funnel with suction. The solid was washed with minimal MeCN (~1 mL) and several portions of $Et_2O$ (total volume ~35 mL). The white solid was suction dried and then placed in a vacuum oven at 60° C. overnight to give 3-(4-((4-((4-(2-methyl-6-(trifluoromethyl)pyrimidin-4-yl)piperazin-1-yl)methyl)benzyl)oxy)-1-oxoisoindolin-2-yl)piperidine-2,6-dione as a white solid (276 mg, 67% yield): HPLC: Waters Symmetry $C_{18}$, 5 μm, 3.9×150 mm, 1 ml/min, 240 nm, 22/78 $CH_3CN/0.1\%$ $H_3PO_4$, 7.59 min (99.7%); mp: 165-167° C.; $^1H$ NMR (DMSO-$d_6$) δ 1.89-2.07 (m, 1H, CHH), 2.38-2.48 (m, 8H, $CH_2$, $CH_2$, CHH. $CH_3$), 2.53-2.65 (m, 1H, CHH), 2.79-2.99 (m, 1H, CHH), 3.53 (s, 2H, $CH_2$), 3.59-3.91 (m, 4H, $CH_2$, $CH_2$), 4.26 (d, J=17.4 Hz, 1H, CHH), 4.43 (d, J=17.6 Hz, 1H, CHH), 5.11 (dd, J=5.1, 13.2 Hz, 1H, CH), 5.24 (s, 2H, $CH_2$), 7.05 (s, 1H, Pyr), 7.28-7.40 (m, 4H, Ar), 7.42-7.55 (m, 3H, Ar), 10.97 (s, 1H, NH); $^{13}C$ NMR (DMSO-$d_6$) δ 22.34, 25.65, 31.18, 43.53, 45.07, 51.56, 52.06, 61.43, 69.38, 96.73 (q, J=3.3 Hz, $\underline{C}CCF_3$), 114.97, 115.22, 121.18 (q, J=275.1 Hz, $CF_3$), 127.66, 128.97, 129.78, 129.95, 133.30, 135.38, 137.66, 153.26 (q, J=34.1 Hz, $\underline{C}CF_3$), 153.49, 161.75, 167.64, 167.99, 170.96, 172.81. $CF_3$ quartet at 121.18 ppm is observed as a doublet (outer signals are missing); LCMS: MH=609; Anal Calcd for $C_{31}H_{31}F_3N_6O_4+0.4\ H_2O$: C, 60.46; H, 5.20; N, 13.65; F, 9.25; Found: C, 60.51; H, 5.13; N, 13.61; F, 8.97.

5.282 3-{1-Oxo-4-[4-(4-Phenoxy-Piperidin-1-ylmethyl)-Benzyloxy]-1,3-Dihydro-Isoindol-2-yl}-Piperidine-2,6-Dione

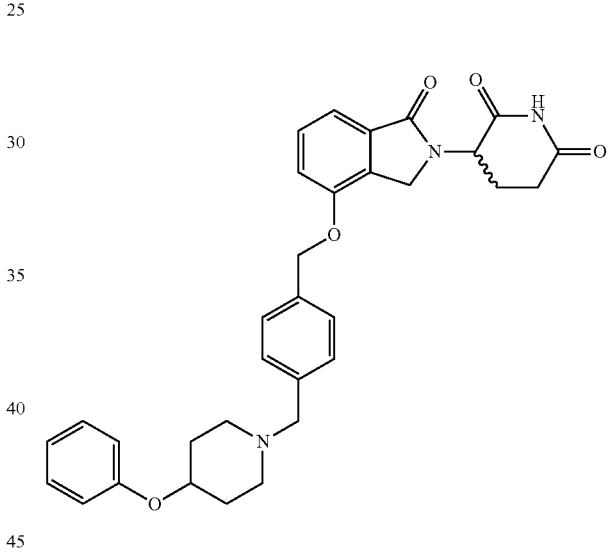

To a 20-mL reaction vial charged with 3-(4-((4-(bromomethyl)benzyl)oxy)-1-oxoisoindolin-2-yl)piperidine-2,6-dione (300 mg, 0.677 mmol) and 4-phenoxypiperidine (126 mg, 0.711 mmol), was added dry MeCN (10 mL) followed by DIEA (0.236 mL, 1.35 mmol). The resulting suspension was warmed to 50° C. to give a clear solution. After ~30 min, the temperature was raised further to 70° C. and the reaction mixture was stirred for ~16 h at 70° C. The mixture was allowed to cool to room temperature and then placed at 4° C. overnight forming a white solid. The slurry was gently agitated and the solid was collected on a 15-mL medium fritted funnel with suction. The cake was washed with $Et_2O$ (~50 mL) and suction dried to give a tan solid. The solid was triturated and washed with water (~50 mL), suction dried, and then dried further in a vacuum oven at 50° C. to give 3-{1-oxo-4-[4-(4-phenoxy-piperidin-1-ylmethyl)-benzyloxy]-1,3-dihydro-isoindol-2-yl}-piperidine-2,6-dione as a light tan solid (254 mg, 70% yield): HPLC: Waters Symmetry $C_{18}$, 5 μm, 3.9×150 mm, 1 ml/min, 240 nm, 27/73 $CH_3CN/0.1\%$ $H_3PO_4$, 4.54 min (99.0%); mp: 180-182° C.; $^1H$ NMR (DMSO-$d_6$) δ 1.49-1.71 (m, 2H, $CH_2$), 1.82-2.07 (m, 3H, CHH, $CH_2$), 2.15-2.31 (m, 2H, $CH_2$), 2.36-2.49 (m, 1H, CHH), 2.52-2.62 (m, 1H, CHH), 2.63-2.75 (m, 2H, CH$_2$), 2.81-3.00 (m, 1H, CHH), 3.49 (s, 2H, CH$_2$), 4.25 (d, J=17.4 Hz, 1H, CHH), 4.32-4.49 (m, 2H, CHH, CHO), 5.11 (dd, J=5.1, 13.2 Hz, 1H, CH), 5.23 (s, 2H, CH$_2$), 6.78-7.04 (m, 3H, Ar), 7.19-7.30 (m, 2H, Ar), 7.33 (dd, J=1.7, 7.7 Hz, 4H, Ar), 7.42-7.62 (m, 3H, Ar), 10.97 (s, 1H, NH); $^{13}$C NMR (DMSO-d$_6$) δ 68 22.33, 30.62, 31.16, 45.07, 50.10, 51.55, 61.64, 69.41, 72.13, 114.96, 115.20, 115.76, 120.42, 127.61, 128.81, 129.46, 129.78, 129.93, 133.28, 135.15, 138.40, 153.49, 157.04, 167.97, 170.95, 172.80; LCMS: MH=540; Anal Calcd for C$_{32}$H$_{33}$N$_3$O$_5$+0.5 H$_2$O: C, 70.06; H, 6.25; N, 7.66; Found: C, 70.11; H, 5.97; N, 7.62.

5.283 2-(2,6-Dioxo-Piperidin-3-yl)-4-{4-[4-(4-Fluoro-Phenyl)-Piperidin-1-ylmethyl]-Benzyloxy}-Isoindole-1,3-Dione

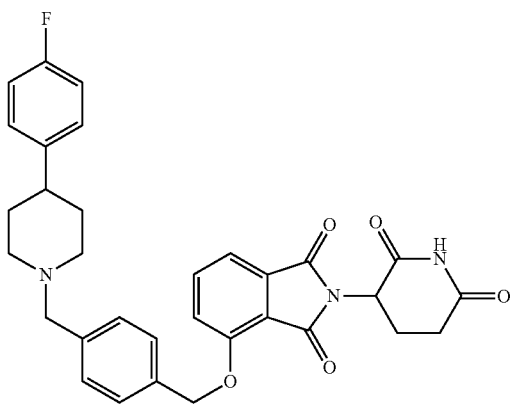 [SMILES: O=C1CCC(N2C(=O)c3cccc(OCc4ccc(CN5CCC(c6ccc(F)cc6)CC5)cc4)c3C2=O)C(=O)N1]

To the CH$_2$Cl$_2$ suspension of 2-(2,6-dioxopiperidin-3-yl)-4-(4-((4-(4-fluorophenyl)piperidin-1-yl)methyl)benzyloxy) isoindoline-1,3-dione (170 mg, 0.306 mmol, 56.0% yield) was added 4-(4-fluorophenyl)piperidine hydrochloride (130 mg, 0.601 mmol) and N-ethyl-N-isopropylpropan-2-amine (0.292 ml, 1.640 mmol). The mixture was stirred at room temperature overnight. The mixture was added CH$_2$Cl$_2$ and water and extracted. The organic layer was concentrated. The resulted solid was stirred in CH$_2$Cl$_2$ (5 mL) and the suspension was filtered to give a white solid (170 mg, 56%). Melting point: 155-157° C. LC-MS m/e=556. HPLC Waters Symmetry C-18, 3.9×150 mm, 5 micro, 1 mL/min, 240 nm, isocratic 25/75 CH$_3$CN/0.1% H$_3$PO$_4$ in H$_2$O: t$_R$=4.06 min (98.5%); $^1$H NMR (DMSO-d$_6$) δ 1.53-1.76 (m, 4H, CH$_2$, CH$_2$), 2.03 (t, J=11.3 Hz, 3H, CHH, CH$_2$), 2.41-2.46 (m, 1H, CHH), 2.54-2.65 (m, 2H, CHH. CH), 2.80-2.99 (m, 4H, CHH, CH$_2$), 3.50 (s, 2H, CH$_2$), 5.09 (dd, J=4.2, 13.4 Hz, 1H, CNH), 5.35 (s, 2H, CH$_2$), 7.03-7.16 (m, 2H, Ar), 7.22-7.31 (m, 2H, Ar), 7.32-7.40 (m, 2H, Ar), 7.43-7.50 (m, 3H, Ar), 7.54-7.68 (m, 1H, Ar), 7.81 (d, J=7.2 Hz, 1H, Ar), 11.10 (br. s., 1H, NH). $^{13}$C NMR (DMSO-d$_6$) δ 21.95, 30.90, 33.13, 38.66, 41.00, 48.73, 53.51, 62.06, 69.99, 114.71, 114.99, 115.48, 116.58, 120.19, 127.23, 128.33, 128.43, 128.92, 133.26, 134.63, 136.97, 138.42, 142.34, 155.53, 158.96, 162.17, 165.27, 166.75, 169.85, 172.71; Anal Calcd for C$_{32}$H$_{30}$FN$_3$O$_5$+0.6 CH$_2$Cl$_2$: C: 64.55%; H: 5.10%; N: 6.93%. Found: C: 64.49%; H: 4.89%; N: 7.03%.

5.284 2-(2,6-Dioxo-Piperidin-3-yl)-4-{4-[4-(2,2,2-Trifluoro-Ethyl)-Piperazin-1-ylmethyl]-Benzyloxy}-Isoindole-1,3-Dione

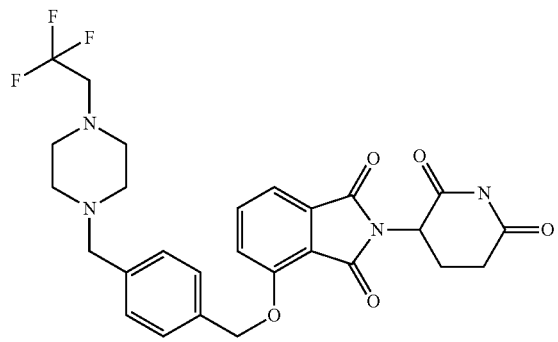 [SMILES: O=C1CCC(N2C(=O)c3cccc(OCc4ccc(CN5CCN(CC(F)(F)F)CC5)cc4)c3C2=O)C(=O)N1]

To the CH$_2$Cl$_2$ solution of 4-(4-(bromomethyl)benzyloxy)-2-(2,6-dioxopiperidin-3-yl)isoindoline-1,3-dione (250 mg, 0.547 mmol) was added 1-(2,2,2-trifluoroethyl)piperazine hydrochloride (123 mg, 0.601 mmol) and N-ethyl-N-isopropylpropan-2-amine (292 μl, 1.640 mmol). The mixture was stirred at room temperature overnight. The reaction mixture was added CH$_2$Cl$_2$ (15 mL) and water (10 mL). and extracted. The organic layer was concentrated and purified on silica gel column eluted with MeOH and CH$_2$Cl$_2$ to give 2-(2,6-dioxo-piperidin-3-yl)-4-{4-[4-(2,2,2-trifluoro-ethyl)-piperazin-1-ylmethyl]-benzyloxy}-isoindole-1,3-dione as a white solid (170 mg, 57%). Melting point: 163-165° C. LC-MS m/e=545. HPLC Waters Symmetry C-18, 3.9×150 mm, 5 micro, mL/min, 240 nm, isocratic 25/75 CH$_3$CN/0.1% H$_3$PO$_4$ in H$_2$O: t$_R$=5.40 min (99%); $^1$H NMR (DMSO-d$_6$) δ 1.96-2.10 (m, 1H, CHH), 2.37 (br. s., 4H, CH$_2$, CH$_2$), 2.43-2.47 (m, OH, CHH), 2.52-2.66 (m, J=4.5 Hz, 6H, CH$_2$, CH$_2$, CH$_2$, CH), 2.79-2.97 (m, 1H, CHH), 3.14 (d, J=10.2 Hz, 2H, CH$_2$), 3.46 (s, 2H, CH$_2$), 5.09 (dd, J=5.4, 12.7 Hz, 1H, NCH), 5.35 (s, 2H, CH$_2$), 7.33 (d, J=8.1 Hz, 2H, Ar), 7.46 (dd, J=4.1, 7.6 Hz, 3H, Ar), 7.60 (d, J=8.5 Hz, 1H, Ar), 7.83 (dd, J=7.4, 8.5 Hz, 1H, Ar), 11.11 (s, 1H, NH). $^{13}$C NMR (DMSO-d$_6$) δ 21.93, 30.90, 48.73, 52.45, 53.06, 56.23, 56.62, 57.39, 57.01, 61.58, 69.95, 115.48, 116.58, 120.19, 127.23, 127.80, 128.87, 133.26, 134.71, 136.96, 137.98, 155.52, 165.27, 166.75, 169.85, 172.71. Anal Calcd for C$_{27}$H$_{27}$F$_3$N$_4$O$_5$, C: 59.56%; H: 5.00%; N: 10.29%; Found: C: 59.44%; H: 4.87%; N: 10.23%.

5.285 3-(4-((4-((4-(2,4-Difluorophenyl)Piperazin-1-yl)Methyl)Benzyl)Oxy)-1-Oxoisoindolin-2-yl)Piperidine-2,6-Dione

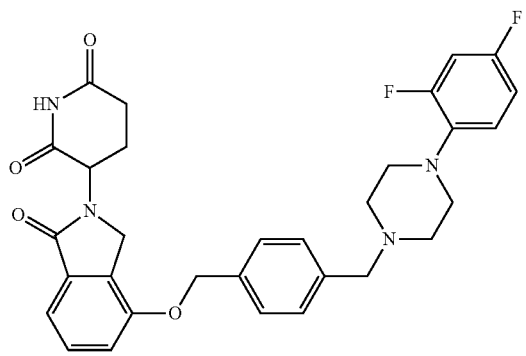 [SMILES: O=C1CCC(N2Cc3c(OCc4ccc(CN5CCN(c6ccc(F)cc6F)CC5)cc4)cccc3C2=O)C(=O)N1]

To the CH$_2$Cl$_2$ solution of 3-(4-(4-(bromomethyl)benzyloxy)-1-oxoisoindolin-2-yl)piperidine-2,6-dione (0.5 g, 1.128 mmol) was added 1-(2,4-difluorophenyl)piperazine (0.235 g, 1.184 mmol) and N-ethyl-N-isopropylpropan-2-amine (0.602 ml, 3.38 mmol). The mixture was stirred at room temperature overnight. The reaction mixture was added water (15 mL), extracted and concentrated to give a yellowish solid. The solid was recrystallized from CH$_3$CN (10 mL) to give 3-(4-((4-((4-(2,4-difluorophenyl)piperazin-1-yl)methyl)benzyl)oxy)-1-oxoisoindolin-2-yl)piperidine-2,6-dione as a white solid (330 mg, 52%). Melting point (determined in house): 207-209° C. LC-MS m/e=561. HPLC Waters Symmetry C-18, 3.9×150 mm, 5 micro, 1 mL/min, 240 nm, isocratic 25/75 CH$_3$CN/0.1% H$_3$PO$_4$ in H$_2$O: 6.80 min (98.8%). $^1$H NMR (DMSO-d$_6$) δ 1.90-2.06 (m, 1H, CHH), 2.36-2.45 (m, J=4.2 Hz, 1H, CHH), 2.53-2.59 (m, 5H, CHH, CH$_2$, CH$_2$), 2.83-3.01 (m, 5H, CH$_2$, CH$_2$, CHH), 3.54 (s, 2H, CH$_2$), 4.05-4.58 (m, 2H, CH$_2$), 5.11 (dd, J=5.0, 13.1 Hz, 1H, NCH), 5.24 (s, 2H, CH$_2$), 6.89-7.12 (m, 2H, Ar), 7.17 (ddd, J=2.8, 9.2, 12.4 Hz, 1H, Ar), 7.27-7.41 (m, 4H, Ar), 7.41-7.51 (m, 3H, Ar), 10.97 (s, 1H, Ar). $^{13}$C NMR (DMSO-d$_6$) δ 22.33, 31.16, 45.07, 50.44, 51.55, 52.52, 61.64, 69.39, 104.18, 104.52, 104.87, 110.80, 111.03, 114.96, 115.22, 119.86, 119.91, 127.63, 128.98, 129.80, 129.95, 133.30, 135.28, 137.88, 153.49, 167.99, 170.95, 172.80. Anal Calcd for C$_{31}$H$_{30}$F$_2$N$_4$O$_4$: C %:66.42, H %:5.39, N %:,9.99. Found: C %:65.08, H %:5.02, N %:9.66.

5.286 4-((4-((4-(2,4-Difluorophenyl)Piperidin-1-yl) Methyl)Benzyl)Oxy)-2-(2,6-Dioxopiperidin-3-yl) Isoindoline-1,3-Dione

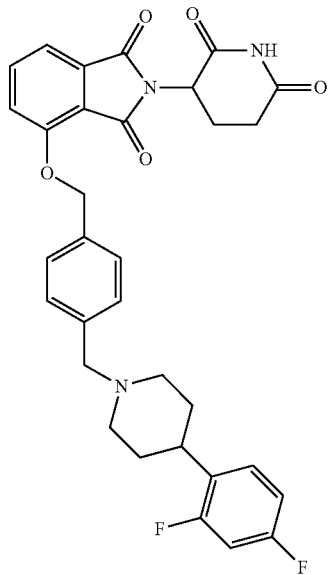 [SMILES: O=C1CCC(N2C(=O)c3cccc(OCc4ccc(CN5CCC(c6ccc(F)cc6F)CC5)cc4)c3C2=O)C(=O)N1]

To the CH$_2$Cl$_2$ suspension of 4-(4-(bromomethyl)benzyloxy)-2-(2,6-dioxopiperidin-3-yl)isoindoline-1,3-dione (0.5 g, 1.093 mmol) was added 4-(2,4-difluorophenyl)piperidine (0.216 g, 1.093 mmol) and N-ethyl-N-isopropylpropan-2-amine (0.584 ml, 3.28 mmol). The suspension was stirred at room temperature overnight. The mixture was added water (10 mL), CH$_2$Cl$_2$ (10 mL), extracted and concentrated. The resulted oil was purified on silica gel column eluted with MeOH and CH$_2$Cl$_2$ to give a solid which was stirred with CH$_2$Cl$_2$ (3 mL) and filtered to give 4-((4-((4-(2,4-difluorophenyl)piperidin-1-yl)methyl)benzyl)oxy)-2-(2,6-dioxopiperidin-3-yl)isoindoline-1,3-dione as white solid (50 mg, 8%). Melting point: 153-155° C. LC-MS m/e=574. HPLC Waters Symmetry C-18, 3.9×150 mm, 5 micro, 1 mL/min, 240 nm, isocratic 30/70 CH$_3$CN/0.1% H$_3$PO$_4$ in H$_2$O: 4.69 min (97.6%). $^1$H NMR (DMSO-d$_6$) δ 1.55-1.75 (m, 4H, CH$_2$, CH$_2$), 2.05 (d, J=2.1 Hz, 3H, CH$_2$, CHH), 2.43-2.48 (m, 1H, CHH), 2.55-2.67 (m, 2H, CHH), 2.68-2.86 (m, 2H, CHH, CH), 2.82-2.82 (m, OH, M$_{01}$), 2.86-2.99 (m, 3H, CHH, CH$_2$), 3.51 (s, 2H, CH$_2$), 4.89-5.18 (m, 1H, NCH), 5.36 (s, 2H, CH$_2$), 6.91-7.08 (m, 1H, Ar), 7.09-7.23 (m, 1H, Ar), 7.27-7.54 (m, 7H, Ar), 7.61 (d, J=8.3 Hz, 1H, Ar), 7.74-7.95 (m, 1H, Ar), 11.10 (s, 1H, NH). $^{13}$C NMR (DMSO-d$_6$) δ 21.93, 30.90, 31.63, 34.63, 48.73, 53.47, 62.01, 69.98, 103.20, 103.57, 103.90, 115.48, 116.58, 120.21, 127.25, 128.91, 129.09, 133.26, 134.65, 136.97, 138.40, 138.53, 155.53, 165.29, 166.75, 169.87, 172.71.

5.287 4-((4-((4-(4-Chlorophenyl)Piperidin-1-yl) Methyl)Benzyl)Oxy)-2-(2,6-Dioxopiperidin-3-yl) Isoindoline-1,3-Dione

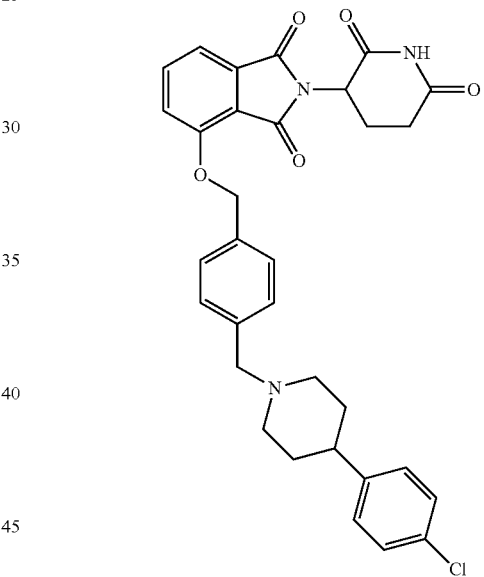

To the CH$_2$Cl$_2$ suspension of 4-(4-(bromomethyl)benzyloxy)-2-(2,6-dioxopiperidin-3-yl)isoindoline-1,3-dione (0.35 g, 0.765 mmol) was added 4-(4-chlorophenyl)piperidine (0.157 g, 0.804 mmol) and N-ethyl-N-isopropylpropan-2-amine (0.409 ml, 2.296 mmol). The suspension was stirred at room temperature overnight. The reaction mixture was loaded on the silica gel column and eluted with MeOH and CH$_2$Cl$_2$ to give 4-((4-((4-(4-chlorophenyl)piperidin-1-yl)methyl)benzyl)oxy)-2-(2,6-dioxopiperidin-3-yl)isoindoline-1,3-dione as a white solid (320 mg, 73%). Melting point: 236-238° C. LC-MS m/e=572, 574. HPLC Waters Symmetry C-18, 3.9×150 mm, 5 micro, 1 mL/min, 240 nm, isocratic 30/70 CH$_3$CN/0.1% H$_3$PO$_4$ in H$_2$O: 6.17 min (98.4%). $^1$H NMR (DMSO-d$_6$) δ 1.50-1.79 (m, 4H, CH$_2$, CH$_2$), 1.96-2.11 (m, 3H, CHH, CH$_2$), 2.46-2.66 (m, 3H, CH, CHH, CHH), 2.79-2.99 (m, 3H, CH$_2$, CHH), 3.50 (s, 2H, CH$_2$), 5.09 (dd, J=5.4, 12.7 Hz, 1H, NCH), 5.36 (s, 2H, CH$_2$), 7.19-7.40 (m, 6H, Ar), 7.42-7.52 (m, 3H, Ar), 7.61 (d, J=8.5 Hz, 1H, Ar), 7.74-7.96 (m, 1H, Ar), 11.11 (s, 1H, NH). $^{13}$C NMR (DMSO-d$_6$) δ 21.95, 30.90, 32.88, 41.11, 48.73, 53.44, 62.03, 69.98, 115.48, 116.58, 120.19, 127.23, 128.15, 128.57, 128.91, 130.40, 133.26, 134.63, 136.97, 138.40, 145.21, 155.53, 165.27, 166.75, 169.85, 172.70. Anal Calcd for C$_{32}$H$_{30}$ClN$_3$O$_5$: C %:67.19; H %:5.29; N %:7.35. Found: C %:66.83; H %:5.31; N %:7.13.

5.288 2-(2,6-Dioxopiperidin-3-yl)-4-((4-((4-((Trifluoromethyl)Sulfonyl)Piperazin-1-yl)Methyl)Benzyl)Oxy) Isoindoline-1,3-Dione

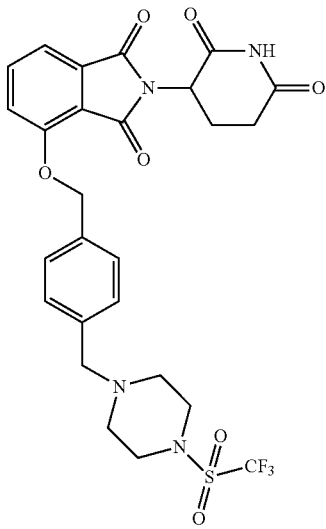 [SMILES: O=C1CCC(N2C(=O)c3cccc(OCc4ccc(CN5CCN(S(=O)(=O)C(F)(F)F)CC5)cc4)c3C2=O)C(=O)N1]

To the CH$_2$Cl$_2$ solution of 4-(4-(bromomethyl)benzyloxy)-2-(2,6-dioxopiperidin-3-yl)isoindoline-1,3-dione (0.25 g, 0.547 mmol) was added 1-(trifluoromethylsulfonyl)piperazine (0.143 g, 0.656 mmol) and N-ethyl-N-isopropylpropan-2-amine (0.212 g, 1.640 mmol). The suspension was stirred at room temperature overnight. The mixture was added water (15 mL), CH$_2$Cl$_2$ (20 mL), extracted, concentrated and the resulted oil was purified on silica gel column to give a solid. The solid was purified on prep-HPLC to give 2-(2,6-dioxopiperidin-3-yl)-4-((4-((4-((trifluoromethyl)sulfonyl)piperazin-1-yl)methyl)benzyl)oxy)isoindoline-1,3-dione solid (80 mg, 25%). Melting point: 229-231° C. LC-MS m/e=595. HPLC Waters Symmetry C-18, 3.9×150 mm, 5 micro, 1 mL/min, 240 nm, isocratic 30/70 CH$_3$CN/0.1% H$_3$PO$_4$ in H$_2$O: 3.79 (97%). $^1$H NMR (DMSO-d$_6$) δ 1.94-2.12 (m, 1H, CHH), 2.35-2.45 (m, 1H, CHH), 2.53-2.67 (m, 5H, CHH, CH$_2$, CH$_2$), 2.80-2.98 (m, 1H, CHH), 3.48 (br. s., 4H, CH$_2$, CH$_2$), 3.56 (s, 2H, CH$_2$), 5.09 (dd, J=5.4, 12.7 Hz, 1H, NCH), 5.35 (s, 2H, CH$_2$), 7.27-7.42 (m, 2H, Ar), 7.48 (d, J=6.8 Hz, 3H, Ar), 7.60 (d, J=8.5 Hz, 1H, Ar), 7.83 (dd, J=7.4, 8.3 Hz, 1H, Ar), 11.11 (s, 1H, NH). $^{13}$C NMR (DMSO-d$_6$) δ 21.95, 30.89, 46.38, 48.73, 51.87, 61.01, 69.90, 115.50, 120.18, 127.35, 128.97, 133.26, 133.75, 134.99, 136.97, 137.34, 155.50, 165.29, 166.79, 169.85, 172.71. Anal Calcd for C$_{26}$H$_{25}$F$_3$N$_4$O$_7$S+1.1 H$_2$O: C %: 51.17; H %: 4.30; N %: 9.12. Found: C %: 50.83; H %: 4.46; N %: 8.74.

5.289 2-(2,6-Dioxo-Piperidin-3-yl)-4-{4-[4-(4-Fluoro-Phenyl)-Piperazin-1-ylmethyl]-Benzyloxy}-Isoindole-1,3-Dione

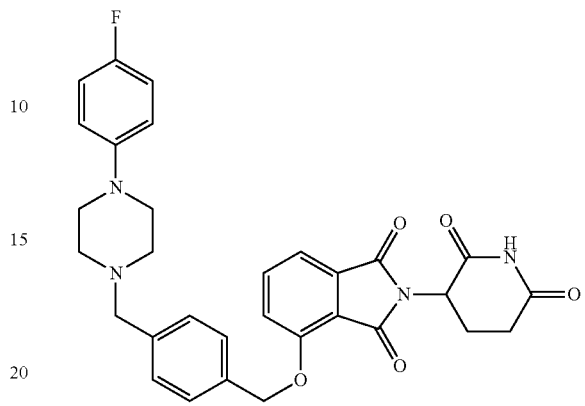

To the CH$_2$Cl$_2$ suspension of 4-(4-(bromomethyl)benzyloxy)-2-(2,6-dioxopiperidin-3-yl)isoindoline-1,3-dione (0.25 g, 0.547 mmol) was added 1-(4-fluorophenyl)piperazine (0.108 g, 0.601 mmol) and N-ethyl-N-isopropylpropan-2-amine (0.212 g, 1.640 mmol). The mixture was stirred at room temperature overnight. The reaction mixture was added water (10 mL) and CH$_2$Cl$_2$ (15 mL) and extracted. The organic layer was concentrated then purified on silica gel column eluted with CHCl$_2$ and MeOH to give 2-(2,6-dioxo-piperidin-3-yl)-4-{4-[4-(4-fluoro-phenyl)-piperazin-1-ylmethyl]-benzyloxy}-isoindole-1,3-dione as yellowish solid (0.24 g, 79%). Melting point: 135-137° C. LC-MS m/e=557. HPLC Waters Symmetry C-18, 3.9×150 mm, 5 micro, 1 mL/min, 240 nm, isocratic 25/75 CH$_3$CN/0.1% H$_3$PO$_4$ in H$_2$O: t$_R$=7.07 min (99%); $^1$H NMR (DMSO-d$_6$) δ 1.92-2.13 (m, 1H, CHH), 2.41-2.47 (m, 1H, CHH), 2.54-2.67 (m, 5H, CHH, CH$_2$, CH$_2$), 2.79-2.97 (m, 1H, CHH), 2.98-3.19 (m, 4H, CH$_2$, CH$_2$), 3.53 (s, 2H, CH$_2$), 5.09 (dd, J=5.4, 12.7 Hz, 1H, NCH), 5.36 (s, 2H, CH$_2$), 6.80-6.97 (m, 2H, Ar), 6.97-7.15 (m, 2H, Ar), 7.29-7.41 (m, 2H, Ar), 7.42-7.55 (m, 3H, Ar), 7.61 (d, J=8.5 Hz, 1H, Ar), 7.83 (dd, J=7.4, 8.5 Hz, 1H, Ar), 11.11 (s, 1H, NH). $^{13}$C NMR (DMSO-d$_6$) δ 21.95, 30.90, 48.75, 48.97, 52.51, 61.65, 69.96, 115.03, 115.31, 115.50, 116.98, 117.09, 120.21, 127.28, 129.00, 133.26, 134.79, 136.97, 137.94, 147.92, 154.35, 155.53, 157.47, 165.29, 166.75, 169.87, 172.71; Anal Calcd for C$_{31}$H$_{29}$FN$_4$O$_5$+0.2 H$_2$O: C: 66.47%; H: 5.29%; N: 10.00%; Found: C: 66.16%; H: 5.17%; N: 9.93%.

5.290 3-(4-Benzo[D]Thiazol-2-yloxy-1-Oxoisoindolin-2-yl)Piperidine-2,6-Dione

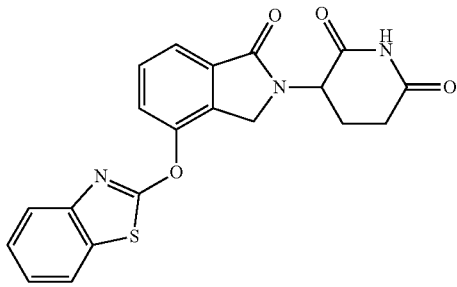 [SMILES: O=C1CCC(N2Cc3c(Oc4nc5ccccc5s4)cccc3C2=O)C(=O)N1]

Step 1: Cesium carbonate (4.6 g, 14.1 mmol) was added to a stirred solution of methyl 3-hydroxy-2-methylbenzoate (2.0 g, 12.0 mmol) and 2-chlorobenzothiazole (3.1 g, 18.1 mmol) in acetonitrile (50 mL). The resulting mixture was stirred at room temperature overnight. The reaction mixture was filtered and washed with acetonitrile (25 mL), the filtrate was concentrated, and the residue was purified by chromatography (SiO$_2$, EtOAc:Hexane 1:9) to give methyl 3-(benzo[d]thiazol-2-yloxy)-2-methylbenzoate (3.4 g, 93% yield): $^1$H NMR (CDCl$_3$) δ 2.52 (s, 3H, CH$_3$), 3.92 (s, 3H, OCH$_3$), 7.23-7.43 (m, 4H, Ar), 7.63-7.75 (m, 2H, Ar), 7.86 (dd, J=1.2 and 7.8 Hz, 1H, Ar).

Step 2: N-Bromosuccinimide (2.2 g, 12.1 mmol) was added to a stirred solution of methyl 3-(benzo[d]thiazol-2-yloxy)-2-methylbenzoate (3.3 g, 11.0 mmol) in CCl$_4$ (70 mL). The resulting mixture was heated at 70° C. oil bath with a 300 W bulb shining on the reaction mixture for 2 hours. The reaction mixture was cooled and filtered. Filtrate was washed with water (2×40 mL) and brine (40 mL), and dried. The solvent was removed and the residue was purified by chromatography (SiO$_2$, EtOAc:Hexane 1:9) to give methyl 3-(benzo[d]thiazol-2-yloxy)-2-(bromomethyl)benzoate (3.4 g, 81% yield): $^1$H NMR (DMSO-d6) δ 3.92 (s, 3H, CH$_3$), 4.98 (s, 2H, CH$_2$), 7.21-7.50 (m, 2H, Ar), 7.56-7.76 (m, 2H), 7.79-7.93 (m, 2H, Ar), 7.99 (d, J=7.2 Hz, 1H, Ar).

Step 3: Triethylamine (2.0 g, 19.8 mmol) was added to a stirred suspension of methyl 3-(benzo[d]thiazol-2-yloxy)-2-(bromomethyl)benzoate (3.0 g, 7.9 mmol) and α-aminoglutarimide hydrochloride (1.3 g, 7.9 mmol) in acetonitrile (100 mL). After addition, the mixture was heated at 45° C. for 3 hours then heated to 85° C. overnight. The reaction mixture was cooled and concentrated. The residue was stirred with water (50 mL) to give a solid, which was reslurried with acetone (20 mL) to give a light blue solid (1.5 g, 46%) of 3-(4-benzo[d]thiazol-2-yloxy)-1-oxoisoindolin-2-yl)piperidine-2,6-dione. The color was removed by dissolving in acetone, treating with decolorizing carbon, and filtering through Millpole (0.45 pM): mp 258-260° C.; $^1$H NMR (DMSO-d$_6$) δ 1.90-2.04 (m, 1H), 2.31-2.45 (m, 1H), 2.57 (b, 1H), 2.78-2.99 (m, 1H), 4.33 (d, J=17.7 Hz, 1H), 4.48 (d, J=17.4 Hz, 1H), 5.12 (dd, J=5.1 and 13.2 Hz, 1H), 7.30-7.49 (m, 2H), 7.64-7.84 (m, 4H), 7.99 (d, J=7.2 Hz, 1H), 10.96 (s, 1H); $^{13}$C NMR (DMSO-d$_6$) δ 22.15, 31.07, 45.10, 51.66, 121.29, 121.43, 122.33, 124.42, 124.44, 126.56, 130.40, 131.94, 133.22, 134.39, 148.20, 148.92, 167.03, 170.52, 170.75, 172.73; Calcd. For C$_{20}$H$_{15}$N$_3$O$_4$S: C, 61.06: H, 3.84; N, 10.68; S, 8.15. Found: C, 61.00; H, 3.72; N, 10.59; S, 8.20.

5.291 3-[4-(4-Methyl-Cyclohexylmethoxy)-1-Oxo-1,3-Dihydro-Isoindol-2-yl]-Piperidine-2,6-Dione

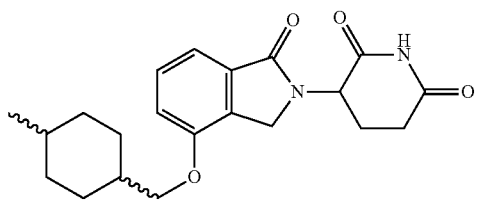

isomer ratio ~ 62% to 38% by HNMR

Step 1: Polymer-supported triphenylphosphene (1.6 mmol/g, 1.90 g, 2.36 mmol) was added to a stirred solution of 4-carbamoyl-4-(4-hydroxy-1-oxo-1,3-dihydro-isoindol-2-yl)-butyric acid methyl ester (0.31 g, 1.07 mmol) in THF (20 mL) at 0° C., followed by addition of diisopropyl diazene-1,2-dicarboxylate (0.27 ml, 2.14 mmol). After stirring for 30 minutes, (4-methyl-cyclohexyl)-methanol (cis & trans mixture, 0.41 g, 1.85 mmol) was added. The mixture was stirred overnight at room temperature then filtered, washed with methanol (3×10 mL), then with methylene chloride (3×10 mL). The combined filtrate was evaporated in vacuo to give an oil, which was purified on silica gel column (MeOH/CH$_2$Cl$_2$ gradient from 0% to 9% in 60 min) to give 4-carbamoyl-4-[4-(4-methyl-cyclohexylmethoxy)-1-oxo-1,3-dihydro-isoindol-2-yl]-butyric acid methyl ester as a clear oil (0.35 g, 81% yield). $^1$H NMR showed 61% to 39% ratio. It was used in the next step without further purification.

Step 2: Potassium tert-butoxide (0.10 g, 0.87 mmol) was added to a stirred solution of 4-carbamoyl-4-[4-(4-methyl-cyclohexylmethoxy)-1-oxo-1,3-dihydro-isoindol-2-yl]-butyric acid methyl ester (0.35 g, 0.87 mmol) in THF (10 mL) at 0° C. The mixture was stirred for ten minutes and quenched with 1N HCl (3 mL), neutralized by saturated sodium bicarbonate (4 mL to pH=7), and quickly extracted by ethyl acetate (2×30 mL). The combined ethyl acetate phases were evaporated to an off-white solid, which was purified by preparative HPLC (0.1% formic acid/water, and 0.1% formic acid/acetonitrile) to give 3-[4-(4-methyl-cyclohexylmethoxy)-1-oxo-1,3-dihydro-isoindol-2-yl]-piperidine-2,6-dione as an off-white solid (0.03 g, 10% yield); HPLC: Waters Symmetry C-18, 3.9×150 mm, 5 μm, 1 mL/min, 240 nm, isocratic at 40/60 in 10 min (acetonitrile/0.1% H$_3$PO$_4$), 4.68 min (60.2%), 5.07 min (37.3%); mp: N/A due to limited sample available; $^1$H NMR (DMSO-d$_6$) δ 0.78-2.08 (m, 15H, CH$_3$, 5CH$_2$, CH, CHH), 2.38-2.46 (m, 1H, CHH), 2.54-2.65 (m, 1H, CHH), 2.80-3.01 (m, 1H, CHH), 3.87-4.08 (m, 2H, CH$_2$(62% to 38%)), 4.15-4.46 (m, 2H, ArCH$_2$), 5.11 (dd, 1H, NCH), 7.16-7.34 (m, 2H, Ar), 7.41-7.54 (m, 1H, Ar), 10.97 (s, 1H, NH); $^{13}$C NMR (DMSO-d$_6$) δ 19.94, 22.35, 22.57, 24.87, 29.04, 29.39, 30.10, 31.20, 32.23, 34.10, 34.51, 36.82, 44.99, 51.58, 70.85, 73.02, 114.43, 114.54, 114.84, 129.71, 129.84, 133.18, 153.91, 168.08, 171.02, 172.85; LCMS MH=371.

5.292 3-[4-(2-Benzofuran-2-yl-Ethoxy)-1-Oxo-1,3-Dihydro-Isoindol-2-yl]-Piperidine-2,6-Dione

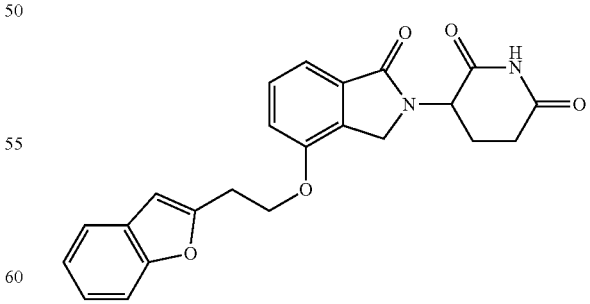

Step 1: To the suspension of 2-iodo phenyl (0.22 g, 1 mmol) in water (3 mL), was added s-prolinol (0.29 mL, 3 mmol) followed by Pd on carbon (70 mg, 0.03 mmol), tripehenylphosphine (35 mg, 0.13 mmol), and cupper iodide (13 mg, 0.07 mmol). The mixture was stirred at room temperature for 1 hour. 3-Butyn-1-ol (0.23 mL, 3 mmol) was added and the mixture was stirred at 80° C. for 3 hours. The mixture was cooled to room temperature and concentrated on rota-vap. The resulting mixture was purified on silica gel column eluted with ethyl acetate and hexane (gradient, product came out at 6% methanol) to give 2-benzofuran-2-yl-ethanol (0.1 g, 62%).

Step 2: To the THF solution (10 mL) of 4-carbamoyl-4-(4-hydroxy-1-oxo-1,3-dihydro-isoindol-2-yl)-butyric acid methyl ester (0.54 g, 1.85 mmol), were added triphenyl phosphine resin (2.4 g, 1.5 mmol/g loading, 3.7 mmol) and DIAD (0.72 mL, 3.7 mmol) at 0° C. After being stirred at 0° C. for 10 minutes, the mixture was added 2-benzofuran-2-yl-ethanol (0.36 g, 2.2 mmol) and stirred at room temperature overnight. The mixture was filtered, and the filtrate was concentrated and extracted with EtOAc (30 mL) and Na$_2$CO$_3$ (20 mL). The organic layer was washed with water (20 mL) and brine (20 mL), and concentrated. The resulting oil was purified on silica gel column to give 4-[4-(2-benzofuran-2-yl-ethoxy)-1-oxo-1,3-dihydro-isoindol-2-yl]-4-carbamoyl-butyric acid methyl ester (0.20 g, 21%).

Step 3: To the THF solution (10 mL) of 4-[4-(2-benzofuran-2-yl-ethoxy)-1-oxo-1,3-dihydro-isoindol-2-yl]-4-carbamoyl-butyric acid methyl ester (0.7 g, 1.5 mmol), was added potassium tert-butoxide (0.45 mL, 0.45 mmol) at 0° C. The mixture was stirred at 0° C. for 10 minutes and was quenched with 1N HCl (5 mL, 5 mmol), followed by saturated NaHCO$_3$ (25 mL). The mixture was extracted with EtOAc (50 mL×2). The organic layer was washed with water (30 mL) and brine (30 mL), dried over MgSO$_4$, and concentrated. The resulting solid was purified on silica gel column eluted with CH$_2$Cl$_2$/MeOH to give 3-[4-(2-benzofuran-2-yl-ethoxy)-1-oxo-1,3-dihydro-isoindol-2-yl]-piperidine-2,6-dione as white solid (0.15 g, 83%). mp: 160-162° C.; HPLC: Waters Symmetry C$_{18}$, 5 μm, 3.9×150 mm, 1 mL/min, 240 nm, gradient to 95/5 acetonitrile/0.1% H$_3$PO$_4$ in 5 min: t$_R$=5.01 min (99%); $^1$H NMR (DMSO-d$_6$) δ 1.87-1.98 (m, 1H, CHH), 2.37 (qd, J=4.5, 13.2 Hz, 1H, CHH), 2.59 (d, J=1.9 Hz, 1H, CHH), 2.80-2.97 (m, 1H, CHH), 3.29 (t, J=6.2 Hz, 2H, CH$_2$), 4.10-4.36 (m, 2H, CH$_2$), 4.49 (t, J=6.3 Hz, 2H, CH$_2$), 5.09 (dd, J=5.1, 13.4 Hz, 1H, NCH), 6.74 (s, 1H, Ar), 7.11-7.29 (m, 2H, Ar), 7.29-7.40 (m, 2H, Ar), 7.44-7.62 (m, 3H, Ar), 10.96 (s, 1H, NH). $^{13}$C NMR (DMSO-d$_6$) δ 22.33, 28.11, 31.18, 44.97, 51.56, 65.86, 103.43, 110.70, 115.01, 115.36, 120.52, 122.66, 123.52, 128.42, 129.84, 129.91, 133.31, 153.44, 153.99, 155.72, 167.95, 170.96, 172.80; LCMS: 405; Anal Calcd for C$_{23}$H$_{20}$N$_2$O$_5$+0.06 EtOAc: C, 68.13; H, 5.04; N, 6.84; Found: C, 67.73; H, 5.16; N, 6.75.

5.293 4-((2-(2,6-Dioxopiperidin-3-yl)-1-Oxoisoindolin-4-yloxy)Methyl)Benzonitrile

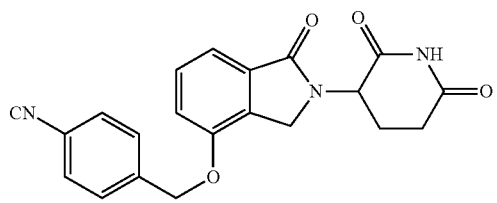

To a mixture of methyl 5-amino-4-(4-hydroxy-1-oxoisoindolin-2-yl)-5-oxopentanoate (0.25 g, 0.86 mmol) and K$_2$CO$_3$ (0.38 g, 2.74 mmol) in DMF (40 mL), was slowly added 4-(bromomethyl)benzonitrile (0.48 mL, 2.46 mmol). The reaction mixture was stirred at room temperature overnight. Additional K$_2$CO$_3$ (0.38 g, 2.74 mmol) was added and the reaction mixture was heated at 80° C. overnight. Acetic acid (5 drops) was added to reaction mixture. The solvent was evaporated and the residue was partitioned between ethyl acetate (100 mL) and saturated solution of sodium bicarbonate (100 mL). Solid that did not go into solution was filtered and it was stirred in methanol (400 mL). Solid was then filtered, washed with methanol (100 mL) and dried to give 4-((2-(2,6-dioxopiperidin-3-yl)-1-oxoisoindolin-4-yloxy)methyl)benzonitrile as a white solid (0.31 g, 66% yield): HPLC: Waters Symmetry C-18, 3.9×150 mm, 5 μm, 1 mL/min, 240 nm, acetonitrile/0.1% H3PO4: gradient 10/90 to 90/10 in 15 min; 5 min at 90/10:10.45 min (98.49%); mp: 290-292° C.; 1H NMR (DMSO-d6) δ 1.85-2.12 (m, 1H, CHH), 2.34-2.47 (m, 1H, CHH), 2.54-2.70 (m, 1H, CHH), 2.78-3.07 (m, 1H, CHH), 4.13-4.39 (d, J=17.6 Hz, 1H, CHH), 4.47 (d, J=17.6 Hz, 1H, CHH), 5.12 (dd, J=5.1, 13.2 Hz, 1H, CH), 5.37 (s, 2H, CH$_2$), 7.32 (dd, J=7.6, 16.7 Hz, 2H, Ar), 7.41-7.57 (m, 1H, Ar), 7.69 (d, J=8.1 Hz, 2H, Ar), 7.88 (d, J=8.3 Hz, 2H, Ar), 10.98 (s, 1H, NH); 13C NMR (DMSO-d6) δ 22.37, 31.16, 45.03, 51.58, 68.49, 110.60, 114.93, 115.53, 118.67, 128.01, 129.83, 129.97, 132.41, 133.40, 142.41, 153.07, 167.90, 170.95, 172.81; LCMS MH=376; Anal Calcd for C$_{21}$H$_{17}$N$_3$O$_4$+0.1 H$_2$O: C, 66.87; H, 4.60; N, 11.14; Found: C, 66.43; H, 4.47; N, 11.05.

5.294 3-[4-(4-Hexylaminomethyl-Benzyloxy)-1-Oxo-1,3-Dihydro-Isoindol-2-yl]-Piperidine-2,6-Dione

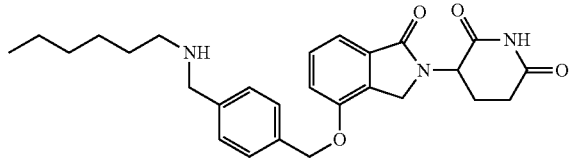 [SMILES: CCCCCCNCc1ccc(COc2cccc3c2CN(C2CCC(=O)NC2=O)C3=O)cc1]

Step 1: To the acetonitrile solution (20 mL) of 4-carbamoyl-4-[4-(4-chloromethyl-benzyloxy)-1-oxo-1,3-dihydroisoindol-2-yl]-butyric acid methyl ester (0.7 g, 1.62 mmol), was added hexyl amine (1.07 ml, 8.1 mmol). The mixture was stirred at room temperature overnight. The reaction mixture was concentrated and the resulting oil was used in next step without purification.

Step 2: To the DMF solution (10 mL) of 4-carbamoyl-4-[4-(4-hexylaminomethyl-benzyloxy)-1-oxo-1,3-dihydroisoindol-2-yl]-butyric acid methyl ester (0.8 g, 1.62 mmol), was added potassium carbonate (0.22 g, 1.62 mmol). The mixture was stirred at 70° C. for 9 hours. The mixture was filtered. The filtrate was concentrated on rota-vap. The resulting mixture was purified on silica gel column and eluted with CH$_2$Cl$_2$/MeOH to give 3-[4-(4-hexylaminomethyl-benzyloxy)-1-oxo-1,3-dihydro-isoindol-2-yl]-piperidine-2,6-dione as a white solid (84 mg, 12%). mp: 155-157° C. HPLC: Waters Symmetry C-18, 3.9×150 mm, 5 micro, 1 mL/min, 240 nm, gradient acetonitrile/0.1% H$_3$PO$_4$ in H$_2$O from 5/95 to 100/0 in 5 min and stayed at 100/0 for 5 min: t$_R$=5.09 min (96%). $^1$H NMR (DMSO-d$_6$) δ 0.65-0.98 (m, 3H, CH$_3$), 1.11-1.33 (m, 6H, CH$_2$, CH$_2$, CH$_2$), 1.41 (d, J=6.8 Hz, 2H, CH$_2$), 1.86-2.07 (m, 1H, CHH), 2.35-2.47 (m, 1H, CHH), 2.54-2.66 (m, 1H, CHH), 2.78-3.09 (m, 1H, CHH), 3.71 (s, 2H, CH$_2$), 4.17-4.53 (m, 2H, CH$_2$), 5.10 (dd, J=5.1, 13.2 Hz, 1H, NCH), 5.22 (s, 2H, CH$_2$), 7.12-7.63 (m, 7H, Ar). $^{13}$C NMR (DMSO-d$_6$) δ 13.84, 21.99, 22.30, 26.35, 28.87, 31.13, 45.04, 48.35, 51.53, 52.28, 69.36, 114.94, 115.15, 127.56, 128.15, 129.73, 129.90, 133.24, 134.95, 139.89, 153.40, 167.94, 170.91, 172.7; LCMS MH=464. Anal Calcd for C$_{27}$H$_{33}$N$_3$O$_4$: C, 69.96; H, 7.18; N, 9.06; Found: C, 61.67; H, 6.22; N, 7.96.

5.295 4-[2-(2,6-Dioxo-Piperidin-3-yl)-1-Oxo-2,3-Dihydro-1H-Isoindol-4-yloxymethyl]-N-(2-Morpholin-4-yl-Ethyl)-Benzamide

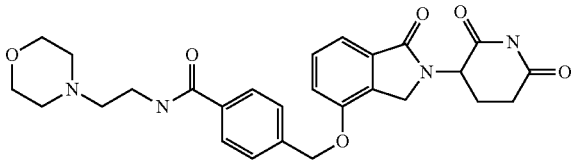 [SMILES: O=C1CCC(N2Cc3c(OCc4ccc(C(=O)NCCN5CCOCC5)cc4)cccc3C2=O)C(=O)N1]

Step 1: 4-(Chloromethyl)benzoyl chloride (1.452 g, 7.68 mmol) was added to a stirred solution of 2-morpholinoethanamine (1 g, 7.68 mmol) in acetonitrile (25 mL). The resulting solution was stirred for 2 hours and the reaction was complete. The reaction mixture concentrated and purified with ISCO to give 4-chloromethyl-N-(2-morpholin-4-yl-ethyl)-benzamide as white solid (1.7 g, 78% yield); LCMS MH=283, 285. $^1$H NMR (DMSO-d$_6$) δ 2.43 (d, J=14.5 Hz, 6H, CH$_2$, CH$_2$, CH$_2$), 3.35-3.44 (m, 2H, CH$_2$), 3.50-3.63 (m, 4H, CH$_2$, CH$_2$), 4.81 (s, 2H, CH$_2$), 7.52 (d, J=8.1 Hz, 2H, Ar), 7.83 (d, J=8.3 Hz, 2H, Ar), 8.34-8.49 (m, 1H, NH).

Step 2: To a stirred solution of methyl 5-amino-4-(4-hydroxy-1-oxoisoindolin-2-yl)-5-oxopentanoate (400 mg, 1.36 mmol), 4-(chloromethyl)-N-(2-morpholinoethyl)benzamide (387 mg, 1.36 mmol) and K$_2$CO$_3$ (189 mg, 1.36 mmol) in DMF (10 mL), was added DIPEA (0.24 ml, 1.36 mmol) at room temperature. The resulting reaction mixture was stirred at room temperature for 21 hours and heated at 50° C. for 4 days. Then mixture was heated at 80° C. overnight and concentrated for purification with ISCO to give a white solid, which was triturated in acetonitrile (3 mL) to give 4-[2-(2,6-dioxo-piperidin-3-yl)-1-oxo-2,3-dihydro-1H-isoindol-4-yloxymethyl]-N-(2-morpholin-4-yl-ethyl)-benzamide as a white solid (123 mg, 17.7% yield). HPLC: Waters Symmetry C-18, 3.9×150 mm, 5 µm, 1 mL/min, 240 nm, gradient 5-50% in 10 min (acetonitrile/0.1% H$_3$PO$_4$), 7.28 min (97.4%); mp: 193-195° C. $^1$H NMR (DMSO-d$_6$) δ 1.91-2.10 (m, 1H, CHH), 2.36-2.48 (m, 7H, CHH, CH$_2$, CH$_2$, CH$_2$), 2.54-2.65 (m, 1H, CHH), 2.83-3.02 (m, 1H, CHH), 3.34-3.44 (m, 2H, CH$_2$), 3.51-3.62 (m, 4H, CH$_2$, CH$_2$), 4.22-4.53 (m, 2H, CHH, CHH), 5.05-5.18 (m, 1H, CHN), 5.32 (s, 2H, CH$_2$), 7.27-7.37 (m, 2H, Ar), 7.44-7.52 (m, 1H, Ar), 7.57 (d, J=8.3 Hz, 2H, Ar), 7.85 (d, J=8.3 Hz, 2H, Ar), 8.40 (s, 1H, NH), 10.98 (s, 1H, NH). $^{13}$C NMR (DMSO-d$_6$) δ 22.34, 31.18, 36.51, 45.07, 51.58, 53.25, 57.29, 66.16, 68.97, 115.01, 115.35, 127.23, 127.29, 129.78, 129.97, 133.34, 134.16, 139.67, 153.27, 165.78, 167.94, 170.96, 172.81. LCMS MH=507. Anal. Calcd for C$_{27}$H$_{30}$N$_4$O$_6$+1.2 H$_2$O: C, 61.40; H, 6.18; N, 10.61; Found: C, 61.10; H, 6.11; N, 10.26.

5.296 3-(4-((6-((Diethylamino)Methyl)Benzofuran-2-yl)Methoxy)-1-Oxoisoindolin-2-yl)Piperidine-2,6-Dione

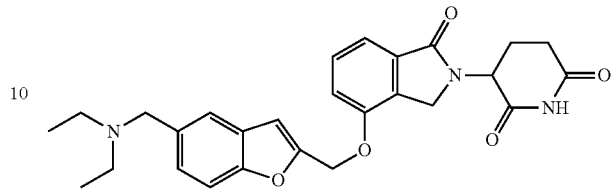

Step 1: A mixture of ethyl 5-formylbenzofuran-2-carboxylate (1.1 g, 4.8 mmol), diethylamine (0.4 g, 5.3 mmol) and acetic acid (0.3 g, 5.5 mmol) in THF (45 mL) was stirred at room temperature for 30 minutes. Sodium triacetoxyborohydride (2.0 g, 9.6 mmol) was added and the mixture was stirred at room temperature overnight. The reaction mixture was diluted with EtOAc (70 mL) and water (40 mL) and basified with NH$_4$OH to pH~11. Layers were separated and aqueous layer was extracted with EtOAc (40 mL). Combined EtOAc solution was dried and concentrated. Residue was purified by chromatography (SiO$_2$, CH$_3$OH:CH$_2$Cl$_2$ 3:97) to give ethyl 5-(diethylaminomethyl)benzofuran-2-carboxylate (0.9 g, 70% yield): $^1$H NMR (CDCl$_3$) δ 1.05 (t, J=6.9 Hz, 6H), 1.42 (t, J=7.2 Hz, 3H), 2.50-2.75 (q, J=7.2 Hz, 4H), 3.64 (s, 2H), 4.40-4.47 (q, J=7.2 Hz, 2H), 7.42-7.53 (m, 3H), 7.62 (d, J=0.9 Hz, 1H).

Step 2: A solution of ethyl 5-(diethylaminomethyl)-benzofuran-2-carboxylate (0.9 g, 3.3 mmol) in THF (15 mL) was added slowly to a stirred solution of LiAlH$_4$/THF (1M, 4.3 mL, 4.3 mmol) in THF (10 mL) at 5° C. The reaction mixture was stirred at 5° C. for 30 minutes then quenched with sat. Na$_2$CO$_3$ (30 mL). The mixture was stirred with CH$_2$Cl$_2$ (50 mL) and aqueous layer was extracted with CH$_2$Cl$_2$ (3×40 mL). Combined CH$_2$Cl$_2$ solution was washed with brine (40 mL) and dried. The solvent was removed and the residue was purified by chromatography (SiO$_2$, CH$_3$OH:CH$_2$Cl$_2$ 3:97) to give [5-(diethylaminomethyl)benzofuran-2-yl]methanol (0.6 g, 87%); $^1$H NMR (CDCl$_3$) δ 1.05 (t, J=7.2 Hz, 6H), 2.50-2.57 (q, J=7.2 Hz, 4H), 2.93 (b, 1H), 3.62 (s, 2H), 4.71 (s, 2H), 6.56 (d, J=0.3 Hz, 1H), 7.21-7.24 (dd, J=1.8 and 8.4 Hz, 1H), 7.32 (d, J=8.4 Hz, 1H), 7.47 (d, J=1.2 Hz, 1H).

Step 3: Diisopropyl azodicarboxylate (0.8 g, 4.2 mmol) was added to a stirred suspension of triphenylphosphine-polymer bound (3.5 g, 4.4 mmol) in THF (40 mL) at 3-5° C. After stirred at 3° C. for 10 minutes, a solution of methyl 5-amino-4-(4-hydroxy-1-oxoisoindolin-2-yl)-5-oxopentanoate (0.8 g, 2.8 mmol) and [5-(diethylaminomethyl)benzofuran-2-yl]methanol (0.7 g, 2.8 mmol) in THF (60 mL) was added at 3-6° C. After stirred at 3° C. for 5 minutes, mixture was stirred at room temperature overnight. The reaction mixture was filtered and solid was washed with CH$_2$Cl$_2$ (40 mL). Filtrate was concentrated and the residue was dissolved in CH$_2$Cl$_2$ (100 mL) and washed with sat. NaHCO$_3$ (40 mL), water (40 mL), and brine (40 mL), and dried. The solvent was removed and the residue was purified by chromatography (SiO$_2$, CH$_3$OH:CH$_2$Cl$_2$ 3:97) to give methyl 5-amino-4-(4-((5-((diethylamino)methyl)benzofuran-2-yl)methoxy)-1-oxoisoindolin-2-yl)-5-oxopentanoate (0.7, 47% yield): $^1$H NMR (CDCl$_3$) δ 1.05 (t, J=7.2 Hz, 6H), 2.12-2.44 (m, 4H), 2.50-2.57 (q, J=7.2 Hz, 4H), 3.62-3.64 (m, 5H), 4.40 (d, J=17.4 Hz, 1H), 4.45 (d, J=17.4 Hz, 1H), 4.87-4.92 (dd, J=5.7 and 8.7 Hz, 1H), 5.23 (s, 2H), 5.49 (s, 1H), 6.40 (s, 1H), 6.77 (s, 1H), 7.15-7.18 (dd, J=2.4 and 6.6 Hz, 1H), 7.22-7.29 (m, 1H), 7.39-7.46 (m, 3H), 7.53 (d, J=0.9 Hz, 1H).

Step 4: A mixture of methyl 5-amino-4-(4-((5-((diethylamino)methyl) benzofuran-2-yl)methoxy)-1-oxoisoindolin-2-yl)-5-oxopentanoate (0.7 g, 1.3 mmol) and $K_2CO_3$ (0.2 g, 1.3 mmol) in DMF (10 mL) was heated at 80° C. oil bath for 6 hours. The reaction mixture was cooled and concentrated. Residue was stirred with EtOAc (10 mL) and water (20 mL). Solid was collected and purified by chromatography ($SiO_2$, $CH_3OH$:$CH_2Cl_2$ 3:97 to 5:95) to give 3-(4-((6-diethylamino)methyl)benzofuran-2-yl)methoxy)-1-oxoisoindolin-2-yl)piperidine-2,6-dione (0.3 g, 51% yield): mp 193-195° C.; $^1$H NMR (DMSO-$d_6$) δ 0.97 (t, J=6.9 Hz, 6H), 1.94-1.98 (m, 1H), 2.39-2.58 (m, 6H), 2.84-2.94 (m, 1H), 3.59 (s, 2H), 4.25 (d, J=17.7 Hz, 1H), 4.35 (d, J=17.7 Hz, 1H), 5.07-5.13 (dd, J=5.1 and 13.2 Hz, 1H), 5.41 (s, 2H), 7.07 (s, 1H), 7.26-7.29 (dd, J=1.2 and 8.4 Hz, 1H), 7.34-7.37 (dd, J=0.9 and 6.9 Hz, 1H), 7.46-7.56 (m, 4H), 10.96 (s, 1H); $^{13}$C NMR (DMSO-$d_6$) δ 11.59, 22.28, 31.16, 45.03, 45.96, 51.55, 56.73, 62.55, 107.05, 110.68, 115.11, 115.64, 121.08, 125.66, 127.40, 129.81, 129.94, 133.42, 134.69, 152.67, 152.98, 153.68, 167.88, 170.93, 172.79; Calcd for $C_{27}H_{29}N_3O_5$+0.2 $H_2O$: C, 67.68; H, 6.18; N, 8.77. Found: C, 67.70; H, 5.94; N, 8.63.

5.297 3-(4-((6-((Diethylamino)Methyl)Benzo[B]Thiophen-2-yl)Methoxy)-1-Oxoisoindolin-2-yl)Piperidine-2,6-Dione

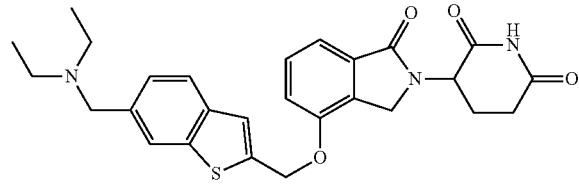 [SMILES: CCN(CC)Cc1ccc2cc(COc3cccc4c3CN(C3CCC(=O)NC3=O)C4=O)sc2c1]

Step 1: A suspension mixture of rhodanine (6.0 g, 45 mmol) and sodium acetate (11.3 g, 137 mmol) in glacial acetic acid (60 mL) was heated at 75° C. oil bath. P-tolualdehyde (5.8 g, 47.9 mmol) was added slowly and mixture was heated at 120° C. for 1 hour. The mixture was cooled to room temperature and poured into ice water (400 mL). After stirred for 30 minutes, mixture was filtered to give 14 g of orange solid. Solid was dissolved in 5% NaOH (200 mL) and heated in 80° C. oil bath for 1 hour then cooled to room temperature. The mixture was acidified with concentrated HCl and solid was collected to give 2-mercapto-3-p-tolylacrylic acid (6.4 g, 73% yield): $^1$H NMR (DMSO-$d_6$) δ 2.34 (s, 3H), 7.28-7.31 (d, J=8.1 Hz, 2H), 7.57-7.60 (d, J=8.1 Hz, 2H), 7.71 (s, 1H).

Step 2: A mixture of 2-mercapto-3-p-tolylacrylic acid (1.5 g, 7.7 mmol) and 12 (2.9 g, 11.6 mmol) in 1,4-dioxane (12 mL) was irradiated in microwave at 160° C. for 12 minutes. The mixture was cooled to room temperature and poured into sat. sodium bisulfite (300 mL). Solid was collected and dried to give 6-methylbenzo[b]thiophene-2-carboxylic acid (1.8 g, 100%). Compound was used in next reaction without further purification.

Step 3: Concentrated $H_2SO_4$ (5 mL) was added to a stirred mixture of 6-methylbenzo[b]thiophene-2-carboxylic acid (4.4 g, 23.2 mmol) in methanol (100 mL). The resulting mixture was heated to reflux for 3 hours. The mixture was cooled and concentrated. Residue was dissolved in $CH_2Cl_2$ (150 mL) and washed with 2N NaOH (40 mL), water (2×40 mL), and brine (40 mL), and dried. The solvent was removed and the residue was purified by chromatography ($SiO_2$, EtOAc:Hexane 1:9) to give methyl 6-methylbenzo[b]thiophene-2carboxylate (2.9 g, 60% yield): $^1$H NMR (CDCl$_3$) δ 2.49 (s, 3H), 3.93 (s, 3H), 7.20-7.26 (m, 1H), 7.65 (s, 1H), 7.74 (d, J=6 Hz, 1H), 8.01 (s, 1H).

Step 4: N-bromosuccinimide (4.0 g, 22.5 mmol) was added to a stirred solution of methyl 6-methylbenzo[b]thiophene-2-carboxylate (3.6 g, 17.4 mmol) in $CCl_4$ (55 mL). The reaction mixture was heated at a 75° C. oil bath with a 300 W bulb shining for 17 hours. The reaction mixture was cooled and filtered and filtrate was washed with water (2×40 mL) and brine (40 mL), and dried. The solvent was removed and the residue was purified by chromatography ($SiO_2$, EtOAc:Hexane 1:9) to give methyl 6-(bromomethyl)benzo[b]thiophene-2-carboxylate (2.2 g, 44% yield): $^1$H NMR (CDCl$_3$) δ 3.90 (s, 3H), 4.40 (s, 2H), 7.39-7.44 (m, 4H).

Step 5: A mixture of diethylamine (1.0 g, 13.7 mmol), $K_2CO_3$ (3.5 g, 25.3 mmol) and 18-crown-6 (catalytic amount) in acetone (15 mL) was heated at 35° C. oil bath. A solution of methyl 6-(bromomethyl)benzo[b]thiophene-2-carboxylate (1.6 g, 5.6 mmol) in acetone (15 mL) was added. The reaction mixture was stirred at 45° C. oil bath for 3 hours and then cooled to room temperature. The mixture was filtered and filtrate was concentrated. Residue was dissolved in EtOAc (70 mL) and washed with water (2×30 mL) and brine (30 mL), and dried. The solvent was removed and the residue was purified by chromatography ($SiO_2$, $CH_3OH$:$CH_2Cl_2$ 3:97) to give methyl 6-[(diethylamino)methyl]benzo[b]thiophene-2-carboxylate (1.3 g, 84% yield): $^1$H NMR (CDCl$_3$) δ 1.06 (t, J=6.9 Hz, 6H), 2.52-2.59 (q, J=7.2 Hz, 4H), 3.68 (s, 2H), 3.93 (s, 3H), 7.38-7.41 (dd, J=1.2 and 8.4 Hz, 1H), 7.78-7.84 (m, 2H), 8.03 (s, 1H).

Step 6: A solution of methyl 6-[(diethylamino)methyl]benzo[b]thiophene-2-carboxylate (1.3 g, 4.7 mmol) in THF (20 mL) was added slowly to a stirred solution of LiAlH$_4$/THF (1M, 6 mL, 6 mmol) in THF (10 mL) at 3-6° C. The resulting solution was stirred at 3° C. for 30 minutes and then quenched with water (5 mL). The mixture was stirred with $CH_2Cl_2$ (40 mL) and sat. NaHCO$_3$ (20 mL). The aqueous layer was extracted with $CH_2Cl_2$ (2×30 mL) and combined $CH_2Cl_2$ solution was washed with water (30 mL) and brine (30 mL), and dried. The solvent was removed and the residue was purified by chromatography ($SiO_2$, $CH_3OH$:$CH_2Cl_2$ 3:97) to give [6-[(diethylamino)methyl]benzo[b]thiophen-2-yl]methanol (1.0 g, 84% yield): $^1$H NMR (CDCl$_3$) δ 1.05 (t, J=6 Hz, 6H), 2.51-2.58 (q, J=6 Hz, 4H), 2.72 (b, 1H), 3.65 (s, 2H), 4.87 (s, 2H), 7.13 (d, J=3 Hz, 1H), 7.29-7.32 (d, J=9 Hz, 1H), 7.61 (d, J=9 Hz, 1H), 7.77 (s, 1H).

Step 7: Diisopropyl azodicarboxylate (0.9 g, 4.3 mmol) was added to a stirred suspension of triphenylphosphine-polymer bound (3.4 g, 5.4 mmol) in THF (40 mL) at 3-5° C. After stirred at 3° C. for 10 minutes, a solution of methyl 5-amino-4-(4-hydroxy-1-oxoisoindolin-2-yl)-5-oxopentanoate (1.1 g, 3.6 mmol) and [6-[(diethylamino)methyl]benzo[b]thiophen-2-yl]methanol (0.9 g, 3.6 mmol) in THF (80 mL) was added slowly at 3-6° C. The resulting mixture was stirred at room temperature overnight. The mixture was filtered and solid was washed with $CH_2Cl_2$ (40 mL). Filtrate was concentrated and the residue was dissolved in $CH_2Cl_2$ (100 mL) and washed with sat. NaHCO$_3$ (30 mL), water (30 mL), and brine (30 mL), and dried. The solvent was removed and the residue was purified by chromatography (SiO$_2$, CH$_3$OH:CH$_2$Cl$_2$ 3:97) to give methyl 5-amino-4-(4-((6-((diethylamino)methyl)benzo[b]thiophen-2-yl)methoxy)-1-oxoisoindolin-2-yl)-5-oxopentanoate (0.7 g, 35% yield).

Step 8: A mixture of methyl 5-amino-4-(4-((6-((diethylamino)methyl)benzo[b]thiophen-2-yl)methoxy)-1-oxoisoindolin-2-yl)-5-oxopentanoate (0.7 g, 1.2 mmol) and K$_2$CO$_3$ (0.2 g, 1.2 mmol) in DMF (10 mL) was heated at 80° C. oil bath for 3 hours. The reaction mixture was cooled and diluted with EtOAc (80 mL) and washed with water (3×35 mL) and brine (35 mL), and dried. The solvent was removed and the residue was crystallizing from hot EtOAc (10 mL) to give 3-(4-((6-((diethylamino)methyl)benzo[b]thiophen-2-yl)methoxy)-1-oxoisoindolin-2-yl)piperidine-2,6-dione (0.3 g, 44% yield): mp 190-192° C.; $^1$H NMR (DMSO-d$_6$) δ 0.98 (t, J=6 Hz, 6H), 1.96-2.02 (m, 1H), 2.43-2.60 (m, 6H), 2.90-2.93 (m, 1H), 3.32 (s, 2H), 4.29 (d, J=18 Hz, 1H), 4.38 (d, J=18 Hz, 1H), 5.08-5.14 (dd, J=3 and 12 Hz, 1H), 5.57 (s, 2H), 7.73-7.53 (m, 5H), 7.75-7.85 (m, 2H), 10.97 (s, 1H); $^{13}$C NMR (DMSO-d$_6$) δ 11.60, 22.31, 31.18, 45.04, 46.11, 51.59, 56.82, 65.28, 115.26, 115.62, 121.94, 123.35, 123.52, 125.56, 129.79, 130.05, 133.40, 137.83, 139.42, 152.87, 167.89, 170.95, 172.80; Calcd for C$_{27}$H$_{29}$N$_3$O$_4$S+0.2 H$_2$O: C, 65.49; H, 5.98; N, 8.49; S, 6.48. Found: C, 65.25; H, 5.82; N, 8.38; S, 6.63.

5.298 3-(4-(4-(8-Oxa-3-Azabicyclo[3.2.1]Octan-3-ylmethyl)Benzyloxy)-1-Oxoisoindolin-2-yl)Piperidine-2,6-Dione

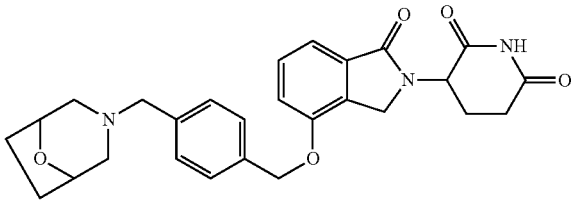 [SMILES: O=C1CCC(N2Cc3c(OCc4ccc(CN5CC6CCC(C5)O6)cc4)cccc3C2=O)C(=O)N1]

Step 1: Polymer-supported triphenylphosphine (1.6 mmol/g, 14.2 g, 22.73 mmol) was added to a stirred suspension of tert-butyl 5-amino-2-(4-hydroxy-1-oxoisoindolin-2-yl)-5-oxopentanoate (3.8 g, 11.36 mmol) in THF (140 mL) at 0° C., followed by diisopropyl azodicarboxylate (4.6 g, 22.73 mmol). After stirring for 10 minutes, (4-(chloromethyl)phenyl)methanol (2.67 g, 17.05 mmol) was added. The mixture was stirred at room temperature overnight and filtered. The resin was washed with dichloromethane (2×70 mL). The combined filtrates were concentrated in vacuo to give a syrup which was partitioned between EtOAc (300 ml) and water (100 ml). The organic layer was washed with brine, dried (Na$_2$SO$_4$,) and concentrated in vacuo to give a crude product as yellow oil. The crude was purified by ISCO (330 g column, MeOH/CH$_2$Cl$_2$ gradient from 0% to 5% in 50 min) to give tert-butyl 5-amino-2-(4-(4-(chloromethyl)benzyloxy)-1-oxoisoindolin-2-yl)-5-oxopentanoate (4 g, 74% yield); $^1$H NMR (DMSO-d$_6$) δ 1.39 (s, 9H, CH$_3$, CH$_3$, CH$_3$), 2.07 (d, J=1.1 Hz, 4H, CH$_2$, CH$_2$), 4.43 (s, 2H, CH$_2$), 4.64-4.75 (m, 1H, CH), 4.78 (s, 2H, CH$_2$), 5.27 (s, 2H, CH$_2$), 6.67-6.86 (m, 1H, NHH), 7.17-7.27 (m, 1H, NHH), 7.32 (d, J=2.6 Hz, 2H, Ar), 7.49 (d, J=5.1 Hz, 5H, Ar).

Step 2: To a solution of tert-butyl 5-amino-2-(4-(4-(chloromethyl)benzyloxy)-1-oxoisoindolin-2-yl)-5-oxopentanoate (500 mg, 1.06 mmol) in acetontrile (10 ml), were added 8-oxa-3-azabicyclo[3.2.1]octane hydrochloride (190 mg, 1.27 mmol) and N,N-diisopropylethylamine (410 mg, 3.17 mmol). The mixture formed was stirred at room temperature overnight. The solvent was evaporated under vacuo. The residue was taken in ethyl acetate (100 ml), washed with water (10 ml) and brine, and dried over MgSO$_4$. The solvent was evaporated to give tert-butyl 2-(4-(4-(8-oxa-3-azabicyclo[3.2.1]octan-3-ylmethyl)benzyloxy)-1-oxoisoindolin-2-yl)-5-amino-5-oxopentanoate (560 mg, 96% yield). $^1$H NMR (DMSO-d$_6$) δ 1.39 (s, 9H, CH$_3$, CH$_3$, CH$_3$), 1.66-1.78 (m, 2H, CH$_2$), 1.82-1.92 (m, 2H, CH$_2$), 1.97-2.30 (m, 6H, CH$_2$, CH$_2$, CH$_2$), 3.44 (s, 2H, CH$_2$), 4.13-4.28 (m, 2H, CH, CH), 4.42 (s, 2H, CH$_2$), 4.63-4.80 (m, 1H, CH), 5.23 (s, 2H, CH$_2$), 6.65-6.87 (m, 1H, NHH), 7.15-7.27 (m, 1H, NHH), 7.33 (d, J=9.3 Hz, 4H, Ar), 7.41-7.54 (m, 3H, Ar).

Step 3: To a slurry of tert-butyl 2-(4-(4-(8-oxa-3-azabicyclo[3.2.1]octan-3-ylmethyl)benzyloxy)-1-oxoisoindolin-2-yl)-5-amino-5-oxopentanoate (560 mg, 1.019 mmol) in THF (20 ml), was added potassium tert-butoxide (137 mg, 1.223 mmol) at 0° C. The mixture was stirred at 0° C. for 10 minutes, warmed up to room temperature and stirred overnight. The reaction was quenched with acetic acid (3 ml), THF was removed under vacuum, and the residue was partitioned between ethyl acetate (70 ml) and saturated sodium bicarbonate (10 ml). The precipitate formed was filtered and the filtrate was washed with brine and dried over magnesium sulfate. The solvent was evaporated and the crude was purified by prep HPLC to give 3-(4-(4-(8-oxa-3-azabicyclo[3.2.1]octan-3-ylmethyl)benzyloxy)-1-oxoisoindolin-2-yl)piperidine-2,6-dione as a white solid (80 mg, 17% yield); mp: 228-230° C.; $^1$H NMR (DMSO-d$_6$) δ 1.58-2.31 (m, 6H, 6×CHH), 2.31-2.50 (m, 2H, CHH, CHH), 2.58 (d, J=18.3 Hz, 2H, CHH, CHH), 2.82-3.03 (m, 1H, CHH), 3.12 (br. s., 1H, CHH), 3.39-3.60 (m, 2H, CH$_2$), 3.92-4.76 (m, 4H, CH$_2$, CH, CH), 5.11 (dd, J=5.0, 13.1 Hz, 1H, CH), 5.25 (br. s., 2H, CH$_2$), 7.12-7.84 (m, 7H, Ar), 10.97 (s, 1H, NH); $^{13}$C NMR (DMSO-d$_6$) δ 22.34, 27.94, 31.16, 45.06, 51.56, 58.19, 60.95, 69.25, 73.58, 114.94, 115.26, 127.64, 129.80, 129.93, 133.30, 137.72, 153.43, 157.78, 158.20, 162.96, 167.97, 170.96, 172.81; LCMS MH=476; HPLC: Waters Xterra C-18, 3.9×150 mm, 5 μm, 1 mL/min, 240 nm, Gradient (acetonitrile/0.1% HCOONH$_4$) 5/95 to 95/5 in 5 min, 95/5 10 min: t$_R$=5.26 (100%).

5.299 3-(4-(4-(8-Oxa-3-Azabicyclo[3.2.1]Octan-3-ylmethyl)Benzyloxy)-1-Oxoisoindolin-2-yl)Piperidine-2,6-Dione

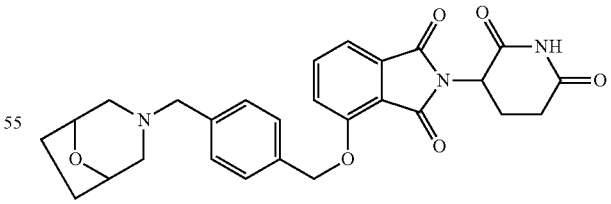

Step 1: To a solution of tert-butyl 5-amino-2-(4-(4-(chloromethyl)benzyloxy)-1-oxoisoindolin-2-yl)-5-oxopentanoate (500 mg, 1.06 mmol) in acetontrile (10 ml) was added 8-oxa-3-azabicyclo[3.2.1]octane hydrochloride (190 mg, 1.27 mmol) and N,N-Diisopropylethyl-amine (410 mg, 3.17 mmol). The formed mixture was stirred at room temperature overnight. The solvent was evaporated under vacuo. The residue was taken in ethyl acetate (100 ml) and washed with water (10 ml), brine, dried over MgSO$_4$, the solvent was evaporated to give tert-butyl 2-(4-(4-(8-oxa-3-azabicyclo[3.2.1]octan-3-ylmethyl)benzyloxy)-1-oxoisoindolin-2-yl)-5-amino-5-oxopentanoate (560 mg, 96% yield). $^1$H NMR (DMSO-d$_6$) δ 1.39 (s, 9H, CH$_3$, CH$_3$, CH$_3$), 1.66-1.78 (m, 2H, CH$_2$), 1.82-1.92 (m, 2H, CH$_2$), 1.97-2.30 (m, 6H, CH$_2$, CH$_2$, CH$_2$), 3.44 (s, 2H, CH$_2$), 4.13-4.28 (m, 2H, CH, CH), 4.42 (s, 2H, CH$_2$), 4.63-4.80 (m, 1H, CH), 5.23 (s, 2H, CH$_2$), 6.65-6.87 (m, 1H, NHH), 7.15-7.27 (m, 1H, NHH), 7.33 (d, J=9.3 Hz, 4H, Ar), 7.41-7.54 (m, 3H, Ar).

Step 2: To a slurry of tert-butyl 2-(4-(4-(8-oxa-3-azabicyclo[3.2.1]octan-3-ylmethyl)benzyloxy)-1-oxoisoindolin-2-yl)-5-amino-5-oxopentanoate (560 mg, 1.019 mmol) in THF (20 ml) was added potassium tert-butoxide (137 mg, 1.223 mmol) at 0° C. The mixture was stirred at 0° C. for 10 minutes, warmed up to room temperature and stirred overnight. The reaction was quenched with acetic acid (3 ml), THF was removed under vacuum, the residue was partitioned between ethyl acetate (70 ml) and saturated sodium bicarbonate (10 ml), the formed precipitate was filtered to give 2-((4-(8-oxa-3-azabicyclo[3.2.1]octan-3-ylmethyl)benzyl)oxy)-6-((2,6-dioxopiperidin-3-yl)carbamoyl)benzoic acid (210 mg, 38% yield). $^1$H NMR (DMSO-d$_6$) δ 1.65-1.79 (m, 2H, CHH, CHH), 1.81-1.90 (m, 2H, CHH, CHH), 1.97 (d, J=3.4 Hz, 1H, CHH), 2.04 (br. s., 1H, CHH), 2.16 (d, J=1.7 Hz, 1H, CHH), 2.20 (d, J=1.7 Hz, 1H, CHH), 2.41-2.50 (m, 2H, CHH, CHH), 2.57 (br. s., 1H, CHH), 2.77 (s, 1H, CHH), 3.42 (s, 2H, CH$_2$), 4.19 (dd, J=2.0, 4.2 Hz, 2H, CH, CH), 4.70 (s, 1H, CH), 5.16 (s, 2H, CH$_2$), 7.17-7.35 (m, 4H, Ar), 7.35-7.53 (m, 3H, Ar), 8.72 (d, J=8.5 Hz, 1H, NH), 10.85 (s, 1H, NH).

Step 3: The mixture of 2-(4-(8-oxa-3-azabicyclo[3.2.1]octan-3-ylmethyl)benzyloxy)-6-(2,6-dioxopiperidin-3-yl-carbamoyl)benzoic acid (210 mg, 0.41 mmol) and triethyl amine (83 mg, 0.82 mmol) in acetic acid (5 ml) was refluxed overnight. The mixture was cooled to room temperature, acetic acid was removed under vacuum, the residue was partitioned between EtOAc (50 ml) and saturated NaHCO$_3$, the organic layer was washed with water, brine, dried (MgSO$_4$) and concentrated in vacuo to give a crude. The crude was reslurried in ether (2×5 ml) and filtered to give 4-(4-(8-oxa-3-azabicyclo[3.2.1]octan-3-ylmethyl)benzyloxy)-2-(2,6-dioxopiperidin-3-yl)isoindoline-1,3-dione (120 mg, 78% yield); m.p: 196-198° C.; $^1$H NMR (DMSO-d$_6$) δ 1.56-1.76 (m, 2H, CHH, CHH), 1.76-1.87 (m, 2H, CHH, CHH), 1.88-2.05 (m, 1H, CHH), 2.12 (d, J=10.6 Hz, 2H, CHH, CHH), 2.41 (br. s., 2H, CHH, CHH), 2.45-2.63 (m, 2H, CHH, CHH), 2.79 (d, J=11.7 Hz, 1H, CHH), 3.37 (s, 2H, CH$_2$), 4.12 (d, J=1.7 Hz, 2H, CH, CH), 5.02 (dd, J=5.4, 12.7 Hz, 1H, CH), 5.28 (s, 2H, CH$_2$), 7.27 (d, J=7.9 Hz, 2H, Ar), 7.40 (dd, J=3.1, 7.6 Hz, 3H, Ar), 7.53 (d, J=8.5 Hz, 1H, Ar), 7.69-7.85 (m, 1H, Ar), 11.04 (s, 1H, NH); $^{13}$C NMR (DMSO-d$_6$) δ 21.95, 28.29, 30.90, 48.73, 58.06, 61.11, 69.95, 73.69, 115.48, 16.56, 120.19, 127.28, 128.56, 133.24, 134.68, 136.97, 155.53, 165.29, 166.75, 169.87, 172.71; HPLC: Waters Xterra C-18, 3.9×150 mm, 5 μm, 1 mL/min, 240 nm, 25/75 CH$_3$CN/0.1% HCOONH$_4$ t$_R$=3.97 (100%); Anal. Calcd for C$_{27}$H$_{27}$N$_3$O$_7$+0.1 H$_2$O; C, 66.00; H, 5.58; N, 8.55; Found: C, 65.96; H, 5.68; N, 8.27.

5.300 3-(4-(4-(3-Oxa-8-Azabicyclo[3.2.1]Octan-8-ylmethyl)Benzyloxy)-1-Oxoisoindolin-2-yl)Piperidine-2,6-Dione

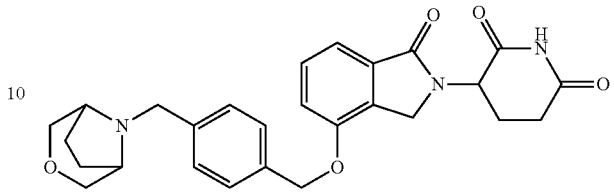

Step 1: tert-butyl 2-(4-(4-(3-oxa-8-azabicyclo[3.2.1]octan-8-ylmethyl)benzyloxy)-1-oxoisoindolin-2-yl)-5-amino-5-oxopentanoate To a suspension of tert-butyl 5-amino-2-(4-(4-(chloromethyl)benzyloxy)-1-oxoisoindolin-2-yl)-5-oxopentanoate (500 mg, 1.06 mmol) in MeCN (10 mL), was added (1R,5S)-3-oxa-8-azabicyclo[3.2.1]octane hydrochloride (316 mg, 2.114 mmol) and N,N-diisopropylethylamine (0.41 mL, 2.33 mmol). The mixture was warmed up to 60° C. and stirred overnight. After ~15 h, the reaction mixture was concentrated to dryness and the solid residue was partitioned between EtOAc (150 mL) and 1N NaHCO$_3$ (30 mL). The aqueous layer was washed with additional EtOAc (150 mL). The organic layers were combined, washed with brine, dried (Na$_2$SO$_4$), and concentrated in vacuo and then dried in a vacuum oven at 60° C. to a provide tert-butyl 2-(4-(4-(3-oxa-8-azabicyclo[3.2.1]octan-8-ylmethyl)benzyloxy)-1-oxoisoindolin-2-yl)-5-amino-5-oxopentanoate as a white solid (580 mg, 100% yield); LC/MS M+H=550. The solid was used in the next step without further purification.

Step 2: tert-Butyl 2-(4-(4-(3-oxa-8-azabicyclo[3.2.1]octan-8-ylmethyl)benzyloxy)-1-oxoisoindolin-2-yl)-5-amino-5-oxopentanoate To a cooled solution of tert-butyl 2-(4-(4-(3-oxa-8-azabicyclo[3.2.1]octan-8-ylmethyl)benzyloxy)-1-oxoisoindolin-2-yl)-5-amino-5-oxopentanoate (580 mg, 1.06 mmol) in THF (10 mL) in an ice bath, was added KO$^t$Bu (154 mg, 1.38 mmol) as a solid in one portion. The ice bath was immediately removed and the reaction mixture was stirred at room temperature for 90 min. The reaction mixture was cooled in an ice bath and quenched by addition of acetic acid (0.162 mL, 2.82 mmol). The volatiles were removed in vacuo to give a white solid that was partitioned between EtOAc (125 mL) and 1N NaHCO$_3$ (30 mL). The aqueous layer was extracted with additional EtOAc (~75 mL). The combined organic layer was washed with brine, dried (Na$_2$SO$_4$), and concentrated in vacuo to give an off-white solid (400 mg crude yield). The solid was triturated with Et$_2$O (40 mL) with the aid of sonication, collected on filter funnel and washed with additional Et$_2$O. A similar trituration was carried out with water (35 mL) and the solid was collected on a filter funnel, suction dried, then placed in vacuum oven at 60° C. for several hours to give tert-butyl 2-(4-(4-(3-oxa-8-azabicyclo[3.2.1]octan-8-ylmethyl)benzyloxy)-1-oxoisoindolin-2-yl)-5-amino-5-oxopentanoate as a white solid (305 mg, 61% yield): HPLC: Waters Symmetry Cis, 5 μm, 3.9×150 mm, 1 ml/min, 240 nm, 15/85 CH$_3$CN/0.1% H$_3$PO$_4$, 6.81 min (95.0%); mp: 243-245° C.; $^1$H NMR (DMSO-d$_6$) δ 1.69-1.81 (m, 2H, CH$_2$), 1.86-2.06 (m, 3H, 3×CHH), 2.33-2.48 (m, 1H, CHH), 2.52-2.64 (m, 1H, CHH), 2.81-3.02 (m, 3H, 3×CHH), 3.35-3.46 (m, 4H, CH$_2$, CHH, CHH), 3.48-3.59 (m, 2H, CHH, CHH), 4.25 (d, J=17.4 Hz, 1H, CHH), 4.42 (d, J=17.6 Hz, 1H, CHH), 5.11 (dd, J=5.1, 13.2 Hz, 1H, CH), 5.22 (s, 2H, CH$_2$), 7.27-7.55

(m, 7H, Ar), 10.97 (s, 1H, Ar); $^{13}$C NMR (DMSO-d$_6$) δ 22.33, 24.56, 31.18, 45.06, 51.55, 56.42, 59.89, 69.41, 72.51, 114.94, 115.19, 127.61, 128.60, 129.78, 129.93, 133.28, 134.99, 139.32, 153.49, 167.99, 170.96, 172.81; LC/MS M+H=476; Anal Calcd for C$_{27}$H$_{29}$N$_3$O$_5$+0.17 H2O+0.26 EtOAc: C, 67.15; H, 6.31; N, 8.38. Found: C, 67.15; H, 6.23; N, 8.49.

5.301 3-[5-Chloro-4-(4-Morpholin-4-ylmethyl-Benzyloxy)-1-Oxo-1,3-Dihydro-Isoindol-2-yl]-Piperidine-2,6-Dione

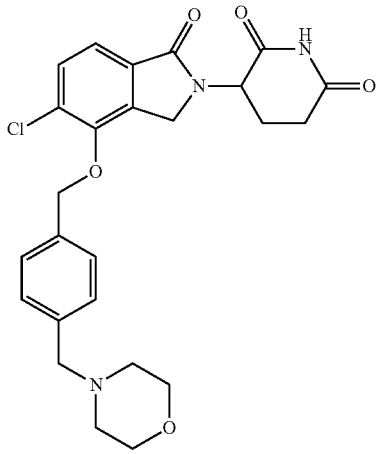 [SMILES: O=C1CCC(N2Cc3c(ccc(Cl)c3OCc3ccc(CN4CCOCC4)cc3)C2=O)C(=O)N1]

Step 1: Preparation of 4-Chloro-3-hydroxy-2-methyl-benzoic acid methyl ester To the stirred solution of 4-chloro-3-hydroxy-2-methylbenzoic acid (2.5 g, 13.40 mmol) in MeOH (20 ml) was added sulfuric acid (0.263 g, 2.68 mmol). The resulting solution was reacted at 62° C. for two days. The reaction mixture was concentrated to give brown solution (30 mL), to which was added water (80 mL). The mixture was stirred and light brown solid precipitated out. The mixture was extracted with EtOAc (100 mL). Organic layer was concentrated and purified by silica gel column (120 g EtOAc/Hexanes) to give 4-Chloro-3-hydroxy-2-methyl-benzoic acid methyl ester as a white solid (6.9 g, 74% yield). It was used in the next step without further work or purification.

Step 2: Preparation of 3-(tert-Butyl-dimethyl-silanyloxy)-4-chloro-2-methyl-benzoic acid methyl ester To a stirred solution of methyl 4-chloro-3-hydroxy-2-methylbenzoate (6.34 g, 31.6 mmol) and 1H-imidazole (5.38 g, 79 mmol) in DMF (60 ml) in a 250 ml RBF in an ice-bath was added tert-butylchlorodimethylsilane (5.24 g, 34.8 mmol). After 20 minutes, the ice-bath was removed and the mixture was stirred at room temperature for 2 hours. Ice-water (50 ml) was added to the mixture, the resulting precipitate was extracted with ethyl acetate (2×40 ml). The combined EtOAc phases were washed with water (40 ml), brine (40 ml), and concentrated to an oil (14.08 g), which was purified by silica gel column to give 3-(tert-Butyl-dimethyl-silanyloxy)-4-chloro-2-methyl-benzoic acid methyl ester as an oil, 8.38 g, 84% yield. The product was used in the next step without further purification.

Step 3: Preparation of 2-Bromomethyl-3-(tert-butyl-dimethyl-silanyloxy)-4-chloro-benzoic acid methyl ester To a solution of methyl 3-(tert-butyldimethylsilyloxy)-4-chloro-2-methylbenzoate (8.38 g, 26.6 mmol) in methyl acetate (50 ml, 26.6 mmol) was added 1-bromopyrrolidine-2,5-dione (4.74 g, 26.6 mmol) at room temperature. The mixture was heated to 50° C. for one hour. The reaction mixture was cooled to room temperature and washed with 50% sodium sulfite (Na$_2$SO$_3$, 50 ml), water (50 ml) and brine (50 ml). The organic phase was dried in MgSO$_4$ and concentrated to an oil, which was purified by silica gel column (120 g, 1% EtOAc in Hex gradient to 5% in 18 minutes) to give 2-Bromomethyl-3-(tert-butyl-dimethyl-silanyloxy)-4-chloro-benzoic acid methyl ester as an oil (9.53 g, 91% yield). The product was used in the next step without further purification.

Step 4: Preparation of 4-[4-(tert-Butyl-dimethyl-silanyloxy)-5-chloro-1-oxo-1,3-dihydro-isoindol-2-yl]-4-carbamoyl-butyric acid methyl ester To a stirred solution of methyl 2-(bromomethyl)-3-(tert-butyldimethylsilyloxy)-4-chlorobenzoate (9.5 g, 24.13 mmol) in acetonitrile (90 ml) at room temperature was added (S)-methyl 4,5-diamino-5-oxopentanoate hydrochloride (5.22 g, 26.5 mmol). To the suspension was slowly added N-ethyl-N-isopropylpropan-2-amine (8.37 ml, 50.7 mmol). The suspension was heated at 40° C. for 24 hours. Solvent was evaporated to give a yellow oil, which was stirred in ether (150 ml) overnight. The suspension was filtered and rinsed with extra diethyl ether (50 ml) to give a light yellow solid and the filtrate. The filtrated was washed with 1N HCl (50 ml), saturated sodium bicarbonate (80 ml), brine (50 ml). The ether phase was evaporated to give 4-[4-(tert-Butyl-dimethyl-silanyloxy)-5-chloro-1-oxo-1,3-dihydro-isoindol-2-yl]-4-carbamoyl-butyric acid methyl ester as an oil, 8.18 g, 76% crude yield. It was used in the next step without further purification.

Step 5: Preparation of 4-Carbamoyl-4-(5-chloro-4-hydroxy-1-oxo-1,3-dihydro-isoindol-2-yl)-butyric acid methyl ester To a stirred solution of (S)-methyl 5-amino-4-(4-(tert-butyldimethylsilyloxy)-5-chloro-1-oxoisoindolin-2-yl)-5-oxopentanoate (8.16 g, 18.50 mmol) in DMF (25 ml) and Water (10 ml) in an ice bath was added potassium carbonate (1.279 g, 9.25 mmol). The mixture was stirred at room temperature for one hour. To the brown mixture was added acetonitrile (15 ml) and stirred at room temperature for 10 minutes. Solvent was evaporated. The resulting oil was purified by silica gel column (MeOH/CH$_2$Cl$_2$, 0.5% grad to 8% in 60 min) to give 4-Carbamoyl-4-(5-chloro-4-hydroxy-1-oxo-1,3-dihydro-isoindol-2-yl)-butyric acid methyl ester as an off-white solid (4.62 g, 76% yield). It was used in the next step without further purification.

Step 6: Preparation of 4-[4-(4-Bromomethyl-benzyloxy)-5-chloro-1-oxo-1,3-dihydro-isoindol-2-yl]-4-carbamoyl-butyric acid methyl ester A mixture of methyl 5-amino-4-(5-chloro-4-hydroxy-1-oxoisoindolin-2-yl)-5-oxopentanoate (4.6 g, 14.08 mmol), 1,4-bis(bromomethyl)benzene (11.15 g, 42.2 mmol) and potassium carbonate (1.946 g, 14.08 mmol) in acetonitrile (70 ml) was stirred at room temperature for 10 min then heated at 50° C. for 5 hours. The reaction mixture was cooled to room temperature, filtered and rinsed with acetonitrile to give a gel-like white solid. The filtrate was purified by silica gel column (MeOH/CH$_2$Cl$_2$) to a white solid (1.17 g, 16% yield). It was used in the next step without further purification.

Step 7: Preparation of 4-Carbamoyl-4-[5-chloro-4-(4-morpholin-4-ylmethyl-benzyloxy)-1-oxo-1,3-dihydro-isoindol-2-yl]-butyric acid methyl ester To a stirred suspension of methyl 5-amino-4-(4-(4-(bromomethyl)benzyloxy)-5-chloro-1-oxoisoindolin-2-yl)-5-oxopentanoate (0.436 g, 0.855 mmol) in acetonitrile (10 ml) at room temperature was added morpholine (0.745 ml, 8.55 mmol) and stirred for one hour. The solvent was evaporated to give an oil, which was stirred in water (15 ml) and EtOAc (20 ml). The mixture was washed with water (2×30 ml), brine (15 ml), dried and concentrated to give a clear oil (0.46 g, 104% crude yield). It was used in the next step without further purification.

Step 8: Preparation of 3-[5-Chloro-4-(4-morpholin-4-yl-methyl-benzyloxy)-1-oxo-1,3-dihydro-isoindol-2-yl]-piperidine-2,6-dione To a stirred solution of methyl 5-amino-4-(5-chloro-4-(4-(morpholinomethyl)benzyloxy)-1-oxoisoindolin-2-yl)-5-oxopentanoate (0.44 g, 0.853 mmol) in THF (10 ml) in a 0° C. ice-bath was added potassium 2-methylpropan-2-olate (0.192 g, 1.706 mmol) and stirred for 10 minutes. The reaction was quickly quenched with 1 N HCl to pH~4, and neutralized with saturated NaHCO$_3$ to pH~7. The mixture was extracted with EtOAc (2×30 ml), dried and evaporated to a white solid, which was purified by silica gel column to give 3-[5-Chloro-4-(4-(morpholin-4-ylmethyl-benzyloxy)-1-oxo-1,3-dihydro-isoindol-2-yl]-piperidine-2,6-dione as a white solid (72 mg, 17% yield); mp, 224-226° C. HPLC: Waters Symmetry C-18, 3.9×150 mm, 5 µm, 1 mL/min, 240 nm, gradient from 10/90 to 95/5 in 5 min, isocratic at 95/5 in 5 min (CH$_3$CN/0.1% H$_3$PO$_4$), 4.62 min (98.7%). $^1$H NMR (DMSO-d$_6$) δ 1.92-2.05 (m, 1H, CHH), 2.26-2.46 (m, 5H, CHH, CH$_2$, CH$_2$), 2.55-2.67 (m, 1H, CHH), 2.83-3.01 (m, 1H, CHH), 3.47 (s, 2H, CH$_2$), 3.52-3.62 (m, 4H, CH$_2$, CH$_2$), 4.39-4.66 (m, 2H, CH$_2$), 5.11 (dd, J=5.1, 13.2 Hz, 1H, NCH), 5.21 (s, 2H, CH$_2$), 7.29-7.39 (m, 2H, Ar), 7.41-7.53 (m, 3H, Ar), 7.66 (d, J=8.1 Hz, 1H, Ar), 11.02 (s, 1H, NH). $^1$H NMR (DMSO-d$_6$) $^{13}$C NMR (DMSO-d$_6$) δ 22.30, 31.11, 45.79, 51.68, 53.14, 62.07, 66.17, 73.52, 118.96, 128.10, 128.95, 130.65, 132.74, 133.96, 135.16, 138.06, 149.42, 166.80, 170.69, 172.80. LC/MS (M+1)$^+$=484; Anal Calcd for C$_{25}$H$_{26}$N$_3$O$_5$Cl, C, 62.05; H, 5.42; N, 8.68; Cl, 7.33. Found: C, 61.93; H, 5.42; N, 8.61; Cl, 7.22.

5.302 3-[5-Methyl-4-(4-Morpholin-4-ylmethyl-Benzyloxy)-1-Oxo-1,3-Dihydro-Isoindol-2-yl]-Piperidine-2,6-Dione

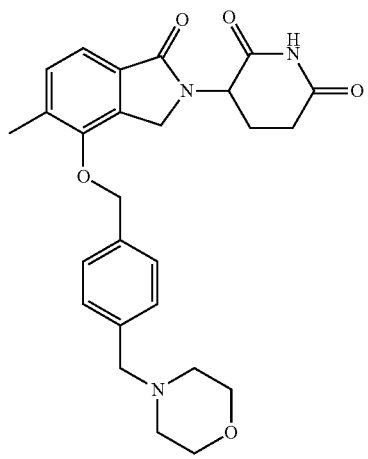 [SMILES: Cc1ccc2c(c1OCc1ccc(CN3CCOCC3)cc1)CN(C1CCC(=O)NC1=O)C2=O]

A mixture of 3-(5-chloro-4-(4-(morpholinomethyl)benzyloxy)-1-oxoisoindolin-2-yl)piperidine-2,6-dione (0.2 g, 0.413 mmol), tetrakis(triphenylphosphine)palladium (0) (0.096 g, 0.083 mmol) was flushed with nitrogen, and added tetramethylstannane (0.114 ml, 0.827 mmol) in Toluene (3 ml) and DMF (1 ml). It was heated in a 2-5 ml microwave vial to 130° C. from 12:20 µm for 2 hours. The mixture was purified by preparative HPLC (Water/MeCN, all with 0.1% HCOOH) to give 3-[5-Methyl-4-(4-morpholin-4-ylmethyl-benzyloxy)-1-oxo-1,3-dihydro-isoindol-2-yl]-piperidine-2,6-dione as a white solid (66 mg, 20% yield); mp, 232-234° C. HPLC: Waters Symmetry C-18, 3.9×150 mm, 5 µm, 1 mL/min, 240 nm, gradient from 10/90 to 70/30 in 5 min, isocratic at 70/30 in 5 min (CH$_3$CN/0.1% H$_3$PO$_4$), 4.78 min (96.3%). $^1$H NMR (DMSO-d$_6$) δ 1.90-2.07 (m, 1H, CHH), 2.23-2.48 (m, 8H, CHH, CH$_2$CH$_2$, CH$_3$), 2.55-2.67 (m, 1H, CHH), 2.83-3.02 (m, 1H, CHH), 3.42-3.50 (m, 2H, CH$_2$), 3.52-3.66 (m, 4H, CH$_2$CH$_2$), 4.35-4.64 (m, 2H, CH$_2$), 5.01-5.19 (m, 3H, NCH, CH$_2$), 7.26-7.52 (m, 6H, Ar), 11.00 (s, 1H, NH). $^{13}$C NMR (DMSO-d$_6$) δ 16.47, 22.42, 31.18, 45.77, 51.55, 53.15, 62.13, 66.20, 72.82, 117.80, 127.97, 128.98, 131.30, 131.89, 133.74, 135.93, 137.80, 151.86, 167.74, 170.95, 172.90. LC/MS m/e=464. Anal Calcd for C$_{26}$H$_{29}$N$_3$O$_5$: C, 67.37; H, 6.31; N, 9.07. Found: C, 67.07; H, 6.24; N, 9.04.

5.303 3-(4-((3-((Methylamino)Methyl)Isoxazol-5-yl)Methoxy)-1-Oxoisoindolin-2-yl)Piperidine-2,6-Dione

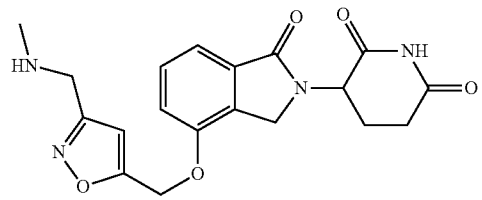 [SMILES: CNCc1cc(COc2cccc3c2CN(C2CCC(=O)NC2=O)C3=O)on1]

Step 1: (5-(((tert-Butyldimethylsilyl)oxy)methyl)isoxazol-3-yl)methanol Sodium borohydride (0.596 g, 15.77 mmol) was added to a stirred mixture of ethyl 5-((tert-butyldimethylsilyloxy)methyl)isoxazole-3-carboxylate (4.5 g, 15.77 mmol) in ethanol (25 mL), and the mixture stirred at room temperature for 4 h. Water (50 mL) was added and the mixture was evaporated to remove the ethanol. The remaining aqueous was extracted with EtOAc (2×75 mL), and the combined organic layers were washed with brine (100 mL), dried (MgSO$_4$), and evaporated, providing 3.67 g as a colorless oil; $^1$H NMR (CDCl$_3$) δ 0.12 (s, 6H), 0.92 (s, 9H), 4.70-4.82 (m, 4H), 6.25 (s, 1H).

Step 2: 3-(Bromomethyl)-5-(((tert-butyldimethylsilyl)oxy)methyl)isoxazole A solution of (5-((tert-butyldimethylsilyloxy)methyl)isoxazol-3-yl)methanol (3.47 g, 14.26 mmol) in dichloromethane (25 mL) was cooled to 0° C., and triphenylphosphine (4.11 g, 15.68 mmol) and carbon tetrabromide (4.49 g, 13.54 mmol) were added. After 2 h, the mixture was evaporated under vacuum and the residue was loaded directly onto a silica gel column, running with a hexanes-ethyl acetate gradient, and eluting the product at 5% EtOAc. The product was obtained as a colorless oil, 3.7 g, in 85% yield; $^1$H NMR (CDCl$_3$) δ 0.13 (s, 6H), 0.93 (s, 9H), 4.41 (s, 2H), 4.77 (s, 2H), 6.29 (s, 1H).

Step 3: tert-Butyl ((5-(hydroxymethyl)isoxazol-3-yl)methyl)methyl) Carbamate 3-(Bromomethyl)-5-((tert-butyldimethylsilyloxy)methyl)isoxazole (3.7 g, 12.08 mmol) was dissolved in Methylamine, 33% wt. solution in absolute ethanol (100 ml, 12.08 mmol) (100 mL), and the mixture was stirred at room temperature for 1 h, and was then evaporated to dryness. The residue was dissolved in THF, and Di-tert butyl dicarbonate (5.80 g, 26.6 mmol) and DIEA (6.94 ml, 39.9 mmol) were added. The mixture stirred at ambient temperature for 16 h. Then, 5 mL of pH 7 buffer solution were added, and 1M TBAF in THF (20 mL) were added, and the mixture stirred at ambient temperature for 3 h. Then, the mixture was evaporated under vacuum. The residue was partitioned between EtOAc (75 mL) and water (100 mL). The aqueous phase was extracted with EtOAc (75 mL), and the combined organic layers were washed with water (2×100 mL) and brine (100 mL), dried (MgSO$_4$), and evaporated. This crude product was used directly as such in the next step, without further characterization or purification.

Step 4: Methyl 5-amino-4-(4-((3-(((tert-butoxycarbonyl) methylamino) methyl)isoxazol-5-yl)methoxy)-1-oxoisoindolin-2-yl)-5-oxopentanoate A mixture of methyl 5-amino-4-(4-hydroxy-1-oxoisoindolin-2-yl)-5-oxopentanoate (1.206 g, 4.13 mmol) and tert-butyl (5-(hydroxymethyl) isoxazol-3-yl)methyl(methyl)carbamate (1 g, 4.13 mmol) was cooled to 0° C. Triphenylphosphine, polymer-bound, 3 mmol/g (2.75 g, 8.26 mmol) was added, followed by DIAD (1.625 ml, 8.26 mmol). The ice bath was allowed to melt, and the mixture stirred at room temperature for 16 h. The mixture was filtered and the filtrate was evaporated. The residue was dissolved in EtOAc (100 mL) and washed with 10% aqueous Na$_2$CO$_3$ (2×100 mL) and water (2×100 mL), and was evaporated. The residue was chromatographed using a methylene chloride-acetonitrile gradient, eluting the product at 70-80% acetonitrile, and providing 0.50 g was obtained as an oil, in 24% yield.

Step 5: 3-(4-((3-((Methylamino)methyl)isoxazol-5-yl) methoxy)-1-oxoisoindolin-2-yl)piperidine-2,6-dione A solution of methyl 5-amino-4-(4-((3-(((tert-butoxycarbonyl (methyl)amino) methyl)isoxazol-5-yl)methoxy)-1-oxoisoindolin-2-yl)-5-oxopentanoate (0.5 g, 0.968 mmol) in THF (100 mL) was cooled to 0° C., and potassium tert-butoxide (0.109 g, 0.968 mmol) was added. Stirring proceeded at this temperature, commencing at t=2:00 PM. After 30 min, the mixture was quenched with AcOH (5 mL) and was then partitioned between saturated aqueous NaHCO$_3$ (100 mL) and EtOAc (100 mL), and the aqueous phase was extracted with EtOAc (100 mL). The combined organic phases were washed with saturated aqueous NaHCO$_3$ (100 mL), water (100 mL), and brine (100 mL), were dried (MgSO$_4$) and evaporated, providing 0.39 g as an oil. The residue was dissolved in CH$_2$Cl$_2$ (20 mL) with stirring at rt, and 2M HCl in Et$_2$O (4 mL) was added. The mixture was stirred at ambient temperature, for 16 h. Then, the mixture partitioned between water (50 mL) and CH$_2$Cl$_2$ (50 mL), and the aqueous phase was made basic using 10% aqueous sodium carbonate solution. The mixture was extracted into EtOAc (3×50 mL), and the combined extracts were dried (MgSO$_4$) and evaporated. After drying, 160 mg were obtained as a white solid, in 43% yield; mp 220-222° C. HPLC: Waters X-Terra, 3.9×150 mm, 5 µm, 1 mL/min, 240 nm, 5/95 to 95/5 CH$_3$CN-0.1% NH$_4$(HCO$_2$) over 5 min then 10 min 95/5 CH$_3$CN-0.1% NH$_4$(HCO$_2$): 3.70 (100%). $^1$H NMR (DMSO-d$_6$) δ 1.94-2.04 (m, 1H), 2.26 (s, 3H), 2.35-2.47 (m, 1H), 2.58 (d, J=17.8 Hz, 1H), 2.82-3.00 (m, 1H), 3.70 (s, ?H), 4.24 (d, J=17.6 Hz, 1H), 4.34-4.47 (m, J=17.6 Hz, 1H), 5.11 (dd, J=5.0, 13.1 Hz, 1H), 5.44 (s, 2H), 6.64 (s, 1H), 7.30-7.44 (m, 2H), 7.46-7.58 (m, 1H), 10.98 (s, 1H). $^{13}$C NMR (DMSO-d$_6$) δ 22.33, 31.20, 35.23, 45.02, 45.54, 51.62, 60.72, 103.86, 115.07, 115.96, 129.87, 129.94, 133.50, 152.68, 162.90, 166.98, 167.82, 170.94, 172.80. Anal. Calcd for C$_{19}$H$_{20}$N$_4$O$_5$+0.5 H2O: C, 58.01%; H, 5.38%; N, 14.24%; Found: C, 58.00%; H, 5.20%; N, 13.90%.

5.304 3-(1-Oxo-4-((4-((4-(5-(2-Oxohexahydro-1H-Thieno[3,4-D]Imidazol-4-yl)Pentanoyl)Piperazin-1-yl)Methyl)Benzyl)Oxy)Isoindolin-2-yl)Piperidine-2,6-Dione

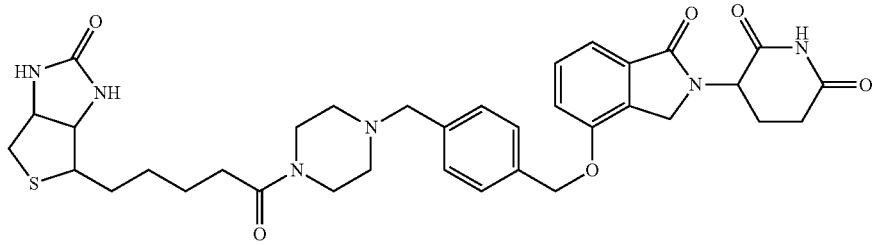 [SMILES: O=C1CCC(N2Cc3c(OCc4ccc(CN5CCN(C(=O)CCCCC6SCC7NC(=O)NC76)CC5)cc4)cccc3C2=O)C(=O)N1]

Step 1: tert-Butyl piperazine-1-carboxylate (0.6 g, 3.2 mmol) and N,N-diisopropylethylamine (9.6 mL, 3.2 mmol) were added to a stirred solution of 3-(4-(4-(bromomethyl) benzyloxy)-1-oxoisoindolin-2-yl)piperidine-2,6-dione (0.7 g, 1.6 mmol) in CH$_2$Cl$_2$ (60 mL). The resulting mixture was stirred at room temperature overnight. The reaction mixture was washed with water (2×35 mL), brine (35 mL) and dried. Solvent was removed and residue was purified by chromatography (SiO$_2$, 3% CH$_3$OH/CH$_2$Cl$_2$ for 15 min then to 5% over 5 min and hold for 15 min then to 10% over 5 min and hold for 15 min) to give tert-butyl 4-(4-((2-(2,6-dioxopiperidin-3-yl)-1-oxoisoindolin-4-yloxy)methyl)benzyl)piperazine-1-carboxylate (0.7 g, 83%): $^1$H NMR (DMSO-d$_6$) δ 1.38 (s, 9H), 1.96-2.00 (m, 1H), 2.28-2.32 (m, 4H), 2.54-2.60 (m, 2H), 2.87-2.93 (m, 1H), 3.29-3.32 (m, 4H), 3.48 (s, 2H), 4.22-4.28 (d, J=18 Hz, 1H), 4.39-4.45 (d, J=18 Hz, 1H), 5.08-5.14 (dd, J=6 and 12 Hz, 1H), 5.23 (s, 2H), 7.31-7.51 (m, 7H), 10.97 (s, 1H); $^{13}$C NMR (DMSO-d$_6$) δ 22.33, 28.00, 31.16, 45.06, 51.55, 52.30, 61.59, 69.36, 78.68, 114.94, 115.20, 127.63, 128.94, 129.78, 129.92, 133.27, 135.28, 137.72, 153.46, 153.74, 167.99, 170.95, 172.81.

Step 2: 4M HCL/dioxane (1.7 mL, 6.8 mmol) was added to a stirred solution of tert-butyl 4-(4-((2-(2,6-dioxopiperidin-3-yl)-1-oxoisoindolin-4-yloxy)methyl)benzyl) piperazine-1-carboxylate (0.7 g, 1.3 mmol) in 1,4-dioxane (10 mL) and CH$_2$Cl$_2$ (10 mL). The resulting mixture was stirred at room temperature overnight. 4M HCl/dioxane (1 mL) was added and mixture was stirred overnight. Ether (20 mL) was added and solid was collected by filtration and dried to give 3-(1-oxo-4-(4-(piperazine-1-ylmethyl)benzyloxy)isoindolin-2-yl)piperidine-2,6-dione (0.7 g, 100%): $^1$H NMR (DMSO-d$_6$) δ 1.97-2.01 (m, 1H), 2.42-2.62 (m, 2H), 2.86-2.98 (m, 1H), 3.35-3.37 (m, 8H), 4.25-4.48 (m, 4H), 5.09-5.15 (dd, J=6 and 12 Hz, 1H), 5.29 (s, 2H), 7.35-7.68 (m, 7H), 9.62 (b, 2H), 10.98 (s, 1H); $^{13}$C NMR (DMSO-d$_6$) δ

22.36, 31.16, 45.06, 47.35, 51.58, 59.00, 66.30, 69.00, 114.96, 115.35, 127.83, 129.83, 129.95, 131.50, 133.34, 139.00, 153.35, 167.94, 170.96, 172.81.

Step 3: 3-(1-Oxo-4-(4-(piperazin-1-ylmethyl)benzyloxy)isoindolin-2-yl)piperidine-2,6-dione (0.7 g, 1.3 mmol) was dissolved in DMF (10 mL). To this solution was added triethylamine (0.4 g, 4.0 mmol) and biotin N-hydroxysuccinimide ester (0.4 g, 1.3 mmol). The resulting mixture was stirred at room temperature overnight. The reaction mixture was concentrated under vacuum and residue was dissolved in $CH_2Cl_2$ (120 mL). $CH_2Cl_2$ solution was washed with water (2×40 mL), brine (40 mL) and dried. Solvent was removed and residue was purified by chromatography ($SiO_2$, 3% $CH_3OH/CH_2Cl_2$ for 10 min then to 10% over 10 min and hold for 10 min then to 15% over 5 min and hold for 15 min) to give 3-(1-oxo-4-((4-((4-(5-(2-oxohexahydro-1H-thieno[3,4-d]imidazol-4-yl)pentanoyl)piperazin-1-yl)methyl)benzyl)oxy)isoindolin-2-yl)piperidine-2,6-dione (0.5 g, 55%): mp 168-170° C.; $^1$H NMR (DMSO-d$_6$) δ 1.35-1.63 (m, 5H), 1.98-2.09 (m, 1H), 2.25-2.60 (m, 9H), 2.82-2.85 (m, 2H), 3.05-3.15 (m, 1H), 3.37-3.49 (m, 7H), 4.11-4.45 (m, 4H), 5.08-5.14 (dd, J=6 and 15 Hz, 1H), 5.23 (s, 2H), 6.35 (s, 1H), 6.42 (s, 1H), 7.32-7.51 (m, 7H), 10.97 (s, 1H); $^{13}$C NMR (DMSO-d$_6$) δ 22.33, 24.82, 28.06, 28.23, 31.16, 32.04, 40.93, 45.07, 51.56, 52.50, 52.90, 55.41, 59.13, 60.98, 61.52, 69.36, 114.97, 115.22, 127.64, 128.95, 129.93, 133.28, 135.33, 137.72, 153.48, 162.63, 167.99, 170.44, 170.96, 172.83; Calcd for $C_{35}H_{42}N_6O_6S+1.0H_2O$; C, 60.68; H, 6.40; N, 12.13; S, 4.68. Found: C, 60.32; H, 6.16; N, 11.68; S, 5.28.

5.305 3-(4-((4-((Bis(3,3-Trifluoropropyl)Amino)Methyl)Benzyl)Oxy)-1-Oxoisoindolin-2-yl)Piperidine-2,6-Dione

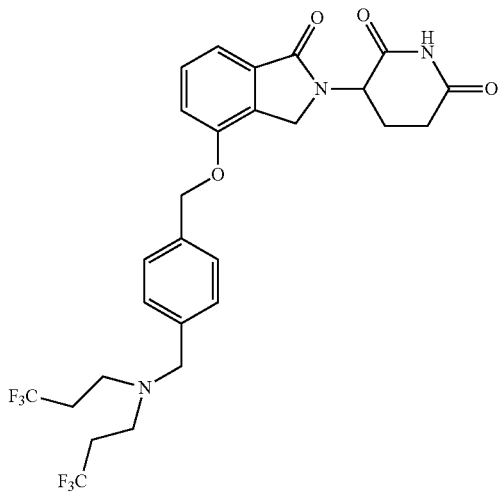 [SMILES: O=C1CCC(N2Cc3c(OCc4ccc(CN(CCC(F)(F)F)CCC(F)(F)F)cc4)cccc3C2=O)C(=O)N1]

Step 1: Methyl 5-amino-4-(4-((4-((bis(3,3,3-trifluoropropyl)amino)methyl) benzyl)oxy)-1-oxoisoindolin-2-yl)-5-oxopentanoate To a solution of methyl 5-amino-4-(4-(4-(bromomethyl)benzyloxy-1-oxoisoindolin-2-yl)-5-oxopentanoate (182 mg, 0.383 mmol) in MeCN (5 mL), was added bis(3,3,3-trifluoropropyl)amine (80 mg, 0.383 mmol) and DIEA (0.100 mL, 0.574 mmol). The clear solution was stirred at room temperature for 2 h and then at 70° C. overnight. After 24 h, the reaction was cooled to room temperature and concentrated in vacuo to give methyl 5-amino-4-(4-((4-((bis(3,3,3-trifluoropropyl)amino)methyl)benzyl)oxy)-1-oxoisoindolin-2-yl)-5-oxopentanoate Methyl 5-amino-4-(4-((4-((bis(3,3,3-trifluoropropyl)amino)methyl)benzyl)oxy)-1-oxoisoindolin-2-yl)-5-oxopentanoate as an oil. The crude product was used in the next step without further purification, assuming quantitative conversion. LCMS: MH=604, ~95 area % at 240 nm.

Step 2: 3-(4-((4-((Bis(3,3,3-trifluoropropyl)amino)methyl)benzyl)oxy)-1-oxoisoindolin-2-yl)piperidine-2,6-dione The crude product obtained in step 1, methyl 5-amino-4-(4-(4-((bis(3,3,3-trifluoropropyl)amino)methyl) benzyloxy)-1-oxoisoindolin-2-yl)-5-oxopentanoate (231 mg, 0.383 mmol) was dissolved in DMF (5 mL). To the solution was added anhydrous $K_2CO_3$ (159 mg, 1.148 mmol). The mixture stirred for 20 h at 85° C. and then allowed to stand at room temperature overnight. The reaction mixture was diluted with EtOAc (~150 mL) and washed with 1N aq. $NaHCO_3$ (30 mL). The organic layer was washed with water (30 mL) and brine, dried over $Na_2SO_4$, and concentrated in vacuo to give a tan oil. The oil was dissolved in DMF (7 mL) and purified using reversed-phase preparatory HPLC. The product was eluted with an acetonitrile/water gradient (0.1% formic acid in both mobile phases, 30 to 95% MeCN over 20 minutes) and fractions were collected by mass trigger. The desired fractions were combined and concentrated in vacuo until a thick slurry was obtained. The solid was collected on a fritted funnel, washed with additional water, and suction dried. Further drying of the solid in a vacuum oven at 60° C. provided 3-(4-((4-((bis(3,3,3-trifluoropropyl)amino)methyl)benzyl)oxy)-1-oxoisoindolin-2-yl)piperidine-2,6-dione as a white solid (57 mg, 26% yield): HPLC: Waters Symmetry $C_{18}$, 5 µm, 3.9×150 mm, 1 ml/min, 240 nm, 50/50 $CH_3CN/0.1\%$ $H_3PO_4$, 3.77 min (99.9%); mp: 107-109° C.; $^1$H NMR (DMSO-d$_6$) δ 1.88-2.06 (m, 1H, CHH), 2.34-2.49 (m, 5H, $CH_2$, $CH_2$, CHH), 2.53-2.76 (m, 5H, $CH_2$, $CH_2$, CHH), 2.82-3.03 (m, 1H, CHH), 3.63 (br. s., 2H, $CH_2$), 4.26 (d, J=17.6 Hz, 1H, CHH), 4.43 (d, J=17.4 Hz, 1H, CHH), 5.11 (dd, J=5.1, 13.2 Hz, 1H, CH), 5.24 (s, 2H, $CH_2$), 7.26-7.41 (m, 4H, Ar), 7.41-7.60 (m, 3H, Ar), 10.96 (s, 1H, NH); $^{13}$C NMR (DMSO-d$_6$) δ 22.33, 30.17 (q, J=20.9 Hz, $M_{02}$), 31.16, 45.07, 45.39, 51.58, 56.40, 69.35, 115.01, 115.22, 127.58, 128.62, 128.68, 128.92, 129.76, 129.96, 133.30, 153.46, 167.97, 170.93, 172.80. $\underline{C}CF_3$ at 30.17 ppm appears as doublet. $CF_3$ is not detected, possibly due to splitting; LCMS: MH=572; Anal Calcd for $C_{27}H_{27}F_6N_3O_4+0.6 H_2O$: C, 55.69; H, 4.88; N, 7.22; Found: C, 55.72; H, 4.83; N, 7.16.

5.306 3-{4-[4-(1H-Benzoimidazol-2-ylsulfanylmethyl)-Benzyloxy]-1-Oxo-1,3-Dihydro-Isoindol-2-yl}-Piperidine-2,6-Dione

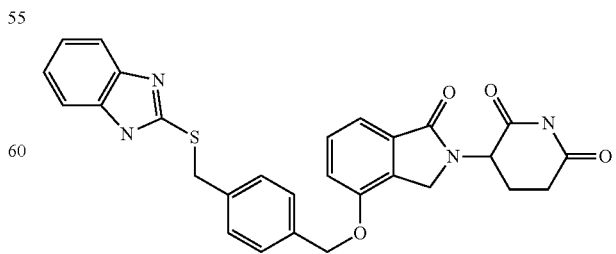

To the $CH_2Cl_2$ solution of 3-(4-(4-(bromomethyl)benzyloxy)-1-oxoisoindolin-2-yl)piperidine-2,6-dione (0.35 g, 0.790 mmol) was added 1H-benzo[d]imidazole-2-thiol (0.119 g, 0.790 mmol) and DIPEA (0.276 ml, 1.579 mmol). The mixture was stirred at room temperature overnight. The reaction mixture 7545-071-B showed product and SM. The mixture was added water and $CH_2Cl_2$ then extracted. The organic layer was purified on silica gel column eluted with $CH_2Cl_2$ and MeOH to give 3-{4-[4-(1H-benzoimidazol-2-ylsulfanylmethyl)-benzyloxy]-1-oxo-1,3-dihydro-isoindol-2-yl}-piperidine-2,6-dione as a white solid (0.2 g, 49%). Melting point: 160-162° C. LC-MS m/e=513. HPLC Waters Symmetry C-18, 3.9×150 mm, 5 micro, 1 mL/min, 240 nm, gradient 5/95 to 5/95 $CH_3CN/0.1\%$ $H_3PO_4$ in $H_2O$ during 5 min and stay at 95/5 for 5 min:7.02 min (97%). $^1H$ NMR (DMSO-$d_6$) δ 1.81-2.03 (m, 1H, CHH), 2.26-2.47 (m, 1H, CHH), 2.53-2.63 (m, 1H, CHH), 2.82-3.00 (m, 1H, CHH), 4.13-4.47 (m, 2H, $CH_2$), 4.58 (s, 2H, $CH_2$), 5.09 (dd, J=5.1, 13.2 Hz, 1H, NCH), 5.20 (s, 2H, $CH_2$), 7.04-7.18 (m, 2H, Ar), 7.26-7.34 (m, 2H, AR), 7.37-7.63 (m, 7H, Ar), 10.95 (s, 1H, NH), 12.56 (br. s., 1H, NH); $^{13}C$ NMR (DMSO-$d_6$) δ 22.30, 31.16, 34.75, 45.06, 51.55, 69.22, 114.88, 115.22, 127.86, 128.92, 129.77, 129.95, 133.28, 135.66, 137.57, 149.59, 153.41, 167.97, 170.92, 172.80. Anal Calcd for $C_{28}H_{24}N_4O_4S$, C: 63.27%; H: 4.55%; N: 10.54%; Found, C: 62.94%; H: 4.59%; N: 10.40%.

5.307 3-[4-(4-{[Ethyl-(2-Phenoxy-Ethyl)-Amino]-Methyl}-Benzyloxy)-1-Oxo-1,3-Dihydro-Isoindol-2-yl]-Piperidine-2,6-Dione

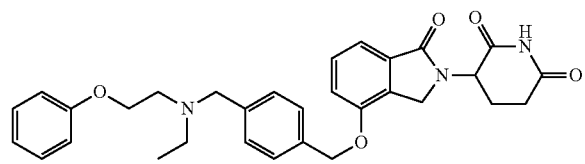 [SMILES: CCN(CCOc1ccccc1)Cc1ccc(COc2cccc3c2CN(C2CCC(=O)NC2=O)C3=O)cc1]

To the $CH_3CN$ (10 ml) solution of 3-(4-(4-(bromomethyl)benzyloxy)-1-oxoisoindolin-2-yl)piperidine-2,6-dione (0.358 g, 0.808 mmol) at room temperature was added N-ethyl-2-phenoxyethanamine (0.160 g, 0.969 mmol) and N-ethyl-N-isopropylpropan-2-amine (0.267 ml, 1.615 mmol). The resulting solution was stirred at room temperature for four hours. Solvent was evaporated and to the residue was added methylene chloride (80 ml). The mixture was washed with water (2×50 ml), brine (50 ml), dried and concentrated to an oil, which was purified by silica gel column (MeOH/$CH_2Cl_2$) to give 3-[4-(4-{[Ethyl-(2-phenoxy-ethyl)-amino]-methyl}-benzyloxy)-1-oxo-1,3-dihydro-isoindol-2-yl]-piperidine-2,6-dione as a white solid (0.334 g, 78% yield); mp, 94-96° C. HPLC: Waters Symmetry C-18, 3.9×150 mm, 5 μm, 1 mL/min, 240 nm, gradient from 10/90 to 90/10 in 5 min, isocratic at 90/10 for 5 min ($CH_3CN/0.1\%$ $H_3PO_4$), 4.72 min (96.2%). $^1H$ NMR (DMSO-$d_6$) δ 1.01 (t, J=7.0 Hz, 3H, $CH_3$), 1.91-2.05 (m, 1H, CHH), 2.35-2.48 (m, 1H, CHH), 2.52-2.64 (m, 3H, CHH, $CH_2$), 2.80 (t, J=6.1 Hz, 2H, $CH_2$), 2.84-2.99 (m, 1H, CHH), 3.66 (s, 2H, $CH_2$), 4.03 (t, J=6.1 Hz, 2H, $CH_2$), 4.19-4.47 (m, 2H, $CH_2$), 5.11 (dd, J=5.1, 13.2 Hz, 1H, NCH), 5.22 (s, 2H, $CH_2$), 6.84-6.95 (m, 3H, Ar), 7.21-7.29 (m, 2H, Ar), 7.30-7.53 (m, 7H, Ar), 10.97 (s, 1H, NH); $^{13}C$ NMR (DMSO-$d_6$) δ 11.81, 22.36, 31.20, 45.09, 47.42, 51.37, 51.58, 57.50, 65.95, 69.47, 114.38, 114.97, 115.20, 120.39, 127.59, 128.61, 129.40, 129.79, 129.94, 133.29, 135.00, 139.65, 153.51, 158.40, 168.01, 170.95, 172.82. LC/MS MH=528. Anal Calcd for $C_{31}H_{33}N_3O_5$ (+0.1 $H_2O$): C, 70.33; H, 6.32; N, 7.94. Found: C, 70.10; H, 6.22; N, 7.83.

5.308 3-{4-[4-(2-Diethylamino-Ethylsulfanylmethyl)-Benzyloxy]-1-Oxo-1,3-Dihydro-Isoindol-2-yl}-Piperidine-2,6-Dione

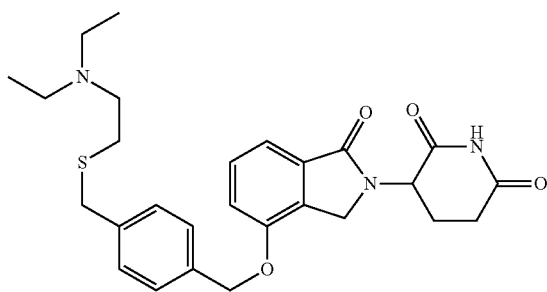 [SMILES: CCN(CC)CCSCc1ccc(COc2cccc3c2CN(C2CCC(=O)NC2=O)C3=O)cc1]

In a 20 mL scint. vial, 2-(diethylamino)ethanethiol hydrochloride (100 mg, 0.590 mmol) was added to a solution of 3-(4-(4-(bromomethyl)benzyloxy)-1-oxoisoindolin-2-yl)piperidine-2,6-dione (200 mg, 0.451 mmol) in acetonitrile (5 mL, 96 mmol). All the solids dissolved with swirling. To the mixture was added N-ethyl-N-isopropylpropan-2-amine (0.197 mL, 1.128 mmol), tetrabutylammonium bromide (29 mg, 0.09 mmol) and the yellowish solution was stirred at room temperature overnight. The crude mixture was evaporated to an oil, which was purified by preparative HPLC to give 3-{4-[4-(2-Diethylamino-ethylsulfanylmethyl)-benzyloxy]-1-oxo-1,3-dihydro-isoindol-2-yl}-piperidine-2,6-dione as an off-white solid (69 mg, 30% yield); mp, 135-137° C. HPLC (Waters Symmetry C-18, 3.9×150 mm, 5 μm, 1 mL/min, 240 nm, isocratic at 23%/77% MeCN/0.1% $H_3PO_4$): 3.99 min (96.4%). HPLC (LC5 grad):4.69 min (95.5%). $^1H$ NMR (DMSO-$d_6$) δ 0.92 (t, J=7.2 Hz, 6H, $_2CH_3$), 1.91-2.06 (m, 1H, CHH), 2.40-2.48 (m, 5H, $CH_2$, $CH_2$, CHH), 2.52-2.64 (m, 3H, CHH, $CH_2$), 2.83-3.01 (m, 1H, CHH), 3.76 (s, 2H, $CH_2$), 4.21-4.47 (m, 3H, $CH_2$), 5.11 (dd, J=5.2, 13.3 Hz, 1H, NCH), 5.23 (s, 2H, $CH_2$), 7.29-7.38 (m, 4H, Ar), 7.41-7.53 (m, 3H, Ar), 8.21 (s, 1H, NH). $^{13}C$ NMR (DMSO-$d_6$) δ 11.53, 22.38, 28.21, 31.20, 34.96, 45.09, 46.17, 51.58, 52.12, 69.33, 115.00, 115.23, 127.77, 128.90, 129.78, 129.95, 133.31, 135.10, 138.67, 153.46, 163.65 (from HCOOH), 167.99, 170.95, 172.82. LC/MS m/e=496. Anal Calcd for $C_{27}H_{33}N_3O_4S$: C, 65.43; H, 6.71; N, 8.48.

5.309 Assays 5.309.1 TNFα Inhibition Assay in hPMBC

Human peripheral blood mononuclear cells (hPBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bio-products, Woodland, Calif., USA), 2 mM L-glutamine, 100 U/ml penicillin, and 100 μg/ml streptomycin (Life Technologies).

PBMC (2×10$^5$ cells) are plated in 96-well flat-bottom Costar tissue culture plates (Corning, N.Y., USA) in triplicate. Cells are stimulated with LPS (from *Salmonella abortus equi*, Sigma cat. no. L-1887, St. Louis, Mo., USA) at 1 ng/ml final in the absence or presence of compounds.

Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% CO2, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

5.309.2 IL-2 and MIP-3α Production by T Cells

PBMC are depleted of adherent monocytes by placing $1 \times 10^8$ PBMC in 10 ml complete medium (RPMI 1640 supplemented with 10% heat-inactivated fetal bovine serum, 2 mM L-glutamine, 100 U/ml penicillin, and 100 µg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every $1 \times 10^8$ non-adherent PBMC: 0.3 ml Sheep anti-mouse IgG beads, 15 µl anti-CD16, 15 µl anti-CD33, 15 µl anti-CD56, 0.23 ml anti-CD19 beads, 0.23 ml anti-HLA class II beads, and 56 µl anti-CD14 beads. The cells and bead/antibody mixture is rotated end-over-end for 30-60 minutes at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 µg/ml in PBS, 100 µl per well, incubated at 37° C. for 3-6 hours, then washed four times with complete medium 100 µl/well just before T cells are added. Compounds are diluted to 20 times of final in a round bottom tissue culture 96-well plate. Final concentrations are about 10 µM to about 0.00064 µM. A 10 mM stock of compounds provided herein is diluted 1:50 in complete for the first 20× dilution of 200 M in 2% DMSO and serially diluted 1:5 into 2% DMSO. Compound is added at 10 µl per 200 µl culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3α levels are normalized to the amount produced in the presence of an amount of a compound provided herein, and $EC_{50}$s calculated using non-linear regression, sigmoidal dose-response, constraining the top to 100% and bottom to 0%, allowing variable slope (GraphPad Prism v3.02).

5.309.3 Cell Proliferation Assay

Cell lines (e.g., Namalwa, MUTZ-5, UT-7, and various NHL cell lines) are obtained from the Deutsche Sammlung von Mikroorganismen und Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 µM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

5.309.4 Immunoprecipitation and Immunoblot

Cells (e.g., various NHL cell lines) are treated with DMSO or an amount of a compound provided herein for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospo-Akt (Ser473 or Thr308), phospho-Gab1 (Y627), Gab1, IRS2, actin and IRF-1 Abs and analyzed on a Storm 860 Imager using ImageQuant software (Molecular Dynamics).

5.309.5 Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

5.309.6 Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

5.309.7 Luciferase Assay

Namalwa cells are transfected with 4 g of API-luciferase (Stratagene) per $1 \times 10^6$ cells and 3 µl Lipofectamine 2000 (Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

5.309.8 TNFα Inhibition

Using procedures substantially similar to those provided in Section 5.309.1 above, $IC_{50}$ values for certain of the compounds provided herein for TNFα inhibition were determined. Tested compounds include the compounds of Examples 5.2, 5.6-5.24, 5.29-5.46, 5.48-5.69, 5.71-5.133, 5.136-5.143, 5.151-5.155, 5.158-5.188, 5.193-5.201, 5.207, 5.224-5.289, 5.293-5.296 and 5.299-5.308.

The determined $IC_{50}$ values ranged from about 0.02 nM to about 2 µM. These results show that compounds provided herein are useful as inhibitors of TNFα.

5.309.9 IL-2 Production

Using procedures substantially similar to those described in Section 5.309.2. above, $EC_{50}$ values of certain compounds provided herein for the production of IL-2 were also determined. Tested compounds include the compounds of Examples 5.2, 5.6-5.24, 5.30-5.46, 5.48-5.57, 5.59-5.69, 5.71-5.133, 5.136-5.137, 5.139-5.143, 5.151-5.188, 5.194-5.201, 5.207, 5.216-5.289, 5.293-5.296, 5.300 and 5.303-5.308.

The determined $EC_{50}$ values ranged from about 0.01 nM to about 1.4 μM. These results show that compounds provided herein are useful as stimulators of IL-2 production.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

All of the patents, patent applications and publications referred to herein are incorporated herein in their entireties. Citation or identification of any reference in this application is not an admission that such reference is available as prior art to the claimed subject matter. The full scope of the invention is better understood with reference to the appended claims.

What is claimed is:

1. A compound of the formula:

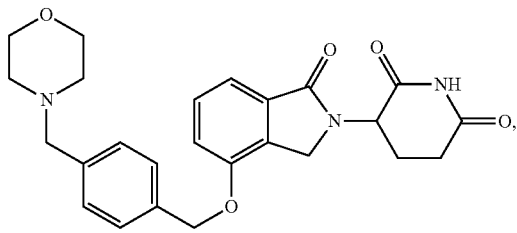 [SMILES: O=C1CCC(N2Cc3c(OCc4ccc(CN5CCOCC5)cc4)cccc3C2=O)C(=O)N1]

or a pharmaceutically acceptable salt or stereoisomer thereof.

2. The compound of claim 1, which is

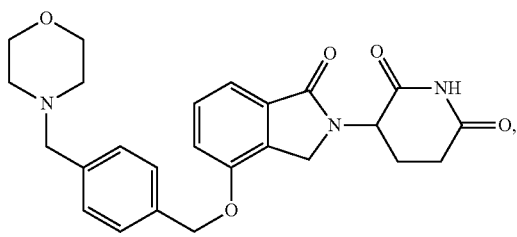 [SMILES: O=C1CCC(N2Cc3c(OCc4ccc(CN5CCOCC5)cc4)cccc3C2=O)C(=O)N1]

or a pharmaceutically acceptable salt thereof.

3. The compound of claim 2, which is

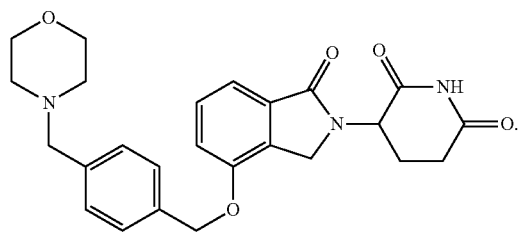 [SMILES: O=C1CCC(N2Cc3c(OCc4ccc(CN5CCOCC5)cc4)cccc3C2=O)C(=O)N1]

4. The compound of claim 1, which is

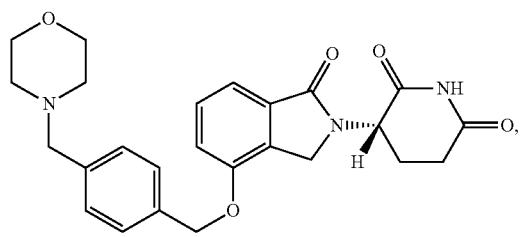 [SMILES: O=C1CC[C@H](N2Cc3c(OCc4ccc(CN5CCOCC5)cc4)cccc3C2=O)C(=O)N1]

or a pharmaceutically acceptable salt thereof.

5. The compound of claim 4, which is

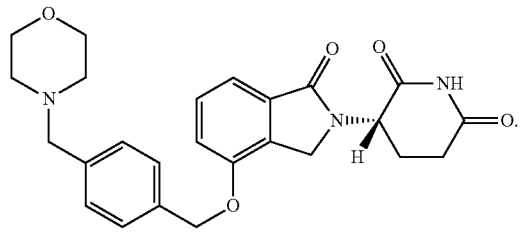 [SMILES: O=C1CC[C@H](N2Cc3c(OCc4ccc(CN5CCOCC5)cc4)cccc3C2=O)C(=O)N1]

6. A pharmaceutical composition comprising a compound of claim 1 and one or more excipients.

7. A pharmaceutical composition comprising a compound of claim 2 and one or more excipients.

8. A pharmaceutical composition comprising a compound of claim 3 and one or more excipients.

9. A pharmaceutical composition comprising a compound of claim 4 and one or more excipients.

10. A pharmaceutical composition comprising a compound of claim 5 and one or more excipients.

* * * * *